US010131695B2

(12) United States Patent
Garcia-Sastre et al.

(10) Patent No.: US 10,131,695 B2
(45) Date of Patent: Nov. 20, 2018

(54) INFLUENZA VIRUS VACCINES AND USES THEREOF

(71) Applicant: Icahn School of Medicine at Mount Sinai, New York, NY (US)

(72) Inventors: Adolfo Garcia-Sastre, New York, NY (US); Peter Palese, New York, NY (US); Florian Krammer, New York, NY (US); Natalie Pica, New York, NY (US); Dirk Eggink, New York, NY (US); Rafael A. Medina-Silva, Santiago (CL); Rong Hai, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 285 days.

(21) Appl. No.: 14/345,816

(22) PCT Filed: Sep. 19, 2012

(86) PCT No.: PCT/US2012/056122
§ 371 (c)(1),
(2) Date: Mar. 19, 2014

(87) PCT Pub. No.: WO2013/043729
PCT Pub. Date: Mar. 28, 2013

(65) Prior Publication Data
US 2015/0132330 A1    May 14, 2015

Related U.S. Application Data

(60) Provisional application No. 61/684,481, filed on Aug. 17, 2012, provisional application No. 61/670,108, filed on Jul. 10, 2012, provisional application No. 61/648,525, filed on May 17, 2012, provisional application No. 61/607,526, filed on Mar. 6, 2012, provisional application No. 61/565,899, filed on Dec. 1, 2011, provisional application No. 61/536,924, filed on Sep. 20, 2011.

(51) Int. Cl.
| | | |
|---|---|---|
| C07K 14/005 | (2006.01) | |
| A61K 39/145 | (2006.01) | |
| A61K 39/12 | (2006.01) | |
| C12N 7/00 | (2006.01) | |
| A61K 39/00 | (2006.01) | |

(52) U.S. Cl.
CPC ............ *C07K 14/005* (2013.01); *A61K 39/12* (2013.01); *A61K 39/145* (2013.01); *C12N 7/00* (2013.01); *A61K 2039/521* (2013.01); *A61K 2039/5258* (2013.01); *A61K 2039/53* (2013.01); *C07K 2319/00* (2013.01); *C12N 2710/14143* (2013.01); *C12N 2760/16122* (2013.01); *C12N 2760/16123* (2013.01); *C12N 2760/16134* (2013.01); *C12N 2760/16162* (2013.01); *C12N 2760/16171* (2013.01)

(58) Field of Classification Search
None
See application file for complete search history.

(56) References Cited

U.S. PATENT DOCUMENTS

| | | |
|---|---|---|
| 5,182,192 A | 1/1993 | Steplewski et al. |
| 5,413,923 A | 5/1995 | Kucherlapati et al. |
| 5,545,806 A | 8/1996 | Lonberg et al. |
| 5,569,825 A | 10/1996 | Lonberg et al. |
| 5,571,709 A | 11/1996 | Devauchelle et al. |
| 5,573,916 A | 11/1996 | Cheronis et al. |
| 5,589,174 A | 12/1996 | Okuno et al. |
| 5,625,126 A | 4/1997 | Lonberg et al. |
| 5,631,350 A | 5/1997 | Okuno et al. |
| 5,633,425 A | 5/1997 | Lonberg et al. |
| 5,661,016 A | 8/1997 | Lonberg et al. |
| 5,820,871 A | 10/1998 | Palese et al. |
| 5,854,037 A | 12/1998 | Palese et al. |
| 5,885,793 A | 3/1999 | Griffiths et al. |
| 5,916,771 A | 6/1999 | Hori et al. |
| 6,001,634 A | 12/1999 | Palese et al. |
| 6,165,476 A | 12/2000 | Strom et al. |
| 6,337,070 B1 | 1/2002 | Okuno et al. |
| 6,720,409 B2 | 4/2004 | Okuno et al. |
| 6,867,293 B2 | 3/2005 | Andrews et al. |
| 6,887,699 B1 | 5/2005 | Palese et al. |
| 6,942,861 B2 | 9/2005 | McKee et al. |
| 7,566,458 B2 | 7/2009 | Yang et al. |

(Continued)

FOREIGN PATENT DOCUMENTS

| | | |
|---|---|---|
| CA | 2121559 | 10/1994 |
| CA | 2121559 A1 | 10/1994 |

(Continued)

OTHER PUBLICATIONS

Horimoto T, Takada A, Iwatsuki-Horimoto K, Hatta M, Goto H, Kawaoka Y. Generation of influenza A viruses with chimeric (type A/B) hemagglutinins. J Virol. Jul. 2003;77(14):8031-8.8038.*
Reid et. al. Hemagglutinin [Influenza A virus (A/South Carolina/1/1918(H1N1))]. GenBank Acc. No. AAD17229.1. Dep. Oct. 11, 2000.*
Gibbs MJ, Armstrong JS, Gibbs AJ. Recombination in the hemagglutinin gene of the 1918 "Spanish flu". Science. Sep. 7, 2001;293(5536):1842-5.*

(Continued)

*Primary Examiner* — Benjamin P Blumel
(74) *Attorney, Agent, or Firm* — Jones Day

(57) ABSTRACT

Provided herein are flu hemagglutinin polypeptides, including chimeric influenza virus hemagglutinin polypeptides, and flu hemagglutinin polypeptides comprising modified glycosylation sites and non-naturally glycosylation sites, compositions comprising the same, vaccines comprising the same and methods of their use.

47 Claims, 84 Drawing Sheets

Figure 4:
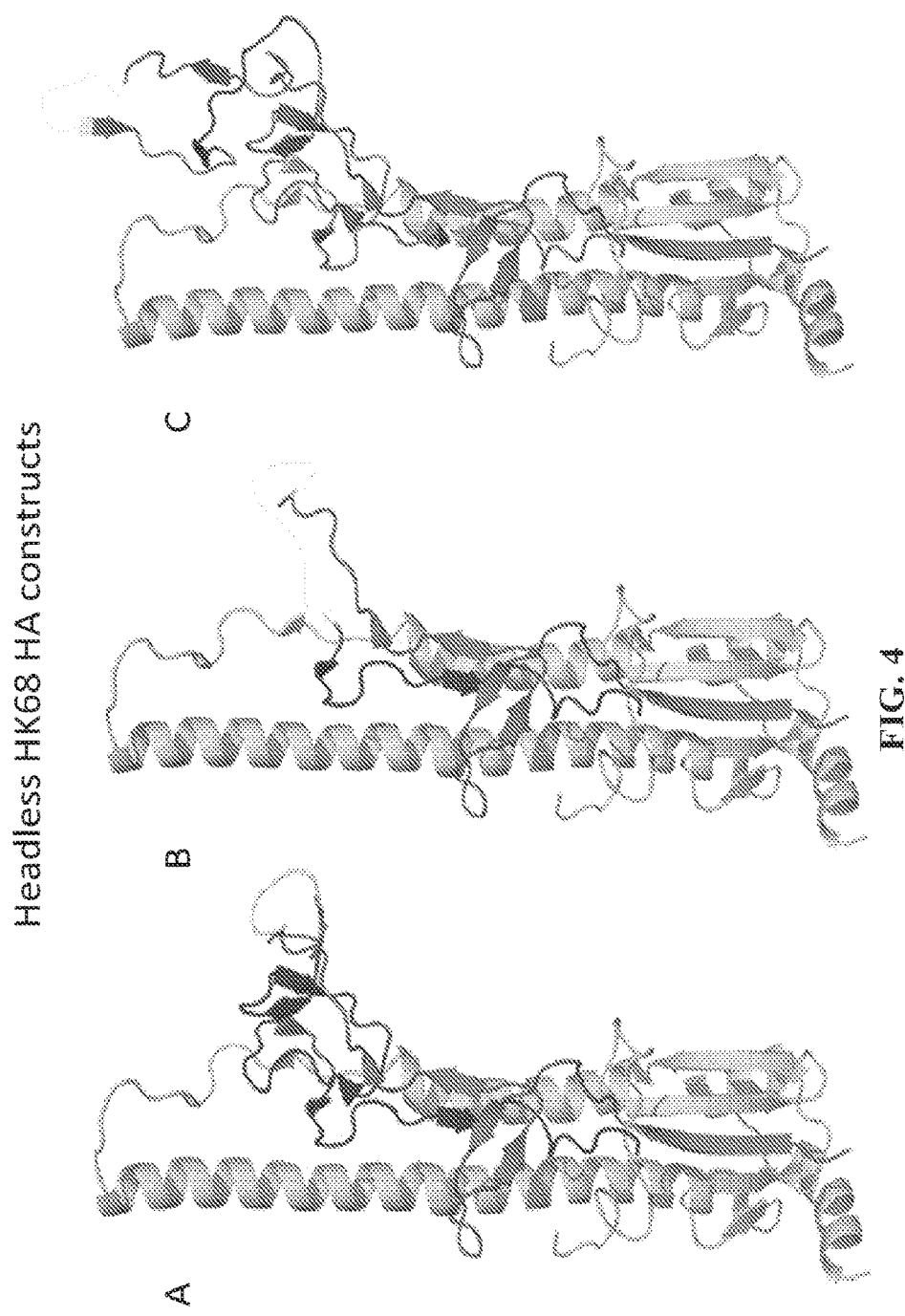

Specification includes a Sequence Listing.

(56) References Cited

U.S. PATENT DOCUMENTS

| | | | |
|---|---|---|---|
| 8,367,077 B2 | 2/2013 | Zurbriggen et al. | |
| 8,603,467 B2 | 12/2013 | Chen et al. | |
| 8,673,314 B2 | 3/2014 | Garcia Sastre et al. | |
| 8,828,406 B2 | 9/2014 | Garcia-Sastre et al. | |
| 9,051,359 B2 | 6/2015 | Garcia-Sastre et al. | |
| 9,175,069 B2 | 11/2015 | Garcia-Sastre et al. | |
| 9,371,366 B2 | 6/2016 | Garcia-Sastre et al. | |
| 9,452,211 B2 | 9/2016 | Meijberg et al. | |
| 9,701,723 B2 | 7/2017 | Garcia-Sastre et al. | |
| 9,707,288 B2 | 7/2017 | Schrader | |
| 9,708,373 B2 | 7/2017 | Garcia-Sastre et al. | |
| 9,849,172 B2 | 12/2017 | Garcia-Sastre et al. | |
| 2002/0164770 A1 | 11/2002 | Hoffman | |
| 2003/0134338 A1 | 7/2003 | Makarocskiy | |
| 2004/0002061 A1 | 1/2004 | Kawaoka | |
| 2005/0009008 A1 | 1/2005 | Robinson et al. | |
| 2005/0042229 A1 | 2/2005 | Yang et al. | |
| 2005/0048074 A1 | 3/2005 | Cardineau et al. | |
| 2005/0064391 A1 | 3/2005 | Segal et al. | |
| 2005/0106178 A1 | 5/2005 | O'hagan et al. | |
| 2005/0201946 A1 | 9/2005 | Friede et al. | |
| 2006/0008473 A1 | 1/2006 | Yana et al. | |
| 2006/0280754 A1 | 12/2006 | Garry et al. | |
| 2007/0020238 A1 | 1/2007 | Baltimore et al. | |
| 2007/0036809 A1 | 2/2007 | Michl et al. | |
| 2008/0019998 A1 | 1/2008 | Wang et al. | |
| 2008/0032921 A1 | 2/2008 | Alexander et al. | |
| 2008/0152657 A1 | 6/2008 | Horowitz et al. | |
| 2008/0176247 A1 | 7/2008 | Chou et al. | |
| 2009/0081255 A1 | 3/2009 | Bublot et al. | |
| 2009/0291472 A1 | 11/2009 | Lu et al. | |
| 2009/0304730 A1 | 12/2009 | Amon et al. | |
| 2009/0304739 A1 | 12/2009 | Rappouli et al. | |
| 2009/0311265 A1 | 12/2009 | Van Den Brink et al. | |
| 2009/0311669 A1 | 12/2009 | Kawaoka | |
| 2010/0184192 A1 | 7/2010 | Smith et al. | |
| 2010/0297165 A1 | 11/2010 | Berzofsky et al. | |
| 2010/0297174 A1 | 11/2010 | Garcia-Sastre et al. | |
| 2011/0027270 A1 | 2/2011 | Garcia-Sastre et al. | |
| 2011/0111494 A1 | 5/2011 | Hill et al. | |
| 2011/0182938 A1 | 7/2011 | Weiner et al. | |
| 2012/0039898 A1 | 2/2012 | Throsby et al. | |
| 2012/0122185 A1 | 5/2012 | Palese et al. | |
| 2012/0189658 A1 | 7/2012 | Couture et al. | |
| 2012/0244183 A1 | 9/2012 | Garcia-Sastre et al. | |
| 2013/0129747 A1 | 5/2013 | Schrader | |
| 2013/0129761 A1 | 5/2013 | Garcia-Sastre et al. | |
| 2013/0209499 A1 | 8/2013 | Garcia-Sastre et al. | |
| 2014/0170163 A1 | 6/2014 | Garcia Sastre et al. | |
| 2014/0193484 A1 | 7/2014 | Bertholet Girardin et al. | |
| 2014/0328875 A1 | 11/2014 | Garcia Sastre et al. | |
| 2015/0239960 A1 | 8/2015 | Garcia-Sastre et al. | |
| 2015/0297712 A1 | 10/2015 | Garcia-Sastre et al. | |
| 2015/0299270 A1 | 10/2015 | Galarza et al. | |
| 2015/0335729 A1 | 11/2015 | Garcia-Sastre et al. | |
| 2016/0022806 A1 | 1/2016 | Weiner et al. | |
| 2016/0038585 A1 | 2/2016 | Dormitzer et al. | |
| 2016/0355553 A1 | 12/2016 | Meijberg et al. | |
| 2016/0361408 A1 | 12/2016 | Garcia-Sastre et al. | |
| 2016/0362455 A1 | 12/2016 | Meijberg et al. | |
| 2016/0376347 A1 | 12/2016 | Saelens et al. | |
| 2017/0327565 A1 | 11/2017 | Schrader | |
| 2018/0002385 A1 | 1/2018 | Garcia-Sastre et al. | |
| 2018/0008696 A1 | 1/2018 | Palese et al. | |

FOREIGN PATENT DOCUMENTS

| | | |
|---|---|---|
| CA | 2718923 | 9/2009 |
| EP | 0621339 A2 | 10/1994 |
| EP | 2 540 312 A1 | 1/2013 |
| JP | A-H7-89992 | 4/1995 |
| JP | 2004-258814 | 9/2004 |
| JP | 2006-347922 | 12/2006 |
| JP | 2008-249712 A | 10/2008 |
| JP | 2011-057653 | 3/2011 |
| JP | 2012-530499 A | 12/2012 |
| WO | WO 1984/000687 | 3/1984 |
| WO | WO 1992/001047 | 1/1992 |
| WO | WO 1994/009136 | 4/1994 |
| WO | WO 1994/016109 | 7/1994 |
| WO | WO 1994/017826 | 8/1994 |
| WO | WO 1995/034324 | 12/1994 |
| WO | WO 1996/033735 | 10/1996 |
| WO | WO 1996/034096 | 10/1996 |
| WO | WO 97/40161 A1 | 10/1997 |
| WO | WO 1997/040177 A1 | 10/1997 |
| WO | WO 1998/024893 | 6/1998 |
| WO | WO 2007/045674 | 4/2007 |
| WO | WO 2007/064802 | 6/2007 |
| WO | WO 2007/103322 | 9/2007 |
| WO | WO 2007/134327 | 11/2007 |
| WO | WO 2008/005777 | 1/2008 |
| WO | WO 2008/028946 | 3/2008 |
| WO | WO 2008/032219 | 3/2008 |
| WO | WO 2009/009876 | 1/2009 |
| WO | WO 2009/012489 A1 | 1/2009 |
| WO | WO 2009/025770 | 2/2009 |
| WO | WO 2009/036157 | 3/2009 |
| WO | WO 2009/068992 | 6/2009 |
| WO | WO 2009/076778 | 6/2009 |
| WO | WO 2009/079259 | 6/2009 |
| WO | WO 2009079259 A2 * | 6/2009 |
| WO | WO 2009/092038 | 7/2009 |
| WO | WO 2009/121004 | 10/2009 |
| WO | WO 2009/150532 | 12/2009 |
| WO | WO 2009/156405 | 12/2009 |
| WO | WO 2010/003235 | 1/2010 |
| WO | WO 2010/036948 | 4/2010 |
| WO | WO 2010/117786 | 10/2010 |
| WO | WO 2010/130636 | 11/2010 |
| WO | WO 2010/138564 | 12/2010 |
| WO | WO 2010/148511 | 12/2010 |
| WO | WO/2010/148511 * | 12/2010 |
| WO | WO 2010/148511 A1 | 12/2010 |
| WO | WO 2010148511 A1 * | 12/2010 |
| WO | WO 2011/014645 | 2/2011 |
| WO | WO 2011/044152 | 4/2011 |
| WO | WO 2011/087092 | 7/2011 |
| WO | WO 2011/103453 | 8/2011 |
| WO | WO 2011/111966 | 9/2011 |
| WO | WO 2011/123495 | 10/2011 |
| WO | WO 2012/009790 | 1/2012 |
| WO | WO 2013/043729 | 3/2013 |
| WO | WO 2013/079473 | 6/2013 |
| WO | WO 2014/159960 | 1/2014 |
| WO | WO 2014/099931 | 6/2014 |
| WO | WO 2014/152841 A1 | 9/2014 |
| WO | WO 2015/199564 A1 | 12/2015 |
| WO | WO 2016/118937 A1 | 7/2016 |
| WO | WO 2016/205347 A1 | 12/2016 |
| WO | WO 2017/210445 A1 | 12/2017 |
| WO | WO 2017/218624 A1 | 12/2017 |

OTHER PUBLICATIONS

Webby R, Webster RG, Govorkova E, Duan S. Hemagglutinin [Influenza A virus (A/Brisbane/59/2007(H1N1))]. GenBank Acc. No. ADE28750.1. Dep. Mar. 29, 2010.*

Horimoto et al., Generation of influenza A viruses with chimeric (typeAIR) hemagglutinins, 2003, Journal of Virology, vol. 77, No. 14, pp. 8031-8038.*

Babai et al., A novel liposomal influenza vaccine (INFLUSOME-VAC) containing hemagglutinin-neuraminidase and IL-2 or GM-CSF induces protective anti-neuraminidase antibodies cross-reacting with a wide spectrum of influenza A viral strains. Vaccine. 200; 20(3-4);505-15.

Bianchi et al., 2005, "Universal influenza B vaccine based on the maturational cleavage site of the hemagglutinin precursor", Journal of Virology; 79(12):7380-7388.

Copeland et al., 2005, "Functional chimeras of human immunodeficiency virus type 1 Gp120 and influenza A virus (H3) hemagglutinin", Journal of Virology; 79:6459-6471.

(56) References Cited

OTHER PUBLICATIONS

Corti et al., 2011, "A neutralizing antibody selected from plasma cells that binds to group 1 and group 2 influenza A hemagglutinins", Science. 333(6044):850-856.
D'Aoust et al., 2008, "Influenza virus-like particles produced by transient expression in Nicotiana benthaminana induce a protective immune response against a lethal viral challenge in mice", J. Plant Biotechnology, 6(9):930-940.
Database Geneseq "Influenza A virus hemagglutinin protein, 1-11PR8", Accession No. AJG95109, dated Nov. 15, 2007.
Ekiert et al., 2009, "Antibody recognition of a highly conserved influenza virus epitope", Science; 324(5924):246-251.
Ekiert et al., 2011, "A highly conserved neutralizing epitope on group 2 influenza A viruses", Science 333:843-850.
Ekiert et al., 2012, "Cross-neutralization of influenza A viruses mediated by a single antibody loop", Nature, 489:526-532.
Fodor et al., 1999, "Rescue of influenza A virus from recombinant DNA", J Virol 73:9679-9682.
Fujii et al., 2003, "Selective incorporation of influenza virus RNA segments into virions", Proc. Natl. Acad. Sci. USA 100:2002-2007.
Gao & Palese, 2009, "Rewiring the RNAs of influenza virus to prevent reassortment", PNAS 106:15891-15896.
Gao et al., 2013, "Human infection with a novel avian-origin influenza A(H7N9) virus", N. Engl. J. Med. 368:1888-1897.
García-Sastre et al., 1994, "Introduction of foreign sequences into the genome of influenza A virus", Dev. Biol. Stand, 82:237-246.
García-Sastre et al., 1994, "Use of a mammalian internal ribosomal entry site element for expression of a foreign protein by a transfectant influenza virus", J. Virol. 68:6254-6261.
Gerhard et al., 2006, -Prospects for universal influenza virus vaccine, Emerging Infectious Diseases; 12(4):569-574.
Gocnik et al., 2008, "Antibodies Induced by the HA2 Glycopolypeptide of Influenza Virus Haemagglutinin Improve Recovery from Influenza A Virus Infection," J Gen Virol., 89:958-967.
Goff et al., 2013, "Adjuvants and immunization strategies to induce influenza virus hemagglutinin stalk antibodies", PLoS One 8:e79194.
Gould et al., 1987, "Mouse H-2k-Restricted Cytotoxic T Cells Recognize Antigenic Determinants in Both The HA1 and HA2 Subunits of the Influenza A/PR/8/34 Hemagglutinin," J. Exp. Med., 166:693-701.
Graves et al., 1983, "Preparation of influenza virus subviral particles lacking the HAI subunit of hemagglutinin: unmasking of cross-reactive HA2 determinants," Virology, 126(1):106-1 16).
Hai et al., 2008, "Influenza B virus NS1-truncated mutants: live-attenuated vaccine approach", J Virol 82:10580-10590.
Hai et al., 2011, "A reassortment-incompetent live attenuated influenza virus vaccine for protection against pandemic virus strains", Journal of virology 85:6832-6843.
Hai et al., 2012, "Influenza viruses expressing chimeric hemagglutinins: globular head and stalk domains derived from different subtypes", J. Virol. 86:5774-5781.
Horimoto et al., Generation of influenza A viruses with chimeric (type AIR) hemagglutinins. J Virol. Jul. 2003;77(14):8031-8.
Horvath et al., 1998, -Hemagglutinin-based multipeptide construct elicits enhanced protective immune response in mice against influenza A virus infection, Immunology Letters; 60(2/03):127-136.
International Search Report dated Feb. 19, 2013 or PCT Application No. PCT/US2012/056122, Published as WO 2013/043729.
International Search Report dated Apr. 28, 2014 of PCT Application No. PCT/US2013/075697, Published as WO 2014/099931.
International Search Report dated Jul. 13, 2011 of PCT Application No. PCT/US2011/030441, Published as WO 2011/123495.
International Search Report dated Aug. 24, 2010 or PCT Application No. PCT/US2010/029202, Published as WO 2010/117786.
International Search Report of International application No. PCT/US20011/025467, dated Oct. 19, 2011.
International Search Report of International application No. PCT/US2010/036170, dated Aug. 17, 2010.
Kashyap et al., 2008, "Combinatorial antibody libraries from survivors of the Turkish H5N1 avian influenza outbreak reveal virus neutralization strategies", Proc Natl Acad Sci USA; 105:5986-5991.
Kistner et al.. 2007, "Cell culture (Vero) derived whole virus (H5N1) vaccine based on wild-type virus strain induces cross-protective immune responses", Vaccine; 25(32):6028-6036.
Krammer et al., 2013, "Influenza virus hemagglutinin stalk-based antibodies and vaccines", Current Opinion in Virology 3:521-530.
Krammer et al., 2012, "A carboxy-terminal trimerization domain stabilizes conformational epitopes on the stalk domain of soluble recombinant hemagglutinin substrates", PLoS One. 7:e43603.doi:10.1371/journal.pone.0043603.
Krammer et al., 2013, "Chimeric hemagglutinin influenza virus vaccine constructs elicit broadly protective stalk-specific antibodies", J. Virol. 87:6542-6550.
Krammer et al., 2010, "Trichoplusia ni cells (High Five) are highly efficient for the production of influenza A virus-like particles: a comparison of two insect cell lines as production platforms for influenza vaccines", Mol Biotechnol; 45:226-34.
Krause et al., 2012, "Human monoclonal antibodies to pandemic 1957 H2N2 and pandemic 1968 H3N2 influenza viruses", J. Virol. 86:6334-6340.
Landry et al., 2008, "Three-dimensional structure determines the pattern of CD4+ T-cell epitope dominance in influenza virus hemagglutinin", Journal of Virology; 82(3):1238-1248.
Lee et al., 2012, "Heterosubtypic antibody recognition of the influenza virus hemagglutinin receptor binding site enhanced by avidity", Proc. Natl. Acad. Sci. U.S.A. 109:17040-17045.
Leroux-Roels, et al. 2008. "Broad Glade 2 cross-reactive immunity induced by an adjuvanted Gladen 1 rH5N1 pandemic influenza vaccine", PLOS One; 3(2):1-5.
Li et al., 1992, "Influenza A virus transfectants with chimeric haemagglutinins containing epitopes from different subtypes", Journal of Virology, 66(1):399-404.
Lowen et al. 2009, "Blocking interhost transmission of influenza virus by vaccination in the guinea pig model", Journal of Virology; 8307):2803-2818.
Marasco et al.. 2007, -The growth and potential of human antiviral monoclonal antibody therapeutics, Nat Biotechnol: 25(12):1421-1434.
Margine et al., 2013, "H3N2 influenza virus infection induces broadly reactive hemagglutinin stalk antibodies in humans and mice", J. Virol. 87:4728-4737.
Miller et al., 2013, "1976 and 2009 H1N1 influenza virus vaccines boost anti-hemagglutinin stalk antibodies in humans", J. Infect. Dis. 207:98-105.
Mo et al., 2003. -Coexpression of complementary fragments of CIC-5 and restoration of chloride channel function in a Dent's disease mutation, Am J Physiol Cell Physiol; 286:C79-C89.
Mok et al., 2008, "Enhancement of the CD8<+> T cell response to a subdominant epitope respiratory syncytial virus by deletion of an immunodominant epitope", Vaccine: 26(37):4775-4782.
Neumann et al., 1999, "Generation of influenza A viruses entirely from cloned cDNAs", PNAS 96:9345-9350.
Okuno et al., 1993, "A common neutralizing epitope conserved between the hemagglutinins of influenza A virus H1 and H2 strains," J. Virol., 67(5):2552-2558.
Okuno et al., 1994, "Protection against the mouse-adapted A/FM/1/47 strain of influenza A virus in mice by a monoclonal antibody with cross-neutralizing activity among E11 and H2 strains," J. Virol., 68(1):517-520.
Ott et al., 2000. The Adjuvant MF59: A 10-Year Perspective, p. 211-228. In O'Hagan DT (ed.), Vaccine Adjuvants, vol. 42. Springer.
Papanikolopoulou et al., 2004, "Formation of highly stable chimeric trimers by fusion of an adenovirus fiber shaft fragment with the foldon domain of bacteriophage t4 fibritin", J. Biol. Chem. 279(10):8991-8998.
Pica et al., Hemagglutinin stalk antibodies elicited by the 2009 pandemic influenza virus as a mechanism for the extinction or seasonal H1N1 viruses. Proc Nat Acad Sci U S A. 2012; 109(7):2573-8.
Pleschka et al., 1996, "A plasmid-based reverse genetics system for influenza A virus", J Virol 70:4188-92.

(56) References Cited

OTHER PUBLICATIONS

Ponomarenko et al., "B-Cell Epitope Prediction" Chap. 35 in Structural Bioinformatics, 2nd Edition, Gu and Bourne. Editors; 2009 John Wiley & Sons. Inc. pp. 849-879.

Roberts el al., Role of conserved glycosylation sites in maturation and transport of influenza A virus hemagglutinin. J Virol, 1993; 67(6):3048-60.

Rudikoff et al., Single amino acid substitution altering antigen-binding specificity. Proc Nat Acad Sci U S A. 1982; 79(6): 1979-1983.

Sagawa et al., 1996, "The immunological activity of a deletion mutant of influenza virus haemagglutinin lacking the globular region", J Gen Virol; 77:1483-1487.

Salem, 2000, "In vivo acute depletion of CD8(+) T cells before murine cytomegalovirus infection upregulated innate antiviral activity of natural killer cells", Int. J. Immunopharmacol. 22:707-718.

Santak, M., Old and new ways to combat human influenza virus. Periodicus Biologorum, 2012;114(2):221-34.

Schneeman et al., 2012, "A Virus-Like Particle That Elicits Cross-Reactive Antibodies to the Conserved Stem of Influenza Virus Hemagglutinin," J. Virol., 86(21): 11686-22697.

Shoji et al., 2008, "Plant-expressed HA as a seasonal influenza vaccine candidate", Vaccine, 26(23):2930-2934.

Simmons et al._ 2007. "Prophylactic and therapeutic efficacy of human monoclonal antibodies against H5N1 Influenza", PLOS Medicine; 4(5):928-936.

Song et al., 2007, "Influenza A Virus Hemagglutinin Protein, H1PR8," GENESEQ, XP002595511.

Stech et al., 2005, "A new approach to an influenza live vaccine: modification of the cleavage site of hemagglutinin", Nature Med. 11(6):683-689.

Steel et al., 2010. -Influenza Virus Vaccine Based on the Conserved Hemagglutinin Stalk Domain, mBIO, 1(0:1-9, pii: e00018-10.

Stephenson et al., Cross-reactivity to highly pathogenic avian influenza H5N1 viruses alter vaccination with nonadjuvantcd and MF59-adjuvanted influenza A/Duck/Singapore/97 (H5N3) vaccine: a potential priming strategy. J Infect Dis. 2005; 191(8):1210-1215.

Strobel et al., 2000, Human Gene Therapy 11:2207-2218.

Sui et al.. 2009, "Structural and functional bases for broad-spectrum neutralization of avian and human influenza A viruses", Nat Struct Mol Biol; 16(3):265-273.

Tamura et al., 1998, "Definition of amino acid residues on the epitope responsible for recognition by influenza A virus H1-specific, H2-specific, and H1- and H2-cross-reactive murine cytotoxic T-lymphocyte clones", J. Virol. 72:9404-9406.

Tan et al., 2012, "A pan-H1 anti-hemagglutinin monoclonal antibody with potent broad-spectrum efficacy in vivo", J. Virol. 86:6179-6188.

Tao et al., 2009, "Enhanced protective immunity against H5N1 influenza virus challenge by vaccination with DNA expressing a chimeric hemagglutinin in combination with an MHC class I-restricted epitope of nucleoprotein in mice", Antiviral research. 2009; 81(3); 253-260.

Thoennes et al., 2008, "Analysis of residues near the fusion peptide in the influenza hemagglutinin structure for roles in triggering membrane fusion", Virology; 370(2):403-414.

Thomson et al., 2012 "Pandemic H1N1 Influenza Infection and Vaccination in Humans Induces Cross-Protective Antibodies that Target the Hemagglutinin Stem", Front. Immunol 3.87.

Throsby et al., 2008, "Heterosubtypic neutralizing monoclonal antibodies cross-protective against H5N1 and H1N1 recovered from human IgM+ memory B cells", PLoS ONE; 3(12):e3942.

Vanlandschoot et al., 1998. An antibody which binds to the membrane-proximal end of influenza virus haemagglutinin (1-13 subtype) inhibits the low-pH-induced conformational change and cell-cell fusion but does not neutralize virus, Journal of General Virology; 79:1781-1791.

Vareckova et al., 2008, "HA2-specific monoclonal antibodies as tools for differential recognition of influenza A virus antigenic subtypes," Virus Research, 132:181-186.

Wang et al., 2008, "Simplified recombinational approach for influenza A virus reverse genetics", J. Virol. Methods 151:74-78.

Wang et al., 2009, "Universal epitopes of influenza virus hemagglutinins?", Nature Structural and Molecular Biology; 16(3):233-234.

Wang et al., 2009, -Characterization of cross-reactive antibodies against the influenza virus hemagglutinin, American Society for Virology 28th Annual Meeting, University of British Columbia, Vancouver, BC, Canada dated Jul. 11-15, 2009; Abstract W30-6.

Wang et al., 2010, "Broadly protective monoclonal antibodies against H3 influenza viruses following sequential immunization with different hemagglutinins", PLOS Pathogens; 6(2):1-9.

Weldon et al., 2010, "Enhanced immunogenicity of stabilized trimeric soluble influenza hemagglutinin", PLoSONE 5(9): e12466.

Wrammert et al., 2011, "Broadly cross-reactive antibodies dominate the human B cell response against 2009 pandemic H1N1 influenza virus infection", J. Exp. Med. 208:181-193.

Written Opinion dated Feb. 19, 2013 for PCT Application No. PCT/US2012/056122, Published as WO 2013/043729.

Written Opinion dated Apr. 28, 2014 for PCT Application No. PCT/US2013/075697, Published as WO 2014/099931.

Written Opinion dated Jul. 13, 2011 for PCT Application No. PCT/US2011/030441, Published as WO 2011/123495.

Written Opinion dated Sep. 30, 2011 for PCT Application No. PCT/US2010/029202, Published as WO 2010/117786.

Written Opinion of International application No. PCT/US2010/036170, dated Aug. 17, 2010.

Written Opinion of International application No. PCT/US2011/25467, dated Oct. 19, 2011.

Yang et al., 2006, "Targeting lentiviral vectors to specific cell types in vivo", PNAS 103: 11479-11484.

Yasugi et al., 2013, "Human monoclonal antibodies broadly neutralizing against influenza B virus", PLoS Pathog. 9(2):e1003150.

Yoshida et al., A. Cross-protective potential of a novel monoclonal antibody directed against antigenic site B of the hemagglutinin of influenza A viruses. PLoS Pathog. 2009; 5(3);e1000350.

Zheng, et al., 1996, "Nonconserved nucleotides at the 3' and 5' ends of an influenza A virus RNA play an important role in viral RNA replication", Virology 217:242-251.

Eda et al., 2006, "Sequential immunization with V3 peptides from primary human immunodeficiency virus type 1 produces cross-neutralizing antibodies against primary isolates with a matching narrow-neutralization sequence motif" J Virol, 80(11):5552-5562.

Berry, 2007, "Cross-reactive MAb to the binding domain of botulinum neurotoxin A, B, and E developed using a sequential immunization strategy: anti-botulinum neurotoxin", Hybridoma, 26(6).

Sui et al.. 2009, "Structural and functional bases for broad-spectrum neutralization of avian and human influenza A viruses", Nat Struct Mol Biol; 16(3):265-273; Supplementary Information.

Flandorfer et al., 2003, "Chimeric Influenza A Viruses with a Functional Influenza B Virus Neuraminidase or Hemagglutinin", J. Virol., 77(17):9116-9123.

Chen et al., 2011, "Vaccine design of hemagglutinin glycoprotein against influenza", Trends in Biotechnology, 29(9):426-434.

Igarashi et al.: 2008, "Genetically destined potentials for N-linked glycosylation of influenza virus hemagglutinin" Virology, 376:323-329.

Schulze, 1997, "Effects of Glycosylation on the Properites and Functions of Influenza Virus Hemagglutinin", The Journal of Infectious Diseases, 176(S1):S24-S28.

Stevens et al., 2006, "Structure and Receptor Specificity of the Hemagglutinin from an H5N1 Influenza Virus" Science, 312:404-409.

Vigerust et al., 2007, "N-Linked Glycosylation Attenuates H3N2 Influenza Viruses", Journal of Virology, 81(16): 8593-8600.

Wang et al., 2010, "Vaccination with a synthetic peptide from the influenza virus hemagglutinin provides protection against distinct viral subtypes". PNAS. 107(44): 18979-18984.

Wohlbold et al., 2015, "Vaccination with soluble headless hemagglutinin protects mice from challenge with divergent influenza viruses." Vaccine, 33(29):3314-3321.

(56) References Cited

OTHER PUBLICATIONS

Wohlbold et al., 2015, "Vaccination with adjuvanted recombinant neuraminidase induces broad heterologous, but not heterosubtypic, cross-protection against influenza virus infection in mice." MBio, 6(2):e02556.
Zamarin et al., 2006, "Influenza A virus PB1-F2 protein contributes to viral pathogenesis in mice". J Virol. 80(16):7976-7983.
Kaverin et al., 2004, "Structural Differences Among Hemagglutinins of Influenza A Virus Subtypes Are Reflected in Their Antigenic Architecture: Analysis of H9 Escape Mutants", Journal of Virology, 78(1):240-249.
Dillon et al., 1992, "Induction of protective class I MHC-restricted CTL in mice by a recombinant influenza vaccine in aluminum hydroxide adjuvant", Vaccine, 10(5):309-318.
Mbawuike et al. 1994, "Influenza A subtype cross-protection after immunization of outbred mice with purified chimeric NS1/HA2 influenza virus protein", Vaccine, 1994: 12(14):1340-1348.
Worobey et al., 2002, "Questioning the Evidence for Genetic Recombination in the 1918 "Spanish Flu" Virus", Science, 296(5566): 211a.
Boni et al., 2010, "Guidelines for identifying homologous recombination events in influenza A virus", PLoS One, 5(5):e10434.
Boni et al., 2012, "No evidence for intra-segment recombination of 2009 H1N1 influenza virus in swine", Gene, 494(2):242-245.
Haynes, 2009, "Influenza virus-like particle vaccines", Expert Rev. Vaccines, 8(4): 435-445.
Wiley 1987, "The Structure and Function of the Hemagglutinin Membrane Glycoprotein of Influenza Virus", Ann. Rev. Biochem. 56:365-394.
Landry et al., 2010, "Preclinical and Clinical Development of Plant-Made Virus-Like Particle Vaccine against Avian H5N1 Influenza", PLoS One, 5(12): e15559.
D'Aoust et al., 2010, "The production of hemagglutinin-based virus-like particles in plants: a rapid, efficient and safe response to pandemic influenza", Plant Biotechnology, 8(5):607-619.
Mett et al., 2008, "A plant-produced influenza subunit vaccine protects ferrets against virus challenge", Influenza and Other Respiratory Viruses, 2(1):33-40.
U.S. Appl. No. 15/158,785, Garcia-Sastre et al.
Babu et al., 2014, "Live attenuated H7N7 influenza vaccine primes for a vigorous antibody response to inactivated H7N7 influenza vaccine," Vaccine, 32:6798-6804.
Bommakanti et al., 2012, "Design of *Eschericia coli*-Expressed Stalk Domain Immunogens of H1N1 Hemagglutinin That Protect Mice from Lethal Challenge." J. Virol., 86(24):13434-13444.
Bowie, et al., 1990, "Deciphering the Message in Protein Sequences: Tolerance to Amino Acid Substitutions." Science, 247: 1306-1310.
Bullough et al., 1994, "Structure of influenza haemagglutinin at the pH of membrane fusion." Nature, 371:37-43.
Casali et al., 2008, "Site-directed mutagenesis of the hinge peptide from the hemagglutinin protein: enhancement of the pH-responsive conformational change." Protein Engineering Design & Selection, 21(6):395-404.
Chen et al., 1999, "N- and C-terminal residues combine in the fusion-pH influenza hemagglutinin HA2 subunit to form an N cap that terminates the triple-stranded coiled coil." Proc. Natl. Acad Sci., 91:8967-8972.
Chen et al., 2007, "Influenza Virus Hemagglutinin and Neuraminidase, but Not the Matrix Protein, Are Required for Assembly and Budding of Plasmid-Derived Virus-Like Particles", J. Virol. 81(13):7111-7123.
Chen et al., 2016, "Influenza A viruses expressing intra- or intergroup chimeric hemagglutinins", J Virol, 90:3789-3793.
Das et al., 2010, "Glycosylation Focuses Sequence Variation in the Influenza A Virus H1 Hemagglutinin Globular Domain " PLoS Pathogens, 6(11):e1001211.
Database GenPept "Hemagglutinin precursor [Contains. Hemagglutinin HA1 chain; Hemagglutinin HA2 chain]", Accession No. P03437, dated Jul. 21, 1986.
Doms RW & Moore JP, 2000, "HIV-1 Membrane Fusion: Targets of Opportunity," JCB, 151(2): F9-F13.
Doyle et al., 1986, "Analysis of Progressive Deletions of the Transmembrane and Cytoplasmic Domains of Influenza Hemagglutinin", JCB, 103:1193-1204.
Dunand et al., 2016, "Both Neutralizing and Non-Neutralizing Human H7N9 Influenza Vaccine-Induced Monoclonal Antibodies Confer Protection," Cell Host & Microbe, 19:1-14.
Fluzone®, 2009-2010 Fluzone Seasonal influenza vaccine package insert, 2009.
Genbank, NCBI Reference Sequence: YP_163736.1, HA2 [Influenza A virus (A/Puerto Rico/8/1934(H1N1))].
Giddings et al., 2000, "Transgenic plants as factories for biopharmaceuticals", Nature Biotechnology, 18:1151-1155.
Gomord et al., 2005, "Biopharmaceutical production in plants: problems, solutions and opportunities." TRENDS in Biotechnology, 23(11):559-565.
Graham et al., 2013, "DNA Vaccine Delivered by a Needle-Free Injection Device Improves Potency of Priming for Antibody and CD8+ TCell Responses after rAd5 Boost in a Randomized Clinical Trial," PLoS ONE, 8(4): 1-11, e59340.
Hallily et al., 2015, "High-Affinity H7 Head and Stalk Domain-Specific Antibody Response to an Inactivated Influenza H7N7 Vaccine After Priming With Live Attenuated Influenza Vaccine," Journal of Infectious Diseases, 212: 1270-1278.
Horimoto et al., 2004, "Influenza A viruses possessing type B hemagglutinin and neuraminidase: potential as vaccine components." Microbes and Infection, 6(6): 579-583.
Impagliazzo et al., 2015, "A stable trimeric influenza hemagglutinin stem as a broadly protective immunogen." Science, 349(6254):1301-1306.
Kanekiyo et al., 2013, "Self-assembling influenza nanoparticle vaccines elicit broadly neutralizing H1N1 antibodies." Nature, 499(7456):102-6.
Khurana et al., 2013, "DNA Priming Prior to Inactivated Influenza A(H5N1) Vaccination Expands the Antibody Epitope Repertoire and Increases Affinity Maturation in a Boost-Interval—Dependent Manner in Adults," Journal of Infectious Disease, 208:413-417.
Krause et al., 2011, "A broadly neutralizing human monoclonal antibody that recognizes a conserved, novel epitope on the globular head of the influenza H1N1 virus hemagglutinin", J. Virol., 85(20):10905-10908.
Lebendiker M. "Purification Protocols." The Wolfson Centre for Applied Structural Biology, http://wolfson.huji.ac.il/purification/Purification_Protocols.html. Apr. 5, 2006.
Ledgerwood, et al., 2013, "Prime-Boost Interval Matters: A Randomized Phase 1 Study to Identify the Minimum Interval Necessary to Observe the H5 DNA Influenza Vaccine Priming Effect," Journal of Infectious Diseases, 208:418-422.
Lorieau, et al., 2010, "The complete influenza hemagglutinin fusion domain adopts a tight helical hairpin arrangement at the lipid:water interface." PNAS, 107(25):11341-11346.
Lu et al., 2013, "Production and stabilization of the trimeric influenza hemagglutinin stem domain for potentially broadly protective influenza vaccines." PNAS, 111(1):125-130.
Luke et al., 2014, "Improving pandemic H5N1 influenza vaccines by combining different vaccine platforms," Expert Review of Vaccines 13(7):873-883.
Mallajosyula et al., 2014, "Influenza hemagglutinin stem-fragment immunogen elicits broadly neutralizing antibodies and confers heterologous protection." PNAS, 111(25):E2514-23.
Nachbagauer et al., 2015, "Hemagglutinin stalk immunity reduces influenza virus replication and transmission in ferrets", J. Virol., doi:10.1128/JVI.02481-15.
Palese P & Shaw M (2007). Orthomyxoviridae: The Viruses and Their Replication. In D.M. Knipe, & P.M. Howley (Eds.), Fields Virology (pp. 1647-1689). Philadelphia, PA: Wolters Kluwer Lippincott Williams & Wilkins.
Robertson, 1987, "Sequence Analysis of the Haemagglutinin of A/Taiwan/1/86, a New Variant of Human Influenza A(H1/N1) Virus," J. Gen. Virol., 68:1205-1208.
Rudenko et al., 2015, "Assessment of immune responses to H5N1 inactivated influenza vaccine among individuals previously primed

(56) References Cited

OTHER PUBLICATIONS with H5N2 live attenuated influenza vaccine," Human Vaccines & Immunotherapeutics, 11(12):2839-2848.
Ryder et al., 2016, "Vaccination with VSV-vectored chimeric hemagglutinins protects mice against divergent influenza virus challenge strains", J. Virol., 90(5):2544-2550.
Sun et al., 2011, "Glycosylation Site Alteration in the Evolution of Influenza A (H1N1) Viruses." PLoS Pathogens, 6(7):e22844.
Talaat et al., 2014, "A Live Attenuated Influenza A(H5N1) Vaccine Induces Long-Term Immunity in the Absence of a Primary Antibody Response," Journal of Infectious Disease; 208:1860-1869.
Tate et al., 2001, "Specific Sites of N-Linked Glycosylation on the Hemagglutinin of H1N1 Subtype Influenza A Virus Determine Sensitivity to Inhibitors of the Innate Immune Systema nd Virulence in Mice." Journal of Immunology, 187(4):1884-1894.
Vajdos et al., 2002, "Comprehensive Functional Maps of the Antigenbinding Site of an Anti-ErbB2 Antibody Obtained with Shotgun Scanning Mutagenesis," Journal of Molecular Biology, 320:415-428.
Vanlandschoot et al., 1995. "A fairly conserved epitope on the hemagglutinin of influenza A (H3N2) virus with variable accessibility to neutralizing antibody." Virology, 212(2)526-34.
Wang et al., 2007, "Incorporation of High Levels of Chimeric Human Immunodeficiency Virus Envelope Glycoproteins into Virus-Like Particles", J. Virol., 81(20):10869-10878.
Wang et al., 2009, "Glycans on influenza hemagglutinin affect receptor binding and immune response." PNAS, 106(43): 18137-18142.
Wei et al., 2010, "Induction of Broadly Neutralizing H1N1 Influenza Antibodies by Vaccination," Science; 329: 1060-1064.
Weis and Brunger, 1990, "Refinement of the Influenza Virus Hemagglutinin by Simulated Annealing." J. Mol. Biol. 212:737-761.
Weis et al., 1988, "Structure of the influenza virus haemagglutinin complexed with its receptor, sialic acid." Nature, 333:426-431.
Wiley and Skehel, 1983, "The three-dimensional structure and antigenic variation of the influenza virus haemagglutinin." Division of Virology, 107-111.
Wiley, 1987, "The Structure and Function of the Hemagglutinin Membrane Glycoprotein of Influenza Virus." Ann. Rev. Biochem., 56:365-94.
Wilson et al., 1981, "Structure of the haemagglutinin membrane glycoprotein of influenza virus at 3 A resolution." Nature, 289:366-373.
Winter et al., 1981, "Nucleotide Sequence of the Haemagglutinin Gene of A Human Influenza Virus H1 Subtype" Nature, 292:72-75.
Yang et al., 2007, "Immunization by Avian H5 Influenza Hemagglutinin Mutants with Altered Receptor Binding Specificity", Science, 317(5839):825-828.
Yassine et al., 2015, "Hemagglutinin-stem nanoparticles generate heterosubtypic influenza protection." Nat. Med. 21(9):1065-70.
Krammer, 2016, "Novel universal influenza virus vaccine approaches", Current Opinion in Virology, 17:95-103.
Krammer, 2015, "The quest for a universal flu vaccine: headless HA 2.0", Cell Host Microbe, 18:395-397.
Bommakanti et al., 2010, "Design of an HA2-based *Escherichia coli* expressed influenza immunogen that protects mice from pathogenic challenge", Proc Natl Acad Sci USA, 107:13701-13706.
Krammer et al., 2012, "Hemagglutinin stalk-reactive antibodies are boosted following sequential infection with seasonal and pandemic H1N1 influenza virus in mice", J Virol, 86:10302-10307.
Krammer et al., 2014, "H3 stalk-based chimeric hemagglutinin influenza virus constructs protect mice from H7N9 challenge", J Virol, 88:2340-2343.
Margine et al., 2013, "Hemagglutinin stalk-based universal vaccine constructs protect against group 2 influenza A viruses", J Virol, 87(19): 10435-10446.
Krammer et al., 2014, "Assessment of influenza virus hemagglutinin stalk-based immunity in ferrets", J Virol, 88:3432-3442.
Tran et al., 2016, "Cryo-electron microscopy structures of chimeric hemagglutinin displayed on a universal influenza vaccine candidate", MBio, 7(2): e00257-16.
Chen et al., 2010, "Generation of Live Attenuated Novel Influenza Virus A/California/7/09 (H1N1) Vaccines with High Yield in Embryonated Chicken Eggs." J. Virol. 84(1):44-51.
Clementi et al., 2011, "A Human Monoclonal Antibody with Neutralizing Activity against Highly Divergent Influenza Subtypes". PLoS ONE, 6(12):e28001.
Cotter et al., 2014, "A Single Amino Acid in the Stalk Region of the H1N1pdm Influenza Virus HA Protein Affects Viral Fusion, Stability and Infectivity." PLoS Pathogens, 10(1):e1003831.
International Search Report dated Jun. 26, 2014 for PCT Application No. PCT/US2014/025526, Published as WO 2014/149960.
NCT01676402, Clinical Trial, Seasonal Influenza HA DNA With Trivalent Inactivated Vaccine (TIV) Administered ID or IM in Healthy Adults 18-70 Years.
Oshima et al., 2011, "Naturally Occurring Antibodies in Humans Can Neutralize a Variety of Influenza Virus Strains, Including H3, H1, H2, and H5". Journal of Virology, 85(21):11048-11057.
Wang et al., 2012, "Generation of recombinant pandemic H1N1 influenza virus with the HA cleavable by bromelain and identification of the residues influencing HA bromelain cleavage." Vaccine, 30(4):872-8.
Written Opinion dated Jun. 26, 2014 for PCT Application No. PCT/US2014/025526, Published as WO 2014/159960.
Yang et al., 2014, "Structural stability of influenza A(H1N1)pdm09 virus hemagglutinins." J. Virol., 88(9):4828-38.
Zhang et al., 2011, "Determination of serum neutralization antibodies against seasonal influenza A strain H3N2 and the emerging strains 2009 H1N1 and avian H5N1". Scandinavian Journal of Infectious Diseases, 43:216-220.
Centers for Disease Control and Prevention Metropolitan Atlanta Congenital Defects Program (CDC MACDP) guidelines. Birth defects and genetic diseases branch 6-digit code for reportable congenital anomalies; http://www.cdc.govincbddd/birthdefects/documents/MACDPcode0807.pdf (2007).
Cox and Fukuda, "Influenza," Infect. Dis. Clin. North Am. 12(1):27-38 (1998).
Crotty et al., "Tracking human antigen-specific memory B cells: a sensitive and generalized ELISPOT system," J. Immunol. Methods 286 (1-2):111-122 (2004).
EMA Guideline on the exposure to medicinal products during pregnancy: need for post-authorization data (Doc. Ref. EMEA/CHMP/313666/2005 ) adopted at Community level in May 2006); http://www.ema.europa.eu/docs/en_GB/document_library/Regulatoly_and_procedural_guideline/2009/11/WC500011303.pdf.
Gauger et al., "Enhanced pneumonia and disease in pigs vaccinated with an inactivated human-like (δ-cluster) H1N2 vaccine and challenged with pandemic 2009 H1N1 influenza virus," Vaccine 29(15):2712-2719 (2011).
Goff et al., 2013, "Induction of cross-reactive antibodies to novel H7N9 influenza virus by recombinant Newcastle disease virus expressing a North American lineage H7 subtype hemagglutinin," J. Virol., 87 (14): 8235-40.
Heaton et al., "In Vivo Bioluminescent Imaging of Influenza A Virus Infection and Characterization of Novel Cross-Protective Monoclonal Antibodies," J. Virol. 87(15):8272-8281 (2013).
Hong et al., "Antibody recognition of the pandemic H1N1 Influenza virus hemagglutinin receptor binding site," J. Virol. 87(22):12471-12480 (2013) (Epub Sep. 11, 2013).
International Search Report of International Application No. PCT/US2017/037384, dated Nov. 3, 2017.
Izurieta et al., 2000, "Influenza and the rates of hospitalization for respiratory disease among infants and young children," NEJM,342(4):232-239.
Krammer and Palese, 2013, "Influenza virus hemagglutinin stalk-based antibodies and vaccines," Curr. Opin. Virol., 3, 521-530.
Montgomery et al., "Heterologous and homologous protection against influenza a by DNA vaccination: optimization of DNA vectors," DNA Cell Biol. 12(9):777-783 (1993).

(56) References Cited

OTHER PUBLICATIONS

Montplaisir et al., 2009, "Risk of narcolepsy associated with inactivated adjuvanted (AS03) A/H1N1 (2009) pandemic influenza vaccine in Quebec," *PLoS One,* 9 (9): e108489. doi: 10.1371/journal. pone.0108489.
Nachbagauer et al., 2014, "Induction of broadly reactive antihemagglutinin stalk antibodies by an H5N1 vaccine in humans," *J. Virol.,* 88 (22): 13260-13268.
Nachbagauer et al., 2016, "A chimeric haemagglutinin-based influenza split virion vaccine adjuvanted with AS03 induces protective stalk-reactive antibodies in mice." Nature Partner Journals (NPJ) Vaccines, Article No. 16015 (2016) doi:10.1038/npjvaccines.2016.15.
Ni et al, "Structural basis for the divergent evolution of influenza B virus hemagglutinin," Virology 446(1-2):112-122 (2013) (Epub Aug. 27, 2013).
O'Brien MA, Uyeki TM, Shay DK, Thompson WW, Kleinman K, McAdam A, Yu XJ, Platt R, Lieu TA. Incidence of outpatient visits and hospitalizations related to influenza in infants and young. children. Pediatrics. 2004; 113: 585-593.
Ohkura et al., "Epitope mapping of neutralizing monoclonal antibody in avian influenza A H5N1 virus hemagglutinin," Biochem. Biophys. Res. Commun. 418(1):38-43 (2012) (Epub Dec. 27, 2011).
Perricone et al., 2013, "Autoimmune/inflammatory syndrome induced by adjuvants (ASIA) 2013:.Unveiling the pathogenic, clinical and diagnostic aspects," J Autoimmun 47:1-16.
Rivera et al., "Probing the structure of influenza B hemagglutinin using site-directed mutagenesis," Virology 206(2):787-795 (1995).
Sparrow et al., 2016, "Passive immunization for influenza through antibody therapies, a review of the pipeline, challenges, and potential applications." Vaccine, 34: 5442-5448.
Tete et al., 2016, "Dissecting the hemagglutinin head and stalk-specific IgG antibody response in healthcare workers following pandemic H1N1 vaccination," Nature Partner Journals (NPJ) Vaccine, Article No. 16001 doi:10.1038/npjvaccines.2016.1.
Tong et al., 2013. "New world bats harbor diverse influenza A viruses," PLoS Pathog. 9: e1003657.
Vincent et al., 2008, "Failure of protection and enhanced pneumonia with a US H1N2 swine influenza virus in pigs vaccinated with an inactivated classical swine H1N1 vaccine," *Vet Microbiol.,* 126 (4): 310-23.

Wang et al., "Crystal structure of unliganded influenza B virus hemagglutinin," J. Virol. 82(6):3011-3020 (2008) (Epub Jan. 9, 2008).
WHO World Health Organization Factsheet No. 211. Influenza Nov. 2016. https://www.who. int/mediacentre/factsheets/fs211/en.
Wohlbold et al., "In the Shadow of Hemagglutinin: A Growing Interest in Influenza Viral Neuraminidase and Its Role as a Vaccine Antigen," Viruses 6(6):2465-2494 (2014).
Written Opinion of the International Searching Authority for International Application No. PCT/US2017/037384, dated Nov. 3, 2017.
Zhang et al., "Crystal structure of the swine-origin A (H1N1)-2009 influenza A virus hemagglutinin (HA) reveals similar antigenicity to that of the 1918 pandemic virus," Protein Cell 1(5):459-467 (2010) (Epub Jun. 4, 2010).
International Search Report of International Application No. PCT/US2016/014640, dated Jun. 3, 2016.
Written Opinion of the International Searching Authority for International Application No. PCT/US2016/014640, dated Jun. 3, 2016.
International Search Report of International Application No. PCT/US2016/037595, dated Sep. 15, 2016.
Written Opinion of the International Searching Authority for International Application No. PCT/US2016/037595, dated Sep. 15, 2016.
International Search Report of International Application No. PCT/US2017/035479, dated Oct. 25, 2017.
Written Opinion of the International Searching Authority for International Application No. PCT/US2017/035479, dated Oct. 25, 2017.
Q0PZR5, UniProtKB Accession No. Q0PZR5, Oct. 29, 2014 [online]. [Retrieved on Sep. 2, 2016]. Retrieved from the internet <URL: http://www.uniprot.org/uniprot/Q0PZR5.txt?version=53> Entire document.
Ermler et al., "Chimeric Hemagglutinin Constructs Induce Broad Protection against Influenza B Virus Challenge in the Mouse Model," J. Virol. 91(12): e00286-17 (2017).
Extended European Search Report for European Application No. 11763347.9, dated Feb. 2, 2015.
International Preliminary Report on Patentability of International application No. PCT/US11/30441, dated Oct. 2, 2012.

* cited by examiner

```
                                    ▼(Mature residue 1)
         H1     -MKANLLVLLCALA--AAD---------ADTICIGYHANNSTDTVDTVLEKNVTVTHSVNL
         H2     ---MAIIYLILLFT--AVR---------GDQICIGYHSNNSTEKVDTILERNVTVTHAQNI
         H3     --MKTIIALSYIFCLALGQDLPGNDNSTATLCLGHHAVPNGTLVKTITDDQIEVTNATEL
         H4     ---MLSIVILFLLIAENS-----SQNYTGNPVICMGHHAVANGTMVKTLADDQVEVVTAQEL
         H5     --MERIVLLLAIVS--LVK---------SDQICIGYHANKSTKQVDTIMEKNVTVTHAQDI
         H6     --MIAIIVVAILAT--AGR---------SDKICIGYHANNSTTQIDTILEKNVTVTHSVEL
         H7     --MNTQILVFALVAVIPTN---------ADKICLGHHAVSNGTKVNTLTERGVEVVNATET
         H8     --MEKFIAIAT-LASTNA----------YDRICIGYQSNNSTDTVNTLIEQNVPVTQTMEL
         H9     --METKAIIAALLMVTAAN---------ADKICIGYQSTNSTETVDTLTESNVPVTHTKEL
         H10    --MYKVVVIIALLGAVKG----------LDRICLGHHAVANGTIVKTLTNEQEEVTNATET
         H11    --MEKTLLFAAIFL--CVK---------ADEICIGYLSNNSTDKVDTIIENNVTVTSSVEL
         H12    --MEKFIILSTVLAASFA----------YDKICIGYQTNNSTETVNTLSEQNVPVTQVEEL
         H13    -MALNVIATLTLIS-VCVH---------ADRICVGYLSTNSSERVDTLLENGVPVTSSIDL
         H14    --MIALILVALALSHTAYSQITNGTTGNPIICLGHHAVENGTSVKTLTDNHVEVVSAKEL
         H15    --MNTQIIVILVLGLSMVK---------SDKICLGHHAVANGTKVNTLTERGVEVVNATET
         H16    -MMIKVLYFLIIVLGRYSK---------ADKICIGYLSNNSSDTVDTLTENGVPVTSSVDL
         H17    MELIVLLILLNPYT--FVL---------GDRICIGYQANQNNQTVNTLLEQNVPVTGAQEI
                                    ▲(Mature residue 1)
                  ▼(Residue Ap)                         (Residue Cp)▼
         H1     LEDSHNGKLCRLKGIAPLQLGKCNIAGWLLGNPECDPLLPVRSWSYIVETPNSENGICYP
         H2     LEKTHNGKLCKLNGIPPLELGDCSIAGWLLGNPECDRLLTVPEWSYIMEKENPRNGLCYP
         H3     VQSSSTGKICNN-PHRILDGIDCTLIDALLGDPHCDVFQNET-WDLFVERSKAFS-NCYP
         H4     VESQNLPELCPS-PLRLVDGQTCDIINGALGSPGCDHLNGAE-WDVFIERPNAVD-TCYP
         H5     LERTHNGKLCSLNGVKPLILRDCSVAGWLLGNPMCDEFINLPEWLYIVEKDNPINSLCYP
         H6     LENQKEERFCKILKKAPLDLKGCTIEGWILGNPQCDLLLGDQSWSYIVERPTAQNGICYP
         H7     VERTNIPKICSK-GKRTTDLGQCGLLGTITGPPQCDQFLEFS-ADLIIERREGND-VCYP
         H8     VETEKHPAYCNTDLGAPLELRDCKIEAVIYGNPKCDIHLKDQGWSYIVERPSAPEGMCYP
         H9     LHTEHNGMLCATDLGHPLILDTCTIEGLIYGNPSCDILLGGKEWSYIVERSSAVNGMCYP
         H10    VESTNLNKLCMK-GRSYKDLGNCHPVGMLIGTPVCDPHLTGT-WDTLIERENAIA-HCYP
         H11    VETEHTGSFCSINGKQPISLGDCSFAGWILGNPMCDELIGKTSWSYIVEKPNPTNGICYP
         H12    VHRGIDPILCGTELGSPLVLDDCSLEGLILGNPKCDYLNGREWSYIVERPKEMEGVCYP
         H13    IETNHTGTYCSLNGVSPVHLGDCSFEGWIVGNPACTSNFGIREWSYLIEDPAAPHGLCYP
         H14    VETNHTDELCPS-PLKLVDGQDCHLINGALGSPGCDRLQDTT-WDVFIERPTAVD-TCYP
         H15    VEITGIDKVCTK-GKKAVDLGSCGILGTIIGPPQCDLHLEFR-ADLIIERRNSSD-ICYP
         H16    VETNHTGTYCSLNGISPIHLGDCSFEGWIVGNPSCATNINIREWSYLIEDPNAPNKFCYP
         H17    LETNHNGKLCSLNGVPPLDLQSCTLAGWLLGNPNCDSLLEAEEWSYIKINESAPDDLCFP
                  ▲(Residue Ap)                         (Residue Cp)▲

H1     GDFIDYEELREQLSSVSSFERFEIFPKESSWPNHNTNGVTAACSHE-GKSSFYRNLLWLT
         H2     GSFNDYEELKHLLSSVTHFEKVKILPKDRWTQHTTTGG-SRACAVS-GNPSFFRNMVWLT
         H3     YDVPDYASLRSLVASSGTLE--FITEGFTW-TGVTQNGGSNACKRG-PGNGFFSRLNWLT
         H4     FDVPEYQSLRSILANNGKFE--FIAEEFQW-NTVKQNGKSGACKRA-NVDDFFNRLNWLV
         H5     GDFNDYEELKYLLSSTNHFEKIRIIPRSSWSNHDASSGVSSACPYI-GRSSFLRNVVWLI
         H6     GVLNEVEELKALIGSGERVERFEMFPKSTWTGVDTSSGVTRACPYN-SGSSFYRNLLWII
         H7     GKFVNEEEALRQILRGSGGID--KETMGFTY-SGIRTNGTTSACRRS-G-SSFYAEMEWLL
         H8     GSVENLEELRFVFSSAASYKRIRLFDYSRWNVTRS--GTSKACNASTGGQSFYRSINWLT
         H9     GNVENLERSLFSSAKSYKRIQIFPDKTWNVTYS--GTSRACSN-----SFYRSMRWLT
         H10    GATINEEALRQKIMESGGIS--KMSTGFTYGSSITSAGTTKACMPN-GGDSFYAELKWLV
         H11    GTLESEEEELRLKFSGVLEFNKFEVFTSNGWGAVNSGVGVTAACKFG-GSNSFFRNMVWLI
         H12    GSIENQEELRSLFSSIKKYERVKMFDFTKWNVTYT--GTSKACNNTSNQGSFYRSMRWLT
         H13    GELNNNGELRHLFSGIRSFSRTELIPPTSWGEVLD--GTTSACRDNTGTNSFYRNLVWFI
         H14    FDVPDYQSLRSILASSGSLE--FIAEQFTW-NGVKVDGSSSACLPG-GRNSFFSRLNWLT
         H15    GRFTNEEALRQIIRESGGID--KESMGFRY-SGIRTDGATSACKRT-V-SSFYSEMKWLS
         H16    GELDNNGELRHLFSGVNSFSRTELINPSKWGNVLD--GVTASCLDR-GASSFYRNLVWIV
         H17    GNFENLQDLLLEMSGVQNFTKVKLFNPQSMTG-VTTNNVDQTCFFE-GKPSFYRNLNWIQ
```

FIG. 1A

```
H1   E-K-EGSYPKLKNSYVNKKGKEVLVLWGIHHPPNSKEQQNLYQNENAYVSVVTSNYNRRF
H2   K-K-GSNYPIAKGSYNNTSGEQMLIIWGVHHPNDETEQRTLYQNVGTYVSIGTSTLNKRS
H3   KS--GSTYPVLNVTMPNNDNFDKLYIWGVHHPSTNQEQTSLYVQESGRVTVSTRRSQQSI
H4   KSD-GNAYPLQNLTKINNGDYARLYIWGVHHPSTSTEQTNLYKNNPGRVTVSTKTSQTSV
H5   K-K-NNTYPTIKRSYNNTNQEDLLILWGIHHPNDAAEQTKLYQNPTTYVSVGTSTLNQRS
H6   KTK-SAAYSVIKGAYNNTGNQPILYFWGVHHPPDTNEQNTLYGSGDRYVRMGTESMNFAK
H7   SNTDNASFPQMTKSYKNTRRESALIVWGIHHSGSTTEQTKLYGSGNKLITVGSSKYHQSF
H8   KKE-PDTYDFNEGAYVNNEDGDIIFLWGIHHPPDTKEQTTLYKNANTLSSVTTNTINRSF
H9   HK--SNSYPFQNAHYTNNERENILFMWGIHHPPTDTEQTDLYKNADTTTSVTTEDINRTF
H10  SKTKGQNFPQTTNTYRNTDTAEHLIIWGIHHPSSTQEKNDLYGTQSLSISVESSTYQNNF
H11  H-Q-SGTYPVIKRTFNNTKGRDVLIVWGIHHPATLTEHQDLYKKDSSYVAVGSETYNRRF
H12  LK--SGQFPVQTDEYKNTRDSDIVFTWAIHHPPTSDEQVKLYKNPDTLSSVTTVEINRSF
H13  K-K-NTRYPVISKTYNNTTGRDVLVLWGIHHPVSVDETKTLYVNSDPYTLVSTKSWSEKY
H14  KAT-NGNYGPINVTKENTGSYVRLYLWGVHHPSSDNEQTDLYKVATGRVTVSTRSDQISI
H15  SSMNNQVFPQLNQTYRNTRKEPALIVWGVHHSSSLDEQNKLYGTGNKLITVGSSKYQQSF
H16  K-K-DEKYPVIKGDYNNTTGRDVLVLWGIHHPDTETTATNLYVNKNPYTLVSTKEWSKRY
H17  G----NSGLPFNIEIKNPTSNPLLLLWGIHNTKDAAQQRNLYGNDYSYTIFNFGEKSEEF

▼(Residue Cq)
H1   TPEIAERPKVRDQAGRMNYYWTLLKPGDTIIFEANGNLIAPMYAFALSRGFG--------
H2   IPVIATRPKVNGQGGRMEFSWTILDIWDTINFESTGNLIAPEYGFRISKRGS--------
H3   IPNIGSRPWVRGQSSRISIYWTIVKPGDVLVINSNGNLIAPRGYFKMRTG---------K
H4   VPDIGSRPLVRGQSGRVSFYWTIVEPGDLIVFNTIGNLIAPRGHYKLNNQK--------K
H5   IPEIATRPKVNGQSGRMEFFWTILKPNDAINFESNGNFIAPRYAYKIVKKGD--------
H6   SPEIAARPAVNGQRGRIDYYWSILKPGETLNVESNGNLIAPWYAFRFVSTSNK-------
H7   VPSPGTRPQINGQSGRIDFHWLILDPNDTVTFSFNGAFIAPNRASFLR---------GK
H8   QPNIGPRPLVRGQQGRMDYYWGILKRGETLKIRTNGNLIAPEFGYLLKGESY--------
H9   KPVIGPRPLVNGQQGRIDYYWSVLKPGQTLRIRSNGNLIAPWYGHVLTGESH--------
H10  VPVVGARPQVNGQSGRIDFHWTLVQPGDNITFSDNGGLIAPSRVSKLT----------GR
H11  TPEINTRPRVNGQAGRMTFYWKIVKPGESITFESNGAFLAPRYAFEIVSVGN--------
H12  KPNIGPRPLVRGQQGRMDYYWAVLKPGQTVKIQTNGNLIAPEYGHLITGKSH--------
H13  KLETGVRPGYNGQRSWMKIYWSLIHPGEMITFESNGGFLAPRYGYIIEEYGK--------
H14  VPNIGSRPRVRNQSGRISIYWTLVNPGDSIIFNSIGNLIAPRGHYKISKST--------K
H15  SPSPGARPKVNGQAGRIDFHWMLLDPGDTVTFTFNGAFIAPDRATFLRSNAPSGIEYNGK
H16  ELEIGTRIG-DGQRSWMKLYWHLMHPGERIMFESNGGLIAPRYGYIIEKYGT--------
H17  RPEIGQRDEVKAHQDRIDYYWGSLPAQSTLRIESTGNLIAPEYGFYYKRKEGK-------
                                                    ▲(Residue Cq)

▼(Residue Aq)            ▼(Residue Bq)
H1   SGIITS-NASMHECNTKCQTPLGAINSSLPYQNIHPVTIGECPKYVRSAKLRMVTGLRNN
H2   SGIMKT-EGTLENCETKCQTPLGAINTTLPFHNVHPLTIGECPKYVKSERLVLATGLRNV
H3   SSIMSSDAPIDT-CISECITPNGSIPNDKPFQNVNKITYGACPKYVKQNTLKLATGMRNV
H4   STILNTAIPIGS-CVSKCHTDKGSLSTTKPFQNISRIAVGDCPRYVKQGSLKLATGMRNI
H5   SAIMKS-GLAYGNCDTKCQTPVGEINSSMPFHNIHPHTIGECPKYVKSDRLVLATGLRNV
H6   GAVFKS-NLPIENCDATCQTVAGVLRTNKTFQNVSPLWIGECPKYVKSESLRLATGLRNV
H7   SMGIQSDVQVDANCEGECYHSGGTITSRLPFQNINSRAVGKCPRYVKQESLLLATGMKNV
H8   GRIIQNEDIPIGNCNTKCQTYAGAINSSKPFQNASRHYMGECPKYVKKASLRLAVGLRNT
H9   GRILKT-DLNNGNCVVQCQTEKGGLNTTLPFHNISKYAFGNCPKYVGVKSLKLPVGLRNV
H10  DLGIQSEALIDNSCESKCFWRGGSINTKLPFQNLSPRTVGQCPKYVNQRSLLLATGMRNV
H11  GKLFRS-ELNIESCSTKCQTEIGGINTNKSFHNVHRNTIGDCPKYVNVKSLKLATGPRNV
H12  GRILKN-NLPMGQCVTECQLNEGVMNTSKPFQNTSKHYIGKCPKYIPSGSLKLAIGLRNV
H13  GRIFQS-RIRMSRCNTKCQTSVGGINTNRTFQNIDKNALGDCPKYIKSGQLKLATGLRNV
H14  STVLKSDKRIGS-CTSPCLTDKGSIQSDKPFQNVSRIAIGNCPKYVKQGSLMLATGMRNI
H15  SLGIQSDAQIDESCEGECFYSGGTINSPLPFQNIDSRAVGKCPRYVKQSSLPLALGMKNV
H16  GRIFQS-GVRMARCNTKCQTSLGGINTNKTFQNIERNALGDCPKYIKSGQLKLATGLRNV
H17  GGLMKS-KLPISDCSTKCQTPLGALNSTLPFQNVHQQTIGNCPKYVKATSLMLATGLRNN
            ▲(Residue Aq)            ▲(Residue Bq)
```

FIG. 1B

```
                    ▼(HA2 domain starts)
H1      P----SIQSRGLFGAIAGFIEGGWTGMIDGWYGYHHQNEQGSGYAADQKSTQNAINGITN
H2      P----QIESRGLFGAIAGFIEGGWQGMIDGWYGYHHSNDQGSGYAADKESTQKAIDGITN
H3      P----EKQTRGLFGAIAGFIENGWEGMIDGWYGFRHQNSEGTGQAADLKSTQAAIDQING
H4      P----EKASRGLFGAIAGFIENGWQGLIDGWYGFRHQNAEGTGTAADLKSTQAAIDQING
H5      P----QRKKRGLFGAIAGFIEGGWQGMVDGWYGYHHSNEQGSGYAADKESTQKAIDGITN
H6      P----QIETRGLFGAIAGFIEGGWTGMIDGWYGYHHENSQGSGYAADRESTQKAVDGITN
H7      PEPSKKRKKRGLFGAIAGFIENGWEGLVDGWYGFRHQNAQGEGTAADYKSTQSAIDQITG
H8      P----SVEPRGLFGAIAGFIEGGWSGMIDGWYGFHHSNSEGTGMAADQKSTQEAIDKITN
H9      P----AVSSRGLFGAIAGFIEGGWPGLVAGWYGFQHSNDQGVGMAADKGSTQKAIDKITS
H10     P----EVVQGRGLFGAIAGFIENGWEGMVDGWYGFRHQNAQGTGQAADYKSTQAAIDQITG
H11     P----AIASRGLFGAIAGFIEGGWPGLINGWYGFQHRDEEGTGIAADKESTQKAIDQITS
H12     P----QVQDRGLFGAIAGFIEGGWPGLVAGWYGFQHQNAEGTGIAADRDSTQRAIDNMQN
H13     P----AISNRGLFGAIAGFIEGGWPGLINGWYGFQHQNEQGTGIAADKESTQKAIDQITT
H14     P----GKQAKGLFGAIAGFIENGWQGLIDGWYGFRHQNAEGTGTAADLKSTQAAIDQING
H15     P---EKIRTRGLFGAIAGFIENGWEGLIDGWYGFRHQNAQGQGTAADYKSTQAAIDQITG
H16     P----SIGERGLFGAIAGFIEGGWPGLINGWYGFQHQNEQGTGIAADKASTQKAINEITT
H17     P----QMEGRGLFGAIAGFIEGGWQGMIDGWYGYHHENQEGSGYAADKEATQKAVDAITN
                    ▲(HA2 domain starts)

H1      KVNTVIEKMNIQFTAVGKEFNKLEKRMENLNKKVDDGFLDIWTYNAELLVLLENERTLDF
H2      RVNSVIEKMNTQFEAVGKEFSNLEKRLENLNKKMEDGFLDVWTYNAELLVLMENERTLDF
H3      KLNRVIEKTNEKFHQIEKEFSEVEGRIQDLEKYVEDTKIDLWSYNAELLVALENQHTIDL
H4      KLNRLIEKTNDKYHQIEKEFEQVEGRIQDLENYVEDTKIDLWSYNAELLVALENQHTIDV
H5      KVNSIIDKMNTRFEAVGKEFNNLERRVENLNKKMEDGFLDVWTYNVELLVLMENERTLDF
H6      KVNSIIDKMNTQFEAVDHEFSNLERRIDNLNKRMEDGFLDVWTYNAELLVLLENERTLDL
H7      KLNRLIEKTNQQFELIDNEFTEVEKQIGNLINWTKDSITEVWSYNAELIVAMENQHTIDL
H8      KVNNIVDKMNREFEVVNHEFSEVEKRINMINDKIDDQIEDLWAYNAELLVLLENQKTLDE
H9      KVNNIIDKMNKQYEVIDHEFNELEARLNMINNKIDDQIQDIWAYNAELLVLLENQKTLDE
H10     KLNRLIEKTNTEFESIESEFSETEHQIGNVINWTKDSITDIWTYNAELLVAMENQHTIDM
H11     KVNNIVDRMNTNFESVQHEFSEIEERINQLSKHVDDSVVDIWSYNAQLLVLLENEKTLDL
H12     KLNNVIDKMNKQFEVVNHEFSEVESRINMINSKIDDQITDIWAYNAELLVLLENQKTLDE
H13     KINNIIDKMNGNYDSIRGEFNQVEKRINMLADRIDDAVTDIWSYNAKLLVLLENDKTLDM
H14     KLNRLIEKTNEKYHQIEKEFEQVEGRIQDLEKYVEDTKIDLWSYNAELLVALENQHTIDV
H15     KLNRLIEKTNKQFELIDNEFTEVEQQIGNVINWTRDSLTEIWSYNAELLVAMENQHTIDL
H16     KINNIIEKMNGNYDSIRGEFNQVEKRINMLADRVDDAVTDIWSYNAKLLVLLENDRTLDL
H17     KVNSIIDKMNSQFESNIKEFNRLELRIQHLSDRVDDALLDIWSYNTELLVLLENERTLDF

H1      HDSNVKNLYEKVKSQLKNNAKEIGNGCFEFYHKCDNECMESVRNGTYDYPKYSEESKLNR
H2      HDSNVKNLYDRVRMQLRDNAKELGNGCFEFYHKCDDECMNSVKNGTYDYPKYEEESKLNR
H3      TDSEMNKLFEKTRRQLRENAEDMGNGCFKIYHKCDNACIESIRNGTYDHVYRDEALNNR
H4      TDSEMNKLFERVRRQLRENAEDKGNGCFEIFHKCDNNCIESIRNGTYDHDIYRDEAINNR
H5      HDSNVNNLYDKVRLQLKDNARELGNGCFEFYHKCDNECMESVRNGTYDYPQYSEEARLNR
H6      HDANVKNLYERVKSQLRDNAMILGNGCFEFWHKCDDECMESVKNGTYDYPKYQDESKLNR
H7      ADSEMNRLYERVRKQLRENAEEDGTGCFEIFHKCDDDCMASIRNNTYDHSKYREEAMQNR
H8      HDSNVKNLFDEVKRRLSANAIDAGNGCFDILHKCDNECMETIKNGTYDHKEYEEEAKLER
H9      HDANVNNLYNKVKPRALGSNAVEDGNGCFELYHKCDDQCMETIRNGTYDRQKYQEESRLER
H10     ADSEMLNLYERVRKQLRQNAEEDGKGCFEIYHTCDDSCMESIRNNTYDHSQYREEALLNR
H11     HDSNVRNLHEKVRRMLKDNAKDEGNGCFTFYHKCDNKCIERVRNGTYDHKEFEEESKINR
H12     HDANVRNLHDRVRRVLRENAIDTGDGCFEILHKCDNNCMDTIRNGTYNHKEYEEESKIER
H13     HDANVKNLHEQVRRELKDNAIDEGNGCFELLHKCNDSCMETIRNGTYDHTEYAEESKLKR
H14     TDSEMNKLFERVRRQLRENAEDQGNGCFEIFHQCDNNCIESIRNGTYDHNIYRDEAINNR
H15     ADSEMNKLYERVRRQLRENAEEDGTGCFEIFHRCDDQCMESIRNNTYNHTEYRQEALQNR
H16     HDANVRNLHDQVKRALKSNAIDEGDGCFNLLHKCNDSCMETIRNGTYNHEDYREESQLKR
H17     HDANVKNLFEKVKAQLKDNAIDEGNGCFLLLHKCNNSCMDDIKNGTYKYMDYREESHIEK
```

FIG. 1C

```
H1   EKVDGVKLESMG-IYQILAIYSTVASSLVLLVSLGAISFWMCSNGSLQCRICI
H2   NEIKGVKLSNMG-VYQILAIYATVAGSLSLAIMIAGISLWMCSNGSLQCRICI
H3   FQIKGVELKSGY--KDWILWISFAISCFLLCVVLLGFIMWACQRGNIRCNICI
H4   FQIQGVKLTQGY--KDIILWISFSISCFLLVALLLAFILWACQNGNIRCQICI
H5   EEISGVKLESMG-VYQILSIYSTVASSLALAIMIAGLSFWMCSNGSLQCRICI
H6   QEIESVKLESLG-VYQILAIYSTVSSSLVLVGLIIAVGLWMCSNGSMQCRICI
H7   IQIDPVKLSSGY--KDVILWFSFGASCFLLLAIAMGLVFICVKNGNMRCTICI
H8   SKINGVKLEENT-TYKILSIYSTVAASLCLAILIAGGLILGMQNGSCRCMFCI
H9   QKIEGVKLESEG-TYKILTIYSTVASSLVLAMGFAAFLFWAMSNGSCRCNICI
H10  LNINPVKLSSGY--KDIILWFSFGESCFVLLAVVMGLVFFCLKNGNMRCTICI
H11  QEIEGVKLDSSGNVYKILSIYSCIASSLVLAALIMGFMFWACSNGSCRCTICI
H12  QKVNGVKLEENS-TYKILSIYSSVASSLVLLLMIIGGFIFGCQNGNVRCTFCI
H13  QEIDGIKLKSEDNVYKALSIYSCIASSVVLVGLILSFIMWACSSGNCRFNVCI
H14  IKINPVTLTMGY--KDIILWISFSMSCFVFVALILGFVLWACQNGNIRCQICI
H15  IMINPVKLSSGY--KDVILWFSFGASCVMLLAIAMGLIFMCVKNGNLRCTICI
H16  QEIEGIKLKTEDNVYKVLSIYSCIASSIVLVGLILAFIMWACSNGSCRFNVCI
H17  QKIDGVKLTDYS-RYYIMTLYSTIASSVVLGSLIIAAFLWGCQKGSIQCKICI
```

FIG. 1D

```
H1    MK---ANLLVLLCALAAADAD--------TICIGYHANNSTDTVDTVLEKNVTVTHSVNLLE
H3    MKTIIALSYIFCLALGQDLPGNDNSTATLCLGHHAVPNGTLVKTITDDQIEVTNATELVQ
HB    MK---AIIVILMVVTSNADR--------ICTGITSSNSPHVVKTATQGEVNVTGVIPLTT

▼(Cys52,HA1)
H1    DSHNGKLCRLKG------IAPLQLGKCNIAGWLLGNPECDPLLPVRSWSYIVETPNSENG-
H3    SSSTGKICNNP-------HRILDGIDCTLIDALLGDPHCD-VFQNETWDLFVERSKAFS--
HB    TPTKSHFANLKGTETRGKLCPKCLNCTDLDVALGRPKCTGKIPSARVSILHEVRPVTSGC
                    ▲(Arg50,B-HA1)  ▲(Ala66,B-HA1)▲(Arg80,B-HA1)

H1    ICYPGDFIDYEELREQLSSVSSF--ERFEIFPKESSWPNHNTNGVTAACS-HEGKSSFYR
H3    NCYPYDVPDYASLRSLVASSG----T-LEFITEGFTWTGVTQNGGSNACK-RGPGNGFFS
HB    FPIMHDRTKIRQLPNLLRGYEHIRLSTHNVINAENAPGGPYKIGTSGSCPNITNGNGFFA

H1    NLLWLTEKE------GSYPKLKNSYVNKKGKEVLVLWGIHHPPNSKEQQNLYQNENAYVS
H3    RLNWLTKSG------STYPVLNVTMPNNDNFDKLYIWGVHHPSTNQEQTSLYVQESGRVT
HB    TMAWAVPKNDKNKTATNPLTIEVPYICTEGEDQITVWGFHSDSETQMAKLYGDSKPQKFT

H1    VVTSNYNRRFTPEIAERPKVRD-----QAGRMNYYWTLLKPGDTIIFEANGNLIAPMYAF
H3    VSTRRSQQSIIPNIGSRPWVRG-----QSSRISIYWTIVKPGDVLVINSNGNLIAPRGYF
HB    SSANGVTTHYVSQIGGFPNQTEDGGLPQSGRIVVDYMVQKSGKTGTITYQRGILLPQKVW

▲(Trp271)

H1    ALSRGFGSGIITSNASMHECNTKCQTPLGAINSSLPYQNIHPVTIGECPKYVRSAKLRMV
H3    KMRTGKSS-IMSSDAPIDTCISECITPNGSIPNDKPFQNVNKITYGACPKYVKQNTLKLA
HB    CASGRSKV-IKGSLPLIGEADCLHEKYGGLNKSKPYYTGEHAKAIGNCPIWVKTP-LKLA
              ▲(Ser277,B-HA1)
```

FIG. 2A

```
                    ▼(HA2 domain starts)
H1    TGLRNNP----SIQSRGLFGAIAGFIEGGWTGMIDGWYGYHHQNEQGSGYAADQKSTQNAI
H3    TGMRNVP---EKQTRGLFGAIAGFIENGWEGMIDGWYGFRHQNSEGTGQAADLKSTQAAI
HB    NGTKYRPPAKLLKERGFFGAIAGFLEGGWEGMIAGWHGYTSHGAHGVAVAADLKSTQEAI
                ▲(B-HA2 domain starts)

H1    NGITNKVNTVIEKMNIQFTAVGKEFNKLEKRMENLNKKVDDGFLDIWTYNAELLVLLENE
H3    DQINGKLNRVIEKTNEKFHQIEKEFSEVEGRIQDLEKYVEDTKIDLWSYNAELLVALENQ
HB    NKITKNLNSLSELEVKNLQRLSGAMDELHNEILELDEKVDDLRADTISSQIELAVLLSNE

H1    RTLDFHDSNVKNLYEKVKSQLKNNAKEIGNGCFEFYHKCDNECMESVRNGTYDYPKYSEE
H3    HTIDLTDSEMNKLFEKTRRQLRENAEDMGNGCFKIYHKCDNACIESIRNGTYDHDVYRDE
HB    GIINSEDEHLLALERKLKKMLGPSAVEIGNGCFETKHKCNQTCLDRIAAGTFDAGEFSLP

H1    SKLNR-EKVDGVKLESMGIYQILAIYSTVASSLVLLVSLGAISFWMCSNGSLQCRICI
H3    ALNNR-FQIKGVELKSGYKDWILWISFAISCFLLCVVLLGFI-MWACQRGNIRCNICI
HB    TFDSLNITAASLNDDGLDNHTILLYYSTAASSLAVTLMIAIFVVYMVSRDNVSCSICL
```

FIG. 2B

```
  1       DRICTGITSS NSPHVVKTAT QGEVNVTGVI PLTTTPTKSH FANLKGTQTR
                                                              ▲(Arg50)

51       GKLCPNCLNC TDLDVALGRP KCMGTIPSAK ASILHEVKPV TSGCFPIMHD
          ▲(Cys54)   ▲(Ala66)             ▲(Arg/Lys80)         ▲(Cys94)

101       RTKIRQLPNL LRGYENIRLS ARNVTNAETA PGGPYIVGTS GSCPNVTNGN
                                                              ▲(Cys143)

151       GFFATMAWAV PKNKTATNPL TVEVPYICTK GEDQITVWGF HSDDETQMVK
                                          ▲(Cys178)

201       LYGDSKPQKF TSSANGVTTH YVSQIGGFPN QAEDEGLPQS GRIVVDYMVQ
                                                     (Cys272)▼ ▼(Ser277)

251       KPGKTGTIAY QRGVLLPQKV WCASGRSKVI KGSLPLIGEA DCLHEKYGGL
                                ▲(Trp271)

301       NKSKPYYTGE HAKAIGNCPI WVKTPLKLAN GTKYRPPAKL LK
```

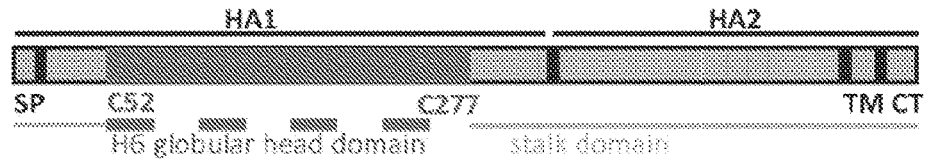
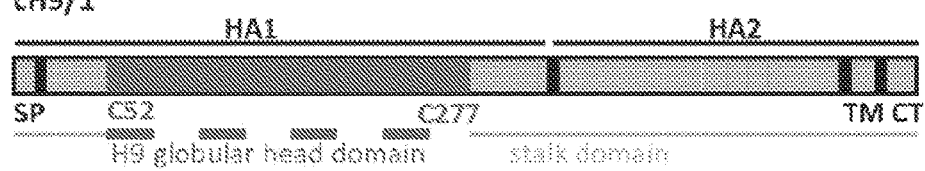
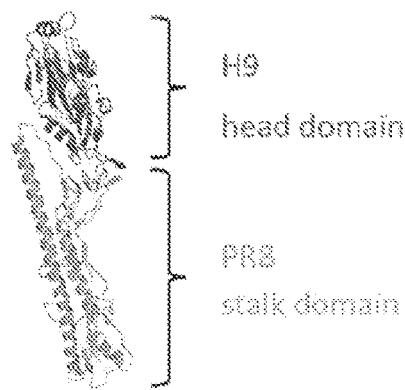
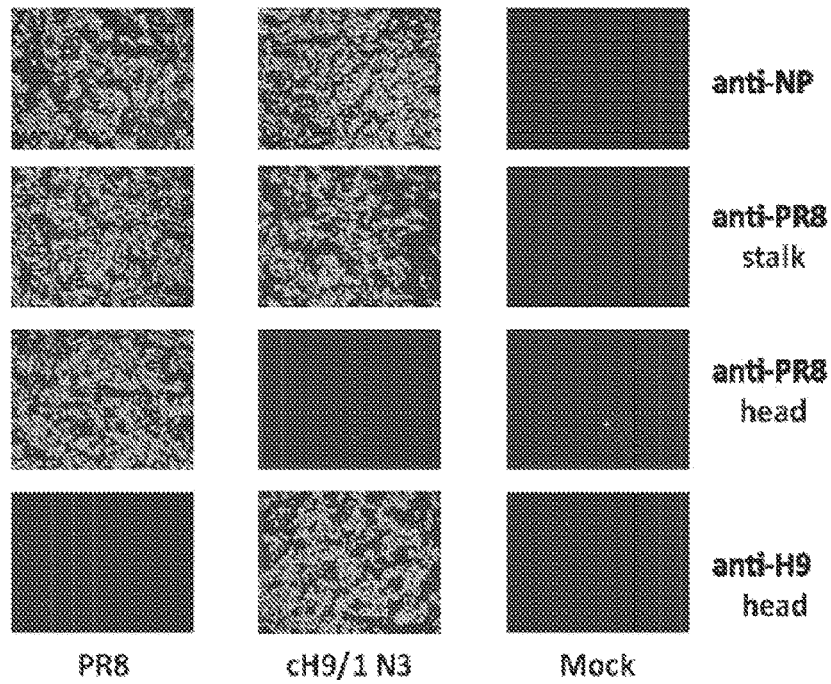
Fig. 26

Percent amino acid identity in the globular head domain

| | A/PR/8/34 (H1) | A/Cal/4/09 (H1) | A/VN/1203/04 (H5) | A/Perth/16/09 (H3) | A/mallard/Alb/24/01 (H7) |
|---|---|---|---|---|---|
| A/PR/8/34 (H1) | | 70 | 50 | 31 | 32 |
| A/Cal/4/09 (H1) | | | 46 | 31 | 27 |
| A/VN/1203/04 (H5) | | | | 34 | 31 |
| A/Perth/16/09 (H3) | | | | | 30 |
| A/mallard/Alb/24/01 (H7) | | | | | |

Percent amino acid identity in the stalk domain

| | A/PR/8/34 (H1) | A/Cal/4/09 (H1) | A/VN/1203/04 (H5) | A/Perth/16/09 (H3) | A/mallard/Alb/24/01 (H7) |
|---|---|---|---|---|---|
| A/PR/8/34 (H1) | | 90 | 77 | 47 | 47 |
| A/Cal/4/09 (H1) | | | 78 | 50 | 48 |
| A/VN/1203/04 (H5) | | | | 46 | 49 |
| A/Perth/16/09 (H3) | | | | | 61 |
| A/mallard/Alb/24/01 (H7) | | | | | |

Percent amino acid identity of the full length hemagglutinin

| | A/PR/8/34 (H1) | A/Cal/4/09 (H1) | A/VN/1203/04 (H5) | A/Perth/16/09 (H3) | A/mallard/Alb/24/01 (H7) |
|---|---|---|---|---|---|
| A/PR/8/34 (H1) | | 82 | 65 | 40 | 42 |
| A/Cal/4/09 (H1) | | | 65 | 42 | 40 |
| A/VN/1203/04 (H5) | | | | 41 | 42 |
| A/Perth/16/09 (H3) | | | | | 49 |
| A/mallard/Alb/24/01 (H7) | | | | | |

Fig. 32

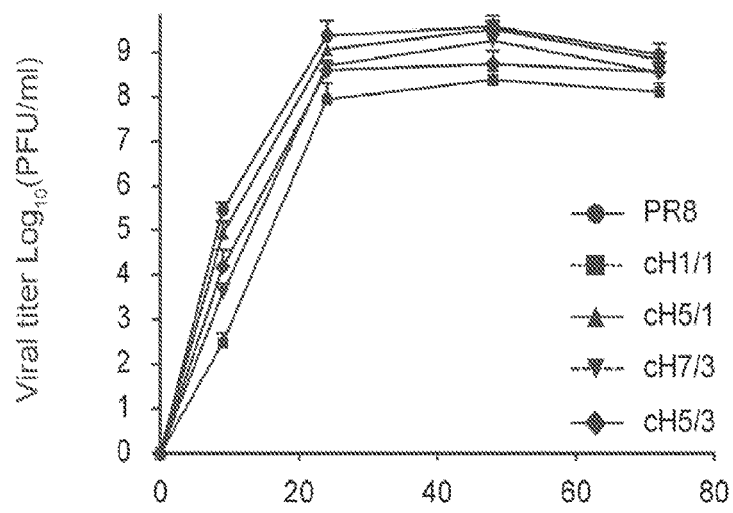
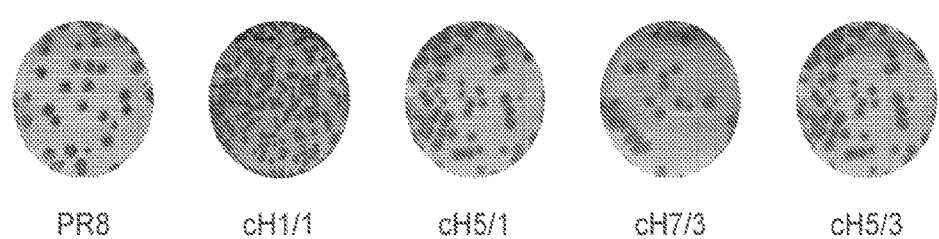
Fig. 37

Fig. 42 B

Figure 43:
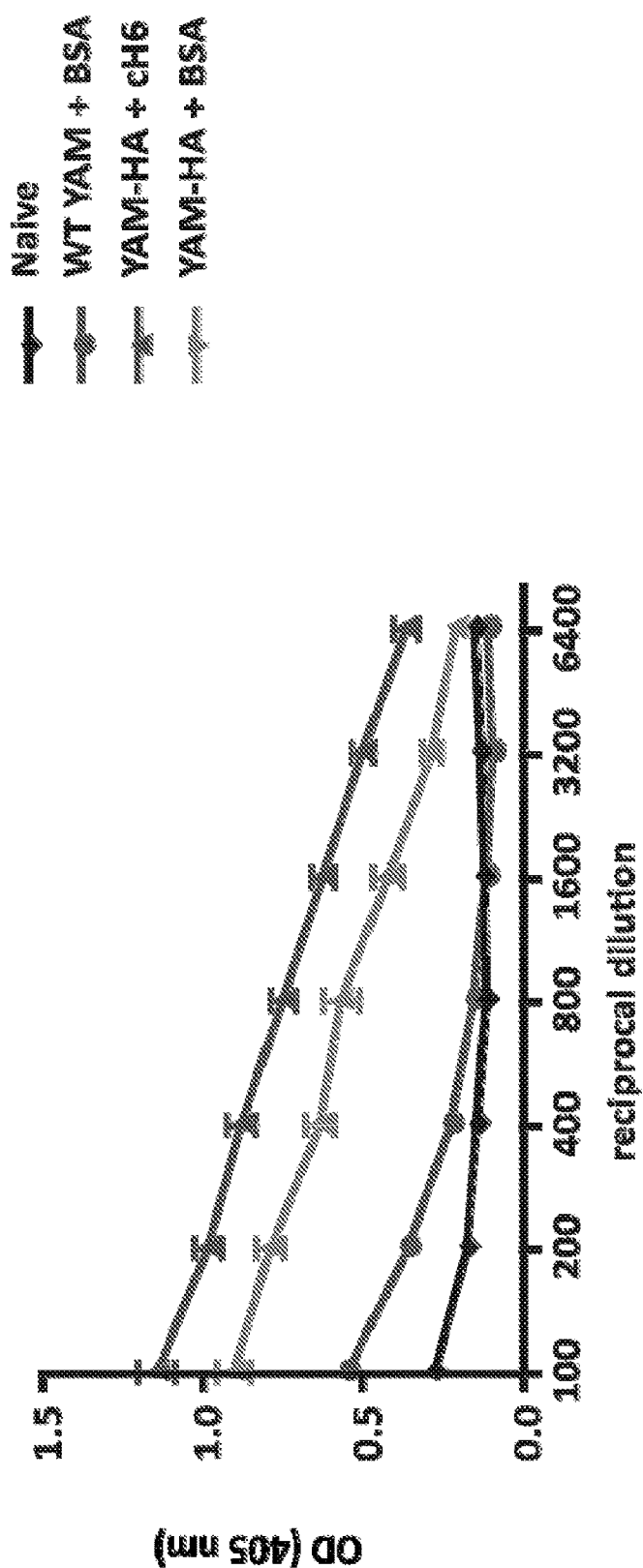

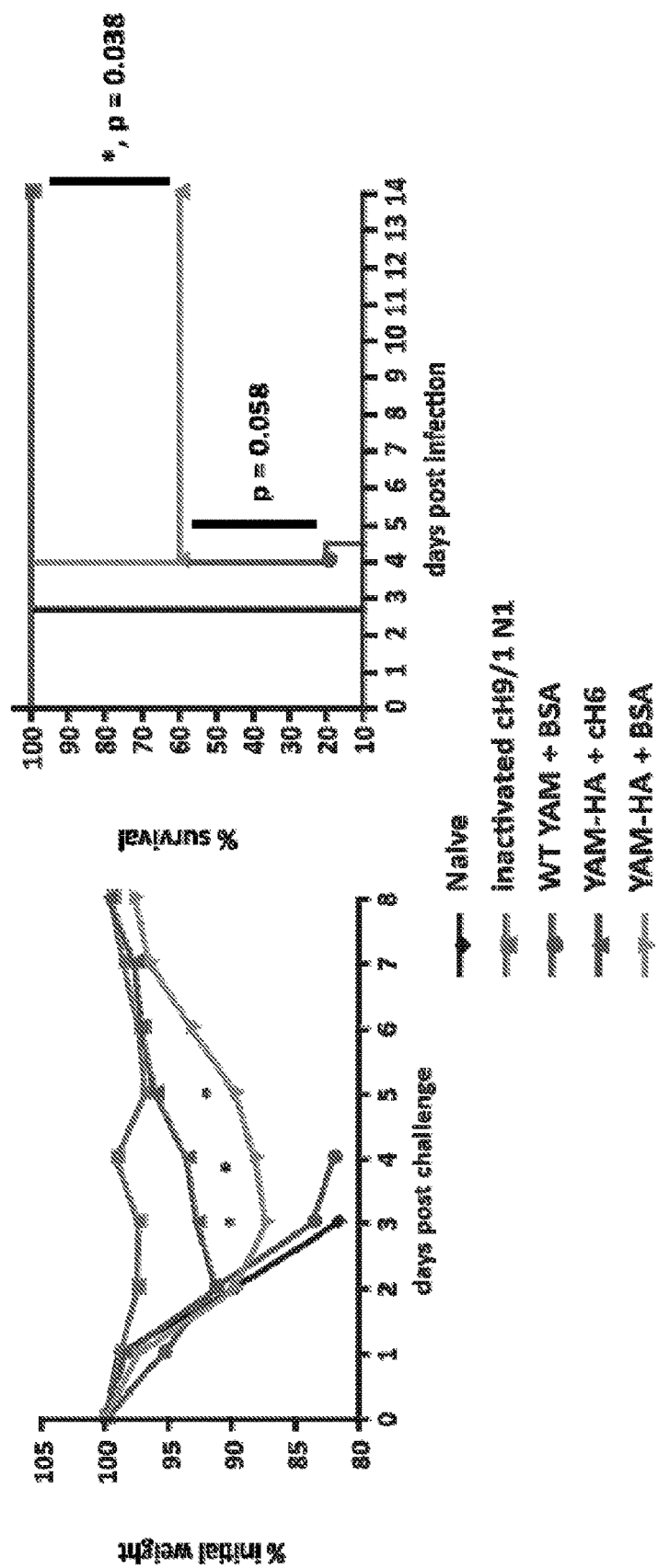
Fig. 43 A-B

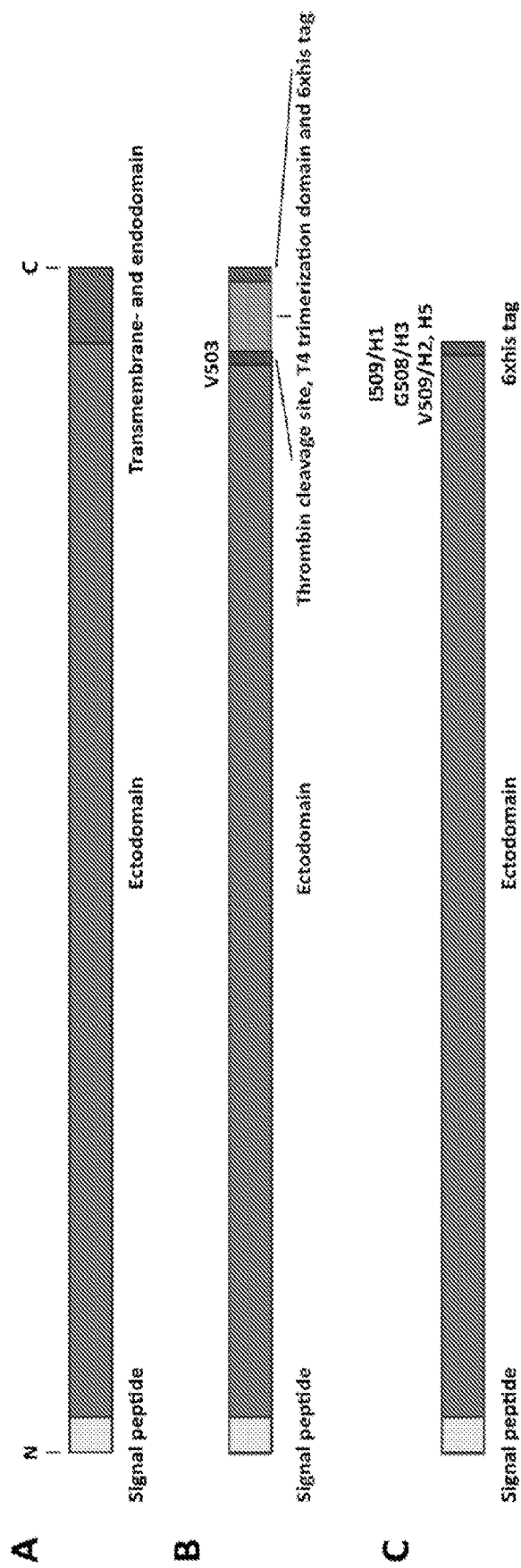
FIG. 52A-C

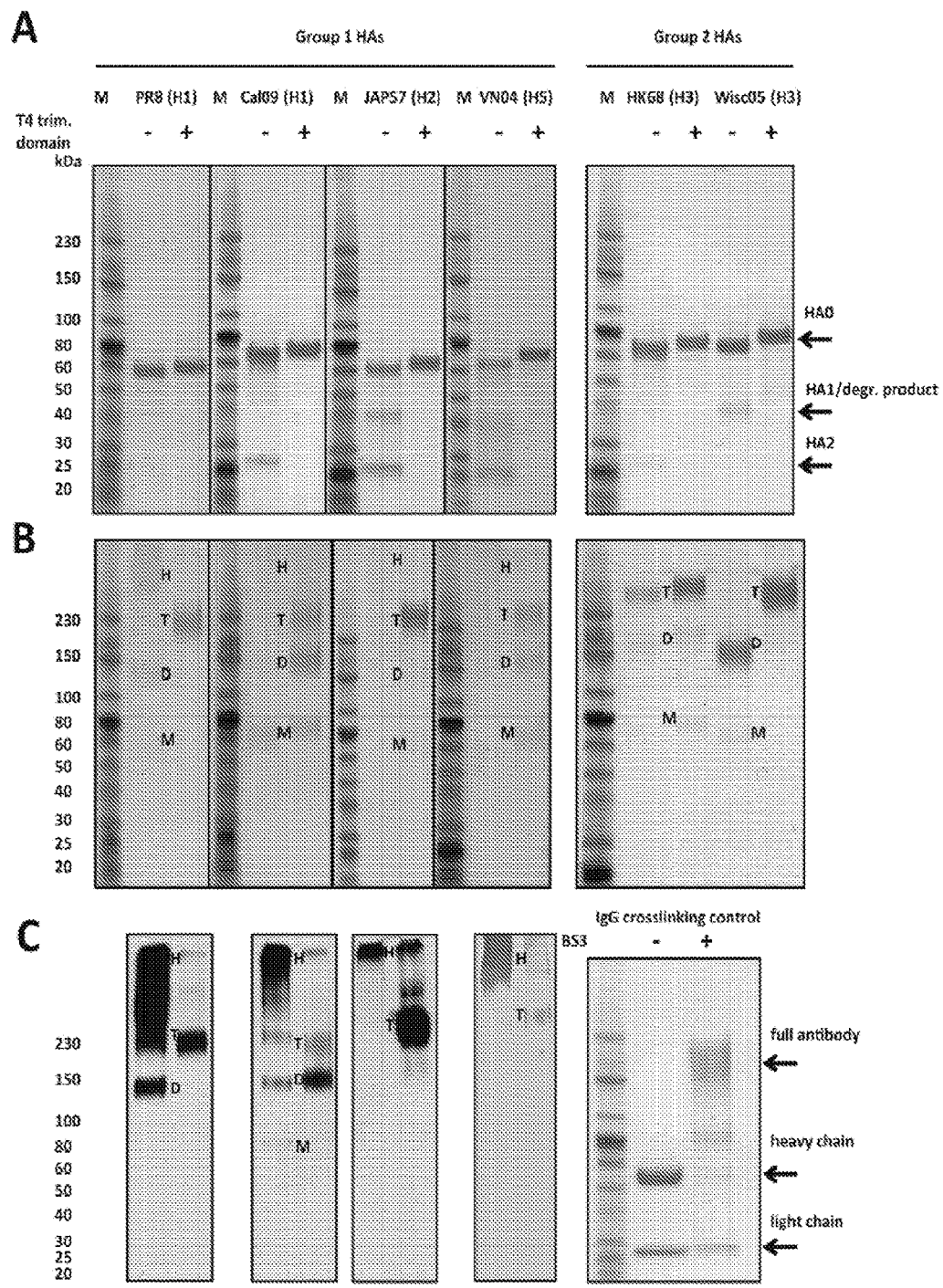
FIG. 53A-C

SEQUENCE LISTING

<160> NUMBER OF SEQ ID NOS: 604

<210> SEQ ID NO 1

<211> LENGTH: 565
<212> TYPE: PRT
<213> ORGANISM: Influenza virus A
<220> FEATURE:
<223> OTHER INFORMATION: influenza virus A hemagglutinin subtype H1

<400> SEQUENCE: 1

```
Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Asn Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380
```

```
Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
            405                 410                 415

Glu Lys Arg Met Glu Asn Leu Asn Lys Lys Val Asp Asp Gly Phe Leu
        420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
            485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 2
<211> LENGTH: 562
<212> TYPE: PRT
<213> ORGANISM: Influenza virus A
<220> FEATURE:
<223> OTHER INFORMATION: influenza virus A hemagglutinin subtype H2

<400> SEQUENCE: 2

Met Ala Ile Ile Tyr Leu Ile Leu Leu Phe Thr Ala Val Arg Gly Asp
 1               5                  10                  15

Gln Ile Cys Ile Gly Tyr His Ser Asn Asn Ser Thr Glu Lys Val Asp
            20                  25                  30

Thr Ile Leu Glu Arg Asn Val Thr Val Thr His Ala Gln Asn Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Thr Val Pro Glu Trp Ser Tyr Ile Met Glu
            85                  90                  95

Lys Glu Asn Pro Arg Asn Gly Leu Cys Tyr Pro Gly Ser Phe Asn Asp
            100                 105                 110

Tyr Glu Glu Leu Lys His Leu Leu Ser Ser Val Thr His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Ile Ala Lys Gly
            165                 170                 175
```

-continued

```
Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
            195                 200                 205

Gly Thr Tyr Val Ser Ile Gly Thr Ser Thr Leu Asn Lys Arg Ser Ile
210                 215                 220

Pro Val Ile Ala Thr Arg Pro Lys Val Asn Gly Gln Gly Gly Arg Met
225                 230                 235                 240

Glu Phe Ser Trp Thr Ile Leu Asp Ile Trp Asp Thr Ile Asn Phe Glu
                245                 250                 255

Ser Thr Gly Asn Leu Ile Ala Pro Glu Tyr Gly Phe Arg Ile Ser Lys
            260                 265                 270

Arg Gly Ser Ser Gly Ile Met Lys Thr Glu Gly Thr Leu Glu Asn Cys
            275                 280                 285

Glu Thr Lys Cys Gln Thr Pro Leu Gly Ala Ile Asn Thr Thr Leu Pro
290                 295                 300

Phe His Asn Val His Pro Leu Thr Ile Gly Glu Cys Pro Lys Tyr Val
305                 310                 315                 320

Lys Ser Glu Arg Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Ile Asp Gly Trp Tyr Gly Tyr His His Ser Asn
            355                 360                 365

Asp Gln Gly Ser Gly Tyr Ala Ala Asp Lys Glu Ser Thr Gln Lys Ala
370                 375                 380

Ile Asp Gly Ile Thr Asn Arg Val Asn Ser Val Ile Glu Lys Met Asn
385                 390                 395                 400

Thr Gln Phe Glu Ala Val Gly Lys Glu Phe Ser Asn Leu Glu Lys Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
            435                 440                 445

Asp Phe His Asp Ser Asn Val Lys Asn Leu Tyr Asp Arg Val Arg Met
450                 455                 460

Gln Leu Arg Asp Asn Ala Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Asn Met Gly Val Tyr Gln Ile Leu Ala
            515                 520                 525

Ile Tyr Ala Thr Val Ala Gly Ser Leu Ser Leu Ala Ile Met Ile Ala
            530                 535                 540

Gly Ile Ser Leu Trp Met Cys Ser Asn Gly Ser Leu Gln Cys Arg Ile
545                 550                 555                 560

Cys Ile
```

<210> SEQ ID NO 3
<211> LENGTH: 566
<212> TYPE: PRT

-continued

<213> ORGANISM: Influenza virus A
<220> FEATURE:
<223> OTHER INFORMATION: influenza virus A hemagglutinin subtype H3

<400> SEQUENCE: 3

```
Met Lys Thr Ile Ile Ala Leu Ser Tyr Ile Phe Cys Leu Ala Leu Gly
 1               5                  10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
 50                  55                  60

Gly Lys Ile Cys Asn Asn Pro His Arg Ile Leu Asp Gly Ile Asp Cys
 65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
130                 135                 140

Gly Val Thr Gln Asn Gly Gly Ser Asn Ala Cys Lys Arg Gly Pro Gly
145                 150                 155                 160

Asn Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Glu Ser Gly Arg Val Thr Val Ser Thr Arg Arg
        210                 215                 220

Ser Gln Gln Ser Ile Ile Pro Asn Ile Gly Ser Arg Pro Trp Val Arg
225                 230                 235                 240

Gly Gln Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Ser Ser Asp Ala
        275                 280                 285

Pro Ile Asp Thr Cys Ile Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
        370                 375                 380

Ser Thr Gln Ala Ala Ile Asp Gln Ile Asn Gly Lys Leu Asn Arg Val
```

```
385                 390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
                420                 425                 430
Lys Ile Asp Leu Trp Ser Tyr Asn Ala Glu Leu Leu Val Ala Leu Glu
                435                 440                 445
Asn Gln His Thr Ile Asp Leu Thr Asp Ser Glu Met Asn Lys Leu Phe
            450                 455                 460
Glu Lys Thr Arg Arg Gln Leu Arg Glu Asn Ala Glu Asp Met Gly Asn
465                 470                 475                 480
Gly Cys Phe Lys Ile Tyr His Lys Cys Asp Asn Ala Cys Ile Glu Ser
                485                 490                 495
Ile Arg Asn Gly Thr Tyr Asp His Asp Val Tyr Arg Asp Glu Ala Leu
                500                 505                 510
Asn Asn Arg Phe Gln Ile Lys Gly Val Glu Leu Lys Ser Gly Tyr Lys
                515                 520                 525
Asp Trp Ile Leu Trp Ile Ser Phe Ala Ile Ser Cys Phe Leu Leu Cys
            530                 535                 540
Val Val Leu Leu Gly Phe Ile Met Trp Ala Cys Gln Arg Gly Asn Ile
545                 550                 555                 560
Arg Cys Asn Ile Cys Ile
                565

<210> SEQ ID NO 4
<211> LENGTH: 564
<212> TYPE: PRT
<213> ORGANISM: Influenza virus A
<220> FEATURE:
<223> OTHER INFORMATION: influenza virus A hemagglutinin subtype H4

<400> SEQUENCE: 4

Met Leu Ser Ile Val Ile Leu Phe Leu Leu Ile Ala Glu Asn Ser Ser
 1               5                  10                  15
Gln Asn Tyr Thr Gly Asn Pro Val Ile Cys Met Gly His His Ala Val
                20                  25                  30
Ala Asn Gly Thr Met Val Lys Thr Leu Ala Asp Asp Gln Val Glu Val
                35                  40                  45
Val Thr Ala Gln Glu Leu Val Glu Ser Gln Asn Leu Pro Glu Leu Cys
            50                  55                  60
Pro Ser Pro Leu Arg Leu Val Asp Gly Gln Thr Cys Asp Ile Ile Asn
65                  70                  75                  80
Gly Ala Leu Gly Ser Pro Gly Cys Asp His Leu Asn Gly Ala Glu Trp
                85                  90                  95
Asp Val Phe Ile Glu Arg Pro Asn Ala Val Asp Thr Cys Tyr Pro Phe
                100                 105                 110
Asp Val Pro Glu Tyr Gln Ser Leu Arg Ser Ile Leu Ala Asn Asn Gly
                115                 120                 125
Lys Phe Glu Phe Ile Ala Glu Glu Phe Gln Trp Asn Thr Val Lys Gln
            130                 135                 140
Asn Gly Lys Ser Gly Ala Cys Lys Arg Ala Asn Val Asp Asp Phe Phe
145                 150                 155                 160
Asn Arg Leu Asn Trp Leu Val Lys Ser Asp Gly Asn Ala Tyr Pro Leu
                165                 170                 175
Gln Asn Leu Thr Lys Ile Asn Asn Gly Asp Tyr Ala Arg Leu Tyr Ile
```

```
                180             185             190
Trp Gly Val His His Pro Ser Thr Ser Thr Glu Gln Thr Asn Leu Tyr
            195             200             205
Lys Asn Asn Pro Gly Arg Val Thr Val Ser Thr Lys Thr Ser Gln Thr
            210             215             220
Ser Val Val Pro Asp Ile Gly Ser Arg Pro Leu Val Arg Gly Gln Ser
225             230             235             240
Gly Arg Val Ser Phe Tyr Trp Thr Ile Val Glu Pro Gly Asp Leu Ile
            245             250             255
Val Phe Asn Thr Ile Gly Asn Leu Ile Ala Pro Arg Gly His Tyr Lys
            260             265             270
Leu Asn Asn Gln Lys Lys Ser Thr Ile Leu Asn Thr Ala Ile Pro Ile
            275             280             285
Gly Ser Cys Val Ser Lys Cys His Thr Asp Lys Gly Ser Leu Ser Thr
            290             295             300
Thr Lys Pro Phe Gln Asn Ile Ser Arg Ile Ala Val Gly Asp Cys Pro
305             310             315             320
Arg Tyr Val Lys Gln Gly Ser Leu Lys Leu Ala Thr Gly Met Arg Asn
            325             330             335
Ile Pro Glu Lys Ala Ser Arg Gly Leu Phe Gly Ala Ile Ala Gly Phe
            340             345             350
Ile Glu Asn Gly Trp Gln Gly Leu Ile Asp Gly Trp Tyr Gly Phe Arg
            355             360             365
His Gln Asn Ala Glu Gly Thr Gly Thr Ala Ala Asp Leu Lys Ser Thr
            370             375             380
Gln Ala Ala Ile Asp Gln Ile Asn Gly Lys Leu Asn Arg Leu Ile Glu
385             390             395             400
Lys Thr Asn Asp Lys Tyr His Gln Ile Glu Lys Glu Phe Glu Gln Val
            405             410             415
Glu Gly Arg Ile Gln Asp Leu Glu Asn Tyr Val Glu Asp Thr Lys Ile
            420             425             430
Asp Leu Trp Ser Tyr Asn Ala Glu Leu Leu Val Ala Leu Glu Asn Gln
            435             440             445
His Thr Ile Asp Val Thr Asp Ser Glu Met Asn Lys Leu Phe Glu Arg
            450             455             460
Val Arg Arg Gln Leu Arg Glu Asn Ala Glu Asp Lys Gly Asn Gly Cys
465             470             475             480
Phe Glu Ile Phe His Lys Cys Asp Asn Cys Ile Glu Ser Ile Arg
            485             490             495
Asn Gly Thr Tyr Asp His Asp Ile Tyr Arg Asp Glu Ala Ile Asn Asn
            500             505             510
Arg Phe Gln Ile Gln Gly Val Lys Leu Thr Gln Gly Tyr Lys Asp Ile
            515             520             525
Ile Leu Trp Ile Ser Phe Ser Ile Ser Cys Phe Leu Leu Val Ala Leu
            530             535             540
Leu Leu Ala Phe Ile Leu Trp Ala Cys Gln Asn Gly Asn Ile Arg Cys
545             550             555             560
Gln Ile Cys Ile

<210> SEQ ID NO 5
<211> LENGTH: 564
<212> TYPE: PRT
<213> ORGANISM: Influenza virus A
<220> FEATURE:
```

<223> OTHER INFORMATION: influenza virus A hemagglutinin subtype H5

<400> SEQUENCE: 5

```
Met Glu Arg Ile Val Leu Leu Leu Ala Ile Val Ser Leu Val Lys Ser
 1               5                  10                  15

Asp Gln Ile Cys Ile Gly Tyr His Ala Asn Lys Ser Thr Lys Gln Val
            20                  25                  30

Asp Thr Ile Met Glu Lys Asn Val Thr Val Thr His Ala Gln Asp Ile
        35                  40                  45

Leu Glu Arg Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Leu Pro Glu Trp Leu Tyr Ile Val
                85                  90                  95

Glu Lys Asp Asn Pro Ile Asn Ser Leu Cys Tyr Pro Gly Asp Phe Asn
            100                 105                 110

Asp Tyr Glu Glu Leu Lys Tyr Leu Leu Ser Ser Thr Asn His Phe Glu
        115                 120                 125

Lys Ile Arg Ile Ile Pro Arg Ser Ser Trp Ser Asn His Asp Ala Ser
130                 135                 140

Ser Gly Val Ser Ser Ala Cys Pro Tyr Ile Gly Arg Ser Ser Phe Leu
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Pro Asn Asp Ala Ala Glu Gln Thr Lys Leu Tyr Gln
        195                 200                 205

Asn Pro Thr Thr Tyr Val Ser Val Gly Thr Ser Thr Leu Asn Gln Arg
    210                 215                 220

Ser Ile Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Arg Tyr Ala Tyr Lys Ile
            260                 265                 270

Val Lys Lys Gly Asp Ser Ala Ile Met Lys Ser Gly Leu Ala Tyr Gly
        275                 280                 285

Asn Cys Asp Thr Lys Cys Gln Thr Pro Val Gly Glu Ile Asn Ser Ser
    290                 295                 300

Met Pro Phe His Asn Ile His Pro His Thr Ile Gly Glu Cys Pro Lys
305                 310                 315                 320

Tyr Val Lys Ser Asp Arg Leu Val Leu Ala Thr Gly Leu Arg Asn Val
                325                 330                 335

Pro Gln Arg Lys Lys Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Ile Thr Asn Lys Val Asn Ser Ile Ile Asp Lys
385                 390                 395                 400
```

```
Met Asn Thr Arg Phe Glu Ala Val Gly Lys Glu Phe Asn Asn Leu Glu
            405                 410                 415
Arg Arg Val Glu Asn Leu Asn Lys Lys Met Glu Asp Gly Phe Leu Asp
        420                 425                 430
Val Trp Thr Tyr Asn Val Glu Leu Leu Val Leu Met Glu Asn Glu Arg
        435                 440                 445
Thr Leu Asp Phe His Asp Ser Asn Val Asn Asn Leu Tyr Asp Lys Val
450                 455                 460
Arg Leu Gln Leu Lys Asp Asn Ala Arg Glu Leu Gly Asn Gly Cys Phe
465                 470                 475                 480
Glu Phe Tyr His Lys Cys Asp Asn Glu Cys Met Glu Ser Val Arg Asn
                485                 490                 495
Gly Thr Tyr Asp Tyr Pro Gln Tyr Ser Glu Glu Ala Arg Leu Asn Arg
            500                 505                 510
Glu Glu Ile Ser Gly Val Lys Leu Glu Ser Met Gly Val Tyr Gln Ile
            515                 520                 525
Leu Ser Ile Tyr Ser Thr Val Ala Ser Ser Leu Ala Leu Ala Ile Met
        530                 535                 540
Ile Ala Gly Leu Ser Phe Trp Met Cys Ser Asn Gly Ser Leu Gln Cys
545                 550                 555                 560
Arg Ile Cys Ile

<210> SEQ ID NO 6
<211> LENGTH: 566
<212> TYPE: PRT
<213> ORGANISM: Influenza virus A
<220> FEATURE:
<223> OTHER INFORMATION: influenza virus A hemagglutinin subtype H6

<400> SEQUENCE: 6

Met Ile Ala Ile Ile Val Val Ala Ile Leu Ala Thr Ala Gly Arg Ser
 1               5                  10                  15
Asp Lys Ile Cys Ile Gly Tyr His Ala Asn Asn Ser Thr Thr Gln Ile
            20                  25                  30
Asp Thr Ile Leu Glu Lys Asn Val Thr Val Thr His Ser Val Glu Leu
        35                  40                  45
Leu Glu Asn Gln Lys Glu Glu Arg Phe Cys Lys Ile Leu Lys Lys Ala
50                  55                  60
Pro Leu Asp Leu Lys Gly Cys Thr Ile Glu Gly Trp Ile Leu Gly Asn
65                  70                  75                  80
Pro Gln Cys Asp Leu Leu Leu Gly Asp Gln Ser Trp Ser Tyr Ile Val
                85                  90                  95
Glu Arg Pro Thr Ala Gln Asn Gly Ile Cys Tyr Pro Gly Val Leu Asn
            100                 105                 110
Glu Val Glu Glu Leu Lys Ala Leu Ile Gly Ser Gly Glu Arg Val Glu
        115                 120                 125
Arg Phe Glu Met Phe Pro Lys Ser Thr Trp Thr Gly Val Asp Thr Ser
    130                 135                 140
Ser Gly Val Thr Arg Ala Cys Pro Tyr Asn Ser Gly Ser Ser Phe Tyr
145                 150                 155                 160
Arg Asn Leu Leu Trp Ile Ile Lys Thr Lys Ser Ala Ala Tyr Ser Val
                165                 170                 175
Ile Lys Gly Ala Tyr Asn Asn Thr Gly Asn Gln Pro Ile Leu Tyr Phe
            180                 185                 190
Trp Gly Val His His Pro Pro Asp Thr Asn Glu Gln Asn Thr Leu Tyr
```

```
                195                 200                 205
Gly Ser Gly Asp Arg Tyr Val Arg Met Gly Thr Glu Ser Met Asn Phe
210                 215                 220
Ala Lys Ser Pro Glu Ile Ala Ala Arg Pro Ala Val Asn Gly Gln Arg
225                 230                 235                 240
Gly Arg Ile Asp Tyr Tyr Trp Ser Ile Leu Lys Pro Gly Glu Thr Leu
                245                 250                 255
Asn Val Glu Ser Asn Gly Asn Leu Ile Ala Pro Trp Tyr Ala Phe Arg
            260                 265                 270
Phe Val Ser Thr Ser Asn Lys Gly Ala Val Phe Lys Ser Asn Leu Pro
            275                 280                 285
Ile Glu Asn Cys Asp Ala Thr Cys Gln Thr Val Ala Gly Val Leu Arg
            290                 295                 300
Thr Asn Lys Thr Phe Gln Asn Val Ser Pro Leu Trp Ile Gly Glu Cys
305                 310                 315                 320
Pro Lys Tyr Val Lys Ser Glu Ser Leu Arg Leu Ala Thr Gly Leu Arg
                325                 330                 335
Asn Val Pro Gln Ile Glu Thr Arg Gly Leu Phe Gly Ala Ile Ala Gly
                340                 345                 350
Phe Ile Glu Gly Gly Trp Thr Gly Met Ile Asp Gly Trp Tyr Gly Tyr
            355                 360                 365
His His Glu Asn Ser Gln Gly Ser Gly Tyr Ala Ala Asp Arg Glu Ser
    370                 375                 380
Thr Gln Lys Ala Val Asp Gly Ile Thr Asn Lys Val Asn Ser Ile Ile
385                 390                 395                 400
Asp Lys Met Asn Thr Gln Phe Glu Ala Val Asp His Glu Phe Ser Asn
                405                 410                 415
Leu Glu Arg Arg Ile Asp Asn Leu Asn Lys Arg Met Glu Asp Gly Phe
                420                 425                 430
Leu Asp Val Trp Thr Tyr Asn Ala Glu Leu Leu Val Leu Leu Glu Asn
            435                 440                 445
Glu Arg Thr Leu Asp Leu His Asp Ala Asn Val Lys Asn Leu Tyr Glu
    450                 455                 460
Arg Val Lys Ser Gln Leu Arg Asp Asn Ala Met Ile Leu Gly Asn Gly
465                 470                 475                 480
Cys Phe Glu Phe Trp His Lys Cys Asp Asp Glu Cys Met Glu Ser Val
                485                 490                 495
Lys Asn Gly Thr Tyr Asp Tyr Pro Lys Tyr Gln Asp Glu Ser Lys Leu
            500                 505                 510
Asn Arg Gln Glu Ile Glu Ser Val Lys Leu Glu Ser Leu Gly Val Tyr
        515                 520                 525
Gln Ile Leu Ala Ile Tyr Ser Thr Val Ser Ser Leu Val Leu Val
    530                 535                 540
Gly Leu Ile Ile Ala Val Gly Leu Trp Met Cys Ser Asn Gly Ser Met
545                 550                 555                 560
Gln Cys Arg Ile Cys Ile
            565

<210> SEQ ID NO 7
<211> LENGTH: 563
<212> TYPE: PRT
<213> ORGANISM: Influenza virus A
<220> FEATURE:
<223> OTHER INFORMATION: influenza virus A hemagglutinin subtype H7
```

```
<400> SEQUENCE: 7

Met Asn Thr Gln Ile Leu Val Phe Ala Leu Val Ala Val Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
                35                  40                  45

Glu Thr Val Glu Arg Thr Asn Ile Pro Lys Ile Cys Ser Lys Gly Lys
50                  55                      60

Arg Thr Thr Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Asn Asp Val Cys Tyr Pro Gly Lys Phe Val Asn
                100                 105                 110

Glu Glu Ala Leu Arg Gln Ile Leu Arg Gly Ser Gly Ile Asp Lys
                115                 120                 125

Glu Thr Met Gly Phe Thr Tyr Ser Gly Ile Arg Thr Asn Gly Thr Thr
                130                 135                 140

Ser Ala Cys Arg Arg Ser Gly Ser Ser Phe Tyr Ala Glu Met Glu Trp
145                 150                 155                 160

Leu Leu Ser Asn Thr Asp Asn Ala Ser Phe Pro Gln Met Thr Lys Ser
                165                 170                 175

Tyr Lys Asn Thr Arg Arg Glu Ser Ala Leu Ile Val Trp Gly Ile His
                180                 185                 190

His Ser Gly Ser Thr Thr Glu Gln Thr Lys Leu Tyr Gly Ser Gly Asn
                195                 200                 205

Lys Leu Ile Thr Val Gly Ser Ser Lys Tyr His Gln Ser Phe Val Pro
                210                 215                 220

Ser Pro Gly Thr Arg Pro Gln Ile Asn Gly Gln Ser Gly Arg Ile Asp
225                 230                 235                 240

Phe His Trp Leu Ile Leu Asp Pro Asn Asp Thr Val Thr Phe Ser Phe
                245                 250                 255

Asn Gly Ala Phe Ile Ala Pro Asn Arg Ala Ser Phe Leu Arg Gly Lys
                260                 265                 270

Ser Met Gly Ile Gln Ser Asp Val Gln Val Asp Ala Asn Cys Glu Gly
                275                 280                 285

Glu Cys Tyr His Ser Gly Gly Thr Ile Thr Ser Arg Leu Pro Phe Gln
                290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Pro Ser
                325                 330                 335

Lys Lys Arg Lys Lys Arg Gly Leu Phe Gly Ala Ile Ala Gly Phe Ile
                340                 345                 350

Glu Asn Gly Trp Glu Gly Leu Val Asp Gly Trp Tyr Gly Phe Arg His
                355                 360                 365

Gln Asn Ala Gln Gly Glu Gly Thr Ala Ala Asp Tyr Lys Ser Thr Gln
                370                 375                 380

Ser Ala Ile Asp Gln Ile Thr Gly Lys Leu Asn Arg Leu Ile Glu Lys
385                 390                 395                 400

Thr Asn Gln Gln Phe Glu Leu Ile Asp Asn Glu Phe Thr Glu Val Glu
                405                 410                 415
```

Lys Gln Ile Gly Asn Leu Ile Asn Trp Thr Lys Asp Ser Ile Thr Glu
              420                 425                 430

Val Trp Ser Tyr Asn Ala Glu Leu Ile Val Ala Met Glu Asn Gln His
         435                 440                 445

Thr Ile Asp Leu Ala Asp Ser Glu Met Asn Arg Leu Tyr Glu Arg Val
    450                 455                 460

Arg Lys Gln Leu Arg Glu Asn Ala Glu Glu Asp Gly Thr Gly Cys Phe
465                 470                 475                 480

Glu Ile Phe His Lys Cys Asp Asp Cys Met Ala Ser Ile Arg Asn
              485                 490                 495

Asn Thr Tyr Asp His Ser Lys Tyr Arg Glu Glu Ala Met Gln Asn Arg
              500                 505                 510

Ile Gln Ile Asp Pro Val Lys Leu Ser Ser Gly Tyr Lys Asp Val Ile
         515                 520                 525

Leu Trp Phe Ser Phe Gly Ala Ser Cys Phe Leu Leu Leu Ala Ile Ala
    530                 535                 540

Met Gly Leu Val Phe Ile Cys Val Lys Asn Gly Asn Met Arg Cys Thr
545                 550                 555                 560

Ile Cys Ile

<210> SEQ ID NO 8
<211> LENGTH: 565
<212> TYPE: PRT
<213> ORGANISM: Influenza virus A
<220> FEATURE:
<223> OTHER INFORMATION: influenza virus A hemagglutinin subtype H8

<400> SEQUENCE: 8

Met Glu Lys Phe Ile Ala Ile Ala Thr Leu Ala Ser Thr Asn Ala Tyr
1               5                   10                  15

Asp Arg Ile Cys Ile Gly Tyr Gln Ser Asn Asn Ser Thr Asp Thr Val
              20                  25                  30

Asn Thr Leu Ile Glu Gln Asn Val Pro Val Thr Gln Thr Met Glu Leu
         35                  40                  45

Val Glu Thr Glu Lys His Pro Ala Tyr Cys Asn Thr Asp Leu Gly Ala
    50                  55                  60

Pro Leu Glu Leu Arg Asp Cys Lys Ile Glu Ala Val Ile Tyr Gly Asn
65                  70                  75                  80

Pro Lys Cys Asp Ile His Leu Lys Asp Gln Gly Trp Ser Tyr Ile Val
              85                  90                  95

Glu Arg Pro Ser Ala Pro Glu Gly Met Cys Tyr Pro Gly Ser Val Glu
              100                 105                 110

Asn Leu Glu Glu Leu Arg Phe Val Phe Ser Ser Ala Ala Ser Tyr Lys
         115                 120                 125

Arg Ile Arg Leu Phe Asp Tyr Ser Arg Trp Asn Val Thr Arg Ser Gly
130                 135                 140

Thr Ser Lys Ala Cys Asn Ala Ser Thr Gly Gly Gln Ser Phe Tyr Arg
145                 150                 155                 160

Ser Ile Asn Trp Leu Thr Lys Lys Glu Pro Asp Thr Tyr Asp Phe Asn
              165                 170                 175

Glu Gly Ala Tyr Val Asn Asn Glu Asp Gly Asp Ile Ile Phe Leu Trp
              180                 185                 190

Gly Ile His His Pro Pro Asp Thr Lys Glu Gln Thr Thr Leu Tyr Lys
         195                 200                 205

Asn Ala Asn Thr Leu Ser Ser Val Thr Thr Asn Thr Ile Asn Arg Ser
210                 215                 220

Phe Gln Pro Asn Ile Gly Pro Arg Pro Leu Val Arg Gly Gln Gln Gly
225                 230                 235                 240

Arg Met Asp Tyr Tyr Trp Gly Ile Leu Lys Arg Gly Glu Thr Leu Lys
                245                 250                 255

Ile Arg Thr Asn Gly Asn Leu Ile Ala Pro Glu Phe Gly Tyr Leu Leu
                260                 265                 270

Lys Gly Glu Ser Tyr Gly Arg Ile Ile Gln Asn Glu Asp Ile Pro Ile
            275                 280                 285

Gly Asn Cys Asn Thr Lys Cys Gln Thr Tyr Ala Gly Ala Ile Asn Ser
290                 295                 300

Ser Lys Pro Phe Gln Asn Ala Ser Arg His Tyr Met Gly Glu Cys Pro
305                 310                 315                 320

Lys Tyr Val Lys Lys Ala Ser Leu Arg Leu Ala Val Gly Leu Arg Asn
                325                 330                 335

Thr Pro Ser Val Glu Pro Arg Gly Leu Phe Gly Ala Ile Ala Gly Phe
                340                 345                 350

Ile Glu Gly Gly Trp Ser Gly Met Ile Asp Gly Trp Tyr Gly Phe His
            355                 360                 365

His Ser Asn Ser Glu Gly Thr Gly Met Ala Ala Asp Gln Lys Ser Thr
370                 375                 380

Gln Glu Ala Ile Asp Lys Ile Thr Asn Lys Val Asn Asn Ile Val Asp
385                 390                 395                 400

Lys Met Asn Arg Glu Phe Glu Val Val Asn His Glu Phe Ser Glu Val
                405                 410                 415

Glu Lys Arg Ile Asn Met Ile Asn Asp Lys Ile Asp Asp Gln Ile Glu
            420                 425                 430

Asp Leu Trp Ala Tyr Asn Ala Glu Leu Leu Val Leu Leu Glu Asn Gln
435                 440                 445

Lys Thr Leu Asp Glu His Asp Ser Asn Val Lys Asn Leu Phe Asp Glu
    450                 455                 460

Val Lys Arg Arg Leu Ser Ala Asn Ala Ile Asp Ala Gly Asn Gly Cys
465                 470                 475                 480

Phe Asp Ile Leu His Lys Cys Asp Asn Glu Cys Met Glu Thr Ile Lys
                485                 490                 495

Asn Gly Thr Tyr Asp His Lys Glu Tyr Glu Glu Ala Lys Leu Glu
                500                 505                 510

Arg Ser Lys Ile Asn Gly Val Lys Leu Glu Glu Asn Thr Thr Tyr Lys
            515                 520                 525

Ile Leu Ser Ile Tyr Ser Thr Val Ala Ala Ser Leu Cys Leu Ala Ile
530                 535                 540

Leu Ile Ala Gly Gly Leu Ile Leu Gly Met Gln Asn Gly Ser Cys Arg
545                 550                 555                 560

Cys Met Phe Cys Ile
            565

<210> SEQ ID NO 9
<211> LENGTH: 560
<212> TYPE: PRT
<213> ORGANISM: Influenza virus A
<220> FEATURE:
<223> OTHER INFORMATION: influenza virus A hemagglutinin subtype H9

<400> SEQUENCE: 9

-continued

```
Met Glu Thr Lys Ala Ile Ile Ala Ala Leu Leu Met Val Thr Ala Ala
 1               5                  10                  15

Asn Ala Asp Lys Ile Cys Ile Gly Tyr Gln Ser Thr Asn Ser Thr Glu
                20                  25                  30

Thr Val Asp Thr Leu Thr Glu Ser Asn Val Pro Val Thr His Thr Lys
             35                  40                  45

Glu Leu Leu His Thr Glu His Asn Gly Met Leu Cys Ala Thr Asp Leu
         50                  55                  60

Gly His Pro Leu Ile Leu Asp Thr Cys Thr Ile Glu Gly Leu Ile Tyr
 65                  70                  75                  80

Gly Asn Pro Ser Cys Asp Ile Leu Leu Gly Gly Lys Glu Trp Ser Tyr
                 85                  90                  95

Ile Val Glu Arg Ser Ser Ala Val Asn Gly Met Cys Tyr Pro Gly Asn
                100                 105                 110

Val Glu Asn Leu Glu Glu Leu Arg Ser Leu Phe Ser Ser Ala Lys Ser
             115                 120                 125

Tyr Lys Arg Ile Gln Ile Phe Pro Asp Lys Thr Trp Asn Val Thr Tyr
             130                 135                 140

Ser Gly Thr Ser Arg Ala Cys Ser Asn Ser Phe Tyr Arg Ser Met Arg
145                 150                 155                 160

Trp Leu Thr His Lys Ser Asn Ser Tyr Pro Phe Gln Asn Ala His Tyr
                 165                 170                 175

Thr Asn Asn Glu Arg Glu Asn Ile Leu Phe Met Trp Gly Ile His His
                 180                 185                 190

Pro Pro Thr Asp Thr Glu Gln Thr Asp Leu Tyr Lys Asn Ala Asp Thr
             195                 200                 205

Thr Thr Ser Val Thr Thr Glu Asp Ile Asn Arg Thr Phe Lys Pro Val
 210                 215                 220

Ile Gly Pro Arg Pro Leu Val Asn Gly Gln Gln Gly Arg Ile Asp Tyr
225                 230                 235                 240

Tyr Trp Ser Val Leu Lys Pro Gly Gln Thr Leu Arg Ile Arg Ser Asn
                 245                 250                 255

Gly Asn Leu Ile Ala Pro Trp Tyr Gly His Val Leu Thr Gly Glu Ser
                 260                 265                 270

His Gly Arg Ile Leu Lys Thr Asp Leu Asn Asn Gly Asn Cys Val Val
             275                 280                 285

Gln Cys Gln Thr Glu Lys Gly Gly Leu Asn Thr Thr Leu Pro Phe His
             290                 295                 300

Asn Ile Ser Lys Tyr Ala Phe Gly Asn Cys Pro Lys Tyr Val Gly Val
305                 310                 315                 320

Lys Ser Leu Lys Leu Pro Val Gly Leu Arg Asn Val Pro Ala Val Ser
                 325                 330                 335

Ser Arg Gly Leu Phe Gly Ala Ile Ala Gly Phe Ile Glu Gly Gly Trp
             340                 345                 350

Pro Gly Leu Val Ala Gly Trp Tyr Gly Phe Gln His Ser Asn Asp Gln
             355                 360                 365

Gly Val Gly Met Ala Ala Asp Lys Gly Ser Thr Gln Lys Ala Ile Asp
 370                 375                 380

Lys Ile Thr Ser Lys Val Asn Asn Ile Ile Asp Lys Met Asn Lys Gln
385                 390                 395                 400

Tyr Glu Val Ile Asp His Glu Phe Asn Glu Leu Glu Ala Arg Leu Asn
                 405                 410                 415

Met Ile Asn Asn Lys Ile Asp Asp Gln Ile Gln Asp Ile Trp Ala Tyr
```

```
                420             425             430
Asn Ala Glu Leu Leu Val Leu Leu Glu Asn Gln Lys Thr Leu Asp Glu
            435                 440                 445
His Asp Ala Asn Val Asn Asn Leu Tyr Asn Lys Val Lys Arg Ala Leu
            450                 455                 460
Gly Ser Asn Ala Val Glu Asp Gly Asn Gly Cys Phe Glu Leu Tyr His
465                 470                 475                 480
Lys Cys Asp Asp Gln Cys Met Glu Thr Ile Arg Asn Gly Thr Tyr Asp
                485                 490                 495
Arg Gln Lys Tyr Gln Glu Glu Ser Arg Leu Glu Arg Gln Lys Ile Glu
                500                 505                 510
Gly Val Lys Leu Glu Ser Glu Gly Thr Tyr Lys Ile Leu Thr Ile Tyr
            515                 520                 525
Ser Thr Val Ala Ser Ser Leu Val Leu Ala Met Gly Phe Ala Ala Phe
            530                 535                 540
Leu Phe Trp Ala Met Ser Asn Gly Ser Cys Arg Cys Asn Ile Cys Ile
545                 550                 555                 560

<210> SEQ ID NO 10
<211> LENGTH: 561
<212> TYPE: PRT
<213> ORGANISM: Influenza virus A
<220> FEATURE:
<223> OTHER INFORMATION: influenza virus A hemagglutinin subtype H10

<400> SEQUENCE: 10

Met Tyr Lys Val Val Ile Ile Ala Leu Leu Gly Ala Val Lys Gly
1               5                   10                  15
Leu Asp Arg Ile Cys Leu Gly His His Ala Val Ala Asn Gly Thr Ile
                20                  25                  30
Val Lys Thr Leu Thr Asn Glu Gln Glu Glu Val Thr Asn Ala Thr Glu
            35                  40                  45
Thr Val Glu Ser Thr Asn Leu Asn Lys Leu Cys Met Lys Gly Arg Ser
50                  55                  60
Tyr Lys Asp Leu Gly Asn Cys His Pro Val Gly Met Leu Ile Gly Thr
65                  70                  75                  80
Pro Val Cys Asp Pro His Leu Thr Gly Thr Trp Asp Thr Leu Ile Glu
                85                  90                  95
Arg Glu Asn Ala Ile Ala His Cys Tyr Pro Gly Ala Thr Ile Asn Glu
                100                 105                 110
Glu Ala Leu Arg Gln Lys Ile Met Glu Ser Gly Gly Ile Ser Lys Met
            115                 120                 125
Ser Thr Gly Phe Thr Tyr Gly Ser Ser Ile Thr Ser Ala Gly Thr Thr
130                 135                 140
Lys Ala Cys Met Arg Asn Gly Gly Asp Ser Phe Tyr Ala Glu Leu Lys
145                 150                 155                 160
Trp Leu Val Ser Lys Thr Lys Gly Gln Asn Phe Pro Gln Thr Thr Asn
                165                 170                 175
Thr Tyr Arg Asn Thr Asp Thr Ala Glu His Leu Ile Ile Trp Gly Ile
                180                 185                 190
His His Pro Ser Ser Thr Gln Glu Lys Asn Asp Leu Tyr Gly Thr Gln
            195                 200                 205
Ser Leu Ser Ile Ser Val Glu Ser Ser Thr Tyr Gln Asn Asn Phe Val
            210                 215                 220
Pro Val Val Gly Ala Arg Pro Gln Val Asn Gly Gln Ser Gly Arg Ile
```

```
            225                 230                 235                 240

Asp Phe His Trp Thr Leu Val Gln Pro Gly Asp Asn Ile Thr Phe Ser
            245                 250                 255

Asp Asn Gly Gly Leu Ile Ala Pro Ser Arg Val Ser Lys Leu Thr Gly
            260                 265                 270

Arg Asp Leu Gly Ile Gln Ser Glu Ala Leu Ile Asp Asn Ser Cys Glu
            275                 280                 285

Ser Lys Cys Phe Trp Arg Gly Ser Ile Asn Thr Lys Leu Pro Phe
            290                 295                 300

Gln Asn Leu Ser Pro Arg Thr Val Gly Gln Cys Pro Lys Tyr Val Asn
305                 310                 315                 320

Gln Arg Ser Leu Leu Leu Ala Thr Gly Met Arg Asn Val Pro Glu Val
            325                 330                 335

Val Gln Gly Arg Gly Leu Phe Gly Ala Ile Ala Gly Phe Ile Glu Asn
            340                 345                 350

Gly Trp Glu Gly Met Val Asp Gly Trp Tyr Gly Phe Arg His Gln Asn
            355                 360                 365

Ala Gln Gly Thr Gly Gln Ala Ala Asp Tyr Lys Ser Thr Gln Ala Ala
            370                 375                 380

Ile Asp Gln Ile Thr Gly Lys Leu Asn Arg Leu Ile Glu Lys Thr Asn
385                 390                 395                 400

Thr Glu Phe Glu Ser Ile Glu Ser Glu Phe Ser Glu Thr Glu His Gln
            405                 410                 415

Ile Gly Asn Val Ile Asn Trp Thr Lys Asp Ser Ile Thr Asp Ile Trp
            420                 425                 430

Thr Tyr Asn Ala Glu Leu Leu Val Ala Met Glu Asn Gln His Thr Ile
            435                 440                 445

Asp Met Ala Asp Ser Glu Met Leu Asn Leu Tyr Glu Arg Val Arg Lys
            450                 455                 460

Gln Leu Arg Gln Asn Ala Glu Glu Asp Gly Lys Gly Cys Phe Glu Ile
465                 470                 475                 480

Tyr His Thr Cys Asp Asp Ser Cys Met Glu Ser Ile Arg Asn Asn Thr
            485                 490                 495

Tyr Asp His Ser Gln Tyr Arg Glu Glu Ala Leu Leu Asn Arg Leu Asn
            500                 505                 510

Ile Asn Pro Val Lys Leu Ser Ser Gly Tyr Lys Asp Ile Ile Leu Trp
            515                 520                 525

Phe Ser Phe Gly Glu Ser Cys Phe Val Leu Leu Ala Val Val Met Gly
            530                 535                 540

Leu Val Phe Phe Cys Leu Lys Asn Gly Asn Met Arg Cys Thr Ile Cys
545                 550                 555                 560

Ile

<210> SEQ ID NO 11
<211> LENGTH: 565
<212> TYPE: PRT
<213> ORGANISM: Influenza virus A
<220> FEATURE:
<223> OTHER INFORMATION: influenza virus A hemagglutinin subtype H11

<400> SEQUENCE: 11

Met Glu Lys Thr Leu Leu Phe Ala Ala Ile Phe Leu Cys Val Lys Ala
1               5                   10                  15

Asp Glu Ile Cys Ile Gly Tyr Leu Ser Asn Asn Ser Thr Asp Lys Val
                20                  25                  30
```

```
Asp Thr Ile Ile Glu Asn Asn Val Thr Val Thr Ser Ser Val Glu Leu
            35                  40                  45

Val Glu Thr Glu His Thr Gly Ser Phe Cys Ser Ile Asn Gly Lys Gln
 50                  55                  60

Pro Ile Ser Leu Gly Asp Cys Ser Phe Ala Gly Trp Ile Leu Gly Asn
 65                  70                  75                  80

Pro Met Cys Asp Glu Leu Ile Gly Lys Thr Ser Trp Ser Tyr Ile Val
                 85                  90                  95

Glu Lys Pro Asn Pro Thr Asn Gly Ile Cys Tyr Pro Gly Thr Leu Glu
                100                 105                 110

Ser Glu Glu Glu Leu Arg Leu Lys Phe Ser Gly Val Leu Glu Phe Asn
                115                 120                 125

Lys Phe Glu Val Phe Thr Ser Asn Gly Trp Gly Ala Val Asn Ser Gly
130                 135                 140

Val Gly Val Thr Ala Ala Cys Lys Phe Gly Gly Ser Asn Ser Phe Phe
145                 150                 155                 160

Arg Asn Met Val Trp Leu Ile His Gln Ser Gly Thr Tyr Pro Val Ile
                165                 170                 175

Lys Arg Thr Phe Asn Asn Thr Lys Gly Arg Asp Val Leu Ile Val Trp
                180                 185                 190

Gly Ile His His Pro Ala Thr Leu Thr Glu His Gln Asp Leu Tyr Lys
                195                 200                 205

Lys Asp Ser Ser Tyr Val Ala Val Gly Ser Glu Thr Tyr Asn Arg Arg
210                 215                 220

Phe Thr Pro Glu Ile Asn Thr Arg Pro Arg Val Asn Gly Gln Ala Gly
225                 230                 235                 240

Arg Met Thr Phe Tyr Trp Lys Ile Val Lys Pro Gly Glu Ser Ile Thr
                245                 250                 255

Phe Glu Ser Asn Gly Ala Phe Leu Ala Pro Arg Tyr Ala Phe Glu Ile
                260                 265                 270

Val Ser Val Gly Asn Gly Lys Leu Phe Arg Ser Glu Leu Asn Ile Glu
                275                 280                 285

Ser Cys Ser Thr Lys Cys Gln Thr Glu Ile Gly Gly Ile Asn Thr Asn
                290                 295                 300

Lys Ser Phe His Asn Val His Arg Asn Thr Ile Gly Asp Cys Pro Lys
305                 310                 315                 320

Tyr Val Asn Val Lys Ser Leu Lys Leu Ala Thr Gly Pro Arg Asn Val
                325                 330                 335

Pro Ala Ile Ala Ser Arg Gly Leu Phe Gly Ala Ile Ala Gly Phe Ile
                340                 345                 350

Glu Gly Gly Trp Pro Gly Leu Ile Asn Gly Trp Tyr Gly Phe Gln His
                355                 360                 365

Arg Asp Glu Glu Gly Thr Gly Ile Ala Ala Asp Lys Glu Ser Thr Gln
370                 375                 380

Lys Ala Ile Asp Gln Ile Thr Ser Lys Val Asn Asn Ile Val Asp Arg
385                 390                 395                 400

Met Asn Thr Asn Phe Glu Ser Val Gln His Glu Phe Ser Glu Ile Glu
                405                 410                 415

Glu Arg Ile Asn Gln Leu Ser Lys His Val Asp Asp Ser Val Val Asp
                420                 425                 430

Ile Trp Ser Tyr Asn Ala Gln Leu Leu Val Leu Leu Glu Asn Glu Lys
                435                 440                 445
```

```
Thr Leu Asp Leu His Asp Ser Asn Val Arg Asn Leu His Glu Lys Val
    450                 455                 460

Arg Arg Met Leu Lys Asp Asn Ala Lys Asp Glu Gly Asn Gly Cys Phe
465                 470                 475                 480

Thr Phe Tyr His Lys Cys Asp Asn Lys Cys Ile Glu Arg Val Arg Asn
                485                 490                 495

Gly Thr Tyr Asp His Lys Glu Phe Glu Glu Ser Lys Ile Asn Arg
            500                 505                 510

Gln Glu Ile Glu Gly Val Lys Leu Asp Ser Ser Gly Asn Val Tyr Lys
                515                 520                 525

Ile Leu Ser Ile Tyr Ser Cys Ile Ala Ser Ser Leu Val Leu Ala Ala
530                 535                 540

Leu Ile Met Gly Phe Met Phe Trp Ala Cys Ser Asn Gly Ser Cys Arg
545                 550                 555                 560

Cys Thr Ile Cys Ile
                565

<210> SEQ ID NO 12
<211> LENGTH: 564
<212> TYPE: PRT
<213> ORGANISM: Influenza virus A
<220> FEATURE:
<223> OTHER INFORMATION: influenza virus A hemagglutinin subtype H12

<400> SEQUENCE: 12

Met Glu Lys Phe Ile Ile Leu Ser Thr Val Leu Ala Ala Ser Phe Ala
1               5                   10                  15

Tyr Asp Lys Ile Cys Ile Gly Tyr Gln Thr Asn Asn Ser Thr Glu Thr
            20                  25                  30

Val Asn Thr Leu Ser Glu Gln Asn Val Pro Val Thr Gln Val Glu Glu
        35                  40                  45

Leu Val His Arg Gly Ile Asp Pro Ile Leu Cys Gly Thr Glu Leu Gly
    50                  55                  60

Ser Pro Leu Val Leu Asp Asp Cys Ser Leu Glu Gly Leu Ile Leu Gly
65                  70                  75                  80

Asn Pro Lys Cys Asp Leu Tyr Leu Asn Gly Arg Glu Trp Ser Tyr Ile
                85                  90                  95

Val Glu Arg Pro Lys Glu Met Glu Gly Val Cys Tyr Pro Gly Ser Ile
            100                 105                 110

Glu Asn Gln Glu Glu Leu Arg Ser Leu Phe Ser Ser Ile Lys Lys Tyr
        115                 120                 125

Glu Arg Val Lys Met Phe Asp Phe Thr Lys Trp Asn Val Thr Tyr Thr
    130                 135                 140

Gly Thr Ser Lys Ala Cys Asn Asn Thr Ser Asn Gln Gly Ser Phe Tyr
145                 150                 155                 160

Arg Ser Met Arg Trp Leu Thr Leu Lys Ser Gly Gln Phe Pro Val Gln
                165                 170                 175

Thr Asp Glu Tyr Lys Asn Thr Arg Asp Ser Asp Ile Val Phe Thr Trp
            180                 185                 190

Ala Ile His His Pro Pro Thr Ser Asp Glu Gln Val Lys Leu Tyr Lys
        195                 200                 205

Asn Pro Asp Thr Leu Ser Ser Val Thr Thr Val Glu Ile Asn Arg Ser
    210                 215                 220

Phe Lys Pro Asn Ile Gly Pro Arg Pro Leu Val Arg Gly Gln Gln Gly
225                 230                 235                 240
```

```
Arg Met Asp Tyr Tyr Trp Ala Val Leu Lys Pro Gly Gln Thr Val Lys
                245                 250                 255

Ile Gln Thr Asn Gly Asn Leu Ile Ala Pro Glu Tyr Gly His Leu Ile
        260                 265                 270

Thr Gly Lys Ser His Gly Arg Ile Leu Lys Asn Asn Leu Pro Met Gly
            275                 280                 285

Gln Cys Val Thr Glu Cys Gln Leu Asn Glu Gly Val Met Asn Thr Ser
        290                 295                 300

Lys Pro Phe Gln Asn Thr Ser Lys His Tyr Ile Gly Lys Cys Pro Lys
305                 310                 315                 320

Tyr Ile Pro Ser Gly Ser Leu Lys Leu Ala Ile Gly Leu Arg Asn Val
                325                 330                 335

Pro Gln Val Gln Asp Arg Gly Leu Phe Gly Ala Ile Ala Gly Phe Ile
            340                 345                 350

Glu Gly Gly Trp Pro Gly Leu Val Ala Gly Trp Tyr Gly Phe Gln His
        355                 360                 365

Gln Asn Ala Glu Gly Thr Gly Ile Ala Ala Asp Arg Asp Ser Thr Gln
    370                 375                 380

Arg Ala Ile Asp Asn Met Gln Asn Lys Leu Asn Asn Val Ile Asp Lys
385                 390                 395                 400

Met Asn Lys Gln Phe Glu Val Val Asn His Glu Phe Ser Glu Val Glu
                405                 410                 415

Ser Arg Ile Asn Met Ile Asn Ser Lys Ile Asp Asp Gln Ile Thr Asp
            420                 425                 430

Ile Trp Ala Tyr Asn Ala Glu Leu Leu Val Leu Leu Glu Asn Gln Lys
        435                 440                 445

Thr Leu Asp Glu His Asp Ala Asn Val Arg Asn Leu His Asp Arg Val
    450                 455                 460

Arg Arg Val Leu Arg Glu Asn Ala Ile Asp Thr Gly Asp Gly Cys Phe
465                 470                 475                 480

Glu Ile Leu His Lys Cys Asp Asn Asn Cys Met Asp Thr Ile Arg Asn
                485                 490                 495

Gly Thr Tyr Asn His Lys Glu Tyr Glu Glu Ser Lys Ile Glu Arg
            500                 505                 510

Gln Lys Val Asn Gly Val Lys Leu Glu Glu Asn Ser Thr Tyr Lys Ile
        515                 520                 525

Leu Ser Ile Tyr Ser Ser Val Ala Ser Ser Leu Val Leu Leu Met
    530                 535                 540

Ile Ile Gly Gly Phe Ile Phe Gly Cys Gln Asn Gly Asn Val Arg Cys
545                 550                 555                 560

Thr Phe Cys Ile

<210> SEQ ID NO 13
<211> LENGTH: 566
<212> TYPE: PRT
<213> ORGANISM: Influenza virus A
<220> FEATURE:
<223> OTHER INFORMATION: influenza virus A hemagglutinin subtype H13

<400> SEQUENCE: 13

Met Ala Leu Asn Val Ile Ala Thr Leu Thr Leu Ile Ser Val Cys Val
 1               5                  10                  15

His Ala Asp Arg Ile Cys Val Gly Tyr Leu Ser Thr Asn Ser Ser Glu
            20                  25                  30

Arg Val Asp Thr Leu Leu Glu Asn Gly Val Pro Val Thr Ser Ser Ile
```

```
            35                  40                  45
Asp Leu Ile Glu Thr Asn His Thr Gly Thr Tyr Cys Ser Leu Asn Gly
     50                  55                  60

Val Ser Pro Val His Leu Gly Asp Cys Ser Phe Glu Gly Trp Ile Val
 65                  70                  75                  80

Gly Asn Pro Ala Cys Thr Ser Asn Phe Gly Ile Arg Glu Trp Ser Tyr
                 85                  90                  95

Leu Ile Glu Asp Pro Ala Ala Pro His Gly Leu Cys Tyr Pro Gly Glu
            100                 105                 110

Leu Asn Asn Asn Gly Glu Leu Arg His Leu Phe Ser Gly Ile Arg Ser
        115                 120                 125

Phe Ser Arg Thr Glu Leu Ile Pro Pro Thr Ser Trp Gly Glu Val Leu
    130                 135                 140

Asp Gly Thr Thr Ser Ala Cys Arg Asp Asn Thr Gly Thr Asn Ser Phe
145                 150                 155                 160

Tyr Arg Asn Leu Val Trp Phe Ile Lys Lys Asn Thr Arg Tyr Pro Val
                165                 170                 175

Ile Ser Lys Thr Tyr Asn Asn Thr Thr Gly Arg Asp Val Leu Val Leu
            180                 185                 190

Trp Gly Ile His His Pro Val Ser Val Asp Glu Thr Lys Thr Leu Tyr
        195                 200                 205

Val Asn Ser Asp Pro Tyr Thr Leu Val Ser Thr Lys Ser Trp Ser Glu
    210                 215                 220

Lys Tyr Lys Leu Glu Thr Gly Val Arg Pro Gly Tyr Asn Gly Gln Arg
225                 230                 235                 240

Ser Trp Met Lys Ile Tyr Trp Ser Leu Ile His Pro Gly Glu Met Ile
                245                 250                 255

Thr Phe Glu Ser Asn Gly Gly Phe Leu Ala Pro Arg Tyr Gly Tyr Ile
            260                 265                 270

Ile Glu Glu Tyr Gly Lys Gly Arg Ile Phe Gln Ser Arg Ile Arg Met
        275                 280                 285

Ser Arg Cys Asn Thr Lys Cys Gln Thr Ser Val Gly Gly Ile Asn Thr
    290                 295                 300

Asn Arg Thr Phe Gln Asn Ile Asp Lys Asn Ala Leu Gly Asp Cys Pro
305                 310                 315                 320

Lys Tyr Ile Lys Ser Gly Gln Leu Lys Leu Ala Thr Gly Leu Arg Asn
                325                 330                 335

Val Pro Ala Ile Ser Asn Arg Gly Leu Phe Gly Ala Ile Ala Gly Phe
            340                 345                 350

Ile Glu Gly Gly Trp Pro Gly Leu Ile Asn Gly Trp Tyr Gly Phe Gln
        355                 360                 365

His Gln Asn Glu Gln Gly Thr Gly Ile Ala Ala Asp Lys Glu Ser Thr
    370                 375                 380

Gln Lys Ala Ile Asp Gln Ile Thr Thr Lys Ile Asn Asn Ile Ile Asp
385                 390                 395                 400

Lys Met Asn Gly Asn Tyr Asp Ser Ile Arg Gly Glu Phe Asn Gln Val
                405                 410                 415

Glu Lys Arg Ile Asn Met Leu Ala Asp Arg Ile Asp Asp Ala Val Thr
            420                 425                 430

Asp Ile Trp Ser Tyr Asn Ala Lys Leu Leu Val Leu Leu Glu Asn Asp
        435                 440                 445

Lys Thr Leu Asp Met His Asp Ala Asn Val Lys Asn Leu His Glu Gln
    450                 455                 460
```

Val Arg Arg Glu Leu Lys Asp Asn Ala Ile Asp Glu Gly Asn Gly Cys
465                 470                 475                 480

Phe Glu Leu Leu His Lys Cys Asn Asp Ser Cys Met Glu Thr Ile Arg
            485                 490                 495

Asn Gly Thr Tyr Asp His Thr Gly Tyr Ala Glu Glu Ser Lys Leu Lys
        500                 505                 510

Arg Gln Glu Ile Asp Gly Ile Lys Leu Lys Ser Glu Asp Asn Val Tyr
    515                 520                 525

Lys Ala Leu Ser Ile Tyr Ser Cys Ile Ala Ser Ser Val Val Leu Val
530                 535                 540

Gly Leu Ile Leu Ser Phe Ile Met Trp Ala Cys Ser Ser Gly Asn Cys
545                 550                 555                 560

Arg Phe Asn Val Cys Ile
                565

<210> SEQ ID NO 14
<211> LENGTH: 568
<212> TYPE: PRT
<213> ORGANISM: Influenza virus A
<220> FEATURE:
<223> OTHER INFORMATION: influenza virus A hemagglutinin subtype H14

<400> SEQUENCE: 14

Met Ile Ala Leu Ile Leu Val Ala Leu Ala Leu Ser His Thr Ala Tyr
1               5                   10                  15

Ser Gln Ile Thr Asn Gly Thr Thr Gly Asn Pro Ile Ile Cys Leu Gly
            20                  25                  30

His His Ala Val Glu Asn Gly Thr Ser Val Lys Thr Leu Thr Asp Asn
        35                  40                  45

His Val Glu Val Val Ser Ala Lys Glu Leu Val Glu Thr Asn His Thr
    50                  55                  60

Asp Glu Leu Cys Pro Ser Pro Leu Lys Leu Val Asp Gly Gln Asp Cys
65                  70                  75                  80

His Leu Ile Asn Gly Ala Leu Gly Ser Pro Gly Cys Asp Arg Leu Gln
                85                  90                  95

Asp Thr Thr Trp Asp Val Phe Ile Glu Arg Pro Thr Ala Val Asp Thr
            100                 105                 110

Cys Tyr Pro Phe Asp Val Pro Asp Tyr Gln Ser Leu Arg Ser Ile Leu
        115                 120                 125

Ala Ser Ser Gly Ser Leu Glu Phe Ile Ala Glu Gln Phe Thr Trp Asn
    130                 135                 140

Gly Val Lys Val Asp Gly Ser Ser Ser Ala Cys Leu Arg Gly Gly Arg
145                 150                 155                 160

Asn Ser Phe Phe Ser Arg Leu Asn Trp Leu Thr Lys Ala Thr Asn Gly
                165                 170                 175

Asn Tyr Gly Pro Ile Asn Val Thr Lys Glu Asn Thr Gly Ser Tyr Val
            180                 185                 190

Arg Leu Tyr Leu Trp Gly Val His His Pro Ser Ser Asp Asn Glu Gln
        195                 200                 205

Thr Asp Leu Tyr Lys Val Ala Thr Gly Arg Val Thr Val Ser Thr Arg
    210                 215                 220

Ser Asp Gln Ile Ser Ile Val Pro Asn Ile Gly Ser Arg Pro Arg Val
225                 230                 235                 240

Arg Asn Gln Ser Gly Arg Ile Ser Ile Tyr Trp Thr Leu Val Asn Pro
                245                 250                 255

Gly Asp Ser Ile Ile Phe Asn Ser Ile Gly Asn Leu Ile Ala Pro Arg
            260                 265                 270

Gly His Tyr Lys Ile Ser Lys Ser Thr Lys Ser Thr Val Leu Lys Ser
            275                 280                 285

Asp Lys Arg Ile Gly Ser Cys Thr Ser Pro Cys Leu Thr Asp Lys Gly
            290                 295                 300

Ser Ile Gln Ser Asp Lys Pro Phe Gln Asn Val Ser Arg Ile Ala Ile
305                 310                 315                 320

Gly Asn Cys Pro Lys Tyr Val Lys Gln Gly Ser Leu Met Leu Ala Thr
                325                 330                 335

Gly Met Arg Asn Ile Pro Gly Lys Gln Ala Lys Gly Leu Phe Gly Ala
            340                 345                 350

Ile Ala Gly Phe Ile Glu Asn Gly Trp Gln Gly Leu Ile Asp Gly Trp
            355                 360                 365

Tyr Gly Phe Arg His Gln Asn Ala Glu Gly Thr Gly Thr Ala Ala Asp
            370                 375                 380

Leu Lys Ser Thr Gln Ala Ala Ile Asp Gln Ile Asn Gly Lys Leu Asn
385                 390                 395                 400

Arg Leu Ile Glu Lys Thr Asn Glu Lys Tyr His Gln Ile Glu Lys Glu
                405                 410                 415

Phe Glu Gln Val Glu Gly Arg Ile Gln Asp Leu Glu Lys Tyr Val Glu
            420                 425                 430

Asp Thr Lys Ile Asp Leu Trp Ser Tyr Asn Ala Glu Leu Leu Val Ala
            435                 440                 445

Leu Glu Asn Gln His Thr Ile Asp Val Thr Asp Ser Glu Met Asn Lys
        450                 455                 460

Leu Phe Glu Arg Val Arg Arg Gln Leu Arg Glu Asn Ala Glu Asp Gln
465                 470                 475                 480

Gly Asn Gly Cys Phe Glu Ile Phe His Gln Cys Asp Asn Asn Cys Ile
                485                 490                 495

Glu Ser Ile Arg Asn Gly Thr Tyr Asp His Asn Ile Tyr Arg Asp Glu
            500                 505                 510

Ala Ile Asn Asn Arg Ile Lys Ile Asn Pro Val Thr Leu Thr Met Gly
            515                 520                 525

Tyr Lys Asp Ile Ile Leu Trp Ile Ser Phe Ser Met Ser Cys Phe Val
            530                 535                 540

Phe Val Ala Leu Ile Leu Gly Phe Val Leu Trp Ala Cys Gln Asn Gly
545                 550                 555                 560

Asn Ile Arg Cys Gln Ile Cys Ile
                565

<210> SEQ ID NO 15
<211> LENGTH: 570
<212> TYPE: PRT
<213> ORGANISM: Influenza virus A
<220> FEATURE:
<223> OTHER INFORMATION: influenza virus A hemagglutinin subtype H15

<400> SEQUENCE: 15

Met Asn Thr Gln Ile Ile Val Ile Leu Val Leu Gly Leu Ser Met Val
 1               5                  10                  15

Lys Ser Asp Lys Ile Cys Leu Gly His His Ala Val Ala Asn Gly Thr
            20                  25                  30

Lys Val Asn Thr Leu Thr Glu Arg Gly Val Glu Val Val Asn Ala Thr
        35                  40                  45

-continued

Glu Thr Val Glu Ile Thr Gly Ile Asp Lys Val Cys Thr Lys Gly Lys
    50                  55                  60

Lys Ala Val Asp Leu Gly Ser Cys Gly Ile Leu Gly Thr Ile Ile Gly
65                  70                  75                  80

Pro Pro Gln Cys Asp Leu His Leu Glu Phe Lys Ala Asp Leu Ile Ile
                    85                  90                  95

Glu Arg Arg Asn Ser Ser Asp Ile Cys Tyr Pro Gly Arg Phe Thr Asn
                100                 105                 110

Glu Glu Ala Leu Arg Gln Ile Ile Arg Glu Ser Gly Ile Asp Lys
            115                 120                 125

Glu Ser Met Gly Phe Arg Tyr Ser Gly Ile Arg Thr Asp Gly Ala Thr
    130                 135                 140

Ser Ala Cys Lys Arg Thr Val Ser Ser Phe Tyr Ser Glu Met Lys Trp
145                 150                 155                 160

Leu Ser Ser Met Asn Asn Gln Val Phe Pro Gln Leu Asn Gln Thr
                165                 170                 175

Tyr Arg Asn Thr Arg Lys Glu Pro Ala Leu Ile Val Trp Gly Val His
                180                 185                 190

His Ser Ser Leu Asp Glu Gln Asn Lys Leu Tyr Gly Thr Gly Asn
    195                 200                 205

Lys Leu Ile Thr Val Gly Ser Ser Lys Tyr Gln Gln Ser Phe Ser Pro
210                 215                 220

Ser Pro Gly Ala Arg Pro Lys Val Asn Gly Gln Ala Gly Arg Ile Asp
225                 230                 235                 240

Phe His Trp Met Leu Leu Asp Pro Gly Asp Thr Val Thr Phe Thr Phe
                245                 250                 255

Asn Gly Ala Phe Ile Ala Pro Asp Arg Ala Thr Phe Leu Arg Ser Asn
                260                 265                 270

Ala Pro Ser Gly Ile Glu Tyr Asn Gly Lys Ser Leu Gly Ile Gln Ser
            275                 280                 285

Asp Ala Gln Ile Asp Glu Ser Cys Glu Gly Glu Cys Phe Tyr Ser Gly
    290                 295                 300

Gly Thr Ile Asn Ser Pro Leu Pro Phe Gln Asn Ile Asp Ser Arg Ala
305                 310                 315                 320

Val Gly Lys Cys Pro Arg Tyr Val Lys Gln Ser Ser Leu Pro Leu Ala
                325                 330                 335

Leu Gly Met Lys Asn Val Pro Glu Lys Ile Arg Thr Arg Gly Leu Phe
                340                 345                 350

Gly Ala Ile Ala Gly Phe Ile Glu Asn Gly Trp Glu Gly Leu Ile Asp
            355                 360                 365

Gly Trp Tyr Gly Phe Arg His Gln Asn Ala Gln Gly Gln Gly Thr Ala
    370                 375                 380

Ala Asp Tyr Lys Ser Thr Gln Ala Ala Ile Asp Gln Ile Thr Gly Lys
385                 390                 395                 400

Leu Asn Arg Leu Ile Glu Lys Thr Asn Lys Gln Phe Glu Leu Ile Asp
                405                 410                 415

Asn Glu Phe Thr Glu Val Glu Gln Gln Ile Gly Asn Val Ile Asn Trp
                420                 425                 430

Thr Arg Asp Ser Leu Thr Glu Ile Trp Ser Tyr Asn Ala Glu Leu Leu
            435                 440                 445

Val Ala Met Glu Asn Gln His Thr Ile Asp Leu Ala Asp Ser Glu Met
    450                 455                 460

```
Asn Lys Leu Tyr Glu Arg Val Arg Arg Gln Leu Arg Glu Asn Ala Glu
465                 470                 475                 480

Glu Asp Gly Thr Gly Cys Phe Glu Ile Phe His Arg Cys Asp Asp Gln
            485                 490                 495

Cys Met Glu Ser Ile Arg Asn Asn Thr Tyr Asn His Thr Glu Tyr Arg
            500                 505                 510

Gln Glu Ala Leu Gln Asn Arg Ile Met Ile Asn Pro Val Lys Leu Ser
            515                 520                 525

Ser Gly Tyr Lys Asp Val Ile Leu Trp Phe Ser Phe Gly Ala Ser Cys
        530                 535                 540

Val Met Leu Leu Ala Ile Ala Met Gly Leu Ile Phe Met Cys Val Lys
545                 550                 555                 560

Asn Gly Asn Leu Arg Cys Thr Ile Cys Ile
                565                 570

<210> SEQ ID NO 16
<211> LENGTH: 565
<212> TYPE: PRT
<213> ORGANISM: Influenza virus A
<220> FEATURE:
<223> OTHER INFORMATION: influenza virus A hemagglutinin subtype H16

<400> SEQUENCE: 16

Met Met Ile Lys Val Leu Tyr Phe Leu Ile Ile Val Leu Gly Arg Tyr
1               5                   10                  15

Ser Lys Ala Asp Lys Ile Cys Ile Gly Tyr Leu Ser Asn Asn Ser Ser
            20                  25                  30

Asp Thr Val Asp Thr Leu Thr Glu Asn Gly Val Pro Val Thr Ser Ser
            35                  40                  45

Val Asp Leu Val Glu Thr Asn His Thr Gly Thr Tyr Cys Ser Leu Asn
50                  55                  60

Gly Ile Ser Pro Ile His Leu Gly Asp Cys Ser Phe Glu Gly Trp Ile
65                  70                  75                  80

Val Gly Asn Pro Ser Cys Ala Thr Asn Ile Asn Ile Arg Glu Trp Ser
                85                  90                  95

Tyr Leu Ile Glu Asp Pro Asn Ala Pro Asn Lys Phe Cys Tyr Pro Gly
            100                 105                 110

Glu Leu Asp Asn Asn Gly Glu Leu Arg His Leu Phe Ser Gly Val Asn
            115                 120                 125

Ser Phe Ser Arg Thr Glu Leu Ile Asn Pro Ser Lys Trp Gly Asn Val
130                 135                 140

Leu Asp Gly Val Thr Ala Ser Cys Leu Asp Arg Gly Ala Ser Ser Phe
145                 150                 155                 160

Tyr Arg Asn Leu Val Trp Ile Val Lys Lys Asp Glu Lys Tyr Pro Val
                165                 170                 175

Ile Lys Gly Asp Tyr Asn Asn Thr Thr Gly Arg Asp Val Leu Val Leu
            180                 185                 190

Trp Gly Ile His His Pro Asp Thr Glu Thr Thr Ala Thr Asn Leu Tyr
            195                 200                 205

Val Asn Lys Asn Pro Tyr Thr Leu Val Ser Thr Lys Glu Trp Ser Lys
210                 215                 220

Arg Tyr Glu Leu Glu Ile Gly Thr Arg Ile Gly Asp Gly Gln Arg Ser
225                 230                 235                 240

Trp Met Lys Leu Tyr Trp His Leu Met His Pro Gly Glu Arg Ile Met
                245                 250                 255
```

Phe Glu Ser Asn Gly Gly Leu Ile Ala Pro Arg Tyr Gly Tyr Ile Ile
                260                 265                 270

Glu Lys Tyr Gly Thr Gly Arg Ile Phe Gln Ser Gly Val Arg Met Ala
            275                 280                 285

Arg Cys Asn Thr Lys Cys Gln Thr Ser Leu Gly Gly Ile Asn Thr Asn
        290                 295                 300

Lys Thr Phe Gln Asn Ile Glu Arg Asn Ala Leu Gly Asp Cys Pro Lys
305                 310                 315                 320

Tyr Ile Lys Ser Gly Gln Leu Lys Leu Ala Thr Gly Leu Arg Asn Val
                325                 330                 335

Pro Ser Ile Gly Glu Arg Gly Leu Phe Gly Ala Ile Ala Gly Phe Ile
            340                 345                 350

Glu Gly Gly Trp Pro Gly Leu Ile Asn Gly Trp Tyr Gly Phe Gln His
        355                 360                 365

Gln Asn Glu Gln Gly Thr Gly Ile Ala Ala Asp Lys Ala Ser Thr Gln
    370                 375                 380

Lys Ala Ile Asn Glu Ile Thr Thr Lys Ile Asn Asn Ile Ile Glu Lys
385                 390                 395                 400

Met Asn Gly Asn Tyr Asp Ser Ile Arg Gly Glu Phe Asn Gln Val Glu
                405                 410                 415

Lys Arg Ile Asn Met Leu Ala Asp Arg Val Asp Asp Ala Val Thr Asp
            420                 425                 430

Ile Trp Ser Tyr Asn Ala Lys Leu Leu Val Leu Leu Glu Asn Asp Arg
        435                 440                 445

Thr Leu Asp Leu His Asp Ala Asn Val Arg Asn Leu His Asp Gln Val
    450                 455                 460

Lys Arg Ala Leu Lys Ser Asn Ala Ile Asp Glu Gly Asp Gly Cys Phe
465                 470                 475                 480

Asn Leu Leu His Lys Cys Asn Asp Ser Cys Met Glu Thr Ile Arg Asn
                485                 490                 495

Gly Thr Tyr Asn His Glu Asp Tyr Arg Glu Gly Ser Gln Leu Lys Arg
            500                 505                 510

Gln Glu Ile Glu Gly Ile Lys Leu Lys Thr Glu Asp Asn Val Tyr Lys
        515                 520                 525

Val Leu Ser Ile Tyr Ser Cys Ile Ala Ser Ser Ile Val Leu Val Gly
    530                 535                 540

Leu Ile Leu Ala Phe Ile Met Trp Ala Cys Ser Asn Gly Ser Cys Arg
545                 550                 555                 560

Phe Asn Val Cys Ile
                565

<210> SEQ ID NO 17
<211> LENGTH: 342
<212> TYPE: PRT
<213> ORGANISM: Influenza virus B
<220> FEATURE:
<223> OTHER INFORMATION: influenza B virus hemagglutinin (in Fig. 3)

<400> SEQUENCE: 17

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Gln
        35                  40                  45

-continued

```
Thr Arg Gly Lys Leu Cys Pro Asn Cys Leu Asn Cys Thr Asp Leu Asp
    50                  55                  60

Val Ala Leu Gly Arg Pro Lys Cys Met Gly Thr Ile Pro Ser Ala Lys
65                  70                  75                  80

Ala Ser Ile Leu His Glu Val Lys Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Ala Arg Asn Val Thr Asn Ala Glu
        115                 120                 125

Thr Ala Pro Gly Gly Pro Tyr Ile Val Gly Thr Ser Gly Ser Cys Pro
    130                 135                 140

Asn Val Thr Asn Gly Asn Gly Phe Phe Ala Thr Met Ala Trp Ala Val
145                 150                 155                 160

Pro Lys Asn Lys Thr Ala Thr Asn Pro Leu Thr Val Glu Val Pro Tyr
                165                 170                 175

Ile Cys Thr Lys Gly Glu Asp Gln Ile Thr Val Trp Gly Phe His Ser
            180                 185                 190

Asp Asp Glu Thr Gln Met Val Lys Leu Tyr Gly Asp Ser Lys Pro Gln
        195                 200                 205

Lys Phe Thr Ser Ser Ala Asn Gly Val Thr Thr His Tyr Val Ser Gln
    210                 215                 220

Ile Gly Gly Phe Pro Asn Gln Ala Glu Asp Glu Gly Leu Pro Gln Ser
225                 230                 235                 240

Gly Arg Ile Val Val Asp Tyr Met Val Gln Lys Pro Gly Lys Thr Gly
                245                 250                 255

Thr Ile Ala Tyr Gln Arg Gly Val Leu Leu Pro Gln Lys Val Trp Cys
            260                 265                 270

Ala Ser Gly Arg Ser Lys Val Ile Lys Gly Ser Leu Pro Leu Ile Gly
        275                 280                 285

Glu Ala Asp Cys Leu His Glu Lys Tyr Gly Gly Leu Asn Lys Ser Lys
    290                 295                 300

Pro Tyr Tyr Thr Gly Glu His Ala Lys Ala Ile Gly Asn Cys Pro Ile
305                 310                 315                 320

Trp Val Lys Thr Pro Leu Lys Leu Ala Asn Gly Thr Lys Tyr Arg Pro
                325                 330                 335

Pro Ala Lys Leu Leu Lys
            340

<210> SEQ ID NO 18
<211> LENGTH: 17
<212> TYPE: PRT
<213> ORGANISM: Influenza virus A
<220> FEATURE:
<223> OTHER INFORMATION: influenza A HA subtype H1 signal peptides

<400> SEQUENCE: 18

Met Lys Ala Asn Leu Leu Val Leu Leu Cys Ala Leu Ala Ala Ala Asp
 1               5                  10                  15

Ala

<210> SEQ ID NO 19
<211> LENGTH: 15
<212> TYPE: PRT
<213> ORGANISM: Influenza virus A
<220> FEATURE:
<223> OTHER INFORMATION: influenza A HA subtype H2 signal peptides
```
<400> SEQUENCE: 19

Met Ala Ile Ile Tyr Leu Ile Leu Leu Phe Thr Ala Val Arg Gly
1 5 10 15

<210> SEQ ID NO 20
<211> LENGTH: 16
<212> TYPE: PRT
<213> ORGANISM: Influenza virus A
<220> FEATURE:
<223> OTHER INFORMATION: influenza A HA subtype H3 signal peptides

<400> SEQUENCE: 20

Met Lys Thr Ile Ile Ala Leu Ser Tyr Ile Phe Cys Leu Ala Leu Gly
1 5 10 15

<210> SEQ ID NO 21
<211> LENGTH: 16
<212> TYPE: PRT
<213> ORGANISM: Influenza virus A
<220> FEATURE:
<223> OTHER INFORMATION: influenza A HA subtype H4 signal peptides

<400> SEQUENCE: 21

Met Leu Ser Ile Val Ile Leu Phe Leu Leu Ile Ala Glu Asn Ser Ser
1 5 10 15

<210> SEQ ID NO 22
<211> LENGTH: 16
<212> TYPE: PRT
<213> ORGANISM: Influenza virus A
<220> FEATURE:
<223> OTHER INFORMATION: influenza A HA subtype H5 signal peptides

<400> SEQUENCE: 22

Met Glu Arg Ile Val Leu Leu Leu Ala Ile Val Ser Leu Val Lys Ser
1 5 10 15

<210> SEQ ID NO 23
<211> LENGTH: 16
<212> TYPE: PRT
<213> ORGANISM: Influenza virus A
<220> FEATURE:
<223> OTHER INFORMATION: influenza A HA subtype H6 signal peptides

<400> SEQUENCE: 23

Met Ile Ala Ile Ile Val Val Ala Ile Leu Ala Thr Ala Gly Arg Ser
1 5 10 15

<210> SEQ ID NO 24
<211> LENGTH: 18
<212> TYPE: PRT
<213> ORGANISM: Influenza virus A
<220> FEATURE:
<223> OTHER INFORMATION: influenza A HA subtype H7 signal peptides

<400> SEQUENCE: 24

Met Asn Thr Gln Ile Leu Val Phe Ala Leu Val Ala Val Ile Pro Thr
1 5 10 15

Asn Ala

<210> SEQ ID NO 25
<211> LENGTH: 16
<212> TYPE: PRT
<213> ORGANISM: Influenza virus A
<220> FEATURE:

```
<223> OTHER INFORMATION: influenza A HA subtype H8 signal peptides

<400> SEQUENCE: 25

Met Glu Lys Phe Ile Ala Ile Ala Thr Leu Ala Ser Thr Asn Ala Tyr
1               5                   10                  15

<210> SEQ ID NO 26
<211> LENGTH: 18
<212> TYPE: PRT
<213> ORGANISM: Influenza virus A
<220> FEATURE:
<223> OTHER INFORMATION: influenza A HA subtype H9 signal peptides

<400> SEQUENCE: 26

Met Glu Thr Lys Ala Ile Ile Ala Ala Leu Leu Met Val Thr Ala Ala
1               5                   10                  15

Asn Ala

<210> SEQ ID NO 27
<211> LENGTH: 16
<212> TYPE: PRT
<213> ORGANISM: Influenza virus A
<220> FEATURE:
<223> OTHER INFORMATION: influenza A HA subtype H10 signal peptides

<400> SEQUENCE: 27

Met Tyr Lys Val Val Val Ile Ile Ala Leu Leu Gly Ala Val Lys Gly
1               5                   10                  15

<210> SEQ ID NO 28
<211> LENGTH: 16
<212> TYPE: PRT
<213> ORGANISM: Influenza virus A
<220> FEATURE:
<223> OTHER INFORMATION: influenza A HA subtype H11 signal peptides

<400> SEQUENCE: 28

Met Glu Lys Thr Leu Leu Phe Ala Ala Ile Phe Leu Cys Val Lys Ala
1               5                   10                  15

<210> SEQ ID NO 29
<211> LENGTH: 17
<212> TYPE: PRT
<213> ORGANISM: Influenza virus A
<220> FEATURE:
<223> OTHER INFORMATION: influenza A HA subtype H12 signal peptides

<400> SEQUENCE: 29

Met Glu Lys Phe Ile Ile Leu Ser Thr Val Leu Ala Ala Ser Phe Ala
1               5                   10                  15

Tyr

<210> SEQ ID NO 30
<211> LENGTH: 18
<212> TYPE: PRT
<213> ORGANISM: Influenza virus A
<220> FEATURE:
<223> OTHER INFORMATION: influenza A HA subtype H13 signal peptides

<400> SEQUENCE: 30

Met Ala Leu Asn Val Ile Ala Thr Leu Thr Leu Ile Ser Val Cys Val
1               5                   10                  15

His Ala
```

```
<210> SEQ ID NO 31
<211> LENGTH: 17
<212> TYPE: PRT
<213> ORGANISM: Influenza virus A
<220> FEATURE:
<223> OTHER INFORMATION: influenza A HA subtype H14 signal peptides

<400> SEQUENCE: 31

Met Ile Ala Leu Ile Leu Val Ala Leu Ala Leu Ser His Thr Ala Tyr
1               5                   10                  15

Ser

<210> SEQ ID NO 32
<211> LENGTH: 18
<212> TYPE: PRT
<213> ORGANISM: Influenza virus A
<220> FEATURE:
<223> OTHER INFORMATION: influenza A HA subtype H15 signal peptides

<400> SEQUENCE: 32

Met Asn Thr Gln Ile Ile Val Ile Leu Val Leu Gly Leu Ser Met Val
1               5                   10                  15

Lys Ser

<210> SEQ ID NO 33
<211> LENGTH: 19
<212> TYPE: PRT
<213> ORGANISM: Influenza virus A
<220> FEATURE:
<223> OTHER INFORMATION: influenza A HA subtype H16 signal peptides

<400> SEQUENCE: 33

Met Met Ile Lys Val Leu Tyr Phe Leu Ile Ile Val Leu Gly Arg Tyr
1               5                   10                  15

Ser Lys Ala

<210> SEQ ID NO 34
<211> LENGTH: 42
<212> TYPE: PRT
<213> ORGANISM: Influenza virus A
<220> FEATURE:
<223> OTHER INFORMATION: influenza A HA subtype H1 N-terminal stem
      segment

<400> SEQUENCE: 34

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys
        35                  40

<210> SEQ ID NO 35
<211> LENGTH: 42
<212> TYPE: PRT
<213> ORGANISM: Influenza virus A
<220> FEATURE:
<223> OTHER INFORMATION: influenza A HA subtype H2 N-terminal stem
      segment

<400> SEQUENCE: 35

Asp Gln Ile Cys Ile Gly Tyr His Ser Asn Asn Ser Thr Glu Lys Val
1               5                   10                  15

Asp Thr Ile Leu Glu Arg Asn Val Thr Val Thr His Ala Gln Asn Ile
```

```
                20                  25                  30

Leu Glu Lys Thr His Asn Gly Lys Leu Cys
        35                  40

<210> SEQ ID NO 36
<211> LENGTH: 52
<212> TYPE: PRT
<213> ORGANISM: Influenza virus A
<220> FEATURE:
<223> OTHER INFORMATION: influenza A HA subtype H3 N-terminal stem
      segment

<400> SEQUENCE: 36

Gln Asp Leu Pro Gly Asn Asp Asn Ser Thr Ala Thr Leu Cys Leu Gly
  1               5                  10                  15

His His Ala Val Pro Asn Gly Thr Leu Val Lys Thr Ile Thr Asp Asp
                20                  25                  30

Gln Ile Glu Val Thr Asn Ala Thr Glu Leu Val Gln Ser Ser Ser Thr
        35                  40                  45

Gly Lys Ile Cys
    50

<210> SEQ ID NO 37
<211> LENGTH: 48
<212> TYPE: PRT
<213> ORGANISM: Influenza virus A
<220> FEATURE:
<223> OTHER INFORMATION: influenza A HA subtype H4 N-terminal stem
      segment

<400> SEQUENCE: 37

Gln Asn Tyr Thr Gly Asn Pro Val Ile Cys Met Gly His His Ala Val
  1               5                  10                  15

Ala Asn Gly Thr Met Val Lys Thr Leu Ala Asp Asp Gln Val Glu Val
                20                  25                  30

Val Thr Ala Gln Glu Leu Val Glu Ser Gln Asn Leu Pro Glu Leu Cys
        35                  40                  45

<210> SEQ ID NO 38
<211> LENGTH: 42
<212> TYPE: PRT
<213> ORGANISM: Influenza virus A
<220> FEATURE:
<223> OTHER INFORMATION: influenza A HA subtype H5 N-terminal stem
      segment

<400> SEQUENCE: 38

Asp Gln Ile Cys Ile Gly Tyr His Ala Asn Lys Ser Thr Lys Gln Val
  1               5                  10                  15

Asp Thr Ile Met Glu Lys Asn Val Thr Val Thr His Ala Gln Asp Ile
                20                  25                  30

Leu Glu Arg Thr His Asn Gly Lys Leu Cys
        35                  40

<210> SEQ ID NO 39
<211> LENGTH: 42
<212> TYPE: PRT
<213> ORGANISM: Influenza virus A
<220> FEATURE:
<223> OTHER INFORMATION: influenza A HA subtype H6 N-terminal stem
      segment

<400> SEQUENCE: 39
```

Asp Lys Ile Cys Ile Gly Tyr His Ala Asn Asn Ser Thr Thr Gln Ile
1               5                   10                  15

Asp Thr Ile Leu Glu Lys Asn Val Thr Val Thr His Ser Val Glu Leu
            20                  25                  30

Leu Glu Asn Gln Lys Glu Glu Arg Phe Cys
        35                  40

<210> SEQ ID NO 40
<211> LENGTH: 42
<212> TYPE: PRT
<213> ORGANISM: Influenza virus A
<220> FEATURE:
<223> OTHER INFORMATION: influenza A HA subtype H7 N-terminal stem
      segment

<400> SEQUENCE: 40

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Thr Asn Ile Pro Lys Ile Cys
        35                  40

<210> SEQ ID NO 41
<211> LENGTH: 42
<212> TYPE: PRT
<213> ORGANISM: Influenza virus A
<220> FEATURE:
<223> OTHER INFORMATION: influenza A HA subtype H8 N-terminal stem
      segment

<400> SEQUENCE: 41

Asp Arg Ile Cys Ile Gly Tyr Gln Ser Asn Asn Ser Thr Asp Thr Val
1               5                   10                  15

Asn Thr Leu Ile Glu Gln Asn Val Pro Val Thr Gln Thr Met Glu Leu
            20                  25                  30

Val Glu Thr Glu Lys His Pro Ala Tyr Cys
        35                  40

<210> SEQ ID NO 42
<211> LENGTH: 42
<212> TYPE: PRT
<213> ORGANISM: Influenza virus A
<220> FEATURE:
<223> OTHER INFORMATION: influenza A HA subtype H9 N-terminal stem
      segment

<400> SEQUENCE: 42

Asp Lys Ile Cys Ile Gly Tyr Gln Ser Thr Asn Ser Thr Glu Thr Val
1               5                   10                  15

Asp Thr Leu Thr Glu Ser Asn Val Pro Val Thr His Thr Lys Glu Leu
            20                  25                  30

Leu His Thr Glu His Asn Gly Met Leu Cys
        35                  40

<210> SEQ ID NO 43
<211> LENGTH: 43
<212> TYPE: PRT
<213> ORGANISM: Influenza virus A
<220> FEATURE:
<223> OTHER INFORMATION: influenza A HA subtype H10 N-terminal stem
      segment

<400> SEQUENCE: 43

Leu Asp Arg Ile Cys Leu Gly His His Ala Val Ala Asn Gly Thr Ile
1               5                   10                  15

Val Lys Thr Leu Thr Asn Glu Gln Glu Val Thr Asn Ala Thr Glu
            20                  25                  30

Thr Val Glu Ser Thr Asn Leu Asn Lys Leu Cys
        35                  40

<210> SEQ ID NO 44
<211> LENGTH: 42
<212> TYPE: PRT
<213> ORGANISM: Influenza virus A
<220> FEATURE:
<223> OTHER INFORMATION: influenza A HA subtype H11 N-terminal stem
      segment

<400> SEQUENCE: 44

Asp Glu Ile Cys Ile Gly Tyr Leu Ser Asn Asn Ser Thr Asp Lys Val
1               5                   10                  15

Asp Thr Ile Ile Glu Asn Asn Val Thr Val Thr Ser Ser Val Glu Leu
            20                  25                  30

Val Glu Thr Glu His Thr Gly Ser Phe Cys
        35                  40

<210> SEQ ID NO 45
<211> LENGTH: 42
<212> TYPE: PRT
<213> ORGANISM: Influenza virus A
<220> FEATURE:
<223> OTHER INFORMATION: influenza A HA subtype H12 N-terminal stem
      segment

<400> SEQUENCE: 45

Asp Lys Ile Cys Ile Gly Tyr Gln Thr Asn Asn Ser Thr Glu Thr Val
1               5                   10                  15

Asn Thr Leu Ser Glu Gln Asn Val Pro Val Thr Gln Val Glu Glu Leu
            20                  25                  30

Val His Arg Gly Ile Asp Pro Ile Leu Cys
        35                  40

<210> SEQ ID NO 46
<211> LENGTH: 42
<212> TYPE: PRT
<213> ORGANISM: Influenza virus A
<220> FEATURE:
<223> OTHER INFORMATION: influenza A HA subtype H13 N-terminal stem
      segment

<400> SEQUENCE: 46

Asp Arg Ile Cys Val Gly Tyr Leu Ser Thr Asn Ser Ser Glu Arg Val
1               5                   10                  15

Asp Thr Leu Leu Glu Asn Gly Val Pro Val Thr Ser Ser Ile Asp Leu
            20                  25                  30

Ile Glu Thr Asn His Thr Gly Thr Tyr Cys
        35                  40

<210> SEQ ID NO 47
<211> LENGTH: 51
<212> TYPE: PRT
<213> ORGANISM: Influenza virus A
<220> FEATURE:
<223> OTHER INFORMATION: influenza A HA subtype H14 N-terminal stem
      segment

```
<400> SEQUENCE: 47

Gln Ile Thr Asn Gly Thr Thr Gly Asn Pro Ile Ile Cys Leu Gly His
  1               5                  10                  15

His Ala Val Glu Asn Gly Thr Ser Val Lys Thr Leu Thr Asp Asn His
             20                  25                  30

Val Glu Val Val Ser Ala Lys Glu Leu Val Glu Thr Asn His Thr Asp
         35                  40                  45

Glu Leu Cys
     50

<210> SEQ ID NO 48
<211> LENGTH: 42
<212> TYPE: PRT
<213> ORGANISM: Influenza virus A
<220> FEATURE:
<223> OTHER INFORMATION: influenza A HA subtype H15 N-terminal stem
      segment

<400> SEQUENCE: 48

Asp Lys Ile Cys Leu Gly His His Ala Val Ala Asn Gly Thr Lys Val
  1               5                  10                  15

Asn Thr Leu Thr Glu Arg Gly Val Glu Val Val Asn Ala Thr Glu Thr
             20                  25                  30

Val

```
<211> LENGTH: 53
<212> TYPE: PRT
<213> ORGANISM: Influenza virus A
<220> FEATURE:
<223> OTHER INFORMATION: influenza A HA subtype H2 C-terminal stem
      segment

<400> SEQUENCE: 51

Cys Glu Thr Lys Cys Gln Thr Pro Leu Gly Ala Ile Asn Thr Thr Leu
 1               5                  10                  15

Pro Phe His Asn Val His Pro Leu Thr Ile Gly Glu Cys Pro Lys Tyr
            20                  25                  30

Val Lys Ser Glu Arg Leu Val Leu Ala Thr Gly Leu Arg Asn Val Pro
        35                  40                  45

Gln Ile Glu Ser Arg
    50

<210> SEQ ID NO 52
<211> LENGTH: 53
<212> TYPE: PRT
<213> ORGANISM: Influenza virus A
<220> FEATURE:
<223> OTHER INFORMATION: influenza A HA subtype H3 C-terminal stem
      segment

<400> SEQUENCE: 52

Cys Ile Ser Glu Cys Ile Thr Pro Asn Gly Ser Ile Pro Asn Asp Lys
 1               5                  10                  15

Pro Phe Gln Asn Val Asn Lys Ile Thr Tyr Gly Ala Cys Pro Lys Tyr
            20                  25                  30

Val Lys Gln Asn Thr Leu Lys Leu Ala Thr Gly Met Arg Asn Val Pro
        35                  40                  45

Glu Lys Gln Thr Arg
    50

<210> SEQ ID NO 53
<211> LENGTH: 53
<212> TYPE: PRT
<213> ORGANISM: Influenza virus A
<220> FEATURE:
<223> OTHER INFORMATION: influenza A HA subtype H4 C-terminal stem
      segment

<400> SEQUENCE: 53

Cys Val Ser Lys Cys His Thr Asp Lys Gly Ser Leu Ser Thr Thr Lys
 1               5                  10                  15

Pro Phe Gln Asn Ile Ser Arg Ile Ala Val Gly Asp Cys Pro Arg Tyr
            20                  25                  30

Val Lys Gln Gly Ser Leu Lys Leu Ala Thr Gly Met Arg Asn Ile Pro
        35                  40                  45

Glu Lys Ala Ser Arg
    50

<210> SEQ ID NO 54
<211> LENGTH: 53
<212> TYPE: PRT
<213> ORGANISM: Influenza virus A
<220> FEATURE:
<223> OTHER INFORMATION: influenza A HA subtype H5 C-terminal stem
      segment

<400> SEQUENCE: 54

Cys Asp Thr Lys Cys Gln Thr Pro Val Gly Glu Ile Asn Ser Ser Met
```

```
                1               5                   10                  15
Pro Phe His Asn Ile His Pro His Thr Ile Gly Glu Cys Pro Lys Tyr
                20                  25                  30

Val Lys Ser Asp Arg Leu Val Leu Ala Thr Gly Leu Arg Asn Val Pro
            35                  40                  45

Gln Arg Lys Lys Arg
    50
```

<210> SEQ ID NO 55
<211> LENGTH: 53
<212> TYPE: PRT
<213> ORGANISM: Influenza virus A
<220> FEATURE:
<223> OTHER INFORMATION: influenza A HA subtype H6 C-terminal stem
      segment

<400> SEQUENCE: 55

```
Cys Asp Ala Thr Cys Gln Thr Val Ala Gly Val Leu Arg Thr Asn Lys
 1               5                   10                  15

Thr Phe Gln Asn Val Ser Pro Leu Trp Ile Gly Glu Cys Pro Lys Tyr
                20                  25                  30

Val Lys Ser Glu Ser Leu Arg Leu Ala Thr Gly Leu Arg Asn Val Pro
            35                  40                  45

Gln Ile Glu Thr Arg
    50
```

<210> SEQ ID NO 56
<211> LENGTH: 57
<212> TYPE: PRT
<213> ORGANISM: Influenza virus A
<220> FEATURE:
<223> OTHER INFORMATION: influenza A HA subtype H7 C-terminal stem
      segment

<400> SEQUENCE: 56

```
Cys Glu Gly Glu Cys Tyr His Ser Gly Gly Thr Ile Thr Ser Arg Leu
 1               5                   10                  15

Pro Phe Gln Asn Ile Asn Ser Arg Ala Val Gly Lys Cys Pro Arg Tyr
                20                  25                  30

Val Lys Gln Glu Ser Leu Leu Leu Ala Thr Gly Met Lys Asn Val Pro
            35                  40                  45

Glu Pro Ser Lys Lys Arg Lys Lys Arg
    50                  55
```

<210> SEQ ID NO 57
<211> LENGTH: 53
<212> TYPE: PRT
<213> ORGANISM: Influenza virus A
<220> FEATURE:
<223> OTHER INFORMATION: influenza A HA subtype H8 C-terminal stem
      segment

<400> SEQUENCE: 57

```
Cys Asn Thr Lys Cys Gln Thr Tyr Ala Gly Ala Ile Asn Ser Ser Lys
 1               5                   10                  15

Pro Phe Gln Asn Ala Ser Arg His Tyr Met Gly Glu Cys Pro Lys Tyr
                20                  25                  30

Val Lys Lys Ala Ser Leu Arg Leu Ala Val Gly Leu Arg Asn Thr Pro
            35                  40                  45

Ser Val Glu Pro Arg
    50
```

<210> SEQ ID NO 58
<211> LENGTH: 53
<212> TYPE: PRT
<213> ORGANISM: Influenza virus A
<220> FEATURE:
<223> OTHER INFORMATION: influenza A HA subtype H9 C-terminal stem segment

<400> SEQUENCE: 58

Cys Val Val Gln Cys Gln Thr Glu Lys Gly Gly Leu Asn Thr Thr Leu
 1               5                  10                  15

Pro Phe His Asn Ile Ser Lys Tyr Ala Phe Gly Asn Cys Pro Lys Tyr
            20                  25                  30

Val Gly Val Lys Ser Leu Lys Leu Pro Val Gly Leu Arg Asn Val Pro
        35                  40                  45

Ala Val Ser Ser Arg
    50

<210> SEQ ID NO 59
<211> LENGTH: 54
<212> TYPE: PRT
<213> ORGANISM: Influenza virus A
<220> FEATURE:
<223> OTHER INFORMATION: influenza A HA subtype H10 C-terminal stem segment

<400> SEQUENCE: 59

Cys Glu Ser Lys Cys Phe Trp Arg Gly Gly Ser Ile Asn Thr Lys Leu
 1               5                  10                  15

Pro Phe Gln Asn Leu Ser Pro Arg Thr Val Gly Gln Cys Pro Lys Tyr
            20                  25                  30

Val Asn Gln Arg Ser Leu Leu Leu Ala Thr Gly Met Arg Asn Val Pro
        35                  40                  45

Glu Val Val Gln Gly Arg
    50

<210> SEQ ID NO 60
<211> LENGTH: 53
<212> TYPE: PRT
<213> ORGANISM: Influenza virus A
<220> FEATURE:
<223> OTHER INFORMATION: influenza A HA subtype H11 C-terminal stem segment

<400> SEQUENCE: 60

Cys Ser Thr Lys Cys Gln Thr Glu Ile Gly Gly Ile Asn Thr Asn Lys
 1               5                  10                  15

Ser Phe His Asn Val His Arg Asn Thr Ile Gly Asp Cys Pro Lys Tyr
            20                  25                  30

Val Asn Val Lys Ser Leu Lys Leu Ala Thr Gly Pro Arg Asn Val Pro
        35                  40                  45

Ala Ile Ala Ser Arg
    50

<210> SEQ ID NO 61
<211> LENGTH: 53
<212> TYPE: PRT
<213> ORGANISM: Influenza virus A
<220> FEATURE:
<223> OTHER INFORMATION: influenza A HA subtype H12 C-terminal stem segment

```
<400> SEQUENCE: 61

Cys Val Thr Glu Cys Gln Leu Asn Glu Gly Val Met Asn Thr Ser Lys
1               5                   10                  15

Pro Phe Gln Asn Thr Ser Lys His Tyr Ile Gly Lys Cys Pro Lys Tyr
            20                  25                  30

Ile Pro Ser Gly Ser Leu Lys Leu Ala Ile Gly Leu Arg Asn Val Pro
        35                  40                  45

Gln Val Gln Asp Arg
    50

<210> SEQ ID NO 62
<211> LENGTH: 53
<212> TYPE: PRT
<213> ORGANISM: Influenza virus A
<220> FEATURE:
<223> OTHER INFORMATION: influenza A HA subtype H13 C-terminal stem
      segment

<400> SEQUENCE: 62

Cys Asn Thr Lys Cys Gln Thr Ser Val Gly Gly Ile Asn Thr Asn Arg
1               5                   10                  15

Thr Phe Gln Asn Ile Asp Lys Asn Ala Leu Gly Asp Cys Pro Lys Tyr
            20                  25                  30

Ile Lys Ser Gly Gln Leu Lys Leu Ala Thr Gly Leu Arg Asn Val Pro
        35                  40                  45

Ala Ile Ser Asn Arg
    50

<210> SEQ ID NO 63
<211> LENGTH: 53
<212> TYPE: PRT
<213> ORGANISM: Influenza virus A
<220> FEATURE:
<223> OTHER INFORMATION: influenza A HA subtype H14 C-terminal stem
      segment

<400> SEQUENCE: 63

Cys Thr Ser Pro Cys Leu Thr Asp Lys Gly Ser Ile Gln Ser Asp Lys
1               5                   10                  15

Pro Phe Gln Asn Val Ser Arg Ile Ala Ile Gly Asn Cys Pro Lys Tyr
            20                  25                  30

Val Lys Gln Gly Ser Leu Met Leu Ala Thr Gly Met Arg Asn Ile Pro
        35                  40                  45

Gly Lys Gln Ala Lys
    50

<210> SEQ ID NO 64
<211> LENGTH: 54
<212> TYPE: PRT
<213> ORGANISM: Influenza virus A
<220> FEATURE:
<223> OTHER INFORMATION: influenza A HA subtype H15 C-terminal stem
      segment

<400> SEQUENCE: 64

Cys Glu Gly Glu Cys Phe Tyr Ser Gly Gly Thr Ile Asn Ser Pro Leu
1               5                   10                  15

Pro Phe Gln Asn Ile Asp Ser Arg Ala Val Gly Lys Cys Pro Arg Tyr
            20                  25                  30

Val Lys Gln Ser Ser Leu Pro Leu Ala Leu Gly Met Lys Asn Val Pro
        35                  40                  45
```

Glu Lys Ile Arg Thr Arg
    50

<210> SEQ ID NO 65
<211> LENGTH: 53
<212> TYPE: PRT
<213> ORGANISM: Influenza virus A
<220> FEATURE:
<223> OTHER INFORMATION: influenza A HA subtype H16 C-terminal stem
      segment

<400

<210> SEQ ID NO 67
<211> LENGTH: 222
<212> TYPE: PRT
<213> ORGANISM: Influenza virus A
<220> FEATURE:
<223> OTHER INFORMATION: influenza A HA subtype H2 HA2 domain

<400> SEQUENCE: 67

Gly Leu Phe Gly Ala Ile Ala Gly Phe Ile Glu Gly Gly Trp Gln Gly
 1               5                  10                  15

Met Ile Asp Gly Trp Tyr Gly Tyr His His Ser Asn Asp Gln Gly Ser
            20                  25                  30

Gly Tyr Ala Ala Asp Lys Glu Ser Thr Gln Lys Ala Ile Asp Gly Ile
        35                  40                  45

Thr Asn Arg Val Asn Ser Val Ile Glu Lys Met Asn Thr Gln Phe Glu
    50                  55                  60

Ala Val Gly Lys Glu Phe Ser Asn Leu Glu Lys Arg Leu Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Tyr Asp Arg Val Arg Met Gln Leu Arg Asp
        115                 120                 125

Asn Ala Lys Glu Leu Gly Asn Gly Cys Phe Glu Phe Tyr His Lys Cys
    130                 135                 140

Asp Asp Glu Cys Met Asn Ser Val Lys Asn Gly Thr Tyr Asp Tyr Pro
145                 150                 155                 160

Lys Tyr Glu Glu Glu Ser Lys Leu Asn Arg Asn Glu Ile Lys Gly Val
                165                 170                 175

Lys Leu Ser Asn Met Gly Val Tyr Gln Ile Leu Ala Ile Tyr Ala Thr
            180                 185                 190

Val Ala Gly Ser Leu Ser Leu Ala Ile Met Ile Ala Gly Ile Ser Leu
        195                 200                 205

Trp Met Cys Ser Asn Gly Ser Leu Gln Cys Arg Ile Cys Ile
    210                 215                 220

<210> SEQ ID NO 68
<211> LENGTH: 221
<212> TYPE: PRT
<213> ORGANISM: Influenza virus A
<220> FEATURE:
<223> OTHER INFORMATION: influenza A HA subtype H3 HA2 domain

<400> SEQUENCE: 68

Gly Leu Phe Gly Ala Ile Ala Gly Phe Ile Glu Asn Gly Trp Glu Gly
 1               5                  10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

```
Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
            115                 120                 125

Asn Ala Glu Asp Met Gly Asn Gly Cys Phe Lys Ile Tyr His Lys Cys
            130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
            195                 200                 205

Ala Cys Gln Arg Gly Asn Ile Arg Cys Asn Ile Cys Ile
            210                 215                 220

<210> SEQ ID NO 69
<211> LENGTH: 221
<212> TYPE: PRT
<213> ORGANISM: Influenza virus A
<220> FEATURE:
<223> OTHER INFORMATION: influenza A HA subtype H4 HA2 domain

<400> SEQUENCE: 69

Gly Leu Phe Gly Ala Ile Ala Gly Phe Ile Glu Asn Gly Trp Gln Gly
  1               5                  10                  15

Leu Ile Asp Gly Trp Tyr Gly Phe Arg His Gln Asn Ala Glu Gly Thr
             20                  25                  30

Gly Thr Ala Ala Asp Leu Lys Ser Thr Gln Ala Ala Ile Asp Gln Ile
         35                  40                  45

Asn Gly Lys Leu Asn Arg Leu Ile Glu Lys Thr Asn Asp Lys Tyr His
 50                  55                  60

Gln Ile Glu Lys Glu Phe Glu Gln Val Glu Gly Arg Ile Gln Asp Leu
 65                  70                  75                  80

Glu Asn Tyr Val Glu Asp Thr Lys Ile Asp Leu Trp Ser Tyr Asn Ala
             85                  90                  95

Glu Leu Leu Val Ala Leu Glu Asn Gln His Thr Ile Asp Val Thr Asp
            100                 105                 110

Ser Glu Met Asn Lys Leu Phe Glu Arg Val Arg Arg Gln Leu Arg Glu
            115                 120                 125

Asn Ala Glu Asp Lys Gly Asn Gly Cys Phe Glu Ile Phe His Lys Cys
            130                 135                 140

Asp Asn Asn Cys Ile Glu Ser Ile Arg Asn Gly Thr Tyr Asp His Asp
145                 150                 155                 160

Ile Tyr Arg Asp Glu Ala Ile Asn Asn Arg Phe Gln Ile Gln Gly Val
                165                 170                 175

Lys Leu Thr Gln Gly Tyr Lys Asp Ile Ile Leu Trp Ile Ser Phe Ser
            180                 185                 190

Ile Ser Cys Phe Leu Leu Val Ala Leu Leu Ala Phe Ile Leu Trp
            195                 200                 205

Ala Cys Gln Asn Gly Asn Ile Arg Cys Gln Ile Cys Ile
            210                 215                 220

<210> SEQ ID NO 70
```

```
<211> LENGTH: 222
<212> TYPE: PRT
<213> ORGANISM: Influenza virus A
<220> FEATURE:
<223> OTHER INFORMATION: influenza A HA subtype H5 HA2 domain

<400> SEQUENCE: 70
```

| Gly | Leu | Phe | Gly | Ala | Ile | Ala | Gly | Phe | Ile | Glu | Gly | Gly | Trp | Gln | Gly |
|---|---|---|---|---|---|---|---|---|---|---|---|---|---|---|---|
| 1 | | | | 5 | | | | | 10 | | | | | 15 | |

| Met | Val | Asp | Gly | Trp | Tyr | Gly | Tyr | His | His | Ser | Asn | Glu | Gln | Gly | Ser |
|---|---|---|---|---|---|---|---|---|---|---|---|---|---|---|---|
| | | | 20 | | | | | 25 | | | | | 30 | | |

| Gly | Tyr | Ala | Ala | Asp | Lys | Glu | Ser | Thr | Gln | Lys | Ala | Ile | Asp | Gly | Ile |
|---|---|---|---|---|---|---|---|---|---|---|---|---|---|---|---|
| | | 35 | | | | | 40 | | | | | 45 | | | |

| Thr | Asn | Lys | Val | Asn | Ser | Ile | Ile | Asp | Lys | Met | Asn | Thr | Arg | Phe | Glu |
|---|---|---|---|---|---|---|---|---|---|---|---|---|---|---|---|
| 50 | | | | | 55 | | | | | 60 | | | | | |

| Ala | Val | Gly | Lys | Glu | Phe | Asn | Asn | Leu | Glu | Arg | Arg | Val | Glu | Asn | Leu |
|---|---|---|---|---|---|---|---|---|---|---|---|---|---|---|---|
| 65 | | | | | 70 | | | | | 75 | | | | | 80 |

| Asn | Lys | Lys | Met | Glu | Asp | Gly | Phe | Leu | Asp | Val | Trp | Thr | Tyr | Asn | Val |
|---|---|---|---|---|---|---|---|---|---|---|---|---|---|---|---|
| | | | | 85 | | | | | 90 | | | | | 95 | |

| Glu | Leu | Leu | Val | Leu | Met | Glu | Asn | Glu | Arg | Thr | Leu | Asp | Phe | His | Asp |
|---|---|---|---|---|---|---|---|---|---|---|---|---|---|---|---|
| | | | 100 | | | | | 105 | | | | | 110 | | |

| Ser | Asn | Val | Asn | Asn | Leu | Tyr | Asp | Lys | Val | Arg | Leu | Gln | Leu | Lys | Asp |
|---|---|---|---|---|---|---|---|---|---|---|---|---|---|---|---|
| | | 115 | | | | | 120 | | | | | 125 | | | |

| Asn | Ala | Arg | Glu | Leu | Gly | Asn | Gly | Cys | Phe | Glu | Phe | Tyr | His | Lys | Cys |
|---|---|---|---|---|---|---|---|---|---|---|---|---|---|---|---|
| | 130 | | | | | 135 | | | | | 140 | | | | |

| Asp | Asn | Glu | Cys | Met | Glu | Ser | Val | Arg | Asn | Gly | Thr | Tyr | Asp | Tyr | Pro |
|---|---|---|---|---|---|---|---|---|---|---|---|---|---|---|---|
| 145 | | | | | 150 | | | | | 155 | | | | | 160 |

| Gln | Tyr | Ser | Glu | Glu | Ala | Arg | Leu | Asn | Arg | Glu | Glu | Ile | Ser | Gly | Val |
|---|---|---|---|---|---|---|---|---|---|---|---|---|---|---|---|
| | | | | 165 | | | | | 170 | | | | | 175 | |

| Lys | Leu | Glu | Ser | Met | Gly | Val | Tyr | Gln | Ile | Leu | Ser | Ile | Tyr | Ser | Thr |
|---|---|---|---|---|---|---|---|---|---|---|---|---|---|---|---|
| | | | 180 | | | | | 185 | | | | | 190 | | |

| Val | Ala | Ser | Ser | Leu | Ala | Leu | Ala | Ile | Met | Ile | Ala | Gly | Leu | Ser | Phe |
|---|---|---|---|---|---|---|---|---|---|---|---|---|---|---|---|
| | | 195 | | | | | 200 | | | | | 205 | | | |

| Trp | Met | Cys | Ser | Asn | Gly | Ser | Leu | Gln | Cys | Arg | Ile | Cys | Ile |
|---|---|---|---|---|---|---|---|---|---|---|---|---|---|
| 210 | | | | | 215 | | | | | 220 | | | |

```
<210> SEQ ID NO 71
<211> LENGTH: 222
<212> TYPE: PRT
<213> ORGANISM: Influenza virus A
<220> FEATURE:
<223> OTHER INFORMATION: influenza A HA subtype H6 HA2 domain

<400> SEQUENCE: 71
```

| Gly | Leu | Phe | Gly | Ala | Ile | Ala | Gly | Phe | Ile | Glu | Gly | Gly | Trp | Thr | Gly |
|---|---|---|---|---|---|---|---|---|---|---|---|---|---|---|---|
| 1 | | | | 5 | | | | | 10 | | | | | 15 | |

| Met | Ile | Asp | Gly | Trp | Tyr | Gly | Tyr | His | His | Glu | Asn | Ser | Gln | Gly | Ser |
|---|---|---|---|---|---|---|---|---|---|---|---|---|---|---|---|
| | | | 20 | | | | | 25 | | | | | 30 | | |

| Gly | Tyr | Ala | Ala | Asp | Arg | Glu | Ser | Thr | Gln | Lys | Ala | Val | Asp | Gly | Ile |
|---|---|---|---|---|---|---|---|---|---|---|---|---|---|---|---|
| | | 35 | | | | | 40 | | | | | 45 | | | |

| Thr | Asn | Lys | Val | Asn | Ser | Ile | Ile | Asp | Lys | Met | Asn | Thr | Gln | Phe | Glu |
|---|---|---|---|---|---|---|---|---|---|---|---|---|---|---|---|
| 50 | | | | | 55 | | | | | 60 | | | | | |

| Ala | Val | Asp | His | Glu | Phe | Ser | Asn | Leu | Glu | Arg | Arg | Ile | Asp | Asn | Leu |
|---|---|---|---|---|---|---|---|---|---|---|---|---|---|---|---|
| 65 | | | | | 70 | | | | | 75 | | | | | 80 |

| Asn | Lys | Arg | Met | Glu | Asp | Gly | Phe | Leu | Asp | Val | Trp | Thr | Tyr | Asn | Ala |
|---|---|---|---|---|---|---|---|---|---|---|---|---|---|---|---|
| | | | | 85 | | | | | 90 | | | | | 95 | |

| Glu | Leu | Leu | Val | Leu | Leu | Glu | Asn | Glu | Arg | Thr | Leu | Asp | Leu | His | Asp |
|---|---|---|---|---|---|---|---|---|---|---|---|---|---|---|---|

```
                100                 105                 110
Ala Asn Val Lys Asn Leu Tyr Glu Arg Val Lys Ser Gln Leu Arg Asp
                115                 120                 125

Asn Ala Met Ile Leu Gly Asn Gly Cys Phe Glu Phe Trp His Lys Cys
    130                 135                 140

Asp Asp Glu Cys Met Glu Ser Val Lys Asn Gly Thr Tyr Asp Tyr Pro
145                 150                 155                 160

Lys Tyr Gln Asp Glu Ser Lys Leu Asn Arg Gln Glu Ile Glu Ser Val
                165                 170                 175

Lys Leu Glu Ser Leu Gly Val Tyr Gln Ile Leu Ala Ile Tyr Ser Thr
                180                 185                 190

Val Ser Ser Ser Leu Val Leu Val Gly Leu Ile Ile Ala Val Gly Leu
                195                 200                 205

Trp Met Cys Ser Asn Gly Ser Met Gln Cys Arg Ile Cys Ile
                210                 215                 220

<210> SEQ ID NO 72
<211> LENGTH: 221
<212> TYPE: PRT
<213> ORGANISM: Influenza virus A
<220> FEATURE:
<223> OTHER INFORMATION: influenza A HA subtype H7 HA2 domain

<400> SEQUENCE: 72

Gly Leu Phe Gly Ala Ile Ala Gly Phe Ile Glu Asn Gly Trp Glu Gly
1               5                   10                  15

Leu Val Asp Gly Trp Tyr Gly Phe Arg His Gln Asn Ala Gln Gly Glu
                20                  25                  30

Gly Thr Ala Ala Asp Tyr Lys Ser Thr Gln Ser Ala Ile Asp Gln Ile
            35                  40                  45

Thr Gly Lys Leu Asn Arg Leu Ile Glu Lys Thr Asn Gln Gln Phe Glu
    50                  55                  60

Leu Ile Asp Asn Glu Phe Thr Glu Val Glu Lys Gln Ile Gly Asn Leu
65                  70                  75                  80

Ile Asn Trp Thr Lys Asp Ser Ile Thr Glu Val Trp Ser Tyr Asn Ala
                85                  90                  95

Glu Leu Ile Val Ala Met Glu Asn Gln His Thr Ile Asp Leu Ala Asp
                100                 105                 110

Ser Glu Met Asn Arg Leu Tyr Glu Arg Val Arg Lys Gln Leu Arg Glu
                115                 120                 125

Asn Ala Glu Glu Asp Gly Thr Gly Cys Phe Glu Ile Phe His Lys Cys
    130                 135                 140

Asp Asp Asp Cys Met Ala Ser Ile Arg Asn Asn Thr Tyr Asp His Ser
145                 150                 155                 160

Lys Tyr Arg Glu Glu Ala Met Gln Asn Arg Ile Gln Ile Asp Pro Val
                165                 170                 175

Lys Leu Ser Ser Gly Tyr Lys Asp Val Ile Leu Trp Phe Ser Phe Gly
                180                 185                 190

Ala Ser Cys Phe Leu Leu Leu Ala Ile Ala Met Gly Leu Val Phe Ile
                195                 200                 205

Cys Val Lys Asn Gly Asn Met Arg Cys Thr Ile Cys Ile
                210                 215                 220

<210> SEQ ID NO 73
<211> LENGTH: 222
<212> TYPE: PRT
```

<213> ORGANISM: Influenza virus A
<220> FEATURE:
<223> OTHER INFORMATION: influenza A HA subtype H8 HA2 domain

<400> SEQUENCE: 73

```
Gly Leu Phe Gly Ala Ile Ala Gly Phe Ile Glu Gly Gly Trp Ser Gly
1               5                   10                  15

Met Ile Asp Gly Trp Tyr Gly Phe His His Ser Asn Ser Glu Gly Thr
            20                  25                  30

Gly Met Ala Ala Asp Gln Lys Ser Thr Gln Glu Ala Ile Asp Lys Ile
        35                  40                  45

Thr Asn Lys Val Asn Asn Ile Val Asp Lys Met Asn Arg Glu Phe Glu
    50                  55                  60

Val Val Asn His Glu Phe Ser Glu Val Glu Lys Arg Ile Asn Met Ile
65                  70                  75                  80

Asn Asp Lys Ile Asp Asp Gln Ile Glu Asp Leu Trp Ala Tyr Asn Ala
                85                  90                  95

Glu Leu Leu Val Leu Leu Glu Asn Gln Lys Thr Leu Asp Glu His Asp
            100                 105                 110

Ser Asn Val Lys Asn Leu Phe Asp Glu Val Lys Arg Arg Leu Ser Ala
        115                 120                 125

Asn Ala Ile Asp Ala Gly Asn Gly Cys Phe Asp Ile Leu His Lys Cys
    130                 135                 140

Asp Asn Glu Cys Met Glu Thr Ile Lys Asn Gly Thr Tyr Asp His Lys
145                 150                 155                 160

Glu Tyr Glu Glu Glu Ala Lys Leu Glu Arg Ser Lys Ile Asn Gly Val
                165                 170                 175

Lys Leu Glu Glu Asn Thr Thr Tyr Lys Ile Leu Ser Ile Tyr Ser Thr
            180                 185                 190

Val Ala Ala Ser Leu Cys Leu Ala Ile Leu Ile Ala Gly Gly Leu Ile
        195                 200                 205

Leu Gly Met Gln Asn Gly Ser Cys Arg Cys Met Phe Cys Ile
    210                 215                 220
```

<210> SEQ ID NO 74
<211> LENGTH: 222
<212> TYPE: PRT
<213> ORGANISM: Influenza virus A
<220> FEATURE:
<223> OTHER INFORMATION: influenza A HA subtype H9 HA2 domain

<400> SEQUENCE: 74

```
Gly Leu Phe Gly Ala Ile Ala Gly Phe Ile Glu Gly Gly Trp Pro Gly
1               5                   10                  15

Leu Val Ala Gly Trp Tyr Gly Phe Gln His Ser Asn Asp Gln Gly Val
            20                  25                  30

Gly Met Ala Ala Asp Lys Gly Ser Thr Gln Lys Ala Ile Asp Lys Ile
        35                  40                  45

Thr Ser Lys Val Asn Asn Ile Ile Asp Lys Met Asn Lys Gln Tyr Glu
    50                  55                  60

Val Ile Asp His Glu Phe Asn Glu Leu Glu Ala Arg Leu Asn Met Ile
65                  70                  75                  80

Asn Asn Lys Ile Asp Asp Gln Ile Gln Asp Ile Trp Ala Tyr Asn Ala
                85                  90                  95

Glu Leu Leu Val Leu Leu Glu Asn Gln Lys Thr Leu Asp Glu His Asp
            100                 105                 110
```

```
Ala Asn Val Asn Asn Leu Tyr Asn Lys Val Lys Arg Ala Leu Gly Ser
            115                 120                 125

Asn Ala Val Glu Asp Gly Asn Gly Cys Phe Glu Leu Tyr His Lys Cys
        130                 135                 140

Asp Asp Gln Cys Met Glu Thr Ile Arg Asn Gly Thr Tyr Asp Arg Gln
145                 150                 155                 160

Lys Tyr Gln Glu Glu Ser Arg Leu Glu Arg Gln Lys Ile Glu Gly Val
                165                 170                 175

Lys Leu Glu Ser Glu Gly Thr Tyr Lys Ile Leu Thr Ile Tyr Ser Thr
            180                 185                 190

Val Ala Ser Ser Leu Val Leu Ala Met Gly Phe Ala Ala Phe Leu Phe
        195                 200                 205

Trp Ala Met Ser Asn Gly Ser Cys Arg Cys Asn Ile Cys Ile
    210                 215                 220

<210> SEQ ID NO 75
<211> LENGTH: 221
<212> TYPE: PRT
<213> ORGANISM: Influenza virus A
<220> FEATURE:
<223> OTHER INFORMATION: influenza A HA subtype H10 HA2 domain

<400> SEQUENCE: 75

Gly Leu Phe Gly Ala Ile Ala Gly Phe Ile Glu Asn Gly Trp Glu Gly
1               5                   10                  15

Met Val Asp Gly Trp Tyr Gly Phe Arg His Gln Asn Ala Gln Gly Thr
            20                  25                  30

Gly Gln Ala Ala Asp Tyr Lys Ser Thr Gln Ala Ala Ile Asp Gln Ile
        35                  40                  45

Thr Gly Lys Leu Asn Arg Leu Ile Glu Lys Thr Asn Thr Glu Phe Glu
    50                  55                  60

Ser Ile Glu Ser Glu Phe Ser Glu Thr Glu His Gln Ile Gly Asn Val
65                  70                  75                  80

Ile Asn Trp Thr Lys Asp Ser Ile Thr Asp Ile Trp Thr Tyr Asn Ala
                85                  90                  95

Glu Leu Leu Val Ala Met Glu Asn Gln His Thr Ile Asp Met Ala Asp
            100                 105                 110

Ser Glu Met Leu Asn Leu Tyr Glu Arg Val Arg Lys Gln Leu Arg Gln
        115                 120                 125

Asn Ala Glu Glu Asp Gly Lys Gly Cys Phe Glu Ile Tyr His Thr Cys
    130                 135                 140

Asp Asp Ser Cys Met Glu Ser Ile Arg Asn Asn Thr Tyr Asp His Ser
145                 150                 155                 160

Gln Tyr Arg Glu Glu Ala Leu Leu Asn Arg Leu Asn Ile Asn Pro Val
                165                 170                 175

Lys Leu Ser Ser Gly Tyr Lys Asp Ile Ile Leu Trp Phe Ser Phe Gly
            180                 185                 190

Glu Ser Cys Phe Val Leu Leu Ala Val Val Met Gly Leu Val Phe Phe
        195                 200                 205

Cys Leu Lys Asn Gly Asn Met Arg Cys Thr Ile Cys Ile
    210                 215                 220

<210> SEQ ID NO 76
<211> LENGTH: 223
<212> TYPE: PRT
<213> ORGANISM: Influenza virus A
<220> FEATURE:
```

<223> OTHER INFORMATION: influenza A HA subtype H11 HA2 domain

<400> SEQUENCE: 76

Gly Leu Phe Gly Ala Ile Ala Gly Phe Ile Glu Gly Gly Trp Pro Gly
1 5 10 15

Leu Ile Asn Gly Trp Tyr Gly Phe Gln His Arg Asp Glu Glu Gly Thr
20 25 30

Gly Ile Ala Ala Asp Lys Glu Ser Thr Gln Lys Ala Ile Asp Gln Ile
35 40 45

Thr Ser Lys Val Asn Asn Ile Val Asp Arg Met Asn Thr Asn Phe Glu
50 55 60

Ser Val Gln His Glu Phe Ser Glu Ile Glu Glu Arg Ile Asn Gln Leu
65 70 75 80

Ser Lys His Val Asp Asp Ser Val Val Asp Ile Trp Ser Tyr Asn Ala
85 90 95

Gln Leu Leu Val Leu Leu Glu Asn Glu Lys Thr Leu Asp Leu His Asp
100 105 110

Ser Asn Val Arg Asn Leu His Glu Lys Val Arg Arg Met Leu Lys Asp
115 120 125

Asn Ala Lys Asp Glu Gly Asn Gly Cys Phe Thr Phe Tyr His Lys Cys
130 135 140

Asp Asn Lys Cys Ile Glu Arg Val Arg Asn Gly Thr Tyr Asp His Lys
145 150 155 160

Glu Phe Glu Glu Glu Ser Lys Ile Asn Arg Gln Glu Ile Glu Gly Val
165 170 175

Lys Leu Asp Ser Ser Gly Asn Val Tyr Lys Ile Leu Ser Ile Tyr Ser
180 185 190

Cys Ile Ala Ser Ser Leu Val Leu Ala Ala Leu Ile Met Gly Phe Met
195 200 205

Phe Trp Ala Cys Ser Asn Gly Ser Cys Arg Cys Thr Ile Cys Ile
210 215 220

<210> SEQ ID NO 77
<211> LENGTH: 222
<212> TYPE: PRT
<213> ORGANISM: Influenza virus A
<220> FEATURE:
<223> OTHER INFORMATION: influenza A HA subtype H12 HA2 domain

<400> SEQUENCE: 77

Gly Leu Phe Gly Ala Ile Ala Gly Phe Ile Glu Gly Gly Trp Pro Gly
1 5 10 15

Leu Val Ala Gly Trp Tyr Gly Phe Gln His Gln Asn Ala Glu Gly Thr
20 25 30

Gly Ile Ala Ala Asp Arg Asp Ser Thr Gln Arg Ala Ile Asp Asn Met
35 40 45

Gln Asn Lys Leu Asn Asn Val Ile Asp Lys Met Asn Lys Gln Phe Glu
50 55 60

Val Val Asn His Glu Phe Ser Glu Val Glu Ser Arg Ile Asn Met Ile
65 70 75 80

Asn Ser Lys Ile Asp Asp Gln Ile Thr Asp Ile Trp Ala Tyr Asn Ala
85 90 95

Glu Leu Leu Val Leu Leu Glu Asn Gln Lys Thr Leu Asp Glu His Asp
100 105 110

Ala Asn Val Arg Asn Leu His Asp Arg Val Arg Arg Val Leu Arg Glu
115 120 125

Asn Ala Ile Asp Thr Gly Asp Gly Cys Phe Glu Ile Leu His Lys Cys
            130                 135                 140

Asp Asn Asn Cys Met Asp Thr Ile Arg Asn Gly Thr Tyr Asn His Lys
145                 150                 155                 160

Glu Tyr Glu Glu Glu Ser Lys Ile Glu Arg Gln Lys Val Asn Gly Val
                165                 170                 175

Lys Leu Glu Glu Asn Ser Thr Tyr Lys Ile Leu Ser Ile Tyr Ser Ser
            180                 185                 190

Val Ala Ser Ser Leu Val Leu Leu Leu Met Ile Ile Gly Gly Phe Ile
        195                 200                 205

Phe Gly Cys Gln Asn Gly Asn Val Arg Cys Thr Phe Cys Ile
        210                 215                 220

<210> SEQ ID NO 78
<211> LENGTH: 223
<212> TYPE: PRT
<213> ORGANISM: Influenza virus A
<220> FEATURE:
<223> OTHER INFORMATION: influenza A HA subtype H13 HA2 domain

<400> SEQUENCE: 78

Gly Leu Phe Gly Ala Ile Ala Gly Phe Ile Glu Gly Gly Trp Pro Gly
1               5                   10                  15

Leu Ile Asn Gly Trp Tyr Gly Phe Gln His Gln Asn Glu Gln Gly Thr
            20                  25                  30

Gly Ile Ala Ala Asp Lys Glu Ser Thr Gln Lys Ala Ile Asp Gln Ile
        35                  40                  45

Thr Thr Lys Ile Asn Asn Ile Ile Asp Lys Met Asn Gly Asn Tyr Asp
    50                  55                  60

Ser Ile Arg Gly Glu Phe Asn Gln Val Glu Lys Arg Ile Asn Met Leu
65                  70                  75                  80

Ala Asp Arg Ile Asp Asp Ala Val Thr Asp Ile Trp Ser Tyr Asn Ala
                85                  90                  95

Lys Leu Leu Val Leu Leu Glu Asn Asp Lys Thr Leu Asp Met His Asp
            100                 105                 110

Ala Asn Val Lys Asn Leu His Glu Gln Val Arg Arg Glu Leu Lys Asp
        115                 120                 125

Asn Ala Ile Asp Glu Gly Asn Gly Cys Phe Glu Leu Leu His Lys Cys
    130                 135                 140

Asn Asp Ser Cys Met Glu Thr Ile Arg Asn Gly Thr Tyr Asp His Thr
145                 150                 155                 160

Glu Tyr Ala Glu Glu Ser Lys Leu Lys Arg Gln Glu Ile Asp Gly Ile
                165                 170                 175

Lys Leu Lys Ser Glu Asp Asn Val Tyr Lys Ala Leu Ser Ile Tyr Ser
            180                 185                 190

Cys Ile Ala Ser Ser Val Val Leu Val Gly Leu Ile Leu Ser Phe Ile
        195                 200                 205

Met Trp Ala Cys Ser Ser Gly Asn Cys Arg Phe Asn Val Cys Ile
    210                 215                 220

<210> SEQ ID NO 79
<211> LENGTH: 221
<212> TYPE: PRT
<213> ORGANISM: Influenza virus A
<220> FEATURE:
<223> OTHER INFORMATION: influenza A HA subtype H14 HA2 domain

```
<400> SEQUENCE: 79

Gly Leu Phe Gly Ala Ile Ala Gly Phe Ile Glu Asn Gly Trp Gln Gly
1               5                   10                  15

Leu Ile Asp Gly Trp Tyr Gly Phe Arg His Gln Asn Ala Glu Gly Thr
            20                  25                  30

Gly Thr Ala Ala Asp Leu Lys Ser Thr Gln Ala Ala Ile Asp Gln Ile
        35                  40                  45

Asn Gly Lys Leu Asn Arg Leu Ile Glu Lys Thr Asn Glu Lys Tyr His
    50                  55                  60

Gln Ile Glu Lys Glu Phe Glu Gln Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Val Thr Asp
            100                 105                 110

Ser Glu Met Asn Lys Leu Phe Glu Arg Val Arg Arg Gln Leu Arg Glu
        115                 120                 125

Asn Ala Glu Asp Gln Gly Asn Gly Cys Phe Glu Ile Phe His Gln Cys
    130                 135                 140

Asp Asn Asn Cys Ile Glu Ser Ile Arg Asn Gly Thr Tyr Asp His Asn
145                 150                 155                 160

Ile Tyr Arg Asp Glu Ala Ile Asn Asn Arg Ile Lys Ile Asn Pro Val
                165                 170                 175

Thr Leu Thr Met Gly Tyr Lys Asp Ile Ile Leu Trp Ile Ser Phe Ser
            180                 185                 190

Met Ser Cys Phe Val Phe Val Ala Leu Ile Leu Gly Phe Val Leu Trp
        195                 200                 205

Ala Cys Gln Asn Gly Asn Ile Arg Cys Gln Ile Cys Ile
    210                 215                 220

<210> SEQ ID NO 80
<211> LENGTH: 221
<212> TYPE: PRT
<213> ORGANISM: Influenza virus A
<220> FEATURE:
<223> OTHER INFORMATION: influenza A HA subtype H15 HA2 domain

<400> SEQUENCE: 80

Gly Leu Phe Gly Ala Ile Ala Gly Phe Ile Glu Asn Gly Trp Glu Gly
1               5                   10                  15

Leu Ile Asp Gly Trp Tyr Gly Phe Arg His Gln Asn Ala Gln Gly Gln
            20                  25                  30

Gly Thr Ala Ala Asp Tyr Lys Ser Thr Gln Ala Ala Ile Asp Gln Ile
        35                  40                  45

Thr Gly Lys Leu Asn Arg Leu Ile Glu Lys Thr Asn Lys Gln Phe Glu
    50                  55                  60

Leu Ile Asp Asn Glu Phe Thr Glu Val Glu Gln Gln Ile Gly Asn Val
65                  70                  75                  80

Ile Asn Trp Thr Arg Asp Ser Leu Thr Glu Ile Trp Ser Tyr Asn Ala
                85                  90                  95

Glu Leu Leu Val Ala Met Glu Asn Gln His Thr Ile Asp Leu Ala Asp
            100                 105                 110

Ser Glu Met Asn Lys Leu Tyr Glu Arg Val Arg Arg Gln Leu Arg Glu
        115                 120                 125

Asn Ala Glu Glu Asp Gly Thr Gly Cys Phe Glu Ile Phe His Arg Cys
```

```
                130                 135                 140
Asp Asp Gln Cys Met Glu Ser Ile Arg Asn Asn Thr Tyr Asn His Thr
145                 150                 155                 160

Glu Tyr Arg Gln Glu Ala Leu Gln Asn Arg Ile Met Ile Asn Pro Val
                165                 170                 175

Lys Leu Ser Ser Gly Tyr Lys Asp Val Ile Leu Trp Phe Ser Phe Gly
                180                 185                 190

Ala Ser Cys Val Met Leu Leu Ala Ile Ala Met Gly Leu Ile Phe Met
                195                 200                 205

Cys Val Lys Asn Gly Asn Leu Arg Cys Thr Ile Cys Ile
210                 215                 220

<210> SEQ ID NO 81
<211> LENGTH: 223
<212> TYPE: PRT
<213> ORGANISM: Influenza virus A
<220> FEATURE:
<223> OTHER INFORMATION: influenza A HA subtype H16 HA2 domain

<400> SEQUENCE: 81

Gly Leu Phe Gly Ala Ile Ala Gly Phe Ile Glu Gly Gly Trp Pro Gly
1               5                   10                  15

Leu Ile Asn Gly Trp Tyr Gly Phe Gln His Gln Asn Glu Gln Gly Thr
                20                  25                  30

Gly Ile Ala Ala Asp Lys Ala Ser Thr Gln Lys Ala Ile Asn Glu Ile
                35                  40                  45

Thr Thr Lys Ile Asn Asn Ile Ile Glu Lys Met Asn Gly Asn Tyr Asp
50                  55                  60

Ser Ile Arg Gly Glu Phe Asn Gln Val Glu Lys Arg Ile Asn Met Leu
65                  70                  75                  80

Ala Asp Arg Val Asp Asp Ala Val Thr Asp Ile Trp Ser Tyr Asn Ala
                85                  90                  95

Lys Leu Leu Val Leu Leu Glu Asn Asp Arg Thr Leu Asp Leu His Asp
                100                 105                 110

Ala Asn Val Arg Asn Leu His Asp Gln Val Lys Arg Ala Leu Lys Ser
                115                 120                 125

Asn Ala Ile Asp Glu Gly Asp Gly Cys Phe Asn Leu Leu His Lys Cys
                130                 135                 140

Asn Asp Ser Cys Met Glu Thr Ile Arg Asn Gly Thr Tyr Asn His Glu
145                 150                 155                 160

Asp Tyr Arg Glu Glu Ser Gln Leu Lys Arg Gln Glu Ile Glu Gly Ile
                165                 170                 175

Lys Leu Lys Thr Glu Asp Asn Val Tyr Lys Val Leu Ser Ile Tyr Ser
                180                 185                 190

Cys Ile Ala Ser Ser Ile Val Leu Val Gly Leu Ile Leu Ala Phe Ile
                195                 200                 205

Met Trp Ala Cys Ser Asn Gly Ser Cys Arg Phe Asn Val Cys Ile
                210                 215                 220

<210> SEQ ID NO 82
<211> LENGTH: 180
<212> TYPE: PRT
<213> ORGANISM: Influenza virus A
<220> FEATURE:
<223> OTHER INFORMATION: influenza A HA2 domain subtype H1 stem domain

<400> SEQUENCE: 82
```

Gly Leu Phe Gly Ala Ile Ala Gly Phe Ile Glu Gly Gly Trp Thr Gly
1               5                   10                  15

Met Ile Asp Gly Trp Tyr Gly Tyr His His Gln Asn Glu Gln Gly Ser
            20                  25                  30

Gly Tyr Ala Ala Asp Gln Lys Ser Thr Gln Asn Ala Ile Asn Gly Ile
        35                  40                  45

Thr Asn Lys Val Asn Thr Val Ile Glu Lys Met Asn Ile Gln Phe Thr
50                  55                  60

Ala Val Gly Lys Glu Phe Asn Lys Leu Glu Arg Met Glu Asn Leu
65                  70                  75                  80

Asn Lys Lys Val Asp Asp Gly Phe Leu Asp Ile Trp Thr Tyr Asn Ala
                85                  90                  95

Glu Leu Leu Val Leu Leu Glu Asn Glu Arg Thr Leu Asp Phe His Asp
                100                 105                 110

Ser Asn Val Lys Asn Leu Tyr Glu Lys Val Lys Ser Gln Leu Lys Asn
                115                 120                 125

Asn Ala Lys Glu Ile Gly Asn Gly Cys Phe Glu Phe Tyr His Lys Cys
            130                 135                 140

Asp Asn Glu Cys Met Glu Ser Val Arg Asn Gly Thr Tyr Asp Tyr Pro
145                 150                 155                 160

Lys Tyr Ser Glu Glu Ser Lys Leu Asn Arg Glu Lys Val Asp Gly Val
                165                 170                 175

Lys Leu Glu Ser
            180

<210> SEQ ID NO 83
<211> LENGTH: 180
<212> TYPE: PRT
<213> ORGANISM: Influenza virus A
<220> FEATURE:
<223> OTHER INFORMATION: influenza A HA2 domain subtype H2 stem domain

<400> SEQUENCE: 83

Gly Leu Phe Gly Ala Ile Ala Gly Phe Ile Glu Gly Gly Trp Gln Gly
1               5                   10                  15

Met Ile Asp Gly Trp Tyr Gly Tyr His His Ser Asn Asp Gln Gly Ser
            20                  25                  30

Gly Tyr Ala Ala Asp Lys Glu Ser Thr Gln Lys Ala Ile Asp Gly Ile
        35                  40                  45

Thr Asn Arg Val Asn Ser Val Ile Glu Lys Met Asn Thr Gln Phe Glu
50                  55                  60

Ala Val Gly Lys Glu Phe Ser Asn Leu Glu Lys Arg Leu Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
                100                 105                 110

Ser Asn Val Lys Asn Leu Tyr Asp Arg Val Arg Met Gln Leu Arg Asp
                115                 120                 125

Asn Ala Lys Glu Leu Gly Asn Gly Cys Phe Glu Phe Tyr His Lys Cys
            130                 135                 140

Asp Asp Glu Cys Met Asn Ser Val Lys Asn Gly Thr Tyr Asp Tyr Pro
145                 150                 155                 160

Lys Tyr Glu Glu Glu Ser Lys Leu Asn Arg Asn Glu Ile Lys Gly Val
                165                 170                 175

Lys Leu Ser Asn
            180

<210> SEQ ID NO 84
<211> LENGTH: 179
<212> TYPE: PRT
<213> ORGANISM: Influenza virus A
<220> FEATURE:
<223> OTHER INFORMATION: influenza A HA2 domain subtype H3 stem domain

<400> SEQUENCE: 84

Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys

<210> SEQ ID NO 85
<211> LENGTH: 179
<212> TYPE: PRT
<213> ORGANISM: Influenza virus A
<220> FEATURE:
<223> OTHER INFORMATION: influenza A HA2 domain subtype H4 stem domain

<400> SEQUENCE: 85

Gly Leu Phe Gly Ala Ile Ala Gly Phe Ile Glu Asn Gly Trp Gln Gly
1               5                   10                  15

Leu Ile Asp Gly Trp Tyr Gly Phe Arg His Gln Asn Ala Glu Gly Thr
            20                  25                  30

Gly Thr Ala Ala Asp Leu Lys Ser Thr Gln Ala Ala Ile Asp Gln Ile
        35                  40                  45

Asn Gly Lys Leu Asn Arg Leu Ile Glu Lys Thr Asn Asp Lys Tyr His
    50                  55                  60

Gln Ile Glu Lys Glu Phe Glu Gln Val Glu Gly Arg Ile Gln Asp Leu
65                  70                  75                  80

Glu Asn Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Val Thr Asp
            100                 105                 110

```
Ser Glu Met Asn Lys Leu Phe Glu Arg Val Arg Arg Gln Leu Arg Glu
            115                 120                 125

Asn Ala Glu Asp Lys Gly Asn Gly Cys Phe Glu Ile Phe His Lys Cys
        130                 135                 140

Asp Asn Asn Cys Ile Glu Ser Ile Arg Asn Gly Thr Tyr Asp His Asp
145                 150                 155                 160

Ile Tyr Arg Asp Glu Ala Ile Asn Asn Arg Phe Gln Ile Gln Gly Val
                165                 170                 175

Lys Leu Thr

<210> SEQ ID NO 86
<211> LENGTH: 180
<212> TYPE: PRT
<213> ORGANISM: Influenza virus A
<220> FEATURE:
<223> OTHER INFORMATION: influenza A HA2 domain subtype H5 stem domain

<400> SEQUENCE: 86

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
            20                  25                  30

Gly Tyr Ala Ala Asp Lys Glu Ser Thr Gln Lys Ala Ile Asp Gly Ile
        35                  40                  45

Thr Asn Lys Val Asn Ser Ile Ile Asp Lys Met Asn Thr Arg Phe Glu
50                  55                  60

Ala Val Gly Lys Glu Phe Asn Asn Leu Glu Arg Arg Val Glu Asn Leu
65                  70                  75                  80

Asn Lys Lys Met Glu Asp Gly Phe Leu Asp Val Trp Thr Tyr Asn Val
                85                  90                  95

Glu Leu Leu Val Leu Met Glu Asn Glu Arg Thr Leu Asp Phe His Asp
            100                 105                 110

Ser Asn Val Asn Asn Leu Tyr Asp Lys Val Arg Leu Gln Leu Lys Asp
        115                 120                 125

Asn Ala Arg Glu Leu Gly Asn Gly Cys Phe Glu Phe Tyr His Lys Cys
        130                 135                 140

Asp Asn Glu Cys Met Glu Ser Val Arg Asn Gly Thr Tyr Asp Tyr Pro
145                 150                 155                 160

Gln Tyr Ser Glu Glu Ala Arg Leu Asn Arg Glu Glu Ile Ser Gly Val
                165                 170                 175

Lys Leu Glu Ser
            180

<210> SEQ ID NO 87
<211> LENGTH: 180
<212> TYPE: PRT
<213> ORGANISM: Influenza virus A
<220> FEATURE:
<223> OTHER INFORMATION: influenza A HA2 domain subtype H6 stem domain

<400> SEQUENCE: 87

Gly Leu Phe Gly Ala Ile Ala Gly Phe Ile Glu Gly Gly Trp Thr Gly
1               5                   10                  15

Met Ile Asp Gly Trp Tyr Gly Tyr His His Glu Asn Ser Gln Gly Ser
            20                  25                  30

Gly Tyr Ala Ala Asp Arg Glu Ser Thr Gln Lys Ala Val Asp Gly Ile
        35                  40                  45
```

```
Thr Asn Lys Val Asn Ser Ile Ile Asp Lys Met Asn Thr Gln Phe Glu
         50                  55                  60

Ala Val Asp His Glu Phe Ser Asn Leu Glu Arg Arg Ile Asp Asn Leu
 65                  70                  75                  80

Asn Lys Arg Met Glu Asp Gly Phe Leu Asp Val Trp Thr Tyr Asn Ala
                 85                  90                  95

Glu Leu Leu Val Leu Leu Glu Asn Glu Arg Thr Leu Asp Leu His Asp
            100                 105                 110

Ala Asn Val Lys Asn Leu Tyr Glu Arg Val Lys Ser Gln Leu Arg Asp
            115                 120                 125

Asn Ala Met Ile Leu Gly Asn Gly Cys Phe Glu Phe Trp His Lys Cys
130                 135                 140

Asp Asp Glu Cys Met Glu Ser Val Lys Asn Gly Thr Tyr Asp Tyr Pro
145                 150                 155                 160

Lys Tyr Gln Asp Glu Ser Lys Leu Asn Arg Gln Glu Ile Glu Ser Val
                165                 170                 175

Lys Leu Glu Ser
            180

<210> SEQ ID NO 88
<211> LENGTH: 179
<212> TYPE: PRT
<213> ORGANISM: Influenza virus A
<220> FEATURE:
<223> OTHER INFORMATION: influenza A HA2 domain subtype H7 stem domain

<400> SEQUENCE: 88

Gly Leu Phe Gly Ala Ile Ala Gly Phe Ile Glu Asn Gly Trp Glu Gly
  1               5                  10                  15

Leu Val Asp Gly Trp Tyr Gly Phe Arg His Gln Asn Ala Gln Gly Glu
             20                  25                  30

Gly Thr Ala Ala Asp Tyr Lys Ser Thr Gln Ser Ala Ile Asp Gln Ile
         35                  40                  45

Thr Gly Lys Leu Asn Arg Leu Ile Glu Lys Thr Asn Gln Gln Phe Glu
     50                  55                  60

Leu Ile Asp Asn Glu Phe Thr Glu Val Glu Lys Gln Ile Gly Asn Leu
 65                  70                  75                  80

Ile Asn Trp Thr Lys Asp Ser Ile Thr Glu Val Trp Ser Tyr Asn Ala
                 85                  90                  95

Glu Leu Ile Val Ala Met Glu Asn Gln His Thr Ile Asp Leu Ala Asp
            100                 105                 110

Ser Glu Met Asn Arg Leu Tyr Glu Arg Val Arg Lys Gln Leu Arg Glu
            115                 120                 125

Asn Ala Glu Glu Asp Gly Thr Gly Cys Phe Glu Ile Phe His Lys Cys
130                 135                 140

Asp Asp Asp Cys Met Ala Ser Ile Arg Asn Asn Thr Tyr Asp His Ser
145                 150                 155                 160

Lys Tyr Arg Glu Glu Ala Met Gln Asn Arg Ile Gln Ile Asp Pro Val
                165                 170                 175

Lys Leu Ser

<210> SEQ ID NO 89
<211> LENGTH: 180
<212> TYPE: PRT
<213> ORGANISM: Influenza virus A
<220> FEATURE:
<223> OTHER INFORMATION: influenza A HA2 domain subtype H8 stem domain
```

<400> SEQUENCE: 89

Gly Leu Phe Gly Ala Ile Ala Gly Phe Ile Glu Gly Gly Trp Ser Gly
1               5                   10                  15

Met Ile Asp Gly Trp Tyr Gly Phe His His Ser Asn Ser Glu Gly Thr
            20                  25                  30

Gly Met Ala Ala Asp Gln Lys Ser Thr Gln Glu Ala Ile Asp Lys Ile
        35                  40                  45

Thr Asn Lys Val Asn Asn Ile Val Asp Lys Met Asn Arg Glu Phe Glu
50                  55                  60

Val Val Asn His Glu Phe Ser Glu Val Glu Lys Arg Ile Asn Met Ile
65                  70                  75                  80

Asn Asp Lys Ile Asp Asp Gln Ile Glu Asp Leu Trp Ala Tyr Asn Ala
                85                  90                  95

Glu Leu Leu Val Leu Leu Glu Asn Gln Lys Thr Leu Asp Glu His Asp
            100                 105                 110

Ser Asn Val Lys Asn Leu Phe Asp Glu Val Lys Arg Arg Leu Ser Ala
        115                 120                 125

Asn Ala Ile Asp Ala Gly Asn Gly Cys Phe Asp Ile Leu His Lys Cys
130                 135                 140

Asp Asn Glu Cys Met Glu Thr Ile Lys Asn Gly Thr Tyr Asp His Lys
145                 150                 155                 160

Glu Tyr Glu Glu Glu Ala Lys Leu Glu Arg Ser Lys Ile Asn Gly Val
                165                 170                 175

Lys Leu Glu Glu
            180

<210> SEQ ID NO 90
<211> LENGTH: 180
<212> TYPE: PRT
<213> ORGANISM: Influenza virus A
<220> FEATURE:
<223> OTHER INFORMATION: influenza A HA2 domain subtype H9 stem domain

<400> SEQUENCE: 90

Gly Leu Phe Gly Ala Ile Ala Gly Phe Ile Glu Gly Gly Trp Pro Gly
1               5                   10                  15

Leu Val Ala Gly Trp Tyr Gly Phe Gln His Ser Asn Asp Gln Gly Val
            20                  25                  30

Gly Met Ala Ala Asp Lys Gly Ser Thr Gln Lys Ala Ile Asp Lys Ile
        35                  40                  45

Thr Ser Lys Val Asn Asn Ile Ile Asp Lys Met Asn Lys Gln Tyr Glu
50                  55                  60

Val Ile Asp His Glu Phe Asn Glu Leu Glu Ala Arg Leu Asn Met Ile
65                  70                  75                  80

Asn Asn Lys Ile Asp Asp Gln Ile Gln Asp Ile Trp Ala Tyr Asn Ala
                85                  90                  95

Glu Leu Leu Val Leu Leu Glu Asn Gln Lys Thr Leu Asp Glu His Asp
            100                 105                 110

Ala Asn Val Asn Asn Leu Tyr Asn Lys Val Lys Arg Ala Leu Gly Ser
        115                 120                 125

Asn Ala Val Glu Asp Gly Asn Gly Cys Phe Glu Leu Tyr His Lys Cys
130                 135                 140

Asp Asp Gln Cys Met Glu Thr Ile Arg Asn Gly Thr Tyr Asp Arg Gln
145                 150                 155                 160

Lys Tyr Gln Glu Glu Ser Arg Leu Glu Arg Gln Lys Ile Glu Gly Val
                165                 170                 175

Lys Leu Glu Ser
            180

<210> SEQ ID NO 91
<211> LENGTH: 179
<212> TYPE: PRT
<213> ORGANISM: Influenza virus A
<220> FEATURE:
<223> OTHER INFORMATION: influenza A HA2 domain subtype H10 stem domain

<400> SEQUENCE: 91

Gly Leu Phe Gly Ala Ile Ala Gly Phe Ile Glu Asn Gly Trp Glu Gly
1               5                   10                  15

Met Val Asp Gly Trp Tyr Gly Phe Arg His Gln Asn Ala Gln Gly Thr
            20                  25                  30

Gly Gln Ala Ala Asp Tyr Lys Ser Thr Gln Ala Ala Ile Asp Gln Ile
        35                  40                  45

Thr Gly Lys Leu Asn Arg Leu Ile Glu Lys Thr Asn Thr Glu Phe Glu
    50                  55                  60

Ser Ile Glu Ser Glu Phe Ser Glu Thr Glu His Gln Ile Gly Asn Val
65                  70                  75                  80

Ile Asn Trp Thr Lys Asp Ser Ile Thr Asp Ile Trp Thr Tyr Asn Ala
                85                  90                  95

Glu Leu Leu Val Ala Met Glu Asn Gln His Thr Ile Asp Met Ala Asp
            100                 105                 110

Ser Glu Met Leu Asn Leu Tyr Glu Arg Val Arg Lys Gln Leu Arg Gln
        115                 120                 125

Asn Ala Glu Glu Asp Gly Lys Gly Cys Phe Glu Ile Tyr His Thr Cys
    130                 135                 140

Asp Asp Ser Cys Met Glu Ser Ile Arg Asn Asn Thr Tyr Asp His Ser
145                 150                 155                 160

Gln Tyr Arg Glu Glu Ala Leu Leu Asn Arg Leu Asn Ile Asn Pro Val
                165                 170                 175

Lys Leu Ser

<210> SEQ ID NO 92
<211> LENGTH: 181
<212> TYPE: PRT
<213> ORGANISM: Influenza virus A
<220> FEATURE:
<223> OTHER INFORMATION: influenza A HA2 domain subtype H11 stem domain

<400> SEQUENCE: 92

Gly Leu Phe Gly Ala Ile Ala Gly Phe Ile Glu Gly Gly Trp Pro Gly
1               5                   10                  15

Leu Ile Asn Gly Trp Tyr Gly Phe Gln His Arg Asp Glu Glu Gly Thr
            20                  25                  30

Gly Ile Ala Ala Asp Lys Glu Ser Thr Gln Lys Ala Ile Asp Gln Ile
        35                  40                  45

Thr Ser Lys Val Asn Asn Ile Val Asp Arg Met Asn Thr Asn Phe Glu
    50                  55                  60

Ser Val Gln His Glu Phe Ser Glu Ile Glu Glu Arg Ile Asn Gln Leu
65                  70                  75                  80

Ser Lys His Val Asp Asp Ser Val Val Asp Ile Trp Ser Tyr Asn Ala
                85                  90                  95

```
Gln Leu Leu Val Leu Leu Glu Asn Glu Lys Thr Leu Asp Leu His Asp
                100                 105                 110

Ser Asn Val Arg Asn Leu His Glu Lys Val Arg Met Leu Lys Asp
            115                 120                 125

Asn Ala Lys Asp Glu Gly Asn Gly Cys Phe Thr Phe Tyr His Lys Cys
130                 135                 140

Asp Asn Lys Cys Ile Glu Arg Val Arg Asn Gly Thr Tyr Asp His Lys
145                 150                 155                 160

Glu Phe Glu Glu Glu Ser Lys Ile Asn Arg Gln Glu Ile Glu Gly Val
                165                 170                 175

Lys Leu Asp Ser Ser
            180

<210> SEQ ID NO 93
<211> LENGTH: 180
<212> TYPE: PRT
<213> ORGANISM: Influenza virus A
<220> FEATURE:
<223> OTHER INFORMATION: influenza A HA2 domain subtype H12 stem domain

<400> SEQUENCE: 93

Gly Leu Phe Gly Ala Ile Ala Gly Phe Ile Glu Gly Gly Trp Pro Gly
1               5                   10                  15

Leu Val Ala Gly Trp Tyr Gly Phe Gln His Gln Asn Ala Glu Gly Thr
            20                  25                  30

Gly Ile Ala Ala Asp Arg Asp Ser Thr Gln Arg Ala Ile Asp Asn Met
        35                  40                  45

Gln Asn Lys Leu Asn Asn Val Ile Asp Lys Met Asn Lys Gln Phe Glu
    50                  55                  60

Val Val Asn His Glu Phe Ser Glu Val Glu Ser Arg Ile Asn Met Ile
65                  70                  75                  80

Asn Ser Lys Ile Asp Asp Gln Ile Thr Asp Ile Trp Ala Tyr Asn Ala
                85                  90                  95

Glu Leu Leu Val Leu Leu Glu Asn Gln Lys Thr Leu Asp Glu His Asp
                100                 105                 110

Ala Asn Val Arg Asn Leu His Asp Arg Val Arg Val Leu Arg Glu
            115                 120                 125

Asn Ala Ile Asp Thr Gly Asp Gly Cys Phe Glu Ile Leu His Lys Cys
130                 135                 140

Asp Asn Asn Cys Met Asp Thr Ile Arg Asn Gly Thr Tyr Asn His Lys
145                 150                 155                 160

Glu Tyr Glu Glu Glu Ser Lys Ile Glu Arg Gln Lys Val Asn Gly Val
                165                 170                 175

Lys Leu Glu Glu
            180

<210> SEQ ID NO 94
<211> LENGTH: 181
<212> TYPE: PRT
<213> ORGANISM: Influenza virus A
<220> FEATURE:
<223> OTHER INFORMATION: influenza A HA2 domain subtype H13 stem domain

<400> SEQUENCE: 94

Gly Leu Phe Gly Ala Ile Ala Gly Phe Ile Glu Gly Gly Trp Pro Gly
1               5                   10                  15

Leu Ile Asn Gly Trp Tyr Gly Phe Gln His Gln Asn Glu Gln Gly Thr
            20                  25                  30
```

Gly Ile Ala Ala Asp Lys Glu Ser Thr Gln Lys Ala Ile Asp Gln Ile
                35                  40                  45

Thr Thr Lys Ile Asn Asn Ile Ile Asp Lys Met Asn Gly Asn Tyr Asp
    50                  55                  60

Ser Ile Arg Gly Glu Phe Asn Gln Val Glu Lys Arg Ile Asn Met Leu
65                  70                  75                  80

Ala Asp Arg Ile Asp Asp Ala Val Thr Asp Ile Trp Ser Tyr Asn Ala
                85                  90                  95

Lys Leu Leu Val Leu Leu Glu Asn Asp Lys Thr Leu Asp Met His Asp
                100                 105                 110

Ala Asn Val Lys Asn Leu His Glu Gln Val Arg Arg Glu Leu Lys Asp
                115                 120                 125

Asn Ala Ile Asp Glu Gly Asn Gly Cys Phe Glu Leu Leu His Lys Cys
            130                 135                 140

Asn Asp Ser Cys Met Glu Thr Ile Arg Asn Gly Thr Tyr Asp His Thr
145                 150                 155                 160

Glu Tyr Ala Glu Glu Ser Lys Leu Lys Arg Gln Glu Ile Asp Gly Ile
                165                 170                 175

Lys Leu Lys Ser Glu
            180

<210> SEQ ID NO 95
<211> LENGTH: 179
<212> TYPE: PRT
<213> ORGANISM: Influenza virus A
<220> FEATURE:
<223> OTHER INFORMATION: influenza A HA2 domain subtype H14 stem domain

<400> SEQUENCE: 95

Gly Leu Phe Gly Ala Ile Ala Gly Phe Ile Glu Asn Gly Trp Gln Gly
1               5                   10                  15

Leu Ile Asp Gly Trp Tyr Gly Phe Arg His Gln Asn Ala Glu Gly Thr
                20                  25                  30

Gly Thr Ala Ala Asp Leu Lys Ser Thr Gln Ala Ala Ile Asp Gln Ile
                35                  40                  45

Asn Gly Lys Leu Asn Arg Leu Ile Glu Lys Thr Asn Glu Lys Tyr His
    50                  55                  60

Gln Ile Glu Lys Glu Phe Glu Gln Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Val Thr Asp
                100                 105                 110

Ser Glu Met Asn Lys Leu Phe Glu Arg Val Arg Arg Gln Leu Arg Glu
                115                 120                 125

Asn Ala Glu Asp Gln Gly Asn Gly Cys Phe Glu Ile Phe His Gln Cys
            130                 135                 140

Asp Asn Asn Cys Ile Glu Ser Ile Arg Asn Gly Thr Tyr Asp His Asn
145                 150                 155                 160

Ile Tyr Arg Asp Glu Ala Ile Asn Asn Arg Ile Lys Ile Asn Pro Val
                165                 170                 175

Thr Leu Thr

<210> SEQ ID NO 96
<211> LENGTH: 179

```
<212> TYPE: PRT
<213> ORGANISM: Influenza virus A
<220> FEATURE:
<223> OTHER INFORMATION: influenza A HA2 domain subtype H15 stem domain

<400> SEQUENCE: 96

Gly Leu Phe Gly Ala Ile Ala Gly Phe Ile Glu Asn Gly Trp Glu Gly
  1               5                  10                  15

Leu Ile Asp Gly Trp Tyr Gly Phe Arg His Gln Asn Ala Gln Gly Gln
             20                  25                  30

Gly Thr Ala Ala Asp Tyr Lys Ser Thr Gln Ala Ala Ile Asp Gln Ile
         35                  40                  45

Thr Gly Lys Leu Asn Arg Leu Ile Glu Lys Thr Asn Lys Gln Phe Glu
 50                  55                  60

Leu Ile Asp Asn Glu Phe Thr Glu Val Glu Gln Gln Ile Gly Asn Val
 65                  70                  75                  80

Ile Asn Trp Thr Arg Asp Ser Leu Thr Glu Ile Trp Ser Tyr Asn Ala
                 85                  90                  95

Glu Leu Leu Val Ala Met Glu Asn Gln His Thr Ile Asp Leu Ala Asp
            100                 105                 110

Ser Glu Met Asn Lys Leu Tyr Glu Arg Val Arg Arg Gln Leu Arg Glu
        115                 120                 125

Asn Ala Glu Glu Asp Gly Thr Gly Cys Phe Glu Ile Phe His Arg Cys
130                 135                 140

Asp Asp Gln Cys Met Glu Ser Ile Arg Asn Asn Thr Tyr Asn His Thr
145                 150                 155                 160

Glu Tyr Arg Gln Glu Ala Leu Gln Asn Arg Ile Met Ile Asn Pro Val
                165                 170                 175

Lys Leu Ser

<210> SEQ ID NO 97
<211> LENGTH: 181
<212> TYPE: PRT
<213> ORGANISM: Influenza virus A
<220> FEATURE:
<223> OTHER INFORMATION: influenza A HA2 domain subtype H16 stem domain

<400> SEQUENCE: 97

Gly Leu Phe Gly Ala Ile Ala Gly Phe Ile Glu Gly Gly Trp Pro Gly
  1               5                  10                  15

Leu Ile Asn Gly Trp Tyr Gly Phe Gln His Gln Asn Glu Gln Gly Thr
             20                  25                  30

Gly Ile Ala Ala Asp Lys Ala Ser Thr Gln Lys Ala Ile Asn Glu Ile
         35                  40                  45

Thr Thr Lys Ile Asn Asn Ile Ile Glu Lys Met Asn Gly Asn Tyr Asp
 50                  55                  60

Ser Ile Arg Gly Glu Phe Asn Gln Val Glu Lys Arg Ile Asn Met Leu
 65                  70                  75                  80

Ala Asp Arg Val Asp Asp Ala Val Thr Asp Ile Trp Ser Tyr Asn Ala
                 85                  90                  95

Lys Leu Leu Val Leu Leu Glu Asn Asp Arg Thr Leu Asp Leu His Asp
            100                 105                 110

Ala Asn Val Arg Asn Leu His Asp Gln Val Lys Arg Ala Leu Lys Ser
        115                 120                 125

Asn Ala Ile Asp Glu Gly Asp Gly Cys Phe Asn Leu Leu His Lys Cys
130                 135                 140
```

```
Asn Asp Ser Cys Met Glu Thr Ile Arg Asn Gly Thr Tyr Asn His Glu
145                 150                 155                 160

Asp Tyr Arg Glu Glu Ser Gln Leu Lys Arg Gln Glu Ile Glu Gly Ile
                165                 170                 175

Lys Leu Lys Thr Glu
            180

<210> SEQ ID NO 98
<211> LENGTH: 5
<212> TYPE: PRT
<213> ORGANISM: Influenza virus A
<220> FEATURE:
<223> OTHER INFORMATION: influenza A HA2 domain subtype H1 Luminal
      domain

<400> SEQUENCE: 98

Met Gly Ile Tyr Gln
1               5

<210> SEQ ID NO 99
<211> LENGTH: 5
<212> TYPE: PRT
<213> ORGANISM: Influenza virus A
<220> FEATURE:
<223> OTHER INFORMATION: influenza A HA2 domain subtype H2 Luminal
      domain

<400> SEQUENCE: 99

Met Gly Val Tyr Gln
1               5

<210> SEQ ID NO 100
<211> LENGTH: 5
<212> TYPE: PRT
<213> ORGANISM: Influenza virus A
<220> FEATURE:
<223> OTHER INFORMATION: influenza A HA2 domain subtype H3 Luminal
      domain

<400> SEQUENCE: 100

Ser Gly Tyr Lys Asp
1               5

<210> SEQ ID NO 101
<211> LENGTH: 5
<212> TYPE: PRT
<213> ORGANISM: Influenza virus A
<220> FEATURE:
<223> OTHER INFORMATION: influenza A HA2 domain subtype H4 Luminal
      domain

<400> SEQUENCE: 101

Gln Gly Tyr Lys Asp
1               5

<210> SEQ ID NO 102
<211> LENGTH: 5
<212> TYPE: PRT
<213> ORGANISM: Influenza virus A
<220> FEATURE:
<223> OTHER INFORMATION: influenza A HA2 domain subtype H5 Luminal
      domain

<400> SEQUENCE: 102

Met Gly Val Tyr Gln
1               5
```

<210> SEQ ID NO 103
<211> LENGTH: 5
<212> TYPE: PRT
<213> ORGANISM: Influenza virus A
<220> FEATURE:
<223> OTHER INFORMATION: influenza A HA2 domain subtype H6 Luminal
      domain

<400> SEQUENCE: 103

Leu Gly Val Tyr Gln
1               5

<210> SEQ ID NO 104
<211> LENGTH: 5
<212> TYPE: PRT
<213> ORGANISM: Influenza virus A
<220> FEATURE:
<223> OTHER INFORMATION: influenza A HA2 domain subtype H7 Luminal
      domain

<400> SEQUENCE: 104

Ser Gly Tyr Lys Asp
1               5

<210> SEQ ID NO 105
<211> LENGTH: 5
<212> TYPE: PRT
<213> ORGANISM: Influenza virus A
<220> FEATURE:
<223> OTHER INFORMATION: influenza A HA2 domain subtype H8 Luminal
      domain

<400> SEQUENCE: 105

Asn Thr Thr Tyr Lys
1               5

<210> SEQ ID NO 106
<211> LENGTH: 5
<212> TYPE: PRT
<213> ORGANISM: Influenza virus A
<220> FEATURE:
<223> OTHER INFORMATION: influenza A HA2 domain subtype H9 Luminal
      domain

<400> SEQUENCE: 106

Glu Gly Thr Tyr Lys
1               5

<210> SEQ ID NO 107
<211> LENGTH: 5
<212> TYPE: PRT
<213> ORGANISM: Influenza virus A
<220> FEATURE:
<223> OTHER INFORMATION: influenza A HA2 domain subtype H10 Luminal
      domain

<400> SEQUENCE: 107

Ser Gly Tyr Lys Asp
1               5

<210> SEQ ID NO 108
<211> LENGTH: 5
<212> TYPE: PRT
<213> ORGANISM: Influenza virus A
<220> FEATURE:
<223> OTHER INFORMATION: influenza A HA2 domain subtype H11 Luminal
      domain

```
<400> SEQUENCE: 108

Gly Asn Val Tyr Lys
1               5

<210> SEQ ID NO 109
<211> LENGTH: 5
<212> TYPE: PRT
<213> ORGANISM: Influenza virus A
<220> FEATURE:
<223> OTHER INFORMATION: influenza A HA2 domain subtype H12 Luminal
      domain

<400> SEQUENCE: 109

Asn Ser Thr Tyr Lys
1               5

<210> SEQ ID NO 110
<211> LENGTH: 5
<212> TYPE: PRT
<213> ORGANISM: Influenza virus A
<220> FEATURE:
<223> OTHER INFORMATION: influenza A HA2 domain subtype H13 Luminal
      domain

<400> SEQUENCE: 110

Asp Asn Val Tyr Lys
1               5

<210> SEQ ID NO 111
<211> LENGTH: 5
<212> TYPE: PRT
<213> ORGANISM: Influenza virus A
<220> FEATURE:
<223> OTHER INFORMATION: influenza A HA2 domain subtype H14 Luminal
      domain

<400> SEQUENCE: 111

Met Gly Tyr Lys Asp
1               5

<210> SEQ ID NO 112
<211> LENGTH: 5
<212> TYPE: PRT
<213> ORGANISM: Influenza virus A
<220> FEATURE:
<223> OTHER INFORMATION: influenza A HA2 domain subtype H15 Luminal
      domain

<400> SEQUENCE: 112

Ser Gly Tyr Lys Asp
1               5

<210> SEQ ID NO 113
<211> LENGTH: 5
<212> TYPE: PRT
<213> ORGANISM: Influenza virus A
<220> FEATURE:
<223> OTHER INFORMATION: influenza A HA2 domain subtype H16 Luminal
      domain

<400> SEQUENCE: 113

Asp Asn Val Tyr Lys
1               5

<210> SEQ ID NO 114
<211> LENGTH: 27
<212> TYPE: PRT
```

```
<213> ORGANISM: Influenza virus A
<220> FEATURE:
<223> OTHER INFORMATION: influenza A HA2 domain subtype H1 transmembrane
      domain

<400> SEQUENCE: 114

Ile Leu Ala Ile Tyr Ser Thr Val Ala Ser Ser Leu Val Leu Val
1               5                   10                  15

Ser Leu Gly Ala Ile Ser Phe Trp Met Cys Ser
            20                  25

<210> SEQ ID NO 115
<211> LENGTH: 27
<212> TYPE: PRT
<213> ORGANISM: Influenza virus A
<220> FEATURE:
<223> OTHER INFORMATION: influenza A HA2 domain subtype H2 transmembrane
      domain

<400> SEQUENCE: 115

Ile Leu Ala Ile Tyr Ala Thr Val Ala Gly Ser Leu Ser Leu Ala Ile
1               5                   10                  15

Met Ile Ala Gly Ile Ser Leu Trp Met Cys Ser
            20                  25

<210> SEQ ID NO 116
<211> LENGTH: 27
<212> TYPE: PRT
<213> ORGANISM: Influenza virus A
<220> FEATURE:
<223> OTHER INFORMATION: influenza A HA2 domain subtype H3 transmembrane
      domain

<400> SEQUENCE: 116

Trp Ile Leu Trp Ile Ser Phe Ala Ile Ser Cys Phe Leu Leu Cys Val
1               5                   10                  15

Val Leu Leu Gly Phe Ile Met Trp Ala Cys Gln
            20                  25

<210> SEQ ID NO 117
<211> LENGTH: 27
<212> TYPE: PRT
<213> ORGANISM: Influenza virus A
<220> FEATURE:
<223> OTHER INFORMATION: influenza A HA2 domain subtype H4 transmembrane
      domain

<400> SEQUENCE: 117

Ile Ile Leu Trp Ile Ser Phe Ser Ile Ser Cys Phe Leu Leu Val Ala
1               5                   10                  15

Leu Leu Leu Ala Phe Ile Leu Trp Ala Cys Gln
            20                  25

<210> SEQ ID NO 118
<211> LENGTH: 27
<212> TYPE: PRT
<213> ORGANISM: Influenza virus A
<220> FEATURE:
<223> OTHER INFORMATION: influenza A HA2 domain subtype H5 transmembrane
      domain

<400> SEQUENCE: 118

Ile Leu Ser Ile Tyr Ser Thr Val Ala Ser Ser Leu Ala Leu Ala Ile
1               5                   10                  15

Met Ile Ala Gly Leu Ser Phe Trp Met Cys Ser
```

20                  25

<210> SEQ ID NO 119
<211> LENGTH: 27
<212> TYPE: PRT
<213> ORGANISM: Influenza virus A
<220> FEATURE:
<223> OTHER INFORMATION: influenza A HA2 domain subtype H6 transmembrane
      domain

<400> SEQUENCE: 119

Ile Leu Ala Ile Tyr Ser Thr Val Ser Ser Leu Val Leu Val Gly
1               5                   10                  15

Leu Ile Ile Ala Val Gly Leu Trp Met Cys Ser
            20                  25

<210> SEQ ID NO 120
<211> LENGTH: 27
<212> TYPE: PRT
<213> ORGANISM: Influenza virus A
<220> FEATURE:
<223> OTHER INFORMATION: influenza A HA2 domain subtype H7 transmembrane
      domain

<400> SEQUENCE: 120

Val Ile Leu Trp Phe Ser Phe Gly Ala Ser Cys Phe Leu Leu Leu Ala
1               5                   10                  15

Ile Ala Met Gly Leu Val Phe Ile Cys Val Lys
            20                  25

<210> SEQ ID NO 121
<211> LENGTH: 27
<212> TYPE: PRT
<213> ORGANISM: Influenza virus A
<220> FEATURE:
<223> OTHER INFORMATION: influenza A HA2 domain subtype H8 transmembrane
      domain

<400> SEQUENCE: 121

Ile Leu Ser Ile Tyr Ser Thr Val Ala Ala Ser Leu Cys Leu Ala Ile
1               5                   10                  15

Leu Ile Ala Gly Gly Leu Ile Leu Gly Met Gln
            20                  25

<210> SEQ ID NO 122
<211> LENGTH: 27
<212> TYPE: PRT
<213> ORGANISM: Influenza virus A
<220> FEATURE:
<223> OTHER INFORMATION: influenza A HA2 domain subtype H9 transmembrane
      domain

<400> SEQUENCE: 122

Ile Leu Thr Ile Tyr Ser Thr Val Ala Ser Ser Leu Val Leu Ala Met
1               5                   10                  15

Gly Phe Ala Ala Phe Leu Phe Trp Ala Met Ser
            20                  25

<210> SEQ ID NO 123
<211> LENGTH: 27
<212> TYPE: PRT
<213> ORGANISM: Influenza virus A
<220> FEATURE:
<223> OTHER INFORMATION: influenza A HA2 domain subtype H10
      transmembrane domain

```
<400> SEQUENCE: 123

Ile Ile Leu Trp Phe Ser Phe Gly Glu Ser Cys Phe Val Leu Leu Ala
 1               5                  10                  15

Val Val Met Gly Leu Val Phe Phe Cys Leu Lys
                20                  25

<210> SEQ ID NO 124
<211> LENGTH: 27
<212> TYPE: PRT
<213> ORGANISM: Influenza virus A
<220> FEATURE:
<223> OTHER INFORMATION: influenza A HA2 domain subtype H11
      transmembrane domain

<400> SEQUENCE: 124

Ile Leu Ser Ile Tyr Ser Cys Ile Ala Ser Ser Leu Val Leu Ala Ala
 1               5                  10                  15

Leu Ile Met Gly Phe Met Phe Trp Ala Cys Ser
                20                  25

<210> SEQ ID NO 125
<211> LENGTH: 28
<212> TYPE: PRT
<213> ORGANISM: Influenza virus A
<220> FEATURE:
<223> OTHER INFORMATION: influenza A HA2 domain subtype H12
      transmembrane domain

<400> SEQUENCE: 125

Ile Leu Ser Ile Tyr Ser Ser Val Ala Ser Ser Leu Val Leu Leu Leu
 1               5                  10                  15

Met Ile Ile Gly Gly Phe Ile Phe Gly Cys Gln Asn
                20                  25

<210> SEQ ID NO 126
<211> LENGTH: 28
<212> TYPE: PRT
<213> ORGANISM: Influenza virus A
<220> FEATURE:
<223> OTHER INFORMATION: influenza A HA2 domain subtype H13
      transmembrane domain

<400> SEQUENCE: 126

Ala Leu Ser Ile Tyr Ser Cys Ile Ala Ser Ser Val Val Leu Val Gly
 1               5                  10                  15

Leu Ile Leu Ser Phe Ile Met Trp Ala Cys Ser Ser
                20                  25

<210> SEQ ID NO 127
<211> LENGTH: 27
<212> TYPE: PRT
<213> ORGANISM: Influenza virus A
<220> FEATURE:
<223> OTHER INFORMATION: influenza A HA2 domain subtype H14
      transmembrane domain

<400> SEQUENCE: 127

Ile Ile Leu Trp Ile Ser Phe Ser Met Ser Cys Phe Val Phe Val Ala
 1               5                  10                  15

Leu Ile Leu Gly Phe Val Leu Trp Ala Cys Gln
                20                  25

<210> SEQ ID NO 128
<211> LENGTH: 28
```

```
<212> TYPE: PRT
<213> ORGANISM: Influenza virus A
<220> FEATURE:
<223> OTHER INFORMATION: influenza A HA2 domain subtype H15
      transmembrane domain

<400> SEQUENCE: 128

Val Ile Leu Trp Phe Ser Phe Gly Ala Ser Cys Val Met Leu Leu Ala
1               5                   10                  15
Ile Ala Met Gly Leu Ile Phe Met Cys Val Lys Asn
            20                  25

<210> SEQ ID NO 129
<211> LENGTH: 27
<212> TYPE: PRT
<213> ORGANISM: Influenza virus A
<220> FEATURE:
<223> OTHER INFORMATION: influenza A HA2 domain subtype H16
      transmembrane domain

<400> SEQUENCE: 129

Val Leu Ser Ile Tyr Ser Cys Ile Ala Ser Ser Ile Val Leu Val Gly
1               5                   10                  15
Leu Ile Leu Ala Phe Ile Met Trp Ala Cys Ser
            20                  25

<210> SEQ ID NO 130
<211> LENGTH: 10
<212> TYPE: PRT
<213> ORGANISM: Influenza virus A
<220> FEATURE:
<223> OTHER INFORMATION: influenza A HA2 domain subtype H1 cytoplasmic
      domain

<400> SEQUENCE: 130

Asn Gly Ser Leu Gln Cys Arg Ile Cys Ile
1               5                   10

<210> SEQ ID NO 131
<211> LENGTH: 10
<212> TYPE: PRT
<213> ORGANISM: Influenza virus A
<220> FEATURE:
<223> OTHER INFORMATION: influenza A HA2 domain subtype H2 cytoplasmic
      domain

<400> SEQUENCE: 131

Asn Gly Ser Leu Gln Cys Arg Ile Cys Ile
1               5                   10

<210> SEQ ID NO 132
<211> LENGTH: 10
<212> TYPE: PRT
<213> ORGANISM: Influenza virus A
<220> FEATURE:
<223> OTHER INFORMATION: influenza A HA2 domain subtype H3 cytoplasmic
      domain

<400> SEQUENCE: 132

Arg Gly Asn Ile Arg Cys Asn Ile Cys Ile
1               5                   10

<210> SEQ ID NO 133
<211> LENGTH: 10
<212> TYPE: PRT
<213> ORGANISM: Influenza virus A
<220> FEATURE:
```

```
<223> OTHER INFORMATION: influenza A HA2 domain subtype H4 cytoplasmic
      domain

<400> SEQUENCE: 133

Asn Gly Asn Ile Arg Cys Gln Ile Cys Ile
1               5                   10

<210> SEQ ID NO 134
<211> LENGTH: 10
<212> TYPE: PRT
<213> ORGANISM: Influenza virus A
<220> FEATURE:
<223> OTHER INFORMATION: influenza A HA2 domain subtype H5 cytoplasmic
      domain

<400> SEQUENCE: 134

Asn Gly Ser Leu Gln Cys Arg Ile Cys Ile
1               5                   10

<210> SEQ ID NO 135
<211> LENGTH: 10
<212> TYPE: PRT
<213> ORGANISM: Influenza virus A
<220> FEATURE:
<223> OTHER INFORMATION: influenza A HA2 domain subtype H6 cytoplasmic
      domain

<400> SEQUENCE: 135

Asn Gly Ser Met Gln Cys Arg Ile Cys Ile
1               5                   10

<210> SEQ ID NO 136
<211> LENGTH: 10
<212> TYPE: PRT
<213> ORGANISM: Influenza virus A
<220> FEATURE:
<223> OTHER INFORMATION: influenza A HA2 domain subtype H7 cytoplasmic
      domain

<400> SEQUENCE: 136

Asn Gly Asn Met Arg Cys Thr Ile Cys Ile
1               5                   10

<210> SEQ ID NO 137
<211> LENGTH: 10
<212> TYPE: PRT
<213> ORGANISM: Influenza virus A
<220> FEATURE:
<223> OTHER INFORMATION: influenza A HA2 domain subtype H8 cytoplasmic
      domain

<400> SEQUENCE: 137

Asn Gly Ser Cys Arg Cys Met Phe Cys Ile
1               5                   10

<210> SEQ ID NO 138
<211> LENGTH: 10
<212> TYPE: PRT
<213> ORGANISM: Influenza virus A
<220> FEATURE:
<223> OTHER INFORMATION: influenza A HA2 domain subtype H9 cytoplasmic
      domain

<400> SEQUENCE: 138

Asn Gly Ser Cys Arg Cys Asn Ile Cys Ile
1               5                   10
```

```
<210> SEQ ID NO 139
<211> LENGTH: 10
<212> TYPE: PRT
<213> ORGANISM: Influenza virus A
<220> FEATURE:
<223> OTHER INFORMATION: influenza A HA2 domain subtype H10 cytoplasmic
      domain

<400> SEQUENCE: 139

Asn Gly Asn Met Arg Cys Thr Ile Cys Ile
  1               5                  10

<210> SEQ ID NO 140
<211> LENGTH: 10
<212> TYPE: PRT
<213> ORGANISM: Influenza virus A
<220> FEATURE:
<223> OTHER INFORMATION: influenza A HA2 domain subtype H11 cytoplasmic
      domain

<400> SEQUENCE: 140

Asn Gly Ser Cys Arg Cys Thr Ile Cys Ile
  1               5                  10

<210> SEQ ID NO 141
<211> LENGTH: 9
<212> TYPE: PRT
<213> ORGANISM: Influenza virus A
<220> FEATURE:
<223> OTHER INFORMATION: influenza A HA2 domain subtype H12 cytoplasmic
      domain

<400> SEQUENCE: 141

Gly Asn Val Arg Cys Thr Phe Cys Ile
  1               5

<210> SEQ ID NO 142
<211> LENGTH: 9
<212> TYPE: PRT
<213> ORGANISM: Influenza virus A
<220> FEATURE:
<223> OTHER INFORMATION: influenza A HA2 domain subtype H13 cytoplasmic
      domain

<400> SEQUENCE: 142

Gly Asn Cys Arg Phe Asn Val Cys Ile
  1               5

<210> SEQ ID NO 143
<211> LENGTH: 10
<212> TYPE: PRT
<213> ORGANISM: Influenza virus A
<220> FEATURE:
<223> OTHER INFORMATION: influenza A HA2 domain subtype H14 cytoplasmic
      domain

<400> SEQUENCE: 143

Asn Gly Asn Ile Arg Cys Gln Ile Cys Ile
  1               5                  10

<210> SEQ ID NO 144
<211> LENGTH: 9
<212> TYPE: PRT
<213> ORGANISM: Influenza virus A
<220> FEATURE:
<223> OTHER INFORMATION: influenza A HA2 domain subtype H15 cytoplasmic
      domain

<400> SEQUENCE: 144
```

```
Gly Asn Leu Arg Cys Thr Ile Cys Ile
 1               5

<210> SEQ ID NO 145
<211> LENGTH: 10
<212> TYPE: PRT
<213> ORGANISM: Influenza virus A
<220> FEATURE:
<223> OTHER INFORMATION: influenza A HA2 domain subtype H16 cytoplasmic
      domain

<400> SEQUENCE: 145

Asn Gly Ser Cys Arg Phe Asn Val Cys Ile
 1               5                  10

<210> SEQ ID NO 146
<211> LENGTH: 23
<212> TYPE: PRT
<213> ORGANISM: Artificial Sequence
<220> FEATURE:
<223> OTHER INFORMATION: sequence of HA1 N-terminal stem segment
<220> FEATURE:
<221> NAME/KEY: VARIANT
<222> LOCATION: 1
<223> OTHER INFORMATION: Xaa = Tyr or His
<220> FEATURE:
<221> NAME/KEY: VARIANT
<222> LOCATION: 2
<223> OTHER INFORMATION: Xaa = His, Leu or Gln
<220> FEATURE:
<221> NAME/KEY: VARIANT
<222> LOCATION: 3.....20
<223> OTHER INFORMATION: Xaa = any amino acid
<220> FEATURE:
<221> NAME/KEY: VARIANT
<222> LOCATION: 21
<223> OTHER INFORMATION: Xaa = any amino acid or absent
<220> FEATURE:
<221> NAME/KEY: VARIANT
<222> LOCATION: 22
<223> OTHER INFORMATION: Xaa = any amino acid or absent
<220> FEATURE:
<221> NAME/KEY: VARIANT
<222> LOCATION: 23
<223> OTHER INFORMATION: Xaa = His, Ser, Gln, Thr or Asn

<400> SEQUENCE: 146

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa
                20

<210> SEQ ID NO 147
<211> LENGTH: 2
<212> TYPE: PRT
<213> ORGANISM: Artificial Sequence
<220> FEATURE:
<223> OTHER INFORMATION: sequence of HA1 c-terminal stem segment
<220> FEATURE:
<221> NAME/KEY: VARIANT
<222> LOCATION: 1
<223> OTHER INFORMATION: Xaa = Thr, Ser, Asn, Asp, Pro or Lys
<220> FEATURE:
<221> NAME/KEY: VARIANT
<222> LOCATION: 2
<223> OTHER INFORMATION: Xaa = Leu, Met, Lys or Arg

<400> SEQUENCE: 147

Xaa Xaa
 1
```

```
<210> SEQ ID NO 148
<211> LENGTH: 4
<212> TYPE: PRT
<213> ORGANISM: Artificial Sequence
<220> FEATURE:
<223> OTHER INFORMATION: sequence of HA2 domain
<220> FEATURE:
<221> NAME/KEY: VARIANT
<222> LOCATION: 1
<223> OTHER INFORMATION: Xaa = Val or Ile
<220> FEATURE:
<221> NAME/KEY: VARIANT
<222> LOCATION: 2
<223> OTHER INFORMATION: Xaa = Asp, Asn or Ala

<400> SEQUENCE: 148

Xaa Xaa Gly Trp
 1

<210> SEQ ID NO 149
<211> LENGTH: 19
<212> TYPE: PRT
<213> ORGANISM: Artificial Sequence
<220> FEATURE:
<223> OTHER INFORMATION: sequence of HA2 domain
<220> FEATURE:
<221> NAME/KEY: VARIANT
<222> LOCATION: 1
<223> OTHER INFORMATION: Xaa = Lys, Gln, Arg, Leu or Tyr
<220> FEATURE:
<221> NAME/KEY: VARIANT
<222> LOCATION: 2, 3, 6, 10
<223> OTHER INFORMATION: Xaa = any amino acid
<220> FEATURE:
<221> NAME/KEY: VARIANT
<222> LOCATION: 11
<223> OTHER INFORMATION: Xaa = Ile, Val or Met
<220> FEATURE:
<221> NAME/KEY: VARIANT
<222> LOCATION: 12
<223> OTHER INFORMATION: Xaa = Thr, Gln or Asn
<220> FEATURE:
<221> NAME/KEY: VARIANT
<222> LOCATION: 13
<223> OTHER INFORMATION: Xaa = any amino acid
<220> FEATURE:
<221> NAME/KEY: VARIANT
<222> LOCATION: 15
<223> OTHER INFORMATION: Xaa = Val or Leu
<220> FEATURE:
<221> NAME/KEY: VARIANT
<222> LOCATION: 17
<223> OTHER INFORMATION: Xaa = any amino acid
<220> FEATURE:
<221> NAME/KEY: VARIANT
<222> LOCATION: 18
<223> OTHER INFORMATION: Xaa = Val, Ile or Leu
<220> FEATURE:
<221> NAME/KEY: VARIANT
<222> LOCATION: 19
<223> OTHER INFORMATION: Xaa = Val or Ile

<400> SEQUENCE: 149

Xaa Xaa Xaa Thr Gln Xaa Ala Ile Asp Xaa Xaa Xaa Xaa Lys Xaa Asn
 1               5                  10                  15

Xaa Xaa Xaa

<210> SEQ ID NO 150
<211> LENGTH: 15
<212> TYPE: PRT
<213> ORGANISM: Influenza virus B
<220> FEATURE:
<223> OTHER INFORMATION: Signal peptide of Influenza B HA construct
``` variant Arg50-Ser277

<400> SEQUENCE: 150

Met Lys Ala Ile Ile Val Ile Leu Met Val Val Thr Ser Asn Ala
1               5                   10                  15

<210> SEQ ID NO 151
<211> LENGTH: 15
<212> TYPE: PRT
<213> ORGANISM: Influenza virus B
<220> FEATURE:
<223> OTHER INFORMATION: Signal peptide of Influenza B HA construct
      variant Ala66-Trp271

<400> SEQUENCE: 151

Met Lys Ala Ile Ile Val Ile Leu Met Val Val Thr Ser Asn Ala
1               5                   10                  15

<210> SEQ ID NO 152
<211> LENGTH: 15
<212> TYPE: PRT
<213> ORGANISM: Influenza virus B
<220> FEATURE:
<223> OTHER INFORMATION: Signal peptide of Influenza B HA construct
      variant Lys80-Ser277

<400> SEQUENCE: 152

Met Lys Ala Ile Ile Val Ile Leu Met Val Val Thr Ser Asn Ala
1               5                   10                  15

<210> SEQ ID NO 153
<211> LENGTH: 15
<212> TYPE: PRT
<213> ORGANISM: Influenza virus B
<220> FEATURE:
<223> OTHER INFORMATION: Signal peptide of Influenza B HA construct
      variant Arg80-Ser277

<400> SEQUENCE: 153

Met Lys Ala Ile Ile Val Ile Leu Met Val Val Thr Ser Asn Ala
1               5                   10                  15

<210> SEQ ID NO 154
<211> LENGTH: 50
<212> TYPE: PRT
<213> ORGANISM: Influenza virus B
<220> FEATURE:
<223> OTHER INFORMATION: Influenza B HA construct variant R50-S277 HA1
      N-terminal Stem Segment

<400> SEQUENCE: 154

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg
    50

<210> SEQ ID NO 155
<211> LENGTH: 66
<212> TYPE: PRT
<213> ORGANISM: Influenza virus B
<220> FEATURE:
<223> OTHER INFORMATION: Influenza B HA construct variant A66-W271 HA N-terminal Stem Segment

<400> SEQUENCE: 155

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala
65

<210> SEQ ID NO 156
<211> LENGTH: 80
<212> TYPE: PRT
<213> ORGANISM: Influenza virus B
<220> FEATURE:
<223> OTHER INFORMATION: HA1 N-terminal Stem Segment of Influenza B HA
      construct variant Lys80-Ser277

<400> SEQUENCE: 156

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Lys Ile Pro Ser Ala Lys
65                  70                  75                  80

<210> SEQ ID NO 157
<211> LENGTH: 80
<212> TYPE: PRT
<213> ORGANISM: Influenza virus B
<220> FEATURE:
<223> OTHER INFORMATION: HA1 N-terminal Stem Segment of Influenza B HA
      construct variant Arg80-Ser277

<400> SEQUENCE: 157

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Lys Ile Pro Ser Ala Arg
65                  70                  75                  80

<210> SEQ ID NO 158
<211> LENGTH: 68
<212> TYPE: PRT
<213> ORGANISM: Influenza virus B
<220> FEATURE:
<223> OTHER INFORMATION: HA1 C-terminal Stem Segment of Influenza B HA
      construct variant Arg50-Ser277

```
<400> SEQUENCE: 158

Ser Lys Val Ile Lys Gly Ser Leu Pro Leu Ile Gly Glu Ala Asp Cys
1               5                   10                  15

Le

Ser Ala Val Glu Ile Gly Asn Gly Cys Phe Glu Thr Lys His Lys Cys
130                 135                 140

Asn Gln Thr Cys Leu Asp Arg Ile Ala Ala Gly Thr Phe Asp Ala Gly
145                 150                 155                 160

Glu Phe Ser Leu Pro Thr Phe Asp Ser Leu Asn Ile Thr Ala Ala Ser
                165                 170                 175

Leu Asn Asp Asp Gly Leu Asp Asn His Thr Ile Leu Leu Tyr Tyr Ser
            180                 185                 190

Thr Ala Ala Ser Ser Leu Ala Val Thr Leu Met Ile Ala Ile Phe Val
        195                 200                 205

Val Tyr Met Val Ser Arg Asp Asn Val Ser Cys Ser Ile Cys Leu
    210                 215                 220

<210> SEQ ID NO 161
<211> LENGTH: 179
<212> TYPE: PRT
<213> ORGANISM: Influenza virus B
<220> FEATURE:
<223> OTHER INFORMATION: Stem domain of Influenza B HA2 domain subtype
      HA2

<400> SEQUENCE: 161

Gly Phe Phe Gly Ala Ile Ala Gly Phe Leu Glu Gly Gly Trp Glu Gly
1               5                   10                  15

Met Ile Ala Gly Trp His Gly Tyr Thr Ser His Gly Ala His Gly Val
            20                  25                  30

Ala Val Ala Ala Asp Leu Lys Ser Thr Gln Glu Ala Ile Asn Lys Ile
        35                  40                  45

Thr Lys Asn Leu Asn Ser Leu Ser Glu Leu Glu Val Lys Asn Leu Gln
    50                  55                  60

Arg Leu Ser Gly Ala Met Asp Glu Leu His Asn Glu Ile Leu Glu Leu
65                  70                  75                  80

Asp Glu Lys Val Asp Asp Leu Arg Ala Asp Thr Ile Ser Ser Gln Ile
                85                  90                  95

Glu Leu Ala Val Leu Leu Ser Asn Glu Gly Ile Ile Asn Ser Glu Asp
            100                 105                 110

Glu His Leu Leu Ala Leu Glu Arg Lys Leu Lys Lys Met Leu Gly Pro
        115                 120                 125

Ser Ala Val Glu Ile Gly Asn Gly Cys Phe Glu Thr Lys His Lys Cys
130                 135                 140

Asn Gln Thr Cys Leu Asp Arg Ile Ala Ala Gly Thr Phe Asp Ala Gly
145                 150                 155                 160

Glu Phe Ser Leu Pro Thr Phe Asp Ser Leu Asn Ile Thr Ala Ala Ser
                165                 170                 175

Leu Asn Asp

<210> SEQ ID NO 162
<211> LENGTH: 5
<212> TYPE: PRT
<213> ORGANISM: Influenza virus B
<220> FEATURE:
<223> OTHER INFORMATION: luminal domain of Influenza B HA2 domain
      subtype HA2

<400> SEQUENCE: 162

Asp Gly Leu Asp Asn
1               5

```
<210> SEQ ID NO 163
<211> LENGTH: 28
<212> TYPE: PRT
<213> ORGANISM: Influenza virus B
<220> FEATURE:
<223> OTHER INFORMATION: transmembrane domain of Influenza B HA2 domain
      subtype HA2

<400> SEQUENCE: 163

His Thr Ile Leu Leu Tyr Tyr Ser Thr Ala Ala Ser Ser Leu Ala Val
  1               5                  10                  15

Thr Leu Met Ile Ala Ile Phe Val Val Tyr Met Val
             20                  25

<210> SEQ ID NO 164
<211> LENGTH: 11
<212> TYPE: PRT
<213> ORGANISM: Influenza virus B
<220> FEATURE:
<223> OTHER INFORMATION: cytoplasmic domain of Influenza B HA2 domain
      subtype HA2

<400> SEQUENCE: 164

Ser Arg Asp Asn Val Ser Cys Ser Ile Cys Leu
  1               5                  10

<210> SEQ ID NO 165
<211> LENGTH: 23
<212> TYPE: PRT
<213> ORGANISM: Artificial Sequence
<220> FEATURE:
<223> OTHER INFORMATION: turn loop linker sequence

<400> SEQUENCE: 165

Ile Thr Pro Asn Gly Ser Ile Pro Asn Asp Lys Pro Phe Gln Asn Val
  1               5                  10                  15

Asn Lys Ile Thr Tyr Gly Ala
             20

<210> SEQ ID NO 166
<211> LENGTH: 6
<212> TYPE: PRT
<213> ORGANISM: Artificial Sequence
<220> FEATURE:
<223> OTHER INFORMATION: His tag

<400> SEQUENCE: 166

His His His His His His
  1               5

<210> SEQ ID NO 167
<211> LENGTH: 29
<212> TYPE: PRT
<213> ORGANISM: Artificial Sequence
<220> FEATURE:
<223> OTHER INFORMATION: example of a foldon domain

<400> SEQUENCE: 167

Gly Ser Gly Tyr Ile Pro Glu Ala Pro Arg Asp Gly Gln Ala Tyr Val
  1               5                  10                  15

Arg Lys Asp Gly Glu Trp Val Leu Leu Ser Thr Phe Leu
             20                  25

<210> SEQ ID NO 168
<211> LENGTH: 7
<212> TYPE: PRT
```

```
<213> ORGANISM: Artificial Sequence
<220> FEATURE:
<223> OTHER INFORMATION: thrombin cleavage site

<400> SEQUENCE: 168

Leu Val Pro Arg Gly Ser Pro
 1               5

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H1(no Cys) Short Stem Domain sequence

<400> SEQUENCE: 177

Asp Thr Ile Cys Ile Gly Tyr His Ala Asn Asn Ser Thr Asp Thr Val
 1               5                  10                  15
```

Asp Thr Val Leu Glu Lys Asn Val Thr Val Thr His Ser Val Asn Leu
            20                  25                  30

Leu Glu Asp Ser His Asn Gly Lys Leu
        35                  40

<210> SEQ ID NO 178
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H1(no Cys-delta 1) Short Stem Domain sequence

<400> SEQUENCE: 178

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu
        35                  40

<210> SEQ ID NO 179
<211> LENGTH: 40
<212> TYPE: PRT
<213> ORGANISM: Influenza virus A
<220> FEATURE:
<223> OTHER INFORMATION: N-terminal stem segment of Influenza A HA
      subtype H1(no Cys-delta 3) Short Stem Domain sequence

<400> SEQUENCE: 179

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys
        35                  40

<210> SEQ ID NO 180
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H2(no Cys) Short Stem Domain sequence

<400> SEQUENCE: 180

Asp Gln Ile Cys Ile Gly Tyr His Ser Asn Asn Ser Thr Glu Lys Val
1               5                   10                  15

Asp Thr Ile Leu Glu Arg Asn Val Thr Val Thr His Ala Gln Asn Ile
            20                  25                  30

Leu Glu Lys Thr His Asn Gly Lys Leu
        35                  40

<210> SEQ ID NO 181
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H2(no Cys-delta 1) Short Stem Domain sequence

<400> SEQUENCE: 181

Asp Gln Ile Cys Ile Gly Tyr His Ser Asn Asn Ser Thr Glu Lys Val
1               5                   10                  15

-continued

Asp Thr Ile Leu Glu Arg Asn Val Thr Val Thr His Ala Gln Asn Ile
                20                  25                  30

Leu Glu Lys Thr His Asn Gly Lys Leu
            35                  40

<210> SEQ ID NO 182
<211> LENGTH: 40
<212> TYPE: PRT
<213> ORGANISM: Influenza virus A
<220> FEATURE:
<223> OTHER INFORMATION: N-terminal stem segment of Influenza A HA
      subtype H2(no Cys-delta 3) Short Stem Domain sequence

<400> SEQUENCE: 182

Asp Gln Ile Cys Ile Gly Tyr His Ser Asn Asn Ser Thr Glu Lys Val
1               5                   10                  15

Asp Thr Ile Leu Glu Arg Asn Val Thr Val Thr His Ala Gln Asn Ile
                20                  25                  30

Leu Glu Lys Thr His Asn Gly Lys
            35                  40

<210> SEQ ID NO 183
<211> LENGTH: 51
<212> TYPE: PRT
<213> ORGANISM: Influenza virus A
<220> FEATURE:
<223> OTHER INFORMATION: N-terminal stem segment of Influenza A HA
      subtype H3(no Cys) Short Stem Domain sequence

<400> SEQUENCE: 183

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
                20                  25                  30

Gln Ile Glu Val Thr Asn Ala Thr Glu Leu Val Gln Ser Ser Ser Thr
            35                  40                  45

Gly Lys Ile
    50

<210> SEQ ID NO 184
<211> LENGTH: 51
<212> TYPE: PRT
<213> ORGANISM: Influenza virus A
<220> FEATURE:
<223> OTHER INFORMATION: N-terminal stem segment of Influenza A HA
      subtype H3(no Cys-delta 1) Short Stem Domain sequence

<400> SEQUENCE: 184

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
                20                  25                  30

Gln Ile Glu Val Thr Asn Ala Thr Glu Leu Val Gln Ser Ser Ser Thr
            35                  40                  45

Gly Lys Ile
    50

<210> SEQ ID NO 185
<211> LENGTH: 50
<212> TYPE: PRT
<213> ORGANISM: Influenza virus A
<220> FEATURE:

<223> OTHER INFORMATION: N-terminal stem segment of Influenza A HA
      subtype H3(no Cys-delta 3) Short Stem Domain sequence

<400> SEQUENCE: 185

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys
    50

<210> SEQ ID NO 186
<211> LENGTH: 47
<212> TYPE: PRT
<213> ORGANISM: Influenza virus A
<220> FEATURE:
<223> OTHER INFORMATION: N-terminal stem segment of Influenza A HA
      subtype H4(no Cys) Short Stem Domain sequence

<400> SEQUENCE: 186

Gln Asn Tyr Thr Gly Asn Pro Val Ile Cys Met Gly His His Ala Val
1               5                   10                  15

Ala Asn Gly Thr Met Val Lys Thr Leu Ala Asp Asp Gln Val Glu Val
            20                  25                  30

Val Thr Ala Gln Glu Leu Val Glu Ser Gln Asn Leu Pro Glu Leu
        35                  40                  45

<210> SEQ ID NO 187
<211> LENGTH: 47
<212> TYPE: PRT
<213> ORGANISM: Influenza virus A
<220> FEATURE:
<223> OTHER INFORMATION: N-terminal stem segment of Influenza A HA
      subtype H4(no Cys-delta 1) Short Stem Domain sequence

<400> SEQUENCE: 187

Gln Asn Tyr Thr Gly Asn Pro Val Ile Cys Met Gly His His Ala Val
1               5                   10                  15

Ala Asn Gly Thr Met Val Lys Thr Leu Ala Asp Asp Gln Val Glu Val
            20                  25                  30

Val Thr Ala Gln Glu Leu Val Glu Ser Gln Asn Leu Pro Glu Leu
        35                  40                  45

<210> SEQ ID NO 188
<211> LENGTH: 46
<212> TYPE: PRT
<213> ORGANISM: Influenza virus A
<220> FEATURE:
<223> OTHER INFORMATION: N-terminal stem segment of Influenza A HA
      subtype H4(no Cys-delta 3) Short Stem Domain sequence

<400> SEQUENCE: 188

Gln Asn Tyr Thr Gly Asn Pro Val Ile Cys Met Gly His His Ala Val
1               5                   10                  15

Ala Asn Gly Thr Met Val Lys Thr Leu Ala Asp Asp Gln Val Glu Val
            20                  25                  30

Val Thr Ala Gln Glu Leu Val Glu Ser Gln Asn Leu Pro Glu
        35                  40                  45

<210> SEQ ID NO 189

```
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H5(no Cys) Short Stem Domain sequence

<400> SEQUENCE: 189

Asp Gln Ile Cys Ile Gly Tyr His Ala Asn Lys Ser Thr Lys Gln Val
1               5                   10                  15

Asp Thr Ile Met Glu Lys Asn Val Thr Val Thr His Ala Gln Asp Ile
            20                  25                  30

Leu Glu Arg Thr His Asn Gly Lys Leu
        35                  40

<210> SEQ ID NO 190
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H5(no Cys-delta 1) Short Stem Domain sequence

<400> SEQUENCE: 190

Asp Gln Ile Cys Ile Gly Tyr His Ala Asn Lys Ser Thr Lys Gln Val
1               5                   10                  15

Asp Thr Ile Met Glu Lys Asn Val Thr Val Thr His Ala Gln Asp Ile
            20                  25                  30

Leu Glu Arg Thr His Asn Gly Lys Leu
        35                  40

<210> SEQ ID NO 191
<211> LENGTH: 40
<212> TYPE: PRT
<213> ORGANISM: Influenza virus A
<220> FEATURE:
<223> OTHER INFORMATION: N-terminal stem segment of Influenza A HA
      subtype H5(no Cys-delta 3) Short Stem Domain sequence

<400> SEQUENCE: 191

Asp Gln Ile Cys Ile Gly Tyr His Ala Asn Lys Ser Thr Lys Gln Val
1               5                   10                  15

Asp Thr Ile Met Glu Lys Asn Val Thr Val Thr His Ala Gln Asp Ile
            20                  25                  30

Leu Glu Arg Thr His Asn Gly Lys
        35                  40

<210> SEQ ID NO 192
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H6(no Cys) Short Stem Domain sequence

<400> SEQUENCE: 192

Asp Lys Ile Cys Ile Gly Tyr His Ala Asn Asn Ser Thr Thr Gln Ile
1               5                   10                  15

Asp Thr Ile Leu Glu Lys Asn Val Thr Val Thr His Ser Val Glu Leu
            20                  25                  30

Leu Glu Asn Gln Lys Glu Glu Arg Phe
        35                  40
```

```
<210> SEQ ID NO 193
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H6(no Cys-delta 1) Short Stem Domain sequence

<400> SEQUENCE: 193

Asp Lys Ile Cys Ile Gly Tyr His Ala Asn Asn Ser Thr Thr Gln Ile
1               5                   10                  15

Asp Thr Ile Leu Glu Lys Asn Val Thr Val Thr His Ser Val Glu Leu
            20                  25                  30

Leu Glu Asn Gln Lys Glu Glu Arg Phe
        35                  40

<210> SEQ ID NO 194
<211> LENGTH: 40
<212> TYPE: PRT
<213> ORGANISM: Influenza virus A
<220> FEATURE:
<223> OTHER INFORMATION: N-terminal stem segment of Influenza A HA
      subtype H6(no Cys-delta 3) Short Stem Domain sequence

<400> SEQUENCE: 194

Asp Lys Ile Cys Ile Gly Tyr His Ala Asn Asn Ser Thr Thr Gln Ile
1               5                   10                  15

Asp Thr Ile Leu Glu Lys Asn Val Thr Val Thr His Ser Val Glu Leu
            20                  25                  30

Leu Glu Asn Gln Lys Glu Glu Arg
        35                  40

<210> SEQ ID NO 195
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H7(no Cys) Short Stem Domain sequence

<400> SEQUENCE: 195

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Thr Asn Ile Pro Lys Ile
        35                  40

<210> SEQ ID NO 196
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H7(no Cys-delta 1) Short Stem Domain sequence

<400> SEQUENCE: 196

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Thr Asn Ile Pro Lys Ile
        35                  40
```

<210> SEQ ID NO 197
<211> LENGTH: 40
<212> TYPE: PRT
<213> ORGANISM: Influenza virus A
<220> FEATURE:
<223> OTHER INFORMATION: N-terminal stem segment of Influenza A HA
      subtype H7(no Cys-delta 3) Short Stem Domain sequence

<400> SEQUENCE: 197

Asp Lys Ile Cys Le

```
<210> SEQ ID NO 201
<211> LENGTH: 41
<212> TYPE: PRT
<213> ORGANISM: Influenza virus A
<220> FEATURE:
<223> OTHER INFORMATION: N 35                  40

<210> SEQ ID NO 205
<211> LENGTH: 42
<212> TYPE: PRT
<213> ORGANISM: Influenza virus A
<220> FEATURE:
<223> OTHER INFORMATION: N-terminal stem segment of Influenza A HA
      subtype H10(no Cys-delta 1) Short Stem Domain sequence

<400> SEQUENCE: 205

Leu Asp Arg Ile Cys Leu Gly His His Ala Val Ala Asn Gly Thr Ile
1 5 10 15

Val Lys Thr Leu Thr Asn Glu Gln Glu Glu Val Thr Asn Ala Thr Glu
20 25 30

Thr Val Glu Ser Thr Asn Leu Asn Lys Leu
35 40

<210> SEQ ID NO 206
<211> LENGTH: 41
<212> TYPE: PRT
<213> ORGANISM: Influenza virus A
<220> FEATURE:
<223> OTHER INFORMATION: N-terminal stem segment of Influenza A HA subtype H10(no Cys-delta 3) Short Stem Domain sequence

<400> SEQUENCE: 206

Leu Asp Arg Ile Cys Leu Gly His His Ala Val Ala Asn Gly Thr Ile
1 5 10 15

Val Lys Thr Leu Thr Asn Glu Gln Glu Glu Val Thr Asn Ala Thr Glu
20 25 30

Thr Val Glu Ser Thr Asn Leu Asn Lys
35 40

<210> SEQ ID NO 207
<211> LENGTH: 41
<212> TYPE: PRT
<213> ORGANISM: Influenza virus A
<220> FEATURE:
<223> OTHER INFORMATION: N-terminal stem segment of Influenza A HA subtype H11(no Cys) Short Stem Domain sequence

<400> SEQUENCE: 207

Asp Glu Ile Cys Ile Gly Tyr Leu Ser Asn Asn Ser Thr Asp Lys Val
1 5 10 15

Asp Thr Ile Ile Glu Asn Asn Val Thr Val Thr Ser Ser Val Glu Leu
20 25 30

Val Glu Thr Glu His Thr Gly Ser Phe
35 40

<210> SEQ ID NO 208
<211> LENGTH: 41
<212> TYPE: PRT
<213> ORGANISM: Influenza virus A
<220> FEATURE:
<223> OTHER INFORMATION: N-terminal stem segment of Influenza A HA subtype H11(no Cys-delta 1) Short Stem Domain sequence

<400> SEQUENCE: 208

Asp Glu Ile Cys Ile Gly Tyr Leu Ser Asn Asn Ser Thr Asp Lys Val
1 5 10 15

Asp Thr Ile Ile Glu Asn Asn Val Thr Val Thr Ser Ser Val Glu Leu
20 25 30

Val Glu Thr Glu His Thr Gly Ser Phe
            35                  40

<210> SEQ ID NO 209
<211> LENGTH: 40
<212> TYPE: PRT
<213> ORGANISM: Influenza virus A
<220> FEATURE:
<223> OTHER INFORMATION: N-terminal stem segment of Influenza A HA subtype H11(no Cys-delta 3) Short Stem Domain sequence

<400> SEQUENCE: 209

Asp Glu Ile Cys Ile Gly Tyr Leu Ser Asn Asn Ser Thr Asp Lys Val
1 5 10 15

Asp Thr Ile Ile Glu Asn Asn Val Thr Val Thr Ser Ser Val Glu Leu
20 25 30

Val Glu Thr Glu His Thr Gly Ser
35 40

<210> SEQ ID NO 210
<211> LENGTH: 41
<212> TYPE: PRT
<213> ORGANISM: Influenza virus A
<220> FEATURE:
<223> OTHER INFORMATION: N-terminal stem segment of Influenza A HA subtype H12(no Cys) Short Stem Domain sequence

<400> SEQUENCE: 210

Asp Lys Ile Cys Ile Gly Tyr Gln Thr Asn Asn Ser Thr Glu Thr Val
1 5 10 15

Asn Thr Leu Ser Glu Gln Asn Val Pro Val Thr Gln Val Glu Glu Leu
20 25 30

Val His Arg Gly Ile Asp Pro Ile Leu
35 40

<210> SEQ ID NO 211
<211> LENGTH: 41
<212> TYPE: PRT
<213> ORGANISM: Influenza virus A
<220> FEATURE:
<223> OTHER INFORMATION: N-terminal stem segment of Influenza A HA subtype H12(no Cys-delta 1) Short Stem Domain sequence

<400> SEQUENCE: 211

Asp Lys Ile Cys Ile Gly Tyr Gln Thr Asn Asn Ser Thr Glu Thr Val
1 5 10 15

Asn Thr Leu Ser Glu Gln Asn Val Pro Val Thr Gln Val Glu Glu Leu
20 25 30

Val His Arg Gly Ile Asp Pro Ile Leu
35 40

<210> SEQ ID NO 212
<211> LENGTH: 40
<212> TYPE: PRT
<213> ORGANISM: Influenza virus A
<220> FEATURE:
<223> OTHER INFORMATION: N-terminal stem segment of Influenza A HA subtype H12(no Cys-delta 3) Short Stem Domain sequence

<400> SEQUENCE: 212

Asp Lys Ile Cys Ile Gly Tyr Gln Thr Asn Asn Ser Thr Glu Thr Val
1 5 10 15

Asn Thr Leu Ser Glu Gln Asn Val Pro Val Thr Gln Val Glu Glu Leu
20 25 30

```
Val His Arg Gly Ile Asp Pro Ile
        35                  40

<210> SEQ ID NO 213
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H13(no Cys) Short Stem Domain sequence

<400> SEQUENCE: 213

Asp Arg Ile Cys Val Gly Tyr Leu Ser Thr Asn Ser Ser Glu Arg Val
1               5                   10                  15

Asp Thr Leu Leu Glu Asn Gly Val Pro Val Thr Ser Ser Ile Asp Leu
            20                  25                  30

Ile Glu Thr Asn His Thr Gly Thr Tyr
        35                  40

<210> SEQ ID NO 214
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H13(no Cys-delta 1) Short Stem Domain sequence

<400> SEQUENCE: 214

Asp Arg Ile Cys Val Gly Tyr Leu Ser Thr Asn Ser Ser Glu Arg Val
1               5                   10                  15

Asp Thr Leu Leu Glu Asn Gly Val Pro Val Thr Ser Ser Ile Asp Leu
            20                  25                  30

Ile Glu Thr Asn His Thr Gly Thr Tyr
        35                  40

<210> SEQ ID NO 215
<211> LENGTH: 40
<212> TYPE: PRT
<213> ORGANISM: Influenza virus A
<220> FEATURE:
<223> OTHER INFORMATION: N-terminal stem segment of Influenza A HA
      subtype H13(no Cys-delta 3) Short Stem Domain sequence

<400> SEQUENCE: 215

Asp Arg Ile Cys Val Gly Tyr Leu Ser Thr Asn Ser Ser Glu Arg Val
1               5                   10                  15

Asp Thr Leu Leu Glu Asn Gly Val Pro Val Thr Ser Ser Ile Asp Leu
            20                  25                  30

Ile Glu Thr Asn His Thr Gly Thr
        35                  40

<210> SEQ ID NO 216
<211> LENGTH: 50
<212> TYPE: PRT
<213> ORGANISM: Influenza virus A
<220> FEATURE:
<223> OTHER INFORMATION: N-terminal stem segment of Influenza A HA
      subtype H14(no Cys) Short Stem Domain sequence

<400> SEQUENCE: 216

Gln Ile Thr Asn Gly Thr Thr Gly Asn Pro Ile Ile Cys Leu Gly His
1               5                   10                  15

His Ala Val Glu Asn Gly Thr Ser Val Lys Thr Leu Thr Asp Asn His
```

```
                    20                  25                  30

Val Glu Val Val Ser Ala Lys Glu Leu Val Glu Thr Asn His Thr Asp
        35                  40                  45

Glu Leu
    50

<210> SEQ ID NO 217
<211> LENGTH: 50
<212> TYPE: PRT
<213> ORGANISM: Influenza virus A
<220> FEATURE:
<223> OTHER INFORMATION: N-terminal stem segment of Influenza A HA
      subtype H14(no Cys-delta 1) Short Stem Domain sequence

<400> SEQUENCE: 217

Gln Ile Thr Asn Gly Thr Thr Gly Asn Pro Ile Ile Cys Leu Gly His
1               5                   10                  15

His Ala Val Glu Asn Gly Thr Ser Val Lys Thr Leu Thr Asp Asn His
                20                  25                  30

Val Glu Val Val Ser Ala Lys Glu Leu Val Glu Thr Asn His Thr Asp
        35                  40                  45

Glu Leu
    50

<210> SEQ ID NO 218
<211> LENGTH: 49
<212> TYPE: PRT
<213> ORGANISM: Influenza virus A
<220> FEATURE:
<223> OTHER INFORMATION: N-terminal stem segment of Influenza A HA
      subtype H14(no Cys-delta 3) Short Stem Domain sequence

<400> SEQUENCE: 218

Gln Ile Thr Asn Gly Thr Thr Gly Asn Pro Ile Ile Cys Leu Gly His
1               5                   10                  15

His Ala Val Glu Asn Gly Thr Ser Val Lys Thr Leu Thr Asp Asn His
                20                  25                  30

Val Glu Val Val Ser Ala Lys Glu Leu Val Glu Thr Asn His Thr Asp
        35                  40                  45

Glu

<210> SEQ ID NO 219
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H15(no Cys) Short Stem Domain sequence

<400> SEQUENCE: 219

Asp Lys Ile Cys Leu Gly His His Ala Val Ala Asn Gly Thr Lys Val
1               5                   10                  15

Asn Thr Leu Thr Glu Arg Gly Val Glu Val Val Asn Ala Thr Glu Thr
                20                  25                  30

Val Glu Ile Thr Gly Ile Asp Lys Val
        35                  40

<210> SEQ ID NO 220
<211> LENGTH: 41
<212> TYPE: PRT
<213> ORGANISM: Influenza virus A
<220> FEATURE:
```

<223> OTHER INFORMATION: N-terminal stem segment of Influenza A HA
      subtype H15(no Cys-delta 1) Short Stem Domain sequence

<400> SEQUENCE: 220

Asp Lys Ile Cys Leu Gly His His Ala Val Ala Asn Gly Thr Lys Val
1               5                   10                  15

Asn Thr Leu Thr Glu Arg Gly Val Glu Val Val Asn Ala Thr Glu Thr
            20                  25                  30

Val Glu Ile Thr Gly Ile Asp Lys Val
        35                  40

<210> SEQ ID NO 221
<211> LENGTH: 40
<212> TYPE: PRT
<213> ORGANISM: Influenza virus A
<220> FEATURE:
<223> OTHER INFORMATION: N-terminal stem segment of Influenza A HA
      subtype H15(no Cys-delta 3) Short Stem Domain sequence

<400> SEQUENCE: 221

Asp Lys Ile Cys Leu Gly His His Ala Val Ala Asn Gly Thr Lys Val
1               5                   10                  15

Asn Thr Leu Thr Glu Arg Gly Val Glu Val Val Asn Ala Thr Glu Thr
            20                  25                  30

Val Glu Ile Thr Gly Ile Asp Lys
        35                  40

<210> SEQ ID NO 222
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H16(no Cys) Short Stem Domain sequence

<400> SEQUENCE: 222

Asp Lys Ile Cys Ile Gly Tyr Leu Ser Asn Asn Ser Ser Asp Thr Val
1               5                   10                  15

Asp Thr Leu Thr Glu Asn Gly Val Pro Val Thr Ser Ser Val Asp Leu
            20                  25                  30

Val Glu Thr Asn His Thr Gly Thr Tyr
        35                  40

<210> SEQ ID NO 223
<211> LENGTH: 41
<212> TYPE: PRT
<213> ORGANISM: Influenza virus A
<220> FEATURE:
<223> OTHER INFORMATION: N-terminal stem segment of Influenza A HA
      subtype H16(no Cys-delta 1) Short Stem Domain sequence

<400> SEQUENCE: 223

Asp Lys Ile Cys Ile Gly Tyr Leu Ser Asn Asn Ser Ser Asp Thr Val
1               5                   10                  15

Asp Thr Leu Thr Glu Asn Gly Val Pro Val Thr Ser Ser Val Asp Leu
            20                  25                  30

Val Glu Thr Asn His Thr Gly Thr Tyr
        35                  40

<210> SEQ ID NO 224
<211> LENGTH: 40
<212> TYPE: PRT
<213> ORGANISM: Influenza virus A

```
<220> FEATURE:
<223> OTHER INFORMATION: N-terminal stem segment of Influenza A HA
      subtype H16(no Cys-delta 3) Short Stem Domain sequence

<400> SEQUENCE: 224

Asp Lys Ile Cys Ile Gly Tyr Leu Ser Asn Asn Ser Ser Asp Thr Val
1               5                   10                  15

Asp Thr Leu Thr Glu Asn Gly Val Pro Val Thr Ser Ser Val Asp Leu
            20                  25                  30

Val Glu Thr Asn His Thr Gly Thr
            35                  40

<210> SEQ ID NO 225

<400> SEQUENCE: 225

000

<210> SEQ ID NO 226
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H1(no Cys)

<400> SEQUENCE: 226

Asn Thr Lys Cys Gln Thr Pro Leu Gly Ala Ile Asn Ser Ser Leu Pro
1               5                   10                  15

Tyr Gln Asn Ile His Pro Val Thr Ile Gly Glu Cys Pro Lys Tyr Val
            20                  25                  30

Arg Ser Ala Lys Leu Arg Met Val Thr Gly Leu Arg Asn Asn Pro Ser
        35                  40                  45

Ile Gln Ser Arg
    50

<210> SEQ ID NO 227
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H1(no Cys-delta 1)

<400> SEQUENCE: 227

Thr Lys Cys Gln Thr Pro Leu Gly Ala Ile Asn Ser Ser Leu Pro Tyr
1               5                   10                  15

Gln Asn Ile His Pro Val Thr Ile Gly Glu Cys Pro Lys Tyr Val Arg
            20                  25                  30

Ser Ala Lys Leu Arg Met Val Thr Gly Leu Arg Asn Asn Pro Ser Ile
        35                  40                  45

Gln Ser Arg
    50

<210> SEQ ID NO 228
<211> LENGTH: 50
<212> TYPE: PRT
<213> ORGANISM: Influenza virus A
<220> FEATURE:
<223> OTHER INFORMATION: C-terminal stem segment of Influenza A HA
      subtype H1(no Cys-delta 3)

<400> SEQUENCE: 228
```

Lys Cys Gln Thr Pro Leu Gly Ala Ile Asn Ser Ser Leu Pro Tyr Gln
1               5                   10                  15

Asn Ile His Pro Val Thr Ile Gly Glu Cys Pro Lys Tyr Val Arg Ser
            20                  25                  30

Ala Lys Leu Arg Met Val Thr Gly Leu Arg Asn Asn Pro Ser Ile Gln
        35                  40                  45

Ser Arg
    50

<210> SEQ ID NO 229
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H2(no Cys)

<400> SEQUENCE: 229

Glu Thr Lys Cys Gln Thr Pro Leu Gly Ala Ile Asn Thr Thr Leu Pro
1               5                   10                  15

Phe His Asn Val His Pro Leu Thr Ile Gly Glu Cys Pro Lys Tyr Val
            20                  25                  30

Lys Ser Glu Arg Leu Val Leu Ala Thr Gly Leu Arg Asn Val Pro Gln
        35                  40                  45

Ile Glu Ser Arg
    50

<210> SEQ ID NO 230
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H2(no Cys-delta 1)

<400> SEQUENCE: 230

Thr Lys Cys Gln Thr Pro Leu Gly Ala Ile Asn Thr Thr Leu Pro Phe
1               5                   10                  15

His Asn Val His Pro Leu Thr Ile Gly Glu Cys Pro Lys Tyr Val Lys
            20                  25                  30

Ser Glu Arg Leu Val Leu Ala Thr Gly Leu Arg Asn Val Pro Gln Ile
        35                  40                  45

Glu Ser Arg
    50

<210> SEQ ID NO 231
<211> LENGTH: 50
<212> TYPE: PRT
<213> ORGANISM: Influenza virus A
<220> FEATURE:
<223> OTHER INFORMATION: C-terminal stem segment of Influenza A HA
      subtype H2(no Cys-delta 3)

<400> SEQUENCE: 231

Lys Cys Gln Thr Pro Leu Gly Ala Ile Asn Thr Thr Leu Pro Phe His
1               5                   10                  15

Asn Val His Pro Leu Thr Ile Gly Glu Cys Pro Lys Tyr Val Lys Ser
            20                  25                  30

Glu Arg Leu Val Leu Ala Thr Gly Leu Arg Asn Val Pro Gln Ile Glu
        35                  40                  45

Ser Arg

<210> SEQ ID NO 232
<211> LENGTH: 52
<212> TYPE: PRT
<213> ORGANISM: Influenza virus A
<220> FEATURE:
<223> OTHER INFORMATION: C-terminal stem segment of Influenza A HA subtype H3(no Cys)

<400> SEQUENCE: 232

Ile Ser Glu Cys Ile Thr Pro Asn Gly Ser Ile Pro Asn Asp Lys Pro
1               5                   10                  15

Phe Gln Asn Val Asn Lys Ile Thr Tyr Gly Ala Cys Pro Lys Tyr Val
            20                  25                  30

Lys Gln Asn Thr Leu Lys Leu Ala Thr Gly Met Arg Asn Val Pro Glu
        35                  40                  45

Lys Gln Thr Arg
    50

<210> SEQ ID NO 233
<211> LENGTH: 51
<212> TYPE: PRT
<213> ORGANISM: Influenza virus A
<220> FEATURE:
<223> OTHER INFORMATION: C-terminal stem segment of Influenza A HA subtype H3(no Cys-delta 1)

<400> SEQUENCE: 233

Ser Glu Cys Ile Thr Pro Asn Gly Ser Ile Pro Asn Asp Lys Pro Phe
1               5                   10                  15

Gln Asn Val Asn Lys Ile Thr Tyr Gly Ala Cys Pro Lys Tyr Val Lys
            20                  25                  30

Gln Asn Thr Leu Lys Leu Ala Thr Gly Met Arg Asn Val Pro Glu Lys
        35                  40                  45

Gln Thr Arg
    50

<210> SEQ ID NO 234
<211> LENGTH: 50
<212> TYPE: PRT
<213> ORGANISM: Influenza virus A
<220> FEATURE:
<223> OTHER INFORMATION: C-terminal stem segment of Influenza A HA subtype H3(no Cys-delta 3)

<400> SEQUENCE: 234

Glu Cys Ile Thr Pro Asn Gly Ser Ile Pro Asn Asp Lys Pro Phe Gln
1               5                   10                  15

Asn Val Asn Lys Ile Thr Tyr Gly Ala Cys Pro Lys Tyr Val Lys Gln
            20                  25                  30

Asn Thr Leu Lys Leu Ala Thr Gly Met Arg Asn Val Pro Glu Lys Gln
        35                  40                  45

Thr Arg
    50

<210> SEQ ID NO 235
<211> LENGTH: 52
<212> TYPE: PRT
<213> ORGANISM: Influenza virus A
<220> FEATURE:
<223> OTHER INFORMATION: C-terminal stem segment of Influenza A HA subtype H4(no Cys)

<400> SEQUENCE: 235

Val Ser Lys Cys His Thr Asp Lys Gly Ser Leu Ser Thr Thr Lys Pro
1               5                   10                  15

Phe Gln Asn Ile Ser Arg Ile Ala Val Gly Asp Cys Pro Arg Tyr Val
                20                  25                  30

Lys Gln Gly Ser Leu Lys Leu Ala Thr Gly Met Arg Asn Ile Pro Glu
            35                  40                  45

Lys Ala Ser Arg
        50

<210> SEQ ID NO 236
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H4(no Cys-delta 1)

<400> SEQUENCE: 236

Ser Lys Cys His Thr Asp Lys Gly Ser Leu Ser Thr Thr Lys Pro Phe
1               5                   10                  15

Gln Asn Ile Ser Arg Ile Ala Val Gly Asp Cys Pro Arg Tyr Val Lys
                20                  25                  30

Gln Gly Ser Leu Lys Leu Ala Thr Gly Met Arg Asn Ile Pro Glu Lys
            35                  40                  45

Ala Ser Arg
        50

<210> SEQ ID NO 237
<211> LENGTH: 50
<212> TYPE: PRT
<213> ORGANISM: Influenza virus A
<220> FEATURE:
<223> OTHER INFORMATION: C-terminal stem segment of Influenza A HA
      subtype H4(no Cys-delta 3)

<400> SEQUENCE: 237

Lys Cys His Thr Asp Lys Gly Ser Leu Ser Thr Thr Lys Pro Phe Gln
1               5                   10                  15

Asn Ile Ser Arg Ile Ala Val Gly Asp Cys Pro Arg Tyr Val Lys Gln
                20                  25                  30

Gly Ser Leu Lys Leu Ala Thr Gly Met Arg Asn Ile Pro Glu Lys Ala
            35                  40                  45

Ser Arg
        50

<210> SEQ ID NO 238
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H5(no Cys)

<400> SEQUENCE: 238

Asp Thr Lys Cys Gln Thr Pro Val Gly Glu Ile Asn Ser Ser Met Pro
1               5                   10                  15

Phe His Asn Ile His Pro His Thr Ile Gly Glu Cys Pro Lys Tyr Val
                20                  25                  30

Lys Ser Asp Arg Leu Val Leu Ala Thr Gly Leu Arg Asn Val Pro Gln

Arg Lys Lys Arg
    50

<210> SEQ ID NO 239
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H5(no Cys-delta 1)

<400> SEQUENCE: 239

Thr Lys Cys Gln Thr Pro Val Gly Glu Ile Asn Ser Ser Met Pro Phe
1               5                   10                  15

His Asn Ile His Pro His Thr Ile Gly Glu Cys Pro Lys Tyr Val Lys
            20                  25                  30

Ser Asp Arg Leu Val Leu Ala Thr Gly Leu Arg Asn Val Pro Gln Arg
        35                  40                  45

Lys Lys Arg
    50

<210> SEQ ID NO 240
<211> LENGTH: 50
<212> TYPE: PRT
<213> ORGANISM: Influenza virus A
<220> FEATURE:
<223> OTHER INFORMATION: C-terminal stem segment of Influenza A HA
      subtype H5(no Cys-delta 3)

<400> SEQUENCE: 240

Lys Cys Gln Thr Pro Val Gly Glu Ile Asn Ser Ser Met Pro Phe His
1               5                   10                  15

Asn Ile His Pro His Thr Ile Gly Glu Cys Pro Lys Tyr Val Lys Ser
            20                  25                  30

Asp Arg Leu Val Leu Ala Thr Gly Leu Arg Asn Val Pro Gln Arg Lys
        35                  40                  45

Lys Arg
    50

<210> SEQ ID NO 241
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H6(no Cys)

<400> SEQUENCE: 241

Asp Ala Thr Cys Gln Thr Val Ala Gly Val Leu Arg Thr Asn Lys Thr
1               5                   10                  15

Phe Gln Asn Val Ser Pro Leu Trp Ile Gly Glu Cys Pro Lys Tyr Val
            20                  25                  30

Lys Ser Glu Ser Leu Arg Leu Ala Thr Gly Leu Arg Asn Val Pro Gln
        35                  40                  45

Ile Glu Thr Arg
    50

<210> SEQ ID NO 242
<211> LENGTH: 51
<212> TYPE: PRT
<213> ORGANISM: Influenza virus A

```
<220> FEATURE:
<223> OTHER INFORMATION: C-terminal stem segment of Influenza A HA
      subtype H6(no Cys-delta 1)

<400> SEQUENCE: 242

Ala Thr Cys Gln Thr Val Ala Gly Val Leu Arg Thr Asn Lys Thr Phe
  1               5                  10                  15

Gln Asn Val Ser Pro Leu Trp Ile Gly Glu Cys Pro Lys Tyr Val Lys
             20                  25                  30

Ser Glu Ser Leu Arg Leu Ala Thr Gly Leu Arg Asn Val Pro Gln Ile
         35                  40                  45

Glu Thr Arg
     50

<210> SEQ ID NO 243
<211> LENGTH: 50
<212> TYPE: PRT
<213> ORGANISM: Influenza virus A
<220> FEATURE:
<223> OTHER INFORMATION: C-terminal stem segment of Influenza A HA
      subtype H6(no Cys-delta 3)

<400> SEQUENCE: 243

Thr Cys Gln Thr Val Ala Gly Val Leu Arg Thr Asn Lys Thr Phe Gln
  1               5                  10                  15

Asn Val Ser Pro Leu Trp Ile Gly Glu Cys Pro Lys Tyr Val Lys Ser
             20                  25                  30

Glu Ser Leu Arg Leu Ala Thr Gly Leu Arg Asn Val Pro Gln Ile Glu
         35                  40                  45

Thr Arg
     50

<210> SEQ ID NO 244
<211> LENGTH: 56
<212> TYPE: PRT
<213> ORGANISM: Influenza virus A
<220> FEATURE:
<223> OTHER INFORMATION: C-terminal stem segment of Influenza A HA
      subtype H7(no Cys)

<400> SEQUENCE: 244

Glu Gly Glu Cys Tyr His Ser Gly Gly Thr Ile Thr Ser Arg Leu Pro
  1               5                  10                  15

Phe Gln Asn Ile Asn Ser Arg Ala Val Gly Lys Cys Pro Arg Tyr Val
             20                  25                  30

Lys Gln Glu Ser Leu Leu Leu Ala Thr Gly Met Lys Asn Val Pro Glu
         35                  40                  45

Pro Ser Lys Lys Arg Lys Lys Arg
     50                  55

<210> SEQ ID NO 245
<211> LENGTH: 55
<212> TYPE: PRT
<213> ORGANISM: Influenza virus A
<220> FEATURE:
<223> OTHER INFORMATION: C-terminal stem segment of Influenza A HA
      subtype H7(no Cys-delta 1)

<400> SEQUENCE: 245

Gly Glu Cys Tyr His Ser Gly Gly Thr Ile Thr Ser Arg Leu Pro Phe
  1               5                  10                  15

Gln Asn Ile Asn Ser Arg Ala Val Gly Lys Cys Pro Arg Tyr Val Lys
```

```
                    20                  25                  30

Gln Glu Ser Leu Leu Ala Thr Gly Met Lys Asn Val Pro Glu Pro
        35                  40                  45

Ser Lys Lys Arg Lys Lys Arg
    50                  55

<210> SEQ ID NO 246
<211> LENGTH: 54
<212> TYPE: PRT
<213> ORGANISM: Influenza virus A
<220> FEATURE:
<223> OTHER INFORMATION: C-terminal stem segment of Influenza A HA
      subtype H7(no Cys-delta 3)

<400> SEQUENCE: 246

Glu Cys Tyr His Ser Gly Gly Thr Ile Thr Ser Arg Leu Pro Phe Gln
1               5                   10                  15

Asn Ile Asn Ser Arg Ala Val Gly Lys Cys Pro Arg Tyr Val Lys Gln
            20                  25                  30

Glu Ser Leu Leu Leu Ala Thr Gly Met Lys Asn Val Pro Glu Pro Ser
        35                  40                  45

Lys Lys Arg Lys Lys Arg
    50

<210> SEQ ID NO 247
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H8(no Cys)

<400> SEQUENCE: 247

Asn Thr Lys Cys Gln Thr Tyr Ala Gly Ala Ile Asn Ser Ser Lys Pro
1               5                   10                  15

Phe Gln Asn Ala Ser Arg His Tyr Met Gly Glu Cys Pro Lys Tyr Val
            20                  25                  30

Lys Lys Ala Ser Leu Arg Leu Ala Val Gly Leu Arg Asn Thr Pro Ser
        35                  40                  45

Val Glu Pro Arg
    50

<210> SEQ ID NO 248
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H8(no Cys-delta 1)

<400> SEQUENCE: 248

Thr Lys Cys Gln Thr Tyr Ala Gly Ala Ile Asn Ser Ser Lys Pro Phe
1               5                   10                  15

Gln Asn Ala Ser Arg His Tyr Met Gly Glu Cys Pro Lys Tyr Val Lys
            20                  25                  30

Lys Ala Ser Leu Arg Leu Ala Val Gly Leu Arg Asn Thr Pro Ser Val
        35                  40                  45

Glu Pro Arg
    50

<210> SEQ ID NO 249
```

```
<211> LENGTH: 50
<212> TYPE: PRT
<213> ORGANISM: Influenza virus A
<220> FEATURE:
<223> OTHER INFORMATION: C-terminal stem segment of Influenza A HA
      subtype H8(no Cys-delta 3)

<400> SEQUENCE: 249

Lys Cys Gln Thr Tyr Ala Gly Ala Ile Asn Ser Ser Lys Pro Phe Gln
1               5                   10                  15

Asn Ala Ser Arg His Tyr Met Gly Glu Cys Pro Lys Tyr Val Lys Lys
            20                  25                  30

Ala Ser Leu Arg Leu Ala Val Gly Leu Arg Asn Thr Pro Ser Val Glu
        35                  40                  45

Pro Arg
    50

<210> SEQ ID NO 250
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H9(no Cys)

<400> SEQUENCE: 250

Val Val Gln Cys Gln Thr Glu Lys Gly Gly Leu Asn Thr Thr Leu Pro
1               5                   10                  15

Phe His Asn Ile Ser Lys Tyr Ala Phe Gly Asn Cys Pro Lys Tyr Val
            20                  25                  30

Gly Val Lys Ser Leu Lys Leu Pro Val Gly Leu Arg Asn Val Pro Ala
        35                  40                  45

Val Ser Ser Arg
    50

<210> SEQ ID NO 251
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H9(no Cys-delta 1)

<400> SEQUENCE: 251

Val Gln Cys Gln Thr Glu Lys Gly Gly Leu Asn Thr Thr Leu Pro Phe
1               5                   10                  15

His Asn Ile Ser Lys Tyr Ala Phe Gly Asn Cys Pro Lys Tyr Val Gly
            20                  25                  30

Val Lys Ser Leu Lys Leu Pro Val Gly Leu Arg Asn Val Pro Ala Val
        35                  40                  45

Ser Ser Arg
    50

<210> SEQ ID NO 252
<211> LENGTH: 50
<212> TYPE: PRT
<213> ORGANISM: Influenza virus A
<220> FEATURE:
<223> OTHER INFORMATION: C-terminal stem segment of Influenza A HA
      subtype H9(no Cys-delta 3)

<400> SEQUENCE: 252

Gln Cys Gln Thr Glu Lys Gly Gly Leu Asn Thr Thr Leu Pro Phe His
```

```
                1               5                   10                  15
Asn Ile Ser Lys Tyr Ala Phe Gly Asn Cys Pro Lys Tyr Val Gly Val
                20                  25                  30

Lys Ser Leu Lys Leu Pro Val Gly Leu Arg Asn Val Pro Ala Val Ser
        35                  40                  45

Ser Arg
    50

<210> SEQ ID NO 253
<211> LENGTH: 53
<212> TYPE: PRT
<213> ORGANISM: Influenza virus A
<220> FEATURE:
<223> OTHER INFORMATION: C-terminal stem segment of Influenza A HA
      subtype H10(no Cys)

<400> SEQUENCE: 253

Glu Ser Lys Cys Phe Trp Arg Gly Gly Ser Ile Asn Thr Lys Leu Pro
1               5                   10                  15

Phe Gln Asn Leu Ser Pro Arg Thr Val Gly Gln Cys Pro Lys Tyr Val
                20                  25                  30

Asn Gln Arg Ser Leu Leu Leu Ala Thr Gly Met Arg Asn Val Pro Glu
        35                  40                  45

Val Val Gln Gly Arg
    50

<210> SEQ ID NO 254
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H10(no Cys-delta 1)

<400> SEQUENCE: 254

Ser Lys Cys Phe Trp Arg Gly Gly Ser Ile Asn Thr Lys Leu Pro Phe
1               5                   10                  15

Gln Asn Leu Ser Pro Arg Thr Val Gly Gln Cys Pro Lys Tyr Val Asn
                20                  25                  30

Gln Arg Ser Leu Leu Leu Ala Thr Gly Met Arg Asn Val Pro Glu Val
        35                  40                  45

Val Gln Gly Arg
    50

<210> SEQ ID NO 255
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H10(no Cys-delta 3)

<400> SEQUENCE: 255

Lys Cys Phe Trp Arg Gly Gly Ser Ile Asn Thr Lys Leu Pro Phe Gln
1               5                   10                  15

Asn Leu Ser Pro Arg Thr Val Gly Gln Cys Pro Lys Tyr Val Asn Gln
                20                  25                  30

Arg Ser Leu Leu Leu Ala Thr Gly Met Arg Asn Val Pro Glu Val Val
        35                  40                  45

Gln Gly Arg
    50
```

<210> SEQ ID NO 256
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H11(no Cys)

<400> SEQUENCE: 256

Ser Thr Lys Cys Gln Thr Glu Ile Gly Gly Ile Asn Thr Asn Lys Ser
 1               5                   10                  15

Phe His Asn Val His Arg Asn Thr Ile Gly Asp Cys Pro Lys Tyr Val
             20                  25                  30

Asn Val Lys Ser Leu Lys Leu Ala Thr Gly Pro Arg Asn Val Pro Ala
         35                  40                  45

Ile Ala Ser Arg
     50

<210> SEQ ID NO 257
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H11(no Cys-delta 1)

<400> SEQUENCE: 257

Thr Lys Cys Gln Thr Glu Ile Gly Gly Ile Asn Thr Asn Lys Ser Phe
 1               5                   10                  15

His Asn Val His Arg Asn Thr Ile Gly Asp Cys Pro Lys Tyr Val Asn
             20                  25                  30

Val Lys Ser Leu Lys Leu Ala Thr Gly Pro Arg Asn Val Pro Ala Ile
         35                  40                  45

Ala Ser Arg
     50

<210> SEQ ID NO 258
<211> LENGTH: 50
<212> TYPE: PRT
<213> ORGANISM: Influenza virus A
<220> FEATURE:
<223> OTHER INFORMATION: C-terminal stem segment of Influenza A HA
      subtype H11(no Cys-delta 3)

<400> SEQUENCE: 258

Lys Cys Gln Thr Glu Ile Gly Gly Ile Asn Thr Asn Lys Ser Phe His
 1               5                   10                  15

Asn Val His Arg Asn Thr Ile Gly Asp Cys Pro Lys Tyr Val Asn Val
             20                  25                  30

Lys Ser Leu Lys Leu Ala Thr Gly Pro Arg Asn Val Pro Ala Ile Ala
         35                  40                  45

Ser Arg
     50

<210> SEQ ID NO 259
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H12(no Cys)

-continued

<400> SEQUENCE: 259

Val Thr Glu Cys Gln Leu Asn Glu Gly Val Met Asn Thr Ser Lys Pro
1               5                   10                  15

Phe Gln Asn Thr Ser Lys His Tyr Ile Gly Lys Cys Pro Lys Tyr Ile
            20                  25                  30

Pro Ser Gly Ser Leu Lys Leu Ala Ile Gly Leu Arg Asn Val Pro Gln
        35                  40                  45

Val Gln Asp Arg
    50

<210> SEQ ID NO 260
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H12(no Cys-delta 1)

<400> SEQUENCE: 260

Thr Glu Cys Gln Leu Asn Glu Gly Val Met Asn Thr Ser Lys Pro Phe
1               5                   10                  15

Gln Asn Thr Ser Lys His Tyr Ile Gly Lys Cys Pro Lys Tyr Ile Pro
            20                  25                  30

Ser Gly Ser Leu Lys Leu Ala Ile Gly Leu Arg Asn Val Pro Gln Val
        35                  40                  45

Gln Asp Arg
    50

<210> SEQ ID NO 261
<211> LENGTH: 50
<212> TYPE: PRT
<213> ORGANISM: Influenza virus A
<220> FEATURE:
<223> OTHER INFORMATION: C-terminal stem segment of Influenza A HA
      subtype H12(no Cys-delta 3)

<400> SEQUENCE: 261

Glu Cys Gln Leu Asn Glu Gly Val Met Asn Thr Ser Lys Pro Phe Gln
1               5                   10                  15

Asn Thr Ser Lys His Tyr Ile Gly Lys Cys Pro Lys Tyr Ile Pro Ser
            20                  25                  30

Gly Ser Leu Lys Leu Ala Ile Gly Leu Arg Asn Val Pro Gln Val Gln
        35                  40                  45

Asp Arg
    50

<210> SEQ ID NO 262
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H13(no Cys)

<400> SEQUENCE: 262

Asn Thr Lys Cys Gln Thr Ser Val Gly Gly Ile Asn Thr Asn Arg Thr
1               5                   10                  15

Phe Gln Asn Ile Asp Lys Asn Ala Leu Gly Asp Cys Pro Lys Tyr Ile
            20                  25                  30

Lys Ser Gly Gln Leu Lys Leu Ala Thr Gly Leu Arg Asn Val Pro Ala
        35                  40                  45

Ile Ser Asn Arg
    50

<210> SEQ ID NO 263
<211> LENGTH: 51
<212> TYPE: PRT
<213>

<223> OTHER INFORMATION: C-terminal stem segment of Influenza A HA
      subtype H14(no Cys-delta 1)

<400> SEQUENCE: 266

Ser Pro Cys Leu Thr Asp Lys Gly Ser Ile Gln Ser Asp Lys Pro Phe
1               5                   10                  15

Gln Asn Val Ser Arg Ile Ala Ile Gly Asn Cys Pro Lys Tyr Val Lys
            20                  25                  30

Gln Gly Ser Leu Met Leu Ala Thr Gly Met Arg Asn Ile Pro Gly Lys
        35                  40                  45

Gln Ala Lys
    50

<210> SEQ ID NO 267
<211> LENGTH: 50
<212> TYPE: PRT
<213> ORGANISM: Influenza virus A
<220> FEATURE:
<223> OTHER INFORMATION: C-terminal stem segment of Influenza A HA
      subtype H14(no Cys-delta 3)

<400> SEQUENCE: 267

Pro Cys Leu Thr Asp Lys Gly Ser Ile Gln Ser Asp Lys Pro Phe Gln
1               5                   10                  15

Asn Val Ser Arg Ile Ala Ile Gly Asn Cys Pro Lys Tyr Val Lys Gln
            20                  25                  30

Gly Ser Leu Met Leu Ala Thr Gly Met Arg Asn Ile Pro Gly Lys Gln
        35                  40                  45

Ala Lys
    50

<210> SEQ ID NO 268
<211> LENGTH: 53
<212> TYPE: PRT
<213> ORGANISM: Influenza virus A
<220> FEATURE:
<223> OTHER INFORMATION: C-terminal stem segment of Influenza A HA
      subtype H15(no Cys)

<400> SEQUENCE: 268

Glu Gly Glu Cys Phe Tyr Ser Gly Gly Thr Ile Asn Ser Pro Leu Pro
1               5                   10                  15

Phe Gln Asn Ile Asp Ser Arg Ala Val Gly Lys Cys Pro Arg Tyr Val
            20                  25                  30

Lys Gln Ser Ser Leu Pro Leu Ala Leu Gly Met Lys Asn Val Pro Glu
        35                  40                  45

Lys Ile Arg Thr Arg
    50

<210> SEQ ID NO 269
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H15(no Cys-delta 1)

<400> SEQUENCE: 269

Gly Glu Cys Phe Tyr Ser Gly Gly Thr Ile Asn Ser Pro Leu Pro Phe
1               5                   10                  15

Gln Asn Ile Asp Ser Arg Ala Val Gly Lys Cys Pro Arg Tyr Val Lys
            20                  25                  30

```
Gln Ser Ser Leu Pro Leu Ala Leu Gly Met Lys Asn Val Pro Glu Lys
        35                  40                  45

Ile Arg Thr Arg
    50

<210> SEQ ID NO 270
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H15(no Cys-delta 3)

<400> SEQUENCE: 270

Glu Cys Phe Tyr Ser Gly Gly Thr Ile Asn Ser Pro Leu Pro Phe Gln
  1               5                  10                  15

Asn Ile Asp Ser Arg Ala Val Gly Lys Cys Pro Arg Tyr Val Lys Gln
             20                  25                  30

Ser Ser Leu Pro Leu Ala Leu Gly Met Lys Asn Val Pro Glu Lys Ile
        35                  40                  45

Arg Thr Arg
    50

<210> SEQ ID NO 271
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H16(no Cys)

<400> SEQUENCE: 271

Asn Thr Lys Cys Gln Thr Ser Leu Gly Gly Ile Asn Thr Asn Lys Thr
  1               5                  10                  15

Phe Gln Asn Ile Glu Arg Asn Ala Leu Gly Asp Cys Pro Lys Tyr Ile
             20                  25                  30

Lys Ser Gly Gln Leu Lys Leu Ala Thr Gly Leu Arg Asn Val Pro Ser
        35                  40                  45

Ile Gly Glu Arg
    50

<210> SEQ ID NO 272
<211> LENGTH: 51
<212> TYPE: PRT
<213> ORGANISM: Influenza virus A
<220> FEATURE:
<223> OTHER INFORMATION: C-terminal stem segment of Influenza A HA
      subtype H16(no Cys-delta 1)

<400> SEQUENCE: 272

Thr Lys Cys Gln Thr Ser Leu Gly Gly Ile Asn Thr Asn Lys Thr Phe
  1               5                  10                  15

Gln Asn Ile Glu Arg Asn Ala Leu Gly Asp Cys Pro Lys Tyr Ile Lys
             20                  25                  30

Ser Gly Gln Leu Lys Leu Ala Thr Gly Leu Arg Asn Val Pro Ser Ile
        35                  40                  45

Gly Glu Arg
    50

<210> SEQ ID NO 273
<211> LENGTH: 50
```

<212> TYPE: PRT
<213> ORGANISM: Influenza virus A
<220> FEATURE:
<223> OTHER INFORMATION: C-terminal stem segment of Influenza A HA subtype H16(no Cys-delta 3)

<400> SEQUENCE: 273

Lys Cys Gln Thr Ser Leu Gly Gly Ile Asn Thr Asn Lys Thr Phe Gln
1               5                   10                  15

Asn Ile Glu Arg Asn Ala Leu Gly Asp Cys Pro Lys Tyr Ile Lys Ser
            20                  25                  30

Gly Gln Leu Lys Leu Ala Thr Gly Leu Arg Asn Val Pro Ser Ile Gly
        35                  40                  45

Glu Arg
    50

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294
<400> SEQUENCE: 294
000

<210> SEQ ID NO 295
<400> SEQUENCE: 295
000

<210> SEQ ID NO 296
<400> SEQUENCE: 296
000

<210> SEQ ID NO 297
<400> SEQUENCE: 297
000

<210> SEQ ID NO 298
<400> SEQUENCE: 298
000

<210> SEQ ID NO 299
<400> SEQUENCE: 299
000

<210> SEQ ID NO 300
<400> SEQUENCE: 300
000

<210> SEQ ID NO 301
<400> SEQUENCE: 301
000

<210> SEQ ID NO 302
<400> SEQUENCE: 302
000

<210> SEQ ID NO 303
<400> SEQUENCE: 303
000

<210> SEQ ID NO 304
<400> SEQUENCE: 304
000

-continued

```
<210> SEQ ID NO 305
<400> SEQUENCE: 305

000

<210> SEQ ID NO 306
<400> SEQUENCE: 306

000

<210> SEQ ID NO 307
<400> SEQUENCE: 307

000

<210> SEQ ID NO 308
<211> LENGTH: 44
<212> TYPE: PRT
<213> ORGANISM: Influenza virus A
<220> FEATURE:
<223> OTHER INFORMATION: N-terminal stem segment of Influenza A HA
      subtype H3(HK68-CON-A)

<400> SEQUENCE: 308

Ser Thr Ala Thr Leu Cys Leu Gly His His Ala Val Pro Asn Gly Thr
1               5                  10                  15

Leu Val Lys Thr Ile Thr Asp Asp Gln Ile Glu Val Thr Asn Ala Thr
            20                  25                  30

Glu Leu Val Gln Ser Ser Ser Thr Gly Lys Ile Cys
        35                  40

<210> SEQ ID NO 309
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H3(HK68-CON-B)

<400> SEQUENCE: 309

Cys Lys Tyr Val Lys Gln Asn Thr Leu Lys Leu Ala Thr Gly Met Arg
1               5                  10                  15

Asn Val Pro Glu Lys Gln Thr Arg
            20

<210> SEQ ID NO 310
<211> LENGTH: 97
<212> TYPE: PRT
<213> ORGANISM: Influenza virus A
<220> FEATURE:
<223> OTHER INFORMATION: N-terminal stem segment of Influenza A HA
      subtype H3(HK68-CON-C)

<400> SEQUENCE: 310

Gln Asp Leu Pro Gly Asn Asp Asn Ser Thr Ala Thr Leu Cys Leu Gly
1               5                  10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
```

```
                50                  55                  60
Thr Leu Ile Asp Ala Leu Leu Gly Asp Pro His Cys Asp Val Phe Gln
 65                  70                  75                  80

Asn Glu Thr Trp Asp Leu Phe Val Glu Arg Ser Lys Ala Phe Ser Asn
                 85                  90                  95

Cys

<210> SEQ ID NO 311
<211> LENGTH: 74
<212> TYPE: PRT
<213> ORGANISM: Influenza virus A
<220> FEATURE:
<223> OTHER INFORMATION: C-terminal stem segment of Influenza A HA
      subtype H3(HK68-CON-C)

<400> SEQUENCE: 311

Ala Pro Arg Gly Tyr Phe Lys Met Arg Thr Gly Lys Ser Ser Ile Met
  1               5                  10                  15

Ser Ser Asp Ala Pro Ile Asp Thr Cys Ile Ser Glu Cys Ile Thr Pro
                 20                  25                  30

Asn Gly Ser Ile Pro Asn Asp Lys Pro Phe Gln Asn Val Asn Lys Ile
             35                  40                  45

Thr Tyr Gly Ala Cys Pro Lys Tyr Val Lys Gln Asn Thr Leu Lys Leu
 50                  55                  60

Ala Thr Gly Met Arg Asn Val Pro Glu Lys
 65                  70

<210> SEQ ID NO 312
<211> LENGTH: 46
<212> TYPE: PRT
<213> ORGANISM: Influenza virus A
<220> FEATURE:
<223> OTHER INFORMATION: N-terminal stem segment of Influenza A HA
      subtype H1(HK68-CON-A)

<400> SEQUENCE: 312

Asp Thr Ile Cys Ile Gly Tyr His Ala Asn Asn Ser Thr Asp Thr Val
  1               5                  10                  15

Asp Thr Val Leu Glu Lys Asn Val Thr Val Thr His Ser Val Asn Leu
                 20                  25                  30

Leu Glu Asp Ser His Asn Gly Lys Leu Cys Arg Leu Lys Cys
             35                  40                  45

<210> SEQ ID NO 313
<211> LENGTH: 52
<212> TYPE: PRT
<213> ORGANISM: Influenza virus A
<220> FEATURE:
<223> OTHER INFORMATION: C-terminal stem segment of Influenza A HA
      subtype H1(HK68-CON-A)

<400> SEQUENCE: 313

Cys Lys Cys Gln Thr Pro Leu Gly Ala Ile Asn Ser Ser Leu Pro Tyr
  1               5                  10                  15

Gln Asn Ile His Pro Val Thr Ile Gly Glu Cys Pro Lys Tyr Val Arg
                 20                  25                  30

Ser Ala Lys Leu Arg Met Val Thr Gly Leu Arg Asn Asn Pro Ser Ile
             35                  40                  45

Gln Ser Arg Gly
             50
```

-continued

```
<210> SEQ ID NO 314
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H1(HK68-CON-B)

<400> SEQUENCE: 314

Cys Val Arg

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

```
<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340
```

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350
<211> LENGTH: 25
<212> TYPE: PRT
<213> ORGANISM: Influenza virus A
<220> FEATURE:
<223> OTHER INFORMATION: C-terminal short stem segment of Influenza A HA
      subtype H1

<400> SEQUENCE: 350

```
Cys Pro Lys Tyr Val Arg Ser Ala Lys Leu Arg Met Val Thr Gly Leu
 1               5                  10                  15
```

-continued

Arg Asn Asn Pro Ser Ile Gln Ser Arg
            20                  25

<210> SEQ ID NO 351
<211> LENGTH: 25
<212> TYPE: PRT
<213> ORGANISM: Influenza virus A
<220> FEATURE:
<223> OTHER INFORMATION: C-terminal short stem segment of Influenza A HA
      subtype H2

<400> SEQUENCE: 351

Cys Pro Lys Tyr Val Lys Ser Glu Arg Leu Val Leu Ala Thr Gly Leu
1               5                   10                  15

Arg Asn Val Pro Gln Ile Glu Ser Arg
            20                  25

<210> SEQ ID NO 352
<211> LENGTH: 25
<212> TYPE: PRT
<213> ORGANISM: Influenza virus A
<220> FEATURE:
<223> OTHER INFORMATION: C-terminal short stem segment of Influenza A HA
      subtype H3

<400> SEQUENCE: 352

Cys Pro Lys Tyr Val Lys Gln Asn Thr Leu Lys Leu Ala Thr Gly Met
1               5                   10                  15

Arg Asn Val Pro Glu Lys Gln Thr Arg
            20                  25

<210> SEQ ID NO 353
<211> LENGTH: 25
<212> TYPE: PRT
<213> ORGANISM: Influenza virus A
<220> FEATURE:
<223> OTHER INFORMATION: C-terminal short stem segment of Influenza A HA
      subtype H4

<400> SEQUENCE: 353

Cys Pro Arg Tyr Val Lys Gln Gly Ser Leu Lys Leu Ala Thr Gly Met
1               5                   10                  15

Arg Asn Ile Pro Glu Lys Ala Ser Arg
            20                  25

<210> SEQ ID NO 354
<211> LENGTH: 25
<212> TYPE: PRT
<213> ORGANISM: Influenza virus A
<220> FEATURE:
<223> OTHER INFORMATION: C-terminal short stem segment of Influenza A HA
      subtype H5

<400> SEQUENCE: 354

Cys Pro Lys Tyr Val Lys Ser Asp Arg Leu Val Leu Ala Thr Gly Leu
1               5                   10                  15

Arg Asn Val Pro Gln Arg Lys Lys Arg
            20                  25

<210> SEQ ID NO 355
<211> LENGTH: 25
<212> TYPE: PRT
<213> ORGANISM: Influenza virus A
<220> FEATURE:
<223> OTHER INFORMATION: C-terminal short stem segment of Influenza A HA subtype H6

<400> SEQUENCE: 355

Cys Pro Lys Tyr Val Lys Ser Glu Ser Leu Arg Leu Ala Thr Gly Leu
1               5                   10                  15

Arg Asn Val Pro Gln Ile Glu Thr Arg
            20                  25

<210> SEQ ID NO 356
<211> LENGTH: 29
<212> TYPE: PRT
<213> ORGANISM: Influenza virus A
<220> FEATURE:
<223> OTHER INFORMATION: C-terminal short stem segment of Influenza A HA
      subtype H7

<400> SEQUENCE: 356

Cys Pro Arg Tyr Val Lys Gln Glu Ser Leu Leu Leu Ala Thr Gly Met
1               5                   10                  15

Lys Asn Val Pro Glu Pro Ser Lys Lys Arg Lys Lys Arg
            20                  25

<210> SEQ ID NO 357
<211> LENGTH: 25
<212> TYPE: PRT
<213> ORGANISM: Influenza virus A
<220> FEATURE:
<223> OTHER INFORMATION: C-terminal short stem segment of Influenza A HA
      subtype H8

<400> SEQUENCE: 357

Cys Pro Lys Tyr Val Lys Lys Ala Ser Leu Arg Leu Ala Val Gly Leu
1               5                   10                  15

Arg Asn Thr Pro Ser Val Glu Pro Arg
            20                  25

<210> SEQ ID NO 358
<211> LENGTH: 25
<212> TYPE: PRT
<213> ORGANISM: Influenza virus A
<220> FEATURE:
<223> OTHER INFORMATION: C-terminal short stem segment of Influenza A HA
      subtype H9

<400> SEQUENCE: 358

Cys Pro Lys Tyr Val Gly Val Lys Ser Leu Lys Leu Pro Val Gly Leu
1               5                   10                  15

Arg Asn Val Pro Ala Val Ser Ser Arg
            20                  25

<210> SEQ ID NO 359
<211> LENGTH: 26
<212> TYPE: PRT
<213> ORGANISM: Influenza virus A
<220> FEATURE:
<223> OTHER INFORMATION: C-terminal short stem segment of Influenza A HA
      subtype H10

<400> SEQUENCE: 359

Cys Pro Lys Tyr Val Asn Gln Arg Ser Leu Leu Leu Ala Thr Gly Met
1               5                   10                  15

Arg Asn Val Pro Glu Val Val Gln Gly Arg
            20                  25

```
<210> SEQ ID NO 360
<211> LENGTH: 25
<212> TYPE: PRT
<213> ORGANISM: Influenza virus A
<220> FEATURE:
<223> OTHER INFORMATION: C-terminal short stem segment of Influenza A HA
      subtype H11

<400> SEQUENCE: 360

Cys Pro Lys Tyr Val Asn Val Lys Ser Leu Lys Leu Ala Thr Gly Pro
1               5                   10                  15

Arg Asn Val Pro Ala Ile Ala Ser Arg
            20                  25

<210> SEQ ID NO 361
<211> LENGTH: 25
<212> TYPE: PRT
<213> ORGANISM: Influenza virus A
<220> FEATURE:
<223> OTHER INFORMATION: C-terminal short stem segment of Influenza A HA
      subtype H12

<400> SEQUENCE: 361

Cys Pro Lys Tyr Ile Pro Ser Gly Ser Leu Lys Leu Ala Ile Gly Leu
1               5                   10                  15

Arg Asn Val Pro Gln Val Gln Asp Arg
            20                  25

<210> SEQ ID NO 362
<211> LENGTH: 25
<212> TYPE: PRT
<213> ORGANISM: Influenza virus A
<220> FEATURE:
<223> OTHER INFORMATION: C-terminal short stem segment of Influenza A HA
      subtype H13

<400> SEQUENCE: 362

Cys Pro Lys Tyr Ile Lys Ser Gly Gln Leu Lys Leu Ala Thr Gly Leu
1               5                   10                  15

Arg Asn Val Pro Ala Ile Ser Asn Arg
            20                  25

<210> SEQ ID NO 363
<211> LENGTH: 25
<212> TYPE: PRT
<213> ORGANISM: Influenza virus A
<220> FEATURE:
<223> OTHER INFORMATION: C-terminal short stem segment of Influenza A HA
      subtype H14

<400> SEQUENCE: 363

Cys Pro Lys Tyr Val Lys Gln Gly Ser Leu Met Leu Ala Thr Gly Met
1               5                   10                  15

Arg Asn Ile Pro Gly Lys Gln Ala Lys
            20                  25

<210> SEQ ID NO 364
<211> LENGTH: 26
<212> TYPE: PRT
<213> ORGANISM: Influenza virus A
<220> FEATURE:
<223> OTHER INFORMATION: C-terminal short stem segment of Influenza A HA
      subtype H15

<400> SEQUENCE: 364

Cys Pro Arg Tyr Val Lys Gln Ser Ser Leu Pro Leu Ala Leu Gly Met
```

1 5 10 15

Lys Asn Val Pro Glu Lys Ile Arg Thr Arg
20 25

<210> SEQ ID NO 365
<211> LENGTH: 25
<212> TYPE: PRT
<213> ORGANISM: Influenza virus A
<220> FEATURE:
<223> OTHER INFORMATION: C-terminal short stem segment of Influenza A HA subtype H16

<400> SEQUENCE: 365

Cys Pro Lys Tyr Ile Lys Ser Gly Gln Leu Lys Leu Ala Thr Gly Leu
1 5 10 15

Arg Asn Val Pro Ser Ile Gly Glu Arg
20 25

<210> SEQ ID NO 366
<211> LENGTH: 24
<212> TYPE: PRT
<213> ORGANISM: Influenza virus A
<220> FEATURE:
<223> OTHER INFORMATION: C-terminal stem segment of Influenza A HA subtype H1(no Cys)

<400> SEQUENCE: 366

Pro Lys Tyr Val Arg Ser Ala Lys Leu Arg Met Val Thr Gly Leu Arg
1 5 10 15

Asn Asn Pro Ser Ile Gln Ser Arg
20

<210> SEQ ID NO 367
<211> LENGTH: 23
<212> TYPE: PRT
<213> ORGANISM: Influenza virus A
<220> FEATURE:
<223> OTHER INFORMATION: C-terminal stem segment of Influenza A HA subtype H1(no Cys-delta 1)

<400> SEQUENCE: 367

Lys Tyr Val Arg Ser Ala Lys Leu Arg Met Val Thr Gly Leu Arg Asn
1 5 10 15

Asn Pro Ser Ile Gln Ser Arg
20

<210> SEQ ID NO 368
<211> LENGTH: 22
<212> TYPE: PRT
<213> ORGANISM: Influenza virus A
<220> FEATURE:
<223> OTHER INFORMATION: C-terminal stem segment of Influenza A HA subtype H1(no Cys-delta 3)

<400> SEQUENCE: 368

Tyr Val Arg Ser Ala Lys Leu Arg Met Val Thr Gly Leu Arg Asn Asn
1 5 10 15

Pro Ser Ile Gln Ser Arg
20

<210> SEQ ID NO 369
<211> LENGTH: 24
<212> TYPE: PRT
<213> ORGANISM: Influenza virus A
<220> FEATURE:

<223> OTHER INFORMATION: C-terminal stem segment of Influenza A HA
      subtype H2(no Cys)

<400> SEQUENCE: 369

Pro Lys Tyr Val Lys Ser Glu Arg Leu Val Leu Ala Thr Gly Leu Arg
1               5                   10                  15

Asn Val Pro Gln Ile Glu Ser Arg
            20

<210> SEQ ID NO 370
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H2(no Cys-delta 1)

<400> SEQUENCE: 370

Lys Tyr Val Lys Ser Glu Arg Leu Val Leu Ala Thr Gly Leu Arg Asn
1               5                   10                  15

Val Pro Gln Ile Glu Ser Arg
            20

<210> SEQ ID NO 371
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H2(no Cys-delta 3)

<400> SEQUENCE: 371

Tyr Val Lys Ser Glu Arg Leu Val Leu Ala Thr Gly Leu Arg Asn Val
1               5                   10                  15

Pro Gln Ile Glu Ser Arg
            20

<210> SEQ ID NO 372
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H3(no Cys)

<400> SEQUENCE: 372

Pro Lys Tyr Val Lys Gln Asn Thr Leu Lys Leu Ala Thr Gly Met Arg
1               5                   10                  15

Asn Val Pro Glu Lys Gln Thr Arg
            20

<210> SEQ ID NO 373
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H3(no Cys-delta 1)

<400> SEQUENCE: 373

Lys Tyr Val Lys Gln Asn Thr Leu Lys Leu Ala Thr Gly Met Arg Asn
1               5                   10                  15

Val Pro Glu Lys Gln Thr Arg
            20

<210> SEQ ID NO 374
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H3(no Cys-delta 3)

<400> SEQUENCE: 374

Tyr Val Lys Gln Asn Thr Leu Lys Leu Ala Thr Gly Met Arg Asn Val
1               5                   10                  15

Pro Glu Lys Gln Thr Arg
            20

<210> SEQ ID NO 375
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H4(no Cys)

<400> SEQUENCE: 375

Pro Arg Tyr Val Lys Gln Gly Ser Leu Lys Leu Ala Thr Gly Met Arg
1               5                   10                  15

Asn Ile Pro Glu Lys Ala Ser Arg
            20

<210> SEQ ID NO 376
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H4(no Cys-delta 1)

<400> SEQUENCE: 376

Arg Tyr Val Lys Gln Gly Ser Leu Lys Leu Ala Thr Gly Met Arg Asn
1               5                   10                  15

Ile Pro Glu Lys Ala Ser Arg
            20

<210> SEQ ID NO 377
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H4(no Cys-delta 3)

<400> SEQUENCE: 377

Tyr Val Lys Gln Gly Ser Leu Lys Leu Ala Thr Gly Met Arg Asn Ile
1               5                   10                  15

Pro Glu Lys Ala Ser Arg
            20

<210> SEQ ID NO 378
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H5(no Cys)

<400> SEQUENCE: 378

-continued

Pro Lys Tyr Val Lys Ser Asp Arg Leu Val Leu Ala Thr Gly Leu Arg
1               5                   10                  15

Asn Val Pro Gln Arg Lys Lys Arg
            20

<210> SEQ ID NO 379
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H5(no Cys-delta 1)

<400> SEQUENCE: 379

Lys Tyr Val Lys Ser Asp Arg Leu Val Leu Ala Thr Gly Leu Arg Asn
1               5                   10                  15

Val Pro Gln Arg Lys Lys Arg
            20

<210> SEQ ID NO 380
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H5(no Cys-delta 3)

<400> SEQUENCE: 380

Tyr Val Lys Ser Asp Arg Leu Val Leu Ala Thr Gly Leu Arg Asn Val
1               5                   10                  15

Pro Gln Arg Lys Lys Arg
            20

<210> SEQ ID NO 381
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H6(no Cys)

<400> SEQUENCE: 381

Pro Lys Tyr Val Lys Ser Glu Ser Leu Arg Leu Ala Thr Gly Leu Arg
1               5                   10                  15

Asn Val Pro Gln Ile Glu Thr Arg
            20

<210> SEQ ID NO 382
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H6(no Cys-delta 1)

<400> SEQUENCE: 382

Lys Tyr Val Lys Ser Glu Ser Leu Arg Leu Ala Thr Gly Leu Arg Asn
1               5                   10                  15

Val Pro Gln Ile Glu Thr Arg
            20

<210> SEQ ID NO 383
<211> LENGTH: 22
<212> TYPE: PRT
<213> ORGANISM: Influenza virus A
<220> FEATURE:
<223> OTHER INFORMATION: C-terminal stem segment of Influenza A HA
subtype H6(no Cys-delta 3)

<400> SEQUENCE: 383

Tyr Val Lys Ser Glu Ser Leu Arg Leu Ala Thr Gly Leu Arg Asn Val
1 5 10 15

Pro Gln Ile Glu Thr Arg
20

<210> SEQ ID NO 384
<211> LENGTH: 28
<212> TYPE: PRT
<213> ORGANISM: Influenza virus A
<220> FEATURE:
<223> OTHER INFORMATION: C-terminal stem segment of Influenza A HA
subtype H7(no Cys)

<400> SEQUENCE: 384

Pro Arg Tyr Val Lys Gln Glu Ser Leu Leu Leu Ala Thr Gly Met Lys
1 5 10 15

Asn Val Pro Glu Pro Ser Lys Lys Arg Lys Lys Arg
20 25

<210> SEQ ID NO 385
<211> LENGTH: 27
<212> TYPE: PRT
<213> ORGANISM: Influenza virus A
<220> FEATURE:
<223> OTHER INFORMATION: C-terminal stem segment of Influenza A HA
subtype H7(no Cys-delta 1)

<400> SEQUENCE: 385

Arg Tyr Val Lys Gln Glu Ser Leu Leu Leu Ala Thr Gly Met Lys Asn
1 5 10 15

Val Pro Glu Pro Ser Lys Lys Arg Lys Lys Arg
20 25

<210> SEQ ID NO 386
<211> LENGTH: 26
<212> TYPE: PRT
<213> ORGANISM: Influenza virus A
<220> FEATURE:
<223> OTHER INFORMATION: C-terminal stem segment of Influenza A HA
subtype H7(no Cys-delta 3)

<400> SEQUENCE: 386

Tyr Val Lys Gln Glu Ser Leu Leu Leu Ala Thr Gly Met Lys Asn Val
1 5 10 15

Pro Glu Pro Ser Lys Lys Arg Lys Lys Arg
20 25

<210> SEQ ID NO 387
<211> LENGTH: 24
<212> TYPE: PRT
<213> ORGANISM: Influenza virus A
<220> FEATURE:
<223> OTHER INFORMATION: C-terminal stem segment of Influenza A HA
subtype H8(no Cys)

<400> SEQUENCE: 387

Pro Lys Tyr Val Lys Lys Ala Ser Leu Arg Leu Ala Val Gly Leu Arg
1 5 10 15

Asn Thr Pro Ser Val Glu Pro Arg
20

<210> SEQ ID NO 388
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H8(no Cys-delta 1)

<400> SEQUENCE: 388

Lys Tyr Val Lys Lys Ala Ser Leu Arg Leu Ala Val Gly Leu Arg Asn
 1               5                  10                  15

Thr Pro Ser Val Glu Pro Arg
            20

<210> SEQ ID NO 389
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H8(no Cys-delta 3)

<400> SEQUENCE: 389

Tyr Val Lys Lys Ala Ser Leu Arg Leu Ala Val Gly Leu Arg Asn Thr
 1               5                  10                  15

Pro Ser Val Glu Pro Arg
            20

<210> SEQ ID NO 390
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H9(no Cys)

<400> SEQUENCE: 390

Pro Lys Tyr Val Gly Val Lys Ser Leu Lys Leu Pro Val Gly Leu Arg
 1               5                  10                  15

Asn Val Pro Ala Val Ser Ser Arg
            20

<210> SEQ ID NO 391
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H9(no Cys-delta 1)

<400> SEQUENCE: 391

Lys Tyr Val Gly Val Lys Ser Leu Lys Leu Pro Val Gly Leu Arg Asn
 1               5                  10                  15

Val Pro Ala Val Ser Ser Arg
            20

<210> SEQ ID NO 392
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H9(no Cys-delta 3)

<400> SEQUENCE: 392

-continued

```
Tyr Val Gly Val Lys Ser Leu Lys Leu Pro Val Gly Leu Arg Asn Val
1               5                   10                  15

Pro Ala Val Ser Ser Arg
            20

<210> SEQ ID NO 393
<211> LENGTH: 25
<212> TYPE: PRT
<213> ORGANISM: Influenza virus A
<220> FEATURE:
<223> OTHER INFORMATION: C-terminal stem segment of Influenza A HA
      subtype H10(no Cys)

<400> SEQUENCE: 393

Pro Lys Tyr Val Asn Gln Arg Ser Leu Leu Leu Ala Thr Gly Met Arg
1               5                   10                  15

Asn Val Pro Glu Val Val Gln Gly Arg
            20                  25

<210> SEQ ID NO 394
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H10(no Cys-delta 1)

<400> SEQUENCE: 394

Lys Tyr Val Asn Gln Arg Ser Leu Leu Leu Ala Thr Gly Met Arg Asn
1               5                   10                  15

Val Pro Glu Val Val Gln Gly Arg
            20

<210> SEQ ID NO 395
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H10(no Cys-delta 3)

<400> SEQUENCE: 395

Tyr Val Asn Gln Arg Ser Leu Leu Leu Ala Thr Gly Met Arg Asn Val
1               5                   10                  15

Pro Glu Val Val Gln Gly Arg
            20

<210> SEQ ID NO 396
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H11(no Cys)

<400> SEQUENCE: 396

Pro Lys Tyr Val Asn Val Lys Ser Leu Lys Leu Ala Thr Gly Pro Arg
1               5                   10                  15

Asn Val Pro Ala Ile Ala Ser Arg
            20

<210> SEQ ID NO 397
<211> LENGTH: 23
<212> TYPE: PRT
```

```
<213> ORGANISM: Influenza virus A
<220> FEATURE:
<223> OTHER INFORMATION: C-terminal stem segment of Influenza A HA
      subtype H11(no Cys-delta 1)

<400> SEQUENCE: 397

Lys Tyr Val Asn Val Lys Ser Leu Lys Leu Ala Thr Gly Pro Arg Asn
 1               5                  10                  15

Val Pro Ala Ile Ala Ser Arg
            20

<210> SEQ ID NO 398
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H11(no Cys-delta 3)

<400> SEQUENCE: 398

Tyr Val Asn Val Lys Ser Leu Lys Leu Ala Thr Gly Pro Arg Asn Val
 1               5                  10                  15

Pro Ala Ile Ala Ser Arg
            20

<210> SEQ ID NO 399
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H12(no Cys)

<400> SEQUENCE: 399

Pro Lys Tyr Ile Pro Ser Gly Ser Leu Lys Leu Ala Ile Gly Leu Arg
 1               5                  10                  15

Asn Val Pro Gln Val Gln Asp Arg
            20

<210> SEQ ID NO 400
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H12(no Cys-delta 1)

<400> SEQUENCE: 400

Lys Tyr Ile Pro Ser Gly Ser Leu Lys Leu Ala Ile Gly Leu Arg Asn
 1               5                  10                  15

Val Pro Gln Val Gln Asp Arg
            20

<210> SEQ ID NO 401
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H12(no Cys-delta 3)

<400> SEQUENCE: 401

Tyr Ile Pro Ser Gly Ser Leu Lys Leu Ala Ile Gly Leu Arg Asn Val
 1               5                  10                  15

Pro Gln Val Gln Asp Arg
```

-continued

```
                20

<210> SEQ ID NO 402
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H13(no Cys)

<400> SEQUENCE: 402

Pro Lys Tyr Ile Lys Ser Gly Gln Leu Lys Leu Ala Thr Gly Leu Arg
1               5                   10                  15

Asn Val Pro Ala Ile Ser Asn Arg
            20

<210> SEQ ID NO 403
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H13(no Cys-delta 1)

<400> SEQUENCE: 403

Lys Tyr Ile Lys Ser Gly Gln Leu Lys Leu Ala Thr Gly Leu Arg Asn
1               5                   10                  15

Val Pro Ala Ile Ser Asn Arg
            20

<210> SEQ ID NO 404
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H13(no Cys-delta 3)

<400> SEQUENCE: 404

Tyr Ile Lys Ser Gly Gln Leu Lys Leu Ala Thr Gly Leu Arg Asn Val
1               5                   10                  15

Pro Ala Ile Ser Asn Arg
            20

<210> SEQ ID NO 405
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H14(no Cys)

<400> SEQUENCE: 405

Pro Lys Tyr Val Lys Gln Gly Ser Leu Met Leu Ala Thr Gly Met Arg
1               5                   10                  15

Asn Ile Pro Gly Lys Gln Ala Lys
            20

<210> SEQ ID NO 406
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H14(no Cys-delta 1)
```

```
<400> SEQUENCE: 406

Lys Tyr Val Lys Gln Gly Ser Leu Met Leu Ala Thr Gly Met Arg Asn
1               5                   10                  15

Ile Pro Gly Lys Gln Ala Lys
            20

<210> SEQ ID NO 407
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H14(no Cys-delta 3)

<400> SEQUENCE: 407

Tyr Val Lys Gln Gly Ser Leu Met Leu Ala Thr Gly Met Arg Asn Ile
1               5                   10                  15

Pro Gly Lys Gln Ala Lys
            20

<210> SEQ ID NO 408
<211> LENGTH: 25
<212> TYPE: PRT
<213> ORGANISM: Influenza virus A
<220> FEATURE:
<223> OTHER INFORMATION: C-terminal stem segment of Influenza A HA
      subtype H15(no Cys)

<400> SEQUENCE: 408

Pro Arg Tyr Val Lys Gln Ser Ser Leu Pro Leu Ala Leu Gly Met Lys
1               5                   10                  15

Asn Val Pro Glu Lys Ile Arg Thr Arg
            20                  25

<210> SEQ ID NO 409
<211> LENGTH: 24
<212> TYPE: PRT
<213> ORGANISM: Influenza virus A
<220> FEATURE:
<223> OTHER INFORMATION: C-terminal stem segment of Influenza A HA
      subtype H15(no Cys-delta 1)

<400> SEQUENCE: 409

Arg Tyr Val Lys Gln Ser Ser Leu Pro Leu Ala Leu Gly Met Lys Asn
1               5                   10                  15

Val Pro Glu Lys Ile Arg Thr Arg
            20

<210> SEQ ID NO 410
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H15(no Cys-delta 3)

<400> SEQUENCE: 410

Tyr Val Lys Gln Ser Ser Leu Pro Leu Ala Leu Gly Met Lys Asn Val
1               5                   10                  15

Pro Glu Lys Ile Arg Thr Arg
            20

<210> SEQ ID NO 411
<211> LENGTH: 24
```

```
<212> TYPE: PRT
<213> ORGANISM: Influenza virus A
<220> FEATURE:
<223> OTHER INFORMATION: C-terminal stem segment of Influenza A HA
      subtype H16(no Cys)

<400> SEQUENCE: 411

Pro Lys Tyr Ile Lys Ser Gly Gln Leu Lys Leu Ala Thr Gly Leu Arg
 1               5                  10                  15

Asn Val Pro Ser Ile Gly Glu Arg
            20

<210> SEQ ID NO 412
<211> LENGTH: 23
<212> TYPE: PRT
<213> ORGANISM: Influenza virus A
<220> FEATURE:
<223> OTHER INFORMATION: C-terminal stem segment of Influenza A HA
      subtype H16(no Cys-delta 1)

<400> SEQUENCE: 412

Lys Tyr Ile Lys Ser Gly Gln Leu Lys Leu Ala Thr Gly Leu Arg Asn
 1               5                  10                  15

Val Pro Ser Ile Gly Glu Arg
            20

<210> SEQ ID NO 413
<211> LENGTH: 22
<212> TYPE: PRT
<213> ORGANISM: Influenza virus A
<220> FEATURE:
<223> OTHER INFORMATION: C-terminal stem segment of Influenza A HA
      subtype H16(no Cys-delta 3)

<400> SEQUENCE: 413

Tyr Ile Lys Ser Gly Gln Leu Lys Leu Ala Thr Gly Leu Arg Asn Val
 1               5                  10                  15

Pro Ser Ile Gly Glu Arg
            20

<210> SEQ ID NO 414
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H1

<400> SEQUENCE: 414

Asp Thr Ile Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
    50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile Cys
                85                  90

<210> SEQ ID NO 415
```

-continued

```
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H2

<400> SEQUENCE: 415

Asp Gln Ile Cys Ile Gly Tyr His Ser Asn Asn Ser Thr Glu Lys Val
1               5                   10                  15

Asp Thr Ile Leu Glu Arg Asn Val Thr Val Thr His Ala Gln Asn Ile
            20                  25                  30

Leu Glu Lys Thr His Asn Gly Lys Leu Cys Lys Leu Asn Gly Ile Pro
        35                  40                  45

Pro Leu Glu Leu Gly Asp Cys Ser Ile Ala Gly Trp Leu Leu Gly Asn
50                  55                  60

Pro Glu Cys Asp Arg Leu Leu Thr Val Pro Glu Trp Ser Tyr Ile Met
65                  70                  75                  80

Glu Lys Glu Asn Pro Arg Asn Gly Leu Cys
                85                  90

<210> SEQ ID NO 416
<211> LENGTH: 97
<212> TYPE: PRT
<213> ORGANISM: Influenza virus A
<220> FEATURE:
<223> OTHER INFORMATION: N-termianl long stem domain segment of
      Influenza A HA subtype H3

<400> SEQUENCE: 416

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

Cys

<210> SEQ ID NO 417
<211> LENGTH: 93
<212> TYPE: PRT
<213> ORGANISM: Influenza virus A
<220> FEATURE:
<223> OTHER INFORMATION: N-termianl long stem domain segment of
      Influenza A HA subtype H4

<400> SEQUENCE: 417

Gln Asn Tyr Thr Gly Asn Pro Val Ile Cys Met Gly His His Ala Val
1               5                   10                  15

Ala Asn Gly Thr Met Val Lys Thr Leu Ala Asp Asp Gln Val Glu Val
            20                  25                  30

Val Thr Ala Gln Glu Leu Val Glu Ser Gln Asn Leu Pro Glu Leu Cys
        35                  40                  45

Pro Ser Pro Leu Arg Leu Val Asp Gly Gln Thr Cys Asp Ile Ile Asn
```

```
                 50                  55                  60
Gly Ala Leu Gly Ser Pro Gly Cys Asp His Leu Asn Gly Ala Glu Trp
 65                  70                  75                  80

Asp Val Phe Ile Glu Arg Pro Asn Ala Val Asp Thr Cys
                 85                  90

<210> SEQ ID NO 418
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H5

<400> SEQUENCE: 418

Asp Gln Ile Cys Ile Gly Tyr His Ala Asn Lys Ser Thr Lys Gln Val
  1               5                  10                  15

Asp Thr Ile Met Glu Lys Asn Val Thr Val Thr His Ala Gln Asp Ile
                 20                  25                  30

Leu Glu Arg Thr His Asn Gly Lys Leu Cys Ser Leu Asn Gly Val Lys
             35                  40                  45

Pro Leu Ile Leu Arg Asp Cys Ser Val Ala Gly Trp Leu Leu Gly Asn
     50                  55                  60

Pro Met Cys Asp Glu Phe Leu Asn Leu Pro Glu Trp Leu Tyr Ile Val
 65                  70                  75                  80

Glu Lys Asp Asn Pro Ile Asn Ser Leu Cys
                 85                  90

<210> SEQ ID NO 419
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H6

<400> SEQUENCE: 419

Asp Lys Ile Cys Ile Gly Tyr His Ala Asn Asn Ser Thr Thr Gln Ile
  1               5                  10                  15

Asp Thr Ile Leu Glu Lys Asn Val Thr Val Thr His Ser Val Glu Leu
                 20                  25                  30

Leu Glu Asn Gln Lys Glu Glu Arg Phe Cys Lys Ile Leu Lys Lys Ala
             35                  40                  45

Pro Leu Asp Leu Lys Gly Cys Thr Ile Glu Gly Trp Ile Leu Gly Asn
     50                  55                  60

Pro Gln Cys Asp Leu Leu Leu Gly Asp Gln Ser Trp Ser Tyr Ile Val
 65                  70                  75                  80

Glu Arg Pro Thr Ala Gln Asn Gly Ile Cys
                 85                  90

<210> SEQ ID NO 420
<211> LENGTH: 87
<212> TYPE: PRT
<213> ORGANISM: Influenza virus A
<220> FEATURE:
<223> OTHER INFORMATION: N-termianl long stem domain segment of
      Influenza A HA subtype H7

<400> SEQUENCE: 420

Asp Lys Ile Cys Leu Gly His His Ala Val Ser Asn Gly Thr Lys Val
  1               5                  10                  15
```

```
Asn Thr Leu Thr Glu Arg Gly Val Glu Val Asn Ala Thr Glu Thr
             20                  25                  30

Val Glu Arg Thr Asn Ile Pro Lys Ile Cys Ser Lys Gly Lys Arg Thr
         35                  40                  45

Thr Asp Leu Gly Gln Cys Gly Leu Leu Gly Thr Ile Thr Gly Pro Pro
 50                  55                  60

Gln Cys Asp Gln Phe Leu Glu Phe Ser Ala Asp Leu Ile Ile Glu Arg
 65                  70                  75                  80

Arg Glu Gly Asn Asp Val Cys
                 85
```

<210> SEQ ID NO 421
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H8

<400> SEQUENCE: 421

```
Asp Arg Ile Cys Ile Gly Tyr Gln Ser Asn Asn Ser Thr Asp Thr Val
 1               5                  10                  15

Asn Thr Leu Ile Glu Gln Asn Val Pro Val Thr Gln Thr Met Glu Leu
             20                  25                  30

Val Glu Thr Glu Lys His Pro Ala Tyr Cys Asn Thr Asp Leu Gly Ala
         35                  40                  45

Pro Leu Glu Leu Arg Asp Cys Lys Ile Glu Ala Val Ile Tyr Gly Asn
 50                  55                  60

Pro Lys Cys Asp Ile His Leu Lys Asp Gln Gly Trp Ser Tyr Ile Val
 65                  70                  75                  80

Glu Arg Pro Ser Ala Pro Glu Gly Met Cys
                 85                  90
```

<210> SEQ ID NO 422
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H9

<400> SEQUENCE: 422

```
Asp Lys Ile Cys Ile Gly Tyr Gln Ser Thr Asn Ser Thr Glu Thr Val
 1               5                  10                  15

Asp Thr Leu Thr Glu Ser Asn Val Pro Val Thr His Thr Lys Glu Leu
             20                  25                  30

Leu His Thr Glu His Asn Gly Met Leu Cys Ala Thr Asp Leu Gly His
         35                  40                  45

Pro Leu Ile Leu Asp Thr Cys Thr Ile Glu Gly Leu Ile Tyr Gly Asn
 50                  55                  60

Pro Ser Cys Asp Ile Leu Leu Gly Gly Lys Glu Trp Ser Tyr Ile Val
 65                  70                  75                  80

Glu Arg Ser Ser Ala Val Asn Gly Met Cys
                 85                  90
```

<210> SEQ ID NO 423
<211> LENGTH: 88
<212> TYPE: PRT
<213> ORGANISM: Influenza virus A
<220> FEATURE:
<223> OTHER INFORMATION: N-termianl long stem domain segment of Influenza A HA subtype H10

<400> SEQUENCE: 423

Leu Asp Arg Ile Cys Leu Gly His His Ala Val Ala Asn Gly Thr Ile
1 5 10 15

Val Lys Thr Leu Thr Asn Glu Gln Glu Glu Val Thr Asn Ala Thr Glu
20 25 30

Thr Val Glu Ser Thr Asn Leu Asn Lys Leu Cys Met Lys Gly Arg Ser
35 40 45

Tyr Lys Asp Leu Gly Asn Cys His Pro Val Gly Met Leu Ile Gly Thr
50 55 60

Pro Val Cys Asp Pro His Leu Thr Gly Thr Trp Asp Thr Leu Ile Glu
65 70 75 80

Arg Glu Asn Ala Ile Ala His Cys
85

<210> SEQ ID NO 424
<211> LENGTH: 90
<212> TYPE: PRT
<213> ORGANISM: Influenza virus A
<220> FEATURE:
<223> OTHER INFORMATION: N-termianl long stem domain segment of Influenza A HA subtype H11

<400> SEQUENCE: 424

Asp Glu Ile Cys Ile Gly Tyr Leu Ser Asn Asn Ser Thr Asp Lys Val
1 5 10 15

Asp Thr Ile Ile Glu Asn Asn Val Thr Val Thr Ser Ser Val Glu Leu
20 25 30

Val Glu Thr Glu His Thr Gly Ser Phe Cys Ser Ile Asn Gly Lys Gln
35 40 45

Pro Ile Ser Leu Gly Asp Cys Ser Phe Ala Gly Trp Ile Leu Gly Asn
50 55 60

Pro Met Cys Asp Glu Leu Ile Gly Lys Thr Ser Trp Ser Tyr Ile Val
65 70 75 80

Glu Lys Pro Asn Pro Thr Asn Gly Ile Cys
85 90

<210> SEQ ID NO 425
<211> LENGTH: 90
<212> TYPE: PRT
<213> ORGANISM: Influenza virus A
<220> FEATURE:
<223> OTHER INFORMATION: N-termianl long stem domain segment of Influenza A HA subtype H12

<400> SEQUENCE: 425

Asp Lys Ile Cys Ile Gly Tyr Gln Thr Asn Asn Ser Thr Glu Thr Val
1 5 10 15

Asn Thr Leu Ser Glu Gln Asn Val Pro Val Thr Gln Val Glu Glu Leu
20 25 30

Val His Arg Gly Ile Asp Pro Ile Leu Cys Gly Thr Glu Leu Gly Ser
35 40 45

Pro Leu Val Leu Asp Asp Cys Ser Leu Glu Gly Leu Ile Leu Gly Asn
50 55 60

Pro Lys Cys Asp Leu Tyr Leu Asn Gly Arg Glu Trp Ser Tyr Ile Val
65 70 75 80

```
Glu Arg Pro Lys Glu Met Glu Gly Val Cys
                85                  90
```

<210> SEQ ID NO 426
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H13

<400> SEQUENCE: 426

```
Asp Arg Ile Cys Val Gly Tyr Leu Ser Thr Asn Ser Ser Glu Arg Val
  1               5                  10                  15

Asp Thr Leu Leu Glu Asn Gly Val Pro Val Thr Ser Ser Ile Asp Leu
                 20                  25                  30

Ile Glu Thr Asn His Thr Gly Thr Tyr Cys Ser Leu Asn Gly Val Ser
             35                  40                  45

Pro Val His Leu Gly Asp Cys Ser Phe Glu Gly Trp Ile Val Gly Asn
         50                  55                  60

Pro Ala Cys Thr Ser Asn Phe Gly Ile Arg Glu Trp Ser Tyr Leu Ile
 65                  70                  75                  80

Glu Asp Pro Ala Ala Pro His Gly Leu Cys
                 85                  90
```

<210> SEQ ID NO 427
<211> LENGTH: 96
<212> TYPE: PRT
<213> ORGANISM: Influenza virus A
<220> FEATURE:
<223> OTHER INFORMATION: N-termianl long stem domain segment of
      Influenza A HA subtype H14

<400> SEQUENCE: 427

```
Gln Ile Thr Asn Gly Thr Thr Gly Asn Pro Ile Ile Cys Leu Gly His
  1               5                  10                  15

His Ala Val Glu Asn Gly Thr Ser Val Lys Thr Leu Thr Asp Asn His
                 20                  25                  30

Val Glu Val Val Ser Ala Lys Glu Leu Val Glu Thr Asn His Thr Asp
             35                  40                  45

Glu Leu Cys Pro Ser Pro Leu Lys Leu Val Asp Gly Gln Asp Cys His
         50                  55                  60

Leu Ile Asn Gly Ala Leu Gly Ser Pro Gly Cys Asp Arg Leu Gln Asp
 65                  70                  75                  80

Thr Thr Trp Asp Val Phe Ile Glu Arg Pro Thr Ala Val Asp Thr Cys
                 85                  90                  95
```

<210> SEQ ID NO 428
<211> LENGTH: 87
<212> TYPE: PRT
<213> ORGANISM: Influenza virus A
<220> FEATURE:
<223> OTHER INFORMATION: N-termianl long stem domain segment of
      Influenza A HA subtype H15

<400> SEQUENCE: 428

```
Asp Lys Ile Cys Leu Gly His His Ala Val Ala Asn Gly Thr Lys Val
  1               5                  10                  15

Asn Thr Leu Thr Glu Arg Gly Val Glu Val Val Asn Ala Thr Glu Thr
                 20                  25                  30

Val Glu Ile Thr Gly Ile Asp Lys Val Cys Thr Lys Gly Lys Lys Ala
```

```
                35                  40                  45

Val Asp Leu Gly Ser Cys Gly Ile Leu Gly Thr Ile Ile Gly Pro Pro
 50                  55                  60

Gln Cys Asp Leu His Leu Glu Phe Lys Ala Asp Leu Ile Ile Glu Arg
 65                  70                  75                  80

Arg Asn Ser Ser Asp Ile Cys
                 85

<210> SEQ ID NO 429
<211> LENGTH: 90
<212> TYPE: PRT
<213> ORGANISM: Influenza virus A
<220> FEATURE:
<223> OTHER INFORMATION: N-termianl long stem domain segment of
      Influenza A HA subtype H16

<400> SEQUENCE: 429

Asp Lys Ile Cys Ile Gly Tyr Leu Ser Asn Asn Ser Ser Asp Thr Val
  1               5                  10                  15

Asp Thr Leu Thr Glu Asn Gly Val Pro Val Thr Ser Ser Val Asp Leu
                 20                  25                  30

Val Glu Thr Asn His Thr Gly Thr Tyr Cys Ser Leu Asn Gly Ile Ser
                 35                  40                  45

Pro Ile His Leu Gly Asp Cys Ser Phe Glu Gly Trp Ile Val Gly Asn
 50                  55                  60

Pro Ser Cys Ala Thr Asn Ile Asn Ile Arg Glu Trp Ser Tyr Leu Ile
 65                  70                  75                  80

Glu Asp Pro Asn Ala Pro Asn Lys Phe Cys
                 85                  90

<210> SEQ ID NO 430
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H1

<400> SEQUENCE: 430

Ala Pro Met Tyr Ala Phe Ala Leu Ser Arg Gly Phe Gly Ser Gly Ile
  1               5                  10                  15

Ile Thr Ser Asn Ala Ser Met His Glu Cys Asn Thr Lys Cys Gln Thr
                 20                  25                  30

Pro Leu Gly Ala Ile Asn Ser Ser Leu Pro Tyr Gln Asn Ile His Pro
                 35                  40                  45

Val Thr Ile Gly Glu Cys Pro Lys Tyr Val Arg Ser Ala Lys Leu Arg
 50                  55                  60

Met Val Thr Gly Leu Arg Asn Asn Pro Ser Ile Gln Ser Arg
 65                  70                  75

<210> SEQ ID NO 431
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H2

<400> SEQUENCE: 431

Ala Pro Glu Tyr Gly Phe Arg Ile Ser Lys Arg Gly Ser Ser Gly Ile
  1               5                  10                  15
```

Met Lys Thr Glu Gly Thr Leu Glu Asn Cys Glu Thr Lys Cys Gln Thr
            20                  25                  30

Pro Leu Gly Ala Ile Asn Thr Thr Leu Pro Phe His Asn Val His Pro
            35                  40                  45

Leu Thr Ile Gly Glu Cys Pro Lys Tyr Val Ser Glu Arg Leu Val
50                  55                  60

Leu Ala Thr Gly Leu Arg Asn Val Pro Gln Ile Glu Ser Arg
65                  70                  75

<210> SEQ ID NO 432
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H3

<400> SEQUENCE: 432

Ala Pro Arg Gly Tyr Phe Lys Met Arg Thr Gly Lys Ser Ser Ile Met
1               5                   10                  15

Ser Ser Asp Ala Pro Ile Asp Thr Cys Ile Ser Glu Cys Ile Thr Pro
            20                  25                  30

Asn Gly Ser Ile Pro Asn Asp Lys Pro Phe Gln Asn Val Asn Lys Ile
            35                  40                  45

Thr Tyr Gly Ala Cys Pro Lys Tyr Val Lys Gln Asn Thr Leu Lys Leu
50                  55                  60

Ala Thr Gly Met Arg Asn Val Pro Glu Lys Gln Thr Arg
65                  70                  75

<210> SEQ ID NO 433
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H4

<400> SEQUENCE: 433

Ala Pro Arg Gly His Tyr Lys Leu Asn Asn Gln Lys Lys Ser Thr Ile
1               5                   10                  15

Leu Asn Thr Ala Ile Pro Ile Gly Ser Cys Val Ser Lys Cys His Thr
            20                  25                  30

Asp Lys Gly Ser Leu Ser Thr Thr Lys Pro Phe Gln Asn Ile Ser Arg
            35                  40                  45

Ile Ala Val Gly Asp Cys Pro Arg Tyr Val Lys Gln Gly Ser Leu Lys
50                  55                  60

Leu Ala Thr Gly Met Arg Asn Ile Pro Glu Lys Ala Ser Arg
65                  70                  75

<210> SEQ ID NO 434
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H5

<400> SEQUENCE: 434

Ala Pro Arg Tyr Ala Tyr Lys Ile Val Lys Lys Gly Asp Ser Ala Ile
1               5                   10                  15

Met Lys Ser Gly Leu Ala Tyr Gly Asn Cys Asp Thr Lys Cys Gln Thr
            20                  25                  30

Pro Val Gly Glu Ile Asn Ser Ser Met Pro Phe His Asn Ile His Pro
        35                  40                  45

His Thr Ile Gly Glu Cys Pro Lys Tyr Val Lys Ser Asp Arg Leu Val
    50                  55                  60

Leu Ala Thr Gly Leu Arg Asn Val Pro Gln Arg Lys Lys Arg
65                  70                  75

<210> SEQ ID NO 435
<211> LENGTH: 79
<212> TYPE: PRT
<213> ORGANISM: Influenza virus A
<220> FEATURE:
<223> OTHER INFORMATION: C-termianl long stem domain segment of
      Influenza A HA subtype H6

<400> SEQUENCE: 435

Ala Pro Trp Tyr Ala Phe Arg Phe Val Ser Thr Ser Asn Lys Gly Ala
1               5                   10                  15

Val Phe Lys Ser Asn Leu Pro Ile Glu Asn Cys Asp Ala Thr Cys Gln
            20                  25                  30

Thr Val Ala Gly Val Leu Arg Thr Asn Lys Thr Phe Gln Asn Val Ser
        35                  40                  45

Pro Leu Trp Ile Gly Glu Cys Pro Lys Tyr Val Lys Ser Glu Ser Leu
    50                  55                  60

Arg Leu Ala Thr Gly Leu Arg Asn Val Pro Gln Ile Glu Thr Arg
65                  70                  75

<210> SEQ ID NO 436
<211> LENGTH: 81
<212> TYPE: PRT
<213> ORGANISM: Influenza virus A
<220> FEATURE:
<223> OTHER INFORMATION: C-termianl long stem domain segment of
      Influenza A HA subtype H7

<400> SEQUENCE: 436

Ala Pro Asn Arg Ala Ser Phe Leu Arg Gly Lys Ser Met Gly Ile Gln
1               5                   10                  15

Ser Asp Val Gln Val Asp Ala Asn Cys Glu Gly Glu Cys Tyr His Ser
            20                  25                  30

Gly Gly Thr Ile Thr Ser Arg Leu Pro Phe Gln Asn Ile Asn Ser Arg
        35                  40                  45

Ala Val Gly Lys Cys Pro Arg Tyr Val Lys Gln Glu Ser Leu Leu Leu
    50                  55                  60

Ala Thr Gly Met Lys Asn Val Pro Glu Pro Ser Lys Lys Arg Lys Lys
65                  70                  75                  80

Arg

<210> SEQ ID NO 437
<211> LENGTH: 79
<212> TYPE: PRT
<213> ORGANISM: Influenza virus A
<220> FEATURE:
<223> OTHER INFORMATION: C-termianl long stem domain segment of
      Influenza A HA subtype H8

<400> SEQUENCE: 437

Ala Pro Glu Phe Gly Tyr Leu Leu Lys Gly Glu Ser Tyr Gly Arg Ile
1               5                   10                  15

Ile Gln Asn Glu Asp Ile Pro Ile Gly Asn Cys Asn Thr Lys Cys Gln
                20                  25                  30

Thr Tyr Ala Gly Ala Ile Asn Ser Ser Lys Pro Phe Gln Asn Ala Ser
            35                  40                  45

Arg His Tyr Met Gly Glu Cys Pro Lys Tyr Val Lys Lys Ala Ser Leu
        50                  55                  60

Arg Leu Ala Val Gly Leu Arg Asn Thr Pro Ser Val Glu Pro Arg
65                  70                  75

<210> SEQ ID NO 438
<211> LENGTH: 78
<212> TYPE: PRT
<213> ORGANISM: Influenza virus A
<220> FEATURE:
<223> OTHER INFORMATION: C-termianl long stem domain segment of
 Influenza A HA subtype H9

<400> SEQUENCE: 438

Ala Pro Trp Tyr Gly His Val Leu Thr Gly Glu Ser His Gly Arg Ile
1               5                   10                  15

Leu Lys Thr Asp Leu Asn Asn Gly Asn Cys Val Val Gln Cys Gln Thr
                20                  25                  30

Glu Lys Gly Gly Leu Asn Thr Thr Leu Pro Phe His Asn Ile Ser Lys
            35                  40                  45

Tyr Ala Phe Gly Asn Cys Pro Lys Tyr Val Gly Val Lys Ser Leu Lys
        50                  55                  60

Leu Pro Val Gly Leu Arg Asn Val Pro Ala Val Ser Ser Arg
65                  70                  75

<210> SEQ ID NO 439
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H10

<400> SEQUENCE: 439

Ala Pro Ser Arg Val Ser Lys Leu Thr Gly Arg Asp Leu Gly Ile Gln
1               5                   10                  15

Ser Glu Ala Leu Ile Asp Asn Ser Cys Glu Ser Lys Cys Phe Trp Arg
                20                  25                  30

Gly Gly Ser Ile Asn Thr Lys Leu Pro Phe Gln Asn Leu Ser Pro Arg
            35                  40                  45

Thr Val Gly Gln Cys Pro Lys Tyr Val Asn Gln Arg Ser Leu Leu Leu
        50                  55                  60

Ala Thr Gly Met Arg Asn Val Pro Glu Val Val Gln Gly Arg
65                  70                  75

<210> SEQ ID NO 440
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H11

<400> SEQUENCE: 440

Ala Pro Arg Tyr Ala Phe Glu Ile Val Ser Val Gly Asn Gly Lys Leu
1               5                   10                  15

Phe Arg Ser Glu Leu Asn Ile Glu Ser Cys Ser Lys Cys Gln Thr
                20                  25                  30

Glu Ile Gly Gly Ile Asn Thr Asn Lys Ser Phe His Asn Val His Arg
        35                  40                  45

Asn Thr Ile Gly Asp Cys Pro Lys Tyr Val Asn Val Lys Ser Leu Lys
    50                  55                  60

Leu Ala Thr Gly Pro Arg Asn Val Pro Ala Ile Ala Ser Arg
65                  70                  75

<210> SEQ ID NO 441
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H12

<400> SEQUENCE: 441

Ala Pro Glu Tyr Gly His Leu Ile Thr Gly Lys Ser His Gly Arg Ile
1               5                   10                  15

Leu Lys Asn Asn Leu Pro Met Gly Gln Cys Val Thr Glu Cys Gln Leu
                20                  25                  30

Asn Glu Gly Val Met Asn Thr Ser Lys Pro Phe Gln Asn Thr Ser Lys
        35                  40                  45

His Tyr Ile Gly Lys Cys Pro Lys Tyr Ile Pro Ser Gly Ser Leu Lys
    50                  55                  60

Leu Ala Ile Gly Leu Arg Asn Val Pro Gln Val Gln Asp Arg
65                  70                  75

<210> SEQ ID NO 442
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H13

<400> SEQUENCE: 442

Ala Pro Arg Tyr Gly Tyr Ile Ile Glu Glu Tyr Gly Lys Gly Arg Ile
1               5                   10                  15

Phe Gln Ser Arg Ile Arg Met Ser Arg Cys Asn Thr Lys Cys Gln Thr
                20                  25                  30

Ser Val Gly Gly Ile Asn Thr Asn Arg Thr Phe Gln Asn Ile Asp Lys
        35                  40                  45

Asn Ala Leu Gly Asp Cys Pro Lys Tyr Ile Lys Ser Gly Gln Leu Lys
    50                  55                  60

Leu Ala Thr Gly Leu Arg Asn Val Pro Ala Ile Ser Asn Arg
65                  70                  75

<210> SEQ ID NO 443
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H14

<400> SEQUENCE: 443

Ala Pro Arg Gly His Tyr Lys Ile Ser Lys Ser Thr Lys Ser Thr Val
1               5                   10                  15

Leu Lys Ser Asp Lys Arg Ile Gly Ser Cys Thr Ser Pro Cys Leu Thr

```
                    20                  25                  30

Asp Lys Gly Ser Ile Gln Ser Asp Lys Pro Phe Gln Asn Val Ser Arg
            35                  40                  45

Ile Ala Ile Gly Asn Cys Pro Lys Tyr Val Lys Gln Gly Ser Leu Met
        50                  55                  60

Leu Ala Thr Gly Met Arg Asn Ile Pro Gly Lys Gln Ala Lys
 65                  70                  75

<210> SEQ ID NO 444
<211> LENGTH: 88
<212> TYPE: PRT
<213> ORGANISM: Influenza virus A
<220> FEATURE:
<223> OTHER INFORMATION: C-termianl long stem domain segment of
      Influenza A HA subtype H15

<400> SEQUENCE: 444

Ala Pro Asp Arg Ala Thr Phe Leu Arg Ser Asn Ala Pro Ser Gly Ile
 1               5                  10                  15

Glu Tyr Asn Gly Lys Ser Leu Gly Ile Gln Ser Asp Ala Gln Ile Asp
            20                  25                  30

Glu Ser Cys Glu Gly Glu Cys Phe Tyr Ser Gly Gly Thr Ile Asn Ser
        35                  40                  45

Pro Leu Pro Phe Gln Asn Ile Asp Ser Arg Ala Val Gly Lys Cys Pro
    50                  55                  60

Arg Tyr Val Lys Gln Ser Ser Leu Pro Leu Ala Leu Gly Met Lys Asn
 65                  70                  75                  80

Val Pro Glu Lys Ile Arg Thr Arg
                85

<210> SEQ ID NO 445
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H16

<400> SEQUENCE: 445

Ala Pro Arg Tyr Gly Tyr Ile Ile Glu Lys Tyr Gly Thr Gly Arg Ile
 1               5                  10                  15

Phe Gln Ser Gly Val Arg Met Ala Arg Cys Asn Thr Lys Cys Gln Thr
            20                  25                  30

Ser Leu Gly Gly Ile Asn Thr Asn Lys Thr Phe Gln Asn Ile Glu Arg
        35                  40                  45

Asn Ala Leu Gly Asp Cys Pro Lys Tyr Ile Lys Ser Gly Gln Leu Lys
    50                  55                  60

Leu Ala Thr Gly Leu Arg Asn Val Pro Ser Ile Gly Glu Arg
 65                  70                  75

<210> SEQ ID NO 446
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H1(No Cys, Ala)

<400> SEQUENCE: 446

Asp Thr Ile Cys Ile Gly Tyr His Ala Asn Asn Ser Thr Asp Thr Val
 1               5                  10                  15
```

-continued

Asp Thr Val Leu Glu Lys Asn Val Thr Val Thr His Ser Val Asn Leu
                20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile
                85

<210> SEQ ID NO 447
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H1(No Cys, Ala - Delta 1)

<400> SEQUENCE: 447

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile
                85

<210> SEQ ID NO 448
<211> LENGTH: 88
<212> TYPE: PRT
<213> ORGANISM: Influenza virus A
<220> FEATURE:
<223> OTHER INFORMATION: N-termianl long stem domain segment of
      Influenza A HA subtype H1(No Cys, Ala - Delta 3)

<400> SEQUENCE: 448

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly
                85

<210> SEQ ID NO 449
<211> LENGTH: 89
<212> TYPE: PRT
<213> ORGANISM: Influenza virus A
<220> FEATURE:
<223> OTHER INFORMATION: N-termianl long stem domain segment of
     Influenza A HA subtype H2(No Cys, Ala)

<400> SEQUENCE: 449

Asp Gln Ile Cys Ile Gly Tyr His Ser Asn Asn Ser Thr Glu Lys Val
1               5                   10                  15

Asp Thr Ile Leu Glu Arg Asn Val Thr Val Thr His Ala Gln Asn Ile
            20                  25                  30

Leu Glu Lys Thr His Asn Gly Lys Leu Cys Lys Leu Asn Gly Ile Pro
        35                  40                  45

Pro Leu Glu Leu Gly Asp Cys Ser Ile Ala Gly Trp Leu Leu Gly Asn
    50                  55                  60

Pro Glu Cys Asp Arg Leu Leu Thr Val Pro Glu Trp Ser Tyr Ile Met
65                  70                  75                  80

Glu Lys Glu Asn Pro Arg Asn Gly Leu
                85

<210> SEQ ID NO 450
<211> LENGTH: 89
<212> TYPE: PRT
<213> ORGANISM: Influenza virus A
<220> FEATURE:
<223> OTHER INFORMATION: N-termianl long stem domain segment of
     Influenza A HA subtype H2(No Cys, Ala - Delta 1)

<400> SEQUENCE: 450

Asp Gln Ile Cys Ile Gly Tyr His Ser Asn Asn Ser Thr Glu Lys Val
1               5                   10                  15

Asp Thr Ile Leu Glu Arg Asn Val Thr Val Thr His Ala Gln Asn Ile
            20                  25                  30

Leu Glu Lys Thr His Asn Gly Lys Leu Cys Lys Leu Asn Gly Ile Pro
        35                  40                  45

Pro Leu Glu Leu Gly Asp Cys Ser Ile Ala Gly Trp Leu Leu Gly Asn
    50                  55                  60

Pro Glu Cys Asp Arg Leu Leu Thr Val Pro Glu Trp Ser Tyr Ile Met
65                  70                  75                  80

Glu Lys Glu Asn Pro Arg Asn Gly Leu
                85

<210> SEQ ID NO 451
<211> LENGTH: 88
<212> TYPE: PRT
<213> ORGANISM: Influenza virus A
<220> FEATURE:
<223> OTHER INFORMATION: N-termianl long stem domain segment of
     Influenza A HA subtype H2(No Cys, Ala - Delta 3)

<400> SEQUENCE: 451

Asp Gln Ile Cys Ile Gly Tyr His Ser Asn Asn Ser Thr Glu Lys Val
1               5                   10                  15

Asp Thr Ile Leu Glu Arg Asn Val Thr Val Thr His Ala Gln Asn Ile
            20                  25                  30

Leu Glu Lys Thr His Asn Gly Lys Leu Cys Lys Leu Asn Gly Ile Pro
        35                  40                  45

Pro Leu Glu Leu Gly Asp Cys Ser Ile Ala Gly Trp Leu Leu Gly Asn
    50                  55                  60

Pro Glu Cys Asp Arg Leu Leu Thr Val Pro Glu Trp Ser Tyr Ile Met
65                  70                  75                  80

Glu Lys Glu Asn Pro Arg Asn Gly
                85

<210> SEQ ID NO 452
<211> LENGTH: 96
<212> TYPE: PRT
<213> ORGANISM: Influenza virus A
<220> FEATURE:
<223> OTHER INFORMATION: N-termianl long stem domain segment of
      Influenza A HA subtype H3(No Cys, Ala)

<400> SEQUENCE: 452

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
                20                  25                  30

Gln Ile Glu Val Thr Asn Ala Thr Glu Leu Val Gln Ser Ser Ser Thr
            35                  40                  45

Gly Lys Ile Cys Asn Asn Pro His Arg Ile Leu Asp Gly Ile Asp Cys
        50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

<210> SEQ ID NO 453
<211> LENGTH: 96
<212> TYPE: PRT
<213> ORGANISM: Influenza virus A
<220> FEATURE:
<223> OTHER INFORMATION: N-termianl long stem domain segment of
      Influenza A HA subtype H3(No Cys, Ala - Delta 1)

<400> SEQUENCE: 453

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
                20                  25                  30

Gln Ile Glu Val Thr Asn Ala Thr Glu Leu Val Gln Ser Ser Ser Thr
            35                  40                  45

Gly Lys Ile Cys Asn Asn Pro His Arg Ile Leu Asp Gly Ile Asp Cys
        50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

<210> SEQ ID NO 454
<211> LENGTH: 95
<212> TYPE: PRT
<213> ORGANISM: Influenza virus A
<220> FEATURE:
<223> OTHER INFORMATION: N-termianl long stem domain segment of
      Influenza A HA subtype H3(No Cys, Ala - Delta 3)

<400> SEQUENCE: 454

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
                20                  25                  30

Gln Ile Glu Val Thr Asn Ala Thr Glu Leu Val Gln Ser Ser Ser Thr

```
                    35                  40                  45

Gly Lys Ile Cys Asn Asn Pro His Arg Ile Leu Asp Gly Ile Asp Cys
 50                  55                  60

Thr Leu Ile Asp Ala Leu Leu Gly Asp Pro His Cys Asp Val Phe Gln
 65                  70                  75                  80

Asn Glu Thr Trp Asp Leu Phe Val Glu Arg Ser Lys Ala Phe Ser
                 85                  90                  95

<210> SEQ ID NO 455
<211> LENGTH: 92
<212> TYPE: PRT
<213> ORGANISM: Influenza virus A
<220> FEATURE:
<223> OTHER INFORMATION: N-termianl long stem domain segment of
      Influenza A HA subtype H4(No Cys, Ala)

<400> SEQUENCE: 455

Gln Asn Tyr Thr Gly Asn Pro Val Ile Cys Met Gly His His Ala Val
 1               5                  10                  15

Ala Asn Gly Thr Met Val Lys Thr Leu Ala Asp Asp Gln Val Glu Val
                 20                  25                  30

Val Thr Ala Gln Glu Leu Val Glu Ser Gln Asn Leu Pro Glu Leu Cys
             35                  40                  45

Pro Ser Pro Leu Arg Leu Val Asp Gly Gln Thr Cys Asp Ile Ile Asn
 50                  55                  60

Gly Ala Leu Gly Ser Pro Gly Cys Asp His Leu Asn Gly Ala Glu Trp
 65                  70                  75                  80

Asp Val Phe Ile Glu Arg Pro Asn Ala Val Asp Thr
                 85                  90

<210> SEQ ID NO 456
<211> LENGTH: 92
<212> TYPE: PRT
<213> ORGANISM: Influenza virus A
<220> FEATURE:
<223> OTHER INFORMATION: N-termianl long stem domain segment of
      Influenza A HA subtype H4(No Cys, Ala - Delta 1)

<400> SEQUENCE: 456

Gln Asn Tyr Thr Gly Asn Pro Val Ile Cys Met Gly His His Ala Val
 1               5                  10                  15

Ala Asn Gly Thr Met Val Lys Thr Leu Ala Asp Asp Gln Val Glu Val
                 20                  25                  30

Val Thr Ala Gln Glu Leu Val Glu Ser Gln Asn Leu Pro Glu Leu Cys
             35                  40                  45

Pro Ser Pro Leu Arg Leu Val Asp Gly Gln Thr Cys Asp Ile Ile Asn
 50                  55                  60

Gly Ala Leu Gly Ser Pro Gly Cys Asp His Leu Asn Gly Ala Glu Trp
 65                  70                  75                  80

Asp Val Phe Ile Glu Arg Pro Asn Ala Val Asp Thr
                 85                  90

<210> SEQ ID NO 457
<211> LENGTH: 91
<212> TYPE: PRT
<213> ORGANISM: Influenza virus A
<220> FEATURE:
<223> OTHER INFORMATION: N-termianl long stem domain segment of
      Influenza A HA subtype H4(No Cys, Ala - Delta 3)

<400> SEQUENCE: 457
```

Gln Asn Tyr Thr Gly Asn Pro Val Ile Cys Met Gly His His Ala Val
1               5                   10                  15

Ala Asn Gly Thr Met Val Lys Thr Leu Ala Asp Asp Gln Val Glu Val
            20                  25                  30

Val Thr Ala Gln Glu Leu Val Glu Ser Gln Asn Leu Pro Glu Leu Cys
        35                  40                  45

Pro Ser Pro Leu Arg Leu Val Asp Gly Gln Thr Cys Asp Ile Ile Asn
    50                  55                  60

Gly Ala Leu Gly Ser Pro Gly Cys Asp His Leu Asn Gly Ala Glu Trp
65              70                  75                  80

Asp Val Phe Ile Glu Arg Pro Asn Ala Val Asp
            85                  90

<210> SEQ ID NO 458
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H5(No Cys, Ala)

<400> SEQUENCE: 458

Asp Gln Ile Cys Ile Gly Tyr His Ala Asn Lys Ser Thr Lys Gln Val
1               5                   10                  15

Asp Thr Ile Met Glu Lys Asn Val Thr Val Thr His Ala Gln Asp Ile
            20                  25                  30

Leu Glu Arg Thr His Asn Gly Lys Leu Cys Ser Leu Asn Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Leu Asn Leu Pro Glu Trp Leu Tyr Ile Val
65              70                  75                  80

Glu Lys Asp Asn Pro Ile Asn Ser Leu
            85

<210> SEQ ID NO 459
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H5(No Cys, Ala - Delta 1)

<400> SEQUENCE: 459

Asp Gln Ile Cys Ile Gly Tyr His Ala Asn Lys Ser Thr Lys Gln Val
1               5                   10                  15

Asp Thr Ile Met Glu Lys Asn Val Thr Val Thr His Ala Gln Asp Ile
            20                  25                  30

Leu Glu Arg Thr His Asn Gly Lys Leu Cys Ser Leu Asn Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Leu Asn Leu Pro Glu Trp Leu Tyr Ile Val
65              70                  75                  80

Glu Lys Asp Asn Pro Ile Asn Ser Leu
            85

<210> SEQ ID NO 460

```
<211> LENGTH: 88
<212> TYPE: PRT
<213> ORGANISM: Influenza virus A
<220> FEATURE:
<223> OTHER INFORMATION: N-termianl long stem domain segment of
      Influenza A HA subtype H5(No Cys, Ala - Delta 3)

<400> SEQUENCE: 460

Asp Gln Ile Cys Ile Gly Tyr His Ala Asn Lys Ser Thr Lys Gln Val
1               5                   10                  15

Asp Thr Ile Met Glu Lys Asn Val Thr Val Thr His Ala Gln Asp Ile
            20                  25                  30

Leu Glu Arg Thr His Asn Gly Lys Leu Cys Ser Leu Asn Gly Val Lys
        35                  40                  45

Pro Leu Ile Leu Arg Asp Cys Ser Val Ala Gly Trp Leu Leu Gly Asn
50                  55                  60

Pro Met Cys Asp Glu Phe Leu Asn Leu Pro Glu Trp Leu Tyr Ile Val
65                  70                  75                  80

Glu Lys Asp Asn Pro Ile Asn Ser
                85

<210> SEQ ID NO 461
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H6(No Cys, Ala)

<400> SEQUENCE: 461

Asp Lys Ile Cys Ile Gly Tyr His Ala Asn Asn Ser Thr Thr Gln Ile
1               5                   10                  15

Asp Thr Ile Leu Glu Lys Asn Val Thr Val Thr His Ser Val Glu Leu
            20                  25                  30

Leu Glu Asn Gln Lys Glu Glu Arg Phe Cys Lys Ile Leu Lys Lys Ala
        35                  40                  45

Pro Leu Asp Leu Lys Gly Cys Thr Ile Glu Gly Trp Ile Leu Gly Asn
50                  55                  60

Pro Gln Cys Asp Leu Leu Leu Gly Asp Gln Ser Trp Ser Tyr Ile Val
65                  70                  75                  80

Glu Arg Pro Thr Ala Gln Asn Gly Ile
                85

<210> SEQ ID NO 462
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H6(No Cys, Ala - Delta 1)

<400> SEQUENCE: 462

Asp Lys Ile Cys Ile Gly Tyr His Ala Asn Asn Ser Thr Thr Gln Ile
1               5                   10                  15

Asp Thr Ile Leu Glu Lys Asn Val Thr Val Thr His Ser Val Glu Leu
            20                  25                  30

Leu Glu Asn Gln Lys Glu Glu Arg Phe Cys Lys Ile Leu Lys Lys Ala
        35                  40                  45

Pro Leu Asp Leu Lys Gly Cys Thr Ile Glu Gly Trp Ile Leu Gly Asn
50                  55                  60
```

Pro Gln Cys Asp Leu Leu Gly Asp Gln Ser Trp Ser Tyr Ile Val
65                  70                  75                  80

Glu Arg Pro Thr Ala Gln Asn Gly Ile
                85

<210> SEQ ID NO 463
<211> LENGTH: 88
<212> TYPE: PRT
<213> ORGANISM: Influenza virus A
<220> FEATURE:
<223> OTHER INFORMATION: N-termianl long stem domain segment of
      Influenza A HA subtype H6(No Cys, Ala - Delta 3)

<400> SEQUENCE: 463

Asp Lys Ile Cys Ile Gly Tyr His Ala Asn Asn Ser Thr Thr Gln Ile
1               5                   10                  15

Asp Thr Ile Leu Glu Lys Asn Val Thr Val Thr His Ser Val Glu Leu
                20                  25                  30

Leu Glu Asn Gln Lys Glu Glu Arg Phe Cys Lys Ile Leu Lys Lys Ala
            35                  40                  45

Pro Leu Asp Leu Lys Gly Cys Thr Ile Glu Gly Trp Ile Leu Gly Asn
50                  55                  60

Pro Gln Cys Asp Leu Leu Gly Asp Gln Ser Trp Ser Tyr Ile Val
65                  70                  75                  80

Glu Arg Pro Thr Ala Gln Asn Gly
                85

<210> SEQ ID NO 464
<211> LENGTH: 86
<212> TYPE: PRT
<213> ORGANISM: Influenza virus A
<220> FEATURE:
<223> OTHER INFORMATION: N-termianl long stem domain segment of
      Influenza A HA subtype H7(No Cys, Ala)

<400> SEQUENCE: 464

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
                20                  25                  30

Val Glu Arg Thr Asn Ile Pro Lys Ile Cys Ser Lys Gly Lys Arg Thr
            35                  40                  45

Thr Asp Leu Gly Gln Cys Gly Leu Leu Gly Thr Ile Thr Gly Pro Pro
50                  55                  60

Gln Cys Asp Gln Phe Leu Glu Phe Ser Ala Asp Leu Ile Ile Glu Arg
65                  70                  75                  80

Arg Glu Gly Asn Asp Val
                85

<210> SEQ ID NO 465
<211> LENGTH: 86
<212> TYPE: PRT
<213> ORGANISM: Influenza virus A
<220> FEATURE:
<223> OTHER INFORMATION: N-termianl long stem domain segment of
      Influenza A HA subtype H7(No Cys, Ala - Delta 1)

<400> SEQUENCE: 465

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr

```
                    20                  25                  30

Val Glu Arg Thr Asn Ile Pro Lys Ile Cys Ser Lys Gly Lys Arg Thr
                35                  40                  45

Thr Asp Leu Gly Gln Cys Gly Leu Leu Gly Thr Ile Thr Gly Pro Pro
            50                  55                  60

Gln Cys Asp Gln Phe Leu Glu Phe Ser Ala Asp Leu Ile Ile Glu Arg
 65                 70                  75                  80

Arg Glu Gly Asn Asp Val
                85

<210> SEQ ID NO 466
<211> LENGTH: 85
<212> TYPE: PRT
<213> ORGANISM: Influenza virus A
<220> FEATURE:
<223> OTHER INFORMATION: N-termianl long stem domain segment of
      Influenza A HA subtype H7(No Cys, Ala - Delta 3)

<400> SEQUENCE: 466

Asp Lys Ile Cys Leu Gly His His Ala Val Ser Asn Gly Thr Lys Val
 1               5                  10                  15

Asn Thr Leu Thr Glu Arg Gly Val Glu Val Val Asn Ala Thr Glu Thr
                20                  25                  30

Val Glu Arg Thr Asn Ile Pro Lys Ile Cys Ser Lys Gly Lys Arg Thr
                35                  40                  45

Thr Asp Leu Gly Gln Cys Gly Leu Leu Gly Thr Ile Thr Gly Pro Pro
            50                  55                  60

Gln Cys Asp Gln Phe Leu Glu Phe Ser Ala Asp Leu Ile Ile Glu Arg
 65                 70                  75                  80

Arg Glu Gly Asn Asp
                85

<210> SEQ ID NO 467
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H8(No Cys, Ala)

<400> SEQUENCE: 467

Asp Arg Ile Cys Ile Gly Tyr Gln Ser Asn Asn Ser Thr Asp Thr Val
 1               5                  10                  15

Asn Thr Leu Ile Glu Gln Asn Val Pro Val Thr Gln Thr Met Glu Leu
                20                  25                  30

Val Glu Thr Glu Lys His Pro Ala Tyr Cys Asn Thr Asp Leu Gly Ala
                35                  40                  45

Pro Leu Glu Leu Arg Asp Cys Lys Ile Glu Ala Val Ile Tyr Gly Asn
            50                  55                  60

Pro Lys Cys Asp Ile His Leu Lys Asp Gln Gly Trp Ser Tyr Ile Val
 65                 70                  75                  80

Glu Arg Pro Ser Ala Pro Glu Gly Met
                85

<210> SEQ ID NO 468
<211> LENGTH: 89
<212> TYPE: PRT
<213> ORGANISM: Influenza virus A
<220> FEATURE:
<223> OTHER INFORMATION: N-termianl long stem domain segment of
```

Influenza A HA subtype H8(No Cys, Ala - Delta 1)

<400> SEQUENCE: 468

Asp Arg Ile Cys Ile Gly Tyr Gln Ser Asn Asn Ser Thr Asp Thr Val
1               5                   10                  15

Asn Thr Leu Ile Glu Gln Asn Val Pro Val Thr Gln Thr Met Glu Leu
            20                  25                  30

Val Glu Thr Glu Lys His Pro Ala Tyr Cys Asn Thr Asp Leu Gly Ala
        35                  40                  45

Pro Leu Glu Leu Arg Asp Cys Lys Ile Glu Ala Val Ile Tyr Gly Asn
    50                  55                  60

Pro Lys Cys Asp Ile His Leu Lys Asp Gln Gly Trp Ser Tyr Ile Val
65                  70                  75                  80

Glu Arg Pro Ser Ala Pro Glu Gly Met
                85

<210> SEQ ID NO 469
<211> LENGTH: 88
<212> TYPE: PRT
<213> ORGANISM: Influenza virus A
<220> FEATURE:
<223> OTHER INFORMATION: N-termianl long stem domain segment of
      Influenza A HA subtype H8(No Cys, Ala - Delta 3)

<400> SEQUENCE: 469

Asp Arg Ile Cys Ile Gly Tyr Gln Ser Asn Asn Ser Thr Asp Thr Val
1               5                   10                  15

Asn Thr Leu Ile Glu Gln Asn Val Pro Val Thr Gln Thr Met Glu Leu
            20                  25                  30

Val Glu Thr Glu Lys His Pro Ala Tyr Cys Asn Thr Asp Leu Gly Ala
        35                  40                  45

Pro Leu Glu Leu Arg Asp Cys Lys Ile Glu Ala Val Ile Tyr Gly Asn
    50                  55                  60

Pro Lys Cys Asp Ile His Leu Lys Asp Gln Gly Trp Ser Tyr Ile Val
65                  70                  75                  80

Glu Arg Pro Ser Ala Pro Glu Gly
                85

<210> SEQ ID NO 470
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H9(No Cys, Ala)

<400> SEQUENCE: 470

Asp Lys Ile Cys Ile Gly Tyr Gln Ser Thr Asn Ser Thr Glu Thr Val
1               5                   10                  15

Asp Thr Leu Thr Glu Ser Asn Val Pro Val Thr His Thr Lys Glu Leu
            20                  25                  30

Leu His Thr Glu His Asn Gly Met Leu Cys Ala Thr Asp Leu Gly His
        35                  40                  45

Pro Leu Ile Leu Asp Thr Cys Thr Ile Glu Gly Leu Ile Tyr Gly Asn
    50                  55                  60

Pro Ser Cys Asp Ile Leu Leu Gly Gly Lys Glu Trp Ser Tyr Ile Val
65                  70                  75                  80

Glu Arg Ser Ser Ala Val Asn Gly Met
                85

<210> SEQ ID NO 471
<211> LENGTH: 89
<212> TYPE: PRT
<213> ORGANISM: Influenza virus A
<220> FEATURE:
<223> OTHER INFORMATION: N-termianl long stem domain segment of
    Influenza A HA subtype H9(No Cys, Ala - Delta 1)

<400> SEQUENCE: 471

Asp Lys Ile Cys Ile Gly Tyr Gln Ser Thr Asn Ser Thr Glu Thr Val
 1               5                  10                  15

Asp Thr Leu Thr Glu Ser Asn Val Pro Val Thr His Thr Lys Glu Leu
            20                  25                  30

Leu His Thr Glu His Asn Gly Met Leu Cys Ala Thr Asp Leu Gly His
        35                  40                  45

Pro Leu Ile Leu Asp Thr Cys Thr Ile Glu Gly Leu Ile Tyr Gly Asn
    50                  55                  60

Pro Ser Cys Asp Ile Leu Leu Gly Gly Lys Glu Trp Ser Tyr Ile Val
65                  70                  75                  80

Glu Arg Ser Ser Ala Val Asn Gly Met
                85

<210> SEQ ID NO 472
<211> LENGTH: 88
<212> TYPE: PRT
<213> ORGANISM: Influenza virus A
<220> FEATURE:
<223> OTHER INFORMATION: N-termianl long stem domain segment of
    Influenza A HA subtype H9(No Cys, Ala - Delta 3)

<400> SEQUENCE: 472

Asp Lys Ile Cys Ile Gly Tyr Gln Ser Thr Asn Ser Thr Glu Thr Val
 1               5                  10                  15

Asp Thr Leu Thr Glu Ser Asn Val Pro Val Thr His Thr Lys Glu Leu
            20                  25                  30

Leu His Thr Glu His Asn Gly Met Leu Cys Ala Thr Asp Leu Gly His
        35                  40                  45

Pro Leu Ile Leu Asp Thr Cys Thr Ile Glu Gly Leu Ile Tyr Gly Asn
    50                  55                  60

Pro Ser Cys Asp Ile Leu Leu Gly Gly Lys Glu Trp Ser Tyr Ile Val
65                  70                  75                  80

Glu Arg Ser Ser Ala Val Asn Gly
                85

<210> SEQ ID NO 473
<211> LENGTH: 87
<212> TYPE: PRT
<213> ORGANISM: Influenza virus A
<220> FEATURE:
<223> OTHER INFORMATION: N-termianl long stem domain segment of
    Influenza A HA subtype H10(No Cys, Ala)

<400> SEQUENCE: 473

Leu Asp Arg Ile Cys Leu Gly His His Ala Val Ala Asn Gly Thr Ile
 1               5                  10                  15

Val Lys Thr Leu Thr Asn Glu Gln Glu Glu Val Thr Asn Ala Thr Glu
            20                  25                  30

Thr Val Glu Ser Thr Asn Leu Asn Lys Leu Cys Met Lys Gly Arg Ser
        35                  40                  45

```
Tyr Lys Asp Leu Gly Asn Cys His Pro Val Gly Met Leu Ile Gly Thr
 50                  55                  60

Pro Val Cys Asp Pro His Leu Thr Gly Thr Trp Asp Thr Leu Ile Glu
 65                  70                  75                  80

Arg Glu Asn Ala Ile Ala His
                 85

<210> SEQ ID NO 474
<211> LENGTH: 87
<212> TYPE: PRT
<213> ORGANISM: Influenza virus A
<220> FEATURE:
<223> OTHER INFORMATION: N-termianl long stem domain segment of
      Influenza A HA subtype H10(No Cys, Ala - Delta 1)

<400> SEQUENCE: 474

Leu Asp Arg Ile Cys Leu Gly His His Ala Val Ala Asn Gly Thr Ile
  1               5                  10                  15

Val Lys Thr Leu Thr Asn Glu Gln Glu Val Thr Asn Ala Thr Glu
             20                  25                  30

Thr Val Glu Ser Thr Asn Leu Asn Lys Leu Cys Met Lys Gly Arg Ser
         35                  40                  45

Tyr Lys Asp Leu Gly Asn Cys His Pro Val Gly Met Leu Ile Gly Thr
 50                  55                  60

Pro Val Cys Asp Pro His Leu Thr Gly Thr Trp Asp Thr Leu Ile Glu
 65                  70                  75                  80

Arg Glu Asn Ala Ile Ala His
                 85

<210> SEQ ID NO 475
<211> LENGTH: 86
<212> TYPE: PRT
<213> ORGANISM: Influenza virus A
<220> FEATURE:
<223> OTHER INFORMATION: N-termianl long stem domain segment of
      Influenza A HA subtype H10(No Cys, Ala - Delta 3)

<400> SEQUENCE: 475

Leu Asp Arg Ile Cys Leu Gly His His Ala Val Ala Asn Gly Thr Ile
  1               5                  10                  15

Val Lys Thr Leu Thr Asn Glu Gln Glu Val Thr Asn Ala Thr Glu
             20                  25                  30

Thr Val Glu Ser Thr Asn Leu Asn Lys Leu Cys Met Lys Gly Arg Ser
         35                  40                  45

Tyr Lys Asp Leu Gly Asn Cys His Pro Val Gly Met Leu Ile Gly Thr
 50                  55                  60

Pro Val Cys Asp Pro His Leu Thr Gly Thr Trp Asp Thr Leu Ile Glu
 65                  70                  75                  80

Arg Glu Asn Ala Ile Ala
                 85

<210> SEQ ID NO 476
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H11(No Cys, Ala)

<400> SEQUENCE: 476

Asp Glu Ile Cys Ile Gly Tyr Leu Ser Asn Asn Ser Thr Asp Lys Val
```

```
                1               5                   10                  15
Asp Thr Ile Ile Glu Asn Asn Val Thr Val Thr Ser Ser Val Glu Leu
                    20                  25                  30

Val Glu Thr Glu His Thr Gly Ser Phe Cys Ser Ile Asn Gly Lys Gln
            35                  40                  45

Pro Ile Ser Leu Gly Asp Cys Ser Phe Ala Gly Trp Ile Leu Gly Asn
    50                  55                  60

Pro Met Cys Asp Glu Leu Ile Gly Lys Thr Ser Trp Ser Tyr Ile Val
65                  70                  75                  80

Glu Lys Pro Asn Pro Thr Asn Gly Ile
                85
```

<210> SEQ ID NO 477
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H11(No Cys, Ala - Delta 1)

<400> SEQUENCE: 477

```
Asp Glu Ile Cys Ile Gly Tyr Leu Ser Asn Asn Ser Thr Asp Lys Val
1               5                   10                  15

Asp Thr Ile Ile Glu Asn Asn Val Thr Val Thr Ser Ser Val Glu Leu
                    20                  25                  30

Val Glu Thr Glu His Thr Gly Ser Phe Cys Ser Ile Asn Gly Lys Gln
            35                  40                  45

Pro Ile Ser Leu Gly Asp Cys Ser Phe Ala Gly Trp Ile Leu Gly Asn
    50                  55                  60

Pro Met Cys Asp Glu Leu Ile Gly Lys Thr Ser Trp Ser Tyr Ile Val
65                  70                  75                  80

Glu Lys Pro Asn Pro Thr Asn Gly Ile
                85
```

<210> SEQ ID NO 478
<211> LENGTH: 88
<212> TYPE: PRT
<213> ORGANISM: Influenza virus A
<220> FEATURE:
<223> OTHER INFORMATION: N-termianl long stem domain segment of
      Influenza A HA subtype H11(No Cys, Ala - Delta 3)

<400> SEQUENCE: 478

```
Asp Glu Ile Cys Ile Gly Tyr Leu Ser Asn Asn Ser Thr Asp Lys Val
1               5                   10                  15

Asp Thr Ile Ile Glu Asn Asn Val Thr Val Thr Ser Ser Val Glu Leu
                    20                  25                  30

Val Glu Thr Glu His Thr Gly Ser Phe Cys Ser Ile Asn Gly Lys Gln
            35                  40                  45

Pro Ile Ser Leu Gly Asp Cys Ser Phe Ala Gly Trp Ile Leu Gly Asn
    50                  55                  60

Pro Met Cys Asp Glu Leu Ile Gly Lys Thr Ser Trp Ser Tyr Ile Val
65                  70                  75                  80

Glu Lys Pro Asn Pro Thr Asn Gly
                85
```

<210> SEQ ID NO 479
<211> LENGTH: 89
<212> TYPE: PRT

<213> ORGANISM: Influenza virus A
<220> FEATURE:
<223> OTHER INFORMATION: N-termianl long stem domain segment of
    Influenza A HA subtype H12(No Cys, Ala)

<400> SEQUENCE: 479

Asp Lys Ile Cys Ile Gly Tyr Gln Thr Asn Asn Ser Thr Glu Thr Val
1               5                   10                  15

Asn Thr Leu Ser Glu Gln Asn Val Pro Val Thr Gln Val Glu Glu Leu
            20                  25                  30

Val His Arg Gly Ile Asp Pro Ile Leu Cys Gly Thr Glu Leu Gly Ser
        35                  40                  45

Pro Leu Val Leu Asp Asp Cys Ser Leu Glu Gly Leu Ile Leu Gly Asn
    50                  55                  60

Pro Lys Cys Asp Leu Tyr Leu Asn Gly Arg Glu Trp Ser Tyr Ile Val
65                  70                  75                  80

Glu Arg Pro Lys Glu Met Glu Gly Val
                85

<210> SEQ ID NO 480
<211> LENGTH: 89
<212> TYPE: PRT
<213> ORGANISM: Influenza virus A
<220> FEATURE:
<223> OTHER INFORMATION: N-termianl long stem domain segment of
    Influenza A HA subtype H12(No Cys, Ala - Delta 1)

<400> SEQUENCE: 480

Asp Lys Ile Cys Ile Gly Tyr Gln Thr Asn Asn Ser Thr Glu Thr Val
1               5                   10                  15

Asn Thr Leu Ser Glu Gln Asn Val Pro Val Thr Gln Val Glu Glu Leu
            20                  25                  30

Val His Arg Gly Ile Asp Pro Ile Leu Cys Gly Thr Glu Leu Gly Ser
        35                  40                  45

Pro Leu Val Leu Asp Asp Cys Ser Leu Glu Gly Leu Ile Leu Gly Asn
    50                  55                  60

Pro Lys Cys Asp Leu Tyr Leu Asn Gly Arg Glu Trp Ser Tyr Ile Val
65                  70                  75                  80

Glu Arg Pro Lys Glu Met Glu Gly Val
                85

<210> SEQ ID NO 481
<211> LENGTH: 88
<212> TYPE: PRT
<213> ORGANISM: Influenza virus A
<220> FEATURE:
<223> OTHER INFORMATION: N-termianl long stem domain segment of
    Influenza A HA subtype H12(No Cys, Ala - Delta 3)

<400> SEQUENCE: 481

Asp Lys Ile Cys Ile Gly Tyr Gln Thr Asn Asn Ser Thr Glu Thr Val
1               5                   10                  15

Asn Thr Leu Ser Glu Gln Asn Val Pro Val Thr Gln Val Glu Glu Leu
            20                  25                  30

Val His Arg Gly Ile Asp Pro Ile Leu Cys Gly Thr Glu Leu Gly Ser
        35                  40                  45

Pro Leu Val Leu Asp Asp Cys Ser Leu Glu Gly Leu Ile Leu Gly Asn
    50                  55                  60

Pro Lys Cys Asp Leu Tyr Leu Asn Gly Arg Glu Trp Ser Tyr Ile Val
65                  70                  75                  80

Glu Arg Pro Lys Glu Met Glu Gly
            85

<210> SEQ ID NO 482
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H13(No Cys, Ala)

<400> SEQUENCE: 482

Asp Arg Ile Cys Val Gly Tyr Leu Ser Thr Asn Ser Ser Glu Arg Val
1               5                   10                  15

Asp Thr Leu Leu Glu Asn Gly Val Pro Val Thr Ser Ser Ile Asp Leu
            20                  25                  30

Ile Glu Thr Asn His Thr Gly Thr Tyr Cys Ser Leu Asn Gly Val Ser
        35                  40                  45

Pro Val His Leu Gly Asp Cys Ser Phe Glu Gly Trp Ile Val Gly Asn
    50                  55                  60

Pro Ala Cys Thr Ser Asn Phe Gly Ile Arg Glu Trp Ser Tyr Leu Ile
65                  70                  75                  80

Glu Asp Pro Ala Ala Pro His Gly Leu
            85

<210> SEQ ID NO 483
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H13(No Cys, Ala - Delta 1)

<400> SEQUENCE: 483

Asp Arg Ile Cys Val Gly Tyr Leu Ser Thr Asn Ser Ser Glu Arg Val
1               5                   10                  15

Asp Thr Leu Leu Glu Asn Gly Val Pro Val Thr Ser Ser Ile Asp Leu
            20                  25                  30

Ile Glu Thr Asn His Thr Gly Thr Tyr Cys Ser Leu Asn Gly Val Ser
        35                  40                  45

Pro Val His Leu Gly Asp Cys Ser Phe Glu Gly Trp Ile Val Gly Asn
    50                  55                  60

Pro Ala Cys Thr Ser Asn Phe Gly Ile Arg Glu Trp Ser Tyr Leu Ile
65                  70                  75                  80

Glu Asp Pro Ala Ala Pro His Gly Leu
            85

<210> SEQ ID NO 484
<211> LENGTH: 88
<212> TYPE: PRT
<213> ORGANISM: Influenza virus A
<220> FEATURE:
<223> OTHER INFORMATION: N-termianl long stem domain segment of
      Influenza A HA subtype H13(No Cys, Ala - Delta 3)

<400> SEQUENCE: 484

Asp Arg Ile Cys Val Gly Tyr Leu Ser Thr Asn Ser Ser Glu Arg Val
1               5                   10                  15

Asp Thr Leu Leu Glu Asn Gly Val Pro Val Thr Ser Ser Ile Asp Leu
            20                  25                  30

Ile Glu Thr Asn His Thr Gly Thr Tyr Cys Ser Leu Asn Gly Val Ser
35                  40                  45

Pro Val His Leu Gly Asp Cys Ser Phe Glu Gly Trp Ile Val Gly Asn
50                  55                  60

Pro Ala Cys Thr Ser Asn Phe Gly Ile Arg Glu Trp Ser Tyr Leu Ile
65                  70                  75                  80

Glu Asp Pro Ala Ala Pro His Gly
                85

<210> SEQ ID NO 485
<211> LENGTH: 95
<212> TYPE: PRT
<213> ORGANISM: Influenza virus A
<220> FEATURE:
<223> OTHER INFORMATION: N-termianl long stem domain segment of
      Influenza A HA subtype H14(No Cys, Ala)

<400> SEQUENCE: 485

Gln Ile Thr Asn Gly Thr Thr Gly Asn Pro Ile Ile Cys Leu Gly His
1               5                   10                  15

His Ala Val Glu Asn Gly Thr Ser Val Lys Thr Leu Thr Asp Asn His
                20                  25                  30

Val Glu Val Val Ser Ala Lys Glu Leu Val Glu Thr Asn His Thr Asp
            35                  40                  45

Glu Leu Cys Pro Ser Pro Leu Lys Leu Val Asp Gly Gln Asp Cys His
        50                  55                  60

Leu Ile Asn Gly Ala Leu Gly Ser Pro Gly Cys Asp Arg Leu Gln Asp
65                  70                  75                  80

Thr Thr Trp Asp Val Phe Ile Glu Arg Pro Thr Ala Val Asp Thr
                85                  90                  95

<210> SEQ ID NO 486
<211> LENGTH: 95
<212> TYPE: PRT
<213> ORGANISM: Influenza virus A
<220> FEATURE:
<223> OTHER INFORMATION: N-termianl long stem domain segment of
      Influenza A HA subtype H14(No Cys, Ala - Delta 1)

<400> SEQUENCE: 486

Gln Ile Thr Asn Gly Thr Thr Gly Asn Pro Ile Ile Cys Leu Gly His
1               5                   10                  15

His Ala Val Glu Asn Gly Thr Ser Val Lys Thr Leu Thr Asp Asn His
                20                  25                  30

Val Glu Val Val Ser Ala Lys Glu Leu Val Glu Thr Asn His Thr Asp
            35                  40                  45

Glu Leu Cys Pro Ser Pro Leu Lys Leu Val Asp Gly Gln Asp Cys His
        50                  55                  60

Leu Ile Asn Gly Ala Leu Gly Ser Pro Gly Cys Asp Arg Leu Gln Asp
65                  70                  75                  80

Thr Thr Trp Asp Val Phe Ile Glu Arg Pro Thr Ala Val Asp Thr
                85                  90                  95

<210> SEQ ID NO 487
<211> LENGTH: 94
<212> TYPE: PRT
<213> ORGANISM: Influenza virus A
<220> FEATURE:
<223> OTHER INFORMATION: N-termianl long stem domain segment of
      Influenza A HA subtype H14(No Cys, Ala - Delta 3)

<400> SEQUENCE: 487

```
Gln Ile Thr Asn Gly Thr Thr Gly Asn Pro Ile Ile Cys Leu Gly His
  1               5                  10                  15

His Ala Val Glu Asn Gly Thr Ser Val Lys Thr Leu Thr Asp Asn His
             20                  25                  30

Val Glu Val Val Ser Ala Lys Glu Leu Val Glu Thr Asn His Thr Asp
         35                  40                  45

Glu Leu Cys Pro Ser Pro Leu Lys Leu Val Asp Gly Gln Asp Cys His
     50                  55                  60

Leu Ile Asn Gly Ala Leu Gly Ser Pro Gly Cys Asp Arg Leu Gln Asp
 65                  70                  75                  80

Thr Thr Trp Asp Val Phe Ile Glu Arg Pro Thr Ala Val Asp
                 85                  90
```

<210> SEQ ID NO 488
<211> LENGTH: 86
<212> TYPE: PRT
<213> ORGANISM: Influenza virus A
<220> FEATURE:
<223> OTHER INFORMATION: N-termianl long stem domain segment of Influenza A HA subtype H15(No Cys, Ala)

<400> SEQUENCE: 488

```
Asp Lys Ile Cys Leu Gly His His Ala Val Ala Asn Gly Thr Lys Val
  1               5                  10                  15

Asn Thr Leu Thr Glu Arg Gly Val Glu Val Val Asn Ala Thr Glu Thr
             20                  25                  30

Val Glu Ile Thr Gly Ile Asp Lys Val Cys Thr Lys Gly Lys Lys Ala
         35                  40                  45

Val Asp Leu Gly Ser Cys Gly Ile Leu Gly Thr Ile Ile Gly Pro Pro
     50                  55                  60

Gln Cys Asp Leu His Leu Glu Phe Lys Ala Asp Leu Ile Ile Glu Arg
 65                  70                  75                  80

Arg Asn Ser Ser Asp Ile
                 85
```

<210> SEQ ID NO 489
<211> LENGTH: 86
<212> TYPE: PRT
<213> ORGANISM: Influenza virus A
<220> FEATURE:
<223> OTHER INFORMATION: N-termianl long stem domain segment of Influenza A HA subtype H15(No Cys, Ala - Delta 1)

<400> SEQUENCE: 489

```
Asp Lys Ile Cys Leu Gly His His Ala Val Ala Asn Gly Thr Lys Val
  1               5                  10                  15

Asn Thr Leu Thr Glu Arg Gly Val Glu Val Val Asn Ala Thr Glu Thr
             20                  25                  30

Val Glu Ile Thr Gly Ile Asp Lys Val Cys Thr Lys Gly Lys Lys Ala
         35                  40                  45

Val Asp Leu Gly Ser Cys Gly Ile Leu Gly Thr Ile Ile Gly Pro Pro
     50                  55                  60

Gln Cys Asp Leu His Leu Glu Phe Lys Ala Asp Leu Ile Ile Glu Arg
 65                  70                  75                  80

Arg Asn Ser Ser Asp Ile
                 85
```

```
<210> SEQ ID NO 490
<211> LENGTH: 85
<212> TYPE: PRT
<213> ORGANISM: Influenza virus A
<220> FEATURE:
<223> OTHER INFORMATION: N-termianl long stem domain segment of
      Influenza A HA subtype H15(No Cys, Ala - Delta 3)

<400> SEQUENCE: 490

Asp Lys Ile Cys Leu Gly His His Ala Val Ala Asn Gly Thr Lys Val
1               5                   10                  15

Asn Thr Leu Thr Glu Arg Gly Val Glu Val Val Asn Ala Thr Glu Thr
            20                  25                  30

Val Glu Ile Thr Gly Ile Asp Lys Val Cys Thr Lys Gly Lys Lys Ala
        35                  40                  45

Val Asp Leu Gly Ser Cys Gly Ile Leu Gly Thr Ile Ile Gly Pro Pro
    50                  55                  60

Gln Cys Asp Leu His Leu Glu Phe Lys Ala Asp Leu Ile Ile Glu Arg
65                  70                  75                  80

Arg Asn Ser Ser Asp
                85

<210> SEQ ID NO 491
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H16(No Cys, Ala)

<400> SEQUENCE: 491

Asp Lys Ile Cys Ile Gly Tyr Leu Ser Asn Asn Ser Ser Asp Thr Val
1               5                   10                  15

Asp Thr Leu Thr Glu Asn Gly Val Pro Val Thr Ser Ser Val Asp Leu
            20                  25                  30

Val Glu Thr Asn His Thr Gly Thr Tyr Cys Ser Leu Asn Gly Ile Ser
        35                  40                  45

Pro Ile His Leu Gly Asp Cys Ser Phe Glu Gly Trp Ile Val Gly Asn
    50                  55                  60

Pro Ser Cys Ala Thr Asn Ile Asn Ile Arg Glu Trp Ser Tyr Leu Ile
65                  70                  75                  80

Glu Asp Pro Asn Ala Pro Asn Lys Phe
                85

<210> SEQ ID NO 492
<211> LENGTH: 89
<212> TYPE: PRT
<213> ORGANISM: Influenza virus A
<220> FEATURE:
<223> OTHER INFORMATION: N-termianl long stem domain segment of
      Influenza A HA subtype H16(No Cys, Ala - Delta 1)

<400> SEQUENCE: 492

Asp Lys Ile Cys Ile Gly Tyr Leu Ser Asn Asn Ser Ser Asp Thr Val
1               5                   10                  15

Asp Thr Leu Thr Glu Asn Gly Val Pro Val Thr Ser Ser Val Asp Leu
            20                  25                  30

Val Glu Thr Asn His Thr Gly Thr Tyr Cys Ser Leu Asn Gly Ile Ser
        35                  40                  45

Pro Ile His Leu Gly Asp Cys Ser Phe Glu Gly Trp Ile Val Gly Asn
    50                  55                  60
```

```
Pro Ser Cys Ala Thr Asn Ile Asn Ile Arg Glu Trp Ser Tyr Leu Ile
65                  70                  75                  80

Glu Asp Pro Asn Ala Pro Asn Lys Phe
                85
```

<210> SEQ ID NO 493
<211> LENGTH: 88
<212> TYPE: PRT
<213> ORGANISM: Influenza virus A
<220> FEATURE:
<223> OTHER INFORMATION: N-termianl long stem domain segment of
      Influenza A HA subtype H16(No Cys, Ala - Delta 3)

<400> SEQUENCE: 493

```
Asp Lys Ile Cys Ile Gly Tyr Leu Ser Asn Asn Ser Ser Asp Thr Val
1               5                   10                  15

Asp Thr Leu Thr Glu Asn Gly Val Pro Val Thr Ser Ser Val Asp Leu
                20                  25                  30

Val Glu Thr Asn His Thr Gly Thr Tyr Cys Ser Leu Asn Gly Ile Ser
            35                  40                  45

Pro Ile His Leu Gly Asp Cys Ser Phe Glu Gly Trp Ile Val Gly Asn
        50                  55                  60

Pro Ser Cys Ala Thr Asn Ile Asn Ile Arg Glu Trp Ser Tyr Leu Ile
65                  70                  75                  80

Glu Asp Pro Asn Ala Pro Asn Lys
                85
```

<210> SEQ ID NO 494
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H1(No Cys, Ala)

<400> SEQUENCE: 494

```
Pro Met Tyr Ala Phe Ala Leu Ser Arg Gly Phe Gly Ser Gly Ile Ile
1               5                   10                  15

Thr Ser Asn Ala Ser Met His Glu Cys Asn Thr Lys Cys Gln Thr Pro
                20                  25                  30

Leu Gly Ala Ile Asn Ser Ser Leu Pro Tyr Gln Asn Ile His Pro Val
            35                  40                  45

Thr Ile Gly Glu Cys Pro Lys Tyr Val Arg Ser Ala Lys Leu Arg Met
        50                  55                  60

Val Thr Gly Leu Arg Asn Asn Pro Ser Ile Gln Ser Arg
65                  70                  75
```

<210> SEQ ID NO 495
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H1(No Cys, Ala - Delta 1)

<400> SEQUENCE: 495

```
Met Tyr Ala Phe Ala Leu Ser Arg Gly Phe Gly Ser Gly Ile Ile Thr
1               5                   10                  15

Ser Asn Ala Ser Met His Glu Cys Asn Thr Lys Cys Gln Thr Pro Leu
                20                  25                  30
```

```
Gly Ala Ile Asn Ser Ser Leu Pro Tyr Gln Asn Ile His Pro Val Thr
        35                  40                  45

Ile Gly Glu Cys Pro Lys Tyr Val Arg Ser Ala Lys Leu Arg Met Val
    50                  55                  60

Thr Gly Leu Arg Asn Asn Pro Ser Ile Gln Ser Arg
65                  70                  75

<210> SEQ ID NO 496
<211> LENGTH: 75
<212> TYPE: PRT
<213> ORGANISM: Influenza virus A
<220> FEATURE:
<223> OTHER INFORMATION: C-termianl long stem domain segment of
      Influenza A HA subtype H1(No Cys, Ala - Delta 3)

<400> SEQUENCE: 496

Tyr Ala Phe Ala Leu Ser Arg Gly Phe Gly Ser Gly Ile Ile Thr Ser
 1               5                  10                  15

Asn Ala Ser Met His Glu Cys Asn Thr Lys Cys Gln Thr Pro Leu Gly
            20                  25                  30

Ala Ile Asn Ser Ser Leu Pro Tyr Gln Asn Ile His Pro Val Thr Ile
        35                  40                  45

Gly Glu Cys Pro Lys Tyr Val Arg Ser Ala Lys Leu Arg Met Val Thr
    50                  55                  60

Gly Leu Arg Asn Asn Pro Ser Ile Gln Ser Arg
65                  70                  75

<210> SEQ ID NO 497
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H2(No Cys, Ala)

<400> SEQUENCE: 497

Pro Glu Tyr Gly Phe Arg Ile Ser Lys Arg Gly Ser Ser Gly Ile Met
 1               5                  10                  15

Lys Thr Glu Gly Thr Leu Glu Asn Cys Glu Thr Lys Cys Gln Thr Pro
            20                  25                  30

Leu Gly Ala Ile Asn Thr Thr Leu Pro Phe His Asn Val His Pro Leu
        35                  40                  45

Thr Ile Gly Glu Cys Pro Lys Tyr Val Lys Ser Glu Arg Leu Val Leu
    50                  55                  60

Ala Thr Gly Leu Arg Asn Val Pro Gln Ile Glu Ser Arg
65                  70                  75

<210> SEQ ID NO 498
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H2(No Cys, Ala - Delta 1)

<400> SEQUENCE: 498

Glu Tyr Gly Phe Arg Ile Ser Lys Arg Gly Ser Ser Gly Ile Met Lys
 1               5                  10                  15

Thr Glu Gly Thr Leu Glu Asn Cys Glu Thr Lys Cys Gln Thr Pro Leu
            20                  25                  30

Gly Ala Ile Asn Thr Thr Leu Pro Phe His Asn Val His Pro Leu Thr
```

```
                   35                  40                  45

Ile Gly Glu Cys Pro Lys Tyr Val Lys Ser Glu Arg Leu Val Leu Ala
 50                  55                  60

Thr Gly Leu Arg Asn Val Pro Gln Ile Glu Ser Arg
 65                  70                  75

<210> SEQ ID NO 499
<211> LENGTH: 75
<212> TYPE: PRT
<213> ORGANISM: Influenza virus A
<220> FEATURE:
<223> OTHER INFORMATION: C-termianl long stem domain segment of
      Influenza A HA subtype H2(No Cys, Ala - Delta 3)

<400> SEQUENCE: 499

Tyr Gly Phe Arg Ile Ser Lys Arg Gly Ser Gly Ile Met Lys Thr
 1               5                  10                  15

Glu Gly Thr Leu Glu Asn Cys Glu Thr Lys Cys Gln Thr Pro Leu Gly
                 20                  25                  30

Ala Ile Asn Thr Thr Leu Pro Phe His Asn Val His Pro Leu Thr Ile
                 35                  40                  45

Gly Glu Cys Pro Lys Tyr Val Lys Ser Glu Arg Leu Val Leu Ala Thr
 50                  55                  60

Gly Leu Arg Asn Val Pro Gln Ile Glu Ser Arg
 65                  70                  75

<210> SEQ ID NO 500
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H3(No Cys, Ala)

<400> SEQUENCE: 500

Pro Arg Gly Tyr Phe Lys Met Arg Thr Gly Lys Ser Ser Ile Met Ser
 1               5                  10                  15

Ser Asp Ala Pro Ile Asp Thr Cys Ile Ser Glu Cys Ile Thr Pro Asn
                 20                  25                  30

Gly Ser Ile Pro Asn Asp Lys Pro Phe Gln Asn Val Asn Lys Ile Thr
                 35                  40                  45

Tyr Gly Ala Cys Pro Lys Tyr Val Lys Gln Asn Thr Leu Lys Leu Ala
 50                  55                  60

Thr Gly Met Arg Asn Val Pro Glu Lys Gln Thr Arg
 65                  70                  75

<210> SEQ ID NO 501
<211> LENGTH: 75
<212> TYPE: PRT
<213> ORGANISM: Influenza virus A
<220> FEATURE:
<223> OTHER INFORMATION: C-termianl long stem domain segment of
      Influenza A HA subtype H3(No Cys, Ala - Delta 1)

<400> SEQUENCE: 501

Arg Gly Tyr Phe Lys Met Arg Thr Gly Lys Ser Ser Ile Met Ser Ser
 1               5                  10                  15

Asp Ala Pro Ile Asp Thr Cys Ile Ser Glu Cys Ile Thr Pro Asn Gly
                 20                  25                  30

Ser Ile Pro Asn Asp Lys Pro Phe Gln Asn Val Asn Lys Ile Thr Tyr
                 35                  40                  45
```

```
Gly Ala Cys Pro Lys Tyr Val Lys Gln Asn Thr Leu Lys Leu Ala Thr
         50                  55                  60

Gly Met Arg Asn Val Pro Glu Lys Gln Thr Arg
 65                  70                  75
```

<210> SEQ ID NO 502
<211> LENGTH: 74
<212> TYPE: PRT
<213> ORGANISM: Influenza virus A
<220> FEATURE:
<223> OTHER INFORMATION: C-termianl long stem domain segment of
      Influenza A HA subtype H3(No Cys, Ala - Delta 3)

<400> SEQUENCE: 502

```
Gly Tyr Phe Lys Met Arg Thr Gly Lys Ser Ser Ile Met Ser Ser Asp
 1               5                  10                  15

Val Gly Asp Cys Pro Arg Tyr Val Lys Gln Gly Ser Leu Lys Leu Ala
    50                  55                  60

Thr Gly Met Arg Asn Ile Pro Glu Lys Ala Ser Arg
65                  70                  75

<210> SEQ ID NO 505
<211> LENGTH: 75
<212> TYPE: PRT
<213> ORGANISM: Influenza virus A
<220> FEATURE:
<223> OTHER INFORMATION: C-termianl long stem domain segment of
      Influenza A HA subtype H4(No Cys, Ala - Delta 3)

<400> SEQUENCE: 505

Gly His Tyr Lys Leu Asn Asn Gln Lys Lys Ser Thr Ile Leu Asn Thr
1               5                   10                  15

Ala Ile Pro Ile Gly Ser Cys Val Ser Lys Cys His Thr Asp Lys Gly
                20                  25                  30

Ser Leu Ser Thr Thr Lys Pro Phe Gln Asn Ile Ser Arg Ile Ala Val
            35                  40                  45

Gly Asp Cys Pro Arg Tyr Val Lys Gln Gly Ser Leu Lys Leu Ala Thr
        50                  55                  60

Gly Met Arg Asn Ile Pro Glu Lys Ala Ser Arg
65                  70                  75

<210> SEQ ID NO 506
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H5(No Cys, Ala)

<400> SEQUENCE: 506

Pro Arg Tyr Ala Tyr Lys Ile Val Lys Lys Gly Asp Ser Ala Ile Met
1               5                   10                  15

Lys Ser Gly Leu Ala Tyr Gly Asn Cys Asp Thr Lys Cys Gln Thr Pro
                20                  25                  30

Val Gly Glu Ile Asn Ser Ser Met Pro Phe His Asn Ile His Pro His
            35                  40                  45

Thr Ile Gly Glu Cys Pro Lys Tyr Val Lys Ser Asp Arg Leu Val Leu
        50                  55                  60

Ala Thr Gly Leu Arg Asn Val Pro Gln Arg Lys Lys Arg
65                  70                  75

<210> SEQ ID NO 507
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H5(No Cys, Ala - Delta 1)

<400> SEQUENCE: 507

Arg Tyr Ala Tyr Lys Ile Val Lys Lys Gly Asp Ser Ala Ile Met Lys
1               5                   10                  15

Ser Gly Leu Ala Tyr Gly Asn Cys Asp Thr Lys Cys Gln Thr Pro Val
                20                  25                  30

Gly Glu Ile Asn Ser Ser Met Pro Phe His Asn Ile His Pro His Thr
            35                  40                  45

Ile Gly Glu Cys Pro Lys Tyr Val Lys Ser Asp Arg Leu Val Leu Ala

```
                    50                  55                  60

Thr Gly Leu Arg Asn Val Pro Gln Arg Lys Lys Arg
 65                  70                  75

<210> SEQ ID NO 508
<211> LENGTH: 75
<212> TYPE: PRT
<213> ORGANISM: Influenza virus A
<220> FEATURE:
<223> OTHER INFORMATION: C-termianl long stem domain segment of
      Influenza A HA subtype H5(No Cys, Ala - Delta 3)

<400> SEQUENCE: 508

Tyr Ala Tyr Lys Ile Val Lys Lys Gly Asp Ser Ala Ile Met Lys Ser
 1               5                  10                  15

Gly Leu Ala Tyr Gly Asn Cys Asp Thr Lys Cys Gln Thr Pro Val Gly
                20                  25                  30

Glu Ile Asn Ser Ser Met Pro Phe His Asn Ile His Pro His Thr Ile
             35                  40                  45

Gly Glu Cys Pro Lys Tyr Val Lys Ser Asp Arg Leu Val Leu Ala Thr
         50                  55                  60

Gly Leu Arg Asn Val Pro Gln Arg Lys Lys Arg
 65                  70                  75

<210> SEQ ID NO 509
<211> LENGTH: 78
<212> TYPE: PRT
<213> ORGANISM: Influenza virus A
<220> FEATURE:
<223> OTHER INFORMATION: C-termianl long stem domain segment of
      Influenza A HA
      subtype H6(No Cys, Ala)

<400> SEQUENCE: 509

Pro Trp Tyr Ala Phe Arg Phe Val Ser Thr Ser Asn Lys Gly Ala Val
 1               5                  10                  15

Phe Lys Ser Asn Leu Pro Ile Glu Asn Cys Asp Ala Thr Cys Gln Thr
                20                  25                  30

Val Ala Gly Val Leu Arg Thr Asn Lys Thr Phe Gln Asn Val Ser Pro
             35                  40                  45

Leu Trp Ile Gly Glu Cys Pro Lys Tyr Val Lys Ser Glu Ser Leu Arg
         50                  55                  60

Leu Ala Thr Gly Leu Arg Asn Val Pro Gln Ile Glu Thr Arg
 65                  70                  75

<210> SEQ ID NO 510
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H6(No Cys, Ala - Delta 1)

<400> SEQUENCE: 510

Trp Tyr Ala Phe Arg Phe Val Ser Thr Ser Asn Lys Gly Ala Val Phe
 1               5                  10                  15

Lys Ser Asn Leu Pro Ile Glu Asn Cys Asp Ala Thr Cys Gln Thr Val
                20                  25                  30

Ala Gly Val Leu Arg Thr Asn Lys Thr Phe Gln Asn Val Ser Pro Leu
             35                  40                  45

Trp Ile Gly Glu Cys Pro Lys Tyr Val Lys Ser Glu Ser Leu Arg Leu
```

Ala Thr Gly Leu Arg Asn Val Pro Gln Ile Glu Thr Arg
65                  70                  75

<210> SEQ ID NO 511
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H6(No Cys, Ala - Delta 3)

<400> SEQUENCE: 511

Tyr Ala Phe Arg Phe Val Ser Thr Ser Asn Lys Gly Ala Val Phe Lys
1               5                   10                  15

Ser Asn Leu Pro Ile Glu Asn Cys Asp Ala Thr Cys Gln Thr Val Ala
                20                  25                  30

Gly Val Leu Arg Thr Asn Lys Thr Phe Gln Asn Val Ser Pro Leu Trp
            35                  40                  45

Ile Gly Glu Cys Pro Lys Tyr Val Lys Ser Glu Ser Leu Arg Leu Ala
        50                  55                  60

Thr Gly Leu Arg Asn Val Pro Gln Ile Glu Thr Arg
65                  70                  75

<210> SEQ ID NO 512
<211> LENGTH: 80
<212> TYPE: PRT
<213> ORGANISM: Influenza virus A
<220> FEATURE:
<223> OTHER INFORMATION: C-termianl long stem domain segment of
      Influenza A HA subtype H7(No Cys, Ala)

<400> SEQUENCE: 512

Pro Asn Arg Ala Ser Phe Leu Arg Gly Lys Ser Met Gly Ile Gln Ser
1               5                   10                  15

Asp Val Gln Val Asp Ala Asn Cys Glu Gly Glu Cys Tyr His Ser Gly
                20                  25                  30

Gly Thr Ile Thr Ser Arg Leu Pro Phe Gln Asn Ile Asn Ser Arg Ala
            35                  40                  45

Val Gly Lys Cys Pro Arg Tyr Val Lys Gln Glu Ser Leu Leu Leu Ala
        50                  55                  60

Thr Gly Met Lys Asn Val Pro Glu Pro Ser Lys Lys Arg Lys Lys Arg
65                  70                  75                  80

<210> SEQ ID NO 513
<211> LENGTH: 79
<212> TYPE: PRT
<213> ORGANISM: Influenza virus A
<220> FEATURE:
<223> OTHER INFORMATION: C-termianl long stem domain segment of
      Influenza A HA subtype H7(No Cys, Ala - Delta 1)

<400> SEQUENCE: 513

Asn Arg Ala Ser Phe Leu Arg Gly Lys Ser Met Gly Ile Gln Ser Asp
1               5                   10                  15

Val Gln Val Asp Ala Asn Cys Glu Gly Glu Cys Tyr His Ser Gly Gly
                20                  25                  30

Thr Ile Thr Ser Arg Leu Pro Phe Gln Asn Ile Asn Ser Arg Ala Val
            35                  40                  45

Gly Lys Cys Pro Arg Tyr Val Lys Gln Glu Ser Leu Leu Leu Ala Thr
        50                  55                  60

```
Gly Met Lys Asn Val Pro Glu Pro Ser Lys Lys Arg Lys Lys Arg
65                  70                  75
```

<210> SEQ ID NO 514
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H7(No Cys, Ala - Delta 3)

<400> SEQUENCE: 514

```
Arg Ala Ser Phe Leu Arg Gly Lys Ser Met Gly Ile Gln Ser Asp Val
1               5                   10                  15

Gln Val Asp Ala Asn Cys Glu Gly Glu Cys Tyr His Ser Gly Gly Thr
                20                  25                  30

Ile Thr Ser Arg Leu Pro Phe Gln Asn Ile Asn Ser Arg Ala Val Gly
            35                  40                  45

Lys Cys Pro Arg Tyr Val Lys Gln Glu Ser Leu Leu Leu Ala Thr Gly
    50                  55                  60

Met Lys Asn Val Pro Glu Pro Ser Lys Lys Arg Lys Lys Arg
65                  70                  75
```

<210> SEQ ID NO 515
<211> LENGTH: 78
<212> TYPE: PRT
<213> ORGANISM: Influenza virus A
<220> FEATURE:
<223> OTHER INFORMATION: C-termianl long stem domain segment of
      Influenza A HA subtype H8(No Cys, Ala)

<400> SEQUENCE: 515

```
Pro Glu Phe Gly Tyr Leu Leu Lys Gly Glu Ser Tyr Gly Arg Ile Ile
1               5                   10                  15

Gln Asn Glu Asp Ile Pro Ile Gly Asn Cys Asn Thr Lys Cys Gln Thr
                20                  25                  30

Tyr Ala Gly Ala Ile Asn Ser Ser Lys Pro Phe Gln Asn Ala Ser Arg
            35                  40                  45

His Tyr Met Gly Glu Cys Pro Lys Tyr Val Lys Lys Ala Ser Leu Arg
    50                  55                  60

Leu Ala Val Gly Leu Arg Asn Thr Pro Ser Val Glu Pro Arg
65                  70                  75
```

<210> SEQ ID NO 516
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H8(No Cys, Ala - Delta 1)

<400> SEQUENCE: 516

```
Glu Phe Gly Tyr Leu Leu Lys Gly Glu Ser Tyr Gly Arg Ile Ile Gln
1               5                   10                  15

Asn Glu Asp Ile Pro Ile Gly Asn Cys Asn Thr Lys Cys Gln Thr Tyr
                20                  25                  30

Ala Gly Ala Ile Asn Ser Ser Lys Pro Phe Gln Asn Ala Ser Arg His
            35                  40                  45

Tyr Met Gly Glu Cys Pro Lys Tyr Val Lys Lys Ala Ser Leu Arg Leu
    50                  55                  60
```

Ala Val Gly Leu Arg Asn Thr Pro Ser Val Glu Pro Arg
65                  70                  75

<210> SEQ ID NO 517
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H8(No Cys, Ala - Delta 3)

<400> SEQUENCE: 517

Phe Gly Tyr Leu Leu Lys Gly Glu Ser Tyr Gly Arg Ile Ile Gln Asn
1                   5                   10                  15

Glu Asp Ile Pro Ile Gly Asn Cys Asn Thr Lys Cys Gln Thr Tyr Ala
                20                  25                  30

Gly Ala Ile Asn Ser Ser Lys Pro Phe Gln Asn Ala Ser Arg His Tyr
            35                  40                  45

Met Gly Glu Cys Pro Lys Tyr Val Lys Lys Ala Ser Leu Arg Leu Ala
        50                  55                  60

Val Gly Leu Arg Asn Thr Pro Ser Val Glu Pro Arg
65                  70                  75

<210> SEQ ID NO 518
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H9(No Cys, Ala)

<400> SEQUENCE: 518

Pro Trp Tyr Gly His Val Leu Thr Gly Glu Ser His Gly Arg Ile Leu
1                   5                   10                  15

Lys Thr Asp Leu Asn Asn Gly Asn Cys Val Val Gln Cys Gln Thr Glu
                20                  25                  30

Lys Gly Gly Leu Asn Thr Thr Leu Pro Phe His Asn Ile Ser Lys Tyr
            35                  40                  45

Ala Phe Gly Asn Cys Pro Lys Tyr Val Gly Val Lys Ser Leu Lys Leu
        50                  55                  60

Pro Val Gly Leu Arg Asn Val Pro Ala Val Ser Ser Arg
65                  70                  75

<210> SEQ ID NO 519
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H9(No Cys, Ala - Delta 1)

<400> SEQUENCE: 519

Trp Tyr Gly His Val Leu Thr Gly Glu Ser His Gly Arg Ile Leu Lys
1                   5                   10                  15

Thr Asp Leu Asn Asn Gly Asn Cys Val Val Gln Cys Gln Thr Glu Lys
                20                  25                  30

Gly Gly Leu Asn Thr Thr Leu Pro Phe His Asn Ile Ser Lys Tyr Ala
            35                  40                  45

Phe Gly Asn Cys Pro Lys Tyr Val Gly Val Lys Ser Leu Lys Leu Pro
        50                  55                  60

Val Gly Leu Arg Asn Val Pro Ala Val Ser Ser Arg 65              70              75

<210> SEQ ID NO 520
<211> LENGTH: 75
<212> TYPE: PRT
<213> ORGANISM: Influenza virus A
<220> FEATURE:
<223> OTHER INFORMATION: C-termianl long stem domain segment of
      Influenza A HA subtype H9(No Cys, Ala - Delta 3)

<400> SEQUENCE: 520

Tyr Gly His Val Leu Thr Gly Glu Ser His Gly Arg Ile Leu Lys Thr
1               5                   10                  15

Asp Leu Asn Asn Gly Asn Cys Val Val Gln Cys Gln Thr Glu Lys Gly
            20                  25                  30

Gly Leu Asn Thr Thr Leu Pro Phe His Asn Ile Ser Lys Tyr Ala Phe
        35                  40                  45

Gly Asn Cys Pro Lys Tyr Val Gly Val Lys Ser Leu Lys Leu Pro Val
    50                  55                  60

Gly Leu Arg Asn Val Pro Ala Val Ser Ser Arg
65                  70                  75

<210> SEQ ID NO 521
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H10(No Cys, Ala)

<400> SEQUENCE: 521

Pro Ser Arg Val Ser Lys Leu Thr Gly Arg Asp Leu Gly Ile Gln Ser
1               5                   10                  15

Glu Ala Leu Ile Asp Asn Ser Cys Glu Ser Lys Cys Phe Trp Arg Gly
            20                  25                  30

Gly Ser Ile Asn Thr Lys Leu Pro Phe Gln Asn Leu Ser Pro Arg Thr
        35                  40                  45

Val Gly Gln Cys Pro Lys Tyr Val Asn Gln Arg Ser Leu Leu Leu Ala
    50                  55                  60

Thr Gly Met Arg Asn Val Pro Glu Val Val Gln Gly Arg
65                  70                  75

<210> SEQ ID NO 522
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H10(No Cys, Ala - Delta 1)

<400> SEQUENCE: 522

Ser Arg Val Ser Lys Leu Thr Gly Arg Asp Leu Gly Ile Gln Ser Glu
1               5                   10                  15

Ala Leu Ile Asp Asn Ser Cys Glu Ser Lys Cys Phe Trp Arg Gly Gly
            20                  25                  30

Ser Ile Asn Thr Lys Leu Pro Phe Gln Asn Leu Ser Pro Arg Thr Val
        35                  40                  45

Gly Gln Cys Pro Lys Tyr Val Asn Gln Arg Ser Leu Leu Leu Ala Thr
    50                  55                  60

Gly Met Arg Asn Val Pro Glu Val Val Gln Gly Arg
65                  70                  75

<210> SEQ ID NO 523
<211> LENGTH: 75
<212> TYPE: PRT
<213> ORGANISM: Influenza virus A
<220> FEATURE:
<223> OTHER INFORMATION: C-termianl long stem domain segment of
      Influenza A HA subtype H10(No Cys, Ala - Delta 3)

<400> SEQUENCE: 523

Arg Val Ser Lys Leu Thr Gly Arg Asp Leu Gly Ile Gln Ser Glu Ala
 1               5                  10                  15

Leu Ile Asp Asn Ser Cys Glu Ser Lys Cys Phe Trp Arg Gly Gly Ser
            20                  25                  30

Ile Asn Thr Lys Leu Pro Phe Gln Asn Leu Ser Pro Arg Thr Val Gly
        35                  40                  45

Gln Cys Pro Lys Tyr Val Asn Gln Arg Ser Leu Leu Leu Ala Thr Gly
    50                  55                  60

Met Arg Asn Val Pro Glu Val Val Gln Gly Arg
65                  70                  75

<210> SEQ ID NO 524
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H11(No Cys, Ala)

<400> SEQUENCE: 524

Pro Arg Tyr Ala Phe Glu Ile Val Ser Val Gly Asn Gly Lys Leu Phe
 1               5                  10                  15

Arg Ser Glu Leu Asn Ile Glu Ser Cys Ser Thr Lys Cys Gln Thr Glu
            20                  25                  30

Ile Gly Gly Ile Asn Thr Asn Lys Ser Phe His Asn Val His Arg Asn
        35                  40                  45

Thr Ile Gly Asp Cys Pro Lys Tyr Val Asn Val Lys Ser Leu Lys Leu
    50                  55                  60

Ala Thr Gly Pro Arg Asn Val Pro Ala Ile Ala Ser Arg
65                  70                  75

<210> SEQ ID NO 525
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H11(No Cys, Ala - Delta 1)

<400> SEQUENCE: 525

Arg Tyr Ala Phe Glu Ile Val Ser Val Gly Asn Gly Lys Leu Phe Arg
 1               5                  10                  15

Ser Glu Leu Asn Ile Glu Ser Cys Ser Thr Lys Cys Gln Thr Glu Ile
            20                  25                  30

Gly Gly Ile Asn Thr Asn Lys Ser Phe His Asn Val His Arg Asn Thr
        35                  40                  45

Ile Gly Asp Cys Pro Lys Tyr Val Asn Val Lys Ser Leu Lys Leu Ala
    50                  55                  60

Thr Gly Pro Arg Asn Val Pro Ala Ile Ala Ser Arg
65                  70                  75

<210> SEQ ID NO 526
<211> LENGTH: 75
<212> TYPE: PRT
<213> ORGANISM: Influenza virus A
<220> FEATURE:
<223> OTHER INFORMAT

```
<210> SEQ ID NO 529
<211> LENGTH: 75
<212> TYPE: PRT
<213> ORGANISM: Influenza virus A
<220> FEATURE:
<223> OTHER INFORMATION: C-termianl long stem domain segment of
      Influenza A HA subtype H12(No Cys, Ala - Delta 3)

<400> SEQUENCE: 529

Tyr Gly His Leu Ile Thr Gly Lys Ser His Gly Arg Ile Leu Lys Asn
  1               5                  10                  15

Asn Leu Pro Met Gly Gln Cys Val Thr Glu Cys Gln Leu Asn Glu Gly
             20                  25                  30

Val Met Asn Thr Ser Lys Pro Phe Gln Asn Thr Ser Lys His Tyr Ile
         35                  40                  45

Gly Lys Cys Pro Lys Tyr Ile Pro Ser Gly Ser Leu Lys Leu Ala Ile
     50                  55                  60

Gly Leu Arg Asn Val Pro Gln Val Gln Asp Arg
 65                  70                  75

<210> SEQ ID NO 530
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H13(No Cys, Ala)

<400> SEQUENCE: 530

Pro Arg Tyr Gly Tyr Ile Ile Glu Glu Tyr Gly Lys Gly Arg Ile Phe
  1               5                  10                  15

Gln Ser Arg Ile Arg Met Ser Arg Cys Asn Thr Lys Cys Gln Thr Ser
             20                  25                  30

Val Gly Gly Ile Asn Thr Asn Arg Thr Phe Gln Asn Ile Asp Lys Asn
         35                  40                  45

Ala Leu Gly Asp Cys Pro Lys Tyr Ile Lys Ser Gly Gln Leu Lys Leu
     50                  55                  60

Ala Thr Gly Leu Arg Asn Val Pro Ala Ile Ser Asn Arg
 65                  70                  75

<210> SEQ ID NO 531
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H13(No Cys, Ala - Delta 1)

<400> SEQUENCE: 531

Arg Tyr Gly Tyr Ile Ile Glu Glu Tyr Gly Lys Gly Arg Ile Phe Gln
  1               5                  10                  15

Ser Arg Ile Arg Met Ser Arg Cys Asn Thr Lys Cys Gln Thr Ser Val
             20                  25                  30

Gly Gly Ile Asn Thr Asn Arg Thr Phe Gln Asn Ile Asp Lys Asn Ala
         35                  40                  45

Leu Gly Asp Cys Pro Lys Tyr Ile Lys Ser Gly Gln Leu Lys Leu Ala
     50                  55                  60

Thr Gly Leu Arg Asn Val Pro Ala Ile Ser Asn Arg
 65                  70                  75

<210> SEQ ID NO 532
```

```
<211> LENGTH: 75
<212> TYPE: PRT
<213> ORGANISM: Influenza virus A
<220> FEATURE:
<223> OTHER INFORMATION: C-termianl long stem domain segment of
      Influenza A HA subtype H13(No Cys, Ala - Delta 3)

<400> SEQUENCE: 532

Tyr Gly Tyr Ile Ile Glu Glu Tyr Gly Lys Gly Arg Ile Phe Gln Ser
1               5                   10                  15

Arg Ile Arg Met Ser Arg Cys Asn Thr Lys Cys Gln Thr Ser Val Gly
            20                  25                  30

Gly Ile Asn Thr Asn Arg Thr Phe Gln Asn Ile Asp Lys Asn Ala Leu
        35                  40                  45

Gly Asp Cys Pro Lys Tyr Ile Lys Ser Gly Gln Leu Lys Leu Ala Thr
    50                  55                  60

Gly Leu Arg Asn Val Pro Ala Ile Ser Asn Arg
65                  70                  75

<210> SEQ ID NO 533
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H14(No Cys, Ala)

<400> SEQUENCE: 533

Pro Arg Gly His Tyr Lys Ile Ser Lys Ser Thr Lys Ser Thr Val Leu
1               5                   10                  15

Lys Ser Asp Lys Arg Ile Gly Ser Cys Thr Ser Pro Cys Leu Thr Asp
            20                  25                  30

Lys Gly Ser Ile Gln Ser Asp Lys Pro Phe Gln Asn Val Ser Arg Ile
        35                  40                  45

Ala Ile Gly Asn Cys Pro Lys Tyr Val Lys Gln Gly Ser Leu Met Leu
    50                  55                  60

Ala Thr Gly Met Arg Asn Ile Pro Gly Lys Gln Ala Lys
65                  70                  75

<210> SEQ ID NO 534
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H14(No Cys, Ala - Delta 1)

<400> SEQUENCE: 534

Arg Gly His Tyr Lys Ile Ser Lys Ser Thr Lys Ser Thr Val Leu Lys
1               5                   10                  15

Ser Asp Lys Arg Ile Gly Ser Cys Thr Ser Pro Cys Leu Thr Asp Lys
            20                  25                  30

Gly Ser Ile Gln Ser Asp Lys Pro Phe Gln Asn Val Ser Arg Ile Ala
        35                  40                  45

Ile Gly Asn Cys Pro Lys Tyr Val Lys Gln Gly Ser Leu Met Leu Ala
    50                  55                  60

Thr Gly Met Arg Asn Ile Pro Gly Lys Gln Ala Lys
65                  70                  75

<210> SEQ ID NO 535
<211> LENGTH: 75
```

```
<212> TYPE: PRT
<213> ORGANISM: Influenza virus A
<220> FEATURE:
<223> OTHER INFORMATION: C-termianl long stem domain segment of
      Influenza A HA subtype H14(No Cys, Ala - Delta 3)

<400> SEQUENCE: 535

Gly His Tyr Lys Ile Ser Lys Ser Thr Lys Ser Thr Val Leu Lys Ser
1               5                   10                  15

Asp Lys Arg Ile Gly Ser Cys Thr Ser Pro Cys Leu Thr Asp Lys Gly
            20                  25                  30

Ser Ile Gln Ser Asp Lys Pro Phe Gln Asn Val Ser Arg Ile Ala Ile
        35                  40                  45

Gly Asn Cys Pro Lys Tyr Val Lys Gln Gly Ser Leu Met Leu Ala Thr
    50                  55                  60

Gly Met Arg Asn Ile Pro Gly Lys Gln Ala Lys
65                  70                  75

<210> SEQ ID NO 536
<211> LENGTH: 87
<212> TYPE: PRT
<213> ORGANISM: Influenza virus A
<220> FEATURE:
<223> OTHER INFORMATION: C-termianl long stem domain segment of
      Influenza A HA subtype H15(No Cys, Ala)

<400> SEQUENCE: 536

Pro Asp Arg Ala Thr Phe Leu Arg Ser Asn Ala Pro Ser Gly Ile Glu
1               5                   10                  15

Tyr Asn Gly Lys Ser Leu Gly Ile Gln Ser Asp Ala Gln Ile Asp Glu
            20                  25                  30

Ser Cys Glu Gly Glu Cys Phe Tyr Ser Gly Gly Thr Ile Asn Ser Pro
        35                  40                  45

Leu Pro Phe Gln Asn Ile Asp Ser Arg Ala Val Gly Lys Cys Pro Arg
    50                  55                  60

Tyr Val Lys Gln Ser Ser Leu Pro Leu Ala Leu Gly Met Lys Asn Val
65                  70                  75                  80

Pro Glu Lys Ile Arg Thr Arg
                85

<210> SEQ ID NO 537
<211> LENGTH: 86
<212> TYPE: PRT
<213> ORGANISM: Influenza virus A
<220> FEATURE:
<223> OTHER INFORMATION: C-termianl long stem domain segment of
      Influenza A HA subtype H15(No Cys, Ala - Delta 1)

<400> SEQUENCE: 537

Asp Arg Ala Thr Phe Leu Arg Ser Asn Ala Pro Ser Gly Ile Glu Tyr
1               5                   10                  15

Asn Gly Lys Ser Leu Gly Ile Gln Ser Asp Ala Gln Ile Asp Glu Ser
            20                  25                  30

Cys Glu Gly Glu Cys Phe Tyr Ser Gly Gly Thr Ile Asn Ser Pro Leu
        35                  40                  45

Pro Phe Gln Asn Ile Asp Ser Arg Ala Val Gly Lys Cys Pro Arg Tyr
    50                  55                  60

Val Lys Gln Ser Ser Leu Pro Leu Ala Leu Gly Met Lys Asn Val Pro
65                  70                  75                  80

Glu Lys Ile Arg Thr Arg
```

-continued

```
                85

<210> SEQ ID NO 538
<211> LENGTH: 85
<212> TYPE: PRT
<213> ORGANISM: Influenza virus A
<220> FEATURE:
<223> OTHER INFORMATION: C-termianl long stem domain segment of
      Influenza A HA subtype H15(No Cys, Ala - Delta 3)

<400> SEQUENCE: 538

Arg Ala Thr Phe Leu Arg Ser Asn Ala Pro Ser Gly Ile Glu Tyr Asn
1               5                   10                  15

Gly Lys Ser Leu Gly Ile Gln Ser Asp Ala Gln Ile Asp Glu Ser Cys
            20                  25                  30

Glu Gly Glu Cys Phe Tyr Ser Gly Gly Thr Ile Asn Ser Pro Leu Pro
        35                  40                  45

Phe Gln Asn Ile Asp Ser Arg Ala Val Gly Lys Cys Pro Arg Tyr Val
    50                  55                  60

Lys Gln Ser Ser Leu Pro Leu Ala Leu Gly Met Lys Asn Val Pro Glu
65                  70                  75                  80

Lys Ile Arg Thr Arg
                85

<210> SEQ ID NO 539
<211> LENGTH: 77
<212> TYPE: PRT
<213> ORGANISM: Influenza virus A
<220> FEATURE:
<223> OTHER INFORMATION: C-termianl long stem domain segment of
      Influenza A HA subtype H16(No Cys, Ala)

<400> SEQUENCE: 539

Pro Arg Tyr Gly Tyr Ile Ile Glu Lys Tyr Gly Thr Gly Arg Ile Phe
1               5                   10                  15

Gln Ser Gly Val Arg Met Ala Arg Cys Asn Thr Lys Cys Gln Thr Ser
            20                  25                  30

Leu Gly Gly Ile Asn Thr Asn Lys Thr Phe Gln Asn Ile Glu Arg Asn
        35                  40                  45

Ala Leu Gly Asp Cys Pro Lys Tyr Ile Lys Ser Gly Gln Leu Lys Leu
    50                  55                  60

Ala Thr Gly Leu Arg Asn Val Pro Ser Ile Gly Glu Arg
65                  70                  75

<210> SEQ ID NO 540
<211> LENGTH: 76
<212> TYPE: PRT
<213> ORGANISM: Influenza virus A
<220> FEATURE:
<223> OTHER INFORMATION: C-termianl long stem domain segment of
      Influenza A HA subtype H16(No Cys, Ala - Delta 1)

<400> SEQUENCE: 540

Arg Tyr Gly Tyr Ile Ile Glu Lys Tyr Gly Thr Gly Arg Ile Phe Gln
1               5                   10                  15

Ser Gly Val Arg Met Ala Arg Cys Asn Thr Lys Cys Gln Thr Ser Leu
            20                  25                  30

Gly Gly Ile Asn Thr Asn Lys Thr Phe Gln Asn Ile Glu Arg Asn Ala
        35                  40                  45

Leu Gly Asp Cys Pro Lys Tyr Ile Lys Ser Gly Gln Leu Lys Leu Ala
    50                  55                  60
```

```
Thr Gly Leu Arg Asn Val Pro Ser Ile Gly Glu Arg
 65                  70                  75

<210> SEQ ID NO 541
<211> LENGTH: 75
<212> TYPE: PRT
<213> ORGANISM: Influenza virus A
<220> FEATURE:
<223> OTHER INFORMATION: C-termianl long stem domain segment of
      Influenza A HA subtype H16(No Cys, Ala - Delta 3)

<400> SEQUENCE: 541

Tyr Gly Tyr Ile Ile Glu Lys Tyr Gly Thr Gly Arg Ile Phe Gln Ser
  1               5                  10                  15

Gly Val Arg Met Ala Arg Cys Asn Thr Lys Cys Gln Thr Ser Leu Gly
                 20                  25                  30

Gly Ile Asn Thr Asn Lys Thr Phe Gln Asn Ile Glu Arg Asn Ala Leu
             35                  40                  45

Gly Asp Cys Pro Lys Tyr Ile Lys Ser Gly Gln Leu Lys Leu Ala Thr
         50                  55                  60

Gly Leu Arg Asn Val Pro Ser Ile Gly Glu Arg
 65                  70                  75

<210> SEQ ID NO 542
<211> LENGTH: 16
<212> TYPE: PRT
<213> ORGANISM: Artificial Sequence
<220> FEATURE:
<223> OTHER INFORMATION: linker sequence

<400> SEQUENCE: 542

Lys Leu Asn Gly Ser Gly Ile Met Lys Thr Glu Gly Thr Leu Glu Asn
  1               5                  10                  15

<210> SEQ ID NO 543
<211> LENGTH: 5
<212> TYPE: PRT
<213> ORGANISM: Artificial Sequence
<220> FEATURE:
<223> OTHER INFORMATION: linker sequence

<400> SEQUENCE: 543

Asn Asn Ile Asp Thr
  1               5

<210> SEQ ID NO 544
<211> LENGTH: 5
<212> TYPE: PRT
<213> ORGANISM: Artificial Sequence
<220> FEATURE:
<223> OTHER INFORMATION: sequence of influenza HA polypeptide

<400> SEQUENCE: 544

Thr Gly Leu Arg Asn
  1               5

<210> SEQ ID NO 545
<211> LENGTH: 12
<212> TYPE: PRT
<213> ORGANISM: Artificial Sequence
<220> FEATURE:
<223> OTHER INFORMATION: sequence of influenza HA polypeptide

<400> SEQUENCE: 545
```

```
Gly Ile Thr Asn Lys Val Asn Ser Val Ile Glu Lys
1               5                   10
```

<210> SEQ ID NO 546
<211> LENGTH: 5
<212> TYPE: PRT
<213> ORGANISM: Artificial Sequence
<220> FEATURE:
<223> OTHER INFORMATION: linker sequence

<400> SEQUENCE: 546

```
Asn Asn Ile Asp Thr
1               5
```

<210> SEQ ID NO 547
<211> LENGTH: 5
<212> TYPE: PRT
<213> ORGANISM: Artificial Sequence
<220> FEATURE:
<223> OTHER INFORMATION: sequence of influenza HA polypeptide

<400> SEQUENCE: 547

```
Thr Gly Met Arg Asn
1               5
```

<210> SEQ ID NO 548
<211> LENGTH: 12
<212> TYPE: PRT
<213> ORGANISM: Artificial Sequence
<220> FEATURE:
<223> OTHER INFORMATION: sequence of influenza HA polypeptide

<400> SEQUENCE: 548

```

```
                65                  70                  75                  80
Ala Ser Ile Leu His Glu Val Lys Pro Val Thr Ser Gly Cys
                85                  90

<210> SEQ ID NO 551
<211> LENGTH: 178
<212> TYPE: PRT
<213> ORGANISM: Influenza virus B
<220> FEATURE:
<223> OTHER INFORMATION: HA1 N-terminal Stem Segment of Influenza B HA
      construct variant Cys178-Cys272

<400> SEQUENCE: 551

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
                20                  25                  30

Thr Thr Thr Pro Thr Lys Ser His Phe Ala Asn Leu Lys Gly Thr Gln
            35                  40                  45

Thr Arg Gly Lys Leu Cys Pro Asn Cys Leu Asn Cys Thr Asp Leu Asp
    50                  55                  60

Val Ala Leu Gly Arg Pro Lys Cys Met Gly Thr Ile Pro Ser Ala Lys
65                  70                  75                  80

Ala Ser Ile Leu His Glu Val Lys Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Ala Arg Asn Val Thr Asn Ala Glu
        115                 120                 125

Thr Ala Pro Gly Gly Pro Tyr Ile Val Gly Thr Ser Gly Ser Cys Pro
    130                 135                 140

Asn Val Thr Asn Gly Asn Gly Phe Phe Ala Thr Met Ala Trp Ala Val
145                 150                 155                 160

Pro Lys Asn Lys Thr Ala Thr Asn Pro Leu Thr Val Glu Val Pro Tyr
                165                 170                 175

Ile Cys

<210> SEQ ID NO 552
<211> LENGTH: 54
<212> TYPE: PRT
<213> ORGANISM: Influenza virus B
<220> FEATURE:
<223> OTHER INFORMATION: HA1 N-terminal Stem Segment of Influenza B HA
      construct variant Cys54-Cys272

<400> SEQUENCE: 552

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
                20                  25                  30

Thr Thr Thr Pro Thr Lys Ser His Phe Ala Asn Leu Lys Gly Thr Gln
            35                  40                  45

Thr Arg Gly Lys Leu Cys
    50

<210> SEQ ID NO 553
<211> LENGTH: 200
<212> TYPE: PRT
<213> ORGANISM: Influenza virus B
```

<220> FEATURE:
<223> OTHER INFORMATION: HA1 C-terminal Stem Segment of Influenza B HA
      construct variant Cys94-Cys143

<400> SEQUENCE: 553

Cys Pro Asn Val Thr Asn Gly Asn Gly Phe Phe Ala Thr Met Ala Trp
1               5                   10                  15

Ala Val Pro Lys Asn Lys Thr Ala Thr Asn Pro Leu Thr Val Glu Val
            20                  25                  30

Pro Tyr Ile Cys Thr Lys Gly Glu Asp Gln Ile Thr Val Trp Gly Phe
        35                  40                  45

His Ser Asp Asp Glu Thr Gln Met Val Lys Leu Tyr Gly Asp Ser Lys
50                  55                  60

Pro Gln Lys Phe Thr Ser Ser Ala Asn Gly Val Thr Thr His Tyr Val
65                  70                  75                  80

Ser Gln Ile Gly Gly Phe Pro Asn Gln Ala Glu Asp Glu Gly Leu Pro
                85                  90                  95

Gln Ser Gly Arg Ile Val Val Asp Tyr Met Val Gln Lys Pro Gly Lys
            100                 105                 110

Thr Gly Thr Ile Ala Tyr Gln Arg Gly Val Leu Leu Pro Gln Lys Val
        115                 120                 125

Trp Cys Ala Ser Gly Arg Ser Lys Val Ile Lys Gly Ser Leu Pro Leu
    130                 135                 140

Ile Gly Glu Ala Asp Cys Leu His Glu Lys Tyr Gly Gly Leu Asn Lys
145                 150                 155                 160

Ser Lys Pro Tyr Tyr Thr Gly Glu His Ala Lys Ala Ile Gly Asn Cys
                165                 170                 175

Pro Ile Trp Val Lys Thr Pro Leu Lys Leu Ala Asn Gly Thr Lys Tyr
            180                 185                 190

Arg Pro Pro Ala Lys Leu Leu Lys
        195                 200

<210> SEQ ID NO 554
<211> LENGTH: 71
<212> TYPE: PRT
<213> ORGANISM: Influenza virus B
<220> FEATURE:
<223> OTHER INFORMATION: HA1 C-terminal Stem Segment of Influenza B HA
      construct variant Cys178-Cys272

<400> SEQUENCE: 554

Cys Ala Ser Gly Arg Ser Lys Val Ile Lys Gly Ser Leu Pro Leu Ile
1               5                   10                  15

Gly Glu Ala Asp Cys Leu His Glu Lys Tyr Gly Gly Leu Asn Lys Ser
            20                  25                  30

Lys Pro Tyr Tyr Thr Gly Glu His Ala Lys Ala Ile Gly Asn Cys Pro
        35                  40                  45

Ile Trp Val Lys Thr Pro Leu Lys Leu Ala Asn Gly Thr Lys Tyr Arg
    50                  55                  60

Pro Pro Ala Lys Leu Leu Lys
65                  70

<210> SEQ ID NO 555
<211> LENGTH: 94
<212> TYPE: PRT
<213> ORGANISM: Influenza virus B
<220> FEATURE:
<223> OTHER INFORMATION: HA1 N-terminal Stem Segment of Influenza B HA
      construct variant Cys94-Cys143-Cys178-Cys272

<400> SEQUENCE: 555

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Gln
        35                  40                  45

Thr Arg Gly Lys Leu Cys Pro Asn Cys Leu Asn Cys Thr Asp Leu Asp
    50                  55                  60

Val Ala Leu Gly Arg Pro Lys Cys Met Gly Thr Ile Pro Ser Ala Lys
65                  70                  75                  80

Ala Ser Ile Leu His Glu Val Lys Pro Val Thr Ser Gly Cys
                85                  90

<210> SEQ ID NO 556
<211> LENGTH: 36
<212> TYPE: PRT
<213> ORGANISM: Influenza virus B
<220> FEATURE:
<223> OTHER INFORMATION: HA1 intermediate Segment of Influenza B HA
      construct variant Cys94-Cys143-Cys178-Cys272

<400> SEQUENCE: 556

Cys Pro Asn Val Thr Asn Gly Asn Gly Phe Phe Ala Thr Met Ala Trp
1               5                   10                  15

Ala Val Pro Lys Asn Lys Thr Ala Thr Asn Pro Leu Thr Val Glu Val
            20                  25                  30

Pro Tyr Ile Cys
        35

<210> SEQ ID NO 557
<211> LENGTH: 71
<212> TYPE: PRT
<213> ORGANISM: Influenza virus B
<220> FEATURE:
<223> OTHER INFORMATION: HA1 C-terminal Stem Segment of Influenza B HA
      construct variant Cys94-Cys143-Cys178-Cys272

<400> SEQUENCE: 557

Cys Ala Ser Gly Arg Ser Lys Val Ile Lys Gly Ser Leu Pro Leu Ile
1               5                   10                  15

Gly Glu Ala Asp Cys Leu His Glu Lys Tyr Gly Gly Leu Asn Lys Ser
            20                  25                  30

Lys Pro Tyr Tyr Thr Gly Glu His Ala Lys Ala Ile Gly Asn Cys Pro
        35                  40                  45

Ile Trp Val Lys Thr Pro Leu Lys Leu Ala Asn Gly Thr Lys Tyr Arg
    50                  55                  60

Pro Pro Ala Lys Leu Leu Lys
65                  70

<210> SEQ ID NO 558
<211> LENGTH: 585
<212> TYPE: PRT
<213> ORGANISM: Influenza virus B
<220> FEATURE:
<223> OTHER INFORMATION: representative sequence of influenza virus B
      hemagglutinin (in Fig. 2)

<400> SEQUENCE: 558

Met Lys Ala Ile Ile Val Ile Leu Met Val Val Thr Ser Asn Ala Asp

```
            1               5              10              15
          Arg Ile Cys Thr Gly Ile Thr Ser Ser Asn Ser Pro His Val Val Lys
                          20              25              30
          Thr Ala Thr Gln Gly Glu Val Asn Val Thr Gly Val Ile Pro Leu Thr
                          35              40              45
          Thr Thr Pro Thr Lys Ser His Phe Ala Asn Leu Lys Gly Thr Glu Thr
           50              55                      60
          Arg Gly Lys Leu Cys Pro Lys Cys Leu Asn Cys Thr Asp Leu Asp Val
           65              70              75                      80
          Ala Leu Gly Arg Pro Lys Cys Thr Gly Lys Ile Pro Ser Ala Arg Val
                          85              90              95
          Ser Ile Leu His Glu Val Arg Pro Val Thr Ser Gly Cys Phe Pro Ile
                         100             105             110
          Met His Asp Arg Thr Lys Ile Arg Gln Leu Pro Asn Leu Leu Arg Gly
                         115             120             125
          Tyr Glu His Ile Arg Leu Ser Thr His Asn Val Ile Asn Ala Glu Asn
                         130             135             140
          Ala Pro Gly Gly Pro Tyr Lys Ile Gly Thr Ser Gly Ser Cys Pro Asn
          145             150             155                     160
          Ile Thr Asn Gly Asn Gly Phe Phe Ala Thr Met Ala Trp Ala Val Pro
                         165             170             175
          Lys Asn Asp Lys Asn Lys Thr Ala Thr Asn Pro Leu Thr Ile Glu Val
                         180             185             190
          Pro Tyr Ile Cys Thr Glu Gly Glu Asp Gln Ile Thr Val Trp Gly Phe
                         195             200             205
          His Ser Asp Ser Glu Thr Gln Met Ala Lys Leu Tyr Gly Asp Ser Lys
                         210             215             220
          Pro Gln Lys Phe Thr Ser Ser Ala Asn Gly Val Thr Thr His Tyr Val
          225             230             235                     240
          Ser Gln Ile Gly Gly Phe Pro Asn Gln Thr Glu Asp Gly Gly Leu Pro
                         245             250             255
          Gln Ser Gly Arg Ile Val Val Asp Tyr Met Val Gln Lys Ser Gly Lys
                         260             265             270
          Thr Gly Thr Ile Thr Tyr Gln Arg Gly Ile Leu Leu Pro Gln Lys Val
                         275             280             285
          Trp Cys Ala Ser Gly Arg Ser Lys Val Ile Lys Gly Ser Leu Pro Leu
                         290             295             300
          Ile Gly Glu Ala Asp Cys Leu His Glu Lys Tyr Gly Gly Leu Asn Lys
          305             310             315                     320
          Ser Lys Pro Tyr Tyr Thr Gly Glu His Ala Lys Ala Ile Gly Asn Cys
                         325             330             335
          Pro Ile Trp Val Lys Thr Pro Leu Lys Leu Ala Asn Gly Thr Lys Tyr
                         340             345             350
          Arg Pro Pro Ala Lys Leu Leu Lys Glu Arg Gly Phe Phe Gly Ala Ile
                         355             360             365
          Ala Gly Phe Leu Glu Gly Gly Trp Glu Gly Met Ile Ala Gly Trp His
                         370             375             380
          Gly Tyr Thr Ser His Gly Ala His Gly Val Ala Val Ala Ala Asp Leu
          385             390             395                     400
          Lys Ser Thr Gln Glu Ala Ile Asn Lys Ile Thr Lys Asn Leu Asn Ser
                         405             410             415
          Leu Ser Glu Leu Glu Val Lys Asn Leu Gln Arg Leu Ser Gly Ala Met
                         420             425             430
```

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
        450                 455                 460

Ser Asn Glu Thr Phe Asp Ser Leu Asn Ile Thr Ala Ala Ser Leu Asn
465                 470                 475                 480

Asp Asp Gly Leu Asp Asn His Thr Ile Leu Leu Tyr Tyr Ser Thr Ala
                485                 490                 495

Ala Ser Ser Leu Ala Val Thr Leu Met Ile Ala Ile Phe Val Val Tyr
            500                 505                 510

Met Val Ser Arg Asp Asn Val Ser Cys Ser Ile Cys Leu Gly Ile Ile
        515                 520                 525

Asn Ser Glu Asp Glu His Leu Leu Ala Leu Arg Lys Leu Lys Lys
530                 535                 540

Met Leu Gly Pro Ser Ala Val Glu Ile Gly Asn Gly Cys Phe Glu Thr
545                 550                 555                 560

Lys His Lys Cys Asn Gln Thr Cys Leu Asp Arg Ile Ala Ala Gly Thr
                565                 570                 575

Phe Asp Ala Gly Glu Phe Ser Leu Pro
            580                 585

<210> SEQ ID NO 559
<211> LENGTH: 16
<212> TYPE: PRT
<213> ORGANISM: Artificial Sequence
<220> FEATURE:
<223> OTHER INFORMATION: linker sequence

<400> SEQUENCE: 559

Lys Leu Asn Gly Ser Gly Ile Met Lys Thr Glu Gly Thr Leu Glu Asn
1               5                   10                  15

<210> SEQ ID NO 560
<211> LENGTH: 18
<212> TYPE: PRT
<213> ORGANISM: Artificial Sequence
<220> FEATURE:
<223> OTHER INFORMATION: influenza A HA subtype H17 signal peptides

<400> SEQUENCE: 560

Met Glu Leu Ile Val Leu Leu Ile Leu Leu Asn Pro Tyr Thr Phe Val
1               5                   10                  15

Leu Gly

<210> SEQ ID NO 561
<211> LENGTH: 42
<212> TYPE: PRT
<213> ORGANISM: Artificial Sequence
<220> FEATURE:
<223> OTHER INFORMATION: influenza A HA subtype H17 N-terminal stem
      segment

<400> SEQUENCE: 561

Asp Arg Ile Cys Ile Gly Tyr Gln Ala Asn Gln Asn Asn Gln Thr Val
1               5                   10                  15

Asn Thr Leu Leu Glu Gln Asn Val Pro Val Thr Gly Ala Gln Glu Ile
            20                  25                  30

Leu Glu Thr Asn His Asn Gly Lys Leu Cys
        35                  40

```
<210> SEQ ID NO 562
<211> LENGTH: 53
<212> TYPE: PRT
<213> ORGANISM: Artificial Sequence
<220> FEATURE:
<223> OTHER INFORMATION: influenza A HA subtype H17 C-terminal stem
      segment

<400> SEQUENCE: 562

Cys Ser Thr Lys Cys Gln Thr Pro Leu Gly Ala Leu Asn Ser Thr Leu
 1               5                  10                  15

Pro Phe Gln Asn Val His Gln Gln Thr Ile Gly Asn Cys Pro Lys Tyr
             20                  25                  30

Val Lys Ala Thr Ser Leu Met Leu Ala Thr Gly Leu Arg Asn Asn Pro
         35                  40                  45

Gln Met Glu Gly Arg
     50

<210> SEQ ID NO 563
<211> LENGTH: 222
<212> TYPE: PRT
<213> ORGANISM: Artificial Sequence
<220> FEATURE:
<223> OTHER INFORMATION: influenza A HA subtype H17 HA2 domain

<400> SEQUENCE: 563

Gly Leu Phe Gly Ala Ile Ala Gly Phe Ile Glu Gly Gly Trp Gln Gly
 1               5                  10                  15

Met Ile Asp Gly Trp Tyr Gly Tyr His His Glu Asn Gln Glu Gly Ser
             20                  25                  30

Gly Tyr Ala Ala Asp Lys Glu Ala Thr Gln Lys Ala Val Asp Ala Ile
         35                  40                  45

Thr Asn Lys Val Asn Ser Ile Ile Asp Lys Met Asn Ser Gln Phe Glu
     50                  55                  60

Ser Asn Ile Lys Glu Phe Asn Arg Leu Glu Leu Arg Ile Gln His Leu
65                  70                  75                  80

Ser Asp Arg Val Asp Asp Ala Leu Leu Asp Ile Trp Ser Tyr Asn Thr
                 85                  90                  95

Glu Leu Leu Val Leu Leu Glu Asn Glu Arg Thr Leu Asp Phe His Asp
            100                 105                 110

Ala Asn Val Lys Asn Leu Phe Glu Lys Val Lys Ala Gln Leu Lys Asp
        115                 120                 125

Asn Ala Ile Asp Glu Gly Asn Gly Cys Phe Leu Leu Leu His Lys Cys
    130                 135                 140

Asn Asn Ser Cys Met Asp Asp Ile Lys Asn Gly Thr Tyr Lys Tyr Met
145                 150                 155                 160

Asp Tyr Arg Glu Glu Ser His Ile Glu Lys Gln Lys Ile Asp Gly Val
                165                 170                 175

Lys Leu Thr Asp Tyr Ser Arg Tyr Tyr Ile Met Thr Leu Tyr Ser Thr
            180                 185                 190

Ile Ala Ser Ser Val Val Leu Gly Ser Leu Ile Ile Ala Ala Phe Leu
        195                 200                 205

Trp Gly Cys Gln Lys Gly Ser Ile Gln Cys Lys Ile Cys Ile
    210                 215                 220

<210> SEQ ID NO 564
<211> LENGTH: 41
<212> TYPE: PRT
```

<213> ORGANISM: Artificial Sequence
<220> FEATURE:
<223> OTHER INFORMATION: N-terminal stem segment of Influenza A HA
      subtype H17(no Cys)

<400> SEQUENCE: 564

Asp Arg Ile Cys Ile Gly Tyr Gln Ala Asn Gln Asn Asn Gln Thr Val
1               5                   10                  15

Asn Thr Leu Leu Glu Gln Asn Val Pro Val Thr Gly Ala Gln Glu Ile
            20                  25                  30

Leu Glu Thr Asn His Asn Gly Lys Leu
            35                  40

<210> SEQ ID NO 565
<211> LENGTH: 52
<212> TYPE: PRT
<213> ORGANISM: Artificial Sequence
<220> FEATURE:
<223> OTHER INFORMATION: C-terminal stem segment of Influenza A HA
      subtype H17(no Cys)

<400> SEQUENCE: 565

Ser Thr Lys Cys Gln Thr Pro Leu Gly Ala Leu Asn Ser Thr Leu Pro
1               5                   10                  15

Phe Gln Asn Val His Gln Gln Thr Ile Gly Asn Cys Pro Lys Tyr Val
            20                  25                  30

Lys Ala Thr Ser Leu Met Leu Ala Thr Gly Leu Arg Asn Asn Pro Gln
            35                  40                  45

Met Glu Gly Arg
    50

<210> SEQ ID NO 566
<211> LENGTH: 180
<212> TYPE: PRT
<213> ORGANISM: Artificial Sequence
<220> FEATURE:
<223> OTHER INFORMATION: influenza A HA2 domain subtype H17 stem domain

<400> SEQUENCE: 566

Gly Leu Phe Gly Ala Ile Ala Gly Phe Ile Glu Gly Gly Trp Gln Gly
1               5                   10                  15

Met Ile Asp Gly Trp Tyr Gly Tyr His His Glu Asn Gln Glu Gly Ser
            20                  25                  30

Gly Tyr Ala Ala Asp Lys Glu Ala Thr Gln Lys Ala Val Asp Ala Ile
            35                  40                  45

Thr Asn Lys Val Asn Ser Ile Ile Asp Lys Met Asn Ser Gln Phe Glu
50                  55                  60

Ser Asn Ile Lys Glu Phe Asn Arg Leu Glu Leu Arg Ile Gln His Leu
65                  70                  75                  80

Ser Asp Arg Val Asp Asp Ala Leu Leu Asp Ile Trp Ser Tyr Asn Thr
            85                  90                  95

Glu Leu Leu Val Leu Leu Glu Asn Glu Arg Thr Leu Asp Phe His Asp
            100                 105                 110

Ala Asn Val Lys Asn Leu Phe Glu Lys Val Lys Ala Gln Leu Lys Asp
            115                 120                 125

Asn Ala Ile Asp Glu Gly Asn Gly Cys Phe Leu Leu Leu His Lys Cys
            130                 135                 140

Asn Asn Ser Cys Met Asp Asp Ile Lys Asn Gly Thr Tyr Lys Tyr Met
145                 150                 155                 160

```
Asp Tyr Arg Glu Glu Ser His Ile Glu Lys Gln Lys Ile Asp Gly Val
            165                 170                 175

Lys Leu Thr Asp
        180

<210> SEQ ID NO 567
<211> LENGTH: 5
<212> TYPE: PRT
<213> ORGANISM: Artificial Sequence
<220> FEATURE:
<223> OTHER INFORMATION: influenza A HA2 domain subtype H17 luminal
      domain

<400> SEQUENCE: 567

Tyr Ser Arg Tyr Tyr
1               5

<210> SEQ ID NO 568
<211> LENGTH: 27
<212> TYPE: PRT
<213> ORGANISM: Artificial Sequence
<220> FEATURE:
<223> OTHER INFORMATION: influenza A HA2 domain subtype H17
      transmembrane domain

<400> SEQUENCE: 568

Ile Met Thr Leu Tyr Ser Thr Ile Ala Ser Ser Val Val Leu Gly Ser
1               5                   10                  15

Leu Ile Ile Ala Ala Phe Leu Trp Gly Cys Gln
            20                  25

<210> SEQ ID NO 569
<211> LENGTH: 10
<212> TYPE: PRT
<213> ORGANISM: Artificial Sequence
<220> FEATURE:
<223> OTHER INFORMATION: influenza A HA2 domain subtype H17 cytoplasmic
      domain

<400> SEQUENCE: 569

Lys Gly Ser Ile Gln Cys Lys Ile Cys Ile
1               5                   10

<210> SEQ ID NO 570
<211> LENGTH: 18
<212> TYPE: PRT
<213> ORGANISM: Artificial Sequence
<220> FEATURE:
<223> OTHER INFORMATION: influenza A HA subtype H17 signal peptide

<400> SEQUENCE: 570

Met Glu Leu Ile Val Leu Leu Ile Leu Leu Asn Pro Tyr Thr Phe Val
1               5                   10                  15

Leu Gly

<210> SEQ ID NO 571
<211> LENGTH: 42
<212> TYPE: PRT
<213> ORGANISM: Artificial Sequence
<220> FEATURE:
<223> OTHER INFORMATION: influenza A HA subtype H17 N-terminal stem
      segment

<400> SEQUENCE: 571

Asp Arg Ile Cys Ile Gly Tyr Gln Ala Asn Gln Asn Asn Gln Thr Val
1               5                   10                  15
```

```
Asn Thr Leu Leu Glu Gln Asn Val Pro Val Thr Gly Ala Gln Glu Ile
             20                  25                  30

Leu Glu Thr Asn His Asn Gly Lys Leu Cys
             35                  40

<210> SEQ ID NO 572
<211> LENGTH: 25
<212> TYPE: PRT
<213> ORGANISM: Artificial Sequence
<220> FEATURE:
<223> OTHER INFORMATION: influenza A HA subtype H17 C-terminal short
      stem segment

<400> SEQUENCE: 572

Cys Pro Lys Tyr Val Lys Ala Thr Ser Leu Met Leu Ala Thr Gly Leu
1               5                   10                  15

Arg Asn Asn Pro Gln Met Glu Gly Arg
             20                  25

<210> SEQ ID NO 573
<211> LENGTH: 222
<212> TYPE: PRT
<213> ORGANISM: Artificial Sequence
<220> FEATURE:
<223> OTHER INFORMATION: influenza A HA subtype H17 HA2 domain

<400> SEQUENCE: 573

Gly Leu Phe Gly Ala Ile Ala Gly Phe Ile Glu Gly Gly Trp Gln Gly
1               5                   10                  15

Met Ile Asp Gly Trp Tyr Gly Tyr His His Glu Asn Gln Glu Gly Ser
             20                  25                  30

Gly Tyr Ala Ala Asp Lys Glu Ala Thr Gln Lys Ala Val Asp Ala Ile
             35                  40                  45

Thr Asn Lys Val Asn Ser Ile Ile Asp Lys Met Asn Ser Gln Phe Glu
         50                  55                  60

Ser Asn Ile Lys Glu Phe Asn Arg Leu Glu Leu Arg Ile Gln His Leu
65                  70                  75                  80

Ser Asp Arg Val Asp Asp Ala Leu Leu Asp Ile Trp Ser Tyr Asn Thr
             85                  90                  95

Glu Leu Leu Val Leu Leu Glu Asn Glu Arg Thr Leu Asp Phe His Asp
            100                 105                 110

Ala Asn Val Lys Asn Leu Phe Glu Lys Val Lys Ala Gln Leu Lys Asp
            115                 120                 125

Asn Ala Ile Asp Glu Gly Asn Gly Cys Phe Leu Leu Leu His Lys Cys
        130                 135                 140

Asn Asn Ser Cys Met Asp Asp Ile Lys Asn Gly Thr Tyr Lys Tyr Met
145                 150                 155                 160

Asp Tyr Arg Glu Glu Ser His Ile Glu Lys Gln Lys Ile Asp Gly Val
            165                 170                 175

Lys Leu Thr Asp Tyr Ser Arg Tyr Tyr Ile Met Thr Leu Tyr Ser Thr
            180                 185                 190

Ile Ala Ser Ser Val Val Leu Gly Ser Leu Ile Ile Ala Ala Phe Leu
            195                 200                 205

Trp Gly Cys Gln Lys Gly Ser Ile Gln Cys Lys Ile Cys Ile
            210                 215                 220

<210> SEQ ID NO 574
<211> LENGTH: 41
```

```
<212> TYPE: PRT
<213> ORGANISM: Artificial Sequence
<220> FEATURE:
<223> OTHER INFORMATION: influenza A HA subtype H17 N-terminal stem
      segment

<400> SEQUENCE: 574

Asp Arg Ile Cys Ile Gly Tyr Gln Ala Asn Gln Asn Asn Gln Thr Val
1               5                   10                  15

Asn Thr Leu Leu Glu Gln Asn Val Pro Val Thr Gly Ala Gln Glu Ile
            20                  25                  30

Leu Glu Thr Asn His Asn Gly Lys Leu
        35                  40

<210> SEQ ID NO 575
<211> LENGTH: 24
<212> TYPE: PRT
<213> ORGANISM: Artificial Sequence
<220> FEATURE:
<223> OTHER INFORMATION: influenza A HA subtype H17 C-terminal stem
      segment

<400> SEQUENCE: 575

Pro Lys Tyr Val Lys Ala Thr Ser Leu Met Leu Ala Thr Gly Leu Arg
1               5                   10                  15

Asn Asn Pro Gln Met Glu Gly Arg
            20

<210> SEQ ID NO 576
<211> LENGTH: 18
<212> TYPE: PRT
<213> ORGANISM: Artificial Sequence
<220> FEATURE:
<223> OTHER INFORMATION: influenza A HA subtype H17 signal peptide

<400> SEQUENCE: 576

Met Glu Leu Ile Val Leu Leu Ile Leu Leu Asn Pro Tyr Thr Phe Val
1               5                   10                  15

Leu Gly

<210> SEQ ID NO 577
<211> LENGTH: 90
<212> TYPE: PRT
<213> ORGANISM: Artificial Sequence
<220> FEATURE:
<223> OTHER INFORMATION: influenza A HA subtype H17 N-terminal long stem
      segment

<400> SEQUENCE: 577

Asp Arg Ile Cys Ile Gly Tyr Gln Ala Asn Gln Asn Asn Gln Thr Val
1               5                   10                  15

Asn Thr Leu Leu Glu Gln Asn Val Pro Val Thr Gly Ala Gln Glu Ile
            20                  25                  30

Leu Glu Thr Asn His Asn Gly Lys Leu Cys Ser Leu Asn Gly Val Pro
        35                  40                  45

Pro Leu Asp Leu Gln Ser Cys Thr Leu Ala Gly Trp Leu Leu Gly Asn
    50                  55                  60

Pro Asn Cys Asp Ser Leu Leu Glu Ala Glu Trp Ser Tyr Ile Lys
65                  70                  75                  80

Ile Asn Glu Ser Ala Pro Asp Asp Leu Cys
            85                  90
```

<210> SEQ ID NO 578
<211> LENGTH: 79
<212> TYPE: PRT
<213> ORGANISM: Artificial Sequence
<220> FEATURE:
<223> OTHER INFORMATION: influenza A HA subtype H17 C-terminal long stem segment

<400> SEQUENCE: 578

Ala Pro Glu Tyr Gly Phe Tyr Tyr Lys Arg Lys Glu Gly Lys Gly Gly
 1               5                  10                  15

Leu Met Lys Ser Lys Leu Pro Ile Ser Asp Cys Ser Thr Lys Cys Gln
            20                  25                  30

Thr Pro Leu Gly Ala Leu Asn Ser Thr Leu Pro Phe Gln Asn Val His
        35                  40                  45

Gln Gln Thr Ile Gly Asn Cys Pro Lys Tyr Val Lys Ala Thr Ser Leu
    50                  55                  60

Met Leu Ala Thr Gly Leu Arg Asn Asn Pro Gln Met Glu Gly Arg
65                  70                  75

<210> SEQ ID NO 579
<211> LENGTH: 222
<212> TYPE: PRT
<213> ORGANISM: Artificial Sequence
<220> FEATURE:
<223> OTHER INFORMATION: influenza A HA subtype H17 HA2 domain

<400> SEQUENCE: 579

Gly Leu Phe Gly Ala Ile Ala Gly Phe Ile Glu Gly Gly Trp Gln Gly
 1               5                  10                  15

Met Ile Asp Gly Trp Tyr Gly Tyr His His Glu Asn Gln Glu Gly Ser
            20                  25                  30

Gly Tyr Ala Ala Asp Lys Glu Ala Thr Gln Lys Ala Val Asp Ala Ile
        35                  40                  45

Thr Asn Lys Val Asn Ser Ile Ile Asp Lys Met Asn Ser Gln Phe Glu
    50                  55                  60

Ser Asn Ile Lys Glu Phe Asn Arg Leu Glu Leu Arg Ile Gln His Leu
65                  70                  75                  80

Ser Asp Arg Val Asp Asp Ala Leu Leu Asp Ile Trp Ser Tyr Asn Thr
                85                  90                  95

Glu Leu Leu Val Leu Leu Glu Asn Glu Arg Thr Leu Asp Phe His Asp
            100                 105                 110

Ala Asn Val Lys Asn Leu Phe Glu Lys Val Lys Ala Gln Leu Lys Asp
        115                 120                 125

Asn Ala Ile Asp Glu Gly Asn Gly Cys Phe Leu Leu Leu His Lys Cys
    130                 135                 140

Asn Asn Ser Cys Met Asp Asp Ile Lys Asn Gly Thr Tyr Lys Tyr Met
145                 150                 155                 160

Asp Tyr Arg Glu Glu Ser His Ile Glu Lys Gln Lys Ile Asp Gly Val
                165                 170                 175

Lys Leu Thr Asp Tyr Ser Arg Tyr Tyr Ile Met Thr Leu Tyr Ser Thr
            180                 185                 190

Ile Ala Ser Ser Val Val Leu Gly Ser Leu Ile Ile Ala Ala Phe Leu
        195                 200                 205

Trp Gly Cys Gln Lys Gly Ser Ile Gln Cys Lys Ile Cys Ile
    210                 215                 220

<210> SEQ ID NO 580

```
<211> LENGTH: 89
<212> TYPE: PRT
<213> ORGANISM: Artificial Sequence
<220> FEATURE:
<223> OTHER INFORMATION: influenza A HA subtype H17 N-terminal long
      stem segment

<400> SEQUENCE: 580

Asp Arg Ile Cys Ile Gly Tyr Gln Ala Asn Gln Asn Asn Gln Thr Val
1               5                   10                  15

Asn Thr Leu Leu Glu Gln Asn Val Pro Val Thr Gly Ala Gln Glu Ile
            20                  25                  30

Leu Glu Thr Asn His Asn Gly Lys Leu Cys Ser Leu Asn Gly Val Pro
        35                  40                  45

Pro Leu Asp Leu Gln Ser Cys Thr Leu Ala Gly Trp Leu Leu Gly Asn
    50                  55                  60

Pro Asn Cys Asp Ser Leu Leu Glu Ala Glu Glu Trp Ser Tyr Ile Lys
65                  70                  75                  80

Ile Asn Glu Ser Ala Pro Asp Asp Leu
                85

<210> SEQ ID NO 581
<211> LENGTH: 78
<212> TYPE: PRT
<213> ORGANISM: Artificial Sequence
<220> FEATURE:
<223> OTHER INFORMATION: influenza A HA subtype H17 C-terminal long stem
      segment

<400> SEQUENCE: 581

Pro Glu Tyr Gly Phe Tyr Tyr Lys Arg Lys Glu Gly Lys Gly Gly Leu
1               5                   10                  15

Met Lys Ser Lys Leu Pro Ile Ser Asp Cys Ser Thr Lys Cys Gln Thr
            20                  25                  30

Pro Leu Gly Ala Leu Asn Ser Thr Leu Pro Phe Gln Asn Val His Gln
        35                  40                  45

Gln Thr Ile Gly Asn Cys Pro Lys Tyr Val Lys Ala Thr Ser Leu Met
    50                  55                  60

Leu Ala Thr Gly Leu Arg Asn Asn Pro Gln Met Glu Gly Arg
65                  70                  75

<210> SEQ ID NO 582
<211> LENGTH: 7
<212> TYPE: PRT
<213> ORGANISM: Artificial Sequence
<220> FEATURE:
<223> OTHER INFORMATION: a cleavage site recognized by Tobacco Etch
      Virus (TEV) protease
<220> FEATURE:
<221> NAME/KEY: Variant
<222> LOCATION: 7
<223> OTHER INFORMATION: Xaa = Gly or Ser

<400> SEQUENCE: 582

Glu Asn Leu Tyr Phe Gln Xaa
1               5

<210> SEQ ID NO 583
<211> LENGTH: 564
<212> TYPE: PRT
<213> ORGANISM: Artificial Sequence
<220> FEATURE:
<223> OTHER INFORMATION: influenza B virus HA
```

<400> SEQUENCE: 583

```
Met Glu Leu Ile Val Leu Leu Ile Leu Leu Asn Pro Tyr Thr Phe Val
1               5                   10                  15

Leu Gly Asp Arg Ile Cys Ile Gly Tyr Gln Ala Asn Gln Asn Asn Gln
            20                  25                  30

Thr Val Asn Thr Leu Leu Glu Gln Asn Val Pro Val Thr Gly Ala Gln
        35                  40                  45

Glu Ile Leu Glu Thr Asn His Asn Gly Lys Leu Cys Ser Leu Asn Gly
    50                  55                  60

Val Pro Pro Leu Asp Leu Gln Ser Cys Thr Leu Ala Gly Trp Leu Leu
65                  70                  75                  80

Gly Asn Pro Asn Cys Asp Ser Leu Leu Glu Ala Glu Trp Ser Tyr
                85                  90                  95

Ile Lys Ile Asn Glu Ser Ala Pro Asp Asp Leu Cys Phe Pro Gly Asn
            100                 105                 110

Phe Glu Asn Leu Gln Asp Leu Leu Glu Met Ser Gly Val Gln Asn
        115                 120                 125

Phe Thr Lys Val Lys Leu Phe Asn Pro Gln Ser Met Thr Gly Val Thr
    130                 135                 140

Thr Asn Asn Val Asp Gln Thr Cys Pro Phe Glu Gly Lys Pro Ser Phe
145                 150                 155                 160

Tyr Arg Asn Leu Asn Trp Ile Gln Gly Asn Ser Gly Leu Pro Phe Asn
                165                 170                 175

Ile Glu Ile Lys Asn Pro Thr Ser Asn Pro Leu Leu Leu Leu Trp Gly
            180                 185                 190

Ile His Asn Thr Lys Asp Ala Ala Gln Gln Arg Asn Leu Tyr Gly Asn
        195                 200                 205

Asp Tyr Ser Tyr Thr Ile Phe Asn Phe Gly Glu Lys Ser Glu Glu Phe
    210                 215                 220

Arg Pro Glu Ile Gly Gln Arg Asp Glu Val Lys Ala His Gln Asp Arg
225                 230                 235                 240

Ile Asp Tyr Tyr Trp Gly Ser Leu Pro Ala Gln Ser Thr Leu Arg Ile
                245                 250                 255

Glu Ser Thr Gly Asn Leu Ile Ala Pro Glu Tyr Gly Phe Tyr Tyr Lys
            260                 265                 270

Arg Lys Glu Gly Lys Gly Leu Met Lys Ser Lys Leu Pro Ile Ser
        275                 280                 285

Asp Cys Ser Thr Lys Cys Gln Thr Pro Leu Gly Ala Leu Asn Ser Thr
    290                 295                 300

Leu Pro Phe Gln Asn Val His Gln Gln Thr Ile Gly Asn Cys Pro Lys
305                 310                 315                 320

Tyr Val Lys Ala Thr Ser Leu Met Leu Ala Thr Gly Leu Arg Asn Asn
                325                 330                 335

Pro Gln Met Glu Gly Arg Gly Leu Phe Gly Ala Ile Ala Gly Phe Ile
            340                 345                 350

Glu Gly Gly Trp Gln Gly Met Ile Asp Gly Trp Tyr Gly Tyr His His
        355                 360                 365

Glu Asn Gln Glu Gly Ser Gly Tyr Ala Ala Asp Lys Glu Ala Thr Gln
    370                 375                 380

Lys Ala Val Asp Ala Ile Thr Asn Lys Val Asn Ser Ile Ile Asp Lys
385                 390                 395                 400

Met Asn Ser Gln Phe Glu Ser Asn Ile Lys Glu Phe Asn Arg Leu Glu
                405                 410                 415
```

Leu Arg Ile Gln His Leu Ser Asp Arg Val Asp Asp Ala Leu Leu Asp
            420                 425                 430

Ile Trp Ser Tyr Asn Thr Glu Leu Val Leu Leu Glu Asn Glu Arg
            435                 440                 445

Thr Leu Asp Phe His Asp Ala Asn Val Lys Asn Leu Phe Glu Lys Val
450                 455                 460

Lys Ala Gln Leu Lys Asp Asn Ala Ile Asp Glu Gly Asn Gly Cys Phe
465                 470                 475                 480

Leu Leu Leu His Lys Cys Asn Asn Ser Cys Met Asp Asp Ile Lys Asn
            485                 490                 495

Gly Thr Tyr Lys Tyr Met Asp Tyr Arg Glu Glu Ser His Ile Glu Lys
            500                 505                 510

Gln Lys Ile Asp Gly Val Lys Leu Thr Asp Tyr Ser Arg Tyr Tyr Ile
            515                 520                 525

Met Thr Leu Tyr Ser Thr Ile Ala Ser Ser Val Val Leu Gly Ser Leu
530                 535                 540

Ile Ile Ala Ala Phe Leu Trp Gly Cys Gln Lys Gly Ser Ile Gln Cys
545                 550                 555                 560

Lys Ile Cys Ile

<210> SEQ ID NO 584
<211> LENGTH: 52
<212> TYPE: PRT
<213> ORGANISM: Artificial Sequence
<220> FEATURE:
<223> OTHER INFORMATION: HA1 region of hemagglutinin protein sequence
      of A/Hong Kong/1/1968(H3)

<400> SEQUENCE: 584

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys
    50

<210> SEQ ID NO 585
<211> LENGTH: 52
<212> TYPE: PRT
<213> ORGANISM: Artificial Sequence
<220> FEATURE:
<223> OTHER INFORMATION: HA1 region of hemagglutinin protein sequence of
      A/Perth/16/2009 (H3)

<400> SEQUENCE: 585

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Glu Ile Cys
    50

<210> SEQ ID NO 586
<211> LENGTH: 42

-continued

```
<212> TYPE: PRT
<213> ORGANISM: Artificial Sequence
<220> FEATURE:
<223> OTHER INFORMATION: HA1 region of hemagglutinin protein sequence of
      A/PR/8/34(H1)

<400> SEQUENCE: 586

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys
        35                  40

<210> SEQ ID NO 587
<211> LENGTH: 42
<212> TYPE: PRT
<213> ORGANISM: Artificial Sequence
<220> FEATURE:
<223> OTHER INFORMATION: HA1 region of hemagglutinin protein sequence of
      A/Cal/4/09(H1)

<400> SEQUENCE: 587

Asp Thr Ile Cys Ile Gly Tyr His Ala Asn Asn Ser Thr Asp Thr Val
1               5                   10                  15

Asp Thr Val Leu Lys Lys Asn Val Thr Val Thr His Ser Val Asn Leu
            20                  25                  30

Leu Glu Asp Lys His Asn Gly Lys Leu Cys
        35                  40

<210> SEQ ID NO 588
<211> LENGTH: 42
<212> TYPE: PRT
<213> ORGANISM: Artificial Sequence
<220> FEATURE:
<223> OTHER INFORMATION: HA1 region of hemagglutinin protein sequence of
      A/VietNam/1203/04(H5)

<400> SEQUENCE: 588

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Lys His Asn Gly Lys Leu Cys
        35                  40

<210> SEQ ID NO 589
<211> LENGTH: 42
<212> TYPE: PRT
<213> ORGANISM: Artificial Sequence
<220> FEATURE:
<223> OTHER INFORMATION: HA1 region of hemagglutinin protein sequence of
      A/mallard/Alberta/24/01(H7)

<400> SEQUENCE: 589

Asp Lys Ile Cys Leu Gly His His Ala Val Ala Asn Gly Thr Lys Val
1               5                   10                  15

Asn Thr Leu Thr Glu Lys Gly Ile Glu Val Val Asn Ala Thr Glu Thr
            20                  25                  30

Val Glu Thr Val Asn Ile Lys Lys Ile Cys
        35                  40

<210> SEQ ID NO 590
```

<211> LENGTH: 264
<212> TYPE: PRT
<213> ORGANISM: Artificial Sequence
<220> FEATURE:
<223> OTHER INFORMATION: HA2 region of hemagglutinin protein sequence of A/Hong Kong/1/1968(H3)

<400> SEQUENCE: 590

```
Cys Ile Ser Glu Cys Ile Thr Pro Asn Gly Ser Ile Pro Asn Asp Lys
1               5                   10                  15

Pro Phe Gln Asn Val Asn Lys Ile Thr Tyr Gly Ala Cys Pro Lys Tyr
                20                  25                  30

Val Lys Gln Asn Thr Leu Lys Leu Ala Thr Gly Met Arg Asn Val Pro
            35                  40                  45

Glu Lys Gln Thr Arg Gly Leu Phe Gly Ala Ile Ala Gly Phe Ile Glu
        50                  55                  60

Asn Gly Trp Glu Gly Met Ile Asp Gly Trp Tyr Gly Phe Arg His Gln
65                  70                  75                  80

Asn Ser Glu Gly Thr Gly Gln Ala Ala Asp Leu Lys Ser Thr Gln Ala
                85                  90                  95

Ala Ile Asp Gln Ile Asn Gly Lys Leu Asn Arg Val Ile Glu Lys Thr
            100                 105                 110

Asn Glu Lys Phe His Gln Ile Glu Lys Glu Phe Ser Glu Val Glu Gly
        115                 120                 125

Arg Ile Gln Asp Leu Glu Lys Tyr Val Glu Asp Thr Lys Ile Asp Leu
    130                 135                 140

Trp Ser Tyr Asn Ala Glu Leu Leu Val Ala Leu Glu Asn Gln His Thr
145                 150                 155                 160

Ile Asp Leu Thr Asp Ser Glu Met Asn Lys Leu Phe Glu Lys Thr Arg
                165                 170                 175

Arg Gln Leu Arg Glu Asn Ala Glu Asp Met Gly Asn Gly Cys Phe Lys
            180                 185                 190

Ile Tyr His Lys Cys Asp Asn Ala Cys Ile Glu Ser Ile Arg Asn Gly
        195                 200                 205

Thr Tyr Asp His Asp Val Tyr Arg Asp Glu Ala Leu Asn Asn Arg Phe
    210                 215                 220

Gln Ile Lys Gly Val Glu Leu Lys Ser Gly Tyr Lys Asp Trp Ile Leu
225                 230                 235                 240

Trp Ile Ser Phe Ala Ile Ser Cys Phe Leu Leu Cys Cys Gln Arg Gly
                245                 250                 255

Asn Ile Arg Cys Asn Ile Cys Ile
            260
```

<210> SEQ ID NO 591
<211> LENGTH: 264
<212> TYPE: PRT
<213> ORGANISM: Artificial Sequence
<220> FEATURE:
<223> OTHER INFORMATION: HA2 region of hemagglutinin protein sequence of A/Perth/16/2009 (H3)

<400> SEQUENCE: 591

```
Cys Asn Ser Glu Cys Ile Thr Pro Asn Gly Ser Ile Pro Asn Asp Lys
1               5                   10                  15

Pro Phe Gln Asn Val Asn Arg Ile Thr Tyr Gly Ala Cys Pro Arg Tyr
                20                  25                  30

Val Lys Gln Asn Thr Leu Lys Leu Ala Thr Gly Met Arg Asn Val Pro
            35                  40                  45
```

```
Glu Lys Gln Thr Arg Gly Ile Phe Gly Ala Ile Ala Gly Phe Ile Glu
             50                  55                  60

Asn Gly Trp Glu Gly Met Val Asp Gly Trp Tyr Gly Phe Arg His Gln
 65                  70                  75                  80

Asn Ser Glu Gly Arg Gly Gln Ala Ala Asp Leu Lys Ser Thr Gln Ala
                 85                  90                  95

Ala Ile Asp Gln Ile Asn Gly Lys Leu Asn Arg Leu Ile Gly Lys Thr
                100                 105                 110

Asn Glu Lys Phe His Gln Ile Glu Lys Glu Phe Ser Glu Val Glu Gly
             115                 120                 125

Arg Ile Gln Asp Leu Glu Lys Tyr Val Glu Asp Thr Lys Ile Asp Leu
        130                 135                 140

Trp Ser Tyr Asn Ala Glu Leu Leu Val Ala Leu Glu Asn Gln His Thr
145                 150                 155                 160

Ile Asp Leu Thr Asp Ser Glu Met Asn Lys Leu Phe Glu Lys Thr Lys
                165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
            195                 200                 205

Thr Tyr Asp His Asp Val Tyr Arg Asp Glu Ala Leu Asn Asn Arg Phe
    210                 215                 220

Gln Ile Lys Gly Val Glu Leu Lys Ser Gly Tyr Lys Asp Trp Ile Leu
225                 230                 235                 240

Trp Ile Ser Phe Ala Ile Ser Cys Phe Leu Leu Cys Cys Gln Lys Gly
                245                 250                 255

Asn Ile Arg Cys Asn Ile Cys Ile
            260

<210> SEQ ID NO 592
<211> LENGTH: 275
<212> TYPE: PRT
<213> ORGANISM: Artificial Sequence
<220> FEATURE:
<223> OTHER INFORMATION: HA2 region of hemagglutinin protein sequence
      of A/PR/8/34(H1)

<400> SEQUENCE: 592

Cys Asn Thr Lys Cys Gln Thr Pro Leu Gly Ala Ile Asn Ser Ser Leu
 1               5                  10                  15

Pro Tyr Gln Asn Ile His Pro Val Thr Ile Gly Glu Cys Pro Lys Tyr
                 20                  25                  30

Val Arg Ser Ala Lys Leu Arg Met Val Thr Gly Leu Arg Asn Thr Pro
             35                  40                  45

Ser Ile Gln Ser Arg Gly Leu Phe Gly Ala Ile Ala Gly Phe Ile Glu
         50                  55                  60

Gly Gly Trp Thr Gly Met Ile Asp Gly Trp Tyr Gly Tyr His His Gln
 65                  70                  75                  80

Asn Glu Gln Gly Ser Gly Tyr Ala Ala Asp Gln Lys Ser Thr Gln Asn
                 85                  90                  95

Ala Ile Asn Gly Ile Thr Asn Lys Val Asn Thr Val Ile Glu Lys Met
                100                 105                 110

Asn Ile Gln Phe Thr Ala Val Gly Lys Glu Phe Asn Lys Leu Glu Lys
            115                 120                 125

Arg Met Glu Asn Leu Asn Lys Lys Val Asp Asp Gly Phe Leu Asp Ile
```

```
              130                 135                 140
Trp Thr Tyr Asn Ala Glu Leu Leu Val Leu Leu Glu Asn Glu Arg Thr
145                 150                 155                 160

Leu Asp Phe His Asp Ser Asn Val Lys Asn Leu Tyr Glu Lys Val Lys
                165                 170                 175

Ser Gln Leu Lys Asn Asn Ala Lys Glu Ile Gly Asn Gly Cys Phe Glu
                180                 185                 190

Phe Tyr His Lys Cys Asp Asn Glu Cys Met Glu Ser Val Arg Asn Gly
                195                 200                 205

Thr Tyr Asp Tyr Pro Lys Tyr Ser Glu Glu Ser Lys Leu Asn Arg Glu
                210                 215                 220

Lys Val Asp Gly Val Lys Leu Glu Ser Met Gly Ile Tyr Gln Ile Leu
225                 230                 235                 240

Ala Ile Tyr Ser Thr Val Ala Ser Ser Leu Val Leu Leu Val Ser Leu
                245                 250                 255

Gly Ala Ile Ser Phe Trp Met Cys Ser Asn Gly Ser Leu Gln Cys Arg
                260                 265                 270

Ile Cys Ile
        275

<210> SEQ ID NO 593
<211> LENGTH: 275
<212> TYPE: PRT
<213> ORGANISM: Artificial Sequence
<220> FEATURE:
<223> OTHER INFORMATION: HA2 region of hemagglutinin protein sequence of
      A/Cal/4/09(H1)

<400> SEQUENCE: 593

Cys Asn Thr Thr Cys Gln Thr Pro Lys Gly Ala Ile Asn Thr Ser Leu
1               5                   10                  15

Pro Phe Gln Asn Ile His Pro Ile Thr Ile Gly Lys Cys Pro Lys Tyr
                20                  25                  30

Val Lys Ser Thr Lys Leu Arg Leu Ala Thr Gly Leu Arg Asn Ile Pro
            35                  40                  45

Ser Ile Gln Ser Arg Gly Leu Phe Gly Ala Ile Ala Gly Phe Ile Glu
        50                  55                  60

Gly Gly Trp Thr Gly Met Val Asp Gly Trp Tyr Gly Tyr His His Gln
65                  70                  75                  80

Asn Glu Gln Gly Ser Gly Tyr Ala Ala Asp Leu Lys Ser Thr Gln Asn
                85                  90                  95

Ala Ile Asp Glu Ile Thr Asn Lys Val Asn Ser Val Ile Glu Lys Met
                100                 105                 110

Asn Thr Gln Phe Thr Ala Val Gly Lys Glu Phe Asn His Leu Glu Lys
            115                 120                 125

Arg Ile Glu Asn Leu Asn Lys Lys Val Asp Asp Gly Phe Leu Asp Ile
        130                 135                 140

Trp Thr Tyr Asn Ala Glu Leu Leu Val Leu Leu Glu Asn Glu Arg Thr
145                 150                 155                 160

Leu Asp Tyr His Asp Ser Asn Val Lys Asn Leu Tyr Glu Lys Val Arg
                165                 170                 175

Ser Gln Leu Lys Asn Asn Ala Lys Glu Ile Gly Asn Gly Cys Phe Glu
                180                 185                 190

Phe Tyr His Lys Cys Asp Asn Thr Cys Met Glu Ser Val Lys Asn Gly
                195                 200                 205
```

```
Thr Tyr Asp Tyr Pro Lys Tyr Ser Glu Glu Ala Lys Leu Asn Arg Glu
    210                 215                 220

Glu Ile Asp Gly Val Lys Leu Glu Ser Thr Arg Ile Tyr Gln Ile Leu
225                 230                 235                 240

Ala Ile Tyr Ser Thr Val Ala Ser Ser Leu Val Leu Val Val Ser Leu
                245                 250                 255

Gly Ala Ile Ser Phe Trp Met Cys Ser Asn Gly Ser Leu Gln Cys Arg
                260                 265                 270

Ile Cys Ile
        275
```

<210> SEQ ID NO 594
<211> LENGTH: 275
<212> TYPE: PRT
<213> ORGANISM: Artificial Sequence
<220> FEATURE:
<223> OTHER INFORMATION: HA1 region of hemagglutinin protein sequence of
      A/VietNam/1203/04(H5)

<400> SEQUENCE: 594

```
Cys Asn Thr Lys Cys Gln Thr Pro Met Gly Ala Ile Asn Ser Ser Met
1               5                   10                  15

Pro Phe His Asn Ile His Pro Leu Thr Ile Gly Glu Cys Pro Lys Tyr
                20                  25                  30

Val Lys Ser Asn Arg Leu Val Leu Ala Thr Gly Leu Arg Asn Ser Pro
            35                  40                  45

Gln Arg Glu Thr Arg Gly Leu Phe Gly Ala Ile Ala Gly Phe Ile Glu
    50                  55                  60

Gly Gly Trp Gln Gly Met Val Asp Gly Trp Tyr Gly Tyr His His Ser
65                  70                  75                  80

Asn Glu Gln Gly Ser Gly Tyr Ala Ala Asp Lys Glu Ser Thr Gln Lys
                85                  90                  95

Ala Ile Asp Gly Val Thr Asn Lys Val Asn Ser Ile Ile Asp Lys Met
            100                 105                 110

Asn Thr Gln Phe Glu Ala Val Gly Arg Glu Phe Asn Asn Leu Glu Arg
        115                 120                 125

Arg Ile Glu Asn Leu Asn Lys Lys Met Glu Asp Gly Phe Leu Asp Val
    130                 135                 140

Trp Thr Tyr Asn Ala Glu Leu Leu Val Leu Met Glu Asn Glu Arg Thr
145                 150                 155                 160

Leu Asp Phe His Asp Ser Asn Val Lys Asn Leu Tyr Asp Lys Val Arg
                165                 170                 175

Leu Gln Leu Arg Asp Asn Ala Lys Glu Leu Gly Asn Gly Cys Phe Glu
            180                 185                 190

Phe Tyr His Lys Cys Asp Asn Glu Cys Met Glu Ser Val Arg Asn Gly
        195                 200                 205

Thr Tyr Asp Tyr Pro Gln Tyr Ser Glu Glu Ala Arg Leu Lys Arg Glu
    210                 215                 220

Glu Ile Ser Gly Val Lys Leu Glu Ser Ile Gly Ile Tyr Gln Ile Leu
225                 230                 235                 240

Ser Ile Tyr Ser Thr Val Ala Ser Ser Leu Ala Leu Ala Ile Met Val
                245                 250                 255

Ala Gly Leu Ser Leu Trp Met Cys Ser Asn Gly Ser Leu Gln Cys Arg
            260                 265                 270

Ile Cys Ile
        275
```

<210> SEQ ID NO 595
<211> LENGTH: 275
<212> TYPE: PRT
<213> ORGANISM: Artificial Sequence
<220> FEATURE:
<223> OTHER INFORMATION: HA1 region of hemagglutinin protein sequence of
    A/mallard/Alberta/24/01(H7)

<400> SEQUENCE: 595

```
Cys Glu Gly Asp Cys Phe His Ser Gly Gly Thr Ile Val Ser Ser Leu
1               5                   10                  15

Pro Phe Gln Asn Ile Asn Pro Arg Thr Val Gly Lys Cys Pro Arg Tyr
            20                  25                  30

Val Lys Gln Thr Ser Leu Leu Leu Ala Thr Gly Met Arg Asn Val Pro
        35                  40                  45

Glu Asn Pro Lys Thr Arg Gly Leu Phe Gly Ala Ile Ala Gly Phe Ile
    50                  55                  60

Glu Asn Gly Trp Glu Gly Leu Ile Asp Gly Trp Tyr Gly Phe Arg His
65                  70                  75                  80

Gln Asn Ala Gln Gly Glu Gly Thr Ala Ala Asp Tyr Lys Ser Thr Gln
                85                  90                  95

Ser Ala Ile Asp Gln Ile Thr Gly Lys Leu Asn Arg Leu Ile Asp Lys
            100                 105                 110

Thr Asn Gln Gln Phe Glu Leu Ile Asp Asn Glu Phe Ser Glu Ile Glu
        115                 120                 125

Gln Gln Ile Gly Asn Val Ile Asn Trp Thr Arg Asp Ser Met Thr Glu
    130                 135                 140

Val Trp Ser Tyr Asn Ala Glu Leu Leu Val Ala Met Glu Asn Gln His
145                 150                 155                 160

Thr Ile Asp Leu Ala Asn Ser Glu Met Asn Lys Leu Tyr Glu Arg Val
                165                 170                 175

Arg Lys Gln Leu Arg Glu Asn Ala Glu Glu Asp Gly Thr Gly Cys Phe
            180                 185                 190

Glu Ile Phe His Lys Cys Asp Asp Gln Cys Met Glu Ser Ile Arg Asn
        195                 200                 205

Asn Thr Tyr Asp His Thr Gln Tyr Arg Thr Glu Ser Leu Gln Asn Arg
    210                 215                 220

Ile Gln Ile Asp Pro Val Lys Leu Ser Ser Gly Tyr Lys Asp Ile Ile
225                 230                 235                 240

Leu Trp Phe Ser Phe Gly Ala Ser Cys Phe Ile Leu Leu Ala Ile Ala
                245                 250                 255

Met Gly Leu Val Phe Ile Cys Ile Lys Asn Gly Asn Met Arg Cys Thr
            260                 265                 270

Ile Cys Ile
        275
```

<210> SEQ ID NO 596
<211> LENGTH: 565
<212> TYPE: PRT
<213> ORGANISM: Artificial Sequence
<220> FEATURE:
<223> OTHER INFORMATION: hemagglutinin (HA) sequence of A/PR/8/34
    (PR8)(H1)

<400> SEQUENCE: 596

```
Met Lys Ala Asn Leu Leu Val Leu Leu Ser Ala Leu Ala Ala Ala Asp
1               5                   10                  15
```

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
 50                  55                  60

Ala Pro Leu Gln Leu Gly Lys Cys Asn Ile Ala Gly Trp Leu Leu Gly
 65                  70                  75                  80

Asn Pro Glu Cys Asp Pro Leu Leu Pro Val Arg Ser Trp Ser Tyr Ile
            85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
 130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
            165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
            195                 200                 205

Gln Asn Glu Asn Ala Tyr Val Ser Val Val Thr Ser Asn Tyr Asn Arg
 210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
            245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
            275                 280                 285

His Glu Cys Asn Thr Lys Cys Gln Thr Pro Leu Gly Ala Ile Asn Ser
 290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
            325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
            405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
            485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 597
<211> LENGTH: 563
<212> TYPE: PRT
<213> ORGANISM: Artificial Sequence
<220> FEATURE:
<223> OTHER INFORMATION: hemagglutinin (HA) sequence of A/HK/1/68(HK68)
      (H3)

<400> SEQUENCE: 597

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
            245                 250                 255

Asp Val Leu Val Ile Asn Ser Asn Gly Asn Leu Ile Ala Pro Arg Gly
        260                 265                 270

Tyr Phe Lys Met Arg Thr Gly Lys Ser Ser Ile Met Arg Ser Asp Ala
    275                 280                 285

Pro Ile Asp Thr Cys Ile Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Lys Leu Ala Thr Gly Met Arg
            325                 330                 335

Asn Val Pro Glu Lys Gln Thr Arg Gly Leu Phe Gly Ala Ile Ala Gly
        340                 345                 350

Phe Ile Glu Asn Gly Trp Glu Gly Met Ile Asp Gly Trp Tyr Gly Phe
    355                 360                 365

Arg His Gln Asn Ser Glu Gly Thr Gly Gln Ala Ala Asp Leu Lys Ser
370                 375                 380

Thr Gln Ala Ala Ile Asp Gln Ile Asn Gly Lys Leu Asn Arg Val Ile
385                 390                 395                 400

Glu Lys Thr Asn Glu Lys Phe His Gln Ile Glu Lys Glu Phe Ser Glu
            405                 410                 415

Val Glu Gly Arg Ile Gln Asp Leu Glu Lys Tyr Val Glu Asp Thr Lys
        420                 425                 430

Ile Asp Leu Trp Ser Tyr Asn Ala Glu Leu Leu Val Ala Leu Glu Asn
    435                 440                 445

Gln His Thr Ile Asp Leu Thr Asp Ser Glu Met Asn Lys Leu Phe Glu
450                 455                 460

Lys Thr Arg Arg Gln Leu Arg Glu Asn Ala Glu Asp Met Gly Asn Gly
465                 470                 475                 480

Cys Phe Lys Ile Tyr His Lys Cys Asp Asn Ala Cys Ile Glu Ile Arg
            485                 490                 495

Asn Gly Thr Tyr Asp His Asp Val Tyr Arg Asp Glu Ala Leu Asn Asn
        500                 505                 510

Arg Phe Gln Ile Lys Gly Val Glu Leu Lys Ser Gly Tyr Lys Asp Trp
    515                 520                 525

Ile Leu Trp Ile Ser Phe Ala Ile Ser Cys Phe Leu Leu Cys Val Val
    530                 535                 540

Leu Leu Gly Phe Ile Trp Ala Cys Gln Arg Gly Asn Ile Arg Cys Asn
545                 550                 555                 560

Ile Cys Ile

<210> SEQ ID NO 598
<211> LENGTH: 6
<212> TYPE: PRT
<213> ORGANISM: Artificial Sequence
<220> FEATURE:
<223> OTHER INFORMATION: non-anturally occurring glycosylation site in
      A/Pr/8/34 H1

<400> SEQUENCE: 598

Leu Leu Pro Val Arg Ser
1               5

```
<210> SEQ ID NO 599
<211> LENGTH: 5
<212> TYPE: PRT
<213> ORGANISM: Artificial Sequence
<220> FEATURE:
<223> OTHER INFORMATION: non-anturally occurring glycosylation site in
      A/Pr/8/34 H1

<400> SEQUENCE: 599

Glu Lys Glu Gly Ser
1               5

<210> SEQ ID NO 600
<211> LENGTH: 6
<212> TYPE: PRT
<213> ORGANISM: Artificial Sequence
<220> FEATURE:
<223> OTHER INFORMATION: non-anturally occurring glycosylation site in
      A/Pr/8/34 H1

<400> SEQUENCE: 600

Pro Lys Leu Lys Asn Ser
1               5

<210> SEQ ID NO 601
<211> LENGTH: 5
<212> TYPE: PRT
<213> ORGANISM: Artificial Sequence
<220> FEATURE:
<223> OTHER INFORMATION: non-anturally occurring glycosylation site in
      A/Pr/8/34 H1

<400> SEQUENCE: 601

Val Asn Lys Lys Gly
1               5

<210> SEQ ID NO 602
<211> LENGTH: 6
<212> TYPE: PRT
<213> ORGANISM: Artificial Sequence
<220> FEATURE:
<223> OTHER INFORMATION: non-anturally occurring glycosylation site in
      A/Pr/8/34 H1

<400> SEQUENCE: 602

Ser His Glu Gly Lys Ser
1               5

<210> SEQ ID NO 603
<211> LENGTH: 12
<212> TYPE: PRT
<213> ORGANISM: Artificial Sequence
<220> FEATURE:
<223> OTHER INFORMATION: non-anturally occurring glycosylation site in
      A/Pr/8/34 H1

<400> SEQUENCE: 603

Asn Ser Lys Asp Gln Gln Asn Ile Tyr Gln Asn Glu
1               5                   10

<210> SEQ ID NO 604
<211> LENGTH: 113
<212> TYPE: PRT
<213> ORGANISM: Artificial Sequence
<220> FEATURE:
<223> OTHER INFORMATION: glycosylation site in HA of Human H1 subtype
      A/South Carolina/1/18
```

```
<400> SEQUENCE: 604

His Ala Asn Asn Ser Thr Asp Thr Val Asp Thr Val Leu Glu Lys Asn
 1               5                  10                  15

Val Thr Val Thr His Leu Gly Lys Cys Asn Ile Ala Gly Trp Leu Leu
            20                  25                  30

Gly Asn Pro Glu Cys Asp Leu Leu Leu Thr Ala Ser Ser Trp Ser Tyr
        35                  40                  45

Ile Val Glu Thr Ser Asn Ser Glu Asn Gly Thr Cys Tyr Thr Ser Ser
 50                  55                  60

Trp Pro Asn His Glu Thr Thr Lys Gly Val Thr Ala Ala Cys Ser Tyr
65                  70                  75                  80

Ala Gly Ala Ser Ser Phe Tyr Arg Asn Leu Leu Trp Leu Thr Lys Lys
            85                  90                  95

Gly Ser Ser Tyr Pro Lys Leu Ser Lys Ser Tyr Val Asn Asn Lys Gly
            100                 105                 110

Lys
```

INFLUENZA VIRUS VACCINES AND USES THEREOF

This application is a national stage entry of International patent application No. PCT/US2012/056122, filed Sep. 19, 2012, which claims priority benefit of U.S. Provisional Application No. 61/536,924, filed Sep. 20, 2011, U.S. Provisional Application No. 61/565,899, filed Dec. 1, 2011, U.S. Provisional Application No. 61/607,526, filed Mar. 6, 2012, U.S. Provisional Application No. 61/648,525, filed May 17, 2012, U.S. Provisional Application No. 61/670,108, filed Jul. 10, 2012, and U.S. Provisional Application No. 61/684,481, filed Aug. 17, 2012, which are herein incorporated by reference in their entireties.

This invention was made with government support under Grant Nos. AI070469, AI086061 and HHSN266200700010C awarded by the National Institutes of Health. The government has certain rights in the invention.

1. INTRODUCTION

Provided herein are flu hemagglutinin polypeptides, for example, chimeric influenza virus hemagglutinin polypeptides, and compositions comprising the same, vaccines comprising the same and methods of their use.

2. BACKGROUND

Influenza viruses are enveloped RNA viruses that belong to the family of Orthomyxoviridae (Palese and Shaw (2007) Orthomyxoviridae: The Viruses and Their Replication, 5th ed. Fields' Virology, edited by B. N. Fields, D. M. Knipe and P. M. Howley. Wolters Kluwer Health/Lippincott Williams & Wilkins, Philadelphia, USA, p 1647-1689). The natural host of influenza A viruses are mainly avians, but influenza A viruses (including those of avian origin) also can infect and cause illness in humans and other animal hosts (bats, canines, pigs, horses, sea mammals, and mustelids). For example, the H5N1 avian influenza A virus circulating in Asia has been found in pigs in China and Indonesia and has also expanded its host range to include cats, leopards, and tigers, which generally have not been considered susceptible to influenza A (CIDRAP—Avian Influenza: Agricultural and Wildlife Considerations). The occurrence of influenza virus infections in animals could potentially give rise to human pandemic influenza strains.

Influenza A and B viruses are major human pathogens, causing a respiratory disease that ranges in severity from sub-clinical infection to primary viral pneumonia which can result in death. The clinical effects of infection vary with the virulence of the influenza strain and the exposure, history, age, and immune status of the host. The cumulative morbidity and mortality caused by seasonal influenza is substantial due to the relatively high attack rate. In a normal season, influenza can cause between 3-5 million cases of severe illness and up to 500,000 deaths worldwide (World Health Organization (2003) Influenza: Overview; March 2003). In the United States, influenza viruses infect an estimated 10-15% of the population (Glezen and Couch R B (1978) Interpandemic influenza in the Houston area, 1974-76. N Engl J Med 298: 587-592; Fox et al. (1982) Influenza virus infections in Seattle families, 1975-1979. II. Pattern of infection in invaded households and relation of age and prior antibody to occurrence of infection and related illness. Am J Epidemiol 116: 228-242) and are associated with approximately 30,000 deaths each year (Thompson W W et al. (2003) Mortality Associated with Influenza and Respiratory Syncytial Virus in the United States. JAMA 289: 179-186; Belshe (2007) Translational research on vaccines: influenza as an example. Clin Pharmacol Ther 82: 745-749).

In addition to annual epidemics, influenza viruses are the cause of infrequent pandemics. For example, influenza A viruses can cause pandemics such as those that occurred in 1918, 1957, 1968, and 2009. Due to the lack of pre-formed immunity against the major viral antigen, hemagglutinin (HA), pandemic influenza can affect greater than 50% of the population in a single year and often causes more severe disease than epidemic influenza. A stark example is the pandemic of 1918, in which an estimated 50-100 million people were killed (Johnson and Mueller (2002) Updating the Accounts: Global Mortality of the 1918-1920 "Spanish" Influenza Pandemic Bulletin of the History of Medicine 76: 105-115). Since the emergence of the highly pathogenic avian H5N1 influenza virus in the late 1990s (Claas et al. (1998) Human influenza A H5N1 virus related to a highly pathogenic avian influenza virus. Lancet 351: 472-7), there have been concerns that it may be the next pandemic virus. Further, H7 and H9 strains are candidates for new pandemics since these strains infect humans on occasion.

An effective way to protect against influenza virus infection is through vaccination; however, current vaccination approaches rely on achieving a good match between circulating strains and the isolates included in the vaccine. Such a match is often difficult to attain due to a combination of factors. First, influenza viruses are constantly undergoing change: every 3-5 years the predominant strain of influenza A virus is replaced by a variant that has undergone sufficient antigenic drift to evade existing antibody responses. Isolates to be included in vaccine preparations must therefore be selected each year based on the intensive surveillance efforts of the World Health Organization (WHO) collaborating centers. Second, to allow sufficient time for vaccine manufacture and distribution, strains must be selected approximately six months prior to the initiation of the influenza season. Often, the predictions of the vaccine strain selection committee are inaccurate, resulting in a substantial drop in the efficacy of vaccination.

The possibility of a novel subtype of influenza A virus entering the human population also presents a significant challenge to current vaccination strategies. Since it is impossible to predict what subtype and strain of influenza virus will cause the next pandemic, current, strain-specific approaches cannot be used to prepare a pandemic influenza vaccine.

3. SUMMARY

Provided herein are flu hemagglutinin (HA) polypeptides that induce a cross-protective immune response against the conserved HA stem domain (sometimes referred to herein as the "stalk" domain) of influenza viruses. In one aspect, the invention concerns the design and construct of chimeric influenza virus hemagglutinin polypeptides having a stable HA stalk that displays a globular HA head heterologous to the stalk (i.e. chimeric influenza virus hemagglutinin polypeptides described herein). The HA immunogens designed for vaccination share the HA stalk region but are highly divergent in their globular heads. Such constructs are engineered into vaccine formulations such as live influenza viruses, killed influenza viruses, virus/viral-like particles ("VLPs"), subunit vaccines, split vaccines, etc., that elicit highly potent and broadly neutralizing antibodies against the conserved HA stalk. Such "universal" vaccines can be used to induce and/or boost cross-protective immune responses across influenza virus subtypes.

By way of background, neutralizing antibodies against influenza viruses target the HA glycoprotein and prevent either the binding or the fusion step involved in viral entry. Two basic subsets of neutralizing antibodies are elicited by exposure to influenza viruses: those directed to the strain-specific globular head (a domain that is non-conserved across the various strains and subtypes of influenza virus), and those directed to the highly conserved stem of the HA glycoprotein. The non-conserved HA globular head carries the immunodominant epitopes. Without being bound by theory, the strain-specific anti-globular head antibodies are thought to be more potent than anti-stem antibodies, thus explaining the largely strain-specific immunity conferred by infection with current vaccines.

The invention is based, in part, on the inventors' rational design strategies for influenza virus vaccines that elicit highly potent and broadly neutralizing antibodies against the HA stem. In this regard, the chimeric HA immunogen is designed to share a relatively well conserved stalk domain from previous exposures/vaccinations, but contain a heterologous HA globular head—preferably one to which the intended vaccinate is naïve. Exposure to this construct should mainly boost antibodies directed to the conserved HA stem. Repeated immunizations with the conserved HA stem and changing the globular head should induce robust cross-neutralizing antibodies against the common stem region of HA.

When designing the chimeric HA constructs, care should be taken to maintain the stability of the resulting protein. In this regard it is recommended that the cysteine residues identified as Ap and Aq in FIG. 1 be maintained since they contribute to the stability of the HA stalk as discussed in more detail in Section 5.1 infra. For the best stability, it is preferred to "swap" the HA globular domain as a whole (between the Ap and Aq cysteine residues as shown in FIG. 1) since the resulting conformation would be closest to the native structure. In other words the "linker" referred to in Section 5.1.2 can be the entire globular head domain of a heterologous HA.

Instead of "swapping out" the native globular head of the HA stalk, the globular head can be made heterologous to the conserved stalk by altering the loops that contribute to the HA globular head epitopes. This approach may not work as well for generating the desired immune response against the conserved stalk, unless the altered globular head is designed to be vastly different from the native globular HA head—especially when using an HA to which the population has been exposed. Nevertheless, such alterations can be accomplished, e.g., by altering a majority of the five loops that contribute to the HA globular head epitopes. In one useful approach, all five loops can be altered. Alternatively, or in addition, the epitopes in the five loops can be masked by introducing glycosylation sites into the globular head domain.

The constructs used for vaccination can advantageously be designed for the particular subjects/population to be vaccinated. There are three influenza subtypes to which human beings living today have been exposed: subtypes H1, H2, and H3. Influenza viruses of the H2 subtype disappeared from the population in 1968, whereas influenza viruses of the H1 and H3 subtypes persist in the population to the present day. As a result, adults living today that were born before 1968 have likely been exposed to each of the H1, H2, and H3 subtypes. In contrast, adults living today that were born after 1968 have likely only been exposed to the H1 and H3 subtypes.

Thus, in preferred embodiments for vaccination of adults, the chimeric influenza hemagglutinin polypeptides do not possess a globular head domain from the HA of an influenza virus of subtype H1, H2, or H3, but do possess a stem domain from the HA of one of these three subtypes. The heterologous globular head can be selected from the HA of any non-H1, non-H2, or non-H3 subtype. Also, separate chimeric constructs made using H1/H2 stems on the one hand, and H3 stems on the other may beneficially be used in a vaccination program—the H1 and H2 subtypes are Group 1 HA subtypes that share a conserved stalk domain; whereas H3 is a Group 2 subtype that has a stalk domain that is structurally different from the Group 1 stalk. The use of H1 and H3 constructs would ensure generating/boosting an immune response against each stem domain. Immunization of adult subjects with such chimeric influenza hemagglutinin polypeptides will boost the memory immune response of the subject, resulting in the large scale production of cross-reactive, broadly neutralizing anti-stem domain antibodies that provide long-lasting immunity to influenza virus in the subject.

Infants who have not been exposed, of course, are naïve to all influenza virus subtypes. As a result, a wide range of HA stem/globular head combinations can be constructed for use in vaccines for infants. In a preferred embodiment, naïve infants can be vaccinated with constructs made using the HA stalk of a Group 1 (H1 or H2) or Group 2 (H3) strain, and a globular head from a heterologous strain; i.e., non-H1, non-H2, and/or non-H3 strains. Three different chimeric HA constructs for each HA stalk can be used advantageously in three sequential vaccinations to induce a cross-protective response.

The chimeric influenza hemagglutinin polypeptides used for vaccination can also advantageously be designed to effectively elicit highly potent and broadly neutralizing antibodies against the HA stem domain in a subject by the addition or modification of glycosylation sites in these polypeptides. It is believed that glycosylation of the HA globular head and stem domain can mask antigenic sites, thereby allowing an influenza virus to evade an immune response within a subject. Within the context of an influenza virus HA polypeptide, however, glycosylation within the stem domain of the chimeric influenza hemagglutinin polypeptide can hinder or prevent desired immune responses against antigenic regions within this domain that are shielded by glycosylation. Therefore, in certain preferred embodiments, the chimeric influenza hemagglutinin polypeptide comprises one or more modified glycosylation sites that disrupts the binding of glycan to the stem domain, thereby making the stem domain more accessible for eliciting an immune response. To further increase the immunogenicity of the stem domain, the constructs can further comprise non-naturally occurring glycosylation sites in the globular head domain that, when glycosylated, shield immunodominant antigenic regions found in the globular head domain from eliciting an immune response. One example of a non-naturally occurring glycosylation sites is the addition of a glycosylation site to the globular head domain of an influenza virus HA of one subtype, wherein the glycosylation site is naturally found in the globular head domain of an influenza virus HA of another subtype. Another example of a non-naturally occurring glycosylation site is the addition of a glycosylation site to the globular head domain of an influenza virus HA from one strain, wherein the glycosylation site is naturally found in the globular head of an HA from another strain of influenza virus. Yet another example of a non-naturally occurring glycosylation site is the addition of a glycosylation site to the globular head of an HA from one strain, wherein the glycosylation site is not naturally found in the globular head of an HA from another subtype or strain of influenza virus. While not being bound by any particular theory of operation, it is believed that the additional glycosylation within the globular head domain will increase the immune response to the conserved stem domain, while reducing the immune response to the globular head domain.

It should be understood that use of the chimeric influenza hemagglutinin polypeptides described herein is advantageous because (i) said polypeptides are highly stable (by virtue of possessing an intact globular head domain) and (ii) the immune systems of the subjects to which said polypeptides are administered have not previously been exposed to the globular head domains of the chimeric influenza hemagglutinin, but have been exposed to the conserved epitopes of the stem domains of the chimeric influenza hemagglutinin.

In another aspect, provided herein is a flu HA polypeptide (e.g., influenza virus hemagglutinin stem domain polypeptides and non-chimeric influenza virus hemagglutinin polypeptides) that comprises a stem domain comprising one or more modified glycosylation sites that disrupt the binding of glycan to the stem domain.

In another aspect, provided herein is a flu HA polypeptide (e.g., influenza virus hemagglutinin stem domain polypeptides and non-chimeric influenza virus hemagglutinin polypeptides) that comprises a globular head domain comprising one or more non-naturally occurring glycosylation sites.

In yet another aspect, provided herein, is a flu HA polypeptide (e.g., influenza virus hemagglutinin stem domain polypeptides and non-chimeric influenza virus hemagglutinin polypeptides) that comprises (1) a stem domain comprising one or more modified glycosylation sites that disrupt the binding of glycan to the stem domain; and (2) a globular head domain comprising one or more non-naturally occurring glycosylation sites.

In a specific embodiment, provided herein is a chimeric influenza virus hemagglutinin (HA) polypeptide comprising an HA stem domain and an HA globular head domain, wherein: (1) the HA globular head domain is heterologous to the HA stem domain; and (2) the HA stem domain comprises one or more modified glycosylation site(s), wherein the modified glycosylation site(s) comprises a modification to a glycosylation site that disrupts/interferes with binding of a glycan to the glycosylation site in the stem domain. In specific embodiments, the modified glycosylation site comprises a modification of a naturally occurring glycosylation site having an amino acid sequence Asn-Xaa-Ser/Thr/Cys, and wherein Xaa is any amino acid. In certain embodiments, the HA globular head domain further comprises one or more non-naturally occurring glycosylation sites having an amino acid sequence Asn-Xaa-Ser/Thr/Cys, wherein Xaa is any amino acid.

In another embodiment, provided herein is a non-chimeric influenza virus hemagglutinin (HA) polypeptide comprising an HA stem domain and an HA globular head domain, wherein: (1) the HA globular head domain is homologous to the HA stem domain, and (2) the HA stem domain comprises one or more modified glycosylation site(s), wherein the modified glycosylation site(s) comprises a modification to a glycosylation site that disrupts/interferes with binding of a glycan to the glycosylation site in the stem domain. In specific embodiments, the modified glycosylation site comprises a modification of a naturally occurring glycosylation site having an amino acid sequence Asn-Xaa-Ser/Thr/Cys, wherein the modification disrupts the ability of a glycan to attach to the modified glycosylation site, wherein Xaa is any amino acid.

In another embodiment, provided herein is a an influenza virus hemagglutinin (HA) stem domain polypeptide comprising: an influenza hemagglutinin HA1 domain that comprises an HA1 N-terminal stem segment covalently linked to a linker of 1 to 50 heterologous residues that is in turn covalently linked to an HA1 C-terminal short stem segment; said HA1 domain in tertiary or quaternary association with an influenza hemagglutinin HA2 domain, wherein the influenza virus HA stem domain polypeptide domain further comprises one or more modified glycosylation site(s), wherein the modified glycosylation site(s) comprises a modification to a glycosylation site that disrupts/interferes with binding of a glycan to the glycosylation site in the stem domain. In specific embodiments, the modified glycosylation site comprises a modification of a naturally occurring glycosylation site having an amino acid sequence Asn-Xaa-Ser/Thr/Cys, where the modification disrupts the ability of a glycan to attach to the modified glycosylation site, and wherein Xaa is any amino acid.

In another embodiment, provided herein is an influenza virus hemagglutinin (HA) stem domain polypeptide comprising: an influenza hemagglutinin HA1 domain that comprises an HA1 N-terminal long stem segment covalently linked to a linker of 1 to 50 heterologous residues that is in turn covalently linked to an HA1 C-terminal long stem segment; said HA1 domain in tertiary or quaternary association with an influenza hemagglutinin HA2 domain, wherein the influenza virus HA stem domain polypeptide domain further comprises one or more modified glycosylation site(s), wherein the modified glycosylation site(s) comprises a modification to a glycosylation site that disrupts/interferes with binding of a glycan to the glycosylation site in the stem domain. In specific embodiments, the modified glycosylation site comprises a modification of a naturally occurring glycosylation site having an amino acid sequence Asn-Xaa-Ser/Thr/Cys, where the modification disrupts the ability of a glycan to attach to the modified glycosylation site, and wherein Xaa is any amino acid.

In another embodiment, provided herein is an influenza virus hemagglutinin (HA) stem domain polypeptide comprising: an influenza hemagglutinin HA1 domain that comprises an HA1 N-terminal stem segment covalently linked to a linker of 1 to 50 heterologous residues that is in turn covalently linked to an HA1 C-terminal stem segment; said HA1 domain in tertiary or quaternary association with an influenza hemagglutinin HA2 domain, wherein the influenza virus HA stem domain polypeptide domain further comprises one or more modified glycosylation site(s), wherein the modified glycosylation site(s) comprises a modification to a glycosylation site that disrupts/interferes with binding of a glycan to the glycosylation site in the stem domain. In specific embodiments, the modified glycosylation site comprises a modification of a naturally occurring glycosylation site having an amino acid sequence Asn-Xaa-Ser/Thr/Cys, where the modification disrupts the ability of a glycan to attach to the modified glycosylation site, and wherein Xaa is any amino acid.

In another embodiment, provided herein is an influenza virus hemagglutinin (HA) stem domain polypeptide comprising: an influenza hemagglutinin HA1 domain that comprises, linked in the following order: an HA1 N-terminal stem segment, a first linker of 1 to 50 heterologous residues, an HA1 intermediate stem segment, a second linker of 1 to 50 heterologous residues and an HA1 C-terminal stem segment; said HA1 domain in tertiary or quaternary association with an influenza hemagglutinin HA2 domain, wherein the influenza virus hemagglutinin (HA) stem domain polypeptide domain further comprises one or more modified glycosylation site(s), wherein the modified glycosylation site(s) comprises a modification to a glycosylation site that disrupts/interferes with binding of a glycan to the glycosylation site in the stem domain. In specific embodiments, the modified glycosylation site comprises a modification of a naturally occurring glycosylation site having an amino acid sequence Asn-Xaa-Ser/Thr/Cys, where the modification disrupts the ability of a glycan to attach to the modified glycosylation site, and wherein Xaa is any amino acid.

The invention is illustrated by the working Examples (e.g., Section 6, Examples) which demonstrate, inter alia, the construction of a chimeric influenza HA polypeptide comprising an HA stem and displaying a heterologous HA head, and the production of a stable chimeric HA protein from this polypeptide that cross-reacts with antibodies to both the stem domain and the head domain. The working Examples also illustrate the use of such constructs in the generation of a protective immune response in subjects against multiple different strains and subtypes of influenza virus, i.e., the Examples demonstrate that the chimeric influenza HA polypeptides described herein can be used as a universal influenza vaccine. In addition, the working Examples (e.g., Section 6.11, Example 11) demonstrate the construction of flu HA polypeptides comprising an HA stem domain with one or more modified glycosylation sites and/or an HA globular head domain with one or more non-naturally occurring glycosylation sites, wherein the modified glycosylations sites are modifications to one or more naturally occurring glycosylation sites that disrupt the ability of a glycan to attach to the glycosylation sites. The working Examples (see Section 6.11, Example 11) also demonstrate the ability of these influenza HA polypeptides to elicit an increased immune response to the conserved stalk domain of an influenza virus.

3.1 Terminology

The terms "about" or "approximate," when used in reference to an amino acid position refer to the particular amino acid position in a sequence or any amino acid that is within five, four, three, two, or one residues of that amino acid position, either in an N-terminal direction or a C-terminal direction.

As used herein, the term "about" or "approximately" when used in conjunction with a number refers to any number within 1, 5 or 10% of the referenced number. In certain embodiments, the term "about" encompasses the exact number recited.

The term "amino acid sequence identity" refers to the degree of identity or similarity between a pair of aligned amino acid sequences, usually expressed as a percentage. Percent identity is the percentage of amino acid residues in a candidate sequence that are identical (i.e., the amino acid residues at a given position in the alignment are the same residue) or similar (i.e., the amino acid substitution at a given position in the alignment is a conservative substitution, as discussed below), to the corresponding amino acid residue in the peptide after aligning the sequences and introducing gaps, if necessary, to achieve the maximum percent sequence homology. Sequence homology, including percentages of sequence identity and similarity, may be determined using sequence alignment techniques well-known in the art, preferably computer algorithms designed for this purpose, using the default parameters of said computer algorithms or the software packages containing them. Non-limiting examples of computer algorithms and software packages incorporating such algorithms include the following. The BLAST family of programs exemplify a particular, non-limiting example of a mathematical algorithm utilized for the comparison of two sequences (e.g., Karlin & Altschul, 1990, *Proc. Natl. Acad. Sci. USA* 87:2264-2268 (modified as in Karlin & Altschul, 1993, *Proc. Natl. Acad. Sci. USA* 90:5873-5877), Altschul et al., 1990, *J. Mol. Biol.* 215:403-410, (describing NBLAST and XBLAST), Altschul et al., 1997, *Nucleic Acids Res.* 25:3389-3402 (describing Gapped BLAST, and PSI-Blast). Another particular example is the algorithm of Myers and Miller (1988 CABIOS 4:11-17) which is incorporated into the ALIGN program (version 2.0) and is available as part of the GCG sequence alignment software package. Also particular is the FASTA program (Pearson W. R. and Lipman D. J., *Proc. Nat. Acad. Sci. USA,* 85:2444-2448, 1988), available as part of the Wisconsin Sequence Analysis Package. Additional examples include BESTFIT, which uses the "local homology" algorithm of Smith and Waterman (Advances in Applied Mathematics, 2:482-489, 1981) to find best single region of similarity between two sequences, and which is preferable where the two sequences being compared are dissimilar in length; and GAP, which aligns two sequences by finding a "maximum similarity" according to the algorithm of Neddleman and Wunsch (*J. Mol. Biol.* 48:443-354, 1970), and is preferable where the two sequences are approximately the same length and an alignment is expected over the entire length.

"Conservative substitution" refers to replacement of an amino acid of one class is with another amino acid of the same class. In particular embodiments, a conservative substitution does not alter the structure or function, or both, of a polypeptide. Classes of amino acids for the purposes of conservative substitution include hydrophobic (Met, Ala, Val, Leu, Ile), neutral hydrophilic (Cys, Ser, Thr), acidic (Asp, Glu), basic (Asn, Gln, H is, Lys, Arg), conformation disrupters (Gly, Pro) and aromatic (Trp, Tyr, Phe).

As used herein, the term "fragment" in the context of a nucleic acid sequence refers to a nucleotide sequence comprising a portion of consecutive nucleotides from a parent sequence. In a specific embodiment, the term refers to a nucleotide sequence of 5 to 15, 5 to 25, 10 to 30, 15 to 30, 10 to 60, 25 to 100, 150 to 300 or more consecutive nucleotides from a parent sequence. In another embodiment, the term refers to a nucleotide sequence of at least 5, 10, 15, 20, 25, 30, 35, 40, 45, 50, 55, 60, 65, 70, 75, 80, 85, 90, 95, 100, 110, 125, 150, 175, 200, 250, 275, 300, 325, 350, 375, 400, 425, 450 or 475 consecutive nucleotides of a parent sequence.

As used herein, the term "fragment" in the context of an amino acid sequence refers to an amino acid sequence comprising a portion of consecutive amino acid residues from a parent sequence. In a specific embodiment, the term refers to an amino acid sequence of 2 to 30, 5 to 30, 10 to 60, 25 to 100, 150 to 300 or more consecutive amino acid residues from a parent sequence. In another embodiment, the term refers to an amino acid sequence of at least 5, 10, 15, 20, 25, 30, 35, 40, 45, 50, 55, 60, 65, 70, 75, 80, 85, 90, 95, 100, 110, 125, 150, 175, or 200 consecutive amino acid residues of a parent sequence.

As used herein, the terms "disease" and "disorder" are used interchangeably to refer to a condition in a subject. In some embodiments, the condition is a viral infection. In specific embodiments, a term "disease" refers to the pathological state resulting from the presence of the virus in a cell or a subject, or by the invasion of a cell or subject by the virus. In certain embodiments, the condition is a disease in a subject, the severity of which is decreased by inducing an immune response in the subject through the administration of an immunogenic composition.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve one, two, three, four, or more of the following effects: (i) reduce or ameliorate the severity of an influenza virus infection, disease or symptom associated therewith; (ii) reduce the duration of an influenza virus infection, disease or symptom associated therewith; (iii) prevent the progression of an influenza virus infection, disease or symptom associated therewith; (iv) cause regression of an influenza virus infection, disease or symptom associated therewith; (v) prevent the development or onset of an influenza virus infection, disease or symptom associated therewith; (vi) prevent the recurrence of an influenza virus infection, disease or symptom associated therewith; (vii) reduce or prevent the spread of an influenza virus from one cell to another cell, one tissue to another tissue, or one organ to another organ; (ix) prevent or reduce the spread of an influenza virus from one subject to another subject; (x) reduce organ failure associated with an influenza virus infection; (xi) reduce hospitalization of a subject; (xii) reduce hospitalization length; (xiii) increase the survival of a subject with an influenza virus infection or disease associated therewith; (xiv) eliminate an influenza virus infection or disease associated therewith; (xv) inhibit or reduce influenza virus replication; (xvi) inhibit or reduce the entry of an influenza virus into a host cell(s); (xviii) inhibit or reduce replication of the influenza virus genome; (xix) inhibit or reduce synthesis of influenza virus proteins; (xx) inhibit or reduce assembly of influenza virus particles; (xxi) inhibit or reduce release of influenza virus particles from a host cell(s); (xxii) reduce influenza virus titer; and/or (xxiii) enhance or improve the prophylactic or therapeutic effect(s) of another therapy.

In certain embodiments, the effective amount does not result in complete protection from an influenza virus disease, but results in a lower titer or reduced number of influenza viruses compared to an untreated subject. In certain embodiments, the effective amount results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, the effective amount results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titer, number or total burden of influenza virus include, but are not limited to, less severe symptoms of the infection, fewer symptoms of the infection and a reduction in the length of the disease associated with the infection.

As used herein, the term "flu hemagglutinin polypeptide" and "flu HA polypeptide" refer to (i) the chimeric influenza hemagglutinin (HA) polypeptides disclosed herein; and (ii) any of the polypeptides disclosed herein that comprise an influenza virus hemagglutinin head domain and/or an influenza virus hemagglutinin stem domain or fragment thereof, wherein either the influenza virus hemagglutinin stem domain comprises one or more modified glycosylation sites; the influenza virus hemagglutinin head domain comprises one or more non-naturally occurring glycosylation sites; or both. Flu HA polypeptides include, but are not limited to, chimeric influenza virus hemagglutinin polypeptides, non-chimeric influenza virus hemagglutinin polypeptides, influenza virus hemagglutinin head domain polypeptides and influenza virus hemagglutinin stem domain polypeptides. In a specific embodiment, the flu HA polypeptide is a chimeric influenza virus hemagglutinin polypeptide that comprises either one or more modified glycosylation sites in the influenza virus hemagglutinin stem domain that disrupts glycan binding to the stem domain; an influenza virus hemagglutinin globular head domain comprising one or more non-naturally occurring glycosylation sites; or both. In another embodiment, the flu HA polypeptide is an influenza hemagglutinin polypeptide (of or from any strain, subtype, or type of influenza virus) that comprises one or more modified glycosylation sites in the influenza virus hemagglutinin stem domain that disrupts glycan binding to the stem domain, an influenza virus hemagglutinin globular head domain comprising one or more non-naturally occurring glycosylation sites; or both. See, e.g., Example 11, infra, for such a flu polypeptide.

"Hemagglutinin" and "HA" refer to any hemagglutinin known to those of skill in the art. In certain embodiments, the hemagglutinin is influenza hemagglutinin, such as an influenza A hemagglutinin, an influenza B hemagglutinin, or an influenza C hemagglutinin. A typical hemagglutinin comprises domains known to those of skill in the art including a signal peptide (optional herein), a stem domain, a globular head domain, a luminal domain (optional herein), a transmembrane domain (optional herein) and a cytoplasmic domain (optional herein). In certain embodiments, a hemagglutinin consists of a single polypeptide chain, such as HA0. In certain embodiments, a hemagglutinin consists of more than one polypeptide chain in quaternary association, e.g. HA1 and HA2. Those of skill in the art will recognize that an immature HA0 might be cleaved to release a signal peptide (approximately 20 amino acids) yielding a mature hemagglutinin HA0. A hemagglutinin HA0 might be cleaved at another site to yield HA1 polypeptide (approximately 320 amino acids, including the globular head domain and a portion of the stem domain) and HA2 polypeptide (approximately 220 amino acids, including the remainder of the stem domain, a luminal domain, a transmembrane domain and a cytoplasmic domain). In certain embodiments, a hemagglutinin comprises a signal peptide, a transmembrane domain and a cytoplasmic domain. In certain embodiments, a hemagglutinin lacks a signal peptide, i.e. the hemagglutinin is a mature hemagglutinin. In certain embodiments, a hemagglutinin lacks a transmembrane domain or cytoplasmic domain, or both. As used herein, the terms "hemagglutinin" and "HA" encompass hemagglutinin polypeptides that are modified by post-translational processing such as signal peptide cleavage, disulfide bond formation, glycosylation (e.g., N-linked glycosylation), protease cleavage and lipid modification (e.g. S-palmitoylation).

As used herein, the terms "chimeric influenza virus hemagglutinin polypeptide," "chimeric influenza virus HA polypeptide," "chimeric hemagglutinin polypeptide" and "chimeric influenza hemagglutinin polypeptide" refer to an influenza hemagglutinin that comprises an influenza virus hemagglutinin stem domain and an influenza virus hemagglutinin head domain, wherein the influenza virus hemagglutinin head domain is heterologous to the influenza virus hemagglutinin stem domain. In certain embodiments, the influenza virus hemagglutinin head domain of a chimeric influenza virus hemagglutinin polypeptide is from a different strain or subtype of influenza virus than the influenza virus hemagglutinin stem domain. In certain embodiments, in the context of the chimeric influenza virus hemagglutinin polypeptides described herein, a heterologous influenza virus hemagglutinin head domain refers to an influenza virus hemagglutinin head that is at least 5%, at least 10%, at least 15%, at least 20%, at least 25%, at least 5-10%, at least 10-15%, at least 10-20%, at least 15-20%, or at least 20-25% different from the homologous head (i.e., the head domain that would normally be associated with the stem domain of the chimeric influenza virus hemagglutinin polypeptide). Those of skill in the art will recognize that such a difference can be measured using approaches known in the art and described herein, e.g., comparing sequence identity or sequence homology of the head domains. In certain embodiments, in the context of the chimeric influenza virus hemagglutinin polypeptides described herein, a heterologous influenza virus hemagglutinin head domain refers to an influenza virus hemagglutinin head that, in a hemagglutination inhibition assay, results in antisera with at least 2, at least 3, at least 4, at least 5, or at least 6 times less hemagglutination inhibition titers relative to the hemagglutination inhibition titers of the antisera raised against the homologous heads (i.e., the head domain that would normally be associated with the stem domain of the chimeric influenza virus hemagglutinin polypeptide). Those of skill in the art will recognize that such a difference can be measured using approaches known in the art and described herein (see, e.g., Section 5.14, infra).

"HA1 N-terminal stem segment" refers to a polypeptide segment that corresponds to the amino-terminal portion of the stem domain of an influenza hemagglutinin HA1 polypeptide. In certain embodiments, an HA1 N-terminal stem segment consists of amino acid residues corresponding approximately to amino acids $HA1_{N-term}$ through $A_p$ of an HA1 domain. $HA1_{N-term}$ is the N-terminal amino acid of HA1 as recognized by those of skill in the art. $A_p$ is the cysteine residue in the HA1 N-terminal stem segment that forms or is capable of forming a disulfide bond with a cysteine residue in an HA1 C-terminal stem segment. Residue $A_p$ is identified in influenza A hemagglutinin polypeptides in FIG. 1. Exemplary HA1 N-terminal stem segments are described herein. In certain embodiments, an HA1 N-terminal stem segment consists of amino acid residues corresponding approximately to amino acids 1-52 of HA1 from an H3 hemagglutinin. Note that, in this numbering system, 1 refers to the N-terminal amino acid of the mature HA0 protein, from which the signal peptide has been removed. Those of skill in the art will readily be able recognize the amino acid residues that correspond to the HA1 N-terminal stem segment of other influenza HA polypeptides, e.g., the amino acid residues that correspond to the HA1 N-terminal stem segment of HA1 from an H1 hemagglutinin (see, e.g., FIG. 1).

"HA1 C-terminal stem segment" refers to a polypeptide segment that corresponds to the carboxy-terminal portion of the stem domain of an influenza hemagglutinin HA1 polypeptide. In certain embodiments, an HA1 C-terminal stem segment consists of amino acid residues corresponding approximately to amino acids $A_q$ through $HA1_{C-term}$ of an HA1 domain. $HA1_{C-term}$ is the C-terminal amino acid of the HA1 domain as recognized by those of skill in the art. Residue $A_q$ is identified in influenza A hemagglutinin polypeptides in FIG. 1. Exemplary HA1 C-terminal stem segments are described herein. In certain embodiments, an HA1 C-terminal stem segment consists of amino acid residues corresponding approximately to amino acids 277-346 of HA1 from an H3 hemagglutinin. Note that, in this numbering system, 1 refers to the N-terminal amino acid of the mature HA0 protein, from which the signal peptide has been removed. Those of skill in the art will readily be able recognize the amino acid residues that correspond to the HA1 C-terminal stem segment of other influenza HA polypeptides, e.g., the amino acid residues that correspond to the HA1 C-terminal stem segment of HA1 from an H1 hemagglutinin (see, e.g., FIG. 1).

"HA1 C-terminal short stem segment" refers to a polypeptide segment that corresponds to the carboxyl-terminal portion of the stem domain of an influenza hemagglutinin HA1 polypeptide. In certain embodiments, an HA1 C-terminal short stem segment consists of amino acid residues corresponding approximately to amino acids $B_q$ through $HA1_{C-term}$ of an HA1 domain. Residue $B_q$ is identified in influenza A hemagglutinin polypeptides in FIG. 1. Exemplary HA1 C-terminal short stem segments are described herein. In certain embodiments, an HA1 C-terminal short stem segment consists of amino acid residues corresponding approximately to amino acids 305-346 of HA1 from an H3 hemagglutinin. Note that, in this numbering system, 1 refers to the N-terminal amino acid of the mature HA0 protein, from which the signal peptide has been removed.

"HA1 N-terminal long stem segment" refers to a polypeptide segment that corresponds to the amino-terminal portion of the stem domain of an influenza hemagglutinin HA1 polypeptide. In certain embodiments, an HA1 N-terminal long stem segment consists of amino acid residues corresponding approximately to amino acids $HA1_{N-term}$ through $C_p$ of an HA1 domain. $C_p$ is a cysteine residue in the HA1 N-terminal long stem segment that is or is capable of being linked to an alanine residue in an HA1 C-terminal long stem segment. Residue $C_p$ is identified in influenza A hemagglutinin polypeptides in FIG. 1. Exemplary HA1 N-terminal long stem segments are described herein. In certain embodiments, an HA1 N-terminal long stem segment consists of amino acid residues corresponding approximately to amino acids 1-97 of HA1 from an H3 hemagglutinin. Note that, in this numbering system, 1 refers to the N-terminal amino acid of the mature HA0 protein, from which the signal peptide has been removed.

"HA1 C-terminal long stem segment" refers to a polypeptide segment that corresponds to the carboxyl-terminal portion of the stem domain of an influenza hemagglutinin HA1 polypeptide. In certain embodiments, an HA1 C-terminal long stem segment consists of amino acid residues corresponding approximately to amino acids $C_q$ through $HA1_{C-term}$ of an HA1 domain. $C_q$ is an alanine residue in the HA1 C-terminal long stem segment that is or is capable of being linked to a cystine residue in an HA1 N-terminal long stem segment. Residue $C_q$ is identified in influenza A hemagglutinin polypeptides in FIG. 1. Exemplary HA1 C-terminal long stem segments are described herein. In certain embodiments, an HA1 C-terminal long stem segment consists of amino acid residues corresponding approximately to amino acids 252-346 of HA1 from an H3 hemagglutinin. Note that, in this numbering system, 1 refers to the N-terminal amino acid of the mature HA0 protein, from which the signal peptide has been removed.

"HA2" refers to a polypeptide domain that corresponds to the HA2 domain of an influenza hemagglutinin polypeptide known to those of skill in the art. In certain embodiments, an HA2 consists of a stem domain, a luminal domain, a transmembrane domain and a cytoplasmic domain (see, e.g., Scheiffle et al., 2007, *EMBO J.* 16(18):5501-5508, the contents of which are incorporated by reference in their entirety). In certain embodiments, an HA2 consists of a stem domain, a luminal domain and a transmembrane domain. In certain embodiments, an HA2 consists of a stem domain and a luminal domain; in such embodiments, the HA2 might be soluble. In certain embodiments, an HA2 consists of a stem domain; in such embodiments, the HA2 might be soluble.

As used herein, the term "heterologous" in the context of a polypeptide, nucleic acid or virus refers to a polypeptide, nucleic acid or virus, respectively, that is not normally found in nature or not normally associated in nature with a polypeptide, nucleic acid or virus of interest. For example, a "heterologous polypeptide" may refer to a polypeptide derived from a different virus, e.g., a different influenza strain or subtype, or an unrelated virus or different species. In specific embodiments, when used in the context of a globular head domain of a chimeric influenza virus hemagglutinin described herein, the term heterologous refers to an influenza HA globular head domain that is associated with an influenza HA stem domain that it would not normally be found associated with (e.g., the head and stem domains of the HA would not be found together in nature). As described above, in certain embodiments, a heterologous influenza HA globular head domain of a chimeric influenza virus hemagglutinin described herein is at least 5%, at least 10%, at least 15%, at least 20%, at least 25%, at least 5-10%, at least 10-15%, at least 10-20%, at least 15-20%, or at least 20-25% different from the homologous head of the hemagglutinin (i.e., the head domain that would normally be associated with the stem domain of the chimeric influenza virus hemagglutinin polypeptide).

As used herein, the term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject. For example, a first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

As used herein, the term "influenza virus disease" refers to the pathological state resulting from the presence of an influenza (e.g., influenza A or B virus) virus in a cell or subject or the invasion of a cell or subject by an influenza virus. In specific embodiments, the term refers to a respiratory illness caused by an influenza virus.

As used herein, the phrases "IFN deficient system" or "IFN-deficient substrate" refer to systems, e.g., cells, cell lines and animals, such as pigs, mice, chickens, turkeys, rabbits, rats, etc., which do not produce IFN or produce low levels of IFN (i.e., a reduction in IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to IFN, and/or are deficient in the activity of one or more antiviral genes induced by IFN.

As used herein, the numeric term "log" refers to $\log_{10}$.

As used herein, the term "modified glycosylation site" refers to a naturally-occurring glycosylation site in an influenza virus hemagglutinin polypeptide that has been modified by the addition, substitution or deletion of one or more amino acids. In certain embodiments, the modified glycosylation site is unable to bind glycan. In certain embodiments, the modified glycosylation site disrupts or interferes with the glycosylation at the modified glycosylation site. In certain embodiments, the modified glycosylation site does not interfere with the proper folding of a flu HA polypeptide (e.g., a chimeric influenza virus HA polypeptide) described herein. In certain embodiments, the modified glycosylation site comprises a modification of a naturally occurring glycosylation site having the amino acid motif Asn-Xaa-Ser/Thr/Cys, wherein Xaa is any amino acid. In particular embodiments, the modified glycosylation site comprises one or more amino acid substitutions in a naturally occurring glycosylation site having the amino acid motif Asn-Xaa-Ser/Thr/Cys, wherein Xaa is any amino acid.

As used herein, the phrase "multiplicity of infection" or "MOI" is the average number of infectious virus particles per infected cell. The MOI is determined by dividing the number of infectious virus particles added (ml added×PFU/ml) by the number of cells added (ml added×cells/ml).

As used herein, the term "non-chimeric influenza virus hemagglutinin polypeptide" refers to an influenza virus hemagglutinin polypeptide comprising an HA stem domain and an HA head domain from the same subtype or strain, and wherein the polypeptide comprises one or more non-naturally occurring glycosylation sites as discussed in Section 5.4.2, infra, and/or one or more modified glycosylation sites as discussed in Section 5.4.1, infra. In certain embodiments, the non-chimeric influenza virus hemagglutinin polypeptide comprises an HA stem domain and HA globular head domain from the same influenza virus subtype. In specific embodiments, the influenza virus subtype is an H1, H2, H3, H4, H5, H6, H7, H8, H9, H10, H11, H12, H13, H14, H15, H16, or H17 subtype. In certain embodiments, the non-chimeric influenza virus hemagglutinin polypeptide comprises an HA stem domain and HA globular head domain from the same influenza virus strain. In certain embodiments, the influenza virus strain is A/Netherlands/602/2009.

As used herein, the term "non-naturally occurring glycosylation site" refers to a glycosylation site that is located at any amino acid positions within a particular globular head domain where a naturally occurring glycosylation site, with respect to a particular HA subtype or strain, is not located. One example of a non-naturally occurring glycosylation site is the addition of a glycosylation site to the globular head domain of an influenza virus hemagglutinin of one subtype, wherein the glycosylation is naturally found in the globular head domain of a hemagglutinin from an influenza virus of another subtype. Another example of a non-naturally occurring glycosylation is the addition of a glycosylation site to the globular head domain of an influenza virus hemagglutinin from one strain, wherein the glycosylation site is naturally found in the globular head of an hemagglutinin from another influenza virus strain. Yet another example of a non-naturally occurring glycosylation site is the addition of a glycosylation site to the globular head domain of an influenza virus hemagglutinin from one strain, wherein the glycosylation site is not naturally found in the globular head of a hemagglutinin from another subtype or strain of influenza virus. In preferred embodiments, the non-naturally occurring glycosylation site has the amino acid motif Asn-Xaa-Ser/Thr/Cys, wherein Xaa is any amino acid, or, in certain embodiments, wherein Xaa is any amino acid except Pro.

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded.

"Polypeptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked glycosylation), protease cleavage and lipid modification (e.g. S-palmitoylation).

As used herein, the terms "prevent," "preventing" and "prevention" in the context of the administration of a therapy(ies) to a subject to prevent an influenza virus disease refer to one or more of the prophylactic/beneficial effects resulting from the administration of a therapy or a combination of therapies. In a specific embodiment, the terms "prevent," "preventing" and "prevention" in the context of the administration of a therapy(ies) to a subject to prevent an influenza virus disease refer to one or more of the following effects resulting from the administration of a therapy or a combination of therapies: (i) the inhibition of the development or onset of an influenza virus disease or a symptom thereof; (ii) the inhibition of the recurrence of an influenza virus disease or a symptom associated therewith; and (iii) the reduction or inhibition in influenza virus infection and/or replication.

As used herein, the terms "purified" and "isolated" when used in the context of a polypeptide (including an antibody) that is obtained from a natural source, e.g., cells, refers to a polypeptide which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide (including an antibody) that is chemically synthesized refers to a polypeptide which is substantially free of chemical precursors or other chemicals which are involved in the syntheses of the polypeptide. In a specific embodiment, a flu HA polypeptide (e.g., an influenza hemagglutinin stem domain polypeptide, an influenza hemagglutinin head domain polypeptide, a chimeric influenza hemagglutinin polypeptide and/or a non-chimeric influenza hemagglutinin polypeptide) is chemically synthesized. In another specific embodiment, an influenza hemagglutinin stem domain polypeptide, an influenza hemagglutinin head domain polypeptide, and/or a chimeric influenza hemagglutinin polypeptide is isolated.

As used herein, the terms "replication," "viral replication" and "virus replication" in the context of a virus refer to one or more, or all, of the stages of a viral life cycle which result in the propagation of virus. The steps of a viral life cycle include, but are not limited to, virus attachment to the host cell surface, penetration or entry of the host cell (e.g., through receptor mediated endocytosis or membrane fusion), uncoating (the process whereby the viral capsid is removed and degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In some embodiments, the terms "replication," "viral replication" and "virus replication" refer to the replication of the viral genome. In other embodiments, the terms "replication," "viral replication" and "virus replication" refer to the synthesis of viral proteins.

As used herein, the terms "stem domain polypeptide" and "influenza virus hemagglutinin stem domain polypeptide" refer to a derivative, e.g. an engineered derivative, of a hemagglutinin polypeptide that comprises one or more polypeptide chains that make up a stem domain of hemagglutinin. A stem domain polypeptide might be a single polypeptide chain, two polypeptide chains or more polypeptide chains. Typically, a stem domain polypeptide is a single polypeptide chain (i.e. corresponding to the stem domain of a hemagglutinin HA0 polypeptide) or two polypeptide chains (i.e. corresponding to the stem domain of a hemagglutinin HA1 polypeptide in association with a hemagglutinin HA2 polypeptide). In certain embodiments, a stem domain polypeptide is derived from an influenza hemagglutinin. In specific embodiments, a stem domain polypeptide is derived from an H1 or H3 influenza virus hemagglutinin. Engineered stem domain polypeptides can comprise one or more linkers as described below.

As used herein, the terms "influenza virus hemagglutinin head domain polypeptide," "influenza virus hemagglutinin head domain," "HA globular head domain," and "HA head domain" refer to the globular head domain of an influenza hemagglutinin polypeptide. An influenza virus hemagglutinin head domain polypeptide or influenza virus hemagglutinin head domain may comprise or consist of a known (e.g., wild-type) influenza virus hemagglutinin head domain or may comprise or consist of a derivative, e.g. an engineered derivative, of a known (e.g., wild-type) influenza virus hemagglutinin head domain.

As used herein, the terms "subject" or "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet. In another embodiment, a subject is a human. In another embodiment, a subject is a human infant. In another embodiment, a subject is a human child. In another embodiment, a subject is a human adult. In another embodiment, a subject is an elderly human. In another embodiment, a subject is a premature human infant.

As used herein, the term "premature human infant" refers to a human infant born at less than 37 weeks of gestational age.

As used herein, the term "human infant" refers to a newborn to 1 year old human.

As used herein, the term "human child" refers to a human that is 1 year to 18 years old.

As used herein, the term "human adult" refers to a human that is 18 years or older.

As used herein, the term "elderly human" refers to a human 65 years or older.

The terms "tertiary structure" and "quaternary structure" have the meanings understood by those of skill in the art. Tertiary structure refers to the three-dimensional structure of a single polypeptide chain. Quaternary structure refers to the three dimensional structure of a polypeptide having multiple polypeptide chains.

As used herein, the term "seasonal influenza virus strain" refers to a strain of influenza virus to which a subject population is exposed to on a seasonal basis. In specific embodiments, the term seasonal influenza virus strain refers to a strain of influenza A virus. In specific embodiments, the term seasonal influenza virus strain refers to a strain of influenza virus that belongs to the H1 or the H3 subtype, i.e., the two subtypes that presently persist in the human subject population. In other embodiments, the term seasonal influenza virus strain refers to a strain of influenza B virus.

As used herein, the terms "therapies" and "therapy" can refer to any protocol(s), method(s), compound(s), composition(s), formulation(s), and/or agent(s) that can be used in the prevention or treatment of a viral infection or a disease or symptom associated therewith. In certain embodiments, the terms "therapies" and "therapy" refer to biological therapy, supportive therapy, and/or other therapies useful in treatment or prevention of a viral infection or a disease or symptom associated therewith known to one of skill in the art. In some embodiments, the term "therapy" refers to (i) a nucleic acid encoding a flu HA polypeptide (e.g., an chimeric influenza virus hemagglutinin polypeptide), (ii) a flu HA polypeptide (e.g., chimeric influenza virus hemagglutinin polypeptide), or (iii) a vector or composition comprising a nucleic acid encoding a flu HA polypeptide (e.g., chimeric influenza virus hemagglutinin polypeptide) or comprising a flu HA polypeptide. In some embodiments, the term "therapy" refers to an antibody that specifically binds to a chimeric influenza virus hemagglutinin polypeptide.

As used herein, the terms "treat," "treatment," and "treating" refer in the context of administration of a therapy(ies) to a subject to treat an influenza virus disease or infection to obtain a beneficial or therapeutic effect of a therapy or a combination of therapies. In specific embodiments, such terms refer to one, two, three, four, five or more of the following effects resulting from the administration of a therapy or a combination of therapies: (i) the reduction or amelioration of the severity of an influenza virus infection or a disease or a symptom associated therewith; (ii) the reduction in the duration of an influenza virus infection or a disease or a symptom associated therewith; (iii) the regression of an influenza virus infection or a disease or a symptom associated therewith; (iv) the reduction of the titer of an influenza virus; (v) the reduction in organ failure associated with an influenza virus infection or a disease associated therewith; (vi) the reduction in hospitalization of a subject; (vii) the reduction in hospitalization length; (viii) the increase in the survival of a subject; (ix) the elimination of an influenza virus infection or a disease or symptom associated therewith; (x) the inhibition of the progression of an influenza virus infection or a disease or a symptom associated therewith; (xi) the prevention of the spread of an influenza virus from a cell, tissue, organ or subject to another cell, tissue, organ or subject; (xii) the inhibition or reduction in the entry of an influenza virus into a host cell(s); (xiii) the inhibition or reduction in the replication of an influenza virus genome; (xiv) the inhibition or reduction in the synthesis of influenza virus proteins; (xv) the inhibition or reduction in the release of influenza virus particles from a host cell(s); and/or (xvi) the enhancement or improvement the therapeutic effect of another therapy.

As used herein, in some embodiments, the phrase "wild-type" in the context of a virus refers to the types of a virus that are prevalent, circulating naturally and producing typical outbreaks of disease. In other embodiments, the term "wild-type" in the context of a virus refers to a parental virus.

4. BRIEF DESCRIPTION OF THE DRAWINGS

FIG. 1 presents a sequence alignment by CLUSTALW of representative sequences of 17 subtypes of influenza virus A hemagglutinin (SEQ ID NOS:1-16 and 583, respectively). The residue designated $A_p$ is the cysteine residue in the HA1 N-terminal stem segment that forms or is capable of forming a disulfide bond with the residue designated $A_q$, a cysteine residue in an HA1 C-terminal stem segment. The residue designated $B_q$ represents the approximate N-terminal amino acid of the HA1 C-terminal short stem segments described herein. The residue designated $C_q$ represents the approximate N-terminal amino acid of the HA1 C-terminal long stem segments described herein. The residue designated $C_p$ represents the approximate C-terminal amino acid of the HA1 N-terminal long stem segments described herein.

FIG. 2 presents a sequence alignment by CLUSTALW of a representative sequence of influenza virus B hemagglutinin (SEQ ID NO:558) aligned with influenza A HK68-H3N2 (SEQ ID NO:3) and PR8-H1N1 (SEQ ID NO:1) hemagglutinins.

FIG. 3 presents a sequence listing of influenza B virus hemagglutinin (SEQ ID NO:17), noting amino acids that constitute boundaries for various N- and C-terminal stem segments and intermediate stem segments described herein.

FIG. 4 provides putative structures of influenza A HA stem domain polypeptides based on an HK68-H3N2 hemagglutinin protein. FIG. 4A provides the putative structure of an influenza A HA stem domain polypeptide based on an HK68-H3N2 hemagglutinin protein, HA1 N-terminal stem segment SEQ ID NO:36 and C-terminal stem segment SEQ ID NO:52. FIG. 4B provides the putative structure of an influenza A HA short stem domain polypeptide based on an HK68-H3N2 hemagglutinin protein, HA1 N-terminal stem segment SEQ ID NO:36 and C-terminal short stem segment SEQ ID NO:352. FIG. 4C provides the putative structure of an influenza A HA long stem domain polypeptide based on an HK68-H3N2 hemagglutinin protein, HA1 N-terminal long stem segment SEQ ID NO:417 and C-terminal long stem segment SEQ ID NO:433.

Figure 5:
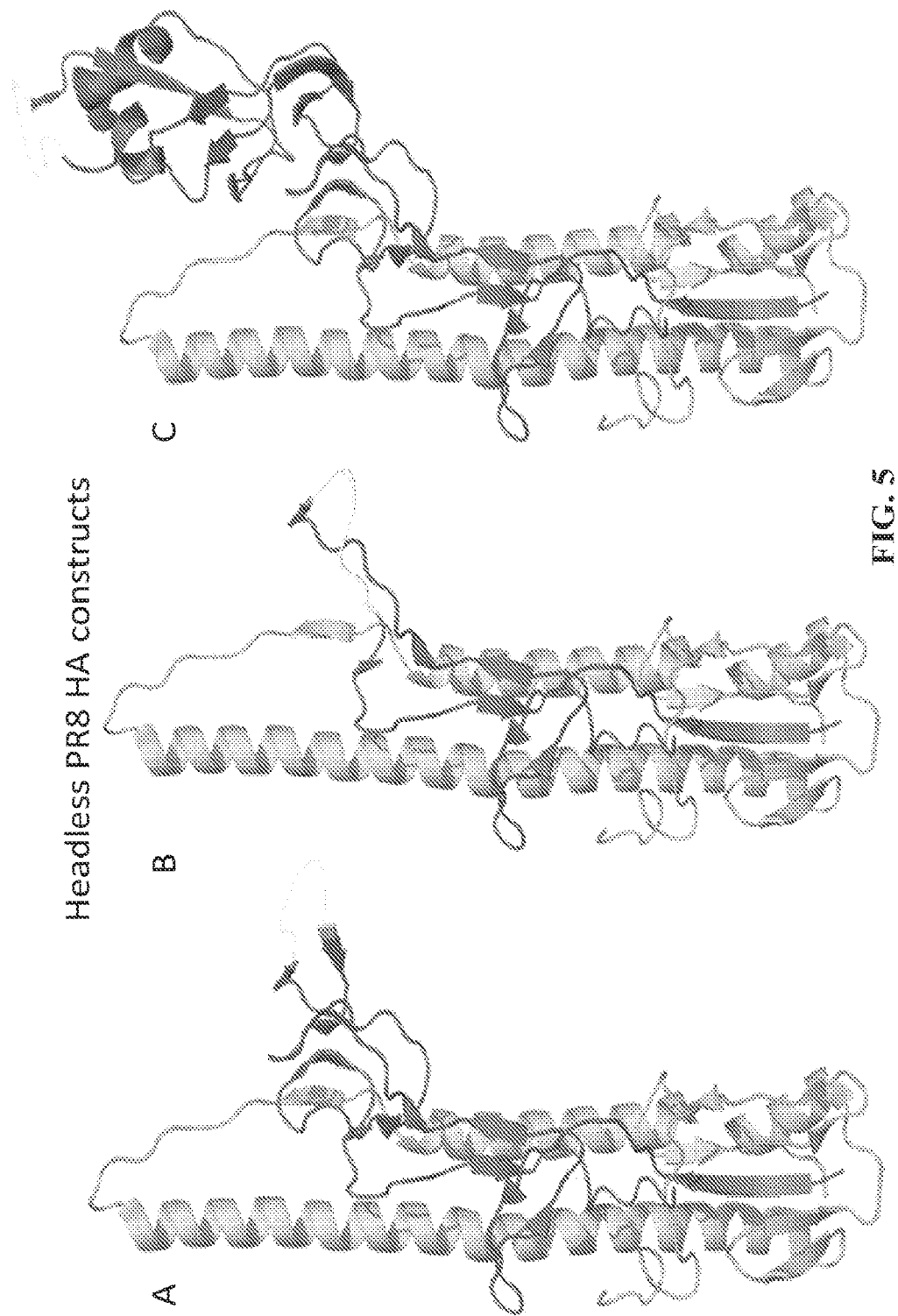

FIG. 5 provides putative structures of influenza A HA stem domain polypeptides based on a PR8-H1N1 hemagglutinin protein. FIG. 5A provides the putative structure of an influenza A HA stem domain polypeptide based on a PR8-H1N1 hemagglutinin protein, HA1 N-terminal stem segment SEQ ID NO:18 and C-terminal stem segment SEQ ID NO:34. FIG. 5B provides the putative structure of an influenza A HA short stem domain polypeptide, HA1 N-terminal stem segment SEQ ID NO:18 and C-terminal short stem segment SEQ ID NO:350. FIG. 5C provides the putative structure of an influenza A HA long stem domain polypeptide based on a PR8-H1N1 hemagglutinin protein, HA1 N-terminal long stem segment SEQ ID NO:414 and C-terminal long stem segment SEQ ID NO:430.

Figure 6:
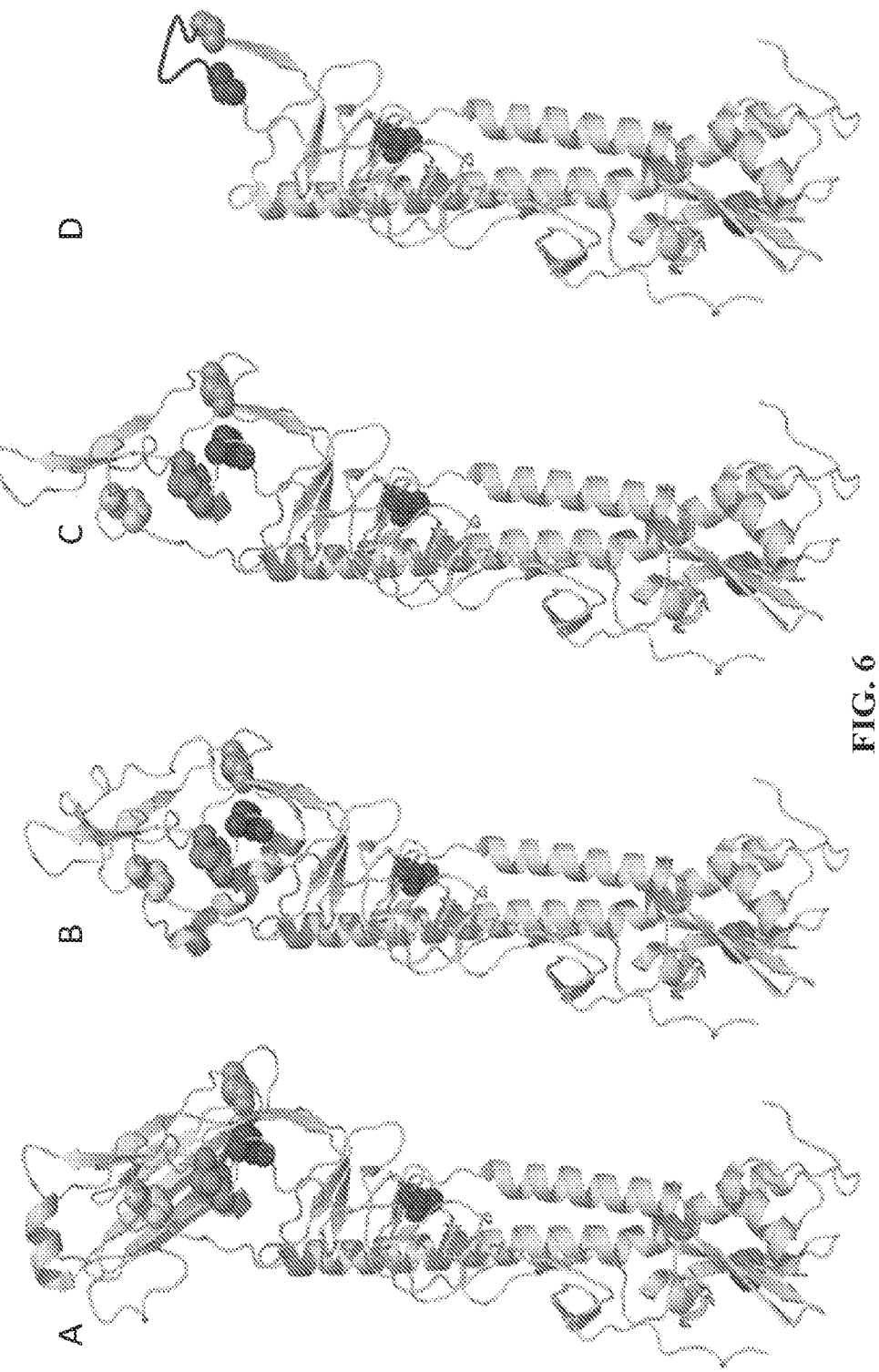

FIG. 6 provides putative structures of influenza B HA stem domain polypeptides. FIG. 6A provides a partially headless HA molecule based on the B/Hong Kong/8/73 hemagglutinin protein, in which the first 94 amino acids of the HA1 domain of the HA are retained (SEQ ID NO:550), and where Cys94 is linked directly to Cys143 of the HA1 domain (SEQ ID NO: 553), by means of a linker bridge. FIG. 6B depicts a partially headless HA molecule based on the B/Hong Kong/8/73 hemagglutinin protein, in which the first 178 amino acids of the HA1 domain of the HA are retained (SEQ ID NO:551), and where Cys178 is linked directly to Cys272 of the HA1 domain (SEQ ID NO:554), by means of a linker bridge. FIG. 6C depicts a headless HA molecule based on the B/Hong Kong/8/73 hemagglutinin protein, in which the first 94 amino acids of the HA1 domain of the HA are retained (SEQ ID NO:555), and where Cys94 is linked directly to Cys143 of the HA1 domain, by means of a linker bridge. Amino acids 143 to 178 of the HA1 domain are furthermore retained (SEQ ID NO:556), and Cys178 is linked directly to Cys272 of the HA1 domain (SEQ ID NO:557), by means of a linker bridge. FIG. 6D depicts a headless HA molecule based on the B/Hong Kong/8/73 hemagglutinin protein, in which the first 54 amino acids of the HA1 domain of the HA are retained (SEQ ID NO:552), and where Cys54 is linked directly to Cys272 of the HA1 domain (SEQ ID NO:554), by means of a linker bridge.

Figure 7:
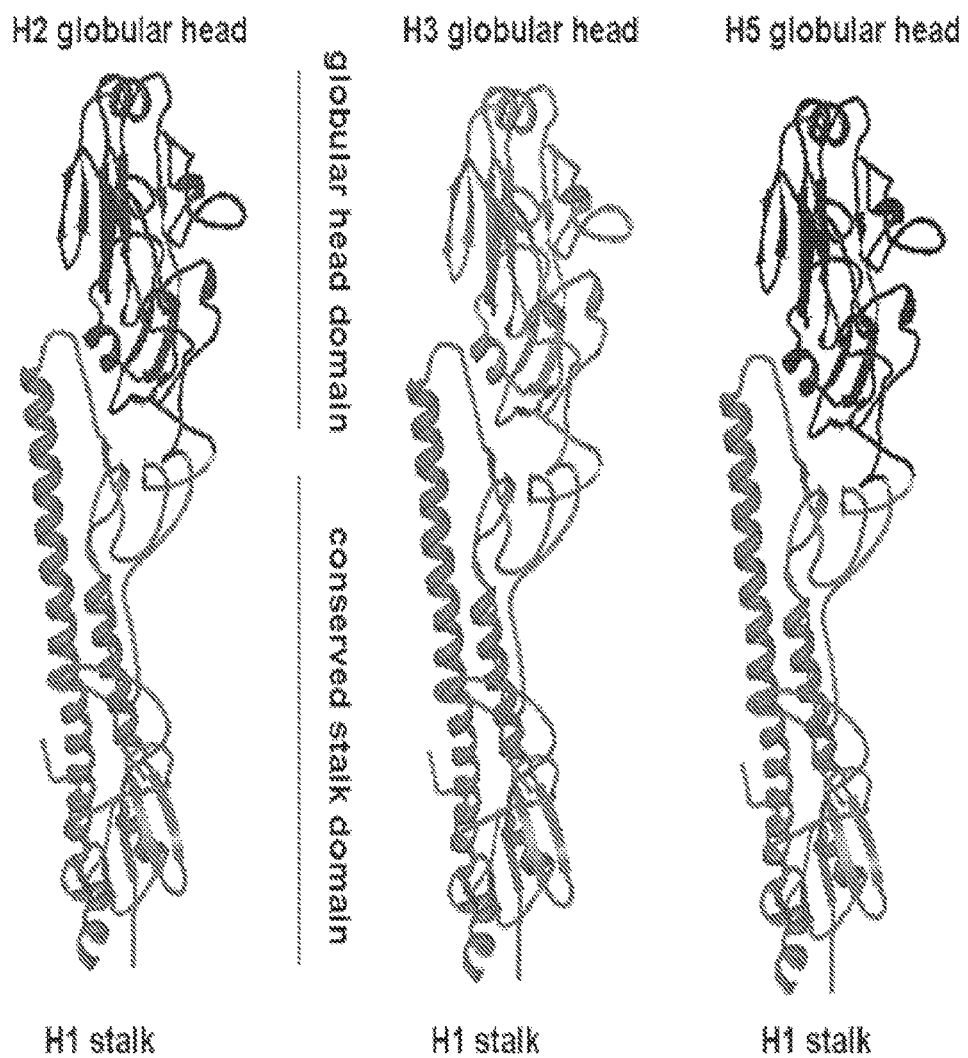

FIG. 7 provides a schematic of chimeric HAs with a conserved H1 stalk domain and different globular head domains from distinct subtype HAs.

Figure 8:
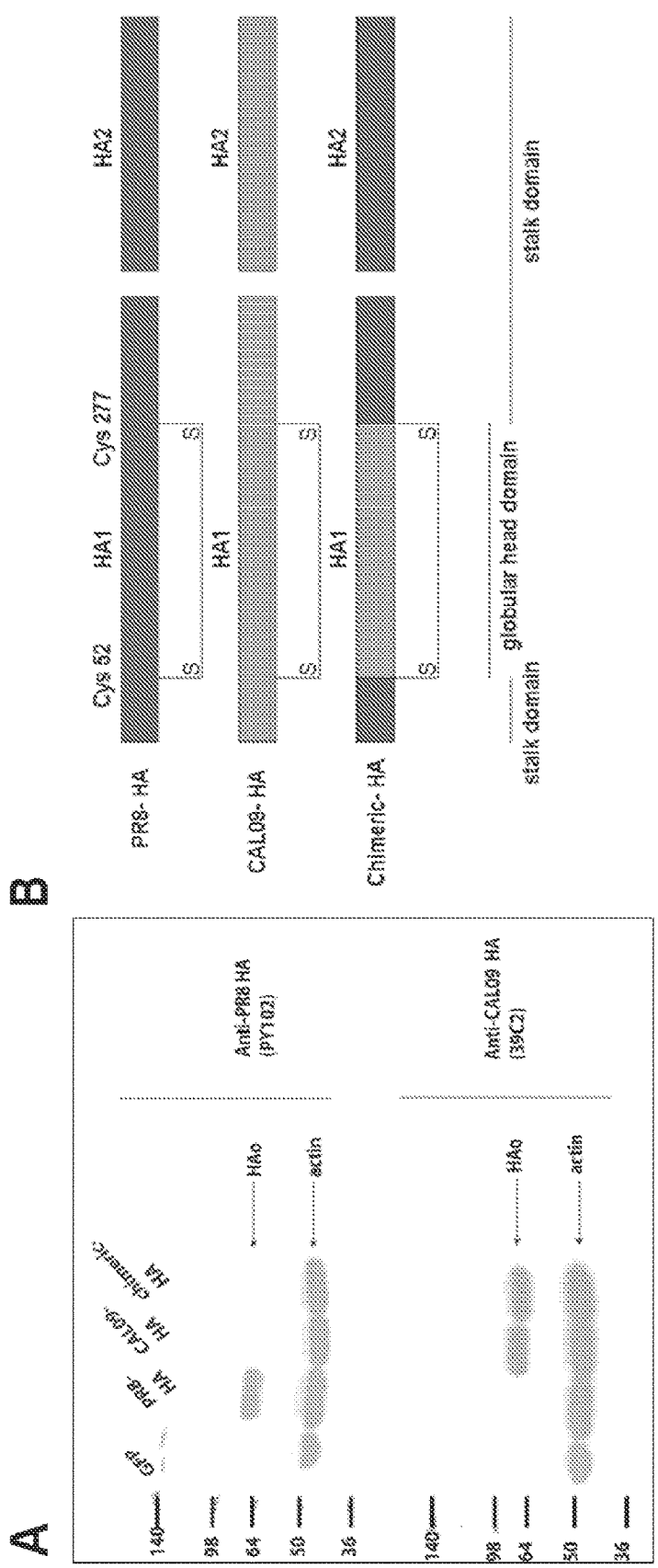

FIG. 8 provides a novel influenza vaccine and diagnostic tool platform to induce and analyze antibodies and reactive sera. A) Expression of chimeric HAs. Chimeric HAs consisting of the stalk domain of A/PR8/34 HA and the globular head domain of A/California/4/09 (chimeric HA) as well as wild type HAs (PR8-HA and CAL09-HA) and a GFP control were expressed in 293T cells. The upper Western blot was probed with a PR8-specific antibody (PY102) whereas the blot on the lower side was probed with an antibody specific for Cal09 (39C2). B) Schematic drawing of HA constructs expressed in A. The chimeric HA is composed of the A/PR/8/34 HA stalk domain and the 2009 A/California/04/09 globular head domain.

Figure 9:
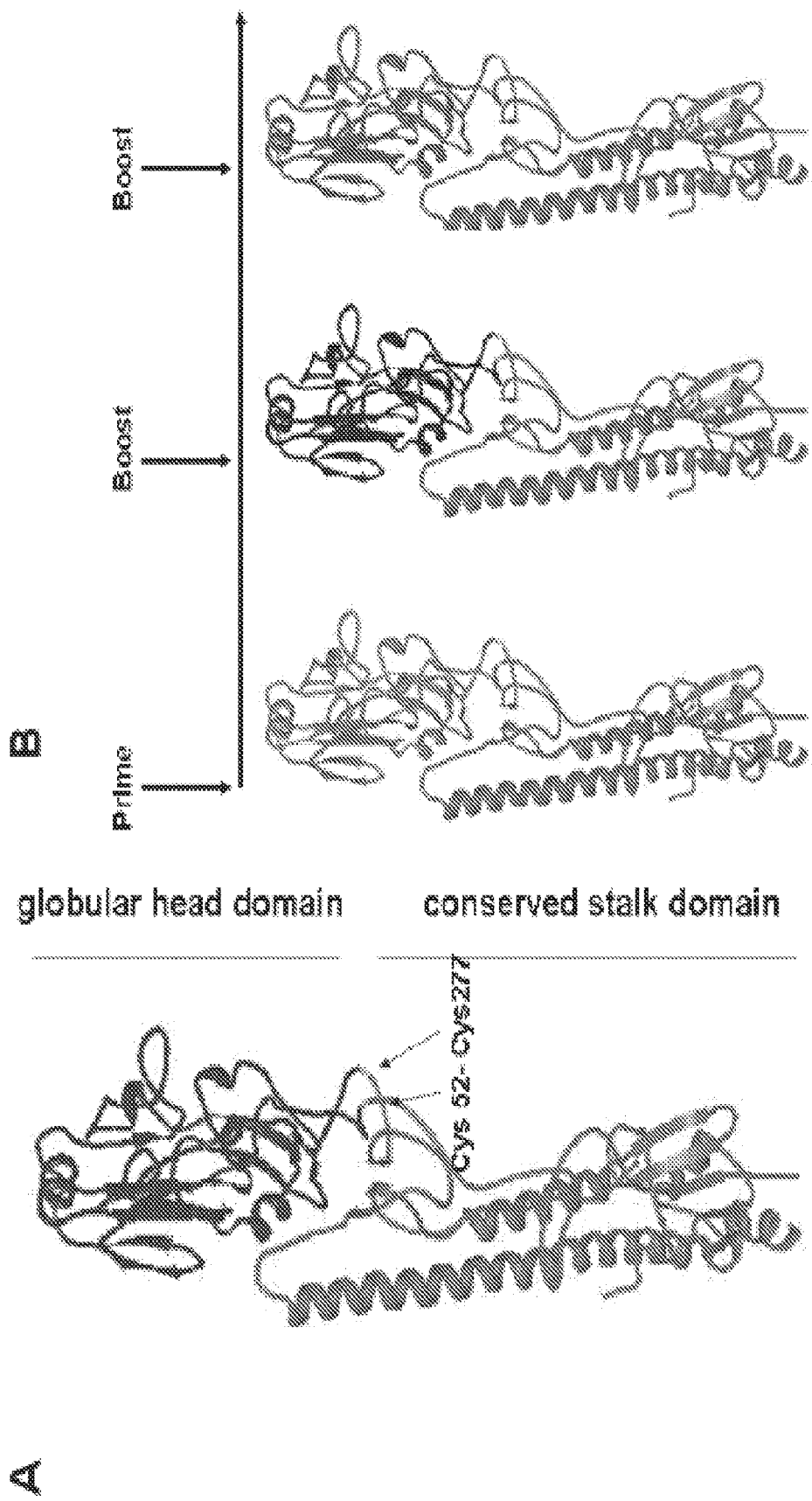

FIG. 9 provides a schematic of chimeric HAs. A) Basic structure of a chimeric HA. The globular head can be exchanged conveniently at disulfide bond Cys 52-Cys 277. B) Prime-boost regime with sequential administration of chimeric HAs consisting of a completely conserved stalk domain and a varying globular head domain.

Figure 10:
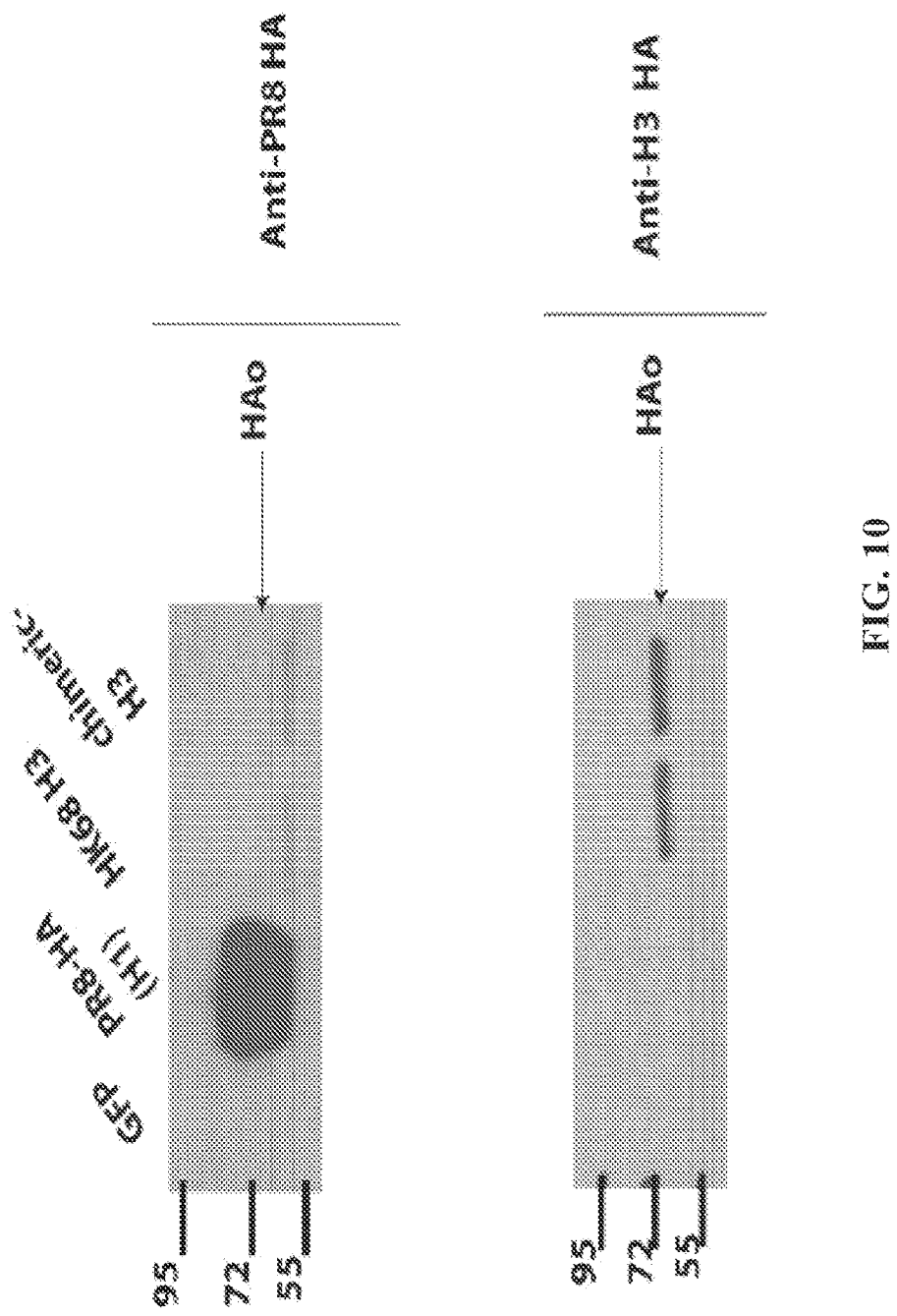

FIG. 10 describes generation of a chimeric HA with the stalk of an H1 HA and the globular head of an H3 HA. A chimeric HA consisting of the stalk domain of A/PR8/34 HA and the globular head domain of HK/68 (chimeric H3) as well as wild type HAs (PR8-HA and HK68 HA) were expressed in 293T cells. The upper Western blot was probed with a PR8-specific antibody whereas the blot on the lower side was probed with an antibody specific for H3.

Figure 11:
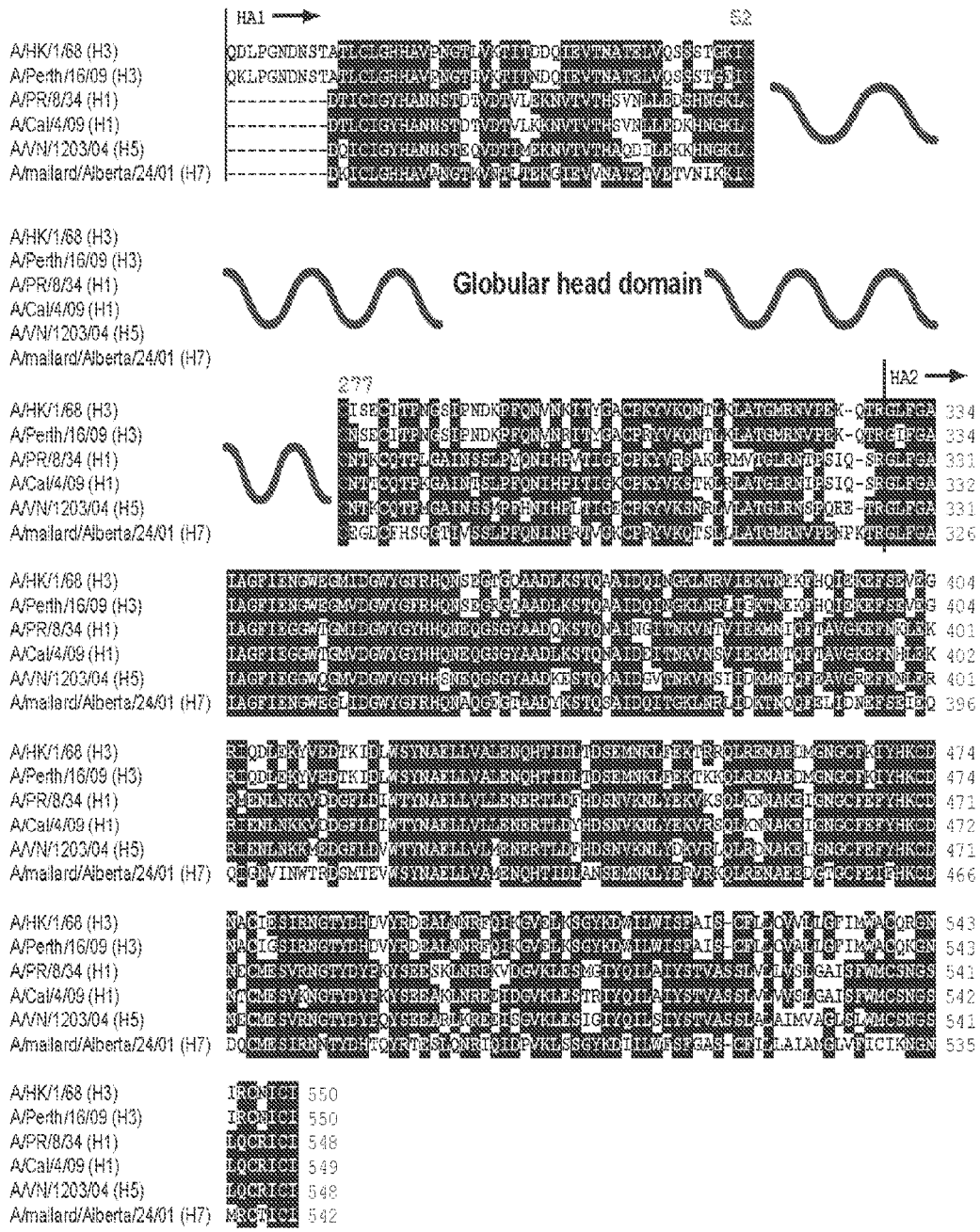

FIG. 11 depicts a sequence comparison of the hemagglutinin protein sequences of A/Hong Kong/1/1968 (H3), A/Perth/16/2009 (H3), A/PR/8/34 (H1), A/Cal/4/09 (H1), A/Viet Nam/1203/04 (H5), and A/mallard/Alberta/24/01 (H7). The Cys52 and Cys272 amino acid residues are specified (based on H3 numbering). The black shade indicates conserved amino acids. The black wavy line represents the globular head region of HAs. The starting points of HA1 and HA2 are indicated. SEQ ID NOs: 584-589 represent the amino acid sequences ending with the Cys52 amino acid residues for A/Hong Kong/1/1968 (H3), A/Perth/16/2009 (H3), A/PR/8/34 (HI), A/Cal/4/09 (H1), A/Viet Nam/1203/04 (H5), and A/mallard/Alberta/24/01 (H7), respectively. SEQ ID NOs: 590-595 represent the amino acid sequences beginning with the Cys277 amino acid residue for A/Hong Kong/1/1968 (H3), A/Perth/16/2009 (H3), A/PR/8/34 (H1), A/Cal/4/09 (H1), A/Viet Nam/1203/04 (H5), and A/mallard/Alberta/24/01 (H7), respectively.

FIG. 12 depicts a schematic of chimeric hemagglutinins (A) Construction diagram of the chimeric PR8-cH1 HA. The chimeric HA was constructed by swapping the globular head domain located between Cys52 and Cys277 of A/PR/8/34 (H1) HA with that of the A/California/4/09(H1) HA. The resulting chimeric HA has the stalk region of A/PR/8/34 (H1) HA with a globular head domain of the A/California/4/09 (H1) HA designated as PR8-cH1. (B) Schematic of the folded structures of the different wild type and chimeric HAs, such as wild the type PR8 HA, the chimeric PR8-cH1 HA, the chimeric PR8-cH5 HA, the wild type Perth HA, and the chimeric Perth-cH7 HA (from left to right). The full-length HA structures were downloaded from the Protein Database (PDB): PR8 HA (PDB ID 1RU7) and Perth HA (represented by HK68 HA, PDB ID 1MQN). Final images were generated with PyMol (Delano Scientific).

FIG. 13 depicts the surface expression and functional analysis of chimeric HA constructs. (A) Surface expression of chimeric HA constructs was evaluated in transiently transfected cells. At 24 h post-transfection, 293T cells were trypsinized and cell surface expression of chimeric HA proteins were analyzed by flow cytometry. In the upper panels, mock-transfected cells (left shaded region) are compared to cells transfected with PR8 HA (right) or cells transfected with PR8-cH1 (right) or PR8-cH5 (right). In the bottom panels, mock-transfected cells (left shaded region) are compared to cells transfected with Perth and Perth-cH7 constructs (right). (B) Luciferase-encoding pseudo-particles expressing chimeric HAs were used to infect MDCK cells. The relative light units (RLU) generated in the luciferase assay indicate that pseudo-particles expressing chimeric HAs were able to enter the cells.

FIG. 14 describes the generation of recombinant viruses bearing chimeric hemagglutinins (A) Western blot analysis of the recombinant viruses. Extracts from MDCK cells mock infected or infected with the indicated viruses (16 hpi) at an MOI of 2 were prepared and probed with antibodies: anti-A/PR8/HA(H1) (PY102), anti-A/Cal/09/HA(H1) (29C1), anti-A/VN/HA(H5) (M08), anti-H3/HA (12D1), anti-H7 (NR-3125), anti-A/NP (HT103) and anti-GAPDH as an internal loading control. (B) Immunofluorescence analysis of the MDCK cells infected with recombinant viruses using antibodies: anti-A/NP (HT103), anti-A/H1 HA (6F12), anti-A/PR8/HA (PY102), anti-A/Cal/09/HA (29C1), anti-A/VN/HA (M08), anti-H3/HA (12D1), and anti-A/H7 virus (NR-3152).

Figure 15:
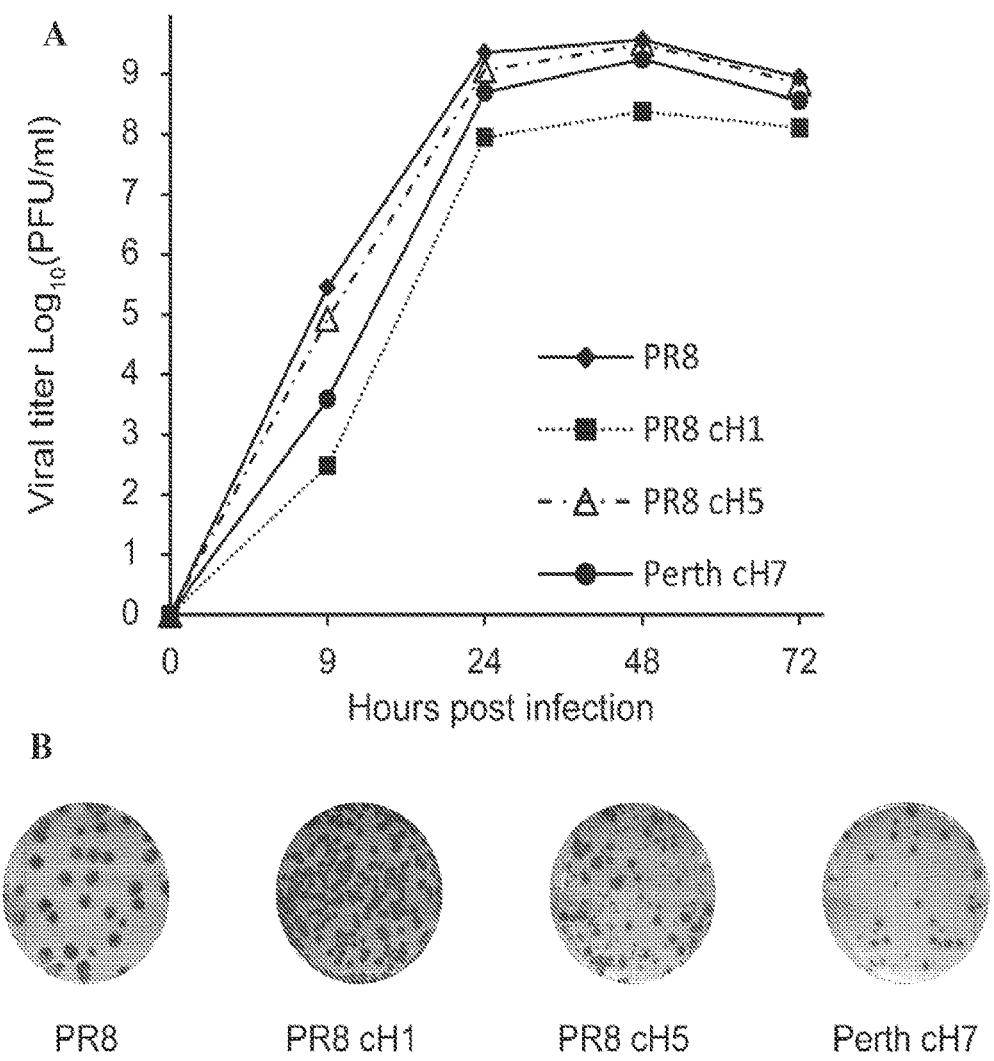

FIG. 15 describes the growth kinetics and plaque phenotypes of recombinant viruses. (A) 10-day old embryonated chicken eggs were infected with wild-type or recombinant virus with 100 pfu per egg and viral growth monitored for 72 hours post infection. (B) The plaque phenotype of recombinant viruses was assessed by plaque assay. MDCK cells were infected with either a wild-type or recombinant virus and at 48 hours post infection immuno-stained to reveal plaque phenotype using the antibody against A/NP (HT103).

FIG. 16A-FIG. 16F depict an immunofluorescence analysis of cells transfected with chimeric H6 hemagglutinin. 293T cells were transfected with 1 μg of pCAGGS plasmid expressing chimeric H6 hemagglutinin. Sera from animals that received DNA (FIG. 16A), Cal/09 infection (FIG. 16B), DNA and Cal/09 infection (FIG. 16C), or Cal/09 split vaccine (D) were added to transfected cells and visualized by fluorescence microscopy following incubation with an Alexa Fluor 594-conjugated anti-mouse IgG. As controls, the cross-reactive H1 stem antibody C179 (FIG. 16E) or the antibody PY102 (FIG. 16F) directed against the globular head of PR8were added to transfected cells and visualized by fluorescence microscopy followed by incubation with an Alexa Fluor 594-conjugated anti-mouse IgG.

Figure 17:
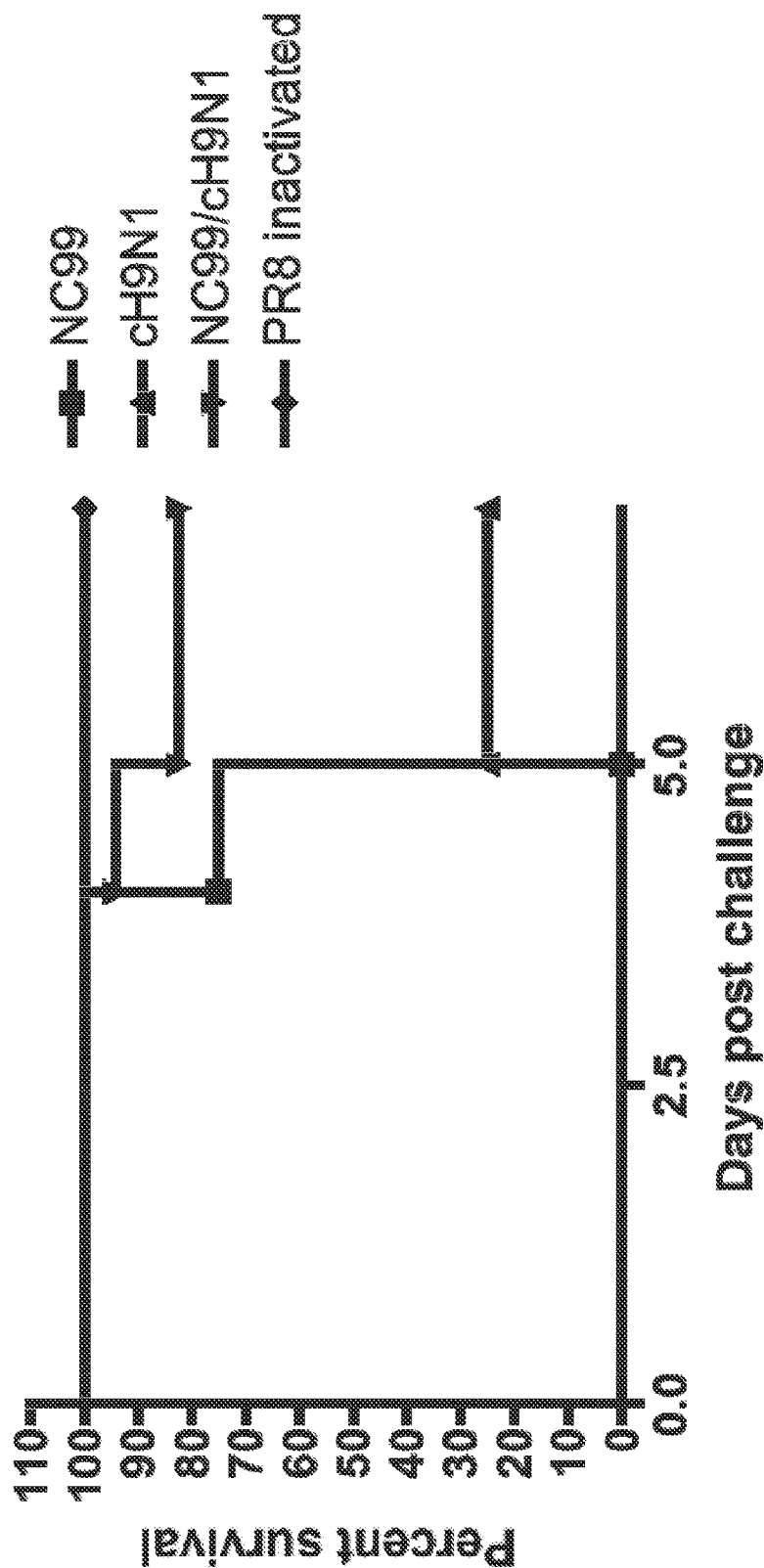

FIG. 17 demonstrates that DNA prime and chimeric virus boost confer protection to animals challenged with lethal influenza virus challenge. Animals were either treated with DNA alone, chimeric H9 virus alone, DNA prime and chimeric H9 virus boost, or with inactivated PR8 virus. Mice were then challenged with $5 \times 10^4$ PFU of PR8 virus, instilled intranasally, and the weight of the animals was monitored for 14 days.

Figure 18:
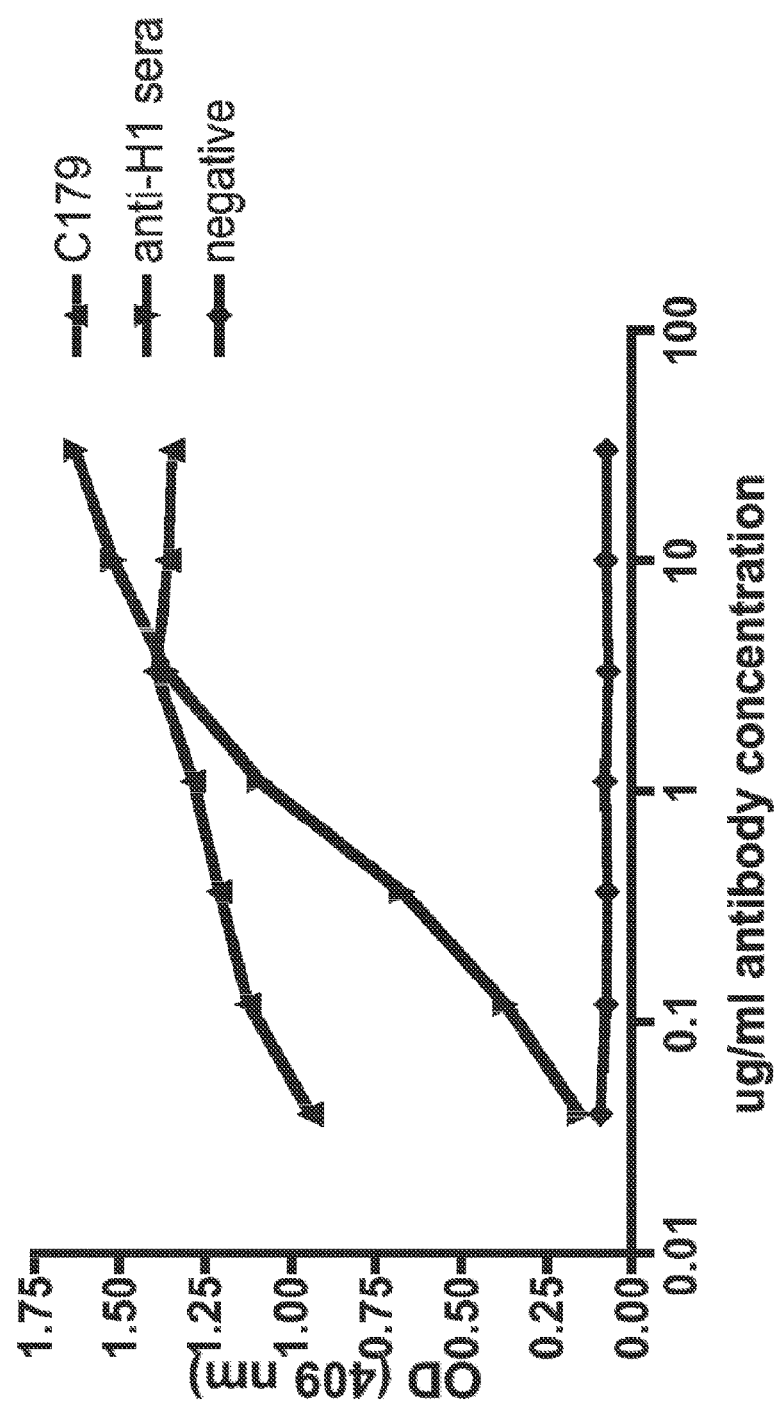

FIG. 18 demonstrates reactivity of stalk specific antibodies to cH6 protein as determined by ELISA.

Figure 19:
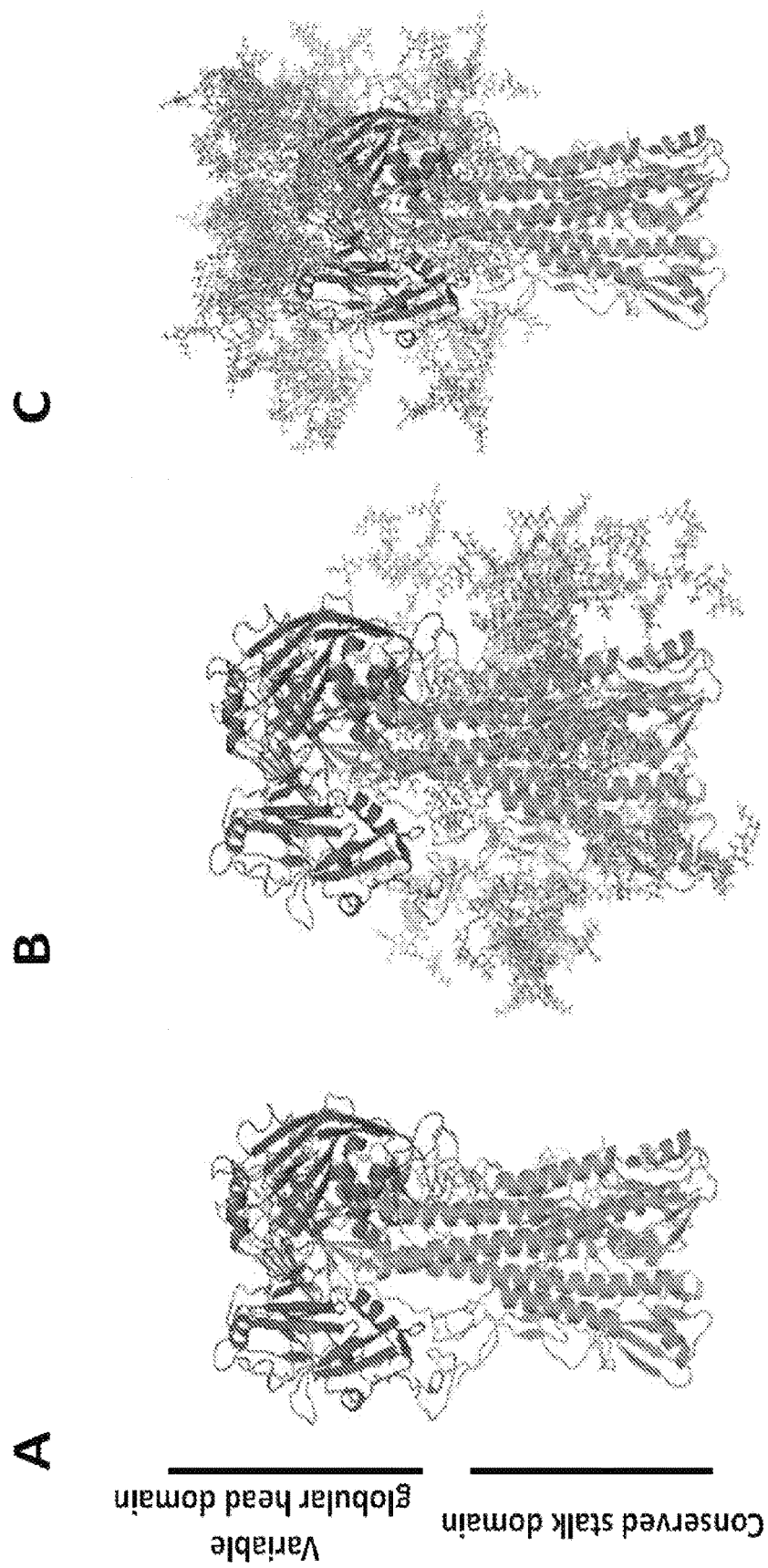

FIG. 19 depicts the structure of A/PR/8/34 H1 hemagglutinin trimer having a stem domain and globular head domain. The hemagglutinin trimer is depicted without glycans (A), in wild type form, with glycan structures (B), and in mutant form wherein the glycan structures are removed from the stalk domain and added to the globular head domain (C).

Figure 20:
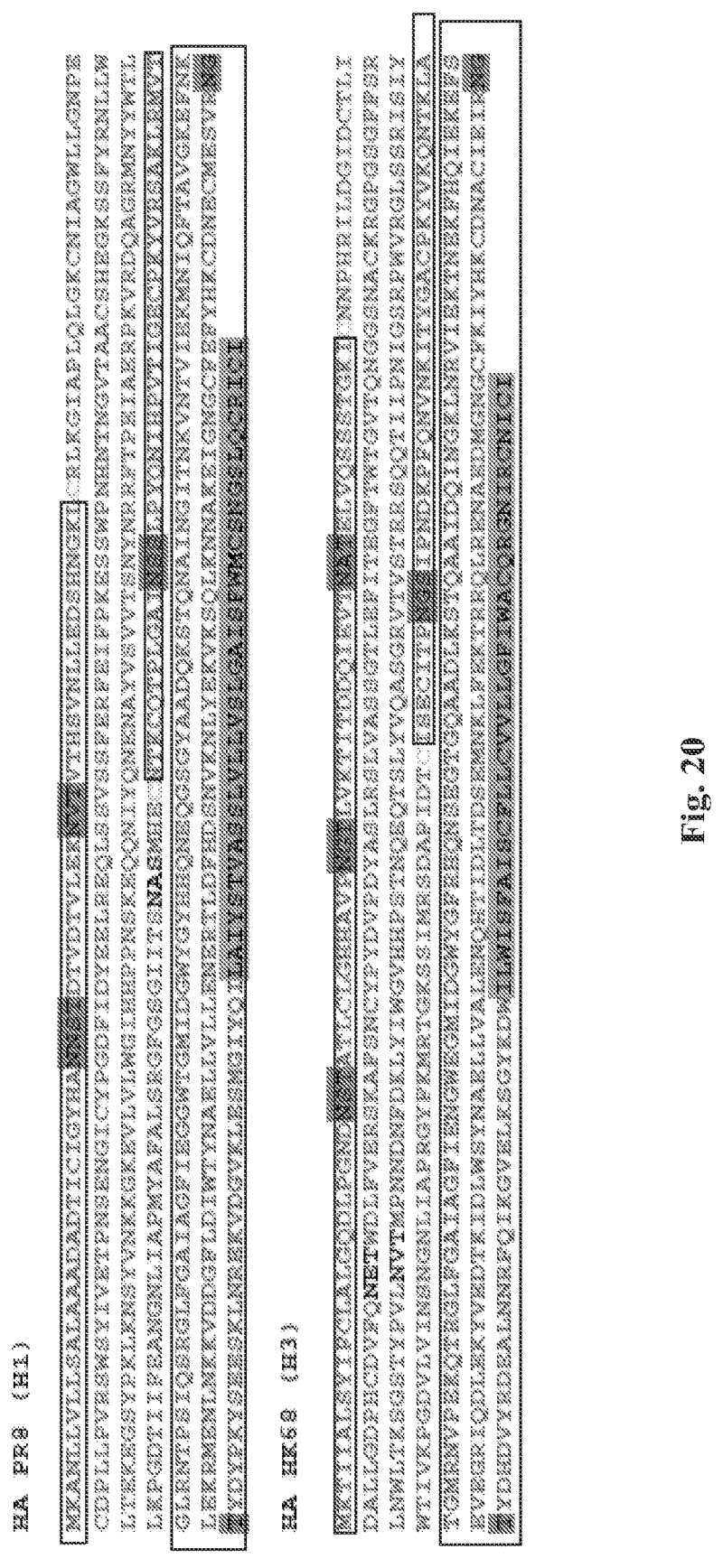

FIG. 20 depicts the sequences of A/PR/8/34 (PR8; SEQ ID NO: 596) and A/HK/1/68 (HK68; SEQ ID NO: 597) hemagglutinin (HA). Amino acids that form the stem domain are boxed. The cysteines ("C") that form the border between stalk and globular head domain are those shown at after the first box of amino acids that form the stem domain and before the second box of amino acids that form the stem domain. The remaining amino acids (the non-boxed amino acids, not including the cysteines present after the first box of amino acids that form the stem domain and before the second box of amino acids that form the stem domain) are those that form the globular head domain. Naturally occurring glycosylation sites are indicated by darkened letters in the sections of amino acids corresponding to the globular head domain. The transmembrane and ectodomain are represented by the highlighted stretch of amino acids at the end of each sequence. Glycosylation sites that can be mutated in order to disrupt binding of glycans to the stem domain are indicated; these include the following sequences: NNST, NVT, NSS, NGT (in HA PR8) and NST, NGT, NAT, NGS, NGT (in HA HK68).

Figure 21:
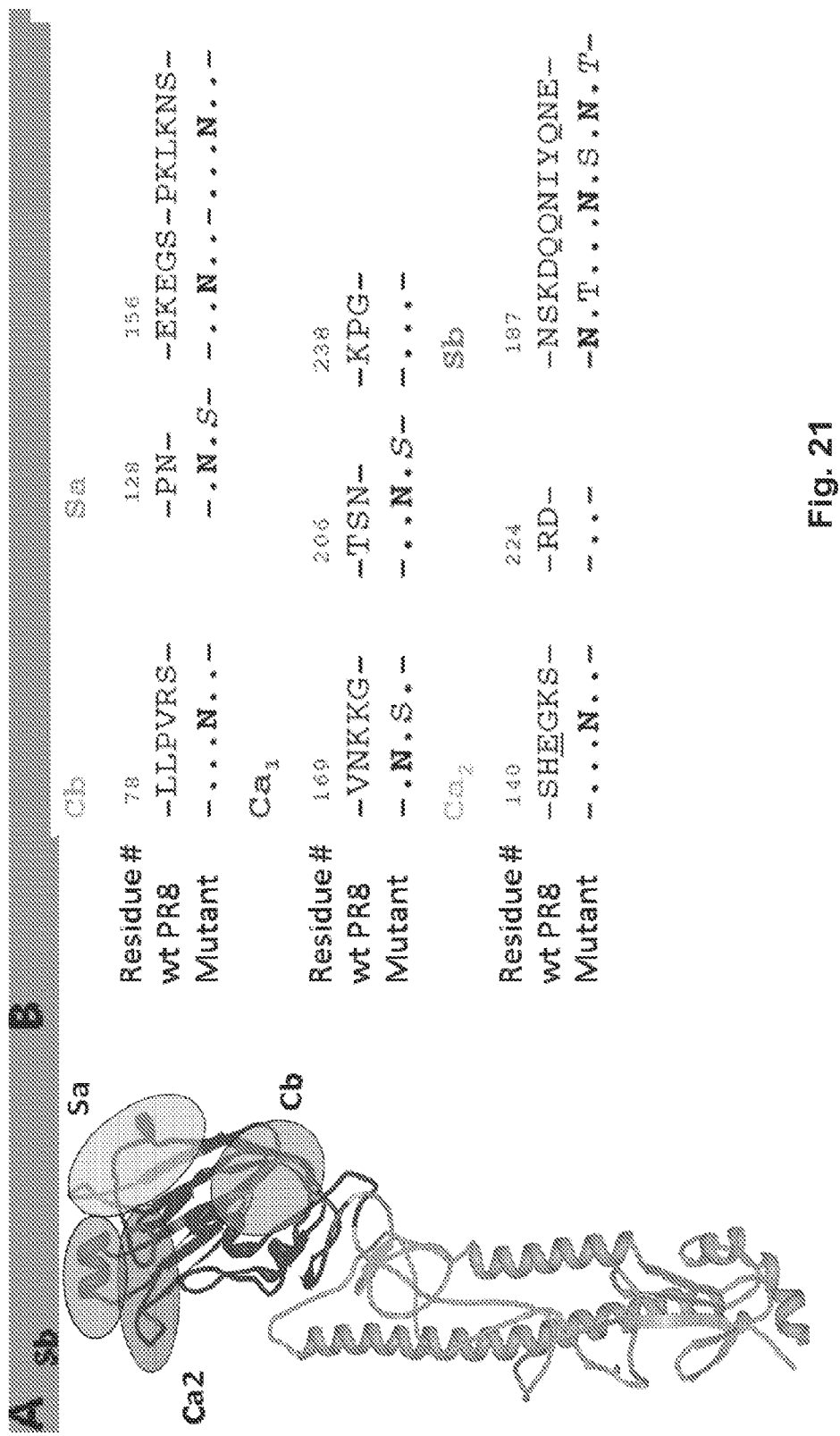

FIG. 21 depicts a schematic drawing of immunodominant antigenic sites on the globular head domain of a monomer of influenza hemagglutinin (H1) (A). Exemplary mutations that introduce non-naturally occurring glycosylation sites into the antigenic sites of A/Pr/8/34 H1 hemagglutinin (B). These non-naturally occurring glycosylation sites are indicated by the amino acid motif N-Xaa-S/T, wherein Xaa can be any amino acid. Amino acid sequence LLPVRS is SEQ ID NO: 598. Amino acid sequence EKEGS is SEQ ID NO 599. Amino acid sequence PKLKNS is SEQ ID NO: 600. Amino acid sequence VNKKG is SEQ ID NO: 601. Amino acid sequence SHEGKS is SEQ ID NO: 602. Amino acid sequence NSKDQQNIYQNE is SEQ ID NO: 603.

FIG. 22 depicts the acquisition of glycosylation sites in HA of human H1 subtype over time (up to and including 2009 H1N1 virus, and other 2009 influenza viruses). Amino acid alignment of antigenic sites in the HA1 of seasonal H1N1 strains circulating in humans since 1918 and prior to the emergence of the 2009 H1N1 pandemic virus (A). For simplicity the alignment was made with selected prototypical reference strains and vaccine strains obtained from the Influenza Research Database and the Influenza Virus Resource Database (accession numbers are listed in methods). Years not represented correspond to either a lack of an isolate sequence for that year or an unclear prototype sequence due to few sequences available. The sequence depicted for A/South Carolina/1/18 is as set forth in SEQ ID NO: 604. The shaded regions depict the known antigenic sites listed on top. Boxed text in the regions designated 1, 2, and 3 represent conserved glycosylation; boxed text in the regions designated 4, 5, 6, and 7 represent glycosylations that appear overtime. Time line depicting the year of acquisition of glycosylations in the globular head of the HA protein (B). Numbers indicate the amino acid position of the glycosylation site that appearing in the specific years shown at the bottom. Arrows denote the persistence of the glycosylation site through time, and circles represent the disappearance of specific glycosylation sites. Discontinuous lines show the time period during which H1N1 did not circulate in humans. Structural representation of the specific position of each glycosylation as they appear overtime from 1918 to the emergence of the 2009 pH1N1 virus (C). The HA is represented as ribbons that form the HA trimeric molecule. Position refers to the H1 nomenclature (71, 142, 144, 172 and 177 correspond to H3 numbering 58, 128, 130, 158 and 163, respectively).

Figure 23:
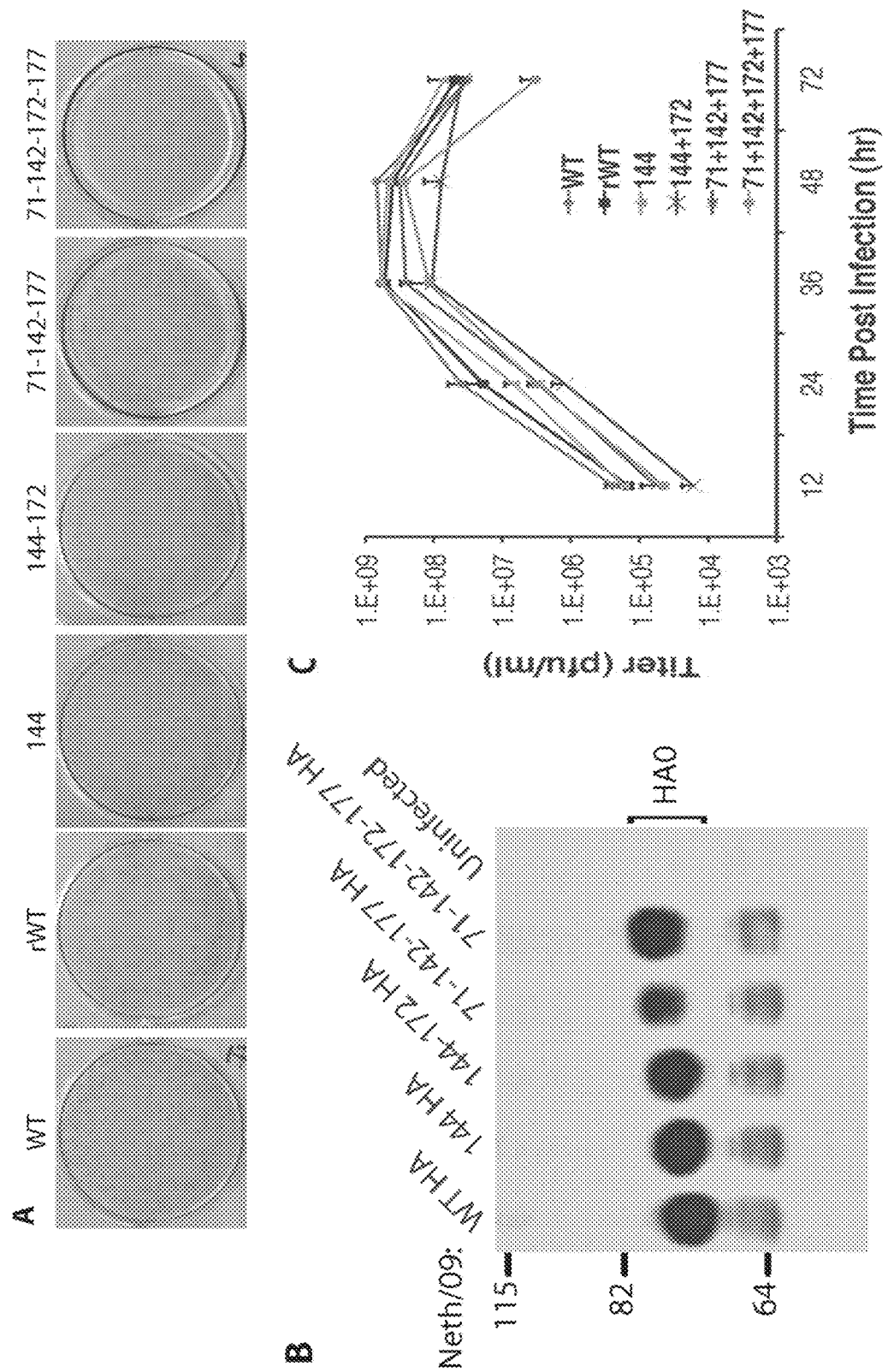

FIG. 23 depicts the phenotypic characterization of HA glycosylation mutant 2009 pH1N1 viruses. Plaque size phenotype of rescued A/Netherlands/602/2009 HA glycosylation mutant viruses in MDCK cells (A). Western blot analysis of whole cell lysates obtained from MDCK cells infected at an MOI of 5 for 12 h (B). Lysates were run under non-reducing conditions and blots were detected with a rabbit polyclonal antibody 3851 raised against a PR8 virus lacking H1, which had been removed by acid and DTT treatment. Growth kinetics of rescued viruses in differentiated human tracheobrochial epithelial cells infected at an MOI of 0.001 (C). Virus titrations were conducted for each time point shown by standard plaques assay in MDCK cells.

FIG. 24 shows that 2009 pH1N1 viruses with additional glycosylations in the HA are attenuated in mice and ferrets.

(A-E) Infection of 9-week-old C57B/6 female mice with Neth/09 glycosylation mutant viruses. Groups of n=5 mice per recombinant virus were infected i.n. with the indicated virus doses. Body weight represent the average of each group and the error bars indicate the standard deviation (s.d.) at each time point. (F) Titer of lungs from mice infected with $1\times10^3$ pfu of each mutant virus were obtained on days 2 (circle), 3 (square), and 7 (triangle) p.i. as shown. Black bar represent the average viral titer for 2 (arrows) or 3 mice per group at each time point as compared to the rNeth/09 WT virus. (G) Body weight changes in ferrets infected (n=3 per group) with the indicated viruses. Weights are shown as the average and the error bars represent the s.d. of each time point. (H) Viral titers in nasal washes obtained every other day from ferrets shown in (G). (I) Viral load in tissues from ferrets (n=3) at day 3 p.i. with the indicated viruses. Values are represented as in (F). Statistically significant differences of the body weight of ferrets were estimated with the Wilcoxon-matched pairs test (G).

FIG. 25 depicts that Viruses containing glycosylation deletions in the HA of Tx/91 exhibit increased virulence in mice and cross-protect against the 2009 pH1N1 strain. Phenotypic characterization of recombinant influenza A viruses carrying either the wild type or glycosylation deletion mutant A/Texas/36/1991 HAs and the remainder 7 genes from PR8 (viruses are rPR87:1 Tx/91 HA). (A) Western blot analysis of lysates obtained from MDCK cells infected at an MOI of 5 for 12 h with the respective glycosylation deletion mutant viruses. Lysates were run under reducing conditions and blots were detected with the polyclonal 3951 antibody. (B) 8-week-old C57B/6 female mice infected with $1\times10^4$ pfu of each virus shown. Average body weight of mice n=5 per group. Error bars denote the s.d. for each time point. (C) Mice infected in (B) were allowed to seroconvert for 27 days at which time they were challenged with a 100 LD50 of Neth/09. Body weight represent the average of each group with their respective s.d. (D) Percent survival are shown for mice in (C). The student's t-test was used to determine significance in body weight loss and the log-rank test was used to assess significance (* $P<0.05$) for survival outcome.

FIG. 26 depicts a schematic representation of chimeric HA (cHA) proteins (A) and cHA expression in MDCK cells (B). Chimeric HA (cHA) proteins and recombinant chimeric virus. (A) Schematic representation of cHAs. The globular head domain is defined as the intervening amino acid sequence between residues C52 and C277 (H3 numbering). Using this disulfide bond as the demarcation between head and stalk, exotic HA heads were introduced atop heterologous stalks. The stalk domain is defined as the remaining portions of HA1 and HA2 subunits. CT, cytoplasmic tail; SP, signal peptide; TM, transmembrane domain. The full-length HA structures were downloaded from the Protein Database (PDB): PR8 (H1) HA (PDB ID 1RU7) and A/guinea fowl/Hong Kong/WF10/99 HA [represented by A/swine/Hong Kong/9/98 (H9; PDB ID 1JSD)]. Final images were generated with PyMol (Delano Scientific). Because no structure of an H6 HA has been published, the image of the head-folding of the PR8 HA is used for the cH6/1 construct. (B) Immunofluorescence to confirm expression of cHA. MDCK cells were infected with either WT PR8 or cH9/1 N3 virus, or they were mock-infected. Antibodies specific for the head and stalk of PR8 virus as well as an antibody with H9 reactivity were used to confirm cHA expression. (Magnification bar: 40×).

FIG. 27 shows that adult patients infected with pandemic H1N1 virus have high titers of neutralizing antibodies that are reactive with the HA stalk. Reactivity of sera of pH1N1-infected adults (n=9), children not infected with pH1N1 (n=5), and adults not infected with pH1N1 virus (n=11) with cH6/1 protein (A), cH9/1 protein; (B), the LAH of the HA2 protein (anti-LAH antibody was used as a positive control; (C), H5 HA protein (mouse polyclonal serum raised against H5 HA was used as a positive control and a pan-H3 antibody, 12D1, was used as negative control; (D) (13), or H3 HA protein (12D1 was used as a positive control and mouse polyclonal serum raised against H5 HA was used as a negative control; (E). All were assessed by ELISA; data points represent average titers with SE or reactivity of pooled samples.

Figure 28:
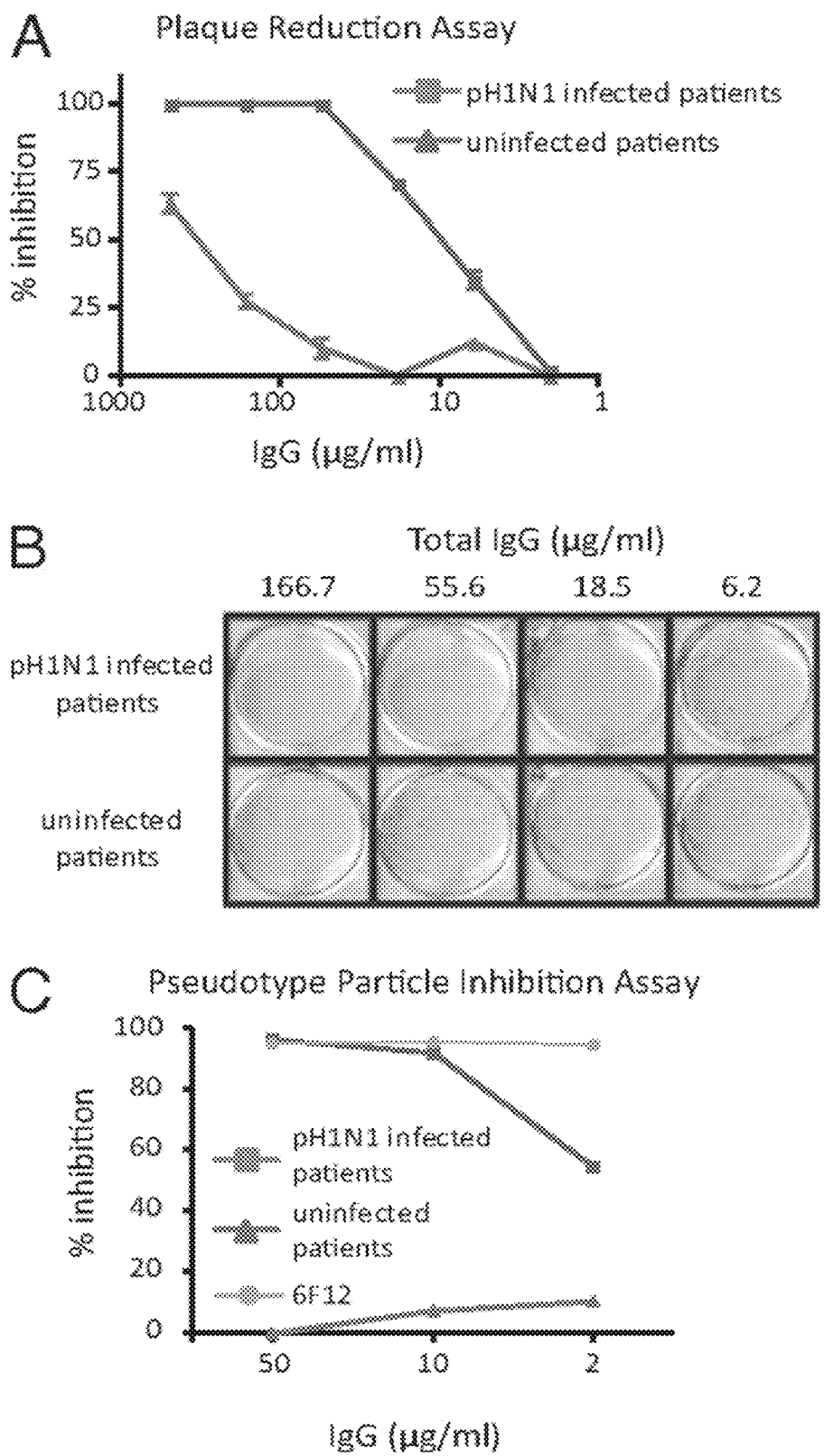

FIG. 28 shows that adult patients infected with pandemic H1N1 virus have high titers of neutralizing antibodies that are specific for the HA stalk (A and B). Sera from pH1N1-infected (n=14) and adults not infected with pH1N1 (n=5) were pooled separately, and total IgG from both pools was purified. Neutralizing capability of stalk antibodies was assessed by plaque reduction assay using cH9/1 N3 virus. Data points represent the mean and SE of two experiments. Plaques were immunostained with anti-H9 antibody G1-26. (B) shows plaque reduction of the four dilutions of sera shown along the top. (C) Pseudotype particle neutralization assay measures neutralizing antibody activity of the human-purified IgG preparations (sera from pH1N1-infected adults and adults not infected with pH1N1). Total IgG concentrations were 50, 10, and 2 µg/mL. As a positive control, the stalk-specific monoclonal antibody 6F12 was used.

Figure 29:
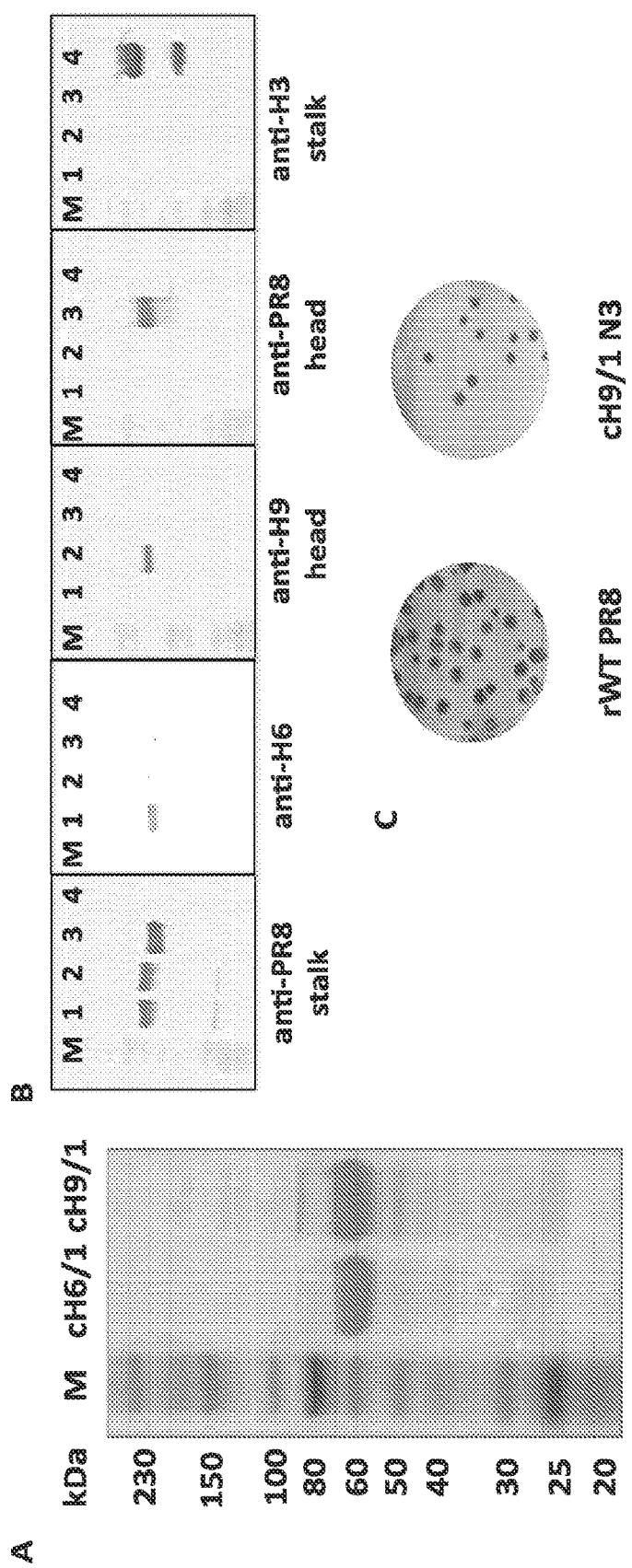

FIG. 29 shows expression and function of cH6/1 and cH9/1 protein. A) Coomasie gel of 2 µg cH6/1 and cH9/1 protein. M, marker proteins. (B) Western blot analysis of baculovirus expressed cHA proteins. Lane 1, cH6/1 protein; lane 2, cH9/1 protein; lane 3, WT PR8 HA; lane 4, WT H3 HA. Blots were probed with antibodies known to react with the stalk of PR8 virus (rabbit polyclonal anti-HA2) or H3 viruses (mouse mAb 12D1) and the globular head of H6 (goat polyclonal anti-H6) or H9 viruses (mouse mAb G1-26) to confirm the identity of baculovirus expressed cHAs. mAb 12D1 reacts with both HA0 and HA2 (H3 protein preparation is cleaved, resulting in two distinct bands). (C) Plaque assay of cH9/1 N3 reassortant virus. Reassortant cH9/1 N3 virus plaque phenotype is similar to plaques made by WT PR8 virus. Plaques were immunostained with PY102 and anti-H9 antibody G1-26.

Figure 30:
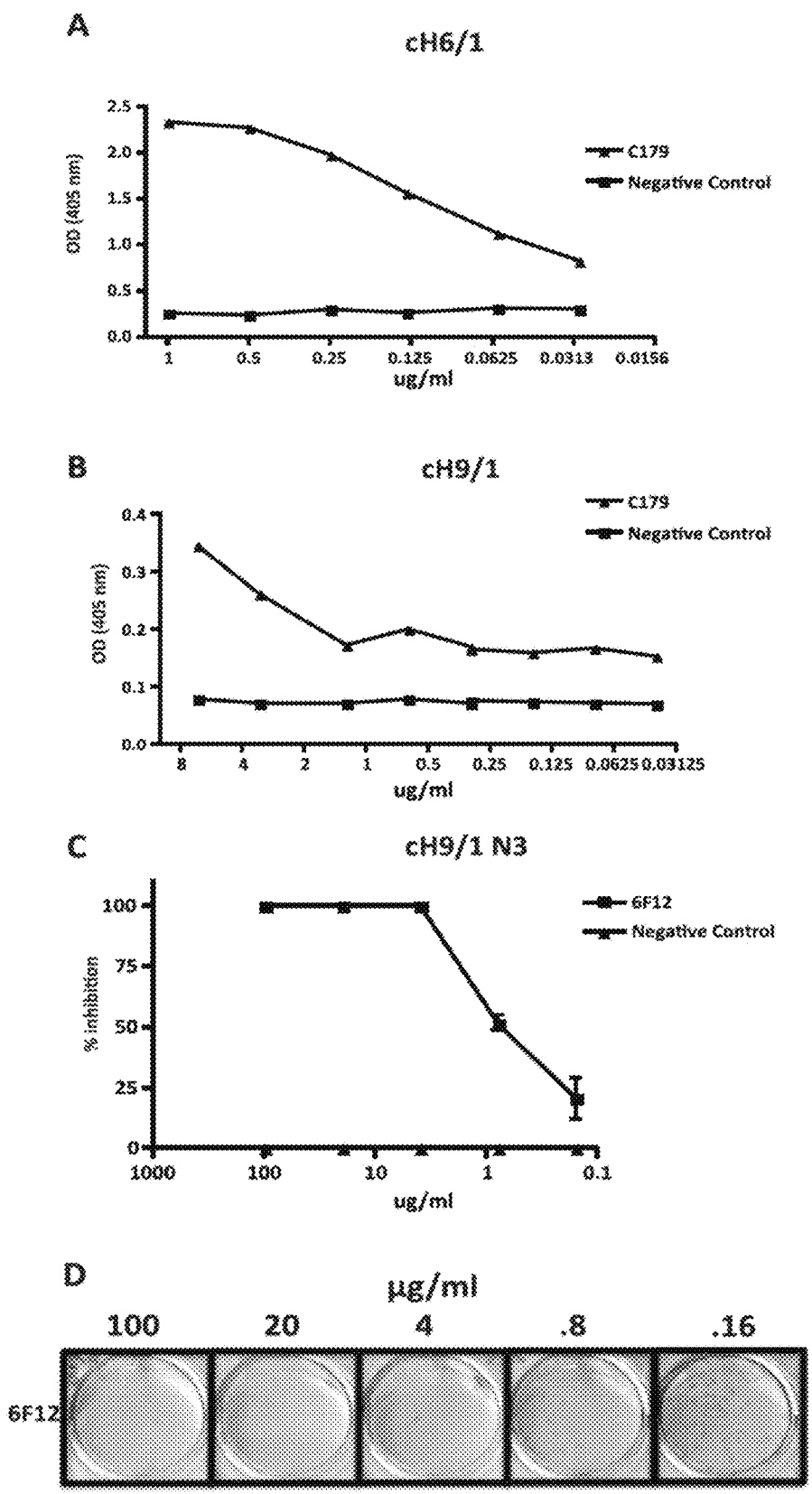

FIG. 30 shows that monoclonal antibodies directed against the stalk of influenza virus HA bind and neutralize cHAs. (A) Stalk antibody C179 was used to test reactivity to cH6/1 baculovirus-expressed protein by ELISA. C179 reacted with cH9/1 in a dose-dependent manner. (B) Stalk antibody C179 was used to test reactivity to cH9/1 baculovirus-expressed protein by ELISA. C179 reacted with cH9/1 in a dose-dependent manner (C and D). Antibody 6F12 neutralizes cH9/1 N3 virus replication. 6F12 was used to assess the ability of stalk-specific monoclonal antibodies to neutralize cH9/1 N3 virus by plaque reduction assay. D shows plaque reduction of cH9/1 N3 virus using five dilutions of mAb 6F12 (100, 20, 4, 0.8, and 0.16 µg/mL). Plaques were immunostained with anti-H9 antibody G1-26.

Figure 31:
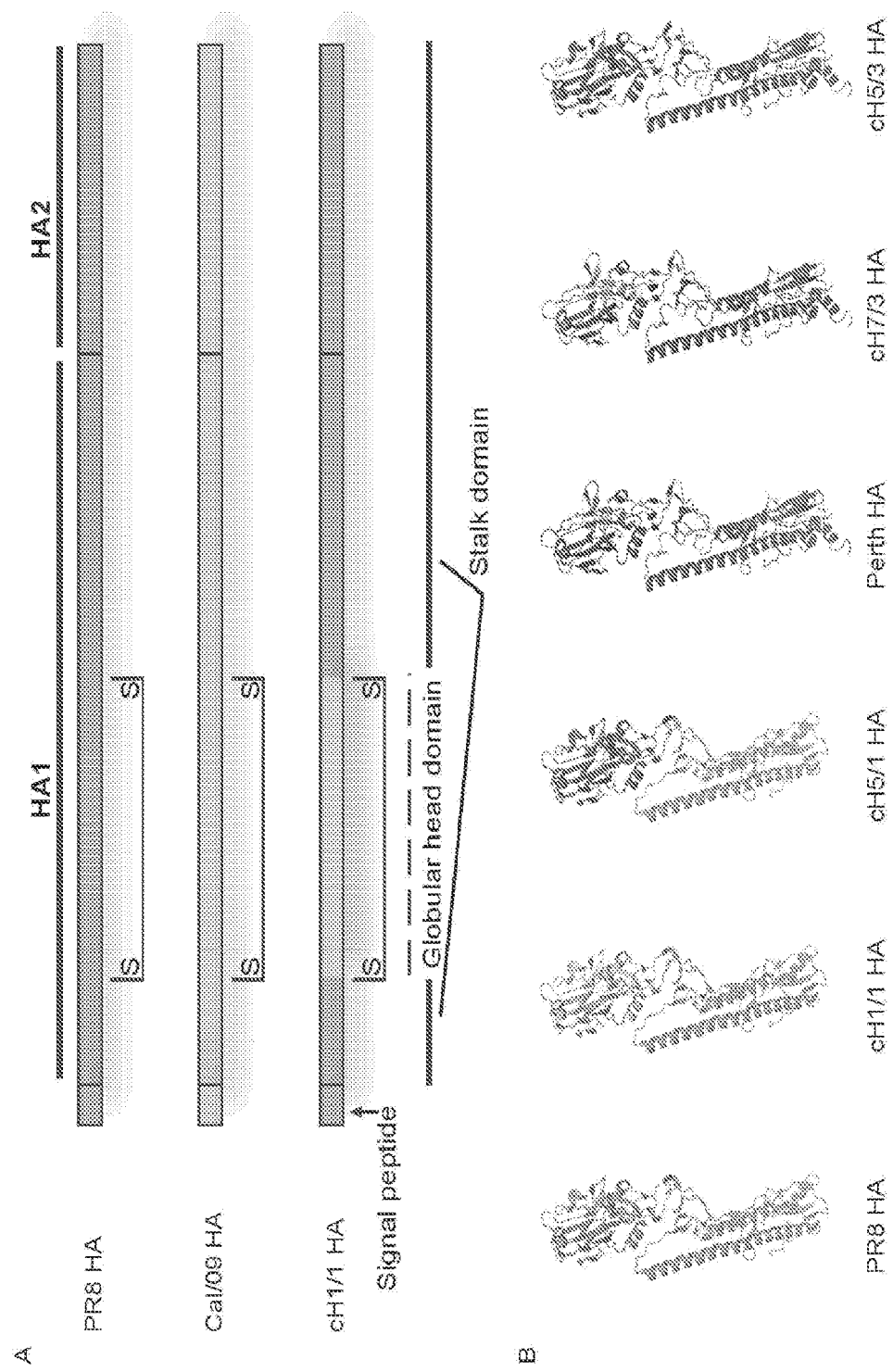

FIG. 31 depicts schematics of chimeric hemagglutinins FIG. 31A shows a diagram of wild-type and cH1/1 viruses. The chimeric HA was constructed by swapping the globular head domain located between Cys52 and Cys277 of PR8 (H1) HA with that of the A/California/4/09 (H1) HA. The resulting chimeric HA has the stalk region of A/PR8/34 (H1) HA with a globular head domain of the A/California/4/09 (H1) HA and is designated as cH1/1. FIG. 31B shows theoretical schematics of the folded structures of the different wild type and chimeric HAs. From left to right: wild type PR8 HA, the chimeric cH1/1 HA, the chimeric cH5/1 HA, the wild type Perth HA, the chimeric cH7/3 HA, and the chimeric cH5/3 HA.

FIG. 32 depicts a table comparing amino acid identity between H1, H3, H5 and H7 HAs used in this study. Percent amino acid identity was calculated using ClustalW (excluding the signal peptide). Percent amino acid identity is compared for full length HA, as well as the globular head and stalk domains. Grey bars indicate 100% identity.

Figure 33:
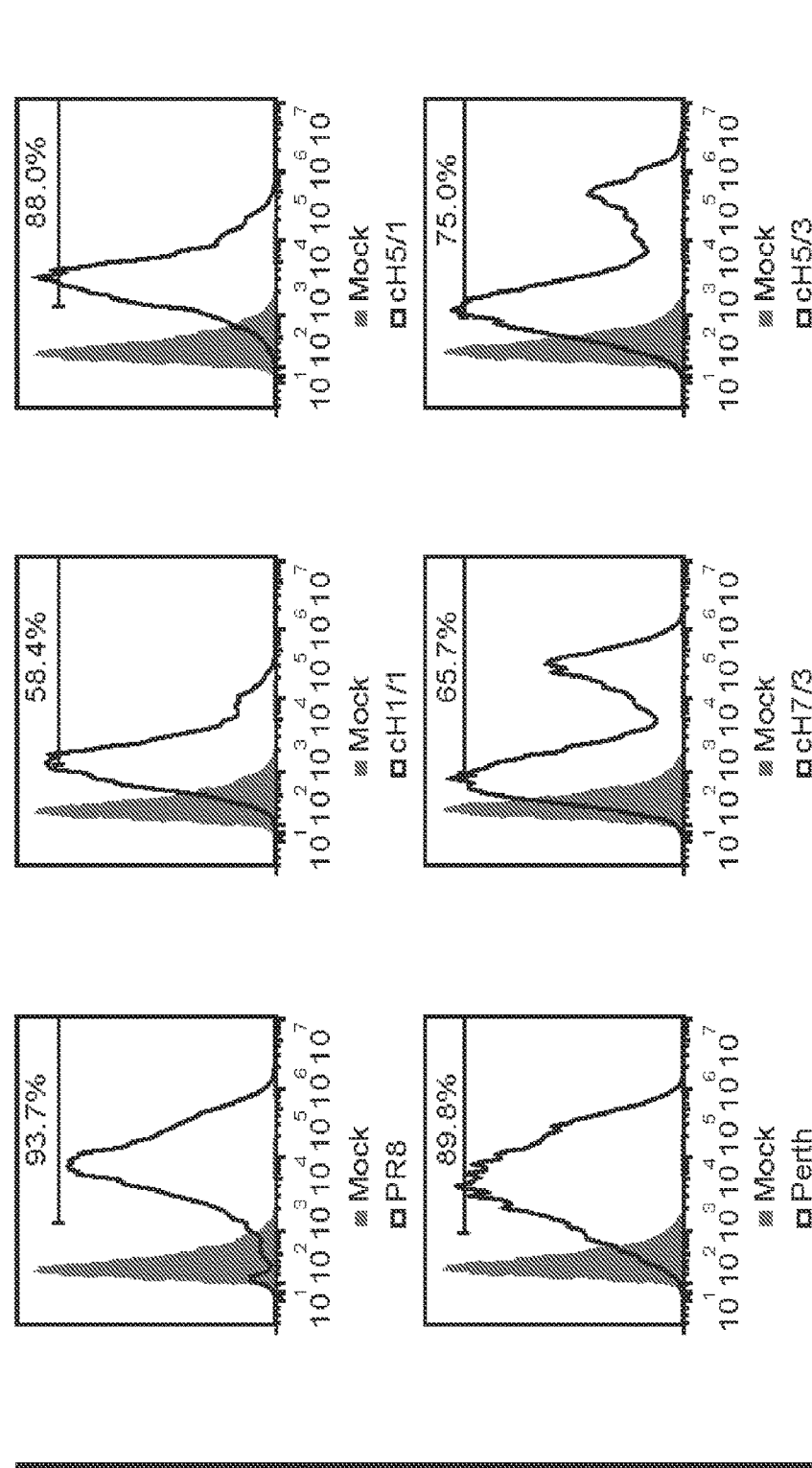

FIG. 33 shows the surface expression of chimeric HA constructs. Surface expression of chimeric HA constructs was evaluated in transiently transfected or infected cells. At 48 h post-transfection, 293T cells were trypsinized and cell surface expression of chimeric HA proteins were analyzed by flow cytometry. In the upper panels, mock-transfected cells (grey) are compared to cells transfected with PR8 HA (black line) or cells transfected with cH1/1 (black line) or cH5/1 (black line). In the center panels, mock-transfected cells (grey) are compared to cells transfected with Perth/09, cH7/3 (black line) and cH5/3 constructs (black line). In the bottom panels, MDCK cells were infected with Perth/09, cH7/3 and cH5/3 expressing recombinant viruses. At 12 h post-infection the cell surface expression of the different HAs were analyzed using flow cytometry.

Figure 34:
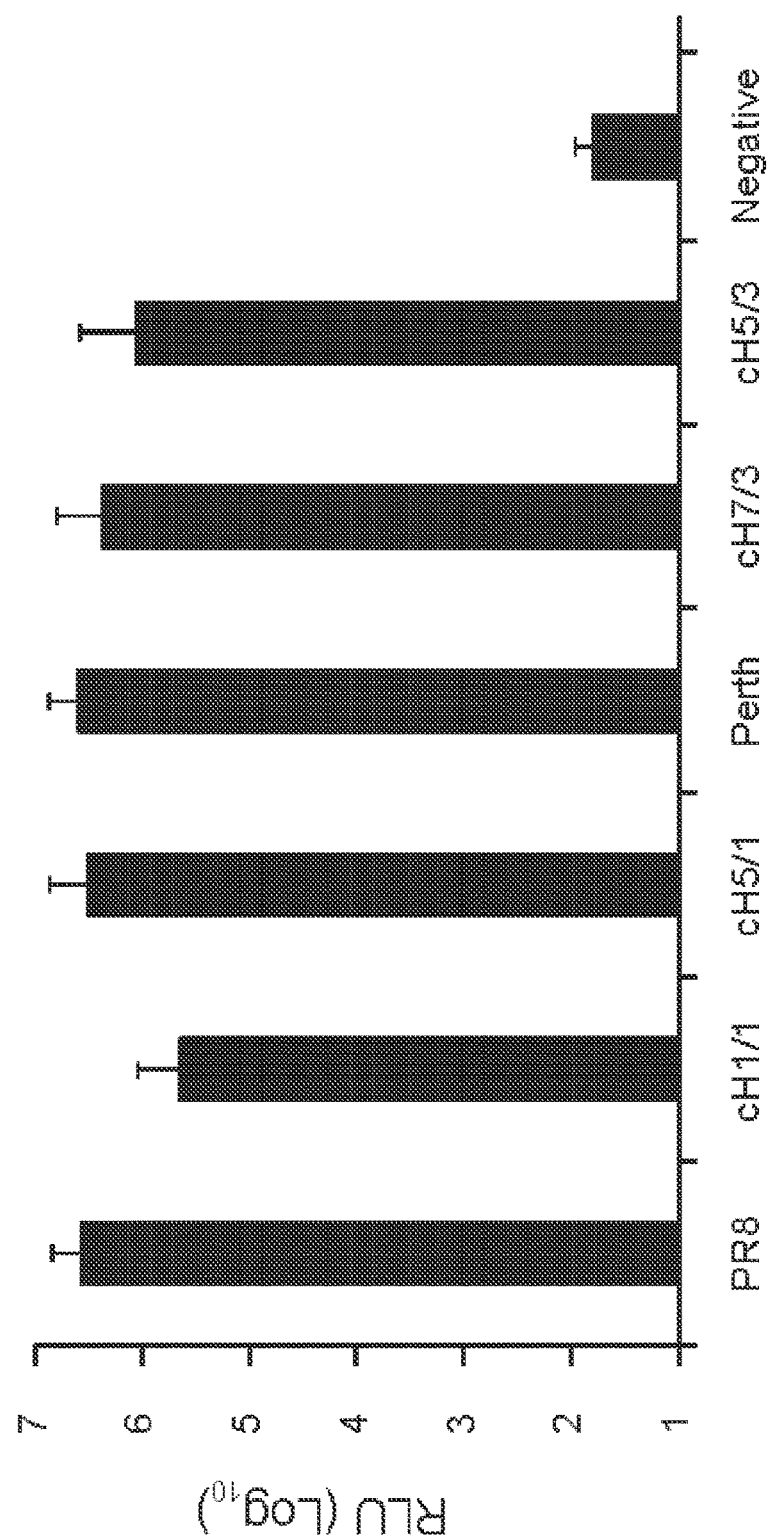

FIG. 34 demonstrates the ability of the chimeric HAs to enter MDCK cells. Luciferase-encoding pseudoparticles expressing chimeric HAs were used to transduce MDCK cells. The relative light units (RLU) generated in the luciferase assay indicates that pseudoparticles expressing chimeric HAs are able to enter cells.

Figure 35:
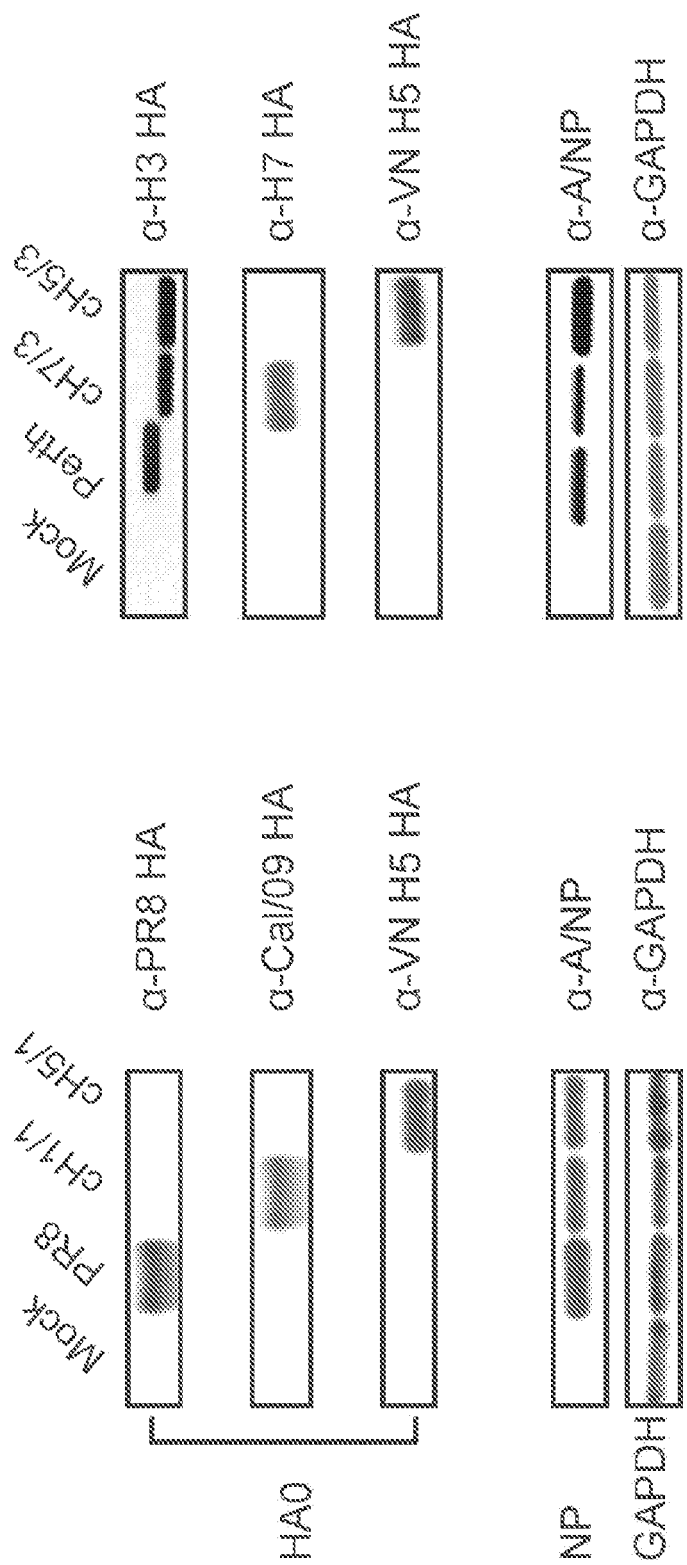

FIG. 35 shows a Western blot analysis of cells infected with the recombinant cHA-expressing viruses. Extracts from MDCK cells mock infected or infected with the indicated viruses at an MOI of 2 were prepared and probed with antibodies at 16 hpi: anti-A/PR8/HA (H1) (PY102), anti-A/Cal/09/HA (H1) (29E3), anti-A/VN/HA (H5) (mAb #8), anti-H3/HA (12D1), anti-H7 (NR-3152), anti-A/NP (HT103) and anti-GAPDH as an loading control.

Figure 36:
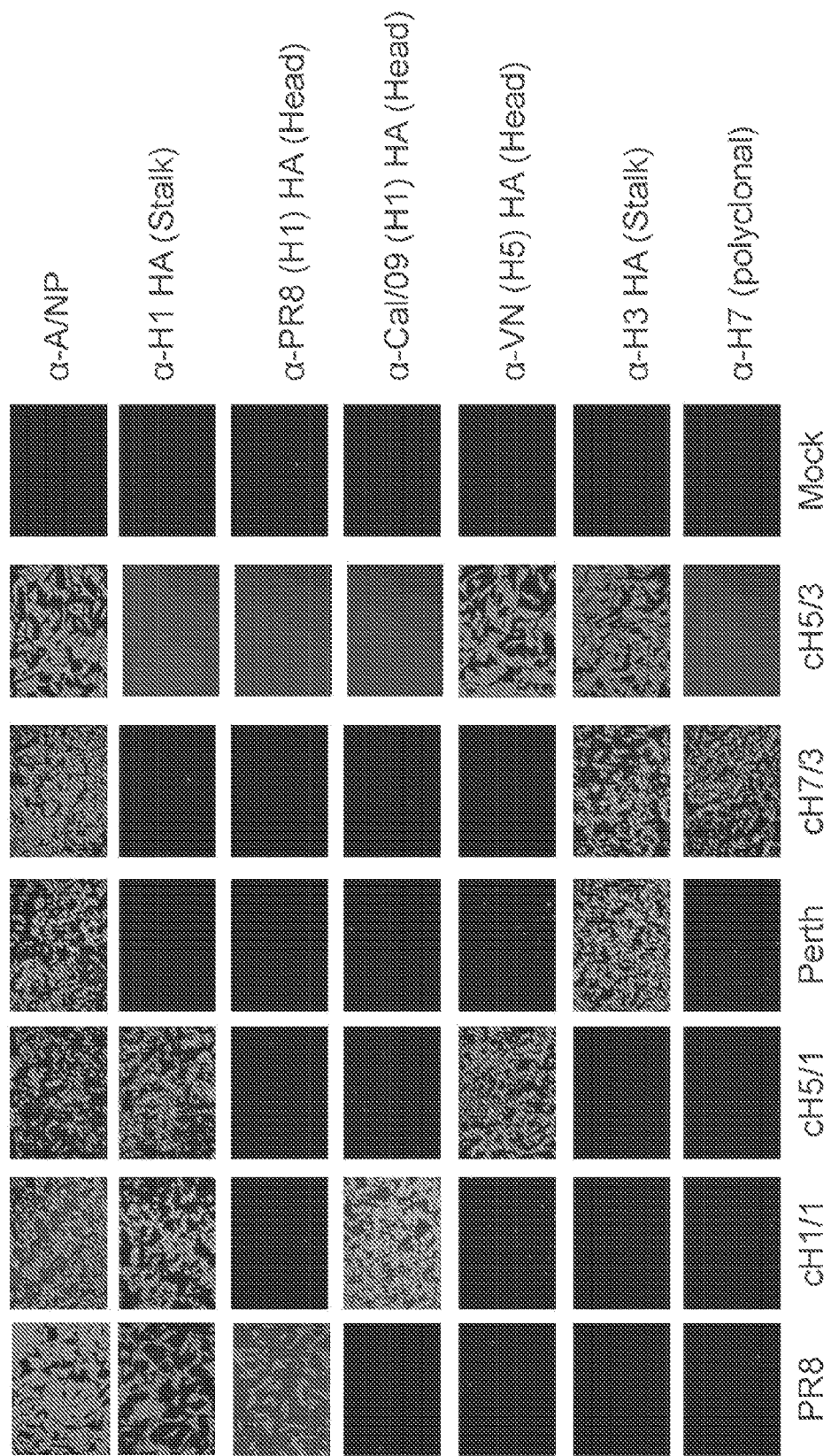

FIG. 36 depicts an immunofluorescence analysis of MDCK cells infected with recombinant viruses using antibodies: anti-A/NP (HT103), anti-A/H1 HA (6F12), anti-A/PR8/HA (PY102), anti-A/Cal/09/HA (29E3), anti-A/VN/HA (mAb #8), anti-H3/HA (12D1), and anti-A/H7 virus (NR-3152).

FIG. 37 depicts the growth kinetics and plaque phenotypes of wild type and recombinant viruses. (A) 10-day old embryonated chicken eggs were infected with 100 pfu per egg of wild-type or recombinant virus and viral growth was monitored for 72 hours post infection. Data points represent the average and standard deviation of experimental replicates. (B) The plaque phenotypes of recombinant viruses were assessed by plaque assay. MDCK cells were infected with either a wild-type or recombinant virus. Cells were fixed 48 hours post infection and immunostained to reveal plaque phenotypes using the antibody against A/NP (HT103).

Figure 38:
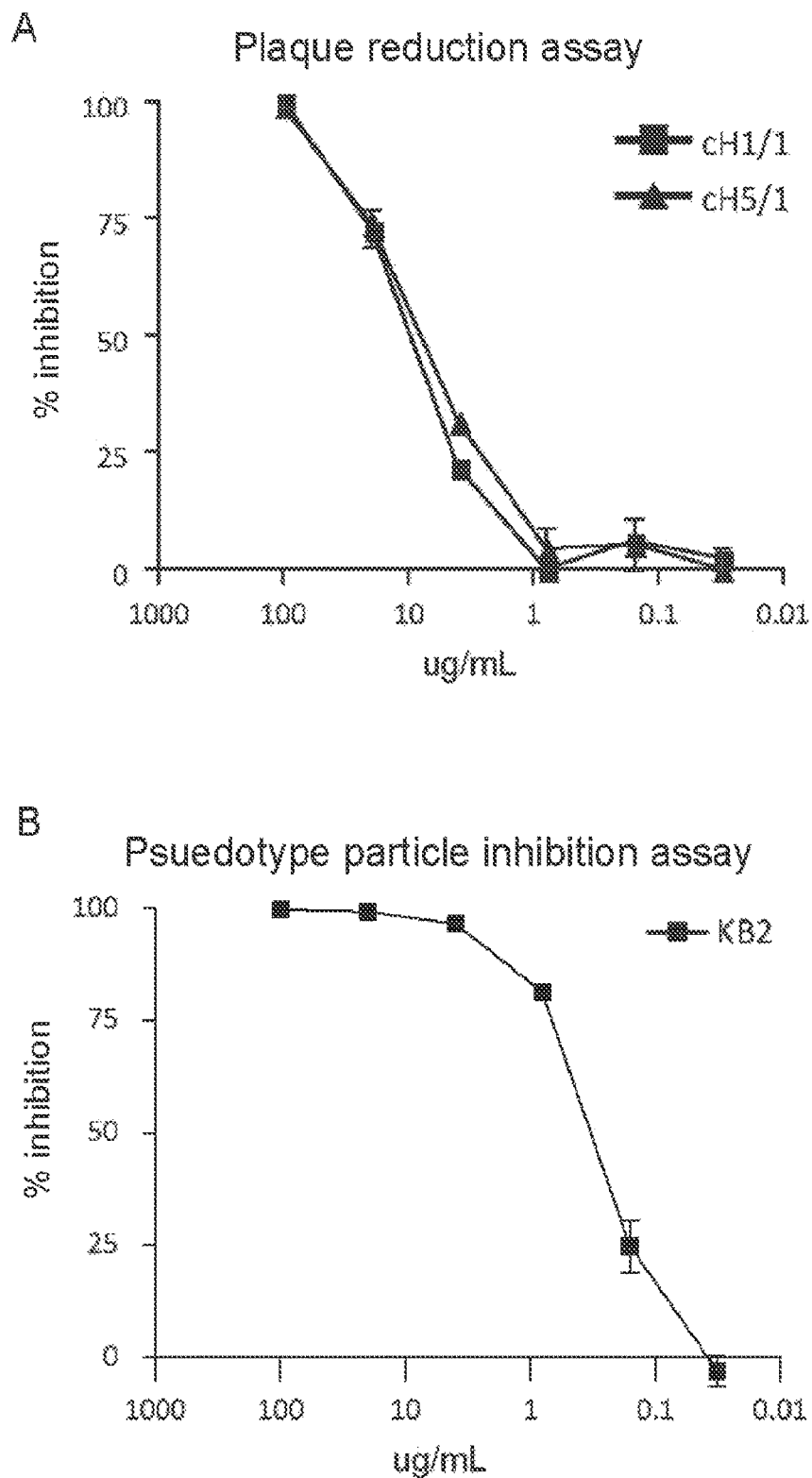

FIGS. 38A-38B depict that stalk-specific monoclonal antibody neutralizes cHA-expressing viruses and pseudotype particles. The ability of a mAb (KB2) to neutralize cHA-expressing viruses or pseudotype particles was assessed by plaque reduction assay or pseudotype particle inhibition assay. MDCK cells were infected or transduce with cHA-expressing viruses or pseudotype particles in the presence of the indicated amount (ug/mL) of the mAb or without antibody. Plaque formation or luciferase activity was used as a readout to determine the degree of inhibition by the mAb. (FIG. 38A) The mAb neutralizes cH1/1 (black boxes) and cH5/1 (black triangles) virus replication in a dose dependent manner, with 100% inhibition at concentrations above 100 ug/mL. Data points represent the average and standard deviation of experimental replicates. (FIG. 38B) The mAb also inhibits entry of cH1/1 (black boxes) pseudotype particles in a dose dependent manner, with complete inhibition above 4 ug/mL. Data points represent the average and standard deviation of experimental replicates. The pseudotype inhibition assays were processed independently.

Figure 39:
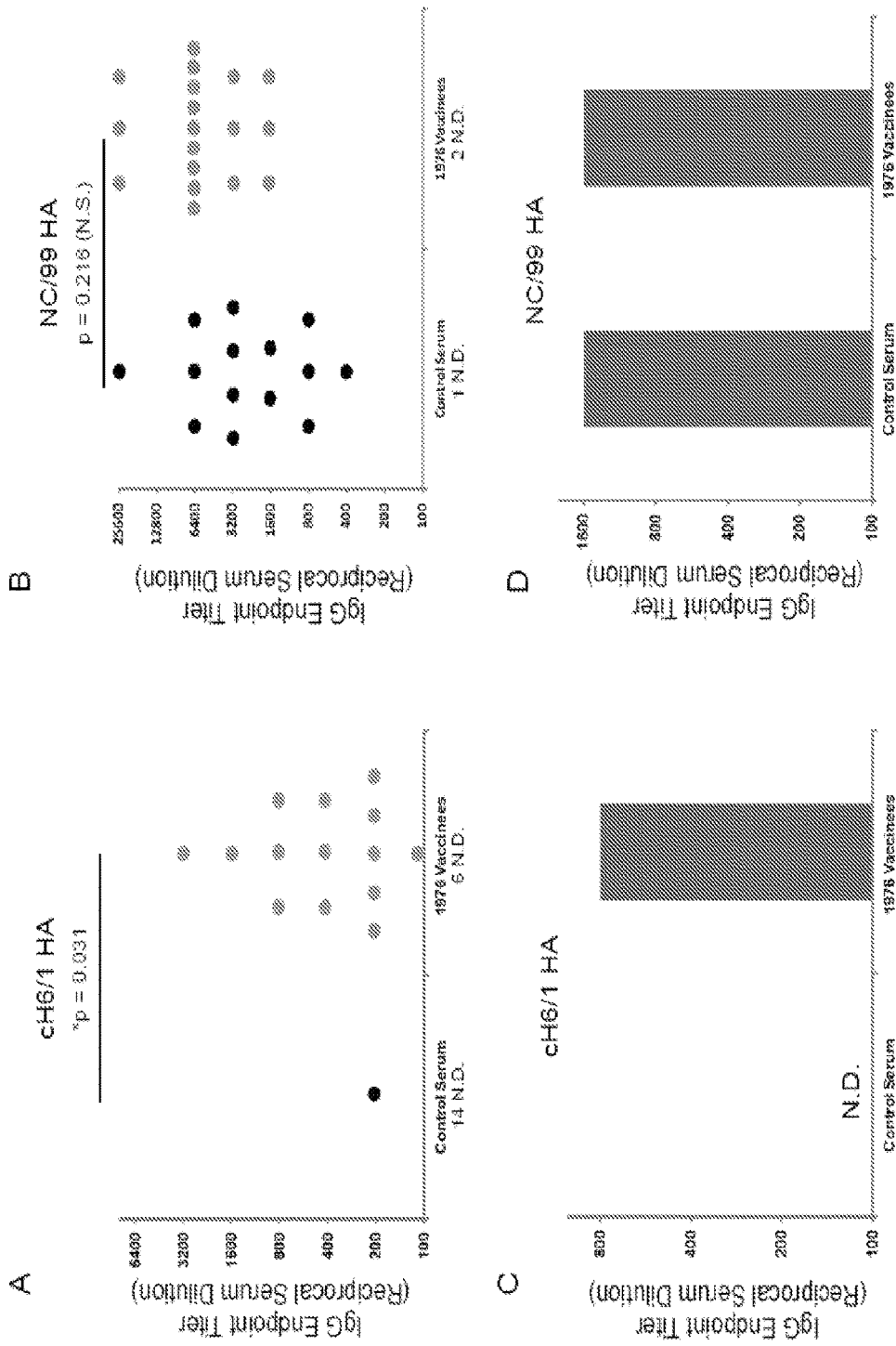

FIG. 39 demonstrates that NJ/76 vaccine recipients had elevated anti-HA stalk antibodies prior to Cal/09 vaccination. Serial dilutions of serum from NJ/76 vaccinees (n=20) or age-matched control subjects (n=15) were tested for their reactivity to A) cH6/1 HA or B) NC/99 HA by ELISA and IgG endpoint titers were calculated. Due to limited quantities of available serum, pre-Cal/09 vaccination IgG endpoint titers were also determined for pooled NJ/76 vaccinees (N=5) and control subjects (n=7) against C) cH6/1 and D) NC/99. Each pool consisted of all individuals from each group for whom both pre- and post-Cal/09 vaccination samples were available. Unpaired Student T-tests were performed and two-tailed p-values <0.05 were considered statistically significant. N.D.=not detected. N.S=not significant. *statistically significant.

Figure 40:
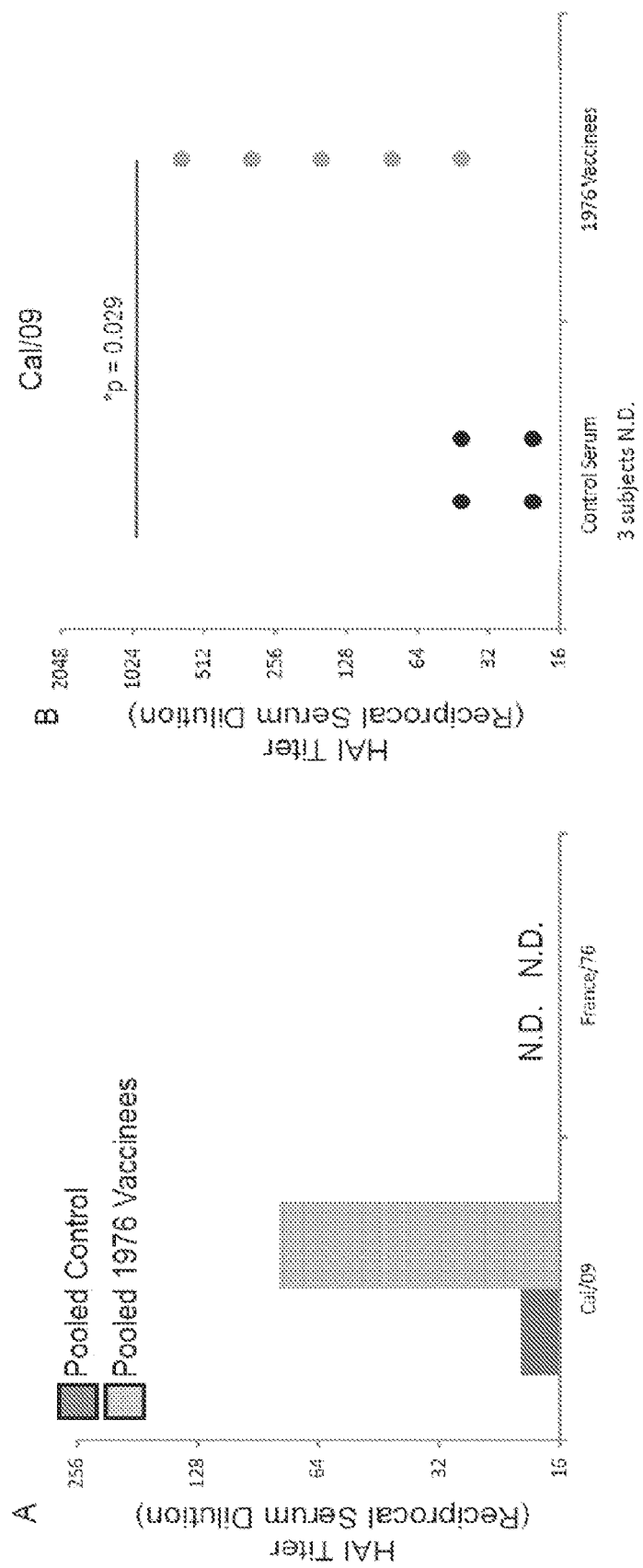

FIG. 40 demonstrates that NJ/76 vaccine recipients had elevated HAI titers against Cal/09 prior to Cal/09 vaccination. A) HAI titers were determined for pre-Cal/09 vaccination pooled serum samples from NJ/76 vaccinees (n=5) and control subjects (n=7) against Cal/09 and France/76 using cRBCs. B) HAI assays against Cal/09 were also performed using serum samples corresponding to the individual subjects from within each pool in order to ensure that the pooled results were representative of the group as a whole. Unpaired Student T-tests were performed and two-tailed p-values<0.05 were considered statistically significant. N.D.=not detected. *statistically significant.

Figure 41:
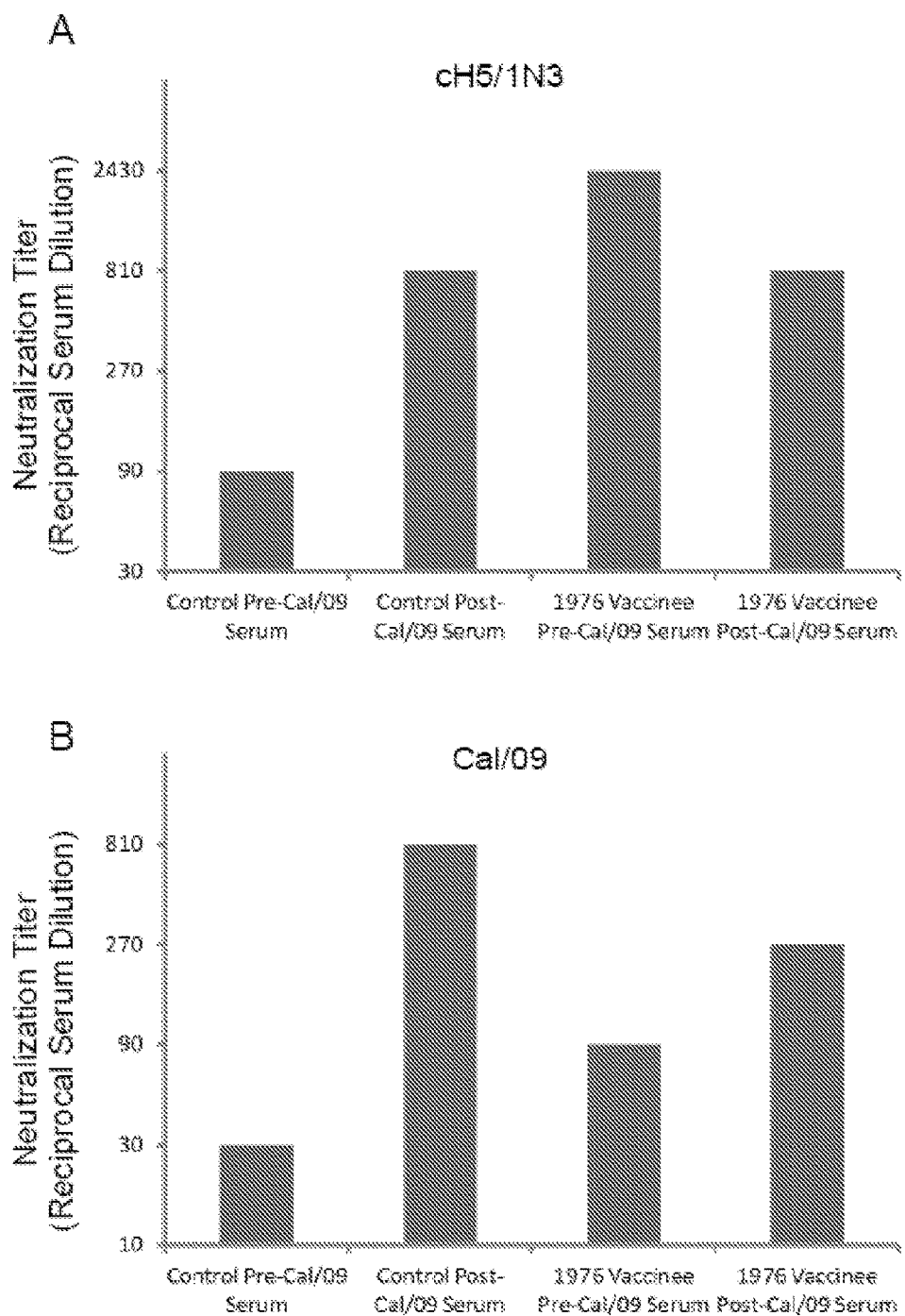

FIG. 41 demonstrates that NJ/76 and Cal/09 vaccines boosted broadly-neutralizing antibodies. Microneutralization assays were performed on MDCK against A) cH5/1 N3 and B) Cal/09 virus using TPCK-trypsin-treated, pooled serum samples collected from NJ/76 vaccinees (n=5) and control subjects (n=7) before and after Cal/09 vaccination. Following infection, cells were stained with an anti-NP antibody and an HRP-conjugated secondary antibody. Neutralization titers were defined as the lowest serum dilution that resulted in at least 50% reduction in specific signal.

Figure 42:
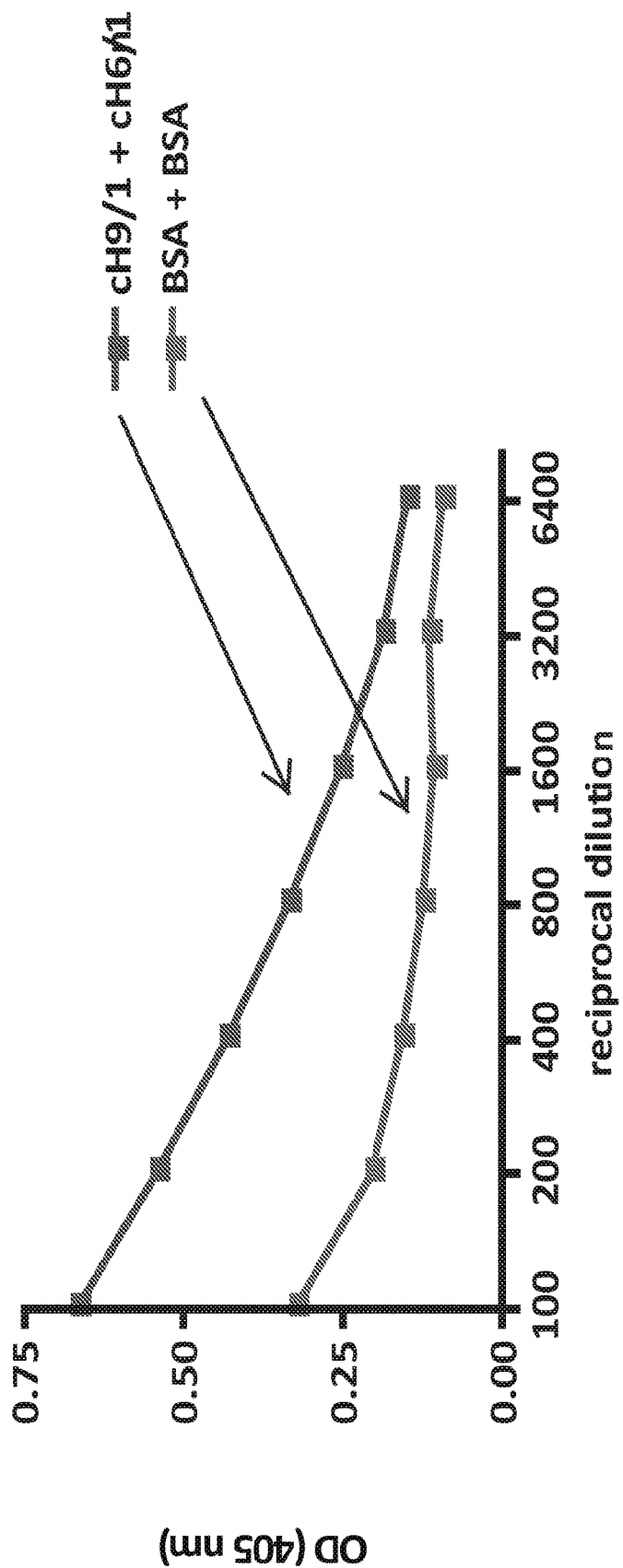
Figure 42B:
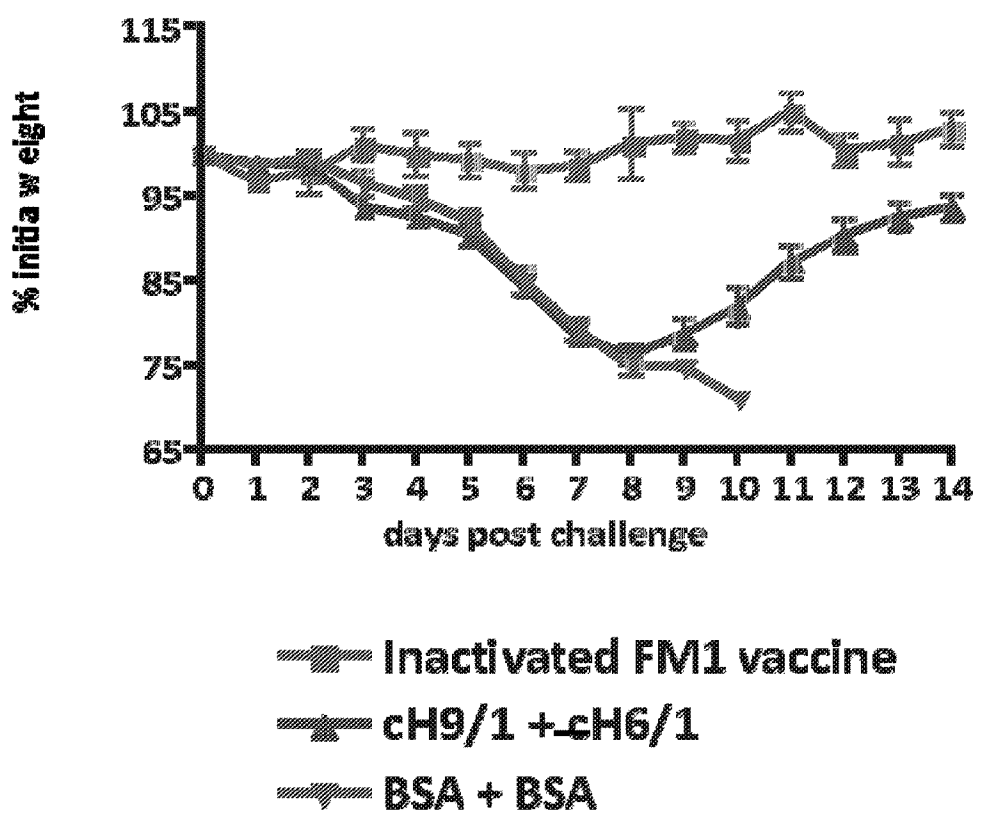
Figure 42:
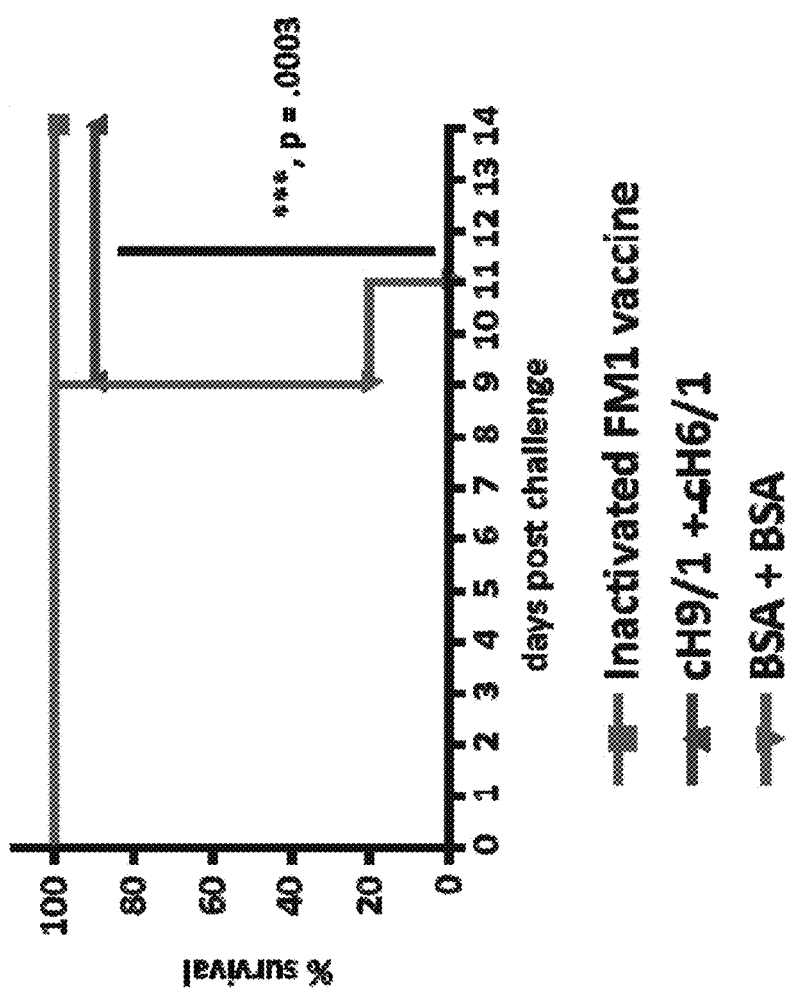

FIG. 42 demonstrates that sequential vaccination with cHA constructs elicits HA stalk-specific antibodies and provides protection from lethal challenge. Mice were primed with 20 μg of cH9/1 protein, administered with adjuvant intranasally and intraperitoneally. Three weeks later, mice were boosted with 20 μg cH6/1 protein, administered with adjuvant intranasally and intraperitoneally. As controls, mice were primed and boosted in a similar fashion using BSA, or given inactivated FM1 virus intramuscularly. Animals were bled and challenged three weeks after the last vaccination with 5LD50 of A/Fort Monmouth/1/1947 (FM1) virus. (A) ELISA plates were coated with cH5/1 N1 virus in order to assess the degree of stalk reactivity elicited through vaccination. (B) Mice were weighed daily for 14 days to assess protection from challenge. (C) Kaplan Meier curve depicting survival rate post challenge. cH9/1+cH6/1 vaccinated mice had a statistically higher survival rate compared to BSA controls (p=0.0003)

FIG. 43 demonstrates that vaccination with cH6/1 elicits stalk-specific immunity that mediates protection from cH9/1 N1 viral challenge. Animals were inoculated with YAM-HA virus in order to simulate prior infection with or vaccination against influenza virus. Three weeks later, animals were vaccinated with cH6/1 or BSA with adjuvant, intranasally and intraperitoneally. Control animals were inoculated with wild-type B/Yamagata/16/1988 and vaccinated in a similar fashion with BSA, or given inactivated cH9/1 N1 virus intramuscularly. Animals were bled and challenged with 250LD$_{50}$ cH9/1 N1 virus three weeks after vaccination. (A) Animals were weighed for 8 days in order to assess protection from challenge. On days 3-5, YAM-HA+cH6/1 animals demonstrated statistically less weight loss compared to the YAM-HA+BSA cohort (p<0.05). (B) Kaplan Meier curve depicting survival. Statistically different survival rates were seen in the YAM-HA+cH6/1 group compared to the YAM-HA+BSA cohort (p=0.038), as well as naïve and WT YAM+BSA animals (p<0.0001). Survival rate of YAM-HA+BSA cohort was not statistically different from that of the WT-YAM+BSA cohort (p=0.058). (C) ELISA plates were coated with cH5/1 N1 virus in order to assess the degree of stalk reactivity elicited through vaccination. (D) Results of a plaque reduction assay using the cH5/1 virus are depicted. (E) Animals were vaccinated, bled and total IgG was harvested for H5-based pseudoparticle entry inhibition assay. Percent inhibition was assessed as a decrease in luciferase expression compared to controls.

FIG. 44 demonstrates that vaccination with cH6/1 protects mice from lethal H5 influenza virus challenge. Animals were inoculated with YAM-HA virus in order to simulate prior infection with or vaccination against influenza virus. Three weeks later, animals were vaccinated with cH6/1 or BSA with adjuvant, intranasally and intraperitoneally. Control animals were inoculated with wild-type B/Yamagata/16/1988 and vaccinated in a similar fashion with BSA or given inactivated cH5/1 N1 virus intramuscularly. Animals were bled and challenged with 10LD$_{50}$ of the 2:6 H5 reassortant in the PR8 background (see, e.g., Steel et al., 2009, J Virol 83:1742-1753). (A) Kaplan Meier curve depicting survival. Differences in survival rates approached statistical significance when comparing the YAM-HA+cH6/1 group to the YAM-HA+BSA cohort (p=0.06). (B) Length of survival was on average longer in animals inoculated with YAM-HA and vaccinated with cH6/1 than animals vaccinated with BSA (p=0.037), as well as naïve and WT YAM/BSA controls (p<0.001). (C) ELISA plates were coated with cH5/1 N1 virus in order to assess the degree of stalk reactivity elicited through vaccination. 1:50 serum dilutions were plotted against % maximum weight loss. One value was determined to be an outlier and was omitted from analysis. For linear regression, $R^2$=0.56 and p=0.02.

FIG. 45 demonstrates that vaccination with cHA elicits stalk-specific immunity that mediates protection from H1N1 virus challenge. (A-F) Animals were primed with DNA encoding cH9/1 and then were vaccinated with cH6/1 and boosted with cH5/1 soluble protein (n=10) or BSA (n=5), while positive control mice received inactivated virus intramuscularly (n=5). (A) Animals were vaccinated and challenged with FM1 virus; mice were weighed daily, and weight loss over time is shown as change in percentage of initial weight. (B) Graph depicting survival of challenged mice in (A). (C) Animals were vaccinated and challenged with pH1N1 virus; mice were weighed daily, and weight loss over time is shown as change in percentage of initial weight. (D) Graph depicting survival of challenged mice in (C). (E) Animals were vaccinated and challenged with PR8 virus; mice were weighed daily, and weight loss over time is shown as change in percentage of initial weight. (F) Graph depicting survival of challenged mice in (E). (G) Reactivity to H1 HA of serum from animals vaccinated as described above in A-F and below in H-I and challenged with 5 LD$_{50}$ of A/FM/1/1947 (A, B), 10 LD$_{50}$ of A/Netherland/602/2009 (C, D), or 5 LD$_{50}$ of A/PR/8/1934 (E, F, H, I). (H) Animals were vaccinated as described above in A-F (square, n=4) or were naive (triangle, n=3), while positive control mice received inactivated PR8 virus intramuscularly (X mark, n=5). CD8 T cells were depleted prior to challenge with PR8 virus. Mice were weighed daily, and weight loss over time is shown as change in percentage of initial weight. (I) Graph depicting survival of challenged mice in (H). (J) Animals were vaccinated as described for A-F. Total IgG was purified for use in H2-based pseudoparticle entry inhibition assay. Percent inhibition was assessed as a decrease in luciferase expression compared to controls. Fab fragment CR6261 was used as a positive control.

Figure 46:
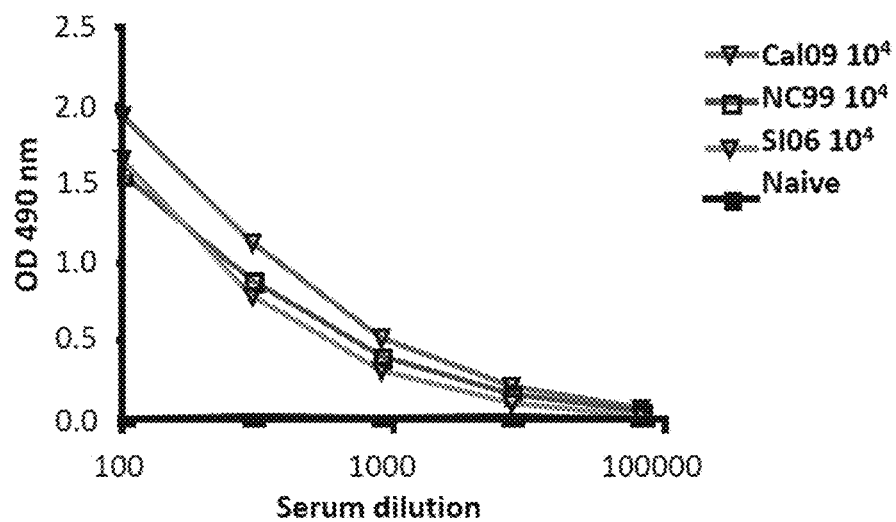

FIG. 46 demonstrates that hemagglutinin stalk antibodies are produced following replicative infection. Animals were infected with 10$^4$ PFU of A/California/04/09 (Cal09), A/New Caledonia/20/99 (NC99), or A/Solomon Islands/3/06 (SI06) virus. Sera were harvested from mice four weeks after infection and hemagglutinin stalk-specific antibodies were assayed by ELISA using cH6/1 protein.

Figure 47:
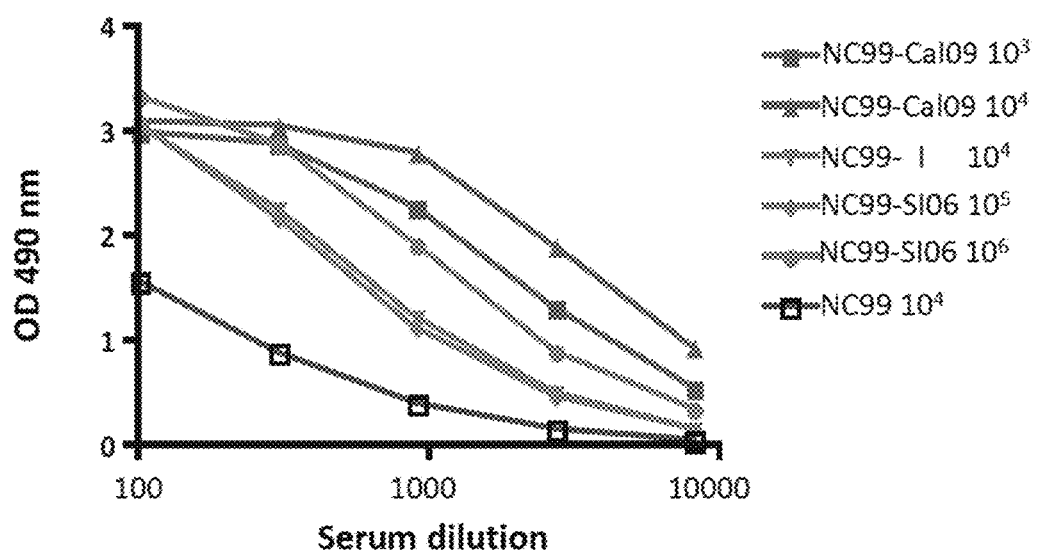

FIG. 47 demonstrates that hemagglutinin stalk antibodies are boosted following a second exposure to influenza virus. Animals were infected with 10$^4$ PFU of NC99 and then boosted four weeks later with 10$^5$ or 10$^6$ PFU of SI06 virus or 10$^3$ or 10$^4$ PFU of Cal09 virus. Sera were harvested from mice four weeks after the second infection and hemagglutinin stalk-specific antibodies were assayed by ELISA using cH6/1 protein. Values shown in FIG. 46 for animals that only received one inoculation of NC99 virus were included to serve as a comparison.

Figure 48:
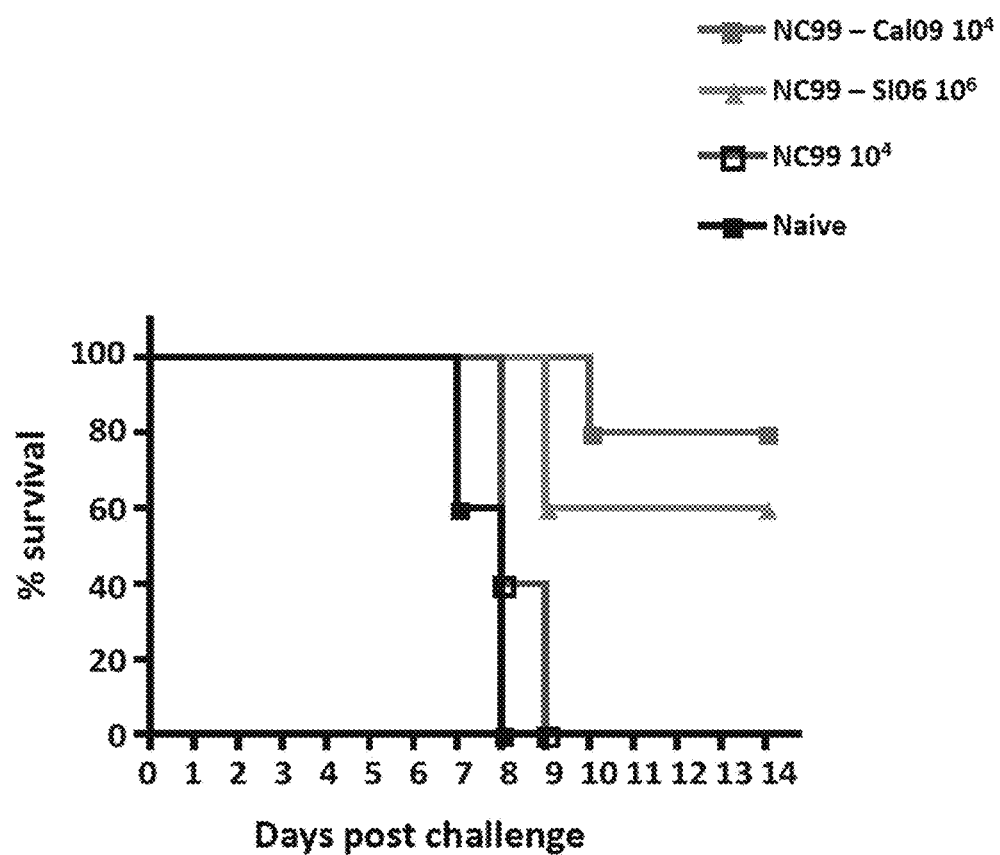

FIG. 48 demonstrates that serum from sequentially infected mice protects naive animals from lethal H5 virus challenge. Animals were infected with 10$^4$ PFU of NC99 and then boosted four weeks later with 10$^6$ PFU of SI06 or 10$^4$ PFU of Cal09 virus. Serum collected from these animals was transferred intraperitoneally to naïve animals that were challenged with a lethal dose of recombinant H5 virus. Animals that received serum from animals that only experienced one NC99 infection were not protected from challenge and died with similar kinetics to controls. Serum from animals exposed to NC99 and SI06 viruses protected 60% of challenged animals, while serum from animals infected with NC99 and Cal09 viruses protected 80% of challenged mice from death. Survival rates between NC99-SI06 and NC99-Cal09 groups were similar (p=0.575) whereas differences in survival rates compared to NC99-only groups were statistically significant (NC99-SI06 versus NC99 p=0.018, NC99-Cal09 versus NC99 p=0.0023).

Figure 49:
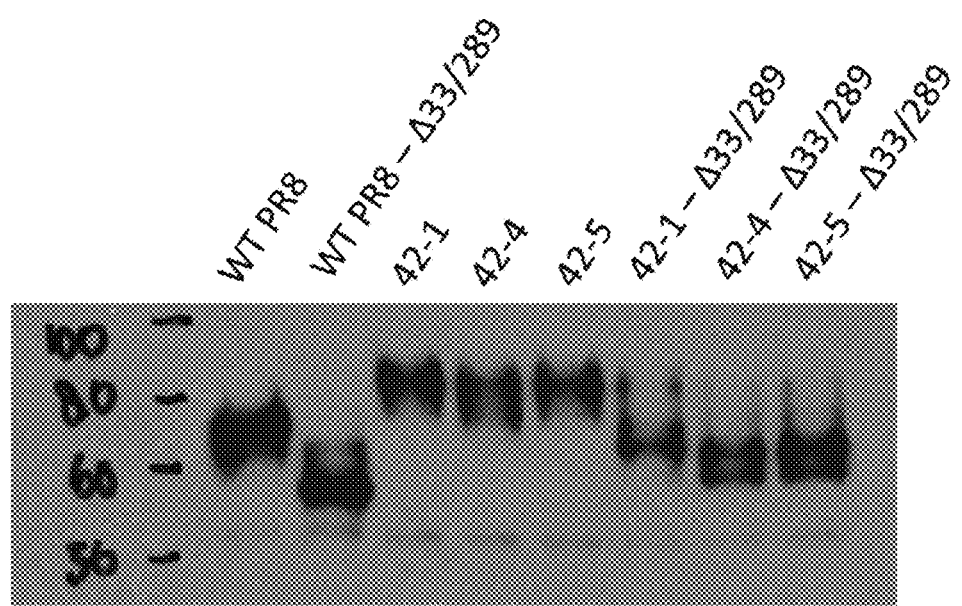

FIG. 49 demonstrates that influenza virus glycosylation mutants are expressed and appropriately glycosylated. 293 T cells were tranfected with wild type A/PR/8/34 HA virus (PR8) or PR8 constructs having glycosylation sites introduced in the PR8 head domain and/or glycosylation sites removed by mutation from the PR8 stalk domain. Western blot analysis was performed with NR-4539 anti-influenza A virus HA2 antibody and visualized with an anti-mouse horseradish peroxidase conjugated secondary antibody. Mutant viral proteins having glycosylation sites introduced migrated at a higher molecular weight than wildtype PR8; those having glycosylation sites eliminated migrated at a lower molecular weight that wildtype PR8. All mutant viral proteins migrated at the expected molecular weight, indicating that glycans had been successfully added or eliminated in vitro at the relevant glycosylation sites. Sites of introduced glycosylation sites are indicated for mutants 42-1, 42-4, and 42-5.

FIG. 50 demonstrates that the addition of glycosylation sites and elimination of glycosylation sites in PR8 has no effect on the expression of the viral proteins or their ability to fold into proper conformation. 293 T cells were transfected with wildtype PR8 or glycosylation mutants of PR8 or cH5/1 hemagglutinin. Twenty-four hours after transfection, cells were fixed and stained with the appropriate anti-head domain (PY 102) or anti-stalk domain (KB2, C179 and 6F12) antibody and incubated with a fluorescent donkey anti-mouse antibody. Fluorescence reactivity was visualized using an inverted fluorescence microscope. (A) Introduction of glycosylation sites in the head domain of PR8 did not effect viral protein expression or stalk antibody (6F12) binding. (B) Immunfluorescent staining of viral proteins in which glycosylation sites had been introduced into the head domain had reduced anti-head antibody binding, indicating that hyperglycosylation of the head domain masked the antibody binding site. There was no change in the binding of anti-stalk domain antibodies that bound conformation epitopes of the stalk domain, indicating that the viral mutants were properly folded. (C) Immunofluorescence of PR8 viral mutants with glycosylation sites introduced into the head domain and eliminated from the stalk domain using anti-head and anti-stalk specific antibodies demonstrated that the proteins were expressed and properly folded. No difference in the ability of anti-stalk antibodies to bind the stalk domain of mutant constructs in which glycosylation sites had been introduced into the head domain (42-1, 42-4 and 42-5) and removed from the stalk domain (Δ33/289) as compared to wildtype PR8 was observed.

Figure 51:
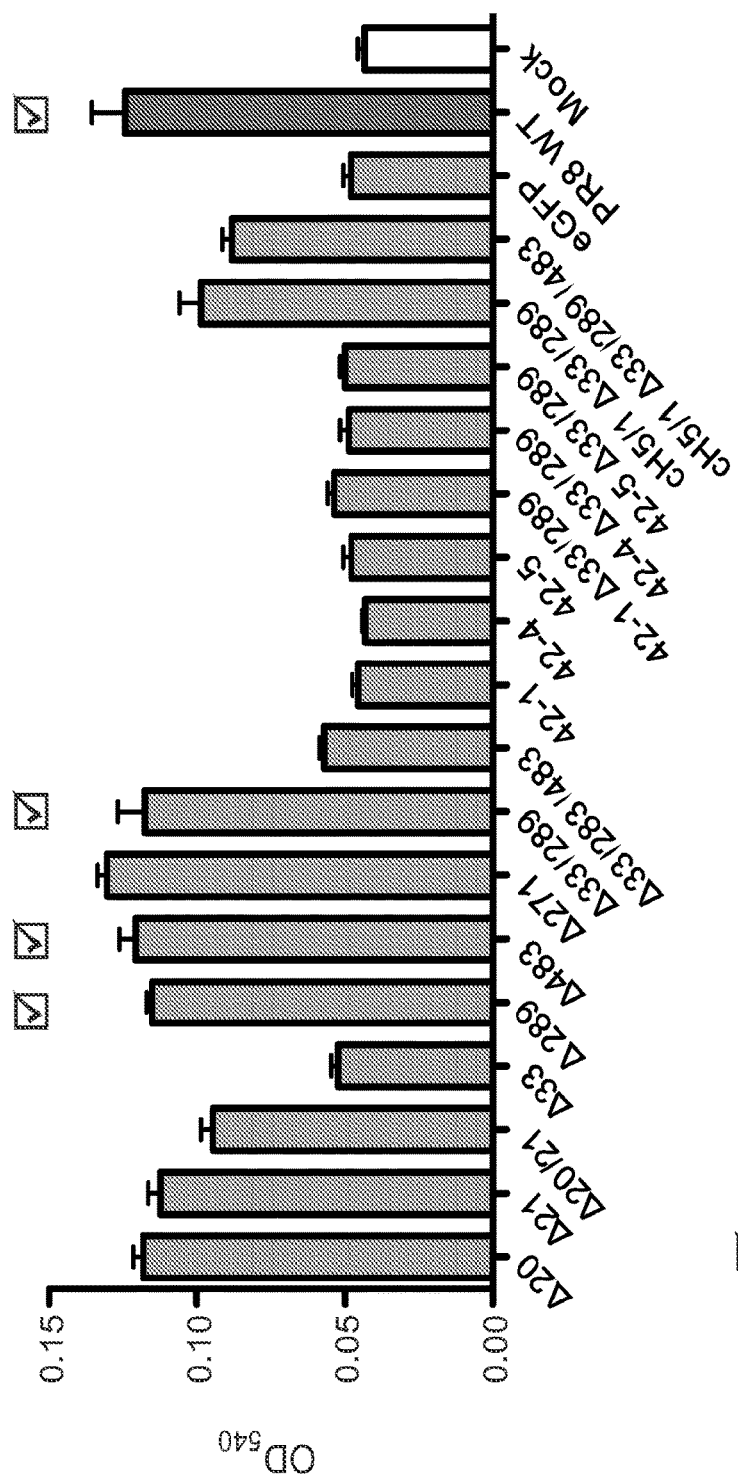

FIG. 51 demonstrates viral glycosylation mutants that can bind sialylated receptors and viable mutant virus rescued. Transfected cells were incubated with neuraminidase (sialidase) at 37° C. for 1 hour, then with a 2% suspension of chicken red blood cells. Attached red blood cells were lysed and absorbance of the lysate measured at 540 nm. To rescue influenza A mutant virus, 293T cells were co-transfected with 1 μg of 8 pDZ PR8 rescue plasmids. Twenty-four hours after transfection, virus-containing supernatant was inoculated into 8-day old embryonated chicken eggs. Allantoic fluid was harvested after 2 days of incubation at 37° C. and assayed for the prescence of virus by hemagglutination of chicken red blood cells and by plaque formation in MDCK cells. Influenza A stalk viral mutants Δ289, Δ483 and Δ33/289 bound chicken red blood cells and were able to be rescued.

FIG. 52. Schematic of wild type HA and expression constructs. (A) Uncleaved full length influenza virus hemagglutinin. The signal peptide is the leftmost component, the HA ectodomain is the middle component and the transmembrane- and endodomain are the rightmost component. (B) Expression construct with trimerization domain. The transmembrane- and endodomain was swapped with a thrombin cleavage site (third component from left), a T4 trimerization domain (fourth component from left) and a hexahistidine tag (6×his tag, fifth component from left) at position V503 (H3 numbering). (C) Expression construct without trimerization domain. The transmembrane- and endodomain was swapped with a hexahistidine tag (6×his tag, rightmost component) at amino acid position 509 (H1, H2 and H5) or 508 (H3) respectively (H3 numbering).

FIG. 53. Introduction of a trimerization domain influences stability and formation of oligomers in recombinant HAs. (A) Analysis of recombinant HAs with and without trimerization domain by reducing, denaturing SDS-PAGE. Recombinant HAs that are expressed with trimerization domain (+) show higher stability than HAs expressed without (−). Uncleaved HA (HA0) and cleavage products (HA1/degr. product; HA2) are indicated by arrows. (B) Reducing, denaturing SDS-PAGE analysis of crosslinked HAs. Different species of HA are indicated in the blot. High molecular multimers are indicated by H, trimers by T, dimers by D and monomers by M. (C) Left panel (boxes 1-4): Western blot analysis of reduced, denatured and cross-linked group 1 HAs from B probed with a anti-hexahistidine-tag antibody. Right panel (rightmost box): Cross-linking control (IgG) with BS$^3$ analyzed on a SDS-PAGE. Different species (full antibody, heavy chain, light chain) are indicated by arrows. Molecular weights of the marker bands are indicated on the left of each panel.

FIG. 54. Binding of stalk-reactive antibodies to recombinant PR8 (H1) and Cal09 (H1) HAs. (A) Binding of stalk-reactive antibodies C179, CR6261 and 6F12 and head-reactive antibody PY102 and PR8 antiserum to recombinant soluble PR8 HA without (w/o T4 trim. domain, black lines) or with (w/ T4 trim. domain, red line) trimerization domain. (B) Binding of stalk-reactive antibodies C179, CR6261 and 6F12 and head-reactive antibody 7B2 and Cal09 antiserum to recombinant soluble Cal09 HA without (w/o T4 trim. domain, black lines) or with (w/ T4 trim. domain, red line) trimerization domain.

FIG. 55. Binding of stalk-reactive antibodies to recombinant JAP57 (H2) and VN04 (H5) HAs. (A) Binding of stalk-reactive antibodies C179 and CR6261 and head-reactive antibody 8F8 and H2 antiserum to recombinant soluble JAP57 HA without (w/o T4 trim. domain, black lines) or with (w/ T4 trim. domain, red line) trimerization domain. (B) Binding of stalk-reactive antibodies C179 and CR6261 and head-reactive antibody mAb#8 and H5 antiserum to recombinant soluble VN04 HA without (w/o T4 trim. domain, black lines) or with (w/ T4 trim. domain, red line) trimerization domain.

FIG. 56. Binding of stalk-reactive antibodies to group 2 HAs. (A) Binding of stalk-reactive antibodies 12D1 and CR8020 and head-reactive antibody XY102 and H3 antiserum to recombinant soluble HK68 HA without (w/o T4 trim. domain, black lines) or with (w/ T4 trim. domain, red line) trimerization domain. (B) Binding of stalk-reactive antibodies 12D1 and CR8020 and H3 antiserum to recombinant soluble Wisc05 HA without (w/o T4 trim. domain, black lines) or with (w/ T4 trim. domain, red line) trimerization domain.

5. DETAILED DESCRIPTION

This invention relates to influenza hemagglutinin (HA) virus immunogens (i.e., flu HA polypeptides), that induce a cross-protective immune response against the conserved HA stem domain (sometimes referred to herein as the "stalk" domain) of influenza viruses.

In one aspect, provided herein are chimeric influenza virus hemagglutinin (HA) polypeptides. Such chimeric influenza virus hemagglutinin (HA) polypeptides comprise an HA stem domain that displays a globular HA head domain heterologous to the stem domain. The chimeric influenza virus hemagglutinin polypeptides designed for vaccination share the HA same stem domain but are highly divergent in their globular heads. Such constructs are engineered into vaccine formulations such as live influenza viruses, killed influenza viruses, virus-like particles ("VLPs"), subunit vaccines, split vaccines, etc., that elicit highly potent and broadly neutralizing antibodies against the conserved HA stem. Such "universal" vaccines can be used to induce and/or boost cross-protective immune responses across influenza virus subtypes.

By way of background, neutralizing antibodies against influenza viruses target the HA glycoprotein and prevent either the binding or the fusion step involved in viral entry. Two basic subsets of neutralizing antibodies are elicited by exposure to influenza viruses: those directed to the strain-specific globular head (a domain that is non-conserved across the various strains and subtypes of influenza virus), and those directed to the highly conserved stem of the HA glycoprotein. The non-conserved HA globular head carries the immunodominant epitopes—the strain-specific anti-globular head antibodies are thought to be more potent than the anti-stem antibody specificities, thus explaining the largely strain-specific immunity conferred by infection with current vaccines.

The chimeric influenza virus hemagglutinin (HA) polypeptides disclosed herein are based, in part, on the inventors' rational design strategies for influenza virus vaccines that elicit highly potent and broadly neutralizing antibodies against the HA stem. In this regard, the chimeric influenza virus hemagglutinin (HA) polypeptide is designed to share a relatively well conserved stem domain from previous exposures/vaccinations, but contain a heterologous HA globular head domain—preferably one to which the intended vaccinate is naïve. Exposure to this construct should mainly boost antibodies directed to the conserved HA stem. Repeated immunizations with the conserved HA stem and changing the globular head should induce robust cross-neutralizing antibodies against the common stem region of HA.

When designing the chimeric influenza virus hemagglutinin (HA) polypeptides, care should be taken to maintain the stability of the resulting protein. In this regard it is recommended that the cysteine residues identified as Ap and Aq in FIG. 1 be maintained since they contribute to the stability of the HA stalk as discussed in more detail in Section 5.1 infra. For the best stability, it is preferred to "swap" the HA globular domain as a whole (between the Ap and Aq cysteine residues as shown in FIG. 1) since the resulting conformation would be closest to the native structure. In other words the "linker" referred to in Section 5.1.2 can be the entire globular head domain of a heterologous HA.

Instead of "swapping out" the native globular head of the HA stalk, the globular head can be made heterologous to the conserved stalk by altering the loops that contribute to the HA globular head epitopes. This approach may not work as well for generating the desired immune response against the conserved stalk, unless the altered globular head is designed to be vastly different from the native globular HA head—especially when using an HA to which the population has been exposed. Nevertheless, such alterations can be accomplished, e.g., by altering a majority of the five loops that contribute to the HA globular head epitopes. In one useful approach, all five loops can be altered.

The constructs used for vaccination can advantageously be designed for the particular subjects/population to be vaccinated. There are three influenza subtypes to which human beings living today have been exposed: subtypes H1, H2, and H3. Influenza viruses of the H2 subtype disappeared from the population in 1968, whereas influenza viruses of the H1 and H3 subtypes persist in the population to the present day. As a result, adults living today that were born before 1968 have likely been exposed to each of the H1, H2, and H3 subtypes. In contrast, adults living today that were born after 1968 have likely only been exposed to the H1 and H3 subtypes.

Thus, in preferred embodiments for vaccination of adults, the chimeric influenza hemagglutinin polypeptides do not possess a globular head domain from the HA of an influenza virus of subtype H1, H2, or H3, but do possess a stem domain from the HA of one of these three subtypes. The heterologous globular head can be selected from the HA of any non-H1, non-H2, or non-H3 subtype. Also, separate chimeric constructs made using H1/H2 stems on the one hand, and H3 stems on the other may beneficially be used in a vaccination program—the H1 and H2 subtypes are Group 1 HA subtypes that share a conserved stalk domain; whereas H3 is a Group 2 subtype that has a stalk domain that is structurally different from the Group1 stalk. The use of H1 and H3 constructs would ensure generating/boosting an immune response against each stem domain. Immunization of adult subjects with such chimeric influenza hemagglutinin polypeptides will boost the memory immune response of the subject, resulting in the large scale production of cross-reactive, broadly neutralizing anti-stem domain antibodies that provide long-lasting immunity to influenza virus in the subject.

Infants who have not been exposed, of course, are naïve to all influenza virus subtypes. As a result, a wide range of HA stem/globular head combinations can be constructed for use in vaccines for infants. In a preferred embodiment, naïve infants can be vaccinated with constructs made using the HA stalk of a Group 1 (H1 or H2) or Group 2 (H3) strain, and a globular head from a heterologous strain; i.e., non-H1, non-H2, and/or non-H3 strains. Three different chimeric HA constructs for each HA stalk can be used advantageously in three sequential vaccinations to induce a cross-protective response.

It should be understood that use of the chimeric influenza hemagglutinin polypeptides described herein is advantageous because (i) said polypeptides are highly stable (by virtue of possessing an intact globular head domain) and (ii) the immune systems of the subjects to which said polypeptides are administered have not previously been exposed to the globular head domains of the chimeric influenza hemagglutinin, but have been exposed to the conserved epitopes of the stem domains of the chimeric influenza hemagglutinin.

The chimeric influenza virus hemagglutinin (HA) polypeptide is illustrated by the working Examples (e.g., Section 6.2) which demonstrate the construction of a chimeric influenza HA polypeptide comprising an HA stem and displaying a heterologous HA head, and the production of a stable chimeric HA protein from this polypeptide that cross-reacts with antibodies to both the stem domain and the head domain.

In one aspect, provided herein are chimeric influenza virus hemagglutinin polypeptides comprising an influenza virus hemagglutinin head domain polypeptide and an influenza virus hemagglutinin stem domain polypeptide, wherein said influenza virus hemagglutinin head domain polypeptide is heterologous to said influenza virus hemagglutinin stem domain polypeptide (e.g., the influenza virus hemagglutinin head domain polypeptide and the influenza virus hemagglutinin stem domain polypeptide are derived from different influenza virus hemagglutinin subtypes). The chimeric influenza virus hemagglutinin polypeptides provided herein may be generated by combining an influenza virus hemagglutinin head domain polypeptide (see Section 5.2) with an influenza virus hemagglutinin stem domain polypeptide (Section 5.3). That is, using the principles of the invention, the influenza virus hemagglutinin head domain polypeptides described herein (see Section 5.1.1, infra) and the influenza virus hemagglutinin stem domain polypeptides described herein (Section 5.1.2, infra) can be mixed and matched so as to generate a chimeric influenza virus hemagglutinin polypeptide.

In another aspect, provided herein are flu hemagglutinin (HA) polypeptides (e.g., chimeric influenza virus hemagglutinin (HA) polypeptides, influenza virus hemagglutinin (HA) stem domain polypeptides) comprising one or more modified glycosylation sites and/or one or more non-naturally occurring glycosylation sites. As shown in FIG. 19B, glycosylation of wild type hemagglutinin occurs in both the globular head and stem domains. It is believed that glycosylation within these domains can mask antigenic regions, thereby allowing an influenza virus to evade a host immune system response. For example, seasonal influenza virus strains (e.g., H1N1 and H3N2) have been known to acquire additional glycosylation sites overtime in immunodominant antigenic regions of the globular head domain. Within the context of an influenza virus HA polypeptide described herein, however, glycosylation within the stem domain of the polypeptide can hinder or prevent desired immune responses against the conserved antigenic regions found in this domain. See FIG. 19C. In one embodiment, provided herein is a flu HA polypeptide comprising a stem domain having at least one modified glycosylation site, wherein the modified glycosylation site, wherein the modification disrupts the ability of a glycan to attach to the modified glycosylation site. In another embodiment, provided herein is a flu HA polypeptide comprising an HA globular head domain, wherein the HA globular head domain comprises at least one non-naturally occurring glycosylation site having an amino acid sequence Asn-Xaa-Ser/Thr/Cys, and wherein Xaa is any amino acid. In another embodiment, the flu HA polypeptide comprises (1) a stem domain comprising one or more modified glycosylation site(s), wherein the modified glycosylation site(s) comprises a modification of a naturally occurring glycosylation site, wherein the modification disrupts the ability of a glycan to attach to the modified glycosylation site; and (2) an HA globular head domain that comprises one or more non-naturally occurring glycosylation site(s) having an amino acid sequence Asn-Xaa-Ser/Thr/Cys, wherein Xaa is any amino acid. In specific embodiments, the modified glycosylation site in the stem domain of the flu HA polypeptide comprises a modification of a naturally occurring glycosylation site having the amino acid sequence Asn-Xaa-Ser/Thr/Cys, wherein Xaa is any amino acid.

Without being bound by any particular theory of operation, it is believed that an immune response to conserved antigenic regions within the stem domain of the influenza virus HA polypeptide provided herein can be increased by modifying one or more glycosylation sites within the stem domain in a manner that disrupts the glycosylation (i.e. the attachment of a glycan) at the sites. In addition, it is believed that masking of the immunodominant antigenic regions of the HA globular head domain by the addition of one or more non-naturally occurring glycosylation sites in these immunodominant regions can also increase the immunogenicity of conserved subimmunodominant antigenic regions within the stem domain.

In another aspect, provided herein are methods of using the flu HA polypeptides (e.g., chimeric influenza virus hemagglutinin polypeptides) described herein in the prevent and/or treatment of and/or immunization against influenza virus disease and/or infection in a subject, i.e., the flu HA polypeptides can be used to vaccinate a subject against an influenza virus disease or infection or to treat a subject suffering from an influenza virus disease or infection. In one embodiment, the method of using the flu HA polypeptide is for the prevention of an influenza virus disease in a subject comprising administering to a subject an effective amount of a flu HA polypeptide. In another embodiment, the method of using the flu HA polypeptide is for the treatment of an influenza virus disease and/or infection in a subject comprising administering to a subject an effective amount of a flu HA polypeptide. In yet another embodiment, the method of using the flu HA polypeptide is for the immunization against influenza virus disease and/or infection in a subject.

In one embodiment, provided herein are influenza viruses engineered to express one or more of the flu HA polypeptides (e.g., chimeric influenza virus hemagglutinin polypeptides) described herein. Such viruses can be utilized as vaccines against influenza virus, e.g., the influenza viruses provided herein that express one or more of the flu HA polypeptides (e.g., chimeric influenza virus hemagglutinin (HA) polypeptides) herein can be utilized in a subunit vaccine, a split vaccine, an inactivated vaccine, and/or a live, attenuated virus vaccine.

In certain embodiments, the influenza viruses engineered to express one or more of the flu HA polypeptides (e.g., chimeric influenza virus hemagglutinin (HA) polypeptides) described herein comprise a neuraminidase (NA), or fragment thereof, that is from the same source (e.g., influenza virus strain or subtype) as that from which the influenza virus hemagglutinin head domain polypeptide of the flu HA polypeptides is derived. In certain embodiments, the influenza viruses engineered to express one or more of the flu HA polypeptides (e.g., chimeric influenza virus hemagglutinin (HA) polypeptides) comprises a neuraminidase from a different strain of influenza virus than the globular head domain and/or stem domain of the flu HA polypeptide. In certain embodiments, the influenza viruses engineered to express one or more of the flu HA polypeptides comprise a neuraminidase from a different influenza virus relative to the other proteins encoded by the influenza viruses engineered to express the one or more of the flu HA polypeptides.

In one embodiment, provided herein are nucleic acids that encode the flu HA polypeptides (e.g., chimeric influenza virus hemagglutinin polypeptides) described herein (see, e.g., Section 5.5, infra).

In another embodiment, provided herein are vectors, e.g., expression vectors, containing a nucleic acid encoding a flu HA polypeptide described herein (see, e.g., Section 5.6, infra). In a specific embodiment, the vector is a plasmid vector. In another specific embodiment, the vector is a viral vector (see, e.g., Sections 5.7 and 5.8, infra), e.g., an influenza virus vector into which a flu HA polypeptide (e.g., a chimeric influenza virus hemagglutinin (HA) polypeptide) described herein has been incorporated into the virions or an influenza virus vector comprising a genome engineered to express a chimeric influenza virus hemagglutinin polypeptide. In another specific embodiment, the vector is a bacterial vector (see, e.g., Section 5.10, infra). In another specific embodiment, the vector is a baculovirus. The vectors provided herein can be designed for expression of a chimeric influenza virus hemagglutinin polypeptide using prokaryotic cells (e.g., bacterial) or eukaryotic cells (e.g., insect cells, yeast cells, plant cells, algae and mammalian cells). As such, also provided herein are cells (i.e., prokaryotic and eukaryotic cells) comprising the vectors provided herein, and capable of producing one or more flu HA polypeptide (e.g. chimeric influenza virus hemagglutinin polypeptide) described herein.

In another embodiment, provided herein are virus-like particles (VLPs) and virosomes into which flu HA polypeptides (e.g. chimeric influenza virus hemagglutinin polypeptides) described herein have been incorporated (see Section 5.9, infra).

In another embodiment, provided herein are compositions comprising one or more of flu HA polypeptides (e.g. chimeric influenza virus hemagglutinin polypeptides) described herein, and/or one or more of the nucleic acids, vectors, VLPs, bacteria, or virosomes described herein (see, e.g., Section 5.14). In a specific embodiment, a composition provided herein comprises a flu HA polypeptide (e.g. chimeric influenza virus hemagglutinin polypeptide) described herein. In another specific embodiment, a composition provided herein comprises a nucleic acid encoding a flu HA polypeptide (e.g. chimeric influenza virus hemagglutinin polypeptide) described herein. In another specific embodiment, a composition provided herein comprises an expression vector comprising a nucleic acid encoding a flu HA polypeptide (e.g. chimeric influenza virus hemagglutinin polypeptide) described herein. In another specific embodiment, a composition provided herein comprises an influenza virus or non-influenza virus having a genome engineered to express a flu HA polypeptide (e.g. chimeric influenza virus hemagglutinin polypeptide) described herein.

In certain embodiments, one or more flu HA polypeptides described herein (see, e.g., a chimeric influenza virus hemagglutinin polypeptide, Section 5.1, infra) or a composition thereof, and/or one or more of the nucleic acids, vectors, VLPs, or virosomes described herein, is administered to a subject to immunize the subject against multiple strains or subtypes of influenza virus. In a specific embodiment, said administration is sufficient to generate a host immune response in said individual against any one, two, three, four, five, six, seven, eight, nine, ten, eleven, twelve, thirteen, fourteen, fifteen, sixteen or seventeen known influenza A hemagglutinin subtypes or a later identified influenza A hemagglutinin subtype. In another specific embodiment, said administration is sufficient to generate a host immune response in said individual against any influenza B hemagglutinin subtype now known or later identified.

In certain embodiments, one or more flu HA polypeptides described herein (see, e.g., a chimeric influenza virus hemagglutinin polypeptide see Section 5.1, infra) or a composition thereof and/or one or more of the nucleic acids, vectors, VLPs, or virosomes described herein, is administered to a subject once as a single dose. In a specific embodiment, the subject is a human child. In another specific embodiment, the subject is a human adult. In another specific embodiment, the subject is an elderly human. In certain embodiments, a first flu HA polypeptide described herein or a composition nucleic acid, vector, VLP, or virosome described herein, is administered to a subject as a single dose, followed by the administration of a second flu HA polypeptide described herein or a composition nucleic acid, vector, VLP, or virosome described herein 3 to 6 weeks later.

In certain embodiments, one or more flu HA polypeptides described herein (see, e.g., a chimeric influenza virus hemagglutinin polypeptide) or a composition thereof and/or one or more of the nucleic acids, vectors, VLPs, or virosomes described herein, is administered to a subject as a single dose, followed by the administration of a second dose 3 to 6 weeks later, wherein the influenza virus hemagglutinin head domain of the flu HA polypeptides (e.g., chimeric influenza virus hemagglutinin polypeptide) used in the first dose is from a different strain or subtype than the influenza virus hemagglutinin head domain of the flu HA polypeptides (e.g. chimeric influenza virus hemagglutinin polypeptide) used in the second dose. In certain embodiments, booster inoculations may be administered to the subject at 6 to 12 month intervals following the second inoculation. In certain embodiments, the influenza virus hemagglutinin head domain of the flu HA polypeptide used in the booster is from a different strain or subtype than the influenza virus hemagglutinin head domain of the flu HA polypeptide used in the first and second doses. In a specific embodiment, the subject is a human child. In another specific embodiment, the subject is a human adult. In another specific embodiment, the subject is an elderly human.

In a specific embodiment, for administration to human infants, two doses of flu HA polypeptides (e.g. chimeric influenza virus hemagglutinin polypeptides) described herein (see, e.g., a chimeric influenza virus hemagglutinin polypeptide, Section 5.1, infra) or a composition thereof and/or one or more of the nucleic acids, vectors, VLPs, or virosomes described herein, are administered to an infant, wherein the influenza virus hemagglutinin head domain of the flu HA polypeptide used in the first dose is from a different strain or subtype than the influenza virus hemagglutinin head domain of the flu HA polypeptides used in the second dose.

In a specific embodiment, for administration to human infants, three doses of flu HA polypeptides (e.g. chimeric influenza virus hemagglutinin polypeptides, Section 5.1, infra) or a composition thereof and/or one or more of the nucleic acids, vectors, VLPs, or virosomes described herein, are administered to an infant, wherein the influenza virus hemagglutinin head domains of the flu HA polypeptide used in the first, second, and third doses are from different strains or subtypes of influenza virus.

In another aspect, provided herein are methods of immunizing a subject against an influenza virus disease or infection comprising exposing the subject to a hemagglutinin of an influenza virus to which the subject is naive, i.e., the subject has not previously been exposed to the influenza virus and/or the hemagglutinin of the influenza virus. In a specific embodiment the hemagglutinin is a flu HA polypeptide described herein. In a specific embodiment, the hemagglutinin is a chimeric influenza virus hemagglutinin (HA) polypeptide.

In one embodiment, provided herein is a method of immunizing a subject against an influenza virus disease or infection comprising administering to said subject one or more influenza viruses, wherein each of said one or more influenza viruses comprises a hemagglutinin polypeptide to which the subject is naive, i.e., the subject has not previously been exposed to the one or more influenza viruses. In a specific embodiment, the one or more influenza viruses is an influenza virus of subtype H2, H4, H5, H6, H7, H8, H9, H10, H11, H12, H13, H14, H15, H16 and/or H17. In another specific embodiment, the method comprises (i) a first administration of an influenza virus of subtype H2, H4, H5, H6, H7, H8, H9, H10, H11, H12, H13, H14, H15, H16 or H17 and (ii) a second administration of an influenza virus of subtype H2, H4, H5, H6, H7, H8, H9, H10, H11, H12, H13, H14, H15, H16, or H17 wherein the influenza virus of the first administration is of a different subtype than the influenza virus of the second administration. In another specific embodiment, the method comprises (i) a first administration of an influenza virus of subtype H2, H4, H5, H6, H7, H8, H9, H10, H11, H12, H13, H14, H15, H16, or H17; (ii) a second administration of an influenza virus of subtype H2, H4, H5, H6, H7, H8, H9, H10, H11, H12, H13, H14, H15, H16, or H17; and (iii) a third administration of an influenza virus of subtype H2, H4, H5, H6, H7, H8, H9, H10, H11, H12, H13, H14, H15, H16, or H17, wherein the influenza viruses of the first, second, and third administrations are of different subtypes.

In another embodiment, provided herein is a method of immunizing a subject against an influenza virus disease or infection comprising administering to said subject one or more influenza virus hemagglutinin polypeptides to which the subject is naive, i.e., the subject has not previously been exposed to the one or more influenza virus hemagglutinin polypeptides. In certain embodiments, said one or more influenza virus hemagglutinin polypeptides to which the subject is naive are in a composition (e.g., a composition comprising a vaccine). In certain embodiments, one or more influenza virus hemagglutinin polypeptides to which the subject is naive are in a vector, e.g., an influenza virus vector. In certain embodiments, one or more influenza virus hemagglutinin polypeptides to which the subject is naive are in a VLP. In certain embodiments, one or more influenza virus hemagglutinin polypeptides to which the subject is naive are in a virosome. In a specific embodiment, the one or more influenza viruses hemagglutinin polypeptides is an influenza virus hemagglutinin polypeptide from an influenza virus of subtype H2, H4, H5, H6, H7, H8, H9, H10, H11, H12, H13, H14, H15, H16, and/or H17. In another specific embodiment, the method comprises (i) a first administration of an influenza virus hemagglutinin polypeptide of subtype H2, H4, H5, H6, H7, H8, H9, H10, H11, H12, H13, H14, H15, H16, or H17 and (ii) a second administration of an influenza virus hemagglutinin polypeptide of subtype H2, H4, H5, H6, H7, H8, H9, H10, H11, H12, H13, H14, H15, H16, or H17, wherein the influenza virus hemagglutinin polypeptide of the first administration is of a different subtype than the influenza virus hemagglutinin polypeptide of the second administration. In another specific embodiment, the method comprises (i) a first administration of an influenza virus hemagglutinin polypeptide of subtype H2, H4, H5, H6, H7, H8, H9, H10, H11, H12, H13, H14, H15, H16, or H17; (ii) a second administration of an influenza virus hemagglutinin polypeptide of subtype H2, H4, H5, H6, H7, H8, H9, H10, H11, H12, H13, H14, H15, H16, or H17; and (iii) a third administration of an influenza virus hemagglutinin polypeptide of subtype H2, H4, H5, H6, H7, H8, H9, H10, H11, H12, H13, H14, H15, H16, or H17, wherein the influenza virus hemagglutinin polypeptides of the first, second, and third administrations are from different influenza virus subtypes.

In another embodiment, provided herein is a method of immunizing a subject against an influenza virus disease or infection comprising (i) priming said subject by administering to said subject an influenza virus hemagglutinin polypeptide (or a nucleic acid encoding said hemagglutinin polypeptide, a virus expressing said hemagglutinin polypeptide, a VLP expressing said hemagglutinin polypeptide, etc.) from an influenza subtype (e.g., an H1 hemagglutinin) and, after a period of time, and (ii) boosting said subject with a flu HA polypeptide (e.g. chimeric influenza virus hemagglutinin polypeptide) described herein (or a nucleic acid encoding said flu HA polypeptide, a virus expressing said flu HA polypeptide, a VLP expressing said flu HA polypeptide, etc.). In a specific embodiment, the flu HA polypeptide is a chimeric influenza virus hemagglutinin HA polypeptide that comprises an influenza virus hemagglutinin head domain polypeptide (or portion thereof) to which the subject is naive and an influenza virus hemagglutinin stem domain polypeptide (or portion thereof) that is the same as or similar to (e.g., from the same influenza virus strain or subtype) the influenza virus hemagglutinin stem domain polypeptide in the hemagglutinin polypeptide used in the priming of step (i). In certain embodiments, the subject may be administered a second boost, comprising a second administration of the same or a different flu HA polypeptide described herein (or a nucleic acid encoding said flu HA polypeptide, a virus expressing said flu HA polypeptide, a VLP expressing said flu HA polypeptide, etc.). In certain embodiments, the subject may be administered a third boost, comprising a third administration of the same or a different flu HA polypeptide described herein (or a nucleic acid encoding said flu HA polypeptide, a virus expressing said flu HA polypeptide, a VLP expressing said flu HA polypeptide, etc.). In certain embodiments, the period of time between the priming and boosting, or between the boosts if more than one boost is administered, of said subject may, for example, be 1 week, 2 weeks, 3 weeks, 4 weeks, 1 month, 2 months, 3 months, or longer. In certain embodiments, the period of time between the priming and boosting (or between the first and second boosts) of said subject may, for example, range from 3-5 days, 7-10 days, 7-14 days, 14-21 days, 14-28 days, 21-28 days, 21 days to 1 month, 1 month to 2 months, 1 month to 3 months, 2 months to 3 months, 2 months to 4 months, or 4 months to 6 months.

In another embodiment, provided herein is a method of immunizing a subject against an influenza virus disease or infection comprising (i) priming said subject by administering to said subject a headless influenza virus hemagglutinin polypeptide (i.e. influenza virus hemagglutinin stem domain polypeptide, or a nucleic acid encoding said hemagglutinin polypeptide, a virus expressing said hemagglutinin polypeptide, a VLP expressing said hemagglutinin polypeptide, etc.) such as those described herein from an influenza subtype (e.g., an H1 hemagglutinin) and, after a period of time, and (ii) boosting said subject with a flu HA polypeptide (e.g., chimeric influenza virus hemagglutinin polypeptide) described herein (or a nucleic acid encoding said flu HA polypeptide, a virus expressing said flu HA polypeptide, a VLP expressing said flu HA polypeptide, etc.). In a specific embodiment, the flu HA polypeptide is a chimeric influenza virus hemagglutinin polypeptide that comprises an influenza virus hemagglutinin head domain polypeptide (or portion thereof) to which the subject is naive and an influenza virus hemagglutinin stem domain polypeptide (or portion thereof) that is the same as or similar to (e.g., from the same influenza virus strain or subtype) the influenza virus hemagglutinin stem domain polypeptide in the headless hemagglutinin polypeptide (i.e. influenza virus hemagglutinin stem domain polypeptide) used in the priming of step (i). In certain embodiments, the subject may be administered a second boost, comprising a second administration of the same or a different flu HA polypeptide described herein (or a nucleic acid encoding said flu HA polypeptide, a virus expressing said flu HA polypeptide, a VLP expressing said flu HA polypeptide, etc.). In certain embodiments, the subject may be administered a third boost, comprising a third administration of the same or a different flu HA polypeptide described herein (or a nucleic acid encoding said flu HA polypeptide, a virus expressing said flu HA polypeptide, a VLP expressing said flu HA polypeptide, etc.). In specific embodiments, the flu HA polypeptide (which in specific embodiments is a chimeric influenza virus hemagglutinin polypeptide) used in the second and/or third boost comprises an influenza virus hemagglutinin stem domain polypeptide that is the same or is similar to the influenza virus hemagglutinin stem domain polypeptide of the headless HA and may or may not comprise a different head. In certain embodiments, the period of time between the priming and boosting, or between the boosts if more than one boost is administered, of said subject may, for example, be 1 week, 2 weeks, 3 weeks, 4 weeks, 1 month, 2 months, 3 months, or longer. In certain embodiments, the period of time between the priming and boosting (or between the first and second boosts) of said subject may, for example, range from 3-5 days, 7-10 days, 7-14 days, 14-21 days, 14-28 days, 21-28 days, 21 days to 1 month, 1 month to 2 months, 1 month to 3 months, 2 months to 3 months, 2 months to 4 months, or 4 months to 6 months.

In another embodiment, provided herein is a method of immunizing a subject against an influenza virus disease or infection comprising (i) priming said subject by administering to said subject a first flu HA polypeptide (e.g., chimeric influenza virus hemagglutinin polypeptide) described herein (or a nucleic acid encoding said flu HA polypeptide, a virus expressing said flu HA polypeptide, a VLP expressing said flu HA polypeptide, etc.) and, after a period of time, and (ii) boosting said subject with a second flu HA polypeptide (e.g., chimeric influenza virus hemagglutinin polypeptide) described herein (or a nucleic acid encoding said flu HA polypeptide, a virus expressing said flu HA polypeptide, a VLP expressing said flu HA polypeptide, etc.). In a specific embodiment, the second flu HA polypeptide is a chimeric influenza virus hemagglutinin polypeptide that comprises an influenza virus hemagglutinin head domain polypeptide (or portion thereof) to which the subject is naive and an influenza virus hemagglutinin stem domain polypeptide (or portion thereof) that is the same as or similar to (e.g., from the same influenza virus strain or subtype) the influenza virus hemagglutinin stem domain polypeptide of the first chimeric influenza virus hemagglutinin polypeptide used in the priming of step (i). In certain embodiments, the subject may be administered a second boost, comprising a second administration of the first or second flu HA polypeptide (e.g., a chimeric influenza virus hemagglutinin polypeptide), or a different flu HA polypeptide (e.g., a chimeric influenza virus hemagglutinin polypeptide) described herein (or a nucleic acid encoding said flu HA polypeptide, a virus expressing said flu HA polypeptide, a VLP expressing said flu HA polypeptide, etc.). In certain embodiments, the subject may be administered a third boost, comprising administration of one of the same flu HA polypeptides (e.g., a chimeric influenza virus hemagglutinin polypeptide) previously administered or a different flu HA polypeptide (e.g., a chimeric influenza virus hemagglutinin polypeptide) described herein (or a nucleic acid encoding said flu HA polypeptide, a virus expressing said flu HA polypeptide e, a VLP expressing said flu HA polypeptide, etc.). In specific embodiments, the flu HA polypeptide used in the second and/or third boost is a chimeric influenza virus hemagglutinin polypeptide that comprises an influenza virus hemagglutinin stem domain polypeptide that is the same or is similar to the influenza virus hemagglutinin stem domain polypeptide of the first flu HA polypeptide (which in specific embodiments, is a chimeric influenza virus hemagglutinin polypeptide) and may or may not comprise a different head. In certain embodiments, the period of time between the priming and boosting, or between the boosts if more than one boost is administered, of said subject may, for example, be 1 week, 2 weeks, 3 weeks, 4 weeks, 1 month, 2 months, 3 months, or longer. In certain embodiments, the period of time between the priming and boosting (or between the first and second boosts) of said subject may, for example, range from 3-5 days, 7-10 days, 7-14 days, 14-21 days, 14-28 days, 21-28 days, 21 days to 1 month, 1 month to 2 months, 1 month to 3 months, 2 months to 3 months, 2 months to 4 months, or 4 months to 6 months.

5.1 Chimeric Influenza Virus Hemagglutinin Polypeptides

Provided herein are chimeric influenza virus hemagglutinin polypeptides comprising or consisting of an influenza virus hemagglutinin head domain polypeptide and an influenza virus hemagglutinin stem domain polypeptide, wherein said influenza virus hemagglutinin head domain polypeptide is heterologous to said influenza virus hemagglutinin stem domain polypeptide (e.g., the influenza virus hemagglutinin head domain polypeptide and the influenza virus hemagglutinin stem domain polypeptide are derived from different influenza virus hemagglutinin subtypes). Influenza virus hemagglutinin head domain polypeptides are described in Section 5.2, infra. Influenza virus hemagglutinin stem domain polypeptides, which are capable of forming stable, headless stem domains, are described in Section 5.3, infra.

A full-length influenza hemagglutinin typically comprises an HA1 domain and an HA2 domain. The stem domain is formed by two segments of the HA1 domain and most or all of the HA2 domain. The two segments of the HA1 domain are separated, in primary sequence, by the globular head domain (see, e.g., the amino acid residues between the residues designated $A_p$ and $A_q$ in FIG. 1). In certain embodiments, the chimeric influenza virus hemagglutinin polypeptides described herein maintain such a structure. That is, in certain embodiments, the chimeric influenza virus hemagglutinin polypeptides described herein comprise a stable stem structure composed of an HA1 domain and an HA2 domain, and a globular head domain separating the two segments of the HA1 domain (in primary sequence), wherein said globular head domain is heterologous to the stem domain formed by the other segments of the HA1 domain and the HA2 domain.

In certain embodiments, a chimeric influenza virus hemagglutinin polypeptide described herein comprises or consists of (i) an influenza virus hemagglutinin stem domain polypeptide described herein (see, e.g., Section 5.1.2, infra) or an influenza virus hemagglutinin stem domain polypeptide from any known strain or subtype of influenza virus (e.g., any wild-type influenza virus hemagglutinin stem domain polypeptide such as the stem domain of the hemagglutinin of an influenza virus described in Section 5.4, infra) and (ii) an influenza virus hemagglutinin head domain polypeptide described herein (see, e.g., Sections 5.2 and 5.4.2, infra) or an influenza virus hemagglutinin head domain polypeptide from any known strain or subtype of influenza virus (e.g., any wild-type influenza virus hemagglutinin head domain polypeptide), wherein said influenza virus hemagglutinin head domain polypeptide is heterologous to said influenza virus hemagglutinin stem domain polypeptide, and wherein said influenza virus hemagglutinin head domain polypeptide is not an influenza virus hemagglutinin head domain polypeptide of influenza A virus subtype H1 or H3.

In certain embodiments, a chimeric influenza virus hemagglutinin polypeptide described herein comprises or consists of (i) an influenza virus hemagglutinin stem domain polypeptide described herein (see, e.g., Section 5.3 and 5.4.1, infra) or an influenza virus hemagglutinin stem domain polypeptide from any known strain or subtype of influenza virus (e.g., any wild-type influenza virus hemagglutinin stem domain polypeptide) and (ii) an influenza virus hemagglutinin head domain polypeptide described herein (see, e.g., Sections 5.2 and 5.4.2, infra) or an influenza virus hemagglutinin head domain polypeptide from any known strain or subtype of influenza virus (e.g., any wild-type influenza virus hemagglutinin head domain polypeptide), wherein said influenza virus hemagglutinin head domain polypeptide is heterologous to said influenza virus hemagglutinin stem domain polypeptide, and wherein said influenza virus hemagglutinin head domain polypeptide is not an influenza virus hemagglutinin head domain polypeptide of influenza A virus subtype H2.

In certain embodiments, a chimeric influenza virus hemagglutinin polypeptide described herein comprises or consists of (i) an influenza virus hemagglutinin stem domain polypeptide described herein (see, e.g., Sections 5.3 and 5.4.1, infra) or an influenza virus hemagglutinin stem domain polypeptide from any known strain or subtype of influenza virus (e.g., any wild-type influenza virus hemagglutinin stem domain polypeptide) and (ii) an influenza virus hemagglutinin head domain polypeptide described herein (see, e.g., Sections 5.2 and 5.4.2, infra) or an influenza virus hemagglutinin head domain polypeptide from any known strain or subtype of influenza virus (e.g., any wild-type influenza virus hemagglutinin head domain polypeptide), wherein said influenza virus hemagglutinin head domain polypeptide is heterologous to said influenza virus hemagglutinin stem domain polypeptide, and wherein said influenza virus hemagglutinin head domain polypeptide is not an influenza virus hemagglutinin head domain polypeptide of influenza A virus subtype H5.

In a specific embodiment, provided herein is a chimeric influenza virus hemagglutinin polypeptide comprising or consisting of (i) an influenza virus hemagglutinin stem domain polypeptide described herein (see, e.g., Sections 5.3 and 5.4.1, infra) or an influenza virus hemagglutinin stem domain polypeptide from any known strain or subtype of influenza virus (e.g., any wild-type influenza virus hemagglutinin stem domain polypeptide) and (ii) an influenza virus hemagglutinin head domain polypeptide from influenza A virus subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide described herein (see, e.g., Section 5.3 and 5.4.1, infra) or an influenza virus hemagglutinin stem domain polypeptide from any known strain or subtype of influenza virus (e.g., any wild-type influenza virus hemagglutinin stem domain polypeptide) and (ii) an influenza virus hemagglutinin head domain polypeptide from influenza A virus subtype H4, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide described herein (see, e.g., Section 5.3 and 5.4.1, infra) or an influenza virus hemagglutinin stem domain polypeptide from any known strain or subtype of influenza virus (e.g., any wild-type influenza virus hemagglutinin stem domain polypeptide) and (ii) an influenza virus hemagglutinin head domain polypeptide from avian influenza virus subtype H1, H2, or H3, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide described herein (see, e.g., Section 5.3 and 5.4.1, infra) or an influenza virus hemagglutinin stem domain polypeptide from any known strain or subtype of influenza virus (e.g., any wild-type influenza virus hemagglutinin stem domain polypeptide) and (ii) an influenza virus hemagglutinin head domain polypeptide from horse influenza virus subtype H3, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide from an influenza A virus of subtype H1 and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H5, H6, H8, H9, H11, H12, H13, H16, or H17. In another specific embodiment, the influenza virus hemagglutinin head domain polypeptide is not from an influenza A virus of subtype H1, H2, or H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from an influenza A virus of subtype H3 and (ii) an influenza virus hemagglutinin head domain polypeptide from an influenza A virus of subtype H1, H2, H3, H4, H5, H6, H7, H8, H9, H10, H11, H12, H13, H14, H15, H16, or H17 wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H7, H10, H14, or H15. In another specific embodiment, the influenza virus hemagglutinin head domain polypeptide is not from an influenza A virus of subtype H1, H2, or H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from an influenza A virus of subtype H2 and (ii) an influenza virus hemagglutinin head domain polypeptide from an influenza A virus of subtype H1, H2, H3, H4, H5, H6, H7, H8, H9, H10, H11, H12, H13, H14, H15, H16, or H17 wherein said influenza virus hemagglutinin head domain polypeptide is heterologous to said influenza virus hemagglutinin stem domain polypeptide. In a specific embodiment, the influenza virus hemagglutinin head domain polypeptide is not from an influenza A virus of subtype H1, H2, or H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from an influenza A virus of subtype H1, H2, H3, H4, H5, H6, H7, H8, H9, H10, H11, H12, H13, H14, H15, H16, or H17 and (ii) an influenza virus hemagglutinin head domain polypeptide from an influenza B virus, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide from an influenza B virus and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H5, H6, H7, H8, H9, H10, H11, H12, H13, H14, H15, H16, or H17. In another specific embodiment, the influenza virus hemagglutinin head domain polypeptide is not from an influenza A virus of subtype H1, H2, or H3. In another specific embodiment, the influenza virus hemagglutinin head domain polypeptide is not from an influenza A virus of subtype H5.

In another specific embodiment provided herein is a chimeric influenza virus hemagglutinin polypeptide comprising or consisting of (i) an influenza virus hemagglutinin stem domain polypeptide from an influenza B virus and (ii) an influenza virus hemagglutinin head domain polypeptide from an influenza B virus, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide from influenza A virus A/California/7/2009 (H1) and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H5, H6, H8, H9, H11, H12, H13, or H16. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/California/7/2009 (H1) and (ii) an influenza virus hemagglutinin head domain polypeptide from an influenza A virus of subtype H2, H4, H5, H6, H7, H8, H9, H10, H11, H12, H13, H14, H15, H16, or H17. In a specific embodiment, the influenza virus hemagglutinin head domain polypeptide is from an influenza A virus of subtype H4. In a specific embodiment, the influenza virus hemagglutinin head domain polypeptide is from an influenza A virus of subtype H5. In a specific embodiment, the influenza virus hemagglutinin head domain polypeptide is from an influenza A virus of subtype H6. In a specific embodiment, the influenza virus hemagglutinin head domain polypeptide is from an influenza A virus of subtype H7. In a specific embodiment, the influenza virus hemagglutinin head domain polypeptide is from an influenza A virus of subtype H8. In a specific embodiment, the influenza virus hemagglutinin head domain polypeptide is from an influenza A virus of subtype H9. In a specific embodiment, the influenza virus hemagglutinin head domain polypeptide is from an influenza A virus of subtype H10. In a specific embodiment, the influenza virus hemagglutinin head domain polypeptide is from an influenza A virus of subtype H11. In a specific embodiment, the influenza virus hemagglutinin head domain polypeptide is from an influenza A virus of subtype H12. In a specific embodiment, the influenza virus hemagglutinin head domain polypeptide is from an influenza A virus of subtype H13. In a specific embodiment, the influenza virus hemagglutinin head domain polypeptide is from an influenza A virus of subtype H14. In a specific embodiment, the influenza virus hemagglutinin head domain polypeptide is from an influenza A virus of subtype H15. In a specific embodiment, the influenza virus hemagglutinin head domain polypeptide is from an influenza A virus of subtype H16.

In another specific embodiment, provided herein is a chimeric influenza virus hemagglutinin polypeptide comprising or consisting of (i) an influenza virus hemagglutinin stem domain polypeptide from influenza A virus A/Brisbane/59/2007-like (H1) and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H5, H6, H8, H9, H11, H12, H13, or H16. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/South Carolina/1918 (H1) and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H5, H6, H8, H9, H11, H12, H13, or H16. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/USSR/92/1977 (H1) and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H5, H6, H8, H9, H11, H12, H13, or H16. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/California/04/2009 (H1) and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H5, H6, H8, H9, H11, H12, H13, or H16. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/Perth/16/2009 (H3) and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H7, H10, H14, or H15. In another specific embodiment, the influenza virus hemagglutinin head domain polyp tide is from an influenza A virus of subtype H5. In another specific embodiment, the influenza virus hemagglutinin head domain polyp tide is from A/Viet Nam/1203/04 (H5). In another specific embodiment, the influenza virus hemagglutinin head domain polypeptide is from an influenza A virus of subtype H7. In another specific embodiment, the influenza virus hemagglutinin head domain polyp tide is from A/Alberta/24/01 (H7). In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/Brisbane/10/2007-like (H3) and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H7, H10, H14, or H15. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/Hong Kong/1/1968 (H3) and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H7, H10, H14, or H15. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/California/1/1988 (H3) and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H7, H10, H14, or H15. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/Ann Arbor/6/60 (H2) and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H7, H10, H14, or H15. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/Puerto Rico/8/1934 (H1) and (ii) an influenza virus hemagglutinin head domain polypeptide from an influenza A virus of subtype H1, H2, H3, H4, H5, H6, H7, H8, H9, H10, H11, H12, H13, H14, H15, H16, or H17, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H1, H2, H4, H5, H6, H7, H9, H10, H14, or H15. In another specific embodiment, the influenza virus hemagglutinin head domain polypeptide is from an influenza A virus of subtype H1, H2, H5, H6, or H9. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5. In another specific embodiment, the influenza virus hemagglutinin head domain polypeptide is from an influenza A virus of subtype H5. In another specific embodiment, the influenza virus hemagglutinin head domain polyptide is from A/Viet Nam/1203/04 (H5). In another specific embodiment, the influenza virus hemagglutinin head domain polypeptide is from an influenza A virus of subtype H6. In another specific embodiment, the influenza virus hemagglutinin head domain polypeptide is from A/mallard/Sweden/81/02 (H6). In another specific embodiment, the influenza virus hemagglutinin head domain polypeptide is from an influenza A virus of subtype H9. In another specific embodiment, the influenza virus hemagglutinin head domain polypeptide is from A/guinea fowl/Hong Kong/WF10/99 (H9).

In certain embodiments, a chimeric influenza virus hemagglutinin polypeptide provided herein comprises an influenza virus hemagglutinin stem domain polypeptide and an influenza virus hemagglutinin head domain polypeptide, wherein the influenza virus hemagglutinin head domain polypeptide is heterologous to the influenza virus hemagglutinin stem domain polypeptide, and wherein the chimeric influenza virus hemagglutinin polypeptide has a primary structure of, in the following order: an HA1 N-terminal stem segment, an influenza virus hemagglutinin head domain polypeptide, an HA1 C-terminal stem segment and an HA2. The primary sequence of a chimeric influenza virus hemagglutinin polypeptide provided herein might be formed by a single polypeptide, or it might be formed by multiple polypeptides. Typically, a single polypeptide is expressed by any technique deemed suitable by one of skill in the art.

In certain embodiments, a chimeric influenza virus hemagglutinin polypeptide provided herein is monomeric. In certain embodiments, a chimeric influenza virus hemagglutinin polypeptide provided herein is multimeric. In certain embodiments, a chimeric influenza virus hemagglutinin polypeptide provided herein is trimeric.

In certain embodiments, a chimeric influenza virus hemagglutinin polypeptide provided herein comprises a signal peptide. Typically, the signal peptide is cleaved during or after polypeptide expression and translation to yield a mature chimeric influenza virus hemagglutinin polypeptide. In certain embodiments, also provided herein are mature chimeric influenza virus hemagglutinin polypeptides that lack a signal peptide. In embodiments where a chimeric influenza virus hemagglutinin polypeptide provided herein comprises a signal peptide, the signal peptide might be based on any influenza virus signal peptide known to those of skill in the art. In certain embodiments, the signal peptides are based on influenza A signal peptides. In certain embodiments, the signal peptides are based on the signal peptide of an influenza A hemagglutinin selected from the group consisting of H1, H2, H3, H4, H5, H6, H7, H8, H9, H10, H11, H12, H13, H14, H15, H16, and H17. In certain embodiments, the signal peptide might be any signal peptide deemed useful to one of skill in the art. In certain embodiments, the signal peptide is selected from SEQ ID NOS:18-33.

In certain embodiments, a chimeric influenza virus hemagglutinin polypeptide provided herein comprises a luminal domain. In embodiments where a chimeric influenza virus hemagglutinin polypeptide provided herein comprises a luminal domain, the luminal domain might be based on any influenza luminal domain known to those of skill in the art. In certain embodiments, the luminal domains are based on influenza A luminal domains. In certain embodiments, the luminal domains are based on the luminal domain of an influenza A hemagglutinin selected from the group consisting of H1, H2, H3, H4, H5, H6, H7, H8, H9, H10, H11, H12, H13, H14, H15, H16, and H17. In certain embodiments, the luminal domain might be any luminal domain deemed useful to one of skill in the art. In certain embodiments, the luminal domain is selected from SEQ ID NOS:98-113. In certain embodiments, the luminal domains are from the same hemagglutinin as the stem domain. In certain embodiments, the luminal domains are from influenza virus strain or subtype as the stem domain HA2 subunit.

In certain embodiments, a chimeric influenza virus hemagglutinin polypeptide provided herein comprises a transmembrane domain. In embodiments where a chimeric influenza virus hemagglutinin polypeptide provided herein comprises a transmembrane domain, the transmembrane domain might be based on any influenza transmembrane domain known to those of skill in the art. In certain embodiments, the transmembrane domains are based on influenza A transmembrane domains. In certain embodiments, the transmembrane domains are based on a transmembrane domain of an influenza A hemagglutinin selected from the group consisting of H1, H2, H3, H4, H5, H6, H7, H8, H9, H10, H11, H12, H13, H14, H15, H16, and H17. In certain embodiments, the transmembrane domain might be any transmembrane domain deemed useful to one of skill in the art. In certain embodiments, the transmembrane domain is selected from SEQ ID NOS:114-129. In certain embodiments, the transmembrane domains are from the same hemagglutinin as the stem domain. In certain embodiments, the transmembrane domains are from influenza virus strain or subtype as the stem domain HA2 subunit.

In certain embodiments, a chimeric influenza virus hemagglutinin polypeptide provided herein comprises a cytoplasmic domain. In embodiments where a chimeric influenza virus hemagglutinin polypeptide provided herein comprises a cytoplasmic domain, the cytoplasmic domain might be based on any influenza cytoplasmic domain known to those of skill in the art. In certain embodiments, the cytoplasmic domains are based on influenza A cytoplasmic domains. In certain embodiments, the cytoplasmic domains are based on a cytoplasmic domain of an influenza A hemagglutinin selected from the group consisting of H1, H2, H3, H4, H5, H6, H7, H8, H9, H10, H11, H12, H13, H14, H15, H16, and H17. In certain embodiments, the cytoplasmic domain might be any cytoplasmic domain deemed useful to one of skill in the art. In certain embodiments, the cytoplasmic domain is selected from SEQ ID NOS:130-145. In certain embodiments, the cytoplasmic domains are from the same hemagglutinin as the stem domain. In certain embodiments, the cytoplasmic domains are from influenza virus strain or subtype as the stem domain HA2 subunit.

In certain embodiments, one or more of glycosylation sites in a chimeric influenza virus hemagglutinin polypeptide provided herein are modified (e.g., by amino acid addition, deletion or substitution). In specific embodiments, the one or more glycosylation sites are modified such that glycosylation at these sites will not occur during processing and maturation of the polypeptide. Those of skill in the art will recognize that influenza HA typically comprises one or more glycosylation sites (e.g. Asn-Xaa-Ser/Thr/Cys, wherein Xaa is any amino acid or Asn-Xaa-Ser/Thr/Cys, or, in certain embodiments, wherein Xaa is any amino acid except Pro). In certain embodiments, the modified glycosylation site is located in the stem domain of the chimeric influenza virus hemagglutinin polypeptide. In certain embodiments, one or more amino acid residues in a glycosylation site are conservatively substituted with an amino acid residue that disrupts the glycosylation site. In certain embodiments, one or more amino acid residues in a glycosylation site are substituted with any amino acid residue that disrupts the glycosylation site. In certain embodiments, one or more asparagine residues in a glycosylation site is substituted with alanine. In a particular embodiment, the asparagine at position 38 of an H3 hemagglutinin is changed to an alanine. In certain embodiments, the chimeric influenza virus hemagglutinin polypeptide comprises one or more non-naturally occurring glycosylation sites in its globular head domain. In certain embodiments, the chimeric influenza virus hemagglutinin polypeptide comprises one or more modified glycosylation sites and/or non-naturally occurring glycosylation sites as discussed in Section 5.4, infra.

In certain embodiments, the chimeric influenza virus hemagglutinin polypeptides provided herein are capable of forming a three dimensional structure that is similar to the three dimensional structure of a native influenza hemagglutinin. Structural similarity might be evaluated based on any technique deemed suitable by those of skill in the art. For instance, reaction, e.g. under non-denaturing conditions, of a chimeric influenza virus hemagglutinin polypeptide with a neutralizing antibody or antiserum that recognizes a native influenza hemagglutinin might indicate structural similarity. Useful neutralizing antibodies or antisera are described in, e.g. Sui, et al., 2009, *Nat. Struct. Mol. Biol.* 16(3):265-273, Ekiert et al., Feb. 26, 2009, *Science* [DOI: 10.1126/science.1171491], and Kashyap et al., 2008, *Proc. Natl. Acad. Sci. USA* 105(16):5986-5991, the contents of which are hereby incorporated by reference in their entireties. In certain embodiments, the antibody or antiserum is an antibody or antiserum that reacts with a non-contiguous epitope (i.e., not contiguous in primary sequence) that is formed by the tertiary or quaternary structure of a hemagglutinin.

In certain embodiments, the chimeric influenza virus hemagglutinin polypeptides provided herein further comprise one or more polypeptide domains. Useful polypeptide domains include domains that facilitate purification, folding and cleavage of portions of a polypeptide. For example, a His tag (His-His-His-His-His-His, SEQ ID NO:166), FLAG epitope or other purification tag can facilitate purification of a chimeric influenza virus hemagglutinin polypeptide provided herein. In some embodiments, the His tag has the sequence, $(His)_n$, wherein n is 2, 3, 4, 5, 6, 7, 8, 9, 10, 11, 12, 13, 14, 15, 16, 17, 18, 19, 20 or greater. A foldon, or trimerization, domain from bacteriophage T4 fibritin can facilitate trimerization of polypeptides provided herein. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, *PLoSONE* 5(9): e12466. The foldon domain can have any foldon sequence known to those of skill in the art (see, e.g., Papanikolopoulou et al., 2004, *J.*

*Biol. Chem.* 279(10):8991-8998, the contents of which are hereby incorporated by reference in their entirety. Examples include GSGYIPEAPRDGQAYVRKDGEWVLLSTFL (SEQ ID NO:167). A foldon domain can be useful to facilitate trimerization of soluble polypeptides provided herein. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO:168). In certain embodiments, the cleavage site is a cleavage site recognized by Tobacco Etch Virus (TEV) protease (e.g., amino acid sequence Glu-Asn-Leu-Tyr-Phe-Gln-(Gly/Ser)).

In certain embodiments, the chimeric influenza hemagglutinin hemagglutinin polypeptides are soluble polypeptides, such as those described in Examples 6 and 9, infra.

In certain embodiments, the influenza hemagglutinin stem domain polypeptides of the chimeric influenza virus hemagglutinin polypeptides described herein maintain the cysteine residues identified in influenza hemagglutinin polypeptides as $A_p$ and $A_q$ in FIG. 1, i.e., the cysteine residues identified in influenza hemagglutinin polypeptides as $A_p$ and $A_q$ in FIG. 1 are maintained in the chimeric influenza virus hemagglutinin polypeptides described herein. Thus, in certain embodiments, in the primary sequence of a chimeric influenza virus hemagglutinin polypeptide described herein: (i) the N-terminal segment of an influenza hemagglutinin stem domain polypeptide ends at the cysteine residue identified as $A_p$ in FIG. 1, (ii) the C-terminal segment of an influenza hemagglutinin stem domain polypeptide begins at the cysteine residue identified as $A_q$ in FIG. 1; and (iii) the influenza hemagglutinin head domain polypeptide (which is heterologous to the influenza hemagglutinin stem domain polypeptide) is between the N-terminal and C-terminal segments of the influenza hemagglutinin stem domain polypeptide. Influenza hemagglutinin stem domain polypeptides are described in detail in Section 5.1.2, infra.

In certain embodiments, the HA1 N-terminal stem segment of the chimeric influenza virus hemagglutinin polypeptides described herein does not end exactly at $A_p$ (e.g., $Cys_{52}$ of an HA1 subunit from an H3 hemagglutinin), but at a residue in sequence and structural vicinity to $A_p$. For example, in certain embodiments, the HA1 N-terminal stem segment of the chimeric influenza virus hemagglutinin polypeptides described herein ends at $A_{p-1}$, $A_{p-2}$, $A_{p-3}$, $A_{p-4}$, $A_{p-5}$, $A_{p-6}$, $A_{p-7}$, $A_{p-8}$, $A_{p-9}$, $A_{p-10}$, $A_{p-11}$, $A_{p-12}$, $A_{p-13}$, $A_{p-14}$, $A_{p-15}$, $A_{p-16}$, $A_{p-17}$, $A_{p-18}$, $A_{p-19}$, $A_{p-20}$, $A_{p-21}$, $A_{p-22}$, $A_{p-23}$, $A_{p-23}$, $A_{p-24}$, $A_{p-25}$, $A_{p-26}$, $A_{p-27}$, $A_{p-28}$, $A_{p-29}$, $A_{p-30}$. In certain embodiments, the HA1 N-terminal stem segment of the chimeric influenza virus hemagglutinin polypeptides described herein ends in the range of $A_{p-1}$ to $A_{p-3}$, $A_{p-3}$ to $A_{p-5}$, $A_{p-5}$ to $A_{p-8}$, $A_{p-8}$ to $A_{p-10}$, $A_{p-10}$ to $A_{p-15}$, $A_{p-15}$ to $A_{p-20}$, $A_{p-20}$ to $A_{p-30}$, $A_{p-30}$ to $A_{p-40}$. For example, an HA1 N-terminal stem segment ending at $A_{p-10}$ would end at Lys42 of an H3 hemagglutinin. In certain embodiments, the HA1 N-terminal stem segment of the chimeric influenza virus hemagglutinin polypeptides described herein ends at $A_{p+1}$, $A_{p+2}$, $A_{p+3}$, $A_{p+4}$, $A_{p+5}$, $A_{p+6}$, $A_{p+7}$, $A_{p+8}$, $A_{p+9}$, $A_{p+10}$, $A_{p+11}$, $A_{p+12}$, $A_{p+13}$, $A_{p+14}$, $A_{p+15}$, $A_{p+16}$, $A_{p+17}$, $A_{p+18}$, $A_{p+19}$, $A_{p+20}$, $A_{p+21}$, $A_{p+22}$, $A_{p+23}$, $A_{p+24}$, $A_{p+25}$, $A_{p+26}$, $A_{p+27}$, $A_{p+28}$, $A_{p+29}$, $A_{p+30}$, $A_{p+31}$, $A_{p+32}$, $A_{p+33}$, $A_{p+34}$, $A_{p+35}$, $A_{p+36}$, $A_{p+37}$, $A_{p+38}$, $A_{p+39}$, $A_{p+40}$. In certain embodiments, the HA1 N-terminal stem segment of the chimeric influenza virus hemagglutinin polypeptides described herein ends in the range of $A_{p+1}$ to $A_{p+5}$, $A_{p+5}$ to $A_{p+10}$, $A_{p+10}$ to $A_{p+15}$, $A_{p+15}$ to $A_{p+20}$, $A_{p+20}$ to $A_{p+25}$, $A_{p+25}$ to $A_{p+30}$, $A_{p+30}$ to $A_{p+35}$, $A_{p+35}$ to $A_{p+40}$, or $A_{p+40}$ to $A_{p+50}$. For example, an HA1 N-terminal stem segment ending at $A_{p+38}$ would end at Arg90 of an H3 hemagglutinin. The end of an HA1 N-terminal stem segment should be selected in conjunction with the end of the HA1 C-terminal stem segment and the influenza hemagglutinin head domain polypeptide so that the resulting chimeric influenza virus hemagglutinin polypeptide is capable of forming a three-dimensional structure similar to a wild-type influenza hemagglutinin. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

In certain embodiments, the HA1 C-terminal stem segment of the chimeric influenza virus hemagglutinin polypeptides described herein does not start at $A_q$ (e.g., $Cys_{277}$ of an HA1 subunit from an H3 hemagglutinin), but at a residue in sequence and structural vicinity to $A_q$. For example, in certain embodiments, the HA1 C-terminal stem segment of the chimeric influenza virus hemagglutinin polypeptides described herein starts at about $A_{q-1}$, $A_{q-2}$, $A_{q-3}$, $A_{q-4}$, $A_{q-5}$, $A_{q-6}$, $A_{q-7}$, $A_{q-8}$, $A_{q-9}$, $A_{q-10}$, $A_{q-11}$, $A_{q-12}$, $A_{q-13}$, $A_{q-14}$, $A_{q-15}$, $A_{q-20}$, $A_{q-25}$, $A_{q-30}$, $A_{q-35}$, $A_{q-40}$, $A_{q-45}$, $A_{q-50}$, $A_{q-55}$, $A_{q-60}$, $A_{q-65}$, $A_{q-70}$, $A_{q-75}$, or $A_{q-80}$. In certain embodiments, the HA1 C-terminal stem segment of the chimeric influenza virus hemagglutinin polypeptides described herein starts in the range of $A_{q-1}$ to $A_{q-5}$, $A_{q-5}$ to $A_{q-10}$, $A_{q-10}$ to $A_{q-15}$, $A_{q-15}$ to $A_{q-20}$, $A_{q-20}$ to $A_{q-25}$, $A_{q-25}$ to $A_{q-30}$, $A_{q-30}$ to $A_{q-35}$, $A_{q-35}$ to $A_{q-40}$, $A_{q-40}$ to $A_{q-45}$, $A_{q-45}$ to $A_{q-50}$, $A_{q-50}$ to $A_{q-55}$, $A_{q-55}$ to $A_{q-60}$, $A_{q-60}$ to $A_{q-65}$, $A_{q-65}$ to $A_{q-70}$, $A_{q-75}$ to $A_{q-80}$. For example, an HA1 C-terminal stem segment ending at $A_{q-77}$ would start at Gly200 of an H3 hemagglutinin; and an HA1 C-terminal stem segment ending at $A_{q-10}$ would start at Isoleucine-262 of an H3 hemagglutinin. In certain embodiments, the HA1 C-terminal stem segment of the chimeric influenza virus hemagglutinin polypeptides described herein starts at $A_{q+1}$, $A_{q+2}$, $A_{q+3}$, $A_{q+4}$, $A_{q+5}$, $A_{q+6}$, $A_{q+7}$, $A_{q+8}$, $A_{q+9}$, $A_{q+10}$, $A_{q+11}$, $A_{q+12}$, $A_{q+13}$, $A_{q+14}$, $A_{q+15}$, $A_{q+16}$, $A_{q+17}$, $A_{q+18}$, $A_{q+19}$, $A_{q+20}$, $A_{q+21}$, $A_{q+22}$, $A_{q+23}$, $A_{q+24}$, $A_{q+25}$, $A_{q+26}$, $A_{q+27}$, $A_{q+28}$, $A_{q+29}$, $A_{q+30}$. In certain embodiments, the HA1 C-terminal stem segment of the chimeric influenza virus hemagglutinin polypeptides described herein starts in the range of $A_{q+1}$ to $A_{q+3}$, $A_{q+3}$ to $A_{q+5}$, $A_{q+5}$ to $A_{q+8}$, $A_{q+8}$ to $A_{q+10}$, $A_{q+10}$ to $A_{q+15}$, or $A_{q+15}$ to $A_{q+20}$. The end of an HA1 N-terminal stem segment should be selected in conjunction with the start of the HA1 C-terminal stem segment and the influenza hemagglutinin head domain polypeptide so that the resulting chimeric influenza virus hemagglutinin polypeptide is capable of forming a three-dimensional structure similar to a wild-type influenza hemagglutinin. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

In one example, an HA1 N-terminal stem segment of a chimeric influenza virus hemagglutinin polypeptide described herein may end at any one of hemagglutinin amino acid positions 45-48 (using H3 numbering) and an HA1 C-terminal stem segment of the chimeric influenza virus hemagglutinin polypeptide may start at any one of hemagglutinin amino acid positions 285-290 (using H3 numbering); and the heterologous head domain may begin at any one of amino acid positions 46-49 and end at any one of amino acid position 284-289 (using H3 numbering). In another example, an HA1 N-terminal stem segment of a chimeric influenza virus hemagglutinin polypeptide described herein ends at hemagglutinin amino acid position 90 (using H3 numbering) and an HA1 C-terminal stem segment of the chimeric influenza virus hemagglutinin polypeptide starts hemagglutinin amino acid position 200 (using H3 numbering); and the heterologous head domain begins at amino acid position 91 and ends at amino acid position 199 (using H3 numbering).

In certain embodiments, the end of the N-terminal stem segment of a chimeric influenza virus hemagglutinin polypeptide described herein is $A_{p-1}$, and the start of the C-terminal stem segment of a chimeric influenza virus hemagglutinin polypeptide described herein is $A_{q-1}$. In certain embodiments, the end of the N-terminal stem segment of a chimeric influenza virus hemagglutinin polypeptide described herein is $A_{p-2}$, and the start of the C-terminal stem segment of a chimeric influenza virus hemagglutinin polypeptide described herein is $A_{q-2}$. In certain embodiments, the end of the N-terminal stem segment of a chimeric influenza virus hemagglutinin polypeptide described herein is $A_{p-3}$ and the start of the C-terminal stem segment of a chimeric influenza virus hemagglutinin polypeptide described herein is $A_{q-3}$. In certain embodiments, the end of the N-terminal stem segment of a chimeric influenza virus hemagglutinin polypeptide described herein is $A_{p-4}$, and the start of the C-terminal stem segment of a chimeric influenza virus hemagglutinin polypeptide described herein is $A_{q-4}$. In certain embodiments, the end of the N-terminal stem segment of a chimeric influenza virus hemagglutinin polypeptide described herein is $A_{p-5}$, and the start of the C-terminal stem segment of a chimeric influenza virus hemagglutinin polypeptide described herein is $A_{q-5}$. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

In certain embodiments, the end of the N-terminal stem segment of a chimeric influenza virus hemagglutinin polypeptide described herein is $A_{p+1}$, and the start of the C-terminal stem segment is of a chimeric influenza virus hemagglutinin polypeptide described herein $A_{q+1}$. In certain embodiments, the end of the N-terminal stem segment of a chimeric influenza virus hemagglutinin polypeptide described herein is $A_{p+2}$, and the start of the C-terminal stem segment of a chimeric influenza virus hemagglutinin polypeptide described herein is $A_{q+2}$. In certain embodiments, the end of the N-terminal stem segment of a chimeric influenza virus hemagglutinin polypeptide described herein is $A_{p+3}$, and the start of the C-terminal stem segment is of a chimeric influenza virus hemagglutinin polypeptide described herein $A_{q+3}$. In certain embodiments, the end of the N-terminal stem segment of a chimeric influenza virus hemagglutinin polypeptide described herein is $A_{p+4}$, and the start of the C-terminal stem segment of a chimeric influenza virus hemagglutinin polypeptide described herein is $A_{q+4}$. In certain embodiments, the end of the N-terminal stem segment of a chimeric influenza virus hemagglutinin polypeptide described herein is $A_{p+5}$, and the start of the C-terminal stem segment of a chimeric influenza virus hemagglutinin polypeptide described herein is $A_{q+5}$. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

In certain embodiments, the end of the N-terminal stem segment of a chimeric influenza virus hemagglutinin polypeptide described herein is $A_{p-1}$, and the start of the C-terminal stem segment of a chimeric influenza virus hemagglutinin polypeptide described herein is $A_{q+1}$. In certain embodiments, the end of the N-terminal stem segment of a chimeric influenza virus hemagglutinin polypeptide described herein is $A_{p-2}$, and the start of the C-terminal stem segment of a chimeric influenza virus hemagglutinin polypeptide described herein is $A_{q+2}$. In certain embodiments, the end of the N-terminal stem segment of a chimeric influenza virus hemagglutinin polypeptide described herein is $A_{p-3}$, and the start of the C-terminal stem segment is of a chimeric influenza virus hemagglutinin polypeptide described herein $A_{q+3}$. In certain embodiments, the end of the N-terminal stem segment of a chimeric influenza virus hemagglutinin polypeptide described herein is $A_{p-4}$, and the start of the C-terminal stem segment of a chimeric influenza virus hemagglutinin polypeptide described herein is $A_{q+4}$. In certain embodiments, the end of the N-terminal stem segment of a chimeric influenza virus hemagglutinin polypeptide described herein is $A_{p-5}$, and the start of the C-terminal stem segment of a chimeric influenza virus hemagglutinin polypeptide described herein is $A_{q+5}$. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

In certain embodiments, the end of the N-terminal stem segment of a chimeric influenza virus hemagglutinin polypeptide described herein is $A_{p+1}$, and the start of the C-terminal stem segment of a chimeric influenza virus hemagglutinin polypeptide described herein is $A_{q-1}$. In certain embodiments, the end of the N-terminal stem segment of a chimeric influenza virus hemagglutinin polypeptide described herein is $A_{p+2}$, and the start of the C-terminal stem segment of a chimeric influenza virus hemagglutinin polypeptide described herein is $A_{q-2}$. In certain embodiments, the end of the N-terminal stem segment of a chimeric influenza virus hemagglutinin polypeptide described herein is $A_{p+3}$, and the start of the C-terminal stem segment of a chimeric influenza virus hemagglutinin polypeptide described herein is $A_{q-3}$. In certain embodiments, the end of the N-terminal stem segment of a chimeric influenza virus hemagglutinin polypeptide described herein is $A_{p+4}$, and the start of the C-terminal stem segment of a chimeric influenza virus hemagglutinin polypeptide described herein is $A_{q-4}$. In certain embodiments, the end of the N-terminal stem segment of a chimeric influenza virus hemagglutinin polypeptide described herein is $A_{p+5}$, and the start of the C-terminal stem segment of a chimeric influenza virus hemagglutinin polypeptide described herein is $A_{q-5}$. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

Also provided herein are chimeric influenza hemagglutinin polypeptides comprising an HA2 subunit and a chimeric HA1 subunit. In certain embodiments, the chimeric HA1 subunit comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 60, 51, 52, 53, 54, 55, 56, 57, 58, 59, 60, 61, 62, 63, 64, 65, 66, 67, 68, 69, 70, 71, 72, 73, 75, 75, 76, 77, 78, 79, or 80 amino acids of the HA1 subunit of a first influenza virus strain or subtype and the remainder of amino acids of the chimeric HA1 subunit are from a second influenza virus strain or subtype. In certain embodiments, the chimeric HA1 subunit comprises 1-10, 10-20, 20-30, 30-40, 40-50, 50-60, 60-70, 70-80, 80-90, or 90-100 amino acids of the HA1 subunit of a first influenza virus strain or subtype and the remainder of amino acids of the chimeric HA1 subunit are from a second influenza virus strain or subtype. In certain embodiments, the amino acids from the first influenza virus strain or subtype can be consecutive, or can represent portions of the N- and/or C-termini of a chimeric HA1 domain. In specific embodiments, the chimeric HA1 subunit comprises an influenza virus hemagglutinin head domain polypeptide comprising amino acids of two or more different subtypes or strains of influenza virus. In specific embodiments, the chimeric HA1 subunit comprises a globular head with amino acids of two or more different subtypes or strains of influenza virus.

It will be understood by those of skill in the art that the chimeric influenza virus hemagglutinin polypeptides provided herein can be prepared according to any technique known by and deemed suitable to those of skill in the art, including the techniques described herein. In certain embodiments, the chimeric influenza virus hemagglutinin polypeptides are isolated.

5.2 Influenza Hemagglutinin Head Domain Polypeptides

Provided herein are influenza hemagglutinin head domain polypeptides for use in the generation of the flu HA polypeptides, including chimeric influenza virus hemagglutinin polypeptides, described herein.

Generally, the influenza hemagglutinin head domain polypeptides provided herein are polypeptides that comprise or consist essentially of the globular head domain of an influenza hemagglutinin polypeptide. The head domain of an influenza hemagglutinin polypeptide is the head domain that is generally recognized by those of skill in the art.

In certain embodiments, the influenza hemagglutinin head domain polypeptides provided herein comprise an influenza hemagglutinin head domain having at least 70%, 75%, 80%, 85%, 90%, 95%, 96%, 98%, or 99% amino acid sequence identity to an influenza hemagglutinin head domain known to those of skill in the art.

Also provided herein are influenza hemagglutinin head domain polypeptides comprising amino acids from two or more strains or subtypes of influenza virus. In certain embodiments, a chimeric HA1 subunit comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 60, 51, 52, 53, 54, 55, 56, 57, 58, 59, 60, 61, 62, 63, 64, 65, 66, 67, 68, 69, 70, 71, 72, 73, 75, 75, 76, 77, 78, 79, or 80 amino acids of the HA1 subunit of a first influenza virus strain or subtype and the remainder of amino acids of the chimeric HA1 subunit are from a second influenza virus strain or subtype. In certain embodiments, a chimeric HA1 subunit comprises 1-10, 10-20, 20-30, 30-40, 40-50, 50-60, 60-70, 70-80, 80-90, or 90-100 amino acids of the HA1 subunit of a first influenza virus strain or subtype and the remainder of amino acids of the chimeric HA1 subunit are from a second influenza virus strain or subtype. In certain embodiments, the amino acids from the first influenza virus strain or subtype can be consecutive, and/or can represent portions of the N- and/or C-termini of a chimeric HA1 domain.

Also provided herein are influenza hemagglutinin head domain polypeptides comprising deleted forms of a known influenza hemagglutinin head domain, wherein up to about 150, 145, 140, 135, 130, 125, 120, 115, 110, 105, 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from the head domain. Also provided herein are influenza hemagglutinin head domain polypeptides comprising deleted forms of a known influenza hemagglutinin head domain, wherein about 1-10, 10-20, 20-30, 30-40, 40-50, 50-60, 60-70, 70-80, 80-90, 90-100, 100-110, 110-120, 120-130, 130-140, or 140-150 amino acid residues are deleted from the head domain. Further provided herein are influenza hemagglutinin head domain polypeptides comprising altered forms of a known influenza hemagglutinin head domain, wherein up to about 80, 75, 70 65, 60, 55, 50, 45, 40, 35, 30, 25, 20, 15, 10, 9, 8, 7, 6, 5, 4, 3, 2 or 1 amino acid residues of the head domain are substituted (e.g., conservatively substituted) with other amino acids. Also provided herein are influenza hemagglutinin head domain polypeptides comprising altered forms of a known influenza hemagglutinin head domain, wherein up to about 1-10, 10-20, 20-30, 30-40, 40-50, 50-60, 60-70, 70-80, 80-90, or 90-100 amino acid residues of the head domain are substituted (e.g., conservatively substituted) with other amino acids. In certain embodiments, up to 50, 60, or more amino acids are deleted from the N-terminus of an influenza hemagglutinin head domain (as viewed from the primary amino acid sequence) and up to 70, 80, or more amino acids are deleted from the C-terminus of an influenza hemagglutinin head domain (as viewed from the primary amino acid sequence).

Also provided herein are influenza hemagglutinin head domain polypeptides comprising a deletion of one or more of the antigenic regions (e.g., a region of the head domain known to comprise or consist of an epitope) associated with the influenza hemagglutinin head domain (e.g., antigenic sites A, B, C, and D, wherein the head domain is from subtype H3 or antigenic sites Sa, Sb, Ca and Cb, wherein the head domain is from subtype H1). In a specific embodiment, provided herein is an influenza hemagglutinin head domain polypeptide comprising a deletion of one antigenic region (e.g., a region of the head domain known to comprise or consist of an epitope). In another specific embodiment, provided herein is an influenza hemagglutinin head domain polypeptide comprising a deletion of two antigenic region (e.g., two regions of the head domain known to comprise or consist of an epitope). In another specific embodiment, provided herein is an influenza hemagglutinin head domain polypeptide comprising a deletion of three antigenic region (e.g., three regions of the head domain known to comprise or consist of an epitope). In another specific embodiment, provided herein is an influenza hemagglutinin head domain polypeptide comprising a deletion of four antigenic regions (e.g., four regions of the head domain known to comprise or consist of an epitope). In another specific embodiment, provided herein is an influenza hemagglutinin head domain polypeptide comprising a deletion of five antigenic region (e.g., five regions of the head domain known to comprise or consist of an epitope). Those of skill in the art can readily determine the antigenic regions (e.g., epitopes) of influenza head domains known in the art or later identified using techniques known to those of skill in the art and described herein.

In certain embodiments, the influenza hemagglutinin head domain polypeptides of the chimeric influenza virus hemagglutinin polypeptides described herein comprise (i) one, two, three, or more antigenic regions from an influenza hemagglutinin head domain polypeptide that are homologous to the stem domain (i.e., derived from the same influenza virus strain or subtype) and (ii) one, two, three, or more antigenic regions from an influenza hemagglutinin head domain polypeptide that are heterologous to the stem domain (i.e., derived from a different influenza virus strain or subtype). In a specific embodiment, the C antigenic site/region of the head domain is homologous to the stem domain (i.e., derived from the same influenza virus strain or subtype). In another specific embodiment, the D antigenic site/region of the head domain is homologous to the stem domain (i.e., derived from the same influenza virus strain or subtype). In another specific embodiment, the C and D antigenic sites/regions of the head domain are homologous to the stem domain (i.e., derived from the same influenza virus strain or subtype). In yet another specific embodiment, the Ca and/or Cb antigenic sites/regions of the head domain are homologous to the stem domain (i.e., derived from the same influenza virus strain or subtype).

Also provided herein are influenza hemagglutinin head domain polypeptides comprising a replacement of one or more of the antigenic regions (e.g., a region of the head domain known to comprise or consist of an epitope) associated with the influenza hemagglutinin head domain with a non-antigenic polypeptide sequence (e.g., a polypeptide sequence that is known to not induce an immune response or is known to generate an immune response that is not specific to influenza). In a specific embodiment, provided herein is an influenza hemagglutinin head domain polypeptide comprising a replacement of one antigenic region (e.g., a region of the head domain known to comprise or consist of an epitope) with a non-antigenic polypeptide sequence (e.g., a polypeptide sequence that is known to not induce an immune response or is known to generate an immune response that is not specific to influenza). In another specific embodiment, provided herein is an influenza hemagglutinin head domain polypeptide comprising a replacement of two antigenic regions (e.g., two regions of the head domain known to comprise or consist of an epitope) with non-antigenic polypeptide sequences (e.g., polypeptide sequences that are known to not induce an immune response or are known to generate an immune response that is not specific to influenza). In another specific embodiment, provided herein is an influenza hemagglutinin head domain polypeptide comprising a replacement of three antigenic regions (e.g., three regions of the head domain known to comprise or consist of an epitope) with non-antigenic polypeptide sequences (e.g., polypeptide sequences that are known to not induce an immune response or are known to generate an immune response that is not specific to influenza). In another specific embodiment, provided herein is an influenza hemagglutinin head domain polypeptide comprising a replacement of four antigenic regions (e.g., four regions of the head domain known to comprise or consist of an epitope) with non-antigenic polypeptide sequences (e.g., polypeptide sequences that are known to not induce an immune response or are known to generate an immune response that is not specific to influenza). In another specific embodiment, provided herein is an influenza hemagglutinin head domain polypeptide comprising a replacement of five antigenic regions (e.g., five regions of the head domain known to comprise or consist of an epitope) with non-antigenic polypeptide sequences (e.g., polypeptide sequences that are known to not induce an immune response or are known to generate an immune response that is not specific to influenza). Those of skill in the art can readily determine the antigenic regions (e.g., epitopes) of influenza head domains known in the art or later identified using techniques known to those of skill in the art and described herein.

In another specific embodiment, provided herein is an influenza hemagglutinin head domain polypeptide comprising one, two, three, or more heterologous antigenic regions, i.e., one, two, three, or more antigenic regions from the hemagglutinin of a different influenza virus strain or subtype (e.g., an influenza virus strain or subtype to which all or part of the population is naïve). In another specific embodiment, the heterologous antigenic regions of the influenza hemagglutinin head domain polypeptide comprises one or more non-naturally occurring glycosylation sites as discussed, infra in Section 5.4.2. Without being bound by any particular theory of operation, it is believed that the immunogenicity of conserved subimmunodominant antigenic regions within the stem domain can be increased by the addition of one or more non-naturally occurring glycosylation sites in these immunodominant regions in the influenza hemagglutinin head domain. In specific embodiments, the influenza hemagglutinin head domain polypeptide comprises one, two, three, or more heterologous antigenic regions wherein the heterologous antigenic regions comprises one or more non-naturally occurring glycosylation sites.

The influenza hemagglutinin head domain polypeptides provided herein might be based on (i.e. might have sequence identity to) the head domain of any influenza hemagglutinin known to those of skill or later discovered. In certain embodiments, influenza hemagglutinin head domain polypeptides are based on the head domain of an influenza A hemagglutinin (e.g., the head domain of the hemagglutinin of an influenza A virus described in Section 5.4, infra). In certain embodiments, the influenza hemagglutinin head domain polypeptides are based on the head domain of an influenza A hemagglutinin selected from the group consisting of H1, H2, H3, H4, H5, H6, H7, H8, H9, H10, H11, H12, H13, H14, H15, H16, and H17. In certain embodiments, influenza hemagglutinin head domain polypeptides are based on the head domain of an influenza B hemagglutinin (e.g., the head domain of the hemagglutinin of an influenza B virus described in Section 5.4, infra). In some embodiments, the influenza hemagglutinin head domain polypeptides are based on the head domain of B/Seal/Netherlands/1/99. In a specific embodiment, the influenza hemagglutinin head domain polypeptides are based on the head domain of an influenza A hemagglutinin selected from an H5, H6, and/or H9 group. In another specific embodiment, the influenza hemagglutinin head domain polypeptides are based on the head domain of an influenza A hemagglutinin selected from an H5, H7, and/or H9 group.

5.3 Influenza Hemagglutinin Stem Domain Polypeptides

Provided herein are influenza hemagglutinin stem domain polypeptides for use in the generation of flu hemagglutinin polypeptides (e.g., chimeric influenza virus hemagglutinin polypeptides). While not intending to be bound by any particular theory of operation, it is believed that, in the context of the flu hemagglutinin polypeptides (e.g., chimeric influenza virus hemagglutinin polypeptides) provided herein, the influenza hemagglutinin stem domain polypeptides are useful for presenting one or more relatively conserved antigenic regions to a host immune system in order to generate an immune response that is capable of cross-reacting with a plurality of influenza strains. Since the one or more antigenic regions are well conserved across influenza hemagglutinin subtypes, such an immune response might cross-react with several subtypes of full-length influenza hemagglutinin polypeptides.

Generally, the influenza hemagglutinin stem domain polypeptides provided herein are polypeptides that comprise or consist essentially of the stem domain of an influenza hemagglutinin polypeptide. The stem domain of an influenza hemagglutinin polypeptide is the stem domain that is generally recognized by those of skill in the art.

In certain embodiments, the influenza hemagglutinin stem domain polypeptides provided herein comprise little or no globular head domain of an influenza hemagglutinin polypeptide. In certain embodiments, an influenza hemagglutinin stem domain polypeptide is an influenza hemagglutinin that has had its globular head domain deleted by any technique deemed suitable by one of skill in the art.

In certain embodiments, influenza hemagglutinin stem domain polypeptides described herein maintain the cysteine residues identified in influenza hemagglutinin polypeptides as $A_p$ and $A_q$ in FIG. 1. In certain embodiments, influenza hemagglutinin stem domain polypeptides described herein have greater stability at a pH lower than the hemagglutinin of a wild-type influenza virus (e.g., a pH less than 5.2, less than 5.1, less than 5.0, or less than 4.9, such as 4.8, 4.7, 4.6, 4.5, 4.4, 4.3, 4.2, 4.1, 4.0, 3.9, 3.8, etc.). In particular embodiments, influenza hemagglutinin stem domain polypeptides described herein undergo conformational changes from the pre-fusion to the fusion conformation at a pH lower than the hemagglutinin of wild-type influenza viruses. In some embodiments, influenza hemagglutinin stem domain polypeptides described herein comprise one or more amino acid substitutions, such as HA1 H17Y (H3 numbering) that increases the stability of the polypeptides at a low pH (e.g., a pH of between 4.9 to 5.2, 4.5 to 3.5, 3.5 to 2.5, 2.5 to 1.5, 1.5 to 0.5). The stability of influenza hemagglutinin stem domain polypeptides can be assessed using techniques known in the art, such as sensitivity of the hemagglutinin molecules to trypsin digestion, as described in, e.g., Thoennes et al., 2008, Virology 370: 403-414.

The influenza hemagglutinin stem domain polypeptides can be prepared according to any technique deemed suitable to one of skill in the art, including techniques described below. In certain embodiments, the stem domain polypeptides are isolated.

In some embodiments, the primary structure of an influenza hemagglutinin stem domain polypeptide comprises, in the following order: an HA1 N-terminal stem segment, a linker, an HA1 C-terminal stem segment and an HA2. In some embodiments, the primary structure of an influenza hemagglutinin stem domain polypeptide comprises, in the following order: an HA1 N-terminal stem segment, a linker, an HA1 C-terminal short stem segment and an HA2. In some embodiments, the primary structure of an influenza hemagglutinin stem domain polypeptide comprises, in the following order: an HA1 N-terminal long stem segment, a linker, an HA1 C-terminal long stem segment and an HA2. In some embodiments, the influenza hemagglutinin stem domain polypeptide comprises in the following order: an HA1 N-terminal stem segment, a linker, an HA1 intermediate stem segment, a second linker, an HA1 C-terminal stem segment and an HA2.

The primary sequence might be formed by a single polypeptide, or it might be formed by multiple polypeptides. Typically, a single polypeptide is expressed by any technique deemed suitable by one of skill in the art. In single polypeptide embodiments, the HA1 segments and the HA2 are in tertiary association. As is known to those of skill in the art, a single HA polypeptide might be cleaved, for example by a protease, under appropriate expression conditions to yield two polypeptides in quaternary association. The cleavage is typically between the HA1 C-terminal stem segment and the HA2. In certain embodiments, provided herein are multiple polypeptide, for example two polypeptide, influenza hemagglutinin stem domains. In multiple polypeptide embodiments, the HA1 segments and HA2 are in quaternary association.

In certain embodiments, an influenza hemagglutinin stem domain polypeptide provided herein is monomeric. In certain embodiments, an influenza hemagglutinin stem domain polypeptide provided herein is multimeric. In certain embodiments, an influenza hemagglutinin stem domain polypeptide provided herein is trimeric. Those of skill in the art will recognize that native influenza hemagglutinin polypeptides are capable of trimerization in vivo and that certain influenza hemagglutinin stem domain polypeptides provided herein are capable of trimerization. In particular embodiments described below, influenza hemagglutinin stem domain polypeptides provided herein comprise trimerization domains to facilitate trimerization.

In certain embodiments, an influenza hemagglutinin stem domain polypeptide comprises a signal peptide. Typically, the signal peptide is cleaved during or after polypeptide expression and translation to yield a mature influenza hemagglutinin stem domain polypeptide. The signal peptide might be advantageous for expression of the influenza hemagglutinin stem domain polypeptides. In certain embodiments, also provided herein are mature influenza hemagglutinin stem domain polypeptides that lack a signal peptide.

Influenza hemagglutinin HA2 typically comprises a stem domain, transmembrane domain and a cytoplasmic domain. In certain embodiments, provided herein are influenza hemagglutinin stem domain polypeptides that comprise an HA2 stem domain, an HA2 luminal domain, an HA2 transmembrane domain and an HA2 cytoplasmic domain. Such influenza hemagglutinin stem domain polypeptides might be expressed as membrane-bound antigens. In certain embodiments, provided herein are influenza hemagglutinin stem domain polypeptides that comprise an HA2 stem domain, an HA2 luminal domain, and an HA2 transmembrane domain but lack some or all of the typical cytoplasmic domain. Such influenza hemagglutinin stem domain polypeptides might be expressed as membrane-bound antigens. In certain embodiments, provided herein are influenza hemagglutinin stem domain polypeptides that comprise an HA2 stem domain and an HA2 luminal domain but lack both an HA2 transmembrane domain and an HA2 cytoplasmic domain. Such influenza hemagglutinin stem domain polypeptides might advantageously be expressed as soluble polypeptides. In certain embodiments, provided herein are influenza hemagglutinin stem domain polypeptides that comprise an HA2 stem domain but lack an HA2 luminal domain, an HA2 transmembrane domain and an HA2 cytoplasmic domain. Such influenza hemagglutinin stem domain polypeptides might advantageously be expressed as soluble polypeptides. In certain embodiments, the influenza hemagglutinin stem domain polypeptides comprise an HA2 stem domain having at least 70%, 75%, 80%, 85%, 90%, 95%, 96% or 98% amino acid sequence identity to an influenza HA2 stem domain known to those of skill in the art. Exemplary known HA2 stem domains from known influenza A and influenza B hemagglutinins are provided in the tables below.

Also provided herein are influenza hemagglutinin stem domain polypeptides comprising deleted forms of HA2 stem domains wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA2 stem domain. Further provided herein are influenza hemagglutinin stem domain polypeptides comprising altered forms of HA2 stem domains wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are conservatively substituted with other amino acids. Further provided are influenza hemagglutinin stem domain polypeptides comprising deleted and altered HA2 stem domains. In certain embodiments, the influenza hemagglutinin stem domain polypeptides comprises an HA2 stem domain comprising one or more modified glycosylation sites, wherein the modified glycosylation site comprises a modification of a naturally occurring glycosylation site that disrupts the ability of a glycan to attach to the modified glycosylation site, as described in Section 5.4.1, infra. Without being bound by any particular theory of operation, it is believed that immunogenicity and accessibility antigenic regions within the stem domain can be increased by modifying one or more glycosylation sites within the stem domain in a manner that disrupts the glycosylation (i.e. the attachment of a glycan) at the sites.

In some embodiments, the primary structure of an influenza hemagglutinin stem domain polypeptide comprises, in the following order: an HA1 N-terminal stem segment, a linker, an HA1 C-terminal stem segment and an HA2. The HA1 N-terminal stem segment might be any HA1 N-terminal stem segment recognized by one of skill in the art based on the definition provided herein. Typically, an HA1 N-terminal stem segment corresponds to a polypeptide consisting of the N-terminal amino acid of a mature HA1 (i.e. an HA1 lacking a signal peptide) through the cysteine residue located in sequence at approximately the $52^{nd}$ residue of the HA1. This cysteine residue, termed $A_p$ herein, is generally capable of forming a disulfide bridge with a cysteine residue in the C-terminal stem segment of HA1. Sequences of 16 representative influenza A hemagglutinins are presented in FIG. 1, and residue $A_p$ is identified in each.

In certain embodiments, the HA1 N-terminal stem segment does not end exactly at $A_p$ (e.g., $Cys_{52}$ of an HA1 subunit from an H3 hemagglutinin), but at a residue in sequence and structural vicinity to $A_p$. For example, in certain embodiments, the HA1 N-terminal stem segment ends at $A_{p-1}$, $A_{p-2}$, $A_{p-3}$, $A_{p-4}$, $A_{p-5}$, $A_{p-6}$, $A_{p-7}$, $A_{p-8}$, $A_{p-9}$, $A_{p-10}$, $A_{p-11}$, $A_{p-12}$, $A_{p-13}$, $A_{p-14}$, $A_{p-15}$, $A_{p-16}$, $A_{p-17}$, $A_{p-18}$, $A_{p-19}$, $A_{p-20}$, $A_{p-21}$, $A_{p-22}$, $A_{p-23}$, $A_{p-23}$, $A_{p-24}$, $A_{p-25}$, $A_{p-26}$, $A_{p-27}$, $A_{p-28}$, $A_{p-29}$, $A_{p-30}$. In certain embodiments, the HA1 N-terminal stem segment of the flu hemagglutinin polypeptides described herein ends in the range of $A_{p-1}$ to $A_{p-3}$, $A_{p-3}$ to $A_{p-5}$, $A_{p-5}$ to $A_{p-8}$, $A_{p-8}$ to $A_{p-10}$, $A_{p-10}$ to $A_{p-15}$, $A_{p-15}$ to $A_{p-20}$, $A_{p-20}$ to $A_{p-30}$, $A_{p-30}$ to $A_{p-40}$. In other embodiments, the HA1 N-terminal stem segment ends at $A_{p+1}$, $A_{p+2}$, $A_{p+3}$, $A_{p+4}$, $A_{p+5}$, $A_{p+6}$, $A_{p+7}$, $A_{p+8}$, $A_{p+9}$, $A_{p+10}$, $A_{p+11}$, $A_{p+12}$, $A_{p+13}$, $A_{p+14}$, $A_{p+15}$, $A_{p+16}$, $A_{p+17}$, $A_{p+18}$, $A_{p+19}$, $A_{p+20}$, $A_{p+21}$, $A_{p+22}$, $A_{p+23}$, $A_{p+24}$, $A_{p+25}$, $A_{p+26}$, $A_{p+27}$, $A_{p+28}$, $A_{p+29}$, $A_{p+30}$, $A_{p+31}$, $A_{p+32}$, $A_{p+33}$, $A_{p+34}$, $A_{p+35}$, $A_{p+36}$, $A_{p+37}$, $A_{p+38}$, $A_{p+39}$, $A_{p+40}$. In certain embodiments, the HA1 N-terminal stem segment of the flu hemagglutinin polypeptides described herein ends in the range of $A_{p+1}$ to $A_{p+5}$, $A_{p+5}$ to $A_{p+10}$, $A_{p+10}$ to $A_{p+15}$, $A_{p+15}$ to $A_{p+20}$, $A_{p+20}$ to $A_{p+25}$, $A_{p+25}$ to $A_{p+30}$, $A_{p+30}$ to $A_{p+35}$, $A_{p+35}$ to $A_{p+40}$, or $A_{p+40}$ to $A_{p+50}$. The end of an HA1 N-terminal stem segment should be selected in conjunction with the end of the HA1 C-terminal stem segment and the linker so that the resulting linked HA1 stem domain is capable of forming a three-dimensional structure similar, as described below, to an influenza hemagglutinin stem domain.

In certain embodiments, the influenza hemagglutinin stem domain polypeptides comprise an HA1 N-terminal stem segment having at least 70%, 75%, 80%, 85%, 90%, 95%, 96% or 98% amino acid sequence identity to an influenza HA1 N-terminal stem segment known to those of skill in the art. Exemplary known HA1 N-terminal stem segments are provided in the tables below.

Also provided herein are influenza hemagglutinin stem domain polypeptides comprising deleted forms of HA1 N-terminal stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA1 N-terminal stem segment. Also provided herein are influenza hemagglutinin stem domain polypeptides comprising deleted forms of a known influenza hemagglutinin stem domain, wherein about 1-10, 10-20, 20-30, 30-40, 40-50, 50-60, 60-70, 70-80, 80-90, 90-100 amino acid residues are deleted from the stem domain. In certain embodiments, provided herein are influenza hemagglutinin stem domain polypeptides that comprise expanded forms of HA1 N-terminal stem segments wherein 1, 2, 3, 4, 5, 6, 7, 8, 9, 10 or more residues are added to the C-terminus of the HA1 N-terminal stem segments; these added residues might be derived from the amino acid sequence of a globular head domain adjacent to an HA1 N-terminal stem segment. Further provided herein are influenza hemagglutinin stem domain polypeptides comprising altered forms of HA1 N-terminal stem segments wherein up to 80, 75, 70 65, 60, 55, 50, 45, 40, 35, 30, 25, 20, 15, 10, 9, 8, 7, 6, 5, 4, 3, 2 or 1 amino acid residues are conservatively substituted with other amino acids. Also provided herein are influenza hemagglutinin stem domain polypeptides comprising altered forms of a known influenza hemagglutinin stem domain, wherein up to about 1-10, 10-20, 20-30, 30-40, 40-50, 50-60, 60-70, 70-80, 80-90, or 90-100 amino acid residues of the stem domain are substituted (e.g., conservatively substituted) with other amino acids. Further provided are influenza hemagglutinin stem domain polypeptides comprising deleted and altered HA1 N-terminal stem segments. In certain embodiments, up to 50, 60, or more amino acids are deleted from the N-terminus of an influenza hemagglutinin stem domain (as viewed from the primary amino acid sequence) and up to 70, 80, or more amino acids are deleted from the C-terminus of an influenza hemagglutinin stem domain (as viewed from the primary amino acid sequence).

The HA1 C-terminal stem segment might be any HA1 C-terminal stem segment recognized by one of skill in the art based on the definition provided herein. Typically, an HA1 C-terminal stem segment corresponds to a polypeptide consisting of the cysteine residue located in sequence at approximately the $277^{th}$ residue of an HA1 (using H3 numbering) through the C-terminal amino acid of the HA1. This cysteine residue, termed $A_q$ herein, is generally capable of forming a disulfide bridge with cysteine residue $A_p$ in the N-terminal stem segment of HA1. Sequences of 17 representative influenza A hemagglutinins are presented in FIG. 1, and residue $A_q$ is identified in each.

In certain embodiments, the HA1 C-terminal stem segment does not start at $A_q$ (e.g., $Cys_{277}$ of an HA1 subunit from an H3 hemagglutinin), but at a residue in sequence and structural vicinity to $A_q$. For example, in certain embodiments, the HA1 C-terminal stem segment starts at about $A_{q-1}$, $A_{q-2}$, $A_{q-3}$, $A_{q-4}$, $A_{q-5}$, $A_{q-6}$, $A_{q-7}$, $A_{q-8}$, $A_{q-9}$, $A_{q-10}$, $A_{q-11}$, $A_{q-12}$, $A_{q-13}$, $A_{q-14}$, $A_{q-15}$, $A_{q-20}$, $A_{q-25}$, $A_{q-30}$, $A_{q-35}$, $A_{q-40}$, $A_{q-45}$, $A_{q-50}$, $A_{q-55}$, $A_{q-60}$, $A_{q-65}$, $A_{q-70}$, $A_{q-75}$, or $A_{q-80}$. In certain embodiments, the HA1 C-terminal stem segment starts at in the range of $A_{q-1}$ to $A_{q-5}$, $A_{q-5}$ to $A_{q-10}$, $A_{q-10}$ to $A_{q-15}$, $A_{q-15}$ to $A_{q-20}$, $A_{q-20}$ to $A_{q-25}$, $A_{q-25}$ to $A_{q-30}$, $A_{q-30}$ to $A_{q-35}$, $A_{q-35}$ to $A_{q-40}$, $A_{q-40}$ to $A_{q-45}$, $A_{q-45}$ to $A_{q-50}$, $A_{q-50}$ to $A_{q-55}$, $A_{q-55}$ to $A_{q-60}$, $A_{q-60}$ to $A_{q-65}$, $A_{q-65}$ to $A_{q-70}$, $A_{q-75}$ to $A_{q-80}$. In other embodiments, the HA1 C-terminal stem segment starts at $A_{q+1}$, $A_{q+2}$, $A_{q+3}$, $A_{q+4}$, $A_{q+5}$, $A_{q+6}$, $A_{q+7}$, $A_{q+8}$, $A_{q+9}$, or $A_{q+10}$. In certain embodiments, the HA1 C-terminal stem segment of the flu hemagglutinin polypeptides described herein starts in the range of $A_{q+1}$ to $A_{q+3}$, $A_{q+3}$ to $A_{q+5}$, $A_{q+5}$ to $A_{q+8}$, $A_{q+8}$ to $A_{q+10}$, $A_{g+10}$ to $A_{q+15}$, or $A_{q+15}$ to $A_{q+20}$. The end of an HA1 N-terminal stem segment should be selected in conjunction with the start of the HA1 C-terminal stem segment and the linker so that the resulting HA1 stem domain is capable of forming a three-dimensional structure similar, as described below, to an influenza hemagglutinin.

In certain embodiments, the influenza hemagglutinin stem domain polypeptides comprise an HA1 C-terminal stem segment having at least 70%, 75%, 80%, 85%, 90%, 95%, 96% or 98% amino acid sequence identity to an influenza HA1 C-terminal stem segment known to those of skill in the art. Exemplary known HA1 C-terminal stem segments are provided in the tables below.

In certain embodiments, the end of the N-terminal stem segment is $A_{p-1}$, and the start of the C-terminal stem segment is $A_{q-1}$. In certain embodiments, the end of the N-terminal stem segment is $A_{p-2}$, and the start of the C-terminal stem segment is $A_{q-2}$. In certain embodiments, the end of the N-terminal stem segment is $A_{p-3}$, and the start of the C-terminal stem segment is $A_{q-3}$. In certain embodiments, the end of the N-terminal stem segment is $A_{p+4}$, and the start of the C-terminal stem segment is $A_{q-4}$. In certain embodiments, the end of the N-terminal stem segment is $A_{p-5}$ and the start of the C-terminal stem segment is $A_{q-5}$.

In certain embodiments, the end of the N-terminal stem segment is $A_{p+1}$, and the start of the C-terminal stem segment is $A_{q+1}$. In certain embodiments, the end of the N-terminal stem segment is $A_{p+2}$, and the start of the C-terminal stem segment is $A_{q+2}$. In certain embodiments, the end of the N-terminal stem segment is $A_{p+3}$ and the start of the C-terminal stem segment is $A_{q+3}$. In certain embodiments, the end of the N-terminal stem segment is $A_{p+4}$, and the start of the C-terminal stem segment is $A_{q+4}$. In certain embodiments, the end of the N-terminal stem segment is $A_{p+5}$ and the start of the C-terminal stem segment is $A_{q+5}$.

In certain embodiments, the end of the N-terminal stem segment is $A_{p-1}$, and the start of the C-terminal stem segment is $A_{q+1}$. In certain embodiments, the end of the N-terminal stem segment is $A_{p-2}$, and the start of the C-terminal stem segment is $A_{q+2}$. In certain embodiments, the end of the N-terminal stem segment is $A_{p-3}$ and the start of the C-terminal stem segment is $A_{q+3}$. In certain embodiments, the end of the N-terminal stem segment is $A_{p-4}$, and the start of the C-terminal stem segment is $A_{q+4}$. In certain embodiments, the end of the N-terminal stem segment is $A_{p-5}$ and the start of the C-terminal stem segment is $A_{q+5}$.

In certain embodiments, the end of the N-terminal stem segment is $A_{p+1}$, and the start of the C-terminal stem segment is $A_{q-1}$. In certain embodiments, the end of the N-terminal stem segment is $A_{p+2}$, and the start of the C-terminal stem segment is $A_{q-2}$. In certain embodiments, the end of the N-terminal stem segment is $A_{p+3}$ and the start of the C-terminal stem segment is $A_{q-3}$. In certain embodiments, the end of the N-terminal stem segment is $A_{p+4}$, and the start of the C-terminal stem segment is $A_{q-4}$. In certain embodiments, the end of the N-terminal stem segment is $A_{p+5}$, and the start of the C-terminal stem segment is $A_{q-5}$.

Also provided herein are influenza hemagglutinin stem domain polypeptides comprising deleted forms of HA1 C-terminal stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA1 C-terminal stem segment. Also provided herein are influenza hemagglutinin stem domain polypeptides comprising deleted forms of a known influenza hemagglutinin stem domain, wherein about 1-10, 10-20, 20-30, 30-40, 40-50, 50-60, 60-70, 70-80, 80-90, or 90-100 amino acid residues are deleted from the stem domain. In certain embodiments, provided herein are influenza hemagglutinin stem domain polypeptides that comprise expanded forms of HA1 C-terminal stem segments wherein 1, 2, 3, 4, 5, 6, 7, 8, 9, 10 or more residues are added to the N-terminus of the HA1 C-terminal stem segments; these added residues might be derived from the amino acid sequence of a globular head domain adjacent to an HA1 C-terminal stem segment. In particular embodiments, if one residue is added to the C-terminal stem segment, then one residue is added to the N-terminal stem segment; if two residues are added to the C-terminal stem segment, then two residues are added to the N-terminal stem segment; if three residues are added to the C-terminal stem segment, then three residues are added to the N-terminal stem segment. Further provided herein are influenza hemagglutinin stem domain polypeptides comprising altered forms of HA1 C-terminal stem segments wherein up to about 80, 75, 70 65, 60, 55, 50, 45, 40, 35, 30, 25, 20, 15, 10, 9, 8, 7, 6, 5, 4, 3, 2 or 1 amino acid residues are conservatively substituted with other amino acids. Also provided herein are influenza hemagglutinin stem domain polypeptides comprising altered forms of HA1 C-terminal stem segments, wherein up to about 1-10, 10-20, 20-30, 30-40, 40-50, 50-60, 60-70, 70-80, 80-90, or 90-100 amino acid residues of the HA1 C-terminal stem segment are substituted (e.g., conservatively substituted) with other amino acids. Further provided are influenza hemagglutinin stem domain polypeptides comprising deleted and altered HA1 C-terminal stem segments. In certain embodiments, the C-terminal stem segment comprises or more modified glycosylation sites. In certain embodiments, the N-terminal stem segment comprises or more modified glycosylation sites. In other embodiments, the C-terminal stem segment and N-terminal stem segment comprise one or more modified glycosylation sites.

In certain embodiments, the influenza hemagglutinin stem domain polypeptides provided herein comprise a chimeric/hybrid of the stem domain of the HA1 subunit. The chimeric of the stem domain of the HA1 subunit may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 60, 51, 52, 53, 54, 55, 56, 57, 58, 59, 60, 61, 62, 63, 64, 65, 66, 67, 68, 69, 70, 71, 72, 73, 75, 75, 76, 77, 78, 79, or 80 amino acids of the stem domain of the HA1 subunit of a first influenza virus strain or subtype and the remainder of amino acids of the chimeric of the stem domain of the HA1 subunit may be from a second influenza virus strain or subtype. In certain embodiments, the chimeric of the stem domain of the HA1 subunit comprises 1-10, 10-20, 20-30, 30-40, 40-50, 50-60, 60-70, 70-80, 80-90, or 90-100 amino acids of the stem domain of the HA1 subunit of a first influenza virus strain or subtype and the remainder of amino acids of the chimeric of the stem domain of the HA1 subunit are from a second influenza virus strain or subtype. In certain embodiments, the influenza hemagglutinin stem domain polypeptides provided herein comprise an HA2 subunit and a chimeric of the stem domain of the HA1 subunit. In certain embodiments, the influenza hemagglutinin stem domain polypeptide comprises a chimeric/hybrid of the stem domain of an HA1 subunit in which one or more naturally occurring glycosylation sites have been modified such that the modification, disrupts the ability of a glycan to attach to the modified glycosylation site, as described in Section 5.4.1, infra. Without being bound by any particular theory of operation, it is believed that immunogenicity and accessibility antigenic regions within the stem domain can be increased by modifying one or more glycosylation sites within the stem domain in a manner that disrupts the glycosylation (i.e. the attachment of a glycan) at the sites.

The influenza hemagglutinin stem domain polypeptides might be based on (i.e. might have sequence identity, as described above) any influenza hemagglutinin known to those of skill or later discovered. In certain embodiments, influenza hemagglutinin stem domain polypeptides are based on an influenza A hemagglutinin. In certain embodiments, the influenza hemagglutinin stem domain polypeptides are based on an influenza A hemagglutinin selected from the group consisting of H1, H2, H3, H4, H5, H6, H7, H8, H9, H10, H11, H12, H13, H14, H15, H16, and H17. In certain embodiments, influenza hemagglutinin stem domain polypeptides are based on an influenza B hemagglutinin, as described in detail below.

The HA1 N-terminal stem segments might be based on (i.e. might have sequence identity, as described above) any HA1 N-terminal stem segments known to those of skill or later discovered. In certain embodiments, the HA1 N-terminal stem segments are based on influenza A HA1 N-terminal stem segments. In certain embodiments, the HA1 N-terminal stem segments are based on an influenza A hemagglutinin selected from the group consisting of H1, H2, H3, H4, H5, H6, H7, H8, H9, H10, H11, H12, H13, H14, H15, H16, and H17. In certain embodiments, the HA1 N-terminal stem segment is selected from SEQ ID NOS: 34-49. In certain embodiments, the HA1 N-terminal stem segment is selected from SEQ ID NOS:34-49, each having one amino acid deleted from its C-terminus. In certain embodiments, the HA1 N-terminal stem segment is selected from SEQ ID NOS:34-49, each having two amino acids deleted from its C-terminus. In certain embodiments, the HA1 N-terminal stem segment is selected from SEQ ID NOS:34-49, each having three amino acids deleted from its C-terminus. In certain embodiments, the HA1 N-terminal stem segment is selected from SEQ ID NOS:34-49, each having four amino acids deleted from its C-terminus. In certain embodiments, the HA1 N-terminal stem segment is selected from SEQ ID NOS:34-49, each having five amino acids deleted from its C-terminus. In certain embodiments, the HA1 N-terminal stem segment is selected from SEQ ID NOS:177-224. In certain embodiments, the HA1 N-terminal stem segment is or is based on the HA-1 N-terminal stem segment of an Ann Arbor/6/60, A/Puerto Rico/8/34, or A/Perth/16/2009 influenza virus.

The HA1 C-terminal stem segments might be based on (i.e. might have sequence identity, as described above) any HA1 C-terminal stem segments known to those of skill or later discovered. In certain embodiments, the HA1 C-terminal stem segments are based on influenza A HA1 C-terminal stem segments. In certain embodiments, the HA1 C-terminal stem segments are based on an influenza A hemagglutinin selected from the group consisting of H1, H2, H3, H4, H5, H6, H7, H8, H9, H10, H11, H12, H13, H14, H15, H16, and H17. In certain embodiments, the HA1 C-terminal stem segment is selected from SEQ ID NOS:50-65. In certain embodiments, the HA1 C-terminal stem segment is selected from SEQ ID NOS: 50-65, each having one amino acid deleted from its N-terminus. In certain embodiments, the HA1 C-terminal stem segment is selected from SEQ ID NOS: 50-65, each having two amino acids deleted from its N-terminus. In certain embodiments, the HA1 C-terminal stem segment is selected from SEQ ID NOS: 50-65, each having three amino acids deleted from its N-terminus. In certain embodiments, the HA1 C-terminal stem segment is selected from SEQ ID NOS: 50-65, each having four amino acids deleted from its N-terminus. In certain embodiments, the HA1 C-terminal stem segment is selected from SEQ ID NOS: 50-65, each having five amino acids deleted from its N-terminus. In certain embodiments, the HA1 C-terminal stem segment is selected from SEQ ID NOS:226-273. In certain embodiments, the HA1 C-terminal stem segment is or is based on the HA-1 N-terminal stem segment of an Ann Arbor/6/60, A/Puerto Rico/8/34, or A/Perth/16/2009 influenza virus.

The HA2 stem domains might be based on (i.e. might have sequence identity, as described above) any HA2 stem domains known to those of skill or later discovered. In certain embodiments, the HA2 stem domains are based on influenza A HA2 stem domains. In certain embodiments, the HA2 stem domains are based on an influenza A hemagglutinin selected from the group consisting of H1, H2, H3, H4, H5, H6, H7, H8, H9, H10, H11, H12, H13, H14, H15, H16, and H17. In certain embodiments, the HA2 stem domain is selected from SEQ ID NOS:66-97. In certain embodiments, the HA2 stem domain is or is based on the HA stem domain of an A/Ann Arbor/6/60-like, A/Puerto Rico/8/1934-like, A/Perth/16/2009-like, A/California/07/2009-like, A/Brisbane/59/07-like, A/New Calcdonia/20/1999-like or A/Victoria/361/201-like influenza virus. In certain embodiments, the HA2 stem domain is or is based on a later discovered HA2 stem domain.

In certain embodiments, the HA2 stem domains are from the same influenza virus strain or subtype as the stem domain of the HA1 subunit.

In embodiments comprising a signal peptide, the signal peptide might be based on any influenza virus signal peptide known to those of skill in the art. In certain embodiments, the signal peptides are based on influenza A signal peptides. In certain embodiments, the signal peptides are based on an influenza A hemagglutinin selected from the group consisting of H1, H2, H3, H4, H5, H6, H7, H8, H9, H10, H11, H12, H13, H14, H15 and H16. In certain embodiments, the signal peptide might be any signal peptide deemed useful to one of skill in the art. In certain embodiments, the signal peptide is selected from SEQ ID NOS:18-33.

In embodiments comprising a luminal domain, the luminal domain might be based on any influenza luminal domain known to those of skill in the art. In certain embodiments, the luminal domains are based on influenza A luminal domains. In certain embodiments, the HA2 luminal domains are based on an influenza A hemagglutinin selected from the group consisting of H1, H2, H3, H4, H5, H6, H7, H8, H9, H10, H11, H12, H13, H14, H15, H16, and H17. In certain embodiments, the luminal domain might be any luminal domain deemed useful to one of skill in the art. In certain embodiments, the luminal domain is selected from SEQ ID NOS:98-113. In certain embodiments, the luminal domain is from the same influenza virus strain or subtype as the stem domain of the HA2 subunit.

In certain embodiments, the cytoplasmic, transmembrane and luminal domains are from the same influenza virus strain or subtype as the stem domain of the HA2 subunit. In other embodiments, the cytoplasmic and transmembrane domains are from the same influenza virus strain or subtype as the stem domain of the HA2 subunit. In certain embodiments, the cytoplasmic and luminal domain are from the same influenza virus strain or subtype as the stem domain of the HA2 subunit.

In embodiments comprising a transmembrane domain, the transmembrane domain might be based on any influenza transmembrane domain known to those of skill in the art. In certain embodiments, the transmembrane domains are based on influenza A transmembrane domains. In certain embodiments, the HA2 transmembrane domains are based on an influenza A hemagglutinin selected from the group consisting of H1, H2, H3, H4, H5, H6, H7, H8, H9, H10, H11, H12, H13, H14, H15, H16, and H17. In certain embodiments, the transmembrane domain might be any transmembrane domain deemed useful to one of skill in the art. In certain embodiments, the transmembrane domain is selected from SEQ ID NOS:114-129. In certain embodiments, the transmembrane domains are from the same influenza virus strain or subtype as the stem domain of the HA2 subunit.

In embodiments comprising a cytoplasmic domain, the cytoplasmic domain might be based on any influenza cytoplasmic domain known to those of skill in the art. In certain embodiments, the cytoplasmic domains are based on influenza A cytoplasmic domains. In certain embodiments, the HA2 cytoplasmic domains are based on an influenza A hemagglutinin selected from the group consisting of H1, H2, H3, H4, H5, H6, H7, H8, H9, H10, H11, H12, H13, H14, H15, H16, and H17. In certain embodiments, the cytoplasmic domain might be any cytoplasmic domain deemed useful to one of skill in the art. In certain embodiments, the cytoplasmic domain is selected from SEQ ID NOS:130-145. In certain embodiments, the cytoplasmic domains are from the same influenza virus strain or subtype as the stem domain of the HA2 subunit.

In certain embodiments, one or more of the glycosylation sites in the hemagglutinin stem domain are modified (e.g., by amino acid addition, deletion or substitution) such that glycosylation at these sites will not occur during processing and maturation of the polypeptide. Those of skill in the art will recognize that influenza HA typically comprises one or more glycosylation sites (e.g. Asn-Xaa-Ser/Thr/Cys, wherein Xaa is any amino acid or, in certain embodiments, wherein Xaa is any amino acid except Pro). In certain embodiments, one or more amino acid residues in a glycosylation site are conservatively substituted with an amino acid residue that disrupts the glycosylation site. In certain embodiments, one or more amino acid residues in a glycosylation site are substituted with any amino acid residue that disrupts the glycosylation site. In certain embodiments, one or more asparagine residues in a glycosylation sequence is substituted with alanine. In a particular embodiment, the asparagine at position 38 of an H3 hemagglutinin is changed to an alanine. In certain embodiments, the hemagglutinin stem domain comprises one or more modified glycosylation sites as discussed in Section 5.4.1, infra.

Table 1, below, identifies signal peptides, HA1 N-terminal stem segments, HA1 C-terminal stem segments and HA2 domains of influenza A hemagglutinin polypeptides. These signal peptides, stem segments and domains are useful in the polypeptides and methods described herein.

TABLE 1

Exemplary Influenza A Hemagglutinin Sequences

| HA Subtype (Genbank No.) | Signal peptide | HA1 N-terminal Stem Segment | HA1 C-terminal Stem Segment | HA2 Domain |
|---|---|---|---|---|
| H1 PR8-H1N1 (EF467821.1) | MKAN LLVLL CALAA ADA [SEQ ID NO: 18] | DTICIGYHANN STDTVDTVLE KNVTVTHSVN LLEDSHNGKL C [SEQ ID NO: 34] | CNTKCQTPLG AINSSLPYQNI HPVTIGECPKY VRSAKLRMVT GLRNNPSIQSR [SEQ ID NO: 50] | GLFGAIAGFIEGGW TGMIDGWYGYHHQ NEQGSGYAADQKST QNAINGITNKVNTVI EKMNIQFTAVGKEF NKLEKRMENLNKK VDDGFLDIWTYNAE LLVLLENERTLDFH DSNVKNLYEKVKSQ LKNNAKEIGNGCFE FYHKCDNECMESVR NGTYDYPKYSEESK LNREKVDGVKLES |

TABLE 1-continued

Exemplary Influenza A Hemagglutinin Sequences

| HA Subtype (Genbank No.) | Signal peptide | HA1 N-terminal Stem Segment | HA1 C-terminal Stem Segment | HA2 Domain |
|---|---|---|---|---|
| | | | | MGIYQILAIYSTVAS<br>SLVLLVSLGAISFW<br>MCSNGSLQCRICI<br>[SEQ ID<br>NO: 66] |
| H2<br>(L11136) | MAIIY<br>LILLFT<br>AVRG<br>[SEQ ID<br>NO: 19] | DQICIGYHSNN<br>STEKVDTILER<br>NVTVTHAQNI<br>LEKTHNGKLC<br>[SEQ ID<br>NO: 35] | CETKCQTPLG<br>AINTTLPFHNV<br>HPLTIGECPKY<br>VKSERLVLAT<br>GLRNVPQIESR<br>[SEQ ID<br>NO: 51] | GLFGAIAGFIEGGW<br>QGMIDGWYGYHHS<br>NDQGSGYAADKEST<br>QKAIDGITNRVNSVI<br>EKMNTQFEAVGKEF<br>SNLEKRLENLNKKM<br>EDGFLDVWTYNAE<br>LLVLMENERTLDFH<br>DSNVKNLYDRVRM<br>QLRDNAKELGNGCF<br>EFYHKCDDECMNS<br>VKNGTYDYPKYEEE<br>SKLNRNEIKGVKLS<br>NMGVYQILAIYATV<br>AGSLSLAIMIAGISL<br>WMCSNGSLQCRICI<br>[SEQ ID<br>NO: 67] |
| H3<br>HK68-H3N2<br>(EF409245)<br>PDB: IHGJ | MKTII<br>ALSYIF<br>CLALG<br>[SEQ ID<br>NO: 20] | QDLPGNDNST<br>ATLCLGHHAV<br>PNGTLVKTITD<br>DQIEVTNATEL<br>VQSSSTGKIC<br>[SEQ ID<br>NO: 36] | CISECITPNGSI<br>PNDKPFQNVN<br>KITYGACPKY<br>VKQNTLKLAT<br>GMRNVPEKQT<br>R<br>[SEQ ID<br>NO: 52] | GLFGAIAGFIENGW<br>EGMIDGWYGFRHQ<br>NSEGTGQAADLKST<br>QAAIDQINGKLNRVI<br>EKTNEKFHQIEKEFS<br>EVEGRIQDLEKYVE<br>DTKIDLWSYNAELL<br>VALENQHTIDLTDS<br>EMNKLFEKTRRQLR<br>ENAEDMGNGCFKIY<br>HKCDNACIESIRNGT<br>YDHDVYRDEALNN<br>RFQIKGVELKSGYK<br>DWILWISFAISCFLL<br>CVVLLGFIMWACQR<br>GNIRCNICI<br>[SEQ ID<br>NO: 68] |
| H4<br>(D90302) | MLSIVI<br>LFLLIA<br>ENSS<br>[SEQ ID<br>NO: 21] | QNYTGNPVIC<br>MGHHAVANG<br>TMVKTLADDQ<br>VEVVTAQELV<br>ESQNLPELC<br>[SEQ ID<br>NO: 37] | CVSKCHTDKG<br>SLSTTKPFQNI<br>SRIAVGDCPRY<br>VKQGSLKLAT<br>GMRNIPEKAS<br>R<br>[SEQ ID<br>NO: 53] | GLFGAIAGFIENGW<br>QGLIDGWYGFRHQ<br>NAEGTGTAADLKST<br>QAAIDQINGKLNRLI<br>EKTNDKYHQIEKEF<br>EQVEGRIQDLENYV<br>EDTKIDLWSYNAEL<br>LVALENQHTIDVTD<br>SEMNKLFERVRRQL<br>RENAEDKGNGCFEI<br>FHKCDNNCIESIRNG<br>TYDHDIYRDEAINN<br>RFQIQGVKLTQGYK<br>DIILWISFSISCFLLV<br>ALLLAFILWACQNG<br>NIRCQICI<br>[SEQ ID<br>NO: 69] |
| H5<br>(X07826) | MERIV<br>LLLAI<br>VSLVK<br>S<br>[SEQ ID<br>NO: 22] | DQICIGYHAN<br>KSTKQVDTIM<br>EKNVTVTHAQ<br>DILERTHNGKL<br>C<br>[SEQ ID<br>NO: 38] | CDTKCQTPVG<br>EINSSMPFHNI<br>HPHTIGECPKY<br>VKSDRLVLAT<br>GLRNVPQRKK<br>R<br>[SEQ ID<br>NO: 54] | GLFGAIAGFIEGGW<br>QGMVDGWYGYHH<br>SNEQGSGYAADKES<br>TQKAIDGITNKVNSI<br>IDKMNTRFEAVGKE<br>FNNLERRVENLNKK<br>MEDGFLDVWTYNV<br>ELLVLMENERTLDF<br>HDSNVNNLYDKVR<br>LQLKDNARELGNGC<br>FEFYHKCDNECMES |

TABLE 1-continued

Exemplary Influenza A Hemagglutinin Sequences

| HA Subtype (Genbank No.) | Signal peptide | HA1 N-terminal Stem Segment | HA1

TABLE 1-continued

Exemplary Influenza A Hemagglutinin Sequences

| HA Subtype (Genbank No.) | Signal peptide | HA1 N-terminal Stem Segment | HA1 C-terminal Stem Segment | HA2 Domain |
|---|---|---|---|---|
| | | | | LGSNAVEDGNGCFE LYHKCDDQCMETIR NGTYDRQKYQEESR LERQKIEGVKLESEG TYKILTIYSTVASSL VLAMGFAAFLFWA MSNGSCRCNICI [SEQ ID NO: 74] |
| H10 (M21647) | MYKV VVIIAL LGAVK G [SEQ ID NO: 27] | LDRICLGHHA VANGTIVKTL TNEQEEVTNA TETVESTNLN KLC [SEQ ID NO: 43] | CESKCFWRGG SINTKLPFQNL SPRTVGQCPK YVNQRSLLLA TGMRNVPEVV QGR [SEQ ID NO: 59] | GLFGAIAGFIENGW EGMVDGWYGFRHQ NAQGTGQAADYKS TQAAIDQITGKLNRL IEKTNTEFESIESEFS ETEHQIGNVINWTK DSITDIWTYNAELLV AMENQHTIDMADSE MLNLYERVRKQLR QNAEEDGKGCFEIY HTCDDSCMESIRNN TYDHSQYREEALLN RLNINPVKLSSGYK DIILWFSFGESCFVL LAVVMGLVFFCLKN GNMRCTICI [SEQ ID NO: 75] |
| H11 (D90306) | MEKTL LFAAIF LCVKA [SEQ ID NO: 28] | DEICIGYLSNN STDKVDTIIEN NVTVTSSVEL VETEHTGSFC [SEQ ID NO: 44] | CSTKCQTEIGG INTNKSFHNV HRNTIGDCPK YVNVKSLKLA TGPRNVPAIAS R [SEQ ID NO: 60] | GLFGAIAGFIEGGWP GLINGWYGFQHRDE EGTGIAADKESTQK AIDQITSKVNNIVDR MNTNFESVQHEFSEI EERINQLSKHVDDS VVDIWSYNAQLLVL LENEKTLDLHDSNV RNLHEKVRRMLKD NAKDEGNGCFTFYH KCDNKCIERVRNGT YDHKEFEEESKINR QEIEGVKLDSSGNV YKILSIYSCIASSLVL AALIMGFMFWACS NGSCRCTICI [SEQ ID NO: 76] |
| H12 (D90307) | MEKFII LSTVL AASFA Y [SEQ ID NO: 29] | DKICIGYQTNN STETVNTLSEQ NVPVTQVEEL VHRGIDPILC [SEQ ID NO: 45] | CVTECQLNEG VMNTSKPFQN TSKHYIGKCPK YIPSGSLKLAI GLRNVPQVQD R [SEQ ID NO: 61] | GLFGAIAGFIEGGWP GLVAGWYGFQHQN AEGTGIAADRDSTQ RAIDNMQNKLNNVI DKMNKQFEVVNHE FSEVESRINMINSKI DDQITDIWAYNAEL LVLLENQKTLDEHD ANVRNLHDRVRRV LRENAIDTGDGCFEI LHKCDNNCMDTIRN GTYNHKEYEEESKI ERQKVNGVKLEENS TYKILSIYSSVASSL VLLLMIIGGFIFGCQ NGNVRCTFCI [SEQ ID NO: 77] |
| H13 (D90308) | MALN VIATL TLISVC VHA [SEQ ID NO: 30] | DRICVGYLSTN SSERVDTLLEN GVPVTSSIDLIE TNHTGTYC [SEQ ID NO: 46] | CNTKCQTSVG GINTNRTFQNI DKNALGDCPK YIKSGQLKLAT GLRNVPAISNR [SEQ ID NO: 62] | GLFGAIAGFIEGGWP GLINGWYGFQHQNE QGTGIAADKESTQK AIDQITTKINNIIDKM NGNYDSIRGEFNQV EKRINMLADRIDDA VTDIWSYNAKLLVL |

TABLE 1-continued

Exemplary Influenza A Hemagglutinin Sequences

| HA Subtype (Genbank No.) | Signal peptide | HA1 N-terminal Stem Segment | HA1 C-terminal Stem Segment | HA2 Domain |
|---|---|---|---|---|
| | | | | LENDKTLDMHDAN VKNLHEQVRRELKD NAIDEGNGCFELLH KCNDSCMETIRNGT YDHTEYAEESKLKR QEIDGIKLKSEDNVY KALSIYSCIASSVVL VGLILSFIMWACSSG NCRFNVCI [SEQ ID NO: 78] |
| H14 (M35997) | MIALIL VALAL SHTAY S [SEQ ID NO: 31] | QITNGTTGNPII CLGHHAVENG TSVKTLTDNH VEVVSAKELV ETNHTDELC [SEQ ID NO: 47] | CTSPCLTDKGS IQSDKPFQNVS RIAIGNCPKYV KQGSLMLATG MRNIPGKQAK [SEQ ID NO: 63] | GLFGAIAGFIENGW QGLIDGWYGFRHQ NAEGTGTAADLKST QAAIDQINGKLNRLI EKTNEKYHQIEKEF EQVEGRIQDLEKYV EDTKIDLWSYNAEL LVALENQHTIDVTD SEMNKLFERVRRQL RENAEDQGNGCFEI FHQCDNNCIESIRNG TYDHNIYRDEAINN RIKINPVTLTMGYK DIILWISFSMSCFVF VALILGFVLWACQN GNIRCQICI [SEQ ID NO: 79] |
| H15 (L43917) | MNTQI IVILVL GLSMV KS [SEQ ID NO: 32] | DKICLGHHAV ANGTKVNTLT ERGVEVVNAT ETVEITGIDKV C [SEQ ID NO: 48] | CEGECFYSGG TINSPLPFQNID SRAVGKCPRY VKQSSLPLAL GMKNVPEKIR TR [SEQ ID NO: 64] | GLFGAIAGFIENGW EGLIDGWYGFRHQN AQGQGTAADYKST QAAIDQITGKLNRLI EKTNKQFELIDNEFT EVEQQIGNVINWTR DSLTEIWSYNAELL VAMENQHTIDLADS EMNKLYERVRRQL RENAEEDGTGCFEIF HRCDDQCMESIRNN TYNHTEYRQEALQN RIMINPVKLSSGYKD VILWFSFGASCVML LAIAMGLIFMCVKN GNLRCTICI [SEQ ID NO: 80] |
| H16 (EU293865) | MMIK VLYFLI IVLGR YSKA [SEQ ID NO: 33] | DKICIGYLSNN SSDTVDTLTEN GVPVTSSVDL VETNHTGTYC [SEQ ID NO: 49] | CNTKCQTSLG GINTNKTFQNI ERNALGDCPK YIKSGQLKLAT GLRNVPSIGER [SEQ ID NO: 65] | GLFGAIAGFIEGGWP GLINGWYGFQHQNE QGTGIAADKASTQK AINEITTKINNIIEKM NGNYDSIRGEFNQV EKRINMLADRVDDA VTDIWSYNAKLLVL LENDRTLDLHDANV RNLHDQVKRALKS NAIDEGDGCFNLLH KCNDSCMETIRNGT YNHEDYREESQLKR QEIEGIKLKTEDNVY KVLSIYSCIASSIVLV GLILAFIMWACSNG SCRFNVCI [SEQ ID NO: 81] |
| H17 (CY103876) | MELIV LLILLN PYTFV LG | DRICIGYQANQ NNQTVNTLLE QNVPVTGAQE ILETNHNGKLC | CSTKCQTPLG ALNSTLPFQN VHQQTIGNCP KYVKATSLML ATGLRNNPQM | GLFGAIAGFIEGGW QGMIDGWYGYHHE NQEGSGYAADKEA TQKAVDAITNKVNS IIDKMNSQFESNIKE |

TABLE 1-continued

Exemplary Influenza A Hemagglutinin Sequences

| HA Subtype (Genbank No.) | Signal peptide | HA1 N-terminal Stem Segment | HA1 C-terminal Stem Segment | HA2 Domain |
|---|---|---|---|---|
| | | | EGR | FNRLELRIQHLSDRV DDALLDIWSYNTEL LVLLENERTLDFHD ANVKNLFEKVKAQ LKDNAIDEGNGCFL LLHKCNNSCMDDIK NGTYKYMDYREES HIEKQKIDGVKLTD YSRYYIMTLYSTIAS SVVLGSLIIAAFLWG CQKGSIQCKICI |

Table 1A, below, identifies useful HA1 N-terminal stem segments and HA1 C-terminal stem segments for the polypeptides and methods described herein.

TABLE 1A

Exemplary Influenza A Hemagglutinin Sequences

| HA Subtype (Genbank No.) | HA1 N-terminal Stem Segment | HA1 C-terminal Stem Segment |
|---|---|---|
| H1 PR8-H1N1 (EF467821.1) No Cys | DTICIGYHANNSTDTVDT VLEKNVTVTHSVNLLED SHNGKL [SEQ ID NO: 177] | NTKCQTPLGAINSSLPYQNIHPVTIGEC PKYVRSAKLRMVTGLRNNPSIQSR [SEQ ID NO: 226] |
| H1 PR8-H1N1 (EF467821.1) No Cys Δ1 | DTICIGYHANNSTDTVDT VLEKNVTVTHSVNLLED SHNGKL [SEQ ID NO: 178] | TKCQTPLGAINSSLPYQNIHPVTIGECP KYVRSAKLRMVTGLRNNPSIQSR [SEQ ID NO: 227] |
| H1 PR8-H1N1 (EF467821.1) No Cys Δ3 | DTICIGYHANNSTDTVDT VLEKNVTVTHSVNLLED SHNGK [SEQ ID NO: 179] | KCQTPLGAINSSLPYQNIHPVTIGECPK YVRSAKLRMVTGLRNNPSIQSR [SEQ ID NO: 228] |
| H1 PR8-H1N1 (EF467821.1) PR8-CON-A | DTICIGYHANNSTDTVDT VLEKNVTVTHSVNLLED SHNGKLCRLKC [SEQ ID NO: 312] | CKCQTPLGAINSSLPYQNIHPVTIGECP KYVRSAKLRMVTGLRNNPSIQSRG [SEQ ID NO: 313] |
| H1 PR8-H1N1 (EF467821.1) PR8-CON-B | DTICIGYHANNSTDTVDT VLEKNVTVTHSVNLLED SHNGKLC [SEQ ID NO: 34] | CVRSAKLRMVTGLRNNPSIQSRG [SEQ ID NO: 314] |
| H1 PR8-H1N1 (EF467821.1) PR8-CON-C | DTICIGYHANNSTDTVDT VLEKNVTVTHSVNLLED SHNGKLCRLKGIAPLQL GKCNIAGWLLGNPECDP LLPVRSWSYIVETPNSEN GICYPGC [SEQ ID NO: 315] | AFALSRGFGSGIITSNASMHECNTKCQ TPLGAINSSLPYQNIHPVTIGECPKYVR SAKLRMVTGLRNNPSIQSRG [SEQ ID NO: 316] |
| H2 (L11136) No Cys | DQICIGYHSNNSTEKVDT ILERNVTVTHAQNILEKT HNGKL [SEQ ID NO: 180] | ETKCQTPLGAINTTLPFHNVHPLTIGE CPKYVKSERLVLATGLRNVPQIESR [SEQ ID NO: 229] |
| H2 (L11136) No Cys Δ1 | DQICIGYHSNNSTEKVDT ILERNVTVTHAQNILEKT HNGKL [SEQ ID NO: 181] | TKCQTPLGAINTTLPFHNVHPLTIGECP KYVKSERLVLATGLRNVPQIESR [SEQ ID NO: 230] |
| H2 (L11136) No Cys Δ3 | DQICIGYHSNNSTEKVDT ILERNVTVTHAQNILEKT HNGK [SEQ ID NO: 182] | KCQTPLGAINTTLPFHNVHPLTIGECP KYVKSERLVLATGLRNVPQIESR [SEQ ID NO: 231] |

TABLE 1A-continued

Exemplary Influenza A Hemagglutinin Sequences

| HA Subtype (Genbank No.) | HA1 N-terminal Stem Segment | HA1 C-terminal Stem Segment |
|---|---|---|
| H3 HK68-H3N2 (EF409245) PDB: 1HGJ No Cys | QDLPGNDNSTATLCLGH HAVPNGTLVKTITDDQIE VTNATELVQSSSTGKI [SEQ ID NO: 183] | ISECITPNGSIPNDKPFQNVNKITYGAC PKYVKQNTLKLATGMRNVPEKQTR [SEQ ID NO: 232] |
| H3 HK68-H3N2 (EF409245) PDB: 1HGJ No Cys Δ1 | QDLPGNDNSTATLCLGH HAVPNGTLVKTITDDQIE VTNATELVQSSSTGKI [SEQ ID NO: 184] | SECITPNGSIPNDKPFQNVNKITYGACP KYVKQNTLKLATGMRNVPEKQTR [SEQ ID NO: 233] |
| H3 HK68-H3N2 (EF409245) PDB: 1HGJ No Cys Δ3 | QDLPGNDNSTATLCLGH HAVPNGTLVKTITDDQIE VTNATELVQSSSTGK [SEQ ID NO: 185] | ECITPNGSIPNDKPFQNVNKITYGACP KYVKQNTLKLATGMRNVPEKQTR [SEQ ID NO: 234] |
| H3 HK68-H3N2 PDB: 1HGJ (EF409245) HK68-CON-A | STATLCLGHHAVPNGTL VKTITDDQIEVTNATELV QSSSTGKIC [SEQ ID NO: 308] | CISECITPNGSIPNDKPFQNVNKITYGA CPKYVKQNTLKLATGMRNVPEKQTR [SEQ ID NO: 52] |
| H3 HK68-H3N2 PDB: 1HGJ (EF409245) HK68-CON-B | QDLPGNDNSTATLCLGH HAVPNGTLVKTITDDQIE VTNATELVQSSSTGKIC [SEQ ID NO: 36] | CKYVKQNTLKLATGMRNVPEKQTR [SEQ ID NO: 309] |
| H3 HK68-H3N2 PDB: 1HGJ (EF409245) HK68-CON-C | QDLPGNDNSTATLCLGH HAVPNGTLVKTITDDQIE VTNATELVQSSSTGKICN NPHRILDGIDCTLIDALL GDPHCDVFQNETWDLF VERSKAFSNC [SEQ ID NO: 310] | APRGYFKMRTGKSSIMSSDAPIDTCIS ECITPNGSIPNDKPFQNVNKITYGACP KYVKQNTLKLATGMRNVPEK [SEQ ID NO: 311] |
| H4 (D90302) No Cys | QNYTGNPVICMGHHAV ANGTMVKTLADDQVEV VTAQELVESQNLPEL [SEQ ID NO: 186] | VSKCHTDKGSLSTTKPFQNISRIAVGD CPRYVKQGSLKLATGMRNIPEKASR [SEQ ID NO: 235] |
| H4 (D90302) No Cys Δ1 | QNYTGNPVICMGHHAV ANGTMVKTLADDQVEV VTAQELVESQNLPEL [SEQ ID NO: 187] | SKCHTDKGSLSTTKPFQNISRIAVGDC PRYVKQGSLKLATGMRNIPEKASR [SEQ ID NO: 236] |
| H4 (D90302) No Cys Δ3 | QNYTGNPVICMGHHAV ANGTMVKTLADDQVEV VTAQELVESQNLPE [SEQ ID NO: 188] | KCHTDKGSLSTTKPFQNISRIAVGDCP RYVKQGSLKLATGMRNIPEKASR [SEQ ID NO: 237] |
| H5 (X07826) No Cys | DQICIGYHANKSTKQVD TIMEKNVTVTHAQDILE RTHNGKL [SEQ ID NO: 189] | DTKCQTPVGEINSSMPFHNIHPHTIGE CPKYVKSDRLVLATGLRNVPQRKKR [SEQ ID NO: 238] |
| H5 (X07826) No Cys Δ1 | DQICIGYHANKSTKQVD TIMEKNVTVTHAQDILE RTHNGKL [SEQ ID NO: 190] | TKCQTPVGEINSSMPFHNIHPHTIGECP KYVKSDRLVLATGLRNVPQRKKR [SEQ ID NO: 239] |
| H5 (X07826) No Cys Δ3 | DQICIGYHANKSTKQVD TIMEKNVTVTHAQDILE RTHNGK [SEQ ID NO: 191] | KCQTPVGEINSSMPFHNIHPHTIGECPK YVKSDRLVLATGLRNVPQRKKR [SEQ ID NO: 240] |
| H6 (D90303) No Cys | DKICIGYHANNSTTQIDT ILEKNVTVTHSVELLENQ KEERF [SEQ ID NO: 192] | DATCQTVAGVLRTNKTFQNVSPLWIG ECPKYVKSESLRLATGLRNVPQIETR [SEQ ID NO: 241] |

TABLE 1A-continued

Exemplary Influenza A Hemagglutinin Sequences

| HA Subtype (Genbank No.) | HA1 N-terminal Stem Segment | HA1 C-terminal Stem Segment |
|---|---|---|
| H6 (D90303) No Cys Δ1 | DKICIGYHANNSTTQIDT ILEKNVTVTHSVELLENQ KEERF [SEQ ID NO: 193] | ATCQTVAGVLRTNKTFQNVSPLWIGE CPKYVKSESLRLATGLRNVPQIETR [SEQ ID NO: 242] |
| H6 (D90303) No Cys Δ3 | DKICIGYHANNSTTQIDT ILEKNVTVTHSVELLENQ KEER [SEQ ID NO: 194] | TCQTVAGVLRTNKTFQNVSPLWIGEC PKYVKSESLRLATGLRNVPQIETR [SEQ ID NO: 243] |
| H7 (M24457) No Cys | DKICLGHHAVSNGTKVN TLTERGVEVVNATETVE RTNIPKI [SEQ ID NO: 195] | EGECYHSGGTITSRLPFQNINSRAVGK CPRYVKQESLLLATGMKNVPEPSKKR KKR [SEQ ID NO: 244] |
| H7 (M24457) No Cys Δ1 | DKICLGHHAVSNGTKVN TLTERGVEVVNATETVE RTNIPKI [SEQ ID NO: 196] | GECYHSGGTITSRLPFQNINSRAVGKC PRYVKQESLLLATGMKNVPEPSKKRK KR [SEQ ID NO: 245] |
| H7 (M24457) No Cys Δ3 | DKICLGHHAVSNGTKVN TLTERGVEVVNATETVE RTNIPK [SEQ ID NO: 197] | ECYHSGGTITSRLPFQNINSRAVGKCP RYVKQESLLLATGMKNVPEPSKKRKK R [SEQ ID NO: 246] |
| H8 (D90304) No Cys | DRICIGYQSNNSTDTVNT LIEQNVPVTQTMELVET EKHPAY [SEQ ID NO: 198] | NTKCQTYAGAINSSKPFQNASRHYMG ECPKYVKKASLRLAVGLRNTPSVEPR [SEQ ID NO: 247] |
| H8 (D90304) No Cys Δ1 | DRICIGYQSNNSTDTVNT LIEQNVPVTQTMELVET EKHPAY [SEQ ID NO: 199] | TKCQTYAGAINSSKPFQNASRHYMGE CPKYVKKASLRLAVGLRNTPSVEPR [SEQ ID NO: 248] |
| H8 (D90304) No Cys Δ3 | DRICIGYQSNNSTDTVNT LIEQNVPVTQTMELVET EKHPA [SEQ ID NO: 200] | KCQTYAGAINSSKPFQNASRHYMGEC PKYVKKASLRLAVGLRNTPSVEPR [SEQ ID NO: 249] |
| H9 (D90305) No Cys | DKICIGYQSTNSTETVDT LTESNVPVTHTKELLHTE HNGML [SEQ ID NO: 201] | VVQCQTEKGGLNTTLPFHNISKYAFG NCPKYVGVKSLKLPVGLRNVPAVSSR [SEQ ID NO: 250] |
| H9 (D90305) No Cys Δ1 | DKICIGYQSTNSTETVDT LTESNVPVTHTKELLHTE HNGML [SEQ ID NO: 202] | VQCQTEKGGLNTTLPFHNISKYAFGN CPKYVGVKSLKLPVGLRNVPAVSSR [SEQ ID NO: 251] |
| H9 (D90305) No Cys Δ3 | DKICIGYQSTNSTETVDT LTESNVPVTHTKELLHTE HNGM [SEQ ID NO: 203] | QCQTEKGGLNTTLPFHNISKYAFGNCP KYVGVKSLKLPVGLRNVPAVSSR [SEQ ID NO: 252] |
| H10 (M21647) No Cys | LDRICLGHHAVANGTIV KTLTNEQEEVTNATETV ESTNLNKL [SEQ ID NO: 204] | ESKCFWRGGSINTKLPFQNLSPRTVGQ CPKYVNQRSLLLATGMRNVPEVVQG R [SEQ ID NO: 253] |
| H10 (M21647) No Cys Δ1 | LDRICLGHHAVANGTIV KTLTNEQEEVTNATETV ESTNLNKL [SEQ ID NO: 205] | SKCFWRGGSINTKLPFQNLSPRTVGQC PKYVNQRSLLLATGMRNVPEVVQGR [SEQ ID NO: 254] |
| H10 (M21647) No Cys Δ3 | LDRICLGHHAVANGTIV KTLTNEQEEVTNATETV ESTNLNK [SEQ ID NO: 206] | KCFWRGGSINTKLPFQNLSPRTVGQCP KYVNQRSLLLATGMRNVPEVVQGR [SEQ ID NO: 255] |
| H11 (D90306) No Cys | DEICIGYLSNNSTDKVDT IIENNVTVTSSVELVETE HTGSF [SEQ ID NO: 207] | STKCQTEIGGINTNKSFHNVHRNTIGD CPKYVNVKSLKLATGPRNVPAIASR [SEQ ID NO: 256] |

TABLE 1A-continued

Exemplary Influenza A Hemagglutinin Sequences

| HA Subtype (Genbank No.) | HA1 N-terminal Stem Segment | HA1 C-terminal Stem Segment |
|---|---|---|
| H11 (D90306) No Cys Δ1 | DEICIGYLSNNSTDKVDT IIENNVTVTSSVELVETE HTGSF [SEQ ID NO: 208] | TKCQTEIGGINTNKSFHNVHRNTIGDC PKYVNVKSLKLATGPRNVPAIASR [SEQ ID NO: 257] |
| H11 (D90306) No Cys Δ3 | DEICIGYLSNNSTDKVDT IIENNVTVTSSVELVETE HTGS [SEQ ID NO: 209] | KCQTEIGGINTNKSFHNVHRNTIGDCP KYVNVKSLKLATGPRNVPAIASR [SEQ ID NO: 258] |
| H12 (D90307) No Cys | DKICIGYQTNNSTETVNT LSEQNVPVTQVEELVHR GIDPIL [SEQ ID NO: 210] | VTECQLNEGVMNTSKPFQNTSKHYIG KCPKYIPSGSLKLAIGLRNVPQVQDR [SEQ ID NO: 259] |
| H12 (D90307) No Cys Δ1 | DKICIGYQTNNSTETVNT LSEQNVPVTQVEELVHR GIDPIL [SEQ ID NO: 211] | TECQLNEGVMNTSKPFQNTSKHYIGK CPKYIPSGSLKLAIGLRNVPQVQDR [SEQ ID NO: 260] |
| H12 (D90307) No Cys Δ3 | DKICIGYQTNNSTETVNT LSEQNVPVTQVEELVHR GIDPI [SEQ ID NO: 212] | ECQLNEGVMNTSKPFQNTSKHYIGKC PKYIPSGSLKLAIGLRNVPQVQDR [SEQ ID NO: 261] |
| H13 (D90308) No Cys | DRICVGYLSTNSSERVDT LLENGVPVTSSIDLIETN HTGTY [SEQ ID NO: 213] | NTKCQTSVGGINTNRTFQNIDKNALG DCPKYIKSGQLKLATGLRNVPAISNR [SEQ ID NO: 262] |
| H13 (D90308) No Cys Δ1 | DRICVGYLSTNSSERVDT LLENGVPVTSSIDLIETN HTGTY [SEQ ID NO: 214] | TKCQTSVGGINTNRTFQNIDKNALGD CPKYIKSGQLKLATGLRNVPAISNR [SEQ ID NO: 263] |
| H13 (D90308) No Cys Δ3 | DRICVGYLSTNSSERVDT LLENGVPVTSSIDLIETN HTGT [SEQ ID NO: 215] | KCQTSVGGINTNRTFQNIDKNALGDC PKYIKSGQLKLATGLRNVPAISNR [SEQ ID NO: 264] |
| H14 (M35997) No Cys | QITNGTTGNPIICLGHHA VENGTSVKTLTDNHVEV VSAKELVETNHTDEL [SEQ ID NO: 216] | TSPCLTDKGSIQSDKPFQNVSRIAIGNC PKYVKQGSLMLATGMRNIPGKQAK [SEQ ID NO: 265] |
| H14 (M35997) No Cys Δ1 | QITNGTTGNPIICLGHHA VENGTSVKTLTDNHVEV VSAKELVETNHTDEL [SEQ ID NO: 217] | SPCLTDKGSIQSDKPFQNVSRIAIGNCP KYVKQGSLMLATGMRNIPGKQAK [SEQ ID NO: 266] |
| H14 (M35997) No Cys Δ3 | QITNGTTGNPIICLGHHA VENGTSVKTLTDNHVEV VSAKELVETNHTDE [SEQ ID NO: 218] | PCLTDKGSIQSDKPFQNVSRIAIGNCPK YVKQGSLMLATGMRNIPGKQAK [SEQ ID NO: 267] |
| H15 (L43917) No Cys | DKICLGHHAVANGTKV NTLTERGVEVVNATETV EITGIDKV [SEQ ID NO: 219] | EGECFYSGGTINSPLPFQNIDSRAVGK CPRYVKQSSLPLALGMKNVPEKIRTR [SEQ ID NO: 268] |
| H15 (L43917) No Cys Δ1 | DKICLGHHAVANGTKV NTLTERGVEVVNATETV EITGIDKV [SEQ ID NO: 220] | GECFYSGGTINSPLPFQNIDSRAVGKC PRYVKQSSLPLALGMKNVPEKIRTR [SEQ ID NO: 269] |
| H15 (L43917) No Cys Δ3 | DKICLGHHAVANGTKV NTLTERGVEVVNATETV EITGIDK [SEQ ID NO: 221] | ECFYSGGTINSPLPFQNIDSRAVGKCP RYVKQSSLPLALGMKNVPEKIRTR [SEQ ID NO: 270] |

TABLE 1A-continued

Exemplary Influenza A Hemagglutinin Sequences

| HA Subtype (Genbank No.) | HA1 N-terminal Stem Segment | HA1 C-terminal Stem Segment |
|---|---|---|
| H16 (EU293865) No Cys | DKICIGYLSNNSSDTVDT LTENGVPVTSSVDLVET NHTGTY [SEQ ID NO: 222] | NTKCQTSLGGINTNKTFQNIERNALGD CPKYIKSGQLKLATGLRNVPSIGER [SEQ ID NO: 271] |
| H16 (EU293865) No Cys Δ1 | DKICIGYLSNNSSDTVDT LTENGVPVTSSVDLVET NHTGTY [SEQ ID NO: 223] | TKCQT TABLE 2-continued Exemplary Influenza A Hemagglutinin Sequences

| HA2 Domain Subtype (Genbank No.) | Stem Domain | Luminal Domain | Transmembrane Domain | Cytoplasmic Domain |
|---|---|---|---|---|
| | DLWSYNAELLVALE NQHTIDLTDSEMNKL FEKTRRQLRENAED MGNGCFKIYHKCDN ACIESIRNGTYDHDV YRDEALNNRFQIKGV ELK [SEQ ID NO: 84] | | | |
| H4 (D90302) | GLFGAIAGFIENGWQ GLIDGWYGFRHQNA EGTGTAADLKSTQA AIDQINGKLNRLIEKT NDKYHQIEKEFEQVE GRIQDLENYVEDTKI DLWSYNAELLVALE NQHTIDVTDSEMNKL FERVRRQLRENAEDK GNGCFEIFHKCDNNC IESIRNGTYDHDIYRD EAINNRFQIQGVKLT [SEQ ID NO: 85] | QGYKD [SEQ ID NO: 101] | IILWISFSISCFLL VALLLAFILWA CQ [SEQ ID NO: 117] | NGNIRCQIC I [SEQ ID NO: 133] |
| H5 (X07826) | GLFGAIAGFIEGGWQ GMVDGWYGYHHSN EQGSGYAADKESTQ KAIDGITNKVNSIIDK MNTRFEAVGKEFNN LERRVENLNKKMED GFLDVWTYNVELLV LMENERTLDFHDSNV NNLYDKVRLQLKDN ARELGNGCFEFYHKC DNECMESVRNGTYD YPQYSEEARLNREEIS GVKLES [SEQ ID NO: 86] | MGVYQ [SEQ ID NO: 102] | ILSIYSTVASSL ALAIMIAGLSF WMCS [SEQ ID NO: 118] | NGSLQCRIC I [SEQ ID NO: 134] |
| H6 (D90303) | GLFGAIAGFIEGGWT GMIDGWYGYHHENS QGSGYAADRESTQK AVDGITNKVNSIIDK MNTQFEAVDHEFSNL ERRIDNLNKRMEDGF LDVWTYNAELLVLL ENERTLDLHDANVK NLYERVKSQLRDNA MILGNGCFEFWHKC DDECMESVKNGTYD YPKYQDESKLNRQEI ESVKLES [SEQ ID NO: 87] | LGVYQ [SEQ ID NO: 103] | ILAIYSTVSSSL VLVGLIIAVGL WMCS [SEQ ID NO: 119] | NGSMQCRI CI [SEQ ID NO: 135] |
| H7 (M24457) | GLFGAIAGFIENGWE GLVDGWYGFRHQNA QGEGTAADYKSTQS AIDQITGKLNRLIEKT NQQFELIDNEFTEVE KQIGNLINWTKDSITE VWSYNAELIVAMEN QHTIDLADSEMNRLY ERVRKQLRENAEED GTGCFEIFHKCDDDC MASIRNNTYDHSKYR EEAMQNRIQIDPVKL S [SEQ ID NO: 88] | SGYKD [SEQ ID NO: 104] | VILWFSFGASCF LLLAIAMGLVFI CVK [SEQ ID NO: 120] | NGNMRCTI CI [SEQ ID NO: 136] |

TABLE 2-continued

Exemplary Influenza A Hemagglutinin Sequences

| HA2 Domain Subtype (Genbank No.) | Stem Domain | Luminal Dom

TABLE 2-continued

Exemplary Influenza A Hemagglutinin Sequences

| HA2 Domain Subtype (Genbank No.) | Stem Domain | Luminal Domain | Transmembrane Domain | Cytoplasmic Domain |
|---|---|---|---|---|
| | CMDTIRNGTYNHKE YEEESKIERQKVNGV KLEE [SEQ ID NO: 93] | | | |
| H13 (D90308) | GLFGAIAGFIEGGWP GLINGWYGFQHQNE QGTGIAADKESTQKA IDQITTKINNIIDKMN GNYDSIRGEFNQVEK RINMLADRIDDAVTD IWSYNAKLLVLLEND KTLDMHDANVKNLH EQVRRELKDNAIDEG NGCFELLHKCNDSC METIRNGTYDHTEYA EESKLKRQEIDGIKLK SE [SEQ ID NO: 94] | DNVYK [SEQ ID NO: 110] | ALSIYSCIASSV VLVGLILSFIM WACSS [SEQ ID NO: 126] | GNCRFNVCI [SEQ ID NO: 142] |
| H14 (M35997) | GLFGAIAGFIENGWQ GLIDGWYGFRHQNA EGTGTAADLKSTQA AIDQINGKLNRLIEKT NEKYHQIEKEFEQVE GRIQDLEKYVEDTKI DLWSYNAELLVALE NQHTIDVTDSEMNKL FERVRRQLRENAEDQ GNGCFEIFHQCDNNC IESIRNGTYDHNIYRD EAINNRIKINPVTLT [SEQ ID NO: 95] | MGYKD [SEQ ID NO: 111] | IILWISFSMSCF VFVALILGFVL WACQ [SEQ ID NO: 127] | NGNIRCQIC I [SEQ ID NO: 143] |
| H15 (L43917) | GLFGAIAGFIENGWE GLIDGWYGFRHQNA QGQGTAADYKSTQA AIDQITGKLNRLIEKT NKQFELIDNEFTEVE QQIGNVINWTRDSLT EIWSYNAELLVAME NQHTIDLADSEMNKL YERVRRQLRENAEED GTGCFEIFHRCDDQC MESIRNNTYNHTEYR QEALQNRIMINPVKL S [SEQ ID NO: 96] | SGYKD [SEQ ID NO: 112] | VILWFSFGASC VMLLAIAMGLI FMCVKN [SEQ ID NO: 128] | GNLRCTICI [SEQ ID NO: 144] |
| H16 (EU293865) | GLFGAIAGFIEGGWP GLINGWYGFQHQNE QGTGIAADKASTQKA INEITTKINNIIEKMNG NYDSIRGEFNQVEKR INMLADRVDDAVTDI WSYNAKLLVLLEND RTLDLHDANVRNLH DQVKRALKSNAIDEG DGCFNLLHKCNDSC METIRNGTYNHEDYR EESQLKRQEIEGIKLK TE [SEQ ID NO: 97] | DNVYK [SEQ ID NO: 113] | VLSIYSCIASSIV LVGLILAFIMW ACS [SEQ ID NO: 129] | NGSCRFNV CI [SEQ ID NO: 145] |
| H17 (CY103876) | GLFGAIAGFIEGGWQ GMIDGWYGYHHENQ EGSGYAADKEATQK AVDAITNKVNSIIDK | YSRYY | IMTLYSTIASSV VLGSLIIAAFLW GCQ | KGSIQCKICI |

TABLE 2-continued

Exemplary Influenza A Hemagglutinin Sequences

| HA2 Domain Subtype (Genbank No.) | Stem Domain | Luminal Domain | Transmembrane Domain | Cytoplasmic Domain |
|---|---|---|---|---|
| | MNSQFESNIKEFNRL ELRIQHLSDRVDDAL LDIWSYNTELLVLLE NERTLDFHDANVKN LFEKVKAQLKDNAID EGNGCFLLLHKCNNS CMDDIKNGTYKYMD YREESHIEKQKIDGV KLTD | | | |

In certain embodiments, the influenza hemagglutinin stem domain polypeptides comprise one or more immunogenic epitopes in the tertiary or quaternary structure of an influenza hemagglutinin polypeptide.

In certain embodiments, the HA1 N-terminal stem segment comprises the amino acid sequence $A_{17}$-$A_{18}$-$(Xaa)_n$-$A_{38}$ (SEQ ID NO:146), wherein
  $A_{17}$ is Y or H;
  $A_{18}$ is H, L, or Q;
  $(Xaa)_n$ represents a sequence of 18-20 amino acid residues; and
  $A_{38}$ is H, S, Q, T or N.

In certain embodiments, the HA1 C-terminal stem segment comprises the amino acid sequence $A_{291}$-$A_{292}$ (SEQ ID NO:147), wherein
  $A_{291}$ is T, S, N, D, P or K; and
  $A_{292}$ is L, M, K or R.

In certain embodiments, the HA2 domain comprises the amino acid sequence $A_{18}$-$A_{19}$-$A_{20}$-$A_{21}$ (SEQ ID NO:148), wherein
  $A_{18}$ is V or I;
  $A_{19}$ is D, N or A;
  $A_{20}$ is G, and
  $A_{21}$ is W.

In certain embodiments, the HA2 domain comprises the amino acid sequence $A_{38}$-$A_{39}$-$A_{40}$-$A_{41}$-$A_{42}$-$A_{43}$-$A_{44}$-$A_{45}$-$A_{46}$-$A_{47}$-$A_{48}$-$A_{49}$-$A_{50}$-$A_{51}$-$A_{52}$-$A_{53}$-$A_{54}$-$A_{55}$-$A_{56}$ (SEQ ID NO:149), wherein
  $A_{38}$ is K, Q, R, L or Y;
  $A_{39}$ is any amino acid residue;
  $A_{40}$ is any amino acid residue;
  $A_{41}$ is T;
  $A_{42}$ is Q;
  $A_{43}$ is any amino acid residue;
  $A_{44}$ is A;
  $A_{45}$ is I;
  $A_{46}$ is D;
  $A_{47}$ is any amino acid residue;
  $A_{48}$ is I, V or M;
  $A_{49}$ is T, Q or N;
  $A_{50}$ is any amino acid residue;
  $A_{51}$ is K;
  $A_{52}$ is V or L;
  $A_{53}$ is N;
  $A_{54}$ is any amino acid residue;
  $A_{55}$ is V, I or L; and
  $A_{56}$ is V or I.

In certain embodiments, the influenza stem domain polypeptides comprise two amino acid sequences selected from SEQ ID NOS:146-149. In certain embodiments, the influenza stem domain polypeptides comprise three amino acid sequences selected from SEQ ID NOS:146-149. In certain embodiments, the influenza stem domain polypeptides comprise four amino acid sequences selected from SEQ ID NOS:146-149.

In certain embodiments, the HA1 N-terminal stem segments are based on an influenza B hemagglutinin. In certain embodiments, the HA1 N-terminal stem segment is selected from SEQ ID NOS:154-157, presented in Table 3 below.

In certain embodiments, the HA1 C-terminal stem segments are based on an influenza B hemagglutinin. In certain embodiments, the HA1 C-terminal stem segment is selected from SEQ ID NOS:158-159 and 553-554, presented in Table 3 below.

In certain embodiments, the HA2 stem domains are based on an influenza B hemagglutinin. Exemplary residues for the end of an N-terminal stem segment and the end of a C-terminal stem segment of an influenza B hemagglutinin are indicated in FIG. 2. In certain embodiments, the HA2 stem domain is according to SEQ ID NO:160, presented in Tables 3 and 4 below.

In particular embodiments, the boundaries of the influenza B virus HA1 N-terminal stem segment and influenza B virus HA1 C-terminal segment are defined with respect to six pairs of amino acid residues: $Arg_{50}$ and $Ser_{277}$; $Ala_{66}$ and $Trp_{271}$; $Lys_{80}$ and $Ser_{277}$; $Cys_{94}$ and $Cys_{143}$; $Cys_{178}$ and $Cys_{272}$ and $Cys_{54}$ and $Cys_{272}$. Positions of these six pairs of residues are also highlighted in FIG. 3. The residue numbers are based on the numbering of the B-HA from influenza virus B as described in Protein Data Bank accession No. 3BT6. The amino acid sequence corresponding to the X-ray crystal structure of the B-HA protein in Protein Data Bank accession No. 3BT6 is aligned with representative H1 and H3 amino acid sequence and shown in FIG. 2.

In certain embodiments, an influenza B virus HA1 N-terminal stem segment starts at residue 1 (based on numbering of an influenza B virus HA1 subunit as in PDB file 3BT6) and ends at $Arg_{50}$. In certain embodiments, an influenza B virus HA1 N-terminal stem segment starts at residue 1 and ends at $Ala_{66}$. In some embodiments, an influenza B virus HA1 N-terminal stem segment starts at residue 1 and ends at $Lys_{80}$. In some embodiments, an influenza B virus N-terminal stem segment starts at residue 1 and ends at $Arg_{80}$. In some embodiments, an influenza B virus N-terminal stem segment starts at residue 1 and ends at Cys54. In some embodiments, an influenza B virus N-terminal stem segment starts at residue 1 and ends at $Cys_{94}$. In some embodiments, an influenza B virus N-terminal stem segment starts at residue 1 and ends at $Cys_{178}$.

In some embodiments, an influenza B virus HA1 N-terminal stem segment has an amino acid sequence according to any one of SEQ ID NOS:154-157 and 550-552, as illustrated in TABLE 3. In some embodiments, an influenza B virus HA1 N-terminal stem segment has an amino acid sequence that is at least 70%, 75%, 80%, 85%, 90%, 95%, 96% or 98% identical to any one of the amino acid sequences of any one of SEQ ID NOS:154-157 or 550-552.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:154, which corresponds to residues 1-50 of the influenza B virus HA1.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:155, which corresponds to residues 1-66 of the influenza B virus HA1.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:156, which corresponds to residues 1-80 of the influenza B virus HA1.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:157, which corresponds to residues 1-80 of the influenza B virus HA1 in which the lysine at position 80 is replaced with an arginine.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:550, which corresponds to residues 1-94 of the influenza B virus HA1.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:551, which corresponds to residues 1-178 of the influenza B virus HA1.

In some embodiments, an influenza B virus HA1 N-terminal stem segment has an amino acid sequence that is at least 70%, 75%, 80%, 85%, 90%, 95%, 96% or 98% identical to the amino acid sequence SEQ ID NO:552, which corresponds to residues 1-54 of the influenza B virus HA1.

In some embodiments, an influenza B virus HA1 C-terminal stem segment has an amino acid sequence that starts at $Ser_{277}$, $Trp_{271}$, $Cys_{143}$, $Cys_{272}$ or corresponding residues in other influenza B virus HA subtypes.

In some embodiments, an influenza B virus HA1 C-terminal stem segment has an amino acid sequence according to any one of SEQ ID NOS:158-159 or 553-554, as illustrated in TABLE 3. In some embodiments, an influenza B virus HA1 C-terminal stem segment has an amino acid sequence that is at least 70%, 75%, 80%, 85%, 90%, 95%, 96% or 98% identical to SEQ ID NO:158, which correspond to residues 277-344 of influenza B virus HA1. In some embodiments, an influenza B virus HA1 C-terminal stem segment has an amino acid sequence that is at least 70%, 75%, 80%, 85%, 90%, 95%, 96% or 98% identical to SEQ ID NO:159, which correspond to residues 271-344 of influenza B virus HA1. In some embodiments, an influenza B virus HA1 C-terminal stem segment has an amino acid sequence that is at least 70%, 75%, 80%, 85%, 90%, 95%, 96% or 98% identical to SEQ ID NO:553, which correspond to residues 137-344 of influenza B virus HA1. In some embodiments, an influenza B virus HA1 C-terminal stem segment has an amino acid sequence that is at least 70%, 75%, 80%, 85%, 90%, 95%, 96% or 98% identical to SEQ ID NO:554, which correspond to residues 272-344 of influenza B virus HA1.

In some embodiments, an influenza B virus HA1 C-terminal stem segment starts at residue-276, residue-275, residue-274, residue-273, or residue-272. In other embodiments, an influenza B virus HA1 C-terminal stem segment starts at residue-278, residue-279, residue-280, residue-281, or residue-282.

In certain embodiments, the influenza B virus HA2 domain is in tertiary or quaternary association with the influenza B virus HA1 domain through the influenza B virus HA1 N-terminal segment, the influenza B virus HA1 C-terminal segment, or both.

In some embodiments, the influenza B virus HA1 C-terminal segment and the influenza B virus HA2 subunit are covalently linked. For example, at its C-terminus (e.g., at the ending residue of the second sequence), the influenza B virus HA1 C-terminal segment is covalently linked to the influenza B virus HA2 domain in such embodiments. In some embodiments, the influenza B virus HA1 C-terminal segment and influenza B virus HA2 domain form a continuous polypeptide chain.

In some embodiments, the influenza B virus HA2 domain has the amino acid sequence of SEQ ID NO:160 or 161, as illustrated in TABLE 3 or 4. In some embodiments, the amino acid sequence of the HA2 domain is at least 70%, 75%, 80%, 85%, 90%, 95%, 96% or 98% identical to any one of SEQ ID NOS:160-161.

In certain embodiments, the influenza B stem domain polypeptides comprise a signal peptide. The signal peptide can be any signal peptide deemed suitable to those of skill in the art, including any signal peptide described herein. In certain embodiments, the signal peptide is at least 70%, 75%, 80%, 85%, 90%, 95%, 96% or 98% identical to any of SEQ ID NOS:150-153. In certain embodiments, the signal peptide is according to any of SEQ ID NOS:150-153.

In certain embodiments, the influenza B stem domain polypeptides comprise a luminal domain. The luminal domain can be any luminal domain deemed suitable to those of skill in the art, including any luminal domain described herein. In certain embodiments, the luminal is at least 60% or 80%, identical to SEQ ID NO:162. In certain embodiments, the luminal domain is according to SEQ ID NO:162.

In certain embodiments, the influenza B stem domain polypeptides comprise a transmembrane domain. The transmembrane domain can be any transmembrane domain deemed suitable to those of skill in the art, including any transmembrane domain described herein. In certain embodiments, the transmembrane domain is at least 70%, 75%, 80%, 85%, 90%, 95%, 96% or 98% identical to SEQ ID NO:163. In certain embodiments, the transmembrane domain is according to SEQ ID NO:163.

In certain embodiments, the influenza B stem domain polypeptides comprise a cytoplasmic domain. The cytoplasmic domain can be any cytoplasmic domain deemed suitable to those of skill in the art, including any cytoplasmic domain described herein. In certain embodiments, the cytoplasmic domain is at least 70%, 75%, 80%, 85%, 90%, 95%, 96% or 98% identical to SEQ ID NO:164. In certain embodiments, the cytoplasmic domain is according to SEQ ID NO:164.

TABLE 3

Exemplary Influenza B Hemagglutinin Sequences

| HA construct variants | Signal peptide | HA1 N-terminal Stem Segment | HA1 C-terminal Stem Segment | HA2 Domain |
|---|---|---|---|---|
| Arg50-<br>Ser277 | MKAIIVILMV<br>VTSNA<br>[SEQ ID<br>NO: 150] | DRICTGITSSNS<br>PHVVKTATQG<br>EVNVTGVIPLT<br>TTPTKSHFANL<br>KGTETR<br>[SEQ ID<br>NO: 154] | SKVIKGSLPLI<br>GEADCLHEKY<br>GGLNKSKPYY<br>TGEHAKAIGN<br>CPIWVKTPLKL<br>ANGTKYRPPA<br>KLLKER<br>[SEQ ID<br>NO: 158] | GFFGAIAGFLEGG<br>WEGMIAGWHGY<br>TSHGAHGVAVAA<br>DLKSTQEAINKIT<br>KNLNSLSELEVKN<br>LQRLSGAMDELH<br>NEILELDEKVDDL<br>RADTISSQIELAVL<br>LSNEGIINSEDEHL<br>LALERKLKKMLG<br>PSAVEIGNGCFET<br>KHKCNQTCLDRI<br>AAGTFDAGEFSLP<br>TFDSLNITAASLN<br>DDGLDNHTILLYY<br>STAASSLAVTLMI<br>AIFVVYMVSRDN<br>VSCSICL<br>[SEQ ID<br>NO: 160] |
| Ala66-<br>Trp271 | MKAIIVILMV<br>VTSNA<br>[SEQ ID<br>NO: 151] | DRICTGITSSNS<br>PHVVKTATQG<br>EVNVTGVIPLT<br>TTPTKSHFANL<br>KGTETRGKLC<br>PKCLNCTDLD<br>VA<br>[SEQ ID<br>NO: 155] | WCASGRSKVI<br>KGSLPLIGEAD<br>CLHEKYGGLN<br>KSKPYYTGEH<br>AKAIGNCPIW<br>VKTPLKLANG<br>TKYRPPAKLL<br>KER<br>[SEQ ID<br>NO: 159] | GFFGAIAGFLEGG<br>WEGMIAGWHGY<br>TSHGAHGVAVAA<br>DLKSTQEAINKIT<br>KNLNSLSELEVKN<br>LQRLSGAMDELH<br>NEILELDEKVDDL<br>RADTISSQIELAVL<br>LSNEGIINSEDEHL<br>LALERKLKKMLG<br>PSAVEIGNGCFET<br>KHKCNQTCLDRI<br>AAGTFDAGEFSLP<br>TFDSLNITAASLN<br>DDGLDNHTILLYY<br>STAASSLAVTLMI<br>AIFVVYMVSRDN<br>VSCSICL<br>[SEQ ID<br>NO: 160] |
| Lys80-<br>Ser277 | MKAIIVILMV<br>VTSNA<br>[SEQ ID<br>NO: 152] | DRICTGITSSNS<br>PHVVKTATQG<br>EVNVTGVIPLT<br>TTPTKSHFANL<br>KGTETRGKLC<br>PKCLNCTDLD<br>VALGRPKCTG<br>KIPSAK<br>[SEQ ID<br>NO: 156] | SKVIKGSLPLI<br>GEADCLHEKY<br>GGLNKSKPYY<br>TGEHAKAIGN<br>CPIWVKTPLKL<br>ANGTKYRPPA<br>KLLKER<br>[SEQ ID<br>NO: 158] | GFFGAIAGFLEGG<br>WEGMIAGWHGY<br>TSHGAHGVAVAA<br>DLKSTQEAINKIT<br>KNLNSLSELEVKN<br>LQRLSGAMDELH<br>NEILELDEKVDDL<br>RADTISSQIELAVL<br>LSNEGIINSEDEHL<br>LALERKLKKMLG<br>PSAVEIGNGCFET<br>KHKCNQTCLDRI<br>AAGTFDAGEFSLP<br>TFDSLNITAASLN<br>DDGLDNHTILLYY<br>STAASSLAVTLMI<br>AIFVVYMVSRDN<br>VSCSICL<br>[SEQ ID<br>NO: 160] |
| Arg80-<br>Ser277 | MKAIIVILMV<br>VTSNA<br>[SEQ ID<br>NO: 153] | DRICTGITSSNS<br>PHVVKTATQG<br>EVNVTGVIPLT<br>TTPTKSHFANL<br>KGTETRGKLC<br>PKCLNCTDLD<br>VALGRPKCTG<br>KIPSAR<br>[SEQ ID<br>NO: 157] | SKVIKGSLPLI<br>GEADCLHEKY<br>GGLNKSKPYY<br>TGEHAKAIGN<br>CPIWVKTPLKL<br>ANGTKYRPPA<br>KLLKER<br>[SEQ ID<br>NO: 158] | GFFGAIAGFLEGG<br>WEGMIAGWHGY<br>TSHGAHGVAVAA<br>DLKSTQEAINKIT<br>KNLNSLSELEVKN<br>LQRLSGAMDELH<br>NEILELDEKVDDL<br>RADTISSQIELAVL<br>LSNEGIINSEDEHL<br>LALERKLKKMLG<br>PSAVEIGNGCFET |

TABLE 3-continued

Exemplary Influenza B Hemagglutinin Sequences

| HA construct variants | Signal peptide | HA1 N-terminal Stem Segment | HA1 C-terminal Stem Segment | HA2 Domain |
|---|---|---|---|---|
| | | | | KHKCNQTCLDRI AAGTFDAGEFSLP TFDSLNITAASLN DDGLDNHTILLYY STAASSLAVTLMI AIFVVYMVSRDN VSCSICL [SEQ ID NO: 160] |
| Cys94-Cys143 | MKAIIVILMVDRICTGITSSNS VTSNA [SEQ ID NO: 150] | PHVVKTATQG EVNVTGVIPLT TTPTKSHFANL KGTQTRGKLC PNCLNCTDLD VALGRPKCMG TIPSAKASILHE VKPVTSGC [SEQ ID NO: 550] | CPNVTNGNGF FATMAWAVP KNKTATNPLT VEVPYICTKGE DQITVWGFHS DDETQMVKLY GDSKPQKFTSS ANGVTTHYVS QIGGFPNQAE DEGLPQSGRIV VDYMVQKPG KTGTIAYQRG VLLPQKVWCA SGRSKVIKGSL PLIGEADCLHE KYGGLNKSKP YYTGEHAKAI GNCPIWVKTP LKLANGTKYR PPAKLLK [SEQ ID NO: 553] | GFFGAIAGFLEGG WEGMIAGWHGY TSHGAHGVAVAA DLKSTQEAINKIT KNLNSLSELEVKN LQRLSGAMDELH NEILELDEKVDDL RADTISSQIELAVL LSNEGIINSEDEHL LALERKLKKMLG PSAVEIGNGCFET KHKCNQTCLDRI AAGTFDAGEFSLP TFDSLNITAASLN DDGLDNHTILLYY STAASSLAVTLMI AIFVVYMVSRDN VSCSICL [SEQ ID NO: 160] |
| Cys178-Cys272 | MKAIIVILMVDRICTGITSSNS VTSNA [SEQ ID NO: 150] | PHVVKTATQG EVNVTGVIPLT TTPTKSHFANL KGTQTRGKLC PNCLNCTDLD VALGRPKCMG TIPSAKASILHE VKPVTSGCFPI MHDRTKIRQL PNLLRGYENIR LSARNVTNAE TAPGGPYIVGT SGSCPNVTNG NGFFATMAW AVPKNKTATN PLTVEVPYIC [SEQ ID NO: 551] | CASGRSKVIK GSLPLIGEADC LHEKYGGLNK SKPYYTGEHA KAIGNCPIWV KTPLKLANGT KYRPPAKLLK [SEQ ID NO: 554] | GFFGAIAGFLEGG WEGMIAGWHGY TSHGAHGVAVAA DLKSTQEAINKIT KNLNSLSELEVKN LQRLSGAMDELH NEILELDEKVDDL RADTISSQIELAVL LSNEGIINSEDEHL LALERKLKKMLG PSAVEIGNGCFET KHKCNQTCLDRI AAGTFDAGEFSLP TFDSLNITAASLN DDGLDNHTILLYY STAASSLAVTLMI AIFVVYMVSRDN VSCSICL [SEQ ID NO: 160] |
| Cys54-Cys272 | MKAIIVILMVDRICTGITSSNS VTSNA [SEQ ID NO: 150] | PHVVKTATQG EVNVTGVIPLT TTPTKSHFANL KGTQTRGKLC [SEQ ID NO: 552] | CASGRSKVIK GSLPLIGEADC LHEKYGGLNK SKPYYTGEHA KAIGNCPIWV KTPLKLANGT KYRPPAKLLK [SEQ ID NO: 554] | GFFGAIAGFLEGG WEGMIAGWHGY TSHGAHGVAVAA DLKSTQEAINKIT KNLNSLSELEVKN LQRLSGAMDELH NEILELDEKVDDL RADTISSQIELAVL LSNEGIINSEDEHL LALERKLKKMLG PSAVEIGNGCFET KHKCNQTCLDRI AAGTFDAGEFSLP TFDSLNITAASLN DDGLDNHTILLYY |

TABLE 3-continued

Exemplary Influenza B Hemagglutinin Sequences

| HA construct variants | Signal peptide | HA1 N-terminal Stem Segment | HA1 C-terminal Stem Segment | HA2 Domain |
|---|---|---|---|---|
| | | | | STAASSLAVTLMI AIFVVYMVSRDN VSCSICL [SEQ ID NO: 160] |

Table 4 provides the putative stem domain, luminal domain, transmembrane domain and cytoplasmic domain of HA from influenza B.

TABLE 4

Exemplary Influenza B Hemagglutinin Sequences

| HA2 domain Subtype (Genbank No.) | Stem Domain | Luminal Domain | Transmembrane Domain | Cytoplasmic Domain |
|---|---|---|---|---|
| HA2 (AY096185) | GFFGAIAGFLEG GWEGMIAGWH GYTSHGAHGV AVAADLKSTQE AINKITKNLNSL SELEVKNLQRL SGAMDELHNEI LELDEKVDDLR ADTISSQIELAV LLSNEGIINSED EHLLALERKLK KMLGPSAVEIG NGCFETKHKCN QTCLDRIAAGT FDAGEFSLPTFD SLNITAASLND [SEQ ID NO: 161] | DGLDN [SEQ ID NO: 162] | HTILLYYSTAAS SLAVTLMIAIFV VYMV [SEQ ID NO: 163] | SRDNVSCSIC L [SEQ ID NO: 164] |

As illustrated in FIGS. 1 and 2, HA1 N-terminal stem segments share sequence identity between influenza A and influenza B and additionally across influenza A subtypes. Similarly, HA1 C-terminal stem segments also share sequence identity between influenza A and influenza B and additionally across influenza A subtypes. Further, HA2 domains also share sequence identity between influenza A and influenza B and additionally across influenza A subtypes.

In some embodiments, the influenza hemagglutinin stem domain polypeptide comprises in the following order: an HA1 N-terminal stem segment, a linker, an HA1 intermediate stem segment, a second linker, an HA1 C-terminal stem segment and an HA2. In some embodiments, the HA1 N-terminal stem segment has an amino acid sequence that is at least 70%, 75%, 80%, 85%, 90%, 95%, 96% or 98% identical to SEQ ID NO:555, as illustrated in Table 5. SEQ ID NO:555 corresponds to residues 1-94 of influenza B virus HA1. In some embodiments, the HA 1 C-terminal stem segment has an amino acid sequence that is at least 70%, 75%, 80%, 85%, 90%, 95%, 96% or 98% identical to SEQ ID NO:557, as illustrated in Table 5. SEQ ID NO:557 corresponds to residues 272-344 of influenza B virus HA1. In some embodiments, the HA1 intermediate segment has an amino acid sequence that is at least 70%, 75%, 80%, 85%, 90%, 95%, 96% or 98% identical to SEQ ID NO:556, as illustrated in Table 5. SEQ ID NO:556 corresponds to residues 143-178 of influenza B virus HA1. In some embodiments, the HA2 domain has an amino acid sequence that is at least 70%, 75%, 80%, 85%, 90%, 95%, 96% or 98% identical to SEQ ID NO:160, as described herein. In some embodiments, the first and second linker can be any linker known to those skilled in the art including, but not limited to, linkers described herein.

TABLE 5

Exemplary Influenza B Hemagglutinin Sequences

| HA construct variant | HA1 N-terminal Stem Segment | HA1 Intermediate Segment | HA1 C-terminal Stem Segment | HA2 Domain |
|---|---|---|---|---|
| Cys94-Cys143 Cys178-Cys272 | DRICTGITSSNS PHVVKTATQGE VNVTGVIPLTTT PTKSHFANLKG TQTRGKLCPNC LNCTDLDVALG RPKCMGTIPSA KASILHEVKPV TSGC [SEQ ID NO: 555] | CPNVTNGNGF FATMAWAVP KNKTATNPLT VEVPYIC [SEQ ID NO: 556] | CASGRSKVIKG SLPLIGEADCLH EKYGGLNKSKP YYTGEHAKAIG NCPIWVKTPLK LANGTKYRPPA KLLK [SEQ ID NO: 557] | GFFGAIAGFL EGGWEGMIA GWHGYTSHG AHGVAVAAD LKSTQEAINK ITKNLNSLSE LEVKNLQRLS GAMDELHNE ILELDEKVDD LRADTISSQIE LAVLLSNEGII NSEDEHLLAL ERKLKKMLG PSAVEIGNGC FETKHKCNQ TCLDRIAAGT FDAGEFSLPT FDSLNITAAS LNDDGLDNH TILLYYSTAA SSLAVTLMIA IFVVYMVSR DNVSCSICL [SEQ ID NO: 160] |

In some embodiments, the influenza hemagglutinin stem domain polypeptide is a hybrid polypeptide that comprises or consists essentially of segments and/or domains from a plurality of influenza strains or subtypes. For example, an influenza hemagglutinin stem domain polypeptide might comprise HA1 N-terminal and HA1 C-terminal stem segments from different influenza A virus HA subtypes. In some embodiments, the HA1 N-terminal stem segment is from influenza A virus while the HA1 C-terminal stem segment is from influenza B virus. Similarly, HA2 may also be from influenza A virus while the HA1 N-terminal and/or C-terminal stem segment is from influenza B virus.

It will be understood that any combination of the sequence elements listed in Tables 1-4 or the variants thereof may be used to form the hemagglutinin HA stem domain polypeptides of the present invention.

In an influenza stem domain polypeptide provided herein, a linker covalently connects the HA1 N-terminal stem segment to the HA1 C-terminal stem segment. In certain embodiments, the linker is a direct bond. In certain embodiments, the linker is a globular head, or a fragment thereof, from an influenza virus heterologous to the influenza stem domain. In certain embodiments, the linker is a globular head, or a fragment thereof, from an influenza virus heterologous to the stem domain of the HA2 subunit of a chimeric influenza virus hemagglutinin. In certain embodiments, the linker is a globular head, or a fragment thereof, from an influenza virus heterologous to the stem domain of the HA1 and/or HA2 subunit of a chimeric influenza virus hemagglutinin. In certain embodiments, the linker is an antibody Fab region or fragment thereof. In other embodiments, the linker is a non-influenza, viral glycoprotein or fragment thereof. In certain embodiments, the linker is a peptide that comprises one amino acid residue, two or fewer amino acid residues, three or fewer amino acid residues, four or fewer amino acid residues, five or fewer amino acid residues, ten or fewer amino acid residues, 15 or fewer amino acid residues, 20 or fewer amino acid residues, 30 or fewer amino acid residues, 40 or fewer amino acid residues, or 50 or fewer amino acid residues. In certain embodiments, the linker peptide comprises 50 or more amino acid residues. In certain embodiments, the linker substantially lacks a globular head domain. In other words, the linker comprises no more than 10, 9, 8, 7, 6, 5 or 4 contiguous, sequential amino acid residues from the amino acid sequence of an influenza globular head domain. In certain embodiments, the linker is other than Lys-Leu-Asn-Gly-Ser-Gly-Ile-Met-Lys-Thr-Glu-Gly-Thr-Leu-Glu-Asn (SEQ ID NO:542). In certain embodiments, the linker is other than Asn-Asn-Ile-Asp-Thr (SEQ ID NO:546) or Lys-Leu-Asn-Gly-Ser-Gly-Ile-Met-Lys-Thr-Glu-Gly-Thr-Leu-Glu-Asn (SEQ ID NO:559). In certain embodiments, the linker is other than Asn-Asn-Ile-Asp-Thr (SEQ ID NO:546).

In certain embodiments, the linker is covalently connected, at one end, to the C-terminus of the HA1 N-terminal stem segment. The linker peptide is also covalently connected, at the other end, to the N-terminus of the HA1 C-terminal stem segment. In certain embodiments, one of the covalent links is an amide bond. In certain embodiments, both covalent links are amide bonds.

The linker might be any linker deemed suitable by one of skill in the art. In certain embodiments, the linker is selected based on the HA1 N-terminal stem segment and the HA1 C-terminal stem segment. In these embodiments, the linker might be selected with molecular modeling programs such as InsightII and Quanta, both from Accelrys. In certain embodiments, the linker is a structural motif that allows structural alignment of the HA1 N-terminal stem segment and the HA1 C-terminal stem segment that is consistent with the structure of a hemagglutinin stem domain as recognized by those of skill in the art. In certain embodiments, the linker is selected from a library of candidate linkers. In certain embodiments, the library includes three dimensional polypeptide structures in a publicly available database such as the Protein Data Bank (PDB) or the Macromolecular Structure Database at the European Molecular Biology Laboratory (EMBL) or European Bioinformatics Institute (EBI). In certain embodiments, the library includes proprietary three-dimensional polypeptide structures associated with commercial programs such as InsightII and Quanta, both from Accelrys. Additionally, any databases or collections of protein structures or structural elements can be used to select the linker. Exemplary database or collections of protein structural elements include but are not limited to the Structural Classification of Proteins (SCOP, maintained by and available through Cambridge University); the database of protein families (Pfam, maintained by and available through the Wellcome Trust Sanger Institute); the Universal Protein Resource (UniProt, maintained by and available through the UniProt Consortium); the Integrated resource for protein families (InterPro; maintained by and available through EMBL-EBI); the Class Architecture Topology Homologous superfamily (CATH, maintained by and available through Institute of Structural and Molecular Biology at the University College London); and the families of structurally similar proteins (FSSP, maintained by and available through EBI). Any algorithm deemed suitable by one of skill in the art may be used to select the linker, including but not limited by those used by SCOP, CATH and FSSP. Useful examples include but are not limited to Pymol (Delano Scientific LLC), InsightII and Quanta (both from Accelrys), MIDAS (University of California, San Francisco), SwissPDB viewer (Swiss Institute of Bioinformatics), TOPOFIT (Northeastern University), CBSU LOOPP (Cornell University), and Super-Pose (University of Alberta, Edmonton).

In certain embodiments, the linker is a direct bond. In certain embodiments, the linker is selected from the group consisting of Gly, Gly-Gly, Gly-Gly-Gly, Gly-Gly-Gly-Gly and Gly-Gly-Gly-Gly-Gly. In certain embodiments, the linker is selected from the group consisting of Gly-Pro and Pro-Gly. In certain embodiments, the linker is a 281 turn loop, e.g. having the sequence ITPNGSIPNDKPFQN-VNKITYGA (SEQ ID NO:165).

In certain embodiments, the linker comprises a glycosylation sequence. In certain embodiments, the linker comprises an amino acid sequence according to Asn-Xaa-Ser/Thr/Cys where Xaa is any amino acid or, in certain embodiments, wherein Xaa is any amino acid except Pro and Ser/Thr/Cys is serine, threonine or cysteine. In certain embodiments, the linker comprises the amino acid sequence Asn-Ala-Ser. In certain embodiments, the linker is a glycosylation sequence. In certain embodiments, the linker is an amino acid sequence according to Asn-Xaa-Ser/Thr/Cys where Xaa is any amino acid or, in certain embodiments, wherein Xaa is any amino acid except Pro and Ser/Thr/Cys is serine, threonine or cysteine. In certain embodiments, the linker is the amino acid sequence Asn-Ala-Ser.

In certain embodiments, influenza hemagglutinin stem domain polypeptides are capable of forming a three dimensional structure that is similar to the three dimensional structure of the stem domain of a native influenza hemagglutinin. Structural similarity might be evaluated based on any technique deemed suitable by those of skill in the art. For instance, reaction, e.g. under non-denaturing conditions, of an influenza hemagglutinin stem domain polypeptide with a neutralizing antibody or antiserum that recognizes a native influenza hemagglutinin might indicate structural similarity. Useful neutralizing antibodies or antisera are described in, e.g. Sui, et al., 2009, *Nat. Struct. Mol. Biol.* 16(3):265-273, Ekiert et al., Feb. 26, 2009, *Science* [DOI: 10.1126/science.1171491], and Kashyap et al., 2008, *Proc. Natl. Acad. Sci. USA* 105(16):5986-5991, the contents of which are hereby incorporated by reference in their entireties. In certain embodiments, the antibody or antiserum is an antibody or antiserum that reacts with a non-contiguous epitope (i.e., not contiguous in primary sequence) that is formed by the tertiary or quaternary structure of a hemagglutinin.

In certain embodiments, structural similarity might be assessed by spectroscopic techniques such as circular dichroism, Raman spectroscopy, NMR, 3D NMR and X-ray crystallography. Known influenza hemagglutinin structures determined by X-ray crystallography are described in structural coordinates in Protein Data Bank files including but not limited to 1HGJ (an HA H3N2 strain) and 1RUZ (an HA H1N1 strain).

In certain embodiments, structural similarity is evaluated by RMS deviation between corresponding superimposed portions of two structures. In order to create a meaningful superimposition, in certain embodiments, the coordinates of at least 20 corresponding atoms, 25 corresponding atoms, 30 corresponding atoms, 40 corresponding atoms, 50 corresponding atoms, 60 corresponding atoms, 70 corresponding atoms, 80 corresponding atoms, 90 corresponding atoms, 100 corresponding atoms, 120 corresponding atoms, 150 corresponding atoms, 200 corresponding atoms, or 250 corresponding atoms are used to calculate an RMS deviation.

In certain embodiments, the coordinates of all corresponding atoms in amino acid backbones are used to calculate an RMS deviation. In certain embodiments, the coordinates of all corresponding alpha carbon-atoms in the amino acid backbones are used to calculate an RMS deviation. In certain embodiments, the coordinates of all corresponding identical residues, including side chains, are used to calculate an RMS deviation.

In certain embodiments, coordinates of all or a portion of the corresponding atoms in a HA1 N-terminal segment are used to calculate an RMS deviation. In certain embodiments, coordinates of all or a portion of the corresponding atoms in a HA1 C-terminal segment are used to calculate an RMS deviation. In certain embodiments, coordinates of all or a portion of the corresponding atoms in both a HA1 N-terminal segment and a C-terminal segment are used to calculate an RMS deviation. In certain embodiments, coordinates of all or a portion of corresponding atoms in HA2 domains are used to calculate an RMS deviation.

In certain embodiments, the RMS deviation between the structures of a influenza hemagglutinin stem domain polypeptide and corresponding portions of a known influenza A virus hemagglutinin stem domain (e.g., from 1HGJ or 1RUZ) is 5 Å or less, 4 Å or less, 3 Å or less, 2.5 Å or less, 2 Å or less, 1.5 Å or less, 1 Å or less, 0.75 Å or less, 0.5 Å or less, 0.3 Å or less, 0.2 Å or less, or 0.1 Å or less. Commercially available or open source software might be used to perform the structural superimpositions and/or RMS deviation calculations. Useful examples include but are not limited to Pymol (Delano Scientific LLC), InsightII and Quanta (both from Accelrys), MIDAS (University of California, San Francisco), SwissPDB viewer (Swiss Institute of Bioinformatics), TOPOFIT (Northeastern University), CBSU LOOPP (Cornell University), and SuperPose (University of Alberta, Edmonton).

In certain embodiments, any influenza hemagglutinin stem domain polypeptide provided herein can further comprise one or more polypeptide domains deemed suitable to those of skill in the art. Useful polypeptide domains include domains that facilitate purification, folding and cleavage of portions of a polypeptide. For example, a His tag (His-His-His-His-His-His, SEQ ID NO:166), FLAG epitope or other purification tag can facilitate purification of a polypeptide provided herein. In some embodiments, the His tag has the sequence, (His)$_n$, wherein n is 2, 3, 4, 5, 6, 7, 8, 9, 10, 11, 12, 13, 14, 15, 16, 17, 18, 19, 20 or greater. A foldon, or trimerization, domain from bacteriophage T4 fibritin can facilitate trimerization of polypeptides provided herein. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. The foldon domain can have any foldon sequence known to those of skill in the art (see, e.g., Papanikolopoulou et al., 2004, *J. Biol. Chem.* 279(10):8991-8998, the contents of which are hereby incorporated by reference in their entirety. Examples include GSGYIPEAPRDGQAYVRKDGEWVLLSTFL (SEQ ID NO:167). A foldon domain can be useful to facilitate trimerization of soluble polypeptides provided herein. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO:168). In certain embodiments, the cleavage site is a cleavage site recognized by Tobacco Etch Virus (TEV) protease (e.g., amino acid sequence Glu-Asn-Leu-Tyr-Phe-Gln-(Gly/Ser)).

In certain embodiments, provided are influenza hemagglutinin stem domain polypeptides comprising an elastase cleavage site. Those of skill in the art will recognize that the trypsin cleavage site at the linkage between HA1 and HA2 can be mutated to an elastase cleavage site by substituting valine for the arginine or lysine at the HA1-HA2 cleavage site in a hemagglutinin sequence (see, e.g., Stech et al., 2005, *Nature Med.* 11(6):683-689). Accordingly, provided herein are influenza hemagglutinin stem domain polypeptides having a valine substitution at the C-terminus of the C-terminal stem segment (i.e., the C-terminus of the HA1 domain). In particular embodiments, provided herein are influenza hemagglutinin stem domain polypeptides comprising any of SEQ ID NOS:50-65 or 158-159 wherein the C-terminal amino acid residue, e.g. arginine or lysine, of SEQ ID NOS:50-65 or 158-159 is substituted with a valine residue.

In certain embodiments, provided herein are influenza hemagglutinin stem domain polypeptides that are predicted to be resistant to protease cleavage at the junction between HA1 and HA2. Those of skill in the art should recognize that the Arg-Gly sequence spanning HA1 and HA2 is a recognition site for trypsin and is typically cleaved for hemagglutinin activation. Since the stem domain polypeptides described herein need not be activated, provided herein are influenza hemagglutinin stem domain polypeptides that are predicted to be resistant to protease cleavage. In certain embodiments, provided is any influenza hemagglutinin stem domain polypeptide described herein wherein the protease site spanning HA1 and HA2 is mutated to a sequence that is resistant to protease cleavage. In certain embodiments, provided is any influenza hemagglutinin stem domain polypeptide described herein wherein the C-terminal residue of the HA1 C-terminal stem segment is any residue other than Lys or Arg. In certain embodiments, provided is any influenza hemagglutinin stem domain polypeptide described herein wherein the N-terminal residue of the HA2 domain is proline. In certain embodiments, provided is any influenza hemagglutinin stem domain polypeptide described herein wherein the C-terminal residue of the HA1 C-terminal stem segment is Ala and the N-terminal residue of the HA2 domain is also Ala.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to an HA2 luminal domain. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to an HA2 luminal domain. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to an HA2 luminal domain.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to, in sequence, a protease cleavage site, a trimerization domain, and a purification tag. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to, in sequence, a cleavage site, a trimerization domain and a purification tag. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to, in sequence, a protease cleavage site, a trimerization domain and a purification tag. In certain embodiments, the protease cleavage site is a thrombin cleavage site. In certain embodiments, the cleavage site has the amino acid sequence LVPRGSP (SEQ ID NO:168). In certain embodiments, the cleavage site is a cleavage site recognized by Tobacco Etch Virus (TEV) protease (e.g., amino acid sequence Glu-Asn-Leu-Tyr-Phe-Gln-(Gly/Ser)). In certain embodiments, the trimerization domain is a foldon domain. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to an HA2 luminal domain that is covalently linked to, in sequence, a cleavage site, a trimerization domain and a purification tag. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to an HA2 luminal domain that is covalently linked to, in sequence, a cleavage site, a trimerization domain and a purification tag. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to an HA2 luminal domain that is covalently linked to, in sequence, a cleavage site, a trimerization domain and a purification tag. In certain embodiments, the protease cleavage site is a thrombin cleavage site. In certain embodiments, the cleavage site has the amino acid sequence LVPRGSP (SEQ ID NO:168). In certain embodiments, the cleavage site is a cleavage site recognized by Tobacco Etch Virus (TEV) protease (e.g., amino acid sequence Glu-Asn-Leu-Tyr-Phe-Gln-(Gly/Ser)). In certain embodiments, the trimerization domain is a foldon domain. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, *PLoSONE* 5(9): e12466. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to an HA2 luminal domain that is in turn covalently linked to an HA2 transmembrane domain. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to an HA2 luminal domain that is in turn covalently linked to an HA2 transmembrane domain. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to an HA2 luminal domain that is in turn covalently linked to an HA2 transmembrane domain.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to an HA2 luminal domain that is in turn covalently linked to an HA2 transmembrane domain that is in turn covalently linked to an HA2 cytoplasmic domain.

In certain embodiments, provided herein is an influenza hemagglutinin polypeptide having a sequence selected from the group consisting of:
(SEQ ID NO:34)-LL-(SEQ ID NO:50)-(SEQ ID NO:66),
(SEQ ID NO:35)-LL-(SEQ ID NO:51)-(SEQ ID NO:67),
(SEQ ID NO:36)-LL-(SEQ ID NO:52)-(SEQ ID NO:68),
(SEQ ID NO:37)-LL-(SEQ ID NO:53)-(SEQ ID NO:69),
(SEQ ID NO:38)-LL-(SEQ ID NO:54)-(SEQ ID NO:70),
(SEQ ID NO:39)-LL-(SEQ ID NO:55)-(SEQ ID NO:71),
(SEQ ID NO:40)-LL-(SEQ ID NO:56)-(SEQ ID NO:72),
(SEQ ID NO:41)-LL-(SEQ ID NO:57)-(SEQ ID NO:73),
(SEQ ID NO:42)-LL-(SEQ ID NO:58)-(SEQ ID NO:74),
(SEQ ID NO:43)-LL-(SEQ ID NO:59)-(SEQ ID NO:75),
(SEQ ID NO:44)-LL-(SEQ ID NO:60)-(SEQ ID NO:76),
(SEQ ID NO:45)-LL-(SEQ ID NO:61)-(SEQ ID NO:77),
(SEQ ID NO:46)-LL-(SEQ ID NO:62)-(SEQ ID NO:78),
(SEQ ID NO:47)-LL-(SEQ ID NO:63)-(SEQ ID NO:79),
(SEQ ID NO:48)-LL-(SEQ ID NO:64)-(SEQ ID NO:80), and
(SEQ ID NO:49)-LL-(SEQ ID NO:65)-(SEQ ID NO:81),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n (wherein n indicates any number of Glycine residues so long as there is flexibility in the peptide linker; in certain embodiments, n is 2, 3, 4, 5, 6, or 7 Glycine residues), Gly-Pro, ITPNGSIPNDKPFQN-VNKITYGA (SEQ ID NO:165) and Asn-Ala-Ser.

In certain embodiments, provided herein is an influenza hemagglutinin polypeptide having a sequence selected from the group consisting of:
(SEQ ID NO:34)-LL-(SEQ ID NO:50)-(SEQ ID NO:82),
(SEQ ID NO:35)-LL-(SEQ ID NO:51)-(SEQ ID NO:83),
(SEQ ID NO:36)-LL-(SEQ ID NO:52)-(SEQ ID NO:84),
(SEQ ID NO:37)-LL-(SEQ ID NO:53)-(SEQ ID NO:85),
(SEQ ID NO:38)-LL-(SEQ ID NO:54)-(SEQ ID NO:86),
(SEQ ID NO:39)-LL-(SEQ ID NO:55)-(SEQ ID NO:87),
(SEQ ID NO:40)-LL-(SEQ ID NO:56)-(SEQ ID NO:88),
(SEQ ID NO:41)-LL-(SEQ ID NO:57)-(SEQ ID NO:89), (SEQ ID NO:42)-LL-(SEQ ID NO:58)-(SEQ ID NO:90),
(SEQ ID NO:43)-LL-(SEQ ID NO:59)-(SEQ ID NO:91),
(SEQ ID NO:44)-LL-(SEQ ID NO:60)-(SEQ ID NO:92),
(SEQ ID NO:45)-LL-(SEQ ID NO:61)-(SEQ ID NO:93),
(SEQ ID NO:46)-LL-(SEQ ID NO:62)-(SEQ ID NO:94),
(SEQ ID NO:47)-LL-(SEQ ID NO:63)-(SEQ ID NO:95),
(SEQ ID NO:48)-LL-(SEQ ID NO:64)-(SEQ ID NO:96), and
(SEQ ID NO:49)-LL-(SEQ ID NO:65)-(SEQ ID NO:97),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:
(SEQ ID NO:34)-LL-(SEQ ID NO:50)-(SEQ ID NO:82)-(SEQ ID NO:98),
(SEQ ID NO:35)-LL-(SEQ ID NO:51)-(SEQ ID NO:83)-(SEQ ID NO:99),
(SEQ ID NO:36)-LL-(SEQ ID NO:52)-(SEQ ID NO:84)-(SEQ ID NO:100),
(SEQ ID NO:37)-LL-(SEQ ID NO:53)-(SEQ ID NO:85)-(SEQ ID NO:101),
(SEQ ID NO:38)-LL-(SEQ ID NO:54)-(SEQ ID NO:86)-(SEQ ID NO:102),
(SEQ ID NO:39)-LL-(SEQ ID NO:55)-(SEQ ID NO:87)-(SEQ ID NO:103),
(SEQ ID NO:40)-LL-(SEQ ID NO:56)-(SEQ ID NO:88)-(SEQ ID NO:104),
(SEQ ID NO:41)-LL-(SEQ ID NO:57)-(SEQ ID NO:89)-(SEQ ID NO:105),
(SEQ ID NO:42)-LL-(SEQ ID NO:58)-(SEQ ID NO:90)-(SEQ ID NO:106),
(SEQ ID NO:43)-LL-(SEQ ID NO:59)-(SEQ ID NO:91)-(SEQ ID NO:107),
(SEQ ID NO:44)-LL-(SEQ ID NO:60)-(SEQ ID NO:92)-(SEQ ID NO:108),
(SEQ ID NO:45)-LL-(SEQ ID NO:61)-(SEQ ID NO:93)-(SEQ ID NO:109),
(SEQ ID NO:46)-LL-(SEQ ID NO:62)-(SEQ ID NO:94)-(SEQ ID NO:110),
(SEQ ID NO:47)-LL-(SEQ ID NO:63)-(SEQ ID NO:95)-(SEQ ID NO:111),
(SEQ ID NO:48)-LL-(SEQ ID NO:64)-(SEQ ID NO:96)-(SEQ ID NO:112), and
(SEQ ID NO:49)-LL-(SEQ ID NO:65)-(SEQ ID NO:97)-(SEQ ID NO:113),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:
(SEQ ID NO:34)-LL-(SEQ ID NO:50)-(SEQ ID NO:82)-(SEQ ID NO:168)-(SEQ ID NO:167)-(SEQ ID NO:166),
(SEQ ID NO:35)-LL-(SEQ ID NO:51)-(SEQ ID NO:83)-(SEQ ID NO:168)-(SEQ ID NO:167)-(SEQ ID NO:166),
(SEQ ID NO:36)-LL-(SEQ ID NO:52)-(SEQ ID NO:84)-(SEQ ID NO:168)-(SEQ ID NO:167)-(SEQ ID NO:166),
(SEQ ID NO:37)-LL-(SEQ ID NO:53)-(SEQ ID NO:85)-(SEQ ID NO:168)-(SEQ ID NO:167)-(SEQ ID NO:166),
(SEQ ID NO:38)-LL-(SEQ ID NO:54)-(SEQ ID NO:86)-(SEQ ID NO:168)-(SEQ ID NO:167)-(SEQ ID NO:166),
(SEQ ID NO:39)-LL-(SEQ ID NO:55)-(SEQ ID NO:87)-(SEQ ID NO:168)-(SEQ ID NO:167)-(SEQ ID NO:166),
(SEQ ID NO:40)-LL-(SEQ ID NO:56)-(SEQ ID NO:88)-(SEQ ID NO:168)-(SEQ ID NO:167)-(SEQ ID NO:166),
(SEQ ID NO:41)-LL-(SEQ ID NO:57)-(SEQ ID NO:89)-(SEQ ID NO:168)-(SEQ ID NO:167)-(SEQ ID NO:166),
(SEQ ID NO:42)-LL-(SEQ ID NO:58)-(SEQ ID NO:90)-(SEQ ID NO:168)-(SEQ ID NO:167)-(SEQ ID NO:166),
(SEQ ID NO:43)-LL-(SEQ ID NO:59)-(SEQ ID NO:91)-(SEQ ID NO:168)-(SEQ ID NO:167)-(SEQ ID NO:166),
(SEQ ID NO:44)-LL-(SEQ ID NO:60)-(SEQ ID NO:92)-(SEQ ID NO:168)-(SEQ ID NO:167)-(SEQ ID NO:166),
(SEQ ID NO:45)-LL-(SEQ ID NO:61)-(SEQ ID NO:93)-(SEQ ID NO:168)-(SEQ ID NO:167)-(SEQ ID NO:166),
(SEQ ID NO:46)-LL-(SEQ ID NO:62)-(SEQ ID NO:94)-(SEQ ID NO:168)-(SEQ ID NO:167)-(SEQ ID NO:166),
(SEQ ID NO:47)-LL-(SEQ ID NO:63)-(SEQ ID NO:95)-(SEQ ID NO:168)-(SEQ ID NO:167)-(SEQ ID NO:166),
(SEQ ID NO:48)-LL-(SEQ ID NO:64)-(SEQ ID NO:96)-(SEQ ID NO:168)-(SEQ ID NO:167)-(SEQ ID NO:166), and
(SEQ ID NO:49)-LL-(SEQ ID NO:65)-(SEQ ID NO:97)-(SEQ ID NO:168)-(SEQ ID NO:167)-(SEQ ID NO:166),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKPFQNVNKITYGA (SEQ ID NO:165) and Asn-Ala-Ser.

In certain embodiments, provided herein is an influenza hemagglutinin polypeptide having a sequence selected from the group consisting of:
(SEQ ID NO:34)-LL-(SEQ ID NO:50)-(SEQ ID NO:82)-(SEQ ID NO:98)-(SEQ ID NO:168)-(SEQ ID NO:167)-(SEQ ID NO:166),
(SEQ ID NO:35)-LL-(SEQ ID NO:51)-(SEQ ID NO:83)-(SEQ ID NO:99)-(SEQ ID NO:168)-(SEQ ID NO:167)-(SEQ ID NO:166),
(SEQ ID NO:36)-LL-(SEQ ID NO:52)-(SEQ ID NO:84)-(SEQ ID NO:100)-(SEQ ID NO:168)-(SEQ ID NO:167)-(SEQ ID NO:166),
(SEQ ID NO:37)-LL-(SEQ ID NO:53)-(SEQ ID NO:85)-(SEQ ID NO:101)-(SEQ ID NO:168)-(SEQ ID NO:167)-(SEQ ID NO:166),
(SEQ ID NO:38)-LL-(SEQ ID NO:54)-(SEQ ID NO:86)-(SEQ ID NO:102)-(SEQ ID NO:168)-(SEQ ID NO:167)-(SEQ ID NO:166),
(SEQ ID NO:39)-LL-(SEQ ID NO:55)-(SEQ ID NO:87)-(SEQ ID NO:103)-(SEQ ID NO:168)-(SEQ ID NO:167)-(SEQ ID NO:166),
(SEQ ID NO:40)-LL-(SEQ ID NO:56)-(SEQ ID NO:88)-(SEQ ID NO:104)-(SEQ ID NO:168)-(SEQ ID NO:167)-(SEQ ID NO:166),
(SEQ ID NO:41)-LL-(SEQ ID NO:57)-(SEQ ID NO:89)-(SEQ ID NO:105)-(SEQ ID NO:168)-(SEQ ID NO:167)-(SEQ ID NO:166),
(SEQ ID NO:42)-LL-(SEQ ID NO:58)-(SEQ ID NO:90)-(SEQ ID NO:106)-(SEQ ID NO:168)-(SEQ ID NO:167)-(SEQ ID NO:166), (SEQ ID NO:43)-LL-(SEQ ID NO:59)-(SEQ ID NO:91)-(SEQ ID NO:107)-(SEQ ID NO:168)-(SEQ ID NO:167)-(SEQ ID NO:166),
(SEQ ID NO:44)-LL-(SEQ ID NO:60)-(SEQ ID NO:92)-(SEQ ID NO:108)-(SEQ ID NO:168)-(SEQ ID NO:167)-(SEQ ID NO:166),
(SEQ ID NO:45)-LL-(SEQ ID NO:61)-(SEQ ID NO:93)-(SEQ ID NO:109)-(SEQ ID NO:168)-(SEQ ID NO:167)-(SEQ ID NO:166),
(SEQ ID NO:46)-LL-(SEQ ID NO:62)-(SEQ ID NO:94)-(SEQ ID NO:110)-(SEQ ID NO:168)-(SEQ ID NO:167)-(SEQ ID NO:166),
(SEQ ID NO:47)-LL-(SEQ ID NO:63)-(SEQ ID NO:95)-(SEQ ID NO:111)-(SEQ ID NO:168)-(SEQ ID NO:167)-(SEQ ID NO:166),
(SEQ ID NO:48)-LL-(SEQ ID NO:64)-(SEQ ID NO:96)-(SEQ ID NO:112)-(SEQ ID NO:168)-(SEQ ID NO:167)-(SEQ ID NO:166), and
(SEQ ID NO:49)-LL-(SEQ ID NO:65)-(SEQ ID NO:97)-(SEQ ID NO:113)-(SEQ ID NO:168)-(SEQ ID NO:167)-(SEQ ID NO:166),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKP-FQNVNKITYGA (SEQ ID NO:165) and Asn-Ala-Ser.

In certain embodiments, provided herein is an influenza hemagglutinin polypeptide having a sequence selected from the group consisting of:
(SEQ ID NO:177)-LL-(SEQ ID NO:226)-(SEQ ID NO:66),
(SEQ ID NO:178)-LL-(SEQ ID NO:227)-(SEQ ID NO:66),
(SEQ ID NO:179)-LL-(SEQ ID NO:228)-(SEQ ID NO:66),
(SEQ ID NO:180)-LL-(SEQ ID NO:229)-(SEQ ID NO:67),
(SEQ ID NO:181)-LL-(SEQ ID NO:230)-(SEQ ID NO:67),
(SEQ ID NO:182)-LL-(SEQ ID NO:231)-(SEQ ID NO:67),
(SEQ ID NO:183)-LL-(SEQ ID NO:232)-(SEQ ID NO:68),
(SEQ ID NO:184)-LL-(SEQ ID NO:233)-(SEQ ID NO:68),
(SEQ ID NO:185)-LL-(SEQ ID NO:234)-(SEQ ID NO:68),
(SEQ ID NO:186)-LL-(SEQ ID NO:235)-(SEQ ID NO:69),
(SEQ ID NO:187)-LL-(SEQ ID NO:236)-(SEQ ID NO:69),
(SEQ ID NO:188)-LL-(SEQ ID NO:237)-(SEQ ID NO:69),
(SEQ ID NO:189)-LL-(SEQ ID NO:238)-(SEQ ID NO:70),
(SEQ ID NO:190)-LL-(SEQ ID NO:239)-(SEQ ID NO:70),
(SEQ ID NO:191)-LL-(SEQ ID NO:240)-(SEQ ID NO:70),
(SEQ ID NO:192)-LL-(SEQ ID NO:241)-(SEQ ID NO:71),
(SEQ ID NO:193)-LL-(SEQ ID NO:242)-(SEQ ID NO:71),
(SEQ ID NO:194)-LL-(SEQ ID NO:243)-(SEQ ID NO:71),
(SEQ ID NO:195)-LL-(SEQ ID NO:244)-(SEQ ID NO:72),
(SEQ ID NO:196)-LL-(SEQ ID NO:245)-(SEQ ID NO:72),
(SEQ ID NO:197)-LL-(SEQ ID NO:246)-(SEQ ID NO:72),
(SEQ ID NO:198)-LL-(SEQ ID NO:247)-(SEQ ID NO:73),
(SEQ ID NO:199)-LL-(SEQ ID NO:248)-(SEQ ID NO:73),
(SEQ ID NO:200)-LL-(SEQ ID NO:249)-(SEQ ID NO:73),
(SEQ ID NO:201)-LL-(SEQ ID NO:250)-(SEQ ID NO:74),
(SEQ ID NO:202)-LL-(SEQ ID NO:251)-(SEQ ID NO:74),
(SEQ ID NO:203)-LL-(SEQ ID NO:252)-(SEQ ID NO:74),
(SEQ ID NO:204)-LL-(SEQ ID NO:253)-(SEQ ID NO:75),
(SEQ ID NO:205)-LL-(SEQ ID NO:254)-(SEQ ID NO:75),
(SEQ ID NO:206)-LL-(SEQ ID NO:255)-(SEQ ID NO:75),
(SEQ ID NO:207)-LL-(SEQ ID NO:256)-(SEQ ID NO:76),
(SEQ ID NO:208)-LL-(SEQ ID NO:257)-(SEQ ID NO:76),
(SEQ ID NO:209)-LL-(SEQ ID NO:258)-(SEQ ID NO:76),
(SEQ ID NO:210)-LL-(SEQ ID NO:259)-(SEQ ID NO:77),
(SEQ ID NO:211)-LL-(SEQ ID NO:260)-(SEQ ID NO:77),
(SEQ ID NO:212)-LL-(SEQ ID NO:261)-(SEQ ID NO:77),
(SEQ ID NO:213)-LL-(SEQ ID NO:262)-(SEQ ID NO:78),
(SEQ ID NO:214)-LL-(SEQ ID NO:263)-(SEQ ID NO:78),
(SEQ ID NO:215)-LL-(SEQ ID NO:264)-(SEQ ID NO:78),
(SEQ ID NO:216)-LL-(SEQ ID NO:265)-(SEQ ID NO:79),
(SEQ ID NO:217)-LL-(SEQ ID NO:266)-(SEQ ID NO:79),
(SEQ ID NO:218)-LL-(SEQ ID NO:267)-(SEQ ID NO:79),
(SEQ ID NO:219)-LL-(SEQ ID NO:268)-(SEQ ID NO:80),
(SEQ ID NO:220)-LL-(SEQ ID NO:269)-(SEQ ID NO:80),
(SEQ ID NO:221)-LL-(SEQ ID NO:270)-(SEQ ID NO:80),
(SEQ ID NO:222)-LL-(SEQ ID NO:271)-(SEQ ID NO:81),
(SEQ ID NO:223)-LL-(SEQ ID NO:272)-(SEQ ID NO:81),
(SEQ ID NO:224)-LL-(SEQ ID NO:273)-(SEQ ID NO:81),
(SEQ ID NO:312)-LL-(SEQ ID NO:313)-(SEQ ID NO:66),
(SEQ ID NO:34)-LL-(SEQ ID NO:314)-(SEQ ID NO:66),
(SEQ ID NO:315)-LL-(SEQ ID NO:316)-(SEQ ID NO:66),
(SEQ ID NO:308)-LL-(SEQ ID NO:52)-(SEQ ID NO:68),
(SEQ ID NO:36)-LL-(SEQ ID NO:309)-(SEQ ID NO:68), and
(SEQ ID NO:310)-LL-(SEQ ID NO:311)-(SEQ ID NO:68),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKP-FQNVNKITYGA (SEQ ID NO:165) and Asn-Ala-Ser.

In certain embodiments, provided herein is an influenza hemagglutinin polypeptide having a sequence selected from the group consisting of:
(SEQ ID NO:154)-LL-(SEQ ID NO:158)-(SEQ ID NO:160),
(SEQ ID NO:155)-LL-(SEQ ID NO:159)-(SEQ ID NO:160),
(SEQ ID NO:156)-LL-(SEQ ID NO:158)-(SEQ ID NO:160),
(SEQ ID NO:157)-LL-(SEQ ID NO:158)-(SEQ ID NO:160),
(SEQ ID NO:550)-LL-(SEQ ID NO:553)-(SEQ ID NO:160),
(SEQ ID NO:551)-LL-(SEQ ID NO:554)-(SEQ ID NO:160), and
(SEQ ID NO:552)-LL-(SEQ ID NO:555)-(SEQ ID NO:160),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKP-FQNVNKITYGA (SEQ ID NO:165) and Asn-Ala-Ser.

In certain embodiments, provided herein is an influenza hemagglutinin polypeptide having a sequence selected from the group consisting of:
(SEQ ID NO:154)-LL-(SEQ ID NO:158)-(SEQ ID NO:161),
(SEQ ID NO:155)-LL-(SEQ ID NO:159)-(SEQ ID NO:161),
(SEQ ID NO:156)-LL-(SEQ ID NO:158)-(SEQ ID NO:161),
(SEQ ID NO:157)-LL-(SEQ ID NO:158)-(SEQ ID NO:161),
(SEQ ID NO:550)-LL-(SEQ ID NO:553)-(SEQ ID NO:161), (SEQ ID NO:551)-LL-(SEQ ID NO:554)-(SEQ ID NO:161),
(SEQ ID NO:552)-LL-(SEQ ID NO:555)-(SEQ ID NO:161), and
(SEQ ID NO:555)-LL-(SEQ ID NO:556)-LL-(SeQ ID NO:557)-(SEQ ID NO:161),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKP-FQNVNKITYGA (SEQ ID NO:165) and Asn-Ala-Ser.

In certain embodiments, provided herein is an influenza hemagglutinin polypeptide having a sequence selected from the group consisting of:
(SEQ ID NO:154)-LL-(SEQ ID NO:158)-(SEQ ID NO:161)-(SEQ ID NO:162),
(SEQ ID NO:155)-LL-(SEQ ID NO:159)-(SEQ ID NO:161)-(SEQ ID NO:162),
(SEQ ID NO:156)-LL-(SEQ ID NO:158)-(SEQ ID NO:161)-(SEQ ID NO:162),
(SEQ ID NO:157)-LL-(SEQ ID NO:158)-(SEQ ID NO:161)-(SEQ ID NO:162),
(SEQ ID NO:550)-LL-(SEQ ID NO:553)-)-(SEQ ID NO:161)-(SEQ ID NO:162),
(SEQ ID NO:551)-LL-(SEQ ID NO:554)-(SEQ ID NO:161)-(SEQ ID NO:162),
(SEQ ID NO:552)-LL-(SEQ ID NO:555)-(SEQ ID NO:161)-(SEQ ID NO:162), and
(SEQ ID NO:555)-LL-(SEQ ID NO:556)-LL-(SeQ ID NO:557)-(SEQ ID NO:161)-(SEQ ID NO:162),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKP-FQNVNKITYGA (SEQ ID NO:165) and Asn-Ala-Ser.

In certain embodiments, provided herein is an influenza hemagglutinin polypeptide having a sequence selected from the group consisting of:
(SEQ ID NO:154)-LL-(SEQ ID NO:158)-(SEQ ID NO:161)-(SEQ ID NO:168)-(SEQ ID NO:167)-SEQ ID NO:166),
(SEQ ID NO:155)-LL-(SEQ ID NO:159)-(SEQ ID NO:161)-(SEQ ID NO:168)-(SEQ ID NO:167)-SEQ ID NO:166),
(SEQ ID NO:156)-LL-(SEQ ID NO:158)-(SEQ ID NO:161)-(SEQ ID NO:168)-(SEQ ID NO:167)-SEQ ID NO:166),
(SEQ ID NO:157)-LL-(SEQ ID NO:159)-(SEQ ID NO:161)-(SEQ ID NO:168)-(SEQ ID NO:167)-SEQ ID NO:166),
(SEQ ID NO:550)-LL-(SEQ ID NO:553)-)-(SEQ ID NO:161)-(SEQ ID NO:168)-(SEQ ID NO:167)-SEQ ID NO:166),
(SEQ ID NO:551)-LL-(SEQ ID NO:554)-(SEQ ID NO:161)-(SEQ ID NO:168)-(SEQ ID NO:167)-SEQ ID NO:166),
(SEQ ID NO:552)-LL-(SEQ ID NO:555)-(SEQ ID NO:161)-(SEQ ID NO:168)-(SEQ ID NO:167)-SEQ ID NO:166), and
(SEQ ID NO:555)-LL-(SEQ ID NO:556)-LL-(SeQ ID NO:557)-)-(SEQ ID NO:161)-(SEQ ID NO:168)-(SEQ ID NO:167)-SEQ ID NO:166),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKP-FQNVNKITYGA (SEQ ID NO:165) and Asn-Ala-Ser.

In certain embodiments, provided herein is an influenza hemagglutinin polypeptide having a sequence selected from the group consisting of:
(SEQ ID NO:154)-LL-(SEQ ID NO:158)-(SEQ ID NO:161)-(SEQ ID NO:162)-(SEQ ID NO:168)-(SEQ ID NO:167)-(SEQ ID NO:166),
(SEQ ID NO:155)-LL-(SEQ ID NO:159)-(SEQ ID NO:161)-(SEQ ID NO:162)-(SEQ ID NO:168)-(SEQ ID NO:167)-(SEQ ID NO:166),
(SEQ ID NO:156)-LL-(SEQ ID NO:158)-(SEQ ID NO:161)-(SEQ ID NO:162)-(SEQ ID NO:168)-(SEQ ID NO:167)-(SEQ ID NO:166), and
(SEQ ID NO:157)-LL-(SEQ ID NO:159)-(SEQ ID NO:161)-(SEQ ID NO:162)-(SEQ ID NO:168)-(SEQ ID NO:167)-(SEQ ID NO:166),
(SEQ ID NO:550)-LL-(SEQ ID NO:553)-)-(SEQ ID NO:161)-(SEQ ID NO:162)-(SEQ ID NO:168)-(SEQ ID NO:167)-(SEQ ID NO:166),
(SEQ ID NO:551)-LL-(SEQ ID NO:554)-(SEQ ID NO:161)-\(SEQ ID NO:162)-(SEQ ID NO:168)-(SEQ ID NO:167)-(SEQ ID NO:166),
(SEQ ID NO:552)-LL-(SEQ ID NO:555)-)-(SEQ ID NO:161)-(SEQ ID NO:162)-(SEQ ID NO:168)-(SEQ ID NO:167)-(SEQ ID NO:166), and
(SEQ ID NO:555)-LL-(SEQ ID NO:556)-LL-(SEQ ID NO:557)-(SEQ ID NO:161)-(SEQ ID NO:162)-(SEQ ID NO:168)-(SEQ ID NO:167)-(SEQ ID NO:166),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKP-FQNVNKITYGA (SEQ ID NO:165) and Asn-Ala-Ser.

In certain embodiments, the influenza hemagglutinin polypeptides described herein do not comprise polypeptides having the amino acid sequence of either Thr-Gly-Leu-Arg-Asn (SEQ ID NO:544) or Gly-Ile-Thr-Asn-Lys-Val-Asn-Ser-Val-Ile-Glu-Lys (SEQ ID NO:545). In certain embodiments, the influenza hemagglutinin polypeptides described herein do not comprise polypeptides having the amino acid sequence of Thr-Gly-Leu-Arg-Asn (SEQ ID NO:544) and Gly-Ile-Thr-Asn-Lys-Val-Asn-Ser-Val-Ile-Glu-Lys (SEQ ID NO:545). In certain embodiments, the influenza hemagglutinin polypeptides described herein do not comprise polypeptides having the amino acid sequence of either Thr-Gly-Met-Arg-Asn (SEQ ID NO:547) or Gln-Ile-Asn-Gly-Lys-Leu-Asn-Arg-Leu-Ile-Glu-Lys (SEQ ID NO:548). In certain embodiments, the influenza hemagglutinin polypeptides described herein do not comprise polypeptides having the amino acid sequence of Thr-Gly-Met-Arg-Asn (SEQ ID NO:547) and Gln-Ile-Asn-Gly-Lys-Leu-Asn-Arg-Leu-Ile-Glu-Lys (SEQ ID NO:548). In certain embodiments, the influenza hemagglutinin polypeptides described herein do not comprise polypeptides having the amino acid sequence of either Thr-Gly-Met-Arg-Asn (SEQ ID NO:547) or Gln-Ile-Asn-Gly-Lys-Leu-Asn-Arg-Val-Ile-Glu-Lys (SEQ ID NO:549). In certain embodiments, the influenza hemagglutinin polypeptides described herein do not comprise polypeptides having the amino acid sequence of Thr-Gly-Met-Arg-Asn (SEQ ID NO:547) and Gln-Ile-Asn-Gly-Lys-Leu-Asn-Arg-Val-Ile-Glu-Lys (SEQ ID NO:549).

In certain embodiments, the influenza hemagglutinin polypeptides described herein are not recognized by the antibody CR6261, CR6325, CR6329, CR6307, CR6323, 2A, D7, D8, F10, G17, H40, A66, D80, E88, E90, H98, C179 (produced by hybridoma FERM BP-4517; clones sold by Takara Bio, Inc. (Otsu, Shiga, Japan)), AI3C (FERM BP-4516), any other antibody described in Ekiert D C et al. (2009) Antibody Recognition of a Highly Conserved Influenza Virus Epitope. Science (published in Science Express Feb. 26, 2009); Kashyap et al. (2008), or any other similar antibodies.

5.3.1 Influenza Hemagglutinin Short Stem Domain Polypeptides

In certain embodiments, the influenza hemagglutinin stem domain polypeptide is an influenza hemagglutinin short stem domain polypeptide. The typical primary structure of an influenza hemagglutinin short stem domain polypeptide provided herein comprises, in the following order: an HA1 N-terminal stem segment, a linker, an HA1 C-terminal short stem segment and an HA2. The primary sequence can be formed by a single polypeptide, or it can be formed by multiple polypeptides. Typically, a single polypeptide is expressed by any technique deemed suitable by one of skill in the art. In single polypeptide embodiments, the HA1 segments and the HA2 are in tertiary association. As is known to those of skill in the art, a single HA polypeptide can be cleaved, for example by a protease, under appropriate expression conditions to yield two polypeptides in quaternary association. The cleavage is typically between the HA1 C-terminal short stem segment and the HA2. In certain embodiments, provided herein are multiple polypeptides. In multiple polypeptide embodiments, the HA1 segments and HA2 are in quaternary association.

In certain embodiments, an influenza hemagglutinin short stem domain polypeptide provided herein is monomeric. In certain embodiments, an influenza hemagglutinin short stem domain polypeptide provided herein is multimeric. In certain embodiments, an influenza hemagglutinin short stem domain polypeptide provided herein is trimeric. Those of skill in the art will recognize that native influenza hemagglutinin polypeptides are capable of trimerization in vivo and that certain influenza hemagglutinin short stem domain polypeptides provided herein are capable of trimerization. In particular embodiments described below, influenza hemagglutinin short stem domain polypeptides provided herein comprise trimerization domains to facilitate trimerization.

In certain embodiments, an influenza hemagglutinin short stem domain polypeptide comprises a signal peptide. Typically, the signal peptide is cleaved during or after polypeptide expression and translation to yield a mature influenza hemagglutinin short stem domain polypeptide. The signal peptide can be advantageous for expression of the influenza hemagglutinin short stem domain polypeptides. In certain embodiments, also provided herein are mature influenza hemagglutinin short stem domain polypeptides that lack a signal peptide.

Influenza hemagglutinin HA2 typically comprises a stem domain, transmembrane domain and a cytoplasmic domain. In certain embodiments, provided herein are influenza hemagglutinin short stem domain polypeptides that comprise an HA2 stem domain, an HA2 luminal domain, an HA2 transmembrane domain and an HA2 cytoplasmic domain. In certain embodiments, provided herein are influenza hemagglutinin short stem domain polypeptides that comprise an HA2 stem domain, an HA2 luminal domain, and an HA2 transmembrane domain but lack some or all of the typical cytoplasmic domain. In certain embodiments, provided herein are influenza hemagglutinin short stem domain polypeptides that comprise an HA2 stem domain and an HA2 luminal domain but lack both an HA2 transmembrane domain and an HA2 cytoplasmic domain. In certain embodiments, provided herein are influenza hemagglutinin short stem domain polypeptides that comprise an HA2 stem domain but lack an HA2 luminal domain, an HA2 transmembrane domain and an HA2 cytoplasmic domain. In certain embodiments, the influenza hemagglutinin short stem domain polypeptides comprise an HA2 stem domain having at least 70%, 75%, 80%, 85%, 90%, 95%, 96% or 98% amino acid sequence identity to an influenza HA2 stem domain known to those of skill in the art. Exemplary known HA2 stem domains from known influenza A and influenza B hemagglutinins are provided in the tables above.

Also provided herein are influenza hemagglutinin short stem domain polypeptides comprising deleted forms of HA2 stem domains wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA2 stem domain. Further provided herein are influenza hemagglutinin short stem domain polypeptides comprising altered forms of HA2 stem domains wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are conservatively substituted with other amino acids. Further provided are influenza hemagglutinin short stem domain polypeptides comprising deleted and altered HA2 stem domains.

The HA1 N-terminal stem segment can be any HA1 N-terminal stem provided herein. Exemplary known HA1 N-terminal stem segments are provided in the tables below.

The HA1 C-terminal short stem segment can be any HA1 C-terminal short stem segment recognized by one of skill in the art based on the definition provided herein. Typically, an HA1 C-terminal short stem segment corresponds to a polypeptide consisting of the cysteine residue located in sequence at approximately the $305^{th}$ residue of an HA1 (using H3 numbering) through the C-terminal amino acid of the HA1. This cysteine residue, termed $B_q$ herein, is capable of being linked to a cysteine residue $A_p$ in the N-terminal stem segment of HA1. Sequences of 17 representative influenza A hemagglutinins are presented in FIG. 1, and residue $B_q$ is identified in each.

In certain embodiments, the HA1 C-terminal short stem segment does not start at $B_q$ (e.g., $Cys_{305}$ of an HA1 subunit from an H3 hemagglutinin), but at a residue in sequence and structural vicinity to $B_q$. For example, in certain embodiments, the HA1 C-terminal short stem segment starts at $B_{q-1}$, $B_{q-2}$, $B_{q-3}$, $B_{q-4}$, $B_{q-5}$, $B_{q-6}$, $B_{q-7}$, $B_{q-8}$, $B_{q-9}$, $B_{q-10}$, $B_{q-11}$, $B_{q-12}$, $B_{q-13}$, $B_{q-14}$, $B_{q-15}$, $B_{q-20}$, $B_{q-25}$, $B_{q-30}$, $B_{q-35}$, $B_{q-40}$, $B_{q-45}$, $B_{q-50}$, $B_{q-55}$, $B_{q-60}$, $B_{q-65}$, $B_{q-70}$, $B_{q-75}$, or $B_{q-80}$. In other embodiments, the HA1 C-terminal short stem segment starts at $B_{q+1}$, $B_{q+2}$, $B_{q+3}$, $B_{q+4}$, $B_{q+5}$, $B_{q+6}$, $B_{q+7}$, $B_{q+8}$, $B_{q+9}$, or $B_{q+10}$. The end of an HA1 N-terminal stem segment should be selected in conjunction with the start of the HA1 C-terminal short stem segment and the linker so that the resulting HA1 stem domain is capable of forming a three-dimensional structure similar, as described below, to an influenza hemagglutinin.

In certain embodiments, the influenza hemagglutinin short stem domain polypeptides comprise an HA1 C-terminal short stem segment having at least 70%, 75%, 80%, 85%, 90%, 95%, 96% or 98% amino acid sequence identity to an influenza HA1 C-terminal short stem segment known to those of skill in the art. Exemplary known HA1 C-terminal short stem segments are provided in the tables below.

In certain embodiments, the end of the N-terminal stem segment is $A_{p-1}$, and the start of the C-terminal short stem segment is $B_{q-1}$. In certain embodiments, the end of the N-terminal stem segment is $A_{p-2}$, and the start of the C-terminal short stem segment is $B_{q-2}$. In certain embodiments, the end of the N-terminal stem segment is $A_{p-3}$, and the start of the C-terminal short stem segment is $B_{q-3}$. In certain embodiments, the end of the N-terminal stem segment is $A_{p-4}$, and the start of the C-terminal short stem segment is $B_{q-4}$. In certain embodiments, the end of the N-terminal stem segment is $A_{p-5}$, and the start of the C-terminal short stem segment is $B_{q-5}$.

In certain embodiments, the end of the N-terminal stem segment is $A_{p+1}$, and the start of the C-terminal short stem segment is $B_{q+1}$. In certain embodiments, the end of the N-terminal stem segment is $A_{p+2}$, and the start of the C-terminal short stem segment is $B_{q+2}$. In certain embodiments, the end of the N-terminal stem segment is $A_{p+3}$, and the start of the C-terminal short stem segment is $B_{q+3}$. In certain embodiments, the end of the N-terminal stem segment is $A_{p+4}$, and the start of the C-terminal short stem segment is $B_{q+4}$. In certain embodiments, the end of the N-terminal stem segment is $A_{p+5}$, and the start of the C-terminal short stem segment is $B_{q+5}$.

In certain embodiments, the end of the N-terminal stem segment is $A_{p-1}$, and the start of the C-terminal short stem segment is $B_{q+1}$. In certain embodiments, the end of the N-terminal stem segment is $A_{p-2}$, and the start of the C-terminal short stem segment is $B_{q+2}$. In certain embodiments, the end of the N-terminal stem segment is $A_{p-3}$, and the start of the C-terminal short stem segment is $B_{q+3}$. In certain embodiments, the end of the N-terminal stem segment is $A_{p-4}$, and the start of the C-terminal short stem segment is $B_{q+4}$. In certain embodiments, the end of the N-terminal stem segment is $A_{p-5}$, and the start of the C-terminal short stem segment is $B_{q+5}$.

In certain embodiments, the end of the N-terminal stem segment is $A_p$ (i.e., the end of the N-terminal stem segment is Cysteine), and the start of the C-terminal stem segment is $A_q$ (i.e., the start of the C-terminal stem segment is Cysteine). In certain embodiments, the end of the N-terminal stem segment is $A_{p+1}$, and the start of the C-terminal short stem segment is $B_{q-1}$. In certain embodiments, the end of the N-terminal stem segment is $A_{p+2}$, and the start of the C-terminal short stem segment is $B_{q-2}$. In certain embodiments, the end of the N-terminal stem segment is $A_{p+3}$, and the start of the C-terminal short stem segment is $B_{q-3}$. In certain embodiments, the end of the N-terminal stem segment is $A_{p+4}$, and the start of the C-terminal short stem segment is $B_{q-4}$. In certain embodiments, the end of the N-terminal stem segment is $A_{p+5}$, and the start of the C-terminal short stem segment is $B_{q-5}$.

Also provided herein are influenza hemagglutinin short stem domain polypeptides comprising deleted forms of HA1 C-terminal short stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA1 C-terminal short stem segment. In certain embodiments, provided herein are influenza hemagglutinin short stem domain polypeptides that comprise expanded forms of HA1 C-terminal short stem segments wherein 1, 2, 3, 4, 5, 6, 7, 8, 9, 10 or more residues are added to the N-terminus of the HA1 C-terminal short stem segments. In particular embodiments, if one residue is added to the C-terminal short stem segment, then one residue is added to the N-terminal stem segment; if two residues are added to the C-terminal short stem segment, then two residues are added to the N-terminal stem segment; if three residues are added to the C-terminal short stem segment, then three residues are added to the N-terminal stem segment. Further provided herein are influenza hemagglutinin short stem domain polypeptides comprising altered forms of HA1 C-terminal short stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are conservatively substituted with other amino acids. Further provided are influenza hemagglutinin short stem domain polypeptides comprising deleted and altered HA1 C-terminal short stem segments.

The influenza hemagglutinin short stem domain polypeptides can be based on (i.e. can have sequence identity, as described above) any influenza hemagglutinin known to those of skill or later discovered. In certain embodiments, influenza hemagglutinin short stem domain polypeptides are based on an influenza A hemagglutinin. In certain embodiments, the influenza hemagglutinin short stem domain polypeptides are based on an influenza A hemagglutinin selected from the group consisting of H1, H2, H3, H4, H5, H6, H7, H8, H9, H10, H11, H12, H13, H14, H15, H16, and H17. In certain embodiments, influenza hemagglutinin short stem domain polypeptides are based on an influenza B hemagglutinin, as described in detail below.

The HA1 N-terminal stem segments can be based on (i.e. can have sequence identity, as described above) any HA1 N-terminal stem segments known to those of skill or later discovered. In certain embodiments, the HA1 N-terminal stem segments are based on influenza A HA1 N-terminal stem segments. In certain embodiments, the HA1 N-terminal stem segments are based on an influenza A hemagglutinin selected from the group consisting of H1, H2, H3, H4, H5, H6, H7, H8, H9, H10, H11, H12, H13, H14, H15, H16, and H17. In certain embodiments, the HA1 N-terminal stem segment is selected from SEQ ID NOS:34-49. In certain embodiments, the HA1 N-terminal stem segment is selected from SEQ ID NOS:34-49, each having one amino acid deleted from its C-terminus. In certain embodiments, the HA1 N-terminal stem segment is selected from SEQ ID NOS:34-49, each having two amino acids deleted from its C-terminus. In certain embodiments, the HA1 N-terminal stem segment is selected from SEQ ID NOS:34-49, each having three amino acids deleted from its C-terminus. In certain embodiments, the HA1 N-terminal stem segment is selected from SEQ ID NOS:34-49, each having four amino acids deleted from its C-terminus. In certain embodiments, the HA1 N-terminal stem segment is selected from SEQ ID NOS:34-49, each having five amino acids deleted from its C-terminus. In certain embodiments, the HA1 N-terminal stem segment is selected from SEQ ID NOS:177-224.

The HA1 C-terminal short stem segments can be based on (i.e. can have sequence identity, as described above) any HA1 C-terminal short stem segments known to those of skill or later discovered. In certain embodiments, the HA1 C-terminal short stem segments are based on influenza A HA1 C-terminal short stem segments. In certain embodiments, the HA1 C-terminal short stem segments are based on an influenza A hemagglutinin selected from the group consisting of H1, H2, H3, H4, H5, H6, H7, H8, H9, H10, H11, H12, H13, H14, H15, H16, and H17. In certain embodiments, the HA1 C-terminal short stem segment is selected from SEQ ID NOS:350-365. In certain embodiments, the HA1 C-terminal short stem segment is selected from SEQ ID NOS: 350-365, each having one amino acid deleted from its N-terminus. In certain embodiments, the HA1 C-terminal short stem segment is selected from SEQ ID NOS:350-365, each having two amino acids deleted from its N-terminus. In certain embodiments, the HA1 C-terminal short stem segment is selected from SEQ ID NOS:350-365, each having three amino acids deleted from its N-terminus. In certain embodiments, the HA1 C-terminal short stem segment is selected from SEQ ID NOS:350-365, each having four amino acids deleted from its N-terminus. In certain embodiments, the HA1 C-terminal short stem segment is selected from SEQ ID NOS: 350-365, each having five amino acids deleted from its N-terminus. In certain embodiments, the HA1 C-terminal short stem segment is selected from SEQ ID NOS:366-413.

The HA2 stem domains can be based on (i.e. can have sequence identity, as described above) any HA2 stem domains known to those of skill, later discovered or described herein. In certain embodiments, the HA2 stem domains are based on influenza A HA2 stem domains. In certain embodiments, the HA2 stem domains are based on an influenza A hemagglutinin selected from the group consisting of H1, H2, H3, H4, H5, H6, H7, H8, H9, H10, H11, H12, H13, H14, H15, H16, and H17. In certain embodiments, the HA2 stem domain is selected from SEQ ID NOS:66-97.

In embodiments comprising a signal peptide, the signal peptide can be based on any influenza signal peptide known to those of skill in the art or described herein. In certain embodiments, the signal peptides are based on influenza A signal peptides.

In embodiments comprising a luminal domain, the luminal domain can be based on any influenza luminal domain known to those of skill in the art or described herein.

In embodiments comprising a transmembrane domain, the transmembrane domain can be based on any influenza transmembrane domain known to those of skill in the art or described herein.

In embodiments comprising a cytoplasmic domain, the cytoplasmic domain can be based on any influenza cytoplasmic domain known to those of skill in the art or described herein.

In certain embodiments, one or more of the glycosylation sites in the hemagglutinin short stem domain are modified (e.g., by amino acid addition, deletion or substitution) such that glycosylation at these sites will not occur during processing and maturation of the polypeptide. Those of skill in the art will recognize that influenza HA typically comprises one or more glycosylation sites (e.g. Ser/Thr/Cys, wherein Xaa is any amino acid, or, in certain embodiments, wherein Xaa is not Pro). In certain embodiments, one or more amino acid residues in a glycosylation sequence is conservatively substituted with an amino acid residue that disrupts the glycosylation site. In certain embodiments, one or more amino acid residues in a glycosylation site are substituted with any amino acid residue that disrupts the glycosylation site. In certain embodiments, one or more asparagine residues in a glycosylation sequence is substituted with alanine. In a particular embodiment, the asparagine at position 38 of an H3 hemagglutinin is changed to an alanine. In certain embodiments, the hemagglutinin short stem domain comprises one or more modified glycosylation sites as discussed in Section 5.4.1, infra.

Table 6, below, identifies signal peptides, HA1 terminal stem segments, HA1 C-terminal short stem segments, and HA2 domains of influenza A hemagglutinin polypeptides. These signal peptides, stem segments, and domains are useful in the polypeptides and methods described herein.

TABLE 6

Exemplary Influenza A Hemagglutinin Short Stem Domain Peptide Sequences

| HA Subtype (Genbank No.) | Signal Peptide | HA1 N-terminal Stem Segment | HA1 C-terminal Short Stem Segment | HA2 Domain |
|---|---|---|---|---|
| H1 PR8-H1N1 (EF467821.1) | MKAN LLVLL CALAA ADA [SEQ ID NO: 18] | DTICIGYHANN STDTVDTVLE KNVTVTHSVN LLEDSHNGKL C [SEQ ID NO: 34] | CPKYVRSAKL RMVTGLRNNP SIQSR [SEQ ID NO: 350] | GLFGAIAGFIEGGW TGMIDGWYGYHHQ NEQGSGYAADQKST QNAINGITNKVNTVI EKMNIQFTAVGKEF NKLEKRMENLNKK VDDGFLDIWTYNAE LLVLLENERTLDFH DSNVKNLYEKVKSQ LKNNAKEIGNGCFE FYHKCDNECMESVR NGTYDYPKYSEESK LNREKVDGVKLES MGIYQILAIYSTVAS SLVLLVSLGAISFW MCSNGSLQCRICI [SEQ ID NO: 66] |
| H2 (L11136) | MAIIY LILLFT AVRG [SEQ ID NO: 19] | DQICIGYHSNN STEKVDTILER NVTVTHAQNI LEKTHNGKLC [SEQ ID NO: 35] | CPKYVKSERL VLATGLRNVP QIESR [SEQ ID NO: 351] | GLFGAIAGFIEGGW QGMIDGWYGYHHS NDQGSGYAADKEST QKAIDGITNRVNSVI EKMNTQFEAVGKEF SNLEKRLENLNKKM EDGFLDVWTYNAE LLVLMENERTLDFH |

TABLE 6-continued

Exemplary Influenza A Hemagglutinin Short Stem Domain Peptide Sequences

| HA Subtype (Genbank No.) | Signal Peptide | HA1 N-terminal Stem Segment | HA1 C-terminal Short Stem Segment | HA2 Domain |
|---|---|---|---|---|
| | | | | DSNVKNLYDRVRM QLRDNAKELGNGCF EFYHKCDDECMNS VKNGTYDYPKYEEE SKLNRNEIKGVKLS NMGVYQILAIYATV AGSLSLAIMIAGISL WMCSNGSLQCRICI [SEQ ID NO: 67] |
| H3 HK68-H3N2 (EF409245) PDB: IHGJ | MKTII ALSYIF CLALG [SEQ ID NO: 20] | QDLPGNDNST ATLCLGHHAV PNGTLVKTITD DQIEVTNATEL VQSSSTGKIC [SEQ ID NO: 36] | CPKYVKQNTL KLATGMRNVP EKQTR [SEQ ID NO: 352] | GLFGAIAGFIENGW EGMIDGWYGFRHQ NSEGTGQAADLKST QAAIDQINGKLNRVI EKTNEKFHQIEKEFS EVEGRIQDLEKYVE DTKIDLWSYNAELL VALENQHTIDLTDS EMNKLFEKTRRQLR ENAEDMGNGCFKIY HKCDNACIESIRNGT YDHDVYRDEALNN RFQIKGVELKSGYK DWILWISFAISCFLL CVVLLGFIMWACQR GNIRCNICI [SEQ ID NO: 68] |
| H4 (D90302) | MLSIVI LFLLIA ENSS [SEQ ID NO: 21] | QNYTGNPVIC MGHHAVANG TMVKTLADDQ VEVVTAQELV ESQNLPELC [SEQ ID NO: 37] | CPRYVKQGSL KLATGMRNIP EKASR [SEQ ID NO: 353] | GLFGAIAGFIENGW QGLIDGWYGFRHQ NAEGTGTAADLKST QAAIDQINGKLNRLI EKTNDKYHQIEKEF EQVEGRIQDLENYV EDTKIDLWSYNAEL LVALENQHTIDVTD SEMNKLFERVRRQL RENAEDKGNGCFEI FHKCDNNCIESIRNG TYDHDIYRDEAINN RFQIQGVKLTQGYK DIILWISFSISCFLLV ALLLAFILWACQNG NIRCQICI [SEQ ID NO: 69] |
| H5 (X07826) | MERIV LLLAI VSLVK S [SEQ ID NO: 22] | DQICIGYHAN KSTKQVDTIM EKNVTVTHAQ DILERTHNGKL C [SEQ ID NO: 38] | CPKYVKSDRL VLATGLRNVP QRKKR [SEQ ID NO: 354] | GLFGAIAGFIEGGW QGMVDGWYGYHH SNEQGSGYAADKES TQKAIDGITNKVNSI IDKMNTRFEAVGKE FNNLERRVENLNKK MEDGFLDVWTYNV ELLVLMENERTLDF HDSNVNNLYDKVR LQLKDNARELGNGC FEFYHKCDNECMES VRNGTYDYPQYSEE ARLNREEISGVKLES MGVYQILSIYSTVAS SLALAIMIAGLSFW MCSNGSLQCRICI [SEQ ID NO: 70] |
| H6 (D90303) | MIAIIV VAILA TAGRS [SEQ ID NO: 23] | DKICIGYHAN NSTTQIDTILE KNVTVTHSVE LLENQKEERF C | CPKYVKSESL RLATGLRNVP QIETR [SEQ ID NO: 355] | GLFGAIAGFIEGGW TGMIDGWYGYHHE NSQGSYAADREST QKAVDGITNKVNSII DKMNTQFEAVDHE |

TABLE 6-continued

Exemplary Influenza A Hemagglutinin Short Stem Domain Peptide Sequences

| HA Subtype (Genbank No.) | Signal Peptide | HA1 N-terminal Stem Segment | HA1 C-terminal Short Stem Segment | HA2 Domain |
|---|---|---|---|---|
| | | [SEQ ID NO: 39] | | FSNLERRIDNLNKR MEDGFLDVWTYNA ELLVLLENERTLDL HDANVKNLYERVK SQLRDNAMILGNGC FEFWHKCDDECMES VKNGTYDYPKYQD ESKLNRQEIESVKLE SLGVYQILAIYSTVS SSLVLVGLIIAVGLW MCSNGSMQCRICI [SEQ ID NO: 71] |
| H7 (M24457) | MNTQI LVFAL VAVIP TNA [SEQ ID NO: 24] | DKICLGHHAV SNGTKVNTLT ERGVEVVNAT ETVERTNIPKI C [SEQ ID NO: 40] | CPRYVKQESL LLATGMKNVP EPSKKRKKR [SEQ ID NO: 356] | GLFGAIAGFIENGW EGLVDGWYGFRHQ NAQGEGTAADYKS TQSAIDQITGKLNRL IEKTNQQFELIDNEF TEVEKQIGNLINWT KDSITEVWSYNAELI VAMENQHTIDLADS EMNRLYERVRKQL RENAEEDGTGCFEIF HKCDDDCMASIRNN TYDHSKYREEAMQ NRIQIDPVKLSSGYK DVILWFSFGASCFLL LAIAMGLVFICVKN GNMRCTICI [SEQ ID NO: 72] |
| H8 (D90304) | MEKFI AIATL ASTNA Y [SEQ ID NO: 25] | DRICIGYQSNN STDTVNTLIEQ NVPVTQTMEL VETEKHPAYC [SEQ ID NO: 41] | CPKYVKKASL RLAVGLRNTP SVEPR [SEQ ID NO: 357] | GLFGAIAGFIEGGWS GMIDGWYGFHHSN SEGTGMAADQKST QEAIDKITNKVNNIV DKMNREFEVVNHEF SEVEKRINMINDKID DQIEDLWAYNAELL VLLENQKTLDEHDS NVKNLFDEVKRRLS ANAIDAGNGCFDIL HKCDNECMETIKNG TYDHKEYEEEAKLE RSKINGVKLEENTT YKILSIYSTVAASLC LAILIAGGLILGMQN GSCRCMFCI [SEQ ID NO: 73] |
| H9 (D90305) | METK AIIAAL LMVTA ANA [SEQ ID NO: 26] | DKICIGYQSTN STETVDTLTES NVPVTHTKEL LHTEHNGMLC [SEQ ID NO: 42] | CPKYVGVKSL KLPVGLRNVP AVSSR [SEQ ID NO: 358] | GLFGAIAGFIEGGWP GLVAGWYGFHHSN DQGVGMAADKGST QKAIDKITSKVNNII DKMNKQYEVIDHEF NELEARLNMINNKI DDQIQDIWAYNAEL LVLLENQKTLDEHD ANVNNLYNKVKRA LGSNAVEDGNGCFE LYHKCDDQCMETIR NGTYDRQKYQEESR LERQKIEGVKLESEG TYKILTIYSTVASSL VLAMGFAAFLFWA MSNGSCRCNICI [SEQ ID NO: 74] |

TABLE 6-continued

Exemplary Influenza A Hemagglutinin Short Stem Domain Peptide Sequences

| HA Subtype (Genbank No.) | Signal Peptide | HA1 N-terminal Stem Segment | HA1 C-terminal Short Stem Segment | HA2 Domain |
|---|---|---|---|---|
| H10 (M21647) | MYKV VVIIAL LGAVK G [SEQ ID NO: 27] | LDRICLGHHA VANGTIVKTL TNEQEEVTNA TETVESTNLN KLC [SEQ ID NO: 43] | CPKYVNQRSL LLATGMRNVP EVVQGR [SEQ ID NO: 359] | GLFGAIAGFIENGW EGMVDGWYGFRHQ NAQGTGQAADYKS TQAAIDQITGKLNRL IEKTNTEFESIESEFS ETEHQIGNVINWTK DSITDIWTYNAELLV AMENQHTIDMADSE MLNLYERVRKQLR QNAEEDGKGCFEIY HTCDDSCMESIRNN TYDHSQYREEALLN RLNINPVKLSSGYK DIILWFSFGESCFVL LAVVMGLVFFCLKN GNMRCTICI [SEQ ID NO: 75] |
| H11 (D90306) | MEKTL LFAAIF LCVKA [SEQ ID NO: 28] | DEICIGYLSNN STDKVDTIIEN NVTVTSSVEL VETEHTGSFC [SEQ ID NO: 44] | CPKYVNVKSL KLATGPRNVP AIASR [SEQ ID NO: 360] | GLFGAIAGFIEGGWP GLINGWYGFQHRDE EGTGIAADKESTQK AIDQITSKVNNIVDR MNTNFESVQHEFSEI EERINQLSKHVDDS VVDIWSYNAQLLVL LENEKTLDLHDSNV RNLHEKVRRMLKD NAKDEGNGCFTFYH KCDNKCIERVRNGT YDHKEFEEESKINR QEIEGVKLDSSGNV YKILSIYSCIASSLVL AALIMGFMFWACS NGSCRCTICI [SEQ ID NO: 76] |
| H12 (D90307) | MEKFII LSTVL AASFA Y [SEQ ID NO: 29] | DKICIGYQTNN STETVNTLSEQ NVPVTQVEEL VHRGIDPILC [SEQ ID NO: 45] | CPKYIPSGSLK LAIGLRNVPQ VQDR [SEQ ID NO: 361] | GLFGAIAGFIEGGWP GLVAGWYGFQHQN AEGTGIAADRDSTQ RAIDNMQNKLNNVI DKMNKQFEVVNHE FSEVESRINMINSKI DDQITDIWAYNAEL LVLLENQKTLDEHD ANVRNLHDRVRRV LRENAIDTGDGCFEI LHKCDNNCMDTIRN GTYNHKEYEEESKI ERQKVNGVKLEENS TYKILSIYSSVASSL VLLLMIIGGFIFGCQ NGNVRCTFCI [SEQ ID NO: 77] |
| H13 (D90308) | MALN VIATL TLISVC VHA [SEQ ID NO: 30] | DRICVGYLSTN SSERVDTLLEN GVPVTSSIDLIE TNHTGTYC [SEQ ID NO: 46] | CPKYIKSGQL KLATGLRNVP AISNR [SEQ ID NO: 362] | GLFGAIAGFIEGGWP GLINGWYGFQHQNE QGTGIAADKESTQK AIDQITTKINNIIDKM NGNYDSIRGEFNQV EKRINMLADRIDDA VTDIWSYNAKLLVL LENDKTLDMHDAN VKNLHEQVRRELKD NAIDEGNGCFELLH KCNDSCMETIRNGT YDHTEYAEESKLKR QEIDGIKLKSEDNVY KALSIYSCIASSVVL VGLILSFIMWACSSG |

TABLE 6-continued

Exemplary Influenza A Hemagglutinin Short Stem Domain Peptide Sequences

| HA Subtype (Genbank No.) | Signal Peptide | HA1 N-terminal Stem Segment | HA1 C-terminal Short Stem Segment | HA2 Domain |
|---|---|---|---|---|
| | | | | NCRFNVCI<br>[SEQ ID<br>NO: 78] |
| H14<br>(M35997) | MIALIL<br>VALAL<br>SHTAY<br>S<br>[SEQ ID<br>NO: 31] | QITNGTTGNPII<br>CLGHHAVENG<br>TSVKTLTDNH<br>VEVVSAKELV<br>ETNHTDELC<br>[SEQ ID<br>NO: 47] | CPKYVKQGSL<br>MLATGMRNIP<br>GKQAK<br>[SEQ ID<br>NO: 363] | GLFGAIAGFIENGW<br>QGLIDGWYGFRHQ<br>NAEGTGTAADLKST<br>QAAIDQINGKLNRLI<br>EKTNEKYHQIEKEF<br>EQVEGRIQDLEKYV<br>EDTKIDLWSYNAEL<br>LVALENQHTIDVTD<br>SEMNKLFERVRRQL<br>RENAEDQGNGCFEI<br>FHQCDNNCIESIRNG<br>TYDHNIYRDEAINN<br>RIKINPVTLTMGYK<br>DIILWISFSMSCFVF<br>VALILGFVLWACQN<br>GNIRCQICI<br>[SEQ ID<br>NO: 79] |
| H15<br>(L43917) | MNTQI<br>IVILVL<br>GLSMV<br>KS<br>[SEQ ID<br>NO: 32] | DKICLGHHAV<br>ANGTKVNTLT<br>ERGVEVVNAT<br>ETVEITGIDKV<br>C<br>[SEQ ID<br>NO: 48] | CPRYVKQSSL<br>PLALGMKNVP<br>EKIRTR<br>[SEQ ID<br>NO: 364] | GLFGAIAGFIENGW<br>EGLIDGWYGFRHQN<br>AQGQGTAADYKST<br>QAAIDQITGKLNRLI<br>EKTNKQFELIDNEFT<br>EVEQQIGNVINWTR<br>DSLTEIWSYNAELL<br>VAMENQHTIDLADS<br>EMNKLYERVRRQL<br>RENAEEDGTGCFEIF<br>HRCDDQCMESIRNN<br>TYNHTEYRQEALQN<br>RIMINPVKLSSGYKD<br>VILWFSFGASCVML<br>LAIAMGLIFMCVKN<br>GNLRCTICI<br>[SEQ ID<br>NO: 80] |
| H16<br>(EU293865) | MMIK<br>VLYFLI<br>IVLGR<br>YSKA<br>[SEQ ID<br>NO: 33] | DKICIGYLSNN<br>SSDTVDTLTEN<br>GVPVTSSVDL<br>VETNHTGTYC<br>[SEQ ID<br>NO: 49] | CPKYIKSGQL<br>KLATGLRNVP<br>SIGER<br>[SEQ ID<br>NO: 365] | GLFGAIAGFIEGGWP<br>GLINGWYGFQHQNE<br>QGTGIAADKASTQK<br>AINEITTKINNIIEKM<br>NGNYDSIRGEFNQV<br>EKRINMLADRVDDA<br>VTDIWSYNAKLLVL<br>LENDRTLDLHDANV<br>RNLHDQVKRALKS<br>NAIDEGDGCFNLLH<br>KCNDSCMETIRNGT<br>YNHEDYREESQLKR<br>QEIEGIKLKTEDNVY<br>KVLSIYSCIASSIVLV<br>GLILAFIMWACSNG<br>SCRFNVCI<br>[SEQ ID<br>NO: 81] |
| H17<br>(CY103876) | MELIV<br>LLILLN<br>PYTFV<br>LG | DRICIGYQANQ<br>NNQTVNTLLE<br>QNVPVTGAQE<br>ILETNHNGKLC | CPKYVKATSL<br>MLATGLRNNP<br>QMEGR | GLFGAIAGFIEGGW<br>QGMIDGWYGYHHE<br>NQEGSGYAADKEA<br>TQKAVDAITNKVNS<br>IIDKMNSQFESNIKE<br>FNRLELRIQHLSDRV<br>DDALLDIWSYNTEL<br>LVLLENERTLDFHD<br>ANVKNLFEKVKAQ<br>LKDNAIDEGNGCFL<br>LLHKCNNSCMDDIK<br>NGTYKYMDYREES |

TABLE 6-continued

Exemplary Influenza A Hemagglutinin Short Stem Domain Peptide Sequences

| HA Subtype (Genbank No.) | Signal Peptide | HA1 N-terminal Stem Segment | HA1 C-terminal Short Stem Segment | HA2 Domain |
|---|---|---|---|---|
| | | | | HIEKQKIDGVKLTD YSRYYIMTLYSTIAS SVVLGSLIIAAFLWG CQKGSIQCKICI |

Table 6A, below, identifies useful HA1 N-terminal stem segments and HA1 C-terminal short stem segments for the polypeptides and methods described herein.

TABLE 6A

Exemplary Influenza A Hemagglutinin Short Stem Domain Peptide Sequences

| HA Subtype (Genbank No.) | HA1 N-terminal Stem Segment | HA1 C-terminal Stem Segment |
|---|---|---|
| H1 PR8-H1N1 (EF467821.1) No Cys | DTICIGYHANNSTDTVDT VLEKNVTVTHSVNLLED SHNGKL [SEQ ID NO: 177] | PKYVRSAKLRMVTGLRNNPSIQSR [SEQ ID NO: 366] |
| H1 PR8-H1N1 (EF467821.1) No Cys Δ1 | DTICIGYHANNSTDTVDT VLEKNVTVTHSVNLLED SHNGKL [SEQ ID NO: 178] | KYVRSAKLRMVTGLRNNPSIQSR [SEQ ID NO: 367] |
| H1 PR8-H1N1 (EF467821.1) No Cys Δ3 | DTICIGYHANNSTDTVDT VLEKNVTVTHSVNLLED SHNGK [SEQ ID NO: 179] | YVRSAKLRMVTGLRNNPSIQSR [SEQ ID NO: 368] |
| H2 (L11136) No Cys | DQICIGYHSNNSTEKVDT ILERNVTVTHAQNILEKT HNGKL [SEQ ID NO: 180] | PKYVKSERLVLATGLRNVPQIESR [SEQ ID NO: 369] |
| H2 (L11136) No Cys Δ1 | DQICIGYHSNNSTEKVDT ILERNVTVTHAQNILEKT HNGKL [SEQ ID NO: 181] | KYVKSERLVLATGLRNVPQIESR [SEQ ID NO: 370] |
| H2 (L11136) No Cys Δ3 | DQICIGYHSNNSTEKVDT ILERNVTVTHAQNILEKT HNGK [SEQ ID NO: 182] | YVKSERLVLATGLRNVPQIESR [SEQ ID NO: 371] |
| H3 HK68-H3N2 (EF409245) PDB: 1HGJ No Cys | QDLPGNDNSTATLCLGH HAVPNGTLVKTITDDQIE VTNATELVQSSSTGKI [SEQ ID NO: 183] | PKYVKQNTLKLATGMRNVPEKQTR [SEQ ID NO: 372] |
| H3 HK68-H3N2 (EF409245) PDB: 1HGJ No Cys Δ1 | QDLPGNDNSTATLCLGH HAVPNGTLVKTITDDQIE VTNATELVQSSSTGKI [SEQ ID NO: 184] | KYVKQNTLKLATGMRNVPEKQTR [SEQ ID NO: 373] |
| H3 HK68-H3N2 (EF409245) PDB: 1HGJ No Cys Δ3 | QDLPGNDNSTATLCLGH HAVPNGTLVKTITDDQIE VTNATELVQSSSTGK [SEQ ID NO: 185] | YVKQNTLKLATGMRNVPEKQTR [SEQ ID NO: 374] |
| H4 (D90302) No Cys | QNYTGNPVICMGHHAV ANGTMVKTLADDQVEV VTAQELVESQNLPEL [SEQ ID NO: 186] | PRYVKQGSLKLATGMRNIPEKASR [SEQ ID NO: 375] |

TABLE 6A-continued

Exemplary Influenza A Hemagglutinin Short Stem Domain Peptide Sequences

| HA Subtype (Genbank No.) | HA1 N-terminal Stem Segment | HA1 C-terminal Stem Segment |
| --- | --- | --- |
| H4 (D90302) No Cys Δ1 | QNYTGNPVICMGHHAV ANGTMVKTLADDQVEV VTAQELVESQNLPEL [SEQ ID NO: 187] | RYVKQGSLKLATGMRNIPEKASR [SEQ ID NO: 376] |
| H4 (D90302) No Cys Δ3 | QNYTGNPVICMGHHAV ANGTMVKTLADDQVEV VTAQELVESQNLPE [SEQ ID NO: 188] | YVKQGSLKLATGMRNIPEKASR [SEQ ID NO: 377] |
| H5 (X07826) No Cys | DQICIGYHANKSTKQVD TIMEKNVTVTHAQDILE RTHNGKL [SEQ ID NO: 189] | PKYVKSDRLVLATGLRNVPQRKKR [SEQ ID NO: 378] |
| H5 (X07826) No Cys Δ1 | DQICIGYHANKSTKQVD TIMEKNVTVTHAQDILE RTHNGKL [SEQ ID NO: 190] | KYVKSDRLVLATGLRNVPQRKKR [SEQ ID NO: 379] |
| H5 (X07826) No Cys Δ3 | DQICIGYHANKSTKQVD TIMEKNVTVTHAQDILE RTHNGK [SEQ ID NO: 191] | YVKSDRLVLATGLRNVPQRKKR [SEQ ID NO: 380] |
| H6 (D90303) No Cys | DKICIGYHANNSTTQIDT ILEKNVTVTHSVELLENQ KEERF [SEQ ID NO: 192] | PKYVKSESLRLATGLRNVPQIETR [SEQ ID NO: 381] |
| H6 (D90303) No Cys Δ1 | DKICIGYHANNSTTQIDT ILEKNVTVTHSVELLENQ KEERF [SEQ ID NO: 193] | KYVKSESLRLATGLRNVPQIETR [SEQ ID NO: 382] |
| H6 (D90303) No Cys Δ3 | DKICIGYHANNSTTQIDT ILEKNVTVTHSVELLENQ KEER [SEQ ID NO: 194] | YVKSESLRLATGLRNVPQIETR [SEQ ID NO: 383] |
| H7 (M24457) No Cys | DKICLGHHAVSNGTKVN TLTERGVEVVNATETVE RTNIPKI [SEQ ID NO: 195] | PRYVKQESLLLATGMKNVPEPSKKRK KR [SEQ ID NO: 384] |
| H7 (M24457) No Cys Δ1 | DKICLGHHAVSNGTKVN TLTERGVEVVNATETVE RTNIPKI [SEQ ID NO: 196] | RYVKQESLLLATGMKNVPEPSKKRKK R [SEQ ID NO: 385] |
| H7 (M24457) No Cys Δ3 | DKICLGHHAVSNGTKVN TLTERGVEVVNATETVE RTNIPK [SEQ ID NO: 197] | YVKQESLLLATGMKNVPEPSKKRKKR [SEQ ID NO: 386] |
| H8 (D90304) No Cys | DRICIGYQSNNSTDTVNT LIEQNVPVTQTMELVET EKHPAY [SEQ ID NO: 198] | PKYVKKASLRLAVGLRNTPSVEPR [SEQ ID NO: 387] |
| H8 (D90304) No Cys Δ1 | DRICIGYQSNNSTDTVNT LIEQNVPVTQTMELVET EKHPAY [SEQ ID NO: 199] | KYVKKASLRLAVGLRNTPSVEPR [SEQ ID NO: 388] |
| H8 (D90304) No Cys Δ3 | DRICIGYQSNNSTDTVNT LIEQNVPVTQTMELVET EKHPA [SEQ ID NO: 200] | YVKKASLRLAVGLRNTPSVEPR [SEQ ID NO: 389] |

TABLE 6A-continued

Exemplary Influenza A Hemagglutinin Short Stem Domain Peptide Sequences

| HA Subtype (Genbank No.) | HA1 N-terminal Stem Segment | HA1 C-terminal Stem Segment |
|---|---|---|
| H9 (D90305) No Cys | DKICIGYQSTNSTETVDT LTESNVPVTHTKELLHTE HNGML [SEQ ID NO: 201] | PKYVGVKSLKLPVGLRNVPAVSSR [SEQ ID NO: 390] |
| H9 (D90305) No Cys Δ1 | DKICIGYQSTNSTETVDT LTESNVPVTHTKELLHTE HNGML [SEQ ID NO: 202] | KYVGVKSLKLPVGLRNVPAVSSR [SEQ ID NO: 391] |
| H9 (D90305) No Cys Δ3 | DKICIGYQSTNSTETVDT LTESNVPVTHTKELLHTE HNGM [SEQ ID NO: 203] | YVGVKSLKLPVGLRNVPAVSSR [SEQ ID NO: 392] |
| H10 (M21647) No Cys | LDRICLGHHAVANGTIV KTLTNEQEEVTNATETV ESTNLNKL [SEQ ID NO: 204] | PKYVNQRSLLLATGMRNVPEVVQGR [SEQ ID NO: 393] |
| H10 (M21647) No Cys Δ1 | LDRICLGHHAVANGTIV KTLTNEQEEVTNATETV ESTNLNKL [SEQ ID NO: 205] | KYVNQRSLLLATGMRNVPEVVQGR [SEQ ID NO: 394] |
| H10 (M21647) No Cys Δ3 | LDRICLGHHAVANGTIV KTLTNEQEEVTNATETV ESTNLNK [SEQ ID NO: 206] | YVNQRSLLLATGMRNVPEVVQGR [SEQ ID NO: 395] |
| H11 (D90306) No Cys | DEICIGYLSNNSTDKVDT IIENNVTVTSSVELVETE HTGSF [SEQ ID NO: 207] | PKYVNVKSLKLATGPRNVPAIASR [SEQ ID NO: 396] |
| H11 (D90306) No Cys Δ1 | DEICIGYLSNNSTDKVDT IIENNVTVTSSVELVETE HTGSF [SEQ ID NO: 208] | KYVNVKSLKLATGPRNVPAIASR [SEQ ID NO: 397] |
| H11 (D90306) No Cys Δ3 | DEICIGYLSNNSTDKVDT IIENNVTVTSSVELVETE HTGS [SEQ ID NO: 209] | YVNVKSLKLATGPRNVPAIASR [SEQ ID NO: 398] |
| H12 (D90307) No Cys | DKICIGYQTNNSTETVNT LSEQNVPVTQVEELVHR GIDPIL [SEQ ID NO: 210] | PKYIPSGSLKLAIGLRNVPQVQDR [SEQ ID NO: 399] |
| H12 (D90307) No Cys Δ1 | DKICIGYQTNNSTETVNT LSEQNVPVTQVEELVHR GIDPIL [SEQ ID NO: 211] | KYIPSGSLKLAIGLRNVPQVQDR [SEQ ID NO: 400] |
| H12 (D90307) No Cys Δ3 | DKICIGYQTNNSTETVNT LSEQNVPVTQVEELVHR GIDPI [SEQ ID NO: 212] | YIPSGSLKLAIGLRNVPQVQDR [SEQ ID NO: 401] |
| H13 (D90308) No Cys | DRICVGYLSTNSSERVDT LLENGVPVTSSIDLIETN HTGTY [SEQ ID NO: 213] | PKYIKSGQLKLATGLRNVPAISNR [SEQ ID NO: 402] |
| H13 (D90308) No Cys Δ1 | DRICVGYLSTNSSERVDT LLENGVPVTSSIDLIETN HTGTY [SEQ ID NO: 214] | KYIKSGQLKLATGLRNVPAISNR [SEQ ID NO: 403] |

TABLE 6A-continued

Exemplary Influenza A Hemagglutinin Short Stem Domain Peptide Sequences

| HA Subtype (Genbank No.) | HA1 N-terminal Stem Segment | HA1 C-terminal Stem Segment |
|---|---|---|
| H13 (D90308) No Cys Δ3 | DRICVGYLSTNSSERVDT LLENGVPVTSSIDLIETN HTGT [SEQ ID NO: 215] | YIKSGQLKLATGLRNVPAISNR [SEQ ID NO: 404] |
| H14 (M35997) No Cys | QITNGTTGNPIICLGHHA VENGTSVKTLTDNHVEV VSAKELVETNHTDEL [SEQ ID NO: 216] | PKYVKQGSLMLATGMRNIPGKQAK [SEQ ID NO: 405] |
| H14 (M35997) No Cys Δ1 | QITNGTTGNPIICLGHHA VENGTSVKTLTDNHVEV VSAKELVETNHTDEL [SEQ ID NO: 217] | KYVKQGSLMLATGMRNIPGKQAK [SEQ ID NO: 406] |
| H14 (M35997) No Cys Δ3 | QITNGTTGNPIICLGHHA VENGTSVKTLTDNHVEV VSAKELVETNHTDE [SEQ ID NO: 218] | YVKQGSLMLATGMRNIPGKQAK [SEQ ID NO: 407] |
| H15 (L43917) No Cys | DKICLGHHAVANGTKV NTLTERGVEVVNATETV EITGIDKV [SEQ ID NO: 219] | PRYVKQSSLPLALGMKNVPEKIRTR [SEQ ID NO: 408] |
| H15 (L43917) No Cys Δ1 | DKICLGHHAVANGTKV NTLTERGVEVVNATETV EITGIDKV [SEQ ID NO: 220] | RYVKQSSLPLALGMKNVPEKIRTR [SEQ ID NO: 409] |
| H15 (L43917) No Cys Δ3 | DKICLGHHAVANGTKV NTLTERGVEVVNATETV EITGIDK [SEQ ID NO: 221] | YVKQSSLPLALGMKNVPEKIRTR [SEQ ID NO: 410] |
| H16 (EU293865) No Cys | DKICIGYLSNNSSDTVDT LTENGVPVTSSVDLVET NHTGTY [SEQ ID NO: 222] | PKYIKSGQLKLATGLRNVPSIGER [SEQ ID NO: 411] |
| H16 (EU293865) No Cys Δ1 | DKICIGYLSNNSSDTVDT LTENGVPVTSSVDLVET NHTGTY [SEQ ID NO: 223] | KYIKSGQLKLATGLRNVPSIGER [SEQ ID NO: 412] |
| H16 (EU293865) No Cys Δ3 | DKICIGYLSNNSSDTVDT LTENGVPVTSSVDLVET NHTGT [SEQ ID NO: 224] | YIKSGQLKLATGLRNVPSIGER [SEQ ID NO: 413] |
| H17 (CY103876) No Cys | DRICIGYQANQNNQTVN TLLEQNVPVTGAQEILET NHNGKL | PKYVKATSLMLATGLRNNPQMEGR |

In certain embodiments, the influenza hemagglutinin short stem domain polypeptides comprise one or more immunogenic epitopes in the tertiary or quaternary structure of an influenza hemagglutinin polypeptide.

In certain embodiments, the HA1 N-terminal stem segment comprises the amino acid sequence $A_{17}$-$A_{18}$-$(Xaa)_n$-$A_{38}$ (SEQ ID NO:146), wherein $A_{17}$ is Y or H;

$A_{18}$ is H, L, or Q;

$(Xaa)_n$ represents a sequence of 18-20 amino acid residues; and $A_{38}$ is H, S, Q, T or N.

In certain embodiments, the HA2 domain comprises the amino acid sequence $A_{18}$-$A_{19}$-$A_{20}$-$A_{21}$ (SEQ ID NO:148), wherein $A_{18}$ is V or I;

$A_{19}$ is D, N or A;

$A_{20}$ is G, and $A_{21}$ is W.

In certain embodiments, the HA2 domain comprises the amino acid sequence $A_{38}$-$A_{39}$-$A_{40}$-$A_{41}$-$A_{42}$-$A_{43}$-$A_{44}$-$A_{45}$-$A_{46}$-$A_{47}$-$A_{48}$-$A_{49}$-$A_{50}$-$A_{51}$-$A_{52}$-$A_{53}$-$A_{54}$-$A_{55}$-$A_{56}$ (SEQ ID NO:149), wherein $A_{38}$ is K, Q, R, L or Y;

$A_{39}$ is any amino acid residue;

$A_{40}$ is any amino acid residue;

$A_{41}$ is T;
$A_{42}$ is Q;
$A_{43}$ is any amino acid residue;
$A_{44}$ is A;
$A_{45}$ is I;
$A_{46}$ is D;
$A_{47}$ is any amino acid residue;
$A_{48}$ is I, V or M;
$A_{49}$ is T, Q or N;
$A_{50}$ is any amino acid residue;
$A_{51}$ is K;
$A_{52}$ is V or L;
$A_{53}$ is N;
$A_{54}$ is any amino acid residue;
$A_{55}$ is V, I or L; and
$A_{56}$ is V or I.

As illustrated in FIGS. 1 and 2, HA1 N-terminal stem segments share sequence identity between influenza A and influenza B and additionally across influenza A subtypes. Similarly, HA1 C-terminal short stem segments also share sequence identity between influenza A and influenza B and additionally across influenza A subtypes. Further, HA2 domains also share sequence identity between influenza A and influenza B and additionally across influenza A subtypes.

In some embodiments, the influenza hemagglutinin short stem domain polypeptide is a hybrid polypeptide that comprises or consists essentially of segments and/or domains from a plurality of influenza strains or subtypes. For example, an influenza hemagglutinin short stem domain polypeptide can comprise HA1 N-terminal and HA1 C-terminal short stem segments from different influenza A virus HA subtypes. In some embodiments, the HA1 N-terminal stem segment is from influenza B virus while the HA1 C-terminal short stem segment is from influenza A virus. Similarly, HA2 and the HA1 C-terminal short stem segment may also be from influenza A virus while the HA1 N-terminal is from influenza B virus.

It will be understood that any combination of the sequence elements listed in Tables 2, 4, 5 and sequences listed under the "Signal peptide," "HA1 N-terminal stem segment," and "HA2 Domain" columns of Table 3 or the variants thereof may be used to form the hemagglutinin HA stem domain polypeptides of the present invention.

In an influenza hemagglutinin short stem domain polypeptide provided herein, a linker covalently connects the HA1 N-terminal stem segment to the HA1 C-terminal short stem segment. The linker can be any linker deemed suitable by one of skill in the art including, but not limited to, those linkers described herein. In certain embodiments, the linker is a globular head, or a fragment thereof, from an influenza virus heterologous to the influenza stem domain.

In certain embodiments, influenza hemagglutinin short stem domain polypeptides are capable of forming a three dimensional structure that is similar to the three dimensional structure of the stem domain of a native influenza hemagglutinin. Structural similarity can be evaluated based on any technique deemed suitable by those of skill in the art including, but not limited to, those techniques described herein.

In certain embodiments, any influenza hemagglutinin short stem domain polypeptide provided herein can further comprise one or more polypeptide domains deemed suitable to those of skill in the art. Useful polypeptide domains include domains that facilitate purification, folding and cleavage of portions of a polypeptide. For example, a His tag (His-His-His-His-His-His, SEQ ID NO:166), FLAG epitope or other purification tag can facilitate purification of a polypeptide provided herein. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

Any trimerization domain, including a foldon from bacteriophage T4 fibritin can facilitate trimerization of polypeptides provided herein. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. The foldon domain can have any foldon sequence known to those of skill in the art (see, e.g., Papanikolopoulou et al., 2004, J. Biol. Chem. 279(10): 8991-8998, the contents of which are hereby incorporated by reference in their entirety. Examples include GSGYIPEAPRDGQAYVRKDGEWVLLSTFL (SEQ ID NO:167). A foldon domain can be useful to facilitate trimerization of soluble polypeptides provided herein. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO:168). In certain embodiments, the cleavage site is a cleavage site recognized by Tobacco Etch Virus (TEV) protease (e.g., amino acid sequence Glu-Asn-Leu-Tyr-Phe-Gln-(Gly/Ser)).

In certain embodiments, provided are influenza hemagglutinin short stem domain polypeptides comprising an elastase cleavage site as described herein. In particular embodiments, provided herein are influenza hemagglutinin short stem domain polypeptides comprising any of SEQ ID NOS:350-365 wherein the C-terminal amino acid residue, e.g. arginine or lysine, of SEQ ID NOS:350-365 is substituted with a valine residue.

In certain embodiments, provided herein are influenza hemagglutinin stem short domain polypeptides that are predicted to be resistant to protease cleavage at the junction between HA1 and HA2. In certain embodiments, provided is any influenza hemagglutinin short stem domain polypeptide described herein wherein the protease site spanning HA1 and HA2 is mutated to a sequence that is resistant to protease cleavage. In certain embodiments, provided is any influenza hemagglutinin short stem domain polypeptide described herein wherein the C-terminal residue of the HA1 C-terminal short stem segment is any residue other than Lys or Arg. In certain embodiments, provided is any influenza hemagglutinin short stem domain polypeptide described herein wherein the N-terminal residue of the HA2 domain is proline. In certain embodiments, provided is any influenza hemagglutinin short stem domain polypeptide described herein wherein the C-terminal residue of the HA1 C-terminal short stem segment is Ala and the N-terminal residue of the HA2 domain is also Ala.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to an HA2 luminal domain. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to an HA2 luminal domain. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to an HA2 luminal domain.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to, in sequence, a cleavage site, a trimerization domain and a purification tag. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to, in sequence, a cleavage site, a trimerization domain and a purification tag. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to, in sequence, a cleavage site, a trimerization domain and a purification tag. In certain embodiments, the protease cleavage site is a thrombin cleavage site. In certain embodiments, the cleavage site has the amino acid sequence LVPRGSP (SEQ ID NO:168). In certain embodiments, the cleavage site is a cleavage site recognized by Tobacco Etch Virus (TEV) protease (e.g., amino acid sequence Glu-Asn-Leu-Tyr-Phe-Gln-(Gly/Ser)). In certain embodiments, the trimerization domain is a foldon domain. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. In some embodiments, the purification tag is a His tag, having the sequence, $(His)_n$, wherein n is 2, 3, 4, 5, 6, 7, 8, 9, 10, 11, 12, 13, 14, 15, 16, 17, 18, 19, 20 or greater.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to an HA2 luminal domain that is covalently linked to, in sequence, a cleavage site, a trimerization domain and a purification tag. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to an HA2 luminal domain that is covalently linked to, in sequence, a cleavage site, a trimerization domain and a purification tag. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to an HA2 luminal domain that is covalently linked to, in sequence, a cleavage site, a trimerization domain and a purification tag. In certain embodiments, the protease cleavage site is a thrombin cleavage site. In certain embodiments, the cleavage site has the amino acid sequence LVPRGSP (SEQ ID NO:168). In certain embodiments, the cleavage site is a cleavage site recognized by Tobacco Etch Virus (TEV) protease (e.g., amino acid sequence Glu-Asn-Leu-Tyr-Phe-Gln-(Gly/Ser)). In certain embodiments, the trimerization domain is a foldon domain. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. In some embodiments, the purification tag is a His tag, having the sequence, $(His)_n$, wherein n is 2, 3, 4, 5, 6, 7, 8, 9, 10, 11, 12, 13, 14, 15, 16, 17, 18, 19, 20 or greater.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to an HA2 luminal domain that is in turn covalently linked to an HA2 transmembrane domain. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to an HA2 luminal domain that is in turn covalently linked to an HA2 transmembrane domain. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to an HA2 luminal domain that is in turn covalently linked to an HA2 transmembrane domain.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to an HA2 luminal domain that is in turn covalently linked to an HA2 transmembrane domain that is in turn covalently linked to an HA2 cytoplasmic domain.

In certain embodiments, provided herein is an influenza hemagglutinin short stem polypeptide having a sequence selected from the group consisting of:
(SEQ ID NO:34)-LL-(SEQ ID NO:350)-(SEQ ID NO:66),
(SEQ ID NO:35)-LL-(SEQ ID NO:351)-(SEQ ID NO:67),
(SEQ ID NO:36)-LL-(SEQ ID NO:352)-(SEQ ID NO:68),
(SEQ ID NO:37)-LL-(SEQ ID NO:353)-(SEQ ID NO:69),
(SEQ ID NO:38)-LL-(SEQ ID NO:354)-(SEQ ID NO:70),
(SEQ ID NO:39)-LL-(SEQ ID NO:355)-(SEQ ID NO:71),
(SEQ ID NO:40)-LL-(SEQ ID NO:356)-(SEQ ID NO:72),
(SEQ ID NO:41)-LL-(SEQ ID NO:357)-(SEQ ID NO:73),
(SEQ ID NO:42)-LL-(SEQ ID NO:358)-(SEQ ID NO:74),
(SEQ ID NO:43)-LL-(SEQ ID NO:359)-(SEQ ID NO:75),
(SEQ ID NO:44)-LL-(SEQ ID NO:360)-(SEQ ID NO:76),
(SEQ ID NO:45)-LL-(SEQ ID NO:361)-(SEQ ID NO:77),
(SEQ ID NO:46)-LL-(SEQ ID NO:362)-(SEQ ID NO:78),
(SEQ ID NO:47)-LL-(SEQ ID NO:363)-(SEQ ID NO:79),
(SEQ ID NO:48)-LL-(SEQ ID NO:364)-(SEQ ID NO:80), and
(SEQ ID NO:49)-LL-(SEQ ID NO:365)-(SEQ ID NO:81),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n (wherein n is any number of Glycine residues so long as there is flexibility in the peptide linker; in certain embodiments, n is 2, 3, 4, 5, 6, or 7 Glycine residues), Gly-Pro, ITPNGSIPNDKPFQNVNKITYGA (SEQ ID NO:165) and Asn-Ala-Ser.

In certain embodiments, provided herein is an influenza hemagglutinin short stem polypeptide having a sequence selected from the group consisting of:
(SEQ ID NO:34)-LL-(SEQ ID NO:350)-(SEQ ID NO:82),
(SEQ ID NO:35)-LL-(SEQ ID NO:351)-(SEQ ID NO:83),
(SEQ ID NO:36)-LL-(SEQ ID NO:352)-(SEQ ID NO:84),
(SEQ ID NO:37)-LL-(SEQ ID NO:353)-(SEQ ID NO:85),
(SEQ ID NO:38)-LL-(SEQ ID NO:354)-(SEQ ID NO:86),
(SEQ ID NO:39)-LL-(SEQ ID NO:355)-(SEQ ID NO:87),
(SEQ ID NO:40)-LL-(SEQ ID NO:356)-(SEQ ID NO:88),
(SEQ ID NO:41)-LL-(SEQ ID NO:357)-(SEQ ID NO:89),
(SEQ ID NO:42)-LL-(SEQ ID NO:358)-(SEQ ID NO:90),
(SEQ ID NO:43)-LL-(SEQ ID NO:359)-(SEQ ID NO:91),
(SEQ ID NO:44)-LL-(SEQ ID NO:360)-(SEQ ID NO:92),
(SEQ ID NO:45)-LL-(SEQ ID NO:361)-(SEQ ID NO:93),
(SEQ ID NO:46)-LL-(SEQ ID NO:362)-(SEQ ID NO:94),
(SEQ ID NO:47)-LL-(SEQ ID NO:363)-(SEQ ID NO:95),
(SEQ ID NO:48)-LL-(SEQ ID NO:364)-(SEQ ID NO:96), and
(SEQ ID NO:49)-LL-(SEQ ID NO:365)-(SEQ ID NO:97),
wherein each sequence above is linked to the adjacent sequence as described herein and wherein LL is a linker as described herein. In particular, the HA1 C-terminal segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKPFQNVNKITYGA (SEQ ID NO:165) and Asn-Ala-Ser.

In certain embodiments, provided herein is an influenza hemagglutinin short stem polypeptide having a sequence selected from the group consisting of:
(SEQ ID NO:34)-LL-(SEQ ID NO:350)-(SEQ ID NO:82)-(SEQ ID NO:98),
(SEQ ID NO:35)-LL-(SEQ ID NO:351)-(SEQ ID NO:83)-(SEQ ID NO:99),
(SEQ ID NO:36)-LL-(SEQ ID NO:352)-(SEQ ID NO:84)-(SEQ ID NO:100),
(SEQ ID NO:37)-LL-(SEQ ID NO:353)-(SEQ ID NO:85)-(SEQ ID NO:101),
(SEQ ID NO:38)-LL-(SEQ ID NO:354)-(SEQ ID NO:86)-(SEQ ID NO:102),
(SEQ ID NO:39)-LL-(SEQ ID NO:355)-(SEQ ID NO:87)-(SEQ ID NO:103),
(SEQ ID NO:40)-LL-(SEQ ID NO:356)-(SEQ ID NO:88)-(SEQ ID NO:104),
(SEQ ID NO:41)-LL-(SEQ ID NO:357)-(SEQ ID NO:89)-(SEQ ID NO:105),
(SEQ ID NO:42)-LL-(SEQ ID NO:358)-(SEQ ID NO:90)-(SEQ ID NO:106),
(SEQ ID NO:43)-LL-(SEQ ID NO:359)-(SEQ ID NO:91)-(SEQ ID NO:107),
(SEQ ID NO:44)-LL-(SEQ ID NO:360)-(SEQ ID NO:92)-(SEQ ID NO:108),
(SEQ ID NO:45)-LL-(SEQ ID NO:361)-(SEQ ID NO:93)-(SEQ ID NO:109),
(SEQ ID NO:46)-LL-(SEQ ID NO:362)-(SEQ ID NO:94)-(SEQ ID NO:110),
(SEQ ID NO:47)-LL-(SEQ ID NO:363)-(SEQ ID NO:95)-(SEQ ID NO:111),
(SEQ ID NO:48)-LL-(SEQ ID NO:364)-(SEQ ID NO:96)-(SEQ ID NO:112), and
(SEQ ID NO:49)-LL-(SEQ ID NO:365)-(SEQ ID NO:97)-(SEQ ID NO:113),
wherein each sequence above is linked to the adjacent sequence as described herein and wherein LL is a linker as described herein. In particular, the HA1 C-terminal short stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKPFQNVNKITYGA (SEQ ID NO:165) and Asn-Ala-Ser.

In certain embodiments, provided herein is an influenza hemagglutinin short stem polypeptide having a sequence selected from the group consisting of:
(SEQ ID NO:34)-LL-(SEQ ID NO:350)-(SEQ ID NO:82)-(SEQ ID NO:168)-(SEQ ID NO:167)-(SEQ ID NO:166),
(SEQ ID NO:35)-LL-(SEQ ID NO:351)-(SEQ ID NO:83)-(SEQ ID NO:168)-(SEQ ID NO:167)-(SEQ ID NO:166),
(SEQ ID NO:36)-LL-(SEQ ID NO:352)-(SEQ ID NO:84)-(SEQ ID NO:168)-(SEQ ID NO:167)-(SEQ ID NO:166),
(SEQ ID NO:37)-LL-(SEQ ID NO:353)-(SEQ ID NO:85)-(SEQ ID NO:168)-(SEQ ID NO:167)-(SEQ ID NO:166),
(SEQ ID NO:38)-LL-(SEQ ID NO:354)-(SEQ ID NO:86)-(SEQ ID NO:168)-(SEQ ID NO:167)-(SEQ ID NO:166),
(SEQ ID NO:39)-LL-(SEQ ID NO:355)-(SEQ ID NO:87)-(SEQ ID NO:168)-(SEQ ID NO:167)-(SEQ ID NO:166), (SEQ ID NO:40)-LL-(SEQ ID NO:356)-(SEQ ID NO:88)-(SEQ ID NO:168)-(SEQ ID NO:167)-(SEQ ID NO:166),
(SEQ ID NO:41)-LL-(SEQ ID NO:357)-(SEQ ID NO:89)-(SEQ ID NO:168)-(SEQ ID NO:167)-(SEQ ID NO:166),
(SEQ ID NO:42)-LL-(SEQ ID NO:358)-(SEQ ID NO:90)-(SEQ ID NO:168)-(SEQ ID NO:167)-(SEQ ID NO:166),
(SEQ ID NO:43)-LL-(SEQ ID NO:359)-(SEQ ID NO:91)-(SEQ ID NO:168)-(SEQ ID NO:167)-(SEQ ID NO:166),
(SEQ ID NO:44)-LL-(SEQ ID NO:360)-(SEQ ID NO:92)-(SEQ ID NO:168)-(SEQ ID NO:167)-(SEQ ID NO:166),
(SEQ ID NO:45)-LL-(SEQ ID NO:361)-(SEQ ID NO:93)-(SEQ ID NO:168)-(SEQ ID NO:167)-(SEQ ID NO:166),
(SEQ ID NO:46)-LL-(SEQ ID NO:362)-(SEQ ID NO:94)-(SEQ ID NO:168)-(SEQ ID NO:167)-(SEQ ID NO:166),
(SEQ ID NO:47)-LL-(SEQ ID NO:363)-(SEQ ID NO:95)-(SEQ ID NO:168)-(SEQ ID NO:167)-(SEQ ID NO:166),
(SEQ ID NO:48)-LL-(SEQ ID NO:364)-(SEQ ID NO:96)-(SEQ ID NO:168)-(SEQ ID NO:167)-(SEQ ID NO:166), and
(SEQ ID NO:49)-LL-(SEQ ID NO:365)-(SEQ ID NO:97)-(SEQ ID NO:168)-(SEQ ID NO:167)-(SEQ ID NO:166),
wherein each sequence above is linked to the adjacent sequence as described herein and wherein LL is a linker as described herein. In particular, the HA1 C-terminal short stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKPFQNVNKITYGA (SEQ ID NO:165) and Asn-Ala-Ser.

In certain embodiments, provided herein is an influenza hemagglutinin short stem polypeptide having a sequence selected from the group consisting of:
(SEQ ID NO:34)-LL-(SEQ ID NO:350)-(SEQ ID NO:82)-(SEQ ID NO:98)-(SEQ ID NO:168)-(SEQ ID NO:167)-(SEQ ID NO:166),
(SEQ ID NO:35)-LL-(SEQ ID NO:351)-(SEQ ID NO:83)-(SEQ ID NO:99)-(SEQ ID NO:168)-(SEQ ID NO:167)-(SEQ ID NO:166),
(SEQ ID NO:36)-LL-(SEQ ID NO:352)-(SEQ ID NO:84)-(SEQ ID NO:100)-(SEQ ID NO:168)-(SEQ ID NO:167)-(SEQ ID NO:166),
(SEQ ID NO:37)-LL-(SEQ ID NO:353)-(SEQ ID NO:85)-(SEQ ID NO:101)-(SEQ ID NO:168)-(SEQ ID NO:167)-(SEQ ID NO:166),
(SEQ ID NO:38)-LL-(SEQ ID NO:354)-(SEQ ID NO:86)-(SEQ ID NO:102)-(SEQ ID NO:168)-(SEQ ID NO:167)-(SEQ ID NO:166),
(SEQ ID NO:39)-LL-(SEQ ID NO:355)-(SEQ ID NO:87)-(SEQ ID NO:103)-(SEQ ID NO:168)-(SEQ ID NO:167)-(SEQ ID NO:166),
(SEQ ID NO:40)-LL-(SEQ ID NO:356)-(SEQ ID NO:88)-(SEQ ID NO:104)-(SEQ ID NO:168)-(SEQ ID NO:167)-(SEQ ID NO:166),
(SEQ ID NO:41)-LL-(SEQ ID NO:357)-(SEQ ID NO:89)-(SEQ ID NO:105)-(SEQ ID NO:168)-(SEQ ID NO:167)-(SEQ ID NO:166),
(SEQ ID NO:42)-LL-(SEQ ID NO:358)-(SEQ ID NO:90)-(SEQ ID NO:106)-(SEQ ID NO:168)-(SEQ ID NO:167)-(SEQ ID NO:166),
(SEQ ID NO:43)-LL-(SEQ ID NO:359)-(SEQ ID NO:91)-(SEQ ID NO:107)-(SEQ ID NO:168)-(SEQ ID NO:167)-(SEQ ID NO:166),
(SEQ ID NO:44)-LL-(SEQ ID NO:360)-(SEQ ID NO:92)-(SEQ ID NO:108)-(SEQ ID NO:168)-(SEQ ID NO:167)-(SEQ ID NO:166),
(SEQ ID NO:45)-LL-(SEQ ID NO:361)-(SEQ ID NO:93)-(SEQ ID NO:109)-(SEQ ID NO:168)-(SEQ ID NO:167)-(SEQ ID NO:166),
(SEQ ID NO:46)-LL-(SEQ ID NO:362)-(SEQ ID NO:94)-(SEQ ID NO:110)-(SEQ ID NO:168)-(SEQ ID NO:167)-(SEQ ID NO:166),
(SEQ ID NO:47)-LL-(SEQ ID NO:363)-(SEQ ID NO:95)-(SEQ ID NO:111)-(SEQ ID NO:168)-(SEQ ID NO:167)-(SEQ ID NO:166),
(SEQ ID NO:48)-LL-(SEQ ID NO:364)-(SEQ ID NO:96)-(SEQ ID NO:112)-(SEQ ID NO:168)-(SEQ ID NO:167)-(SEQ ID NO:166), and
(SEQ ID NO:49)-LL-(SEQ ID NO:365)-(SEQ ID NO:97)-(SEQ ID NO:113)-(SEQ ID NO:168)-(SEQ ID NO:167)-(SEQ ID NO:166),
wherein each sequence above is linked to the adjacent sequence as described herein and wherein LL is a linker as described herein. In particular, the HA1 C-terminal short stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, Gly, (Gly)n, Gly-Pro, ITPNGSIPNDKPFQNVNKITYGA (SEQ ID NO:165) and Asn-Ala-Ser.

In certain embodiments, provided herein is an influenza hemagglutinin short stem polypeptide having a sequence selected from the group consisting of:
(SEQ ID NO:177)-LL-(SEQ ID NO:366)-(SEQ ID NO:66),
(SEQ ID NO:178)-LL-(SEQ ID NO:367)-(SEQ ID NO:66),
(SEQ ID NO:179)-LL-(SEQ ID NO:368)-(SEQ ID NO:66),
(SEQ ID NO:180)-LL-(SEQ ID NO:369)-(SEQ ID NO:67),
(SEQ ID NO:181)-LL-(SEQ ID NO:370)-(SEQ ID NO:67),
(SEQ ID NO:182)-LL-(SEQ ID NO:371)-(SEQ ID NO:67),
(SEQ ID NO:183)-LL-(SEQ ID NO:372)-(SEQ ID NO:68),
(SEQ ID NO:184)-LL-(SEQ ID NO:373)-(SEQ ID NO:68),
(SEQ ID NO:185)-LL-(SEQ ID NO:374)-(SEQ ID NO:68),
(SEQ ID NO:186)-LL-(SEQ ID NO:375)-(SEQ ID NO:69),
(SEQ ID NO:187)-LL-(SEQ ID NO:376)-(SEQ ID NO:69),
(SEQ ID NO:188)-LL-(SEQ ID NO:377)-(SEQ ID NO:69),
(SEQ ID NO:189)-LL-(SEQ ID NO:378)-(SEQ ID NO:70),
(SEQ ID NO:190)-LL-(SEQ ID NO:379)-(SEQ ID NO:70),
(SEQ ID NO:191)-LL-(SEQ ID NO:380)-(SEQ ID NO:70),
(SEQ ID NO:192)-LL-(SEQ ID NO:381)-(SEQ ID NO:71),
(SEQ ID NO:193)-LL-(SEQ ID NO:382)-(SEQ ID NO:71),
(SEQ ID NO:194)-LL-(SEQ ID NO:383)-(SEQ ID NO:71),
(SEQ ID NO:195)-LL-(SEQ ID NO:384)-(SEQ ID NO:72),
(SEQ ID NO:196)-LL-(SEQ ID NO:385)-(SEQ ID NO:72),
(SEQ ID NO:197)-LL-(SEQ ID NO:386)-(SEQ ID NO:72),
(SEQ ID NO:198)-LL-(SEQ ID NO:387)-(SEQ ID NO:73),
(SEQ ID NO:199)-LL-(SEQ ID NO:388)-(SEQ ID NO:73),
(SEQ ID NO:200)-LL-(SEQ ID NO:389)-(SEQ ID NO:73),
(SEQ ID NO:201)-LL-(SEQ ID NO:390)-(SEQ ID NO:74),
(SEQ ID NO:202)-LL-(SEQ ID NO:391)-(SEQ ID NO:74),
(SEQ ID NO:203)-LL-(SEQ ID NO:392)-(SEQ ID NO:74),
(SEQ ID NO:204)-LL-(SEQ ID NO:393)-(SEQ ID NO:75),
(SEQ ID NO:205)-LL-(SEQ ID NO:394)-(SEQ ID NO:75),
(SEQ ID NO:206)-LL-(SEQ ID NO:395)-(SEQ ID NO:75),
(SEQ ID NO:207)-LL-(SEQ ID NO:396)-(SEQ ID NO:76),
(SEQ ID NO:208)-LL-(SEQ ID NO:397)-(SEQ ID NO:76),
(SEQ ID NO:209)-LL-(SEQ ID NO:398)-(SEQ ID NO:76),
(SEQ ID NO:210)-LL-(SEQ ID NO:399)-(SEQ ID NO:77),
(SEQ ID NO:211)-LL-(SEQ ID NO:400)-(SEQ ID NO:77),
(SEQ ID NO:212)-LL-(SEQ ID NO:401)-(SEQ ID NO:77),
(SEQ ID NO:213)-LL-(SEQ ID NO:402)-(SEQ ID NO:78),
(SEQ ID NO:214)-LL-(SEQ ID NO:403)-(SEQ ID NO:78),
(SEQ ID NO:215)-LL-(SEQ ID NO:404)-(SEQ ID NO:78),
(SEQ ID NO:216)-LL-(SEQ ID NO:405)-(SEQ ID NO:79), (SEQ ID NO:217)-LL-(SEQ ID NO:406)-(SEQ ID NO:79),
(SEQ ID NO:218)-LL-(SEQ ID NO:407)-(SEQ ID NO:79),
(SEQ ID NO:219)-LL-(SEQ ID NO:408)-(SEQ ID NO:80),
(SEQ ID NO:220)-LL-(SEQ ID NO:409)-(SEQ ID NO:80),
(SEQ ID NO:221)-LL-(SEQ ID NO:410)-(SEQ ID NO:80),
(SEQ ID NO:222)-LL-(SEQ ID NO:411)-(SEQ ID NO:81),
(SEQ ID NO:223)-LL-(SEQ ID NO:412)-(SEQ ID NO:81), and
(SEQ ID NO:224)-LL-(SEQ ID NO:413)-(SEQ ID NO:81), and
wherein each sequence above is linked to the adjacent sequence as described herein and wherein LL is a linker as described herein. In particular, the HA1 C-terminal short stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNG-SIPNDKPFQNVNKITYGA (SEQ ID NO:165) and Asn-Ala-Ser.

5.3.2 Influenza Hemagglutinin Long Stem Domain Polypeptides

In certain embodiments, the influenza hemagglutinin stem domain polypeptide is an influenza hemagglutinin long stem domain polypeptide. The typical primary structure of an influenza hemagglutinin long stem domain polypeptide provided herein comprises, in the following order: an HA1 N-terminal long stem segment, a linker, an HA1 C-terminal long stem segment and an HA2. The primary sequence can be formed by a single polypeptide, or it can be formed by multiple polypeptides. Typically, a single polypeptide is expressed by any technique deemed suitable by one of skill in the art. In single polypeptide embodiments, the HA1 segments and the HA2 are in tertiary association. As is known to those of skill in the art, a single HA polypeptide can be cleaved, for example by a protease, under appropriate expression conditions to yield two polypeptides in quaternary association. The cleavage is typically between the HA1 C-terminal short stem segment and the HA2. In certain embodiments, provided herein are multiple polypeptides. In multiple polypeptide embodiments, the HA1 segments and HA2 are in quaternary association.

In certain embodiments, an influenza hemagglutinin long stem domain polypeptide provided herein is monomeric. In certain embodiments, an influenza hemagglutinin long stem domain polypeptide provided herein is multimeric. In certain embodiments, an influenza hemagglutinin long stem domain polypeptide provided herein is trimeric. Those of skill in the art will recognize that native influenza hemagglutinin long stem domain polypeptides are capable of trimerization in vivo and that certain influenza hemagglutinin long stem domain polypeptides provided herein are capable of trimerization. In particular embodiments described below, influenza hemagglutinin long stem domain polypeptides provided herein comprise trimerization domains to facilitate trimerization.

In certain embodiments, an influenza hemagglutinin long stem domain polypeptide comprises a signal peptide. In certain embodiments, also provided herein are mature influenza hemagglutinin long stem domain polypeptides that lack a signal peptide.

In certain embodiments, provided herein are influenza hemagglutinin long stem domain polypeptides that comprise an HA2 stem domain, an HA2 luminal domain, an HA2 transmembrane domain and an HA2 cytoplasmic domain. In certain embodiments, provided herein are influenza hemagglutinin long stem domain polypeptides that comprise an HA2 stem domain, an HA2 luminal domain, and an HA2 transmembrane domain but lack some or all of the typical cytoplasmic domain. In certain embodiments, provided herein are influenza hemagglutinin long stem domain polypeptides that comprise an HA2 stem domain and an HA2 luminal domain but lack both an HA2 transmembrane domain and an HA2 cytoplasmic domain. In certain embodiments, provided herein are influenza hemagglutinin long stem domain polypeptides that comprise an HA2 stem domain but lack an HA2 luminal domain, an HA2 transmembrane domain and an HA2 cytoplasmic domain. In certain embodiments, the influenza hemagglutinin long stem domain polypeptides comprise an HA2 stem domain having at least 70%, 75%, 80%, 85%, 90%, 95%, 96% or 98% amino acid sequence identity to an influenza HA2 stem domain known to those of skill in the art. Exemplary known HA2 stem domains from known influenza A hemagglutinins are provided in the tables below.

Also provided herein are influenza hemagglutinin long stem domain polypeptides comprising deleted forms of HA2 stem domains wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA2 stem domain. Further provided herein are influenza hemagglutinin long stem domain polypeptides comprising altered forms of HA2 stem domains wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are conservatively substituted with other amino acids. Further provided are influenza hemagglutinin long stem domain polypeptides comprising deleted and altered HA2 stem domains.

The HA1 N-terminal long stem segment can be any HA1 N-terminal long stem segment recognized by one of skill in the art based on the definition provided herein. Typically, an HA1 N-terminal long stem segment corresponds to a polypeptide consisting of the N-terminal amino acid of a mature HA1 (i.e. an HA1 lacking a signal peptide) through the cysteine residue located in sequence at approximately the 97$^{th}$ residue of the HA1 (using H3 numbering). This cystine residue, termed $C_p$ herein, is generally capable of being linked to a cysteine residue $C_q$ in the C-terminal long stem segment of HA1. Sequences of 17 representative influenza A hemagglutinins are presented in FIG. 1, and residue $C_p$ is identified in each.

In certain embodiments, the HA1 N-terminal long stem segment does not end exactly at $C_p$ (e.g., $Cys_{97}$ of an HA1 subunit from an H3 hemagglutinin), but at a residue in sequence and structural vicinity to $C_p$. For example, in certain embodiments, the HA1 N-terminal long stem segment ends at $C_{p-1}$, $C_{p-2}$, $C_{p-3}$, or $C_{p-4}$. In other embodiments, the HA1 N-terminal long stem segment ends at $C_{p+1}$, $C_{p+2}$, $C_{p+3}$, $C_{p+4}$ or $C_{p+5}$. The end of an HA1 N-terminal long stem segment should be selected in conjunction with the end of the HA1 C-terminal long stem segment and the linker so that the resulting linked HA1 stem domain is capable of forming a three-dimensional structure similar, as described below, to an influenza hemagglutinin stem domain.

In certain embodiments, the influenza hemagglutinin long stem domain polypeptides comprise an HA1 N-terminal long stem segment having at least 70%, 75%, 80%, 85%, 90%, 95%, 96% or 98% amino acid sequence identity to an influenza HA1 N-terminal long stem segment known to those of skill in the art. Exemplary known HA1 N-terminal long stem segments are provided in the tables below.

Also provided herein are influenza hemagglutinin long stem domain polypeptides comprising deleted forms of HA1

N-terminal long stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA1 N-terminal long stem segment. In certain embodiments, provided herein are influenza hemagglutinin long stem domain polypeptides that comprise expanded forms of HA1 N-terminal long stem segments wherein 1, 2, 3, 4, 5, 6, 7, 8, 9, 10 or more residues are added to the C-terminus of the HA1 N-terminal long stem segments; these added residues can be derived from the amino acid sequence of a globular head domain adjacent to an HA1 N-terminal long stem segment. Further provided herein are influenza hemagglutinin long stem domain polypeptides comprising altered forms of HA1 N-terminal long stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are conservatively substituted with other amino acids. Further provided are influenza hemagglutinin long stem domain polypeptides comprising deleted and altered HA1 N-terminal long stem segments.

The HA1 C-terminal long stem segment can be any HA1 C-terminal long stem segment recognized by one of skill in the art based on the definition provided herein. Typically, an HA1 C-terminal long stem segment corresponds to a polypeptide consisting of the alanine residue located in sequence at approximately the $252^{nd}$ residue of an HA1 (using H3 numbering) through the C-terminal amino acid of the HA1. This alanine residue, termed $C_q$ herein, is generally capable of being linked to a cysteine residue $C_p$ in the N-terminal long stem segment of HA1. Sequences of 16 representative influenza A hemagglutinins are presented in FIG. 1, and residue $C_q$ is identified in each.

In certain embodiments, the HA1 C-terminal long stem segment does not start at $C_q$ (e.g., Ala$_{252}$ of an HA1 subunit from an H3 hemagglutinin), but at a residue in sequence and structural vicinity to $C_q$. For example, in certain embodiments, the HA1 C-terminal long stem segment starts at $C_{q-1}$, $C_{q-2}$, $C_{q-3}$, or $C_{q-4}$. In other embodiments, the HA1 C-terminal long stem segment starts at $C_{q+1}$, $C_{q+2}$, $C_{q+3}$, $C_{q+4}$ or $C_{q+5}$. The end of an HA1 N-terminal long stem segment should be selected in conjunction with the start of the HA1 C-terminal long stem segment and the linker so that the resulting HA1 stem domain is capable of forming a three-dimensional structure similar, as described below, to an influenza hemagglutinin.

In certain embodiments, the influenza hemagglutinin long stem domain polypeptides comprise an HA1 C-terminal long stem segment having at least 70%, 75%, 80%, 85%, 90%, 95%, 96% or 98% amino acid sequence identity to an influenza HA1 C-terminal long stem segment known to those of skill in the art. Exemplary known HA1 C-terminal long stem segments are provided in the tables below.

In certain embodiments, the end of the N-terminal long stem segment is $C_{p-1}$, and the start of the C-terminal long stem segment is $C_{q-1}$. In certain embodiments, the end of the N-terminal long stem segment is $A_{p-2}$, and the start of the C-terminal long stem segment is $C_{q-2}$. In certain embodiments, the end of the N-terminal long stem segment is $C_{p-3}$, and the start of the C-terminal long stem segment is $C_{q-3}$. In certain embodiments, the end of the N-terminal long stem segment is $C_{p-4}$, and the start of the C-terminal long stem segment is $C_{q-4}$. In certain embodiments, the end of the N-terminal long stem segment is $C_{p-5}$, and the start of the C-terminal long stem segment is $C_{q-5}$.

In certain embodiments, the end of the N-terminal long stem segment is $C_{p+1}$, and the start of the C-terminal long stem segment is $C_{q+1}$. In certain embodiments, the end of the N-terminal long stem segment is $C_{p+2}$, and the start of the C-terminal long stem segment is $C_{q+2}$. In certain embodiments, the end of the N-terminal long stem segment is $C_{p+3}$, and the start of the C-terminal long stem segment is $C_{q+3}$. In certain embodiments, the end of the N-terminal long stem segment is $C_{p+4}$, and the start of the C-terminal long stem segment is $C_{q+4}$. In certain embodiments, the end of the N-terminal long stem segment is $C_{p+5}$, and the start of the C-terminal long stem segment is $C_{q+5}$.

In certain embodiments, the end of the N-terminal long stem segment is $C_{p-1}$, and the start of the C-terminal long stem segment is $C_{q+1}$. In certain embodiments, the end of the N-terminal long stem segment is $C_{p-2}$, and the start of the C-terminal long stem segment is $C_{q+2}$. In certain embodiments, the end of the N-terminal long stem segment is $C_{p-3}$, and the start of the C-terminal long stem segment is $C_{q+3}$. In certain embodiments, the end of the N-terminal long stem segment is $C_{p-4}$, and the start of the C-terminal long stem segment is $C_{q+4}$. In certain embodiments, the end of the N-terminal long stem segment is $C_{p-5}$, and the start of the C-terminal long stem segment is $C_{q+5}$.

In certain embodiments, the end of the N-terminal long stem segment is $C_{p+1}$, and the start of the C-terminal long stem segment is $C_{q-1}$. In certain embodiments, the end of the N-terminal long stem segment is $C_{p+2}$, and the start of the C-terminal long stem segment is $C_{q-2}$. In certain embodiments, the end of the N-terminal long stem segment is $C_{p+3}$, and the start of the C-terminal long stem segment is $C_{q-3}$. In certain embodiments, the end of the N-terminal long stem segment is $C_{p+4}$, and the start of the C-terminal long stem segment is $C_{q-4}$. In certain embodiments, the end of the N-terminal long stem segment is $C_{p+5}$, and the start of the C-terminal long stem segment is $C_{q-5}$.

Also provided herein are influenza hemagglutinin long stem domain polypeptides comprising deleted forms of HA1 C-terminal long stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA1 C-terminal long stem segment. In certain embodiments, provided herein are influenza hemagglutinin long stem domain polypeptides that comprise expanded forms of HA1 C-terminal long stem segments wherein 1, 2, 3, 4, 5, 6, 7, 8, 9, 10 or more residues are added to the N-terminus of the HA1 C-terminal long stem segments; these added residues can be derived from the amino acid sequence of a globular head domain adjacent to an HA1 C-terminal long stem segment. In particular embodiments, if one residue is added to the C-terminal long stem segment, then one residue is added to the N-terminal long stem segment; if two residues are added to the C-terminal long stem segment, then two residues are added to the N-terminal long stem segment; if three residues are added to the C-terminal long stem segment, then three residues are added to the N-terminal long stem segment. Further provided herein are influenza hemagglutinin long stem domain polypeptides comprising altered forms of HA1 C-terminal long stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are conservatively substituted with other amino acids. Further provided are influenza hemagglutinin long stem domain polypeptides comprising deleted and altered HA1 C-terminal long stem segments.

The influenza hemagglutinin long stem domain polypeptides can be based on (i.e. can have sequence identity, as described above) any influenza hemagglutinin known to those of skill or later discovered. In certain embodiments, influenza hemagglutinin long stem domain polypeptides are based on an influenza A hemagglutinin. In certain embodiments, the influenza hemagglutinin long stem domain polypeptides are based on an influenza A hemagglutinin selected from the group consisting of H1, H2, H3, H4, H5, H6, H7, H8, H9, H10, H11, H12, H13, H14, H15, H16, and H17. In certain embodiments, influenza hemagglutinin long stem domain polypeptides are based on an influenza B hemagglutinin, as described in detail below.

The HA1 N-terminal long stem segments can be based on (i.e. can have sequence identity, as described above) any HA1 N-terminal long stem segments known to those of skill or later discovered. In certain embodiments, the HA1 N-terminal long stem segments are based on influenza A HA1 N-terminal long stem segments. In certain embodiments, the HA1 N-terminal long stem segments are based on an influenza A hemagglutinin selected from the group consisting of H1, H2, H3, H4, H5, H6, H7, H8, H9, H10, H11, H12, H13, H14, H15, H16, and H17. In certain embodiments, the HA1 N-terminal long stem segment is selected from SEQ ID NOS:414-429. In certain embodiments, the HA1 N-terminal long stem segment is selected from SEQ ID NOS:414-429, each having one amino acid deleted from its C-terminus. In certain embodiments, the HA1 N-terminal long stem segment is selected from SEQ ID NOS:414-429, each having two amino acids deleted from its C-terminus. In certain embodiments, the HA1 N-terminal long stem segment is selected from SEQ ID NOS:414-429, each having three amino acids deleted from its C-terminus. In certain embodiments, the HA1 N-terminal long stem segment is selected from SEQ ID NOS:414-429, each having four amino acids deleted from its C-terminus. In certain embodiments, the HA1 N-terminal long stem segment is selected from SEQ ID NOS:414-429, each having five amino acids deleted from its C-terminus. In certain embodiments, the HA1 N-terminal long stem segment is selected from SEQ ID NOS:446-493.

The HA1 C-terminal long stem segments can be based on (i.e. can have sequence identity, as described above) any HA1 C-terminal long stem segments known to those of skill or later discovered. In certain embodiments, the HA1 C-terminal long stem segments are based on influenza A HA1 C-terminal long stem segments. In certain embodiments, the HA1 C-terminal long stem segments are based on an influenza A hemagglutinin selected from the group consisting of H1, H2, H3, H4, H5, H6, H7, H8, H9, H10, H11, H12, H13, H14, H15, H16, and H17. In certain embodiments, the HA1 C-terminal long stem segment is selected from SEQ ID NOS:430-445. In certain embodiments, the HA1 C-terminal long stem segment is selected from SEQ ID NOS: 430-445, each having one amino acid deleted from its N-terminus. In certain embodiments, the HA1 C-terminal long stem segment is selected from SEQ ID NOS: 430-445, each having two amino acids deleted from its N-terminus. In certain embodiments, the HA1 C-terminal long stem segment is selected from SEQ ID NOS: 430-445, each having three amino acids deleted from its N-terminus. In certain embodiments, the HA1 C-terminal long stem segment is selected from SEQ ID NOS: 430-445, each having four amino acids deleted from its N-terminus. In certain embodiments, the HA1 C-terminal long stem segment is selected from SEQ ID NOS: 430-445, each having five amino acids deleted from its N-terminus. In certain embodiments, the HA1 C-terminal long stem segment is selected from SEQ ID NOS:494-541.

The HA2 stem domains can be based on (i.e. can have sequence identity, as described above) any HA2 stem domains known to those of skill, later discovered, or described herein. In certain embodiments, the HA2 stem domains are based on influenza A HA2 stem domains. In certain embodiments, the HA2 stem domains are based on an influenza A hemagglutinin selected from the group consisting of H1, H2, H3, H4, H5, H6, H7, H8, H9, H10, H11, H12, H13, H14, H15, H16, and H17. In certain embodiments, the HA2 stem domain is selected from SEQ ID NOS:66-97.

In embodiments comprising a signal peptide, the signal peptide can be based on any influenza signal peptide known to those of skill in the art or described herein. In certain embodiments, the signal peptide is selected from SEQ ID NOS:18-33.

In embodiments comprising a luminal domain, the luminal domain can be based on any influenza luminal domain known to those of skill in the art or described herein. In certain embodiments, the luminal domain is selected from SEQ ID NOS:98-113.

In embodiments comprising a transmembrane domain, the transmembrane domain can be based on any influenza transmembrane domain known to those of skill in the art or described herein. In certain embodiments, the transmembrane domain is selected from SEQ ID NOS:114-129.

In embodiments comprising a cytoplasmic domain, the cytoplasmic domain can be based on any influenza cytoplasmic domain known to those of skill in the art or described herein. In certain embodiments, the cytoplasmic domain is selected from SEQ ID NOS:130-145.

In certain embodiments, one or more of the glycosylation sites in the hemagglutinin stem domain are modified (e.g., by amino acid addition, deletion or substitution) such that glycosylation at these sites will not occur during processing and maturation of the polypeptide. Those of skill in the art will recognize that influenza HA typically comprises one or more glycosylation sites (e.g. Asn-Xaa-Ser/Thr/Cys, wherein Xaa is any amino acid other, or, in certain embodiments, wherein Xaa is any amino acid except Pro). In certain embodiments, one or more amino acid residues in a glycosylation site are conservatively substituted with an amino acid residue that disrupts the glycosylation site. In certain embodiments, one or more amino acid residues in a glycosylation site are substituted with any amino acid residue that disrupts the glycosylation sequence. In certain embodiments, one or more asparagine residues in a glycosylation sequence is substituted with alanine. In a particular embodiment, the asparagine at position 38 of an H3 hemagglutinin is changed to an alanine. In certain embodiments, the hemagglutinin stem domain comprises one or more modified glycosylation sites as discussed in Section 5.4.1, infra Table 7, below, identifies signal peptides, HA1 N-terminal long stem segments, HA1 C-terminal long stem segments and HA2 domains of influenza A hemagglutinin polypeptides. These signal peptides, stem segments and domains are useful in the polypeptides and methods described herein.

TABLE 7

Exemplary Influenza A Hemagglutinin Long Stem Domain Peptide Sequences

| HA Subtype (Genbank No.) | Signal Peptide | HA1 N-terminal Long Stem Segment | HA1 C-terminal Long Stem Segment | HA2 Domain |
|---|---|---|---|---|
| H1 PR8-H1N1 (EF467821.1) | MKANLLVLLCALAAADA [SEQ ID NO: 18] | DTICIGYHANNSTDTVDTVLEKNVTVTHSVNLLEDSHNGKLCRLKGIAPLQLGKCNIAGWLLGNPECDPLLPVRSWSYIVETPNSENGIC [SEQ ID NO: 414] | APMYAFALSRGFGSGIITSNASMHECNTKCQTPLGAINSSLPYQNIHPVTIGECPKYVRSAKLRMVTGLRNNPSIQSR [SEQ ID NO: 430] | GLFGAIAGFIEGGWTGMIDGWYGYHHQNEQGSGYAADQKSTQNAINGITNKVNTVIEKMNIQFTAVGKEFNKLEKRMENLNKKVDDGFLDIWTYNAELLVLLENERTLDFHDSNVKNLYEKVKSQLKNNAKEIGNGCFEFYHKCDNECMESVRNGTYDYPKYSEESKLNREKVDGVKLESMGIYQILAIYSTVASSLVLLVSLGAISFWMCSNGSLQCRICI [SEQ ID NO: 66] |
| H2 (L11136) | MAIIYLILLFTAVRG [SEQ ID NO: 19] | DQICIGYHSNNSTEKVDTILERNVTVTHAQNILEKTHNGKLCKLNGIPPLELGDCSIAGWLLGNPECDRLLTVPEWSYIMEKENPRNGLC [SEQ ID NO: 415] | APEYGFRISKRGSSGIMKTEGTLENCETKCQTPLGAINTTLPFHNVHPLTIGECPKYVKSERLVLATGLRNVPQIESR [SEQ ID NO: 431] | GLFGAIAGFIEGGWQGMIDGWYGYHHSNDQGSGYAADKESTQKAIDGITNRVNSVIEKMNTQFEAVGKEFSNLEKRLENLNKKMEDGFLDVWTYNAELLVLMENERTLDFHDSNVKNLYDRVRMQLRDNAKELGNGCFEFYHKCDDECMNSVKNGTYDYPKYEEESKLNRNEIKGVKLSNMGVYQILAIYATVAGSLSLAIMIAGISLWMCSNGSLQCRICI [SEQ ID NO: 67] |
| H3 HK68-H3N2 (EF409245) PDB: IHGJ | MKTIIALSYIFCLALG [SEQ ID NO: 20] | QDLPGNDNSTATLCLGHHAVPNGTLVKTITDDQIEVTNATELVQSSSTGKICNNPHRILDGIDCTLIDALLGDPHCDVFQNETWDLFVERSKAFSNC [SEQ ID NO: 416] | APRGYFKMRTGKSSIMSSDAPIDTCISECITPNGSIPNDKPFQNVNKITYGACPKYVKQNTLKLATGMRNVPEKQTR [SEQ ID NO: 432] | GLFGAIAGFIENGWEGMIDGWYGFRHQNSEGTGQAADLKSTQAAIDQINGKLNRVIEKTNEKFHQIEKEFSEVEGRIQDLEKYVEDTKIDLWSYNAELLVALENQHTIDLTDSEMNKLFEKTRRQLRENAEDMGNGCFKIYHKCDNACIESIRNGTYDHDVYRDEALNNRFQIKGVELKSGYKDWILWISFAISCFLLCVVLLGFIMWACQRGNIRCNICI [SEQ ID NO: 68] |
| H4 (D90302) | MLSIVILFLLIAENSS [SEQ ID NO: 21] | QNYTGNPVICMGHHAVANGTMVKTLADDQVEVVTAQELVESQNLPELCPSPLRLVDGQTCDIINGALGSPGCDHLNGAEWDVFIERPNAVDTC [SEQ ID NO: 417] | APRGHYKLNNQKKSTILNTAIPIGSCVSKCHTDKGSLSTTKPFQNISRIAVGDCPRYVKQGSLKLATGMRNIPEKASR [SEQ ID NO: 433] | GLFGAIAGFIENGWQGLIDGWYGFRHQNAEGTGTAADLKSTQAAIDQINGKLNRLIEKTNDKYHQIEKEFEQVEGRIQDLENYVEDTKIDLWSYNAELLVALENQHTIDVTDSEMNKLFERVRRQLRENAEDKGNGCFEIFHKCDNNCIESIRNGTYDHDIYRDEAINNRFQIQGVKLTQGYKDIILWISFSISCFLLVALLLAFILWACQNGNIRCQICI |

TABLE 7-continued

Exemplary Influenza A Hemagglutinin Long Stem Domain Peptide Sequences

| HA Subtype (Genbank No.) | Signal Peptide | HA1 N-terminal Long Stem Segment | HA1 C-terminal Long Stem Segment | HA2 Domain |
|---|---|---|---|---|
| | | | | [SEQ ID NO: 69] |
| H5 (X07826) | MERIV LLLAI VSLVK S [SEQ ID NO: 22] | DQICIGYHAN KSTKQVDTIM EKNVTVTHAQ DILERTHNGKL CSLNGVKPLIL RDCSVAGWLL GNPMCDEFLN LPEWLYIVEK DNPINSLC [SEQ ID NO: 418] | APRYAYKIVK KGDSAIMKSG LAYGNCDTKC QTPVGEINSSM PFHNIHPHTIG ECPKYVKSDR LVLATGLRNV PQRKKR [SEQ ID NO: 434] | GLFGAIAGFIEGGW QGMVDGWYGYHH SNEQGSGYAADKES TQKAIDGITNKVNSI IDKMNTRFEAVGKE FNNLERRVENLNKK MEDGFLDVWTYNV ELLVLMENERTLDF HDSNVNNLYDKVR LQLKDNARELGNGC FEFYHKCDNECMES VRNGTYDYPQYSEE ARLNREEISGVKLES MGVYQILSIYSTVAS SLALAIMIAGLSFW MCSNGSLQCRICI [SEQ ID NO: 70] |
| H6 (D90303) | MIAIIV VAILA TAGRS [SEQ ID NO: 23] | DKICIGYHAN NSTTQIDTILE KNVTVTHSVE LLENQKEERF CKILKKAPLDL KGCTIEGWILG NPQCDLLLGD QSWSYIVERPT AQNGIC [SEQ ID NO: 419] | APWYAFRFVS TSNKGAVFKS NLPIENCDATC QTVAGVLRTN KTFQNVSPLWI GECPKYVKSE SLRLATGLRN VPQIETR [SEQ ID NO: 435] | GLFGAIAGFIEGGW TGMIDGWYGYHHE NSQGSGYAADREST QKAVDGITNKVNSII DKMNTQFEAVDHE FSNLERRIDNLNKR MEDGFLDVWTYNA ELLVLLENERTLDL HDANVKNLYERVK SQLRDNAMILGNGC FEFWHKCDDECMES VKNGTYDYPKYQD ESKLNRQEIESVKLE SLGVYQILAIYSTVS SSLVLVGLIIAVGLW MCSNGSMQCRICI [SEQ ID NO: 71] |
| H7 (M24457) | MNTQI LVFAL VAVIP TNA [SEQ ID NO: 24] | DKICLGHHAV SNGTKVNTLT ERGVEVVNAT ETVERTNIPKI CSKGKRTTDL GQCGLLGTITG PPQCDQFLEFS ADLIIERREGN DVC [SEQ ID NO: 420] | APNRASFLRG KSMGIQSDVQ VDANCEGECY HSGGTITSRLP FQNINSRAVG KCPRYVKQES LLLATGMKNV PEPSKKRKKR [SEQ ID NO: 436] | GLFGAIAGFIENGW EGLVDGWYGFRHQ NAQGEGTAADYKS TQSAIDQITGKLNRL IEKTNQQFELIDNEF TEVEKQIGNLINWT KDSITEVWSYNAELI VAMENQHTIDLADS EMNRLYERVRKQL RENAEEDGTGCFEIF HKCDDDCMASIRNN TYDHSKYREEAMQ NRIQIDPVKLSSGYK DVILWFSFGASCFLL LAIAMGLVFICVKN GNMRCTICI [SEQ ID NO: 72] |
| H8 (D90304) | MEKFI AIATL ASTNA Y [SEQ ID NO: 25] | DRICIGYQSNN STDTVNTLIEQ NVPVTQTMEL VETEKHPAYC NTDLGAPLEL RDCKIEAVIYG NPKCDIHLKD QGWSYIVERP SAPEGMC [SEQ ID NO: 421] | APEFGYLLKG ESYGRIIQNEDI PIGNCNTKCQT YAGAINSSKPF QNASRHYMGE CPKYVKKASL RLAVGLRNTP SVEPR [SEQ ID NO: 437] | GLFGAIAGFIEGGWS GMIDGWYGFHHSN SEGTGMAADQKST QEAIDKITNKVNIV DKMNREFEVVNHEF SEVEKRINMINDKID DQIEDLWAYNAELL VLLENQKTLDEHDS NVKNLFDEVKRRLS ANAIDAGNGCFDIL HKCDNECMETIKNG TYDHKEYEEEAKLE RSKINGVKLEENTT |

TABLE 7-continued

Exemplary Influenza A Hemagglutinin Long Stem Domain Peptide Sequences

| HA Subtype (Genbank No.) | Signal Peptide | HA1 N-terminal Long Stem Segment | HA1 C-terminal Long Stem Segment | HA2 Domain |
| --- | --- | --- | --- | --- |
| | | | | YKILSIYSTVAASLC LAILIAGGLILGMQN GSCRCMFCI [SEQ ID NO: 73] |
| H9 (D90305) | METK AIIAAL LMVTA ANA [SEQ ID NO: 26] | DKICIGYQSTN STETVDTLTES NVPVTHTKEL LHTEHNGMLC ATDLGHPLILD TCTIEGLIYGN PSCDILLGGKE WSYIVERSSA VNGMC [SEQ ID NO: 422] | APWYGHVLT GESHGRILKTD LNNGNCVVQC QTEKGGLNTT LPFHNISKYAF GNCPKYVGVK SLKLPVGLRN VPAVSSR [SEQ ID NO: 438] | GLFGAIAGFIEGGWP GLVAGWYGFQHSN DQGVGMAADKGST QKAIDKITSKVNNII DKMNKQYEVIDHEF NELEARLNMINNKI DDQIQDIWAYNAEL LVLLENQKTLDEHD ANVNNLYNKVKRA LGSNAVEDGNGCFE LYHKCDDQCMETIR NGTYDRQKYQEESR LERQKIEGVKLESEG TYKILTIYSTVASSL VLAMGFAAFLFWA MSNGSCRCNICI [SEQ ID NO: 74] |
| H10 (M21647) | MYKV VVIIAL LGAVK G [SEQ ID NO: 27] | LDRICLGHHA VANGTIVKTL TNEQEEVTNA TETVESTNLN KLCMKGRSYK DLGNCHPVGM LIGTPVCDPHL TGTWDTLIERE NAIAHC [SEQ ID NO: 423] | APSRVSKLTG RDLGIQSEALI DNSCESKCFW RGGSINTKLPF QNLSPRTVGQ CPKYVNQRSL LLATGMRNVP EVVQGR [SEQ ID NO: 439] | GLFGAIAGFIENGW EGMVDGWYGFRHQ NAQGTGQAADYKS TQAAIDQITGKLNRL IEKTNTEFESIESEFS ETEHQIGNVINWTK DSITDIWTYNAELLV AMENQHTIDMADSE MLNLYERVRKQLR QNAEEDGKGCFEIY HTCDDSCMESIRNN TYDHSQYREEALLN RLNINPVKLSSGYK DIILWFSFGESCFVL LAVVMGLVFFCLKN GNMRCTICI [SEQ ID NO: 75] |
| H11 (D90306) | MEKTL LFAAIF LCVKA [SEQ ID NO: 28] | DEICIGYLSNN STDKVDTIIEN NVTVTSSVEL VETEHTGSFCS INGKQPISLGD CSFAGWILGN PMCDELIGKTS WSYIVEKPNPT NGIC [SEQ ID NO: 424] | APRYAFEIVSV GNGKLFRSEL NIESCSTKCQT EIGGINTNKSF HNVHRNTIGD CPKYVNVKSL KLATGPRNVP AIASR [SEQ ID NO: 440] | GLFGAIAGFIEGGWP GLINGWYGFQHRDE EGTGIAADKESTQK AIDQITSKVNNIVDR MNTNFESVQHEFSEI EERINQLSKHVDDS VVDIWSYNAQLLVL LENEKTLDLHDSNV RNLHEKVRRMLKD NAKDEGNGCFTFYH KCDNKCIERVRNGT YDHKEFEEESKINR QEIEGVKLDSSGNV YKILSIYSCIASSLVL AALIMGFMFWACS NGSCRCTICI [SEQ ID NO: 76] |
| H12 (D90307) | MEKFII LSTVL AASFA Y [SEQ ID NO: 29] | DKICIGYQTNN STETVNTLSEQ NVPVTQVEEL VHRGIDPILCG TELGSPLVLDD CSLEGLILGNP KCDLYLNGRE WSYIVERPKE MEGVC [SEQ ID | APEYGHLITG KSHGRILKNN LPMGQCVTEC QLNEGVMNTS KPFQNTSKHYI GKCPKYIPSGS LKLAIGLRNVP QVQDR [SEQ ID NO: 441] | GLFGAIAGFIEGGWP GLVAGWYGFQHQN AEGTGIAADRDSTQ RAIDNMQNKLNNVI DKMNKQPEVVNHE FSEVESRINMINSKI DDQITDIWAYNAEL LVLLENQKTLDEHD ANVRNLHDRVRRV LRENAIDTGDGCFEI |

TABLE 7-continued

Exemplary Influenza A Hemagglutinin Long Stem Domain Peptide Sequences

| HA Subtype (Genbank No.) | Signal Peptide | HA1 N

TABLE 7-continued

Exemplary Influenza A Hemagglutinin Long Stem Domain Peptide Sequences

| HA Subtype (Genbank No.) | Signal Peptide | HA1 N-terminal Long Stem Segment | HA1 C-terminal Long Stem Segment | HA2 Domain |
|---|---|---|---|---|
| | | EWSYLIEDPN APNKFC [SEQ ID NO: 429] | GER [SEQ ID NO: 445] | LENDRTLDLHDANV RNLHDQVKRALKS NAIDEGDGCFNLLH KCNDSCMETIRNGT YNHEDYREESQLKR QEIEGIKLKTEDNVY KVLSIYSCIASSIVLV GLILAFIMWACSNG SCRFNVCI [SEQ ID NO: 81] |
| H17 (CY103876) | MELIV LLILLN PYTFV LG | DRICIGYQANQ NNQTVNTLLE QNVPVTGAQE ILETNHNGKLC SLNGVPPLDL QSCTLAGWLL GNPNCDSLLE AEEWSYIKINE SAPDDLC | APEYGFYYKR KEGKGGLMKS KLPISDCSTKC QTPLGALNSTL PFQNVHQQTI GNCPKYVKAT SLMLATGLRN NPQMEGR | GLFGAIAGFIEGGW QGMIDGWYGYHHE NQEGSGYAADKEA TQKAVDAITNKVNS IIDKMNSQFESNIKE FNRLELRIQHLSDRV DDALLDIWSYNTEL LVLLENERTLDFHD ANVKNLFEKVKAQ LKDNAIDEGNGCFL LLHKCNNSCMDDIK NGTYKYMDYREES HIEKQKIDGVKLTD YSRYYIMTLYSTIAS SVVLGSLIIAAFLWG CQKGSIQCKICI |

Table 7A, below, identifies useful HA1 N-terminal long stem segments and HA1 C-terminal long stem segments for the polypeptides and methods described herein.

TABLE 7A

Exemplary Influenza A Hemagglutinin Long Stem Domain Sequences

| HA Subtype (Genbank No.) | HA1 N-terminal Long Stem Segment | HA1 C-terminal Long Stem Segment |
|---|---|---|
| H1 PR8-H1N1 (EF467821.1) No Cys, Ala | DTICIGYHANNSTDTVDT VLEKNVTVTHSVNLLED SHNGKLCRLKGIAPLQL GKCNIAGWLLGNPECDP LLPVRSWSYIVETPNSEN GI [SEQ ID NO: 446] | PMYAFALSRGFGSGIITSNASMHECNT KCQTPLGAINSSLPYQNIHPVTIGECPK YVRSAKLRMVTGLRNNPSIQSR [SEQ ID NO: 494] |
| H1 PR8-H1N1 (EF467821.1) No Cys, Ala Δ1 | DTICIGYHANNSTDTVDT VLEKNVTVTHSVNLLED SHNGKLCRLKGIAPLQL GKCNIAGWLLGNPECDP LLPVRSWSYIVETPNSEN GI [SEQ ID NO: 447] | MYAFALSRGFGSGIITSNASMHECNTK CQTPLGAINSSLPYQNIHPVTIGECPKY VRSAKLRMVTGLRNNPSIQSR [SEQ ID NO: 495] |
| H1 PR8-H1N1 (EF467821.1) No Cys, Ala Δ3 | DTICIGYHANNSTDTVDT VLEKNVTVTHSVNLLED SHNGKLCRLKGIAPLQL GKCNIAGWLLGNPECDP LLPVRSWSYIVETPNSEN G [SEQ ID NO: 448] | YAFALSRGFGSGIITSNASMHECNTKC QTPLGAINSSLPYQNIHPVTIGECPKYV RSAKLRMVTGLRNNPSIQSR [SEQ ID NO: 496] |
| H2 (L11136) No Cys, Ala | DQICIGYHSNNSTEKVDT ILERNVTVTHAQNILEKT HNGKLCKLNGIPPLELG | PEYGFRISKRGSSGIMKTEGTLENCET KCQTPLGAINTTLPFHNVHPLTIGECP KYVKSERLVLATGLRNVPQIESR |

TABLE 7A-continued

Exemplary Influenza A Hemagglutinin Long Stem Domain Sequences

| HA Subtype (Genbank No.) | HA1 N-terminal Long Stem Segment | HA1 C-terminal Long Stem Segment |
|---|---|---|
| | DCSIAGWLLGNPECDRL LTVPEWSYIMEKENPRN GL [SEQ ID NO: 449] | [SEQ ID NO: 497] |
| H2 (L11136) No Cys, Ala Δ1 | DQICIGYHSNNSTEKVDT ILERNVTVTHAQNILEKT HNGKLCKLNGIPPLELG DCSIAGWLLGNPECDRL LTVPEWSYIMEKENPRN GL [SEQ ID NO: 450] | EYGFRISKRGSSGIMKTEGTLENCETK CQTPLGAINTTLPFHNVHPLTIGECPK YVKSERLVLATGLRNVPQIESR [SEQ ID NO: 498] |
| H2 (L11136) No Cys, Ala Δ3 | DQICIGYHSNNSTEKVDT ILERNVTVTHAQNILEKT HNGKLCKLNGIPPLELG DCSIAGWLLGNPECDRL LTVPEWSYIMEKENPRN G [SEQ ID NO: 451] | YGFRISKRGSSGIMKTEGTLENCETKC QTPLGAINTTLPFHNVHPLTIGECPKY VKSERLVLATGLRNVPQIESR [SEQ ID NO: 499] |
| H3 HK68-H3N2 (EF409245) PDB: 1HGJ No Cys, Ala | QDLPGNDNSTATLCLGH HAVPNGTLVKTITDDQIE VTNATELVQSSSTGKICN NPHRILDGIDCTLIDALL GDPHCDVFQNETWDLF VERSKAFSN [SEQ ID NO: 452] | PRGYFKMRTGKSSIMSSDAPIDTCISEC ITPNGSIPNDKPFQNVNKITYGACPKY VKQNTLKLATGMRNVPEKQTR [SEQ ID NO: 500] |
| H3 HK68-H3N2 (EF409245) PDB: 1HGJ No Cys, Ala Δ1 | QDLPGNDNSTATLCLGH HAVPNGTLVKTITDDQIE VTNATELVQSSSTGKICN NPHRILDGIDCTLIDALL GDPHCDVFQNETWDLF VERSKAFSN [SEQ ID NO: 453] | RGYFKMRTGKSSIMSSDAPIDTCISECI TPNGSIPNDKPFQNVNKITYGACPKYV KQNTLKLATGMRNVPEKQTR [SEQ ID NO: 501] |
| H3 HK68-H3N2 (EF409245) PDB: 1HGJ No Cys, Ala Δ3 | QDLPGNDNSTATLCLGH HAVPNGTLVKTITDDQIE VTNATELVQSSSTGKICN NPHRILDGIDCTLIDALL GDPHCDVFQNETWDLF VERSKAFS [SEQ ID NO: 454] | GYFKMRTGKSSIMSSDAPIDTCISECIT PNGSIPNDKPFQNVNKITYGACPKYVK QNTLKLATGMRNVPEKQTR [SEQ ID NO: 502] |
| H4 (D90302) No Cys, Ala | QNYTGNPVICMGHHAV ANGTMVKTLADDQVEV VTAQELVESQNLPELCPS PLRLVDGQTCDIINGALG SPGCDHLNGAEWDVFIE RPNAVDT [SEQ ID NO: 455] | PRGHYKLNNQKKSTILNTAIPIGSCVS KCHTDKGSLSTTKPFQNISRIAVGDCP RYVKQGSLKLATGMRNIPEKASR [SEQ ID NO: 503] |
| H4 (D90302) No Cys, Ala Δ1 | QNYTGNPVICMGHHAV ANGTMVKTLADDQVEV VTAQELVESQNLPELCPS PLRLVDGQTCDIINGALG SPGCDHLNGAEWDVFIE RPNAVDT [SEQ ID NO: 456] | RGHYKLNNQKKSTILNTAIPIGSCVSK CHTDKGSLSTTKPFQNISRIAVGDCPR YVKQGSLKLATGMRNIPEKASR [SEQ ID NO: 504] |
| H4 (D90302) No Cys, Ala Δ3 | QNYTGNPVICMGHHAV ANGTMVKTLADDQVEV VTAQELVESQNLPELCPS PLRLVDGQTCDIINGALG SPGCDHLNGAEWDVFIE RPNAVD [SEQ ID NO: 457] | GHYKLNNQKKSTILNTAIPIGSCVSKC HTDKGSLSTTKPFQNISRIAVGDCPRY VKQGSLKLATGMRNIPEKASR [SEQ ID NO: 505] |
| H5 (X07826) | DQICIGYHANKSTKQVD TIMEKNVTVTHAQDILE | PRYAYKIVKKGDSAIMKSGLAYGNCD TKCQTPVGEINSSMPFHNIHPHTIGECP |

TABLE 7A-continued

Exemplary Influenza A Hemagglutinin Long Stem Domain Sequences

| HA Subtype (Genbank No.) | HA1 N-terminal Long Stem Segment | HA1 C-terminal Long Stem Segment |
|---|---|---|
| No Cys, Ala | RTHNGKLCSLNGVKPLI LRDCSVAGWLLGNPMC DEFLNLPEWLYIVEKDN PINSL [SEQ ID NO: 458] | KYVKSDRLVLATGLRNVPQRKKR [SEQ ID NO: 506] |
| H5 (X07826) No Cys, Ala Δ1 | DQICIGYHANKSTKQVD TIMEKNVTVTHAQDILE RTHNGKLCSLNGVKPLI LRDCSVAGWLLGNPMC DEFLNLPEWLYIVEKDN PINSL [SEQ ID NO: 459] | RYAYKIVKKGDSAIMKSGLAYGNCDT KCQTPVGEINSSMPFHNIHPHTIGECPK YVKSDRLVLATGLRNVPQRKKR [SEQ ID NO: 507] |
| H5 (X07826) No Cys, Ala Δ3 | DQICIGYHANKSTKQVD TIMEKNVTVTHAQDILE RTHNGKLCSLNGVKPLI LRDCSVAGWLLGNPMC DEFLNLPEWLYIVEKDN PINS [SEQ ID NO: 460] | YAYKIVKKGDSAIMKSGLAYGNCDTK CQTPVGEINSSMPFHNIHPHTIGECPKY VKSDRLVLATGLRNVPQRKKR [SEQ ID NO: 508] |
| H6 (D90303) No Cys, Ala | DKICIGYHANNSTTQIDT ILEKNVTVTHSVELLENQ KEERFCKILKKAPLDLK GCTIEGWILGNPQCDLLL GDQSWSYIVERPTAQNG I [SEQ ID NO: 461] | PWYAFRFVSTSNKGAVFKSNLPIENC DATCQTVAGVLRTNKTFQNVSPLWIG ECPKYVKSESLRLATGLRNVPQIETR [SEQ ID NO: 509] |
| H6 (D90303) No Cys, Ala Δ1 | DKICIGYHANNSTTQIDT ILEKNVTVTHSVELLENQ KEERFCKILKKAPLDLK GCTIEGWILGNPQCDLLL GDQSWSYIVERPTAQNG I [SEQ ID NO: 462] | WYAFRFVSTSNKGAVFKSNLPIENCD ATCQTVAGVLRTNKTFQNVSPLWIGE CPKYVKSESLRLATGLRNVPQIETR [SEQ ID NO: 510] |
| H6 (D90303) No Cys, Ala Δ3 | DKICIGYHANNSTTQIDT ILEKNVTVTHSVELLENQ KEERFCKILKKAPLDLK GCTIEGWILGNPQCDLLL GDQSWSYIVERPTAQNG [SEQ ID NO: 463] | YAFRFVSTSNKGAVFKSNLPIENCDAT CQTVAGVLRTNKTFQNVSPLWIGECP KYVKSESLRLATGLRNVPQIETR [SEQ ID NO: 511] |
| H7 (M24457) No Cys, Ala | DKICLGHHAVSNGTKVN TLTERGVEVVNATETVE RTNIPKICSKGKRTTDLG QCGLLGTITGPPQCDQFL EFSADLIIERREGNDV [SEQ ID NO: 464] | PNRASFLRGKSMGIQSDVQVDANCEG ECYHSGGTITSRLPFQNINSRAVGKCP RYVKQESLLLATGMKNVPEPSKKRKK R [SEQ ID NO: 512] |
| H7 (M24457) No Cys, Ala Δ1 | DKICLGHHAVSNGTKVN TLTERGVEVVNATETVE RTNIPKICSKGKRTTDLG QCGLLGTITGPPQCDQFL EFSADLIIERREGNDV [SEQ ID NO: 465] | NRASFLRGKSMGIQSDVQVDANCEGE CYHSGGTITSRLPFQNINSRAVGKCPR YVKQESLLLATGMKNVPEPSKKRKKR [SEQ ID NO: 513] |
| H7 (M24457) No Cys, Ala Δ3 | DKICLGHHAVSNGTKVN TLTERGVEVVNATETVE RTNIPKICSKGKRTTDLG QCGLLGTITGPPQCDQFL EFSADLIIERREGND [SEQ ID NO: 466] | RASFLRGKSMGIQSDVQVDANCEGEC YHSGGTITSRLPFQNINSRAVGKCPRY VKQESLLLATGMKNVPEPSKKRKKR [SEQ ID NO: 514] |
| H8 (D90304) No Cys, Ala | DRICIGYQSNNSTDTVNT LIEQNVPVTQTMELVET EKHPAYCNTDLGAPLEL RDCKIEAVIYGNPKCDIH LKDQGWSYIVERPSAPE GM [SEQ ID NO: 467] | PEFGYLLKGESYGRIIQNEDIPIGNCNT KCQTYAGAINSSKPFQNASRHYMGEC PKYVKKASLRLAVGLRNTPSVEPR [SEQ ID NO: 515] |

TABLE 7A-continued

Exemplary Influenza A Hemagglutinin Long Stem Domain Sequences

| HA Subtype (Genbank No.) | HA1 N-terminal Long Stem Segment | HA1 C-terminal Long Stem Segment |
|---|---|---|
| H8 (D90304) No Cys, Ala Δ1 | DRICIGYQSNNSTDTVNT LIEQNVPVTQTMELVET EKHPAYCNTDLGAPLEL RDCKIEAVIYGNPKCDIH LKDQGWSYIVERPSAPE GM [SEQ ID NO: 468] | EFGYLLKGESYGRIIQNEDIPIGNCNTK CQTYAGAINSSKPFQNASRHYMGECP KYVKKASLRLAVGLRNTPSVEPR [SEQ ID NO: 516] |
| H8 (D90304) No Cys, Ala Δ3 | DRICIGYQSNNSTDTVNT LIEQNVPVTQTMELVET EKHPAYCNTDLGAPLEL RDCKIEAVIYGNPKCDIH LKDQGWSYIVERPSAPE G [SEQ ID NO: 469] | FGYLLKGESYGRIIQNEDIPIGNCNTKC QTYAGAINSSKPFQNASRHYMGECPK YVKKASLRLAVGLRNTPSVEPR [SEQ ID NO: 517] |
| H9 (D90305) No Cys, Ala | DKICIGYQSTNSTETVDT LTESNVPVTHTKELLHTE HNGMLCATDLGHPLILD TCTIEGLIYGNPSCDILLG GKEWSYIVERSSAVNGM [SEQ ID NO: 470] | PWYGHVLTGESHGRILKTDLNNGNCV VQCQTEKGGLNTTLPFHNISKYAFGN CPKYVGVKSLKLPVGLRNVPAVSSR [SEQ ID NO: 518] |
| H9 (D90305) No Cys, Ala Δ1 | DKICIGYQSTNSTETVDT LTESNVPVTHTKELLHTE HNGMLCATDLGHPLILD TCTIEGLIYGNPSCDILLG GKEWSYIVERSSAVNGM [SEQ ID NO: 471] | WYGHVLTGESHGRILKTDLNNGNCV VQCQTEKGGLNTTLPFHNISKYAFGN CPKYVGVKSLKLPVGLRNVPAVSSR [SEQ ID NO: 519] |
| H9 (D90305) No Cys, Ala Δ3 | DKICIGYQSTNSTETVDT LTESNVPVTHTKELLHTE HNGMLCATDLGHPLILD TCTIEGLIYGNPSCDILLG GKEWSYIVERSSAVNG [SEQ ID NO: 472] | YGHVLTGESHGRILKTDLNNGNCVVQ CQTEKGGLNTTLPFHNISKYAFGNCPK YVGVKSLKLPVGLRNVPAVSSR [SEQ ID NO: 520] |
| H10 (M21647) No Cys, Ala | LDRICLGHHAVANGTIV KTLTNEQEEVTNATETV ESTNLNKLCMKGRSYKD LGNCHPVGMLIGTPVCD PHLTGTWDTLIERENAIA H [SEQ ID NO: 473] | PSRVSKLTGRDLGIQSEALIDNSCESK CFWRGGSINTKLPFQNLSPRTVGQCPK YVNQRSLLLATGMRNVPEVVQGR [SEQ ID NO: 521] |
| H10 (M21647) No Cys, Ala Δ1 | LDRICLGHHAVANGTIV KTLTNEQEEVTNATETV ESTNLNKLCMKGRSYKD LGNCHPVGMLIGTPVCD PHLTGTWDTLIERENAIA H [SEQ ID NO: 474] | SRVSKLTGRDLGIQSEALIDNSCESKC FWRGGSINTKLPFQNLSPRTVGQCPKY VNQRSLLLATGMRNVPEVVQGR [SEQ ID NO: 522] |
| H10 (M21647) No Cys, Ala Δ3 | LDRICLGHHAVANGTIV KTLTNEQEEVTNATETV ESTNLNKLCMKGRSYKD LGNCHPVGMLIGTPVCD PHLTGTWDTLIERENAIA [SEQ ID NO: 475] | RVSKLTGRDLGIQSEALIDNSCESKCF WRGGSINTKLPFQNLSPRTVGQCPKY VNQRSLLLATGMRNVPEVVQGR [SEQ ID NO: 523] |
| H11 (D90306) No Cys, Ala | DEICIGYLSNNSTDKVDT IIENNVTVTSSVELVETE HTGSFCSINGKQPISLGD CSFAGWILGNPMCDELI GKTSWSYIVEKPNPTNGI [SEQ ID NO: 476] | PRYAFEIVSVGNGKLFRSELNIESCSTK CQTEIGGINTNKSFHNVHRNTIGDCPK YVNVKSLKLATGPRNVPAIASR [SEQ ID NO: 524] |
| H11 (D90306) No Cys, Ala Δ1 | DEICIGYLSNNSTDKVDT IIENNVTVTSSVELVETE HTGSFCSINGKQPISLGD CSFAGWILGNPMCDELI GKTSWSYIVEKPNPTNGI [SEQ ID NO: 477] | RYAFEIVSVGNGKLFRSELNIESCSTKC QTEIGGINTNKSFHNVHRNTIGDCPKY VNVKSLKLATGPRNVPAIASR [SEQ ID NO: 525] |

TABLE 7A-continued

Exemplary Influenza A Hemagglutinin Long Stem Domain Sequences

| HA Subtype (Genbank No.) | HA1 N-terminal Long

TABLE 7A-continued

Exemplary Influenza A Hemagglutinin Long Stem Domain Sequences

| HA Subtype (Genbank No.) | HA1 N-terminal Long Stem Segment | HA1 C-terminal Long Stem Segment |
|---|---|---|
| | LGSPGCDRLQDTTWDVF IERPTAVD [SEQ ID NO: 487] | |
| H15 (L43917) No Cys, Ala | DKICLGHHAVANGTKV NTLTERGVEVVNATETV EITGIDKVCTKGKKAVD LGSCGILGTIIGPPQCDLH LEFKADLIIERRNSSDI [SEQ ID NO: 488] | PDRATFLRSNAPSGIEYNGKSLGIQSD AQIDESCEGECFYSGGTINSPLPFQNID SRAVGKCPRYVKQSSLPLALGMKNVP EKIRTR [SEQ ID NO: 536] |
| H15 (L43917) No Cys, Ala Δ1 | DKICLGHHAVANGTKV NTLTERGVEVVNATETV EITGIDKVCTKGKKAVD LGSCGILGTIIGPPQCDLH LEFKADLIIERRNSSDI [SEQ ID NO: 489] | DRATFLRSNAPSGIEYNGKSLGIQSDA QIDESCEGECFYSGGTINSPLPFQNIDS RAVGKCPRYVKQSSLPLALGMKNVPE KIRTR [SEQ ID NO: 537] |
| H15 (L43917) No Cys, Ala Δ3 | DKICLGHHAVANGTKV NTLTERGVEVVNATETV EITGIDKVCTKGKKAVD LGSCGILGTIIGPPQCDLH LEFKADLIIERRNSSD [SEQ ID NO: 490] | RATFLRSNAPSGIEYNGKSLGIQSDAQI DESCEGECFYSGGTINSPLPFQNIDSRA VGKCPRYVKQSSLPLALGMKNVPEKI RTR [SEQ ID NO: 538] |
| H16 (EU293865) No Cys, Ala | DKICIGYLSNNSSDTVDT LTENGVPVTSSVDLVET NHTGTYCSLNGISPIHLG DCSFEGWIVGNPSCATNI NIREWSYLIEDPNAPNKF [SEQ ID NO: 491] | PRYGYIIEKYGTGRIFQSGVRMARCNT KCQTSLGGINTNKTFQNIERNALGDCP KYIKSGQLKLATGLRNVPSIGER [SEQ ID NO: 539] |
| H16 (EU293865) No Cys, Ala Δ1 | DKICIGYLSNNSSDTVDT LTENGVPVTSSVDLVET NHTGTYCSLNGISPIHLG DCSFEGWIVGNPSCATNI NIREWSYLIEDPNAPNKF [SEQ ID NO: 492] | RYGYIIEKYGTGRIFQSGVRMARCNT KCQTSLGGINTNKTFQNIERNALGDCP KYIKSGQLKLATGLRNVPSIGER [SEQ ID NO: 540] |
| H16 (EU293865) No Cys, Ala Δ3 | DKICIGYLSNNSSDTVDT LTENGVPVTSSVDLVET NHTGTYCSLNGISPIHLG DCSFEGWIVGNPSCATNI NIREWSYLIEDPNAPNK [SEQ ID NO: 493] | YGYIIEKYGTGRIFQSGVRMARCNTK CQTSLGGINTNKTFQNIERNALGDCPK YIKSGQLKLATGLRNVPSIGER [SEQ ID NO: 541] |
| H17 (CY103876) No Cys, Ala | DRICIGYQANQNNQTVN TLLEQNVPVTGAQEILET NHNGKLCSLNGVPPLDL QSCTLAGWLLGNPNCDS LLEAEEWSYIKINESAPD DL | PEYGFYYKRKEGKGGLMKSKLPISDC STKCQTPLGALNSTLPFQNVHQQTIGN CPKYVKATSLMLATGLRNNPQMEGR |

In certain embodiments, the influenza hemagglutinin long stem domain polypeptides comprise one or more immunogenic epitopes in the tertiary or quaternary structure of an influenza hemagglutinin long stem domain polypeptide.

In certain embodiments, the HA1 N-terminal long stem segment comprises the amino acid sequence $A_{17}$-$A_{18}$-(Xaa)$_n$-$A_{38}$ (SEQ ID NO:146), wherein $A_{17}$ is Y or H;

$A_{18}$ is H, L, or Q;

(Xaa)$_n$ represents a sequence of 18-20 amino acid residues; and $A_{38}$ is H, S, Q, T or N.

In certain embodiments, the HA1 C-terminal long stem segment comprises the amino acid sequence $A_{291}$-$A_{292}$ (SEQ ID NO:147), wherein $A_{291}$ is T, S, N, D, P or K; and $A_{292}$ is L, M, K or R.

In certain embodiments, the HA2 domain comprises the amino acid sequence $A_{18}$-$A_{19}$-$A_{20}$-$A_{21}$ (SEQ ID NO:148), wherein $A_{18}$ is V or I;

$A_{19}$ is D, N or A;

$A_{20}$ is G, and $A_{21}$ is W.

In certain embodiments, the HA2 domain comprises the amino acid sequence $A_{38}$-$A_{39}$-$A_{40}$-$A_{41}$-$A_{42}$-$A_{43}$-$A_{44}$-$A_{45}$-$A_{46}$-$A_{47}$-$A_{48}$-$A_{49}$-$A_{50}$-$A_{51}$-$A_{52}$-$A_{53}$-$A_{54}$-$A_{55}$-$A_{56}$ (SEQ ID NO:149), wherein $A_{38}$ is K, Q, R, L or Y;

$A_{39}$ is any amino acid residue;

$A_{40}$ is any amino acid residue;

$A_{41}$ is T;

$A_{42}$ is Q;
$A_{43}$ is any amino acid residue;
$A_{44}$ is A;
$A_{45}$ is I;
$A_{46}$ is D;
$A_{47}$ is any amino acid residue;
$A_{48}$ is I, V or M;
$A_{49}$ is T, Q or N;
$A_{50}$ is any amino acid residue;
$A_{51}$ is K;
$A_{52}$ is V or L;
$A_{53}$ is N;
$A_{54}$ is any amino acid residue;
$A_{55}$ is V, I or L; and
$A_{56}$ is V or I.

In certain embodiments, the influenza stem domain polypeptides comprise two amino acid sequences selected from SEQ ID NOS:146-149. In certain embodiments, the influenza stem domain polypeptides comprise three amino acid sequences selected from SEQ ID NOS:146-149. In certain embodiments, the influenza stem domain polypeptides comprise four amino acid sequences selected from SEQ ID NOS:146-149.

As illustrated in FIGS. 1 and 2, HA1 N-terminal long stem segments share sequence identity between influenza A and influenza B and additionally across influenza A subtypes. Similarly, HA1 C-terminal long stem segments also share sequence identity between influenza A and influenza B and additionally across influenza A subtypes. Further, HA2 domains also share sequence identity between influenza A and influenza B and additionally across influenza A subtypes.

In some embodiments, the influenza hemagglutinin long stem domain polypeptide is a hybrid polypeptide that comprises or consists essentially of segments and/or domains from a plurality of influenza strains or subtypes. For example, an influenza hemagglutinin long stem domain polypeptide can comprise HA1 N-terminal and HA1 C-terminal long stem segments from different influenza A virus HA subtypes. In some embodiments, the HA1 N-terminal long stem segment is from influenza A virus while the HA1 C-terminal long stem segment is from influenza B virus. Similarly, HA2 may also be from influenza A virus while the HA1 N-terminal and/or C-terminal long stem segment is from influenza B virus.

It will be understood that any combination of the sequence elements listed in Tables 2-4, 6, 6a or the variants thereof may be used to form the hemagglutinin HA long stem domain polypeptides of the present invention.

In an influenza stem domain polypeptide provided herein, a linker covalently connects the HA1 N-terminal long stem segment to the HA1 C-terminal long stem segment. The linker can be any linked deemed suitable by one of skill in the art including, but not limited to, those linkers described herein.

In certain embodiments, influenza hemagglutinin long stem domain polypeptides are capable of forming a three dimensional structure that is similar to the three dimensional structure of the stem domain of a native influenza hemagglutinin. Structural similarity can be evaluated based on any technique deemed suitable by those of skill in the art including, but not limited to, those techniques described herein.

In certain embodiments, any influenza hemagglutinin long stem domain polypeptide provided herein can further comprise one or more polypeptide domains deemed suitable to those of skill in the art. Useful polypeptide domains include domains that facilitate purification, folding and cleavage of portions of a polypeptide. For example, a His tag (His-His-His-His-His-His, SEQ ID NO:166), FLAG epitope or other purification tag can facilitate purification of a polypeptide provided herein. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

Any trimerization domain, including a foldon from bacteriophage T4 fibritin can facilitate trimerization of polypeptides provided herein. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. The foldon domain can have any foldon sequence known to those of skill in the art (see, e.g., Papanikolopoulou et al., 2004, J. Biol. Chem. 279(10): 8991-8998, the contents of which are hereby incorporated by reference in their entirety. Examples include GSGYIPEAPRDGQAYVRKDGEWVLLSTFL (SEQ ID NO:167). A foldon domain can be useful to facilitate trimerization of soluble polypeptides provided herein. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO:168). In certain embodiments, the cleavage site is a cleavage site recognized by Tobacco Etch Virus (TEV) protease (e.g., amino acid sequence Glu-Asn-Leu-Tyr-Phe-Gln-(Gly/Ser)).

In certain embodiments, provided are influenza hemagglutinin long stem domain polypeptides comprising an elastase cleavage site as described herein. In particular embodiments, provided herein are influenza hemagglutinin long stem domain polypeptides comprising any of SEQ ID NOS:430-445 wherein the C-terminal amino acid residue, e.g. arginine or lysine, of SEQ ID NOS:430-445 is substituted with a valine residue.

In certain embodiments, provided herein are influenza hemagglutinin long stem domain polypeptides that are predicted to be resistant to protease cleavage at the junction between HA1 and HA2. Those of skill in the art should recognize that the Arg-Gly sequence spanning HA1 and HA2 is a recognition site for trypsin and is typically cleaved for hemagglutinin activation. Since the stem domain polypeptides described herein need not be activated, provided herein are influenza hemagglutinin long stem domain polypeptides that are predicted to be resistant to protease cleavage. In certain embodiments, provided is any influenza hemagglutinin long stem domain polypeptide described herein wherein the protease site spanning HA1 and HA2 is mutated to a sequence that is resistant to protease cleavage. In certain embodiments, provided is any influenza hemagglutinin long stem domain polypeptide described herein wherein the C-terminal residue of the HA1 C-terminal long stem segment is any residue other than Lys or Arg. In certain embodiments, provided is any influenza hemagglutinin long stem domain polypeptide described herein wherein the N-terminal residue of the HA2 domain is proline. In certain embodiments, provided is any influenza hemagglutinin long stem domain polypeptide described herein wherein the C-terminal residue of the HA1 C-terminal long stem segment is Ala and the N-terminal residue of the HA2 domain is also Ala. In certain embodiments, provided is any influenza hemagglutinin long stem domain polypeptide described herein wherein the N-terminal residue of the HA2 domain is any residue other than glycine.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain. In certain embodiments, the linker is a globular head, or a fragment thereof, from an influenza virus heterologous to the influenza stem domain. In certain embodiments, the linker is a globular head, or a fragment thereof, from an influenza virus heterologous to the stem domain of the HA2 subunit of the chimeric influenza virus hemagglutinin polypeptide. In certain embodiments, the linker is a globular head, or a fragment thereof, from an influenza virus heterologous to the stem domain of the HA1 and/or HA2 subunit of the chimeric influenza virus hemagglutinin.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to an HA2 luminal domain. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to an HA2 luminal domain. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to an HA2 luminal domain. In certain embodiments, the linker is a globular head, or a fragment thereof, from an influenza virus heterologous to the influenza stem domain. In certain embodiments, the linker is a globular head, or a fragment thereof, from an influenza virus heterologous to the stem domain of the HA2 subunit of the hemagglutinin. In certain embodiments, the linker is a globular head, or a fragment thereof, from an influenza virus heterologous to the stem domain of the HA1 and/or HA2 subunit of the hemagglutinin.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to, in sequence, a cleavage site, a trimerization domain and a purification tag. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to, in sequence, a cleavage site, a trimerization domain and a purification tag. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to, in sequence, a cleavage site, a trimerization domain and a purification tag. In certain embodiments, the protease cleavage site is a thrombin cleavage site. In certain embodiments, the cleavage site has the amino acid sequence LVPRGSP (SEQ ID NO:168). In certain embodiments, the cleavage site is a cleavage site recognized by Tobacco Etch Virus (TEV) protease (e.g., amino acid sequence Glu-Asn-Leu-Tyr-Phe-Gln-(Gly/Ser)). In certain embodiments, the trimerization domain is a foldon domain. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. In some embodiments, the purification tag is a His tag, having the sequence, $(H\ is)_n$, wherein n is 2, 3, 4, 5, 6, 7, 8, 9, 10, 11, 12, 13, 14, 15, 16, 17, 18, 19, 20 or greater.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to an HA2 luminal domain that is covalently linked to, in sequence, a cleavage site, a trimerization domain and a purification tag. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to an HA2 luminal domain that is covalently linked to, in sequence, a cleavage site, a trimerization domain and a purification tag. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to an HA2 luminal domain that is covalently linked to, in sequence, a cleavage site, a trimerization domain and a purification tag. In certain embodiments, the protease cleavage site is a thrombin cleavage site. In certain embodiments, the cleavage site has the amino acid sequence LVPRGSP (SEQ ID NO:168). In certain embodiments, the cleavage site is a cleavage site recognized by Tobacco Etch Virus (TEV) protease (e.g., amino acid sequence Glu-Asn-Leu-Tyr-Phe-Gln-(Gly/Ser)). In certain embodiments, the trimerization domain is a foldon domain. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to an HA2 luminal domain that is in turn covalently linked to an HA2 transmembrane domain. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to an HA2 luminal domain that is in turn covalently linked to an HA2 transmembrane domain. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to an HA2 luminal domain that is in turn covalently linked to an HA2 transmembrane domain.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to an HA2 luminal domain that is in turn covalently linked to an HA2 transmembrane domain that is in turn covalently linked to an HA2 cytoplasmic domain.

In certain embodiments, provided herein is an influenza hemagglutinin long stem domain polypeptide having a sequence selected from the group consisting of:
(SEQ ID NO:414)-LL-(SEQ ID NO:430)-(SEQ ID NO:66),
(SEQ ID NO:415)-LL-(SEQ ID NO:431)-(SEQ ID NO:67),
(SEQ ID NO:416)-LL-(SEQ ID NO:432)-(SEQ ID NO:68),
(SEQ ID NO:417)-LL-(SEQ ID NO:433)-(SEQ ID NO:69),
(SEQ ID NO:418)-LL-(SEQ ID NO:434)-(SEQ ID NO:70),
(SEQ ID NO:419)-LL-(SEQ ID NO:435)-(SEQ ID NO:71),
(SEQ ID NO:420)-LL-(SEQ ID NO:436)-(SEQ ID NO:72),
(SEQ ID NO:421)-LL-(SEQ ID NO:437)-(SEQ ID NO:73),
(SEQ ID NO:422)-LL-(SEQ ID NO:438)-(SEQ ID NO:74),
(SEQ ID NO:423)-LL-(SEQ ID NO:439)-(SEQ ID NO:75),
(SEQ ID NO:424)-LL-(SEQ ID NO:440)-(SEQ ID NO:76),
(SEQ ID NO:425)-LL-(SEQ ID NO:441)-(SEQ ID NO:77),
(SEQ ID NO:426)-LL-(SEQ ID NO:442)-(SEQ ID NO:78),
(SEQ ID NO:427)-LL-(SEQ ID NO:443)-(SEQ ID NO:79),
(SEQ ID NO:428)-LL-(SEQ ID NO:444)-(SEQ ID NO:80), and
(SEQ ID NO:429)-LL-(SEQ ID NO:445)-(SEQ ID NO:81),
wherein each sequence above is linked to the adjacent sequence as described herein and wherein LL is a linker as described herein. In particular, the HA1 C-terminal long stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)$_n$ (wherein n is any number of Glycine residues so long as there is flexibility in the peptide linker; in certain embodiments, n is 2, 3, 4, 5, 6, or 7 Glycine residues), Gly-Pro, ITPNGSIPNDKPFQNVNKITYGA (SEQ ID NO:165) and Asn-Ala-Ser.

In certain embodiments, provided herein is an influenza hemagglutinin long stem domain polypeptide having a sequence selected from the group consisting of:
(SEQ ID NO:414)-LL-(SEQ ID NO:430)-(SEQ ID NO:82),
(SEQ ID NO:415)-LL-(SEQ ID NO:431)-(SEQ ID NO:83),
(SEQ ID NO:416)-LL-(SEQ ID NO:432)-(SEQ ID NO:84),
(SEQ ID NO:417)-LL-(SEQ ID NO:433)-(SEQ ID NO:85),
(SEQ ID NO:418)-LL-(SEQ ID NO:434)-(SEQ ID NO:86),
(SEQ ID NO:419)-LL-(SEQ ID NO:435)-(SEQ ID NO:87),
(SEQ ID NO:420)-LL-(SEQ ID NO:436)-(SEQ ID NO:88),
(SEQ ID NO:421)-LL-(SEQ ID NO:437)-(SEQ ID NO:89),
(SEQ ID NO:422)-LL-(SEQ ID NO:438)-(SEQ ID NO:90),
(SEQ ID NO:423)-LL-(SEQ ID NO:439)-(SEQ ID NO:91),
(SEQ ID NO:424)-LL-(SEQ ID NO:440)-(SEQ ID NO:92),
(SEQ ID NO:425)-LL-(SEQ ID NO:441)-(SEQ ID NO:93),
(SEQ ID NO:426)-LL-(SEQ ID NO:442)-(SEQ ID NO:94),
(SEQ ID NO:427)-LL-(SEQ ID NO:443)-(SEQ ID NO:95),
(SEQ ID NO:428)-LL-(SEQ ID NO:444)-(SEQ ID NO:96), and
(SEQ ID NO:429)-LL-(SEQ ID NO:445)-(SEQ ID NO:97),
wherein each sequence above is linked to the adjacent sequence as described herein and wherein LL is a linker as described herein. In particular, the HA1 C-terminal long stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNGSIPNDKPFQNVNKITYGA (SEQ ID NO:165) and Asn-Ala-Ser.

In certain embodiments, provided herein is an influenza hemagglutinin long stem domain polypeptide having a sequence selected from the group consisting of:
(SEQ ID NO:414)-LL-(SEQ ID NO:430)-(SEQ ID NO:82)-(SEQ ID NO:98),
(SEQ ID NO:415)-LL-(SEQ ID NO:431)-(SEQ ID NO:83)-(SEQ ID NO:99),
(SEQ ID NO:416)-LL-(SEQ ID NO:432)-(SEQ ID NO:84)-(SEQ ID NO:100),
(SEQ ID NO:417)-LL-(SEQ ID NO:433)-(SEQ ID NO:85)-(SEQ ID NO:101),
(SEQ ID NO:418)-LL-(SEQ ID NO:434)-(SEQ ID NO:86)-(SEQ ID NO:102),
(SEQ ID NO:419)-LL-(SEQ ID NO:435)-(SEQ ID NO:87)-(SEQ ID NO:103),
(SEQ ID NO:420)-LL-(SEQ ID NO:436)-(SEQ ID NO:88)-(SEQ ID NO:104),
(SEQ ID NO:421)-LL-(SEQ ID NO:437)-(SEQ ID NO:89)-(SEQ ID NO:105),
(SEQ ID NO:422)-LL-(SEQ ID NO:438)-(SEQ ID NO:90)-(SEQ ID NO:106),
(SEQ ID NO:423)-LL-(SEQ ID NO:439)-(SEQ ID NO:91)-(SEQ ID NO:107), (SEQ ID NO:424)-LL-(SEQ ID NO:440)-(SEQ ID NO:92)-(SEQ ID NO:108),
(SEQ ID NO:425)-LL-(SEQ ID NO:441)-(SEQ ID NO:93)-(SEQ ID NO:109),
(SEQ ID NO:426)-LL-(SEQ ID NO:442)-(SEQ ID NO:94)-(SEQ ID NO:110),
(SEQ ID NO:427)-LL-(SEQ ID NO:443)-(SEQ ID NO:95)-(SEQ ID NO:111),
(SEQ ID NO:428)-LL-(SEQ ID NO:444)-(SEQ ID NO:96)-(SEQ ID NO:112), and
(SEQ ID NO:429)-LL-(SEQ ID NO:445)-(SEQ ID NO:97)-(SEQ ID NO:113),
wherein each sequence above is linked to the adjacent sequence as described herein and wherein LL is a linker as described herein. In particular, the HA1 C-terminal long stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNG-SIPNDKPFQNVNKITYGA (SEQ ID NO:165) and Asn-Ala-Ser.

In certain embodiments, provided herein is an influenza hemagglutinin long stem domain polypeptide having a sequence selected from the group consisting of:
(SEQ ID NO:414)-LL-(SEQ ID NO:430)-(SEQ ID NO:82)-(SEQ ID NO:168)-(SEQ ID NO:167)-(SEQ ID NO:166),
(SEQ ID NO:415)-LL-(SEQ ID NO:431)-(SEQ ID NO:83)-(SEQ ID NO:168)-(SEQ ID NO:167)-(SEQ ID NO:166),
(SEQ ID NO:416)-LL-(SEQ ID NO:432)-(SEQ ID NO:84)-(SEQ ID NO:168)-(SEQ ID NO:167)-(SEQ ID NO:166),
(SEQ ID NO:417)-LL-(SEQ ID NO:433)-(SEQ ID NO:85)-(SEQ ID NO:168)-(SEQ ID NO:167)-(SEQ ID NO:166),
(SEQ ID NO:418)-LL-(SEQ ID NO:434)-(SEQ ID NO:86)-(SEQ ID NO:168)-(SEQ ID NO:167)-(SEQ ID NO:166),
(SEQ ID NO:419)-LL-(SEQ ID NO:435)-(SEQ ID NO:87)-(SEQ ID NO:168)-(SEQ ID NO:167)-(SEQ ID NO:166),
(SEQ ID NO:420)-LL-(SEQ ID NO:436)-(SEQ ID NO:88)-(SEQ ID NO:168)-(SEQ ID NO:167)-(SEQ ID NO:166),
(SEQ ID NO:421)-LL-(SEQ ID NO:437)-(SEQ ID NO:89)-(SEQ ID NO:168)-(SEQ ID NO:167)-(SEQ ID NO:166),
(SEQ ID NO:422)-LL-(SEQ ID NO:438)-(SEQ ID NO:90)-(SEQ ID NO:168)-(SEQ ID NO:167)-(SEQ ID NO:166),
(SEQ ID NO:423)-LL-(SEQ ID NO:439)-(SEQ ID NO:91)-(SEQ ID NO:168)-(SEQ ID NO:167)-(SEQ ID NO:166),
(SEQ ID NO:424)-LL-(SEQ ID NO:440)-(SEQ ID NO:92)-(SEQ ID NO:168)-(SEQ ID NO:167)-(SEQ ID NO:166),
(SEQ ID NO:425)-LL-(SEQ ID NO:441)-(SEQ ID NO:93)-(SEQ ID NO:168)-(SEQ ID NO:167)-(SEQ ID NO:166),
(SEQ ID NO:426)-LL-(SEQ ID NO:442)-(SEQ ID NO:94)-(SEQ ID NO:168)-(SEQ ID NO:167)-(SEQ ID NO:166),
(SEQ ID NO:427)-LL-(SEQ ID NO:443)-(SEQ ID NO:95)-(SEQ ID NO:168)-(SEQ ID NO:167)-(SEQ ID NO:166),
(SEQ ID NO:428)-LL-(SEQ ID NO:444)-(SEQ ID NO:96)-(SEQ ID NO:168)-(SEQ ID NO:167)-(SEQ ID NO:166), and
(SEQ ID NO:429)-LL-(SEQ ID NO:445)-(SEQ ID NO:97)-(SEQ ID NO:113)-(SEQ ID NO:168)-(SEQ ID NO:167)-(SEQ ID NO:166),
wherein each sequence above is linked to the adjacent sequence as described herein and wherein LL is a linker as described herein. In particular, the HA1 C-terminal long stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNG-SIPNDKPFQNVNKITYGA (SEQ ID NO:165) and Asn-Ala-Ser.

In certain embodiments, provided herein is an influenza hemagglutinin long stem domain polypeptide having a sequence selected from the group consisting of:
(SEQ ID NO:446)-LL-(SEQ ID NO:494)-(SEQ ID NO:66),
(SEQ ID NO:447)-LL-(SEQ ID NO:495)-(SEQ ID NO:66),
(SEQ ID NO:448)-LL-(SEQ ID NO:496)-(SEQ ID NO:66),
(SEQ ID NO:449)-LL-(SEQ ID NO:497)-(SEQ ID NO:67), (SEQ ID NO:450)-LL-(SEQ ID NO:498)-(SEQ ID NO:67),
(SEQ ID NO:451)-LL-(SEQ ID NO:499)-(SEQ ID NO:67),
(SEQ ID NO:452)-LL-(SEQ ID NO:500)-(SEQ ID NO:68),
(SEQ ID NO:453)-LL-(SEQ ID NO:501)-(SEQ ID NO:68),
(SEQ ID NO:454)-LL-(SEQ ID NO:502)-(SEQ ID NO:68),
(SEQ ID NO:455)-LL-(SEQ ID NO:503)-(SEQ ID NO:69),
(SEQ ID NO:456)-LL-(SEQ ID NO:504)-(SEQ ID NO:69),
(SEQ ID NO:457)-LL-(SEQ ID NO:505)-(SEQ ID NO:69),
(SEQ ID NO:458)-LL-(SEQ ID NO:506)-(SEQ ID NO:70),
(SEQ ID NO:459)-LL-(SEQ ID NO:507)-(SEQ ID NO:70),
(SEQ ID NO:460)-LL-(SEQ ID NO:508)-(SEQ ID NO:70),
(SEQ ID NO:461)-LL-(SEQ ID NO:509)-(SEQ ID NO:71),
(SEQ ID NO:462)-LL-(SEQ ID NO:510)-(SEQ ID NO:71),
(SEQ ID NO:463)-LL-(SEQ ID NO:511)-(SEQ ID NO:71),
(SEQ ID NO:464)-LL-(SEQ ID NO:512)-(SEQ ID NO:72),
(SEQ ID NO:465)-LL-(SEQ ID NO:513)-(SEQ ID NO:72),
(SEQ ID NO:466)-LL-(SEQ ID NO:514)-(SEQ ID NO:72),
(SEQ ID NO:467)-LL-(SEQ ID NO:515)-(SEQ ID NO:73),
(SEQ ID NO:468)-LL-(SEQ ID NO:516)-(SEQ ID NO:73),
(SEQ ID NO:469)-LL-(SEQ ID NO:517)-(SEQ ID NO:73),
(SEQ ID NO:470)-LL-(SEQ ID NO:518)-(SEQ ID NO:74),
(SEQ ID NO:471)-LL-(SEQ ID NO:519)-(SEQ ID NO:74),
(SEQ ID NO:472)-LL-(SEQ ID NO:520)-(SEQ ID NO:74),
(SEQ ID NO:473)-LL-(SEQ ID NO:521)-(SEQ ID NO:75),
(SEQ ID NO:474)-LL-(SEQ ID NO:522)-(SEQ ID NO:75),
(SEQ ID NO:475)-LL-(SEQ ID NO:523)-(SEQ ID NO:75),
(SEQ ID NO:476)-LL-(SEQ ID NO:524)-(SEQ ID NO:76),
(SEQ ID NO:477)-LL-(SEQ ID NO:525)-(SEQ ID NO:76),
(SEQ ID NO:478)-LL-(SEQ ID NO:526)-(SEQ ID NO:76),
(SEQ ID NO:479)-LL-(SEQ ID NO:527)-(SEQ ID NO:77),
(SEQ ID NO:480)-LL-(SEQ ID NO:528)-(SEQ ID NO:77),
(SEQ ID NO:481)-LL-(SEQ ID NO:529)-(SEQ ID NO:77),
(SEQ ID NO:482)-LL-(SEQ ID NO:530)-(SEQ ID NO:78),
(SEQ ID NO:483)-LL-(SEQ ID NO:531)-(SEQ ID NO:78),
(SEQ ID NO:484)-LL-(SEQ ID NO:532)-(SEQ ID NO:78),
(SEQ ID NO:485)-LL-(SEQ ID NO:533)-(SEQ ID NO:79),
(SEQ ID NO:486)-LL-(SEQ ID NO:534)-(SEQ ID NO:79),
(SEQ ID NO:487)-LL-(SEQ ID NO:535)-(SEQ ID NO:79),
(SEQ ID NO:488)-LL-(SEQ ID NO:536)-(SEQ ID NO:80),
(SEQ ID NO:489)-LL-(SEQ ID NO:537)-(SEQ ID NO:80),
(SEQ ID NO:490)-LL-(SEQ ID NO:538)-(SEQ ID NO:80),
(SEQ ID NO:491)-LL-(SEQ ID NO:539)-(SEQ ID NO:81),
(SEQ ID NO:492)-LL-(SEQ ID NO:540)-(SEQ ID NO:81), and
(SEQ ID NO:493)-LL-(SEQ ID NO:541)-(SEQ ID NO:81), wherein each sequence above is linked to the adjacent sequence as described herein and wherein LL is a linker as described herein. In particular, the HA1 C-terminal long stem segments can be covalently or non-covalently linked to the HA2 domains. In certain embodiments, LL is selected from the group consisting of a direct bond, Gly, Gly-Gly, Gly-Gly-Gly, Gly-Gly-Gly-Gly, (Gly)n, Gly-Pro, ITPNG-SIPNDKPFQNVNKITYGA (SEQ ID NO:165) and Asn-Ala-Ser.

5.4 Glcosylation Variants

In another aspect, provided herein are flu hemagglutinin (HA) polypeptides comprising one or more modified glycosylation sites and/or one or more non-naturally occurring glycosylation sites. In specific embodiments, the flu HA polypeptide is a chimeric influenza virus hemagglutinin polypeptide comprising one or more modified glycosylation sites and/or one or more non-naturally occurring glycosylation sites. As shown in FIGS. 19C and B, glycosylation of a wild type hemagglutinin occurs in both the globular head and stem domains. It is believed that glycosylation within these domains can mask antigenic regions, thereby allowing an influenza virus to evade a host immune system response. For example, seasonal influenza virus strains (e.g., H1N1 and H3N2) have been known to acquire additional glycosylation sites overtime in immunodominant antigenic regions of the globular head domain. Within the context of an influenza virus HA polypeptide described herein, however, glycosylation within the stem domain of the polypeptide can hinder or prevent desired immune responses against the conserved antigenic regions found in this domain.

Without being bound by any particular theory of operation, it is believed that an immune response to conserved antigenic regions within the stem domain of the influenza virus HA polypeptide provided herein can be increased by modifying one or more glycosylation sites within the stem domain in a manner that disrupts the glycosylation (i.e. the attachment of a glycan) at the sites. In addition, it is believed that masking of the immunodominant antigenic regions of the HA globular head domain by the addition of one or more non-naturally occurring glycosylation sites in these immunodominant regions can also increase the immunogenicity of conserved subimmunodominant antigenic regions within the stem domain. See FIG. 19C.

The flu hemagglutinin (HA) polypeptides comprising one or more modified glycosylation sites and/or one or more non-naturally occurring glycosylation sites can be used in accordance with the methods of vaccination described herein, i.e., such mutant HA polypeptides can be administered to a subject so as to elicit influenza virus stalk/stem domain-specific antibodies in the subject. To assess the ability of the mutant HA polypeptides to elicit such stalk-directed antibodies, subjects (e.g., mice) can be immunized with the mutant HA polypeptides described herein, or virus (e.g., influenza virus) expressing the mutant HA polypeptides described herein, and the ability of such mutant HA polypeptides or viruses expressing such mutant HA polypeptides to elicit the production stem/stalk domain specific antibodies can be assessed and compared to the ability of counterepart wild-type HA or wild-type viruses to elicit the production stem/stalk domain specific antibodies in the subject. For example, to assess the ability of the mutant HA polypeptides to elicit stalk-directed antibodies, mice can be immunized with a strain or subtype of wildtype influenza virus, influenza virus expressing HA mutants having glycosylation sites added to the head domain, and influenza virus expressing HA mutants with glycosylation sites removed from the stalk domain, and combinations thereof. Such mice then can be primed with influenza virus DNA or innoculated with viral protein. Three weeks later, such mice can be boosted with viral protein. Three weeks after being boosted with viral protein, the mice can be challenged with various influenza virus strains and monitored for weight loss and survival. The serum titers of anti-head and anti-stalk antibodies in infected mice can be assessed by ELISA as described below.

5.4.1 Modified Glycosylation Sites in the Stem Domain

In one embodiment, the flu hemagglutinin (HA) polypeptide provided herein comprises an HA stem domain comprising at least one modified glycosylation site, wherein the modified glycosylation site comprises a modification of a naturally occurring glycosylation site that disrupts the ability of a glycan to attach to the modified glycosylation site. Without being bound by any particular theory of operation, it is believed that conserved antigenic regions within the stem domain of the flu HA polypeptide are shielded from a subject's immune system (e.g., an antibody response) by glycans that attach to these antigenic regions. Therefore, it is believed that immunogenicity of and accessibility to antigenic regions within the stem domain can be increased by modifying one or more glycosylation sites within the stem domain in a manner that disrupts the glycosylation (i.e. the attachment of a glycan) at the sites.

Modified glycosylation sites in which a naturally occurring glycosylation site is modified in a manner that disrupts the ability of a glycan to attach to the modified glycosylation site can be made by any technique apparent to one of skill in the art, including the methods described herein, including, for example, the site directed mutagenesis techniques discussed in Example 5, infra In certain embodiments, the flu hemagglutinin (HA) polypeptide comprises an HA stem domain comprising at least one, two, three, four, five, six, seven, eight, nine, ten, eleven, twelve, thirteen, fourteen, fifteen, or twenty or more modified glycosylation sites, wherein the modified glycosylation site comprises a modification of a naturally occurring glycosylation site that disrupts the ability of a glycan to attach to the modified glycosylation site. In certain embodiments, the HA stem domain of the flu hemagglutinin (HA) polypeptide comprises 1-3, 4-6, 7-9, 10-12, 13-15, 16-18, 19-21 modified glycosylation sites. In other embodiments, the HA stem domain of the flu hemagglutinin (HA) polypeptide comprises 1-5, 6-10, 11-15, 16-20, 21-25 modified glycosylation sites. In certain embodiments, the HA stem domain of the flu hemagglutinin (HA) polypeptide comprises one modified glycosylation site. In certain embodiments, the HA stem domain of the flu hemagglutinin (HA) polypeptide comprises two modified glycosylation sites. In certain embodiments, the HA stem domain of the flu hemagglutinin (HA) polypeptide comprises three modified glycosylation sites. In certain embodiments, the HA stem domain of the flu hemagglutinin (HA) polypeptide comprises four modified glycosylation site. In certain embodiments, the HA stem domain of the flu hemagglutinin (HA) polypeptide comprises five modified glycosylation sites. In certain embodiments, the HA stem domain of the flu hemagglutinin (HA) polypeptide comprises six modified glycosylation sites. In certain embodiments, the HA stem domain of the flu hemagglutinin (HA) polypeptide comprises seven modified glycosylation sites. In certain embodiments, the HA stem domain of the flu hemagglutinin (HA) polypeptide comprises eight modified glycosylation sites. In certain embodiments, the HA stem domain of the flu hemagglutinin (HA) polypeptide comprises nine modified glycosylation sites. In certain embodiments, the HA stem domain of the flu hemagglutinin (HA) polypeptide comprises ten modified glycosylation sites. In certain embodiments, the HA stem domain of the flu hemagglutinin (HA) polypeptide comprises eleven modified glycosylation sites. In certain embodiments, the HA stem domain of the flu hemagglutinin (HA) polypeptide comprises twelve modified glycosylation sites. In certain embodiments, the HA stem domain of the flu hemagglutinin (HA) polypeptide comprises thirteen modified glycosylation sites. In certain embodiments, the HA stem domain of the flu hemagglutinin (HA) polypeptide comprises fourteen modified glycosylation sites. In certain embodiments, the HA stem domain of the flu hemagglutinin (HA) polypeptide comprises fifteen modified glycosylation sites. In certain embodiments, the HA stem domain of the flu hemagglutinin (HA) polypeptide comprises sixteen modified glycosylation sites. In certain embodiments, the HA stem domain of the flu hemagglutinin (HA) polypeptide comprises seventeen modified glycosylation sites. In certain embodiments, the HA stem domain of the flu hemagglutinin (HA) polypeptide comprises eighteen modified glycosylation sites. In certain embodiments, the HA stem domain of the flu hemagglutinin (HA) polypeptide comprises nineteen modified glycosylation sites. In certain embodiments, the HA stem domain of the flu hemagglutinin (HA) polypeptide comprises twenty or more modified glycosylation sites.

Modified glycosylation sites include, but are not limited to, N-linked and O-linked glycosylation sites. In certain embodiments, the modified glycosylation site is an N-linked glycosylation site. In other embodiments, the modified glycosylation site is an O-linked glycosylation site. In some embodiments, the modified glycosylation site is a modified N-linked glycosylation site having the amino acid motif Asn-Xaa-Ser/Thr/Cys, wherein Xaa is any amino acid or, in certain embodiments, wherein Xaa is any amino acid except Pro.

The modified glycosylation site can comprise any modification that can disrupt the ability of a glycan to attach to the modified glycosylation site. In preferred embodiments, the modification does not interfere with the proper folding of the flu hemagglutinin (HA) polypeptide and/or the ability of the flu hemagglutinin (HA) polypeptide to elicit an immune response in a subject. In certain embodiments, the modification comprises a deletion of one or more amino acid residues in a naturally occurring glycosylation site. In other embodiments, the modification comprises one or more amino acid substitutions in a naturally occurring glycosylation site.

In certain embodiments, the modified glycosylation site comprises one or more amino acid substitutions in a naturally occurring glycosylation site comprising the amino acid sequence Asn-Xaa-Ser/Thr/Cys, wherein Xaa is any amino acid or, in certain embodiments, wherein Xaa is any amino acid except Pro, and wherein the modification disrupts the ability of a glycan to attach to the modified glycosylation site. The modified glycosylation site can comprise any amino acid substitution know to one of skill in art that can disrupt the ability of a glycan to attach to the modified glycosylation site. In preferred embodiments, the one or more amino acid substitutions does not interfere with the ability of the flu hemagglutinin (HA) polypeptide to fold properly or elicit an immune response in a subject. In certain embodiments, the one or more amino acids of a naturally occurring glycosylation site is substituted for an Asn (N), Ser (S), Thr (T) or Asp (D) amino acid residue. Exemplary amino acid substitutions include, but are not limited to, substitution of an Asn (N) for a Lys (K) amino acid residue; substitution of a Ser (S) for an Asn (N) residue; and substitution of a Thr (T) for an Asp (D) residue. In specific embodiments, the modified glycosylation site comprises a substitution of an Asn (N) residue of a naturally occurring glycosylation site for a Lys (K) residue. In other embodiments, the modified glycosylation site comprises a substitution of a Ser (S) residue of a naturally occurring glycosylation site for an Asn (N) amino acid residue. In yet other embodiments, the modified glycosylation site comprises a substitution of a Thr (T) residue of a naturally occurring glycosylation site for an Asp (D) amino acid residue.

In certain embodiments, the modification comprises one or more amino acid substitutions in a naturally occurring glycosylation site comprising the amino acid sequence Asn-Ala-Ser. In certain embodiments, the modification comprises one or more amino acid substitutions in a naturally occurring glycosylation site comprising the amino acid sequence Asn-Asp-Ser. In some embodiments, the modification comprises one or more amino acid substitutions in a naturally occurring glycosylation site comprising the amino acid sequence Asn-Arg-Ser. In other embodiments, the modification comprises one or more amino acid substitutions in a naturally occurring glycosylation site comprising the amino acid sequence Asn-Asn-Ser. In certain embodiments, the modification comprises one or more amino acid substitutions in a naturally occurring glycosylation site comprising the amino acid sequence Asn-Cys-Ser. In certain embodiments, the modification comprises one or more amino acid substitutions in a naturally occurring glycosylation site comprising the amino acid sequence Asn-Glu-Ser. In other embodiments, the modification comprises one or more amino acid substitutions in a naturally occurring glycosylation site comprising the amino acid sequence Asn-Gln-Ser. In some embodiments, the modification comprises one or more amino acid substitutions in a naturally occurring glycosylation site comprising the amino acid sequence Asn-Gly-Ser. In certain embodiments, the modification comprises one or more amino acid substitutions in a naturally occurring glycosylation site comprising the amino acid sequence Asn-His-Ser. In other embodiments, the modification comprises one or more amino acid substitutions in a naturally occurring glycosylation site comprising the amino acid sequence Asn-Ile-Ser. In some embodiments, the modification comprises one or more amino acid substitutions in a naturally occurring glycosylation site comprising the amino acid sequence Asn-Lys-Ser. In certain embodiments, the modification comprises one or more amino acid substitutions in a naturally occurring glycosylation site comprising the amino acid sequence Asn-Leu-Ser. In other embodiments, the modification comprises one or more amino acid substitutions in a naturally occurring glycosylation site comprising the amino acid sequence Asn-Met-Ser. In other embodiments, the modification comprises one or more amino acid substitutions in a naturally occurring glycosylation site comprising the amino acid sequence Asn-Phe-Ser. In certain embodiments, the modification comprises one or more amino acid substitutions in a naturally occurring glycosylation site comprising the amino acid sequence Asn-Pro-Ser. In some embodiments, the modification comprises one or more amino acid substitutions in a naturally occurring glycosylation site comprising the amino acid sequence Asn-Ser-Ser. In certain embodiments, the modification comprises one or more amino acid substitutions in a naturally occurring glycosylation site comprising the amino acid sequence Asn-Thr-Ser. In other embodiments, the modification comprises one or more amino acid substitutions in a naturally occurring glycosylation site comprising the amino acid sequence Asn-Trp-Ser. In certain embodiments, the modification comprises one or more amino acid substitutions in a naturally occurring glycosylation site comprising the amino acid sequence Asn-Tyr-Ser. In certain embodiments, the modification comprises one or more amino acid substitutions in a naturally occurring glycosylation site comprising the amino acid sequence Asn-Val-Ser.

In certain embodiments, the modification comprises one or more amino acid substitutions in a naturally occurring glycosylation site comprising the amino acid sequence Asn-Ala-Thr. In certain embodiments, the modification comprises one or more amino acid substitutions in a naturally occurring glycosylation site comprising the amino acid sequence Asn-Asp-Thr. In some embodiments, the modification comprises one or more amino acid substitutions in a naturally occurring glycosylation site comprising the amino acid sequence Asn-Arg-Thr. In other embodiments, the modification comprises one or more amino acid substitutions in a naturally occurring glycosylation site comprising the amino acid sequence Asn-Asn-Thr. In certain embodiments, the modification comprises one or more amino acid substitutions in a naturally occurring glycosylation site comprising the amino acid sequence Asn-Cys-Thr. In certain embodiments, the modification comprises one or more amino acid substitutions in a naturally occurring glycosylation site comprising the amino acid sequence Asn-Glu-Thr. In other embodiments, the modification comprises one or more amino acid substitutions in a naturally occurring glycosylation site comprising the amino acid sequence Asn-Gln-Thr. In some embodiments, the modification comprises one or more amino acid substitutions in a naturally occurring glycosylation site comprising the amino acid sequence Asn-Gly-Thr. In certain embodiments, the modification comprises one or more amino acid substitutions in a naturally occurring glycosylation site comprising the amino acid sequence Asn-His-Thr. In other embodiments, the modification comprises one or more amino acid substitutions in a naturally occurring glycosylation site comprising the amino acid sequence Asn-Ile-Thr. In some embodiments, the modification comprises one or more amino acid substitutions in a naturally occurring glycosylation site comprising the amino acid sequence Asn-Lys-Thr. In certain embodiments, the modification comprises one or more amino acid substitutions in a naturally occurring glycosylation site comprising the amino acid sequence Asn-Leu-Thr. In other embodiments, the modification comprises one or more amino acid substitutions in a naturally occurring glycosylation site comprising the amino acid sequence Asn-Met-Thr. In other embodiments, the modification comprises one or more amino acid substitutions in a naturally occurring glycosylation site comprising the amino acid sequence Asn-Phe-Thr. In certain embodiments, the modification comprises one or more amino acid substitutions in a naturally occurring glycosylation site comprising the amino acid sequence Asn-Pro-Thr. In some embodiments, the modification comprises one or more amino acid substitutions in a naturally occurring glycosylation site comprising the amino acid sequence Asn-Ser-Thr. In certain embodiments, the modification comprises one or more amino acid substitutions in a naturally occurring glycosylation site comprising the amino acid sequence Asn-Thr-Thr. In other embodiments, the modification comprises one or more amino acid substitutions in a naturally occurring glycosylation site comprising the amino acid sequence Asn-Trp-Thr. In certain embodiments, the modification comprises one or more amino acid substitutions in a naturally occurring glycosylation site comprising the amino acid sequence Asn-Tyr-Thr. In certain embodiments, the modification comprises one or more amino acid substitutions in a naturally occurring glycosylation site comprising the amino acid sequence Asn-Val-Thr.

In certain embodiments, the modification comprises one or more amino acid substitutions in a naturally occurring glycosylation site comprising the amino acid sequence Asn-Ala-Cys. In certain embodiments, the modification comprises one or more amino acid substitutions in a naturally occurring glycosylation site comprising the amino acid sequence Asn-Asp-Cys. In some embodiments, the modification comprises one or more amino acid substitutions in a naturally occurring glycosylation site comprising the amino acid sequence Asn-Arg-Cys. In other embodiments, the modification comprises one or more amino acid substitutions in a naturally occurring glycosylation site comprising the amino acid sequence Asn-Asn-Cys. In certain embodiments, the modification comprises one or more amino acid substitutions in a naturally occurring glycosylation site comprising the amino acid sequence Asn-Cys-Cys. In certain embodiments, the modification comprises one or more amino acid substitutions in a naturally occurring glycosylation site comprising the amino acid sequence Asn-Glu-Cys. In other embodiments, the modification comprises one or more amino acid substitutions in a naturally occurring glycosylation site comprising the amino acid sequence Asn-Gln-Cys. In some embodiments, the modification comprises one or more amino acid substitutions in a naturally occurring glycosylation site comprising the amino acid sequence Asn-Gly-Cys. In certain embodiments, the modification comprises one or more amino acid substitutions in a naturally occurring glycosylation site comprising the amino acid sequence Asn-His-Cys. In other embodiments, the modification comprises one or more amino acid substitutions in a naturally occurring glycosylation site comprising the amino acid sequence Asn-Ile-Cys. In some embodiments, the modification comprises one or more amino acid substitutions in a naturally occurring glycosylation site comprising the amino acid sequence Asn-Lys-Cys. In certain embodiments, the modification comprises one or more amino acid substitutions in a naturally occurring glycosylation site comprising the amino acid sequence Asn-Leu-Cys. In other embodiments, the modification comprises one or more amino acid substitutions in a naturally occurring glycosylation site comprising the amino acid sequence Asn-Met-Cys. In other embodiments, the modification comprises one or more amino acid substitutions in a naturally occurring glycosylation site comprising the amino acid sequence Asn-Phe-Cys. In certain embodiments, the modification comprises one or more amino acid substitutions in a naturally occurring glycosylation site comprising the amino acid sequence Asn-Pro-Cys. In some embodiments, the modification comprises one or more amino acid substitutions in a naturally occurring glycosylation site comprising the amino acid sequence Asn-Ser-Cys. In certain embodiments, the modification comprises one or more amino acid substitutions in a naturally occurring glycosylation site comprising the amino acid sequence Asn-Thr-Cys. In other embodiments, the modification comprises one or more amino acid substitutions in a naturally occurring glycosylation site comprising the amino acid sequence Asn-Trp-Cys. In certain embodiments, the modification comprises one or more amino acid substitutions in a naturally occurring glycosylation site comprising the amino acid sequence Asn-Tyr-Cys. In certain embodiments, the modification comprises one or more amino acid substitutions in a naturally occurring glycosylation site comprising the amino acid sequence Asn-Val-Cys.

Conserved naturally occurring glycosylation sites in the HA stem domain include those shown in FIG. 20. Exemplary naturally occurring N-glycosylation sites in group 1 hemagglutinins (H1, H2, H5, H6, H8, H9, H11, H12, H13, and H16) can be found at, but are not limited to, amino acid positions 20-22 (missing in H9), 21-23, 33-35 (missing in H8, H9, H12, H13, H16), 46-48 (missing in H1, H2, H5, H6, H8, H9, H11, H12), 289-291 (missing in H6, H11, H13, H16), 290-292 (missing in H1, H2, H5, H8, H9, H12), 296-298 (missing in H1, H2, H5, H11, H13, H16) and 481-483, wherein the amino acid positions are according to H3 numbering. In certain embodiments, the hemagglutinin (HA) polypeptide comprises a modified glycosylation site at amino acid positions 20-22, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 21-23, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 33-35, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 46-48, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 289-291, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 290-292, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 296-298, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 481-483, according to H3 numbering, wherein the modified glycosylation site comprises a modification that disrupts glycosylation at the modified glycosylation site.

In certain embodiments, the flu hemagglutinin (HA) polypeptide comprises two modified glycosylation sites at amino acid positions selected from the group consisting of amino acid positions 20-22, 21-23, 33-35, 46-48, 289-291, 290-292, 296-298 and 481-483, according to H3 numbering, wherein each modified glycosylation site comprises a modification that disrupts glycosylation at the modified glycosylation site. In other embodiments, the flu hemagglutinin (HA) polypeptide comprises three modified glycosylation sites at amino acid positions selected from the group consisting of amino acid positions 20-22, 21-23, 33-35, 46-48, 289-291, 290-292, 296-298 and 481-483, according to H3 numbering, wherein each modified glycosylation site comprises a modification that disrupts glycosylation at the modified glycosylation site. In certain embodiments, the flu hemagglutinin (HA) polypeptide comprises four modified glycosylation sites at amino acid positions selected from the group consisting of amino acid positions 20-22, 21-23, 33-35, 46-48, 289-291, 290-292, 296-298 and 481-483, according to H3 numbering, wherein each modified glycosylation site comprises a modification that disrupts glycosylation at the modified glycosylation site. In some embodiments, the flu hemagglutinin (HA) polypeptide comprises five modified glycosylation sites at amino acid positions selected from the group consisting of amino acid positions 20-22, 21-23, 33-35, 46-48, 289-291, 290-292, 296-298 and 481-483, according to H3 numbering, wherein each modified glycosylation site comprises a modification that disrupts glycosylation at the modified glycosylation site. In certain embodiments, the flu hemagglutinin (HA) polypeptide comprises six modified glycosylation sites at amino acid positions selected from the group consisting of amino acid positions 20-22, 21-23, 33-35, 46-48, 289-291, 290-292, 296-298 and 481-483, according to H3 numbering, wherein each modified glycosylation site comprises a modification that disrupts glycosylation at the modified glycosylation site. In other embodiments, the flu hemagglutinin (HA) polypeptide comprises seven modified glycosylation sites at amino acid positions selected from the group consisting of amino acid positions 20-22, 21-23, 33-35, 46-48, 289-291, 290-292, 296-298 and 481-483, according to H3 numbering, wherein each modified glycosylation site comprises a modification that disrupts glycosylation at the modified glycosylation site. In yet other embodiments, the flu hemagglutinin (HA) polypeptide comprises modified glycosylation sites at amino acid positions 20-22, 21-23, 33-35, 46-48, 289-291, 290-292, 296-298 and 481-483, according to H3 numbering, wherein each modified glycosylation site comprises a modification that disrupts glycosylation at the modified glycosylation site.

Exemplary conserved N-glycosylation sites in group 2 hemagglutinins (H3, H4, H7, H10, H14, H15), can be found at, but are not limited to, amino acid positions, 8-10, 22-24, 38-40 (missing in H4, H14), 46-48 (missing in H3, H4, H7, H10, H14) 285-287 (missing in H4, H7, H10, H14, H15), 296-298 (missing in H3, H7, H15), 410-412 (missing in H3, H4, H14) and 481-483, wherein the amino acid positions are according to H3 numbering. In certain embodiments, the flu hemagglutinin (HA) polypeptide comprises a modified glycosylation site at amino acid positions 8-10, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 22-24, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 38-40, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 46-48, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 285-287, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 296-298, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 410-412, according to H3 numbering, wherein the modified glycosylation site comprises a modification that disrupts glycosylation at the modified glycosylation site. In certain embodiments, the flu hemagglutinin (HA) polypeptide comprises a modified glycosylation site at amino acid positions 481-483, according to H3 numbering, wherein the modified glycosylation site comprises a modification that disrupts glycosylation at the modified glycosylation site.

In certain embodiments, the flu hemagglutinin (HA) polypeptide comprises two modified glycosylation sites at amino acid positions selected from the group consisting of amino acid positions 8-10, 22-24, 38-40, 46-48, 285-287, 296-298, 410-412 and 481-483, according to H3 numbering, wherein each of the modified glycosylation sites comprises a modification that disrupts glycosylation at the modified glycosylation site. In certain embodiments, the flu hemagglutinin (HA) polypeptide comprises three modified glycosylation sites at amino acid positions selected from the group consisting of amino acid positions 8-10, 22-24, 38-40, 46-48, 285-287, 296-298, 410-412 and 481-483, according to H3 numbering, wherein each of the modified glycosylation sites comprises a modification that disrupts glycosylation at the modified glycosylation site. In certain embodiments, the flu hemagglutinin (HA) polypeptide comprises four modified glycosylation sites at amino acid positions selected from the group consisting of amino acid positions 8-10, 22-24, 38-40, 46-48, 285-287, 296-298, 410-412 and 481-483, according to H3 numbering, wherein each of the modified glycosylation sites comprises a modification that disrupts glycosylation at the modified glycosylation site. In certain embodiments, the flu hemagglutinin (HA) polypeptide comprises five modified glycosylation sites at amino acid positions selected from the group consisting of amino acid positions 8-10, 22-24, 38-40, 46-48, 285-287, 296-298, 410-412 and 481-483, according to H3 numbering, wherein each of the modified glycosylation sites comprises a modification that disrupts glycosylation at the modified glycosylation site. In certain embodiments, the flu hemagglutinin (HA) polypeptide comprises six modified glycosylation sites at amino acid positions selected from the group consisting of amino acid positions 8-10, 22-24, 38-40, 46-48, 285-287, 296-298, 410-412 and 481-483, according to H3 numbering, wherein each of the modified glycosylation sites comprises a modification that disrupts glycosylation at the modified glycosylation site. In certain embodiments, the flu hemagglutinin (HA) polypeptide comprises seven modified glycosylation sites at amino acid positions selected from the group consisting of amino acid positions 8-10, 22-24, 38-40, 46-48, 285-287, 296-298, 410-412 and 481-483, according to H3 numbering, wherein each of the modified glycosylation sites comprises a modification that disrupts glycosylation at the modified glycosylation site. In certain embodiments, the flu hemagglutinin (HA) polypeptide comprises modified glycosylation sites at amino acid positions 8-10, 22-24, 38-40, 46-48, 285-287, 296-298, 410-412 and 481-483, according to H3 numbering, wherein each of the modified glycosylation sites comprises a modification that disrupts glycosylation at the modified glycosylation site.

In certain embodiments, the flu hemagglutinin (HA) polypeptide comprises one, two or more modified glycosylation sites at amino acid residues 20-23, 33-35, 289-291 and 483-485, according to H3 numbering, wherein the modified glycosylation sites comprise a modification that disrupts glycosylation at the modified glycosylation sites. In other embodiments, the flu hemaglutinin (HA) polypeptide comprises two modified glycosylation sites at amino acid residues 33-35 and 289-291, according to H3 numbering, wherein the modified glycosylation sites comprise a modification that disrupts glycosylation at the modified glycosylation sites.

The flu hemagglutinin polypeptide comprising a HA stem domain comprising at least one modified glycosylation site can be any flu hemagglutinin (HA) polypeptide comprising an HA stem domain described herein, including, but not limited to, a chimeric influenza virus hemagglutinin polypeptide, a non-chimeric influenza virus hemagglutinin polypeptide (i.e., an influenza virus hemagglutinin polypeptide comprising an HA stem domain and an HA head domain from the same subtype or strain), and an influenza virus hemagglutinin stem domain polypeptide.

In certain embodiments, the flu hemagglutinin (HA) polypeptide is a chimeric influenza virus hemagglutinin polypeptide. In specific embodiments, the chimeric influenza virus hemagglutinin (HA) polypeptide comprises an HA stem domain and an HA globular head domain, wherein the HA globular head domain is heterologous to the HA stem domain, and wherein the HA stem domain comprises at least one modified glycosylation site, wherein the modified glycosylation site comprises a modification of a naturally occurring glycosylation site that disrupts the ability of a glycan to attach to the modified glycosylation site. In specific embodiments, the modification comprises one or more amino acid substitutions in a naturally occurring glycosylation site having the amino acid sequence Asn-Xaa-Ser/Thr/Cys, wherein Xaa is any amino acid or, in certain embodiments, wherein Xaa is any amino acid except Pro.

In certain embodiments, the flu hemagglutinin (HA) polypeptide is a non-chimeric influenza virus hemagglutinin polypeptide. In specific embodiments, the non-chimeric influenza virus hemagglutinin polypeptide comprises an HA stem domain and an HA globular head domain, wherein the HA globular head domain is homologous to the HA stem domain (i.e., the globular head domain and stem domain are from the same influenza virus strain or subtype), and wherein the HA stem domain comprises at least one modified glycosylation site, wherein the modified glycosylation site comprises a modification of a naturally occurring glycosylation site that disrupts the ability of a glycan to attach to the modified glycosylation site. In specific embodiments, the modification comprises one or more amino acid substitutions in a naturally occurring glycosylation site having the amino acid sequence Asn-Xaa-Ser/Thr/Cys, wherein Xaa is any amino acid or, in certain embodiments, wherein Xaa is any amino acid except Pro. In certain embodiments, the non-chimeric influenza virus hemagglutinin polypeptide comprises an HA stem domain and HA globular head domain from the same influenza virus subtype. In specific embodiments, the influenza virus subtype is an H1, H2, H3, H4, H5, H6, H7, H8, H9, H10, H11, H12, H13, H14, H15, H16, or H17 subtype. In specific embodiments, the non-chimeric influenza virus hemagglutinin polypeptide comprises an HA stem domain and HA globular head domain from the same influenza virus strain. In certain embodiments, the influenza virus strain is A/Netherlands/602/2009.

In certain embodiments, the flu hemagglutinin (HA) polypeptide is an influenza virus hemagglutinin stem domain polypeptide. Exemplary influenza virus hemagglutinin stem domain polypeptides are disclosed in Section 5.2, supra.

In a specific embodiment, the influenza virus hemagglutinin stem domain polypeptide comprises: (a) an influenza hemagglutinin HA1 domain that comprises an HA1 N-terminal stem segment covalently linked to a linker of 1 to 50 heterologous residues that is in turn covalently linked to an HA1 C-terminal short stem segment; said HA1 domain in tertiary or quaternary association with (b) an influenza hemagglutinin HA2 domain, wherein the influenza virus hemagglutinin stem domain polypeptide further comprises at least one modified glycosylation site, wherein the modified glycosylation site comprises a modification of a naturally occurring glycosylation site that disrupts the ability of a glycan to attach to the modified glycosylation site. In a specific embodiment, the modification comprises one or more amino acid substitutions in a naturally occurring glycosylation site having the amino acid sequence Asn-Xaa-Ser/Thr/Cys, wherein Xaa is any amino acid or, in certain embodiments, wherein Xaa is any amino acid except Pro. In another embodiment, the influenza virus hemagglutinin stem domain polypeptide comprises: (a) an influenza hemagglutinin HA1 domain that comprises an HA1 N-terminal long stem segment covalently linked to a linker of 1 to 50 heterologous residues that is in turn covalently linked to an HA1 C-terminal long stem segment; said HA1 domain in tertiary or quaternary association with (b) an influenza hemagglutinin HA2 domain, wherein the influenza virus hemagglutinin stem domain polypeptide further comprises at least one modified glycosylation site, wherein the modified glycosylation site comprises a modification of a naturally occurring glycosylation site that disrupts the ability of a glycan to attach to the modified glycosylation site. In another embodiment, the modification comprises one or more amino acid substitutions in a naturally occurring glycosylation site having the amino acid sequence Asn-Xaa-Ser/Thr/Cys, wherein Xaa is any amino acid or, in certain embodiments, wherein Xaa is any amino acid except Pro. In another embodiment, the influenza virus hemagglutinin stem domain polypeptide comprises: (a) an influenza hemagglutinin HA1 domain that comprises an HA1 N-terminal stem segment covalently linked to a linker of 1 to 50 heterologous residues that is in turn covalently linked to an HA1 C-terminal stem segment; said HA1 domain in tertiary or quaternary association with (b) an influenza hemagglutinin HA2 domain, wherein the influenza virus hemagglutinin stem domain polypeptide further comprises at least one modified glycosylation site, wherein the modified glycosylation site comprises a modification of a naturally occurring glycosylation site that disrupts the ability of a glycan to attach to the modified glycosylation site. In a specific embodiment, the modification comprises one or more amino acid substitutions in a naturally occurring glycosylation site having the amino acid sequence Asn-Xaa-Ser/Thr/Cys, wherein Xaa is any amino acid or, in certain embodiments, wherein Xaa is any amino acid except Pro. In another embodiment, the influenza virus hemagglutinin stem domain polypeptide comprises: (a) an influenza hemagglutinin HA1 domain that comprises, linked in the following order: an HA1 N-terminal stem segment, a first linker of 1 to 50 heterologous residues, an HA1 intermediate stem segment, a second linker of 1 to 50 heterologous residues and an HA1 C-terminal stem segment; said HA1 domain in tertiary or quaternary association with (b) an influenza hemagglutinin HA2 domain, wherein the influenza virus hemagglutinin stem domain polypeptide further comprises at least one modified glycosylation site, wherein the modified glycosylation site comprises a modification of a naturally occurring glycosylation site that disrupts the ability of a glycan to attach to the modified glycosylation site. In a specific embodiment, the modification comprises one or more amino acid substitutions in a naturally occurring glycosylation site having the amino acid sequence Asn-Xaa-Ser/Thr/Cys, wherein Xaa is any amino acid, or, in certain embodiments, wherein Xaa is any amino acid except Pro.

5.4.2 Non-Naturally Occurring Glycosylation Sites in the Globular Head Domain In another embodiment, the flu hemagglutinin (HA) polypeptide provided herein comprises an HA globular head domain comprising at least one non-naturally occurring glycosylation site. Without being bound by any particular theory of operation, it is believed that masking of the immunodominant antigenic regions of the HA globular head domain by the addition of one or more non-naturally occurring glycosylation sites in these immunodominant regions can also increase immunogenicity to the conserved subimmunodominant antigenic regions in the stem domain of the flu hemagglutinin (HA) polypeptide.

Non-naturally occurring glycosylation sites can be added to the HA globular head domain of the flu hemagglutinin (HA) polypeptide described herein using any known technique known to one of skill in the art, including, for example, the site directed mutagenesis techniques described in Example 5, infra. In preferred/specific embodiments, the non-naturally occurring glycosylation site does not interfere with the proper folding of the flu hemagglutinin (HA) polypeptide and/or interfere with the ability of the stem domain of the flu hemagglutinin (HA) polypeptide from eliciting an immune response (e.g., an antibody response) in a subject.

In certain embodiments, the non-naturally occurring glycosylation sites can be added to an HA globular head domain based on the head domain of an influenza A hemagglutinin. In certain embodiments, the HA globular head domain is based on the head domain of an influenza A hemagglutinin selected from the group consisting of H1, H2, H3, H4, H5, H6, H7, H8, H9, H10, H11, H12, H13, H14, H15, H16, and H17. In certain embodiments, the non-naturally occurring glycosylation sites can be added to an HA globular head domain based on the head domain of an influenza B hemagglutinin. In some embodiments, the HA globular head domain is based on the head domain of B/Seal/Netherlands/1/99.

In certain embodiments, the non-naturally occurring glycosylation site comprises the amino acid sequence Asn-Xaa-Ser/Thr/Cys, wherein Xaa is any amino acid, or, in certain embodiments, wherein Xaa is any amino acid except Pro. In certain embodiments, the non-naturally occurring glycosylation site comprises the amino acid sequence Asn-Ala-Ser. In certain embodiments, the non-naturally occurring glycosylation site comprises Asn-Asp-Ser. In some embodiments, the non-naturally occurring glycosylation site comprises Asn-Arg-Ser. In other embodiments, the non-naturally occurring glycosylation site comprises Asn-Asn-Ser. In certain embodiments, the non-naturally occurring glycosylation site comprises Asn-Cys-Ser. In certain embodiments, the non-naturally occurring glycosylation site comprises Asn-Glu-Ser. In other embodiments, the non-naturally occurring glycosylation site comprises Asn-Gln-Ser. In some embodiments, the non-naturally occurring glycosylation site comprises Asn-Gly-Ser. In certain embodiments, the non-naturally occurring glycosylation site comprises Asn-His-Ser. In other embodiments, the non-naturally occurring glycosylation site comprises Asn-Ile-Ser. In some embodiments, the non-naturally occurring glycosylation site comprises Asn-Lys-Ser. In certain embodiments, the non-naturally occurring glycosylation site comprises Asn-Leu-Ser. In other embodiments, the non-naturally occurring glycosylation site comprises Asn-Met-Ser. In other embodiments, the non-naturally occurring glycosylation site comprises Asn-Phe-Ser. In certain embodiments, the non-naturally occurring glycosylation site comprises Asn-Pro-Ser. In some embodiments, the non-naturally occurring glycosylation site comprises Asn-Ser-Ser. In certain embodiments, the non-naturally occurring glycosylation site comprises Asn-Thr-Ser. In other embodiments, the non-naturally occurring glycosylation site comprises Asn-Trp-Ser. In certain embodiments, the non-naturally occurring glycosylation site comprises Asn-Tyr-Ser. In certain embodiments, the non-naturally occurring glycosylation site comprises Asn-Val-Ser.

In certain embodiments, the non-naturally occurring glycosylation site comprises the amino acid sequence Asn-Ala-Thr. In certain embodiments, the non-naturally occurring glycosylation site comprises Asn-Asp-Thr. In some embodiments, the non-naturally occurring glycosylation site comprises Asn-Arg-Thr. In other embodiments, the non-naturally occurring glycosylation site comprises Asn-Asn-Thr. In certain embodiments, the non-naturally occurring glycosylation site comprises Asn-Cys-Thr. In certain embodiments, the non-naturally occurring glycosylation site comprises Asn-Glu-Thr. In other embodiments, the non-naturally occurring glycosylation site comprises Asn-Gln-Thr. In some embodiments, the non-naturally occurring glycosylation site comprises Asn-Gly-Thr. In certain embodiments, the non-naturally occurring glycosylation site comprises Asn-His-Thr. In other embodiments, the non-naturally occurring glycosylation site comprises Asn-Ile-Thr. In some embodiments, the non-naturally occurring glycosylation site comprises Asn-Lys-Thr. In certain embodiments, the non-naturally occurring glycosylation site comprises Asn-Leu-Thr. In other embodiments, the non-naturally occurring glycosylation site comprises Asn-Met-Thr. In other embodiments, the non-naturally occurring glycosylation site comprises Asn-Phe-Thr. In certain embodiments, the non-naturally occurring glycosylation site comprises Asn-Pro-Thr. In some embodiments, the non-naturally occurring glycosylation site comprises Asn-Ser-Thr. In certain embodiments, the non-naturally occurring glycosylation site comprises Asn-Thr-Thr. In other embodiments, the non-naturally occurring glycosylation site comprises Asn-Trp-Thr. In certain embodiments, the non-naturally occurring glycosylation site comprises Asn-Tyr-Thr. In certain embodiments, the non-naturally occurring glycosylation site comprises Asn-Val-Thr.

In certain embodiments, the non-naturally occurring glycosylation site comprises the amino acid sequence Asn-Ala-Cys. In certain embodiments, the non-naturally occurring glycosylation site comprises Asn-Asp-Cys. In some embodiments, the non-naturally occurring glycosylation site comprises Asn-Arg-Cys. In other embodiments, the non-naturally occurring glycosylation site comprises Asn-Asn-Cys. In certain embodiments, the non-naturally occurring glycosylation site comprises Asn-Cys-Cys. In certain embodiments, the non-naturally occurring glycosylation site comprises Asn-Glu-Cys. In other embodiments, the non-naturally occurring glycosylation site comprises Asn-Gln-Cys. In some embodiments, the non-naturally occurring glycosylation site comprises Asn-Gly-Cys. In certain embodiments, the non-naturally occurring glycosylation site comprises Asn-His-Cys. In other embodiments, the non-naturally occurring glycosylation site comprises Asn-Ile-Cys. In some embodiments, the non-naturally occurring glycosylation site comprises Asn-Lys-Cys. In certain embodiments, the non-naturally occurring glycosylation site comprises Asn-Leu-Cys. In other embodiments, the non-naturally occurring glycosylation site comprises Asn-Met-Cys. In other embodiments, the non-naturally occurring glycosylation site comprises Asn-Phe-Cys. In certain embodiments, the non-naturally occurring glycosylation site comprises Asn-Pro-Cys. In some embodiments, the non-naturally occurring glycosylation site comprises Asn-Ser-Cys. In certain embodiments, the non-naturally occurring glycosylation site comprises Asn-Thr-Cys. In other embodiments, the non-naturally occurring glycosylation site comprises Asn-Trp-Cys. In certain embodiments, the non-naturally occurring glycosylation site comprises Asn-Tyr-Cys. In certain embodiments, the non-naturally occurring glycosylation site comprises Asn-Val-Cys.

The flu hemagglutinin (HA) polypeptide can comprise an HA globular head domain with one, two, three, four, five, six, seven, eight, nine, ten, eleven, twelve, thirteen, fourteen, fifteen, sixteen, seventeen, eighteen, nineteen, or twenty or more non-naturally occurring glycosylation sites. In some embodiments, the flu HA polypeptide comprises 2 to 5, 4 to 6, 5 to 10, or 10 to 15 non-naturally occurring glycosylation sites. In certain embodiments, the flu hemagglutinin (HA) polypeptide comprises an HA globular head domain with one non-naturally occurring glycosylation site. In other embodiments, the flu hemagglutinin (HA) polypeptide comprises an HA globular head domain with two non-naturally occurring glycosylation sites. In specific embodiments, the flu hemagglutinin (HA) polypeptide comprises an HA globular head domain with three non-naturally occurring glycosylation sites. In other embodiments, the flu hemagglutinin (HA) polypeptide comprises an HA globular head domain with four non-naturally occurring glycosylation sites. In certain embodiments, the flu hemagglutinin (HA) polypeptide comprises an HA globular head domain with five non-naturally occurring glycosylation sites. In other embodiments, the flu hemagglutinin (HA) polypeptide comprises an HA globular head domain with six non-naturally occurring glycosylation sites. In other embodiments, the flu hemagglutinin (HA) polypeptide comprises an HA globular head domain with seven non-naturally occurring glycosylation sites. In other embodiments, the flu hemagglutinin (HA) polypeptide comprises an HA globular head domain with eight non-naturally occurring glycosylation sites. In other embodiments, the flu hemagglutinin (HA) polypeptide comprises an HA globular head domain with nine non-naturally occurring glycosylation sites. In other embodiments, the flu hemagglutinin (HA) polypeptide comprises an HA globular head domain with ten non-naturally occurring glycosylation sites. In other embodiments, the flu hemagglutinin (HA) polypeptide an HA globular head domain with eleven non-naturally occurring glycosylation sites. In other embodiments, the flu hemagglutinin (HA) polypeptide comprises an HA globular head domain with twelve non-naturally occurring glycosylation sites. In certain embodiments, the flu hemagglutinin (HA) polypeptide comprises an HA globular head domain with thirteen non-naturally occurring glycosylation sites. In certain embodiments, the flu hemagglutinin (HA) polypeptide comprises an HA globular head domain with fourteen non-naturally occurring glycosylation sites. In other embodiments, the flu hemagglutinin (HA) polypeptide comprises an HA globular head domain with fifteen non-naturally occurring glycosylation sites. In other embodiments, the flu hemagglutinin (HA) polypeptide comprises an HA globular head domain with sixteen non-naturally occurring glycosylation sites. In certain embodiments, the flu hemagglutinin (HA) polypeptide comprises an HA globular head domain with seventeen non-naturally occurring glycosylation sites. In other embodiments, the flu hemagglutinin (HA) polypeptide comprises an HA globular head domain with eighteen non-naturally occurring glycosylation sites. In other embodiments, the flu hemagglutinin (HA) polypeptide comprises an HA globular head domain with nineteen non-naturally occurring glycosylation sites. In other embodiments, the flu hemagglutinin (HA) polypeptide comprises an HA globular head domain with twenty or more non-naturally occurring glycosylation sites.

The one or more non-naturally occurring glycosylation sites can be located at any amino acid positions within a globular head domain where a naturally occurring glycosylation site is not located with respect to a particular influenza virus subtype or strain. Exemplary mutations that introduce non-naturally occurring glycosylation sites into a globular head domain are shown in FIG. 21B. In certain embodiments, the non-naturally occurring glycosylation site is at amino acid positions 59-61, 128-130, 130-132, 158-160, and/or 163-165 according to the H3 numbering system. In certain embodiments, the non-naturally occurring glycosylation site is at amino acid positions 59-61, 81-83, 129-131, 143-145, 158-160, 165-167, 170-172, 187-189, 193-195, 197-199, and/or 208-210 according to the H3 numbering system. In some embodiments, the non-naturally occurring glycosylation site is at amino acid positions 59-61, according to H3 numbering. In other embodiments, the non-naturally occurring glycosylation site is at amino acid position 129-131, according to H3 numbering. In other embodiments, the non-naturally occurring glycosylation sites are at amino acid positions 129-131 and 158-160, according to H3 numbering. In some embodiments, the non-naturally occurring glycosylation sites are at amino acid positions 59-61, 129-131 and 165-167, according to H3 numbering. In some embodiments, the non-naturally occurring glycosylation sites are at amino acid positions 59-61, 129-131, 158-160 and 165-167, according to H3 numbering. In some embodiments, the non-naturally occurring glycosylation sites are at amino acid positions 81-83, 129-131, 158-160, 165-167, 170-172, 187-189 and 208-210, according to H3 numbering. In other embodiments, the non-naturally occurring glycosylation sites are at amino acid positions 81-83, 129-131, 158-160, 170-172, 187-189 and 208-210, according to H3 numbering. In still other embodiments, the non-naturally occurring glycosylation sites are at amino acid positions 129-131, 158-160, 165-167, 170-172, 187-189 and 208-210, according to H3 numbering.

In preferred embodiments, the non-naturally occurring glycosylation site is located in an antigenic region in the globular head domain, thereby shielding the antigenic region from eliciting an immune response. Exemplary antigenic regions in the globular domain include, but are not limited to the Sa, Sb, Ca and Cb antigenic site FIG. 21A in the H1 subtype and the A, B, C, D antigenic regions in the H3 subtype. In some embodiments, the flu hemagglutinin (HA) polypeptide comprises a non-naturally occurring glycosylation site located in the Sa antigenic region of an H1 subtype globular head domain. In certain embodiments, the flu hemagglutinin (HA) polypeptide comprises a non-naturally occurring glycosylation site located in the Sb antigenic region of an H1 subtype globular head domain. In other embodiments, the flu hemagglutinin (HA) polypeptide comprises a non-naturally occurring glycosylation site located in the Ca antigenic region of an H1 subtype globular head domain. In yet other embodiments, the flu hemagglutinin (HA) polypeptide comprises a non-naturally occurring glycosylation site located in the Cb antigenic region of an H1 subtype globular head domain. In another embodiment, the flu hemagglutinin (HA) polypeptide comprises a non-naturally occurring glycosylation site located in the Sa and Sb antigenic regions of an H1 subtype globular head domain. In another embodiment, the flu hemagglutinin (HA) polypeptide comprises a non-naturally occurring glycosylation site located in the Sa and Ca antigenic regions of an H1 subtype globular head domain. In another embodiment, the flu hemagglutinin (HA) polypeptide comprises a non-naturally occurring glycosylation site located in the Sa and Cb antigenic regions of an H1 subtype globular head domain. In another embodiment, the flu hemagglutinin (HA) polypeptide comprises a non-naturally occurring glycosylation site located in the Sb and Ca antigenic regions of an H1 subtype globular head domain. In another embodiment, the flu hemagglutinin (HA) polypeptide comprises a non-naturally occurring glycosylation site located in the Sb and Cb antigenic regions of an H1 subtype globular head domain. In another embodiment, the flu hemagglutinin (HA) polypeptide comprises a non-naturally occurring glycosylation site located in the Ca and Cb antigenic regions of an H1 subtype globular head domain. In another embodiment, the flu hemagglutinin (HA) polypeptide comprises a non-naturally occurring glycosylation site located in the Sa, Sb, and Ca antigenic regions of an H1 subtype globular head domain. In another embodiment, the flu hemagglutinin (HA) polypeptide comprises a non-naturally occurring glycosylation site located in the Sb, Ca and Cb antigenic regions of an H1 subtype globular head domain. In another embodiment, the flu hemagglutinin (HA) polypeptide comprises a non-naturally occurring glycosylation site located in the Sa, Sb, Ca and Cb antigenic regions of an H1 subtype globular head domain.

In some embodiments, the non-naturally occurring glycosylation site is in the A antigenic region of an H3 subtype globular head domain. In some embodiments, the non-naturally occurring glycosylation site is in the B antigenic region of an H3 subtype globular head domain. In some embodiments, the non-naturally occurring glycosylation site is in the C antigenic region of an H3 subtype globular head domain. In some embodiments, the non-naturally occurring glycosylation site is in the D antigenic region of an H3 subtype globular head domain. In another embodiment, the flu hemagglutinin (HA) polypeptide comprises a non-naturally occurring glycosylation site located in the A and B antigenic regions of an H3 subtype globular head domain. In another embodiment, the flu hemagglutinin (HA) polypeptide comprises a non-naturally occurring glycosylation site located in the A and C antigenic regions of an H3 subtype globular head domain. In another embodiment, the flu hemagglutinin (HA) polypeptide comprises a non-naturally occurring glycosylation site located in the A and D antigenic regions of an H3 subtype globular head domain. In another embodiment, the flu hemagglutinin (HA) polypeptide comprises a non-naturally occurring glycosylation site located in the B and C antigenic regions of an H3 subtype globular head domain. In another embodiment, the flu hemagglutinin (HA) polypeptide comprises a non-naturally occurring glycosylation site located in the B and D antigenic regions of an H3 subtype globular head domain. In another embodiment, the flu hemagglutinin (HA) polypeptide comprises a non-naturally occurring glycosylation site located in the C and D antigenic regions of an H3 subtype globular head domain. In another embodiment, the flu hemagglutinin (HA) polypeptide comprises a non-naturally occurring glycosylation site located in the A, B, and C antigenic regions of an H3 subtype globular head domain. In another embodiment, the flu hemagglutinin (HA) polypeptide comprises a non-naturally occurring glycosylation site located in the B, C, and D antigenic regions of an H3 subtype globular head domain. In another embodiment, the flu hemagglutinin (HA) polypeptide comprises a non-naturally occurring glycosylation site located in the A, B, C, and D antigenic regions of an H3 subtype globular head domain.

In other embodiments, a flu hemagglutinin (HA) polypeptide comprises one or more non-naturally occurring glycosylation sites in one or more antigenic regions of an H1, H2, H3, H4, H5, H6, H7, H8, H9, H10, H11, H12, H13, H14, H15, H16 or H17 globular head domain.

In certain embodiments, the flu hemagglutinin (HA) polypeptide comprising an HA globular head domain with one or more non-naturally occurring glycosylation sites is a chimeric influenza virus hemagglutinin polypeptide. In certain embodiments, the flu hemagglutinin (HA) polypeptide comprising an HA globular head domain with one or more non-naturally occurring glycosylation sites is a non-chimeric influenza virus hemagglutinin polypeptide.

5.4.3 Non-Naturally Occurring Glycosylation Sites in the Globular Head Domain and Modified Glycosylation Sites in the Stem Domain In another embodiment, the flu hemagglutinin (HA) polypeptide provided herein comprises an HA stem domain with one, two or more modified glycosylation sites and an HA globular head with one, two or more non-naturally occurring glycosylation sites, wherein the modified glycosylation sites comprises a modification of a naturally occurring glycosylation site that disrupts the ability of a glycan to attach to the modified glycosylation site. The modified glycosylation sites and non-naturally occurring glycosylation sites can be produced using techniques known in the art and/or described herein. In specific embodiments, the modified glycosylation site(s) and non-naturally occurring glycosylation site(s) does not interfere with the proper folding of the flu HA polypeptide and/or interfere with the ability of the stem domain flu HA polypeptide from eliciting an immune response (e.g., an antibody response) in a subject. See Sections 5.4.1 and 5.4.2, supra, for a description of modified glyosylation sites and non-naturally occurring occurring glycosylation sites. The modified glycosylation sites and non-naturally occurring glycosylation sites described in Section 5.4.1 and 5.4.2, supra, can both be incorporated into a flu HA polypeptide.

In certain embodiments, a flu hemagglutinin (HA) polypeptide provided herein comprises an HA stem domain with modified glyosylation sites at positions 33-35 and 289-291 according to H3 numbering; and an HA globular head domain comprising non-naturally occurring glycosylation sites at one, two, three, four, five, six or seven of the following positions: 129-131, 158-160, 165-167, 170-172, 187-189, and 208-210 according to H3 numbering.

In a specific embodiment, provided herein is a chimeric influenza hemagglutinin polypeptide comprising one or more non-naturally occurring glycosylation sites in the globular head domain and one or more modified glycosylation sites in the stem domain, wherein said modified glycosylation sites in the stem domain comprise a modification that disrupts glycosylation at the modified glycosylation site. In another specific embodiment, provided herein is a chimeric influenza hemagglutinin polypeptide comprising one or more non-naturally occurring glycosylation sites in the globular head domain and one or more modified glycosylation sites in the stem domain, wherein said modified glycosylation sites in the stem domain comprise a modification that disrupts glycosylation at the modified glycosylation site, and wherein (i) the non-naturally occurring glycosylation sites are at one, two, three, four, five, six, seven, or more of amino acid positions 81-83, 129-131, 158-160, 165-167, 170-172, 187-189 and 208-210, according to H3 numbering and (ii) the modified glycosylation sites are at one, two, three, or more of amino acid positions 20-23, 33-35, 271-273, 289-291, and/or 483-485 according to H3 numbering. In another specific embodiment, provided herein is a chimeric influenza hemagglutinin polypeptide comprising one or more non-naturally occurring glycosylation sites in the globular head domain and comprising one or more modified glycosylation sites in the stem domain, wherein said modified glycosylation sites in the stem domain comprise a modification that disrupts glycosylation at the modified glycosylation site, and wherein (i) the non-naturally occurring glycosylation sites are at amino acid positions 81-83, 129-131, 158-160, 170-172, 187-189 and 208-210, according to H3 numbering and (ii) the modified glycosylation sites are at amino acid positions 33-35 and 289-291, according to H3 numbering. In another specific embodiment, provided herein is a chimeric influenza hemagglutinin polypeptide comprising one or more non-naturally occurring glycosylation sites in the globular head domain comprising one or more modified glycosylation sites in the stem domain, wherein said modified glycosylation sites in the stem domain comprise a modification that disrupts glycosylation at the modified glycosylation site, and wherein (i) the non-naturally occurring glycosylation sites are at amino acid positions 81-83, 129-131, 158-160, 165-167, 170-172, 187-189 and 208-210, according to H3 numbering and (ii) the modified glycosylation sites are at amino acid positions 33-35 and 289-291, according to H3 numbering. In another specific embodiment, provided herein is a chimeric influenza hemagglutinin polypeptide comprising one or more non-naturally occurring glycosylation sites in the globular head domain comprising one or more modified glycosylation sites in the stem domain, wherein said modified glycosylation sites in the stem domain comprise a modification that disrupts glycosylation at the modified glycosylation site, and wherein (i) the non-naturally occurring glycosylation sites are at amino acid positions 129-131, 158-160, 165-167, 170-172, 187-189 and 208-210, according to H3 numbering and (ii) the modified glycosylation sites are at amino acid positions 33-35 and 289-291, according to H3 numbering. Exemplary chimeric influenza hemagglutinin polypeptide comprising modified glycosylation sites are described in Section 6.11 (Example 11).

5.5 Nucleic Acids Encoding Flu Hemagglutinin (HA) Polypeptide

Provided herein are nucleic acids that encode the flu hemagglutinin (HA) polypeptides (e.g., chimeric influenza virus hemagglutinin polypeptides) described herein. Due to the degeneracy of the genetic code, any nucleic acid that encodes a flu hemagglutinin (HA) polypeptide described herein is encompassed herein. In certain embodiments, nucleic acids corresponding to naturally occurring influenza virus nucleic acids encoding an HA1 N-terminal stem segment, an HA1 C-terminal stem segment, HA2 domain, luminal domain, transmembrane domain, and/or cytoplasmic domain are used to produce a flu hemagglutinin (HA) polypeptide (e.g., a chimeric influenza virus hemagglutinin polypeptide).

Also provided herein are nucleic acids capable of hybridizing to a nucleic acid encoding a flu hemagglutinin (HA) polypeptide (e.g., a chimeric influenza virus hemagglutinin polypeptide). In certain embodiments, provided herein are nucleic acids capable of hybridizing to a fragment of a nucleic acid encoding a flu hemagglutinin (HA) polypeptide (e.g., a chimeric influenza virus hemagglutinin polypeptide). In other embodiments, provided herein are nucleic acids capable of hybridizing to the full length of a nucleic acid encoding a flu hemagglutinin (HA) polypeptide (e.g., a chimeric influenza virus hemagglutinin polypeptide). General parameters for hybridization conditions for nucleic acids are described in Sambrook et al., Molecular Cloning—A Laboratory Manual (2nd Ed.), Vols. 1-3, Cold Spring Harbor Laboratory, Cold Spring Harbor, N.Y. (1989), and in Ausubel et al., Current Protocols in Molecular Biology, vol. 2, Current Protocols Publishing, New York (1994). Hybridization may be performed under high stringency conditions, medium stringency conditions, or low stringency conditions. Those of skill in the art will understand that low, medium and high stringency conditions are contingent upon multiple factors all of which interact and are also dependent upon the nucleic acids in question. For example, high stringency conditions may include temperatures within 5° C. melting temperature of the nucleic acid(s), a low salt concentration (e.g., less than 250 mM), and a high co-solvent concentration (e.g., 1-20% of co-solvent, e.g., DMSO). Low stringency conditions, on the other hand, may include temperatures greater than 10° C. below the melting temperature of the nucleic acid(s), a high salt concentration (e.g., greater than 1000 mM) and the absence of co-solvents.

In some embodiments, a nucleic acid encoding a flu hemagglutinin (HA) polypeptide (e.g., a chimeric influenza virus hemagglutinin polypeptide) is isolated. In certain embodiments, an "isolated" nucleic acid refers to a nucleic acid molecule which is separated from other nucleic acid molecules which are present in the natural source of the nucleic acid. In other words, the isolated nucleic acid can comprise heterologous nucleic acids that are not associated with it in nature. In other embodiments, an "isolated" nucleic acid, such as a cDNA molecule, can be substantially free of other cellular material, or culture medium when produced by recombinant techniques, or substantially free of chemical precursors or other chemicals when chemically synthesized. The term "substantially free of cellular material" includes preparations of nucleic acid in which the nucleic acid is separated from cellular components of the cells from which it is isolated or recombinantly produced. Thus, nucleic acid that is substantially free of cellular material includes preparations of nucleic acid having less than about 30%, 20%, 10%, or 5% (by dry weight) of other nucleic acids. The term "substantially free of culture medium" includes preparations of nucleic acid in which the culture medium represents less than about 50%, 20%, 10%, or 5% of the volume of the preparation. The term "substantially free of chemical precursors or other chemicals" includes preparations in which the nucleic acid is separated from chemical precursors or other chemicals which are involved in the synthesis of the nucleic acid. In specific embodiments, such preparations of the nucleic acid have less than about 50%, 30%, 20%, 10%, 5% (by dry weight) of chemical precursors or compounds other than the nucleic acid of interest.

In addition, provided herein are nucleic acids encoding the individual components of an influenza hemagglutinin stem domain polypeptide. In specific embodiments, nucleic acids encoding an HA1 N-terminal stem segment, an HA1 C-terminal stem segment and/or HA2 domain are provided. Nucleic acids encoding components of an influenza hemagglutinin stem domain polypeptide may be assembled using standard molecular biology techniques known to the one of skill in the art.

5.6 Expression of Flu Hemagglutinin (HA) Polypeptide

Provided herein are vectors, including expression vectors, containing a nucleic acid encoding a flu hemagglutinin (HA) polypeptide (e.g., a chimeric influenza virus hemagglutinin polypeptide) described herein. In a specific embodiment, the vector is an expression vector that is capable of directing the expression of a nucleic acid encoding a flu hemagglutinin (HA) polypeptide (e.g., a chimeric influenza virus hemagglutinin polypeptide). Non-limiting examples of expression vectors include, but are not limited to, plasmids and viral vectors, such as replication defective retroviruses, adenoviruses, adeno-associated viruses and baculoviruses. Expression vectors also may include, without limitation, transgenic animals and non-mammalian cells/organisms, e.g., mammalian cells/organisms that have been engineered to perform mammalian N-linked glycosylatio.

In some embodiments, provided herein are expression vectors encoding components of a flu hemagglutinin (HA) polypeptide (e.g., the stem domain and the head domain, or portions of either domain). Such vectors may be used to express the components in one or more host cells and the components may be isolated and conjugated together with a linker using techniques known to one of skill in the art.

An expression vector comprises a nucleic acid encoding a flu hemagglutinin (HA) polypeptide described herein in a form suitable for expression of the nucleic acid in a host cell. In a specific embodiment, an expression vector includes one or more regulatory sequences, selected on the basis of the host cells to be used for expression, which is operably linked to the nucleic acid to be expressed. Within an expression vector, "operably linked" is intended to mean that a nucleic acid of interest is linked to the regulatory sequence(s) in a manner which allows for expression of the nucleic acid (e.g., in an in vitro transcription/translation system or in a host cell when the vector is introduced into the host cell). Regulatory sequences include promoters, enhancers and other expression control elements (e.g., polyadenylation signals). Regulatory sequences include those which direct constitutive expression of a nucleic acid in many types of host cells, those which direct expression of the nucleic acid only in certain host cells (e.g., tissue-specific regulatory sequences), and those which direct the expression of the nucleic acid upon stimulation with a particular agent (e.g., inducible regulatory sequences). It will be appreciated by those skilled in the art that the design of the expression vector can depend on such factors as the choice of the host cell to be transformed, the level of expression of protein desired, etc. The term "host cell" is intended to include a particular subject cell transformed or transfected with a nucleic acid and the progeny or potential progeny of such a cell. Progeny of such a cell may not be identical to the parent cell transformed or transfected with the nucleic acid due to mutations or environmental influences that may occur in succeeding generations or integration of the nucleic acid into the host cell genome.

Expression vectors can be designed for expression of a flu hemagglutinin (HA) polypeptide described herein using prokaryotic (e.g., *E. coli*) or eukaryotic cells (e.g., insect cells (using baculovirus expression vectors, see, e.g., Treanor et al., 2007, JAMA, 297(14):1577-1582 incorporated by reference herein in its entirety), yeast cells, plant cells, algae or mammalian cells). Examples of yeast host cells include, but are not limited to *S. pombe* and *S. cerevisiae* and examples, infra. Examples of mammalian host cells include, but are not limited to, Crucell Per.C6 cells, Vero cells, CHO cells, VERY cells, BHK cells, HeLa cells, COS cells, MDCK cells, 293 cells, 3T3 cells or WI38 cells. In certain embodiments, the hosts cells are myeloma cells, e.g., NS0 cells, 45.6 TG1.7 cells, AF-2 clone 9B5 cells, AF-2 clone 9B5 cells, J558L cells, MOPC 315 cells, MPC-11 cells, NCI-H929 cells, NP cells, NS0/1 cells, P3 NS1 Ag4 cells, P3/NS1/1-Ag4-1 cells, P3U1 cells, P3X63Ag8 cells, P3X63Ag8.653 cells, P3X63Ag8U1 cells, RPMI 8226 cells, Sp20-Ag14 cells, U266B1 cells, X63AG8.653 cells, Y3.Ag.1.2.3 cells, and YO cells. Non-limiting examples of insect cells include Sf9, Sf21, *Trichoplusia ni, Spodoptera frugiperda* and *Bombyx mori*. In a particular embodiment, a mammalian cell culture system (e.g. Chinese hamster ovary or baby hamster kidney cells) is used for expression of a flu hemagglutinin (HA) polypeptide. In another embodiment, a plant cell culture system is used for expression of a flu hemagglutinin (HA) polypeptide. See, e.g., U.S. Pat. Nos. 7,504,560; 6,770,799; 6,551,820; 6,136,320; 6,034,298; 5,914,935; 5,612,487; and 5,484,719, and U.S. patent application publication Nos. 2009/0208477, 2009/0082548, 2009/0053762, 2008/0038232, 2007/0275014 and 2006/0204487 for plant cells and methods for the production of proteins utilizing plant cell culture systems. In specific embodiments, plant cell culture systems are not used for expression of a flu hemagglutinin (HA) polypeptide. The host cells comprising the nucleic acids that encode the flu hemagglutinin (HA) polypeptides (e.g., a chimeric influenza virus hemagglutinin polypeptides) described herein can be isolated, i.e., the cells are outside of the body of a subject. In certain embodiments, the cells are engineered to express nucleic acids that encode the flu hemagglutinin (HA) polypeptides (e.g., a chimeric influenza virus hemagglutinin polypeptides) described herein.

An expression vector can be introduced into host cells via conventional transformation or transfection techniques. Such techniques include, but are not limited to, calcium phosphate or calcium chloride co-precipitation, DEAE-dextran-mediated transfection, lipofection, and electroporation. Suitable methods for transforming or transfecting host cells can be found in Sambrook et al., 1989, Molecular Cloning—A Laboratory Manual, 2nd Edition, Cold Spring Harbor Press, New York, and other laboratory manuals. In certain embodiments, a host cell is transiently transfected with an expression vector containing a nucleic acid encoding a flu hemagglutinin (HA) polypeptide. In other embodiments, a host cell is stably transfected with an expression vector containing a nucleic acid encoding a flu hemagglutinin (HA) polypeptide.

For stable transfection of mammalian cells, it is known that, depending upon the expression vector and transfection technique used, only a small fraction of cells may integrate the foreign DNA into their genome. In order to identify and select these integrants, a nucleic acid that encodes a selectable marker (e.g., for resistance to antibiotics) is generally introduced into the host cells along with the nucleic acid of interest. Examples of selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

As an alternative to recombinant expression of a flu hemagglutinin (HA) polypeptide using a host cell, an expression vector containing a nucleic acid encoding a flu hemagglutinin (HA) polypeptide can be transcribed and translated in vitro using, e.g., T7 promoter regulatory sequences and T7 polymerase. In a specific embodiment, a coupled transcription/translation system, such as Promega TNT®, or a cell lysate or cell extract comprising the components necessary for transcription and translation may be used to produce a flu hemagglutinin (HA) polypeptide.

Once a flu hemagglutinin (HA) polypeptide has been produced, it may be isolated or purified by any method known in the art for isolation or purification of a protein, for example, by chromatography (e.g., ion exchange, affinity, particularly by affinity for the specific antigen, by Protein A, and sizing column chromatography), centrifugation, differential solubility, or by any other standard technique for the isolation or purification of proteins. In certain embodiments, a flu hemagglutinin (HA) polypeptide may be conjugated to heterologous proteins, e.g., a major histocompatibility complex (MHC) with or without heat shock proteins (e.g., Hsp10, Hsp20, Hsp30, Hsp40, Hsp60, Hsp70, Hsp90, or Hsp100). In certain embodiments, a flu hemagglutinin (HA) polypeptide may be conjugated to immunomodulatory molecules, such as proteins which would target the flu hemagglutinin (HA) polypeptide to immune cells such as B cells (e.g., C3d) or T cells. In certain embodiments, a flu hemagglutinin (HA) polypeptide may be conjugated to proteins which stimulate the innate immune system such as interferon type 1, alpha, beta, or gamma interferon, colony stimulating factors such as granulocyte-macrophage colony-stimulating factor (GM-CSF), interleukin (IL)-1, IL-2, IL-4, IL-5, IL-6, IL-7, IL-12, IL-15, IL-18, IL-21, IL-23, tumor necrosis factor (TNF)-β, TNFα, B7.1, B7.2, 4-1BB, CD40 ligand (CD40L), and drug-inducible CD40 (iCD40).

Accordingly, provided herein are methods for producing a flu hemagglutinin (HA) polypeptide (e.g., a chimeric influenza virus hemagglutinin (HA) polypeptide). In one embodiment, the method comprises culturing a host cell containing a nucleic acid encoding the polypeptide in a suitable medium such that the polypeptide is produced. In some embodiments, the method further comprises isolating the polypeptide from the medium or the host cell.

5.7 Influenza Virus Vectors

In one aspect, provided herein are influenza viruses containing a flu hemagglutinin (HA) polypeptide (e.g., a chimeric influenza virus hemagglutinin polypeptide) described herein. In a specific embodiment, the flu hemagglutinin (HA) polypeptide is incorporated into the virions of the influenza virus. The influenza viruses may be conjugated to moieties that target the viruses to particular cell types, such as immune cells. In some embodiments, the virions of the influenza virus have incorporated into them or express a heterologous polypeptide in addition to a flu hemagglutinin (HA) polypeptide. The heterologous polypeptide may be a polypeptide that has immunopotentiating activity, or that targets the influenza virus to a particular cell type, such as an antibody that binds to an antigen on a specific cell type or a ligand that binds a specific receptor on a specific cell type.

Influenza viruses containing a flu hemagglutinin (HA) polypeptide may be produced by supplying in trans the flu hemagglutinin (HA) polypeptide during production of virions using techniques known to one skilled in the art, such as reverse genetics and helper-free plasmid rescue. Alternatively, the replication of a parental influenza virus comprising a genome engineered to express a flu hemagglutinin (HA) polypeptide in cells susceptible to infection with the virus wherein hemagglutinin function is provided in trans will produce progeny influenza viruses containing the flu hemagglutinin (HA) polypeptide.

In another aspect, provided herein are influenza viruses comprising a genome engineered to express a flu hemagglutinin (HA) polypeptide. In a specific embodiment, the genome of a parental influenza virus is engineered to encode a flu hemagglutinin (HA) polypeptide, which is expressed by progeny influenza virus. In another specific embodiment, the genome of a parental influenza virus is engineered to encode a flu hemagglutinin (HA) polypeptide, which is expressed and incorporated into the virions of progeny influenza virus. Thus, the progeny influenza virus resulting from the replication of the parental influenza virus contain a flu hemagglutinin (HA) polypeptide. The virions of the parental influenza virus may have incorporated into them a flu hemagglutinin (HA) polypeptide that contains a stem or head domain from the same or a different type, subtype or strain of influenza virus. Alternatively, the virions of the parental influenza virus may have incorporated into them a moiety that is capable of functionally replacing one or more of the activities of influenza virus hemagglutinin polypeptide (e.g., the receptor binding and/or fusogenic activities of influenza virus hemagglutinin) In certain embodiments, one or more of the activities of the influenza virus hemagglutinin polypeptide is provided by a fusion protein comprising (i) an ectodomain of a polypeptide heterologous to influenza virus fused to (ii) a transmembrane domain, or a transmembrane domain and a cytoplasmic domain of an influenza virus hemagglutinin polypeptide. In a specific embodiment, the virions of the parental influenza virus may have incorporated into them a fusion protein comprising (i) an ectodomain of a receptor binding/fusogenic polypeptide of an infectious agent other than influenza virus fused to (ii) a transmembrane domain, or a transmembrane domain and a cytoplasmic domain of an influenza virus hemagglutinin. For a description of fusion proteins that provide one or more activities of an influenza virus hemagglutinin polypeptide and methods for the production of influenza viruses engineered to express such fusion proteins, see, e.g., International patent application Publication No. WO 2007/064802, published Jun. 7, 2007 and U.S. patent application Ser. No. 11/633,130, filed on Dec. 1, 2006; each of which is incorporated herein by reference in its entirety.

In certain embodiments, the influenza viruses engineered to express one or more of the flu hemagglutinin (HA) polypeptides described herein comprise a neuraminidase (NA), or fragment thereof, that is from the same source (e.g., influenza virus strain or subtype) as that from which the globular head of the flu hemagglutinin (HA) polypeptide is derived. In certain embodiments, the influenza viruses engineered to express one or more of the chimeric influenza virus hemagglutinin polypeptides described herein comprise a neuraminidase (NA), or fragment thereof, that is from the same source (e.g., influenza virus strain or subtype) as that from which the globular head of the chimeric influenza virus hemagglutinin polypeptide is derived, wherein the globular head is heterologous to the stem domain of the HA1 and/or HA2 subunits of the chimeric influenza virus hemagglutinin polypeptide.

In some embodiments, the virions of the parental influenza virus have incorporated into them a heterologous polypeptide. In certain embodiments, the genome of a parental influenza virus is engineered to encode a heterologous polypeptide and a flu hemagglutinin (HA) polypeptide, which are expressed by progeny influenza virus. In specific embodiments, the flu hemagglutinin (HA) polypeptide, the heterologous polypeptide or both are incorporated into virions of the progeny influenza virus.

The heterologous polypeptide may be a polypeptide that targets the influenza virus to a particular cell type, such as an antibody that recognizes an antigen on a specific cell type or a ligand that binds a specific receptor on a specific cell type. In some embodiments, the targeting polypeptide replaces the target cell recognition function of the virus. In a specific embodiment, the heterologous polypeptide targets the influenza virus to the same cell types that influenza virus infects in nature. In other specific embodiments, the heterologous polypeptide targets the progeny influenza virus to immune cells, such as B cells, T cells, macrophages or dendritic cells. In some embodiments, the heterologous polypeptide recognizes and binds to cell-specific markers of antigen presenting cells, such as dendritic cells (e.g., such as CD44). In one embodiment, the heterologous polypeptide is DC-SIGN which targets the virus to dendritic cells. In another embodiment, the heterologous polypeptide is an antibody (e.g., a single-chain antibody) that targets the virus to an immune cell, which may be fused with a transmembrane domain from another polypeptide so that it is incorporated into the influenza virus virion. In some embodiments, the antibody is a CD20 antibody, a CD34 antibody, or an antibody against DEC-205. Techniques for engineering viruses to express polypeptides with targeting functions are known in the art. See, e.g., Yang et al., 2006, PNAS103: 11479-11484 and United States patent application Publication No. 20080019998, published Jan. 24, 2008, and No. 20070020238, published Jan. 25, 2007, the contents of each of which are incorporated herein in their entirety.

In another embodiment, the heterologous polypeptide is a viral attachment protein. Non-limiting examples of viruses whose attachment protein(s) can be used in this aspect are viruses selected from the group of: Lassa fever virus, Hepatitis B virus, Rabies virus, Newcastle disease virus (NDV), a retrovirus such as human immunodeficiency virus, tick-borne encephalitis virus, vaccinia virus, herpesvirus, poliovirus, alphaviruses such as Semliki Forest virus, Ross River virus, and Aura virus (which comprise surface glycoproteins such as E1, E2, and E3), Borna disease virus, Hantaan virus, foamyvirus, and SARS-CoV virus.

In one embodiment, a flavivirus surface glycoprotein may be used, such as Dengue virus (DV) E protein. In some embodiments, a Sindbis virus glycoprotein from the alphavirus family is used (K. S. Wang, R. J. Kuhn, E. G. Strauss, S. Ou, J. H. Strauss, J. Virol. 66, 4992 (1992)). In certain embodiments, the heterologous polypeptide is derived from an NDV HN or F protein; a human immunodeficiency virus (HIV) gp160 (or a product thereof, such as gp41 or gp120); a hepatitis B virus surface antigen (HBsAg); a glycoprotein of herpesvirus (e.g., gD, gE); or VP1 of poliovirus.

In another embodiment, the heterologous polypeptide is derived from any non-viral targeting system known in the art. In certain embodiments, a protein of a nonviral pathogen such as an intracellular bacteria or protozoa is used. In some embodiments, the bacterial polypeptide is provided by, e.g., *Chlamydia, Rikettsia, Coxelia, Listeria, Brucella*, or *Legionella*. In some embodiments, protozoan polypeptide is provided by, e.g., *Plasmodia* species, *Leishmania* spp., *Toxoplasma gondii*, or *Trypanosoma cruzi*. Other exemplary targeting systems are described in Waehler et al., 2007, "Engineering targeted viral vectors for gene therapy," Nature Reviews Genetics 8: 573-587, which is incorporated herein in its entirety.

In certain embodiments, the heterologous polypeptide expressed by an influenza virus has immunopotentiating (immune stimulating) activity. Non-limiting examples of immunopotentiating polypeptides include, but are not limited to, stimulation molecules, cytokines, chemokines, antibodies and other agents such as Flt-3 ligands. Specific examples of polypeptides with immunopotentiating activity include: interferon type 1, alpha, beta, or gamma interferon, colony stimulating factors such as granulocyte-macrophage colony-stimulating factor (GM-CSF), interleukin (IL)-1, IL-2, IL-4, IL-5, IL-6, IL-7, IL-12, IL-15, IL-18, IL-21, IL-23, tumor necrosis factor (TNF)-13, TNFα, B7.1, B7.2, 4-1BB, CD40 ligand (CD40L), and drug-inducible CD40 (iCD40) (see, e.g., Hanks, B. A., et al. 2005. Nat Med 11:130-137, which is incorporated herein by reference in its entirety.)

Since the genome of influenza A and B viruses consist of eight (8) single-stranded, negative sense segments (influenza C viruses consist of seven (7) single-stranded, negative sense segments), the genome of a parental influenza virus may be engineered to express a flu hemagglutinin (HA) polypeptide (and any other polypeptide, such as a heterologous polypeptide) using a recombinant segment and techniques known to one skilled in the art, such a reverse genetics and helper-free plasmid rescue. In one embodiment, the recombinant segment comprises a nucleic acid encoding the flu hemagglutinin (HA) polypeptide as well as the 3' and 5' incorporation signals which are required for proper replication, transcription and packaging of the vRNAs (Fujii et al., 2003, Proc. Natl. Acad. Sci. USA 100:2002-2007; Zheng, et al., 1996, Virology 217:242-251, both of which are incorporated by reference herein in their entireties). In a specific embodiment, the recombinant segment uses the 3' and 5' noncoding and/or nontranslated sequences of segments of influenza viruses that are from a different or the same type, subtype or strain as the parental influenza virus. In some embodiments, the recombinant segment comprises the 3' noncoding region of an influenza virus hemagglutinin polypeptide, the untranslated regions of an influenza virus hemagglutinin polypeptide, and the 5' non-coding region of an influenza virus hemagglutinin polypeptide. In specific embodiments, the recombinant segment comprises the 3' and 5' noncoding and/or nontranslated sequences of the HA segment of an influenza virus that is the same type, subtype or strain as the influenza virus type, subtype or strain as the HA1 N-terminal stem segment, the HA1 C-terminal stem segment, the globular head domain, and/or the HA2 of a flu hemagglutinin (HA) polypeptide. In certain embodiments, the recombinant segment encoding the flu hemagglutinin (HA) polypeptide may replace the HA segment of a parental influenza virus. In some embodiments, the recombinant segment encoding the flu hemagglutinin (HA) polypeptide may replace the NS1 gene of the parental influenza virus. In some embodiments, the recombinant segment encoding the flu hemagglutinin (HA) polypeptide may replace the NA gene of the parental influenza virus. Exemplary influenza virus strains that can be used to express the flu hemagglutinin (HA) polypeptides include Ann Arbor/1/50, A/Ann Arbor/6/60, A/Puerto Rico/8/34, A/South Dakota/6/2007, A/Uruguay/716/2007, A/California/07/2009, A/Perth/16/2009, A/Brisbane/59/2007, A/Brisbane/10/2007, and B/Brisbane/60/2008.

In some embodiments, a flu hemagglutinin gene segment encodes a flu hemagglutinin (HA) polypeptide. In specific embodiments, the flu hemagglutinin (HA) gene segment and at least one other influenza virus gene segment comprise packaging signals that enable the flu hemagglutinin (HA) gene segment and the at least one other gene segment to segregate together during replication of a recombinant influenza virus (see, Gao & Palese 2009, PNAS106:15891-15896; and International Application Publication No. WO11/014,645).

In some embodiments, the genome of a parental influenza virus may be engineered to express a flu hemagglutinin (HA) polypeptide using a recombinant segment that is bicistronic. Bicistronic techniques allow the engineering of coding sequences of multiple proteins into a single mRNA through the use of internal ribosome entry site (IRES) sequences. IRES sequences direct the internal recruitment of ribosomes to the RNA molecule and allow downstream translation in a cap independent manner. Briefly, a coding region of one protein is inserted into the open reading frame (ORF) of a second protein. The insertion is flanked by an IRES and any untranslated signal sequences necessary for proper expression and/or function. The insertion must not disrupt the ORF, polyadenylation or transcriptional promoters of the second protein (see, e.g., García-Sastre et al., 1994, J. Virol. 68:6254-6261 and García-Sastre et al., 1994 Dev. Biol. Stand. 82:237-246, each of which is hereby incorporated by reference in its entirety). See also, e.g., U.S. Pat. No. 6,887,699, U.S. Pat. No. 6,001,634, U.S. Pat. No. 5,854,037 and U.S. Pat. No. 5,820,871, each of which is incorporated herein by reference in its entirety. Any IRES known in the art or described herein may be used in accordance with the invention (e.g., the IRES of BiP gene, nucleotides 372 to 592 of GenBank database entry HUMGRP78; or the IRES of encephalomyocarditis virus (EMCV), nucleotides 1430-2115 of GenBank database entry CQ867238.). Thus, in certain embodiments, a parental influenza virus is engineered to contain a bicistronic RNA segment that expresses the flu hemagglutinin (HA) polypeptide and another polypeptide, such as a gene expressed by the parental influenza virus. In some embodiments, the parental influenza virus gene is the HA gene. In some embodiments, the parental influenza virus gene is the NA gene. In some embodiments, the parental influenza virus gene is the NS1 gene.

Techniques known to one skilled in the art may be used to produce an influenza virus containing a flu hemagglutinin (HA) polypeptide and an influenza virus comprising a genome engineered to express a flu hemagglutinin (HA) polypeptide. For example, reverse genetics techniques may be used to generate such an influenza virus. Briefly, reverse genetics techniques generally involve the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO 97/12032 published Apr. 3, 1997; WO 96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

Alternatively, helper-free plasmid technology may be used to produce an influenza virus containing a flu hemagglutinin (HA) polypeptide and an influenza virus comprising a genome engineered to express a flu hemagglutinin (HA) polypeptide. Briefly, full length cDNAs of viral segments are amplified using PCR with primers that include unique restriction sites, which allow the insertion of the PCR product into the plasmid vector (Flandorfer et al., 2003, J. Virol. 77:9116-9123; Nakaya et al., 2001, J. Virol. 75:11868-11873; both of which are incorporated herein by reference in their entireties). The plasmid vector is designed so that an exact negative (vRNA sense) transcript is expressed. For example, the plasmid vector may be designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment as well as expression vectors comprising necessary viral proteins may be transfected into cells leading to production of recombinant viral particles. In another example, plasmid vectors from which both the viral genomic RNA and mRNA encoding the necessary viral proteins are expressed may be used. For a detailed description of helper-free plasmid technology see, e.g., International Publication No. WO 01/04333; U.S. Pat. Nos. 6,951,754, 7,384,774, 6,649,372, and 7,312,064; Fodor et al., 1999, J. Virol. 73:9679-9682; Quinlivan et al., 2005, J. Virol. 79:8431-8439; Hoffmann et al., 2000, Proc. Natl. Acad. Sci. USA 97:6108-6113; and Neumann et al., 1999, Proc. Natl. Acad. Sci. USA 96:9345-9350, which are incorporated herein by reference in their entireties.

The influenza viruses described herein may be propagated in any substrate that allows the virus to grow to titers that permit their use in accordance with the methods described herein. In one embodiment, the substrate allows the viruses to grow to titers comparable to those determined for the corresponding wild-type viruses. In certain embodiments, the substrate is one which is biologically relevant to the influenza virus or to the virus from which the HA function is derived. In a specific embodiment, an attenuated influenza virus by virtue of, e.g., a mutation in the NS1 gene, may be propagated in an IFN-deficient substrate. For example, a suitable IFN-deficient substrate may be one that is defective in its ability to produce or respond to interferon, or is one which an IFN-deficient substrate may be used for the growth of any number of viruses which may require interferon-deficient growth environment. See, for example, U.S. Pat. No. 6,573,079, issued Jun. 3, 2003, U.S. Pat. No. 6,852,522, issued Feb. 8, 2005, and U.S. Pat. No. 7,494,808, issued Feb. 24, 2009, the entire contents of each of which is incorporated herein by reference in its entirety. In a specific embodiment, the virus is propagated in embryonated eggs (e.g., chicken eggs). In a specific embodiment, the virus is propagated in 8 day old, 9-day old, 8-10 day old, 10 day old, 11-day old, 10-12 day old, or 12-day old embryonated eggs (e.g., chicken eggs). In certain embodiments, the virus is propagated in MDCK cells, Vero cells, 293T cells, or other cell lines known in the art. In certain embodiments, the virus is propagated in cells derived from embryonated eggs.

The influenza viruses described herein may be isolated and purified by any method known to those of skill in the art. In one embodiment, the virus is removed from cell culture and separated from cellular components, typically by well known clarification procedures, e.g., such as gradient centrifugation and column chromatography, and may be further purified as desired using procedures well known to those skilled in the art, e.g., plaque assays.

In certain embodiments, the influenza viruses, or influenza virus polypeptides, genes or genome segments for use as described herein are obtained or derived from an influenza A virus. In certain embodiments, the influenza viruses, or influenza virus polypeptides, genes or genome segments for use as described herein are obtained or derived from a single influenza A virus subtype or strain. In other embodiments, the influenza viruses, or influenza virus polypeptides, genes or genome segments for use as described herein are obtained or derived from two or more influenza A virus subtypes or strains. In certain embodiments, the influenza viruses for use as described herein comprise a chimeric influenza virus hemagglutinin polypeptide described herein and a neuraminidase (NA), or fragment thereof, wherein the NA is from the same source (e.g., influenza virus strain or subtype) as that from which the globular head of the chimeric influenza virus hemagglutinin polypeptide is derived. In certain embodiments, the influenza viruses engineered to express one or more of the chimeric influenza virus hemagglutinin polypeptides described herein comprise a neuraminidase (NA), or fragment thereof, that is from the same source (e.g., influenza virus strain or subtype) as that from which the globular head of the chimeric influenza virus hemagglutinin polypeptide is derived, wherein the globular head is heterologous to the stem domain of the HA1 and/or HA2 subunits of the chimeric influenza virus hemagglutinin polypeptide.

In some embodiments, the influenza viruses, or influenza virus polypeptides, genes or genome segments for use as described herein are obtained or derived from an influenza B virus. In certain embodiments, the influenza viruses, or influenza virus polypeptides, genes or genome segments for use as described herein are obtained or derived from a single influenza B virus subtype or strain. In other embodiments, the influenza viruses, or influenza virus polypeptides, genes or genome segments for use as described herein are obtained or derived from two or more influenza B virus subtypes or strains. In other embodiments, the influenza viruses, or influenza virus polypeptides, genes or genome segments for use as described herein are obtained or derived from a combination of influenza A and influenza B virus subtypes or strains.

In some embodiments, the influenza viruses, or influenza virus polypeptides, genes or genome segments for use as described herein are obtained or derived from an influenza C virus. In certain embodiments, the influenza viruses, or influenza virus polypeptides, genes or genome segments for use as described herein are obtained or derived from a single influenza C virus subtype or strain. In other embodiments, the influenza viruses, or influenza virus polypeptides, genes or genome segments for use as described herein are obtained or derived from two or more influenza C virus subtypes or strains. In other embodiments, the influenza viruses, or influenza virus polypeptides, genes or genome segments for use as described herein are obtained or derived from a combination of influenza C virus and influenza A virus and/or influenza B virus subtypes or strains.

Non-limiting examples of influenza A viruses include subtype H10N4, subtype H10N5, subtype H10N7, subtype H10N8, subtype H10N9, subtype H11N1, subtype H11N13, subtype H11N2, subtype H11N4, subtype H11N6, subtype H11N8, subtype H11N9, subtype H12N1, subtype H12N4, subtype H12N5, subtype H12N8, subtype H13N2, subtype H13N3, subtype H13N6, subtype H13N7, subtype H14N5, subtype H14N6, subtype H15N8, subtype H15N9, subtype H16N3, subtype H1N1, subtype H1N2, subtype H1N3, subtype H1N6, subtype H1N9, subtype H2N1, subtype H2N2, subtype H2N3, subtype H2N5, subtype H2N7, subtype H2N8, subtype H2N9, subtype H3N1, subtype H3N2, subtype H3N3, subtype H3N4, subtype H3N5, subtype H3N6, subtype H3N8, subtype H3N9, subtype H4N1, subtype H4N2, subtype H4N3, subtype H4N4, subtype H4N5, subtype H4N6, subtype H4N8, subtype H4N9, subtype H5N1, subtype H5N2, subtype H5N3, subtype H5N4, subtype H5N6, subtype H5N7, subtype H5N8, subtype H5N9, subtype H6N1, subtype H6N2, subtype H6N3, subtype H6N4, subtype H6N5, subtype H6N6, subtype H6N7, subtype H6N8, subtype H6N9, subtype H7N1, subtype H7N2, subtype H7N3, subtype H7N4, subtype H7N5, subtype H7N7, subtype H7N8, subtype H7N9, subtype H8N4, subtype H8N5, subtype H9N1, subtype H9N2, subtype H9N3, subtype H9N5, subtype H9N6, subtype H9N7, subtype H9N8, and subtype H9N9.

Specific examples of strains of influenza A virus include, but are not limited to: A/Victoria/361/2011 (H3N2); A/California/4/2009 (H1N1); A/California/7/2009 (H1N1); A/Perth/16/2009 (H3N2); A/Brisbane/59/2007 (H1N1); A/Brisbane/10/2007 ((H3N2); A/sw/Iowa/15/30 (H1N1); A/WSN/33 (H1N1); A/eq/Prague/1/56 (H7N7); A/PR/8/34; A/mallard/Potsdam/178-4/83 (H2N2); A/herring gull/DE/712/88 (H16N3); A/sw/Hong Kong/168/1993 (H1N1); A/mallard/Alberta/211/98 (H1N1); A/shorebird/Delaware/168/06 (H16N3); A/sw/Netherlands/25/80 (H1N1); A/sw/Germany/2/81 (H1N1); A/sw/Hannover/1/81 (H1N1); A/sw/Potsdam/1/81 (H1N1); A/sw/Potsdam/15/81 (H1N1); A/sw/Pots dam/268/81 (H1N1); A/sw/Finistere/2899/82 (H1N1); A/sw/Pots dam/35/82 (H3N2); A/sw/Cote d'Armor/3633/84 (H3N2); A/sw/Gent/1/84 (H3N2); A/sw/Netherlands/12/85 (H1N1); A/sw/Karrenzien/2/87 (H3N2); A/sw/Schwerin/103/89 (H1N1); A/turkey/Germany/3/91 (H1N1); A/sw/Germany/8533/91 (H1N1); A/sw/Belgium/220/92 (H3N2); A/sw/GentN230/92 (H1N1); A/sw/Leipzig/145/92 (H3N2); A/sw/Re220/92hp (H3N2); A/sw/Bakum/909/93 (H3N2); A/sw/Schleswig-Holstein/1/93 (H1N1); A/sw/Scotland/419440/94 (H1N2); A/sw/Bakum/5/95 (H1N1); A/sw/Best/5C/96 (H1N1); A/sw/England/17394/96 (H1N2); A/sw/Jena/5/96 (H3N2); A/sw/Oedenrode/7C/96 (H3N2); A/sw/Lohne/1/97 (H3N2); A/sw/Cote d'Armor/790/97 (H1N1); A/sw/Bakum/1362/98 (H3N2); A/sw/Italy/1521/98 (H1N2); A/sw/Italy/1553-2/98 (H3N2); A/sw/Italy/1566/98 (H1N1); A/sw/Italy/1589/98 (H1N1); A/sw/Bakum/8602/99 (H3N2); A/sw/Cotes d'Armor/604/99 (H1N2); A/sw/Cote d'Armor/1482/99 (H1N1); A/sw/Gent/7625/99 (H1N2); A/Hong Kong/1774/99 (H3N2); A/sw/Hong Kong/5190/99 (H3N2); A/sw/Hong Kong/5200/99 (H3N2); A/sw/Hong Kong/5212/99 (H3N2); A/sw/Ille et Villaine/1455/99 (H1N1); A/sw/Italy/1654-1/99 (H1N2); A/sw/Italy/2034/99 (H1N1); A/sw/Italy/2064/99 (H1N2); A/sw/Berlin/1578/00 (H3N2); A/sw/Bakum/1832/00 (H1N2); A/sw/Bakum/1833/00 (H1N2); A/sw/Cote d'Armor/800/00 (H1N2); A/sw/Hong Kong/7982/00 (H3N2); A/sw/Italy/1081/00 (H1N2); A/sw/Belzig/2/01 (H1N1); A/sw/Belzig/54/01 (H3N2); A/sw/Hong Kong/9296/01 (H3N2); A/sw/Hong Kong/9745/01 (H3N2); A/sw/Spain/33601/01 (H3N2); A/sw/Hong Kong/1144/02 (H3N2); A/sw/Hong Kong/1197/02 (H3N2); A/sw/Spain/39139/02 (H3N2); A/sw/Spain/42386/02 (H3N2); A/Switzerland/8808/2002 (H1N1); A/sw/Bakum/1769/03 (H3N2); A/sw/Bissendorf/IDT1864/03 (H3N2); A/sw/Ehren/IDT2570/03 (H1N2); A/sw/Gescher/IDT2702/03 (H1N2); A/sw/Haselünne/2617/03hp (H1N1); A/sw/Löningen/IDT2530/03 (H1N2); A/sw/IVD/IDT2674/03 (H1N2); A/sw/Nordkirchen/IDT1993/03 (H3N2); A/sw/Nordwalde/IDT2197/03 (H1N2); A/sw/Norden/IDT2308/03 (H1N2); A/sw/Spain/50047/03 (H1N1); A/sw/Spain/51915/03 (H1N1); A/sw/Vechta/2623/03 (H1N1); A/sw/Visbek/IDT2869/03 (H1N2); A/sw/Waltersdorf/IDT2527/03 (H1N2); A/sw/Damme/IDT2890/04 (H3N2); A/sw/Geldern/IDT2888/04 (H1N1); A/sw/Granstedt/IDT3475/04 (H1N2); A/sw/Greven/IDT2889/04 (H1N1); A/sw/Gudensberg/IDT2930/04 (H1N2); A/sw/Gudensberg/IDT2931/04 (H1N2); A/sw/Lohne/IDT3357/04 (H3N2); A/sw/Nortrup/IDT3685/04 (H1N2); A/sw/Seesen/IDT3055/04 (H3N2); A/sw/Spain/53207/04 (H1N1); A/sw/Spain/54008/04 (H3N2); A/sw/Stolzenau/IDT3296/04 (H1N2); A/sw/Wedel/IDT2965/04 (H1N1); A/sw/Bad Griesbach/IDT4191/05 (H3N2); A/sw/Cloppenburg/IDT4777/05 (H1N2); A/sw/Dötlingen/IDT3780/05 (H1N2); A/sw/Dötlingen/IDT4735/05 (H1N2); A/sw/Egglham/IDT5250/05 (H3N2); A/sw/Harkenblek/IDT4097/05 (H3N2); A/sw/Hertzen/IDT4317/

05 (H3N2); A/sw/Krogel/IDT4192/05 (H1N1); A/sw/Laer/IDT3893/05 (H1N1); A/sw/Laer/IDT4126/05 (H3N2); A/sw/Merzen/IDT4114/05 (H3N2); A/sw/Muesleringen-S./IDT4263/05 (H3N2); A/sw/Osterhofen/IDT4004/05 (H3N2); A/sw/Sprenge/IDT3805/05 (H1N2); A/sw/Stadtlohn/IDT3853/05 (H1N2); A/sw/Voglarn/IDT4096/05 (H1N1); A/sw/Wohlerst/IDT4093/05 (H1N1); A/sw/Bad Griesbach/IDT5604/06 (H1N1); A/sw/Herzlake/IDT5335/06 (H3N2); A/sw/Herzlake/IDT5336/06 (H3N2); A/sw/Herzlake/IDT5337/06 (H3N2); and A/wild boar/Germany/R169/2006 (H3N2).

Other specific examples of strains of influenza A virus include, but are not limited to: A/Toronto/3141/2009 (H1N1); A/Regensburg/D6/2009 (H1N1); A/Bayern/62/2009 (H1N1); A/Bayern/62/2009 (H1N1); A/Bradenburg/19/2009 (H1N1); A/Bradenburg/20/2009 (H1N1); A/Distrito Federal/2611/2009 (H1N1); A/Mato Grosso/2329/2009 (H1N1); A/Sao Paulo/1454/2009 (H1N1); A/Sao Paulo/2233/2009 (H1N1); A/Stockholm/37/2009 (H1N1); A/Stockholm/41/2009 (H1N1); A/Stockholm/45/2009 (H1N1); A/swine/Alberta/OTH-33-1/2009 (H1N1); A/swine/Alberta/OTH-33-14/2009 (H1N1); A/swine/Alberta/OTH-33-2/2009 (H1N1); A/swine/Alberta/OTH-33-21/2009 (H1N1); A/swine/Alberta/OTH-33-22/2009 (H1N1); A/swine/Alberta/OTH-33-23/2009 (H1N1); A/swine/Alberta/OTH-33-24/2009 (H1N1); A/swine/Alberta/OTH-33-25/2009 (H1N1); A/swine/Alberta/OTH-33-3/2009 (H1N1); A/swine/Alberta/OTH-33-7/2009 (H1N1); A/Beijing/502/2009 (H1N1); A/Firenze/10/2009 (H1N1); A/Hong Kong/2369/2009 (H1N1); A/Italy/85/2009 (H1N1); A/Santo Domingo/572N/2009 (H1N1); A/Catalonia/385/2009 (H1N1); A/Catalonia/386/2009 (H1N1); A/Catalonia/387/2009 (H1N1); A/Catalonia/390/2009 (H1N1); A/Catalonia/394/2009 (H1N1); A/Catalonia/397/2009 (H1N1); A/Catalonia/398/2009 (H1N1); A/Catalonia/399/2009 (H1N1); A/Sao Paulo/2303/2009 (H1N1); A/Akita/1/2009 (H1N1); A/Castro/JXP/2009 (H1N1); A/Fukushima/1/2009 (H1N1); A/Israel/276/2009 (H1N1); A/Israel/277/2009 (H1N1); A/Israel/70/2009 (H1N1); A/Iwate/1/2009 (H1N1); A/Iwate/2/2009 (H1N1); A/Kagoshima/1/2009 (H1N1); A/Osaka/180/2009 (H1N1); A/Puerto Montt/Bio87/2009 (H1N1); A/Sao Paulo/2303/2009 (H1N1); A/Sapporo/1/2009 (H1N1); A/Stockholm/30/2009 (H1N1); A/Stockholm/31/2009 (H1N1); A/Stockholm/32/2009 (H1N1); A/Stockholm/33/2009 (H1N1); A/Stockholm/34/2009 (H1N1); A/Stockholm/35/2009 (H1N1); A/Stockholm/36/2009 (H1N1); A/Stockholm/38/2009 (H1N1); A/Stockholm/39/2009 (H1N1); A/Stockholm/40/2009 (H1N1;) A/Stockholm/42/2009 (H1N1); A/Stockholm/43/2009 (H1N1); A/Stockholm/44/2009 (H1N1); A/Utsunomiya/2/2009 (H1N1); A/WRAIR/0573N/2009 (H1N1); and A/Zhejiang/DTID-ZJU01/2009 (H1N1).

Non-limiting examples of influenza B viruses include strain Aichi/5/88, strain B/Brisbane/60/2008; Akita/27/2001, strain Akita/5/2001, strain Alaska/16/2000, strain Alaska/1777/2005, strain Argentina/69/2001, strain Arizona/146/2005, strain Arizona/148/2005, strain Bangkok/163/90, strain Bangkok/34/99, strain Bangkok/460/03, strain Bangkok/54/99, strain Barcelona/215/03, strain Beijing/15/84, strain Beijing/184/93, strain Beijing/243/97, strain Beijing/43/75, strain Beijing/5/76, strain Beijing/76/98, strain Belgium/WV106/2002, strain Belgium/WV107/2002, strain Belgium/WV109/2002, strain Belgium/WV114/2002, strain Belgium/WV122/2002, strain Bonn/43, strain Brazil/952/2001, strain Bucharest/795/03, strain Buenos Aires/161/00), strain Buenos Aires/9/95, strain Buenos Aires/SW16/97, strain Buenos Aires/VL518/99, strain Canada/464/2001, strain Canada/464/2002, strain Chaco/366/00, strain Chaco/R113/00, strain Cheju/303/03, strain Chiba/447/98, strain Chongqing/3/2000, strain clinical isolate SA1 Thailand/2002, strain clinical isolate SA10 Thailand/2002, strain clinical isolate SA100 Philippines/2002, strain clinical isolate SA101 Philippines/2002, strain clinical isolate SA110 Philippines/2002), strain clinical isolate SA112 Philippines/2002, strain clinical isolate SA113 Philippines/2002, strain clinical isolate SA114 Philippines/2002, strain clinical isolate SA2 Thailand/2002, strain clinical isolate SA20 Thailand/2002, strain clinical isolate SA38 Philippines/2002, strain clinical isolate SA39 Thailand/2002, strain clinical isolate SA99 Philippines/2002, strain CNIC/27/2001, strain Colorado/2597/2004, strain Cordoba/VA418/99, strain Czechoslovakia/16/89, strain Czechoslovakia/69/90, strain Daeku/10/97, strain Daeku/45/97, strain Daeku/47/97, strain Daeku/9/97, strain B/Du/4/78, strain B/Durban/39/98, strain Durban/43/98, strain Durban/44/98, strain B/Durban/52/98, strain Durban/55/98, strain Durban/56/98, strain England/1716/2005, strain England/2054/2005), strain England/23/04, strain Finland/154/2002, strain Finland/159/2002, strain Finland/160/2002, strain Finland/161/2002, strain Finland/162/03, strain Finland/162/2002, strain Finland/162/91, strain Finland/164/2003, strain Finland/172/91, strain Finland/173/2003, strain Finland/176/2003, strain Finland/184/91, strain Finland/188/2003, strain Finland/190/2003, strain Finland/220/2003, strain Finland/WV5/2002, strain Fujian/36/82, strain Geneva/5079/03, strain Genoa/11/02, strain Genoa/2/02, strain Genoa/21/02, strain Genova/54/02, strain Genova/55/02, strain Guangdong/05/94, strain Guangdong/08/93, strain Guangdong/5/94, strain Guangdong/55/89, strain Guangdong/8/93, strain Guangzhou/7/97, strain Guangzhou/86/92, strain Guangzhou/87/92, strain Gyeonggi/592/2005, strain Hannover/2/90, strain Harbin/07/94, strain Hawaii/10/2001, strain Hawaii/1990/2004, strain Hawaii/38/2001, strain Hawaii/9/2001, strain Hebei/19/94, strain Hebei/3/94), strain Henan/22/97, strain Hiroshima/23/2001, strain Hong Kong/110/99, strain Hong Kong/1115/2002, strain Hong Kong/112/2001, strain Hong Kong/123/2001, strain Hong Kong/1351/2002, strain Hong Kong/1434/2002, strain Hong Kong/147/99, strain Hong Kong/156/99, strain Hong Kong/157/99, strain Hong Kong/22/2001, strain Hong Kong/22/89, strain Hong Kong/336/2001, strain Hong Kong/666/2001, strain Hong Kong/9/89, strain Houston/1/91, strain Houston/1/96, strain Houston/2/96, strain Hunan/4/72, strain Ibaraki/2/85, strain ncheon/297/2005, strain India/3/89, strain India/77276/2001, strain Israel/95/03, strain Israel/WV187/2002, strain Japan/1224/2005, strain Jiangsu/10/03, strain Johannesburg/1/99, strain Johannesburg/96/01, strain Kadoma/1076/99, strain Kadoma/122/99, strain Kagoshima/15/94, strain Kansas/22992/99, strain Khazkov/224/91, strain Kobe/1/2002, strain, strain Kouchi/193/99, strain Lazio/1/02, strain Lee/40, strain Leningrad/129/91, strain Lissabon/2/90), strain Los Angeles/1/02, strain Lusaka/270/99, strain Lyon/1271/96, strain Malaysia/83077/2001, strain Maputo/1/99, strain Mar del Plata/595/99, strain Maryland/1/01, strain Memphis/1/01, strain Memphis/12/97-MA, strain Michigan/22572/99, strain Mie/1/93, strain Milano/1/01, strain Minsk/318/90, strain Moscow/3/03, strain Nagoya/20/99, strain Nanchang/1/00, strain Nashville/107/93, strain Nashville/45/91, strain Nebraska/2/01, strain Netherland/801/90, strain Netherlands/429/98, strain New York/1/2002, strain NIB/48/90, strain Ningxia/45/83, strain Norway/1/84, strain Oman/16299/2001, strain Osaka/1059/97, strain Osaka/983/97-V2, strain Oslo/1329/2002, strain Oslo/1846/2002, strain Panama/45/90, strain Paris/329/90, strain Parma/23/02, strain Perth/211/2001, strain Peru/1364/2004, strain Philippines/5072/2001, strain Pusan/270/99, strain Quebec/173/98, strain Quebec/465/98, strain Quebec/7/01, strain Roma/1/03, strain Saga/S172/99, strain Seoul/13/95, strain Seoul/37/91, strain Shangdong/7/97, strain Shanghai/361/2002), strain Shiga/T30/98, strain Sichuan/379/99, strain Singapore/222/79, strain Spain/WV27/2002, strain Stockholm/10/90, strain Switzerland/5441/90, strain Taiwan/0409/00, strain Taiwan/0722/02, strain Taiwan/97271/2001, strain Tehran/80/02, strain Tokyo/6/98, strain Trieste/28/02, strain Ulan Ude/4/02, strain United Kingdom/34304/99, strain USSR/100/83, strain Victoria/103/89, strain Vienna/1/99, strain Wuhan/356/2000, strain WV194/2002, strain Xuanwu/23/82, strain Yamagata/1311/2003, strain Yamagata/K500/2001, strain Alaska/12/96, strain GA/86, strain NAGASAKI/1/87, strain Tokyo/942/96, strain B/Wisconsin/1/2010; and strain Rochester/02/2001.

Non-limiting examples of influenza C viruses include strain Aichi/1/81, strain Ann Arbor/1/50, strain Aomori/74, strain California/78, strain England/83, strain Greece/79, strain Hiroshima/246/2000, strain Hiroshima/252/2000, strain Hyogo/1/83, strain Johannesburg/66, strain Kanagawa/1/76, strain Kyoto/1/79, strain Mississippi/80, strain Miyagi/1/97, strain Miyagi/5/2000, strain Miyagi/9/96, strain Nara/2/85, strain NewJersey/76, strain pig/Beijing/115/81, strain Saitama/3/2000), strain Shizuoka/79, strain Yamagata/2/98, strain Yamagata/6/2000, strain Yamagata/9/96, strain BERLIN/1/85, strain ENGLAND/892/8, strain GREAT LAKES/1167/54, strain JJ/50, strain PIG/BEIJING/10/81, strain PIG/BEIJING/439/82), strain TAYLOR/1233/47, and strain C/YAMAGATA/10/81.

In certain embodiments, the influenza viruses provided herein have an attenuated phenotype. In specific embodiments, the attenuated influenza virus is based on influenza A virus. In other embodiments, the attenuated influenza virus is based on influenza B virus. In yet other embodiments, the attenuated influenza virus is based on influenza C virus. In other embodiments, the attenuated influenza virus may comprise genes or genome segments from one or more strains or subtypes of influenza A, influenza B, and/or influenza C virus. In some embodiments, the attenuated backbone virus comprises genes from an influenza A virus and an influenza B virus.

In specific embodiments, attenuation of influenza virus is desired such that the virus remains, at least partially, infectious and can replicate in vivo, but only generate low titers resulting in subclinical levels of infection that are non-pathogenic. Such attenuated viruses are especially suited for embodiments described herein wherein the virus or an immunogenic composition thereof is administered to a subject to induce an immune response. Attenuation of the influenza virus can be accomplished according to any method known in the art, such as, e.g., selecting viral mutants generated by chemical mutagenesis, mutation of the genome by genetic engineering, selecting reassortant viruses that contain segments with attenuated function, or selecting for conditional virus mutants (e.g., cold-adapted viruses). Alternatively, naturally occurring attenuated influenza viruses may be used as influenza virus backbones for the influenza virus vectors.

In one embodiment, an influenza virus may be attenuated, at least in part, by virtue of substituting the HA gene of the parental influenza virus with a flu hemagglutinin (HA) polypeptide described herein. In some embodiments, an influenza virus may be attenuated, at least in part, by engineering the influenza virus to express a mutated NS1 gene that impairs the ability of the virus to antagonize the cellular interferon (IFN) response. Examples of the types of mutations that can be introduced into the influenza virus NS1 gene include deletions, substitutions, insertions and combinations thereof. One or more mutations can be introduced anywhere throughout the NS1 gene (e.g., the N-terminus, the C-terminus or somewhere in between) and/or the regulatory element of the NS1 gene. In one embodiment, an attenuated influenza virus comprises a genome having a mutation in an influenza virus NS1 gene resulting in a deletion consisting of 5, preferably 10, 15, 20, 25, 30, 35, 40, 45, 50, 55, 60, 65, 75, 80, 85, 90, 95, 99, 100, 105, 110, 115, 120, 125, 126, 130, 135, 140, 145, 150, 155, 160, 165, 170 or 175 amino acid residues from the C-terminus of NS1, or a deletion of between 5-170, 25-170, 50-170, 100-170, 100-160, or 105-160 amino acid residues from the C-terminus. In another embodiment, an attenuated influenza virus comprises a genome having a mutation in an influenza virus NS1 gene such that it encodes an NS1 protein of amino acid residues 1-130, amino acid residues 1-126, amino acid residues 1-120, amino acid residues 1-115, amino acid residues 1-110, amino acid residues 1-100, amino acid residues 1-99, amino acid residues 1-95, amino acid residues 1-85, amino acid residues 1-83, amino acid residues 1-80, amino acid residues 1-75, amino acid residues 1-73, amino acid residues 1-70, amino acid residues 1-65, or amino acid residues 1-60, wherein the N-terminus amino acid is number 1. For examples of NS1 mutations and influenza viruses comprising a mutated NS1, see, e.g., U.S. Pat. Nos. 6,468,544 and 6,669,943; and Li et al., 1999, J. Infect. Dis. 179:1132-1138, each of which is incorporated by reference herein in its entirety.

5.8 Non-Influenza Virus Vectors

In one aspect, provided herein are non-influenza viruses containing a flu hemagglutinin (HA) polypeptide (e.g., a chimeric influenza virus emagglutinin (HA) polypeptide). In a specific embodiment, the flu hemagglutinin (HA) polypeptide is incorporated into the virions of the non-influenza virus. In a specific embodiment, the flu hemagglutinin (HA) polypeptide (e.g., a chimeric influenza virus hemagglutinin polypeptide) is contained in/expressed by a purified (e.g., plaque purified) or isolated virus. The non-influenza viruses may be conjugated to moieties that target the viruses to particular cell types, such as immune cells. In some embodiments, the virions of the non-influenza virus have incorporated into them or express a heterologous polypeptide in addition to a flu hemagglutinin (HA) polypeptide. The heterologous polypeptide may be a polypeptide that has immunopotentiating activity, or that targets the non-influenza virus to a particular cell type, such as an antibody that recognizes an antigen on a specific cell type or a ligand that binds a specific receptor on a specific cell type. See Section 5.4 supra for examples of such heterologous polypeptides.

Non-influenza viruses containing/expressing a flu hemagglutinin (HA) polypeptide can be produced using techniques known to those skilled in the art. Non-influenza viruses containing a flu hemagglutinin (HA) polypeptide may be produced by supplying in trans the flu hemagglutinin (HA) polypeptide during production of virions using techniques known to one skilled in the art. Alternatively, the replication of a parental non-influenza virus comprising a genome engineered to express a flu hemagglutinin (HA) polypeptide in cells susceptible to infection with the virus wherein hemagglutinin function is provided in trans will produce progeny viruses containing the flu hemagglutinin (HA) polypeptide.

Any virus type, subtype or strain including, but not limited to, naturally occurring strains, variants or mutants, mutagenized viruses, reassortants and/or genetically modified viruses may be used as a non-influenza virus vector. In a specific embodiment, the parental non-influenza virus is not a naturally occurring virus. In another specific embodiment, the parental non-influenza virus is a genetically engineered virus. In certain embodiments, an enveloped virus is preferred for the expression of a membrane bound flu hemagglutinin (HA) polypeptide described herein.

In an exemplary embodiment, the non-influenza virus vector is a Newcastle disease virus (NDV). In another embodiment, the non-influenza virus vector is a vaccinia virus. In other exemplary, non-limiting, embodiments, the non-influenza virus vector is adenovirus, adeno-associated virus (AAV), hepatitis B virus, retrovirus (such as, e.g., a gammaretrovirus such as Mouse Stem Cell Virus (MSCV) genome or Murine Leukemia Virus (MLV), e.g., Moloney murine leukemia virus, oncoretrovirus, or lentivirus), an alphavirus (e.g., Venezuelan equine encephalitis virus), a rhabdovirus, such as vesicular stomatitis virus or papillomaviruses, poxvirus (such as, e.g., vaccinia virus, a MVA-T7 vector, or fowlpox), metapneumovirus, measles virus, herpesvirus, such as herpes simplex virus, or foamyvirus. See, e.g., Lawrie and Tumin, 1993, Cur. Opin. Genet. Develop. 3, 102-109 (retroviral vectors); Bett et al., 1993, J. Virol. 67, 5911 (adenoviral vectors); Zhou et al., 1994, J. Exp. Med. 179, 1867 (adeno-associated virus vectors); Dubensky et al., 1996, J. Virol. 70, 508-519 (viral vectors from the pox family including vaccinia virus and the avian pox viruses and viral vectors from the alpha virus genus such as those derived from Sindbis and Semliki Forest Viruses); U.S. Pat. No. 5,643,576 (Venezuelan equine encephalitis virus); WO 96/34625 (VSV); Ohe et al., 1995, Human Gene Therapy 6, 325-333; Woo et al., WO 94/12629; Xiao & Brandsma, 1996, Nucleic Acids. Res. 24, 2630-2622 (papillomaviruses); and Bukreyev and Collins, 2008, Curr Opin Mol. Ther. 10:46-55 (NDV), each of which is incorporated by reference herein in its entirety.

In a specific embodiment, the non-influenza virus vector is NDV. Any NDV type, subtype or strain may serve as the backbone that is engineered to express a flu hemagglutinin (HA) polypeptide, including, but not limited to, naturally-occurring strains, variants or mutants, mutagenized viruses, reassortants and/or genetically engineered viruses. In a specific embodiment, the NDV that serves as the backbone for genetic engineering is a naturally-occurring strain. In certain embodiments, the NDV that serves as the backbone for genetic engineering is a lytic strain. In other embodiments, the NDV that serves as the backbone for genetic engineering is a non-lytic strain. In certain embodiments, the NDV that serves as the backbone for genetic engineering is lentogenic strain. In some embodiments, the NDV that serves as the backbone for genetic engineering is a mesogenic strain. In other embodiments, the NDV that serves as the backbone for genetic engineering is a velogenic strain. Specific examples of NDV strains include, but are not limited to, the 73-T strain, Ulster strain, MTH-68 strain, Italien strain, Hickman strain, PV701 strain, Hitchner B1 strain, La Sota strain, YG97 strain, MET95 strain, and F48E9 strain. In a specific embodiment, the NDV that serves as the backbone for genetic engineering is the Hitchner B1 strain. In another specific embodiment, the NDV that serves as the backbone for genetic engineering is the La Sota strain.

In one embodiment, the NDV used as the backbone for a non-influenza virus vector is engineered to express a modified F protein in which the cleavage site of the F protein is replaced with one containing one or two extra arginine residues, allowing the mutant cleavage site to be activated by ubiquitously expressed proteases of the furin family. Specific examples of NDVs that express such a modified F protein include, but are not limited to, rNDV/F2aa and rNDV/F3aa. For a description of mutations introduced into a NDV F protein to produce a modified F protein with a mutated cleavage site, see, e.g., Park et al. (2006) "Engineered viral vaccine constructs with dual specificity: Avian influenza and Newcastle disease." PNAS USA 103: 8203-2808, which is incorporated herein by reference in its entirety.

In one embodiment, the non-influenza virus vector is a poxvirus. A poxvirus vector may be based on any member of the poxyiridae, in particular, a vaccinia virus or an avipox virus (e.g., such as canarypox, fowlpox, etc.) that provides suitable sequences for vaccine vectors. In a specific embodiment, the poxyiral vector is a vaccinia virus vector. Suitable vaccinia viruses include, but are not limited to, the Copenhagen (VC-2) strain (Goebel, et al., Virol 179: 247-266, 1990; Johnson, et al., Virol. 196: 381-401, 1993), modified Copenhagen strain (NYVAC) (U.S. Pat. No. 6,265,189), the WYETH strain and the modified Ankara (MVA) strain (Antoine, et al., Virol. 244: 365-396, 1998). Other suitable poxviruses include fowlpox strains such as ALVAC and TROVAC vectors that provide desirable properties and are highly attenuated (see, e.g., U.S. Pat. No. 6,265,189; Tartaglia et al., In AIDS Research Reviews, Koff, et al., eds., Vol. 3, Marcel Dekker, N.Y., 1993; and Tartaglia et al., 1990, Reviews in Immunology 10: 13-30, 1990).

Methods of engineering non-influenza viruses to express influenza polypeptides are well known in the art, as are methods for attenuating, propagating, and isolating and purifying such viruses. For such techniques with respect to NDV vectors, see, e.g., International Publication No. WO 01/04333; U.S. Pat. Nos. 7,442,379, 6,146,642, 6,649,372, 6,544,785 and 7,384,774; Swayne et al. (2003). Avian Dis. 47:1047-1050; and Swayne et al. (2001). J. Virol. 11868-11873, each of which is incorporated by reference in its entirety. For such techniques with respect to poxviruses, see, e.g., Piccini, et al., Methods of Enzymology 153: 545-563, 1987; International Publication No. WO 96/11279; U.S. Pat. No. 4,769,330; U.S. Pat. No. 4,722,848; U.S. Pat. No. 4,769,330; U.S. Pat. No. 4,603,112; U.S. Pat. No. 5,110,587; U.S. Pat. No. 5,174,993; EP 83 286; EP 206 920; Mayr et al., Infection 3: 6-14, 1975; and Sutter and Moss, Proc. Natl. Acad. Sci. USA 89: 10847-10851, 1992. In certain embodiments, the non-influenza virus is attenuated.

Exemplary considerations for the selection of a non-influenza virus vector, particularly for use in compositions for administration to a subject, are safety, low toxicity, stability, cell type specificity, and immunogenicity, particularly, antigenicity of the flu hemagglutinin (HA) polypeptide expressed by the non-influenza virus vector.

5.9 Virus-Like Particles and Virosomes

The flu hemagglutinin (HA) polypeptides (e.g., chimeric influenza virus hemagglutinin polypeptides) described herein can be incorporated into virus-like particle (VLP) vectors, e.g., purified/isolated VLPs. VLPs generally comprise a viral polypeptide(s) typically derived from a structural protein(s) of a virus. In some embodiments, the VLPs are not capable of replicating. In certain embodiments, the VLPs may lack the complete genome of a virus or comprise a portion of the genome of a virus. In some embodiments, the VLPs are not capable of infecting a cell. In some embodiments, the VLPs express on their surface one or more of viral (e.g., virus surface glycoprotein) or non-viral (e.g., antibody or protein) targeting moieties known to one skilled in the art or described herein. In some embodiments, the VLPs comprise a flu hemagglutinin (HA) polypeptide and a viral structural protein, such as HIV gag. In a specific embodiment, the VLPs comprise a flu hemagglutinin (HA) polypeptide and an HIV gag polypeptide.

Methods for producing and characterizing recombinantly produced VLPs have been described based on several viruses, including influenza virus (Bright et al. (2007) Vaccine. 25:3871), human papilloma virus type 1 (Hagnesee et al. (1991) J. Virol. 67:315), human papilloma virus type 16 (Kirnbauer et al. Proc. Natl. Acad. Sci. (1992)89:12180), HIV-1 (Haffer et al., (1990) J. Virol. 64:2653), and hepatitis A (Winokur (1991) 65:5029), each of which is incorporated herein in its entirety. Methods for expressing VLPs that contain NDV proteins are provided by Pantua et al. (2006) J. Virol. 80:11062-11073, and in United States patent application Publication No. 20090068221, published Mar. 12, 2009, each of which is incorporated in its entirety herein. In a specific embodiment, the VLPs comprising flu hemagglutinin (HA) polypeptide described herein are generated using baculovirus, as described in the Examples section below. In other embodiments, the VLPs comprising flu hemagglutinin (HA) polypeptides described herein are generated using 293T cells, as described in the Examples section below.

In specific embodiments, VLPs, e.g., VLPs comprising a flu hemagglutinin (HA) polypeptide, are expressed in cells (e.g., 293T cells). In certain embodiments, the VLPs are expressed in cells that express surface glycoproteins that comprise sialic acid. In accordance with such embodiments, the cells are cultured in the presence of neuraminidase (e.g., viral of bacterial neuraminidase). In certain embodiments, VLPs, e.g., VLPs comprising a flu hemagglutinin (HA) polypeptide, are expressed in cells that do not express surface glycoproteins that comprise sialic acid.

In a specific embodiment, a flu hemagglutinin (HA) polypeptide may be incorporated into a virosome. A virosome containing a flu hemagglutinin (HA) polypeptide may be produced using techniques known to those skilled in the art. For example, a virosome may be produced by disrupting a purified virus, extracting the genome, and reassembling particles with the viral proteins (e.g., a flu hemagglutinin (HA) polypeptide) and lipids to form lipid particles containing viral proteins.

5.10 Bacterial Vectors

In a specific embodiment, bacteria may be engineered to express a flu hemagglutinin (HA) polypeptide (e.g., chimeric influenza virus hemagglutinin polypeptide) described herein. Suitable bacteria for expression of a flu hemagglutinin (HA) polypeptide include, but are not limited to, *Listeria, Salmonella, Shigella* sp., *Mycobacterium tuberculosis, E. coli, Neisseria meningitides, Brucella abortus, Brucella melitensis, Borrelia burgdorferi, Lactobacillus, Campylobacter, Lactococcus, Bifidobacterium*, and *Francisella tularensis*. In a specific embodiment, the bacteria engineered to express a flu hemagglutinin (HA) polypeptide are attenuated. Techniques for the production of bacteria engineered to express a heterologous polypeptide are known in the art and can be applied to the expression of a flu hemagglutinin (HA) polypeptide. See, e.g., United States Patent Application Publication No. 20080248066, published Oct. 9, 2008, and United States Patent Application Publication No. 20070207171, published Sep. 6, 2007, each of which are incorporated by reference herein in their entirety. In certain embodiments, the bacterial vectors used herein possess the ability to perform N-linked glycosylation, e.g., such bacteria naturally possess N-glycosylation machinery (e.g., *Campylobacter*) or have been genetically engineered to possess N-glycosylation machinery.

5.11 Plant and Algae Vectors

In certain embodiments, plants (e.g., plants of the genus *Nicotiana*) may be engineered to express a flu hemagglutinin (HA) polypeptide described herein. In specific embodiments, plants are engineered to express a flu hemagglutinin (HA) polypeptide (e.g., a chimeric influenza virus hemagglutinin polypeptide) described herein via an agroinfiltration procedure using methods known in the art. For example, nucleic acids encoding a gene of interest, e.g., a gene encoding a flu hemagglutinin (HA) polypeptide described herein, are introduced into a strain of *Agrobacterium*. Subsequently the strain is grown in a liquid culture and the resulting bacteria are washed and suspended into a buffer solution. The plants are then exposed (e.g., via injection or submersion) to the *Agrobacterium* that comprises the nucleic acids encoding a flu hemagglutinin (HA) polypeptide described herein such that the *Agrobacterium* transforms the gene of interest to a portion of the plant cells. The flu hemagglutinin (HA) polypeptide is then transiently expressed by the plant and can isolated using methods known in the art and described herein. (For specific examples see Shoji et al., 2008, Vaccine, 26(23):2930-2934; and D'Aoust et al., 2008, J. Plant Biotechnology, 6(9):930-940). In a specific embodiment, the plant is a tobacco plant (i.e., *Nicotiana tabacum*). In another specific embodiment, the plant is a relative of the tobacco plant (e.g., *Nicotiana benthamiana*). In another specific embodiment, the flu hemagglutinin (HA) polypeptides described herein are expressed in a species of soy. In another specific embodiment, the flu hemagglutinin (HA) polypeptides described herein are expressed in a species of corn. In another specific embodiment, the flu hemagglutinin (HA) polypeptides described herein are expressed in a species of rice In other embodiments, algae (e.g., *Chlamydomonas reinhardtii*) may be engineered to express a flu hemagglutinin (HA) polypeptide described herein (see, e.g., Rasala et al., 2010, Plant Biotechnology Journal (Published online Mar. 7, 2010)).

In certain embodiments, the plants used to express the flu hemagglutinin (HA) polypeptides described herein are engineered to express components of an N-glycosylation system (e.g., a bacterial or mammalian N-glycosylation system), i.e., the plants can perform N-glycosylation.

Plant cells that can be used to express the flu hemagglutinin (HA) polypeptides and methods for the production of proteins utilizing plant cell culture systems are described in, e.g., U.S. Pat. Nos. 5,929,304; 7,504,560; 6,770,799; 6,551,820; 6,136,320; 6,034,298; 5,914,935; 5,612,487; and 5,484,719, U.S. patent application publication Nos. 2009/0208477, 2009/0082548, 2009/0053762, 2008/0038232, 2007/0275014 and 2006/0204487, and Shoji et al., 2008, Vaccine, 26(23):2930-2934, and D'Aoust et al., 2008, J. Plant Biotechnology, 6(9):930-940 (which are incorporated herein by reference in their entirety).

5.12 Generation of Antibodies Against Flu Hemagglutinin (HA) Polypeptides

The flu hemagglutinin (HA) polypeptides, nucleic acids encoding such polypeptides, or vectors comprising such nucleic acids or polypeptides described herein may be used to elicit neutralizing antibodies against influenza, for example, against the stalk region of an influenza virus hemagglutinin polypeptide. In a specific embodiment, the flu hemagglutinin (HA) polypeptide, nucleic acids encoding such polypeptides, or vectors comprising such nucleic acids or polypeptides described herein may be administered to a non-human subject (e.g., a mouse, rabbit, rat, guinea pig, etc.) to induce an immune response that includes the production of antibodies which may be isolated using techniques known to one of skill in the art (e.g., immunoaffinity chromatography, centrifugation, precipitation, etc.).

Alternatively, the flu hemagglutinin (HA) polypeptide described herein may be used to screen for antibodies from antibody libraries. For example, an isolated flu hemagglutinin (HA) polypeptide may be immobilized to a solid support (e.g., a silica gel, a resin, a derivatized plastic film, a glass bead, cotton, a plastic bead, a polystyrene bead, an alumina gel, or a polysaccharide, a magnetic bead), and screened for binding to antibodies. As an alternative, the antibodies may be immobilized to a solid support and screened for binding to the isolated flu hemagglutinin (HA) polypeptides. Any screening assay, such as a panning assay, ELISA, surface plasmon resonance, or other antibody screening assay known in the art may be used to screen for antibodies that bind to the flu hemagglutinin (HA) polypeptide. The antibody library screened may be a commercially available antibody library, an in vitro generated library, or a library obtained by identifying and cloning or isolating antibodies from an individual infected with influenza. In particular embodiments, the antibody library is generated from a survivor of an influenza virus outbreak. Antibody libraries may be generated in accordance with methods known in the art. In a particular embodiment, the antibody library is generated by cloning the antibodies and using them in phage display libraries or a phagemid display library.

Antibodies identified in the methods described herein may be tested for neutralizing activity and lack of autoreactivity using the biological assays known in the art or described herein. In one embodiment, an antibody isolated from a non-human animal or an antibody library neutralizes a hemagglutinin polypeptide from more than one influenza subtype. In some embodiments, an antibody elicited or identified using a flu hemagglutinin (HA) polypeptide, a nucleic acid encoding such a polypeptide, or a vector encoding such a nucleic acid or polypeptide neutralizes an influenza H3 virus. In some embodiments, an antibody elicited or identified using a flu hemagglutinin (HA) polypeptide, a nucleic acid encoding such a polypeptide, or a vector comprising such a nucleic acid or polypeptide neutralizes 1, 2, 3, 4, 5, 6, 7, 8, 9, 10, 11, 12, 13, 14, 15, or 16 or more subtypes or strains of influenza virus. In one embodiment, the neutralizing antibody neutralizes one or more influenza A viruses and one or more influenza B viruses. In particular embodiments, the neutralizing antibody is not, or does not bind the same epitope as CR6261, CR6325, CR6329, CR6307, CR6323, 2A, D7, D8, F10, G17, H40, A66, D80, E88, E90, H98, C179 (produced by hybridoma FERM BP-4517; clones sold by Takara Bio, Inc. (Otsu, Shiga, Japan)), and/or AI3C (FERM BP-4516); or any other antibody described in Ekiert D C et al. (2009) Antibody Recognition of a Highly Conserved Influenza Virus Epitope. Science (published in Science Express Feb. 26, 2009); Kashyap et al. (2008) Combinatorial antibody libraries from survivors of the Turkish H5N1 avian influenza outbreak reveal virus neutralization strategies. Proc Natl Acad Sci USA 105: 5986-5991; Sui et al. (2009) Structural and functional bases for broad-spectrum neutralization of avian and human influenza A viruses. Nat Struct Mol Biol 16: 265-273; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/US2008/085876 published as International Publication No. WO 2009/079259. In other embodiments, the neutralizing antibody is not an antibody described in Wang et al. (2010) "Broadly Protective Monoclonal Antibodies against H3 Influenza Viruses following Sequential Immunization with Different Hemagglutinins," PLOS Pathogens 6(2):1-9. In particular embodiments, the neutralizing antibody does not use the Ig VH1-69 segment. In some embodiments, the interaction of the neutralizing antibody with the antigen is not mediated exclusively by the heavy chain.

Antibodies identified or elicited using a flu hemagglutinin (HA) polypeptide, a nucleic acid encoding such a polypeptide, or a vector comprising such a nucleic acid or polypeptide include immunoglobulin molecules and immunologically active portions of immunoglobulin molecules, i.e., molecules that contain an antigen binding site that specifically binds to a hemagglutinin polypeptide. The immunoglobulin molecules may be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule. Antibodies include, but are not limited to, monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies elicited or identified using a method described herein), and epitope-binding fragments of any of the above.

Antibodies elicited or identified using a flu hemagglutinin (HA) polypeptides, nucleic acids encoding such a polypeptide or a vector comprising such a nucleic acid or polypeptide may be used in diagnostic immunoassays, passive immunotherapy, and generation of antiidiotypic antibodies. The antibodies before being used in passive immunotherapy may be modified, e.g., the antibodies may be chimerized or humanized. See, e.g., U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741, each of which is incorporated herein by reference in its entirety, for reviews on the generation of chimeric and humanized antibodies. In addition, the ability of the antibodies to neutralize hemagglutinin polypeptides and the specificity of the antibodies for the polypeptides may be tested prior to using the antibodies in passive immunotherapy. See Section 5.11 infra for a discussion regarding use of neutralizing antibodies for the prevention or treatment of disease caused by influenza virus infection.

Antibodies elicited or identified using a flu hemagglutinin (HA) polypeptide, a nucleic acid encoding such a polypeptide, or a vector comprising such a nucleic acid or polypeptide may be used to monitor the efficacy of a therapy and/or disease progression. Any immunoassay system known in the art may be used for this purpose including, but not limited to, competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays, to name but a few.

Antibodies elicited or identified using a flu hemagglutinin (HA) polypeptide, a nucleic acid encoding such a polypeptide, or a vector comprising such a nucleic acid or polypeptide may be used in the production of antiidiotypic antibody. The antiidiotypic antibody can then in turn be used for immunization, in order to produce a subpopulation of antibodies that bind a particular antigen of influenza, e.g., a neutralizing epitope of a hemagglutinin polypeptide (Jerne, 1974, Ann. Immunol. (Paris) 125c:373; Jerne et al., 1982, EMBO J. 1:234, incorporated herein by reference in its entirety).

5.13 Stimulation of Cells with Flu Hemagglutinin (HA) Polypeptides

In another aspect, provided herein are methods for stimulating cells ex vivo with a flu hemagglutinin (HA) polypeptide (e.g., a chimeric influenza virus hemagglutinin polypeptide) described herein. Such cells, e.g., dendritic cells, may be used in vitro to generate antibodies against the flu hemagglutinin (HA) polypeptide or may themselves be administered to a subject by, e.g., an adoptive transfer technique known in the art. See, e.g., United States patent application Publication No. 20080019998, published Jan. 24, 2008, which is incorporated herein by reference in its entirety, for a description of adoptive transfer techniques. In certain embodiments, when cells that have been stimulated ex vivo with a flu hemagglutinin (HA) polypeptide described herein are administered to a subject, the cells are not mammalian cells (e.g., CB-1 cells).

In one non-limiting example, a vector, e.g., an influenza virus vector, engineered to express a flu hemagglutinin (HA) polypeptide described herein can be used to generate dendritic cells (DCs) that express the flu hemagglutinin (HA) polypeptide and display immunostimulatory properties directed against an influenza virus hemagglutinin polypeptide. Such DCs may be used to expand memory T cells and are potent stimulators of T cells, including flu hemagglutinin (HA) polypeptide-specific cytotoxic T lymphocyte clones. See Strobel et al., 2000, Human Gene Therapy 11:2207-2218, which is incorporated herein by reference in its entirety.

A flu hemagglutinin (HA) polypeptide described herein may be delivered to a target cell in any way that allows the polypeptide to contact the target cell, e.g., a DC, and deliver the polypeptide to the target cell. In certain embodiments, the flu hemagglutinin (HA) polypeptide is delivered to a subject, as described herein. In some such embodiments, cells contacted with the polypeptide may be isolated and propagated.

In certain embodiments, a flu hemagglutinin (HA) polypeptide is delivered to a target cell in vitro. Techniques known to one of skill in the art may be used to deliver the polypeptide to target cells. For example, target cells may be contacted with the polypeptide in a tissue culture plate, tube or other container. The polypeptide may be suspended in media and added to the wells of a culture plate, tube or other container. The media containing the polypeptide may be added prior to plating of the cells or after the cells have been plated. The target cells are preferably incubated with the polypeptide for a sufficient amount of time to allow the polypeptide to contact the cells. In certain embodiments, the cells are incubated with the polypeptide for about 1 hour or more, about 5 hours or more, about 10 hours or more, about 12 hours or more, about 16 hours or more, about 24, hours or more, about 48 hours or more, about 1 hour to about 12 hours, about 3 hours to about 6 hours, about 6 hours to about 12 hours, about 12 hours to about 24 hours, or about 24 hours to about 48 hours. In certain embodiments, wherein the flu hemagglutinin (HA) polypeptide is in a virus, the contacting of the target cells comprises infecting the cells with the virus.

The target cells may be from any species, including, e.g., humans, mice, rats, rabbits and guinea pigs. In some embodiments, target cells are DCs obtained from a healthy subject or a subject in need of treatment. In certain embodiments, target cells are DCs obtained from a subject in whom it is desired to stimulate an immune response to the polypeptide. Methods of obtaining cells from a subject are well known in the art.

5.14 Compositions

The nucleic acids, vectors, polypeptides, bacteria, antibodies, or cells described herein (sometimes referred to herein as "active compounds") may be incorporated into compositions. In a specific embodiment, the compositions are pharmaceutical compositions, such as immunogenic compositions (e.g., vaccine formulations). The pharmaceutical compositions provided herein can be in any form that allows for the composition to be administered to a subject. In a specific embodiment, the pharmaceutical compositions are suitable for veterinary and/or human administration. The compositions may be used in methods of preventing or treating an influenza virus disease.

In one embodiment, a pharmaceutical composition comprises a flu hemagglutinin (HA) polypeptide (e.g., a chimeric influenza virus hemagglutinin polypeptide), in an admixture with a pharmaceutically acceptable carrier. In another embodiment, a pharmaceutical composition comprises a nucleic acid encoding a flu hemagglutinin (HA) polypeptide described herein, in an admixture with a pharmaceutically acceptable carrier. In another embodiment, a pharmaceutical composition comprises an expression vector comprising a nucleic acid encoding a flu hemagglutinin (HA) polypeptide, in an admixture with a pharmaceutically acceptable carrier. In another embodiment, a pharmaceutical composition comprises an influenza virus or non-influenza virus containing a flu hemagglutinin (HA) polypeptide, in an admixture with a pharmaceutically acceptable carrier. In another embodiment, a pharmaceutical composition comprises an influenza virus or non-influenza virus having a genome engineered to express a flu hemagglutinin (HA) polypeptide, in admixture with a pharmaceutically acceptable carrier. In another embodiment, a pharmaceutical composition comprises a virus-like particle or virosome containing a flu hemagglutinin (HA) polypeptide, in an admixture with a pharmaceutically acceptable carrier. In another embodiment, a pharmaceutical composition comprises a bacteria expressing or engineered to express a flu hemagglutinin (HA) polypeptide, in an admixture with a pharmaceutically acceptable carrier. In another embodiment, a pharmaceutical composition comprises cells stimulated with a flu hemagglutinin (HA) polypeptide, in an admixture with a pharmaceutically acceptable carrier.

In some embodiments, a pharmaceutical composition may comprise one or more other therapies in addition to a therapy that utilizes a flu hemagglutinin (HA) polypeptide described herein.

As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In a specific embodiment, pharmaceutical compositions are formulated to be suitable for the intended route of administration to a subject. For example, the pharmaceutical composition may be formulated to be suitable for parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, biodegradable polymers, such as ethylene vinyl acetate, polyanhydrides, polyethylene glycol (PEGylation), polymethyl methacrylate polymers, polylactides, poly(lactide-co-glycolides), polyglycolic acid, collagen, polyorthoesters, and polylactic acid, may be used as carriers. In some embodiments, the active compounds are prepared with carriers that increase the protection of the compound against rapid elimination from the body, such as a controlled release formulation, including implants and microencapsulated delivery systems. Methods for preparation of such formulations will be apparent to those skilled in the art. Liposomes or micelles can also be used as pharmaceutically acceptable carriers. These can be prepared according to methods known to those skilled in the art, for example, as described in U.S. Pat. No. 4,522,811. In certain embodiments, the pharmaceutical compositions comprise one or more adjuvants.

In specific embodiments, immunogenic compositions described herein are monovalent formulations. In other embodiments, immunogenic compositions described herein are multivalent formulations. In one example, a multivalent formulation comprises more than one vector expressing a flu hemagglutinin (HA) polypeptide. In certain embodiments, a multivalent formulation may comprise one or more different flu hemagglutinin (HA) polypeptides expressed using a single vector.

In certain embodiments, the pharmaceutical compositions described herein additionally comprise a preservative, e.g., the mercury derivative thimerosal. In a specific embodiment, the pharmaceutical compositions described herein comprises 0.001% to 0.01% thimerosal. In other embodiments, the pharmaceutical compositions described herein do not comprise a preservative. In a specific embodiment, thimerosal is used during the manufacture of a pharmaceutical composition described herein and the thimerosal is removed via purification steps following production of the pharmaceutical composition, i.e., the pharmaceutical composition contains trace amounts of thimerosal (<0.3 µg of mercury per dose after purification; such pharmaceutical compositions are considered thimerosal-free products).

In certain embodiments, the pharmaceutical compositions described herein additionally comprise egg protein (e.g., ovalbumin or other egg proteins). The amount of egg protein in the pharmaceutical compositions described herein may range from about 0.0005 to about 1.2. µg of egg protein to 1 ml of pharmaceutical composition. In other embodiments, the pharmaceutical compositions described herein do not comprise egg protein.

In certain embodiments, the pharmaceutical compositions described herein additionally comprise one or more antimicrobial agents (e.g., antibiotics) including, but not limited to gentamicin, neomycin, polymyxin (e.g., polymyxin B), and kanamycin, streptomycin. In other embodiments, the pharmaceutical compositions described herein do not comprise any antibiotics.

In certain embodiments, the pharmaceutical compositions described herein additionally comprise one or more components used to inactivate a virus, e.g., formalin or formaldehyde or a detergent such as sodium deoxycholate, octoxynol 9 (Triton X-100), and octoxynol 10. In other embodiments, the pharmaceutical compositions described herein do not comprise any components used to inactivate a virus.

In certain embodiments, the pharmaceutical compositions described herein additionally comprise gelatin. In other embodiments, the pharmaceutical compositions described herein do not comprise gelatin.

In certain embodiments, the pharmaceutical compositions described herein additionally comprise one or more buffers, e.g., phosphate buffer and sucrose phosphate glutamate buffer. In other embodiments, the pharmaceutical compositions described herein do not comprise buffers.

In certain embodiments, the pharmaceutical compositions described herein additionally comprise one or more salts, e.g., sodium chloride, calcium chloride, sodium phosphate, monosodium glutamate, and aluminum salts (e.g., aluminum hydroxide, aluminum phosphate, alum (potassium aluminum sulfate), or a mixture of such aluminum salts). In other embodiments, the pharmaceutical compositions described herein do not comprise salts.

In specific embodiments, the pharmaceutical compositions described herein are low-additive influenza virus vaccines, i.e., the pharmaceutical compositions do not comprise one or more additives commonly found in influenza virus vaccines. Low-additive influenza vaccines have been described (see, e.g., International Application No. PCT/IB2008/002238 published as International Publication No. WO 09/001,217 which is herein incorporated by reference in its entirety).

The pharmaceutical compositions described herein can be included in a container, pack, or dispenser together with instructions for administration.

The pharmaceutical compositions described herein can be stored before use, e.g., the pharmaceutical compositions can be stored frozen (e.g., at about −20° C. or at about −70° C.); stored in refrigerated conditions (e.g., at about 4° C.); or stored at room temperature (see International Application No. PCT/IB2007/001149 published as International Publication No. WO 07/110,776, which is herein incorporated by reference in its entirety, for methods of storing compositions comprising influenza vaccines without refrigeration).

In certain embodiments, when the active compound in a pharmaceutical composition described herein is a cell engineered to express a flu hemagglutinin (HA) polypeptide, the cells in the pharmaceutical composition are not mammalian cells (e.g., CB-1 cells).

5.14.1 Subunit Vaccines

In a specific embodiment, provided herein are subunit vaccines comprising a flu hemagglutinin (HA) polypeptide (e.g., a chimeric influenza virus hemagglutinin polypeptide) described herein. In some embodiments, a subunit vaccine comprises a flu hemagglutinin (HA) polypeptide and one or more surface glycoproteins (e.g., influenza virus neuraminidase), other targeting moieties, or adjuvants. In specific embodiments, a subunit vaccine comprises a single flu hemagglutinin (HA) polypeptide. In other embodiments, a subunit vaccine comprises two, three, four or more flu hemagglutinin (HA) polypeptides. In specific embodiments, the flu hemagglutinin (HA) polypeptide (s) used in a subunit vaccine is not membrane-bound, i.e., it is soluble.

In certain embodiments, provided herein are subunit vaccines comprising about 10 μg to about 60 μg of one or more flu hemagglutinin (HA) polypeptides described herein, about 0.001% to 0.01% thimerosal, about 0.1 μg to about 1.0 μg chicken egg protein, about 1.0 μg to about 5.0 μg polymyxin, about 1.0 μg to about 5.0 μg neomycin, about 0.1 μg to about 0.5 μg betapropiolactone, and about 0.001 to about 0.05% w/v of nonylphenol ethoxylate per dose.

In a specific embodiment, a subunit vaccine provided herein comprises or consists of a 0.5 ml dose that comprises 45 μg of flu hemagglutinin (HA) polypeptide (s) provided herein, ≤1.0 μg of mercury (from thimerosal), ≤1.0 μg chicken egg protein (i.e., ovalbumin), ≤3.75 μg polymyxin, and ≤2.5 μg neomycin. In some embodiments, a subunit vaccine provided herein additionally comprises or consists of not more than 0.5 μg betapropiolactone, and not more than 0.015% w/v of nonylphenol ethoxylate per dose. In some embodiments, the 0.5 ml dose subunit vaccine is packaged in a pre-filled syringe.

In a specific embodiment, a subunit vaccine provided herein consists of a 5.0 ml multidose vial (0.5 ml per dose) that comprises 45 μg of flu hemagglutinin (HA) polypeptide (s) provided herein, 25.0 μg of mercury (from thimerosal), ≤1.0 μg chicken egg protein (i.e., ovalbumin), ≤3.75 μg polymyxin, and ≤2.5 μg neomycin. In some embodiments, a subunit vaccine provided herein additionally comprises or consists of not more than 0.5 μg betapropiolactone, and not more than 0.015% w/v of nonylphenol ethoxylate per dose.

In a specific embodiment, the subunit vaccine is prepared using influenza virus that was propagated in embryonated chicken eggs (i.e., the components of the subunit vaccine (e.g., a flu hemagglutinin (HA) polypeptide) are isolated from virus that was propagated in embryonated chicken eggs). In another specific embodiment, the subunit vaccine is prepared using influenza virus that was not propagated in embryonated chicken eggs (i.e., the components of the subunit vaccine (e.g., a flu hemagglutinin (HA) polypeptide) are isolated from virus that was not propagated in embryonated chicken eggs). In another specific embodiment, the subunit vaccine is prepared using influenza virus that was propagated in mammalian cells, e.g., immortalized human cells (see, e.g., International Application No. PCT/EP2006/067566 published as International Publication No. WO 07/045,674 which is herein incorporated by reference in its entirety) or canine kidney cells such as MDCK cells (see, e.g., International Application No. PCT/IB2007/003536 published as International Publication No. WO 08/032,219 which is herein incorporated by reference in its entirety) (i.e., the components of the subunit vaccine (e.g., a flu hemagglutinin (HA) polypeptide) are isolated from virus that was propagated in mammalian cells). In another specific embodiment, the flu hemagglutinin (HA) polypeptide (s) in a subunit vaccine are prepared using an expression vector, e.g., a viral vector, plant vector or a bacterial vector (i.e., the flu hemagglutinin (HA) polypeptide (s) in the subunit vaccine are obtained/isolated from an expression vector).

5.14.2 Live Virus Vaccines

In one embodiment, provided herein are immunogenic compositions (e.g., vaccines) comprising live virus containing a flu hemagglutinin (HA) polypeptide (e.g., a chimeric influenza virus hemagglutinin polypeptide). In another embodiment, provided herein are immunogenic compositions (e.g., vaccines) comprising live virus that is engineered to encode a flu hemagglutinin (HA) polypeptide, which is expressed by progeny virus produced in the subjects administered the compositions. In specific embodiments, the flu hemagglutinin (HA) polypeptide is membrane-bound. In other specific embodiments, the flu hemagglutinin (HA) polypeptide is not membrane-bound, i.e., it is soluble. In particular embodiments, the live virus is an influenza virus, such as described in Section 5.7, supra. In other embodiments, the live virus is a non-influenza virus, such as described in Section 5.8, supra. In some embodiments, the live virus is attenuated. In some embodiments, an immunogenic composition comprises two, three, four or more live viruses containing or engineered to express two, three, four or more different flu hemagglutinin (HA) polypeptides.

In certain embodiments, provided herein are immunogenic compositions (e.g., vaccines) comprising about $10^5$ to about $10^{10}$ fluorescent focus units (FFU) of live attenuated influenza virus containing one or more flu hemagglutinin (HA) polypeptides described herein, about 0.1 to about 0.5 mg monosodium glutamate, about 1.0 to about 5.0 mg hydrolyzed procine gelatin, about 1.0 to about 5.0 mg arginine, about 10 to about 15 mg sucrose, about 1.0 to about 5.0 mg dibasic potassium phosphate, about 0.5 to about 2.0 mg monobasic potassium phosphate, and about 0.001 to about 0.05 μg/ml gentamicin sulfate per dose. In some embodiments, the immunogenic compositions (e.g., vaccines) are packaged as pre-filled sprayers containing single 0.2 ml doses.

In a specific embodiment, provided herein are immunogenic compositions (e.g., vaccines) comprising $10^{65}$ to $10^{75}$ FFU of live attenuated influenza virus containing one or more flu hemagglutinin (HA) polypeptides described herein, 0.188 mg monosodium glutamate, 2.0 mg hydrolyzed procine gelatin, 2.42 mg arginine, 13.68 mg sucrose, 2.26 mg dibasic potassium phosphate, 0.96 mg monobasic potassium phosphate, and ≤0.015 μg/ml gentamicin sulfate per dose. In some embodiments, the immunogenic compositions (e.g., vaccines) are packaged as pre-filled sprayers containing single 0.2 ml doses.

In a specific embodiment, the live virus that contains a flu hemagglutinin (HA) polypeptide is propagated in embryonated chicken eggs before its use in an immunogenic composition described herein. In another specific embodiment, the live virus that contains a flu hemagglutinin (HA) polypeptide is not propagated in embryonated chicken eggs before its use in an immunogenic composition described herein. In another specific embodiment, the live virus that contains a flu hemagglutinin (HA) polypeptide is propagated in mammalian cells, e.g., immortalized human cells (see, e.g., International Application No. PCT/EP2006/067566 published as International Publication No. WO 07/045,674 which is herein incorporated by reference in its entirety) or canine kidney cells such as MDCK cells (see, e.g., International Application No. PCT/IB2007/003536 published as International Publication No. WO 08/032,219 which is herein incorporated by reference in its entirety) before its use in an immunogenic composition described herein.

An immunogenic composition comprising a live virus for administration to a subject may be preferred because multiplication of the virus in the subject may lead to a prolonged stimulus of similar kind and magnitude to that occurring in natural infections, and therefore, confer substantial, long lasting immunity.

5.14.3 Inactivated Virus Vaccines

In one embodiment, provided herein are immunogenic compositions (e.g., vaccines) comprising an inactivated virus containing a flu hemagglutinin (HA) polypeptide (e.g., a chimeric influenza virus hemagglutinin polypeptide). In specific embodiments, the flu hemagglutinin (HA) polypeptide is membrane-bound. In particular embodiments, the inactivated virus is an influenza virus, such as described in Section 5.7, supra. In other embodiments, the inactivated virus is a non-influenza virus, such as described in Section 5.8, supra. In some embodiments, an immunogenic composition comprises two, three, four or more inactivated viruses containing two, three, four or more different flu hemagglutinin (HA) polypeptides. In certain embodiments, the inactivated virus immunogenic compositions comprise one or more adjuvants.

Techniques known to one of skill in the art may be used to inactivate viruses containing a flu hemagglutinin (HA) polypeptide. Common methods use formalin, heat, or detergent for inactivation. See, e.g., U.S. Pat. No. 6,635,246, which is herein incorporated by reference in its entirety. Other methods include those described in U.S. Pat. Nos. 5,891,705; 5,106,619 and 4,693,981, which are incorporated herein by reference in their entireties.

In certain embodiments, provided herein are immunogenic compositions (e.g., vaccines) comprising inactivated influenza virus such that each dose of the immunogenic composition comprises about 15 to about 60 µg of a flu hemagglutinin (HA) polypeptide described herein, about 1.0 to about 5.0 mg sodium chloride, about 20 to about 100 µg monobasic sodium phosphate, about 100 to about 500 µg dibasic sodium phosphate, about 5 to about 30 µg monobasic potassium phosphate, about 5 to about 30 µg potassium chloride, and about 0.5 to about 3.0 µg calcium chloride. In some embodiments, the immunogenic compositions (e.g., vaccines) are packaged as single 0.25 ml or single 0.5 ml doses. In other embodiments, the immunogenic compositions (e.g., vaccines) are packaged as multi-dose formulations.

In certain embodiments, provided herein are immunogenic compositions (e.g., vaccines) comprising inactivated influenza virus such that each dose of the immunogenic composition comprises about 15 to about 60 µg of a flu hemagglutinin (HA) polypeptide described herein, about 0.001% to 0.01% thimerosal, about 1.0 to about 5.0 mg sodium chloride, about 20 to about 100 µg monobasic sodium phosphate, about 100 to about 500 µg dibasic sodium phosphate, about 5 to about 30 µg monobasic potassium phosphate, about 5 to about 30 µg potassium chloride, and about 0.5 to about 3.0 µg calcium chloride per dose. In some embodiments, the immunogenic compositions (e.g., vaccines) are packaged as single 0.25 ml or single 0.5 ml doses. In other embodiments, the immunogenic compositions (e.g., vaccines) are packaged as multi-dose formulations.

In a specific embodiment, immunogenic compositions (e.g., vaccines) provided herein are packaged as single 0.25 ml doses and comprise 22.5 µg of a flu hemagglutinin (HA) polypeptide described herein, 2.05 mg sodium chloride, 40 µg monobasic sodium phosphate, 150 µg dibasic sodium phosphate, 10 µg monobasic potassium phosphate, 10 µg potassium chloride, and 0.75 µg calcium chloride per dose.

In a specific embodiment, immunogenic compositions (e.g., vaccines) provided herein are packaged as single 0.5 ml doses and comprise 45 µg of a flu hemagglutinin (HA) polypeptide described herein, 4.1 mg sodium chloride, 80 µg monobasic sodium phosphate, 300 µg dibasic sodium phosphate, 20 µg monobasic potassium phosphate, 20 µg potassium chloride, and 1.5 µg calcium chloride per dose.

In a specific embodiment, immunogenic compositions (e.g., vaccines) are packaged as multi-dose formulations comprising or consisting of 5.0 ml of vaccine (0.5 ml per dose) and comprise 24.5 µg of mercury (from thimerosal), 45 µg of a flu hemagglutinin (HA) polypeptide described herein, 4.1 mg sodium chloride, 80 µg monobasic sodium phosphate, 300 µg dibasic sodium phosphate, 20 µg monobasic potassium phosphate, 20 µg potassium chloride, and 1.5 µg calcium chloride per dose.

In a specific embodiment, the inactivated virus that contains a flu hemagglutinin (HA) polypeptide was propagated in embryonated chicken eggs before its inactivation and subsequent use in an immunogenic composition described herein. In another specific embodiment, the inactivated virus that contains a flu hemagglutinin (HA) polypeptide was not propagated in embryonated chicken eggs before its inactivation and subsequent use in an immunogenic composition described herein. In another specific embodiment, the inactivated virus that contains a flu hemagglutinin (HA) polypeptide was propagated in mammalian cells, e.g., immortalized human cells (see, e.g., International Application No. PCT/EP2006/067566 published as International Publication No. WO 07/045,674 which is herein incorporated by reference in its entirety) or canine kidney cells such as MDCK cells (see, e.g., International Application No. PCT/IB2007/003536 published as International Publication No. WO 08/032,219 which is herein incorporated by reference in its entirety) before its inactivation and subsequent use in an immunogenic composition described herein.

5.14.4 Split Virus Vaccines

In one embodiment, an immunogenic composition comprising a flu hemagglutinin (HA) polypeptide (e.g., a chimeric influenza virus hemagglutinin polypeptide) is a split virus vaccine. In some embodiments, split virus vaccine contains two, three, four or more different flu hemagglutinin (HA) polypeptides. In certain embodiments, the flu hemagglutinin (HA) polypeptide is/was membrane-bound. In certain embodiments, the split virus vaccines comprise one or more adjuvants.

Techniques for producing split virus vaccines are known to those skilled in the art. By way of non-limiting example, an influenza virus split vaccine may be prepared using inactivated particles disrupted with detergents. One example of a split virus vaccine that can be adapted for use in accordance with the methods described herein is the Fluzone®, Influenza Virus Vaccine (Zonal Purified, Subvirion) for intramuscular use, which is formulated as a sterile suspension prepared from influenza viruses propagated in embryonated chicken eggs. The virus-containing fluids are harvested and inactivated with formaldehyde. Influenza virus is concentrated and purified in a linear sucrose density gradient solution using a continuous flow centrifuge. The virus is then chemically disrupted using a nonionic surfactant, octoxinol-9, (Triton® X-100—A registered trademark of Union Carbide, Co.) producing a "split virus." The split virus is then further purified by chemical means and suspended in sodium phosphate-buffered isotonic sodium chloride solution.

In certain embodiments, provided herein are split virus vaccines comprising about 10 μg to about 60 μg of one or more flu hemagglutinin (HA) polypeptides described herein, about 0.01 to about 1.0 mg octoxynol-10 (TRITON X-100®, about 0.5 to 0.5 mg α-tocopheryl hydrogen succinate, about 0.1 to 1.0 mg polysorbate 80 (Tween 80), about 0.001 to about 0.003 μg hydrocortisone, about 0.05 to about 0.3 μg gentamcin sulfate, about 0.5 to about 2.0 μg chicken egg protein (ovalbumin), about 25 to 75 μg formaldehyde, and about 25 to 75 μg sodium deoxycholate.

In a specific embodiment, a split virus vaccine provided herein comprises or consists of a 0.5 ml dose that comprises 45 μg of a flu hemagglutinin (HA) polypeptide (s) provided herein, ≤0.085 mg octoxynol-10 (TRITON X-100®, ≤0.1 mg α-tocopheryl hydrogen succinate, ≤0.415 mg polysorbate 80 (Tween 80), ≤0.0016 μg hydrocortisone, ≤0.15 μg gentamcin sulfate, ≤1.0 chicken egg protein (ovalbumin), ≤50 μg formaldehyde, and ≤50 μg sodium deoxycholate. In some embodiments, the 0.5 ml dose subunit vaccine is packaged in a pre-filled syringe.

In a specific embodiment, the split virus vaccine is prepared using influenza virus that was propagated in embryonated chicken eggs. In another specific embodiment, the split virus vaccine is prepared using influenza virus that was not propagated in embryonated chicken eggs. In another specific embodiment, the split virus vaccine is prepared using influenza virus that was propagated in mammalian cells, e.g., immortalized human cells (see, e.g., PCT/EP2006/067566 published as WO 07/045,674 which is herein incorporated by reference in its entirety) or canine kidney cells such as MDCK cells (see, e.g., PCT/IB2007/003536 published as WO 08/032,219 which is herein incorporated by reference in its entirety).

5.14.5 Adjuvants

In certain embodiments, the compositions described herein comprise, or are administered in combination with, an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a flu hemagglutinin (HA) polypeptide (e.g., a chimeric influenza virus hemagglutinin polypeptide), but when the compound is administered alone does not generate an immune response to the polypeptide. In some embodiments, the adjuvant generates an immune response to the polypeptide and does not produce an allergy or other adverse reaction. Adjuvants can enhance an immune response by several mechanisms including, e.g., lymphocyte recruitment, stimulation of B and/or T cells, and stimulation of macrophages.

In certain embodiments, an adjuvant augments the intrinsic response to the flu hemagglutinin (HA) polypeptide without causing conformational changes in the polypeptide that affect the qualitative form of the response. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, NY, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine, or other immunopotentiating agents described in Section 5.4, supra. It should be understood that different formulations of flu hemagglutinin (HA) polypeptides may comprise different adjuvants or may comprise the same adjuvant.

5.15 Prophylactic and Therapeutic Uses

In one aspect, provided herein are methods for inducing an immune response in a subject utilizing an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition described herein. In a specific embodiment, a method for inducing an immune response to an influenza virus hemagglutinin polypeptide in a subject comprises administering to a subject in need thereof an effective amount of a flu hemagglutinin (HA) polypeptide described herein or an immunogenic composition thereof. In another embodiment, a method for inducing an immune response to an influenza virus hemagglutinin polypeptide in a subject comprises administering to a subject in need thereof an effective amount of a nucleic acid encoding a flu hemagglutinin (HA) polypeptide described herein or an immunogenic composition thereof. In another embodiment, a method for inducing an immune response to an influenza virus hemagglutinin polypeptide in a subject comprises administering to a subject in need thereof an effective amount of a viral vector containing or expressing a flu hemagglutinin (HA) polypeptide described herein or an immunogenic composition thereof. In yet another embodiment, a method for inducing an immune response to an influenza virus hemagglutinin polypeptide in a subject comprises administering to a subject in need thereof an effective amount of cells stimulated with a flu hemagglutinin (HA) polypeptide described herein or a pharmaceutical composition thereof. In certain embodiments, a flu hemagglutinin (HA) polypeptide described herein used in the method is a purified flu hemagglutinin (HA) polypeptide described herein derived from a mammalian cell, a plant cell, or an insect cell.

In a specific embodiment, a method for inducing an immune response to an influenza virus hemagglutinin polypeptide in a subject comprises administering to a subject in need thereof a subunit vaccine described herein. In another embodiment, a method for inducing an immune response to an influenza virus hemagglutinin polypeptide in a subject comprises administering to a subject in need thereof a live virus vaccine described herein. In particular embodiments, the live virus vaccine comprises an attenuated virus. In another embodiment, a method for inducing an immune response to an influenza virus hemagglutinin polypeptide in a subject comprises administering to a subject in need thereof an inactivated virus vaccine described herein. In another embodiment, a method for inducing an immune response to an influenza virus hemagglutinin polypeptide in a subject comprises administering to a subject in need thereof a split virus vaccine described herein. In another embodiment, a method for inducing an immune response to an influenza virus hemagglutinin polypeptide in a subject comprises administering to a subject in need thereof a virus-like particle vaccine described herein. In another embodiment, a method for inducing an immune response to an influenza hemagglutinin polypeptide comprises administering to a subject in need thereof a virosome described herein. In another embodiment, a method for inducing an immune response to an influenza hemagglutinin polypeptide comprises administering to a subject in need thereof a bacteria expressing or engineered to express a flu hemagglutinin (HA) polypeptide described herein or a composition thereof. In certain embodiments, a flu hemagglutinin (HA) polypeptide described herein used in the method is a purified flu hemagglutinin (HA) polypeptide described herein derived from a mammalian cell, a plant cell, or an insect cell.

In some embodiments, the immune response induced by an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition described herein is effective to prevent and/or treat an influenza virus infection caused by any subtype or strain of influenza virus. In certain embodiments, the immune response induced by an active compound or a composition described herein is effective to prevent and/or treat an influenza virus infection caused by a subtype of influenza virus that belongs to one HA group (e.g., Group 1, which comprises H1, H2, H5, H6, H8, H9, H11, H12, H13, and H16) and not the other HA group (e.g., Group 2, which comprises H3, H4, H7, H10, H14, and H15). For example, the immune response induced may be effective to prevent and/or treat an influenza virus infection caused by an influenza virus that belongs to the HA group consisting of H11, H13, H16, H9, H8, H12, H6, H1, H5 and H2. Alternatively, the immune response induced may be effective to prevent and/or treat an influenza virus infection caused by an influenza virus that belongs to the HA group consisting of H3, H4, H14, H10, H15 and H7. In some embodiments, the immune response induced by an active compound or a composition described herein is effective to prevent and/or treat an influenza virus infection caused by one, two, three, four or five subtypes of influenza virus. In certain embodiments, the immune response induced by an active compound or a composition described herein is effective to prevent and/or treat an influenza virus infection caused by six, seven, eight, nine, ten, eleven, twelve, thirteen, fourteen or fifteen subtypes of influenza virus. In some embodiments, the immune response induced by an active compound or a composition described herein is effective to prevent and/or treat an influenza virus infection caused by one or more variants within the same subtype of influenza virus.

In some embodiments, the immune response induced by an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition described herein is effective to prevent and/or treat an influenza virus infection caused by both H1N1 and H2N2 subtypes. In other embodiments, the immune response induced by an active compound or a composition described herein is not effective to prevent and/or treat an influenza virus infection caused by both H1N1 and H2N2 subtypes. In some embodiments, the immune response induced by an active compound or a composition described herein is effective to prevent and/or treat an influenza virus infection caused by H1N1, H2N2, and H3N2 subtypes. In some embodiments, the immune response induced by an active compound or a composition described herein is effective to prevent and/or treat an influenza virus infection caused by H3N2 subtypes. In other embodiments, the immune response induced by an active compound or a composition described herein is not effective to prevent and/or treat an influenza virus infection caused by H3N2 subtypes.

In some embodiments, the immune response induced by an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition described herein is effective to prevent and/or treat an influenza virus disease caused by any subtype or strain of influenza virus. In certain embodiments, the immune response induced by an active compound or a composition described herein is effective to prevent and/or treat an influenza virus disease caused by a subtype of influenza virus that belongs to one HA group and not the other HA group. For example, the immune response induced may be effective to prevent and/or treat an influenza virus disease caused by an influenza virus that belongs to the HA group consisting of H11, H13, H16, H9, H8, H12, H6, H1, H5 and H2. Alternatively, the immune response induced may be effective to prevent and/or treat an influenza virus disease caused by an influenza virus that belongs to the HA group consisting of H3, H4, H14, H10, H15 and H7. In some embodiments, the immune response induced by an active compound or a composition described herein is effective to prevent and/or treat an influenza virus disease caused by any of one, two, three, four or five subtypes of influenza virus. In certain embodiments, the immune response induced by an active compound or a composition described herein is effective to prevent and/or treat an influenza virus disease caused by any of six, seven, eight, nine, ten, eleven, twelve, thirteen, fourteen or fifteen subtypes of influenza virus. In some embodiments, the immune response induced by an active compound or a composition described herein is effective to prevent and/or treat an influenza virus disease caused by one or more variants within the same subtype of influenza virus.

In some embodiments, the immune response induced by an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition described herein is effective to reduce symptoms resulting from an influenza virus disease/infection. Symptoms of influenza virus disease/infection include, but are not limited to, body aches (especially joints and throat), fever, nausea, headaches, irritated eyes, fatigue, sore throat, reddened eyes or skin, and abdominal pain.

In some embodiments, the immune response induced by an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition described herein is effective to reduce the hospitalization of a subject suffering from an influenza virus disease/infection. In some embodiments, the immune response induced by an active compound or a composition described herein is effective to reduce the duration of hospitalization of a subject suffering from an influenza virus disease/infection.

In another aspect, provided herein are methods for preventing and/or treating an influenza virus infection in a subject utilizing an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or a composition described herein. In one embodiment, a method for preventing or treating an influenza virus infection in a subject comprises administering to a subject in need thereof a flu hemagglutinin (HA) polypeptide, a nucleic acid encoding such a polypeptide, a vector containing or expressing such a polypeptide, or a composition of any one of the foregoing. In a specific embodiment, a method for preventing or treating an influenza virus infection in a subject comprises administering to a subject in need thereof a subunit vaccine, a live virus vaccine, an inactivated virus vaccine, a split virus vaccine or a virus-like particle vaccine.

In another aspect, provided herein are methods for preventing and/or treating an influenza virus disease in a subject utilizing a flu hemagglutinin (HA) polypeptide described herein, a nucleic acid encoding such a polypeptide, a vector containing or expressing such a polypeptide, or cells stimulated with such a polypeptide. In a specific embodiment, a method for preventing or treating an influenza virus disease in a subject comprises administering to a subject in need thereof an effective amount of a flu hemagglutinin (HA) polypeptide or an immunogenic composition thereof. In another embodiment, a method for preventing or treating an influenza virus disease in a subject comprises administering to a subject in need thereof an effective amount of a nucleic acid encoding a flu hemagglutinin (HA) polypeptide or an immunogenic composition thereof. In another embodiment, a method for preventing or treating an influenza virus disease in a subject comprises administering to a subject in need thereof an effective amount of a viral vector containing or expressing a flu hemagglutinin (HA) polypeptide or an immunogenic composition thereof. In yet another embodiment, a method for preventing or treating an influenza virus disease in a subject comprises administering to a subject in need thereof an effective amount of cells stimulated with a flu hemagglutinin (HA) polypeptide or a pharmaceutical composition thereof.

In a specific embodiment, a method for preventing or treating an influenza virus disease in a subject comprises administering to a subject in need thereof a subunit vaccine described herein. In another embodiment, a method for preventing or treating an influenza virus disease in a subject comprises administering to a subject in need thereof a live virus vaccine described herein. In particular embodiments, the live virus vaccine comprises an attenuated virus. In another embodiment, a method for preventing or treating an influenza virus disease in a subject comprises administering to a subject in need thereof an inactivated virus vaccine described herein. In another embodiment, a method for preventing or treating an influenza virus disease in a subject comprises administering to a subject in need thereof a split virus vaccine described herein. In another embodiment, a method for preventing or treating an influenza virus disease comprises administering to a subject in need thereof a virus-like particle vaccine described herein. In another embodiment, a method for preventing or treating an influenza virus disease in a subject, comprising administering to a subject in need thereof a virosome described herein. In another embodiment, a method for preventing or treating an influenza virus disease in a subject comprising administering to a subject in need thereof a bacteria expressing or engineered to express a flu hemagglutinin (HA) polypeptide or a composition thereof.

In another aspect, provided herein are methods of immunizing a subject against an influenza virus disease or infection comprising exposing the hemagglutinin of an influenza virus to which the subject is naive, i.e., the subject has not previously been exposed to the influenza virus and/or the hemagglutinin of the influenza virus.

In one embodiment, provided herein is a method of immunizing a subject against an influenza virus disease or infection comprising administering to said subject one or more influenza viruses, wherein each of said one or more influenza viruses comprises a hemagglutinin polypeptide to which the subject is naive, i.e., the subject has not previously been exposed to the one or more influenza viruses. In a specific embodiment, the one or more influenza viruses is an influenza virus of subtype H2, H4, H5, H6, H7, H8, H9, H10, H11, H12, H13, H14, H15, H16, and/or H17. In another specific embodiment, the method comprises (i) a first administration of an influenza virus of subtype H2, H4, H5, H6, H7, H8, H9, H10, H11, H12, H13, H14, H15, H16, or H17 and (ii) a second administration of an influenza virus of subtype H2, H4, H5, H6, H7, H8, H9, H10, H11, H12, H13, H14, H15, H16, or H17, wherein the influenza virus of the first administration is of a different subtype than the influenza virus of the second administration. The first and second administrations may be separated by at least 1 day, 2 days, 3 days, 5 days, 10 days, 15 days, 30 days, 45 days, 2 months, 75 days, 3 months, or at least 6 months. In another specific embodiment, the method comprises (i) a first administration of an influenza virus of subtype H2, H4, H5, H6, H7, H8, H9, H10, H11, H12, H13, H14, H15, H16, or H17; (ii) a second administration of an influenza virus of subtype H2, H4, H5, H6, H7, H8, H9, H10, H11, H12, H13, H14, H15, H16, or H17; and (iii) a third administration of an influenza virus of subtype H2, H4, H5, H6, H7, H8, H9, H10, H11, H12, H13, H14, H15, H16, or H17, wherein the influenza viruses of the first, second, and third administrations are of different subtypes. The first, second, and third administrations may be separated by at least 1 day, 2 days, 3 days, 5 days, 10 days, 15 days, 30 days, 45 days, 2 months, 75 days, 3 months, or at least 6 months.

In another embodiment, provided herein is a method of immunizing a subject against an influenza virus disease or infection comprising administering to said subject one or more influenza virus hemagglutinin polypeptides to which the subject is naive, i.e., the subject has not previously been exposed to the one or more influenza virus hemagglutinin polypeptides. In certain embodiments, said one or more influenza virus hemagglutinin polypeptides to which the subject is naive are in a composition (e.g., a composition comprising a vaccine). In certain embodiments, one or more influenza virus hemagglutinin polypeptides to which the subject is naive are in a vector, e.g., an influenza virus vector. In certain embodiments, one or more influenza virus hemagglutinin polypeptides to which the subject is naive are in a VLP. In certain embodiments, one or more influenza virus hemagglutinin polypeptides to which the subject is naive are in a virosome. In a specific embodiment, the one or more influenza viruses hemagglutinin polypeptides is an influenza virus hemagglutinin polypeptide from an influenza virus of subtype H2, H4, H5, H6, H7, H8, H9, H10, H11, H12, H13, H14, H15, H16, and/or H17. In another specific embodiment, the method comprises (i) a first administration of an influenza virus hemagglutinin polypeptide of subtype H2, H4, H5, H6, H7, H8, H9, H10, H11, H12, H13, H14, H15, H16, or H17 and (ii) a second administration of an influenza virus hemagglutinin polypeptide of subtype H2, H4, H5, H6, H7, H8, H9, H10, H11, H12, H13, H14, H15, H16, or H17, wherein the influenza virus hemagglutinin polypeptide of the first administration is of a different subtype than the influenza virus hemagglutinin polypeptide of the second administration. The first and second administrations may be separated by at least 1 day, 2 days, 3 days, 5 days, 10 days, 15 days, 30 days, 45 days, 2 months, 75 days, 3 months, or at least 6 months. In another specific embodiment, the method comprises (i) a first administration of an influenza virus hemagglutinin polypeptide of subtype H2, H4, H5, H6, H7, H8, H9, H10, H11, H12, H13, H14, H15, H16, or H17; (ii) a second administration of an influenza virus hemagglutinin polypeptide of subtype H2, H4, H5, H6, H7, H8, H9, H10, H11, H12, H13, H14, H15, H16, or H17; and (iii) a third administration of an influenza virus hemagglutinin polypeptide of subtype H2, H4, H5, H6, H7, H8, H9, H10, H11, H12, H13, H14, H15, H16, or H17, wherein the influenza virus hemagglutinin polypeptides of the first, second, and third administrations are from different influenza virus subtypes. The first, second, and third administrations may be separated by at least 1 day, 2 days, 3 days, 5 days, 10 days, 15 days, 30 days, 45 days, 2 months, 75 days, 3 months, or at least 6 months.

In another embodiment, the method comprises (i) a first administration of a first flu HA polypeptide described herein (e.g., a chimeric influenza virus hemagglutinin polypeptide), a nucleic acid encoding such a polypeptide, a vector containing or expressing such a polypeptide; and (ii) a second administration of a second flu HA polypeptide described herein (e.g., a chimeric influenza virus hemagglutinin polypeptide), wherein the first and second flu HA polypeptides have the same stem domain. In certain embodiments, the globular head domain of the first and second flu HA polypeptides are different. In certain embodiments, the globular head domain of the first and second flu HA polypeptides are from the same strain. The first and second administrations may be separated by at least 1 day, 2 days, 3 days, 5 days, 10 days, 15 days, 30 days, 45 days, 2 months, 75 days, 3 months, or at least 6 months. In certain embodiments, booster inoculations may be administered to the subject at 6 to 12 month intervals following the second inoculation.

In another embodiment, the method comprises (i) a first administration of an influenza virus; and (ii) a second administration of a flu HA polypeptide described herein (e.g., a chimeric influenza virus hemagglutinin polypeptide), wherein the influenza virus and the flu HA polypeptides have the same stem domain. In certain embodiments, the globular head domain of the influenza virus and the flu HA polypeptides are different. The first and second administrations may be separated by at least 1 day, 2 days, 3 days, 5 days, 10 days, 15 days, 30 days, 45 days, 2 months, 75 days, 3 months, or at least 6 months. In certain embodiments, booster inoculations may be administered to the subject at 6 to 12 month intervals following the second inoculation.

In another aspect, provided herein are methods of preventing and/or treating an influenza virus disease in a subject by administering neutralizing antibodies described herein. In a specific embodiment, a method for preventing or treating an influenza virus disease in a subject comprises administering to a subject in need thereof an effective amount of a neutralizing antibody described herein, or a pharmaceutical composition thereof. In particular embodiments, the neutralizing antibody is a monoclonal antibody. In certain embodiments, the neutralizing antibody is not CR6261, CR6325, CR6329, CR6307, CR6323, 2A, D7, D8, F10, G17, H40, A66, D80, E88, E90, H98, C179 (FERM BP-4517), AI3C (FERM BP-4516) or any other antibody described in Ekiert D C et al. (2009) Antibody Recognition of a Highly Conserved Influenza Virus Epitope. Science (published in Science Express Feb. 26, 2009); Kashyap et al. (2008) Combinatorial antibody libraries from survivors of the Turkish H5N1 avian influenza outbreak reveal virus neutralization strategies. Proc Natl Acad Sci USA 105: 5986-5991; Sui et al. (2009) Structural and functional bases for broad-spectrum neutralization of avian and human influenza A viruses. Nat Struct Mol Biol 16: 265-273; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/US2008/085876 published as International Publication No. WO 2009/079259. In other embodiments, the neutralizing antibody is not an antibody described in Wang et al. (2010) "Broadly Protective Monoclonal Antibodies against H3 Influenza Viruses following Sequential Immunization with Different Hemagglutinins," PLOS Pathogens 6(2):1-9.

In certain embodiments, the methods for preventing or treating an influenza virus disease or infection in a subject (e.g., a human or non-human animal) provided herein result in a reduction in the replication of the influenza virus in the subject as measured by in vivo and in vitro assays known to those of skill in the art and described herein. In some embodiments, the replication of the influenza virus is reduced by approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

Example 9, below, sets forth how chimeric influenza virus HA polypeptides may be used to vaccinate subjects against influenza virus infection.

5.15.1 Combination Therapies

In various embodiments, a flu hemagglutinin (HA) polypeptide (e.g., a chimeric influenza virus hemagglutinin polypeptide) described herein, a nucleic acid encoding such a polypeptide, a vector (e.g., a viral vector or a bacteria) containing or expressing such a polypeptide, cells stimulated with such a polypeptide, or a neutralizing antibody may be administered to a subject in combination with one or more other therapies (e.g., antiviral, antibacterial, or immunomodulatory therapies). In some embodiments, a pharmaceutical composition (e.g., an immunogenic composition) described herein may be administered to a subject in combination with one or more therapies. The one or more other therapies may be beneficial in the treatment or prevention of an influenza virus disease or may ameliorate a symptom or condition associated with an influenza virus disease. In some embodiments, the one or more other therapies are pain relievers, anti-fever medications, or therapies that alleviate or assist with breathing. In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patent visit.

Any anti-viral agents well-known to one of skill in the art may used in combination with an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or pharmaceutical composition described herein. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, peramivir, rimantadine, saquinavir, indinavir, ritonavir, alpha-interferons and other interferons, AZT, zanamivir (Relenza®), and oseltamivir (Tamiflu®). Other anti-viral agents include influenza virus vaccines, e.g., Fluarix® (GlaxoSmithKline), FluMist® (MedImmune Vaccines), Fluvirin® (Chiron Corporation), Flulaval® (GlaxoSmithKline), Afluria® (CSL Biotherapies Inc.), Agriflu® (Novartis) or Fluzone® (Aventis Pasteur).

In specific embodiments, the anti-viral agent is an immunomodulatory agent that is specific for a viral antigen. In particular embodiments, the viral antigen is an influenza virus polypeptide other than a hemagglutinin polypeptide. In other embodiments, the viral antigen is an influenza virus hemagglutinin polypeptide.

Any anti-bacterial agents known to one of skill in the art may used in combination with an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or pharmaceutical composition described herein. Non-limiting examples of anti-bacterial agents include Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefinenoxime, Cefoperazone, Cefoperazone-sulbactam, Cefotaxime, Cefoxitin, Cefpirome, Cefpodoxime, Cefpodoxime-clavulanic acid, Cefpodoxime-sulbactam, Cefprozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, and Voriconazole.

In some embodiments, a combination therapy comprises active immunization with a flu hemagglutinin (HA) polypeptide described herein, or one or more vectors described in Sections 5.2-5.7 and passive immunization with one or more neutralizing antibodies described in Section 5.9. In some embodiments, a combination therapy comprises immunization with one or more vectors described in Sections 5.2-5.7 and administration of cells (e.g., by adoptive transfer) described in Section 5.9.

In some embodiments, a combination therapy comprises administration of two or more different vectors described in Sections 5.2-5.7.

In some embodiments, a combination therapy comprises active immunization with an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) that induces an immune response to one, two, three, or more HA subtypes in one HA group (e.g., Group 1) in combination with an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) that induces an immune response to one, two, three, or more HA subtypes in the other HA group (e.g., Group 2).

In some embodiments, a combination therapy comprises active immunization with two or more flu hemagglutinin (HA) polypeptides described herein.

5.15.2 Patient Populations

In certain embodiments, an active compound (i.e., a flu hemagglutinin (HA) polypeptide (e.g., a chimeric influenza virus hemagglutinin polypeptide) described herein, a nucleic acid encoding such a polypeptide, a vector (e.g., a viral vector, or a bacteria) containing or expressing such a polypeptide, cells stimulated with such a polypeptide) or composition described herein may be administered to a naïve subject, i.e., a subject that does not have a disease caused by influenza virus infection or has not been and is not currently infected with an influenza virus infection. In one embodiment, an active compound or composition described herein is administered to a naïve subject that is at risk of acquiring an influenza virus infection. In one embodiment, an active compound or composition described herein is administered to a subject that does not have a disease caused by the specific influenza virus, or has not been and is not infected with the specific influenza virus to which the flu hemagglutinin (HA) polypeptide induces an immune response. An active compound or composition described herein may also be administered to a subject that is and/or has been infected with the influenza virus or another type, subtype or strain of the influenza virus to which the flu hemagglutinin (HA) polypeptide induces an immune response.

In certain embodiments, an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is administered to a patient who has been diagnosed with an influenza virus infection. In some embodiments, an active compound or composition described herein is administered to a patient infected with an influenza virus before symptoms manifest or symptoms become severe (e.g., before the patient requires hospitalization). In some embodiments, an active compound or composition described herein is administered to a patient that is infected with or has been diagnosed with a different type of influenza virus than that of the influenza virus from which the head domain of the flu hemagglutinin (HA) polypeptide of the active compound or composition was derived.

In certain embodiments, an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is administered to a patient that may be or is infected with an influenza virus that belongs to the same HA group as that of the head domain of the flu hemagglutinin (HA) polypeptide. In certain embodiments, an active compound or composition described herein is administered to a patient that may be or is infected with an influenza virus of the same subtype as that of the head domain of the flu hemagglutinin (HA) polypeptide.

In some embodiments, a subject to be administered an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is an animal. In certain embodiments, the animal is a bird. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, mouse, or primate, preferably a human.

In certain embodiments, a subject to be administered an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is a human adult. In certain embodiments, a subject to be administered an active compound or composition described herein is a human adult more than 50 years old. In certain embodiments, a subject to be administered an active compound or composition described herein is an elderly human subject.

In certain embodiments, a subject to be administered an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is a human child. In certain embodiments, a subject to be administered an active compound or composition described herein is a human infant. In certain embodiments, a subject to whom an active compound or composition described herein is administered is not an infant of less than 6 months old. In a specific embodiment, a subject to be administered an active compound or composition described herein is 2 years old or younger.

In specific embodiments, a subject to be administered an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is any infant or child more than 6 months of age and any adult over 50 years of age. In other embodiments, the subject is an individual who is pregnant. In another embodiment, the subject is an individual who may or will be pregnant during the influenza season (e.g., November to April). In specific embodiments, a subject to be administered an active compound or composition described herein is a woman who has given birth 1, 2, 3, 4, 5, 6, 7, or 8 weeks earlier.

In some embodiments, the human subject to be administered an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is any individual at increased risk of influenza virus infection or disease resulting from influenza virus infection (e.g., an immunocompromised or immunodeficient individual). In some embodiments, the human subject to be administered an active compound or composition described herein is any individual in close contact with an individual with increased risk of influenza virus infection or disease resulting from influenza virus infection (e.g., immunocompromised or immunosuppressed individuals).

In some embodiments, the human subject to be administered an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is an individual affected by any condition that increases susceptibility to influenza virus infection or complications or disease resulting from influenza virus infection. In other embodiments, an active compound or composition described herein is administered to a subject in which an influenza virus infection has the potential to increase complications of another condition that the individual is affected by, or for which they are at risk. In particular embodiments, such conditions that increase susceptibility to influenza virus complications or for which influenza virus increases complications associated with the condition are, e.g., conditions that affect the lung, such as cystic fibrosis, emphysema, asthma, or bacterial infections (e.g., infections caused by *Haemophilus influenzae, Streptococcus pneumoniae, Legionella pneumophila*, and *Chlamydia trachomatus*); cardiovascular disease (e.g., congenital heart disease, congestive heart failure, and coronary artery disease); endocrine disorders (e.g., diabetes), neurological and neuron-developmental conditions (e.g., disorders of the brain, the spinal cord, the peripheral nerve, and muscle (such as cerebral palsy, epilepsy (seizure disorders), stroke, intellectual disability (e.g, mental retardation), muscular dystrophy, and spinal cord injury)).

In some embodiments, the human subject to be administered an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is an individual that resides in a group home, such as a nursing home. In some embodiments, the human subject to be administered an active compound or composition described herein works in, or spends a significant amount of time in, a group home, e.g., a nursing home. In some embodiments, the human subject to be administered an active compound or composition described herein is a health care worker (e.g., a doctor or nurse). In some embodiments, the human subject to be administered an active compound or composition described herein is a smoker. In a specific embodiment, the human subject to be administered an active compound or composition described herein is immunocompromised or immunosuppressed.

In addition, subjects at increased risk of developing complications from influenza who may be administered an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein include: any individual who can transmit influenza viruses to those at high risk for complications, such as, e.g., members of households with high-risk individuals, including households that will include infants younger than 6 months, individuals coming into contact with infants less than 6 months of age, or individuals who will come into contact with individuals who live in nursing homes or other long-term care facilities; individuals with long-term disorders of the lungs, heart, or circulation; individuals with metabolic diseases (e.g., diabetes); individuals with kidney disorders; individuals with blood disorders (including anemia or sickle cell disease); individuals with weakened immune systems (including immunosuppression caused by medications, malignancies such as cancer, organ transplant, or HIV infection); children who receive long-term aspirin therapy (and therefore have a higher chance of developing Reye syndrome if infected with influenza).

In other embodiments, subjects for administration of an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein include healthy individuals six months of age or older, who: plan to travel to foreign countries and areas where flu outbreaks may be occurring, such, e.g., as the tropics and the Southern Hemisphere from April through September; travel as a part of large organized tourist groups that may include persons from areas of the world where influenza viruses are circulating; attend school or college and reside in dormitories, or reside in institutional settings; or wish to reduce their risk of becoming ill with influenza.

In some embodiments, a subject for whom administration of an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition described herein is contraindicated include any individual for whom influenza vaccination is contraindicated, such as: infants younger than six months of age; and individuals who have had an anaphylactic reaction (allergic reactions that cause difficulty breathing, which is often followed by shock) to eggs, egg products, or other components used in the production of the immunogenic formulation. In certain embodiments, when administration of an active compound or composition described herein is contraindicated due to one or more components used in the production of the immunogenic formulation (e.g., due to the presence of egg or egg products), the active compound or composition may be produced in a manner that does not include the component that causes the administration of an active compound or composition to be contraindicated (e.g., the active compound or composition may be produced without the use of eggs or egg products).

In some embodiments, it may be advisable not to administer a live virus vaccine to one or more of the following patient populations: elderly humans; infants younger than 6 months old; pregnant individuals; infants under the age of 1 years old; children under the age of 2 years old; children under the age of 3 years old; children under the age of 4 years old; children under the age of 5 years old; adults under the age of 20 years old; adults under the age of 25 years old; adults under the age of 30 years old; adults under the age of 35 years old; adults under the age of 40 years old; adults under the age of 45 years old; adults under the age of 50 years old; elderly humans over the age of 70 years old; elderly humans over the age of 75 years old; elderly humans over the age of 80 years old; elderly humans over the age of 85 years old; elderly humans over the age of 90 years old; elderly humans over the age of 95 years old; children and adolescents (2-17 years of age) receiving aspirin or aspirin-containing medications, because of the complications associated with aspirin and wild-type influenza virus infections in this age group; individuals with a history of asthma or other reactive airway diseases; individuals with chronic underlying medical conditions that may predispose them to severe influenza infections; individuals with a history of Guillain-Barre syndrome; individuals with acute serious illness with fever; or individuals who are moderately or severely ill. For such individuals, administration of inactivated virus vaccines, split virus vaccines, subunit vaccines, virosomes, virus-like particles or the non-viral vectors described herein may be preferred. In certain embodiments, subjects preferably administered a live virus vaccine may include healthy children and adolescents, ages 2-17 years, and healthy adults, ages 18-49.

In certain embodiments, an immunogenic formulation comprising a live virus vector is not given concurrently with other live-virus vaccines.

5.16 Modes of Administration

5.16.1 Routes of Delivery

An active compound (i.e., a flu hemagglutinin (HA) polypeptide described herein (e.g., a chimeric influenza virus hemagglutinin polypeptide), a nucleic acid encoding such a polypeptide, a vector (e.g., a viral vector, or a bacteria) containing or expressing such a polypeptide, cells stimulated with such a polypeptide) or composition described herein may be delivered to a subject by a variety of routes. These include, but are not limited to, intranasal, intratracheal, oral, intradermal, intramuscular, intraperitoneal, transdermal, intravenous, conjunctival and subcutaneous routes. In some embodiments, a composition is formulated for topical administration, for example, for application to the skin. In specific embodiments, the route of administration is nasal, e.g., as part of a nasal spray. In certain embodiments, a composition is formulated for intramuscular administration. In some embodiments, a composition is formulated for subcutaneous administration. In certain embodiments, a composition is not formulated for administration by injection. In specific embodiments for live virus vaccines, the vaccine is formulated for administration by a route other than injection.

In cases where the antigen is a viral vector, a virus-like particle vector, or a bacterial vector, for example, it may be preferable to introduce an immunogenic composition via the natural route of infection of the backbone virus or bacteria from which the vector was derived. Alternatively, it may be preferable to introduce a flu hemagglutinin (HA) polypeptide via the natural route of infection of the influenza virus from which polypeptide is derived. The ability of an antigen, particularly a viral vector, to induce a vigorous secretory and cellular immune response can be used advantageously. For example, infection of the respiratory tract by a viral vector may induce a strong secretory immune response, for example in the urogenital system, with concomitant protection against an influenza virus. In addition, in a preferred embodiment it may be desirable to introduce the pharmaceutical compositions into the lungs by any suitable route. Pulmonary administration can also be employed, e.g., by use of an inhaler or nebulizer, and formulation with an aerosolizing agent for use as a spray.

In a specific embodiment, a subunit vaccine is administered intramuscularly. In another embodiment, a live influenza virus vaccine is administered intranasally. In another embodiment, an inactivated influenza virus vaccine, or a split influenza virus vaccine is administered intramuscularly. In another embodiment, a virus-like particle or composition thereof is administered intramuscularly.

In some embodiments, cells stimulated with a flu hemagglutinin (HA) polypeptide described herein in vitro may be introduced (or re-introduced) into a subject using techniques known to one of skill in the art. In some embodiments, the cells can be introduced into the dermis, under the dermis, or into the peripheral blood stream. In some embodiments, the cells introduced into a subject are preferably cells derived from that subject, to avoid an adverse immune response. In other embodiments, cells also can be used that are derived from a donor host having a similar immune background. Other cells also can be used, including those designed to avoid an adverse immunogenic response.

5.16.2 Dosage and Frequency of Administration

The amount of an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition which will be effective in the treatment and/or prevention of an influenza virus infection or an influenza virus disease will depend on the nature of the disease, and can be determined by standard clinical techniques.

The precise dose to be employed in the formulation will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, other medications administered, and whether treatment is prophylactic or therapeutic. Usually, the patient is a human but nonhuman mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Exemplary doses for nucleic acids encoding a flu hemagglutinin (HA) polypeptide described herein range from about 10 ng to 1 g, 100 ng to 100 mg, 1 μg to 10 mg, or 30-300 μg nucleic acid, e.g., DNA, per patient.

In certain embodiments, exemplary doses for a flu hemagglutinin (HA) polypeptide described herein (e.g., as provided in split virus vaccines and subunit vaccines) range from about 5 μg to 100 mg, 15 μg to 50 mg, 15 μg to 25 mg, 15 μg to 10 mg, 15 μg to 5 mg, 15 μg to 1 mg, 15 μg to 100 μg, 15 μg to 75 μg, 5 μg to 50 μg, 10 μg to 50 μg, 15 μg to 45 μg, 20 μg to 40 μg, or 25 to 35 μg per kilogram of the patient. In other embodiments, exemplary doses for flu hemagglutinin (HA) polypeptide range from about 1 μg to about 50 mg, about 5 μg to about 50 mg, about 1 μg to about 100 mg, about 5 μg to about 100 mg, about 15 μg to about 50 mg, about 15 μg to about 25 mg, about 15 μg to about 10 mg, about 15 μg to about 5 mg, about 15 μg to about 1 mg, about 15 μg to about 100 μg, about 15 μg to about 75 μg, about 5 μg to about 50 μg, about 10 μg to about 50 μg, about 15 μg to about 45 μg, about 20 μg to about 40 μg, or about 25 to about 35 μg of flu hemagglutinin (HA) polypeptide per dose, and can be administered to a subject once, twice, three or more times with intervals as often as needed.

Doses for infectious viral vectors may vary from 10-100, or more, virions per dose. In some embodiments, suitable dosages of a virus vector are $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu, and can be administered to a subject once, twice, three or more times with intervals as often as needed.

In certain embodiments, exemplary doses for VLPs range from about 0.01 μg to about 100 mg, about 0.1 μg to about 100 mg, about 5 μg to about 100 mg, about 15 μg to about 50 mg, about 15 μg to about 25 mg, about 15 μg to about 10 mg, about 15 μg to about 5 mg, about 15 μg to about 1 mg, about 15 μg to about 100 μg, about 15 μg to about 75 μg, about 5 μg to about 50 μg, about 10 μg to about 50 μg, about 15 μg to about 45 μg, about 20 μg to about 40 μg, or about 25 to about 35 μg per kilogram of the patient.

In one embodiment, an inactivated vaccine is formulated such that it contains about 5 μg to about 50 μg, about 10 μg to about 50 μg, about 15 μg to about 100 μg, about 15 μg to about 75 μg, about 15 μg to about 50 μg, about 15 μg to about 30 μg, about 20 μg to about 50 μg, about 25 μg to about 40 μg, about 25 μg to about 35 μg of a flu hemagglutinin (HA) polypeptide.

In certain embodiments, an active compound i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide, or composition is administered to a subject once as a single dose.

In certain embodiments, an active compound or composition is administered to a subject as a single dose followed by a second dose 3 to 6 weeks later. In certain embodiments, an active compound or composition is administered to a subject as a single dose followed by a second dose 3 to 6 weeks later, which is followed by administration of a third dose 3 to 6 weeks later. In certain embodiments, the second and/or third administrations may utilize a different active compound or composition. In accordance with these embodiments, booster inoculations may be administered to the subject at 6 to 12 month intervals following the second inoculation. In certain embodiments, the booster inoculations may utilize a different active compound or composition. In certain embodiments, the first (priming) administration comprises a full-length hemagglutinin or fragment thereof (or a nucleic acid encoding the same) and the second (booster) administration comprises administration of a flu hemagglutinin (HA) polypeptide described herein (or a nucleic acid encoding the same, a VLP comprising the same, or a virus or bacteria expressing the same). In some embodiments, the administration of the same active compound or composition may be repeated and the administrations may be separated by at least 1 day, 2 days, 3 days, 5 days, 10 days, 15 days, 30 days, 45 days, 2 months, 75 days, 3 months, or at least 6 months. In certain embodiments, an active compound or composition is administered to a subject as a single dose once per year.

In specific embodiments for administration to children, two doses of an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition, given at least one month apart, are administered to a child. In specific embodiments for administration to adults, a single dose is given. In another embodiment, two doses of an active compound or composition, given at least one month apart, are administered to an adult. In another embodiment, a young child (six months to nine years old) may be administered an active compound or composition for the first time in two doses given one month apart. In a particular embodiment, a child who received only one dose in their first year of vaccination should receive two doses in the following year. In some embodiments, two doses administered 4 weeks apart are preferred for children 2-8 years of age who are administered an influenza vaccine, e.g., an immunogenic formulation described herein, for the first time. In certain embodiments, for children 6-35 months of age, a half dose (0.25 ml) may be preferred, in contrast to 0.5 ml which may be preferred for subjects over three years of age.

In a specific embodiment, for administration to human infants, two doses of flu hemagglutinin (HA) polypeptides described herein (see Section 5.1, infra) or a composition thereof and/or one or more of the nucleic acids, vectors, VLPs, or virosomes described herein, are administered to an infant, wherein the influenza virus hemagglutinin head domain of the flu hemagglutinin (HA) polypeptide used in the first dose is from a different strain or subtype than the influenza virus hemagglutinin head domain of the flu hemagglutinin (HA) polypeptide used in the second dose. The first and second administrations may be separated by at least 1 day, 2 days, 3 days, 5 days, 10 days, 15 days, 30 days, 45 days, 2 months, 75 days, 3 months, or at least 6 months.

In a specific embodiment, for administration to human infants, three doses of flu hemagglutinin (HA) polypeptides described herein (see Section 5.1, infra) or a composition thereof and/or one or more of the nucleic acids, vectors, VLPs, or virosomes described herein, are administered to an infant, wherein the influenza virus hemagglutinin head domains of the flu hemagglutinin (HA) polypeptides used in the first, second, and third doses are from different strains or subtypes of influenza virus. The first, second, and third administrations may be separated by at least 1 day, 2 days, 3 days, 5 days, 10 days, 15 days, 30 days, 45 days, 2 months, 75 days, 3 months, or at least 6 months.

In particular embodiments, an active compound (i.e., a flu hemagglutinin (HA) polypeptide described herein, a nucleic acid encoding such a polypeptide, a vector (e.g., a viral vector, or a bacteria) containing or expressing such a polypeptide, cells stimulated with such a polypeptide) or composition is administered to a subject in the fall or winter, i.e., prior to or during the influenza season in each hemisphere. In one embodiment, children are administered their first dose early in the season, e.g., late September or early October in the Northern hemisphere, so that the second dose can be given prior to the peak of the influenza season.

For passive immunization with an antibody, the dosage ranges from about 0.0001 to 100 mg/kg, and more usually 0.01 to 5 mg/kg, of the patient body weight. For example, dosages can be 1 mg/kg body weight or 10 mg/kg body weight or within the range of 1-10 mg/kg or in other words, 70 mg or 700 mg or within the range of 70-700 mg, respectively, for a 70 kg patient. An exemplary treatment regime entails administration once per every two weeks or once a month or once every 3 to 6 months for a period of one year or over several years, or over several year-intervals. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to the flu hemagglutinin (HA) polypeptide in the patient.

5.17 Biological Assays 5.17.1 Assays for Testing Activity of Chimeric Influenza Virus Hemagglutinin Polypeptides Assays for testing the expression of a flu hemagglutinin (HA) polypeptide in a vector disclosed herein may be conducted using any assay known in the art. For example, an assay for incorporation into a viral vector comprises growing the virus as described in this section or Sections 5.4 or 5.5, purifying the viral particles by centrifugation through a sucrose cushion, and subsequent analysis for flu hemagglutinin (HA) polypeptide expression by an immunoassay, such as Western blotting, using methods well known in the art. Methods for determining whether a hemagglutinin polypeptide is chimeric are known to those of skill in the art and described herein (see, e.g., the Examples 3 and 4 below).

In one embodiment, a flu hemagglutinin (HA) polypeptide disclosed herein is assayed for proper folding and functionality by testing its ability to bind specifically to a neutralizing antibody directed to an influenza virus hemagglutinin polypeptide, such as the stalk region of the polypeptide, using any assay for antibody-antigen interaction known in the art. Neutralizing antibodies for use in such assays include, for example, the neutralizing antibodies described in Ekiert et al., 2009, *Science Express*, 26 Feb. 2009; Kashyap et al., 2008, *Proc Natl Acad Sci USA* 105: 5986-5991; Sui et al. 2009, *Nature Structural and Molecular Biology*, 16:265-273; Wang et al., 2010, *PLOS Pathogens* 6(2):1-9; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/

US2008/085876 published as International Publication No. WO 2009/079259. These antibodies include CR6261, CR6325, CR6329, CR6307, CR6323, 2A, D7, D8, F10, G17, H40, A66, D80, E88, E90, H98, C179 (FERM BP-4517), AI3C (FERM BP-4516), among others.

In another embodiment, a flu hemagglutinin (HA) polypeptide disclosed herein is assayed for proper folding by determination of the structure or conformation of the flu hemagglutinin (HA) polypeptide using any method known in the art such as, e.g., NMR, X-ray crystallographic methods, or secondary structure prediction methods, e.g., circular dichroism.

5.17.2 Assays for Testing Activity of Antibodies Generated Using Chimeric Influenza Virus Hemagglutinin Polypeptides Antibodies described herein may be characterized in a variety of ways known to one of skill in the art (e.g. ELISA, Surface Plasmon resonance display (BIAcore), Western blot, immunofluorescence, immunostaining and/or microneutralization assays). In some embodiments, antibodies are assayed for the ability to specifically bind to a flu hemagglutinin (HA) polypeptide, or a vector comprising said polypeptide. Such an assay may be performed in solution (e.g., Houghten, 1992, Bio/Techniques 13:412 421), on beads (Lam, 1991, Nature 354:82 84), on chips (Fodor, 1993, Nature 364:555 556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865 1869) or on phage (Scott and Smith, 1990, Science 249:386 390; Cwirla et al., 1990, Proc. Natl. Acad. Sci. USA 87:6378 6382; and Felici, 1991, J. Mol. Biol. 222:301 310) (each of these references is incorporated herein in its entirety by reference).

Specific binding of an antibody to the flu hemagglutinin (HA) polypeptide and cross-reactivity with other antigens can be assessed by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to a flu hemagglutinin (HA) polypeptide and the off-rate of an antibody-antigen interaction can be determined by competitive binding assays. One example of a competitive binding assay is a radioimmunoassay comprising the incubation of labeled antigen (e.g., $^3H$ or $^{125}I$) with the antibody of interest in the presence of increasing amounts of unlabeled antigen, and the detection of the antibody bound to the labeled antigen. The affinity of the antibody for a flu hemagglutinin (HA) polypeptide and the binding off-rates can be determined from the data by Scatchard plot analysis. Competition with a second antibody can also be determined using radioimmunoassays. In this case, a flu hemagglutinin (HA) polypeptide is incubated with the test antibody conjugated to a labeled compound (e.g., $^3H$ or $^{125}I$) in the presence of increasing amounts of an unlabeled second antibody.

In certain embodiments, antibody binding affinity and rate constants are measured using the KinExA 3000 System (Sapidyne Instruments, Boise, Id.). In some embodiments, surface plasmon resonance (e.g., BIAcore kinetic) analysis is used to determine the binding on and off rates of the antibodies to an influenza virus hemagglutinin polypeptide. BIAcore kinetic analysis comprises analyzing the binding and dissociation of a flu hemagglutinin (HA) polypeptide from chips with immobilized antibodies to a flu hemagglutinin (HA) polypeptide on their surface. A typical BIAcore kinetic study involves the injection of 250 μL, of an antibody reagent (mAb, Fab) at varying concentration in HBS buffer containing 0.005% Tween-20 over a sensor chip surface, onto which has been immobilized the flu hemagglutinin (HA) polypeptide. The flow rate is maintained constant at 75 μL/min. Dissociation data is collected for 15 min or longer as necessary. Following each injection/dissociation cycle, the bound antibody is removed from the influenza virus hemagglutinin polypeptide surface using brief, 1 min pulses of dilute acid, typically 10-100 mM HCl, though other regenerants are employed as the circumstances warrant. More specifically, for measurement of the rates of association, $k_{on}$, and dissociation, $k_{off}$, the polypeptide is directly immobilized onto the sensor chip surface through the use of standard amine coupling chemistries, namely the EDC/NHS method (EDC=N-diethylaminopropyl)-carbodiimide). Briefly, a 5-100 nM solution of the polypeptide in 10 mM NaOAc, pH 4 or pH 5 is prepared and passed over the EDC/NHS-activated surface until approximately 30-50 RU's worth of polypeptide are immobilized. Following this, the unreacted active esters are "capped" off with an injection of 1M Et-$NH_2$. A blank surface, containing no polypeptide, is prepared under identical immobilization conditions for reference purposes. Once an appropriate surface has been prepared, a suitable dilution series of each one of the antibody reagents is prepared in HBS/Tween-20, and passed over both the polypeptide and reference cell surfaces, which are connected in series. The range of antibody concentrations that are prepared varies, depending on what the equilibrium binding constant, $K_D$, is estimated to be. As described above, the bound antibody is removed after each injection/dissociation cycle using an appropriate regenerant.

The neutralizing activity of an antibody can be determined utilizing any assay known to one skilled in the art. Antibodies described herein can be assayed for their ability to inhibit the binding of an influenza virus, or any other composition comprising a flu hemagglutinin (HA) polypeptide (e.g., a VLP, liposome, or detergent extract), to its host cell receptor (i.e., sialic acid) using techniques known to those of skill in the art. For example, cells expressing influenza virus receptors can be contacted with a composition comprising a flu hemagglutinin (HA) polypeptide in the presence or absence of the antibody and the ability of the antibody to inhibit the antigen's binding can measured by, for example, flow cytometry or a scintillation assay. The composition comprising a flu hemagglutinin (HA) polypeptide or the antibody can be labeled with a detectable compound such as a radioactive label (e.g., $^{32}P$, $^{35}S$, and $^{125}I$) or a fluorescent label (e.g., fluorescein isothiocyanate, rhodamine, phycoerythrin, phycocyanin, allophycocyanin, o-phthaldehyde and fluorescamine) to enable detection of an interaction between the composition comprising a flu hemagglutinin (HA) polypeptide and a cell receptor. Alternatively, the ability of antibodies to inhibit a flu hemagglutinin (HA) polypeptide from binding to its receptor can be determined in cell-free assays. For example, a composition comprising an influenza virus hemagglutinin polypeptide can be contacted with an antibody and the ability of the antibody to inhibit the composition comprising a flu hemagglutinin (HA) polypeptide from binding to a cell receptor can be determined. In a specific embodiment, the antibody is immobilized on a solid support and the composition comprising an influenza virus hemagglutinin polypeptide is labeled with a detectable compound. Alternatively, a composition comprising a flu hemagglutinin (HA) polypeptide is immobilized on a solid support and the antibody is labeled with a detectable compound. In certain embodiments, the ability of an antibody to inhibit a flu hemagglutinin (HA) polypeptide from binding to a cell receptor is determined by assessing the percentage of binding inhibition of the antibody relative to a control (e.g., an antibody known to inhibit the flu hemagglutinin (HA) polypeptide from binding to the cell receptor).

In other embodiments, an antibody suitable for use in the methods described herein does not inhibit influenza virus receptor binding, yet is still found to be neutralizing in an assay described herein. In some embodiments, an antibody suitable for use in accordance with the methods described herein reduces or inhibits virus-host membrane fusion in an assay known in the art or described herein.

In one embodiment, virus-host membrane fusion is assayed in an in vitro assay using an influenza virus containing a reporter and a host cell capable of being infected with the virus. An antibody inhibits fusion if reporter activity is inhibited or reduced compared to a negative control (e.g., reporter activity in the presence of a control antibody or in the absence of antibody).

In one embodiment, virus-host membrane fusion is detected using a model system of cell fusion. In an exemplary cell fusion assay, cells (e.g., HeLa cells) are transfected with a plasmid encoding a flu hemagglutinin (HA) polypeptide and contacted and exposed to a buffer that allows the flu hemagglutinin (HA) polypeptide fusion function (e.g., pH 5.0 buffer) in the presence of an antibody. An antibody is neutralizing if it reduces or inhibits syncytia formation compared to a negative control (e.g., syncytia formation in the presence of a control antibody or in the absence of antibody).

In other embodiments, virus-host membrane fusion is assayed using an in vitro liposome-based assay. In an exemplary assay, the host cell receptor is reconstituted into liposomes containing one half of a reporter. A flu hemagglutinin (HA) polypeptide is reconstituted into another set of liposomes containing another half of a reporter. When the two liposome populations are mixed together, fusion is detected by reconstitution of the reporter, for example, an enzymatic reaction that can be detected colorimetrically. The antibody inhibits fusion if reporter activity is reduced or inhibited compared to reporter activity in an assay conducted in the absence of antibody or in the presence of a control antibody. In certain embodiments, the ability of an antibody to inhibit fusion is determined by assessing the percentage of fusion in the presence of the antibody relative to the percentage of fusion in the presence a control.

5.17.3 Assays for Testing Activity of Stimulated Cells

Cells stimulated in accordance with the methods described herein may be analyzed, for example, for integration, transcription and/or expression of the polynucleotide or gene(s) of interest, the number of copies of the gene integrated, and the location of the integration. Such analysis may be carried out at any time and may be carried out by any methods known in the art. In other embodiments, successful stimulation of the target cell with a flu hemagglutinin (HA) polypeptide described herein is determined by detecting production of neutralizing antibodies against the flu hemagglutinin (HA) polypeptide using methods known in the art or described herein.

In certain embodiments, subjects in which the stimulated cells, e.g., DCs, are administered can be analyzed for location of the cells, expression of a vector-delivered polynucleotide or gene encoding the flu hemagglutinin (HA) polypeptide, stimulation of an immune response (e.g., production of neutralizing antibodies against the flu hemagglutinin (HA) polypeptide), and/or monitored for symptoms associated with influenza virus infection or a disease associated therewith by any methods known in the art or described herein.

Reporter assays can be used to determine the specificity of the targeting of the flu hemagglutinin (HA) polypeptide. For example, a mixed population of bone marrow cells can be obtained from a subject and cultured in vitro. The flu hemagglutinin (HA) polypeptide can be administered to the mixed population of bone marrow cells, and expression of a reporter gene associated with the flu hemagglutinin (HA) polypeptide can be assayed in the cultured cells. In some embodiments, at least about 50%, more preferably at least about 60%, 70%, 80% or 90%, still more preferably at least about 95% of stimulated cells in the mixed cell population are dendritic cells.

5.17.4 Antiviral Activity Assays

Antibodies described herein or compositions thereof can be assessed in vitro for antiviral activity. In one embodiment, the antibodies or compositions thereof are tested in vitro for their effect on growth of an influenza virus. Growth of influenza virus can be assessed by any method known in the art or described herein (e.g. in cell culture). In a specific embodiment, cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented. Viral titers are determined in the supernatant by hemagglutinin plaques or any other viral assay described herein. Cells in which viral titers can be assessed include, but are not limited to, EFK-2 cells, Vero cells, MDCK cells, primary human umbilical vein endothelial cells (HUVEC), H292 human epithelial cell line and HeLa cells. In vitro assays include those that measure altered viral replication (as determined, e.g., by plaque formation) or the production of viral proteins (as determined, e.g., by Western blot analysis) or viral RNAs (as determined, e.g., by RT-PCR or northern blot analysis) in cultured cells in vitro using methods which are well known in the art or described herein.

In one non-limiting example, a monolayer of the target mammalian cell line is infected with different amounts (e.g., multiplicity of 3 plaque forming units (pfu) or 5 pfu) of virus (e.g., influenza) and subsequently cultured in the presence or absence of various dilutions of antibodies (e.g., 0.1 µg/ml, 1 µg/ml, 5 µg/ml, or 10 µg/ml). Infected cultures are harvested 48 hours or 72 hours post infection and titered by standard plaque assays known in the art on the appropriate target cell line (e.g., Vero cells).

In a non-limiting example of a hemagglutination assay, cells are contacted with an antibody and are concurrently or subsequently infected with the virus (e.g., at an MOI of 1) and the virus is incubated under conditions to permit virus replication (e.g., 20-24 hours). The antibodies are preferably present throughout the course of infection. Viral replication and release of viral particles is then determined by hemagglutination assays using 0.5% chicken red blood cells. See, e.g., Kashyap et al., PNAS USA 105: 5986-5991. In some embodiments, a compound is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more. In other specific embodiments an inhibitor results in a reduction of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs in influenza virus titer in the subject. The log-reduction in Influenza virus titer may be as compared to a negative control, as compared to another treatment, or as compared to the titer in the patient prior to antibody administration.

5.17.5 Cytotoxicity Assays

Many assays well-known in the art can be used to assess viability of cells (infected or uninfected) or cell lines following exposure to an active compound or a composition thereof and, thus, determine the cytotoxicity of the compound or composition. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270: 18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic-very heavy—80%), PH (partially toxic-heavy—60%), P (partially toxic—40%), Ps (partially toxic-slight—20%), or 0 (no toxicity—0%), conforming to the degree of cytotoxicity seen. A 50% cell inhibitory (cytotoxic) concentration ($IC_{50}$) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. In certain embodiments, cytotoxicity is assessed in one or more of the following cell lines: MDCK, MEF, Huh 7.5, Detroit, or human tracheobronchial epithelial (HTBE) cells.

Active compounds or compositions thereof can be tested for in vivo toxicity in animal models. For example, animal models, described herein and/or others known in the art, used to test the activities of active compounds can also be used to determine the in vivo toxicity of these compounds. For example, animals are administered a range of concentrations of active compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of an active compound can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An active compound that exhibits large therapeutic indices is preferred. While an active compound that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of an active compound for use in humans. The dosage of such agents lies preferably within a range of circulating concentrations that include the $ED_{50}$ with little or no toxicity. The dosage may vary within this range depending upon the dosage form employed and the route of administration utilized. For any active compound used in a method described herein, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided herein.

Further, any assays known to those skilled in the art can be used to evaluate the prophylactic and/or therapeutic utility of the active compounds and compositions described herein, for example, by measuring viral infection or a condition or symptoms associated therewith.

5.17.6 In Vivo Antiviral Activity

Active compounds and compositions thereof are preferably assayed in vivo for the desired therapeutic or prophylactic activity prior to use in humans. For example, in vivo assays can be used to determine whether it is preferable to administer an active compound or composition thereof and/or another therapy. For example, to assess the use of an active compound or composition thereof to prevent an influenza virus disease, the composition can be administered before the animal is infected with influenza virus. Alternatively, or in addition, an active compound or composition thereof can be administered to the animal at the same time that the animal is infected with influenza virus. To assess the use of an active compound or composition thereof to treat an influenza virus infection or disease associated therewith, the compound or composition may be administered after infecting the animal with influenza virus. In a specific embodiment, an active compound or composition thereof is administered to the animal more than one time.

Active compounds and compositions thereof can be tested for antiviral activity in animal model systems including, but are not limited to, rats, mice, chicken, cows, monkeys, pigs, ferrets, goats, sheep, dogs, rabbits, guinea pigs, etc. In a specific embodiment, active compounds and compositions thereof are tested in a mouse model system. Such model systems are widely used and well-known to the skilled artisan. In a specific embodiment, active compounds and compositions thereof are tested in a mouse model system. Non-limiting examples of animal models for influenza virus are provided in this section.

In general, animals are infected with influenza virus and concurrently or subsequently treated with an active compound or composition thereof, or placebo. Alternatively, animals are treated with an active compound or composition thereof or placebo and subsequently infected with influenza virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of an active compound or composition thereof on the virulence of a virus can also be determined using in vivo assays in which the titer of the virus in an infected subject administered an active compound or composition thereof, the length of survival of an infected subject administered an active compound or composition thereof, the immune response in an infected subject administered an active compound or composition thereof, the number, duration and/or severity of the symptoms in an infected subject administered an active compound or composition thereof, and/or the time period before onset of one or more symptoms in an infected subject administered an active compound or composition thereof, is assessed. Techniques known to one of skill in the art can be used to measure such effects. In certain embodiments, an active compound or composition thereof results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, an active compound or composition thereof results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

Influenza virus animal models, such as ferret, mouse, guinea pig, squirrel monkey, macaque, and chicken, developed for use to test antiviral agents against influenza virus have been described. See, e.g., Sidwell et al., Antiviral Res., 2000, 48:1-16; Lowen A. C. et al. PNAS., 2006, 103: 9988-92; and McCauley et al., Antiviral Res., 1995, 27:179-186 and Rimmelzwann et al., Avian Diseases, 2003, 47:931-933. For mouse models of influenza, non-limiting examples of parameters that can be used to assay antiviral activity of active compounds administered to the influenza-infected mice include pneumonia-associated death, serum $\alpha$1-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

In other assays, histopathologic evaluations are performed after infection of an animal model subject. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

In one example, the ability to induce lung lesions and cause infection in an animal model of virus infection is compared using wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

In one embodiment, virus is quantified in tissue samples. For example, tissue samples are homogenized in phosphate-buffered saline (PBS), and dilutions of clarified homogenates adsorbed for 1 h at 37° C. onto monolayers of cells (e.g., MDCK cells). Infected monolayers are then overlaid with a solution of minimal essential medium containing 0.1% bovine serum albumin (BSA), 0.01% DEAE-dextran, 0.1% $NaHCO_3$, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., MDCK cells) in 96-well plates are incubated with log dilutions of clarified tissue homogenates in media. Two to three days after inoculation, 0.05-ml aliquots from each well are assessed for viral growth by hemagglutination assay (HA assay).

5.17.6.1.1 Assays in Humans

In one embodiment, an active compound or composition thereof that modulates replication of an influenza virus are assessed in infected human subjects. In accordance with this embodiment, an active compound or composition thereof is administered to the human subject, and the effect of the active compound or composition on viral replication is determined by, e.g., analyzing the level of the virus or viral nucleic acids in a biological sample (e.g., serum or plasma). An active compound or composition thereof that alters virus replication can be identified by comparing the level of virus replication in a subject or group of subjects treated with a control to that in a subject or group of subjects treated with an active compound or composition thereof. Alternatively, alterations in viral replication can be identified by comparing the level of the virus replication in a subject or group of subjects before and after the administration of an active compound or composition thereof. Techniques known to those of skill in the art can be used to obtain the biological sample and analyze the mRNA or protein expression.

In another embodiment, the effect of an active compound or composition thereof on the severity of one or more symptoms associated with an influenza virus infection/disease are assessed in an infected subject. In accordance with this embodiment, an active compound or composition thereof or a control is administered to a human subject suffering from influenza virus infection and the effect of the active compound or composition on one or more symptoms of the virus infection is determined. An active compound or composition thereof that reduces one or more symptoms can be identified by comparing the subjects treated with a control to the subjects treated with the active compound or composition. In a specific embodiment, administration of an active compound (i.e., a flu hemagglutinin (HA) polypeptide described herein) or composition thereof results in a decrease in hospitalization of a human or population of humans caused by influenza virus disease or infection. In another specific embodiment, administration of an active compound (i.e., a flu hemagglutinin (HA) polypeptide described herein) or composition thereof results in a reduced need for respiratory/breathing assistance in a human or population of humans with an influenza virus disease or infection. In another specific embodiment, administration of an active compound (i.e., a flu hemagglutinin (HA) polypeptide described herein) or composition thereof results in a reduced length of illness of a human or population of humans with an influenza virus disease or infection. In another specific embodiment, administration of an active compound (i.e., a flu hemagglutinin (HA) polypeptide described herein) or composition thereof results in improvement (e.g., an increase) in lung volume as assessed by, e.g., whole body or lung plethysmography. In another embodiment, an active compound or composition thereof is administered to a healthy human subject and monitored for efficacy as a vaccine (e.g., the subject is monitored for the onset of symptoms of influenza virus infection; the ability of influenza virus to infect the subject; and/or a reduction in/absence of one or more symptoms associated with influenza virus infection). Techniques known to physicians familiar with infectious diseases can be used to determine whether an active compound or composition thereof reduces one or more symptoms associated with the influenza virus disease.

5.18 Assessment of Antibodies in a Subject

In another aspect, a flu hemagglutinin (HA) polypeptide (e.g., a chimeric influenza virus hemagglutinin polypeptide) described herein, or virus expressing a flu hemagglutinin (HA) polypeptide (e.g., a chimeric influenza virus hemagglutinin polypeptide) described herein, can be used to assess the antibody response of a subject (e.g., a naive subject or an immunized/vaccinated subject) or a population of subjects to an influenza virus hemagglutining polypeptide (e.g., a flu HA polypeptide, such as a chimeric influenza virus hemagglutinin polypeptide (see, e.g., Example 8, below). In specific embodiments, a chimeric influenza virus hemagglutinin polypeptide or a virus expressing a chimeric influenza virus hemagglutinin polypeptide can be used to assess the presence of stem-specific antibodies in the subject or population of subjects. In specific embodiments, the chimeric influenza virus HA polypeptide comprises one or more modified glycosylations sites in the HA stem domain and/or one or more non-naturally occurring glycosylation sites in the globular head domain.

In a specific embodiment, the antibody response of a subject or a population of subjects that has been an immunized/vaccinated with an influenza virus hemagglutinin polypeptide (e.g., a flu hemagglutinin (HA) polypeptide(s) described herein, such as a chimeric influenza virus hemagglutinin polypeptide, or a virus expressing a flu hemagglutinin (HA) polypeptide described herein, such as a chimeric influenza virus hemagglutinin polypeptide), is assessed to identify the types of stalk-specific antibodies in the subject or population of subjects. Such an assessment may allow for the identification surrogate markers/endpoints important in determining the clinical response to administration of an influenza virus HA polypeptide polypeptide (s) (e.g., a flu HA polypeptide such as a chimeric influenza virus hemagglutinin polypeptide) described herein, or a virus expressing a influenza virus HA polypeptide polypeptide (s) (e.g., a flu HA polypeptide such as a chimeric influenza virus hemagglutinin polypeptide) described herein. In such an approach, a biological sample, e.g., blood, from the subject or population of subjects may be isolated and tested directly for the presence of antibodies, or may be processed (e.g., to obtain sera) and subsequently tested for the presence of antibodies.

In another specific embodiment, the antibody profile of a naive subject (i.e., a subject that has not been immunized/vaccinated with an influenza virus HA polypeptide polypeptide (s) (e.g., a flu HA polypeptide such as a chimeric influenza virus hemagglutinin polypeptide described herein), or a virus expressing an influenza virus HA polypeptide polypeptide(s) (e.g., a flu HA polypeptide such as a chimeric influenza virus hemagglutinin polypeptide)) or a population of naive subjects is assessed to determine whether said subject or population of subjects possesses globular head-specific and/or stem specific antibodies against various influenza virus strains or subtypes. Such an assessment may allow for the generation of a flu hemagglutinin (HA) polypeptide (e.g., a chimeric influenza virus hemagglutinin polypeptide), or viruses expressing flu hemagglutinin (HA) polypeptide (e.g., a chimeric influenza virus hemagglutinin polypeptide), that are suitable for administration to said subject or population of subjects, e.g., flu hemagglutinin (HA) polypeptides, such as a chimeric influenza virus hemagglutinin polypeptide, comprising a head domain to which said subject or population of subjects is naive (does not have antibodies against). Such an assessment may determine an immunization strategy for the patient.

In another specific embodiment, provided herein is a method of assessing/detecting the presence of antibodies in a subject that are specific for a stem domain of a particular influenza virus strain or subtype comprising contacting in vitro a biological sample (e.g., blood, sera) from said subject with a chimeric influenza virus hemagglutinin polypeptide described herein, wherein said chimeric influenza virus hemagglutinin polypeptide comprises a stem domain from the strain or subtype of interest. See Examples 6-8, infra, for methods for assessing/detecting the presence of antibodies specific for a stem domain of a particular influenza virus strain or subtype. In another specific embodiment, provided herein is a method of assessing/detecting the presence of antibodies in a subject that are specific for a stem domain of a particular influenza virus strain or subtype comprising contacting in vitro a biological sample (e.g., blood, sera) from said subject with a virus expressing/containing a chimeric influenza virus hemagglutinin polypeptide described herein, wherein said chimeric influenza virus hemagglutinin polypeptide comprises a stem domain from the strain or subtype of interest.

5.19 Kits

Provided herein is a pharmaceutical pack or kit comprising one or more containers filled with one or more of the ingredients of the pharmaceutical/immunogenic compositions described herein, such as one or more active compounds provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in accordance with the methods described herein. In one embodiment, a kit comprises an active compound described herein, preferably one or more flu hemagglutinin (HA) polypeptides (e.g., one or more chimeric influenza virus hemagglutinin polypeptides), in one or more containers. In certain embodiments, a kit comprises a vaccine described herein, e.g., a split virus vaccine, a subunit vaccine, an inactivated influenza virus vaccine, or a live influenza virus vaccine, wherein said vaccine comprises one or more flu hemagglutinin (HA) polypeptides described herein (e.g., one or more chimeric influenza virus hemagglutinin polypeptides). In a specific embodiment, provided herein are kits comprising a chimeric influenza virus hemagglutinin polypeptide described herein and instructions for using the chimeric influenza virus hemagglutinin polypeptide to assess the antibodies present in a subject. In another specific embodiment, provided herein are kits comprising a chimeric influenza virus hemagglutinin polypeptide described herein for use in methods of assaying for the presence of HA stem domain specific antibodies in a sample.

6. EXAMPLES

6.1 Example 1

Influenza Hemagglutinin Stem Domain Polypeptides

TABLE 8

Summary of Constructs

| Name | HA1 N-terminal Stem Se2ment | Linker | HA1 C-terminal Stem Se2ment | HA2 Domain |
|---|---|---|---|---|
| PR8-2G | SEQ ID NO: 34 | Gly-Gly | SEQ ID NO: 50 | SEQ ID NO: 66 |
| PR8-4G | SEQ ID NO: 34 | Gly-Gly-Gly-Gly | SEQ ID NO: 50 | SEQ ID NO: 66 |
| PR8-PG | SEQ ID NO: 34 | Pro-Gly | SEQ ID NO: 50 | SEQ ID NO: 66 |
| PR8-No Cys-1G | SEQ ID NO: 177 | Gly | SEQ ID NO: 226 | SEQ ID NO: 66 |
| PR8-No Cys 2G | SEQ ID NO: 177 | Gly-Gly | SEQ ID NO: 226 | SEQ ID NO: 66 |
| PR8-No Cys 3G | SEQ ID NO: 177 | Gly-Gly-Gly | SEQ ID NO: 226 | SEQ ID NO: 66 |
| PR8-No Cys | SEQ ID NO: 177 | direct bond | SEQ ID NO: 226 | SEQ ID NO: 66 |
| PR8-No Cys Δ1 | SEQ ID NO: 178 | direct bond | SEQ ID NO: 227 | SEQ ID NO: 66 |

TABLE 8-continued

Summary of Constructs

| Name | HA1 N-terminal Stem Se2ment | Linker | HA1 C-terminal Stem Se2ment | HA2 Domain |
|---|---|---|---|---|
| PR8-No Cys Δ3 | SEQ ID NO: 179 | direct bond | SEQ ID NO: 228 | SEQ ID NO: 66 |
| PR8-No Cys NAS | SEQ ID NO: 177 | Asn-Ala-Ser | SEQ ID NO: 226 | SEQ ID NO: 66 |
| PR8-CON-A | SEQ ID NO: 312 | Gly-Gly-Gly-Gly | SEQ ID NO: 313 | SEQ ID NO: 66 |
| PR8-CON-B | SEQ ID NO: 34 | Gly-Gly | SEQ ID NO: 314 | SEQ ID NO: 66 |
| PR8-CON-C | SEQ ID NO: 315 | Gly-Gly | SEQ ID NO: 316 | SEQ ID NO: 66 |
| HK68-2G | SEQ ID NO: 36 | Gly-Gly | SEQ ID NO: 52 | SEQ ID NO: 68 |
| HK68-4G | SEQ ID NO: 36 | Gly-Gly-Gly-Gly | SEQ ID NO: 52 | SEQ ID NO: 68 |
| HK68-PG | SEQ ID NO: 36 | Pro-Gly | SEQ ID NO: 52 | SEQ ID NO: 68 |
| HK68-No Cys | SEQ ID NO: 183 | direct bond | SEQ ID NO: 232 | SEQ ID NO: 68 |
| HK68-No Cys Δ1 | SEQ ID NO: 184 | direct bond | SEQ ID NO: 233 | SEQ ID NO: 68 |
| HK68-No Cys Δ3 | SEQ ID NO: 185 | direct bond | SEQ ID NO: 234 | SEQ ID NO: 68 |
| HK68-No Cys NAS | SEQ ID NO: 183 | Asn-Ala-Ser | SEQ ID NO: 232 | SEQ ID NO: 68 |
| HK68-CON-A | SEQ ID NO: 308 | Gly-Gly-Gly-Gly | SEQ ID NO: 52 | SEQ ID NO: 68 |
| HK68-CON-B | SEQ ID NO: 36 | Gly-Gly | SEQ ID NO: 309 | SEQ ID NO: 68 |
| HK68-CON-C | SEQ ID NO: 310 | Gly-Gly-Gly-Gly | SEQ ID NO: 311 | SEQ ID NO: 68 |

The instant example provides useful polypeptides in Table 8 that can be prepared according to the methods described herein.

6.2 Example 2

Chimeric Influenza Virus Hemagglutinin Polypeptides

This example describes chimeric influenza virus hemagglutinin polypeptides and methods for inducing high levels of cross-neutralizing HA stalk antibodies in a subject comprising administration of said chimeric influenza virus hemagglutinin polypeptides. As described in this example, chimeric influenza virus hemagglutinin were generated that were successfully expressed by influenza virus and by cells engineered to express the chimeric influenza virus hemagglutinin. The chimeric influenza virus hemagglutinin were successfully recovered in their proper conformation, as evidenced by antibody recognition of both the stem and head domains of the chimeric influenza virus hemagglutinin.

FIG. 7 depicts chimeric influenza virus hemagglutinins (HAs), comprising the stem/stalk domain of an H1 subtype of influenza virus and the heterologous globular head domains of other influenza virus subtypes (H2, H3, and H5). Following the strategy outline in FIG. 7, an influenza virus was generated that comprises a chimeric HA composed of a stem domain derived from an H1N1 (PR8-H1N1) influenza virus and the globular head domain of the 2009 pandemic H1 HA (Cal/09). The globular head domains of the HAs of the two viruses are very distinct (~70% amino acid identity) whereas the stem domains are highly conserved but still divergent (~89% amino acid identity). As demonstrated in FIG. 8, the chimeric HAs with the same stem domain but very different HA heads within the same subtype were expressed.

In addition, a chimeric HA consisting of the stalk domain of A/PR8/34 HA and the globular head domain of HK/68 (chimeric H3) as well as wild type HAs (PR8-HA and HK68 HA) were expressed in 293T cells. FIG. 10 demonstrates that it is also possible to express stable chimeric HAs with the same stem domain (derived from the H1 subtype HA) and with a globular head from a different subtype (H3).

Thus, HA immunogens that completely share the HA stem domain but are highly divergent in their globular heads were designed. Repeated immunizations with these constructs should result in high levels of cross-neutralizing antibodies against the common stem domain of the HA. An improved vaccine strategy thus uses chimeric HAs with a constant stem/stalk domain and a changing globular head to induce robust cross-neutralizing anti-stem domain antibodies. A constant stem domain of, e.g., the H1 HA from A/PR/8/34 can be used together with globular heads from different group 1 HAs (H1, H2, H5, H9) to make a panel of either recombinant inactivated viruses, recombinant attenuated viruses or recombinant HAs (FIG. 9). A similar panel for group 2 HAs based on the stem domain of, e.g., H3 HA of an X31 virus, in combination with H3, H4 and H7 globular heads can provide the basis for a group 2 HA universal vaccine. Recombinant viruses can be rescued on an influenza virus vaccine backbone, such as PR/8 or cold-adapted influenza viruses, grown by standard techniques and used as inactivated or attenuated vaccines. Recombinant HAs can be expressed in insect cells that are able to perform mammalian-like glycosylation (MIMIC Sf9) or by transient transfection of, e.g., 293 T or Vero cells, and then can be purified by Ni-chelat chromatography with the help of a C-terminal his tag. Other strategies can include the use of DNA vaccines expressing the chimeric HAs or other vectors, such as adenovirus vectors, expressing the chimeric HAs.

6.3 Example 3

Viruses Expressing Chimeric Influenza Virus Hemagglutinin Polypeptides

This example describes several functional chimeric influenza virus hemagglutinins encompassing a variety of globular head and stalk combinations from different hemagglutinin subtypes as well as recombinant influenza viruses expressing these chimeric hemagglutinins, which had growth properties similar to those of wild-type influenza viruses.

6.3.1 Materials and Methods 6.3.1.1 Cells and Viruses 293T and MDCK cells were obtained from the American Type Culture Collection (ATCC, Manassas, Va.) and were maintained either in Dulbecco's minimal essential medium (DMEM) or in MEM (Gibco, Invitrogen) supplemented with 10% fetal calf serum (HyClone; Thermo Scientific) and penicillin-streptomycin (Gibco, Invitrogen).

All A/PR/8/34 recombinant viruses were grown in 10-day old embryonated chicken eggs at 37° C. for 2 days.

6.3.1.2 Construction of Plasmids

Plasmids encoding the different chimeric hemagglutinins were constructed by a similar strategy adapted from constructing reverse genetics plasmids for generating recombinant viruses as previously described (see, e.g., Fodor et al., 1999, J Virol 73:9679-9682; and Hai et al., 2008, J Virol 82:10580-10590). Briefly, the different segments of chimeric HA were amplified by PCR with primers containing SapI sites, digested with SapI, and cloned into the SapI sites of the pDZ vector that contains the human RNA polymerase I promoter and the mouse RNA polymerase I terminator (see, e.g. Quinlivan et al., 2005, J Virol 79:8431-8439), through multi-segmental ligation.

6.3.1.3 Flow Cytometric Analysis

To assess levels of hemagglutinin proteins at the cell surface, 293T cells were transfected with 1 µg of the appropriate plasmid using Lipofectamine 2000 (Invitrogen) according to the manufacturer's instructions. At 24 h post-transfection, cells were trypsinized and resuspended in PBS containing 2% FBS prior to staining them with the monoclonal antibody (mAb) 6F12 against H1 HAs at a 1/1000 dilution or with the mAb 12D1 against H3 HAs (see Wang et al., 2010, PLoS Pathog 6:e1000796) at a 1/400 dilution. Stained cells were enumerated on a Beckman Coulter Cytomics FC 500 flow cytometer, and the results were analyzed using FlowJo software.

6.3.1.4 Pseudoparticle Generation and Entry Assay

The procedure for pseudo-particle production was adapted from previous studies (see, e.g., Evans et al., 2007, Nature 446:801-805; and Sui et al., 2011, Clin Infect Dis 52:1003-1009). Briefly, 293-T cells were co-transfected with four plasmids encoding (i) a pro-virus containing the desired reporter (V1-GLuc), (ii) HIV Gag-Pol, (iii) the different chimeric hemagglutinin protein and (iv) influenza A PR8 neuraminidase (NA). Supernatants were collected 72 h post-transfection and subsequently, filtered (0.45 µm pore size). All transductions and infection assays using pseudo-particles were performed in the presence of 1 µg/ml polybrene (Sigma, St. Louis, Mo.) (see Sui et al., 2011, Clin Infect Dis 52:1003-1009).

The entry assay was performed through infecting MDCK cells with pseudo-particles with different chimeric hemagglutinin containing the G-Luc reporter. Twenty-four hours post-infection, cells were washed three times with fresh medium to remove G-Luc protein that was present in the pseudo-particle inoculum. Forty-eight hours post-infection luciferase assays were performed (see Evans et al., 2007, Nature 446:801-805).

6.3.1.5 Rescue of Recombinant Chimeric Influenza a Viruses

Rescue of influenza A viruses from plasmid DNA was performed as previously described (see, e.g., Fodor et al., 1999, J Virol 73:9679-9682; and Hai et al., 2008, J Virol 82:10580-10590). To generate the recombinant wild-type (rWT) PR8 virus, 293T cells were co-transfected with 1 µg of each of the 8 pDZ PR8 rescue plasmids using Lipofectamine 2000 (Invitrogen, Carlsbad, Calif.). The viruses expressing different chimeric HA were generated in the same way but substituting the HA plasmid by the corresponding chimeric one to recover the corresponding chimeric viruses. At 6 h post-transfection, the medium was replaced with DMEM containing 0.3% bovine serum albumin (BSA), 10 mM HEPES, and 1.5 µg/ml TPCK (L-1-tosylamide-2-phenylethyl chloromethyl ketone)-treated trypsin. After 24 hours post-transfection, virus-containing supernatant was inoculated into 8-day old embryonated chicken eggs. Allantoic fluid was harvested after 2 days of incubation at 37° C. and assayed for the presence of virus by hemagglutination of chicken red blood cells and by plaque formation in MDCK cells.

6.3.1.6 Virus Growth Kinetics Assay

To analyze the replication characteristics of recombinant viruses, 10-day old embryonated chicken eggs were inoculated with 100 pfu of each respective virus. Allantoic fluid was harvested and subsequently assayed for viral growth at 0, 9, 24, 48, and 72 h post-infection (hpi). The titers of virus present in allantoic fluid were determined by plaque assay on MDCK cells.

6.3.1.7 Immunostaining of Plaques

Plaques were visualized by immunostaining with the mAb (HT103) against the influenza A NP protein.

6.3.1.8 Western Blot and Indirect Immunofluorescence Analysis

One well of a 12-well dish of confluent MDCK cells was infected (multiplicity of infection [MOI] of 2) with indicated recombinant influenza viruses or mock infected with phosphate-buffered saline (PBS) for 1 h at 37° C. At 12 h post-infection (hpi), cells were lysed in 1× protein loading buffer as described previously (see, e.g., Hai et al., 2008, J Virol 82:10580-10590). The reduced cell lysates were analyzed by Western blot analysis by using mAbs against, A/NP (HT103), A/PR8/HA (PY102), A/Cal/09/HA (29C1), A/VN/HA (M08) (20), A/H3/HA (12D1). The detection of Perth-cH7 used a goat polyclonal sera, NR-3152, against A/FPV/Dutch/27 (H7) virus, which was obtained from the BEI Resources. The mAb anti-Glyceraldehyde 3-phosphate dehydrogenase (GAPDH) loading control antibody was from Abcam. All the proteins of interest were visualized using an enhanced chemiluminescence protein detection system (PerkinElmer Life Sciences, Boston, Mass.).

For immunofluorescence analysis, confluent monolayers of MDCK cells on 15-mm coverslips were infected with recombinant viruses at an MOI of 2. At 15 hpi, cells were fixed and permeabilized with methanol-acetone (ratio, 1:1) at −20° C. for 20 min. After being blocked with 1% bovine serum albumin in PBS containing 0.1% Tween 20, cells were incubated for 1 h with the antibody directed against A/NP (HT103), A/H1/HA (6F12), A/PR8/HA (PY102), A/Cal/09/HA (29C1), A/VN/HA (M08) (20), A/H3/HA (12D1), and A/H7 virus (NR-3152) as mentioned above. After three washes with PBS containing 0.1% Tween 20, cells were incubated for 1 h with Alexa Fluor 594-conjugated anti-mouse immunoglobulin G (IgG; Invitrogen, Carlsbad, Calif.) or Alexa Fluor 594-conjugated anti-goat immunoglobulin G (IgG, Invitrogen, Carlsbad, Calif.). Following the final three washes, infected cells were analyzed by fluorescence microscopy with an Olympus IX70 microscope.

6.3.2 Results 6.3.2.1 Generation of Chimeric Hemagglutinins

In order to gain information regarding the conservation of the cysteine residues forming the Cys52-Cys277 disulfide bond, an alignment of the influenza A virus HA sequences of the H1, H3, H5 and H7 subtypes was generated (see FIG. 11). The sequences of the HA1 subunits are less conserved than those of the HA2 subunits, mainly due to the presence of immuno-dominant antigenic sites on the globular head domain. The more conserved HA2 chains comprise the stalk regions anchoring the HA molecules to the viral envelope. The alignment demonstrates that Cys52 and Cys277 and the amino acids towards both ends are conserved across selected subtypes. Henceforth, the hemagglutinin sequences N-terminal to Cys52 and C-terminal to Cys277 are defined as the stalk domain (FIG. 11). The intervening sequence is considered in this example to be the head domain.

Figures 12A, 12B:
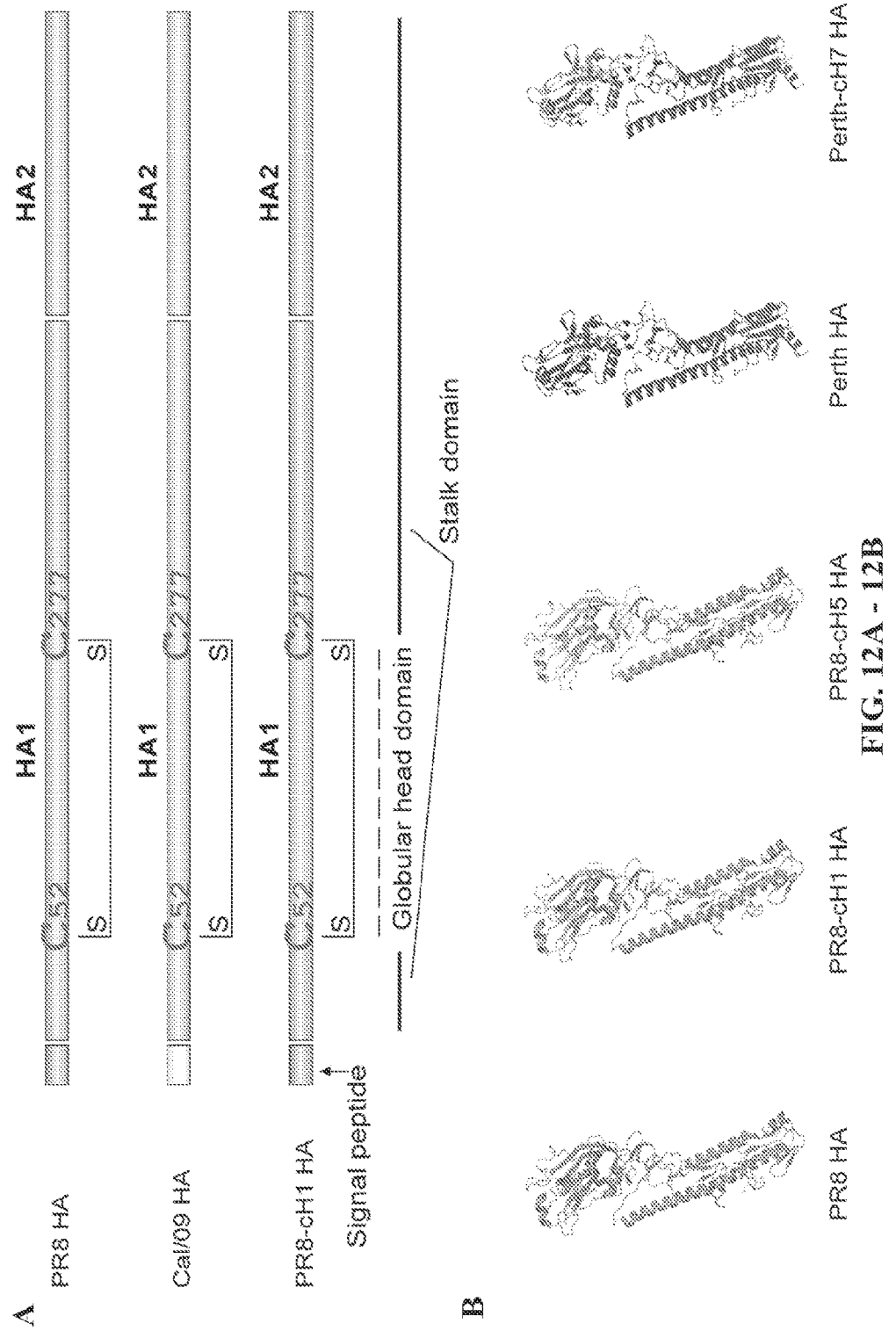

A chimeric hemagglutinin construct (PR8-cH1) containing the pandemic H1 Cal/09 HA globular head domain with the stalk region from the PR8 (H1) HA was first generated (FIG. 12A). A chimeric HA (PR8-cH5) containing the globular head from the VN1203 (H5) HA with the stalk from the PR8 (H1) HA also was generated (FIG. 12B). Since all 16 subtypes of influenza HA are grouped into two phylogenetic groups (groups 1 and 2) (see, e.g., Sui et al., 2009, Nat Struct Mol Biol 16:265-273) and H1 and H5 HAs both belong to group 1, a similar strategy to generate a chimeric HA bearing the A/Alberta/24/01 (H7) head domain with the stalk region from A/Perth/16/2009 (H3) HA (Perth-cH7) (FIG. 12B) was applied. Both H7 and H3 are members from the group 2 phylogenetic group (see, e.g., Sui et al., 2009, Nat Struct Mol Biol 16:265-273).

Figure 13A:
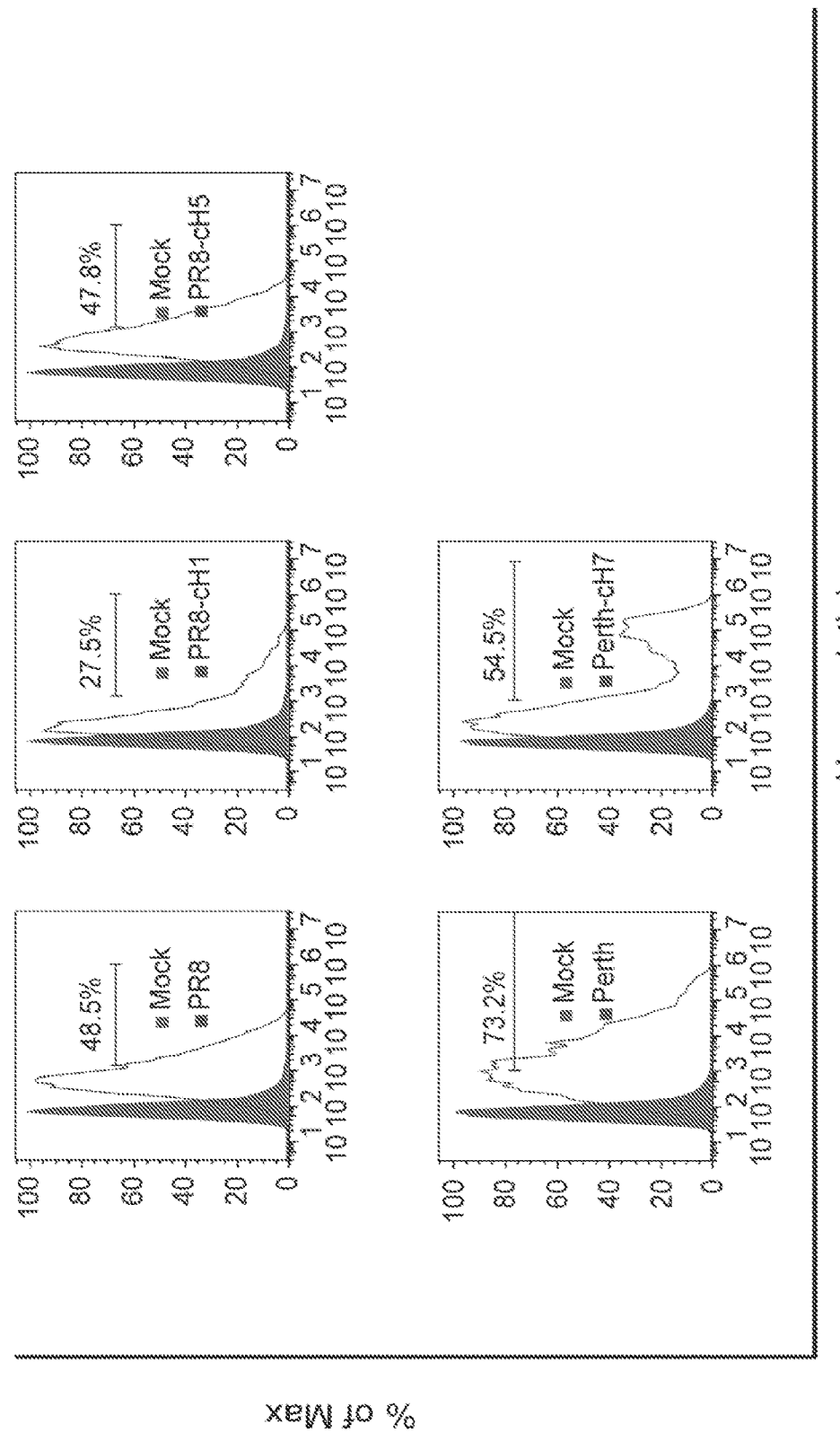

It was next tested whether the different chimeric HA constructs were being expressed and transported to the cell surface. Fluorescence-activated cell sorter (FACS) analysis of transiently transfected 293T cells was performed following surface staining with PR8 and H3 stalk domain specific antibodies, respectively (FIG. 13A). As shown in FIG. 13A, expression of all three chimeric constructs was detected. This detection indicates that the transportation of the chimeric HAs through the Golgi complex to the cell surface is not disrupted.

Figure 13B:
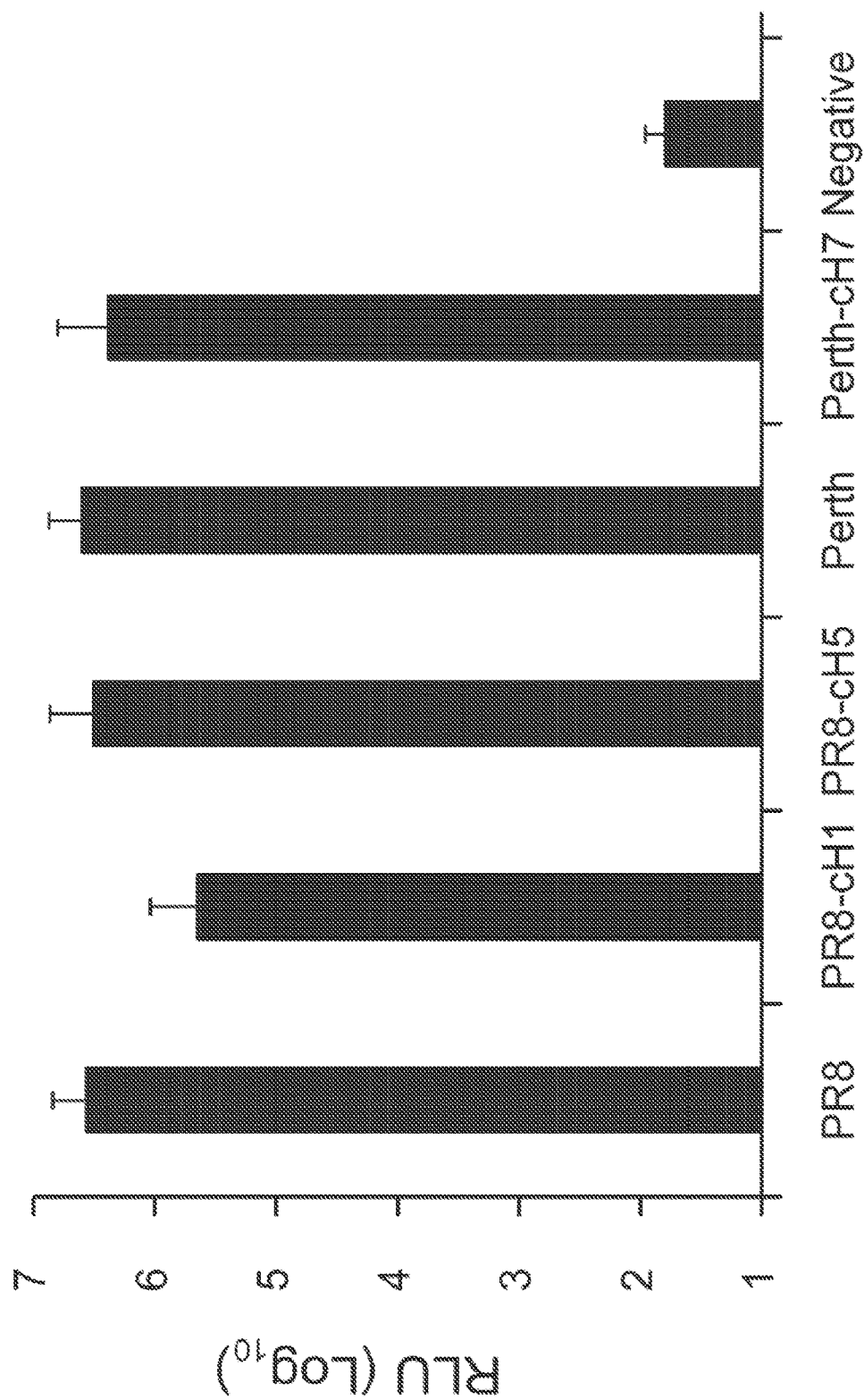

Next the entry characteristics of the different chimeric HAs was examined through infection of MDCK cells with retroviral HA-pseudotyped particles containing the chimeric HA, wild type influenza A PR8NA and HIV-based luciferase. The entry efficiency mediated by the chimeric HA proteins was detected by luciferase read-out. Comparable levels of pseudotyped particle-mediated luciferase delivery were observed for PR8-cH5 and Perth-cH7 chimeric HAs and the corresponding wild type proteins (FIG. 13B). The PR8-cH1 HA showed a lower luciferase level compared to the other HA constructs.

6.3.3 Generation of Recombinant Influenza Viruses Bearing Chimeric Hemagglutinins.

In light of the above results, whether a chimeric HA is functional in the context of a whole virus particle and ultimately would allow the rescue of a recombinant influenza A virus only expressing a chimeric HA was ascertained. Using previously published protocols (see, e.g., Fodor et al., 1999, J Virol 73:9679-9682; and Hai et al., 2008, J Virol 82:10580-10590), viruses containing all of the different chimeric HAs were successfully generated. The resulting viruses were plaque purified, amplified in 10-Day-old embryonic eggs and the chimeric segments were analyzed by RT-PCR and sequenced. In all cases, the virus was found to have the expected chimeric HA segment and no other HA segments.

Figure 14A:
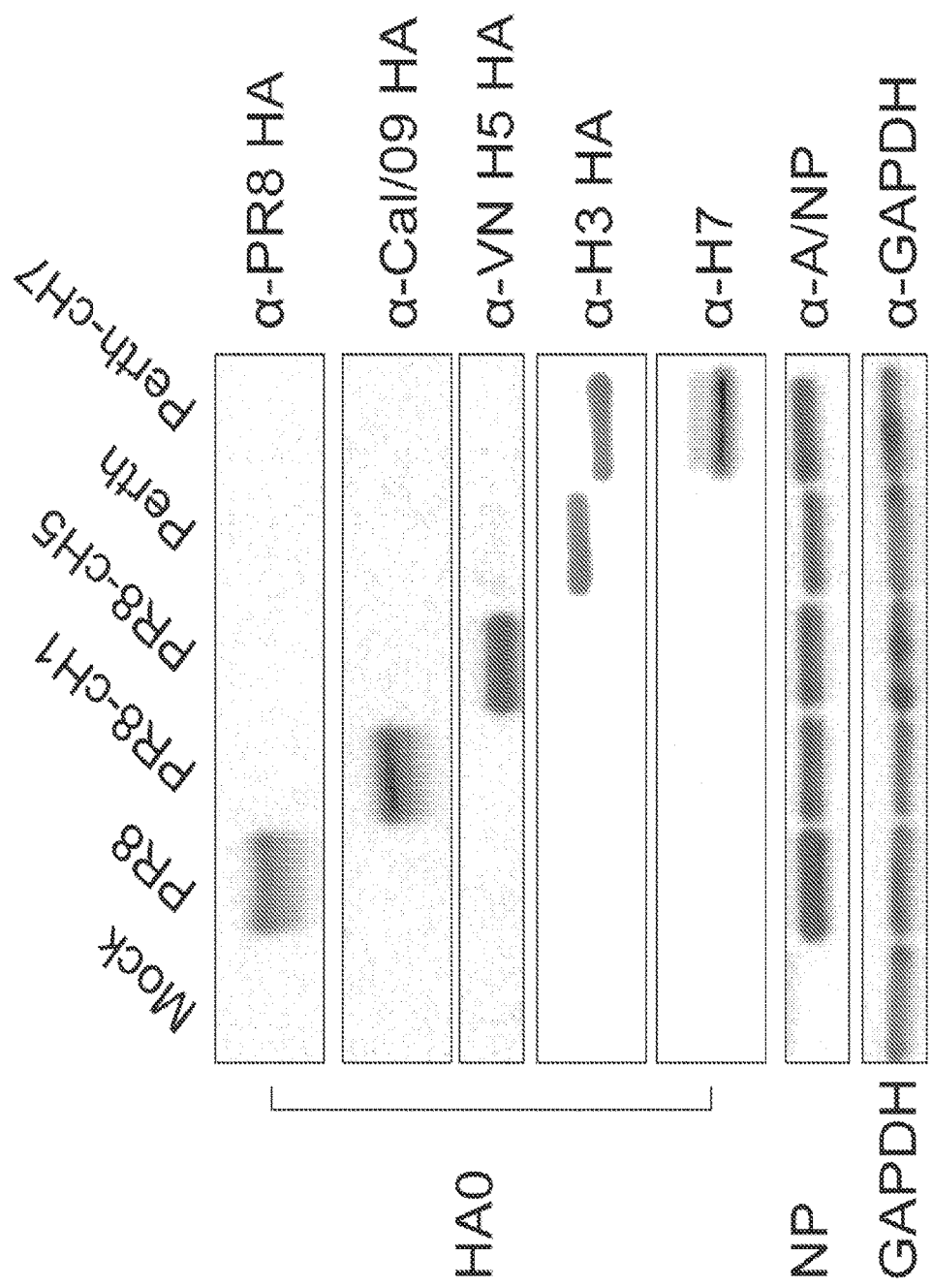
Figure 14B:
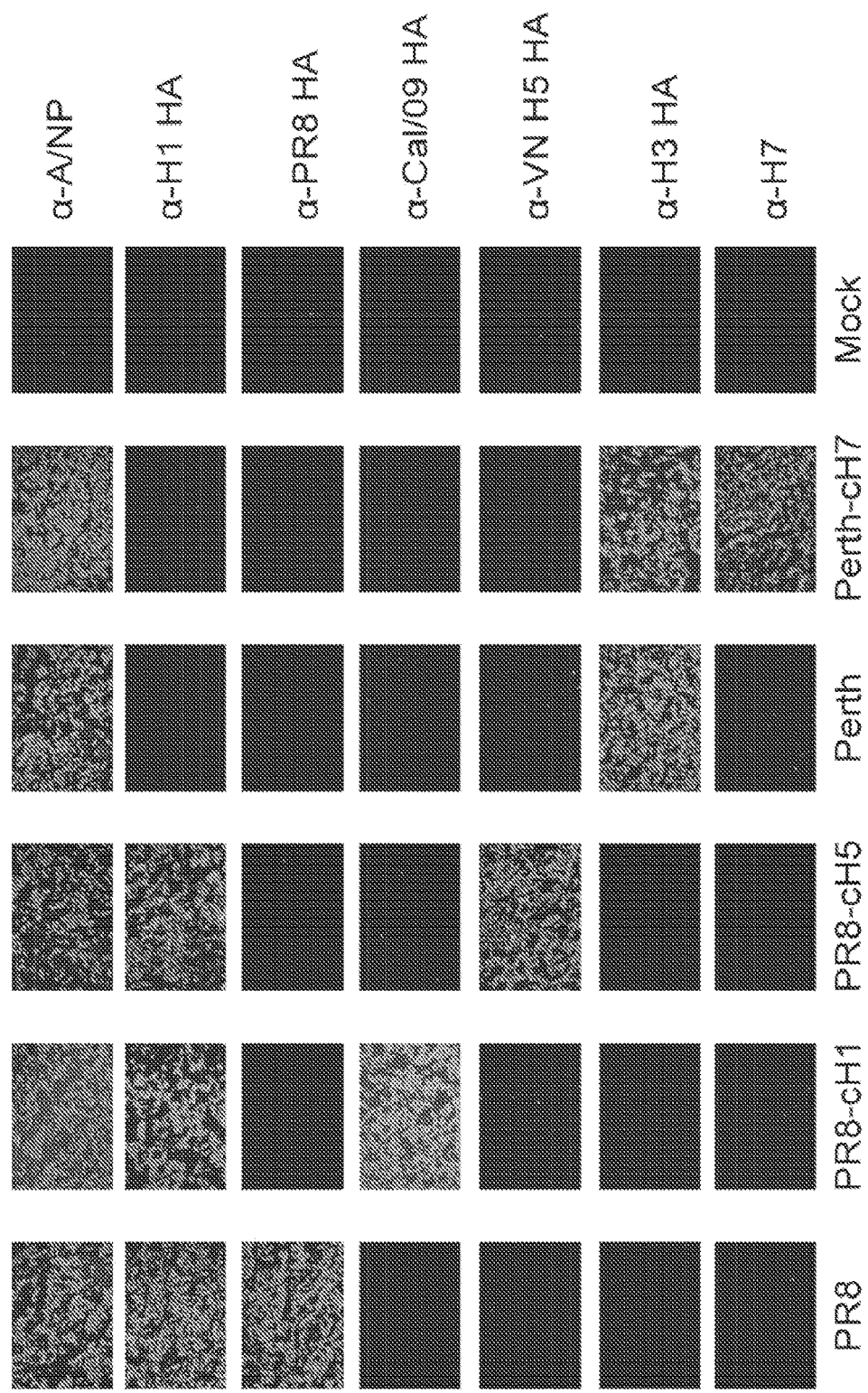

The identity of the chimeric viruses was further demonstrated by Western blotting and indirect immunofluorescence of infected cells (FIGS. 14A and 14B). MDCK cells were infected with rWT A/PR8, wild-type A/Perth, PR8-cH1, PR8-cH5, and Perth-cH7 viruses (FIGS. 14A and 14B). PR8-cH1 and PR8-cH5 chimeric HA proteins were detected in the corresponding samples using antibodies against either Cal/09 HA (29C1) or VN/04 HA (M08) (see Steel et al., 2009, J Virol 83:1742-1753), respectively (FIG. 14A). Using 12D1, a pan H3 stalk mAb (see Wang et al., 2010, PLoS Pathog 6:e1000796), comparable expression levels between the Perth cH7HA and wild type Perth HA were observed. A positive band was only detected for the Perth-cH7 infection sample when using anti-H7 antibodies (NR-3152).

For the immunofluorescence study, the infection conditions were similar to those for the Western analysis. Infected cells were stained with corresponding antibodies as indicated in FIG. 14B. All the infected cells showed the expected expression of the HAs as well as of the A/NP protein (FIG. 14B).

6.3.4 Replication Characteristics of Recombinant Viruses

The growth properties of the viruses were assessed in 10-day-old embryonated chicken eggs at 37° C. (FIG. 15A). The rWT PR8 virus was included for comparison of the growth kinetics of the recombinant viruses expressing chimeric HAs. Regarding the PR8-cH5 virus, a similar replication pattern as compared to PR8 virus was observed. As for Perth-cH7 virus, there was a 2 fold reduction in viral titer compared to the rWT PR8 virus at 9 hpi. Nevertheless, it reached a similar peak titer as the wild type virus (1×109 PFU/ml) at 48 hpi. The PR8-cH1 virus was attenuated when compared to the rWT PR8 virus, as shown by reduction in titers through all the time points. Nonetheless, even this chimeric virus reached a respectable peak titer of approximately 108 PFU/ml. The plaque phenotype of each of the chimeric viruses was also evaluated in MDCK cells. All viruses formed comparably sized plaques as shown in FIG. 15B. These results confirm that the chimeric HA constructs fold correctly in vivo and are biologically functional.

6.3.5 Conclusion

A novel strategy was developed to generate influenza viruses with chimeric HA proteins bearing different HA globular head domains by taking advantage of the conserved disulfide bond Cys52-Cys277 which demarcates the border between the head and stalk domains. Thus, through substituting the parental head domain with the head domain of another HA, a panel of chimeric HAs with the same stalk but different globular heads was generated. The design was tested across multiple subtypes, including the PR8 stalk domain with Cal/09 and VN H5 globular heads. In addition, an H7 globular head was placed on an H3 stalk domain. These constructs cover both phylogenetic groups of the influenza HA protein. Each construct was expressed on the cell surface and retained fusion activity as shown in FIG. 12. The generation of recombinant viruses bearing the chimeric HAs further validated that the HAs fold correctly and retain biological functions.

6.4 Example 4

Diagnostic Applications of Chimeric Influenza Virus Hemagglutinin Polypeptides and Vaccination of Mice with Chimeric Influenza Virus Hemagglutinin Polypeptides This example demonstrates that chimeric influenza virus hemagglutinin polypeptides can be utilized for diagnostic purposes and that viruses expressing chimeric influenza virus hemagglutinin polypeptides can be utilized in vaccines.

6.4.1 Materials and Methods 6.4.1.1 Cells and Plasmids 293T and MDCK cells were obtained from ATCC and were maintained in Dulbeccos's Modified Eagle's medium (DMEM) and Minimal Essential Medium (both from Gibco), respectively, each supplemented with 10% fetal calf serum (HyClone), and 100 units/ml of penicillin-100 ng/ml of streptomycin (Pen/Strep, Gibco). TNM-FH (Sigma-Aldrich) supplemented with 10% fetal calf serum and Hyclone SFX insect culture media (ThermoScientific) were used for Sf9 and BT1-TN5B1-4 (High Five) cell culture.

Chimeric hemagglutinin constructs with the stalk of A/Puerto Rico/8/1934 (PR8) containing the globular head domain from either A/Mallard/Sweden/81/02 ("cH6") virus or A/Guinea fowl/Hong Kong/WF10/99 ("cH9") virus were generated using similar techniques. For the chimeric H6 construct, different components were amplified by PCR and cloned into the pDZ plasmid using a cloning strategy previously described (see, e.g., Fodor et al., 1999, J Virol 73:9679-82; and Hai et al., 2008, Journal of Virology 82:10580-90). Briefly, different components of the chimeric hemagglutinin (cHA) were amplified by PCR with primers containing Sap I sites, digested with Sap I, and cloned into the Sap I sites of thepDZ plasmid. For generation of the baculo-transfer plasmid, cH6 was amplified by PCR, cut with BamHI and NotI, and cloned in frame into a modified pBacPAK8 (Gentech) baculo-transfer vector that harbors a C-terminal T4 phage foldon and a 6-his tag (see Meier et al., 2004, J Mol Biol 344:1051-69). The sequences of all plasmids were confirmed by Sanger sequencing.

6.4.1.2 Rescue of Recombinant cH9 Virus

In order to rescue the recombinant vaccine virus, eight reverse genetics plasmids that encode vRNA and mRNA of the seven wild type viral segments from PR8 and the cH9 were used, as previously described (Fodor et al., 1999, J Virol 73:9679-82; and Pleschka et al., 1996, J Virol 70:4188-92). Briefly, 293T cells were transfected with 1 μg of each of the eight plasmids using Lipofectamine 2000 (Invitrogen). At 12 hours post transfection, the medium was replaced with DMEM containing 0.3% bovine serum albumin, 10 mM HEPES, and 1.5 μg of TPCK (1-1-tosylamide-2-phenylethyl chloromethyl ketone)-treated trypsin/mL. At two days post transfection, virus-containing supernatant was inoculated into 10-day-old embryonated chicken eggs. Allantoic fluid was harvested after 2 days of incubation at 37° C. and assayed for the presence of virus by the hemagglutination of chicken red blood cells. The rescued cH9 virus was then propagated in 10-day old eggs following a 48 hour incubation at 37° C. Virus stocks were tittered by plaque assay as previously described (see, e.g., Steel et al., 2009, Journal of Virology 83:1742-53). The sequence of the cH9 was confirmed by sequencing of reverse transcription-PCR products.

6.4.1.3 Recombinant Baculovirus Generation, Protein Expression and Purification

In order to generate recombinant baculoviruses (rBV) carrying the cH6, plasmids and Baculogold DNA (BDBiosciences) were co-transfected into Sf9 cells with Cellfectin II (Invitrogen) according to the manufacturer's instructions. Recombinant baculovirus was amplified in Sf9 cells grown in TNM-FH medium (Gemini Bioproducts, West Sacramento, Calif.) and titers were determined by plaque assay as previously described (see, e.g., Steel et al., 2009, Journal of Virology 83:1742-53).

High Five cells (see Krammer et al., 2010, Mol Biotechnol 45:226-34) grown in HyClone SFX insect cell media (Thermo Fisher Scientific, Waltham, Mass.) were infected with rBV expressing cH6 at a multiplicity of infection (MOI) of 10 and a cell density of $1\times10^6$ cells/ml in 500 ml shaker flasks. Cells were harvested 96 hours post-infection and separated from supernatant by low speed centrifugation for 10 minutes at 2000×g at room temperature. For purification of cH6 protein, the supernatant was collected and incubated with Ni-NTA resin (Qiagen) for 2 hours at 4° C. The slurry was loaded on columns and washed trice with washing buffer (50 mM Na2HCO3, 300 mMNaCl, 20 mM Imidazole, pH 8). Protein was eluted in 0.5 ml steps with elution buffer (50 mM Na2HCO3, 300 mMNaCl, 250 mM Imidazole, pH 8), tested for protein content with Bradford reagent and fractions containing protein were pooled. Protein purity and identity was tested by SDS-PAGE, Coomassie staining and Western blot. Protein concentration was determined with Bradford reagent.

6.4.1.4 Mouse Experiments

For all procedures, mice were anesthetized with intraperitoneal injections of 0.1 mL of ketamine/xylazine mixtures (1.5 mg ketamine and 0.3 mg xylazine).

Mouse 50% lethal doses ($LD_{50}$) were determined in BALB/c mice (Charles River Laboratories) by infecting groups of four mice with 10-fold serial dilutions of influenza virus. Body weights were monitored for a two week period. Mice that lost greater than 25% of their body weight were considered to have reached experimental endpoint and were euthanized. $LD_{50}$ values were calculated by the method of Reed and Meunch (see Reed and Meunch. 1938, Am. J. Hyg. 27:493-497).

For experiments to assess the stem antibodies produced following A/California/04/09 (Cal/09) virus infection, female, 8-10 week old BALB/c mice were first primed with intramuscular administration of 80 μg of an expression plasmid encoding full length HA from PR8 virus, coupled with the application of electrical stimulation as previously described (TriGrid delivery system, Ichor Medical Systems) (see, e.g., Luxembourg et al., 2007, Expert Opinion on Biological Therapy 7:1647-64). Three weeks later, mice were boosted with a sublethal dose of $10^4$ PFU Cal/09 in a 50 μl volume, intranasally. Control animals either received DNA alone or Cal/09 virus alone, or intramuscular injection of the 2009-2010 vaccine (Cal/09 split vaccine). Three weeks post boost, or the equivalent time point for control animals, mice were bled and sera was harvested to test reactivity to cH6 by immunofluorescence as described below.

For experiments testing the efficacy of cH9 virus as a vaccine construct, PR8 full length DNA was administered as described above. Three weeks post prime, mice were inoculated with $10^3$ PFU of cH9 virus instilled intranasally. Control animals either received DNA alone or Cal/09 virus alone or purified inactivated PR8 virus intramuscularly. Three weeks post boost, or the equivalent time point for control animals, mice were challenged with intranasal inoculation of $5 \times 10^4$ $LD_{50}$ of PR8 virus. Mice were weighed for 14 days post challenge. Animals that lost more than 27.5% of their initial body weight were euthanized and scored as dead.

6.4.1.5 Immunofluorescence to Confirm Expression of Chimeric Hemagglutinin

Confluent monolayers of 293T cells were transfected with 1 μg of pDZ cH6 plasmid. At 48 hours post transfection, cells were fixed and blocked with 1% bovine serum albumin in PBS containing 0.1% Tween 20. Cells were then incubated with sera pooled from the animals of each of the four experimental groups described above (PR8DNA alone, Cal/09 alone, PR8DNA and Cal/09 infection, or Cal/09 split vaccine alone). After three washes with PBS containing 0.1% Tween 20, cells were incubated for 1 hour with Alexa Fluor 488-conjugated anti-mouse IgG (Invitrogen). Infected cells were analyzed by fluorescence microscopy with an Olympus IX70 microscope.

6.4.1.6 ELISA

Ninety-six well ELISA plates (Nunc, MaxiSorp) were coated with 50 ml of baculovirus-expressed cH6 and incubated overnight at 4° C. Plates were blocked 3% milk/PBS and then washed with PBS/0.1% Tween (PBST). Serum from vaccinated mice was serially diluted in PBS and added to the plate, followed by a 1 hour incubation at 37° C. Plates were then washed with PBST and incubated with 1:2500 dilution of horseradish peroxidase linked anti-mouse IgG (GE Healthcare). Following an additional wash with PBST, SigmafastoOPD substrate (Sigma) was added. The reaction was stopped with 3M $H_2SO_4$ and optical density measurements were taken at 490 nm.

6.4.2 Results 6.4.2.1 Chimeric Influenza Virus Hemagglutinin Polypeptides can be Used in Diagnostic Applications A chimeric hemagglutinin construct comprising the globular head domain from the hemagglutinin of an H6 influenza virus subtype and stem/stalk domain from the hemagglutinin of the PR8 virus was generated to serve as analytical tool to assay production of antibodies by the immunized mice against the H6 stem domain. Because the immunized mice were only exposed to the globular head of H1 viruses, antibodies that were generated in the experimental animals would only be reactive to chimeric H6 hemagglutinin (cH6) if they were directed towards its H1 stem.

Figures 16A, 16B, 16C, 16D, 16E, 16F:
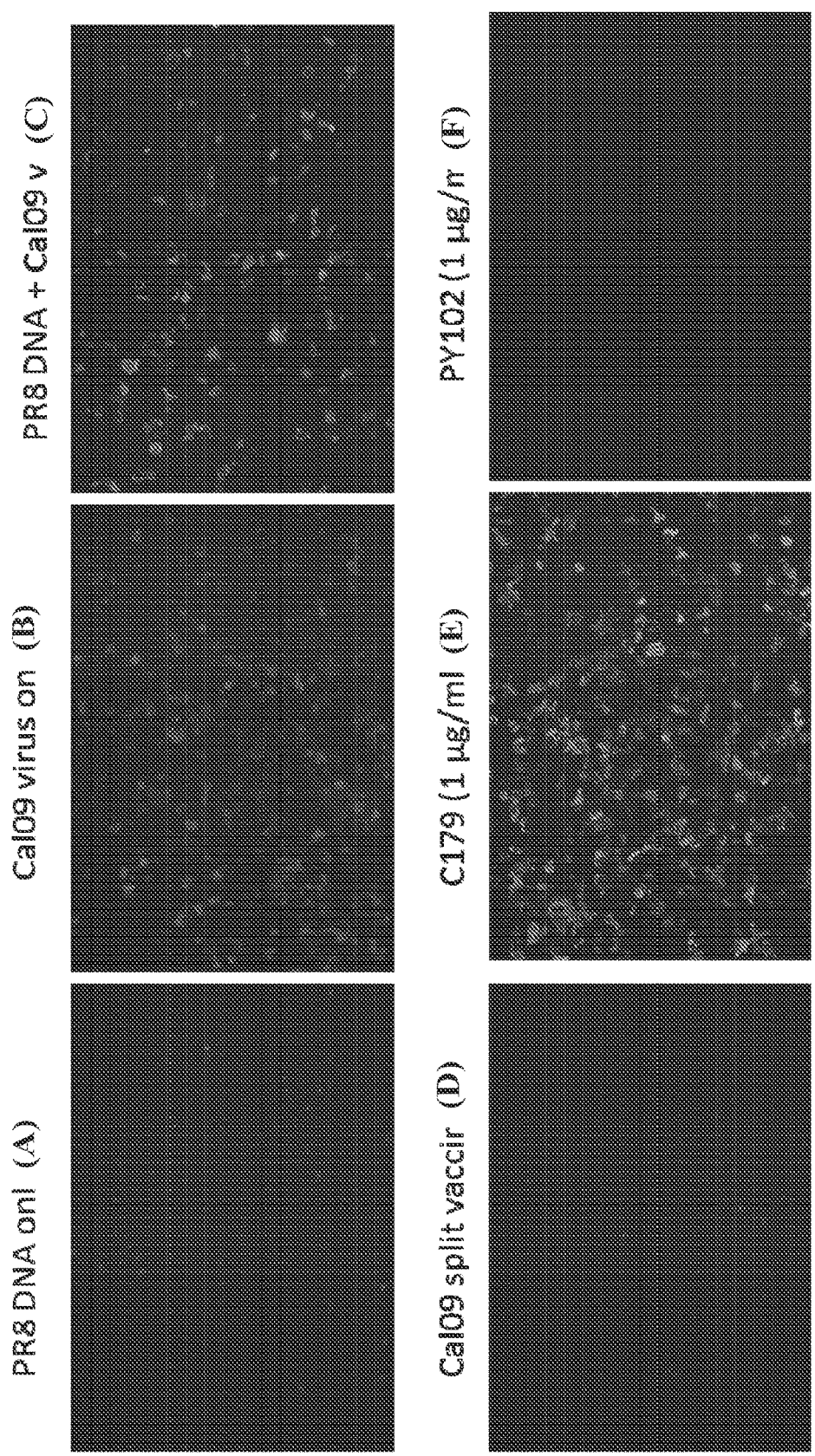

As shown in FIGS. 16A and 16D, treatment with DNA alone or pandemic split vaccine did not elicit any stem reactive antibodies in the vaccinated mice. Conversely, infection with Cal/09 alone generated stem reactive antibodies (FIG. 16B), though not to the extent elicited by DNA electroporation and infection (FIG. 16C). A cross-reactive H1 stem antibody, C179, was used as a control for the transfection (FIG. 16E). As expected, PY102, an antibody directed against the globular head of PR8, did not react to the transfected cH6 HA (FIG. 16F).

As shown in FIG. 18, the utility of the cH6 chimeric influenza virus hemagglutinin polypeptide as a tool in which to detect stem antibody binding was confirmed by ELISA.

6.4.2.2 Chimeric Influenza Virus Hemagglutinin Polypeptides can be Used in Vaccines As shown in FIG. 17, animals that were vaccinated with inactivated PR8 virus were protected from lethal challenge, while animals that received DNA alone completely succumbed to infection by day 5 post challenge. Animals that received cH9 virus alone also were not protected from infection, with only a 25% survival rate. By contrast, animals that were first primed with DNA and then boosted with cH9 virus were protected from challenge, with a survival rate that was statistically the same as animals vaccinated with the inactivated virus preparation.

6.5 Example 5

Glycosylation in the Globular Head Domain of an Influenza Virus Hemagglutinin Polypeptide Modulates the Virulence and Antigenic Properties of the Influenza Viruses This example demonstrates the effects of glycosylation of the globular head domain of an influenza virus hemagglutinin polypeptide on virulence and antigenic cross-reactivity of influenza viruses.

6.5.1 Materials and Methods 6.5.1.1 H1N1 HA Virus Sequences and Alignment

Figure 22A:
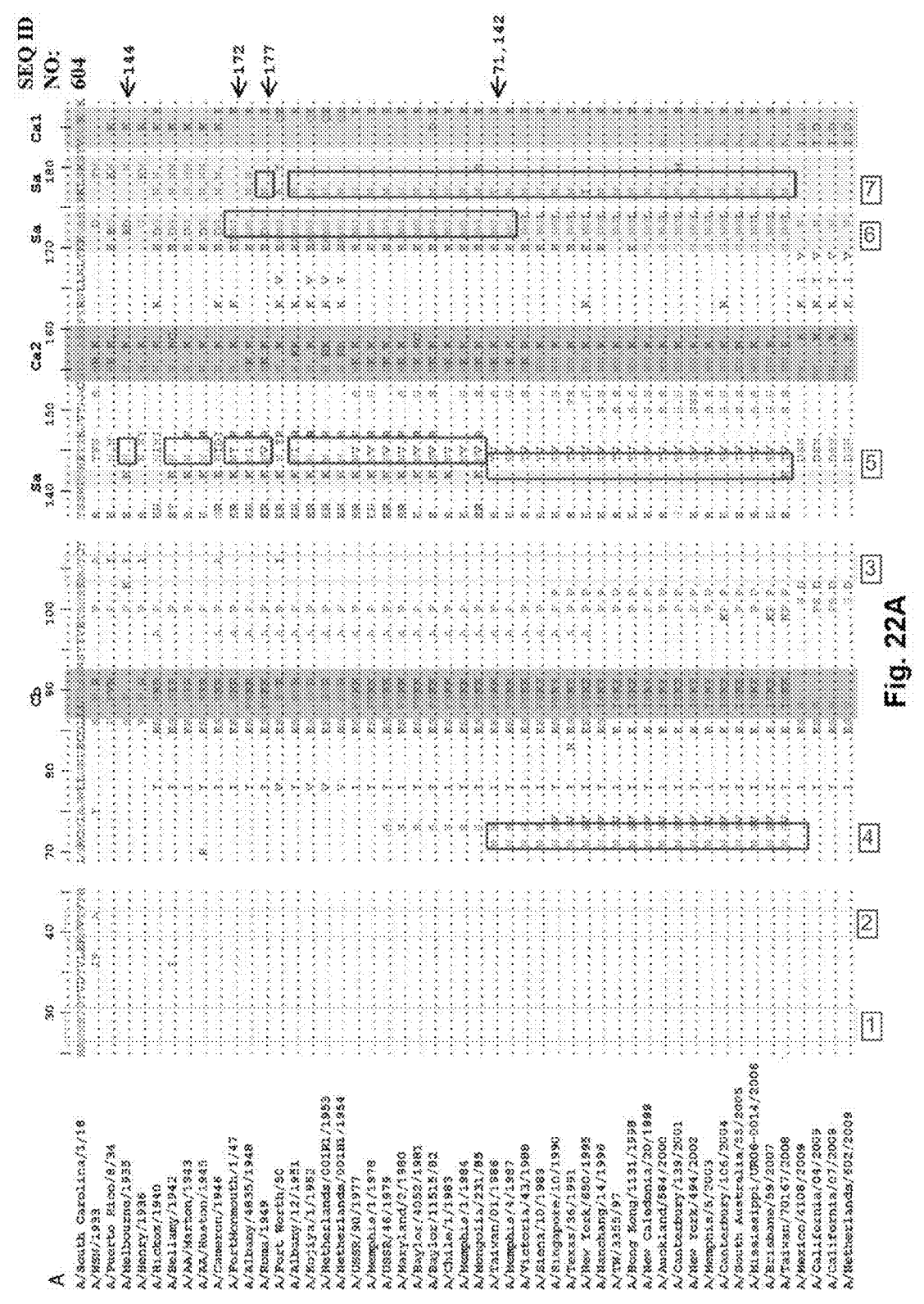

The HA sequence from all the H1N1 human viruses available through the Influenza Research Database (www-_fludb_org) were downloaded and aligned utilizing ClustalW and edited manually with the BioEdit Sequence Alignment Editor software. HA1 sequences containing representative glycosylation patterns based on at least two original isolates per year were selected for further analysis. The GenBank accession numbers of the HAs depicted on FIG. 22A are: AF117241.1, CY034132, AF389118, CY009324, CY020445, CY013271, CY020285, CY021709, CY009612, CY019947, CY019971, CY009332, CY021821, CY009340, CY021053, DQ508897, CY011296, CY021909, CY020181, CY021029, CY010364, CY020437, CY021725, DQ508873, CY019779, CY033655, CY012872, CY017011, DQ415317, EU103824, CY025026, CY010332, CY006675, CY019883, CY007467, CY016675, CY027875, CY058487.1, CY040114, FJ984355, GQ150342, GQ149654, GQ117044, FJ966974, CY039527.2. The glycosylation sites were predicted by the motif N-X-S/T.

6.5.1.2 Cell Lines and Viruses

Human embryonic kidney (293T) cells were maintained in DMEM supplemented with 10% FBS and 1000 U/ml penicillin/streptomycin. Madin-Darby canine kidney (MDCK) cells were maintained in MEM supplemented with 10% FBS and penicillin/streptomycin. Reagents for cell culture were purchased from Gibco Life Technologies. The virus strains A/Texas/36/1991 H1N1 (Texas/91), A/Brisbane/59/2007 H1N1 (Bris/59) and A/Brisbane/10/2007 H3N2 (Bris/10) were grown in 10-day-old embryonated eggs. The A/California/04/2009 (Cal/09) and A/Netherlands/602/2009 (Neth/09) isolates and all recombinant virus stocks were grown in MDCK cells.

6.5.1.3 Generation of Recombinant Viruses 6.5.1.3.1 A/Netherlands/602/2009 Isolate Rescue Plasmids Sequence analysis showed that segments encoding the PB2, PB1, M and NS proteins were identical between the A/California/04/2009 and A/Netherlands/602/2009 isolates. Thus, plasmids pDZ-PB1, -PB2, -M and -NS of strain A/California/04/2009 described previously (Hai et al., 2010, *Journal of Virology* 84: 4442-4450; Quinlivan et al., 2005, *Journal of Virology* 79, 8431-8439) were used. The remaining segments were cloned by isolating viral RNA from supernatants obtained from MDCK cells infected with the A/Netherlands/602/2009 virus isolate using the QIAamp viral RNA mini kit (Qiagen, Hilden, Germany) and used segment-specific primers containing the SapI restriction sites to clone NP, HA and NA into the pPolI plasmid as previously described (Quinlivan et al., 2005, *Journal of Virology* 79, 8431-8439). For PA, site-directed mutagenesis was performed using the A/California/04/2009 pPolI-PA plasmid as template and mutated 3 nt to obtain the WT Neth/09 PA gene. Next, segments PA and NP were subcloned from vector pPolI into the bidirectional vector pDZ using SapI restriction sites. Constructs encoding the glycosylation mutants were generated by site-directed mutagenesis of the WT Neth/09 pPol-HA using the Quick Change Site-Directed Mutagenesis Kit (Stratagene, La Jolla, Calif.). The amino acid changes made in each case to add glycosylation sites were as follows: K71N and N73S for site 71, D144T for site 142, D144N and N146T for site 144, G172S for site 172, and K177N for site 177.

6.5.1.3.2 Rescue of WT a/Netherlands/602/2009 and Respective Glycosylation Mutant Viruses The Neth/09 based recombinant influenza A viruses were generated by transfecting 293T cells with 0.5 μg of each of ten plasmids utilizing Lipofectamine 2000 (Invitrogen, Carlsbad, Calif.) according to the manufacturer's instructions. The plasmid mixture contained the six pDZ vectors encoding the PB2, PB1, PA, NP, M and NS genes and two pPolI vectors encoding the HA and NA genes. The A/WSN/33 expression plasmids pCAGGS-HA and pCAGGS-NA were included to enhance rescue efficiency. At 16-20 hr post-transfection, MDCK cells were added onto the 293T cells and medium was changed to DMEM with penicillin/streptomycin, 0.3% bovine albumin and 1 ug/ml TPCK-treated trypsin (Sigma-Aldrich, St. Louis, Mo.). Supernatants were harvested 24-36 hr post addition of the MDCK cells. The rescued viruses were plaque purified and re-grown in MDCK cells for 48 hrs to make passage 1 stocks, which were used for all experiments shown. Titers of virus stocks were determined in triplicate by plaque assay on MDCK cells. The correct sequences of each recombinant virus were confirmed by sequencing the entire genome.

6.5.1.3.3 Generation and Rescue of A/PR8/34 7:1 Tx/91 HA Glycosylation Deletion Viruses Fusion PCR was performed to generate pDZ-HA plasmids containing glycosylation mutants of the Tx/91 HA to delete 1, 2 or 3 glycosylation sites located in the globular head of this contemporary seasonal H1N1 HA. The following amino acid changes were made to delete each glycosylation site to match the residues found in the Neth/09 isolate: N71K and S73N to delete site 71, T144D to delete site 142, and N177K to delete site 177. The reminder 7 genes of A/PR8/34 (PR/34) were cloned into the pDZ plasmid to rescue PR/34 7:1 TX/91 HA wild type and mutant recombinant viruses as described above.

6.5.1.4 Plaque Phenotype and In Vitro Virus Growth Analysis

The plaque size phenotype was evaluated by performing a plaque assay after infecting MDCK cells with ~100 pfu of each recombinant virus as shown. At 48 hr p.i. the cells were fixed with 4% formaldehyde and plaques were visualized by immunostaning with the mouse monoclonal antibody, E10, that recognizes the amino-terminal peptide that is common to the M1 and M2 proteins. Growth curves were performed in differentiated primary human tracheobronchial epithelial (HTBE) cells (Lonza, MD). Approximately $1\times10^5$ HTBE cells were seeded onto collagen-coated 12-mm permeable membrane transwell inserts (0.4 μm) in a 12 well plate (Corning. MA). The cells were grown submerged in BEGM Bronchial Epithelial Cell Growth Medium (Lonza, MD) for 4 days until confluence was achieved and then differentiation was established by removing the media from the apical surface and further culturing the cells for 4 weeks in this air-liquid interface. During this time the media on the basolateral side was replaced every 2 days. Prior to virus infection the cell monolayers were washed thoroughly with PBS to remove the mucus accumulated on the apical side of the cells. Triplicate wells were inoculated with each virus shown at a multiplicity of infection (MOI) of 0.001 pfu/cell. Virus was collected at the indicated time points by adding 100 μl of PBS to each well for 30 mins at 37 C. Viral titers were performed by standard plaque assay using MDCK cells.

6.5.1.5 Western Blot Assays

MDCK cells infected at an MOI of 5 for 12 h with the indicated viruses were lysed in NP-40 lysis buffer (50 nM Tris, 150 nM NaCl, 5 mM EDTA, 30 mM NaF, 40 mM β-glycerophosphate, 10% glycerol and 0.25% NP-40) containing Complete Mini protease inhibitor (Roche, Ind.). Clarified lysates were boiled for 5 min and proteins were separated on a NuPAGE 4-12% Bis-Tris gradient gel (Invitrogen, CA) under non-reducing conditions for the WT and mutant Neth/09 viruses, or under reducing conditions for the Tx/91 WT and the respective glycosylation deletion mutant viruses. Western blots were performed to detect proteins transferred to PVDF membranes, by incubation with the rabbit polyclonal antibody 3951 raised against a PR8 virus lacking H1, which had been removed by acid and DTT treatment (Steel et al., 2010, mBio 1).

6.5.1.6 Mouse Experiments 6.5.1.6.1 Infections, Body Weight Loss and Survival

All mouse experiments were carried out in accordance with institutional Animal Care and Use Committee (IACUC) guidelines, and have been approved by the IACUC of Mount Sinai School of Medicine. 7 to 9-week-old C57BL/6 female mice (Jackson Laboratories, ME) were anesthetized by intraperitoneal injection of ketamine-xylaxine and were intranasally infected with the indicated virus at doses of $1\times10^2$, $1\times10^3$, $1\times10^4$, $1\times10^5$, $1\times10^6$ pfu of the virus diluted in 50 μl of PBS. Body weight and survival were monitored daily for 14 days. Mice showing more than 25% of body weight loss were considered to have reached the experimental end point and were humanely euthanized.

6.5.1.6.2 Lung Viral Titers

Lungs of infected mice were excised aseptically on the indicated days post-infection and were stored at −80° C. until further possessing. For titrations the tissues were homogenized in 1 ml of PBS using a mechanical homogenizer (MP Biochemicals, OH). The viral titers in the clarified supernatant homogenates were quantified by standard plaque assay on MDCK cells.

6.5.1.6.3 Neth/09 Challenge 8-week old mice were infected with the indicated rTx/91 viruses. Mice were allowed seroconvert for 27 days at which time they were challenged with a 100 times the 50% lethal dose (LD50%) of A/Netherlands/602/2009. Survival and body weight loss were monitored for 13 days p.i.

6.5.1.7 Ferret Experiments

Animal research was conducted under the guidance of the Centers for Disease Control and Prevention's Institutional Animal Care and Use Committee in an Association for Assessment and Accreditation of Laboratory Animal Care International-accredited animal facility.

6.5.1.7.1 Infections, Body Weight Loss and Nasal Wash Titers

Male Fitch ferrets, 8 to 12 months of age (Triple F Farms, PA) that were serologically negative by hemagglutination inhibition for currently circulating seasonal H3N2, the previously circulating seasonal H1N1 and the pandemic 2009 H1N1 influenza A viruses, were used to assess the virulence of the indicated viruses. Three ferrets per group were anesthetized with an intramuscular injection of a ketamine hydrochloride (24 mg/kg)-xylazine (2 mg/kg)-atropine (0.05 mg/kg) cocktail and were infected intranasally with either the WT Neth/09 HA or the HA 144-172 glycosylation mutant virus at $10^6$ pfu in a final volume of 500 µl of PBS. Body weights were measured daily for 12 days and are represented as a percentage weight as compared to the initial weight. The nasal cavities of the ferrets were washed with 1 ml of PBS every other day from days 1 through 7. The viral titers on the nasal washes were determined by standard plaque assay on MDCK cells.

6.5.1.7.2 Tissue Viral Titers

Three ferrets per indicated group were infected with $10^6$ pfu of each virus as described above. On day 3 p.i. the ferrets were euthanized and the lungs, trachea, nasal turbinates and olfactory bulb were aseptically collected. The tissue specimens were immediately frozen on dry ice and stored at −70° C. until they were processed. Frozen tissue specimens were thawed, weighed, and then homogenized in cold PBS using disposable sterile tissue grinders (Kendall, Mass.). Tissue homogenates were clarified and virus titers in the clear supernatants were determined by standard plaque assay on MDCK cells.

6.5.1.8 Human Specimens

The studies involving the use of human sera specimens were reviewed and approved by the Institutional Review Boards of both, the Saint Louis University School of Medicine and of Mount Sinai School of Medicine. Pre- and post-vaccination sera samples obtained from subjects who were 18 years of age or older (adults) and from individuals ages 1 to 17 (pediatric), that were enrolled in clinical trials were used to test the safety and immunogenicity of an inactivated 2009 H1N1 influenza vaccine strain performed at the National Institute of Allergy and Infectious Disease Vaccine and Treatment Evaluation Unit at Saint Louis University. The experiments conducted to assess the reactivity of these human sera against seasonal H3N2, H1N1, 2009 H1N1 and the glycosylation mutant HAs were performed blinded.

6.5.1.9 Hemagglutination Inhibition (HAI) Assay of Mouse and Human Sera

Mouse sera were obtained from animals infected with the indicated viruses on day 28p.i. Experiments performed with mice sera were performed with sera pooled from 3 infected animals per virus that were selected to contain at least 160 HI units against the homologous virus. The HAI assays were conducted essentially as previously described (Manicassamy et al., 2010, *PLoS Pathog* 6, e1000745; Medina et al., 2010, *Nat Commun* 1, doi: 10.1038). Briefly, trypsin-heat-periodate treatment was used to inactivate the mouse, ferret and human sera by mixing half a volume of trypsin 8 mg/ml (Sigma-Aldrich) in 0.1 M phosphate buffer, pH 8.2, with one volume of sera and the samples were incubated tier 30 min at 56° C. The samples were cooled to RT, mixed with three volumes of 0.11 M metapotassium periodate and further incubated at RT for 15 min. The samples were then mixed with three volumes of 1% glycerol saline and incubated for 15 min at RT. The samples were finally mixed and incubated with 2.5 volumes of 85% saline to dilute the samples to a concentration of 1:10. HAI assays of sera were performed following standard protocols (Yu et al., 2008, *Nature* 455, 532-536). Briefly, two-fold serial dilutions of mouse or human sera were mixed and pre-incubated in 96-well plates with 8 HA units of virus per well for 30 min at 4° C. Turkey (for Bris/10 and Neth/09) or Chicken (for Bris/59) red blood cells were added at a final concentration of 0.25%, and the plate was incubated at 4° C. for 30 min. HAI titers were determined as the highest dilution that displayed haemagglutinating activity.

6.5.1.10 Statistical Analysis

For mice studies, statistical significant differences ($P<0.05$) in body weight loss were assessed using a two-tailed unpaired Student's t-test, and for establishing statistical differences for survival curves we utilized the log-rank test. For the ferret experiments statistical significance ($P<0.05$) of the weight loss over time was performed by analysis of the area under the curve (AUC), interpreted as the total weight loss of the animal group (n=3) as a function of time, using the Wilcoxon-matched pairs test.

6.5.2 Introduction

Influenza A virus infections remain a major concern causing a great burden to public health (Molinari et al., 2007, *Vaccine* 25, 5086-5096). The emergence of the 2009 pandemic H1N1 (pH1N1) virus provided the first direct evidence that previously circulating subtypes, given enough time, can cause a novel pandemic due to the great proportion of the human population being naïve to the hemagglutinin (HA) of this new strain (Medina & Garcia-Sastre, 2011, *Nature Reviews* 9, 590-603). Thus, the level and quality of cross-protective HA antibodies play an important role in determining the pandemic potential of a novel influenza A virus strain.

It was previously demonstrated that the HA of the 2009 pH1N1 strain shares antigenic similarities to the HA of human H1N1 viruses that circulated prior to 1950, including great homology to the 1918 virus (Kash et al., 2010, *Influenza and other respiratory viruses* 4, 121-127; Manicassamy et al., 2010, PLoS Pathog 6, e1000745; Skountzou et al., 2010), specifically around antigenic site Sa (Krause et al., 2010, J Virol 84, 3127-3130; Manicassamy et al., 2010, PLoS Pathog 6, e1000745; Xu et al., 2010). In contrast, vaccination (Manicassamy et al., 2010, PLoS Pathog 6, e1000745) or infection (Kash et al., 2010, Influenza and other respiratory viruses 4, 121-127) with contemporary seasonal H1N1 strains induced little or no cross-reactivity to the 2009 pH1N1 virus, which correlates with a greater difference at the amino acid level seen at or near to the known antigenic sites that are located in the globular head of the HA (Manicassamy et al., 2010, PLoS Pathog 6, e1000745).

Previous seasonal H1N1 and H3N2 influenza viruses circulating in humans have been shown to undergo antigenic drift (a gradual accumulation of amino acid changes in or around the HA antigenic sites overtime) due to immune selection pressure. Some of these residue changes result in the acquisition of glycosylation sites in the HA, some of which are maintained, while others are replaced or disappear overtime, suggesting that HA glycosylation plays an important evolutionary role in human influenza A viruses (Das et al., 2010, *PLoS Pathog* 6, e1001211; Igarashi et al., 2008, Virology 376, 323-329; Sun et al., 2011, *PloS one* 6, e22844). Recent studies have shown that HA glycosylation affect the antigenic and receptor binding properties of this viral protein (Wang et al., 2009, *Proc Natl Acad Sci USA* 106, 18137-18142), as well as the virulence of influenza viruses (Tate et al., 2011a, *J Immunol* 187, 1884-1894; Tate et al., 2011b, *Virology* 413, 84-92). Of interest, a number of glycosylation sites on the globular head of the HA have been temporally acquired from 1918 to 2009 by the seasonal H1N1 viruses and most of these are located within or near antigenic site Sa (Das et al., 2010, (Das et al., 2010, *PLoS Pathog* 6, e1001211; Igarashi et al., 2008, *Virology* 376, 323-329; Sun et al., 2011, PloS one 6, e22844). In contrast, the 2009 pH1N1 virus lacks these additional glycosylations and shares the same glycosylation status as the 1918 H1N1 pandemic virus.

The specific role that each of the H1 glycosylation sites has in the virulence and antigenic properties of the 2009 pH1N1 has not been addressed.

The 2009 pH1N1 strain has spread globally since its original outbreak in North America, and it is now circulating seasonally in the Northern and Southern hemispheres, replacing the previous H1N1 viruses. It is then likely that the pH1N1 virus will start undergoing antigenic drift driven by immune selection pressure. Acquisition of glycosylations might contribute to the emergence of H1N1 drift variants. In this example, the specific effects of the acquisition of glycosylations in the globular head of the H1N1 HA on virulence and antigenic properties of H1N1 viruses was investigated. The results indicate that HA glycosylation play a crucial role in both pathogenesis and in escape from pre-existing immunity, as well as in induction of cross-reactive polyclonal antibody responses.

Figures 22B, 22C:
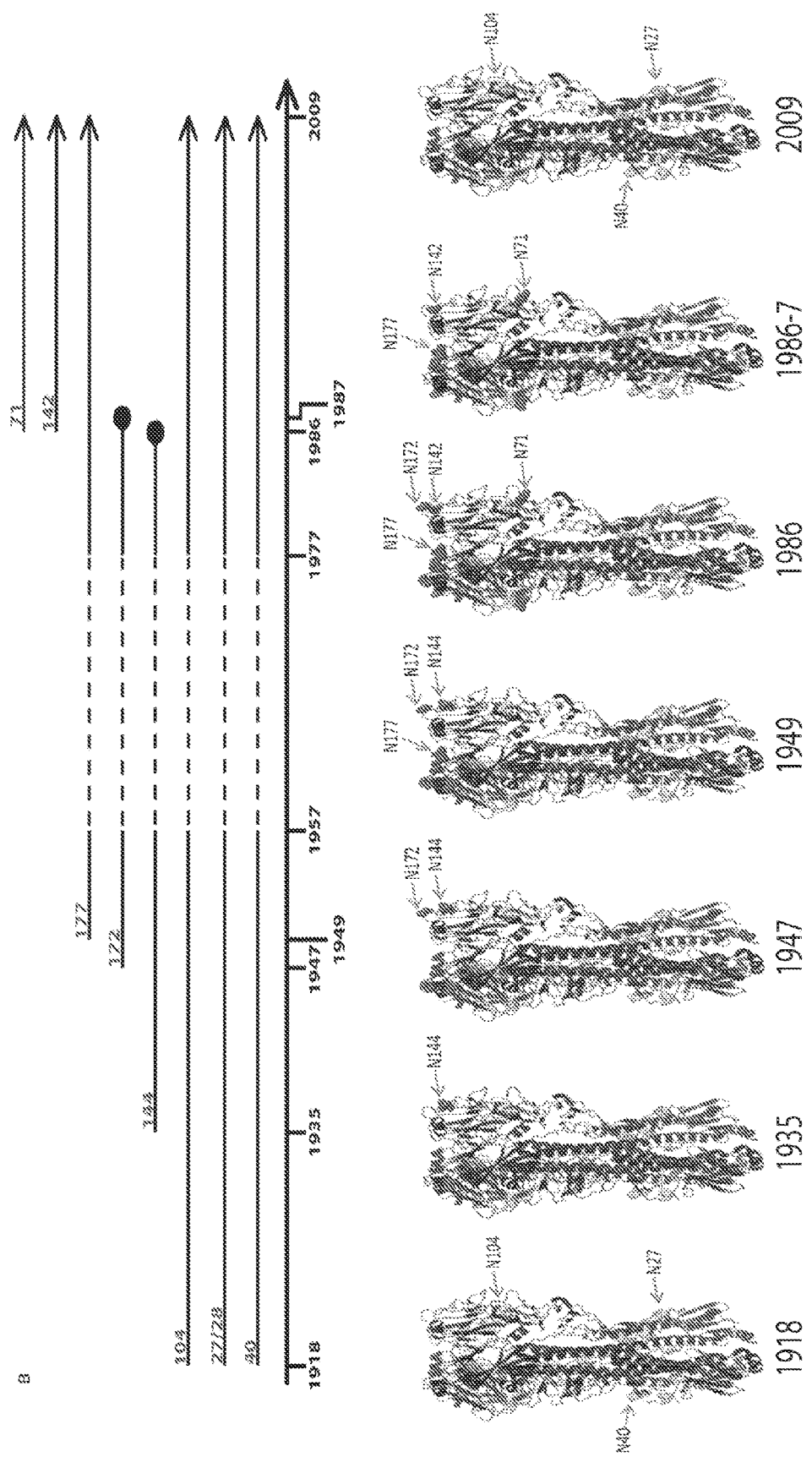

6.5.3 Results 6.5.3.1 H1N1 Human Viruses Acquired Glycosylation Sites in the Globular Head of the HA Protein Overtime An overall analysis of the amino acid sequence of the 1918 and the 2009 H1N1 pandemic viruses revealed that the HA1 of these viruses are glycosylated at the same sites. To better understand the differences that might be responsible for the distinct antigenic properties of the 2009 H1N1 HA protein as compared to the seasonal H1N1 virus strains circulating just prior to the pandemic, particular attention was focused on the amino acid sequences around the known antigenic sites. Sequence alignments revealed that since the introduction in 1918 of the H1N1 viruses into humans, a number of glycosylation sites as predicted by the motif N-X-S/T, have been acquired in the HA globular head overtime (FIGS. 22A and 22B). Of interest, these glycosylation sites appeared predominantly near or within antigenic site Sa (FIG. 22A). Although there are no sequences available of human influenza viruses between 1918 and 1933, and with the caveat that most of the sequences from early H1N1 viruses are from strains that have been passaged extensively in eggs, it appeared that during the years 1935 to 1957, three different HA glycosylations were acquired sequentially (on amino acid residues 144, 172 and 177 [H3 numbering 130, 158 and 163, respectively]) and were consistently found in human isolates. The emergence of the H2N2 pandemic influenza virus in 1957 displaced the H1N1 viruses, which disappeared from human circulation. The H1N1 virus strain re-emerged in humans in 1977 and contained the same glycosylation sites as the H1N1 viruses circulating in the 1950s. In 1986, glycosylation site 144 was replaced by a glycosylation on position 142 (H3 numbering: 128; these glycosylation sites are incompatible), and an additional glycosylation on site 71 (H3 numbering: 59) was acquired almost simultaneously. However, in 1987 glycosylation site 172 was lost, and since then the contemporary H1N1 viruses, including seasonal viruses circulating just prior to the emergence of 2009 pH1N1, contained glycosylation sites 71, 142 and 177 in the globular head of HA (FIGS. 22B and 22C). Since, the glycosylation status of the 2009 pH1N1 is the same as that of the 1918 H1N1 pandemic virus, the 2009 pH1N1 virus might acquire the same or similar glycosylations overtime as a result of immune selection pressure (Wei et al., 2010, *Sci Transl Med* 2, 24ra21). The specific effect of additional glycosylations on virulence and antigenic properties of the 2009 pH1N1 virus was then assessed.

Figures 24A, 24B, 24C:
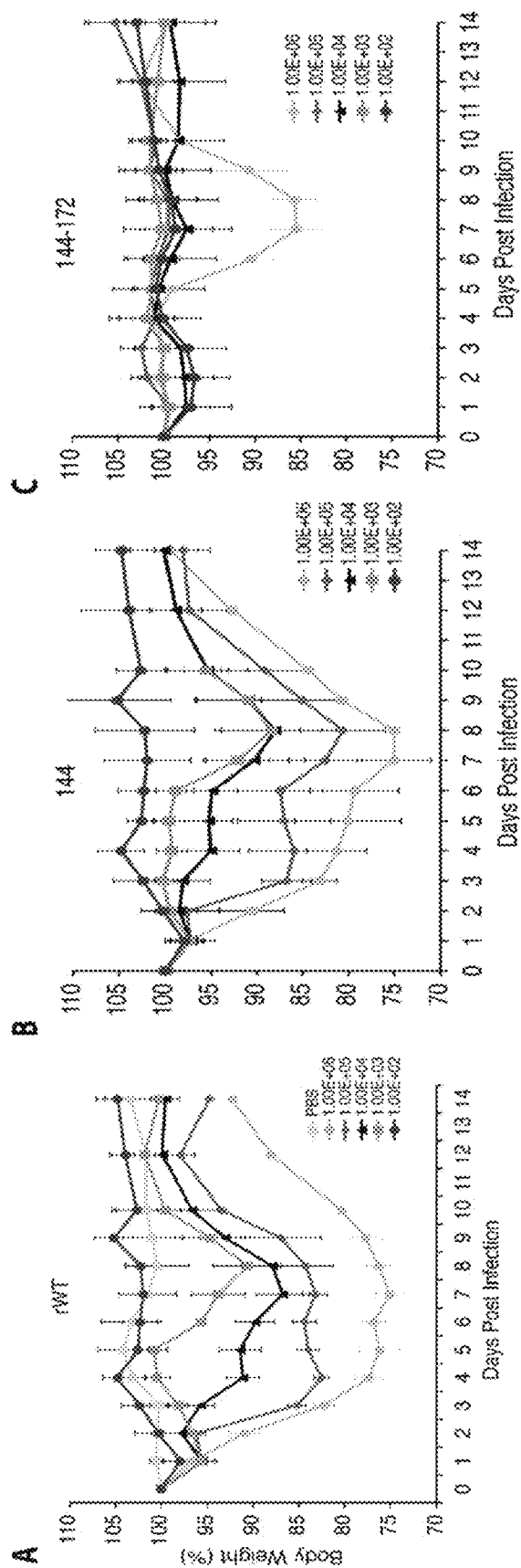
Figures 24D, 24E, 24F:
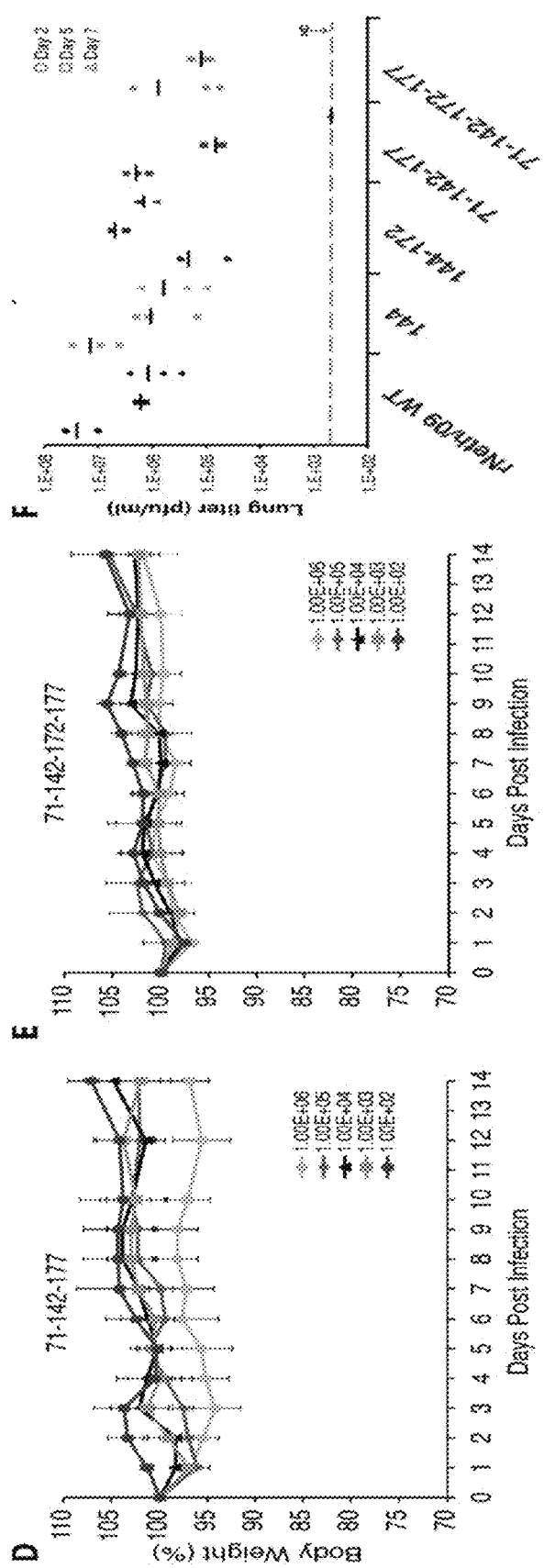
Figures 24G, 24H, 24I:
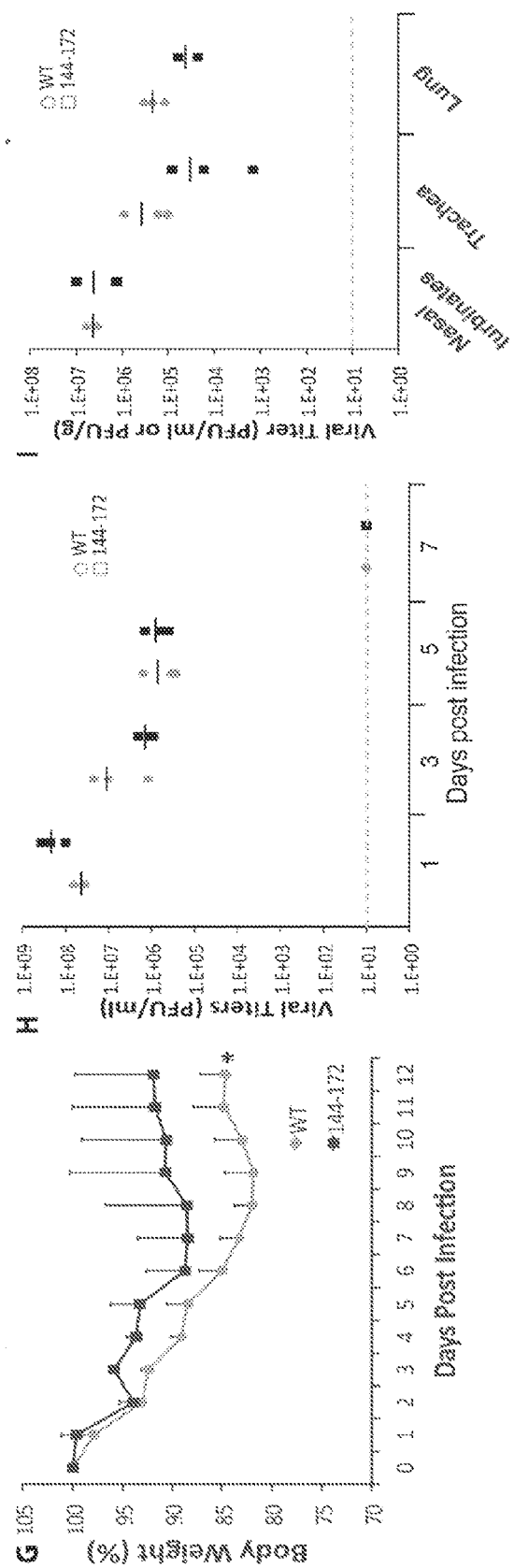

6.5.3.2 Additional Glycosylations in the Globular Head of the HA Attenuate the pH1N1 Virus In Vivo but not In Vitro 2009 pH1N1 (Neth/09 strain) recombinant viruses were generated, differing only by the sequential addition of HA glycosylations to mimic the temporal appearance of these sites in the seasonal H1N1s. Despite several attempts, rescue of a virus containing the HA glycosylation sites 144, 172 and 177 in the Neth/09 background was not possible, suggesting that the combination of these specific glycosylations might require additional compensatory mutations. Nevertheless, all other mutant viruses were successfully rescued. In vitro phenotypic analysis of these recombinant viruses showed that only the virus containing 4 additional glycosylations (Neth/09 HA 71-142-172-177) had a smaller plaque phenotype in MDKCs (FIG. 23A.). Addition of HA glycosylation sites resulted in slower mobility of the HA in SDS-PAGE, consistent with the use of these sites (FIG. 23B.). Growth kinetics were performed to evaluate the effects of glycosylations on the virus' ability to replicate in primary differentiated human tracheobroncheal epithelial cells (HTBE). All viruses replicated at high levels ($>10^7$ pfu/ml), similar to those of the original WT Neth/09 isolate virus (FIG. 23C.), indicating that these additional glycosylations did not affect infection of human cells. The pathogenic potential of the recombinant glycosylated viruses was next evaluated in C57BL/6 mice. From this example, a glycosylation dependent attenuation in the virulence of the viruses in mice (i.e. the more glycosylation sites in the HA the less pathogenic), as assessed by body weight loss (FIG. 24A-E) was found. Only the virus containing glycosylation site 144 showed weight loss patterns similar to those seen in mice infected with WT Neth/09 virus (FIG. 24B). All viruses with two or more extra glycosylation sites were severely attenuated (FIGS. 24C-E). Morbidity correlated with lung viral titers in mice during the initial 7 days of infection. Animals infected with the 144-172, 71-142-177 and 71-142-172-177 had significantly lower titers as compared to WT Neth/09. To determine if this is also the case in a different animal model, the virulence of the 144-172 glycosylated virus as compared to the WT virus in ferrets, which is widely accepted as one of the best animal models to study pathogenesis of influenza viruses, was assessed. There was a statistically significant decrease in the overall weight loss seen in the animals infected with the 144-172 virus (FIG. 24G). Interestingly, the nasal wash titers obtained from both groups through day 7, and titers of the nasal turbinates on day 3 showed no differences (FIGS. 24H and I). However, the trachea and the lungs of ferrets at day 3 showed a decreased infection in the 144-172 virus as compared to WT Neth/09 (FIG. 24I). This suggests that while glycosylated H1N1 viruses can replicate to similar levels in the upper respiratory track (in the nose), they are less able to infect and replicate in the lower respiratory track (trachea and lungs).

6.5.3.3 HA Glycosylation Site 144 Evades the Polyclonal Antibody Response Against WT HA while Inducing a Broader Polyclonal Response in Mice To gain insight into the effects of glycosylation on the antigenic properties of the H1N1 viruses, the HAI activity of sera obtained from mice infected with each of the glycosylation mutant viruses against each other (Table 9, infra) was tested. Infection of mice with rWT virus or the 71-142-177 or 71-142-172-177 glycosylated viruses resulted in low or no detectable sera HAI to the glycosylated viruses 144 and 144-172, while certain level of cross-reactivity remained against the other viruses. Surprisingly, infection with viruses containing the 144 or the 144-172 glycosylations elicited antibody responses capable of cross-reacting to all of the HA glycosylation mutant viruses and the WT Neth/09 virus. Taking all together, this indicates that most of the polyclonal HAI activity induced by the viruses, with the exception of those containing the 144 glycosylation site, is directed against a site, likely Sa, efficiently masked by the 144 glycosylation. By contrast, glycosylation at position 144 changes the pattern of induction of the polyclonal antibody responses, which appear to be against multiple antigenic regions in the HA and is not masked by a single or multiple glycosylation events. In contrast, infection with viruses containing glycosylations at positions 71-142-177 or 71-142-172-177 induced a narrower cross-reactivity pattern, suggesting that the polyclonal humoral response is slightly changed but remains focused, possibly around site Sa.

TABLE 9

HAI titers of mice sera after infection with 2009 pH1N1 glycosylations mutants

| | | | | Virus[b,c] | | |
|---|---|---|---|---|---|---|
| Sera | | | | | 71-142- | 71-142- |
| Species | Infection[a] | rWT | 144 | 144-172 | 177 | 172-177 |
| Mice | rWT HA | 320 | 10 | 20 | 80 | 160 |
| | | | 16 | | | |
| | 144 HA | 320 | 0 | 80 | 160 | 160 |
| | 144-172 HA | 160 | 80 | 160 | 160 | 320 |
| | | | <1 | | | |
| | 71-142-177 HA | 40 | 0 | <10 | 160 | 160 |
| | 71-142-172-177 HA | <1 20 | 0 | 40 | 160 | 160 |

[a]Mice were infected with the Neth/99 recombinant virus containing the indicated HA segment.
[b]HAI titers represent the highest dilution that displayed hemagglutination inhibitory activity.
[c]Homologous titers are in bold.

6.5.3.4 HA Glycosylation Site 144 Evades the Polyclonal Antibody Response Against pH1N1 Inactivated Vaccine in Humans The ability of 2009 pH1N1 inactivated vaccine to elicit antibody responses in humans with inhibitory activity against 2009 H1N1 viruses bearing glycosylated Has was next tested. It was found that most adult individuals that received the 2009 pH1N1 monovalent vaccine had detectable antibody responses to all the glycosylation mutant viruses (Table 10, infra) Nonetheless, the lowest cross-reactivity was seen with viruses containing the 144 (and the 144-172) glycosylation sites, with one individual showing undetectable HAI activity levels when tested against these two viruses. This is in close agreement with the mouse serology results, emphasizing the masking effects of glycosylation at site 144. As expected, the trivalent seasonal vaccine of 2009 containing a previously circulating seasonal H1N1 virus, did not induce significant HAI titers against pH1N1 viruses, independently of their level of glycosylation (Table 10, infra). Since the level of previous exposure to influenza virus in humans could impact their polyclonal antibody responses, an assessment was also made of the sera HAI titers in a more naïve population (children <18 years of age) that were immunized with the monovalent p2009 H1N1 inactivated vaccine. The sera activity of these individuals had similar cross-reactivity pattern to the ones of adults, showing lower HAI activity against the 144 and the 144-172 glycosylation mutant viruses (Table 11, infra). By contrast, some of the pediatric and adult sera showed a considerable activity against the 71-142-177 and 71-142-172-177 glycosylated viruses (Tables 10 and 11, infra)

TABLE 10

HAI titers of adult human sera after vaccination with 2009 pH1N1 inactivated vaccine.

| | | Virus[a] | | | | | | | Vaccine | |
|---|---|---|---|---|---|---|---|---|---|---|
| Sera | | rWT | 144 | 144-172 | 71-142-177 | 71-142-172-177 | Bris/59 | Bris/10 | Age | 2009 H1N1 | 2009 TIV[d] |
| 1 | Pre | 20 | <10 | <10 | 20 | 20 | <10 | <10 | 19[b] | Yes | Yes |
| | Post | 160 | 40 | 20 | 160 | 160 | 80 | 320 | | | |
| 2 | Pre | 10 | 10 | <10 | 20 | 20 | 80 | 80 | 21[b] | Yes | Yes |
| | Post | 640 | 320 | 160 | 1280 | 1280 | 80 | 160 | | | |
| 3 | Pre | <10 | <10 | <10 | <10 | <10 | 20 | 10 | 33[b] | Yes | No |
| | Post | 80 | 20 | 40 | 20 | 80 | 20 | 20 | | | |
| 4 | Pre | <10 | <10 | <10 | <10 | <10 | <10 | <10 | 34[b] | Yes | Yes |
| | Post | 2560 | 1280 | 1280 | 80 | 640 | 20 | 10 | | | |
| 5 | Pre | 10 | 10 | 10 | 20 | 10 | <10 | 40 | 34[b] | Yes | Yes |
| | Post | 160 | <10 | <10 | 320 | 640 | 160 | 1280 | | | |
| 6 | Pre | 20 | 10 | 10 | 20 | 20 | 10 | 20 | 42[b] | Yes | Yes |
| | Post | 640 | 320 | 160 | 320 | 640 | 20 | 40 | | | |
| 7 | Pre | 10 | 10 | 10 | <10 | 10 | 10 | 80 | 43[b] | Yes | Yes |
| | Post | 640 | 320 | 160 | 640 | 640 | 20 | 40 | | | |

TABLE 10-continued

HAI titers of adult human sera after vaccination with 2009 pH1N1 inactivated vaccine.

| | | | | Virus[a] | | | | | Vaccine | |
|---|---|---|---|---|---|---|---|---|---|---|
| Sera | rWT | 144 | 144-172 | 71-142-177 | 71-142-172-177 | Bris/59 | Bris/10 | Age | 2009 H1N1 | 2009 TIV[d] |
| 8 Pre | <10 | <10 | <10 | <10 | <10 | <10 | <10 | 49[b] | Yes | Yes |
| Post | 40 | 20 | 20 | 40 | 160 | 10 | 20 | | | |
| 9 Pre | <10 | <10 | <10 | <10 | <10 | <10 | <10 | 55[b] | Yes | Yes |
| Post | 640 | 320 | 640 | 320 | 640 | 80 | <10 | | | |
| 10 Pre | 20 | 10 | 20 | 20 | 20 | <10 | <10 | 60[c] | Yes | Yes |
| Post | 1280 | 320 | 320 | 320 | 160 | <10 | 10 | | | |
| 11 Pre | 10 | <10 | <10 | 20 | 10 | 20 | 40 | 67[c] | Yes | Yes |
| Post | 1280 | 640 | 320 | 640 | 320 | 40 | 80 | | | |
| 12 Pre | 20 | <10 | 20 | 20 | 20 | 10 | 40 | 67[c] | Yes | Yes |
| Post | 640 | 40 | 320 | 640 | 2560 | 10 | 320 | | | |
| 13 Pre | 40 | 40 | 40 | 40 | 40 | 10 | 40 | 82[c] | Yes | Yes |
| Post | 2560 | 2560 | 160 | 1280 | 160 | 20 | 160 | | | |
| 14 Pre | <10 | <10 | <10 | <10 | <10 | 40 | <10 | 51[c] | No | Yes |
| Post | <10 | <10 | <10 | <10 | <10 | 20 | 40 | | | |
| 15 Pre | <10 | <10 | <10 | <10 | <10 | <10 | 20 | 74[c] | No | Yes |
| Post | 10 | <10 | 10 | <10 | 10 | 320 | 80 | | | |

[a]Bold boxes indicate the lowest cross-reactive titer for each individual.
[b]Human serum samples obtained on days 0 (Pre) and 21 (Post) after vaccination, respectively.
[c]Human serum samples obtained on days 0 (Pre) and 63 (Post) after vaccination, respectively.
[d]2009 TIV: trivalent inactivated influenza virus vaccine which included trains A/Brisbane/57/2007 (H1N1), A/Brisbane/10/2007 (H3N2) and B/Brisbane/60/2008.

TABLE 11

HAI titers of pediatric human sera after vaccination with 2009 pH1N1 inactivated vaccine.

| | | | Virus[b] | | | | | | Vaccine | |
|---|---|---|---|---|---|---|---|---|---|---|
| Sera[a] | rWT | 144 | 144-172 | 71-142-177 | 71-142-172-177 | Bris/59 | Bris/10 | Age | 2009 H1N1 | 2009 TIV |
| 1 Pre | <10 | <10 | <10 | <10 | <10 | 20 | 20 | 1 | Yes[c] | No |
| Post | 20 | 10 | 10 | 20 | 40 | 20 | 20 | | | |
| 2 Pre | <10 | <10 | <10 | <10 | <10 | 80 | <10 | 8 | Yes[c] | No |
| Post | <10 | <10 | <10 | 10 | 10 | 80 | <10 | | | |
| 3 Pre | 10 | 10 | 10 | 10 | 10 | 10 | <10 | 12 | Yes[c] | No |
| Post | 80 | 80 | 40 | 160 | 160 | 10 | 10 | | | |
| 4 Pre | <10 | <10 | <10 | <10 | <10 | <10 | 10 | 13 | Yes[c] | No |
| Post | 80 | 40 | 40 | 160 | 320 | 10 | 10 | | | |
| 5 Pre | <10 | <10 | <10 | <10 | <10 | 80 | 10 | 14 | Yes[c] | No |
| Post | 10 | <10 | <10 | 10 | 20 | 80 | 10 | | | |
| 6 Pre | <10 | <10 | <10 | 10 | 20 | <10 | 10 | 14 | Yes[d] | Yes[d] |
| Post | 160 | 160 | 80 | 640 | 640 | 40 | 40 | | | |
| 7 Pre | <10 | <10 | <10 | <10 | <10 | 160 | 20 | | Yes[c] | No |
| Post | 10 | <10 | <10 | 20 | 10 | 160 | 20 | 16 | | |
| 8 Pre | <10 | <10 | <10 | <10 | <10 | 10 | 10 | 16 | Yes[d] | Yes[d] |
| Post | 20 | 10 | <10 | 20 | 40 | 80 | 80 | | | |
| 9 Pre | <10 | <10 | <10 | 20 | 20 | 10 | <10 | 17 | Yes[c] | No |
| Post | 40 | 10 | 10 | 160 | 160 | 20 | <10 | | | |
| 10 Pre | <10 | <10 | <10 | <10 | <10 | 20 | <10 | 17 | Yes[d] | Yes[d] |
| Post | 160 | 40 | 40 | 640 | 640 | 20 | <10 | | | |

[a]Human serum samples obtained on days 0 (Pre) and 42 (Post) after vaccination, respectively.
[b]Bold boxes highlight the lowest cross-reactive titer for each individual.
[c]2009 H1N1 inactivated vaccine was administered on day 0 and day 21.
[d]2009 TIV: trivalent inactivated influenza virus vaccine which included trains A/Brisbane/57/2007 (H1N1), A/Brisbane/10/2007 (H3N2) and B/Brisbane/60/2008, was given on day 0 and the 2009 H1N1 vaccine was given on day 21.

Figures 25A, 25B:
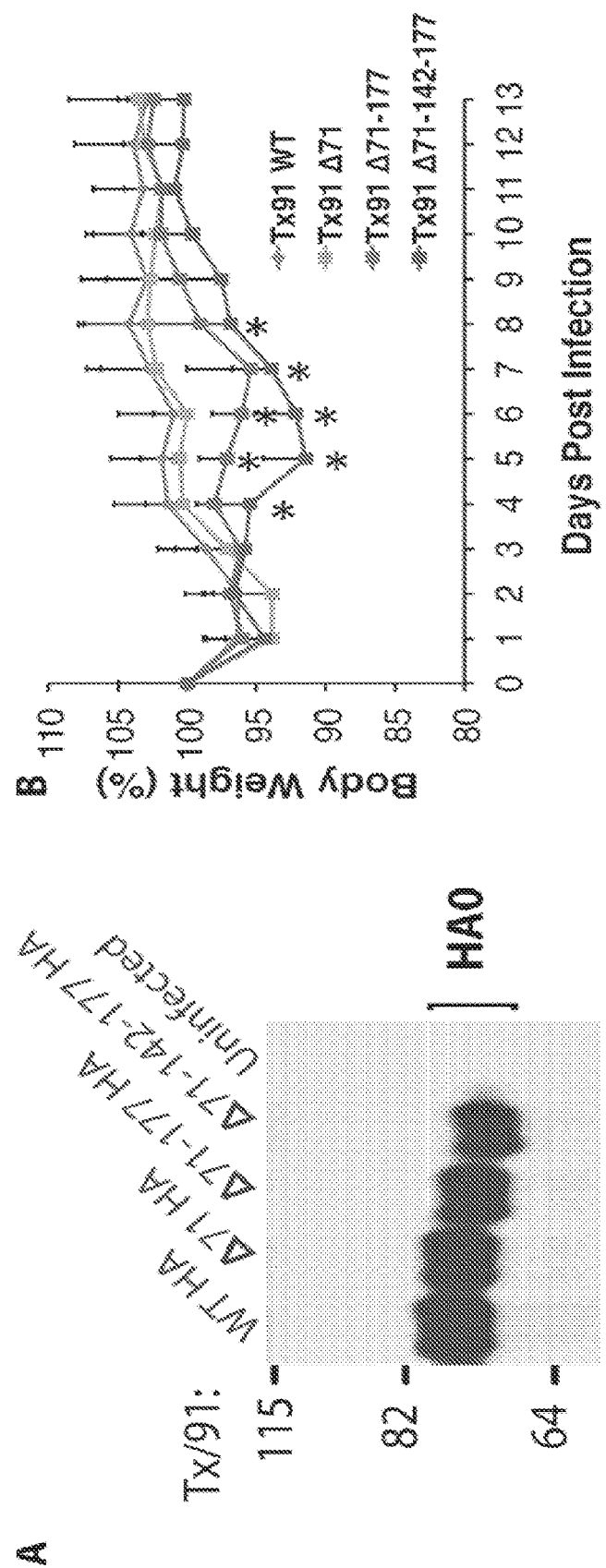
Figures 25C, 25D:
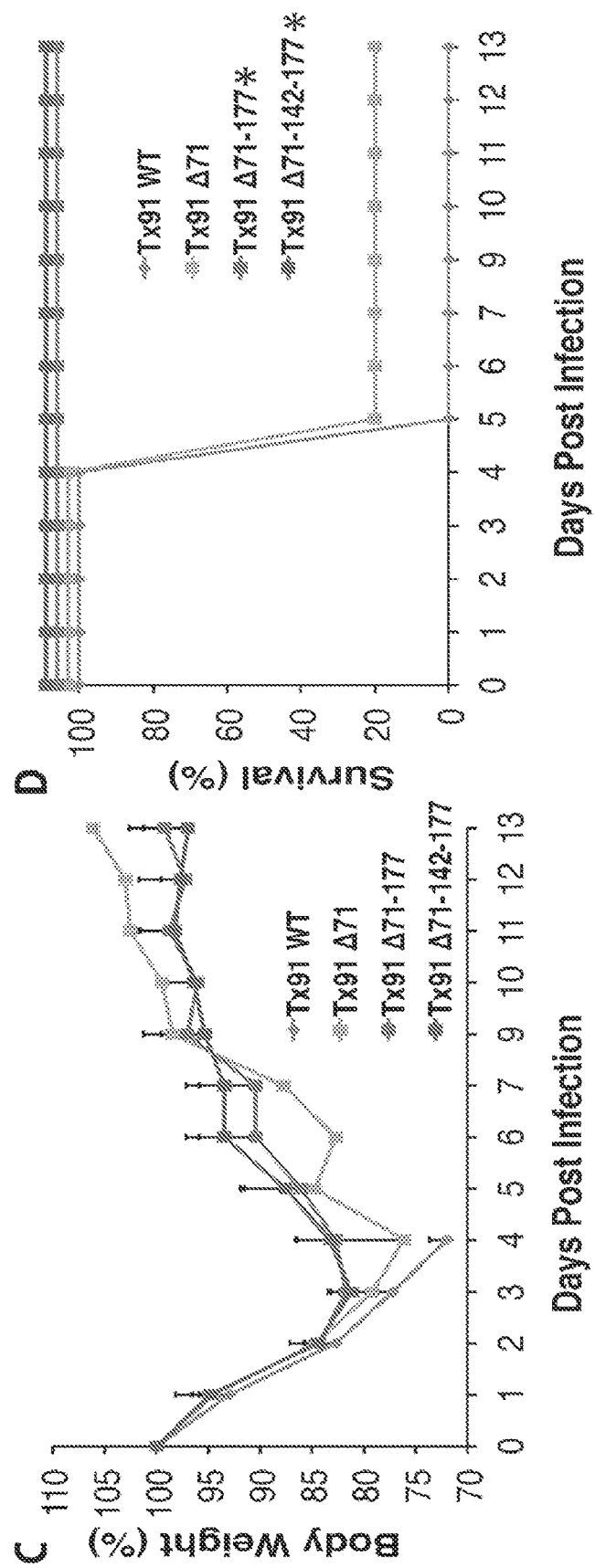

6.5.3.5 Glycosylation Deletions in a Recent Seasonal H1N1 Virus Increase its in Vivo Virulence and Elicit Cross-Protection Against pH1N1 2009 Virus Challenge To further elucidate the role of HA glycosylations in the pathogenic and antigenic properties of H1N1 viruses, a set of glycosylation deletion viruses was generated, based on the contemporary Tx/91 seasonal strain that contains three extra glycosylation sites in its HA, on sites 71, 142 and 177. Elimination of HA glycosylation sites resulted in faster HA mobility in SDS-PAGE, as expected (FIG. 25A). Infection with a sublethal dose of WT Tx/91 virus (at $1 \times 10^3$ pfu) did not result in morbidity in mice, however; infection with viruses containing deletions of 2 or 3 glycosylations (Δ71-177 and Δ71-142-177) resulted in a significant level of weight loss as compared to the rWT virus (FIG. 25B). The highest morbidity was observed in the Δ71-142-177 virus, a virus that resembles the 2009 pH1N1 in that it has no glycosylation sites in the globular head of HA. This again confirmed that glycosylation of HA negatively affect the in vivo pathogenic potential of H1N1 viruses. To investigate if infection with these glycosylation deletion viruses could elicit cross-protective humoral responses to the antigenically highly diverse WT 2009 H1N1 virus, these animals were challenged on day 27 p.i. with 100 times the 50% lethal dose (LD50) of WT Neth/09 virus. The mice previously infected with rWT Tx/91 all succumbed to the Neth/09 challenge, and the mice infected with the virus containing a single deleted glycosylation on site 71 (Δ71) showed substantial weight loss and only a 20% survival rate (FIGS. 25C and D). In contrast, although the animals infected with viruses with glycosylation deletions on sites 71-177 (Δ71-177) and 71-142-177 (Δ71-142-177) showed a substantial loss in body weight (up to ~20%) they all survived the lethal challenge with Neth/09 (FIG. 25D) with animals infected with Δ71-142-177 showing an overall lower morbidity level (FIG. 25C). These data show that HA glycosylations play an important role in masking antigenic sites and in eliciting protective immune responses against antigenically diverse H1N1 influenza virus strains.

6.5.4 Discussion

In this example, the effect of glycosylations in the HA protein on virulence and antigenic cross-reactivity in the context of the current 2009 pH1N1 strain were evaluated. Utilizing a set of recombinant 2009 pH1N1 viruses engineered to mimic the temporal acquisition of glycosylations in the HA protein as those observed for the seasonal H1N1 viruses in the past, it was demonstrated that glycosylations play an important role in modulating the pathogenesis and the antigenic properties of these viruses.

Initial sequence analysis of the 2009 pH1N1 virus revealed a drastic difference as compared to the seasonal H1N1 viruses (Bris/59-like) that were circulating worldwide at the time of the outbreak (Dawood et al., 2009, *N Engl J Med* 360, 2605-2615; Garten et al., 2009, *Science* 325, 197-201; Smith et al., 2009, *Nature* 459, 1122-1125). Close analysis of the HA protein, and experimental studies from us and others (Kash et al., 2010, *Influenza and other respiratory viruses* 4, 121-127; Manicassamy et al., 2010, *PLoS Pathog* 6, e1000745; Skountzou et al., 2010, *J. Immunol.* 1895(3), 1642-1649), showed that the 2009 pandemic virus was more closely related to older H1N1 viruses that circulated in humans before the 1950s. The HA of the H1N1 seasonal viruses has acquired glycosylation sites during its evolution in humans, likely as a result of immune selection pressure. Of interest, a number of glycosylations have emerged but eventually disappeared and some have been fixed in time (FIG. 22). This suggests that during viral evolution, some of these glycosylations can be deleterious for the virus, while others might provide fitness and/or an immune escape advantage for the emergence of drift variants in humans. Because the 2009 pH1N1 and the 1918 H1N1 pandemic viruses have the same glycosylation pattern in HAL there is a possibility that the 2009 pH1N1 strain might undergo a similar evolutionary pattern and might acquire similar glycosylations in the HA with time as observed previously with the seasonal H1N1 (FIG. 22). Therefore, 2009 pH1N1 viruses was engineered with additional glycosylations motifs that occurred naturally in human H1N1 viruses since their emergence in 1918. This also allowed the study of the potential significance of such mutations in the context of protective antibody responses elicited by the 2009 pH1N1 vaccine in humans.

The recombinant Neth/09 viruses containing additional glycosylation sites in the HA were attenuated in mice and ferrets (FIG. 24). Nonetheless, the infection and replication capacity of the glycosylated viruses in MDCK and primary HTBE cells were not significantly affected (FIG. 23). Between the WT and the 144-172 viruses, differences were observed in viral load in the lungs and trachea of the 144-172 infected animals, but not in the nasal turbinates. Infection in these animal models with glycosylated pH1N1 viruses is largely reminiscent of infection with H1N1 seasonal viruses, which do not generally produce disease in mouse models (Bouvier & Lowen, 2010, Viruses 2, 1530-1563; Pica et al., 2011, *Journal of Virology* 85(23), 12825-9) and in ferrets replicate to high titers in the upper respiratory track but not in the lower respiratory track (Maines et al., 2009, *Science* 325, 484-487; Munster et al., 2009, *Science* 325, 481-483). Not only virulence was decreased by adding glycosylation sites in the pH1N1 viruses but also virulence was increased by deleting glycosylations in the context of the Tx/91 H1N1 virus. Therefore acquisition of glycosylations in the HA seems to reduce the virulence of the H1N1 viruses.

Antigenic characterization of the Neth/09 glycosylation mutant viruses suggested that site Sa in the HA is a predominant antigenic region for mice, ferret (data not shown) and humans, since adding 1 or 2 glycosylation on residues around this site (e.g. sites 144 and 144-172) was sufficient to significantly reduce the HAI activity of the polyclonal response elicited by the WT unglycosylated virus. Of these two sites, 144 seems to be the one responsible for this effect, as a dramatic reduction in HAI was not seen in the 71-142-172-177 virus. Immunization of humans with the current inactivated 2009 pH1N1 vaccine strain induced an overall polyclonal antibody immune response reminiscent of the one in pH1N1 immunized mice and ferrets (Table 10, supra), as glycosylation at site 144 was the most efficient in evading HAI reactivity. Similarly, the pediatric post-vaccination sera analyzed show considerable activity against the 71-142-177 and the 71-142-172-177 viruses, but less against 144 and 144-172 viruses. Overall this indicates that glycosylation of human H1N1 viruses greatly affect their antigenic properties. It is also possible that as a consequence of immune mediated antigenic pressure, new changes in HA will evolve and drive the appearance of novel glycosylations sites in the 2009 pH1N1 strain modulating its antigenic properties as it continues to circulate seasonally worldwide. If this is the case, it will be interesting to analyze their impact in virulence and antigenicity.

Importantly, infection with viruses harboring glycosylation sites 144 and 144-172 induced a broader polyclonal response capable of cross-reacting with all the WT and Neth/09 glycosylated viruses generated (Table 9, supra). The increased breath of the polyclonal response is likely due to shielding of the immunodominant site Sa, resulting in a change of the antigenic focus that redirects the humoral response to other epitopes. Remarkably, the cross-protection against the WT Neth/09 virus observed in the mice infected with a sub-lethal dose of the Tx/91 deletion mutants Δ71-177 and Δ71-142-177 emphasize the importance of glycosylations in "distracting" or redirecting the humoral response. These results also point to the crucial evolutionary role of the appearance of glycosylations around site Sa, since deleting glycosylations within or close to this region has a profound effect in cross-reactivity. Altogether, these findings highlight the immune-modulatory effects of specific glycosylations in the antigenic properties of HA, and also the effects of glycosylations on the breath of the immune response to infection and vaccination.

6.6 Example 6

Hemagglutinin Stalk Antibodies Elicited by Infection with the 2009 Pandemic H1N1 Influenza Virus This example describes chimeric influenza virus hemagglutinin polypeptdies that were used to study stem domain specific antibodies. Using these polypeptides, it was determined that infection with the 2009 pandemic H1N1 virus elicited a boost in titer of virus-neutralizing antibodies directed against the hemagglutinin stem. In addition to the chimeric influenza virus hemagglutinin polypeptdies, assays that can be used to measure influenza virus-neutralizing antibodies which are not detected in the traditional hemagglutination-inhibition assay are also described.

6.6.1 Materials and Methods 6.6.1.1 Cells and Plasmids 293T and MDCK cells were obtained from ATCC and were maintained in Dulbeccos's Modified Eagle's medium (DMEM) and Minimal Essential Medium (both from Gibco), respectively, each supplemented with 10% fetal calf serum (HyClone), and 100 units/ml of penicillin-100 µg/ml of streptomycin (Pen/Strep, Gibco). TNM-FH media (Gemini Bioproducts) supplemented with 10% fetal calf serum and Hyclone SFX insect culture media (ThermoScientific) were used for Sf9 and BT1-TN5B1-4 (High Five) cell culture.

Chimeric hemagglutinin (cHA) constructs with the stalk of A/Puerto Rico/8/1934 (PR8) containing the globular head domain from either A/Mallard/Sweden/81/02 (cH6/1) virus or A/Guinea fowl/Hong Kong/WF10/99 (cH9/1) viruses were generated using methods previously described (Hai et al., 2008, *J Virol* 82, 10580; Fodor et al., 1999, *J Virol* 73, 9679). Briefly, different components of the chimeric hemagglutinin (cHA) were amplified by PCR with primers containing Sap I sites, digested with Sap I, and cloned into the Sap I sites of the pDZ plasmid (Quinlivan et al., 2005, *J Virol* 79, 8431). For generation of the baculo-transfer plasmids, cH6/1 and cH9/1 were amplified by PCR, cut with BamHI and NotI, and cloned in frame into a modified pFastBac (Invitrogen) baculo-transfer vector that harbors a C-terminal T4 phage foldon and a 6-his tag (Meier et al., 2004, *J Mol Biol* 344, 1051). The sequences of all plasmids were confirmed by Sanger sequencing.

6.6.1.2 Recombinant Baculovirus Generation, Protein Expression and Purification

In order to generate recombinant cH6/1 and cH9/1 protein, baculo-transfer vectors were transformed into *E. coli* strain DH10Bac (Invitrogen) according to the manufacturer's instructions. DH10Bac colonies showing the right phenotype were picked, grown up and bacmids were prepared using a Plasmid Midi Kit (Qiagen).

Bacmids carrying the cH6/1 or cH9/1 genes were transfected into Sf9 cells with Cellfectin II (Invitrogen) according to the manufacturer's instructions. Recombinant baculovirus was amplified in Sf9 cells grown in TNM-FH medium (Gemini Bioproducts, West Sacramento, Calif.) and titers were determined by plaque assay (King et al., 2007, *Methods Mol Biol* 388, 77).

High Five cells grown in HyClone SFX insect cell media (Thermo Fisher Scientific) were infected with recombinant baculovirus expressing cH6/1 or cH9/1 at a multiplicity of infection (MOI) of 10 and a cell density of $1 \times 10^6$ cells/ml in 500 ml shaker flasks (Krammer et al., 2010, *Mol Biotechnol* 45, 226). Cells were harvested 96 hours post infection and separated from supernatant by low speed centrifugation for 10 minutes at 2000 g and room temperature. For purification of cHA proteins, the supernatant was collected and incubated with Ni-NTA resin (Qiagen) for 2 hours at 4° C. The slurry was loaded onto columns and washed 3× with washing buffer (50 mM Na2HCO3, 300 mM NaCl, 20 mM imidazole, pH 8). Protein was eluted in 0.5 ml steps with elution buffer (50 mM Na2HCO$_3$, 300 mM NaCl, 250 mM imidazole, pH 8), tested for protein content with Bradford reagent and fractions containing protein were pooled. Pooled fractions were buffer exchanged in PBS and concentrated using an Amicon Ultra centrifugal filter unit (Millipore) with a 10 kD molecular weight cut-off in a swinging bucket rotor. Protein purity and identity were tested by SDS-PAGE, Coomassie staining and Western blot. The following antibodies were used to confirm expression of cHA: Anti-H6 goat antiserum (BEI, #NR-663), G1-26 (anti-H9, mouse; BEI# NR-9485), 3951 (rabbit, anti-HA2 PR8) (Graves et al., 1983, *Virology* 126, 106), PY102 (anti-PR8 head, mouse), and 12D1 (anti-H3 stalk, mouse) (Wang et al., 2010, *PLoS Pathog* 6, e1000796). Final protein concentrations were determined with Bradford reagent.

6.6.1.3 Rescue of Recombinant cHA Expressing Viruses

In order to rescue the recombinant virus expressing cH9/1, reverse genetics plasmids that encode vRNA and mRNA of the six wild type viral segments from PR8, as well as plasmids encoding the N3 NA from A/mallard/Alberta/24/01 virus and cH9/1 were used, as previously described (Hai et al., 2008, *J Virol* 82, 10580; Fodor et al., 1999, *J Virol* 73, 9679, 27). Briefly, 293T cells were transfected with 1 µg of each of the eight plasmids using Lipofectamine 2000 (Invitrogen) according to the manufacturer's instructions. At 12 hours post transfection, the medium was replaced with DMEM containing 0.3% bovine serum albumin, 10 mM HEPES, and 1.5 µg of TPCK (1-1-tosylamide-2-phenylethyl chloromethyl ketone)-treated trypsin/mL (Sigma T1426). At two days post transfection, virus-containing supernatant was inoculated into 10-day-old embryonated chicken eggs. Allantoic fluid was harvested after 2 days of incubation at 37° C. and assayed for the presence of virus by the hemagglutination of chicken red blood cells. The rescued cH9/1 virus was then propagated in 10 day old eggs following a 48 hour incubation at 37° C. Virus stocks were titered by plaque assay as previously described on MDCK cells in the presence of TPCK trypsin (Steel et al., 2009, *J Virol* 83, 1742). The sequence of the cH9/1 RNA was confirmed by sequencing of reverse transcription-PCR products.

6.6.1.4 Immunofluorescence to Confirm Expression of Chimeric Hemagglutinin

Confluent monolayers of MDCK cells were infected with cH9/1N3 virus at an MOI of 2. At 48 hours post infection, cells were fixed and blocked with 1% bovine serum albumin in PBS containing 0.1% Tween 20. Cells were then incubated with mouse mAbs: anti-NP antibody HT103, PY102, anti-H9 (BEI NR#9485), or a pan-H1 stalk-specific antibody (6F12). After three washes with PBS containing 0.1% Tween 20, cells were incubated for 1 hour with Alexa Fluor 488-conjugated anti-mouse IgG (Invitrogen). Infected cells were analyzed by fluorescence microscopy with an Olympus IX70 microscope.

6.6.1.5 Human Serum Samples

Human sera samples were collected and used in accordance with insitututional protocols. Sera were collected from three patient cohorts: adults not infected with pH1N1, children not infected with pH1N1, and pH1N1 virus infected adults. Sera were collected from pH1N1 infected patients within the first 3 weeks of symptomatic infection. For experiments using pooled serum, an equal volume of each sample was mixed to generate pool. Confirmation of infection was performed by Wrammert et al. by RT-PCR and by serological assays (Wrammert et al., 2011, *J Exp Med* 208, 181-193).

6.6.1.6 Hemagglutinin Inhibition Assays

Collected sera were first inactivated by trypsin-heat-periodate treatment or by RDE treatment in order to remove non-specific inhibitors of hemagglutination (Coleman, Dowdle, 1969, *Bull World Health Organ* 41, 415 (1969). Hemagglutination inhibition (HI) assays were performed to test reactivity with cH9/1N3 and A/duck/France/MB42/76 (H6 HA) (Desselberger et al., 1978, *Proc Natl Acad Sci USA* 75, 3341 (July, 1978)) viruses as previously described (Lowen et al., 2009, *J Virol* 83, 2803). A sample is considered negative if HI activity is not seen with a 1:10 dilution of the serum.

6.6.1.7 ELISAs

Ninety-six well ELISA plates (Qiagen HisSorb or Nunc Immulon 2) were coated with 50 ul of baculovirus-expressed cH6/1, cH9/1 or full length hemagglutinin (H5 HA, BEI NR#660; H3 HA, BEI NR#15171) proteins or H1 sequence (PR8) long alpha helix (LAH) (Wang et al., 2010, *Proc Natl Acad Sci USA* 107, 18979) diluted in PBS and incubated overnight at 4° C. Plates were blocked with 0.5% milk/2% goat sera/PBS and then washed 3× with PBS/0.1% Tween (PBST). Monoclonal antibodies, sera from human subjects, and mouse sera used as controls were serially diluted in PBS or blocking buffer and then added to the plate, followed by a one hour incubation at room temperature. Plates were then washed 3× with PBST and incubated with 1:5000 dilution of goat anti-Human IgG [Fc] coupled to alkaline phosphatase (AP) (Meridian Life Science) or anti-mouse AP (Invitrogen) for an additional hour. Following washing 3× with PBST, p-nitrophenyl phosphate substrate (Sigma) was added. The reaction was stopped with NaOH after 10 minutes and optical density measurements were taken at 405 nm.

6.6.1.8 Plaque Reduction Assay

Sera from adult infected and naïve (not infected with pH1N1 virus) patients were first pooled and loaded onto a gravity flow column with protein G sepharose (GE Healthcare) for purification of IgG proteins. The column was washed with PBS. The polyclonal antibodies were eluted with a 0.1 M glycine buffer (pH 2.7). A 2 M Tris-HCl buffer (pH 10) was added immediately at a 1:10 ratio to restore the pH. The eluate was buffer exchanged in PBS and concentrated using an Amicon Ultra-15 centrifugal filter unit (Millipore) with a 50 kD MW cut-off in a swinging bucket rotor. Protein concentrations were measured on a NanoDrop 2000 spectrophotometer using the A280 method. Removal of non-specific serum inhibitors was confirmed by HI tests using multiple virus strains that demonstrated an absence of HI activity in the purified IgG preparations (data not shown). Neutralization capability of stalk-reactive antibodies was assessed as previously described (Wang et al., 2010, *PLoS Pathog* 6, e1000796). Virus was first diluted to a concentration that would yield 100 plaque forming units per well. Different concentrations of IgG from pooled sera were then co-incubated with virus at room temperature for an hour. Six-well plates seeded with MDCK cells were washed with PBS and then infected with 200 ul of virus-IgG mixtures. Following a forty-five minute incubation at 37° C., virus and IgG were aspirated from cells and an agar overlay containing appropriate antibody concentration and TPCK trypsin was added to each well. Plates were incubated for 2 days at 37° C. Plaques were visualized by immunostaining (Bouvier et al., 2008, *J Virol* 82, 10052) using anti-H9 antibody G1-26.

6.6.1.9 Pseudotype Particle Neutralization Assay

The procedure for pseudotype particle production was adapted from previous studies (Evans et al., 2007, *Nature* 446, 801). Briefly, 293-T cells were co-transfected with four plasmids encoding (i) a pro-virus containing the desired reporter (V1-GLuc), (ii) HIV Gag-Pol, (iii) the chimeric cH9/1 hemagglutinin protein and (iv) influenza B/Yamagata/16/88 neuraminidase (NA) (Tscherne et al., 2010, *J Virol Methods* 163, 336). The V1-GLuc plasmid encodes a luciferase protein that is secreted from cells and can be detected in the cell supernatant. Supernatants were collected 48 h post-transfection and subsequently filtered (0.45 μm pore size) in order to purify the cH9/1 particle preparations. Particles were then incubated (at quantity determined to give luciferase activity within the linear range after infection) with different concentrations (50 m/ml, 10 m/ml and 2 m/ml) of purified human IgGs and were added to MDCK cells. Infections proceeded for 6 hours before cells were washed and fresh supernatant was placed over cells. All infections using pseudotype particles were performed in the presence of 1 μg/ml polybrene (Sigma, St. Louis, Mo.) (Tscherne et al., 2010, *J Virol Methods* 163, 336). Forty-eight hours post-infection luciferase assays were performed.

6.6.2 Results 6.6.2.1 Development of Chimeric Hemagglutinin-Based Reagents

Chimeric hemagglutinin (cHA) constructs were generated to serve as analytical tools to assess the presence of stalk antibodies in human sera. By taking advantage of a disulfide bond that exists between C52 and C277, and that delineates the boundary between the HA stalk and head, expression plasmids were engineered that encode the globular head domain of an H6 or H9 hemagglutinin atop the stalk domain from the HA of PR8 virus (FIG. 26A). It was hypothesized that human serum samples containing stalk antibodies would likely be negative for hemagglutination inhibition (HI) activity against H6 or H9 viruses (due to lack of prior exposure to these virus subtypes), yet would be reactive with the cH6/1 or cH9/1 constructs due to prior exposure to the H1 hemagglutinin stalk. These tools, recombinantly expressed cHA proteins and viruses expressing the cHAs, could be used to assess relative amounts of stalk antibodies in human serum samples and to measure any neutralizing activity mediated by those stalk-specific antibodies.

In order to generate cH6/1 and cH9/1 protein for analytical assays, plasmids coding for the chimeric HAs were generated and expressed as soluble proteins in a baculovirus expression system. Coomassie staining of 2 μg of total protein suggests a high degree of purity in these preparations (FIG. 29A). The slight delayed migration of cH9/1 is thought to be the result of an increased number of occupied glycosylation sites on the cH9/1 head. The cHA proteins were further characterized by western blot analysis using antibodies reactive with various parts of the HA. As shown in FIG. 29B, only cH6/1, cH9/1 and full length HA from PR8 reacted with a rabbit polyclonal antiserum specific for the PR8 stalk. Monoclonal antibodies against the head domains of H6, H9, and PR8 confirmed that the chimeric constructs were expressing exotic heads atop a PR8 stalk. H3 protein was used as a negative control, and was only detected when using the pan-H3 antibody 12D1 (Wang et al., 2010, *PLoS Pathog* 6, e1000796).

Recombinant viruses expressing the chimeric molecules were also rescued for the purpose of detecting neutralizing stalk antibodies. Because all human influenza viruses over the last century have encoded NA of the N1 or N2 subtype, it was reasoned that the rescue of the cH9/1N3 reassortant virus would allow for the assessment of the neutralizing capability of stalk-specific antibodies, while not measuring any (N1 or N2) neuraminidase antibody activity. The cH9/1N3 virus (expressing the H1 stalk with H9 globular head HA with an N3 subtype neuraminidase) was rescued using reverse genetics and grown to high titers in embryonated chicken eggs. The plaque assay phenotype of this virus was similar to that of PR8 wild type virus (FIG. 29C). To confirm the presence of the H9 head after virus passage, cells were infected with cH9/1N3 virus. Infected cells were then probed with mouse mAb G1-26, an antibody specific for H9 subtype hemagglutinin proteins. A pan-H1 stalk specific antibody, 6F12, was used to detect both wild type PR8 and cH9/1N3 virus infected cells (FIG. 26B).

6.6.2.2 Stalk Specific Antibodies Bind and Neutralize cHA

In order to confirm that cH6/1 and cH9/1 proteins could be used as tools to detect stem antibodies, the use of these cHAs was first validated with an antibody known to react with the HA stalk. Indeed, mouse mAb C179, an antibody reactive with the stalk of H1 HA (Okuno et al., 1993, *J Virol* 67, 2552), bound to baculovirus expressed cH6/1 and cH9/1 protein by ELISA in a dose dependent manner (FIGS. 30A and B).

Next, it was ascertained whether replication of the cH9/1N3 virus could be inhibited by monoclonal antibody 6F12, which has neutralizing activity against H1 influenza viruses (data not shown). Antibody 6F12 was able to bind and neutralize cH9/1N3 virus in a plaque reduction assay (FIGS. 30C and D), in a dose dependent manner, with one hundred percent inhibition seen at concentrations above 4 μg/ml. These results validated the hypothesis that the chimeric proteins and the recombinant cH9/1N3 virus could be used to detect stalk antibodies with neutralizing activity.

6.6.2.3 Patients Infected with pH1N1 have High Titers of Antibodies that Bind and Neutralize cHA Prior to the use of cH6/1 and cH9/1 soluble proteins to quantitate stalk-reactive antibodies in patient blood samples, the sera for HI activity was tested against viruses expressing these two HA subtypes. Using A/duck/France/MB42/76 (H6) and cH9/1N3 viruses, it was confirmed that all adult and pediatric serum samples collected were HI negative (results not shown).

Figures 27A, 27B:
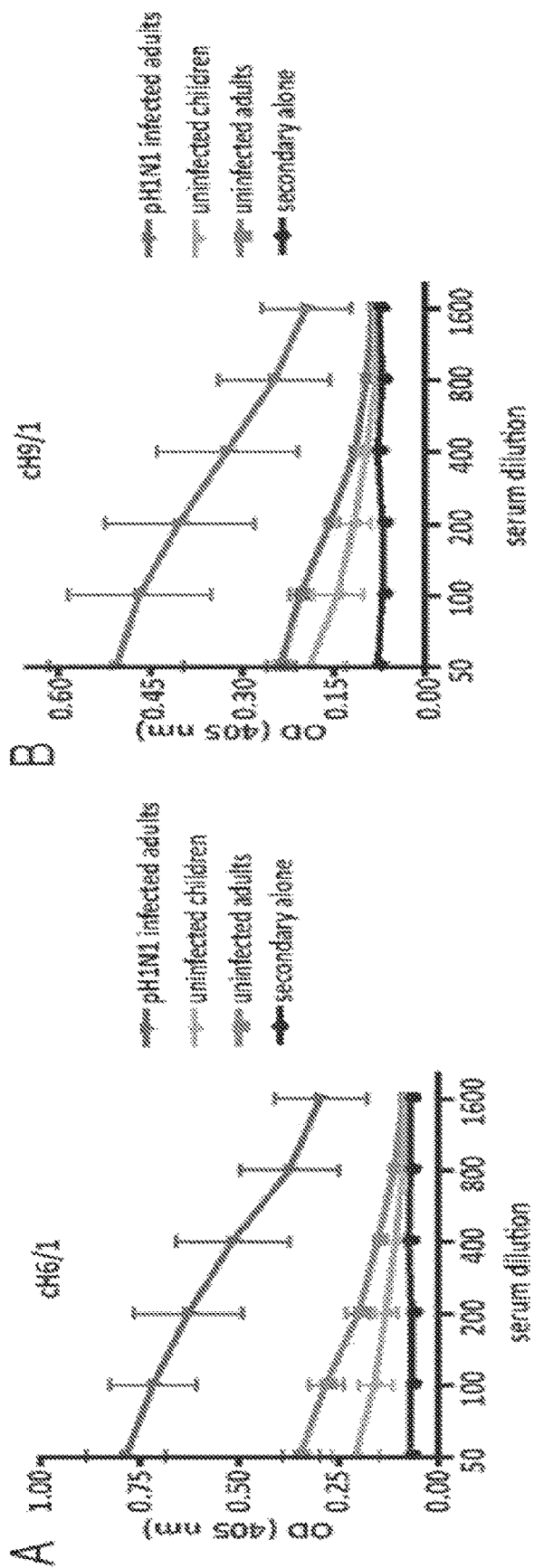

Next, the reactivity of the sera with cH6/1 and cH9/1 proteins was tested by ELISA. Sera collected from adult and pediatric subjects not infected with pH1N1 viruses showed little reactivity with either protein. However, sera collected from patients infected with pH1N1 influenza virus showed enhanced binding to both cHA constructs, with a greater than 30-fold difference in IgG reactivity (comparing dilutions that yield equivalent optical density readings) when comparing serum pools from pH1N1 infected with those of uninfected adults and children (FIGS. 27A and B). It was therefore reasoned, by taking the negative HI data into account, that reactivity with cHA proteins is occurring in the stalk domain.

Using pooled samples of human sera, IgG binding to a portion of the HA stem, the long alpha helix (LAH), was also tested. These IgGs had previously been shown to mediate protective immunity in mice (Wang et al., 2010, *Proc Natl Acad Sci USA* 107, 18979). Sera from patients infected with pH1N1 contained antibody reactive with the H1 LAH, whereas patients unexposed to the pandemic virus had minimal LAH-specific serum antibody (FIG. 27C).

The H5 hemagglutinin subtype is within the same phylogenetic group as the H1 HA, and shares a very similar stalk structure (Ekiert et al., 2009, *Science* 324, 246). Interestingly, patients exposed to the pH1N1 had boosted serum antibody specificities reactive with the H5 protein (FIG. 27D), while not having any serum HI activity against the homologous H5 subtype virus (data not shown). This result suggested that exposure to the pH1N1 virus may have conferred a degree of anti-H5 immunity mediated by stalk-specific antibodies.

Figures 27C, 27D, 27E:
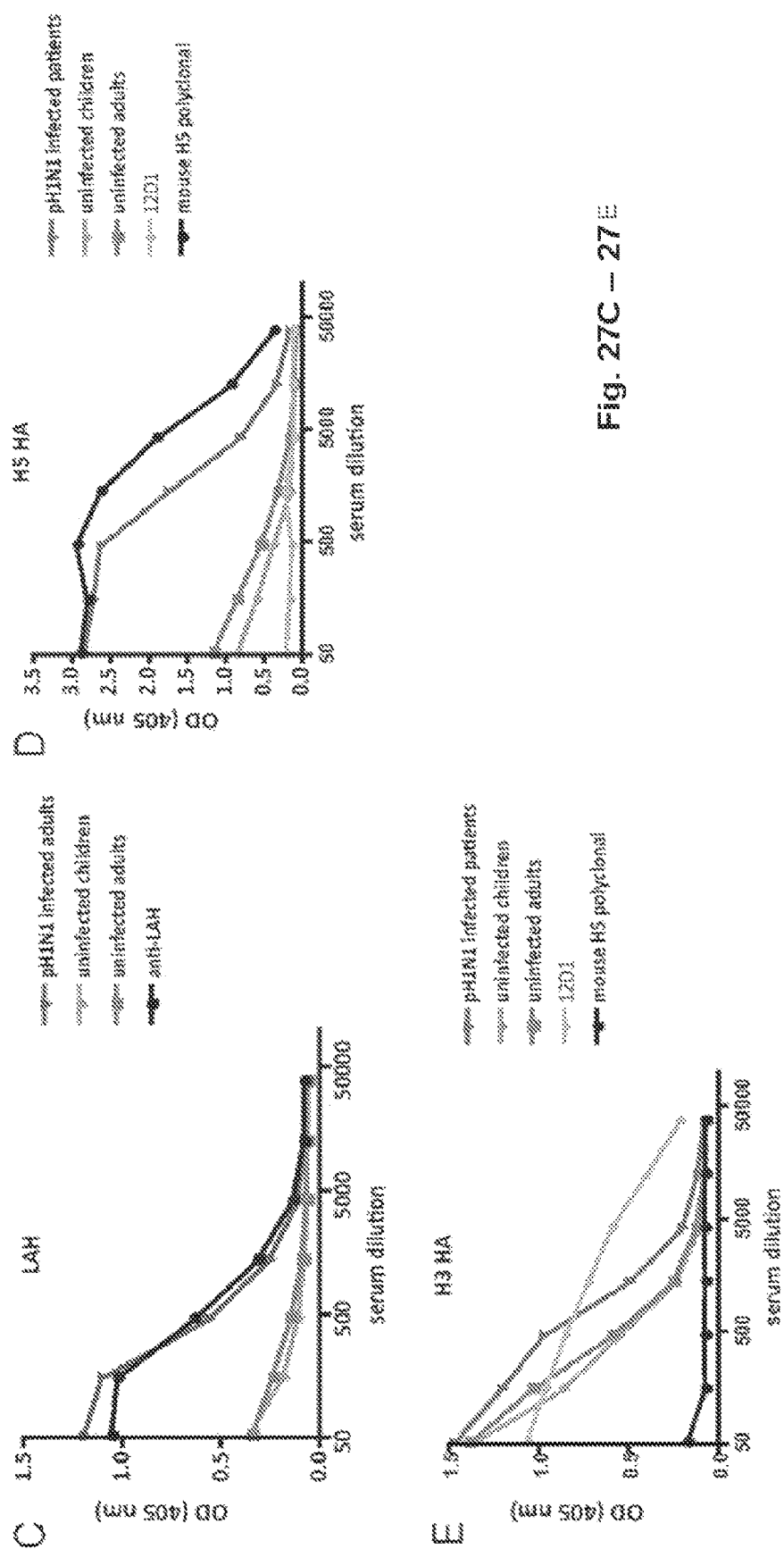

Importantly, patients infected with pH1N1 did not have boosted serum antibody specific for an H3 hemagglutinin protein (H3 being in a separate phylogenetic group from H1 and H5 HAs) (FIG. 27E). This result demonstrates that the enhanced titer of stalk-specific antibodies in sera from pH1N1-infected patients is not a function of general immune stimulation; rather, the H1 stalk antibody specificities were selectively boosted by infection with the pandemic virus strain.

Next, it was assessed whether these stalk reactive antibodies found in these human samples had neutralizing capability. Serum samples from infected and uninfected adults were pooled and total IgG was purified in order to remove non-specific inhibitors (eg: sialic acid containing molecules and lectins) that would bind to the hemagglutinin head. Using these pure IgG preparations, complete inhibition plaque formation at antibody concentrations above 55.5 m/mL total serum IgG (FIGS. 28A and B) was achieved. In accordance with the ELISA data, an approximately 30-fold difference in neutralizing capability was observed when comparing sera from pH1N1 infected with those of uninfected adults. Using mAb 6F12 as a standard, a comparison was able to be made between neutralizing activities mediated by 6F12 and the polyclonal human IgG preparation. By comparing the concentrations of 6F12 and human IgGs that yielded 100% neutralization of cHA virus, it was estimated that 7% of total human IgG from patients infected with pH1N1 during the last 30 days comprised neutralizing stalk antibodies.

Finally, the neutralizing capability of stalk reactive antibodies was evaluated, using a pseudotype particle infection assay that has a read-out of luciferase activity which is generated upon virus entry into host cells. Pseudotyped particles expressing the cH9/1 protein were incubated with purified human IgG and neutralizing activity was measured by inhibition of particle entry resulting in absence of luciferase enzymatic activity in cell supernatants (see methods). Consistent with the plaque reduction assay, the pseudotyped particle assay also showed 100% neutralization of particles at total IgG concentrations of exceeding 10 μg/ml (FIG. 28C).

6.6.3 Conclusion

Novel analytical tools, in the form of chimeric hemagglutinin proteins and viruses expressing those chimeric proteins, were developed that allowed for the selectively detection of stalk-specific antibodies in preparations that also include antibodies that bind the globular head of hemagglutinin proteins. These novel hemagglutinin constructs have a constant H1 subtype stalk, with globular head domains from distinct hemagglutinin subtypes (ex: H1 stalk with H6 head). This was accomplished by taking advantage of a disulfide bond that exists between cysteines 52 and 277 in the hemagglutinin protein (19) to exchange the intervening sequence with that of a different HA subtype.

Using these chimeric hemagglutinin (cHA) constructs, it was demonstrated that a small cohort of humans with confirmed pH1N1 virus infection generated a high titer of stalk specific, neutralizing antibodies compared to uninfected adult and pediatric controls not infected with pH1N1 viruses. These findings support the hypothesis that antibodies reactive with the hemagglutintin stalk, generated in response to pH1N1 infection, likely contributed to the dying out of seasonal H1N1 viruses that were circulating prior to the influenza pandemic of 2009.

6.7 Example 7

Influenza Viruses Expressing Chimeric Hemagglutinins: Globular Head and Stalk Domains Derived from Different Subtypes and Phylogenic Groups This example describes several functional chimeric influenza virus hemagglutinins encompassing a variety of globular head and stalk combinations from different hemagglutinin subtypes and different phylogenic groups as wells as recombinant influenza viruses expressing these chimeric hemagglutinins, which had growth properties similar to those of wild-type influenza viruses. These chimeric recombinant viruses possess growth properties similar to those of wild-type influenza viruses and can be used as reagents to measure domain-specific antibodies in virological and immunological assays.

6.7.1 Materials and Methods 6.7.1.1 Cells and Viruses 293T and MDCK cells were obtained from the American Type Culture Collection (ATCC) and were maintained either in Dulbecco's minimal essential medium (DMEM) or in MEM (Gibco, Invitrogen) supplemented with 10% fetal calf serum (HyClone; Thermo Scientific) and penicillin-streptomycin (Gibco, Invitrogen). The A/Puerto Rico/8/1934 (PR8) and A/Perth/16/2009 (Perth/09) wild type (kindly provided by Alexander Klimov, CDC) and recombinant viruses were grown in 10-day old specific pathogen-free embryonated hen's eggs (Charles River) at 37° C. for 2 days.

6.7.1.2 Construction of Plasmids.

Plasmids encoding the different chimeric hemagglutinins were constructed using a strategy similar to what has been previously described (see, e.g., Fodor et al., 1999, *J Virol* 73:9679-9682; and Hai et al., 2008, *J Virol* 82:10580-10590). Briefly, the different segments of chimeric HA were amplified by PCR with primers containing SapI sites, digested with SapI, and cloned into the SapI sites of the ambisense expression vector pDZ vector in which vRNA transcription is controlled by the human RNA polymerase I promoter and the mouse RNA polymerase I terminator, and mRNA/cRNA transcription is controlled by the chicken beta actin polymerase II promoter (see, e.g., Quinlivan et al., 2005, *J Virol* 79:8431-8439), through multi-segmental ligation. We kindly thank Daniel Perez (University of Maryland) for the H7 HA plasmid (Genbank ID: DQ017504). The plasmids encoding A/Puerto Rico/8/1934 (PR8) genes were used as previously described (Hai et al., 2008, *J Virol* 82:10580-10590).

6.7.1.3 Nucleotide Sequence Accession Number

All constructed cHA genes used in this study have been deposited in the Influenza Research Database under the accession number IRD-RG-684014, IRD-RG-684022, IRD-RG-684030, and IRD-RG-684038. The chimeric cH1/1, cH5/1, cH7/3 and cH5/3 are listed as A/Puerto Rico/8-RGcH1-1/34, A/Puerto Rico/8-RGcH5-1/34, A/Perth/16-RGcH7-3/09, and A/Perth/16-RGcH5-3/09, respectively.

6.7.1.4 Flow Cytometric Analysis

To assess levels of hemagglutinin protein expression at the cell surface, 293T cells were transfected with 1 μg of the appropriate plasmid using Lipofectamine 2000 (Invitrogen) according to the manufacturer's instructions or MDCK cells were infected with cHA-expressing recombinant viruses. At 48 h post-transfection, 293T cells were trypsinized and resuspended in PBS containing 2% FBS prior to staining with the monoclonal antibody (mAb) 6F12 (5 μg/ml), a mAb generated in our laboratory that is broadly reactive to the stalk domain of group 1 HAs (data not shown) or with the mAb 12D1 (5 μg/mL) against H3 HAs (see Wang et al., 2010, *PLoS Pathog* 6:e1000796). At 12 h post-infection, MDCK cells were resuspended by trypsinization and stained with the mAb 12D1. Stained cells were analyzed on a Beckman Coulter Cytomics FC 500 flow cytometer, and the results were analyzed using FlowJo software.

6.7.1.5 Pseudoparticle Generation and Entry Assay

The procedure for pseudoparticle production was adapted from previous studies (see, e.g., Evans et al., 2007, *Nature* 446:801-805 and Tscherne et al, 2010, *J Virol Methods* 163:336-43). Briefly, we co-transfected 293T cells with four plasmids encoding (i) a pro-virus containing the desired reporter (V1-Gaussia luciferase) (Evans et al., 2007, *Nature* 446:801-805), (ii) HIV Gag-Pol (Evans et al., 2007, *Nature* 446:801-805), (iii) chimeric hemagglutinin protein and (iv) B/Yamagata/16/88 virus neuraminidase (NA). Supernatants were collected 72 h post-transfection and subsequently filtered (0.45 μm pore size). The presence of pseudotype virus like particles (VLPs) was evaluated through hemagglutination assay. Different VLP preparations were adjusted to the same 4 hemagglutination units prior to inoculation of MDCK cells. All of the following assays using pseudoparticles were performed in the presence of 1 μg/mL polybrene (Sigma) to increase the efficiency of transduction (see, e.g., Evans et al., 2007, *Nature* 446:801-805 and Tscherne et al, 2010, *J Virol Methods* 163:336-43).

The entry assay was performed by transducing MDCK cells with pseudoparticles that expressed different chimeric hemagglutinins and contained the Gaussia luciferase reporter. Twenty-four hours post-transduction, cells were washed three times with fresh medium to remove any residual Gaussia luciferase protein present in the inoculum. Forty-eight hours post-transduction, luciferase assays were performed (Evans et al., 2007, *Nature* 446:801-805).

6.7.1.6 Rescue of Recombinant Chimeric Influenza A Viruses

Rescue of influenza A viruses from plasmid DNA was performed as previously described (see, e.g., Fodor et al., 1999, *J Virol* 73:9679-9682; and Hai et al., 2008, *J Virol* 82:10580-10590). To generate the recombinant wild-type (rWT) PR8 virus, 293T cells were co-transfected with 1 μg of 8 pDZ PR8 rescue plasmids using Lipofectamine 2000 (Invitrogen). The wild type HA plasmid was substituted with a plasmid encoding the desired chimeric HA in order to generate cHA-expressing recombinant viruses. At 6 h post-transfection, the medium was replaced with DMEM containing 0.3% bovine serum albumin (BSA), 10 mM HEPES, and 1.5 μg/ml TPCK (L-1-tosylamide-2-phenylethyl chloromethyl ketone)-treated trypsin (Sigma). After 24 hours post-transfection, 8-day old embryonated chicken eggs were inoculated with virus-containing supernatant. Allantoic fluid was harvested after 2 days of incubation at 37° C. and assayed for the presence of virus by hemagglutination of chicken red blood cells. Virus stocks were titered by plaque assay on MDCK cells as previously described (Fodor et al., 1999, *J Virol* 73:9679-9682, Hai et al., 2008, *J Virol* 82:10580-10590).

6.7.1.7 Virus Growth Kinetics Assay

To analyze the replication characteristics of recombinant viruses, 10-day old embryonated chicken eggs were inoculated with 100 plaque forming units (pfu) of wild-type or cHA-expressing recombinant viruses. Allantoic fluid was harvested and subsequently assayed for viral growth at 0, 9, 24, 48, and 72 h post-infection (hpi). The titers of virus present in allantoic fluid were determined by plaque assay on MDCK cells as referenced above.

6.7.1.8 Immunostaining of Plaques

Plaques were visualized by immunostaining with mAb HT103 against the influenza A nucleoprotein (NP), using a protocol that has been previously described (Bouvier et al., 2008, *Journal of Virology* 82:10052-8; and Steel et al, 2009, *J Virol* 83:1742-53).

6.7.1.9 Western Blot and Indirect Immunofluorescence Analysis

Confluent MDCK cells were infected (multiplicity of infection [MOI] of 2) with indicated recombinant influenza viruses or mock infected with phosphate-buffered saline (PBS) for 1 h at 37° C. At 12 hpi, cells were lysed in 1×SDS loading buffer as described previously (see, e.g., Hai et al., 2008, *J Virol* 82:10580-10590). The reduced cell lysates were analyzed by Western blot analysis using monoclonal antibodies (mAbs) against influenza A virus nucleoprotein (NP) (HT103), PR8 HA head domain (PY102), Cal/09 HA head domain (29E3), VN/04 HA head domain (mAb #8) and 12D1, a pan-H3 antibody reactive against the HA stalk. In order to detect H7 head domains, polyclonal goat sera NR-3152 was used (raised against A/FPV/Dutch/27 (H7) virus, BEI Resources). An anti-glyceraldehyde 3-phosphate dehydrogenase (GAPDH) antibody (Abcam) was used for the loading control. Proteins were visualized using an enhanced chemiluminescence protein detection system (PerkinElmer Life Sciences).

For immunofluorescence analysis, confluent monolayers of MDCK cells on 15-mm coverslips were infected with recombinant viruses at an MOI of 2. At 15 hpi, cells were fixed and permeabilized with methanol-acetone (ratio, 1:1) at −20° C. for 20 minutes. After being blocked with 1% bovine serum albumin in PBS containing 0.1% Tween 20, cells were incubated for 1 h with the antibodies described above, as well as mAb 6F12. After three washes with PBS containing 0.1% Tween 20, cells were incubated for 1 h with Alexa Fluor 594-conjugated anti-mouse IgG (Invitrogen) or Alexa Fluor 594-conjugated anti-goat IgG (Invitrogen). Following the final three washes, infected cells were analyzed by fluorescence microscopy with an Olympus IX70 microscope.

6.7.1.10 Plaque Reduction Assay

Plaque reduction assay was performed as previously described (see Wang et al., 2010, *PLoS Pathog* 6:e1000796). Approximately 60 to 80 pfu of recombinant viruses expressing cHA made up of Cal/09 or VN/04 globular head domains atop a PR8 stalk were incubated with or without different concentrations (100, 20, 4, 0.8, 0.16 and 0.032 ug/ml) of mAb KB2, a broadly neutralizing anti-HA stalk antibody generated in our laboratory (data not shown) for 60 minutes in a total volume of 240 uL at room temperature. A confluent layer of MDCK cells in 6-well plates was washed twice with PBS and then incubated with the antibody-virus mixture for 40 minutes at 37° C. A TPCK-trypsin agar overlay supplemented with antibody at the above-described concentrations or no antibody was then added to each well after the inoculum had been aspirated off. Plates were incubated for 2 days at 37° C. Plaques were then visualized by immunostaining (Bouvier et al., 2008, *Journal of Virology* 82:10052-8; and Steel et al., 2009, *J Virol* 83:1742-53) with anti-influenza A NP antibody HT103.

6.7.1.11 Pseudotype Particle Neutralization Assay

The procedure for pseudotype particle production was the same as described above, using the cHA construct that is comprised of either a VN/04 (H5) or a Cal/09 (H1) head and a PR8 (H1) stalk with the influenza B/Yamagata/16/88 virus NA. Particles were then incubated with different concentrations of mAb KB2 at 5 fold dilutions from 100 to 0.032 μg/mL. Then, these mixtures were added to MDCK cells. Transductions proceeded for 6 hours before cells were washed and fresh medium was placed over cells. All transductions using pseudotype particles were performed in the presence of 1 μg/mL polybrene (Sigma, St. Louis, Mo.) (Tscherne et al, 2010, *J Virol Methods* 163:336-43). Forty-eight hours post-transduction, luciferase assays were performed in order to assay the degree in which entry was blocked by mAb KB2.

6.7.2 Results:

6.7.2.1 Generation of Chimeric Hemagglutinins

In order to see if the cysteine residues forming the Cys52-Cys277 disulfide bond were conserved, an alignment of influenza A virus HA sequences of the H1, H3, H5 and H7 subtypes were used in this study. Because these cysteine residues are highly conserved across HA subtypes, for both group 1 and group 2 HAs, the Cys52-Cys277 disulfide bond was used as a delineating point between the head and stalk domains. By defining the sequence between Cys52 and Cys277 as the head region, and the remainder of the molecule as the stalk, it was rationalized that constructs could be made that encode novel head and stalk combinations from a variety of HA subtypes (FIGS. 31A and B).

The degree of amino acid identity that exists between the stalk regions of hemagglutinin subtypes further encouraged us that the swapping of head domains might be possible. Higher percentages of amino acid identity were seen in the stalk domains across all subtypes, compared to the head domains (FIG. 32).

All 16 subtypes of influenza HA are classified into two phylogenetic groups (Palese and Shaw, 2006, Orthomyxoviridae: the viruses and their replication, Fields virology, 5th ed., 1647-1690). Because higher percentages of amino acid identity was observed within stalk regions of a particular group (FIG. 32), and because one cHA virus that contained head and stalk domains from group 1 viruses had been successfully generated (Pica et al., 2012, *PNAS* 109:2573-8), an attempt was made to generate intra-group cHAs. For group 1, two chimeric hemagglutinin constructs that encode either the pandemic H1 Cal/09 HA or VN/04 globular head domain with the stalk region from PR8 (H1) HA (cH1/1 and cH5/1, respectively) were generated (FIG. 31B). A similar strategy was applied to generate a chimeric HA that expressed head and stalk domains from different group 2 influenza strains: the head from Alb/01 (H7, group 2) and the stalk region from Perth/09 (H3, group 2) HA (cH7/3) (FIG. 1B). Finally, it was evaluated whether the head and stalk domains could be swaped to make an inter-group chimeric HA containing the head domain of VN/05 HA (H5, group 1) atop a Perth/09 HA (H3, group 2) stalk (cH5/3) (FIG. 31B).

Following the construction of these plasmids, experiments were performed to determine whether the different chimeric HA constructs could be expressed and transported to the cell surface like wild-type HAs. Fluorescence-activated cell sorter (FACS) analysis of transiently transfected 293T cells was performed following surface staining with H1 and H3 stalk domain specific antibodies, respectively. Using this method, cell surface expression of all four chimeric constructs were detected (FIG. 33). However, compared to the wild type PR8 HA less surface protein expression was detected for the cH1/1 construct, which could be attributed to the inherent character associated with the head domain of the Cal/09 HA or a lower transfection efficiency for this chimeric DNA construct. In addition, it is of note that there were differences in the cell surface expression pattern for the cH7/3 and cH5/3 constructs. This "double peak" expression pattern was observed only in transfection conditions, and was reproducible. It was not detected upon infection with either cH7/3 or cH5/3-expressing recombinant viruses (FIG. 33). Therefore, these data indicate that the cHAs can be transported through the Golgi complex to the cell surface.

Next, the entry characteristics of the different cHAs through transduction of MDCK cells were examined using retroviral pseudotype particles that contained a luciferase reporter construct and expressed the cHA and wild-type B/Yamagata/16/88 virus NA on the particle surface. The entry efficiency mediated by the cHA proteins was detected by the luciferase read-out. Comparable levels of pseudotype particle-mediated luciferase expression were observed for cH5/1, cH7/3 and cH5/3 chimeric HAs and the corresponding wild type proteins (FIG. 34). Particles encoding the cH1/1 HA expressed lower luciferase levels compared to the other HA constructs, which could be due to either the lower expression of the cH1/1 in the producer cell line and hence fewer HA trimers per particle or the less efficient entry properties of the cH1/1 HA. It is also possible that when normalizing the pseudotype particles to 4 hemagglutinin units, the actual amount of pseudotype particles may vary due to differences in binding to red blood cells.

6.7.2.2 Generation of Recombinant Influenza Viruses Bearing Chimeric Hemagglutinins Because it had determined that our cHA constructs were efficiently expressed and transported to the cell surface, a study was performed to assess whether a recombinant influenza virus that encodes a cHA could be rescued. Viruses containing the different cHAs were successfully generated using previously published protocols (see, e.g., Fodor et al., 1999, *J Virol* 73:9679-9682; and Hai et al., 2008, *J Virol* 82:10580-10590). The resulting viruses were plaque purified, amplified in 10 day old embryonated eggs and the chimeric segments were analyzed by RT-PCR and sequenced. In all cases, the virus was found to have the expected chimeric HA segment and no other HA segment (data not shown).

The presence of the cHAs in rescued viruses was further confirmed by Western blot and indirect immunofluorescence of infected cells (FIGS. 35 and 36). MDCK cells were infected with rWT PR8, wild-type Perth/09, cH1/1, cH5/1, cH7/3 and cH5/3 viruses (FIGS. 35 and 36). cH1/1 and cH5/1 chimeric HA proteins were detected in the corresponding samples using antibodies reactive against the head domains of Cal/09 (H1) HA (29E3) (Medina et al., 2010, *Nature Communications* 1:28) or VN/04 (H5) HA (mAb #8) (Steel et al., 2009, *J Virol* 83:1742-53) respectively (FIG. 35). Comparable expression levels among the cH7/3, cH5/3 and wild type Perth HA using 12D1, a pan-H3 anti-stalk mAb (see Wang et al., 2010, *PLoS Pathog* 6:e1000796). The wild type Perth HA showed a slower migration on the gel that is likely due to a higher number of glycosylation sites in the globular head domain. It was confirmed that the correct HA head domain was expressed atop an H3 stalk by using anti-H7 polyclonal (NR-3152) or anti-H5 monoclonal antibodies (mAb #8) on cH7/3 or cH5/3 infection samples, respectively. Positive bands were detected in both cases.

For the immunofluorescence study, the infection conditions were similar to those used for Western blot analysis. Infected cells were stained with corresponding antibodies as used in FIG. 35. All infected cells showed the expected expression of the chimeric and wild type HAs, as well as of the influenza A virus NP (FIG. 36).

6.7.2.3 Replication Characteristics of Recombinant Viruses

The growth properties of wild type and recombinant viruses were assessed in 10-day-old embryonated chicken eggs at 37° C. (FIG. 37A). The rWT PR8 virus was included for comparison of the growth kinetics of the recombinant viruses expressing chimeric HAs. cH5/1 and cH5/3 viruses displayed comparable replication kinetics to that of rWT PR8 virus. cH7/3 virus grew to similar peak titers as rWT PR8 at 48 hpi ($1\times10^9$ PFU/mL), though there was a 2 log reduction in viral titer compared to the rWT PR8 virus at 9 hpi. The cH1/1 virus was attenuated as compared to the rWT PR8 virus, as shown by reduced viral titers at all time points. Nonetheless, cH1/1 virus reached a respectable peak titer of approximately $10^8$ PFU/mL. The Perth/09 Wild type virus grows to comparable peak titers in embryonated eggs (data not shown).

The plaque phenotype of each of the chimeric viruses was also evaluated in MDCK cells. All viruses formed comparable sized plaques as shown in FIG. 37B. These data together confirm that the chimeric HA constructs fold correctly and are biologically functional.

6.7.2.4 Stalk Specific Antibodies can Neutralize cHA-Expressing Viruses and Pseudoparticles Finally, stalk-specific antibodies were tested for the ability to neutralize our newly generated recombinant viruses expressing cHAs. Plaque reduction assays were performed in the presence of mAb KB2, an HA-stalk specific antibody with broad group 1 reactivity or without antibody. It was shown that mAb KB2 neutralizes all cHA-expressing viruses with similar efficiency and in a dose dependent manner. At 100 ug/mL, mAb KB2 was able to completely neutralize cH1/1 and cH5/1 viruses with 100% efficiency, with some neutralizing activity at concentrations as low as 4 ug/mL (FIG. 38A).

To confirm these results, a pseudotype particle inhibition assay was performed with mAb KB2. Pseudotype particles expressing cH1/1 or cH5/1 and influenza B virus NA were added to MDCK cells in the presence of mAb KB2, or without antibody. Forty-eight hours post-transduction, supernatant was collected and luciferase activity was analyzed. As expected, mAb KB2 blocked the entry of cH1/1 and cH5/1 pseudotype particles in a dose dependent manner at concentrations above 4 ug/mL. While a lower concentration of mAb KB2 was sufficient to inhibit entry of pseudotype particles compared to concentrations used in the plaque reduction assay, this was an expected result due to the assumed lower incorporation of HA trimers on the surface of pseudotype particles (Corti et al., 2010, *The Journal of Clinical Investigation* 120:1663-73). This phenomenon of different neutralizing potencies of mAbs in assays that involve whole virus versus pseudotype particles has been appreciated in other studies (Corti et al., 2010, *The Journal of Clinical Investigation* 120:1663-7321; Sui et al., 2009, *Nature Structural & Molecular Biology* 16:265-73).

6.7.3 Conclusion

A novel strategy was developed to generate influenza viruses with chimeric HA proteins bearing different HA globular head domains by taking advantage of the conserved disulfide bond Cys52-Cys277 which demarcates the border between the head and stalk domains. Thus, through substituting the parental head domain with the head domain of another HA, a panel of chimeric HAs with the same stalk but different globular heads was generated. The design was tested across multiple subtypes, including the PR8 stalk domain with Cal/09 and VN H5 globular heads. In addition, an H7 globular head was placed on an H3 stalk domain. These constructs cover both phylogenetic groups of the influenza HA protein. Each construct was expressed on the cell surface and retained fusion activity as shown in FIG. 12. The generation of recombinant viruses bearing the chimeric HAs further validated that the HAs fold correctly and retain biological functions.

6.8 Example 8

1976 and 2009 H1N1 Influenza Virus Vaccines Boost Anti-Hemagglutinin Stalk Antibodies in Humans This example demonstrates that individuals who had received the A/New Jersey/1976 influenza virus vaccine showed elevated titers of hemagglutinin stalk antibodies relative to age-matched controls. These control subjects experienced a boost in anti-hemagglutinin stalk antibodies after receiving the A/California/04/09 vaccine, whereas the individuals having received the A/New Jersey/1976 vaccine did not. This demonstrates the utility of chimeric influenza virus hemagglutinin polypeptides to detect the presence of anti-stem/stalk antibodies in sera.

6.8.1 Materials and Methods 6.8.1.1 Human Serum Samples

Human sera were collected in October 2009 from subjects who had received the NJ/76 vaccine (n=20, average age=62) and from age-matched controls (n=15, average age=57). Subjects who had experienced influenza-like illness within the four months prior to the beginning of the study were excluded. All subjects were administered the monovalent Cal/09-like vaccine between October 2009 and January 2010. Six to eight months after receiving the Cal/09 vaccine, subjects returned to have post-vaccination blood drawn (5 of 20 NJ/76 vaccinees; 7 of 15 control subjects). Due to the limited amounts of serum available, equal volumes of pre- and post-Cal/09 vaccination sera were pooled from individuals for whom both samples were available (NJ/76 vaccinees=5; control subjects=7) and these pools were then tested in multiple assays.

6.8.1.2 Cells and Viruses

Madin-Darby Canine Kidney (MDCK) cells were obtained from the ATCC and were maintained in Dulbecco's Modified Eagle Medium (DMEM, Gibco) supplemented with 10% fetal calf serum (FCS, Hyclone) and 100 U/ml penicillin and streptomycin (Gibco). Cal/09 was propagated on MDCK cells in DMEM containing 1 µg/ml 1-1-tosylamide-2-phenylethyl chloromethyl ketone-treated (TPCK)-trypsin (Sigma-Aldrich). A/duck/France/MB42/1976 (France/76) virus was propagated in 10-day old embryonated chicken eggs. The cH5/1 N3 virus was generated using a reverse genetics system described previously (see, e.g., Fodor et al., J Virol 1999; 73:9679-82; Neumann et al., Proc Natl Acad Sci USA 1999; 96:9345-50) The reverse genetics plasmids that encode vRNA and mRNA include the six WT viral segments from A/Puerto Rico/8/34 (PR8) as well as plasmids encoding cH5/1 HA and N3 NA from A/Swine/Missouri/4296424/06 virus (Miss/06). The sequence of the cH5/1 and N3 RNA was confirmed by sequencing of RT-PCR products. All infections were performed using DMEM supplemented with 1 µg/ml TPCK-trypsin (infection media).

6.8.1.3 Expression and Purification of Recombinant Influenza Virus Proteins

Coding sequences for the N-terminal ectodomain of HAs from PR8, A/New Calcdonia/20/99 (NC/99) virus and cH6/1 (see, e.g., Pica et al., Proc Natl Acad Sci USA 2012; 109:2573-80). HAs were cloned in frame into a modified pFastBac vector (Invitrogen) with a C-terminal hexahistidine-tag and T4 trimerization domain. Recombinant baculovirus (rBV) was generated according to the manufacturer's recommendations. BT1-TN5B1-4 (High Five) (Krammer et al., Mol Biotechnol 2010; 45:226-34) cells grown in HyClone SFX insect cell media (Thermo Fisher Scientific) were infected with rBV expressing HAs at a multiplicity of infection (MOI) of 10 and a cell density of $1\times10^6$ cells/ml in 500 ml shaker flasks. Cells were harvested 72 to 96 h post infection and separated from supernatant by low speed centrifugation for 10 min at 2000×g at room temperature (RT). Supernatant (250 ml) was collected and incubated with 3 ml of Ni-NTA resin (Qiagen) for 2 h at 4° C. The slurry was loaded on to columns and washed three times with washing buffer (50 mM Na2HCO3, 300 mM NaCl, 20 mM imidazole, pH 8). Protein was eluted in 0.5 ml steps with elution buffer (50 mM Na2HCO3, 300 mM NaCl, 300 mM imidazole, pH 8) and tested for protein content with Bradford reagent. Fractions containing protein were pooled and concentrated using Amicon Ultracell (Millipore) centrifugation units with a cut-off of 30 kDa and buffer was exchanged to phosphate buffered saline (PBS) of pH 7.4. Protein purity and identity was tested by SDS-PAGE, Coomassie staining and Western blot. Protein concentration was determined with Bradford reagent.

6.8.1.4 Immunoglobulin G (IgG) Endpoint Titer Determination

IgG endpoint titers were determined by enzyme-linked immunosorbent assay (ELISA). Briefly, 96-well plates (Immulon 2; Nunc) were coated with 2 µg/ml of purified recombinant HA or with bovine serum albumin (BSA) in carbonate/bicarbonate buffer, pH 9, overnight at 4° C. Plates were blocked for 1 h at RT with 5% non-fat milk and were washed three times with PBS/0.025% Tween-20 (PBS-T). Serum was diluted serially in 5% non-fat milk and was added to wells. Plates were incubated for 1 h at RT, after which time they were washed three times with PBS-T. Goat anti-human IgG-horseradish peroxidase (HRP) (Meridian Life Science Inc.) secondary antibody was diluted 1:5000 in 5% non-fat milk before adding to wells and incubating for 1 h at RT. Plates were again washed three times with PBS-T prior to the addition of peroxidase substrate (SigmaFAST OPD, Sigma-Aldrich). Incubation with substrate took place for 5 min at RT before reactions were stopped by the addition of 3M HCl. Optical density measurements were taken at 490 nm. Optical densities gathered against HAs were subtracted from those measured against BSA for each individual serum dilution, to normalize against non-specific signal. Background signal was calculated for each specific antigen based on the reactivity of secondary antibody alone. Endpoint titers were defined as having an optical density at least three standard deviations above background after subtraction of non-specific (BSA) signal.

6.8.1.5 Hemagglutination Inhibition (HAI) Assays

Non-specific inhibitors of hemagglutination were removed by treating sera with 0.5 volumes 8 mg/ml TPCK-trypsin (Sigma-Aldrich) at 56° C. for 30 min. Samples were then cooled to RT prior to the addition of three volumes of 11 mM potassium periodate solution (Sigma-Aldrich). Following incubation of samples with potassium periodate for 15 min at RT, three volumes of 1% glycerol saline solution was added to samples which were again incubated for 15 min at RT. Finally, 1.5 volumes of 0.85% saline was added to samples prior to use. All volumes are in relation to the starting volume of serum. Hemagglutination assays were first performed in V-bottom 96 well plates (Nunc) using 0.5% chicken red blood cells (cRBCs, Lampire Biological Laboratories) to determine the dilution of virus that would produce three wells of hemagglutination. Virus and antibodies were mixed and incubated for 30 min at RT. cRBCs were then added to wells and plates were incubated on ice for approximately 30 min prior to reading.

6.8.1.6 Microneutralization Assays

Briefly, 50% tissue culture infectious doses (TCID50) were determined for cH5/1 N3 and Cal/09 viruses by serial dilution on MDCK cells. After infection, cells were incubated for 20 h at 37° C., 5% CO2. Cells were fixed with 80% acetone and were blocked with 3% hydrogen peroxide and 5% non-fat milk. Cells were probed with a 1:2000 dilution of biotin-conjugated mouse anti-NP (Millipore) followed by a 1:5000 dilution of secondary HRP-conjugated streptavidin (Millipore). Peroxidase substrate (SigmaFAST, Sigma-Aldrich) was added to wells for 20 min at RT before reactions were stopped with 3M HCl. For microneutralization assays, 200 $TCID_{50}$/100 μl was added to wells of serially-diluted serum (in infection media) which had been pre-treated with TPCK-trypsin as described earlier. Serum and viruses (cH5/1 N3 or Cal/09) were incubated for 1 h at 37° C. Serum/virus mixtures were transferred onto 96-well plates of confluent MDCK cells which were incubated for 1 h at 37° C., 5% $CO_2$ to allow for adsorption. Plates were washed twice with PBS and were reincubated for 20 h with infection media containing equivalent concentrations of diluted serum. Fixation and antibody treatments were identical to those used during $TCID_{50}$ determination. Neutralization titers were defined as the dilution of serum which resulted in at least 50% inhibition of infectivity.

6.8.2 Results 6.8.2.1 NJ/76 Vaccinees Had Elevated Titers of HA Stalk Antibodies Prior to Cal/09 Vaccination HA stalk antibodies are thought to be boosted most efficiently in the context of infection when individuals are exposed to HAs whose head domains differ substantially from previous exposures, but whose stalk domains remain conserved (see, e.g., Palese and Wang, MBio 2011; 2). An amino acid sequence comparison of HA0 from A/Fort Warren/1/50 (FW/50, seasonal), NJ/76 (swine-origin), NC/99 (seasonal) and Cal/09 (swine-origin) illustrates this point (Table 12). Cal/09 and NJ/76 HAs share overall 79.9% and 82.5% amino acid sequence identity, respectively, when compared to the HA of seasonal strain NC/99. Similarly, the degree of identity between NJ/76 and the pre-circulating seasonal strain FW/50 was 83.0%. However, when analyzed further, it becomes apparent that greatest degree of identity among these proteins is present in the HA stalk domain (Cal09 vs. NC/99=88.9% identity; NJ/76 vs. NC/99=91.6% identity; NJ/76 vs. FW/50=90.9% identity), while the head domains of the swine-origin H1s differ substantially from that of the seasonal H1 (Cal/09 vs. NC/99=67.1% identity; NJ/76 vs. NC/99=69.7% identity; NJ/76 vs. FW/50=69.8% identity). Despite a greater than 30 year gap between their emergence in humans, the swine-origin H1s exhibit a much higher degree of identity to one another than to seasonal H1s (whole HA0=91.0% identity; head domain=85.9% identity; stalk domain=94.6% identity). Therefore, it is possible that in a manner analogous to Cal/09 infection (see, e.g., Pica et al., Proc Natl Acad Sci USA 2012; 109:2573-8), recipients of the NJ/76 vaccine may have experienced a boost in HA stalk antibodies prior to Cal/09 exposure.

TABLE 12

Hemagglutinin amino acid sequence comparison of strains Cal/09, NJ/76, NC/99 and FW/50

| Comparison | Whole Protein (HA0) (% Identity) | Globular Head Residues 52-277 H3 Numbering (% Identity) | Stalk (% Identity) |
| --- | --- | --- | --- |
| Cal/09 vs. NJ/76 | 91.0 | 85.9 | 94.6 |
| Cal/09 vs. NC/99 | 79.9 | 67.1 | 88.9 |
| NJ/76 vs. NC/99 | 82.5 | 69.7 | 91.6 |
| NJ/76 vs. FW/50 | 83.0 | 69.8 | 90.9 |

Given the similarity of the NJ/76 HA to that of the Cal/09 HA (and the degree of difference between NJ/76 HA and FW/50 HA), it was determined whether subjects who received the NJ/76 vaccine would have higher titers of stalk-reactive antibodies than those who did not, prior to vaccination with Cal/09. Sera from individuals who received the 1976 vaccine (n=20) were compared to sera from age-matched individuals who did not receive the vaccine (n=15). Endpoint IgG titers against cH6/1 and NC/99 were determined by ELISA. The cH6/1 HA protein contains an H1 stalk, but an H6 head. Since exposure of humans to H6 IAVs is unlikely, this protein serves as a useful tool for the detection of group 1 HA stalk-binding antibodies, as has recently been shown (see, e.g., Pica et al., Proc Natl Acad Sci USA 2012; 109:2573-8). Strikingly, NJ/76 vaccinees had significantly elevated IgG endpoint titers compared to control subjects against cH6/1 HA (FIG. 39A). No significant difference existed between the two groups in IgG endpoint titers against the seasonal NC/99 HA, demonstrating that this phenomenon was specific for HA stalk antibodies (FIG. 39B). Due to the scarcity of samples available, pre- and post-Cal/09 vaccination serum pools were then generated from all patients in both groups for whom both of the samples were available (NJ/76 vaccinees=5/20; Control subjects=7/15). IgG endpoint titers from the pre-Cal/09 vaccination pools from each group were then determined against cH6/1 and NC/99 HAs, to ensure that they accurately reflected the data collected from individual patients (FIGS. 39A and 39B) and could thus be used for downstream applications. Indeed, the NJ/76 vaccinee pool displayed a substantially elevated endpoint titer against cH6/1 HA compared to the control pool (FIG. 39C). However, no differences existed in IgG endpoint titers against NC/99 HA between the two groups (FIG. 39D). These data demonstrate that NJ/76 vaccinees had elevated titers of anti-HA stalk antibodies prior to receiving the Cal/09 vaccine.

6.8.2.2 NJ/76 Vaccinees Had Protective HAI Titers Against Cal/09 Prior to Cal/09 Vaccination Only NJ/76 vaccine recipients had protective HAI titers against Cal/09, while unvaccinated subjects did not (FIG. 40A). To again ensure the reliability of the pooled HAI results, HAI assays were performed against Cal/09 with serum from each individual included in the pools. As was the case with the endpoint titers, results were consistent and significant, demonstrating that the pooled serum gave an accurate representation of the population (FIG. 40B). No HAI activity was observed against France/76 virus (H6N4) in either sample, confirming that none of the subjects had previous exposure to H6 viruses (FIG. 40A). Taken together, these results confirm that NJ/76 vaccinees experienced a boost in HAI antibodies which bind to the globular head of Cal/09 HA prior to Cal/09 vaccination.

6.8.2.3 Anti-HA Stalk Antibody Titers were Boosted in Control Subjects Subsequent to Cal/09 Vaccination The observation that individuals infected with p2009 IAV had elevated titers of anti-HA stalk antibodies (see, e.g., Pica et al., Proc Natl Acad Sci USA 2012; 109:2573-8), as did those immunized with the NJ/76 vaccine, led to investigation of whether vaccination with Cal/09 would also boost anti-HA stalk antibody titers. To this end, both control subjects and NJ/76 vaccinees were administered the monovalent Cal/09 vaccine between October 2009-January 2010. Subjects returned to have their post-vaccination blood drawn six to eight months later. Endpoint IgG titers against NC/99 HA and cH6/1 HA were determined for pooled post-vaccination serum from both groups by ELISA. These were compared to the pre-vaccination values determined in FIGS. 39B and 39D in order to calculate the fold-change in IgG titers against each HA protein post-Cal/09 vaccination (Table 13). Endpoint IgG titers of control subjects rose greater than two-fold against cH6/1, while IgG endpoint titers of NJ/76 vaccinees did not increase. No boost was observed against NC/99 HA in either group, as would be expected. These data indicate that Cal/09 vaccination is also capable of boosting titers of anti-HA stalk antibodies, but only in individuals who had not been previously exposed to NJ/76.

TABLE 13

Post-Cal/09 vaccination IgG endpoint titer changes against NC/99 HA and cH6/1 HA

| HA Protein | Control | | | 1976 Vaccinees | | |
|---|---|---|---|---|---|---|
| | Pre-Cal/09 Vaccination | Post-Cal/09 Vaccination | Fold Change | Pre-Cal/09 Vaccination | Post-Cal/09 Vaccination | Fold Change |
| cH6/1 | N.D. | 200 | >2 | 800 | 800 | 1 |
| NC/99 | 1600 | 1600 | 1 | 1600 | 800 | 0.5 |

*N.D. = not detected 6.8.2.4 Vaccination with NJ/76 or Cal/09 Boosted Neutralizing Antibodies Against Virus Containing Homologous HA Stalk and a Heterologous HA Head It next determined whether the boost in anti-HA stalk antibodies experienced after NJ/76 or Cal/09 vaccination corresponded to enhanced neutralization titers against virus containing a homologous HA stalk and a heterosubtypic HA head domain. To test this, a microneutralization assay was performed against a cH5/1 N3 virus using the pooled sera. The cH5/1 N3 virus was used to detect the presence of HA stalk neutralizing antibodies, as it contains an H5 HA head domain, a PR8 HA stalk, and an N3 from Miss/06. In agreement with the IgG endpoint titer data against cH6/1, sera from NJ/76 vaccinees also exhibited markedly more potent neutralization titers against cH5/1 N3 than did control subjects prior to vaccination with Cal/09 (2430 vs. 90). However, only control subjects experienced a boost in neutralizing antibodies subsequent to vaccination (810, up from 90) (FIG. 41A). NJ/76 vaccinees had neutralization titers against Cal/09 that were 3-fold more potent than control subjects prior to Cal/09 vaccination (90 vs. 30). Both groups experienced a boost in neutralizing antibody titers against Cal/09 subsequent to Cal/09 vaccination (FIG. 41B). Taken together, these data demonstrate that the anti-HA stalk antibodies boosted by vaccination with 1976 and 2009 H1N1 viruses correspond to an enhanced capacity to neutralize virus harboring a homologous HA stalk and a heterosubtypic HA head domain.

6.8.3 Conclusion

This example demonstrates that the 1976 and 2009 H1N1 vaccines, which both contain classical swine H1 HAs, are capable of boosting titers of HA stalk antibodies. Furthermore, anti-HA stalk antibodies elicited by vaccination appear to be long-lived and may provide partial protection against diverse IAV strains.

6.9 Example 9

Chimeric Hemagglutinin Constructs as a Universal Influenza Vaccine

This example demonstrates the protective efficacy of a stalk-specific immune response that can be elicited through vaccination with chimeric hemagglutinin (cHA) constructs, proteins that contain unique hemagglutinin head and stalk combinations.

6.9.1 Materials and Methods 6.9.1.1 Cells and Viruses 293T and MDCK cells were obtained from ATCC and were maintained in Dulbeccos's Modified Eagle's medium (DMEM) and Minimal Essential Medium (both from Gibco). Each were supplemented with 10% fetal calf serum (HyClone), and 100 units/ml of penicillin-100 µg/ml of streptomycin (Pen/Strep, Gibco).

Influenza virus A/Fort Monmouth/1/1947 (FM1) and A/Netherlands/602/2009 were passaged in mouse lungs and then grown in 10 day old embryonated chicken eggs for 48 hours. Low pathogenicity A/Vietnam/1203/04 (VN04): PR82:6 reassortant virus with the polybasic cleavage site removed (see, e.g., Steel et al., 2009, J Virol 83:1742-1753) and B/Yamagata/16/1988 virus were grown in 10-day old embryonated eggs for 48 hours at 37° C. or 72 hours at 33° C., respectively.

Recombinant influenza viruses were produced by reverse genetics system as described above and as previously described (see, e.g., Quinlivan et al., 2005, J Virol 79:8431-8439). cH9/1 N1 virus, a virus expressing the HA globular head domain of an H9 virus atop an H1 stalk (from PR8 virus), and cH5/1 (H5 head (VN04), H1 stalk) N1 viruses were rescued in a similar manner as previously described (see, e.g., Pica et al., 2012, PNAS USA 109:2573-2578). In order to generate the YAM-HA virus, the extracellular domain of the B/Yamagata/16/1988 (WT YAM) HA was substituted with the corresponding domain of A/Puerto Rico/8/1934 virus HA (see, e.g., Hai et al., 2011, Journal of virology 85:6832-6843). The reverse genetic plasmids encoding the other 7 WT YAM viral segments were constructed in a previous study (see, e.g., Hai et al., 2008, J Virol82:10580-10590). Following rescue, cHA-expressing recombinant viruses were propagated in 10 day old embryonated chicken eggs for 48 hours at 37° C. YAM-HA virus was grown in 8-day old embryonated chicken eggs for 72 hours at 33° C.

Recombinant and wild-type viruses were titered on MDCK cells (ATCC) in the presence of TPCK trypsin as described above. cH5/1 N1 virus was partially purified over a 30% sucrose cushion for use in ELISA assays. cH9/1 N1, cH5/1 N1 and FM1 viruses were purified via gradient centrifugation and inactivated with formaldehyde diluted (1:4000) in PBS to be used as positive control vaccines.

6.9.1.2 Generation of cH6/1 and cH9/1 Protein Constructs

Soluble cH6/1 and cH9/1 proteins were generated using a baculovirus expression system as described above and as previously described (see, e.g., Pica et al., 2012, PNAS USA 109:2573-2578). Briefly, baculotransfer vectors were first generated followed by transfection of bacmids into Sf9 cells. Recombinant baculovirus were then used to infect High Five cells at an MOI of 10. Supernatants were harvested 96 h postinfection and then incubated with Ni-NTA resin (Qiagen) for 2 h at 4° C. to purify His-tagged recombinant cHA proteins. The slurry was loaded onto columns, and following washes, was eluted in pH 8 elution buffer (50 mM Na2HCO3, 300 mM NaCl, 250 mM imidazole). Pooled fractions that contained protein were buffer-exchanged in PBS and concentrated using an Amicon Ultra centrifugal filter unit (Millipore) with a 10-kDa molecular mass cutoff in a swinging bucket rotor. Protein purity and identity were tested by SDS/PAGE, Coomassie staining, and Western blot. Final protein concentrations were determined with Bradford reagent.

6.9.1.3 Animals

Animals were allowed access to food and water ad libitum and kept on a 12 hour light/dark cycle. Female 6-8 week old BALB/c mice (Jackson Laboratories) were anesthetized for all intranasal procedures with intraperitoneal (IP) injection of 0.1 ml of ketamine/xylazine (0.15 mg ketamine and 0.03 mg xylazine).

6.9.1.4 Vaccination and Challenge Experiments

Naïve 6-8 week old female BALB/c mice were vaccinated with cH9/1 protein, intranasally (10 ug) in the presence of adjuvant R848 (Invitrogen) and intraperitoneally (10 ug) with Addavax, an MF59-like adjuvant (Invitrogen). Animals were boosted with cH6/1 protein, or BSA (BioRad) three weeks post prime. Booster vaccinations were also administered intranasally (10 ug) and intraperitoneally (10 ug), though with poly I:C as an adjuvant (Invitrogen). Inactivated FM1 virus (1 ug) was administered intramuscularly in a volume of 50 ul as a positive control. Three weeks post boost, animals were bled and sera was harvested, and animals were challenged with 5 LD50 of FM1 virus. Weights were monitored for 14 days post challenge.

In other experiments, animals were primed with cH9/1 encoding plasmid DNA (80 ug, TriGrid delivery system; Ichor Medical Systems) and then boosted three weeks later with cH6/1 or cH9/1 (control) protein administered with polyI:C intranasally (10 ug) and intramuscularly (10 ug). The boost was repeated three weeks later with cH5/1 or cH9/1 (control) protein. Control animals were DNA electroporated with cH9/1 coding DNA as well but were boosted twice with BSA (in a similar way as the treatment group). Positive control animals received either inactivated FM1 or PR8 virus (1 μg) or 1 μg of pH1N1 monovalent split vaccine intramuscularly (BEI). Animals were then challenged 3-5 weeks post boost with 5 LD50 of PR8 or FM1 or 10 LD50 of pH1N1 virus. Animals used for CD8+ T-cell depletion were treated 48 and 24 hours prior to challenge with 300 μg of a anti-CD8+ T-cell antibody (see, e.g., M. L. Salem, 2000, Int. J. Immunopharmacol. 22:707) (from hybridoma line 2.43, purchased from ATCC) and challenged with 5 LD50 of PR8 virus. Weights were monitored for 14 days post challenge. A 20% cutoff was used for all viruses.

For other experiments, mice were inoculated with YAM-HA or WT YAM virus, and then vaccinated with BSA or cH6/1 protein in the presence of poly I:C intramuscularly and intraperitoneally three weeks later. Naïve animals served as an additional control. All animals were bled and challenged 3-5 weeks following vaccination with 250 LD50 cH9/1 N1 virus, or 10LD50 of 2:6 reassortant H5 virus with the polybasic cleavage site removed in the PR8 background (see, e.g., Steel et al., 2009, J Virol 83:1742-1753). Formaldehyde-inactivated cH9/1 N1 virus (1 ug) and cH5/1 N1 virus were administered intramuscularly in a volume of 50 ul as a positive control for the appropriate viral challenge. Animals were euthanized if they lost more than 30% of their initial body weight following challenge, according to institutional guidelines. A 20% cutoff was used for infection with the less pathogenic cH9/1 N1 and A/Netherlands/602/2009 viruses. For challenges using these two viruses, more stringent doses were used in order to appreciate death or substantial weight losses of all controls (250 or 10 LD50).

6.9.1.5 Enzyme Linked Immunosorbant Assay

Immulon 4HBX (Thermo Scientific) plates were coated overnight with partially purified cH5/1 N1 virus diluted to 5 ug/mL in PBS. Plates were blocked for 1 hour with 0.1% Tween 20-PBS (TPBS) containing 3% non-fat milk powder, and then incubated with mouse sera serially diluted in TPBS containing 1% milk powder for 1 hour at room temperature. After three washes, plates were incubated for 1 hour at room temperature with alkaline phosphate (AP) linked anti-mouse IgG (γ-chain specific, Invitrogen). Plates were then washed three times with TPBS, developed with p-nitrophenylphosphate (PNPP) substrate (Zymed), stopped with 0.5M NaOH, and read at the optical density of 405 nm. For all experiments, a Synergy 4 (BioTek) plate reader was used.

Stalk-specific antibody titers were detected by ELISA as described above. PR8 antigens were used to coat ELISA plates in order to quantify stalk-specific reactivity. To detect the neutralization capability of stalk-specific antibodies in vaccinated mice, sera were pooled and total serum IgG was purified.

Pseudoparticles expressing H5 HA were used in a pseudoparticle entry assay as previously described (see, e.g., Hai et al., 2012, J. Virol. 86:5774-5781 and N. Pica et al., 2012, PNAS109:2573-2578). Upon entry, pseudoparticles express a luciferase reporter. Inhibition of this entry by IgG was quantified as the percentage of expression compared to non-IgG treated controls. Because animals had not been exposed to H5 globular head domains, these assays determined the degree to which stalk-specific antibodies produced by vaccination neutralize virus. Monoclonal antibody CR6261 and purified IgG from influenza B wild type infected mice were used as controls.

6.9.1.6 Plaque Reduction Neutralization Assay (PRNA)

Dilutions of mAbs were first pre-incubated with 60 to 80 plaque-forming units (pfu) of virus (cH9N1 influenza A virus) for 1 hour at RT on a shaker. The virus and purified IgG mixture was then used to infect a monolayer of MDCK cells in duplicate in a 12-well format and incubated at 37° C. for 1 hour with intermittent rocking every 10 minutes. The agar overlay was supplemented with corresponding IgG dilutions. At two days post infection (dpi), the monolayer was fixed with 4% PFA/1×PBS for 30 minutes. Cells were blocked with 5% NF-milk/1×PBS for 30 minutes at RT and were incubated accordingly with either with an H9 specific monoclonal antibody (5 μg/mL) for 1 hour at RT. An anti-mouse secondary conjugated to HRP was used as a secondary at a 1:1000 dilution. Plaques were visualized using TrueBlue peroxidase substrate (KPL Inc.) and the reaction was stopped with tap water. Plaques were counted for each antibody and percent inhibition calculated over the no mAb group.

6.9.1.7 Statistical Tests

Statistical analyses were performed using a one tailed student's T test (Prism4, GraphPad). For FIG. 44C, all values are plotted as averages with standard error of the mean. Differences in survival were calculated with Kaplan Meier survival analysis with log rank significance test.

For analyses with P-values, P-values at or below 0.05 are considered statistically significant. Welch's correction was used if variances were determined to be statistically different. P-values at or below 0.05 are considered statistically significant. When comparing stalk serum reactivity to maximum weight loss in FIG. 3, one value was detected as an outlier (modified Z-score>3.5 standard deviations above the mean) according to the methods of Iglewicz and Hoaglin (see Iglewicz, B. a. H., D. 1993. Volume 16: How to detect and handle outliers. In E. Mykytka (ed.), The ASQC Basic References in Quality Control: Statistical Techniques. American Society of Quality Control), and was omitted from analyses.

6.9.2 Results 6.9.2.1 Sequential Vaccination with cHA Constructs Elicits HA Stalk-Specific Antibodies and Provides Protection from Lethal Influenza Challenge It was hypothesized that constructs that express globular head domains from viruses with different antigenicities could stimulate polyclonal responses towards the stalk domain of the HA. To test this, mice were first vaccinated with cH9/1 soluble protein with adjuvant, whereby the stalk of the HA is from A/Puerto Rico/8/1934 (PR8) virus and the head from an H9 isolate. Three weeks post prime, mice were boosted with a second soluble cHA, cH6/1 (head from H6 virus, stalk from PR8 virus), with the intent of stimulating humoral responses towards the stalk domain of the molecule. (Mice vaccinated with inactivated FM1 virus served as a positive control). Three weeks post boost, mice were bled to assess serum reactivity to the H1 stalk domain, and then challenged with mouse-adapted A/Fort Mounmoth/1/1947 (FM1) virus. As shown in FIG. 42A, vaccinated mice produced serum antibody responses towards the HA stalk domain. Following challenge with FM1, animals lost a considerable amount of weight (FIG. 42B), though recovered after day 7 for an overall survival rate of 90% (FIG. 42C). Even though mice had only been exposed to the globular head domains of H9 and H6 viruses, it was verified that all mice were HI negative to FM1 virus, and thereby confirmed that the protection elicited from vaccination was the result of an immune response specific to the stalk domain. Therefore, vaccination with PR8-based cHAs provides stalk-specific immunity that is protective in the face of an FM1 virus challenge.

6.9.2.2 Vaccination with cH6/1 Protein Elicits Stalk-Specific Immunity that Mediates Protection from cH9/1 N1 Virus Challenge Although antibody responses were generated towards the stalk by administering two different soluble cHA constructs, a substantial degree of morbidity was seen following FM1 challenge. Because mice are immunologically naïve to influenza virus, it was possible that multiple exposures to influenza virus followed by the introduction of an antigenically distinct head was required in order to induce high serum antibody titers against the HA stalk. Enhanced stimulation of serum antibody titers with specificity to the hemagglutinin stalk may also require infection, and may explain why a robust protection following prime and boost with cHA proteins alone was not observed.

In order to stimulate immune responses towards the viral hemagglutinin, but not generate protective immunity to other viral proteins, a recombinant B/Yamagata/16/1988 virus was constructed that expresses the ectodomain of the HA from PR8 virus (YAM-HA) (see, e.g., Hai et al., 2011, Journal of virology 85:6832-6843). Mice were inoculated with YAM-HA in order to mimic prior exposures to influenza virus, and then vaccinated 3 weeks later with BSA or cH6/1 protein. As an additional control, mice were infected with wild-type B/Yamagata/16/1988 (WT YAM) virus and vaccinated with BSA. An influenza A virus that expressed the cH9/1 (H9 head, H1 stalk) was then used as the challenge virus, in order to definitively demonstrate the protective nature of an immune response directed only towards the HA stalk. Again, because animals were exposed to the globular head domains from H1 and H6 viruses, the protection seen following challenge with a virus that expressed the cH9/1 HA was most likely a result of immunity towards the H1 stalk domain.

As shown in FIG. 43A, animals that received cH6/1 protein vaccine following YAM-HA exposure were completely protected from 250 LD50 challenge with a cH9/1 expressing virus in the PR8 background. Animals vaccinated with cH6/1 soluble protein lost statistically less weight on days 3, 4, and 5 compared to animals that were vaccinated with BSA. This protection from weight loss resulted in increased survival in the group vaccinated with cH6/1, compared to the cohort vaccinated with BSA ($p=0.038$; FIG. 43B). Naïve animals and those inoculated with WT YAM were not protected from infection, demonstrating that any protection that was seen in the other vaccination groups was not a result of viral replication, but was instead a specific response to the H1 stalk domain. Because animals were exposed to the globular head domains from H1 and H6 viruses, and were HI negative to the cH9/1 challenge virus, it is believed that the protection seen here is a result of immunity towards the H1 stalk domain.

Figure 43D:
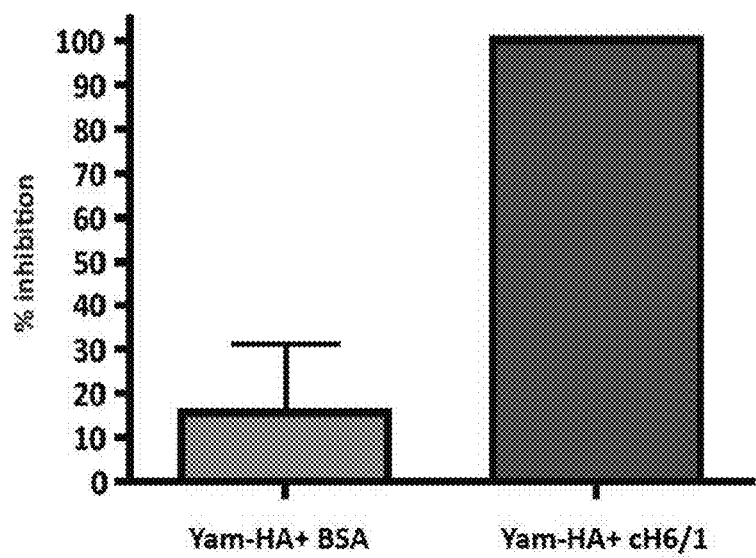
Figure 43E:
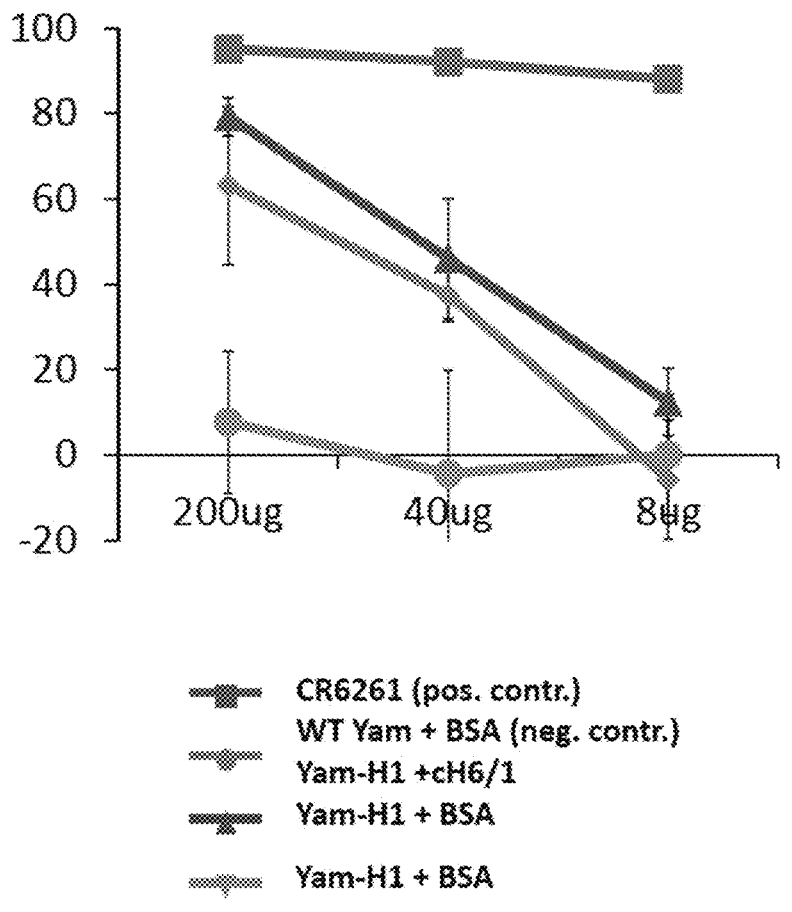

It is of note that monoclonal antibodies with specificities to the HA stalk have been isolated from individuals infected with or vaccinated against seasonal H1N1 viruses (see, e.g., Corti et al., 2010, The Journal of clinical investigation 120:1663-1673; Corti et al., 2011, Science 333:850-856; Ekiert et al., 2011, Science 333:843-850; Sui et al., 2009, Nat Struct Mol Biol 16:265-273; Throsby et al., 2008, PLoS One 3:e3942), and stalk titers have been appreciated in individuals not infected with the pH1N1 virus, although at lower levels (see, e.g., Pica et al., 2012, PNAS USA 109:2573-2578). As such, it is not surprising that YAM-HA inoculated animals were able to generate some degree of stalk titer. Vaccination with the cH6/1 construct, however, increased serum stalk titers by 4 fold (reciprocal dilutions that yielded equivalent OD values) (FIG. 43C, and protected animals from substantial weight loss and death (FIGS. 43A and 43B). Vaccination with the cH6/1 construct elicited the production of stalk-specific IgG that neutralized virus with 100% efficiency (YAM-HA+BSA) (FIG. 43D) whereas serum from prime only animals exhibited neutralizing levels barely above background (YAM-HA+BSA). Indeed, animals inoculated with YAM-HA and then vaccinated with BSA had statistically similar survival rates to those that were inoculated with WT YAM virus and vaccinated with BSA ($p=0.058$). In contrast, the use of cH6/1 protein as a vaccine yielded 100% survival from challenge, a rate that was highly significant when compared to that of animals inoculated with WT YAM (p<0.0001). Survival was also enhanced when compared to that of mice inoculated with YAM-HA and vaccinated with BSA (p=0.038). These differences were not reflected in the pseudoparticle entry assay, as IgG from YAM-HA+BSA mice and YAM-HA+cH6/1 mice inhibited the entry of pseudoparticles encoding an H5 HA with similar efficiency (FIG. 43E). It is important to note that the latter assay only detects the ability of antibodies to block entry of pseudoparticles. Therefore, the effects of stalk-antibodies downstream of entry and/or their interaction with infected (immune) cells would not be detected in this assay. This might explain why differences in neutralization were not observed between the two groups and did not reflect the in vivo findings. Nonetheless, the antibodies elicited by these infection protocols were stalk specific and were broadly neutralizing. Because the challenge virus only encodes the stalk domain from an H1 virus, it can be concluded that the protection seen was the result of the host immune response to the HA stalk domain that was stimulated through cH6/1 vaccination.

Figure 44A:
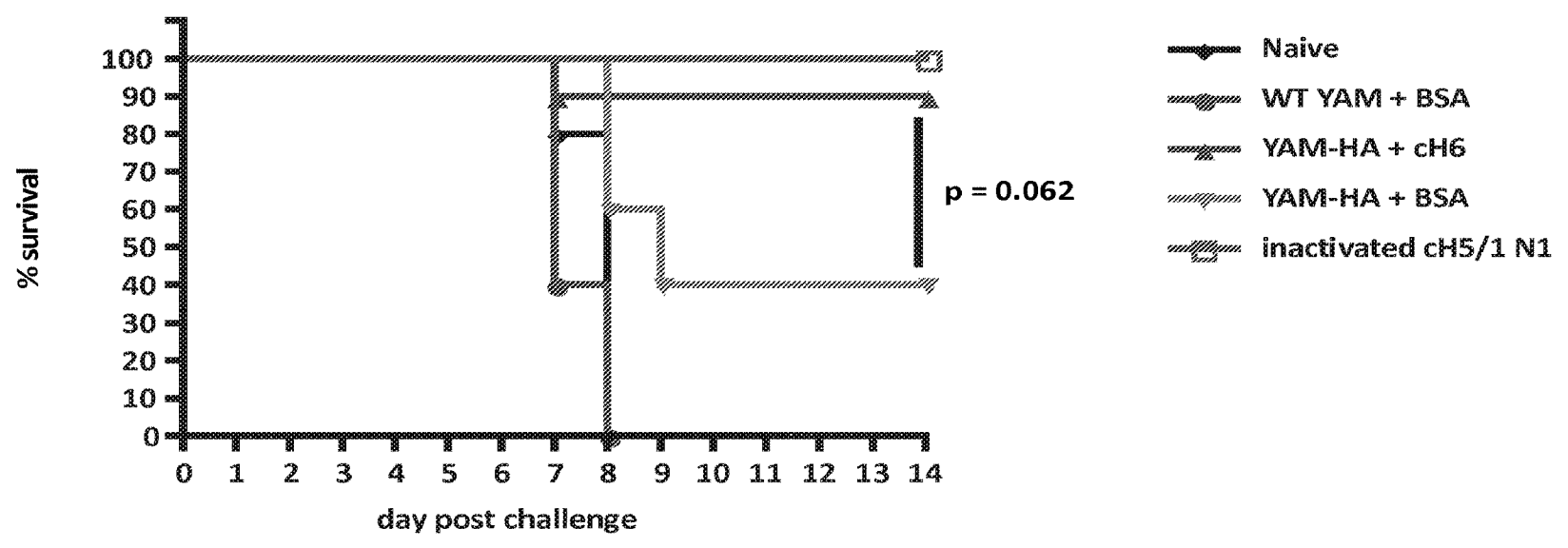
Figure 44B:
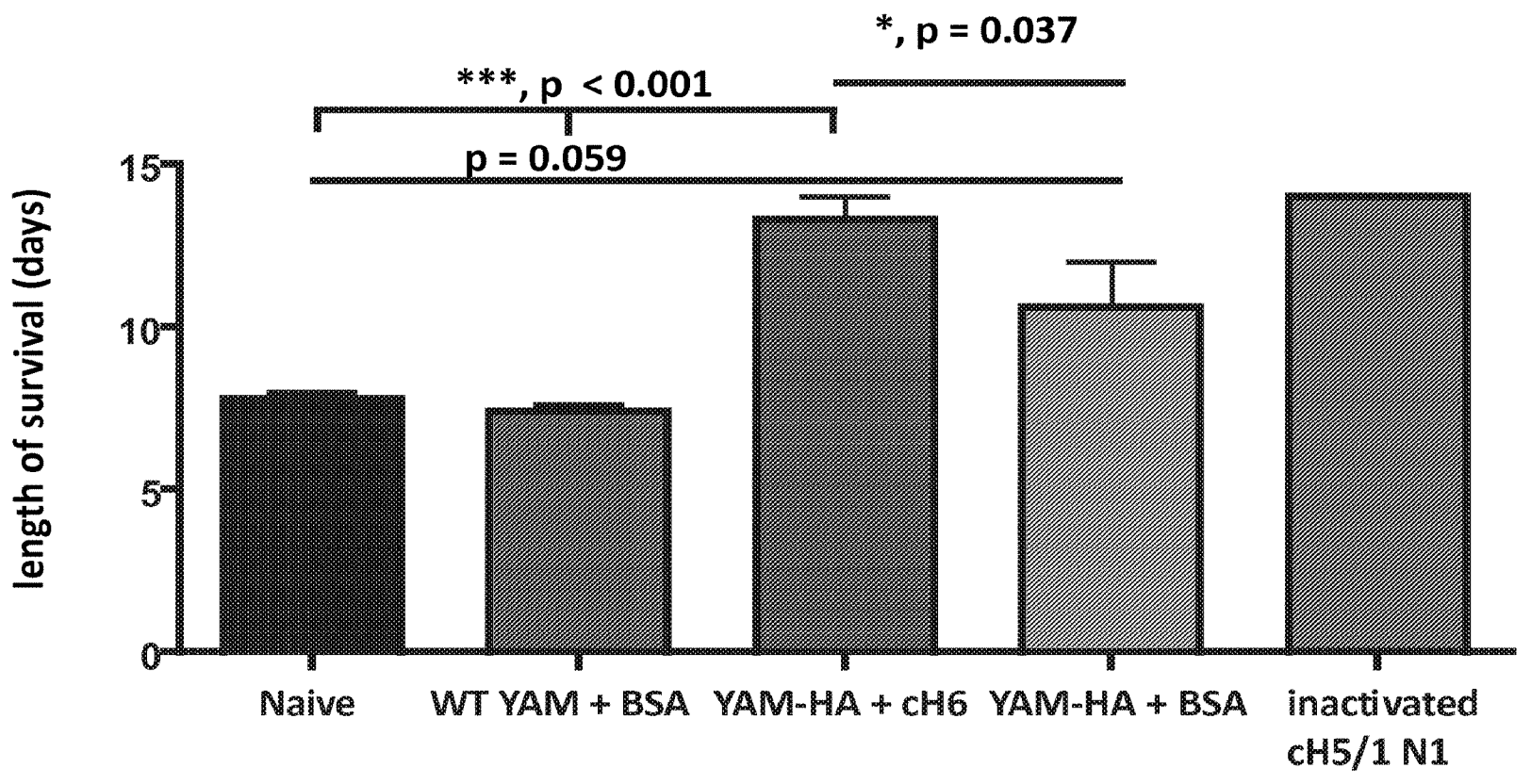
Figure 44C:
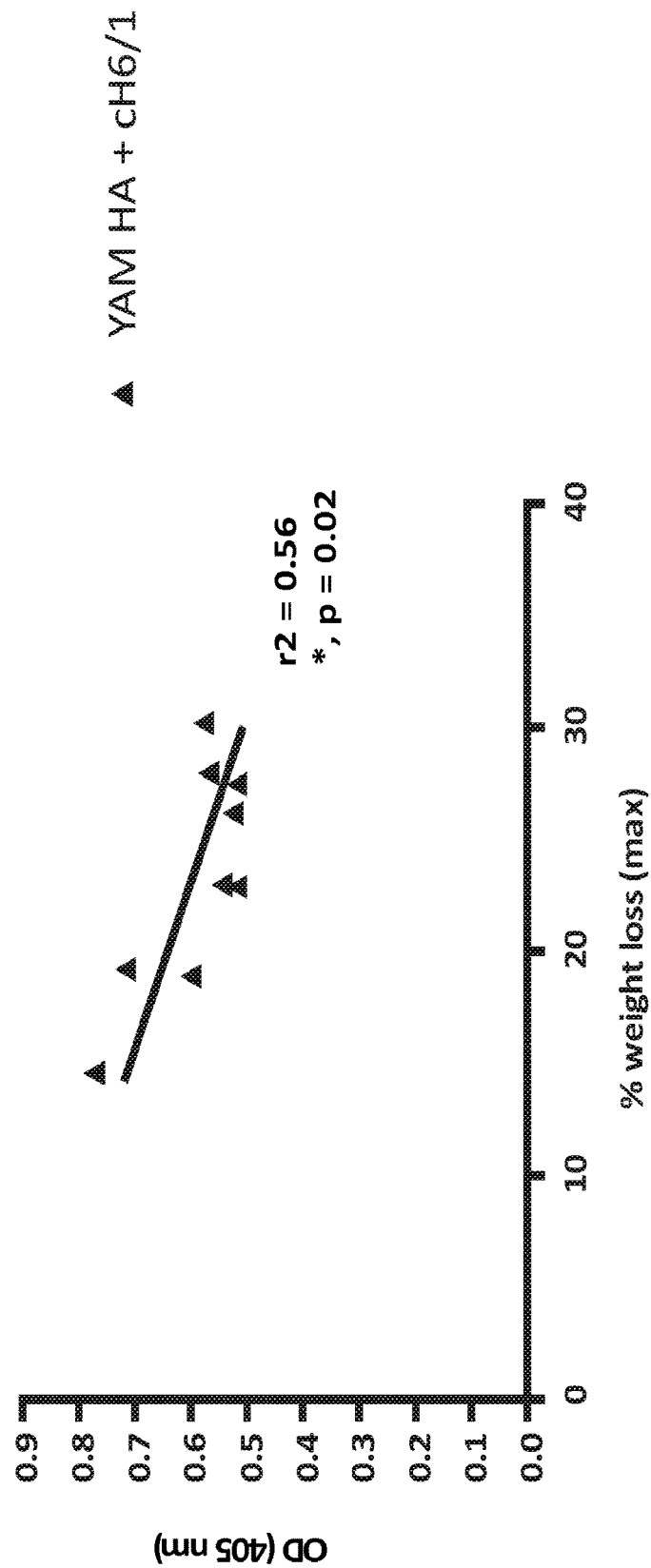

6.9.2.3 Vaccination with cH6/1 Protein Protects Mice from Lethal H5 Influenza Virus Challenge Whether vaccination with cH6/1 protein could protect mice from challenge with an H5 virus was next ascertained. Mice were inoculated and vaccinated as described above, and challenged with 10 LD50 of a 2:6 reassortant virus that expresses the HA and NA from A/Vietnam/1203/2004 virus in the PR8 background (see, e.g., Steel et al., 2009, J Virol 83:1742-1753). As expected, naïve animals and those inoculated with WT YAM virus were not protected from challenge and succumbed to infection by day 8. Animals inoculated with YAM-HA virus and vaccinated with BSA were marginally protected from challenge, with a survival rate of 40%. Increased protection was seen when animals were vaccinated with cH6/1 protein, with 90% survival. The difference in survival rates between the two vaccine groups approached statistical significance (p=0.06), although mice vaccinated with cH6/1 protein survived for a statically longer time (p=0.037) (FIGS. 44A and 44B). When comparing reactivity to the HA stalk to the % maximal weight loss over the monitoring period following H5 challenge, an inverse correlation was detected, whereby animals with higher serum stalk titers tended to lose less weight following challenge (FIG. 44C), supporting the notion that cH6/1 can boost HA-stalk based immunity.

Using challenge viruses with HA globular head domains to which vaccinated mice were immunologically naïve and HI negative, the results indicate that protection from challenge following vaccination was solely based on an immune response towards the HA stalk. To exclude the possibility that cross reactive antibodies towards the receptor binding site could be playing a role in the protection seen here, mice were all tested for HI and found to be HI negative to their respective challenge viruses.

Figure 45A:
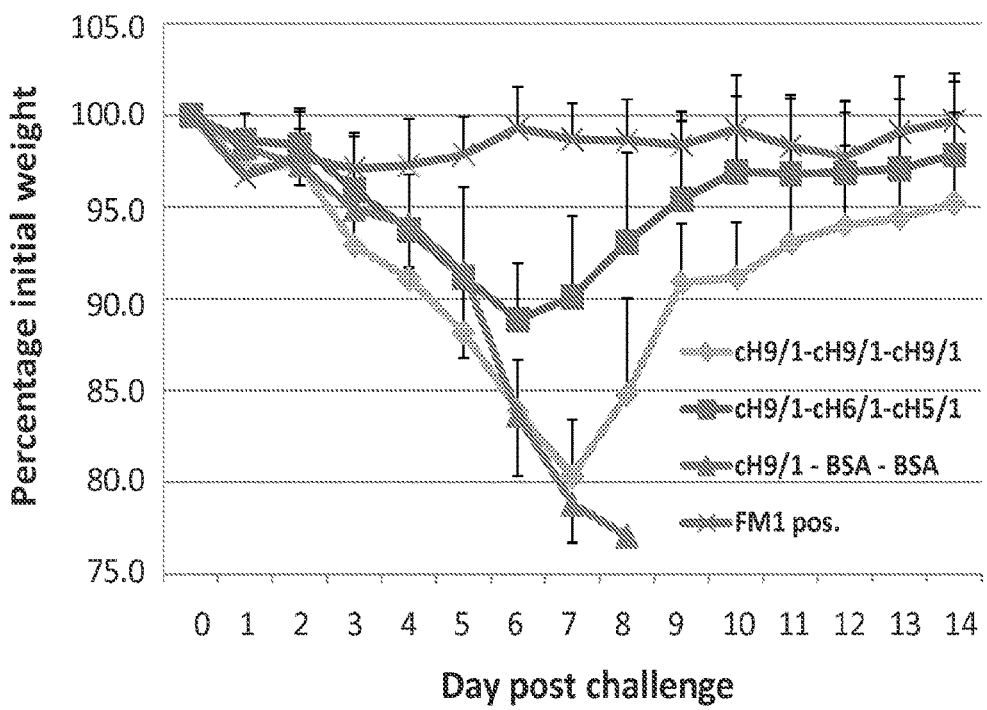
Figure 45B:
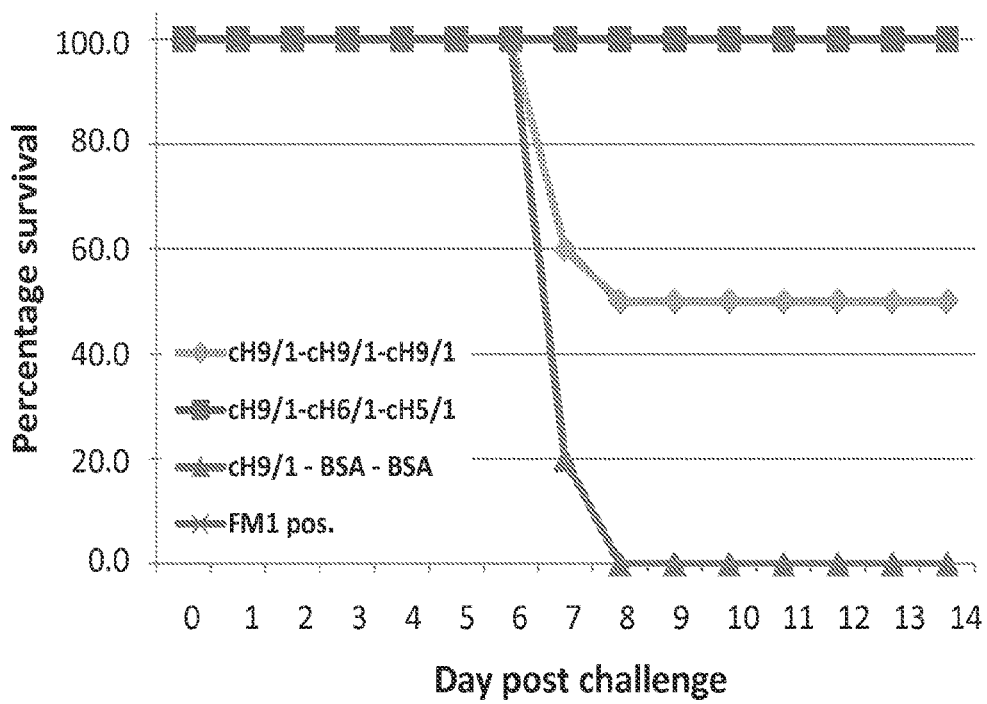
Figure 45C:
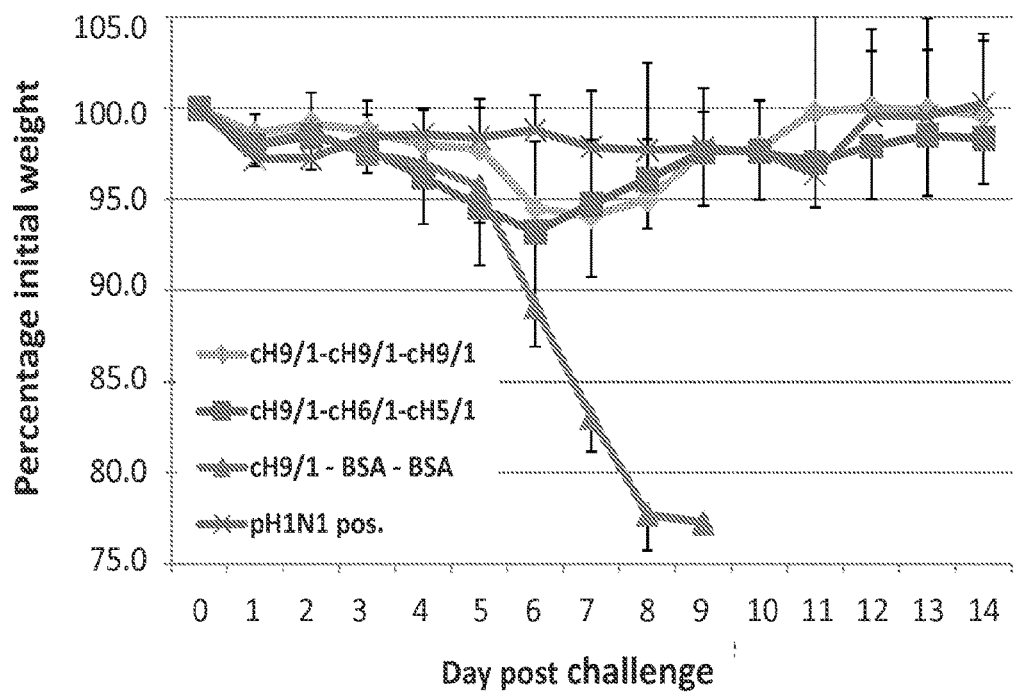
Figure 45D:
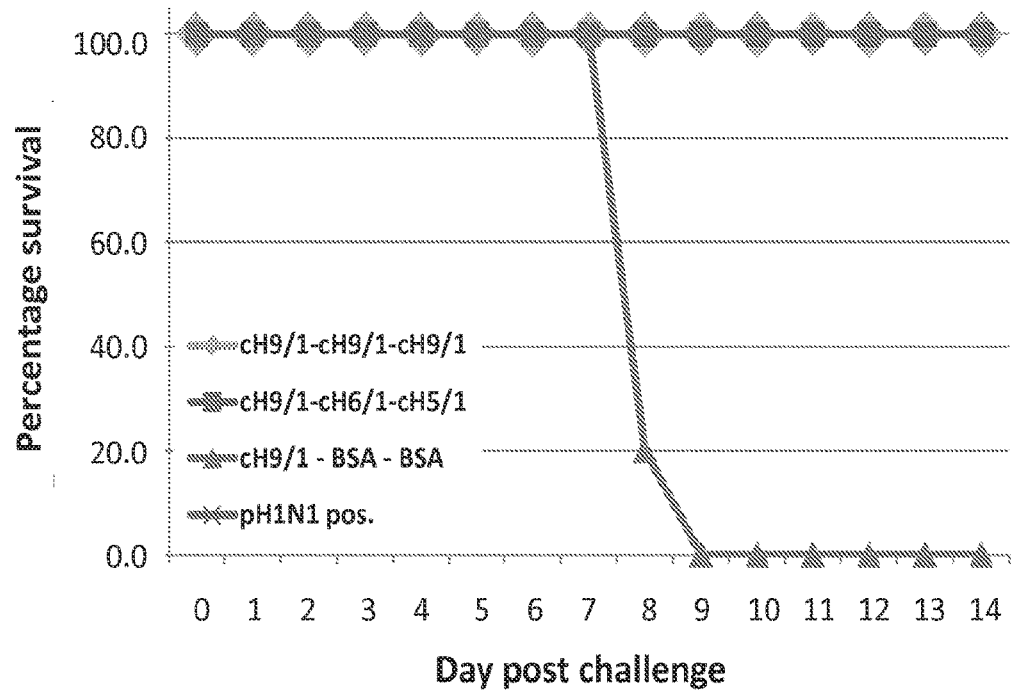
Figure 45E:
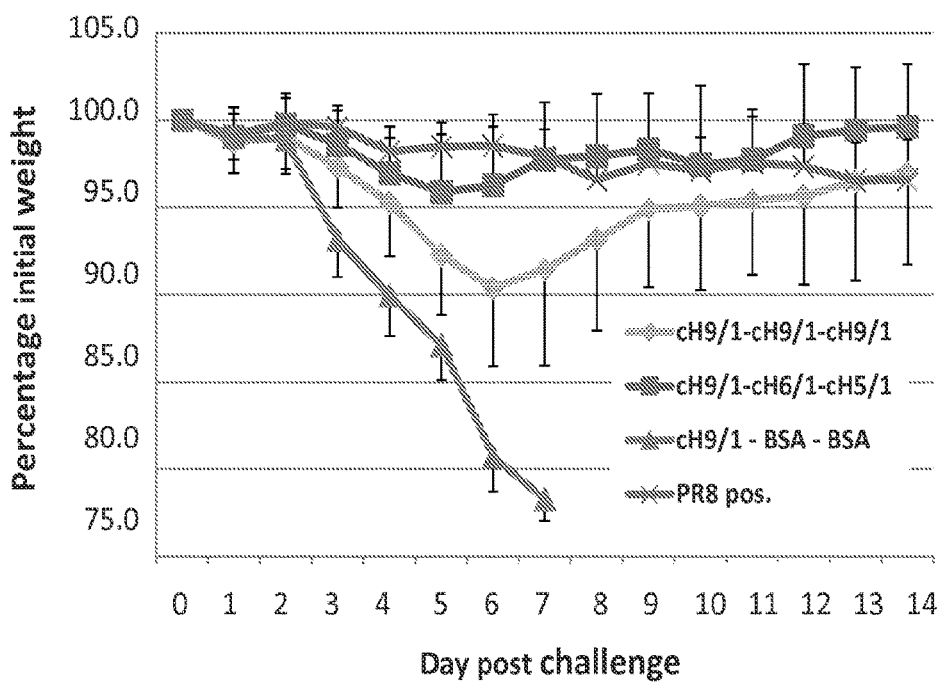
Figure 45F:
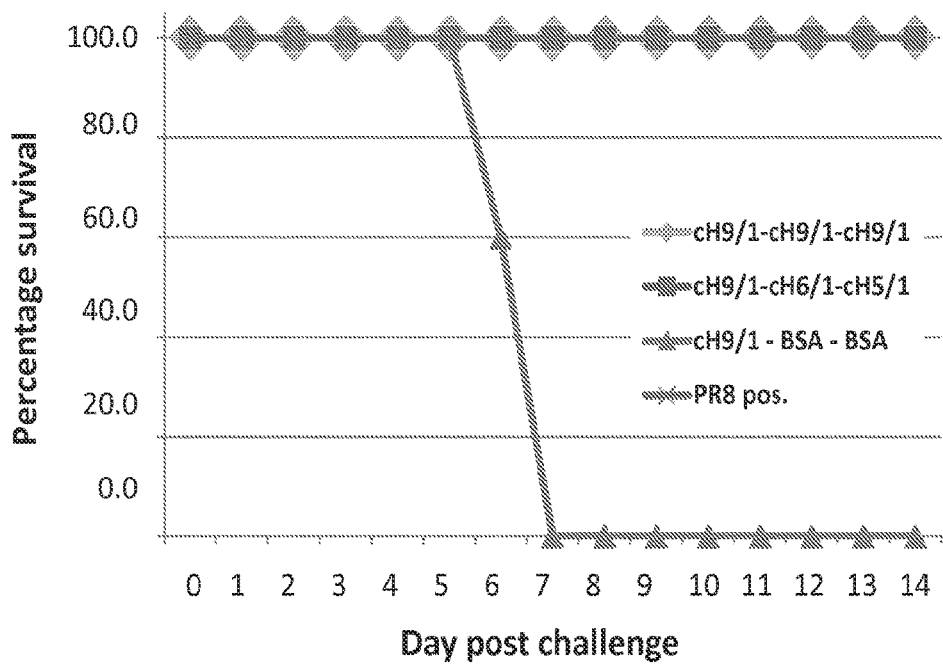
Figure 45G:
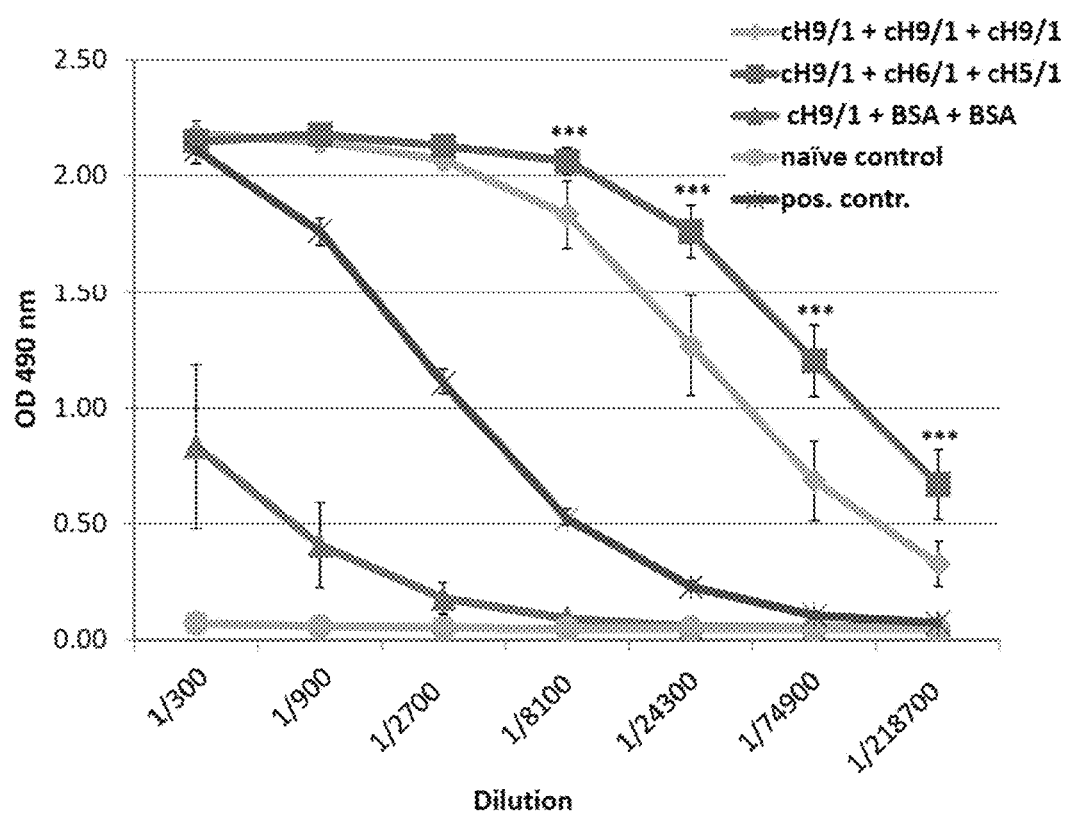
Figure 45H:
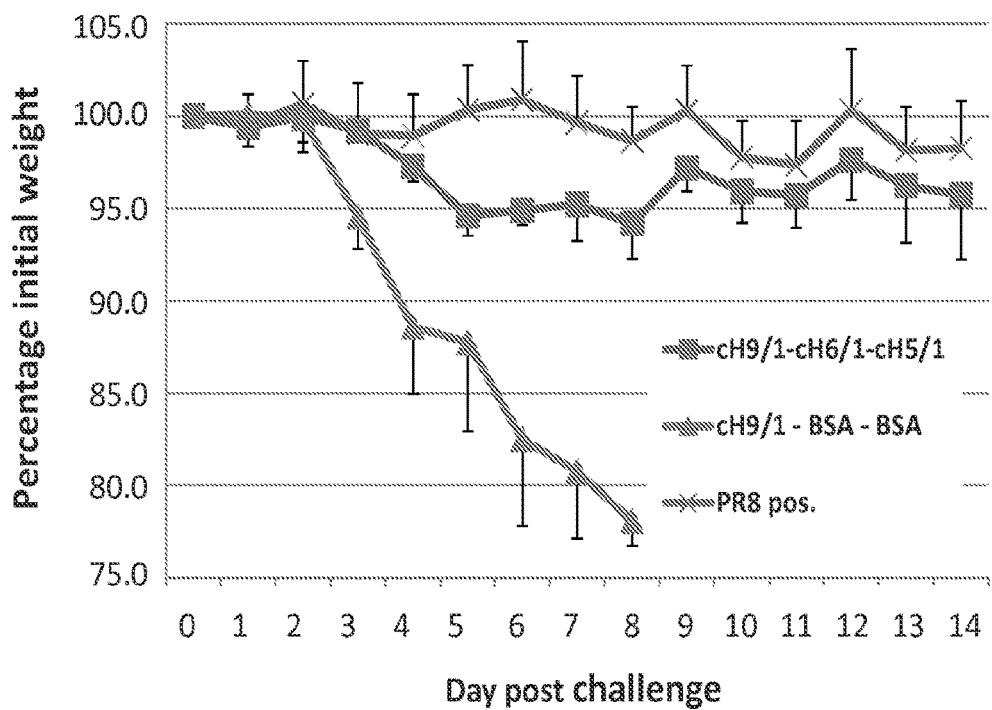
Figure 45I:
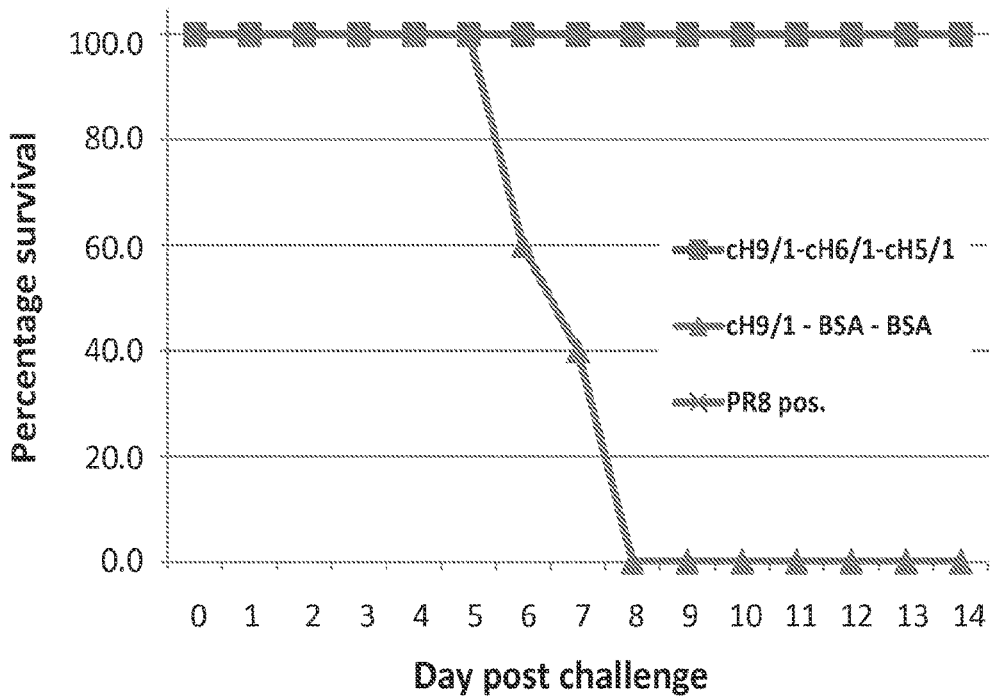

6.9.2.4 Vaccination with cHA Elicits Stalk-Specific Immunity that Mediates Protection from H1N1 Virus Challenges Stalk-specific antibodies have been detected in human sera (see, e.g., FIGS. 27A and 27B; M. Thorsby et al., 2008, PLoS One 3:e3942, D. C. Ekiert et al., 2009, Science 324:246-251, D. C. Ekiert et al., 2011, Science 333:843-850, J. Wrammert et al., 2011, J. Exp. Med. 208:181-193 and N. Pica et al., 2012, PNAS109:2573-2578). Because it is possible that previous exposure to influenza virus HA is critical to the robust production of a stalk specific immune response, it was ascertained whether preexisting immunity to the influenza virus in mice could be recapitulated. It was hypothesized that this would more effectively protect against morbidity following virus challenge. To achieve this, mice were primed with a DNA expression vector (see, e.g., J. Steel et al, 2010, MBio 1(1), pii:e00018-10) that encodes cH9/1, then were boosted with soluble cH6/1 protein, followed by cH5/1 protein (H5 head, H1 stalk), and finally challenged with a panel of H1N1 viruses (FIGS. 45A-45F). Following infection with FM1 (FIGS. 45A and 45B), A/Netherlands/602/2009 (pH1N1) (FIGS. 45C and 45D) and PR8 viruses (FIGS. 45E and 45F), all cHA-vaccinated animals were protected from challenge and displayed only minimal amounts of weight loss, if any. In contrast, negative control animals that received BSA following priming with cH9/1 DNA lost considerable amounts of weight and, with the exception of one animal, succumbed to infection by day 9 (FIGS. 45A-45F). The survival of the cHA-vaccinated animals in each of the challenge experiments was significantly different from that of controls (FIGS. 45B, 45D and 45F). To confirm that the protection elicited was a result of stalk-specific humoral immunity, all mice were confirmed to be HI negative to each challenge virus though the sera were capable of binding H1 HA by ELISA (FIG. 45G), confirming the production of stalk specific antibodies by our vaccination protocol. Because it is possible that CD8 T cells directed towards epitopes within the HA stalk could be playing a role in the protection seen here (see, e.g., M. Tamura et al., J. Virol. 72:9404-9406), mice were vaccinated and depleted of CD8 T cells by administering monoclonal antibody 2.43 prior to PR8 challenge (M. L. Salem, 2000, Int. J. Immunopharmacol. 22:707-718). Depletion did not affect weight loss nor survival outcomes, implicating a humoral response in the protection elicited by vaccination (FIGS. 45H and 45I). Therefore, an adaptive humoral immune response towards the HA stalk, and not the head, was providing protection against the three different H1N1 viruses.

Figure 45J:
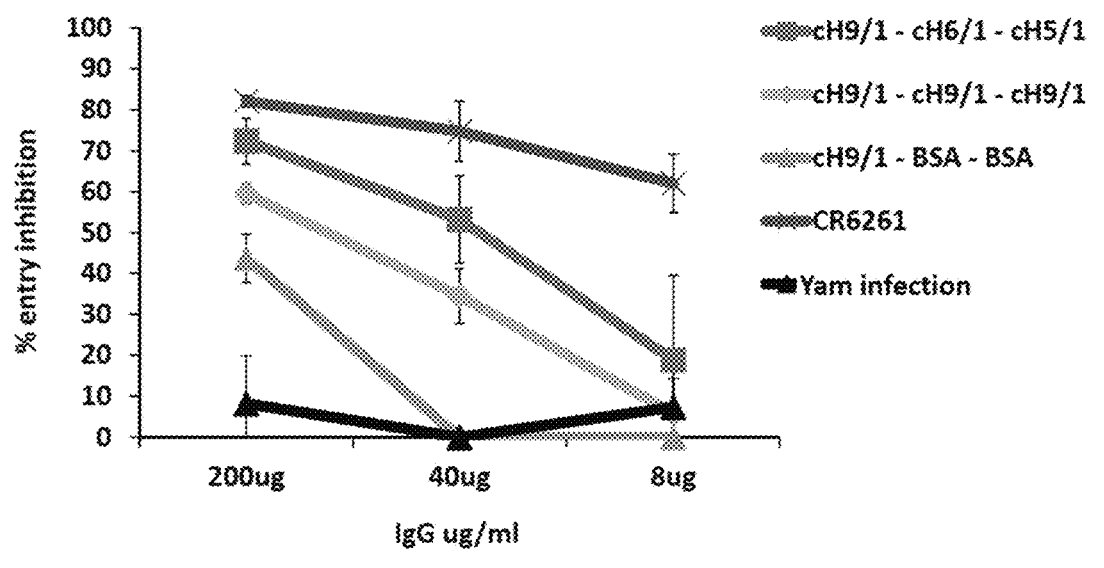

In order to further validate that the cHA-based vaccination protocol induced stalk-specific antibodies with neutralizing capability against other subtypes, the ability of purified IgG from vaccinated mice to block the entry of pseudoparticles that harbor an H2 HA was tested. Because pseudoparticles express a luciferase reporter gene following entry, neutralizing activity was measured by the absence of luciferase enzymatic activity in cell supernatants (R. Hai et al., 2012, J. Virol. 86:5774-5781 and N. Pica et al., 2012, PNAS 109:2573-2578). Consistent with the protection seen following challenge, IgG purified from vaccinated mice inhibited the entry of pseudoparticles in a dose-dependent manner and with similar efficacy to that of CR6261, a monoclonal antibody with specificity to the HA stalk that was used as the positive control (FIG. 45J). The vaccination protocol, therefore, elicited stalk antibodies with broad specificities, capable of neutralizing other group 1 HAs like H2.

6.9.3 Conclusion

This example demonstrates the protective effect of a stalk-specific immune response that can be elicited through vaccination with chimeric HAs. It was demonstrated that an immune response directed towards the HA stalk was sufficient for protection from viral challenge, and that this vaccination protocol provided heterosubtypic protection. A similar strategy could be developed in humans to provide protection against a broad range of influenza viruses, negating the need for annual vaccination, and enhancing pandemic preparedness.

6.10 Example 10

Hemagglutinin Stalk Reactive Antibodies are Boosted Following Sequential Infection of Seasonal and Pandemic H1N1 Influenza Virus in Mice This example demonstrates that infection with a seasonal influenza virus followed by infection with a pandemic influenza strain stimulates the production of stalk-specific antibodies in mice, validating a mouse model of human influenza infection and a concomitant stalk antibody immune response.

6.10.1 Material and Methods

6.10.1.1 Cells and Viruses 293T and MDCK cells were obtained from ATCC and were maintained in Dulbeccos's Modified Eagle's medium (DMEM) and Minimal Essential Medium (both from Gibco), respectively, each supplemented with 10% fetal calf serum (HyClone), and 100 units/ml of penicillin-100 µg/ml of streptomycin (Pen/Strep, Gibco). Influenza virus strains A/New Caledonia/20/99 (NC99) (H1N1), A/Solomon Islands/3/2006 (SI06) (H1N1), A/Puerto Rico/8/1934 (PR8) (H1N1), A/Fort Monmouth/1/1947 (FM1) (H1N1), A/California/04/2009 (Cal09) (93 H1N1) and a low pathogenicity. A/Vietnam/1203/04 (VN04):PR82:6 reassortant virus (H5N1) (see, e.g., J. Steel et al., 2009, J. Virol. 83:1742-1753) were grown in 10-day old embryonated eggs for 48 hours.

In order to construct a cold-adapted virus with PR8 antigenicity, an A/Ann Arbor/6/60 based-rescue system was generated by reverse transcription of viral genes (Transcriptor RT, Roche) from purified virion RNA, PCR amplification (PFU turbo, Stratagene) and cloning into the vector pPOL1 (see, e.g., E. Fodor et al., 1999, J. Virol 73:9679-9682) following the recombinational protocol described by Wang et al. (see, e.g., S. Wang et al., 2008, J. Virol. Methods 151:74-78). A/Ann Arbor/6/60 plasmids encoding PB1, PB2, PA, NP, M, and NS were used with those encoding HA and NA from the PR8 strain to rescue a PR8-based cold-adapted virus. The cold adapted virus was grown in 10 day-old embryonated chicken eggs for 48 hours. In order to construct a PR8 virus with a deletion in the nonstructural protein 1 (NS1), a plasmid that only encodes the first 73 amino acids of NS1 was used in addition to the seven other PR8-based rescue plasmids. Following its rescue, the virus was propagated in 8 day old embryonated chicken eggs for 48 hours (see, e.g., S. A. Kopecky-Bromberg, 2009, Vaccine 27:3766-3774).

Recombinant and wild-type viruses were titered on MDCK cells (ATCC) in the presence of TPCK trypsin as previously described (6). Viruses were inactivated following formaldehyde treatment for 72 hours at 4° C.

6.10.1.2 Recombinant Baculovirus Generation, Protein Expression, and Purification In order to generate NC99, Cal09, cH6/1 (globular head domain from H6N1 A/mallard/Sweden/81/02, stalk domain from PR8), or VN04 HA and VN04 NA, a baculovirus based expression system was employed as previously described (N. Pica et al., 2012, PNAS109:2573-2578). Briefly, baculotransfer vectors were transformed into *Escherichia coli* strain DH10Bac (Invitrogen), and colonies were picked and grown up. Bacmids were prepared using a Plasmid 116 Midi Kit (Qiagen) and then transfected into Sf9 cells with Cellfectin II (Invitrogen) according to the manufacturer's instructions. Recombinant baculovirus was amplified in Sf9 cells grown in TNM-FH medium (Gemini Bioproducts), and then used to infect High Five cells grown in HyClone SFX insect cell media (Thermo Fisher Scientific) at an MOI of 10. Supernatants were harvested 96 hours postinfection and then incubated with Ni-NTA resin (Qiagen) for 2 hours at 4° C. to purify His 122 tagged recombinant HA proteins. The slurry was loaded onto columns and washed three times with washing buffer (50 mM Na2HCO3, 300 mM NaCl, 20 mM imidazole, pH 8). Protein was eluted in 0.5-mL steps with elution buffer (50 mM Na2HCO3, 300 mM NaCl, 250 mM imidazole, pH 8) and tested for protein content with Bradford reagent, and fractions containing protein were pooled. Pooled fractions were buffer-exchanged in PBS and concentrated using an Amicon Ultra centrifugal filter unit (Millipore) with a 10-kDa molecular mass cutoff in a swinging bucket rotor. Protein purity and identity were tested by SDS/PAGE, Coomassie staining, and Western blot. Final protein concentrations were determined with Bradford reagent.

6.10.1.3 Animals

All animal experiments were performed in accordance with the guidelines of the Mount Sinai School of Medicine Institutional Animal Care and Use Committee. Animals were allowed access to food and water ad libitum and kept on a 12 hour light/dark cycle. Female 6-8 week old BALB/c mice (Jackson Laboratories) were anesthetized for all intranasal procedures with intraperitoneal (IP) injection of 0.1 ml of ketamine/xylazine (0.15 mg ketamine and 0.03 mg xylazine).

6.10.1.4 Infection and Vaccination

Groups of five 6-8 week old female BALB/c mice were anesthetized and inoculated intranasally with 50 ul of $10^4$ PFU of either NC99, SI06 or Cal09 viruses, $10^3$ or $10^4$ PFU of cold adapted PR8 virus or $10^3$ or $10^4$ PFU of an NS1-truncated PR8 virus diluted in PBS. Mice also received 1 µg of formaldehyde-inactivated PR8 or FM1 virus or the commercial trivalent split vaccine containing 1 µg of A/Brisbane/57/07 (TIV) H1 HA (the dose also contained 1 µg of the H3 component A/Uruguay/716/07 and the B component B/Brisbane/60/08) administered intramuscularly in a volume of 50 ul. Additionally, two groups of mice were vaccinated with 80 µg of pCAGGS plasmid encoding either PR8 or NC99 HA using a TriGrid electroporation device (Ichor Medical Systems) (see, e.g., J. Steel, 2010, MBio 1(1), pii:e00018-10). Four weeks following infection or vaccination, animals were bled retro-orbitally and serum was harvested from whole blood.

Following infection with NC99 virus, mice were intranasally inoculated with $10^5$ or $10^6$ PFU of SI06 virus or with $10^3$ or $10^4$ PFU of Cal09 virus diluted in PBS. Three days post-boost, three animals per group were euthanized with $CO_2$ and lungs were harvested and homogenized with a FastPrep-24 homogenizer (MP). Lung virus titers were measured by titration on MDCK cells. Four weeks following the second infection, animals were bled retro-orbitally and serum was harvested from whole blood.

6.10.1.5 Enzyme-Linked Immunosorbant Assay and Psuedoparticle Entry Assay

Immulon 4HBX (Thermo Scientific) plates were coated overnight with purified baculovirus expressed NC99, Cal09, cH6/1 or VN04 HA (all with a C-terminal T4 foldon) or VN04 NA (with a N-terminal tetramerization domain) in coating buffer (0.1 M Na2CO3/NaHCO3, pH 9.2, 50 µl/well) or PBS (N. Pica et al., 2012, PNAS109:2573-2578). Plates were blocked for 1 hour with 0.1% Tween 20-PBS (TPBS) containing 3% non-fat milk powder, and then incubated with mouse sera serially diluted in TPBS containing 1% milk powder for 1 hour at room temperature. After three washes, plates were incubated for 1 hour at room temperature with a secondary horseradish peroxidase (HRP) conjugated anti-mouse IgG antibody (Sigma) or an alkaline phosphate (AP) linked anti-mouse IgG (γ-chain specific, Invitrogen). Plates were then washed three times with TPBS and developed. When the HRP secondary was used, plates were developed using SigmaFAST OPD substrate (Sigma) (100 ul/well), stopped with 3M HCl and read at 490 nm. When an AP-linked secondary antibody was used, plates were developed with p-nitrophenylphosphate (PNPP) substrate (Zymed), stopped with 0.5M NaOH, and read at the optical density of 405 nm. For all experiments, a Synergy 4 (BioTek) plate reader was used. For ELISA experiments detecting reactivity to H5 HA, sera from mice infected with $10^5$ PFU of an NS1-truncated A/Vietnam/1203/2004 virus were used as a positive control.

6.10.1.6 Purification of Mouse IgG from Polyclonal Sera

Mouse sera were diluted in PBS (pH 7.4) and passed through a 0.45 um sterile filter unit. Filtered sera were loaded on a column containing 3 ml of 4 FastFlow Sepharose G (GE Healthcare). The column was washed with 60 ml of PBS and total IgG was eluted with a 0.1 M glycine HCl buffer (pH 2.7) and immediately neutralized using a 2 M TRIS-HCl buffer (pH 10) (A. Jungbauer et al., 1989, J. Chromatogr 476:257-268). Eluted IgG was then concentrated and buffer exchanged (to PBS) using Amicon Ultra-cell (Millipore) centrifugation units with a cut-off of 30 kDa. Protein concentration was measured on a NanoDrop 2000 Spectrophotometer using the A280 method.

6.10.1.7 Pseudotyped Particle Neutralization Assay

The procedure for pseudotype particle production was adapted 185 from previous studies and has been previously described (see, e.g, M. J. Evans, 2007, Nature 446:801-805, R. Hai et al., 2012, J. Virol. 86:5774-5781 and N. Pica et al., 2012, PNAS109:2573-2578). Briefly, 293 T cells were co-transfected with four plasmids encoding a pro-virus containing a luciferase reporter gene, HIV Gag-Pol, the chimeric cH5/1 hemagglutinin protein (A/Viet Nam/1203/04 H5 head domain and PR8 stalk domain) an a neuraminidase from influenza B virus B/Yamagata/16/88. Supernatants were collected 48 hours post-transfection and subsequently filtered (0.45 μm pore size) in order to purify the cH5/1 particle preparations. Particles were then incubated with different concentrations of purified mouse IgGs and added to MDCK cells. Transductions proceeded for 6 hours before cells were washed and fresh media was placed over cells. All transductions were performed in the presence of 1 μg/mL polybrene (Sigma, St. Louis, Mo.). Luciferase assays were performed 48 hours after transduction.

6.10.1.8 Passive Transfer Experiment

Mice (n=5 per group) were intraperitoneally inoculated with 200 ul of sera from groups that were infected with NC99 virus, NC99 followed by Cal09 or SI06 virus, or with sera from naïve animals. Two hours post-inoculation mice were anesthetized and challenged with 5 MLD50 of VN04: PR82:6 reassortant (see, e.g., J. Steel et al., 2009, J. Virol. 83:1742-1753). Weight loss was monitored daily for 14 days and mice that lost more than 30% of their initial body weight were scored dead and euthanized. Statistical analyses were performed using Prism4 (GraphPad). Differences in survival were calculated with Kaplan Meier survival analysis with log rank significance test. P-values at or below 0.05 are considered statistically significant.

6.10.2 Results 6.10.2.1 Stalk-Reactive Antibodies are Induced Upon Infection with Seasonal or Pandemic H1N1 Virus, but not by Vaccination Groups of five mice were sublethally infected with $10^4$ PFU of NC99, SI06 or Cal09 virus and bled four weeks later for the assessment of serum stalk antibody titer. In order to determine the degree of stalk antibodies induced by infection, cH6/1 protein, a soluble HA construct that contains the stalk of an H1 virus and the head of an H6 virus, was used (see, e.g., N. Pica et al., 2012, PNAS109:2573-2578). This reagent allows for the direct detection of stalk-specific antibodies in polyclonal sera. All mice infected with a seasonal or a pandemic virus produced antibodies with reactivity to the HA stalk (FIG. 46). In contrast, animals that were primed with DNA encoding PR8 or NC99 HA, or those that received inactivated PR8 or FM1 vaccine or the commercial split vaccine intramuscularly did not have any reactivity to cH6/1 by ELISA, despite their seroconversion to the antigen they were vaccinated with. When animals were vaccinated with $10^3$ or $10^4$ of a cold-adapted or live virus attenuated via NS1 truncation, stalk-specific antibody titers were barely above background. Sera from mice vaccinated with a headless hemagglutinin construct (see, e.g., J. Steel et al., 2010, MBio 1(1), pii:e00018-10) and stalk-specific monoclonal antibody 6F12 were used as positive controls (see, e.g, G. S. Tan et al., 2012, J. Virol. 86:6179-6188). Since the replication level of the attenuated viruses was lower than that of wild type viruses, and inactivated/DNA vaccines did not induce stalk-reactive antibodies, it is hypothesized that the initial induction of these antibodies was greatly enhanced by replication competent virus.

6.10.2.2 A Boost with Pandemic H1N1 Elicits Higher Titers of Stalk-Reactive Antibodies than with a Drifted Seasonal H1N1 Isolate Animals primed with $10^4$ PFU of NC99 virus were boosted four weeks post-prime with two different doses of SI06 ($10^5$, $10^6$ PFU; "NC/SI") or Cal09 ($10^3$, $10^4$ PFU; "NC/Cal"). Four weeks later, mice were terminally bled and sera were analyzed for the presence of stalk reactive antibodies using recombinant cH6/1 protein. All animals that received a second inoculation of virus had elevated stalk titers compared to mice that had only been infected with NC99 (FIG. 47). Indeed, the effect was dose dependent, as animals that received the lower dose ($10^3$ of Cal09 or $10^5$ PFU of SI06 virus) had a weaker boost than those that received a higher dose ($10^4$ PFU of Cal09 or $10^6$ of SI06 virus). It is of note, however, that NC/Cal infected animals exhibited a stronger induction of stalk titer compared to the NC/SI infected group. In fact, in order to generate comparable serum stalk titers to the NC/Cal group, 1000 fold more of the seasonal virus SI06 was required (FIG. 47). In order to confirm seroconversion to primary and secondary infections, all sera were tested for reactivity to recombinant NC99 and Cal09 HA protein by ELISA.

Based on the finding that replication strongly enhances the elicitation of stalk directed antibodies, it was ascertained whether the increased boost in anti-stalk titer seen in Cal09 infected animals could be a result of enhanced replication capability of the virus. Three days post boost, NC/Cal and NC/SI animals were sacrificed and lung tissues were collected. Although SI virus was not detected in the lungs of sequentially infected mice, Cal09 virus grew to $10^5$ PFU/mL by this time point.

6.10.2.3 Elicited Stalk-Reactive Antibodies have Neutralizaing Activity in Vitro In order to assess the neutralizing capability of these stalk-specific antibodies a pseudotyped particle neutralization assay was used. Pseudoparticles that expressed an HA with an H1 stem and an H5 head (cH5/1) were engineered to harbor a luciferase 253 reporter gene that would be expressed following the successful entry of the pseudoparticle into cells. Entry was therefore measured as a function of luciferase expression. Because animals were only exposed to H1N1 viruses, any inhibition of entry would be a result of neutralizing antibodies directed towards the HA (H1) stalk. Due to the limited amount of serum available, only the relative neutralization efficiency of purified IgG preparations of serum from mice that were primed with NC99 virus but then were boosted with $10^3$ Cal09 virus or $10^5$ SI06 virus was tested. Serum from mice that were infected with Cal09 alone was used as an additional point of comparison. Monoclonal antibody 6F12 (see, e.g, G. S. Tan et al., 2012, J. Virol. 86:6179-6188), a stalk specific antibody with broad group 1 specificity, was used as a positive control.

Greater than 90% inhibition was seen with as little as 50 ug/mL of purified IgG from either NC/Cal or NC/SI mice. It is of note that IgG isolated from NC/Cal mice and NC/SI mice were able to inhibit the entry of cH5/1 expressing pseudoparticles with similar efficiencies at 50 or 10 ug/mL. IgG from mice infected with only Cal09 virus displayed low levels of entry inhibition, which was similar to the levels seen for naïve mice. Again, this reflects the relative stalk-antibody titers in this group, as shown in FIG. 47.

6.10.2.4 Stalk-Reactive Antibodies Protect from Heterologous Challenge in a Passive Transfer Experiment In order to assess the in vivo protective efficacy of such antibodies, sera from sequentially infected animals were administered intraperitoneally to naïve mice, followed by challenge with an H5N1 reassortant virus in the PR8 background (VN04). Animals that received sera from mice sequentially infected with seasonal and pandemic viruses (NC99 $10^4$ PFU-Cal09 $10^4$ PFU) were partially protected from challenge, with an 80% rate of survival. Mice that were only exposed to drifted seasonal strains (NC99 $10^4$ PFU-SI06 106 PFU) were also partially protected from challenge (60% survival). Mice that only received a single inoculation of NC99 virus ($10^4$ PFU) were not protected from challenge, and all succumbed to infection by day 9 (FIG. 48).

Differences in survival between the two prime-boost groups were not statistically significant (p=0.575). However, survival of sequentially infected mice was statistically different to that of prime-only (NC99/SI06 p=0.018, NC99/Cal09 p=0.0023) and control mice (NC99/SI06 p=0.0031, NC99/Cal09 p=0.0031), indicating that elevated levels of stalk reactive antibodies are able to protect from heterosubtypic challenge.

Because the findings correlated well with the degree of serum reactivity to the HA stalk for each of the experimental groups, the reactivity of HA from the VN04 virus was assessed. As expected, reactivity to the H5 HA was highest in the group that experienced both seasonal and pandemic virus infections. While mice that were infected with drifted seasonal strains displayed a higher degree of reactivity to the HA from VN04 virus compared to mice inoculated only once with $10^4$ PFU of NC99 virus, this titer was still lower than that of the NC99/Cal09 group, where 100 fold less virus was used for the boost. In order to rule out the potential contribution of N1-specific antibodies to the degree of protection seen here, serum antibody titers were assessed by ELISA. Titers were equivalent irrespective of the virus used to boost the initial NC99 virus infection. Boost with a seasonal or pandemic H1N1 virus similarly enhanced NA antibody titer over the response seen following one virus infection.

6.10.3 Conclusion

This example recapitulates in mice the findings that individuals infected with pH1N1 virus have higher stalk-specific antibody titers compared to uninfected individuals (see, e.g., Example 6.8). In this mouse model of influenza infection, the infection of mice with a seasonal H1N1 virus followed by exposure to the pandemic H1N1 strain boosted HA stalk antibody titers to a greater extent than sequential infection with drifted seasonal H1N1 viruses.

6.11 Example 11

Directing Humoral Immune Response Against Influenza Hemagglutinin Towards the Conserved Stalk Domain by Changing Glycosylation This example demonstrates that the immune system can be guided to produce antibodies to the conserved stalk domain of influenza viruses by masking the antigenic sites in the influenza head domain through the introduction of glycosylation sites and by making antigenic sites more accessible in the stalk domain through the removal of glycosylation sites.

6.11.1 Materials and Methods 6.11.1.1 Generation and Cloning of Deletion and Hyper-Glycosylation Mutants N-linked glycosylation is programmed by the Asn-X-Ser/Thr sequence motif within proteins, where X can be any amino acid but proline. Removal of individual glycosylation sites or combinations thereof of A/PR/8/34 HA, was performed by mutating the Asn residue to the closely related Gln, using site directed mutagenesis (Stratagene, Santa Clara, Calif.). The reverse strategy was used to introduce extra N-linked glycosylation sites on the globular head domain of HA by creating extra Asn-X-Ser/Thr sequence motifs in the variable antigenic sites. Mutated genes were introduced into the pCAGGS protein expression plasmid or pDZ plasmid for virus rescue (see, e.g., E. Fodor et al., 1999, J. Virol. 73:9679-9682 and R. Hai et al., 2008, J. Virol. 82:10580-10590)

6.11.1.2 Immunofluorescence Assays

293 T cells were transfected with pCAGGS plasmid coding for wild type and glycosylation mutants of A/PR/8/34 or cH5/1 hemagglutinin. Twenty-four hours post-transfection cells were fixed with 0.5% PFA/1×PBS for 30 minutes at room temperature (RT) and blocked with 5% NF-milk/1×PBS for 30 minutes at RT. MAbs were diluted in 5% NF-milk/1×PBS and incubated at RT for 1 hour at a final concentration of 5 μg/mL. Positive control sera were diluted 1:100. The cell monolayer was washed three times with 1×PBS and then incubated with an Alexa Fluor 488 donkey anti-mouse IgG (Invitrogen) at a dilution of 1:1000 for 1 hour at RT. Fluorescence reactivity was visualized using an Olympus IX70 inverted fluorescence microscope.

6.11.1.3 Western Blot

SDS-PAGE (Biorad) and Western blot analysis was performed with reduced cell lysates of transfected cells, using antibody NR-4539 and an anti-mouse horseradish peroxidase conjugated secondary antibody (Santa Cruz Biotechnology). The NR-4539 monoclonal anti-influenza A virus HA2 antibody was obtained through the NIH Biodefense and Emerging Infections Research Resources Repository, NIAID.

6.11.1.4 Hemadsorption Assays

Transfected cells were incubated with neuraminidase (Sialidase) from *Vibrio cholera* (Roche) for 1 hour at 37° C. and washed 3 times with 1×PBS containing 0.01% $CaCl_2$ and $MgCl_2$. Next, the cell monolayer was incubated for 30 minutes at ice with a 2% suspension of chicken red blood cells in PBS/CaCl2/MgCl2 and washed again 3 times with PBS/CaCl$_2$/MgCl$_2$. Attached red blood cells were lysed by adding 50 mM NH$_4$Cl and shaking cells for 15 minutes. Lysate was removed from cells and absorbance was measured at 540 nm.

6.11.1.5 Virus Rescue

Rescue of influenza A viruses from plasmid DNA was performed as previously described (see, e.g., E. Fodor et al., 1999, J. Virol. 73:9679-9682, R. Hai et al., 2008, J. Virol. 82:10580-10590 and G. Neumann et al., 1999, PNAS 96:9345-9350). To generate the recombinant wild-type (rWT) PR8 virus, 293T cells were co-transfected with 1 µg of each of the 8 pDZ PR8 rescue plasmids using Lipofectamine 2000 (Invitrogen, Carlsbad, Calif.). The viruses expressing different glycomutant HAs were generated in the same way but substituting the HA plasmid by the corresponding plasmid coding for the mutant HA sequence to recover the corresponding mutant viruses. 24 hours post-transfection, virus-containing supernatant was inoculated into 8-day old embryonated chicken eggs. Allantoic fluid was harvested after 2 days of incubation at 37° C. and assayed for the presence of virus by hemagglutination of chicken red blood cells and by plaque formation in MDCK cells (see, e.g., E. Fodor et al., 1999, J. Virol. 73:9679-9682 and R. Hai et al., 2008, J. Virol. 82:10580-10590).

6.11.2 Results 6.11.2.1 Influenza Glycosylation Mutants are Expressed and Appropriately Hyper- or Hypo-Glycosylated Up to 7 extra glycosylation sites were introduced into the globular head domain of PR8 (see Table 3). In addition, deletions to glycosylation sites 31 and 289 in the stalk domain of PR8 were created. HA mutants bearing such globular head domain mutations alone, as well as in combination with the stalk domain mutations were created and analyzed.

TABLE 3

PR8 head domain glycosylation mutants

| Clone # | Head Glycans (amino acid residue, H3 numbering) | | | | | | | | |
|---|---|---|---|---|---|---|---|---|---|
| | 81 | 131 | 142 | 158 | 165 | 172 | 189 | 195 199 | 210 |
| 42-1 | X | X | | X | X | X | X | | X |
| 42-4 | X | X | | X | | X | X | | X |
| 42-5 | | X | | X | X | X | X | | X |

In order to determine if the mutated HA proteins were expressed and the introduced glycosylation sites had been glycosylated in vitro, 293 T cells were transfected with the HA mutant constructs and Western blot analysis performed on the cell lysates. Probe of the Western blot with an anti-influenza A HA2 antibody showed that all of the viral constructs were expressed (FIG. 49). The differential migration of the influenza protein on the Western blot indicated that glycans had been added in a manner corresponding to the number of glycosylation sites introduced. Constructs in which a glycosylation site(s) had been added migrated at a higher molecular weight compared to wildtype PR8, while those in which a glycosylation site(s) had been deleted migrated at a lower molecular weight relative to wildtype PR8 (FIG. 49). The binding of antisera from mice infected with wildtype PR8 to the constructs was reduced, suggesting that binding sites for the antibodies in the sera were covered by the added additional glycans sites.

Figure 50A:
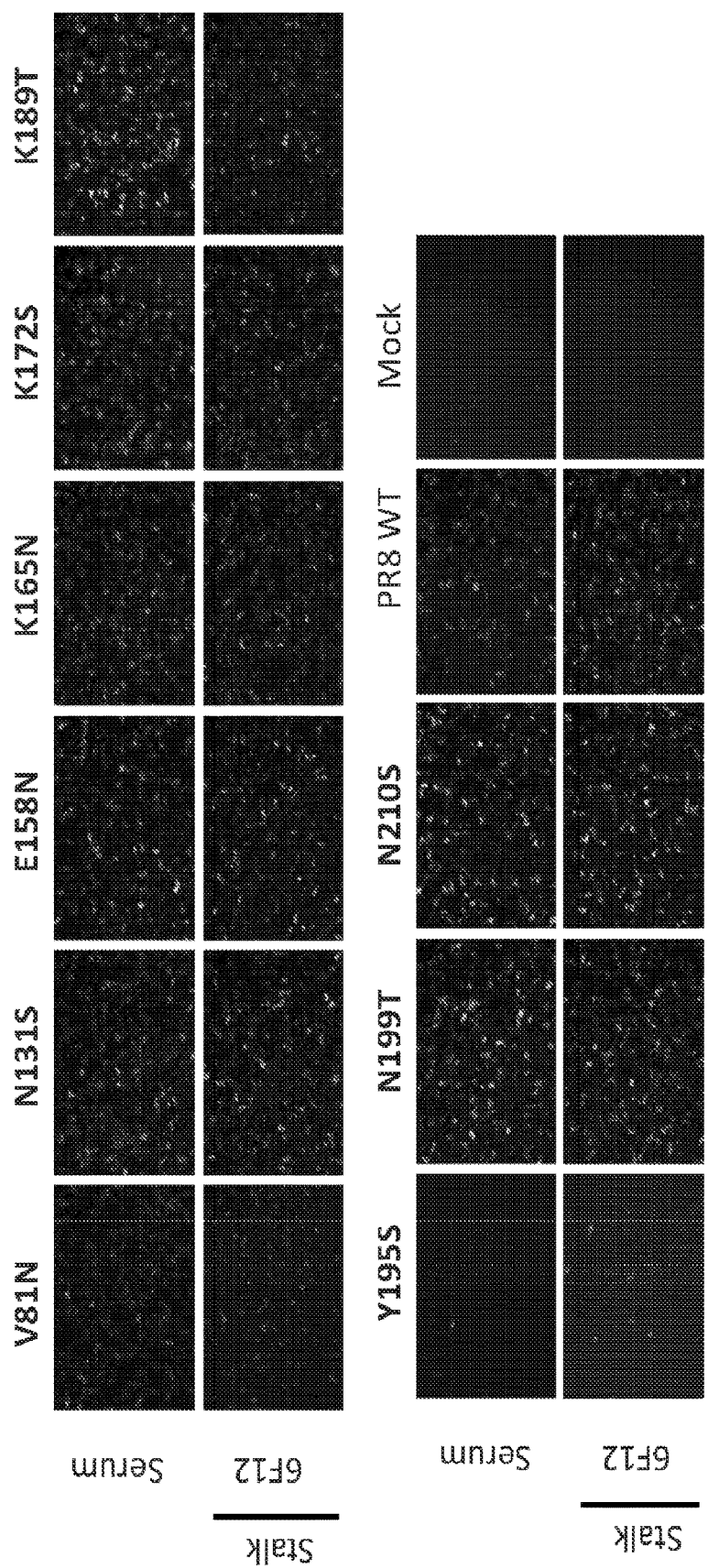
Figure 50B:
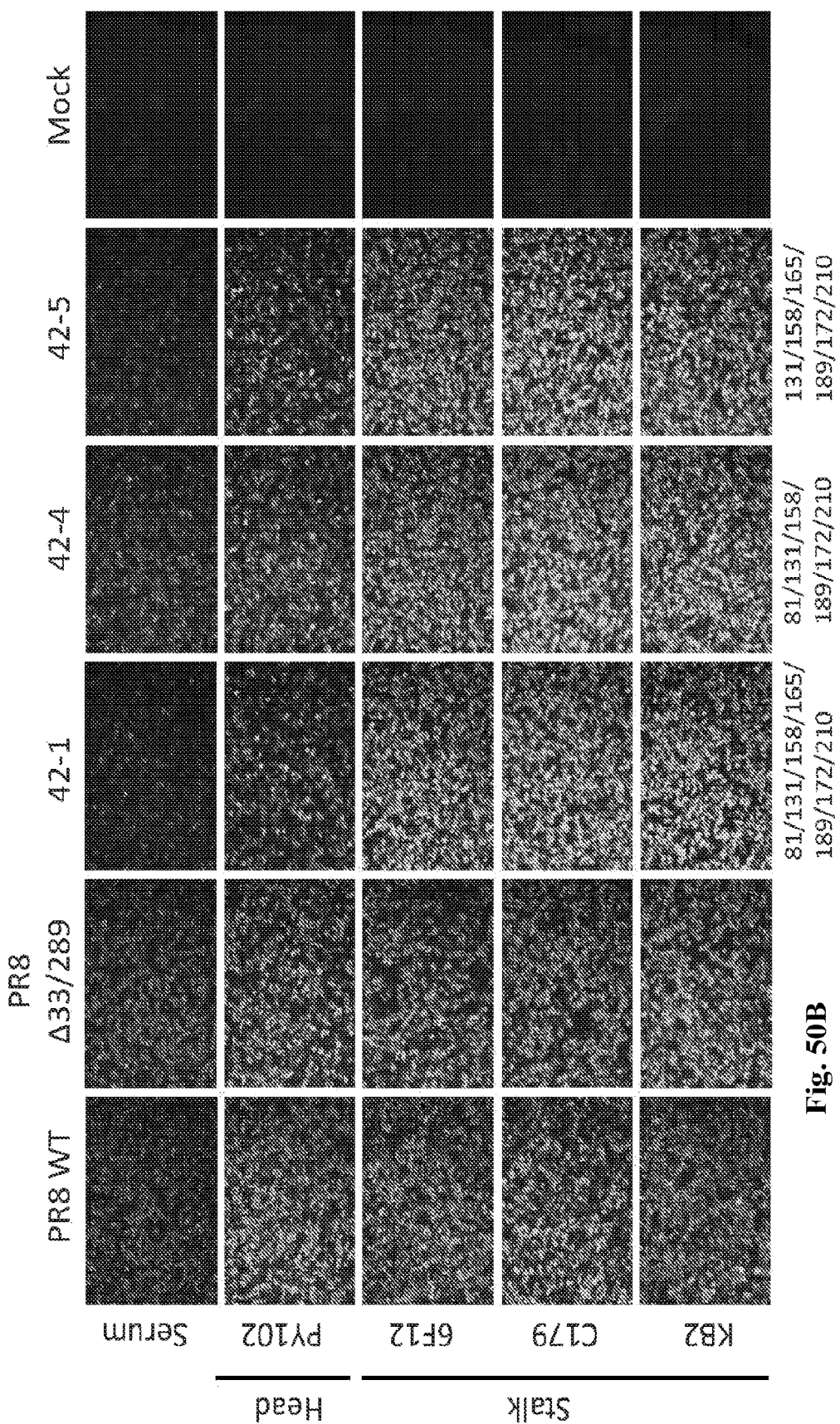

Immunofluorescence was used to compare the expression levels of the mutant HA constructs in vitro and to determine whether the glycosylation mutant HA proteins had properly folded into their native conformation. Introduction of individual glycosylation sites in the globular head domain of HA at all four antigenic sites still allowed protein expression and HA stalk domain-specific antibody binding (FIG. 50A). The addition of glycosylation sites in the HA globular head domain resulted in diminished anti-head domain specific antibody immunofluorescence signal (PY102 antibody) compared to wildtype PR8 HA, indicating that antigenic sites in the head domain of HA were indeed masked by glycosylation at the introduced sites (FIG. 50B and Table 4).

TABLE 4

Expression of and antibody binding to influenza glycosylation mutants

| | | Antibody binding | |
|---|---|---|---|
| Clone # | Expression | Head PY102 | Stalk 6F12/ C179/ KB2 |
| 42-1 | +/− | +/− | ++ |
| 42-4 | + | + | ++ |
| 42-5 | +/− | +/− | ++ |

Figure 50C:
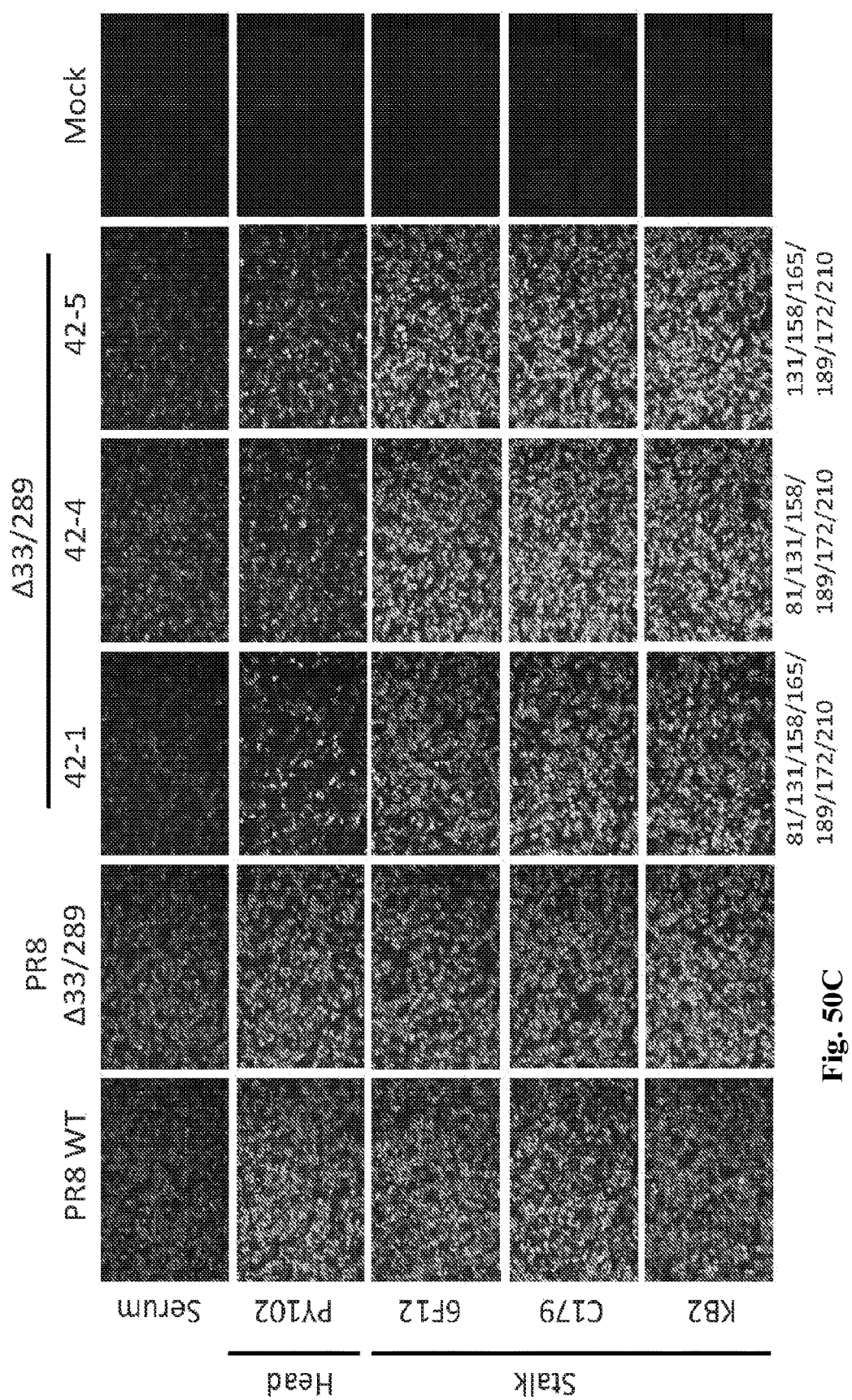

Fluorescence staining of the stalk domain with antibodies that specifically bind conformational epitopes in the stalk (KB2, C179 and 6F12 antibodies) was comparable to that of wildtype PR8, demonstrating that the mutant viral proteins were properly folded in their native conformation despite the addition of glycosylation sites in the head domain (FIG. 50C). Immunofluorescence staining of cells transfected with mutant PR8 HA constructs in which glycosylation sites had been introduced into the head domain (42-1, 42-4 and 42-5) and cells transfected with mutant constructs in which glycosylation sites hs been introduced into the head domain and in which glycosylation sites had been removed from the stalk domain (42-1, Δ33/289; 42-4, Δ33/289; 42-5, Δ33/289) showed diminished binding to the anti-head domain antibody (PY102) compared to cells transfected with wildtype PR8 HA constructs and cells transfected with PR8 HA constructs with only two glycosylation sites in the HA stalk domain removed (433/289) (FIG. 50C). In contrast, there was no difference in the ability of anti-stalk antibodies to bind the stalk domain of cells expressing these same mutants as compared to wildtype PR8 and PR8 with glycosylation sites removed from the stalk domain (FIG. 50C).

To assess whether viable mutant virus could be recovered from infected cells, a hemadsorption assay was used to determine if the viral mutants were still able to bind sialyated receptors on chicken red blood cells. Mutant virus that retained an ability to bind the sialyated receptors would indicate that the virus could enter cells via its receptor. Influenza viruses expressing HA mutants in which certain glycosylation sites had been removed from the HA stalk were able to be rescued (FIG. 51). Next, the ability of virus to be rescued was assessed using a hemagglutinin assay in chicken embryo eggs, as described previously. In particular, Influenza viruses expressing HA mutants in which glycosylation sites at positions 289 and 483, or 33, 289, and 483 had been removed bound to red blood cells as well as wildtype PR8 virus (FIG. 51). In contrast, the addition of glycosylation sites in the head domain of HA seemed to substantially interfere with the ability of viruses expressing the mutant HA proteins to bind red blood cells (FIG. 51).

6.12 Example 12

A Carboxy-Terminal Trimerization Domain Stabilizes Conformational Epitopes on the Stalk Domain of Soluble Recombinant Hemagglutinin Substrates This example demonstrates that a carboxy-terminal trimerization domain is important to the structural integrity of stalk epitopes on recombinant soluble influenza virus hemagglutinin.

6.12.1 Materials and Methods

6.12.1.1 Cells

Sf9 insect cells (ATCC # CRL-1711) were grown in TMN-FH medium (Gemini Bio-Products) supplemented with 10% FBS (Atlanta Biologicals), 0.1% Pluronic F68 (Sigma) and a Penicillin-Streptomycin antibiotic (Gibco) mixture. BTI-TN-5B1-4 cells (High Five—Vienna Institute of Biotechnology subclone) were grown in HyClone SFX serum free medium (Fisher Scientific) supplemented with Penicillin-Streptomycin antibiotic mixture (Gibco).

6.12.1.2 Cloning and Recombinant Baculovirus Generation

Sequences coding for HAs of H1 strains A/Puerto Rico/8/34 (PR8), A/California/04/09 (Cal09), H2 strain A/Japan/305/57 (JAP57), H3 strains A/Hong Kong/1/68 (HK68), A/Wisconsin/67/05 (Wisc05) and H5 strain A/Viet Nam/1203/04 (VN04—with removed polybasic cleavage site; see Steel et al., 2009, J Virol 83: 1742-1753) were amplified from pCAGGS plasmids by polymerase chain reaction and cloned into a modified pFastBac vector (Invitrogen) using BamHI or StuI and NotI restriction endonucleases (NEB). Primer sequences are available upon request. Two sets of constructs, HA without and with trimerization domain, were cloned: HA constructs without trimerization domain were designed so that the C-terminal transmembrane- and endodomain of the HA were replaced with a hexahistidine-tag (HA sequence ends with I509 for H1, V509 for H2 and H5 and G508 for H3; H3 numbering); the other set of constructs, HA with a trimerization domain, also lack the C-terminal transmembrane- and endodomains (HA sequence ends with V503-H3 numbering) but include a thrombin cleavage site and a T4 foldon trimerization domain (see, e.g., Meier et al., 2004, J Mol Biol 344: 1051-1069) in addition to the C-terminal hexahistidine-tag (FIG. 52). Generated recombinant pFastBac clones were transformed into DH10Bac bacteria (Invitrogen) according to the manufacturer's instructions and recombinant bacmids were prepared with a PureLink Plasmid Filter Midiprep kit (Invitrogen). Recombinant bacmids were transformed into Sf9 cells using Cellfectin II (Invitrogen) for rescue of recombinant baculovirus. All sequences were confirmed by Sanger sequencing.

6.12.1.3 Protein Expression, Purification and Characterization

Baculovirus was amplified in Sf9 cells to a passage 3 stock and then used to infect BTI-TN-5B1-4 (High Five) cells at $1\times10^6$ cells/ml in HyClone SFX serum free media (Fisher Scientific) at a multiplicity of infection of 10. Expression was carried out in 1000 ml shaker flasks for 96 hours at 28° C. After 96 hours, supernatants were cleared by low speed centrifugation (5000 g, 4° C., 20 min) and incubated with Ni-NTA (Qiagen) resin (3 ml slurry for 250 ml of culture supernatant) for two hours at room temperature (RT). The resin-supernatant mixture was then passed over 10 ml polypropylene columns (Qiagen). The retained resin was washed four times with 15 ml of washing buffer (50 mM $Na_2HCO_3$, 300 mM NaCl, 20 mM imidazole, pH 8) and protein was eluted with elution buffer (50 mM $Na_2HCO_3$, 300 mM NaCl, 300 mM imidazole, pH 8). The eluate was concentrated using Amicon Ultracell (Millipore) centrifugation units with a cut-off of 30 kDa and buffer was changed to phosphate buffered saline (PBS) of pH 7.4. Protein concentration was quantified using Quickstart Bradford Dye Reagent (Bio-Rad) with a bovine serum albumin standard curve. Protein purity, integrity and identity was assessed by sodium dodecyl sulfate polyacrylamide gel electrophoresis (SDS-PAGE) (4-20% polyacrylamide—Mini PROTEAN TGX gels, Bio-Rad), Coomassie staining and Western blot or enzyme linked immunosorbent assay (ELISA). Extent of trimerization and/or multimerization was tested by cross-linking of HA with bis-[sulfosuccinimidyl]suberate ($BS^3$—Fisher Scientific) according to the manufacturer's recommendations. Briefly, 3 µg of HA were incubated in 30 µA of PBS in the presence of a 25 fold molar excess of $BS^3$ crosslinker. The mixture was incubated at RT for 30 minutes and then $BS^3$ was quenched by adding 1M Tris-HCl buffer (pH 8) to a final concentration of 50 mM. Subsequently SDS-PAGE and/or Western blot analysis with a mouse anti-his primary antibody (Sigma) and anti-mouse horseradish peroxidase (Santa Cruz Biotechnology) or alkaline phosphatase (Santa Cruz Biotechnology) conjugated secondary antibody was performed.

6.12.1.4 Enzyme Linked Immunosorbent Assay

Immunolon 4HBX (Fisher Scientific) plates were coated with recombinant HA with and without trimerization domain at a concentration of 5 µg/ml in coating buffer (0.1 M Na2CO3/NaHCO3, pH 9.2, 50 µl/well) overnight at 4° C. The plates were then blocked for one hour at RT with PBS (pH 7.4) containing 1% Tween 20 (TBPS) and 3% non-fat dry milk powder. After blocking, plates were washed once with TPBS and then incubated with three fold dilutions of monoclonal antibody or sera (100 µl per well in TPBS with 1% milk powder-monoclonal antibody starting concentration 30 µg/ml; 1:100 dilution for sera) for one hour at RT. Plates were then washed trice with 100 µl of TPBS and incubated for another hour at RT with horse radish peroxidase conjugated anti-mouse IgG (Santa Cruz Biotechnology) or anti-human Fab secondary antibody (Sigma) at a dilution of 1:3000 (50 µl per well). After three more washes, plates were developed using SigmaFAST OPD substrate (Sigma) (100 µl/well), stopped with 3M HCl (50 µl/well) and read at an absorption of 490 nm on a Synergy 4 (BioTek) plate reader. The obtained read-out was background subtracted with values from secondary antibody-only incubated wells.

For stability studies, HA from PR8 virus with trimerization domain was stored at 4° C. for 60 days, or at −80° C. and went through one (standard), two, three or four freeze-thaw cycles. Stability of head versus stalk binding antibodies was compared using PY102 and C179 monoclonal antibodies. Antibody-HA combinations in ELISA were done in triplicates except for stability studies where duplicates were used.

6.12.2 Results

6.12.2.1 A C-Terminal Trimerization Domain Stabilizes HAs and Induces Trimer Formation The extracellular domain of various group 1 and group 2 HAs were expressed in soluble form with or without a C-terminal T4 phage trimerization domain (FIG. 52) in the baculoviral expression system. Proteins were harvested 96 hours post infection and purified via a C-terminal hexahistidine-tag using a Ni-NTA column. Purified protein was concentrated using ultrafiltration spin columns, assessed for protein integrity and impurities by SDS-PAGE and Coomassie staining and quantified with Bradford reagent. Based on the amino acid sequence and the fact that baculovirus expressed full length HAs without polybasic cleavage site are usually uncleaved, the extracellular domain of HA would have an expected molecular mass of approximately 60 kDa per monomer (or 180 kDa per trimer) without taking glycosylation into account. Cal09 (H1), JAP57 (H2) and VN04 (H5 without polybasic cleavage site) HA without trimerization domain seemed to be partially cleaved into HA1 and HA2 as indicated by the presence of bands at approximately 40 kDa (HA1) and 25 kDa (HA2) in addition to the uncleaved HA band at 60 kDa (HA0). Based on the exclusive presence of a 60 kDa band for Cal09, JAP57 and VN04 HAs with trimerization domains in the non-reducing, denaturing SDS-PAGE, it can be assumed that these proteins are expressed mostly as an uncleaved HA0 (FIG. 53A). Additionally, preparations of Wisc05 (H3) HA without a trimerization domain showed a degradation product at 40 kDa that was reactive when probed with an anti-stalk antibody (12D1). This species was thus likely a product of non-specific cleavage. Wisc05 HA with trimerization domain appeared only as an HA0 band (FIG. 53A). PR8 and HK68 HA appeared to be very stable (present as HA0) even in the absence of a trimerization domain.

HAs were crosslinked with and without T4 trimerization domain using BS3, a hydrophilic 11 Ångstrom chemical crosslinker that was recently used to show trimerization for HAs (see, e.g., Weldon et al., 2010, PLoS One 5). After crosslinking, samples were diluted in a reducing, denaturing loading dye and resolved on a reducing, denaturing SDS-PAGE gel. Group 1 HAs without trimerization domain formed high molecular weight oligomers that barely ran into the running gel and were mostly retained in the stacking gel (FIGS. 53B and 53C). The strongest phenotype was detected for VN04 and JAP57; other group 1 HAs also formed additional trimers (approximately 230 kDa), dimers (130 to 150 kDa) and monomers (60 kDa) (FIGS. 53B and 53C). Group 1 HAs with trimerization domain formed mostly trimers that ran at approximately 230 kD on the SDS-PAGE gel and formed a defined band in the running gel. However, they also formed dimers (approximately 130 to 150 kDa, strongest for Cal09) and monomers (60 kDa). Group 2 HAs behaved differently: HK68 HA formed predominantly trimers and to some degree dimers regardless of the presence of a trimerization domain. Wisc05 HA showed mainly dimerization in the absence of a trimerization domain, while HA with the T4 domain was mostly trimerized.

Figure 54A:
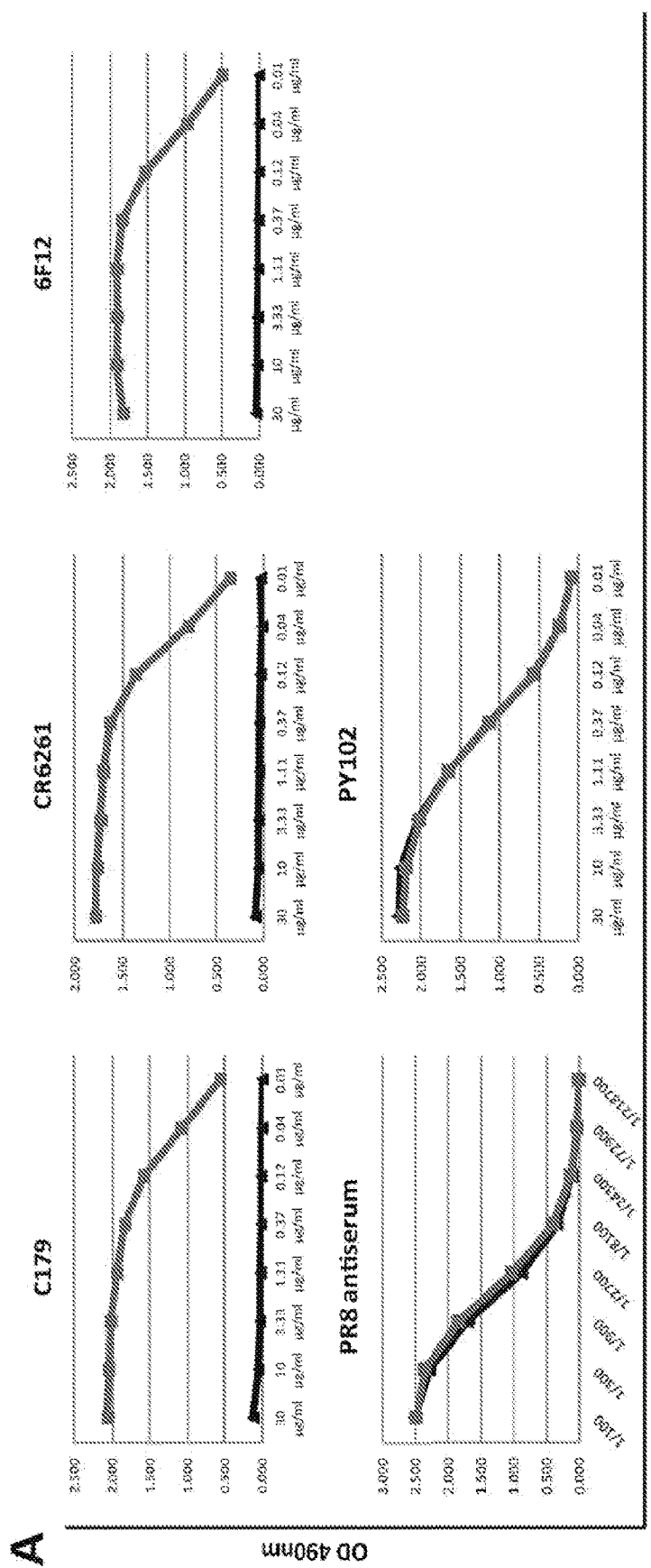
Figure 54B:
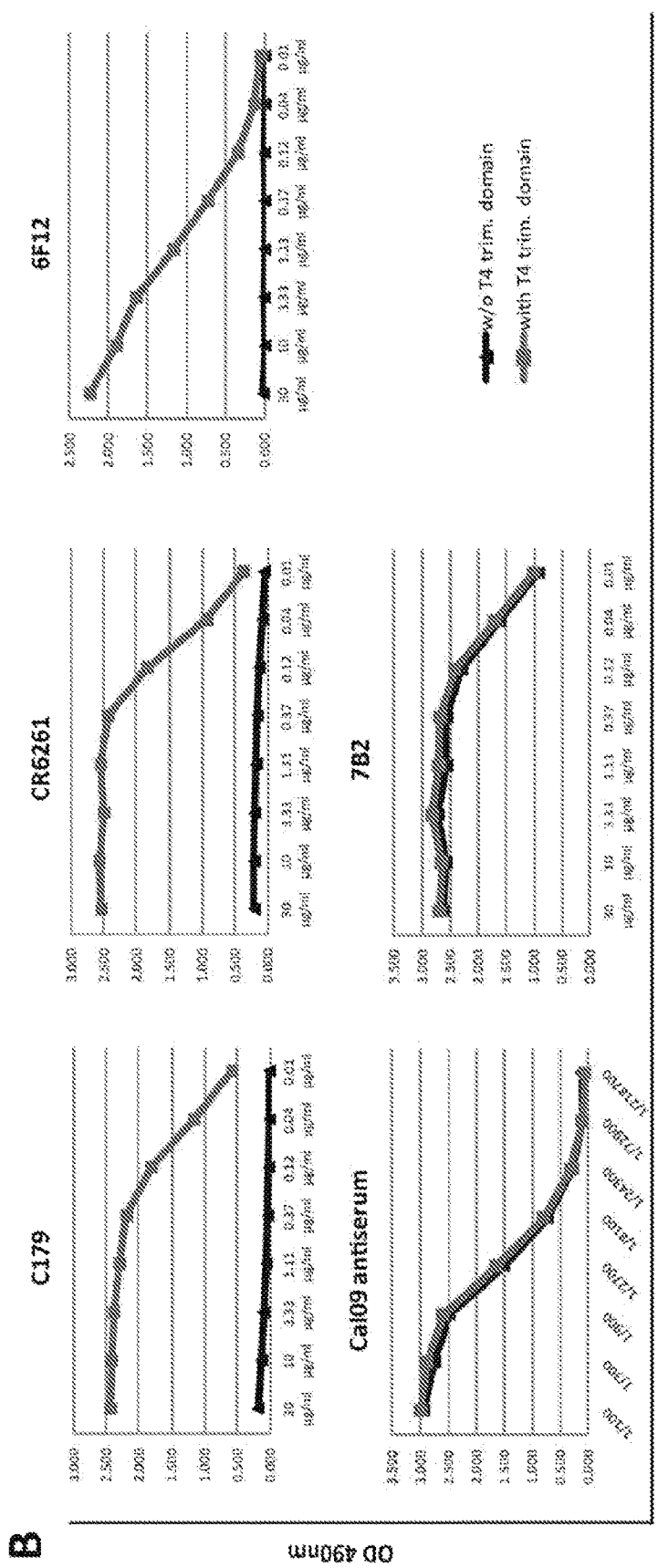

6.12.2.2 A C-Terminal Trimerization Domain Strongly Enhances Binding of Stalk-Reactive Antibodies to HA Substrates The reactivity of a panel of broadly reactive, neutralizing antibodies to the HA constructs was assessed in order to determine differential binding of these antibodies to HA substrates with and without trimerization domain. Stalk-specific antibodies mAb C179, mouse mAb 6F12, human mAb CR6261 (all group 1 specific); and mouse mAb 12D1 and human mAb CR8020 (both group 2 specific) were used in the experiment. Four other stalk-reactive antibodies, KB2, BD3, GG3 and IB11, that were recently isolated and characterized to have reactivity to both H1 and H5 Has also were used in the experiment. As a control, strain specific antibodies that are known to bind to the globular head domain of HA were used. As additional controls, sera of mice sub-lethally infected with influenza virus strains (PR8, Cal09, H3, VN04) or vaccinated with VLPs (JAP57) was used. Antibodies C179, CR6261 and 6F12 showed a strong binding phenotype to both H1 HAs that were tested (Cal09 and PR8). It is of note that they bound exclusively to HAs that had a trimerization domain (FIGS. 54A and 54B); no binding was observed to HAs without a trimerization domain. Similar binding characteristics were seen with the four other stalk-reactive broadly neutralizing H1-H5 antibodies. In contrast, head-specific antibodies, such as 7B2 (Cal09) and PY102 (PR8), reacted with HAs irrespective of the expression of a trimerization domain and these findings were confirmed using sera from Cal09 or PR8 infected animals (FIGS. 54A and 54B).

Figure 55A:
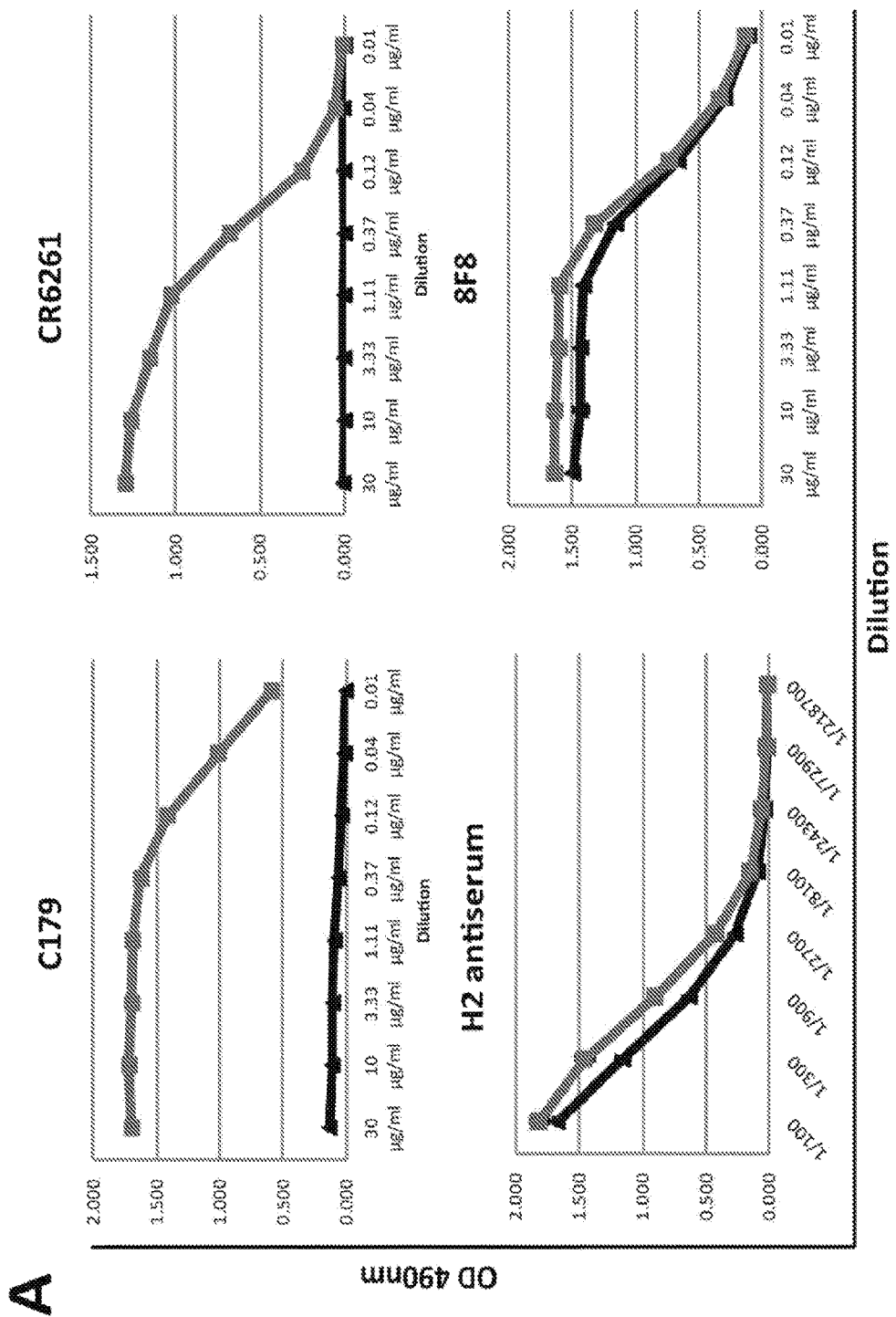
Figure 55B:
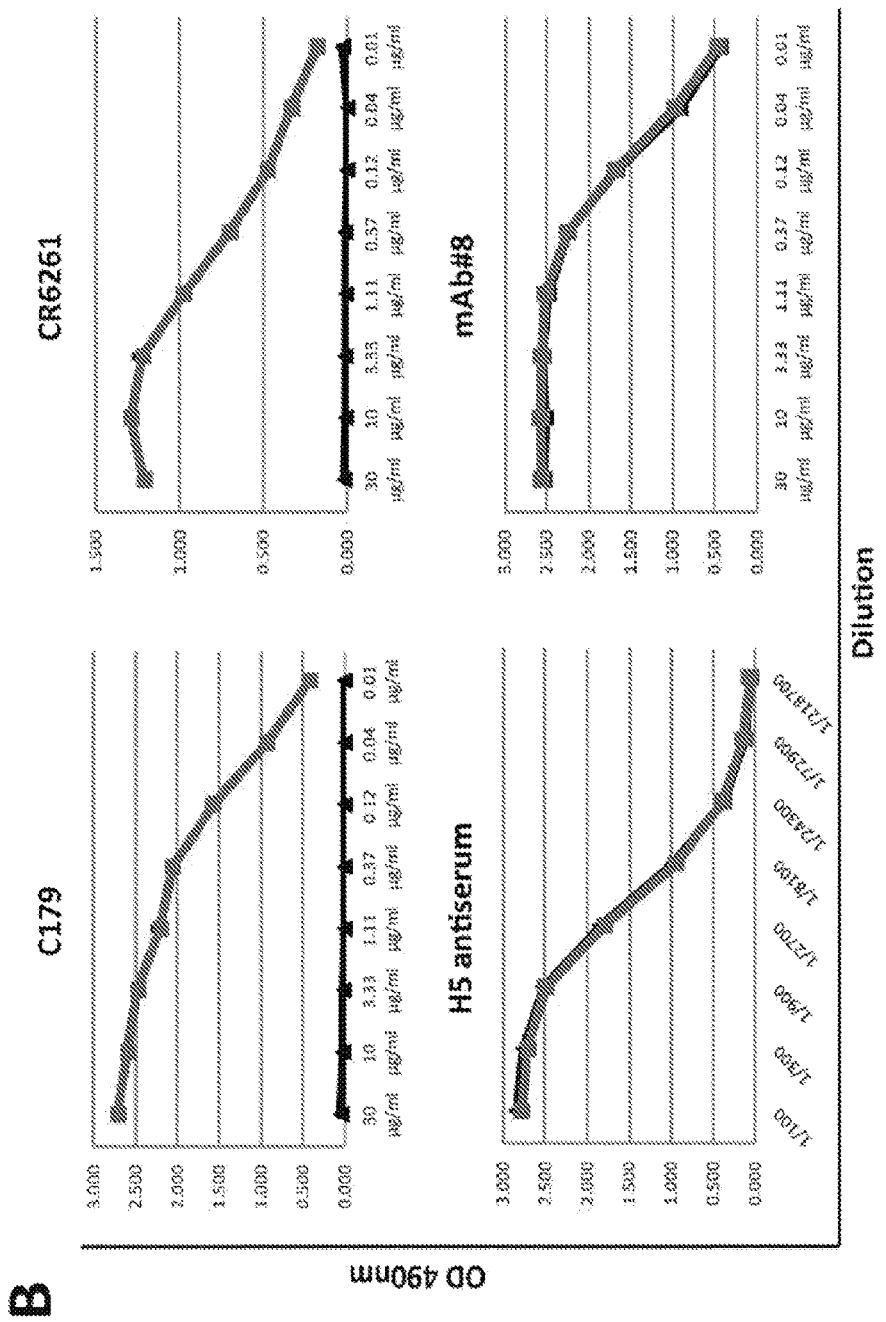

This effect is not specific to the H1 subtype—when testing the binding of C179 and CR6261 to JAP57 (H2) and VN04 (H5) HAs with and without a trimerization domain, a similar phenotype was observed, where these antibodies only reacted with trimerized forms of the protein (FIGS. 55A and 55B). The same result was seen when reactivity of the four H1-H5 antibodies was assessed. Head-specific antibodies 8F8 (JAP57) and mAb#8 (VN04) or polyclonal anti-H2 or anti-H5 sera recognized both forms of HA equally well.

Figure 56A:
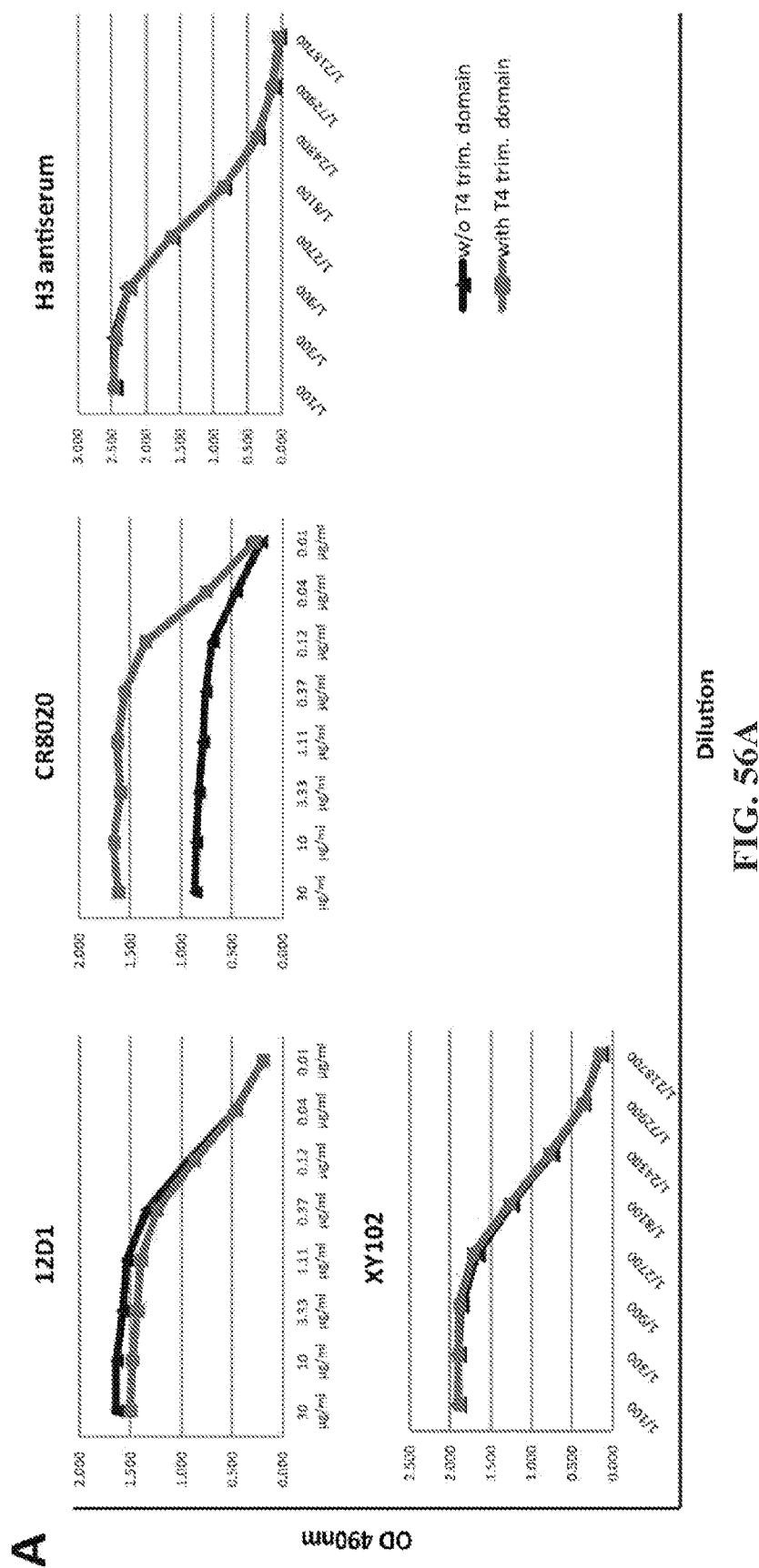
Figure 56B:
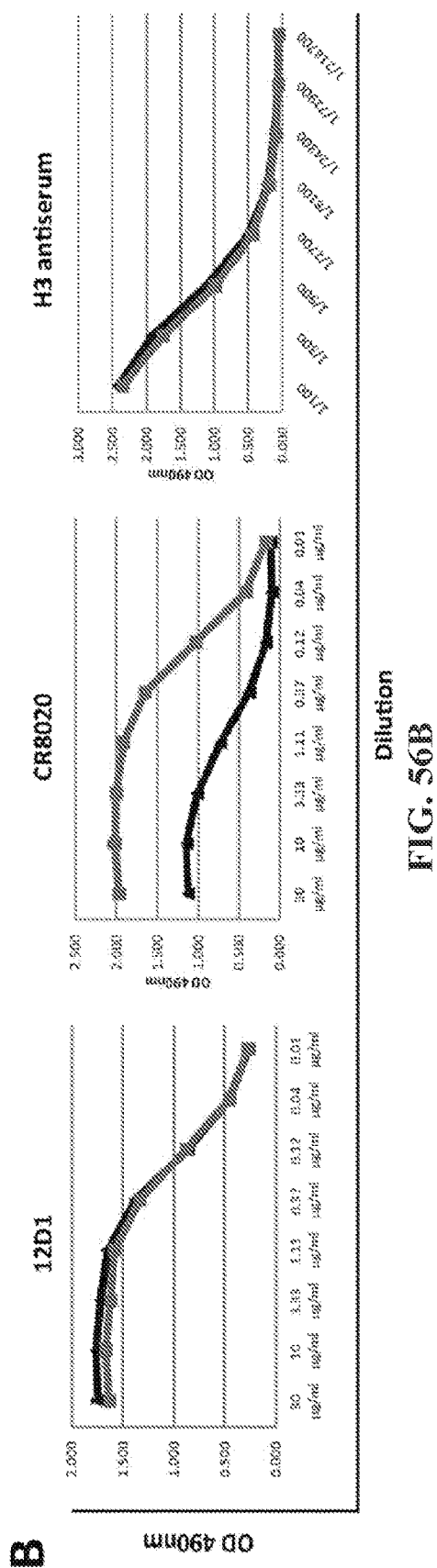

For group 2 HA-binding antibodies a different pattern emerged. In order to test the effects of a trimerization domain on reactivity of stalk antibodies with group 2 HAs, broadly reactive antibodies CR8020 and 12D1 were used. CR8020 binds a conformational epitope in group 2 HAs, while 12D1 is thought to bind to a linear epitope within the long alpha helix (LAH) of the HA2 subunit. CR8020 binding to HK68 and Wisc05 HAs with trimerization domains was greatly enhanced over binding to HAs without trimerization domain (FIGS. 56A and 56B). However, lack of the trimerization domain did not completely abolish binding as seen with group 1 HAs. 12D1 did not distinguish between HAs with or without the trimerization domain (FIG. 56).

6.12.3 Conclusion

The T4 trimerization domain allows for successful trimerization of soluble HA molecules and greatly increases the stability of these molecules following baculovirus expression.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A chimeric influenza virus hemagglutinin (HA) polypeptide comprising an HA stem domain and an HA globular head domain, wherein the HA globular head domain is from a different influenza virus subtype than the influenza virus subtype of the HA stem domain, wherein
   (a) the HA stem domain comprises (i) an HA1 N-terminal stem segment, wherein the HA1 N-terminal stem segment consists of amino acid residues $HA1_{N-term}$ through $A_p$; and (ii) an HA1 C-terminal stem segment, wherein the HA1 C-terminal stem segment consists of amino acid residues $A_q$ through $HA1_{C-term}$; and
   (b) the HA globular head domain comprises the amino acid residues between $A_p$ and $A_q$ of an HA1 domain: and
   wherein $HA1_{N-term}$ is the N-terminal amino acid of a mature HA0 protein lacking a signal peptide; wherein $HA1_{C-term}$ is the C-terminal amino acid of an HA1 domain; and wherein $A_p$ is the Cys that corresponds to amino acid position 52 of an HA1 domain using H3 numbering; and wherein $A_q$ is the Cys that corresponds to amino acid position 277 of an HA1 domain using H3 numbering.

2. The chimeric influenza virus HA polypeptide of claim 1, wherein the HA stem domain comprises an HA2 domain, and wherein the HA stem domain is resistant to protease cleavage at the junction between HA1 and HA2.

3. The chimeric influenza virus HA polypeptide of claim 1, wherein the chimeric influenza virus HA polypeptide is expressed and isolated from a mammalian cell.

4. The chimeric influenza virus HA polypeptide of claim 1, wherein the chimeric influenza virus HA polypeptide is expressed and isolated from an insect cell.

5. The chimeric influenza virus HA polypeptide of claim 1, wherein the chimeric influenza virus HA polypeptide is soluble.

6. The chimeric influenza virus HA polypeptide of claim 1, wherein the HA stem domain is the HA stem domain of an influenza virus of subtype H1.

7. The chimeric influenza virus HA polypeptide of claim 1, wherein the HA stem domain is the HA stem domain of an influenza virus of subtype H3.

8. An immunogenic composition comprising the chimeric influenza virus HA polypeptide of claim 1.

9. The chimeric influenza virus HA polypeptide of claim 5, wherein the chimeric influenza virus HA polypeptide further comprises a foldon or trimerization domain.

10. The chimeric influenza virus HA polypeptide of claim 1, wherein the HA stem domain is from an H1 subtype and the HA globular head domain from an H5 subtype.

11. The chimeric influenza virus HA polypeptide of claim 1, wherein (a) the HA stem domain is from an H1 subtype and the HA globular head domain is from an H6 subtype; or (b) the HA stem domain is from an H1 subtype and the HA globular head domain from an H9 subtype.

12. The chimeric influenza virus HA polypeptide of claim 1, wherein the HA stem domain is from an H3 subtype and the HA globular head domain is from an H7 subtype.

13. The chimeric influenza virus HA polypeptide of claim 1, wherein the HA stem domain is from A/Perth/16/2009 of the H3 subtype and the HA globular head domain is from A/mallard/Alberta/24/2001 of the H7 subtype.

14. A chimeric influenza virus hemagglutinin (HA) polypeptide comprising an HA stem domain and an HA globular head domain, wherein the HA globular head domain is from a different influenza virus subtype than the influenza virus subtype of the HA stem domain, and wherein the chimeric influenza virus HA polypeptide has fusogenic activity of an influenza virus HA, wherein
   (a) the HA stem domain comprises (i) an HA1 N-terminal stem segment, wherein the HA1 N-terminal stem seument consists of amino acid residues $HA1_{N-term}$ throuuh $A_p$; and (ii) an HA1 C-terminal stem segment, wherein the HA1 C-terminal stem segment consists of amino acid residues $A_q$ throuah $HA1_{C-term}$; and
   (b) the HA ulobular head domain comprises the amino acid residues between $A_p$ and $A_q$ of an HA1 domain;
   wherein $HA1_{N-term}$ is the N-terminal amino acid of a mature HA0 protein lacking a signal peptide; wherein $HA1_{C-term}$ is the C-terminal amino acid of an HA1 domain; and wherein $A_p$ is the Cys that corresponds to amino acid position 52 of an HA1 domain usinu H3 numbering; and wherein $A_q$ is the Cys that corresponds to amino acid position 277 of an HA1 domain using H3 numbering.

15. An immunogenic composition comprising the chimeric influenza virus HA polypeptide of claim 14.

16. The chimeric influenza virus HA polypeptide of claim 1, wherein the HA globular head domain is the HA globular head domain of an influenza virus of subtype H4, H6, H7, H8, H9, H10, H11, H12, H13, H14, H15, H16, or H17.

17. The chimeric influenza virus HA polypeptide of claim 1, wherein the HA globular head domain is the HA globular head domain of an influenza virus of subtype H5.

18. The chimeric influenza virus HA polypeptide of claim 1, wherein the HA globular head domain is the HA globular head domain of an influenza virus of subtype H7.

19. The chimeric influenza virus HA polypeptide of claim 6, wherein the H1 subtype is A/Califomia/04/09.

20. The chimeric influenza virus HA polypeptide of claim 7, wherein the H3 subtype is A/Perth/16/2009.

21. The chimeric influenza virus HA polypeptide of claim 1, wherein the HA stem domain is from an H3 subtype and the HA globular head domain from an H5 subtype.

22. The chimeric influenza virus HA polypeptide of claim 21, wherein the H3 subtype is A/Perth/16/2009 and the H5 subtype is A/Vietnam/1203/04.

23. The chimeric influenza virus HA polypeptide of claim 1, wherein the HA globular head domain is from an influenza virus of subtype H4.

24. The chimeric influenza virus HA polypeptide of claim 1, wherein the HA globular head domain is from an influenza vims of subtype H6.

25. The chimeric influenza virus HA polypeptide of claim 1, wherein the HA globular head domain is from an influenza virus of subtype H8.

26. The chimeric influenza virus HA polypeptide of claim 1, wherein the HA globular head domain is from an influenza virus of subtype H9.

27. The chimeric influenza virus HA polypeptide of claim 1, wherein the HA globular head domain is from an influenza virus of subtype H10.

28. The chimeric influenza virus HA polypeptide of claim 1, wherein the HA globular head domain is from an influenza virus of subtype H11.

29. The chimeric influenza virus HA polypeptide of claim 1, wherein the HA globular head domain is from an influenza virus of subtype H12.

30. The chimeric influenza virus HA polypeptide of claim 1, wherein the HA globular head domain is from an influenza virus of subtype H13.

31. The chimeric influenza virus HA polypeptide of claim 1, wherein the HA globular head domain is from an influenza virus of subtype H14.

32. The chimeric influenza virus HA polypeptide of claim 1, wherein the HA globular head domain is from an influenza virus of subtype H15.

33. The chimeric influenza virus HA polypeptide of claim 1, wherein the HA globular head domain is from an influenza virus of subtype H16.

34. The chimeric influenza virus HA polypeptide of claim 27, wherein the HA globular head domain is from an influenza virus of subtype H17.

35. The chimeric influenza virus HA polypeptide of claim 1, wherein the HA stem domain is from an H1 subtype and the HA globular head domain from an H2 subtype.

36. The chimeric influenza virus HA polypeptide of claim 1, wherein the HA stem domain is from an H1 subtype and the HA globular head domain from an H3 subtype.

37. The chimeric influenza virus HA polypeptide of claim 1, wherein the HA stem domain is from an H1 subtype and the HA globular head domain from an H11 subtype.

38. The chimeric influenza virus HA polypeptide of claim 14, wherein the HA stem domain is from an influenza virus of subtype H1.

39. The chimeric influenza virus HA polypeptide of claim 14, wherein the HA stem domain is from an influenza virus of subtype H3.

40. The chimeric influenza virus HA polypeptide of claim 14, wherein the HA globular head domain is the HA globular head domain of an influenza virus of subtype H4, H6, H7, H8, H9, H10, H11, H12, H13, H14, H15, H16, or H17.

41. The chimeric influenza virus HA polypeptide of claim 14, wherein the HA globular head domain is from an influenza virus of subtype H5.

42. The chimeric influenza virus HA polypeptide of claim 14, wherein the HA stem domain is from A/Perth/16/2009 of the H3 subtype and the HA globular head domain is from A/mallard/Alberta/24/2001 of the H7 subtype.

43. The chimeric influenza virus HA polypeptide of claim 38, wherein the H1 subtype is A/California/04/09.

44. The chimeric influenza virus HA polypeptide of claim 39, wherein the H3 subtype is A/Perth/16/2009.

45. The chimeric influenza viais HA polypeptide of claim 14, wherein the HA stem domain is from an H3 subtype and the HA globular head domain from an H5 subtype.

46. The chimeric influenza virus HA polypeptide of claim 45, wherein the H3 subtype is A/Perth/16/2009 and the H5 subtype is A/Vietnam/1203/04.

47. The chimeric influenza virus HA polypeptide of claim 1, wherein (a) the HA stem domain is from A/PR/8/34 of the H1 subtype and the HA globular head domain is from A/California/04/09 of the H1 subtype; (b) the HA stem domain is from A/PR/8/34 of the H1 subtype and the HA globular head domain is from A/Vietnam/1203/04 of the H5 subtype; (c) the HA stem domain is from A/PR/8/34 of the H3 subtype and the HA globular head domain is from A/Hong Kong/1/1968 of the H3 subtype; (d) the HA stem domain is from A/PR/8/34 of the H1 subtype and the HA globular head domain is from A/Mallard/Sweden/81/02 of the H6 subtype; or (e) the HA stem domain is from A/PR/8/34 and the HA globular head domain is from A/Guinea fowl/Hong Kong/WF 10/99 of the H9 subtype.

* * * * *